US007247442B1

(12) United States Patent
Ruben et al.

(10) Patent No.: US 7,247,442 B1
(45) Date of Patent: Jul. 24, 2007

(54) ANTIBODIES TO HHPEN62 POLYPEPTIDE

(75) Inventors: Steven M. Ruben, Brookeville, MD (US); Kimberly A. Florence, Rockville, MD (US); Jian Ni, Germantown, MD (US); Craig A. Rosen, Laytonsville, MD (US); Kenneth C. Carter, North Potomac, MD (US); Paul A. Moore, North Bethesda, MD (US); Henrik S. Olsen, Gaithersburg, MD (US); Yanggu Shi, Gaithersburg, MD (US); Paul E. Young, Gaithersburg, MD (US); Ying-Fei Wei, Berkeley, CA (US); Laurie A. Brewer, St. Paul, MN (US); Daniel R. Soppet, Centreville, VA (US); David W. LaFleur, Washington, DC (US); Gregory A. Endress, Florence, MA (US); Reinhard Ebner, Gaithersburg, MD (US); Charles E. Birse, North Potomac, MD (US)

(73) Assignee: Human Genome Sciences, Inc., Rockville, MD (US)

( * ) Notice: Subject to any disclaimer, the term of this patent is extended or adjusted under 35 U.S.C. 154(b) by 83 days.

(21) Appl. No.: 10/849,979

(22) Filed: May 21, 2004

Related U.S. Application Data

(63) Continuation of application No. 09/948,783, filed on Sep. 10, 2001, now abandoned, which is a continuation-in-part of application No. 09/892,877, filed on Jun. 28, 2001, now abandoned, which is a continuation of application No. 09/437,658, filed on Nov. 10, 1999, now abandoned, which is a continuation-in-part of application No. PCT/US99/09847, filed on May 6, 1999.

(60) Provisional application No. 60/231,846, filed on Sep. 11, 2000, provisional application No. 60/085,927, filed on May 18, 1998, provisional application No. 60/085,906, filed on May 18, 1998, provisional application No. 60/085,920, filed on May 18, 1998, provisional application No. 60/085,924, filed on May 18, 1998, provisional application No. 60/085,922, filed on May 18, 1998, provisional application No. 60/085,923, filed on May 18, 1998, provisional application No. 60/085,921, filed on May 18, 1998, provisional application No. 60/085,925, filed on May 18, 1998, provisional application No. 60/085,928, filed on May 18, 1998, provisional application No. 60/085,093, filed on May 12, 1998, provisional application No. 60/085,094, filed on May 12, 1998, provisional application No. 60/085,105, filed on May 12, 1998, provisional application No. 60/085,180, filed on May 12, 1998.

(51) Int. Cl.
*G01N 33/53* (2006.01)
*C07K 16/40* (2006.01)
*C12N 5/12* (2006.01)

(52) U.S. Cl. ................ 435/7.1; 530/387.1; 530/387.9; 530/388.1; 530/387.3; 530/388.15; 530/388.26; 435/325; 435/326

(58) Field of Classification Search .................... None
See application file for complete search history.

(56) References Cited

FOREIGN PATENT DOCUMENTS

| | | |
|---|---|---|
| EP | 0829538 A2 | 3/1998 |
| EP | 1097997 | 5/2001 |
| WO | WO 92/05256 | 4/1992 |
| WO | WO-97/48799 | 12/1997 |
| WO | WO-97/48800 | 12/1997 |
| WO | WO-97/48801 | 12/1997 |
| WO | WO-99/02686 | 1/1999 |
| WO | WO-00/39327 | 7/2000 |

OTHER PUBLICATIONS

U.S. Appl. No. 09/912,293, Rosen et al., pp. 1-75 (pp. 1 & 2 partially redacted); portion of Table 2; and SEQ ID Nos. 95819, 95820, 96106, 96643 and 96644.
U.S. Appl. No. 09/912,292, Rosen et al., pp.1-75 (pp.1 & 2 partially redacted); portion of Table 2; and SED ID Nos. 11013 and 21531.
GenBank Accession No. AAB51073, Racevskis et al., "Molecular cloning of LMO41, a new human LIM domain gene," Feb. 15, 2000.
GenBank Accession No. U24576, Racevskis, "Human breast tumor autoantigen," May 3, 1995.
Teufel et al., "Sequence identification and characterization of human carnosinase and a closely related non-specific dipeptidase," *J Biol Chem.* 278(8):6521-31 (2003).
Steck et al., "Chondrocyte expressed protein-68 (CEP-68), a novel human marker gene for cultured chondrocytes," Biochem. J. (Great Britain) 353:169-174 (2001).
Peeck, et al., Cell, 50:667 (1987).
Skolnick, et al., Nature Biotechnology, arch 2000, 18:283-287.
Ganong, Review of Molecular Physiology, 17th edition, Appleton & Lange, pp. 220, 446 (1995).
Creighton, Proteins, Freeman & Co., pp. 70-73, Structures & Principles (1984).
GenBank Accession No. AC002518, Chen et al., " *Homo sapiens* chromosome X clone bWXD20, * Sequencing in Progress *, 10 unordered pieces," Sep. 2, 1997.
GenBank Accession No. Z95328, Bird, "Human DNA sequence from clone RP3-447B16 on chromosome Xq13.1-13.3," May 12, 1997.

(Continued)

*Primary Examiner*—Prema Mertz
(74) *Attorney, Agent, or Firm*—Human Genome Sciences, Inc.

(57) ABSTRACT

The present invention relates to novel human secreted proteins and isolated nucleic acids containing the coding regions of the genes encoding such proteins. Also provided are vectors, host cells, antibodies, and recombinant methods for producing human secreted proteins. The invention further relates to diagnostic and therapeutic methods useful for diagnosing and treating diseases, disorders, and/or conditions related to these novel human secreted proteins.

24 Claims, 8 Drawing Sheets

OTHER PUBLICATIONS

Figure 2:
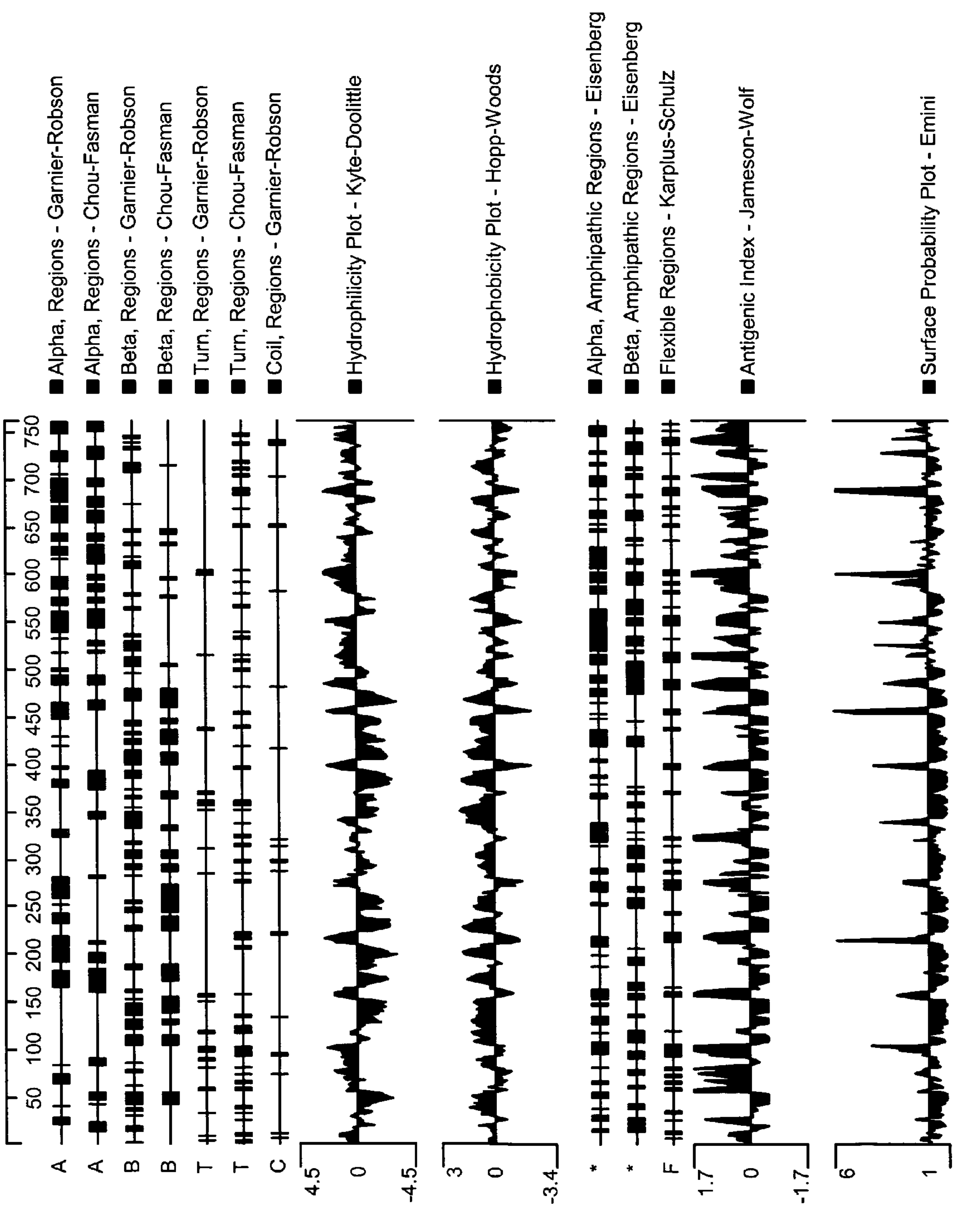

GenBank Accession No. U82207, Smith, " *Homo sapiens* chromosome 10 clone CIT987SK-1119P3 map 10q25.1, * Sequencing in Progress *, 1 ordered pieces," Jan. 22, 1997.
GenBank Accession No. AA238564, Marra et al., "my35f04.r1 Barstead mouse pooled organs MPLRB4 Mus musculus mRNA for TAG7 protein (MOUSE)," Mar. 6, 1997.
GenBank Accession No. H41544, Hillier et al., "yp71d08.s1 Soares adult brain N2b4HB55Y *Homo sapiens* cDNA clone Image: 19287 3', mRNA sequence," Aug. 5, 1995.
GenBank Accession No. AA348503, Adams et al., "EST29899 Cerebellum II *Homo sapiens* cDNA 5' end," April 18, 1997.
GenBank Accession No. AA326679, Adams et al., "EST54964 Hippocampus II Homo sapiens cDNA 5' end, mRNA sequence," Apr. 18, 1997.
GenBank Accession No. AI361251, Strausberg et al., "qy42e02.x1 NCI_CGAP_Brn23 *Homo sapiens* cDNA clone Image: 2014682 3' similar to WP:R11H6.1 CE12770 Yeast Hypothetical 52.9 KD Protein Like; mRNA sequence," Jan. 7, 1999.
GenBank Accession No. AC009704, Birren et al., " *Homo sapiens* chromosome 18, clone RP 11-231E4, complete sequence," Sep. 1, 1999.
Kishi, "Isolation and characterization of human Nramp cDNA," *Biochem Biohys Res Commun* 204(3):1074-80 (1994).
Jackson et al., "Purification and properties of human serum carnosinase," *Clin Chim Acta.* 196(2-3):193-205 (1991).
Jackson et al., "Homocarnosinosis patients and great apes have a serum protein that cross-reacts with human serum carnosinase," *Clin Chim Acta.* 205(1-2):109-16 (1992).
Willi et al., "A deletion in the long arm of chromosome 18 in a child with serum carnosinase deficiency," *Pediatr Res.* 41(2):210-3 (1997).
Lunde et al., "Homocarnosinosis: influence of dietary restriction of histidine," *Neurochem Res.* 11(6):825-38 (1986).
Murphey et al. "Serum carnosinase deficiency concomitant with mental retardation," *Pediatr Res.* 7(7):601-6 (1973).
Fleisher et al., "Carnosinase deficiency: a new variant with high residual activity," *Pediatr Res.* 14(4 Pt 1):269-71 (1980).
Partial European Search Report, Application No. EP 99 92 1691, mailed Mar. 23, 2005.
U.S. Appl. No. 10/100,683, Rosen et al., not yet published.
U.S. Appl. No. 11/001,793, Rosen et al., not yet published.
U.S. Appl. No. 11/366,486, Rosen et al., Nov. 2, 2006.
U.S. Appl. No. 10/664,357, Rosen et al., not yet published.
U.S. Appl. No. 10/472,533, Rosen et al., Nov. 8, 2005.
U.S. Appl. No. 10/405,027, Rosen et al., not yet published.
Nothen et al., "Evaluation of Linkage of Bipolar Affective disorder to Chromsome 18 in a Sample of 57 German Families," *Molecular Psychiatry*, 4:76-84 (1999).
McMahon et al., "Linkage of Bipolar Disorder to Chromosome 18q and the Validity of Bipolar II Disorder," *Arch. Gen. Psychiatry*, 58:1025-1031 (2001).
Wisniewski et al., "Neurological disease in a Child with Carnosinase Deficiency," *Neuropediatrics*, 12:143-151 (1981).
Lenney et al., "Homocarnosinosis: Lack of Serum Carnosinase is the Defect Probably Responsible for Elevated Brain and CSF Homocarnosine," *Clin. Chim. Acta.*, 132:157-165 (1983).
Zheng, Wei-ping and R.A. Flavell, "The Transcription Factor GATA-3 Is Necessary and Sufficient for Th2 Cytokine Gene Expression in CD4 T Cells," *Cell*, 89:587-596 (May 16, 1997).
Serreze et al., "Th1 to Th2 Cytokine Shifts in Nonobese Diabetic Mice: Sometimes an Outcome, Rather Tan the Cause, of Diabetes Resistance Elicited by Immunostimulation," *J. Immunol.*, 166: 1352-1359 (2001).

Figure 1A

```
  1 GCA CCC GGG AGG GAG ATG CGG CCG GGG CTC AGG CTC CTT GCA GTT GTA ATT TAG ATT CGA  60

 61 GAA GTG GTT TAT CCT TTG ACT GGA AAA GAA AAG TAG CTG CAG TAT TCC CCC AGC ACT TGC 120

121 TGA GAG CAT GCC GTA TGC CAG GCT GTG AGG CTC GAG AGA CAA GCA GTG GAA GAG TTG CGG 180

181 CCT GTT TCA TCT CTG GAT TGT AAA TCT GAG CCT CCT TCT GGC CCC TGG AAG GGG ACA GCA 240

241 TCA CCA TGG AAT GAT TCC TAA CCA GCA TAA TGC TGG AGC CGG GAG CCA CCA ACC TGC AGT 300
  1             M   I   P   N   Q   H   N   A   G   A   G   S   H   Q   P   A   V   17

301 TTT CAG AAT GGC CGT GTT GGA CAC TGA TTT GGA TCA CAT TCT TCC ATC TTC TGT TCT TCC 360
 18  F   R   M   A   V   L   D   T   D   L   D   H   I   L   P   S   S   V   L   P   37

361 TCC ATT CTG GGC TAA GTT AGT AGT GGG ATC GGT TGC CAT TGT GTG TTT TGC ACG CAG CTA 420
 38  P   F   W   A   K   L   V   V   G   S   V   A   I   V   C   F   A   R   S   Y   57

421 TGA TGG AGA CTT TGT CTT TGA TGA CTC AGA AGC TAT TGT TAA CAA TAA GGA CCT CCA AGC 480
 58  D   G   D   F   V   F   D   D   S   E   A   I   V   N   N   K   D   L   Q   A   77

481 AGA AAC GCC CCT GGG GGA CCT GTG GCA TCA TGA CTT CTG GGG CAG TAG ACT GAG CAG CAA 540
 78  E   T   P   L   G   D   L   W   H   H   D   F   W   G   S   R   L   S   S   N   97

541 CAC CAG CCA CAA GTC CTA CCG GCC TCT CAC CGT CCT GAC TTT CAG GAT TAA CTA CTA CCT 600
 98  T   S   H   K   S   Y   R   P   L   T   V   L   T   F   R   I   N   Y   Y   L  117
```

Figure 1B

```
601  CTC GGG AGG CTT CCA CCC CGT GGG CTT TCA CGT GGT CAA CAT CCT CCT GCA CAG TGG CAT 660
118   S   G   G   F   H   P   V   G   F   H   V   V   N   I   L   L   H   S   G   I  137

661  CTC TGT CCT CAT GGT GGA CGT CTT CTC GGT TCT GTT TGG CGG CCT GCA GTA CAC CAG TAA 720
138   S   V   L   M   V   D   V   F   S   V   L   F   G   G   L   Q   Y   T   S   K  157

721  AGG CCG GAG GCT GCA CCT CGC CCC CAG GGC GTC CCT GCT GGC CGC GCT GCT GTT TGC TGT 780
158   G   R   R   L   H   L   A   P   R   A   S   L   L   A   A   L   L   F   A   V  177

781  CCA TCC TGT GCA CAC CGA GTG TGT TGC TGG TGT TGT CGG CCG TGC AGA CCT CCT GTG TGC 840
178   H   P   V   H   T   E   C   V   A   G   V   V   G   R   A   D   L   L   C   A  197

841  CCT GTT CTT CTT GTT ATC TTT CCT TGG CTA CTG TAA AGC ATT TAG AGA AAG TAA CAA GGA 900
198   L   F   F   L   L   S   F   L   G   Y   C   K   A   F   R   E   S   N   K   E  217

901  GGG AGC GCA TTC TTC CAC CTT CTG GGT GCT GCT GAG TAT CTT TCT GGG AGC AGT GGC CAT 960
218   G   A   H   S   S   T   F   W   V   L   L   S   I   F   L   G   A   V   A   M  237

961  GCT GTG CAA AGA GCA AGG GAT CAC TGT GCT GGG TTT AAA TGC GGT ATT TGA CAT CTT GGT 1020
238   L   C   K   E   Q   G   I   T   V   L   G   L   N   A   V   F   D   I   L   V  257

1021 GAT AGG CAA ATT CAA TGT TCT GGA AAT TGN CCA GAA GGT ACT ACA TAA GGA CAA GTC ATT 1080
258   I   G   K   F   N   V   L   E   I   X   Q   K   V   L   H   K   D   K   S   L  277

1081 AGA GAA TCT CGG CAT GCT CAG GAA CGG GGG CCT CCT CTT CAG AAT GAC CCT GCT CAC CTC 1140
278   E   N   L   G   M   L   R   N   G   G   L   L   F   R   M   T   L   L   T   S  297
```

Figure 1C

```
1141 TGG AGG GGC TGG GAT GCT CTA CGT GCG CTG GAG GAT CAT GGG CAC GGG CCC GYC GGC CTT 1200
298   G   G   A   G   M   L   Y   V   R   W   R   I   M   G   T   G   P   X   A   F  317

1201 CAC CGA GGT GGA CAA CCC GGC CTC CTT TGC TGA CAG CAT GCT GGT GAG GGC CGT AAA CTA 1260
318   T   E   V   D   N   P   A   S   F   A   D   S   M   L   V   R   A   V   N   Y  337

1261 CAA TTA CTA CTA TTC ATT GAA TGC CTG GCT GCT GCT GTG TCC CTG GTG GCT GTG TTT TGA 1320
338   N   Y   Y   Y   S   L   N   A   W   L   L   L   C   P   W   W   L   C   F   D  357

1321 TTG GTC AAT GGG CTG CAT CCC CCT CAT TAA GTC CAT CAG CGA CTG GAG GGT AAT TGC ACT 1380
358   W   S   M   G   C   I   P   L   I   K   S   I   S   D   W   R   V   I   A   L  377

1381 TGC AGC ACT CTG GTT CTG CCT AAT TGG CCT GAT ATG CCA AGC CCT GTG CTC TGA AGA CGG 1440
378   A   A   L   W   F   C   L   I   G   L   I   C   Q   A   L   C   S   E   D   G  397

1441 CCA CAA GAG AAG GAT CCT TAC TCT GGG CCT GGG ATT TCT CGT TAT CCC ATT TCT CCC CGC 1500
398   H   K   R   R   I   L   T   L   G   L   G   F   L   V   I   P   F   L   P   A  417

1501 GAG TAA CCT GTT CTT CCG AGT GGG CTT CGT GGT CGC GGA GCG TGT CCT CTA CCT CCC CAG 1560
418   S   N   L   F   F   R   V   G   F   V   V   A   E   R   V   L   Y   L   P   S  437

1561 CRT TGG GTA CTG TGT GCT GCT GAC TTT TGG ATT CGG AGC CCT GAG CAA ACA TAC CAA GAA 1620
438   X   G   Y   C   V   L   L   T   F   G   F   G   A   L   S   K   H   T   K   K  457

1621 AAA GAA ACT CAT TGC CGC TGT CGT GCT GGG AAT CTT ATT CAT CAA CAC GCT GAG ATG TGT 1680
458   K   K   L   I   A   A   V   V   L   G   I   L   F   I   N   T   L   R   C   V  477

1681 GCT GCG CAG CGG CGA GTG GCG GAG TGA GGA ACA GCT TTT CAG AAG TGC TCT GTC TGT GTG 1740
478   L   R   S   G   E   W   R   S   E   E   Q   L   F   R   S   A   L   S   V   C  497
```

Figure 1D

```
1741 TCC CCT CAA TGC TAA GGT TCA CTA CAA CAT TGG CAA AAA CCT GGC TGA TAA AGG CAA CCA 1800
 498  P   L   N   A   K   V   H   Y   N   I   G   K   N   L   A   D   K   G   N   Q  517

1801 GAC AGC TGC CAT CAG ATA CTA CCG GGA AGC TGT AAG ATT AAA TCC CAA GTA TGT TCA TGC 1860
 518  T   A   A   I   R   Y   Y   R   E   A   V   R   L   N   P   K   Y   V   H   A  537

1861 CAT GAA TAA TCT TGG AAA TAT CTT AAA AGA AAG GAA TGA GCT ACA GGA AGC TGA GGA GCT 1920
 538  M   N   N   L   G   N   I   L   K   E   R   N   E   L   Q   E   A   E   E   L  557

1921 GCT GTC TTT GGC TGT TCA AAT ACA GCC AGA CTT TGC CGC TGC GTG GAT GAA TCT AGG CAT 1980
 558  L   S   L   A   V   Q   I   Q   P   D   F   A   A   A   W   M   N   L   G   I  577

1981 AGT GCA GAA TAG CCT GAA ACG GTT TGA AGC AGC AGA GCA AAG TTA CCG GAC AGC AAT TAA 2040
 578  V   Q   N   S   L   K   R   F   E   A   A   E   Q   S   Y   R   T   A   I   K  597

2041 ACA CAG AAG GAA ATA CCC AGA CTG TTA CTA CAA CCT CGG GCG TCT GTA TGC AGA TCT CAA 2100
 598  H   R   R   K   Y   P   D   C   Y   Y   N   L   G   R   L   Y   A   D   L   N  617

2101 TCG CCA CGT GGA TGC CTT GAA TGC GTG GAG AAA TGC CAC CGT GCT GAA ACC AGA GCA CAG 2160
 618  R   H   V   D   A   L   N   A   W   R   N   A   T   V   L   K   P   E   H   S  637

2161 CCT GGC CTG GAA CAA CAT GAT TAT ACT CCT CGA CAA TAC AGG TAA TTT AGC CCA AGC TGA 2220
 638  L   A   W   N   N   M   I   I   L   L   D   N   T   G   N   L   A   Q   A   E  657

2221 AGC AGT TGG AAG AGA GGC ACT GGA ATT AAT ACC TAA TGA TCA CTC TCT CAT GTT CTC GTT 2280
 658  A   V   G   R   E   A   L   E   L   I   P   N   D   H   S   L   M   F   S   L  677

2281 GGC AAA CGT GCT GGG GAA ATC CCA GAA ATA CAA GGA ATC TGA AGC TTT ATT CCT CAA GGC 2340
 678  A   N   V   L   G   K   S   Q   K   Y   K   E   S   E   A   L   F   L   K   A  697
```

Figure 1E

```
2341 AAT TAA AGC AAA TCC AAA TGC TGC AAG TTA CCA TGG TAA TTT GGC TGT GCT TTA TCA TCG 2400
 698  I   K   A   N   P   N   A   A   S   Y   H   G   N   L   A   V   L   Y   H   R  717

2401 TTG GGG ACA TCT AGA CTT GGC CAA GAA ACA CTA TGA AAT CTC CTT GCA GCT TGA CCC CAC 2460
 718  W   G   H   L   D   L   A   K   K   H   Y   E   I   S   L   Q   L   D   P   T  737

2461 GGC ATC AGG AAC TAA GGA GAA TTA CGG TCT GCT GAG AAG AAA GCT AGA ACT AAT GCA AAA 2520
 738  A   S   G   T   K   E   N   Y   G   L   L   R   R   K   L   E   L   M   Q   K  757

2521 GAA AGC TGT CTG ATC CTG TTT CCT TCA TGT TTT GAG TTT GAG TGT GTG TGT GCA TGA GGC 2580
 758  K   A   V   *                                                                  760

2581 ATA TCA TTA ATA GTA TGT GGT TAC ATT TAA CCA TTT AAA AGT CTT AGA CAT GTT ATT TTA 2640

2641 CTG ATT TTT TTC TAT GAA AAC AAA GAC ATG CAA AAA GAT TAT AGC ACC AGC AAT ATA CTC 2700

2701 TTG AAT GCG TGA TAT GAT TTT TCA TTG AAA TTG TAT TTT TTC AGA CAA CTC AAA TGT AAT 2760

2761 TCT AAA ATT CCA AAA ATG TCT TTT TTA ATT AAA CAG AAA AAG AGA AAA AAT TAT CTT GAG 2820

2821 CAA CTT TTA GTA GAA TTG AGC TTA CAT TTG GGA TCT GAG CCT TGT CGT GTA TGG ACT AGC 2880

2881 ACT ATT AAA CTT CAA TTA TGA CCA AGA AAG GAT ACA CTG GCC CCT ACA ATT TGT ATA AAT 2940

2941 ATT GAA CAT GTC TAT ATA TTA GCA TTT TTA TTT AAT GAC AAA GCA AAT TAA GTT TTT TTA 3000

3001 TCT CTT TTT TTT AAA ACA ACA TAC TGT GAA CTT TGT AAG GAA ATA TTT ATT TGT ATT TTT 3060
```

Figure 1F

```
3061 ATG TTT TGA ATA GGG CAA ATA ATC GAA TGA GGA ATG GAA GTT TTA ACA TAG TAT ATC TAT 3120

3121 ATG CTT TTC CCC ATA GGA AGA AAT TGA CTC TTG CAG TTT TTG GAT GCT CTG ACT TGT GCA 3180

3181 ATT TCA ATA CAC AGG AGA TTA TGT AAT GTA ATA TTT TTC ATA AGC GGT TAC TAT CAA TTG 3240

3241 AAA GTT CAA GCC ATG CTT TAG GCA AGA GCA GGC AGC CTC ACA TCT TTA TTT TTG TTA CAT 3300

3301 CCA AGG TGA AGA GGG CAA CAC ATC TGT GTA AGC TGC TTT TTA GTG TGT TTA TCT GAA GGC 3360

3361 CGT TTT CCA TTT TGC TTA ATG TAA CTA CAG ACA TTA TCC AGA AAA TGC AAA ATT TTC TAT 3420

3421 CAA ATG GAG CCA CAT TCG GGG AAT TCG TGG TAT TTT TAA GAA TTG AGT TGT TCC TGC TGT 3480

3481 TTT TTA TTT GAT CCA AAC AAT GTT TTG TTT TGT TCT TCT CTG TAT GCT GTT GAC CTA ATG 3540

3541 ATT TAT GCA ATC TCT GTA ATT TCT TAT GCA GTA AAA TTA CTA CAC AAA CTA GCA AAA AAA 3600

3601 AAA AAA AAA AAA AAA GGG CGG CCG CTC TAG AGG ATC CAA GCT TAC GTA CGC GTG CAT GCG 3660

3661 ACG TCA TAG CTC TTC TAT AGT GCA CCT AAA TTC AAT TCA CTG GGC CGT CGT TTT ACA ACG 3720
```

Figure 1G

3721 TCG TGA CTG GGA AAA CCC TGC GNT ACC CAA CTT AAT CGC CTT GCA GCA CAT CCC CCT TTC 3780

3781 GCC AAG CTG GCG TAA TAG CGA AAA GGC CCG GAC CGA CGG CCT TTC CAA CAG TTG CCA ACC 3840

3841 TGA AGG CNA AAG GGA CCC CCC CTG GAC GGG GCA TAA NCC CGN GGN T 3886

SEQUENCE LISTING

<160> NUMBER OF SEQ ID NOS: 465

<210> SEQ ID NO 1
<211> LENGTH: 733
<212> TYPE: DNA
<213> ORGANISM: Homo sapiens

<400> SEQUENCE: 1
gggatccgga gcccaaatct tctgacaaaa ctcacacatg cccaccgtgc ccagcacctg 60
aattcgaggg tgcaccgtca gtcttcctct tccccccaaa acccaaggac accctcatga 120
tctcccggac tcctgaggtc acatgcgtgg tggtggacgt aagccacgaa gaccctgagg 180
tcaagttcaa ctggtacgtg gacggcgtgg aggtgcataa tgccaagaca aagccgcggg 240
aggagcagta caacagcacg taccgtgtgg tcagcgtcct caccgtcctg caccaggact 300
ggctgaatgg caaggagtac aagtgcaagg tctccaacaa agccctccca acccccatcg 360
agaaaaccat ctccaaagcc aaagggcagc cccgagaacc acaggtgtac accctgcccc 420
catcccggga tgagctgacc aagaaccagg tcagcctgac ctgcctggtc aaaggcttct 480
atccaagcga catcgccgtg gagtgggaga gcaatgggca gccggagaac aactacaaga 540
ccacgcctcc cgtgctggac tccgacggct ccttcttcct ctacagcaag ctcaccgtgg 600
acaagagcag gtggcagcag gggaacgtct tctcatgctc cgtgatgcat gaggctctgc 660
acaaccacta cacgcagaag agcctctccc tgtctccggg taaatgagtg cgacggccgc 720
gactctagag gat 733

<210> SEQ ID NO 2
<211> LENGTH: 5
<212> TYPE: PRT
<213> ORGANISM: Homo sapiens
<220> FEATURE:
<221> NAME/KEY: Site
<222> LOCATION: (3)
<223> OTHER INFORMATION: Xaa equals any of the twenty naturally ocurring L-amino acids

<400> SEQUENCE: 2

Trp Ser Xaa Trp Ser
1 5

<210> SEQ ID NO 3
<211> LENGTH: 86
<212> TYPE: DNA
<213> ORGANISM: Homo sapiens

<400> SEQUENCE: 3
gcgcctcgag atttccccga aatctagatt tccccgaaat gatttccccg aaatgatttc 60
cccgaaatat ctgccatctc aattag 86

<210> SEQ ID NO 4
<211> LENGTH: 27
<212> TYPE: DNA
<213> ORGANISM: Homo sapiens

<400> SEQUENCE: 4
gcggcaagct ttttgcaaag cctaggc 27

<210> SEQ ID NO 5
<211> LENGTH: 271

-continued

<212> TYPE: DNA
<213> ORGANISM: Homo sapiens

<400> SEQUENCE: 5
ctcgagattt ccccgaaatc tagatttccc cgaaatgatt tccccgaaat gatttccccg 60
aaatatctgc catctcaatt agtcagcaac catagtcccg cccctaactc cgcccatccc 120
gcccctaact ccgcccagtt ccgcccattc tccgccccat ggctgactaa ttttttttat 180
ttatgcagag gccgaggccg cctcggcctc tgagctattc cagaagtagt gaggaggctt 240
ttttggaggc ctaggctttt gcaaaaagct t 271

<210> SEQ ID NO 6
<211> LENGTH: 32
<212> TYPE: DNA
<213> ORGANISM: Homo sapiens

<400> SEQUENCE: 6
gcgctcgagg gatgacagcg atagaacccc gg 32

<210> SEQ ID NO 7
<211> LENGTH: 31
<212> TYPE: DNA
<213> ORGANISM: Homo sapiens

<400> SEQUENCE: 7
gcgaagcttc gcgactcccc ggatccgcct c 31

<210> SEQ ID NO 8
<211> LENGTH: 12
<212> TYPE: DNA
<213> ORGANISM: Homo sapiens

<400> SEQUENCE: 8
ggggactttc cc 12

<210> SEQ ID NO 9
<211> LENGTH: 73
<212> TYPE: DNA
<213> ORGANISM: Homo sapiens

<400> SEQUENCE: 9
gcggcctcga ggggactttc ccggggactt tccggggact ttccgggact ttccatcctg 60
ccatctcaat tag 73

<210> SEQ ID NO 10
<211> LENGTH: 256
<212> TYPE: DNA
<213> ORGANISM: Homo sapiens

<400> SEQUENCE: 10
ctcgagggga ctttcccggg gactttccgg ggactttccg ggactttcca tctgccatct 60
caattagtca gcaaccatag tcccgcccct aactccgccc atcccgcccc taactccgcc 120
cagttccgcc cattctccgc cccatggctg actaattttt tttatttatg cagaggccga 180
ggccgcctcg gcctctgagc tattccagaa gtagtgagga ggcttttttg gaggcctagg 240

-continued

```
cttttgcaaa aagctt                                                  256

<210> SEQ ID NO 11
<211> LENGTH: 1191
<212> TYPE: DNA
<213> ORGANISM: Homo sapiens

<400> SEQUENCE: 11

gctgggctgg aacacaagar cccacagggc tgccgtccac actctcccgg tcagagtcct     60

gggaccacat ggggacgctg ccatggcttc ttgccttctt cattctgggt ctccaggctt    120

gggatactcc caccatcgtc tcccgcaagg agtggggggc aagaccgctc gcctgcaggg    180

ccctgctgac cctgcctgtg gcctacatca tcacagacca gctcccaggg atgcagtgcc    240

agcagcagag cgtttgcagc cagatgctgc gggggttgca gtcccattcc gtctacacca    300

taggctggtg cgacgtggcg tacaacttcc tggttgggga tgatggcagg gtgtatgaag    360

gtgttggctg gaacatccaa ggcttgcaca cccagggcta caacaacatt tccctgggca    420

tcgccttctt tggcaataag ataagcagca gtcccagccc tgctgcctta tcagctgcag    480

agggtctgat ctcctatgcc atccagaagg gtcacctgtc gcccaggtat attcagccac    540

ttcttctgaa agaagagacc tgcctggacc ctcaacatcc agtgatgccc agraaggttt    600

gccccaacat catcaaacga tctgcttggg aagccagaga gacacactgc cctaaaatga    660

acctcccagc caaatatgtc atcatcatcc acaccgctgg cacaagctgc actgtatcca    720

cagactgcca gactgtcgtc cgaaacatac agtcctttca catggacaca cggaactttt    780

gtgacattgg atatcaataa ggccaggcgt ggcggcgatt acgtctgtaa tcccaggact    840

ttgggaggcc aaggcgggca gatcacttca ggccaggaat tcaagagcag cctggccaat    900

atggcgaaac tctgtctcta ctgaaaacaa acaaacaaac aaacaaacaa acaaagaaac    960

aacaaaaatt agccgggtgt ggtggcacac gcctgtagtc ccagctactc aggaggctga   1020

ggcataagaa ttgcttgaac cctggaggcg gaggttgcag tgagctgaga ttgggccacc   1080

gcactccagt ctgggagaca gagtgagact gtctcaaaac aacaacaaaa aaatccctaa   1140

cataatctca aaaaaaaaaa aaaaaaaaaa aaaaaaaaaa agggcggccg c            1191

<210> SEQ ID NO 12
<211> LENGTH: 1251
<212> TYPE: DNA
<213> ORGANISM: Homo sapiens

<400> SEQUENCE: 12

ggcacaggtc agccaactaa caaatgaagc gcagggaaat gactcaattc ttattgagtc     60

tagttgctct taattgctgc tctatttctt tgggaagatt gacatatcca ggaggttttc    120

atctaaaact agacccctta gaactctgaa gtcagagcaa ctttccctct gtcaatccta    180

ctcactactt ttgtamcctt gaccagagaa gttgcttaat cttttggggc ctgcattctc    240

atatacctaa agtaggaata aaaatacctg cttagagact tgctcagtcc atcaaatrag    300

agattataca caaccttccc acttcaagga tggctgcaag gacaaaaaag aaaaatgaca    360

taataaatat aaaggtccct gcagactgta atactaggat gagttattac tacaaaggct    420

cagggaaaag aggagagatg gagtcttggt tggtcatgtc atcatggtct attttagatt    480

ttgagttttt agaggcaaga ccacagttgt ttaatttagt gtatacagaa cattccactt    540

attcagggag acattatact agggaaaggg gtgggttcat ggtgttcaaa aattcatact    600

cacagttatt attaaaaaga aaggattctc tatgtgcttt tattcagccc atggctttaa    660
```

-continued atatcatcca tgtgcctatg tcttccaaat gtatttttcc agcccagtct ggtccctcga 720
cattcagatc cttatggtgg tgccctcacc ctatatccaa atgccaactt ggtctctact 780
ctagtcagat tagagatatc ccatacttgg catgactaaa atggaacttt aacttgtttc 840
ttatctctat ctcagtaaat cacaccacca cagtgcatca ttttcctaaa tcaaattcct 900
aagaatcatc cttgattttt cccttccttt tgtcccttgc catcccagat tatcctgcaa 960
aaactgtcta tgctacctac aaaagtatct gccacatgtc atactaattg tcratatcct 1020
agagcaccmt tcatctgcct tcacctgtgg tgttgctgca attgtctcct tcctggctgc 1080
cctgattata tccattctcc ctgtctccaa aagcattctg cgcacagcag acacagatgt 1140
ttcataaatg taagtctggt catgcgctcc tctacctaaa accattagat ggtttttcat 1200
tgcactcaca actagagttt cctgaccatg acttgcaggc taagctcgta g 1251

<210> SEQ ID NO 13
<211> LENGTH: 1734
<212> TYPE: DNA
<213> ORGANISM: Homo sapiens
<220> FEATURE:
<221> NAME/KEY: SITE
<222> LOCATION: (1417)
<223> OTHER INFORMATION: n equals a,t,g, or c
<220> FEATURE:
<221> NAME/KEY: SITE
<222> LOCATION: (1703)
<223> OTHER INFORMATION: n equals a,t,g, or c
<220> FEATURE:
<221> NAME/KEY: SITE
<222> LOCATION: (1714)
<223> OTHER INFORMATION: n equals a,t,g, or c
<220> FEATURE:
<221> NAME/KEY: SITE
<222> LOCATION: (1715)
<223> OTHER INFORMATION: n equals a,t,g, or c
<220> FEATURE:
<221> NAME/KEY: SITE
<222> LOCATION: (1731)
<223> OTHER INFORMATION: n equals a,t,g, or c
<220> FEATURE:
<221> NAME/KEY: SITE
<222> LOCATION: (1732)
<223> OTHER INFORMATION: n equals a,t,g, or c

<400> SEQUENCE: 13
gaagcgtgcg gtgccgcagc aatggcggcg ctcacaattg ccacgggtac tggcaattgg 60
ttttcggctt tggcgctcgg ggtgactctt ctcaaatgcc ttctcatccc cacataccat 120
tccacagatt ttgaagtaca ccgaaactgg cttgctatca ctcacagttt gccaatatca 180
cagtggtatt atgaggcaac ttcagagtgg acgttggatt acccccccttt ctttgcatgg 240 tttgagtata tcctgtcaca tgttgccaaa tattttgatc aagaaatgct gaatgtccat 300
aatttgaatt actccagctc aaggacctta cttttccaga gattttccgt catctttatg 360
gatgtactct ttgtgtatgc tgtccgtgag tgctgtaaat gcattgatgg aaaaaaagtg 420
ggtaaagaac ttacagaaaa gccaaaattt attctgtcgg tattacttct gtggaacttc 480
gggttattaa ttgtggacca tattcatttt cagtacaatg gctttttatt tggattaatg 540
ctactctcca ttgcacgatt atttcagaaa aggcatatgg aaggagcatt tctctttgct 600
gttctcctac atttcaagca tatctacctc tatgtagcac cagcttatgg tgtatatctg 660
ctgcgatcct actgtttcac tgcaaataaa ccagatgggt ctattcgatg gaagagtttc 720
agctttgttc gtgttatttc cctgggactg gttgttttct tagtttctgc tctttcattg 780

-continued

```
ggtcctttcc tggccttgaa tcagctgcct caagtctttt cccgactctt tcctttcaag    840
aggggcctct gtcatgcata ttgggctcca aacttctggg ctttgtacaa tgctttggac    900
aaagtgctgt ctgtcatcgg tttgaaattg aaatttcttg atcccaacaa tattcccaag    960
gcctcaatga caagtggttt ggttcagcag ttccaacaca cagtccttcc ctcagtgact   1020
cccttggcaa ccctcatctg cacactgatt gccatattgc cctctatttt ctgtctttgg   1080
tttaaacccc aagggcccag aggctttctc cgatgtctaa ctctttgtgc cttgagctcc   1140
tttatgtttg ggtggcatgt tcatgaaaaa gccatacttc tagcaattct cccaatgagc   1200
cttttgtctg tgggaaaagc aggagacgct tcgatttttc tgattctgac cacaacagga   1260
cattattccc tctttcctct gctcttcact gcaccagaac ttcccattaa aatcttactc   1320
atgttactat tcaccatata tagtatttcg tcactgaaga ctttattcag aaaagaaaaa   1380
cctcttttta attggatgga aactttctac ctgcttngcc tggggcctct ggaagtctgc   1440
tgtgaatttg tattcccttt cacctcctgg aaggtgaagt accccttcat ccctttgtta   1500
ctaacctcag tgtattgtgc agtaggcatc acatatgctt ggttcaaact gtatgtttca   1560
gtattgattg actctgctat tggcaagaca aagaaacaat gaataaagga actgcttaga   1620
aaaaaaaaaa aaaaaaaaaa aaagggcggc cgctctagag gatccctcga gggcccaagc   1680
ttacgcgtgc atgcgagtca tantctctcc tggnntgatc gtatgaagct nngc         1734
```

<210> SEQ ID NO 14
<211> LENGTH: 1540
<212> TYPE: DNA
<213> ORGANISM: Homo sapiens
<220> FEATURE:
<221> NAME/KEY: SITE
<222> LOCATION: (22)
<223> OTHER INFORMATION: n equals a,t,g, or c
<220> FEATURE:
<221> NAME/KEY: SITE
<222> LOCATION: (430)
<223> OTHER INFORMATION: n equals a,t,g, or c

<400> SEQUENCE: 14

```
gcctgggcgc cgtgggcgcg gnactgcgcg ggctgcgcgg gtgccgagga gcgcgaggcg     60
cggggaaggc gcacctgggg tggccctggc gtgcgggcgg cgacatggag gacggcgtgc    120
tcaaggaggg cttcctggtc aagaggggcc acattgtcca caactggaag gcgcgatggt    180
tcatccttcg gcagaacacg ctggtgtact acaagcttga ggggggtcgg agagtgaccc    240
ctcccaaggg ccggatcctc ctggatggct gcaccatcac ctgcccctgc ctggagtatg    300
aaaaccgacc gctcctcatt aagctgaaga ctcaaacatc cacggagtac ttcctggagg    360
cctgttctcg agaggaagcg ggatgcctgg gcctttkaag rtyaccgggg ctattcatgc    420
agggcagccn ggggaaggtc cagcagctgc acagcctgag aaactccttc amgctgcccc    480
cgcacatcar gctgyatcgy attgtggaca agatgcacga tagcaacacc ggwatccgtt    540
caagccccaa catggagcag agaagcacct ataaaaagam cttyctcggc tcctccctgg    600
tggactggyt yatctycaam agcttcamgg gcagccgtct kgaggcggtg amcctggcct    660
ccatgytcat rgaggagaac ttcctcaggt ctgtggctgt acgatgcatg ggaggcattc    720
ggtctgggga tctggccgag cagttcctgg atgactccac agccctgtac acttttsctg    780
agagctacam aaagawgata agccccaagg aagaaattag cctgagcact gtggagttaa    840
gtggcacggt ggtgaaacaa ggctacctgg ccaagcaggg acacaagagg aaaaactgga    900
aggtgcgtcg ctttgttcta aggaaggatc cagctttcct gcattactat gacccttcca    960
```

-continued

```
aagaagagaa caggccagtg ggtgggtttt ctcttcgtgg ttcactcgtg tctgctctgg   1020
aagataatgg cgttcccact ggggttaaag ggaatgtcca gggaaacctc ttcaaagtga   1080
ttactaagga tgacacacac tattacattc aggccagcag caaggctgag cgagccgagt   1140
ggattgaagc tatcaaaaag ctaacatgac aaggacctga gggaaccagg attcctccct   1200
cctaccagat gacacagaca agagttcctg gagaatggga gtgttaagac ttttgacttc   1260
tttgtaagtt ttgtactgct ttggagagtg aatgctgcca agagttcctc agattacaaa   1320
cagcagtggt gccatttcct tccccatctt catgttacaa acctggaaag gctagaacag   1380
ccattaggcg tcagcatctt gacttttccc cagcatcaca aacagccatt tcctcgggca   1440
ccaaagtagg ttccctttgt tggaacaatt acactggcca tgccataatg ttgaataaaa   1500
ctctcttctt atgaaaaaaa aaaaaaaaaa aaaaaaaaaa                         1540
```

<210> SEQ ID NO 15
<211> LENGTH: 1558
<212> TYPE: DNA
<213> ORGANISM: Homo sapiens

<400> SEQUENCE: 15

```
ccacgtcgtc cgaacctttt aaaaatggtc ttgatgtatg tggaagagag tatgtgtatg     60
tgtgttcctg tacatagcat gggtgcagct gtggatgtgt gcaaaagagt gtgagtgtgt    120
gtgtgtgtgt gtaaaggggt ctgtcctaga gcccacatca gtttgttgtg aatctggaaa    180
aagggtcggt gagggccggg agatgttgac cctggtggga gcaggctgag gctgccccgt    240
tctccacatc ctctgttttg cccagtctct gattccatta gggggagtgt gctgaagcca    300
ttctcggatg cttcccagac caggctccct ctgccagagt cacatgcatc cgagctgctg    360
gtctccattg tccagcagga aggcggaaag gcaggcaaga tggtgtgaag cttaaagctt    420
gtatttgatg gaaaaggtct cccctgttca tctgagaggc caagcctggc caccccaggc    480
tcagaacctg ggcttcaaga aatgtgctgg gagctcctaa cttacacatc cctccagcct    540
tccttgaatc ctcccaccac cccctatttc ctttaatttc tcaggtctgc tccctcctcc    600
cccaacccca cagctgggca agaagtctgc aaaagctgca tctgcagctg tctctaactc    660
ttcccagcca tctcccgtat tttttggtac cttgattcct tgactcttaa taagccaagc    720
caccttatct ctgtagttct tatttttttg ttgactaaat ttggggggtt cttttttatg    780
gtcatgtcac tgacctatta aattggggct tggtgctttt ccaccttccc cctctgaatg    840
aaagccaagg aatgggggaa gagcgggaac tctgccgcgg aggtggagca agaacggtga    900
agggccctgg tcccagagag gctggtgggt ccctctccca aaggaaggca gacagtctct    960
gctttgcctt ggaccttggt gctgggggtg gggaggcctg ggggggacac tccccactcc   1020
cattcccctt cctttgtcct aatcctggaa ttaagtacag ggtttatag  gttctatttc   1080
ttcccaagag ccctgcaaag aaccccagtt tcctatttgg atgcccctac actgttgtgt   1140
ttcagtggaa tgtattttca tttaaaaaca actttgaatg gggcactttt tctttcctgt   1200
tttaaaaatt gaaaaattct tacagtacaa acaggactgt cagggtgggg gtgttggtgc   1260
tgtaagaggt tactcttgag tgcattttgg cactgggatg ggatggctgg ggtgggaaga   1320
cccccatccc cacccccaac ttcttttcta atatttaagg agtgttttgt aggattcaac   1380
aaccaccaca acttgaattt gtatcatggg aggtgggagg gagtggctta gaggtgtctg   1440
cctatgctta aagccaactg tggaagtttt gttttccctt ttttgtataa taaagtgaaa   1500
```

-continued

```
aacaaaaaaa aaaaaaaaaa aaaaaaaaaa aaaaaaaaaa aaaaaaaaaa aaaaaaaa     1558


<210> SEQ ID NO 16
<211> LENGTH: 1636
<212> TYPE: DNA
<213> ORGANISM: Homo sapiens
<220> FEATURE:
<221> NAME/KEY: SITE
<222> LOCATION: (424)
<223> OTHER INFORMATION: n equals a,t,g, or c
<220> FEATURE:
<221> NAME/KEY: SITE
<222> LOCATION: (823)
<223> OTHER INFORMATION: n equals a,t,g, or c
<220> FEATURE:
<221> NAME/KEY: SITE
<222> LOCATION: (960)
<223> OTHER INFORMATION: n equals a,t,g, or c

<400> SEQUENCE: 16

gaattcggca cgagttgaaa ttgaaaatca agataaaaat gttcacaatt aagctccttc     60

tttttattgt tcctctagtt atttcctcca gaattgatca agacaattca tcatttgatt    120

ctctatctcc agagccaaaa tcaagatttg ctatgttaga cgatgtaaaa attttagcca    180

atggcctcct tcagttggga catggtctta aagactttgt ccataagacg aagggccaaa    240

ttaatgacat atttcaaaaa ctcaacatat ttgatcagtc tttttatgat ctatcgctgc    300

aaaccagtga aatcaaagar gaagaaaagg aactgagaag aactacmtat aaactacaag    360

tcaaaaatga agaggtaaag aatatgtcac ttgaactcaa ctcaaaactt gaaagcctcc    420

tagnagaaaa aattctactt caacaaaaag tgaaatattt agaagagcaa ctaactaact    480

taattcaaaa tcaacctgaa actccagaac acccagaagt aacttcactt aaaacttttg    540

tagaaaaaca agataatagc atcaaagacy ttctccagac cgtggaagac caatatwaac    600

aattaaacca acagcatagt caaataaaag aratagaaaa tcagctcaga aggactagta    660

ttcaagaacc cacagaaatt tctctatctt ccaagccaag agcaccaaga actactccct    720

ttcttcagtt gaatgaaata agaaatgtaa aacatgatgg cattcctgct gaatgtacca    780

ccatttataa cagaggtgaa catacaagtg gcatgtatgc atncagaccc agcaactctc    840

aagtttttca tgtctactgt gatgttatat caggtagtcc atggacatta attcaacatc    900

gaatagatgg atcacaaaac ttcaatgaaa cgtgggagaa ctacaaatat ggttttgggn    960

aggcttgatg gagaattttg gttgggccta gagaagatat actccatagt gaagcaatct   1020

aattatgttt tacgaattga gttggaagac tggaaagaca acaaacatta tattgaatat   1080

tctttttact tgggaaatca cgaaaccaac tatacgctac atctagttgc gattactggc   1140

aatgtcccca atgcaatccc ggaaaacaaa gatttggtgt tttctacttg ggatcacaaa   1200

gcaaaaggac acttcaactg tccagagggt tattcaggag gctggtggtg gcatgatgag   1260

tgtggagaaa acaacctaaa tggtaaatat aacaaaccaa gagcaaaatc taagccagag   1320

aggagaagag gattatcttg gaagtctcaa aatggaaggt tatactctat aaaatcaacc   1380

aaaatgttga tccatccaac agattcagaa agctttgaat gaactgaggc aaatttaaaa   1440

ggcaataatt taaacattaa cctcattcca agttaatgtg gtctaataat ctggtattaa   1500

atccttaaga gaaagcttga gaaatagatt ttttttatct taaagtcact gtctatttaa   1560

gattaaacat acaatcacat aaccttaaaa aaaaaaaaaa aaaaactcga gggggggcccg  1620

gtacccaatt cgccgg                                                    1636
```

<210> SEQ ID NO 17
<211> LENGTH: 1256
<212> TYPE: DNA
<213> ORGANISM: Homo sapiens
<220> FEATURE:
<221> NAME/KEY: SITE
<222> LOCATION: (1240)
<223> OTHER INFORMATION: n equals a,t,g, or c

<400> SEQUENCE: 17

```
tcgacccacg cgtccgagca accgcagctt ctagtatcca gactccagcg ccgccccggg     60
cgcggacccc aaccccgacc cagagcttct ccagcggcgg cgcacgagca gggctccccg    120
ccttaacttc ctccgcgggg cccagccacc ttcgggagtc cgggttgccc acctgcaaac    180
tctccgcctt ctgcacctgc cacccctgag ccagcgcggg cgcccgagcg agtcatggcc    240
aacgcggggc tgcagctgtt gggcttcatt ctcgccttcc tgggatggat cggcgccatc    300
gtcagcactg ccctgcccca gtggaggatt tactcctatg ccggcgacaa catcgtgacc    360
gcccaggcca tgtacgaggg gctgtggatg tcctgcgtgt cgcagagcac cgggcagatc    420
cagtgcaaag tctttgactc cttgctgaat ctgagcagca cattgcaagc aacccgtgcc    480
ttgatggtgg ttggcatcct cctgggagtg atagcaatct ttgtggccam cgttggcatg    540
aagtgtatga agtgcttgga agacgatgag gtgcagaaga tgaggatggc tgtcattggg    600
ggcgcgatat ttcttcttgc aggtctggct attttagttg ccacagcatg gtatggcaat    660
agaatcgttc aagaattcta tgaccctatg accccagtca atgccaggta cgaatttggt    720
caggctctct tcactggctg ggctgctgct tctctctgcc ttctgggagg tgccctactt    780
tgctgttcct gtccccgaaa aacaacctct tacccaacac caaggcccta tccaaaacct    840
gcaccttcca gcgggaaaga ctacgtgtga cacagaggca aaaggagaaa atcatgttga    900
aacaaaccga aaatggacat tgagatacta tcattaacat taggacctta gaattttggg    960
tattgtaatc tgaagtatgg tattacaaaa caaacaaaca aacaaaaaac ccatgtgtta   1020
aaatactcag tgctaaacat ggcttaatct tattttatct tctttcctca atataggagg   1080
gaagattttt ccatttgtat tactgcttcc cattgagtaa tcatactcaa ctgggggaag   1140
gggtgctcct taaatatata tagatatgta tatatacatg tttttctatt aaaaatagac   1200
agtaaaatwc taaaaaaaaa aaaaaaamcy cgggggggn ccggtaccca ttcgcc        1256
```

<210> SEQ ID NO 18
<211> LENGTH: 1143
<212> TYPE: DNA
<213> ORGANISM: Homo sapiens
<220> FEATURE:
<221> NAME/KEY: SITE
<222> LOCATION: (1100)
<223> OTHER INFORMATION: n equals a,t,g, or c

<400> SEQUENCE: 18

```
ggcacgaggg ctggggtcag caaatataca gggggccgag gcgtcacgtg ggccccatcc     60
tcagcagcag tgcctcggat atcttctgcg acaatgagaa tgggcctaac ttccttttcc    120
acaaccgggg cgatggcacc tttgtggacg ctgcggccag tgctggtgtg gacgaccccc    180
accagcatgg gcgaggtgtc gccctggctg acttcaaccg tgatggcaaa gtggacatcg    240
tctatggcaa ctggaatggc ccccaccgcc tctatctgca gatgagcacc catgggaagg    300
tccgcttccg ggacatcgcc cttcacccaa gttctccatg ccctcccctg ttccgcacgg    360
tcatcaccgg ccgactttga caatgaccag gagctggaga atcttcttca acaacattgc    420
```

-continued ctaccgcagc tcctcagcca accgcctctt ccgcgtcatc cgtagagagc acggagaccc 480
cctcatcgag gagctcaatc ccggcgacgc cttggagcct gagggccggg gcacaggggg 540
tgtggtgacc gacttcgacg gagacgggat gctggacctc atcttgtccc atggagagtc 600
catggctcaa ccgctgtccg tcttccgggg caatcagggc ttcaacaaca actggctgcg 660
agtggtgcca cgcacccggt ttggggcctt tgccagggga gctaaggtcg tgctctacac 720
caagaagagt ggggcccacc tgaggatcat cgacgggggc tcaggctacc tgtgtgagat 780
ggagcccgtg gcacactttg gcctggggaa ggatgaagcc agcagtgtgg aggtgacgtg 840
gccagatggc aagatggtga gccggaacgt ggccagcggg gagatgaact cagtgctgga 900
gatcctctac ccccgggatg aggacacact tcaggaccca gccccactgg agtgtggcca 960
aggattctcc cagcaggaaa atggccattg catggacacc aatgaatgca tccagttccc 1020
attcgtgtgc cctcgagaca agcccgtatg tgtcaacacc tatggaagct acaggtgccg 1080
gaccaacaag aagtgcagtn cggggctacg agtcccaacg aggatggcac atacgggctt 1140
gtc 1143

<210> SEQ ID NO 19
<211> LENGTH: 1537
<212> TYPE: DNA
<213> ORGANISM: Homo sapiens

<400> SEQUENCE: 19
atcatatagg aaacggtagc ctgcagtacc ggtccggaat tcccgggtcg acccacgcgt 60
ccggagcagc aagagatttg tcctggggat ccagaaaccc atgataccct actgaacacc 120
gaatcccctg gaagcccaca gagacagaga cagcaagaga agcagagata aatacactca 180
cgccaggagc tcgctcgctc tctctctctc tctctcactc ctccctccct ctctctctgc 240
ctgtcctagt cctctagtcc tcaaattccc agtcccctgc accccttcct gggacactat 300
gttgttctcc gccctcctgc tggaggtgat ttggatcctg gctgcagatg gggtcaaca 360 ctggacgtat gagggcccac atggtcagga ccattggcca gcctcttacc ctgagtgtgg 420
aaacaatgcc cagtcgccca tcgatattca gacagacagt gtgacatttg accctgattt 480
gcctgctctg cagccccacg gatatgacca gcctggcacc gagcctttgg acctgcacaa 540
caatggccac acagtgcaac tctctctgcc ctctaccctg tatctgggtg gacttccccg 600
aaaatatgta gctgcccagc tccacctgca ctggggtcag aaaggatccc caggggggtc 660
agaacaccag atcaacagtg aagccacatt tgcagagctc cacattgtac attatgactc 720
tgattcctat gacagcttga gtgaggctgc tgagaggcct cagggcctgg ctgtcctggg 780
catcctaatt gagctggaaa agcttcaggg gacattgttc tccacagaag aggagccctc 840
taagcttctg gtacagaact accgagccct tcagcctctc aatcagcgca tggtctttgc 900
ttctttcatc caagcaggat cctcgtatac cacaggtgaa atgctgagtc taggtgtagg 960
aatcttggtt ggctgtctct gccttctcct ggctgtttat ttcattgcta gaaagattcg 1020
gaagaagagg ctggaaaacc gaaagagtgt ggtcttcacc tcagcacaag ccacgactga 1080
ggcataaatt ccttctcaga taccatggat gtggatgact tcccttcatg cctatcagga 1140
agcctctaaa atggggtgta ggatctggcc agaaacactg taggagtagt aagcagatgt 1200
cctccttccc ctggacatct cctagagagg aatggaccca ggctgtcatt ccaggaagaa 1260
ctgcagagcc ttcagcctct ccaaacatgt aggaggaaat gaggaaatcg ctgtgttgtt 1320
aatgcagaga acaaactctg tttagttgca ggggaagttt gggatatacc ccaaagtcct 1380

-continued ctaccccctc acttttatgg ccctttccct agatatactg cgggatctct ccttaggata 1440
aagagttgct gttgaagttg tatatttttg atcaatatat ttggaaatta aagtttctga 1500
ctttaaaaaa aaaaaaaaaa aaaaaactcg aggggggg 1537

<210> SEQ ID NO 20
<211> LENGTH: 2672
<212> TYPE: DNA
<213> ORGANISM: Homo sapiens
<220> FEATURE:
<221> NAME/KEY: SITE
<222> LOCATION: (16)
<223> OTHER INFORMATION: n equals a,t,g, or c
<220> FEATURE:
<221> NAME/KEY: SITE
<222> LOCATION: (28)
<223> OTHER INFORMATION: n equals a,t,g, or c
<220> FEATURE:
<221> NAME/KEY: SITE
<222> LOCATION: (47)
<223> OTHER INFORMATION: n equals a,t,g, or c
<220> FEATURE:
<221> NAME/KEY: SITE
<222> LOCATION: (52)
<223> OTHER INFORMATION: n equals a,t,g, or c
<220> FEATURE:
<221> NAME/KEY: SITE
<222> LOCATION: (93)
<223> OTHER INFORMATION: n equals a,t,g, or c

<400> SEQUENCE: 20
cccaaagttc ggaaantaaa ccttcaanta aagggaaaca aaaagcngga gnttcccacc 60
gcgggtgggc ggcccgttct agaattaagt ggnatccccc cggggctgcc aggaatttcc 120
gagccggggc cgcgccgccg ctgcccgccg ccgcgsgcgg attytgcttc tcagaagatg 180
cactattata gatactctaa cgccaaggtc agctgctggt acaagtacct ccttttcagc 240
tacaacatca tcttctgrtt ggctggagtt gtcttccttg gagtcgggct gtgggcatgg 300
agcgaaaagg gtgtgctgtc cgacctcacc aaagtgaccc ggatgcatgg aatcgaccct 360
gtggtgctgg tcctgatggt gggcgtggtg atgttcaccc tggggttcgc cggctgcgtg 420
ggggctctgc gggagaatat ctgcttgctc aactttttct gtggcaccat cgtgctcatc 480
ttcttcctgg agctggctgt ggccgtgctg gccttcctgt tccaggactg ggtgagggac 540
cggttccggg agttcttcga gagcaacatc aagtcctacc gggacgatat cgatctgcaa 600
aacctcatcg actcccttca gaaagctaac cagtgctgtg gcgcatatgg ccctgaagac 660
tgggacctca acgtctactt caattgcagc ggtgccagct acagccgaga gaagtgcggg 720
gtccccttct cctgctgcgt gccagatcct gcgcaaaaag ttgtgaacac acagtgtgga 780
tatgatgtca ggattcagct gaagagcaag tgggatgagt ccatcttcac gaaaggctgc 840
atccaggcgc tggaaagctg gctcccgcgg aacatttaca ttgtggctgg cgtcttcatc 900
gccatctcgc tgttgcagat atttggcatc ttcctggcaa ggacgctgat ctcagacatc 960
gaggcagtga aggccggcca tcacttctga ggagcagagt tgagggagcc gagctgagcc 1020
acgctgggag gccagagcct ttctctgcca tcagccctac gtccagaggg agaggagccg 1080
acacccccag agccagtgcc ccatcttaag catcagcgtg acgtgacctc tctgtttctg 1140
cttgctggtg ctgaagacca agggtccccc ttgttacctg cccaaacttg tgactgcatc 1200
cctctggagt ctacccagag acagagaatg tgtctttatg tgggagtggt gactctgaaa 1260
gacagagagg gctcctgtgg ctgccaggag ggcttgactc agacccccctg cagctcaagc 1320

-continued atgtctgcag gacaccctgg tcccctctcc actggcatcc agacatctgc tttgggtcat 1380
ccacatctgt gggtgggccg tgggtagagg gacccacagg cgtggacagg gcatctctct 1440
ccatcaagca aagcagcatg ggggcctgcc cgtaacggga ggcggacgtg gccccgctgg 1500
gcctctgagt gccagcgcag tctgctggga catgcacata tcaggggttg tttgcaggat 1560
cctcagccat gttcaagtga agtaagcctg agccagtgcg tggactggtg ccacgggagt 1620
gccttgtcca ctgtcccct gtgtccacca gctattctcc tggcgccgga actgcctctg 1680
gtcttgatag cattaagccc tgatggcgcc ggtggcggtt gggcatggtt cttcactgag 1740
agccggctct ccttttctta aagtgtgtaa atagtttatt tataggggta agaatgttct 1800
cacaccattt cacttcctct tcctctcctc cagcattctc ctctgagcag ccttagatag 1860
tgtccatggc tggagccgac cctttgagtc cccttgagtg tcttaagaac cagcccacaa 1920
cagcctctct ttctcctcca catactgcag cctccctcca tgcatcccac atacaagcac 1980
tcccccactc cccagcgtgg cctcactgtc ttctggtctt ggtgctactg aaattgtcac 2040
ccagaatttg aatcctgacc ctccccactg caagcccagg gagccccagc ccaagatggc 2100
cagcctgaaa ctgttggcca gggctcctct tgtggccatg tacccagggc tggctggcct 2160
gccatttgcc tctccccgga gacagccgtt cttctgcaac cacaccccgt gcctagccac 2220
aaccccaggc tgcagctgct cagaagctcc aggcattttg tttctggtga ccgcccctaa 2280
tgggatatcg gtgatcactg gtccaccctt cctgtcaggg cttttctggg gctgctcttg 2340
gaaatgaagt cttaagtact gaataactcc cctggggata gctggggcat ttgtctagct 2400
gggctacttt ctaacacttt gccatagctc agaccacttc tcatcgttca gggatggact 2460
gcaaccttaa tttacttgcc ggagtgtaca ttctagtgtg gtgtatactg gtggctgttg 2520
atgatgattt tttttttttt tttacacaat tctctgtaga ctaggagaag aatgcttgtg 2580
tttttcggaa gtgtgatgct tctctttgac tgccaaactc ttttatggaa tatatcttta 2640
tattaaaaaa aaaaaaaaac aaaaaaaaaa aa 2672

<210> SEQ ID NO 21
<211> LENGTH: 1508
<212> TYPE: DNA
<213> ORGANISM: Homo sapiens

<400> SEQUENCE: 21
ggcacagaga tagagcggca acctcggaag tgcggacggg tgggcctata tagatgttga 60
ggtgcggagg ccgtgggctt ttgttgggcc tggctgtagc cgcagcagcg gtaatggcag 120
cacggcttat gggctggtgg ggtccccgcg ctggctttcg ccttttcata ccggaggagc 180
tgtctcgcta ccgcggcggc ccaggggacc cgggcctgta cttggcgttg ctcggccgtg 240
tctacgatgt gtcctccggc cggagcacta cgagcctggg tcccactata gcggcttcgc 300
aggccgagac gcatccagag ctttcgtgac cggggactgt tctgaagcag gcctcgtgga 360
tgacgtatcc gacctgtcag ccgctgagat gctgacactt cacaattggc tttcattcta 420
tgagaagaat tatgtgtgtg ttgggagggt gacaggacgg ttctacggag aggatgggct 480
gcccaccccg gcactgaccc aggtagaagc tgcgatcacc agaggcttgg aggccaacaa 540
actacagctg caagagaagc agacattccc gccgtgcaac gcggagtgga gctcagccag 600
gggcagccgg ctctggtgct cccagaagag tggaggtgtg agcagagact ggattggcgt 660
ccccaggaag ctgtataagc caggtgctaa ggagccccgc tgcgtgtgtg tgagaaccac 720 cggccccct agtggccaga tgccggacaa ccctccacac agaaatcgtg ggacctgga 780

-continued ccacccaaac ttggcagagt acacaggctg cccaccgcta gccatcacat gctcctttcc 840
actctaagcc gtagcctctt ctgttaataa cacacagaga gctctgccaa gcacctgagt 900
aggcccttga cacttgtgtg ccctgggatg cctcctggcg cgaatcagga gggtctggaa 960
ggactctggc tatattctgc aaatgtggct catgcccctt accgtggctc ggcgttgtgg 1020
tgcctgaggg acagccggcc acctgcccag tactggtcag cttttcaaca ctattccctt 1080
tgacctactg gccatcttcc tcacagccct cagatatcaa cgggcacaaa taagaccaac 1140
tcaatttcca cttgaattta caaccaaaag cctgctgagt tgattacagc tgggccaata 1200
cagtacgagg caataacaaa ttagtgtggg ttgattctgg aattggaaaa gcttttgctt 1260
gtatggatac agcaaatcca gatgtctctg aacaaagcaa caatttaaag caacgacatt 1320
ttctgtcctt taagcactta aaatcaggtg tggtgtgttt tcaaaggcag aagtctgcat 1380
tttgagcaaa aggtggcttc ccagctctaa caaggtaact ggttagcatg acattaaagc 1440
ttgggcaagg cttcaaactt aaaaaaaaaa aaaaaaaaaa aaaaaaaaaa aaaaaaaaaa 1500
aactcgag 1508

<210> SEQ ID NO 22
<211> LENGTH: 1447
<212> TYPE: DNA
<213> ORGANISM: Homo sapiens

<400> SEQUENCE: 22
aattcggcac gagagattta agtgcagcgt ggattttttt tttctcactt tgccttgtgt 60
tttccaccct gaaagaatgt tgtggctgct ctttttttctg gtgactgcca ttcatgctga 120
actctgtcaa ccaggtgcag aaaatgcttt taaagtgaga cttagtatca gaacagctct 180
gggagataaa gcatatgcct gggataccaa tgaagaatac ctcttcaaag cgatggtagc 240
tttctccatg agaaaagttc ccaacagaga agcaacagaa atttcccatg tcctactttg 300
caatgtaacc cagagggtat cattctggtt tgtggttaca gacccttcaa aaaatcacac 360
ccttcctgct gttgaggtgc aatcagccat aagaatgaac aagaaccgga tcaacaatgc 420
cttctttcta aatgmccaaa ctctggaatt tttaaaaatc ccttccacac ttgcaccacc 480
catggaccca tctgtgccca tctggattat tatatttggt gtgatatttt gcatcatcat 540
agttgcaatt gcactactga ttttatcagg gatctggcaa cgtagaagaa agaacaaaga 600
accatctgaa gtggatgacg ctgaagataa gtgtgaaaac atgatcacaa ttgaaaatgg 660
catcccctct gatcccctgg acatgaaggg agggcatatt aatgatgcct tcatgacaga 720
ggatgagagg ctcacccctc tctgaagggc tgttgttctg cttcctcaag aaattaaaca 780
tttgtttctg tgtgactgct gagcatcctg aaataccaag agcagatcat atattttgtt 840
tcaccattct tcttttgtaa taaattttga atgtgcttga aagtgaaaag caatcaatta 900
tacccaccaa caccactgaa atcataagct attcacgact caaaatattc taaaatattt 960
ttctgacagt atagtgtata aatgtggtca tgtggtattt gtagttattg atttaagcat 1020
ttttagaaat aagatcaggc atatgtatat attttcacac ttcaaagacc taaggaaaaa 1080
taaattttcc agtggagaat acatataata tggtgtagaa atcattgaaa atggatcctt 1140
tttgacgatc acttatatca ctctgkatat gactaagtaa acaaaagtga gaagtaatta 1200
ttgtaaatgg atggataaaa atggaattac tcatatacag ggtggaattt tatcctgtta 1260
tcacaccaac agttgattat atattttctg aatatcagcc cctaatagga caattctatt 1320

-continued

```
tgttgaccat ttctacaatt tgtaaaagtc caatctgtgc taacttaata aagtaataat   1380

catctctttt tgattgtgaa aaaaaaaaaa aaaaaaaaaa aaaaaaaaaa aaaaaaaaaa   1440

actcgag                                                             1447


<210> SEQ ID NO 23
<211> LENGTH: 3886
<212> TYPE: DNA
<213> ORGANISM: Homo sapiens
<220> FEATURE:
<221> NAME/KEY: SITE
<222> LOCATION: (1050)
<223> OTHER INFORMATION: n equals a,t,g, or c
<220> FEATURE:
<221> NAME/KEY: SITE
<222> LOCATION: (3743)
<223> OTHER INFORMATION: n equals a,t,g, or c
<220> FEATURE:
<221> NAME/KEY: SITE
<222> LOCATION: (3848)
<223> OTHER INFORMATION: n equals a,t,g, or c
<220> FEATURE:
<221> NAME/KEY: SITE
<222> LOCATION: (3877)
<223> OTHER INFORMATION: n equals a,t,g, or c
<220> FEATURE:
<221> NAME/KEY: SITE
<222> LOCATION: (3882)
<223> OTHER INFORMATION: n equals a,t,g, or c
<220> FEATURE:
<221> NAME/KEY: SITE
<222> LOCATION: (3885)
<223> OTHER INFORMATION: n equals a,t,g, or c

<400> SEQUENCE: 23

gcacccggga gggagatgcg gccggggctc aggctccttg cagttgtaat ttagattcga     60

gaagtggttt atcctttgac tggaaaagaa aagtagctgc agtattcccc cagcacttgc    120

tgagagcatg ccgtatgcca ggctgtgagg ctcgagagac aagcagtgga agagttgcgg    180

cctgtttcat ctctggattg taaatctgag cctccttctg gcccctggaa ggggacagca    240

tcaccatgga atgattccta accagcataa tgctggagcc gggagccacc aacctgcagt    300

tttcagaatg gccgtgttgg acactgattt ggatcacatt cttccatctt ctgttcttcc    360

tccattctgg gctaagttag tagtgggatc ggttgccatt gtgtgttttg cacgcagcta    420

tgatggagac tttgtctttg atgactcaga agctattgtt aacaataagg acctccaagc    480

agaaacgccc ctgggggacc tgtggcatca tgacttctgg ggcagtagac tgagcagcaa    540

caccagccac aagtcctacc ggcctctcac cgtcctgact ttcaggatta actactacct    600

ctcgggaggc ttccaccccg tgggctttca cgtggtcaac atcctcctgc acagtggcat    660

ctctgtcctc atggtggacg tcttctcggt tctgtttggc ggcctgcagt acaccagtaa    720

aggccggagg ctgcacctcg cccccagggc gtccctgctg gccgcgctgc tgtttgctgt    780

ccatcctgtg cacaccgagt gtgttgctgg tgttgtcggc cgtgcagacc tcctgtgtgc    840

cctgttcttc ttgttatctt tccttggcta ctgtaaagca tttagagaaa gtaacaagga    900

gggagcgcat tcttccacct tctgggtgct gctgagtatc tttctgggag cagtggccat    960

gctgtgcaaa gagcaaggga tcactgtgct gggtttaaat gcggtatttg acatcttggt   1020

gataggcaaa ttcaatgttc tggaaattgn ccagaaggta ctacataagg acaagtcatt   1080

agagaatctc ggcatgctca ggaacggggg cctcctcttc agaatgaccc tgctcacctc   1140

tggaggggct gggatgctct acgtgcgctg gaggatcatg ggcacgggcc cgycggcctt   1200

caccgaggtg gacaacccgg cctcctttgc tgacagcatg ctggtgaggg ccgtaaacta   1260
```

-continued

```
caattactac tattcattga atgcctggct gctgctgtgt ccctggtggc tgtgttttga   1320
ttggtcaatg ggctgcatcc ccctcattaa gtccatcagc gactggaggg taattgcact   1380
tgcagcactc tggttctgcc taattggcct gatatgccaa gccctgtgct ctgaagacgg   1440
ccacaagaga aggatcctta ctctgggcct gggatttctc gttatcccat ttctccccgc   1500
gagtaacctg ttcttccgag tgggcttcgt ggtcgcggag cgtgtcctct acctccccag   1560
crttgggtac tgtgtgctgc tgacttttgg attcggagcc ctgagcaaac ataccaagaa   1620
aaagaaactc attgccgctg tcgtgctggg aatcttattc atcaacacgc tgagatgtgt   1680
gctgcgcagc ggcgagtggc ggagtgagga acagcttttc agaagtgctc tgtctgtgtg   1740
tcccctcaat gctaaggttc actacaacat tggcaaaaac ctggctgata aaggcaacca   1800
gacagctgcc atcagatact accgggaagc tgtaagatta aatcccaagt atgttcatgc   1860
catgaataat cttggaaata tcttaaaaga aaggaatgag ctacaggaag ctgaggagct   1920
gctgtctttg gctgttcaaa tacagccaga ctttgccgct gcgtggatga atctaggcat   1980
agtgcagaat agcctgaaac ggtttgaagc agcagagcaa agttaccgga cagcaattaa   2040
acacagaagg aaatacccag actgttacta caacctcggg cgtctgtatg cagatctcaa   2100
tcgccacgtg gatgccttga atgcgtggag aaatgccacc gtgctgaaac cagagcacag   2160
cctggcctgg aacaacatga ttatactcct cgacaataca ggtaatttag cccaagctga   2220
agcagttgga agagaggcac tggaattaat acctaatgat cactctctca tgttctcgtt   2280
ggcaaacgtg ctggggaaat cccagaaata caaggaatct gaagctttat tcctcaaggc   2340
aattaaagca aatccaaatg ctgcaagtta ccatggtaat ttggctgtgc tttatcatcg   2400
ttggggacat ctagacttgg ccaagaaaca ctatgaaatc tccttgcagc ttgaccccac   2460
ggcatcagga actaaggaga attacggtct gctgagaaga aagctagaac taatgcaaaa   2520
gaaagctgtc tgatcctgtt tccttcatgt tttgagtttg agtgtgtgtg tgcatgaggc   2580
atatcattaa tagtatgtgg ttacatttaa ccatttaaaa gtcttagaca tgttatttta   2640
ctgatttttt tctatgaaaa caaagacatg caaaaagatt atagcaccag caatatactc   2700
ttgaatgcgt gatatgattt ttcattgaaa ttgtattttt tcagacaact caaatgtaat   2760
tctaaaattc caaaaatgtc ttttttaatt aaacagaaaa agagaaaaaa ttatcttgag   2820
caacttttag tagaattgag cttacatttg ggatctgagc cttgtcgtgt atggactagc   2880
actattaaac ttcaattatg accaagaaag gatacactgg cccctacaat ttgtataaat   2940
attgaacatg tctatatatt agcattttta tttaatgaca aagcaaatta agttttttta   3000
tctctttttt ttaaaacaac atactgtgaa ctttgtaagg aaatatttat ttgtattttt   3060
atgttttgaa tagggcaaat aatcgaatga ggaatggaag ttttaacata gtatatctat   3120
atgcttttcc ccataggaag aaattgactc ttgcagtttt tggatgctct gacttgtgca   3180
atttcaatac acaggagatt atgtaatgta atatttttca taagcggtta ctatcaattg   3240
aaagttcaag ccatgcttta ggcaagagca ggcagcctca catctttatt tttgttacat   3300
ccaaggtgaa gagggcaaca catctgtgta agctgctttt tagtgtgttt atctgaaggc   3360
cgttttccat tttgcttaat gtaactacag acattatcca gaaaatgcaa aattttctat   3420
caaatggagc cacattcggg gaattcgtgg tatttttaag aattgagttg ttcctgctgt   3480
tttttatttg atccaaacaa tgttttgttt tgttcttctc tgtatgctgt tgacctaatg   3540
atttatgcaa tctctgtaat ttcttatgca gtaaaattac tacacaaact agcaaaaaaa   3600
```

-continued aaaaaaaaaa aaaaagggcg gccgctctag aggatccaag cttacgtacg cgtgcatgcg 3660
acgtcatagc tcttctatag tgcacctaaa ttcaattcac tgggccgtcg ttttacaacg 3720
tcgtgactgg gaaaaccctg cgntacccaa cttaatcgcc ttgcagcaca tccccctttc 3780
gccaagctgg cgtaatagcg aaaaggcccg gaccgacggc ctttccaaca gttgccaacc 3840
tgaaggcnaa agggaccccc cctggacggg gcataanccc gnggnt 3886

<210> SEQ ID NO 24
<211> LENGTH: 1583
<212> TYPE: DNA
<213> ORGANISM: Homo sapiens

<400> SEQUENCE: 24
ggcacgaggg acaacgacta tctgctacat ggtcatagac ctcccatgtt ctcctttcgg 60
gcttgcttca agagcatctt ccgcattcat acagaaactg gcaacatctg gacccatctg 120
cttggtttcg tgctgtttct ctttttggga atcttgacca tgctcagacc aaatatgtac 180
ttcatggccc ctctacagga gaaggtggtt tttgggatgt tctttttggg tgcagtgctc 240
tgcctcagct tctcctggct ctttcacacc gtctattgtc attcagagaa agtctctcgg 300
actttttcca aactggacta ttcagggatt gctcttctaa ttatggggag ctttgtcccc 360
tggctctatt attccttcta ctgctcccca cagccacggc tcatctacct ctccatcgtc 420
tgtgtcctgg gcatttctgc catcattgtg gcgcagtggg accggtttgc cactcctaag 480
caccggcaga caagagcagg cgtgttcctg ggacttggct tgagtggcgt cgtgcccacc 540
atgcacttta ctatcgctga gggctttgtc aaggccacca cagtgggcca gatgggctgg 600
ttcttcctca tggctgtgat gtacatcact ggagctggcc tttatgctgc tcgaattcct 660
gagcgcttct ttcctggaaa atttgacata tggttccagt ctcatcagat tttccatgtc 720
ctggtggtgg cagcagcctt tgtccacttc tatggagtct ccaaccttca ggaattccgt 780
tacggcctag aaggcggctg tactgatgac acccttctct gagccttccc acctgcgggg 840
tggaggagga acttcccaag tgcttttaaa aataacttct ttgctgaagt gagaggaaga 900
gtctgagttg tctgtttcta gaagaaacct cttagagaat tcagtaccaa ccaagcttca 960
gcccactttc acacccactg ggcaataaac tttccatttc cattctccta gctggggatg 1020
gggcatggtc aaacttagcc atcccctcct cagcaaggca tctaccggcc cctcacagag 1080
acagtacttt gaaactcatg ttgagatttt accctctcct ccaaccattt tgggaaaatt 1140
atggactggg actcttcaga aattctgtct tttcttctgg aagaaaatgt ccctccctta 1200
cccccatcct taactttgta tcctggctta taacaggcca tccatttttg tagcacactt 1260
ttcaaaaaca attatatacc ctggtcccat ctttctaggg cctggatctg cttatagagc 1320
aggaagaata aagccaccaa cttttaccta gcccggctaa tcatggaagt gtgtccaggc 1380
ttcaagtaac ttgagtttta attttttttt ttttcttggc agagtaatgt aaaatttaaa 1440
tggggaaaga tatttaatat ttaatactaa gctttaaaaa gaaacctgct atcattgcta 1500
tgtatcttga tgcaaagact atgatgttaa taaaagaaag tacagaagac acttggcatt 1560
caaaaaaaaa aaaaaaaaaa aaa 1583

<210> SEQ ID NO 25
<211> LENGTH: 1669
<212> TYPE: DNA
<213> ORGANISM: Homo sapiens
<220> FEATURE:
<221> NAME/KEY: SITE -continued
<222> LOCATION: (587)
<223> OTHER INFORMATION: n equals a,t,g, or c
<220> FEATURE:
<221> NAME/KEY: SITE
<222> LOCATION: (1634)
<223> OTHER INFORMATION: n equals a,t,g, or c
<220> FEATURE:
<221> NAME/KEY: SITE
<222> LOCATION: (1648)
<223> OTHER INFORMATION: n equals a,t,g, or c
<220> FEATURE:
<221> NAME/KEY: SITE
<222> LOCATION: (1659)
<223> OTHER INFORMATION: n equals a,t,g, or c
<220> FEATURE:
<221> NAME/KEY: SITE
<222> LOCATION: (1668)
<223> OTHER INFORMATION: n equals a,t,g, or c

<400> SEQUENCE: 25
aggcgcttag gggctgaggc gcgatggcag gtgtcggggc tgggcctctg cgggcgatgg 60
ggcggcaggc cctgctgctt ctcgcgctgt gcgccacagg cgcccagggg ctctacttcc 120
acatcggcga gaccgagaag cgctgtttca tcgaggaaat ccccgacgag accatggtca 180
tcggtcaggc gggctgaggg tggggaggcc ctttgtaccc agctcagccc tcggcggcgc 240
tccctcctcc cgagcccagc cgggtcgctg gctcccccag tacctagcct gagggtgccc 300
cgaggacgcc aggccccctg cctagagctc cgggccgcac gtcggagggg gccgggcgga 360
gaggcggccc actagggccg gtcgtgacta tgtgtctgcc ccgcaggcaa ctatcgtacc 420
cagatgtggg ataagcagaa ggaggtcttc ctgccctcga cccctggcct gggcatgcac 480
gtggaagtga aggaccccga cggcaaggtg gtgctgtccc ggcagtacgg ctcggagggc 540
cgcttcacgt tcacctccca cacgcccggt gaccatcaaa tctgtcngca ctccaattct 600
accaggatgg ctctcttcgc tggtggcaaa ctgcgkgtgc atctcgacat ccaggttggg 660
gagcatgcca acaactaccc tgagattgct gcaaaagata agctgacgga gctacagctc 720
cgcgcccgcc agttgcttga tcaggtggaa cagattcaga aggagcagga ttaccaaagg 780
gcaagtgcat atctccttgt aatttgagag ggcagttgac ctttataccc actataccta 840
ctcaagtttc tgcttgggag atcagctctg cagagaatgg aatgagaagt attggtttag 900
ataggttgtt tgtttgttgt ttttgagacg gagtttcact cttgttgccc atgctggagt 960
gcaatgccat gatcttggct cactgcaacc tccgcctccc caggctgagg caggagaatg 1020
gcgtgagctc gggaggtgga gcttgcagtg agctgagatc gtgccactgc actccagcct 1080
gggcgacaga gtgagactcc ttctaaaaaa caaaaacaaa accaaaacag tagttagggt 1140
acacacacac aaattctagt gattttcccc ccagtactac ccttgacttt tgaaattcct 1200
gctttctcag agtttacaac atccttacca aacagccttc tccctcctta ccacaaaaaa 1260
araaaaaaaa gttctggggt tgaggggaca ctccattctt aacatcctct attatcccag 1320
cccaattccc cagctctcac tgggactagt tgtacctatc ttcattcatt tggtcccagc 1380
atgactacct gttggtgcat gagctgatct ctcctaacct aacagccaga tgctagtctc 1440
tggtactyag atgctgggct gcatcagata ggatgcacag gatcatcctg ggaagcttgt 1500
tgacatagat tcctgtgcaa cacttcagat atagtcttaa tgtagatttg tgttggggtg 1560
gtatggtagg tagaataatg ggcctaccac tgtgtaaaca tatggatatg tttacctaac 1620
atgacagaag aganttaagt tgctaatnag atgactgtna aataaatna 1669

<210> SEQ ID NO 26

-continued

<211> LENGTH: 1053
<212> TYPE: DNA
<213> ORGANISM: Homo sapiens
<220> FEATURE:
<221> NAME/KEY: SITE
<222> LOCATION: (1025)
<223> OTHER INFORMATION: n equals a,t,g, or c

<400> SEQUENCE: 26

```
ctaggagcac cgagcagctt ggctaaaagt aagggtgtcg tgctgatggc cctgtgcgca     60
ctgacccgcg ctctgckctc tctgaacctg gcgcccccga ccgtcgccgc ccctgccccg    120
agtctgttcc ccgccgccca gatgatgaac aatggcctcc tccaacagcc ctctgccttg    180
atgttgctcc cctgccgccc agttcttact tctgtggccc ttaatgccaa ctttgtgtcc    240
tggaagagtc gtaccaagta caccattaca ccagtgaaga tgaggaagtc tgggggccga    300
gaccacacag gccgaatccg ggtgcatggt attggcgggg gccacaagca acgttatcga    360
atgattgact ttctgcgttt ccggcctgag gagaccaagt caggaccctt tgaggagaag    420
gttatccaag tccgctatga tccctgtagg tcagcagaca tagctctggt tgctgggggc    480
agccggaaac gctggatcat cgccacagaa aacatgcagg ctggagatac aatcttgaac    540
tctaaccaca taggccgaat ggcagttgct gctcgggaag gggatgcgca tcctcttggg    600
gctctgcctg tggggaccct catcaacaac gtggaaagtg agccaggccg ggggtgccaa    660
tatatccgag ctgcagggac gtgtggtgtg ctactgcgga aggtgaatgg cacagccatt    720
atccagctgc cctctaagag gcagatgcag gtgctggaaa cgtgcgtagc aacagtaggc    780
cgagtatcca acgttgatca taacaaacgg gtcattggca aggcaggtcg caaccgctgg    840
ctgggcaaga ggcctaacag tgggcggtgg caccgcaagg ggggctgggc tggccgaaag    900
attcggccac taccccccat gaagagttac gtgaagctgc cttctgcttc tgcccaaagc    960
tgatatccct gtactctaat aaaatgcccc ccccccccgt taaaaaaaaa aaaaaaaaaa   1020
ctcgngggg ggcccggtaa ccaattcggc cta                                 1053
```

<210> SEQ ID NO 27
<211> LENGTH: 1477
<212> TYPE: DNA
<213> ORGANISM: Homo sapiens
<220> FEATURE:
<221> NAME/KEY: SITE
<222> LOCATION: (7)
<223> OTHER INFORMATION: n equals a,t,g, or c

<400> SEQUENCE: 27

```
tgcaggnacc ggtccggaat tcccgggatc aaacagtact gttgcacgtc gaattaagga     60
tctagctgct gacattgaag aagagcttgt ttgtagactg aaaatttgcg atgggttttc    120
actgcaacta gatgaatcag ctgatgtttc aggacttgct gtgctgcttg tgtttgttcg    180
ttataggttt aataagtcta ttgaggaaga cctactcctg tgtgaatctt tgcaaagtaa    240
tgctaccggt gaagaaatat tcaactgtat caacagtttt atgcagaaac atgaaattga    300
atgggaaaaa tgtgttgatg tttgtagtga tgcttctagg gcagtggatg ggaaaattgc    360
cgaagctgtc accttaataa aatatgtggc tcccgaaagc accagtagtc actgcctatt    420
atacagacat gcactggcag ttaaaataat gcctacatct ctaaaaaatg tgctagacca    480
ggcagtacaa atcatcaatt atattaaagc tcgaccacat caatccagac tattaaaaat    540
tttatgtgag gaaatgggtg ctcagcacac agcacttctt ctaaatacag aggtgaggtg    600
gctttctcga ggtaaagttc ttgtaagact tttgaactt cgtcgtgaac ttttggtttt    660
```

```
catggattct gcttttcgac tatctgattg tttaacaaat tcatcttggc tgctaagact    720

tgcatatctt gcagatattt ttactaaatt aaatgaagtt aatttgtcaa tgcaaggaaa    780

aaatgtgacc gtttttacag tatttgataa aatgtcgtca ttgttaagaa aattggaatt    840

ttgggcctca tctgtagaag aagaaaactt tgattgtttt cctacactca gtgatttttt    900

gactgaaatt aattctacag ttgataaaga tatttgcagt gccattgtgc agcacctaag    960

gggtttgcgc gctactctgt taaaatactt tcctgtaaca aatgacaata atgcttgggt   1020

tagaaatcca tttacagtta ctgttaaacc agcttcatta gtagcacggg actatgagag   1080

cctgattgat ttaacatctg attctcaagt gaagcaaaat tttagtgaac tttcactaaa   1140

tgatttttgg agtagcctaa ttcaggaata cccaagcatt gcaaggcgtg cagtgcgtgt   1200

acttcttcct tttgctacaa tgcacctgtg tgaaacgggg ttttcatatt acgctgcaac   1260

aaaaacaaaa tataggaaaa gacttgatgc tgcacctcat atgcgaatcc gacttagcaa   1320

tattacacct aatattaagc ggatatgtga taaaaagaca caaaaacact gttctcatta   1380

aaattggagg agtttgcatg tctcatgata accaaatgta agatgaaaat aaaagatgat   1440

ttacttcaaa aaaaaaaaaa aaaaaaaggg cggccgc                            1477
```

<210> SEQ ID NO 28
<211> LENGTH: 2504
<212> TYPE: DNA
<213> ORGANISM: Homo sapiens

<400> SEQUENCE: 28

```
tcgacccacg cgtccgcgag tgcctgcagg actgggcctc cttcctccgc ctggccatcc     60

ccagcatgct catgctgtgc atggagtggt gggcctatga ggtcgggagc ttcctcagtg    120

gcatcctcgg catggtggag ctgggcgctc agtccatcgt gtatgaactg gccatcattg    180

tgtacatggt ccctgcaggc ttcagtgtgg ctgccagtgt ccgggtagga aacgctctgg    240

gtgctggaga catggagcag gcacggaagt cctctaccgt ttccctgctg attacagtgc    300

tctttgctgt agccttcagt gtcctgctgt taagctgtaa ggatcacgtg gggtacattt    360

ttactaccga ccgagacatc attaatctgg tggctcaggt ggttccaatt tatgctgttt    420

cccacctctt tgaagctctt gcttgcacga gtggtggtgt tctgaggggg agtggaaatc    480

agaaagttgg agccattgtg aataccattg ggtamtatgt ggttggcctc cccatcggga    540

tcgcgctgat gtttgcaacc acacttggag tgatgggtct gtggtcaggg atcatcatct    600

gtacagtctt tcaagctgtg tgttttctag gctttattat tcagctaaat tggaaaaaag    660

cctgtcmgca ggctcaggta cacgccaatt tgaaagtaaa caacgtgcct cggagtggga    720

attctgctct ccctcaggat ccgcttcacc cagggtgccc tgaaaacctt gaaggaattt    780

taacgaacga tgttggaaag acaggcgagc ctcagtcaga tcagcagatg cgccaagaag    840

aacctttgcc ggaacatcca caggacggcg ctaaattgtc caggaaacag ctggtgctgc    900

ggcgagggct tctgctcctg ggggtcttct taatcttgct ggtggggatt ttagtgagat    960

tctatgtcag aattcagtga cgtggtagga aagaaagtca ggtcaagtga tgcttttgag   1020

cttacacaca attcacaggc ccaccagtga caatttactg tgagttaatg tcattcaggt   1080

gtgcccatgg attttgaggg ctggaaatgc aaagacacat ttttctataa aaagaaaaag   1140

caactaaggt taaaagctat attgtggccc aagacactgt ctgaaagatg acatgagtag   1200

taattcacca ctatctgaac caagcaagga tcaatgtgct gactgcattg gccaatggct   1260
```

-continued

```
ttgatacttc tgctattttt ttagacacaa acccataaac taactgctta agaattcata   1320
ctgcttgaat tatgtaaaat atattttaca gtatatcttt ccttgggcct tagattacta   1380
ttcactgggc aaatggtatt tgtttttgtt ttaatttttt ttttaataga cggaagtctt   1440
gctctgtcat gcaggctgga gtgcggtggt gcgatcatag ctcactgcag cctcgaactc   1500
ttgggcttca agcaatcctc ctgtgtcagc caccagagta gctgagacta caggggtatg   1560
ccaccatgcc cagctggcat ttgttaatct tcatttgagg tctagatcta ggcactgtgg   1620
acactgaaaa acagttggga aatctttcga gctgtggaaa tccaaacaaa gactgataat   1680
tcctggtarg ggtgtgtgcs tgacgtactg carcctyaam ctyctgggct yaagtgatcc   1740
tcccacctca gcctcctgag tagctgagac cacaggcgtg tgccaccacg cctagctaat   1800
ttttwawacc rgggtcwamc ctttgtttcc caggstggty ttgaattcct gggatcaagc   1860
aatycttcca cctkgsmctc ccaaagtgtt gggattatag gcatgagcca ccasgactgg   1920
ccagaggaca aaattttaat aaaggtctta gcttaagcag taatcytact tcattaagcc   1980
ttcctggggt gcggtacaca ccgttaattc agcaaccctc agtacatact aagtatgctc   2040
agtgctgtga aagtggatta caccaaatta agtcattctt atcacaccca atcaaaagtc   2100
aagaagccag ggataaaagc acctcaggca cataacatta atctagtaat gtaattctct   2160
gcacatccag ctggtgaaac tgcgtgctgt aagctgggac cagctttgtc cataactgct   2220
gagagaactt gctgaagctc taggaataat tttgcctgcc cggttgctca ccagttgtag   2280
cttgccagct cccaacaccc ttcctggtgc caataaactt tctcaaagag caatactgac   2340
atttcttttg ataaaacctc cagccttctc tgtgttgttc cgacataccg aggaccaact   2400
ggtctacatg gatgccctga acatgcaatt ctttcttcca aaataaaaca ttaaatagag   2460
aaaaaaaaaa aaaaaaaaaa aaaaaaaaaa aaaaaagggc ggcc                     2504
```

```
<210> SEQ ID NO 29
<211> LENGTH: 1866
<212> TYPE: DNA
<213> ORGANISM: Homo sapiens

<400> SEQUENCE: 29
```

```
ggcacgagaa tacatacgat ccttgtctac caggagtcta atagaaagat ggacagcgtg     60
gaccctgcca gcagccaggc catggagctc tctgatgtca ccctcattga gggtgtgggt    120
aatgaggtga tggtggtggc aggtgtggtg gtgctgattc tagccttggt cctagcttgg    180
ctctctacct acgtagcaga cagcggtagc aaccagctcc tgggcgctat tgtgtcagca    240
ggcgacacat ccgtcctcca cctggggcat gtggaccacc tggtggcagg ccaaggcaac    300
cccgagccaa ctgaactccc ccatccatca gagggtaatg atgagaaggc tgaagaggcg    360
ggtgaaggtc ggggagactc cactggggag gctggagctg gggtggtgt tgagcccagc    420
cttgagcatc tccttgacat ccaaggcctg cccaaaagac aagcaggtgc aggcagcagc    480
agtccagagg ccccccctgag atctgaggat agcacctgcc tccctcccag ccctggcctc    540
atcactgtgc ggctcaaatt cctcaatgat accgaggagc tggctgtggc taggccagag    600
gataccgtgg gtgccctgaa gagcaaatac ttccctggac aagaaagcca gatgaaactg    660
atctaccagg gccgcctgct acaagaccca gcccgcacac tgcgttctct gaacattacc    720
gacaactgtg tgattcactg ccaccgctca cccccagggt cagctgttcc aggcccctca    780
gcctccttgg ccccctcggc cactgagcca cccagccttg gtgtcaatgt gggcagcctc    840
atggtgcctg tctttgtggt gctgttgggt gtggtctggt acttccgaat caattaccgc    900
```

-continued

```
caattcttca cagcacctgc cactgtctcc ctggtgggag tcaccgtctt cttcagcttc    960
ctagtatttg ggatgtatgg acgataagga cataggaaga aaatgaaagg catggtcttt   1020
ctcctttatg gcctccccac ttttcctggc cagagctggg cccaagggcc ggggagggag   1080
gggtggaaag gatgtgatgg aaatctcctc cataggacac aggaggcaag tatgcggcct   1140
ccccttctca tccacaggag tacagatgtc cctcccgtgc gagcacaact caggtagaaa   1200
tgaggatgtc atcttccttc acttttaggg tcctctgaag gagttcaaag ctgctggcca   1260
agctcagtgg ggagcctggg ctctgagatt ccctcccacc tgtggttctg actcttccca   1320
gtgtcctgca tgtctgcccc cagcacccag ggctgcctgc aagggcagct cagcatggcc   1380
ccagcacaac tccgtaggga gcctggagta tccttccatt tctcagccaa atactcatct   1440
tttgagactg aaatcacact ggcgggaatg aagattgtgc cagccttctc ttatgggcac   1500
ctagccgcct tcaccttctt cctctacccc ttagcaggaa tagggtgtcc tcccttcttt   1560
caaagcactt tgcttgcatt ttattttatt tttttaagag tccttcatag agctcagtca   1620
ggaaggggat ggggcaccaa gccaagcccc cagcattggg agcggccagg ccacagctgc   1680
tgctcccgta gtcctcaggc tgtaagcaag agacagcact ggcccttggc cagcgtccta   1740
ccctgcccaa ctccaaggac tgggtatgga ttgctgggcc ctaggctctt gcttctgggg   1800
ctattggagg gtcagtgtct gtgactgaat aaagttccat tttgtggtaa aaaaaaaaaa   1860
aaaaaa                                                              1866
```

```
<210> SEQ ID NO 30
<211> LENGTH: 1501
<212> TYPE: DNA
<213> ORGANISM: Homo sapiens
<220> FEATURE:
<221> NAME/KEY: SITE
<222> LOCATION: (434)
<223> OTHER INFORMATION: n equals a,t,g, or c
<220> FEATURE:
<221> NAME/KEY: SITE
<222> LOCATION: (441)
<223> OTHER INFORMATION: n equals a,t,g, or c
<220> FEATURE:
<221> NAME/KEY: SITE
<222> LOCATION: (1300)
<223> OTHER INFORMATION: n equals a,t,g, or c

<400> SEQUENCE: 30
```

```
ggacagccgt atcagcctgc tggtgaataa cgccggtgtg ggcgccacgg cttcgctgct     60
ggagtcggat gccgacaaaa tggacgcgat gattctgctg aacgtactgg cgctgacccg    120
cctggccaaa gccgcggcaa ccaactttgt cgcccagggc cgtggcacga tcatcaacat    180
cggctcgatt gtcgctctcg ctcccaaagt gctgaacggc gtgtatggcg gtaccaaagc    240
gttcgtgcag gcgttcagcg aatcgctgca gcatgagctg agtgacaagg gcgtagtggt    300
ccaggtggtg ctgccaggcg ctaccgccac ggagttctgg gacatcgccg gcctgcctgt    360
gaaacaacct gccggaagcc atggtgatga ccaccgaaaa cctggtggac gccgccctgs    420
caggccttgc ccanggcraa ncgtgacgat tccgtccctg ccggacagcg cagattggga    480
cactacgaac gcgcgcggct ggccctgggt ccgaacctgt cgcaccgtga acccgccgct    540
cgttatgggt tgaagtaatc cggactagcg cagccgggtt taaacgcagg cttcctgatt    600
gcctgggagg cctgttcata cccgtaggcg accgacagca acgtggcttc gctcaaattt    660
ttcccataga agtgaacggc tgtcggcatc ccttcgtcgt ccatgcccga tggtatggag    720
```

-continued

```
ataccgggat aaccggccac cgccgagtag tagtaactgt atgagtgaaa gttggacatc    780

attgcatcaa gcttatgctc ggccagcggc ttatcgatgg tgcttttgaa aatcgggccg    840

atggcagccc ataactcatt gcgcgcctca tcactgatat ccatcccgtt gatcatggtg    900

agcatctgtt gatccggcac acccggaccg ctgttgcgct cgttgaattc aatcagctca    960

gccagcgact tcaccggcaa gcctgcccgt ccggccaggt aggcttcaag ctggtgttta   1020

acgtccgata acaacgcgtc gttatattgt tcatgggttt cgtacgggac gccctcaccc   1080

agttgaccca cgggtaccaa tgtcgcgccc ttgcctcgca gcaacgtaat ggcatcctcg   1140

aagtgctsct gtcggctttt ttcgccgggt cgttggcatc ttctacagat aactcaggca   1200

acggcgtata accgatgcgc ttgcccacca aggcgtcagg cttgattccc tgggtgtagc   1260

ggttggtatc cgtcatcgca tccagtgctt gcgccgcatn acgcacgtta cgggtgaagg   1320

tgcccaccgt gtcctggcgg gaactggtca tcacccttcg gtactcacta atccttcggt   1380

cggtttgaaa ccaataacac cgttgtaagc cgccggcgta atgattgaac cattggtttc   1440

gacccccaat gccaagggca caatcccttg tgcaacggct accgcagagc ccgtactcga   1500

g                                                                   1501
```

<210> SEQ ID NO 31
<211> LENGTH: 1752
<212> TYPE: DNA
<213> ORGANISM: Homo sapiens
<220> FEATURE:
<221> NAME/KEY: SITE
<222> LOCATION: (1099)
<223> OTHER INFORMATION: n equals a,t,g, or c

<400> SEQUENCE: 31

```
aaggtacgcc tgcaggtacc ggtccggaat tcccgggtcg acccacgcgt ccgtccagga     60

cagagagtgc acaaactacc cagcacagcc ccctccgccc cctctggagg ctgaagaggg    120

attccagccc ctgccaccca cagacacggg ctgactgggg tgtctgcccc ccttgggggg    180

gggcagcaca gggcctcagg cctgggtgcc acctggcacc tagaagatgc ctgtgccctg    240

gttcttgctg tccttggcac tgggccgaag cccagtggtc ctttctctgg agaggcttgt    300

ggggcctcag gacgctaccc actgctctcc gggcctctcc tgccgcctct gggacagtga    360

catactctgc ctgcctgggg acatcgtgcc tgctccgggc cccgtgctgg cgcctacgca    420

cctgcagaca gagctggtgc tgaggtgcca gaaggagacc gactgtgacc tctgtctgcg    480

tgtggmtgtc cacttggccg tgcatgggca ctgggaagag cctgaagatg aggaaaagtt    540

tggaggagca gctgacttag ggtggagga gcctaggaat gcctctctcc aggcccaagt    600

cgtgctctcc ttccaggcct accctactgc ccgctgcgtc ctgctggagg tgcaagtgcc    660

tgctgccctt gtgcagtttg gtcagtctgt gggctctgtg gtatatgact gcttcgaggc    720

tgccctaggg agtgaggtac gaatctggtc ctatactcag cccaggtacg agaaggaayt    780

caaccacaca cagcagctgc ctgactgcag ggggctcgaa gtctggaaca gcatcccgag    840

ctgctgggcc ctgccctggc tcaacgtgtc agcagatggt gacaacgtgc atctggttct    900

gaatgtctct gaggagcagc acttcggcct ctccctgtac tggaatcagg tccagggccc    960

cccaaaaccc cggtggcaca aaaacctgac tggaccgcag atcattacct tgaaccacac   1020

agacctggtt ccctgcctct gtattcaggt gtggcctctg gaacctgact ccgttagacg   1080

aacatctgcc ccttcaggna ggacccccgc gcacaccaga acctctggca agccgcccga   1140

ctgcgactgc tgaccctgca gagctggctg ctggacgcac cgtgctcgct gcccgcagaa   1200
```

-continued gcggcactgt gctggcgggc tccgggtggg gacccctgcc agccactggt cccaccgctt 1260
tcctgggaga aygtcactgt ggacaaggtt ctcgagttcc cattgctgaa aggccaccct 1320
aacctctgtg ttcaggtgaa cagctcggag aagctgcagc tgcaggagtg cttgtgggct 1380
gactccctgg ggcctctcaa agacgatgtg ctactgttgg agacacgagg cccccaggac 1440
aacagatccc tctgtgcctt ggaacccagt ggctgtactt cactacccag caaagcctcc 1500
acgagggcag ctcgccttgg agagtactta ctacaagacc tgcagtcagg ccagtgtctg 1560
cagctatggg acgatgactt gggagcgcta tgggcctgcc ccatggacaa atacatccac 1620
aagcgctggg ccctcgtgtg gctggcctgc ctactctttg cctgcgcttt ccctcatcct 1680
ccttctcaaa aaggatcacg cgaaagggtg gctgaggctc ttgaaacagg acgtccgctc 1740
gggggcggcc gc 1752

<210> SEQ ID NO 32
<211> LENGTH: 2152
<212> TYPE: DNA
<213> ORGANISM: Homo sapiens

<400> SEQUENCE: 32
ccgctttgtt ctccagatgt gaatagctcc actataccag cctcgtcttc cttccggggg 60
acaacgtggg tcagggcaca gagagatatt taatgtcacc ctcttggggc tttcatggga 120
ctccctctgc cacatttttt ggaggttggg aaagttgcta gaggcttcag aactccagcc 180
taatggatcc caaactcggg agaatggctg cgtccctgct ggctgtgctg ctgctgctgc 240
tgctggagcg cggcatgttc tcctcaccct ccccgccccc ggcgctgtta gagaaagtct 300
tccagtacat tgacctccat caggatgaat ttgtgcagac gctgaaggag tgggtggcca 360
tcgagagcga ctctgtccag cctgtgcctc gcttcagaca agagctcttc agaatgatgg 420
ccgtggctgc ggacacgctg cagcgcctgg gggcccgtgt ggcctcggtg gacatgggtc 480
ctcagcagct gcccgatggt cagagtcttc caatacctcc cgtcatcctg gccgaactgg 540
ggagcgatcc cacgaaaggc accgtgtgct tctacggcca cttggacgtg cagcctgctg 600
accggggcga tgggtggctc acggacccct atgtgctgac ggaggtagac gggaaacttt 660
atggacgagg agcgaccgac aacaaaggcc ctgtcttggc ttggatcaat gctgtgagcg 720
ccttcagagc cctggagcaa gatcttcctg tgaatatcaa attcatcatt gaggggatgg 780
aagaggctgg ctctgttgcc ctggaggaac ttgtggaaaa agaaaaggac cgattcttct 840
ctggtgtgga ctacattgta atttcagata acctgtggat cagccaaagg aagccagcaa 900
tcacttatgg aacccggggg aacagctact tcatggtgga ggtgaaatgc agagaccagg 960
attttcactc aggaaccttt ggtggcatcc ttcatgaacc aatggctgat ctggttgctc 1020
ttctcggtag cctggtagac tcgtctggtc atatcctggt ccctggaatc tatgatgaag 1080
tggttcctct tacagaagag gaaataaata catacaaagc catccatcta gacctagaag 1140
aataccggaa tagcagccgg gttgagaaat ttctgttcga tactaaggag gagattctaa 1200
tgcacctctg gaggtaccca tctctttcta ttcatgggat cgagggcgcg tttgatgagc 1260
ctggaactaa aacagtcata cctggccgag ttataggaaa attttcaatc cgtctagtcc 1320
ctcacatgaa tgtgtctgcg gtggaaaaac aggtgacacg acatcttgaa gatgtgttct 1380
ccaaaagaaa tagttccaac aagatggttg tttccatgac tctaggacta cacccgtgga 1440
ttgcaaatat tgatgacacc cagtatctcg cagcaaaaag agcgatcaga acagtgtttg 1500
gaacagaacc agatatgatc cgggatggat ccaccattcc aattgccaaa atgttccagg 1560
agatcgtcca caagagcgtg gtgctaattc cgctgggagc tgttgatgat ggagaacatt 1620
cgcagaatga gaaaatcaac aggtggaact acatagaggg aaccaaatta tttgctgcct 1680
ttttcttaga gatggcccag ctccattaat cacaagaacc ttctagtctg atctgatcca 1740
ctgacagatt cacctccccc acatccctag acagggatgg aatgtaaata tccagagaat 1800
ttgggtctag tatagtacat tttcccttcc atttaaaatg tcttgggata tctggatcag 1860
taataaaata tttcaaaggc acagatgttg gaaatggttt aaggtccccc actgcacacc 1920
ttcctcaagt catagctgct tgcagcaact tgatttcccc aagtcctgtg caatagcccc 1980
aggattggat tccttccaac cttttagcat atctccaacc ttgcaatttg attggcataa 2040
tcactccggt ttgctttcta ggtcctcaag tgctcgtgac acataatcat tccatccaat 2100
gatcgccttt gctttaccay tctttccttt tatcttatta ataaaaatgt tg 2152

<210> SEQ ID NO 33
<211> LENGTH: 1757
<212> TYPE: DNA
<213> ORGANISM: Homo sapiens

<400> SEQUENCE: 33
aggctttcca cccagaccgt caacttcggg acagtggggg agacggtcac ccttcacatc 60
tgcccagaca gggatgggga tgaggcggca cagcctgatg ctgctgccat ggtggcttgg 120
ggcagcgggg agaaaggagt gtcacaggga gcagctcgtg gctgcagtgg aagtcactga 180
gcaagagact aaagtcccca agaaaaccgt catcatagaa gagaccatca ccactgtggt 240
gaagagccca cgtggccaac gacggtyccc cagcaagtcc ccctcccgct caccttcccg 300
ctgctctgcc agcccgctga ggccaggcct actggccccc gacctgctgt acctgccagg 360
tgctggccag ccccgcaggc cggargcaga accaggccag aagcccrtgg tgcccacact 420
gtatgtgacg gaggccgagg cccactctcc agctctgccc ggactctcgg ggccccagcc 480
caagtgggtg gaggtggagg agaccattga agtccgggtg aagaagatgg gcccgcaggg 540
tgtgtctccc accacagagg tgcccaggag ctcatcgggg catctcttca cactgcccgg 600
tgcgaccccc ggaggggacc ccaattccaa caactccaac aacaagctgc tggcccagga 660
ggcctgggcc cagggcacag ccatggtcgg cgtcagagag ccccttgtct tccgcgtgga 720
tgccagaggc agtgtggact gggctgcttc tggcatgggc agcctggagg aggagggcac 780
catggaggag gcgggagagg aagaggggga agacggagac gcctttgtga cggaggagtc 840
ccaggacaca cacagccttg gggatcgtga ccccaagatc ctcacgcaca acggccgcat 900
gctgacactg gctgacctgg aagattacgt gcctggggaa ggggagacct tccactgtgg 960
tggccctggg cctggcgccc ctgatgaccc tccctgcgag gtctcggtga tccagagaga 1020
gatcggggag cccacggtgg gcagcctgtg ctgctcagcg tggggcatgc actgggtccc 1080
cgaggccctc tcggcctctt taggcctgag ccccgtgggg cgtcaccacc gggaccccag 1140
gtccgtagcc ttgagggcac ctccttcctc ttgcgggagg ccccggctcg gcctgtgggc 1200
agtgctccct ggacgcagtc tttctgcacc cgcatccggc gttctgcgga cagtggccag 1260
agcagcttca ccacagagct ttccacccag accgtcaact tcgggacagt gggggagacg 1320
gtcacccttc acatctgtcs ctggccwcgg gccttcttac ctcactcaac ttcagccagg 1380
aggactgggt ggtgcttgca atgttggaat gaccggctca aagacctcag ctctgggctg 1440
tttcctgtca gcctggcagg agcctcagga ctgtggacga aggatgtggc cttgggcatt 1500

-continued

```
tgtcctgttc ccacatgggc ctggtccctc cctcctggcc ccagccacag ctgccaggcc   1560

tgacatggcc ttgcctctcc tgcagtcttg gtgactgaga cccttgggtg gcgcttccca   1620

gctctgcagg ccctcctggc cttttctgca gggtggacac agggtctgtg tgtgggcagc   1680

agcccctgtc tctcagcaag aataaagcag cttcctgtgc aaaaaaaaaa aaaaaaaaaa   1740

aactcgagcg gcacgag                                                  1757
```

<210> SEQ ID NO 34
<211> LENGTH: 1466
<212> TYPE: DNA
<213> ORGANISM: Homo sapiens

<400> SEQUENCE: 34

```
ggcacaggct gggactttgg gctggctgca gtctgtctga gggcggccga agtggctggc     60

tcatttaaga tgaggcttct gctgcttctc ctagtggcgg cgtctgcgat ggtccggagc    120

gaggcctcgg ccaatctggg cggcgtgccc agcaagagat taaagatgca gtacgccacg    180

gggccgctgc tcaagttcca gatttgtgtt tcctgaggtt ataggcgggt gtttgaggag    240

tacatgcggg ttattagcca gcggtaccca gacatccgca ttgaaggaga gaattacctc    300

cctcaaccaa tatatagaca catagcatct ttcctgtcag tcttcaaact agtattaata    360

ggcttaataa ttgttggcaa ggatcctttt gctttctttg gcatgcaagc tcctagcatc    420

tggcagtggg gccaagaaaa taaggtttat gcatgtatga tggttttctt cttgagcaac    480

atgattgaga accagtgtat gtcaacaggt gcatttgaga taactttaaa tgatgtacct    540

gtgtggtcta agctggaatc tggtcacctt ccatccatgc aacaacttgt tcaaattctt    600

gacaatgaaa tgaagctcaa tgtgcatatg gattcaatcc cacaccatcg atcatagcac    660

cacctatcag cactgaaaac tcttttgcat taagggatca ttgcaagagc agcgtgactg    720

acattatgaa ggcctgtact gaagacagca agctgttagt acagaccaga tgctttcttg    780

gcaggctcgt tgtacctctt ggaaaacctc aatgcaagat agtgtttcag tgctggcata    840

ttttggaatt ctgcacattc atggagtgca ataatactgt atagctttcc ccacctccca    900

caaaatcacc cagttaatgt gtgtgtgtgt ttttttttta aggtaaacat tactacttgt    960

aacttttttt cttagtcata tttgaaaaag tagaaaattg agttacaatt tgattttttt   1020

tccaaagatg tctgttaaat ctgttgtgct tttatatgaa tatttgtttt ttatagttta   1080

aaattgatcc tttgggaatc cagttgaagt tcccaaatac tttataagag tttatcagac   1140

atctctaatt tggccatgtc cagtttatac agtttacaaa atatagcaga tgcaagatta   1200

tgggggaaat cctatattca gagtactcta taaatttttg tgtatgtgtg tatgtgcgtg   1260

tgattaccag agaactacta aaaaaaccaa ctgcttttta aatcctattg tgtagttaaa   1320

gtgtcatgcc ttgaccaatc taatgaattg attaattaac tgggccttta tacttaacta   1380

aataaaaaac taagcagata tgagttaaaa aaaaaaaaaa aaaaaaaaaa aaaaaaaaaa   1440

aaaaaaaaaa aaaaaaaaaa actcga                                        1466
```

<210> SEQ ID NO 35
<211> LENGTH: 526
<212> TYPE: DNA
<213> ORGANISM: Homo sapiens
<220> FEATURE:
<221> NAME/KEY: SITE
<222> LOCATION: (283)
<223> OTHER INFORMATION: n equals a,t,g, or c -continued

<400> SEQUENCE: 35

```
ggggacgtgc acggggccgc cctcctggcc ctgaagctgc gccggcctcc ctgagcgttt     60
cgctgcggag ggaagtccac tctcggggag agatgctgat gccggtccac ttcctgctgc    120
tcctgctgct gctcctgggg ggccccagga caggcctccc ccacaagttc tacaaagcca    180
agcccatctt cagctgcctc aacaccgccc tgtctgaggc tgagaagggc cagtgggagg    240
atgcatccct gctgagcaag aggagcttcc actacctgcg canaagsacg cctcttcggg    300
agaggaggag gagggcaaag agaaaaagac tttccccatc tctggggcca ggggtggarc    360
cagaggcacc cggtacagat acgtgtccca agcacagccc aggggaaagc cacgccagga    420
cacggccaag agtccccacc gcaccaagtt caccctgtcc ctcgacgtcc ccaccaacat    480
catgaacctc ctcttcaaca tcgccaaggc caagaactgc gtgccc                   526
```

<210> SEQ ID NO 36
<211> LENGTH: 2412
<212> TYPE: DNA
<213> ORGANISM: Homo sapiens
<220> FEATURE:
<221> NAME/KEY: SITE
<222> LOCATION: (329)
<223> OTHER INFORMATION: n equals a,t,g, or c
<220> FEATURE:
<221> NAME/KEY: SITE
<222> LOCATION: (340)
<223> OTHER INFORMATION: n equals a,t,g, or c
<220> FEATURE:
<221> NAME/KEY: SITE
<222> LOCATION: (977)
<223> OTHER INFORMATION: n equals a,t,g, or c
<220> FEATURE:
<221> NAME/KEY: SITE
<222> LOCATION: (1117)
<223> OTHER INFORMATION: n equals a,t,g, or c

<400> SEQUENCE: 36

```
cacgagtttt aaatcaattt tttttcaagc aatcagattc ttttctccta gaggagctgt     60
gggcaagaaa actaatgaat tctacatcct tctcatcacc tggtttaaat tgttttctgc    120
tctgagtaaa cagtaattac tgtttaagta catctcagca gaattttatc ccaattgcaa    180
cagttcatgt tcctcctaat gtaatctctg cggaggaaat gatcgtcaag ggaagcaggc    240
tgacctgctc acgggatggc gttcttacaa tctgcatctt atgtaatggt gattctgtgt    300
gcctgtgtca taattattgg aatattatnt tatgcttttn tttttgagac tctatctcca    360
aaaaaaagaa gagacataga aatttgaaga aggatccttt aatggtctac accgtcttcc    420
aaagtcaaga agtggcagct gatatccatt tgaaagtaga atcctagctt ttcagagcta    480
gacmaggcct cagaaactat agttgaattc ctcattgtac caatgagaaa ctcaggccta    540
gatgggtaaa aagaggtgtg ttgtagcagt gctgggacag atctcggttt ttctgcttcc    600
tatacaatcc tcttcaaccc aatactacaa tgtatttatt atcacatatt aagctggaga    660
tttgtagcca tgttattaga gttgcaactg tttatcctat agattccagc cacattttaa    720
acacataact tcatgtagtt aggccactaa aaataaagta atccatcaaa ctagtaatac    780
actagagaat ttgacctaca tactaagatg cctgaaatcc acagtatatg gcaatttaac    840
ccccatctaa tagtggctca atcaagtagc taaacatatt tatttcactc agatggttgg    900
ttgtttggta gaaggaatgg actccttggg ctattttggg aacaaaaaag gactaggaca    960
caaatcaaag ccacatncac agtaagaaat ccgggctgat ctctgccaag aaaagktaca   1020
aagaataatt acttgatcac gtggggaaat ttcgacataa aagaagtaat ggataaaarg   1080
```

-continued

```
aaagaaaaat gaccaattgc tgragmcaat aattatngca accctaaacc agaaagcact   1140
aagccaggaa gtcaaaaact aagtcatmca catatgacaa ggtgcggggg ttggtcctga   1200
gacttcagtg agaatatgtc cgatcaggat atgcaaagaa ccatttggaa gatttctagt   1260
tcataaggga agtaccaaat gaagtggatg ggaccatacg caatttgcat aggaccccca   1320
aggaggaaat agtatgacat ggtagtaaaa aagcaatcac gactacactc acaattttag   1380
gagaaaataa aactaaatcc agaatttgaa gccaacaaca acaaaaaaag tcattattta   1440
gggtatacgt tcctgtgggc agtaccttgc aaagtagaac atcttcaaga agaaatattt   1500
gacttgaggt aaggctttca agattgccat attacattca taaaggcaaa ctcatccttg   1560
agaccaaagt gacagaagat tagaaattaa ggctttgttt taaagaaatg ttgacatcat   1620
actggaaatt attatccagc tacttacaca ttcgttttta aatccatccc tatgtttagc   1680
tgccaaaatg caaactgcgc attgywctct cacggagagc gccacaggtc accagctatt   1740
attctcccag gagtcattga gtaggctgcc ccaagtacca cataggaaac tcaacgaact   1800
attttcattt caaggaccat tagaaacaga aaggaaaaga gaaggtcagg gaaacttagt   1860
ttctaacaaa ggaagtgagg cactttgaaa aagaaaatat ttagagaacg gagaggaagc   1920
taaacccaaa caaccaaaac gcacagctga caattattcc gggaagttgg taacttctgc   1980
ctggtctcta gaagcacagg aagaaaggac tgttagcgtg aagaacactc cagggttctg   2040
ggtatctagg cagagtcagt caacagggct aaccatgtga taatcctggg taattccacc   2100
tcacagttca ctaaaaaaca agcggaaccc tgggcaaagc cctttggggc tttaatagca   2160
atggaggaca tcaccctgtc actttctctg cttctacaca gcaggcaatc aaggaaaact   2220
tgccaagaaa tatgagtgaa taaatgattt tgaaagtttc attgagcagg aacatgaaaa   2280
ggatgatttg gggatagctg gaaggatagt tacttgcatg aataatattt attcaccgtc   2340
agtgtgatat ttctcaatag aaagattgta tttaaaatgt acaactacaa aaaaaaaaaa   2400
aaaaaactcg ag                                                       2412
```

<210> SEQ ID NO 37
<211> LENGTH: 1274
<212> TYPE: DNA
<213> ORGANISM: Homo sapiens

<400> SEQUENCE: 37

```
ggcacgagga aagaccaact ggccggtctt ctgagcagat ggattcctat aggaccagtg     60
gggagaggat tacacagtac ctctgaaccc tcaacacaaa ataatatctc ttctattgtt    120
ggttagtttc actatctgct tcattctttt aaaatgtcaa gtgttttctc ttgagggaac    180
cttctgaatt actttgcctg cactatacct aattcttatt acaatgctgt gaactttgaa    240
ttattaccct tgttcacccc aaatggaaaa tcaaagctca aagaggtgag tgactgccca    300
gctcatgcag ctgatagaat caagatttca tttcaggtgt gtctggatcc tgcacttact    360
tgctcttttc tcaacatggc ctcctaagga tccagaagga agcccgccat cagcaaccag    420
cagcccactc accccccacc tcagtctcac cttgccattc aaacaggctc cagtttcaaa    480
tgtcagttct gccattcacg tgatgctgga caagtcagtt agcctctctg agattcaatt    540
ttctcatatg cctaatggaa aaagagcatc taccttataa attgcatatt tactcttcct    600
tcccactgac tcaatagaac tatattcccc aytcccatag atgctggcct tagacttgtg    660
acttgcattg gccaatgaga tgagacatac accaatcaaa agagaggcat taaatgtgca    720
```

-continued

```
tgactggttt agcttggcct cttatgstcc tgccatgcgt rattagatca tgcctgagta    780

gccactgctc attcagcctg agttctggag tgagaaacag gtggagcagt cctggactcc    840

atccacagcc cagagcagag caccatggcc cacccgtagg gctgtaagtg agaaagaaat    900

gtctattgtt ataaaccagt ggttttcaag gcatggtccc tcagtatcaa cgtcacttag    960

aaatttggag aaatgcacat tctcagtcct catccaaacc tgcttaatca gaaactctgg   1020

gggttgggcc cagcaatctg tattttaaaa aggcctctag gtaattctga tgcaggctca   1080

ggcttggaat ccactgttat aaatcactga catttgggga ttatttgttg ctgtgtgaaa   1140

gctgactaat acatctaccc tttgaggttg ctatgaggac acagtaagat aagatgtgag   1200

aagctcctgg aatgaggttc ctcctgatag tcctaagcct ggcatccaaa attcttcata   1260

atctgatcct cgag                                                     1274
```

```
<210> SEQ ID NO 38
<211> LENGTH: 1036
<212> TYPE: DNA
<213> ORGANISM: Homo sapiens
<220> FEATURE:
<221> NAME/KEY: SITE
<222> LOCATION: (43)
<223> OTHER INFORMATION: n equals a,t,g, or c
<220> FEATURE:
<221> NAME/KEY: SITE
<222> LOCATION: (47)
<223> OTHER INFORMATION: n equals a,t,g, or c
<220> FEATURE:
<221> NAME/KEY: SITE
<222> LOCATION: (58)
<223> OTHER INFORMATION: n equals a,t,g, or c

<400> SEQUENCE: 38

caaaccccat ttacgtgcac actgatacac cgtcacgcct gcnggtnacc ggtccggnat     60

tcccgggtcg acccacgcgt ccgggggaag caagcactta tttggctact tggtgtccat    120

ggggaaagaa ttcctaatgc tccttatgtg ttagaggact ttgttgagaa tgtgaagtcg    180

gaaacatttc cagctgttaa gatggagctg ctcactgctt tgctgcgcct tttcctctcc    240

cgacctgctg agtgccagga catgctagga cgtttgttgt attactgcat agaggaagaa    300

aaagatatgg ctgtacggga ccgaggtctc ttctattatc gcctcctctt agttggcatt    360

gatgaagtta agcggattct gtgtagccct aaatctgacc ctactcttgg acttttggag    420

gatccggcag aaagacctgt gaatagctgg gcctcagact tcaacacact ggtgccagtg    480

tatggcaaag cccactgggc aactatctct aaatgccagg gggcagagcg ttgtgaccca    540

gagcttccta aaacttcatc ctttgccgca tcaggaccct tgattcctga agagaacaag    600

gagagggtac aagaactccc tgattctgga gccctcatgc tagtccccaa tcgccagctt    660

actgctgatt attttgagaa aacttggctt agccttaaag ttgctcatca gcaagtgttg    720

ccttggcggg gagaattcca tcctgacacc ctccagatgg ctcttcaagt agtgaacatc    780

cagaccatcg caatgagtag ggctgggtct cggccatgga aagcatacct cagtgctcag    840

gatgatactg gctgtctgtt cttaacagaa ctgctattgg agcctggaaa ctcagaaatg    900

cagatctctg tgaaacaaaa tgaagcaaga acggagacgc tgaatagttt tatttctgta    960

ttagaaactg tgattggaac aattgaagaa ataaaatcat aacagagaaa aaaaaaaaaa   1020

aaaaaagggc ggccgc                                                   1036

<210> SEQ ID NO 39
<211> LENGTH: 1379
```

-continued

<212> TYPE: DNA
<213> ORGANISM: Homo sapiens

<400> SEQUENCE: 39

```
gcggcgcggg tgggggttgt gcgttttacg caggctgtgg cagcgacgcg gtccccagcc     60
tgggtaaaga tggccccatg gcccccgaag gcctagtccc agctgtgctc tggggcctca    120
gcctcttcct caacctccca ggacctatct ggctccagcc ctctccacct ccccagtctt    180
ctcccccgcc tcagccccat ccgtgtcata cctgccgggg actggttgac agctttaaca    240
agggcctgga gagaaccatc cgggacaact ttggaggtgg aaacactgcc tgggaggaag    300
agaatttgtc caaatacaaa gacagtgaga cccgcctggt agaggtgctg gagggtgtgt    360
gcagcaagtc agacttcgag tgccaccgcc tgctggagct gagtgaggag ctggtggaga    420
gctggtggtt tcacaagcag caggaggccc cggacctctt ccagtggctg tgctcagatt    480
ccctgaagct ctgctgcccc gcaggcacct tcgggccctc ctgccttccc tgtcctgggg    540
gaacagagag gccctgcggt ggctacgggc agtgtgaagg agaagggaca cgagggggca    600
gcgggcactg tgactgccaa gccggctacg gggtgaggc ctgtggccag tgtggccttg    660
gctactttga ggcagaacgc aacgccagcc atctggtatg ttcggcttgt tttggcccct    720
gtgcccgatg ctcaggacct gaggaatcaa actgtttgca atgcaagaag ggctgggccc    780
tgcatcacct caagtgtgta gacattgatg agtgtggcac agagggagcc aactgtggag    840
ctgaccaatt ctgcgtgaac actgagggct cctatgagtg ccgagactgt gccaaggcct    900
gcctaggctg catgggggca gggccaggtc gctgtaagaa gtgtagccct ggctatcagc    960
aggtgggctc caagtgtctc gatgtggatg agtgtgagac agaggtgtgt ccgggagaga   1020
acaagcagtg tgaaaacacc gagggcggtt atcgctgcat ctgtgccgag ggctacaagc   1080
agatggaagg catctgtgtg aaggagcaga tcccaggtgc attccccatc ttaactgatt   1140
taacccctga aacaacccga cgctggaagt tgggttctca tccccactct acatatgtaa   1200
aaatgaagat gcagagagat gaagctactt tcccagggct atatggcaag caagtcgcaa   1260
agctgggatc ccaatccaga cagtctgacc gtggaacgag actcatacac gtaataaatg   1320
ctctgccccc aacttgtcca ccacaaaaaa aaaaaaaaaa aaaaaaaaag ggcggccgc    1379
```

<210> SEQ ID NO 40
<211> LENGTH: 1932
<212> TYPE: DNA
<213> ORGANISM: Homo sapiens
<220> FEATURE:
<221> NAME/KEY: SITE
<222> LOCATION: (293)
<223> OTHER INFORMATION: n equals a,t,g, or c

<400> SEQUENCE: 40

```
ggcacgaggc cgccctgggt gtcagcggct cggctcccgc gcacgctccg gccgtcgcgc     60
asctcggcac ctgcaggtcc gtgcgtcccg cggctggcgc ccctgactcc gtcccggcca    120
gggagggcca tgatttccct cccggggccc ctggtgacca acttgctgcg gtttttgttc    180
ctggggctga gtgccctcgc gcccccctcg cgggcccagc tgcaactgca cttgcccgcc    240
aaccggttgc aggcggtgga gggaggggaa gtggtgcttc cagcgtggta canctttgcac    300
ggggaggtgt cttcatccca gccatgggag gtgccctttg tgatgtggtt cttcaaacag    360
aaagaaaagg aggatcaggt gttgtcctac atcaatgggg tcacaacaag caaacctgga    420
gtatccttgg tctactccat gccctcccgg aacctgtccc tgcggctgga gggtctccag    480
```

-continued

```
gagaaagact ctggccccta cagctgctcc gtgaatgtgc aagacaaaca aggcaaatct    540
aggggccaca gcatcaaaac cttagaactc aatgtactgg ttcctccagc tcctccatcc    600
tgccgtctcc agggtgtgcc ccatgtgggg gcaaacgtga ccctgagctg ccagtctcca    660
aggagtaagc ccgctgtcca ataccagtgg gatcggcagc ttccatcctt ccagactttc    720
tttgcaccag cattagatgt catccgtggg tctttaagcc tcaccaacct ttcgtcttcc    780
atggctggag tctatgtctg caaggcccac aatgaggtgg gcactgccaa tgtaatgtga    840
cgctggaagt gagcacaggg cctggagctg cagtggttgc tggagctgtt gtgggtaccc    900
tggttggact ggggttgctg gctgggctgg tcctcttgta ccaccgccgg ggcaaggccc    960
tggaggagcc agccaatgat atcaaggagg atgccattgc tccccggacc ctgccctggc   1020
ccaagagctc agacacaatc tccaagaatg ggaccctttc ctctgtcacc tccgcacgag   1080
ccctccggcc accccatggc cctcccaggc ctggtgcatt gacccccacg cccagtctct   1140
ccagccaggc cctgccctca ccaagactgc ccacgacaga tggggcccac cctcaaccaa   1200
tatcccccat ccctggtggg gtttcttcct ctggcttgag ccgcatgggt gctgtgcctg   1260
tgatggtgcc tgcccagagt caagctggct ctctggtatg atgaccccac cactcattgg   1320
ctaaaggatt tggggtctct ccttcctata rgggtcacct ctagcacaga ggcctgagtc   1380
atgggaaaga gtcacactcc tgacccttag tactctgccc ccacctctct ttactgtggg   1440
aaaaccatct cagtaagacc taagtgtcca ggagacagaa ggagaagagg aagtggatct   1500
ggaattggga ggagcctcca cccacccctg actcctcctt atgaagccag ctgctgaaat   1560
tagctactca ccaagagtga ggggcagaga cttccagtca ctgagtctcc caggcccccct  1620
tgatctgtac cccaccccta tctaacacca cccttggctc ccactccagc tccctgtatt   1680
gatataacct gtcaggctgg cttggttagg ttttactggg gcagaggata gggaatctct   1740
tattaaaact aacatgaaat atgtgttgtt ttcatttgca aatttaaata aagatacata   1800
atgtttgtat garaaaaaaa aaaaaaaaaa aaaaagggcg gccgctctag aggatccctc   1860
gaggggccca agcttacgcg tgcatgcgac gtcatagctc tctccctata gtgagtcgta   1920
ttataagcta gg                                                       1932
```

<210> SEQ ID NO 41
<211> LENGTH: 1430
<212> TYPE: DNA
<213> ORGANISM: Homo sapiens

<400> SEQUENCE: 41

```
aatttgaccc tacttccctc tcagtcctaa gggcctatct ttcatcacta ggttgaatta     60
tctcccatgt ttgatttgcc tctatctccc tatgggcttg caacaccatg acgggcacat    120
tgcaagtgca cttakacaaa tgagatcaga tgacctgggg aacgtggctt gtacacacct    180
ttctgtgttc tgtagcatca gctaagacct taaaatcagt aagaaagtat ctgtctctct    240
gttcacccat aggaagcagc ttcgtggtga gtgaagggag ctacctggac atctccgact    300
ggttaaaccc ggccaagctt tccctgtatt accagatcaa tgccacctcc ccatgggtga    360
gggacctctg tggacaaagg wcgacagatg cctgtgagca gctctgcgac ccagaaaccg    420
gtgagccatg ggagccggga tggggataga aggtgggaga ggctgggttg aaagaggcat    480
tgtgctccct ctacctaaag aaccatggrk tctgagccat tgacaagtgg ctgaataaga    540
aggcccatca atctaataaa cactaatgta tgtgctgcca ttgcctttca agggggggaaa    600
ttcttagaga gccacagact ctcagagtaa gaaaggacca cagagaacat ctggcctagc    660
```

-continued

```
tccagacaag caaaatgtct gcacttcaga tatccctgca ttcagagcct atcttcttgg    720
tactagctgg gtgatcttga gcaagacact gcttaccttt cagtacaaga gaatgaaaat    780
agcaccaacc cacaaaactg tcattaggat tgaatgagaa gctgtgtgga aatctcacag    840
catattcatt aattcactca acaggtattt ctttagtagc caggcatatt tttaggtatt    900
gggaagacag cagtgatcaa aatatgcaaa atctccaccc tcatgaagct tacatgctag    960
tggggtagac actaaacatg cactgtggaa tatggtagcc actagctaca tgtggcattt   1020
tattttaaat taattgaaat taaataaaag taaacattca ttttcccagt cataccaccc   1080
agatttcaag tgttccatag ccacacacta gcagctacat tgttgcacaa catagmtata   1140
gaatatcttc atcactctga aaatttctca tgggacagtg ctgcagtggt caaacaagca   1200
ggtaaattat atgactctgt taggtgatga tagatgccgg tgtaggggaa aagaatgatg   1260
tacaaagcat gtggagtgct aagctgggag tttgggtgga gtttcattat acagaaagtg   1320
gtcaggggag gcctctctga ggtaagagga tcacttgagc ctaggagttc gagtccagcc   1380
tggacaacat agcaagatct catctctaaa aaaaaaaaaa aagggcggcc              1430
```

<210> SEQ ID NO 42
<211> LENGTH: 1407
<212> TYPE: DNA
<213> ORGANISM: Homo sapiens
<220> FEATURE:
<221> NAME/KEY: SITE
<222> LOCATION: (353)
<223> OTHER INFORMATION: n equals a,t,g, or c

<400> SEQUENCE: 42

```
gcttaagatg aaaagttcct tttcttgtgt taatggatgg cacaactggc ataaaaggtc     60
attaaatgct aatagaccca cttgaggtat gctcgcttaa tggaggatta gagcaaaaca    120
gacttaaaag accaacatgc cagttgtgcc atcccttaag atgaaaagtt ccttttcttg    180
tgttaatgta caaagctttt cttttggcac tgacaactgt gttctacctg ggaattttga    240
atagccattt tcatggctgt gtgttgtgta acacaaatgt ttttaaatgg tattctcacc    300
cagtaggcca gctctccaaa cgttgcttag atgcttcaaa attagcatat ttnaagttta    360
ccagtataaa ataccaatgc aactactcta catagccaaa tgtttgtaaa tcacgtctta    420
ttttcctgak gtttttcact ccaccaaatc ttacaaatsr ttgaaagaaa tatattctaa    480
cagtacgcac tgaatagtga aaataattag acattttaag aaccagagcc atagaattat    540
tttaaattag tagaaaagag gagctatttc cgaatctata gaataaagta ccacctaaaa    600
ctgaatttta tcatataasc aagtaatacc tattagtcat acctaaattt ttcagcactt    660
cattcaatta aaatmcatga attttaaata ttttacatga tgtgaatagg catgataata    720
cttttagtat aaaatctaaa ctttttccat ttatcagaaa tgataaaatc cagttaccac    780
atatcacgtt tataaaatcc ttaattaaat gagtaacttc taaaatataa caatactaaa    840
tatcacactg cgatggaggt cccaaatatg tggtctatca ccactgaatt catgtaatag    900
ataagaaaaa aattagaggt ggatgtcttg ttttgtgtca tgaattacta aaatctctta    960
gtagttgtgg tatatttttg agtaaaatta ccatttccag atttgagttt gaagggcttt   1020
tatagtkgta ttttcctcct cactgttaat aatcataatc ctttttcagt attttagtgg   1080
cctgaacaac tggtttatct acaatctcaa atcctaagtg tataattatg tgcatgttca   1140
atacctcata taatacttgc tcaacagtat agtggtacca tggcattaag atggtgtttt   1200
```

-continued

```
tgttctacat atttttcaat atttattctt tctatgttga aattatatca ggctttaccg   1260

gttttttttag ttgtttaaat aagtaatatt ttcaaaagaa taaaataacc aatgatatct   1320

cttggaataa tctgtaaaac gtagttataa aattctattt tctacttaga aaaaaaaaaa   1380

aaaaaaaaaa aaaaaaaaag ggcggcc                                        1407
```

<210> SEQ ID NO 43
<211> LENGTH: 950
<212> TYPE: DNA
<213> ORGANISM: Homo sapiens

<400> SEQUENCE: 43

```
ggcacgaggt taccagcctg tttaattaca gcagacttcc cacttttctc ccacttagta     60

tttccaattt gctgcttcct gaaacctagg aagaattgaa aattgtctag agaataagca    120

tgccagattt gttaaatcag cgaccttatt ttatatatat ttctaagtca tggccatggg    180

catagaagct tcttttttaa ttaagaagga aaaataaaaa tatgtgaaaa gaaagccata    240

aaggtcattt tacacacatg taactccatg cacgaatgcc agtccttccc cttgtgtgtg    300

cacttgagac tagttctact actatccttc aaaacccaag tgcatgaatt ccatgaagtt    360

tttccccatt attctcattt taattttcct tctctgaaca actatgacat taatttatta    420

cttaatcatg aattatggca tacaactccc taattgatgt ttgtgggttt ttttctcccc    480

cagctagatt ttaatttcct tgaagacaga agccatgctc ttactgtgct agaatatctg    540

tctcccgtag ctcctgacac agtgctctgt gtatagaggg tgcttgttgg ctcaccaatt    600

tgttctttac accaaatgcc cagggaaatc ttacatagag tttataccag gcaagaaaag    660

gatatgctag attctccagc tgccaaagac tggaatgtca ctggtatcca gtcaccacaa    720

tctctaggtc cctcatttg ttcttggtga gaaaggagca ctaaggagat ttcgtccttg    780

aaaaggcaga aagcaagtgt agtatcatct tgccatctag cttggaaatt aacacttgat    840

cctaaattag gtaatcttcc cttcacatct cagagttttc caggcaacag acactcagta    900

cgaacaacaa caacaacaac aacaaaaata ccaaaaaaaa aaaaaaaaaa               950
```

<210> SEQ ID NO 44
<211> LENGTH: 1004
<212> TYPE: DNA
<213> ORGANISM: Homo sapiens

<400> SEQUENCE: 44

```
aattcggcac gagcagcatt ccacttgcaa ttggaagccg agagaaacca ttgtttatga     60

aakkaaagag gctkctcaga tgactgcaaa ccagccttcc ttactggttt tatcactggt    120

aatgttataa agacagttgt ccagtttcat gaatcttgta ggtttttgtt tgtttatttg    180

tttgcttttr atgttgttgt tgttgctgtt gttttccaaa ttcagtattg tagaaaaata    240

tgctgcccca gaagagatga ttggacactc tccagcgtgg tgttggactt tgtcatctct    300

tgcacagcca tctccagacc ttagtgttta cctcacgtta gtttttttata ttctgcaaag   360

acaaamccaa aataatccaa atttgacaca aatacctggg atacatctta tttgagatgt    420

ttaacaaatg tctggatcat cttttcttac attggattat aacgcaggaa acactgtgaa    480

gtaagtaaag ttggaattcc caagtcmaag accatttgaa tatttacaag tagatttgag    540

gcaggaataa tacagggtgg ccgcagggta acaaattcta ggcagcagat ttacatgact    600

tgaggctatg ggctgataag acgctgaaaa accagggtgt ggaccaagct ggctaagact    660

gactggaccc aatgtggtgc tagatttgag gtaggtttta cctaggccct cattatacac    720
```

-continued

```
ttattaacat actaaatcac acacccacca gtgccatgac agttctgaga ccaatatgtg     780
atgtaaaaat ggatggcacc acagttccga gaaatcacct ttacccagga attttcacga     840
atattccact ccttggttaa agaaacccat tgagatgaaa ccccagaacc cattgttctc     900
tctcgggtat gcccgaactc ccctttcttg agtgtgtact ttctgctttg caatacatct     960
cttctttcac tatttgctga ctcatccttg acttggttct cgag                     1004
```

<210> SEQ ID NO 45
<211> LENGTH: 1681
<212> TYPE: DNA
<213> ORGANISM: Homo sapiens

<400> SEQUENCE: 45

```
gaattcggca cgagtcgagt tttttattcc tccactgaga atcacacaaa aagttagaag      60
cacaaaaagt atgatgggta atgatttgct ccacctcgtg ttcttgcaac taagtttagg     120
tgtagcatca gggggatgga ttttgtggcc actgaggaga ttgggtggtg cccatacgag     180
taaggatmca aataaaaatg gmcacsytgt gcattgcttg gtcattacca atgagcctct     240
agtttccamc aagaagattg ggctctcttc tcctcacact tgtccatcaa ctctccaaca     300
gttttgatcc ccactgtaat taaactagta tcttctaaac acaaaatctt cactctacct     360
cagtagcgct tggcagctga aatcttttct atttagaata tcccaccttt ctatcttgaa     420
attttgtcca agctaaatgc ctcctactaa tctctgcgta cctgcgggaa cacaatgtgg     480
ctaccacatt ggctaccagg gctgtaggga ggattgtctc aaaatcctct ccatttatca     540
caraaaggga ggcgggaara ggaaraaagt aggttatgcc ctgaggctca aggctactgg     600
atggccaatc tgtgctaggt ttgctggtca gaaagtagga tgatatgagc tgatatagsa     660
gagaaatata gggtacagtt tctaccctga ggggctgtat tttagttggg gagatacatg     720
caatgactgg acaccaccac caaggataag gaagtcctgg gattgtgtga aagccacagc     780
agttcagaga ggagaaggaa aaagactcca tggaaatgat gggaattgaa ccaggcctgg     840
gttttccccc tctcaggcac actggaggct gtttgcctac cctgttgcat ctcttggctt     900
ttccaagttt ctgtcttgtt acagactctt tcctctcttc ctcctcctag aaatattggc     960
aagcttcttt agtcatttgt gtttctttac attacaggcc agaggtgtat cttctctgat    1020
agataatggc cctcagttaa gactagggaa agctattttg cttgctgtat tagcgcccta    1080
ttttagaata atcctattcc cttgattctt tagtatttac aatttttcta agtaccgatt    1140
atattttcta agtcaaagtg gggtaaaatt agtgcattgt atcctgttgt tgccgctttc    1200
tggagtagtc agtcttacat atttgaacaa taccaccctg gtgtaatttt aaaaagtaag    1260
agcttgattc tttaaaaaac acttagccag gcagtgtgag ctctctctga ggatcctcac    1320
attaggagtg ttttacatac atcacacaaa aggaaaatgc gttctgaggg gatcggggct    1380
cctccgagct gagagctgga cctgatgaat tgtgacaaat gggcctgttt ctgccagctg    1440
cacgttctca gccaggtgac gtctgaggct gcctgccagt aatggtttgt ggtttgggga    1500
gcaagaggga ggccctggac atactcactg gtggggaaca ggaaaaagtc aggcccaatc    1560
agaaatagta actctcctca gtgttcccca gctaagtaag actatgcatt taccatacag    1620
tccccatcct aaaactcatg aaatgaagaa ttagtgacac actgggggag tagtggctcg    1680
a                                                                    1681
```

<210> SEQ ID NO 46

-continued

<211> LENGTH: 1361
<212> TYPE: DNA
<213> ORGANISM: Homo sapiens

<400> SEQUENCE: 46
ggcacgaggg agaactgctt taattagcct aggtgaaaag tagtcctagc agtgtaaata 60
tgtataatta gagttttcta atttcactgt gagatctcta acttttgagt ggcaaacaga 120
tcaagtcttt tgctcataga cttttctgtg gggttattaa aatgcaaaag ctttattttt 180
ttaataatgc catactccat tagtgtcaga tgatggtatg gaatttgttc ccttgctttc 240
ccccactgtt actgcttcag tttatagatt gccagcagag ttcagaaata gagcagggat 300
ttacccgttc tttgcttgga catcccattt tcttttgtcc agacccatgt tggcaatcat 360
gtatgaactg tgttatactt tcagtgcttt ctttttcttt tttgataaga tggatatcaa 420
aaatagttgc tgtgcaaaag ttagagtctt cttcaagaag aaaaccaatt ctttttctaa 480
taatatcctg tgaaattgct tcattcattc atttattttt aagccaaatg tcagcagagt 540
gctgctgctt ttatctagta attttgatat gtaagtatta atgcattttt aaaagatgtc 600
tacattgaaa catgttcttc ccagtgtcct gcttatgatg ctttgttcag attttttgta 660
agagaccagt tagtacactg ggggtgtata ttgtgtacat gtgtcatttt agttaggcat 720
gtaggccaaa tgtgattata aatgaagttg atgaacatta attttgttat tagtgagttt 780
tttgaattgt aaatggattt ccagtttacc ttctgttgtc tacagctttt ttaattttaa 840
ggtttgacta attgtatcca tctcattgta cagtgtttta gttgcaagca gaaagtagaa 900
tttggtataa agcaggttat ttctatattg aaaggagtac agttgaaatt gtagatttaa 960
gattgttaaa atcatgacaa ttctaacttg tctattctaa cctattgtgt acaatctgat 1020
tttttaaaat tgtaaacatg tatgatcttg gtttcatgtg tttttgaaag tgttattgtt 1080
taaaaaatga aaaaagcata tctgctaaag agctgtcagt tttcattact gactctgtaa 1140
aatacactgt tctttgtgta ctgtgtgtta ttttgccagc tgctgcatta gccttcaaaa 1200
gtatttggaa acttaagatg aactacattt cttgcaaagt acattccttt ctgtggtatt 1260
ttgtcctgta actgaagtat agtaattatt ttatggaaat gttagcaatt ctgtaccaac 1320
tttgaataaa atgaaaaatt tataaaaaaa aaaaaaaaaa a 1361

<210> SEQ ID NO 47
<211> LENGTH: 1137
<212> TYPE: DNA
<213> ORGANISM: Homo sapiens

<400> SEQUENCE: 47
gggctttttg tcaacctgaa gcacgttcta agtcgatggt agaaagtgga cacccccaga 60
agacactttt gcccagaaat ctctttcttc ctgacccctc ttccccagag tgcccggaat 120
tccactgtca gaaatgcatt gtctgggtta aaaaacttaa cacctgctat gatttcaaca 180
gtgtcaaaac aggatacgtc aaaactgggc gaggaggaaa tgtatttggg ttctaggata 240
gtgaaagctc tattttttct acttttctgt attttccata tttggtacaa tgagcacgta 300
cttagaacgg ttttagattt acgaaaatat gcaaacacag tacagatagt tcttgcgtcc 360
cccatgccta gttcctctat tgctaacgtc tcaacgttag tgtggtgcgt ttgttgcaat 420
gggtgaatga atattcgtgg gctgttatta aagtcagtgc ttcaccccta tttccccagc 480
tttcctctta catccttttc tgttccaaga tgcatccagg atgccgcgtt acattagtct 540
tcacacttcc ttaggttcct cttggtatga tggtttctca gatttttctt gtttttgata 600

-continued atcttgacag ttcgaggagt atttgtcagg cattttgtca aatgttcttc aactggggtc 660
tctggtggtt ttctcatgat tagtctggga atgtgctttt gggaggaaga ccacagagat 720
gatgtgccag tctcagaaca tcgtactaag aaaaggttct gccaacttga cttaccactg 780
ttgctggtga ctttgagccc ccggctgagg ttactccttt gtaaagttac tctttttttc 840
tcctttccat gctgtatgtt ttagaaggaa gtcactatgc tgctccaagc aactcaagtt 900
tgatgaatgg ggagttccgc cccacctcct tgagggcaga gtagctacat aaattacttg 960
gaatttctca aggagatttg tctgtactcc cagtttatta tataaataaa tgatttattt 1020
atattacagg gacccaggga tctttactgt atgctttggg ttataatcca atggtacttt 1080
actttgtggc tcaagtatac tacttttaaa ttggaaaaaa aaaaaaaaaa aactcga 1137

<210> SEQ ID NO 48
<211> LENGTH: 2763
<212> TYPE: DNA
<213> ORGANISM: Homo sapiens

<400> SEQUENCE: 48
agagtttgac cctggaaagg tgctttgtat atgttctttt cacatagtgc ccagcttgca 60
tgaaatgtac agagaaatgt gtggtcgtat tttttacttt tgtcttgtat atgtatgtat 120
attgggtcct ctgggcagta gaggcaaagc tcacctccca tgtagcacat gaaatgcttg 180
tgagttgttg acattggaca ggtgaacagt agggcattac atttgtgtga attaaatgtg 240
aacttctgta ttacgttgcg gcgtcggcag tcctgcgttc cctggagtaa ctgtacgtat 300
ctgcctttgc tgggaagact gyggggctgc ctgtgttggc tggcgaccag caggattgct 360
ccaggatttt gtgtttacct cgcgtgaagt tcagcacgtg ctgtcgtgta gtcagcttct 420
actctaattt ctgttacagt tctgcaaagg taacctggag tttagaagtt aaaaaaaagc 480
atgggatgtt ggatttgcac catttggagt ttctttaggg aagaaaagtt ttctgctttt 540
ttatagaaaa tcatttcagt ctcccgaggt ctcatgctag caaattttga aataggattc 600
taatcactga tttcaaatat taagcaaaat gtaaagcact ttaatttata gctatggtta 660
taaacaggtt ttagatgttt caaatgactt gtccactgaa tgtcacttga ccttgataag 720
aggccgcctg cacacagagc ccagttaatt ctccgcacct cggttgtgtg cttccgaatg 780
ggctcactcc cgtggtggtg tttgagagcc aacaacacta cctcagagac gggtctttgg 840
gaaactttgg gtctcactgt tgcctggctg gagcactttg gtttatagct ggaatactga 900
gttcagttca gaaggcagga aagacagtca caccgacgtg tcctgaaggt gtaggctctc 960
cacttaggcg cacaagctga cggctgcagc cagcaggccc cggtgacgag acacttccag 1020
gtcttgtggt ggggacgcct ctcagtgcca gtcccgccac tgctgagtga gcctggtgtt 1080
cttgccttct tggaaattac tgctcacctg gtatctgtac gttaatgttt cttgctgagt 1140
tacagttttg ataaagaggc tctcatttcc tgtgtcttgt atattcagtc ctttcaatac 1200
gtccacctgg aggctcacca cttggagaga cacaggaagg taatatttac agctgtcatg 1260
tgacatcccc aggtctttgt gttttgccct gttttacggt gaggtaggag ggaacccatc 1320
tggggaccgg taggtgcagg tgcagtagga cgtgggactt ttggacccgt cctttggtgc 1380
agctcgccag ggatgagagg cacctcccta cttgggtctt caggagctgg tccaaggagc 1440
ttcgaatcta agtcatctag aatgaccctg aaatgactga cagccccggg cccaagaaaa 1500
acccataacc acctcagatg gatctgacgt ggctaaggga caaacagcaa atatttcagt 1560

-continued cattttgatt ttacaaataa aaaatgtgtt gtgtttttgt ccgacattat ttcctgactg 1620
cactgttctg agaatggagt ccacctggtc cctctggttg attagaatct caggtttcag 1680
ctcctgctgt cctgagcgaa cttgcctgat gcagggctgt gctgtgtcca gatgttgctg 1740
gggcctcact ttttctcttg gctggaggtc caattgccag agcctcccac actgcacata 1800
caaaggtytg agcccagggc agcttctggg gccactgcac aggccacctg cttgggttcc 1860
tcggagttta atttgaaagt ctgggtgtct taggatgatg gttaggaaca ttgaaaaatg 1920
gctgcaaata gccaaatcaa acttaagaac cagatctctg ccagattaaa catttttgaa 1980
gcttttaaaa gtcaatattc ctagtggcca ctgagttcca ggcacactgg tgccctttac 2040
tgccacagct gctcaccttg tctggcaaac tggagggacc tcagaaactg gactcctgca 2100
tgtccttggg ggcgcagccc tgtggtgctc aggcagagct ctcaggagcc ggggcacctt 2160
gctgttcgct gctgtgtcgt cttctaatgt gagctcatcc actgctgctg cagcgtggtg 2220
atcaggagtc acagacaaga tcggggatgg tgtgtgtgtg tgtgtgtgtg tgtgtgcacg 2280
tgtgtgtggc taaattaagt catactgtca accacacgtg atctcgtctg aaacagtgtt 2340
tggaagtggg aacagttttg tcctgtatgc tgatgtgtcc agaatttcat ttaatgatag 2400
acggaaaatg tgtggttact gaaaactgta tatgatacag aatttcataa gagccatgct 2460
gttgggcaaa gcaactcttt ttcaaccact gctcatcagt ttctgtagag acaaaaactc 2520
tgtacatatt ttggaatctg aagaatccta tgtaaatcat ttgttactta agtctgtgaa 2580
aaacatattt ctttggagga aaatgtatgc atttataagt gttccatgga atcagttttt 2640
attgtatcga tataattgtc tctaagtgtt gactgtcttc attgcaatat gaaattcatt 2700
aaaatgtcca tgttccataa ttactattat aaaaaaaaaa aaaaaaaaaa aaagggcggc 2760
cgc 2763

<210> SEQ ID NO 49
<211> LENGTH: 1348
<212> TYPE: DNA
<213> ORGANISM: Homo sapiens

<400> SEQUENCE: 49
gttaaaaaac atgtaaaacc gtatttatct tcgaattaca gtgttatgtg tttgaatggt 60
tttagatgtt aaaaagtagc aaattgaaac ttaatgttta aagtctttgt taattgaaaa 120
attgatcttc aatagtggta ctatttgcag tatgattcgt tcctttaatg tacatacgta 180
tatattagta catacgagag tgatgttaga cctgtagaaa tgaaggtgtt gttttaattg 240
aaaacattta tgtttatttt gctgatagtg tttgtatttt caaaaagtaa acaagttctg 300
tcaatatgtt tgaaaatttt taaagttgag ataaatagca tctcattttg taaaaataaa 360
aaatataaag atttaccata tgcgtttgca tcagaaaaga ctggaaggac atactcaaat 420
gtcaacaatg attatctctg aatatgggat tatgggcaga tttttatatt ctttttactt 480
atctgtattt tcaaaaactt ctacagtaag tgaactgcat ttataatact gttttaaaag 540
attgaaccac caaagataga ggttattaaa aattatatcc ctactcacat gattatagta 600
attggattat ttttggattt caagaaacat tagtattagt ttaagagaat gttgctatat 660
gtaaagcatt gtactaaaaa ctatgggaga tatacagaag gaaaagatag cttactttca 720
aggaagctgt atttcaaaaa atgtgtgtag aaagtgccag agtggcaagg aaatttgctc 780
accagttatc ccactcctta atacagtttc ctggcaaatc tttgtttctt tcttagacta 840
atacttggag acctatgtct ccttgtactc ttctttcaaa tctaactttg ttttttttaat 900

-continued

```
ggatcatgaa agataaattt ctgtaattga tgttttattc atagcatgaa gattttcctc    960

taaactgttt cttccttttc tggtaatcat ttacagtggt ctttatgtta caatttgaaa   1020

cacagtagaa gtacaaaaat atggccaggc gcggcggctc acgcctataa tcccagcact   1080

ttgggaggcc aacgtgggtg gatcacttga gctggggagt tcaagaccag cttggtcaac   1140

atggtgaaac cctgtctcta ctaaaaatac gaaaattagt cgggcgtggt ggcacatgcc   1200

tgtaatccca gctgcttggg aggctgaggc acgagaatcg cttgaacatg ggaggtggag   1260

gttgcagtga gccaaggttg caccactgca ctccagccta ggcaaccaag cgagactttg   1320

tctcaaaaaa aaaaaaaaaa aaaaaaaa                                      1348
```

<210> SEQ ID NO 50
<211> LENGTH: 1264
<212> TYPE: DNA
<213> ORGANISM: Homo sapiens

<400> SEQUENCE: 50

```
gacccacgcg tccgcccacg cgtccgcttt cattcacatt cacaaagcaa acatctagta     60

catgtctttc acttcacttt atgatagtgt attggatgat ttgggcatta cgatcacctc    120

ttaccacagc acagaacata cattcttcaa cagcattaac ggagtttgcc aagtgcatta    180

aagaggtcac gtggagggta cgttcatatg aaacaatctg cagaaagtgg ggtaagaaag    240

ggcacatggc acagttaaag ttgtagaaat caaattacta tcattttttg ttgccaaaac    300

aaagtcttac atttaacccc cctttctacc acccccctcc acacttcacg tcagctacat    360

agtttccaca gggtaattca ctaagagctt gtggagcttg gttttaaaat ccttagcctg    420

gtctgacttt aggcatagct tcagttcttc ttccgtgtcc tggtttcttg ttcagtttta    480

cttctaatcc accaccaaaa gaaatgtctg gctggtctca gctagagtct atgtgtctta    540

gagcatgtgt gcgtatctga ccatcatccc tgctctcatc tcagctccct ccaggctgag    600

caccggttcc ttttgtccca tacgtcatga agtccactat tgggaaacct gtgcttccct    660

ctccatggct taactccctg tcagtgtcgg agtgtataag aatgcttgta aatactgtaa    720

tatatttatt aatatttgaa aggcattcat tcagtggaca gtgggaatta actctcccaa    780

ggcaagtgaa aatgaatgat tgacgtacgt tgatttaaca atcttactag attttaattc    840

ttaaggattt caaatgaaac cagaaggtgg ttatgtaaga ggcttaaaat gatcttatgt    900

ttaaagagat tctgttatta gcaccatgaa ctcgtactat gaaattttta agccttttat    960

ttttctaact atattactgt aggactggat attaggtgtc atataggaag cacaaaagtt   1020

tattgctgtt tgctaaagca aaatagcaga aaattttgta tatgcaaaac tgttgaagga   1080

ccatagagaa tgtgtactac tgcggggctt ttactaggct tcctgcgtgt gtaaaagtcg   1140

aggtattgct ggcattcagg gtgacatgat ggtactaaat gttttccatt aaagtcttct   1200

attttaaaat ttagagaaaa ataaaatggc tttccatcag aaaaaaaaaa aaaaaaaaaa   1260

aaaa                                                                1264
```

<210> SEQ ID NO 51
<211> LENGTH: 1660
<212> TYPE: DNA
<213> ORGANISM: Homo sapiens

<400> SEQUENCE: 51

```
acccacgcgt ccgtatacat atctattagt atagtatctc ttgaatgcga ttttttctag     60
```

-continued

```
aatgtgttct gctgatttgt tttagagcca tgagtgcaat ttatacacat acatctattg    120

ggaatgctca gaagttgttt actgatggaa gtgccttcag aagagtccgg gaaccacttc    180

ctaaggaagg aaagagctgg ccacagttag agcaagcctg cctggggccc tgctctgtgt    240

tccagctgca aactgcctgc atcatccctt cctgttactc ttccttcacc tgagacagtc    300

gaggccacag cgtcagccag ggccagagct gggatttgaa cccaggcact cgggctccag    360

agccacactg ccccagtgtg gggcttagtg gcggctcctg gccctgactg aggggctgac    420

tgaagcctgg tgagagcgtg ctgggtcagc ctctccctgg cgggaatcct ctccgtccag    480

tcttctaacc tagcagcctc acgtccacag agctgccttg tgaaactcag cagagccctg    540

gcttcctgca gagccgtgtt ctcccagcct gcttcatggc tccctggttg agccaagctt    600

gcggatccgt ggggtgaagg tacccgcacc gcctgggcct tagtggtatg tacgggcctg    660

catcgtgagc agcgggcggg ggcccaggca ggtgaggcag ctggccacaa gggcagggcc    720

cggcccccct cccaaggctg tgtctsatat tcttgagcct gttcgagttt ccttttccaa    780

gcctcctgtt ctcccacccc camccctgcc atgctgcagt gactaaatct gtggttctca    840

tccttggaga acacctgagt agctgctaca agctggccac agcccagcga ctctgatgtg    900

gttgggctgg gtgtggccag cagccagggc atcgggactt ttcgaagctc ccaggtgact    960

caccggcagc tggggatgag aactgtcagg agggaaggtc agaagtccca ggatgcactt   1020

gaaaagcctc tagctccacc agtgaccagc tcctggctgg actcctggtc tggactcagc   1080

atcagggagg ctctggcctc tcgccctcag gctgggggct tcttcacatg gtcatcaaag   1140

acttggccag ttccgcctct cccacggccg tccttgtctc acccagcatc acgacgcatc   1200

agttcaccaa caaacacgat tcagtgctgc tagtgctggg tcctgttctg ggggctggtg   1260

atgaggccaa gagggaaaga gggagctctg tgttccatcg agggggcgac aagcctggac   1320

cagatgaaag tgactcatgt tgttaattag cggcttaggg ccaaaggtgg cccctggacc   1380

agtggcctca gcatcacctg ggaaaaggtt agaaatgaac attcccaggc cccacctcag   1440

cctcctgaat cagagcatcc ctttggcaaa ccatactgag aaacaaccac gtgcatcacc   1500

aagcgctgtg aagaaggcaa gctttgagac cttgaaggaa tcatcaaact ctgggcctcg   1560

gtgtgctcac ccagggcgag acaaagacgc catgctcctc caagtggcct ccaagattaa   1620

atgagcaatg acttttaaaa aaaaaaaaaa aaaactcgag                          1660
```

<210> SEQ ID NO 52
<211> LENGTH: 1678
<212> TYPE: DNA
<213> ORGANISM: Homo sapiens

<400> SEQUENCE: 52

```
aattcggcac gagccaagct gcactattgg gaatggattg tggctgaaca gcaaatcaaa     60

acaccagaaa tatttttata tgttaacgtc atattatgtt aatgttgctg aaaacaaaac    120

ctaacaaacc ttgatgtacc agtccaatac catgtagcgc tgagtgataa agttaaaatg    180

tgctgtgctt cccacccttg tcagagggaa gggtggctat gtgttatttt cactgtcttt    240

ttgaaagtta cagtatgtgt tttcactttc gtgcagataa ctggaagtaa agcggcaaac    300

agtgctatta catgctaaag ttaccttctc tttgtttttt gcatatctgg aattacacct    360

ttaaagactg atatgaatca gtacggtcac tatacatttt atgatttttc tgtcatctta    420

aaattgtatg atcgtaacat tatttattac cacaaaacag caaaatcttc aatgtctaag    480

aaaactagct taaaatgttt aaatatagtt ctgattgggt attaattact tgattaagaa    540
```

-continued

```
aaaattaaca ttatagatac tctggcatta cgcttctata ccttttaggt cttccttgca    600
atactggaac ataattcttt tgtgtagctc actattagcc agctaagttc atctttttaa    660
taccataaaa aggttatatg tacagttcct attttagctt gcttacaaag ggagcattat    720
ttttatttaa agtattgcta gtaaatgatt tgtagaaact tggttttcta agcatagttc    780
ttccataacc accttttgtt gtttgagcac aagggattct tttcctagtt ctatgtgttt    840
gtttccctat atgcagtctt taaaggatta caacacttaa aattgaatgg acttgtgtca    900
agctttttgc atcatacatt ttttgaaaga tttttaaaaa agcctacaac ttacatatgt    960
agtagaatca gccattgctc tgctcctggc atagagtcac ctgttatgtg gattaaatag   1020
ttttaaaata catatttgaa gmcctttgag aatgctttag tgtttgattt gaaataaaag   1080
gaaattttag caaggattaa agaaaaaagc tatcagctgt atgttaagag agactcttac   1140
taacatgttg taaatattac aattcatgaa atgttattgt aagtctgtaa cttaattttt   1200
tccctgtttt agttatacag gttggtttgg aaatttgtgt tttggcataa acaagtaaaa   1260
tgtgcccatt ttatggkttc catgcttttg taatcctaaa aatattaatg tctagttgtt   1320
ctatattata accacatttg cgctctatgc aagcccttgg aacagaacat actcatcttc   1380
atgtaggacc tatgaaaatt gtctattttt atctatatat ttaaagtttt ctaaaaatga   1440
taaaaggtta ttacgaattt tgttgtacaa aatctgtaca aaaatctgtt tttacatcat   1500
aatgcaagaa ttggaaattt ttctatggta gcctagttat ttgagcctgg tttcaatgtg   1560
agaaccacgt ttactgttat tgtatttaat tttcttttcc ttttcaacaa tctcctaata   1620
aaactgtctg aaatctccct gtgactttaa aaaaaaaaaa aaaaaaaaaa aactcgag     1678
```

<210> SEQ ID NO 53
<211> LENGTH: 1860
<212> TYPE: DNA
<213> ORGANISM: Homo sapiens
<220> FEATURE:
<221> NAME/KEY: SITE
<222> LOCATION: (912)
<223> OTHER INFORMATION: n equals a,t,g, or c

<400> SEQUENCE: 53

```
cctagctgtc cccctgagat gaagaaagag ctccctgttg acagctgcct gccccgctca     60
ctcgagcttc accctcagaa gatggatccc aagagacagc acattcagct cctgagcagc    120
ctgactgagt gcctgacggt ggaccccctc agtgccagcg tctggaggca gctgtaccct    180
aagcacctgt cacagtccag ccttctgctg kagcacttgc tcagctcctg ggagcagatt    240
cccaagaagg tacagaagtc tttgcaagaa accattcagt ccctcaagct taccaaccag    300
gagctgctga ggaagggtag cagtaacaac caggatgtcg tcacctgtga catggcctgc    360
aagggcctgt tgcagcaggt tcagggtcct cggctgccct ggacgcggct cctcctgttg    420
ctgctggtct tcgctgtagg cttcctgtgc catgacctgc cggtcacaca gctccttcca    480
ggctggctgg gggagacact gccgctctgg ggctcccacc tgctcaccgt ggtgcggccc    540
agcttgcagc tggcctgggc tcacaccaat gccacagtca gcttcctttc tgcccactgt    600
gcctctcacc ttgcgtggtt tggtgacagt ctcaccagtc tctctcagag gctacagatc    660
cagctccccg attccgtgaa tcagctactc cgctatctga gagagctgcc cctgcttttc    720
caccagaatg tgctgctgcc actgtggcac ctcttgcttg aggccctggc ctgggcccag    780
gagcactgcc atgaggcatg cagaggtgag gtgacctggg actgcatgaa gacacagctc    840
```

-continued

```
agtgaggctg tccactggac ctggctttgc tacaggacat tacagtggct ttcttggact    900

gggcacttgc cntgatatcc cagcagtagg ccctgccttc ctggccactg atttctgcat    960

gggtagacca tccaagactg cagcgggtag aaggtggcag ttcttcatgg gagtcttttt   1020

aacttggtgc ctgagttctc tcctaggcaa gtggccagtt gcctccacct cagttcttcc   1080

atctttggtg gggacagggc ccagcagcat ctcagcctcc tacccacaat tccactgaac   1140

acttttctgg ccctactgca catggccccc agcctccatc cttgtgctgg tagcctctca   1200

caactccgcc cttgccctct gccttccact tccttccatc tcatttctaa accccaaaca   1260

gctcatctct aaaaagatag aactcccagc aggtggcttc tgtgttcttc tgacaaatga   1320

ttcctgcttc tccagacttt agcagcctcc tgttcccatt cttggtcaca gctctagcca   1380

cagcagaagg aaaggggctt ccagaagaat atagcaccgc attgggaaac agcagcctca   1440

cctccacctg aagcctgggt gtggctgtca gtggacatgg ggagctggat ggaaatgcct   1500

ctcacttcaa aatgcccagc ctgccccaaa tgcctctaag cccctccctg tcccctccct   1560

tgtagtccta cttcttccaa ctttccattc cccatcatgc tgggggtctt ggtcacaagg   1620

ctcagcttct ctccactgtc catccctcct atcatctgta gagcagagca caggcagttg   1680

tgtgccttgg gcccagggaa ccctccatca acctgagaca ggactcagta tatggttctt   1740

gggtatgccc taccaggtgg aataaaggac acagatttga tttctaraaa aaaaaaaaaa   1800

aaaaaaaaaa aaaaaaaaaa aaaaaaaaaa aaaaaaaaaa aaaaaaaaaa aaaaaaaaaa   1860
```

<210> SEQ ID NO 54
<211> LENGTH: 1663
<212> TYPE: DNA
<213> ORGANISM: Homo sapiens
<220> FEATURE:
<221> NAME/KEY: SITE
<222> LOCATION: (975)
<223> OTHER INFORMATION: n equals a,t,g, or c

<400> SEQUENCE: 54

```
aattcggcag agttttctga tcagactctt tttattgttt tgttttttat aaacaagtct     60

caggtggaaa aagaaagaaa gggaggagct agctctctgc cttctcagcc aattgaaatc    120

gtggaaacca atgggcttca gctagcccca ctcatcactg ctgggggga aaagacatcc     180

ctactcccct tccccgtggc actcatgata ttctcaatgc cccaacaagg gtcatcttgg    240

ttcctctcgg cgtttctgtc ctggcctttg gctctggctc cggctctgac tccgactccg    300

gctccggcca gggccccggg agcccctaga gctgctggag cccctggaag agttgctgcc    360

ggccgtggaa catgtgctgg tgccctggcc ccgggacagg aagcttggtc tgctgtatgg    420

gagccaggcc tcttcatctg ggtggagcac ccgctgggct gccaggggca cggcctggac    480

cgctttcctc tccccactgc gctcccgctc cagggaggac atgctgcctg ctgccctcag    540

ctctagggcc cagctcgcct cttcctctgg cggtggcaag ggtggtgggg gcaagtcccc    600

aggactgttc tccctcctgt agggaagagc cttgggtttc ttccggaatc gagcacgggg    660

tccttgaagt gggggagtca tctccccatt cccctgccag gttctgcctg ggcactgct     720

ggctgtgcta ggggcaggac tggggctgag gtggggtgag gctgcagggc cagcacccaa    780

gccagcaggc ctcgcttcac ggatgcccag catgggctgg gatacactga gaggggaact    840

cggcccaagg ggcaccytcc tgggcatctg atggagatgg ggcatgtcag ttgggggctg    900

gggagggtca ggaggtgagg gtgtaagagt ggctgtggac tgctgtccat aggaaggtgt    960

gggagagggg gtttnccttc gggatggggt gaccaggcac cctccactgg agctgggctc   1020
```

-continued

```
cgtcaggtga cttctctcag gcattggcgg gcaccactcc tctggctctg agctgccctc   1080

cagctcctcc tccggccctt ctaggcagct cagttcacaa gaaggaggag gtgggggcag   1140

ggcttctggc cagttcagag agggcatctg cacaggtttc cccagaagct tcactttgcc   1200

tcccttggct ccactgtccc cctggctcca ctctggagga gcgtactggc tccagggacc   1260

cagatctcct gagggatgtt gggggaagcc cccatggaag gtctgcagct cctcccccgc   1320

tgggtcaatg gtgctataga caggaccctc gccaggggcg gccgtgcccc tggccgtctg   1380

agctagatac agggagattc ccgcttcgtt gtaatatctg tcgtccgggt caggattgct   1440

agggcagcag cttcccctgg gttcctgggc cgaggggctt cgagatgggt ggggccacga   1500

atctgccagc catgagtagg gggctttccg tcctcgaact tgccccttct ttatggagat   1560

ggttgcaaag cctggcctcc tcgtggcgtc ttagaggcaa acgtcatcca gatcccgccc   1620

cgtcttggcc cgcagccctc cctagtcctg gcagctcctc gag                     1663
```

<210> SEQ ID NO 55
<211> LENGTH: 1632
<212> TYPE: DNA
<213> ORGANISM: Homo sapiens

<400> SEQUENCE: 55

```
cccgccccgc ggcgcattgt gggatctgtc ggcttgtcag gtggtggagg aaaaggcgct     60

ccgtcatggg gatccagacg agccccgtcc tgctggcctc cctgggggtg gggctggtca    120

ctctgctcgg cctggctgtg ggctcctact tggttcggag gtcccgccgg cctcaggtca    180

ctctcctgga ccccaatgaa aagtacctgc tacgactgct agacaagacg actgtgagcc    240

accacactct ggggctgcct gtgggcaaac atatctacct ctccacccga attgatggca    300

gcctggtcat caggccatac actcctgtca ccagtgatga ggatcaaggc tatgtggatc    360

ttgtcatcaa ggtctacctg aagggtgtgc accccaaatt tcctgaggga gggaagatgt    420

ctcagtacct ggatagcctg aaggttgggg atgtggtgga gtttcggggg ccaagcgggt    480

tgctcactta cactggaaaa gggcatttta acattcagcc caacaagaaa tctccaccag    540

aaccccgagt ggcgaagaaa ctgggaatga ttgccggcgg gacaggaatc accccaatgc    600

tacagctgat ccgggccatc ctgaaagtcc ctgaagatcc aacccagtgc tttctgcttt    660

ttgccaacca gacagaaaag gatatcatct tgcgggagga cttagaggaa ctgcaggccc    720

gctatcccaa tcgctttaag ctctggttca ctctggatca tcccccaaaa gattgggcct    780

acagcaaggg ctttgtgact gccgacatga tccgggaaca cctgcccgct ccaggggatg    840

atgtgctggt actgctttgt gggccacccc caatggtgca gctggcctgc catcccaact    900

tggacaaact gggctactca caaaagatgc gattcaccta ctgagcatcc tccagcttcc    960

ctggtgctgt tcgctgcagt tgttccccat cagtactcaa gcactataag ccttagattc   1020

ctttcctcag agtttcaggt tttttcagtt acatctagag ctgaaatctg gatagtacct   1080

gcaggaacaa tattcctgta gccatggaag agggccaagg ctcagtcact ccttggatgg   1140

cctcctaaat ctccccgtgg caacaggtcc aggagaggcc catggagcag tctcttccat   1200

ggagtaagaa ggaagggagc atgtacgctt ggtccaagat tggctagttc cttgatagca   1260

tcttactctc accttctttg tgtctgtgat gaaaggaaca gtctgtgcaa tgggttttac   1320

ttaaacttca ctgttcaacc tatgagcaaa tctgtatgtg tgagtataag ttgagcatag   1380

catacttcca gaggtggtct tatggagatg gcaagaaagg aggaaatgat ttcttcagat   1440
```

-continued

```
ctcaaaggag tctgaaatat catatttctg tgtgtgtctc tctcagcccc tgcccaggct   1500

agagggaaac agctactgat aatcgaaaac tgctgtttgt ggcaggaacc cctggctgtg   1560

caaataaawr kgctgaggcc cctgtgtgat attgaaaaaa aaaaaaaaaa aaaaaaaaaa   1620

aaaaaactcg ag                                                       1632
```

<210> SEQ ID NO 56
<211> LENGTH: 2233
<212> TYPE: DNA
<213> ORGANISM: Homo sapiens

<400> SEQUENCE: 56

```
ggcacgagct tgatttgata tggtaagcag taatatttaa aatggtgatg gtattcttct     60

taacattttc tggctcccac ggatgtgttc cgacatctca gccctggaag gatgctgaag    120

accaggttgg gtgtgtccat gccgtagctt gggtgaactc agctctttac acagtcctct    180

gccccttct gggaaagccc aaatgttcat tctcatttga taggaacgag agtgaggatt     240

tgaataagca ggaggttaag tgcagggcag tgcctgtctc tgtgtcgagc tcaatgttgt    300

aattgtgctg tgtaaaaggc ctgtgtggtg aacaagggtg agctcactcc agggaggaga    360

aggactgtta gaagactttt gtggcacctg acagccctgt ggggtcagct tattctctcg    420

taccctgaac aacttggtcc taaggcctag tagagatttg aaggaagaaa gcaacccagt    480

cctcaactct gcttttttta gaatgaagaa cagactagca aaatagcatt gccatacatc    540

tcaaggcaga gagatgcgac agggattgga agccaggtaa ttggtcagga aacattctgg    600

agacaaattt ggggaccaag actcaaggat tgggaaggac aaggaaatag gatctaggtg    660

gtctaccgtc taggcctgtt ggttctccct tctccatgat agttagtggg gaaatcccac    720

gtaaggaaag cacgggtagt aagaaacttg ggaacaaata acacctagaa actgaggcag    780

caagatgcac cttagtctag gaagccttct tgaaagaggg gagtctctgg taagaatttg    840

aaagaaaaga aatatggctt gcttagcaag aatataagaa aggctttgag gaagaaaaga    900

tagccagtga gtgccaagca tctggttggg cttgagggtg agcacaaaca ggaagcaacc    960

cggccagccc ctctgtgttt ctgccacagt caaacagtgc tcaaggaata tgaatacggc   1020

tgtcctgatt gtgaaagaag agaggggccc gaggcaaagg aagctggcag gcagctcctg   1080

ctgatcctcc agatgctagt tgataaaggc ccaatttcaa atgaaggttt tgaaagcaaa   1140

aggacagtag gaacccggag gcagggaatg aatcacagga cttgggagcg ggtgtggggt   1200

gaacctgaaa ttgagacagg attaaaaacg acctgtctga gatgggacag gggctggctt   1260

gtttcacgga cttcaatgct tctggcagca atggggaaat tgggcaggct ggctatcata   1320

ggaggctggg cacagaccct gagcccaggg gatggtacat tgagtagcca gtggccccgg   1380

gtgaaagttc tgcagccaaa aacaactggg ggatgaggaa aaaaggaaaa attcaattct   1440

agtctctccc attaagcccc cttcccaatt tgaagactgg cccaagaggc cttcgggaat   1500

acccctcctg tcttccaccc ttctcatcac ttccctgtcc cttctctgtc ctttccccca   1560

actctccccc tcaagcccag tctcgttgtc accaaggctt ctaggtgatt agagaatccc   1620

acctcatctc cacctggaac cctccctcca cttctgcact cctagggata aaccgttgca   1680

cacccctgcc ccacctggaa gggcctacag ggtctccagt gaaaaacctg tgaactgttg   1740

aacctcctgt ttggtggcat attattttga tttttggtga ctttttcttg gaataagtca   1800

acaaatatta accaagtgcc taccacatgc caagcgctgc tctaggtata cagtggtgag   1860

caaagttggg ttgagttttt caatagaaaa tccatgtttg ggtaatttaa gcttaaaata   1920
```

-continued

```
tcatgcaaac aggctggatg cattggctca cacctgtggt cctagtactt tgggaggccg   1980
aggcagacag atcacttgag gtcaggagtt caagactagc ctggccaaca tggcgaaaca   2040
ctgtctctac taaaaaaata caaaaattag ccggacgtgg tggcgggcgc ctgtaatccc   2100
agctacccgg gaggctgagg gatgagaatc gcttgaaccc aggagtcgga ggttgcagtg   2160
agccgagatc ccgccactgc actccagtat gggcagcaga atgagactcc atctcaaaaa   2220
aaaaaaaaaa aaa                                                      2233
```

<210> SEQ ID NO 57
<211> LENGTH: 1963
<212> TYPE: DNA
<213> ORGANISM: Homo sapiens
<220> FEATURE:
<221> NAME/KEY: SITE
<222> LOCATION: (1540)
<223> OTHER INFORMATION: n equals a,t,g, or c
<220> FEATURE:
<221> NAME/KEY: SITE
<222> LOCATION: (1935)
<223> OTHER INFORMATION: n equals a,t,g, or c

<400> SEQUENCE: 57

```
ggcacgagct ttgaagagag agttcaagag ggcgtcatct acccttccat gtgctggatc     60
cgggactccc tggtcagcta catcaccaac ctgggcctct tcagcctggt gtttctgttc    120
aacatggcca tgctagccac catggtggtg cagatcctgc ggctgcgccc ccacacccaa    180
aagtggtcac atgtgctgac actgctgggc ctcagcctgg tccttggcct gccctgggcc    240
ttgatcttct tctcctttgc ttctggcacc ttccagcttg tcgtcctcta ccttttcagc    300
atcatcacct ccttccaagg cttcctcatc ttcatctggt actggtccat gcggctgcag    360
gcccggggtg gcccctcccc tctgaagagc aactcagaca gcgccaggct ccccatcagc    420
tcgggcagca cctcgtccag ccgcatctag gcctccagcc cacctgccca tgtgatgaag    480
cagagatgcg gcctcgtcgm acactgcctg tggcccccga gccmggccca gccccaggcc    540
agtcagccgc agactttgga aagcccaacg accatggaga gatgggccgt tgccatggtg    600
gacggaytcc cgggctgggc ttttgaattg gscttgggga ctactcggct ctcactcagc    660
tcccacggga ctcagaagtg cgccgccatg ctgcctaggg tactgtcccc acatctgtcc    720
caacccagct ggaggcctgg tctctcctta yaacccctgg gcccagccct cattgctggg    780
ggccaggcct tggatcttga gggtctggca catccttaat cctgtgcccc tgcctgggac    840
agaaatgtgg ctccagttgc tctgtctctc gtggtcaccc tgagggcact ctgcatcctc    900
tgtcatttta acctcaggtg gcacccaggg cgaatggggc ccagggcaga ccttcagggc    960
cagagccctg gcggaggaga ggccctttgc caggagcaca gcagcagctc gcctacctct   1020
gagcccaggc cccctccctc cctcagcccc ccagtcctcc ctccatcttc cctggggttc   1080
tcctcctctc ccagggcctc cttgctcctt cgttcacagc tgggggtccc cgattccaat   1140
gctgtttttt ggggagtggt ttccaggagc tgcctggtgt ctgctgtaaa tgtttgtcta   1200
ctgcacaagc ctcggcctgc ccctgagcca ggctcggtac cgatgcgtgg gctgggctag   1260
gtccctctgt ccatctgggc ctttgtatga gctgcattgc ccttgctcac cctgaccaag   1320
cacacgcctc agaggggccc tcagcctctc ctgaagccct cttgtggcaa gaactgtgga   1380
ccatgccagt cccgtctggt ttccatccca ccactccaag gactgagact gacctcctct   1440
ggtgacactg gcctagrgcc tgacactctc ctaagaggtt ctctccaagc ccccaaatag   1500
```

-continued

```
ctccaggcgc cctcggccgc ccatcatggt taattctgtn ccaacaaaca cacacgggta   1560

gattgctggc ctgttgtagg tggtagggac acagatgacc gacctggtca ctcctcctgc   1620

caacattcag tctggtatgt gaggcgtgcg tgaagcaaga actcctggag ctacagggac   1680

agggagccat cattcctgcc tgggaatcct ggaagacttc ctgcaggagt cagcgttcaa   1740

tcttgacctt gaagatggga aggatgttct ttttacgtac caattctttt gtcttttgat   1800

attaaaaaga agtacatgtt cattgtagag aatttggaaa ctgtagaaga gaatcaagaa   1860

gaaaaataaa aatcagctgt tgtaatcacc tagcaaaaaa aaaaaaaaaa aaaaccggca   1920

cgaggggggg cccgntaccc aattcggcct ttggaaatga gat                      1963
```

<210> SEQ ID NO 58
<211> LENGTH: 1267
<212> TYPE: DNA
<213> ORGANISM: Homo sapiens
<220> FEATURE:
<221> NAME/KEY: SITE
<222> LOCATION: (1248)
<223> OTHER INFORMATION: n equals a,t,g, or c
<220> FEATURE:
<221> NAME/KEY: SITE
<222> LOCATION: (1255)
<223> OTHER INFORMATION: n equals a,t,g, or c

<400> SEQUENCE: 58

```
gctgcagcag actatgcaag ccatgctgca ctttgggggc cggctggccc agagccttcg     60

ggggacttcc aaggaagctg cttcagaccc ctctgactct ccaaaccttc ccacaccagg    120

gagctggtgg gagcagttga cccaggcctc ccgggtctat gcctctgggg gcactgaggg    180

ctttcctctt tcccgatggg caccggggcg tcatgggact gcagctgaag aaggtgcaca    240

ggagagaccc ctgcccacag atgagatggc accaggcagg ggcctctggt tgggaagact    300

atttggagtg cctgggggcc ccgcagaaaa tgagaatgga gccctaaagt ccaggagacc    360

atctagctgg ctgcccccga cagtgagtgt gttggctctt gtgaagcggg gggcacctcc    420

cgagatgcct tctcctcagg agcttgaggc ctcagcaccc aggatggtgc aaacccatag    480

ggcagtgcgg gctctctgtg atcacactgc tgcaagacct gaccagttga gcttccggcg    540

tggggaagtg ctgcgtgtca tcaccacagt ggatgaggac tggctccgct gtgggcggga    600

tggcatggag ggtctggtgc ctgtggggta tacctccctt gttctgtagc cctgggaccc    660

tttcctgcgt atgtgtctcc ttcctgtcac ctgggaatgg aatggccagt gaacaccatc    720

ccagaagcat tttccctctg caaaatgacg tttcttccca cgtctgtttc tgctaatatt    780

taaaataaac tttccttctt ccctcctata cccacctgta aggtgaaatc tgctcttctt    840

ccaaatatat aaaaaaggaa ttgccctcca ggtaatccct ttcctttttc ccgtctatat    900

aagggaatgt cttccttcct atctatctgc aaaatggaaa tctagacctc cttcttcatc    960

cataagtgga ctgtgccagt acaatacatg cctcagcccc caagcctaga aggacctcta   1020

gtctccttcc tgtgtggaat cttccccact ccatccctcc caagttgcct gtattgataa   1080

tgtactcact catgctgtac taggtgctga agcctggaca cccttggtgg gtgggcctgt   1140

ggtgatggtt tgcatccttc ctcctttgtc ccaataaagt atgggagttg aaaaaaaaaa   1200

aaaaaaaaaa aaaaaaaaaa aaaaaaaaaa aaaaaaackc gcggccgnaa gcttntttcc   1260

ctttagt                                                              1267
```

<210> SEQ ID NO 59
<211> LENGTH: 1295

<212> TYPE: DNA
<213> ORGANISM: Homo sapiens

<400> SEQUENCE: 59
ggcacgagct tgtcccaggm ctggagcagc tgtggagaaa ctgggaggga agcccgtcca 60
gcctgattcc aagcccacat gctgctcaca ggtcaaggcc gagggactga tttttgccgg 120
tctgactgga ctcaagttac ttcccagttc cttgcagaga gctgtctttg tgagacagtg 180
tcttgggttc tggaatgatg ggagccgtgc tttgcaaatg aggagtgatt gcgtgctcat 240
ctggcagctg gtgggtgtcc tgctggcatc aggcctgagc ggtgaccgtg ctcctctgat 300
tgtcctcact gcgtgtgaca aggcctgggc cactgtgtga gtcgtcttgc gctccatgaa 360
gcctggtgtc tgtgcagatg tgtgggtggc gttaaggttg ggggacattt gtctttcaca 420
ctggagaatg ggagtctgga gctggtgcta ctggtgagga agaggcccgg cctgctgcca 480
ggttcgccca caccttcccc ctggttgttg ggaaaaccaa ccttggaatg gccaaggcag 540
gagatagcac ctccccggtg aagatccagg agctctcatg agctccacgt ggaaagatca 600
aggatctgga gtctggagcc cttcaggcag caactcagtg accatgaacc tcagctctgt 660
ccacccggca cagcattgct gggagctgga cccgggaggc tgccggctcc agagtgagga 720
gggtccagac catgcagaca atatgccctt tttctccaaa caccatttca agcaaacccg 780
caggtctcct ccacggctgt cagcagcttc tcgtagagct tctcatagga ctcatatggt 840
ggaatgtcga tccggttaaa gctgaaaaag gacaaaagag agtcaccgtg tgggcagtcc 900
agccctagga ccaacctcaa ggccaaggac aggcagtgag aaagacaggg tctcgctagg 960
ttgcccaggc tgctctcaaa ctcctggcct caagtgaacc tcctgccttg ccctctcaac 1020
gtgctgggag ccactgtgcc caatcaacac acagtaaagg ggaagctcat ttccagtatt 1080
tgtgcaaaga aaaagacatc ctttaagaag ctatcgtagc aaaccaaaaa atacaaaatt 1140
gtgacccaga ggatgtacag tgacttctgg ctttctaggg tgctgtggca ggtgctgtgg 1200
cttttgagtt ctgatgatga caaaaatatt ttggcagaga ctccatctca aaaaaaaaaa 1260
aaaaaaaaaa aaaaaaaaaa aaaaaaaaac tcgag 1295

<210> SEQ ID NO 60
<211> LENGTH: 915
<212> TYPE: DNA
<213> ORGANISM: Homo sapiens

<400> SEQUENCE: 60
acccacgcgt ccgtgttcac agacagtagt ttcaaagtgt gtaccacatg aagttgcagt 60
cttccaacct tccagccagt gtgtatggaa ataacctgaa ttgtattaat agcagttctt 120
caatgtgggc ctgctggggg atgcttggtt gtattccgtt gtttgttccc tgggtgcccg 180
tcttgggcaa gcatttctct ggatgtcyct atttatgtgg caggtmaccc tgctggattg 240
ccttcatctg tgtgcggact ccctgtggac caactacagc gcctacagct actttgaagt 300
ggtcaccatt kgygacttga taatgawcct cgccttttac ctggtccacc tcttccgctt 360
ctaccgcgtg ctcacctgta tcagctggcc cctgtcggta agagagtggt ctggccctgt 420
cctccgcatg cacaagtcag gatgttagct agagtactga gacctgacag agtttttccc 480
gtctgcccat ctcacctctt taaccattct ttgctgcctc tgccctgaat ttcctattgt 540
ttggtggaca tctctgcttg atgtcctgct ggtttttaaa actcactttc cagctacaag 600
aaggctgtgg ctggccgggc gcggtggctc acgctggtaa tcccagcact ttgggaggct 660

-continued

```
gaggcgggcg gatcacgagg tcaggagttc gagaccacgg tgaaaccccg tctctactaa    720

aaaatacaaa aaatcagccg ggcgtggtgg cgggtgcctg tagtcccagc tactcagaga    780

ggctgaggca ggagaatggc gtgaacccgg gaggcggagc ttgcagtgag ccgagatcga    840

gccactgcac tccagcctgg gtgacagagc gagactcctc tcaaaaaaaa aaaaaaaaaa    900

aaaaagggcg gccgc                                                     915
```

<210> SEQ ID NO 61
<211> LENGTH: 1445
<212> TYPE: DNA
<213> ORGANISM: Homo sapiens
<220> FEATURE:
<221> NAME/KEY: SITE
<222> LOCATION: (1047)
<223> OTHER INFORMATION: n equals a,t,g, or c

<400> SEQUENCE: 61

```
aggaattcgg cacgagcggc acgaggactc cttctcttct gcagaagcag atgggaatat     60

gctcttttaa actatgagat actggacaga catgaggagg aactaccgtg tcacgtatca    120

agtagtgttg ttatttctgt gcttctccct cctaacagaa tgtaaaacct ttgaacccag    180

gtcagagagg tctttatttt catatcccct gtgatgtcta atttatttgg atttacagat    240

aaatgatcgg taaactttag aaacagcact ccagtttata gctctgtgct gtagacttac    300

tgaacaacta cagtgaaacc aattcaaaaa gggatatttt gtattatgat ttagtctcct    360

acttccaagg ctagttttta aggctgtgaa gggaagctga aaatgacaca gtgtttctgg    420

gatgaccaga cagacactgt atccagagat gctgtctgcg cagcggggga tagtaaaccc    480

cttagtacaa cattaattgg catggtggtt tatgagttaa tgtaatacca aatattaaca    540

taaataaaaa tatatttaag tgataactaa gctggacata tatcttaaaa gacaactaca    600

gcccagaaaa caatgaacat tgttgtccta cagctatttt gtcactgtga tgatacctaa    660

ttttaatctt aaagggagct gatgtttata acctagaagt tgattttgat aacatttgag    720

aaaacttcat aaagctggca caggtaacat atttagtttt gtatatctgc tgtccaattt    780

gagtctctaa aaattatctt agaatgaata tgaaattcgc aggtataaag accaagtttt    840

cagaaataaa aaatgtccaa gtactttgaa acatctattt ttcactcatt attcagccta    900

ggatattagc acttgtgtcc ttgaacagag atgagaatgt ttgttatcca aagaccagga    960

aggtcaccag ccaagggata tacagtcgtg cctcatcttc tgtgcctttg tattccttta   1020

tgctttgtag cttaacaaaa ggttttncct tgtacttgtt aagtttccat atatttgtta   1080

aatatatact tcacacttca cagttgctca tgtcagaaca gactattgaa aatgtaaacc   1140

tggccaggca cggtgctcac gcctgtaatc ccagcacatt gggaggctga ggcaggcgga   1200

tcacttgagg tcaggagttt gagaccagcc tggccaacat ggtgaaacct tgtatctgct   1260

aaaaatgcca aaaaattagc taggcatagt ggtgcacgcc tataacccca gctacttggg   1320

aggctgaggc aggagaattg cttgaaccca ggaggcggag gttgcagtga accaagatca   1380

caccactgca ctccagccwa ggtgatagag tgacactctc tcaaaaaaaa aaaaaaaaaa   1440

ctcga                                                               1445
```

<210> SEQ ID NO 62
<211> LENGTH: 1100
<212> TYPE: DNA
<213> ORGANISM: Homo sapiens

<400> SEQUENCE: 62

-continued

```
ggtgactgct ccctagctgg tcatgaaaat tctcctcaag attattaaat cagggattat     60
gtcttgtcca aatataagtg aaatattgtt tgtaacaatg ataagttact tggctttaca    120
ttttagtaac taccctttca tgtttcttta actcttgaaa tattttatta ggggttgagc    180
attcatgatg gtacctggaa gtcagcaatt tatggttttg gagatcagag taatttgaga    240
aaactaagaa atgtatcaaa tctgaaacct gtcccgctca ttggtccaaa attgaagaga    300
aggtggccaa tttcttattg tcgggaactc aaaggttatt ccattccttt tatgggatct    360
gatgtgtctg ttgtaaggag gactcaacgt tacttgtatg aaaatttaga ggaatcacca    420
gttcagtatg ctgcgtatgt aactgtggga ggcatcacct ctgttattaa gctgatgttt    480
gcaggacttt tctttttgtt ctttgtgagg tttggaattg gaaggcaact tctcataaaa    540
ttcccatggt tcttctcctt tggctatttt tcaaaacaag gcccaacaca aaaacagatt    600
gatgctgcct cattcacgct gacattcttt ggtcaaggat acagccaagg cactggtaca    660
gataagaaca aaccaaatat caaaatttgt actcaggtga aaggaccaga ggctggctat    720
gtggctaccc ccatagctat ggttcaggca gccatgactc ttctaagtga tgcttctcat    780
ctgcctaagg cgggcggggt cttcacacct ggagcagctt tttccaaaac aaagttgatt    840
gacagactca acaaacacgg tattgagttt agtgttatta gcagctctga agtctaaaca    900
ctggaagaat taactgaagt cataacgtgc gtgaattaac agcttctcta tttgatattt    960
gaaattcttc tgtaagcctg tctgagtgta tgtggaaacg attgtcaaat ctaaaatatc   1020
tatatattaa aaagtaggaa attgtcctag cttaccctaa atttcaaaaa aaaaaaaaaa   1080
aaaaaaaaaa gggcggccgc                                               1100
```

<210> SEQ ID NO 63
<211> LENGTH: 1499
<212> TYPE: DNA
<213> ORGANISM: Homo sapiens
<220> FEATURE:
<221> NAME/KEY: SITE
<222> LOCATION: (52)
<223> OTHER INFORMATION: n equals a,t,g, or c
<220> FEATURE:
<221> NAME/KEY: SITE
<222> LOCATION: (66)
<223> OTHER INFORMATION: n equals a,t,g, or c
<220> FEATURE:
<221> NAME/KEY: SITE
<222> LOCATION: (84)
<223> OTHER INFORMATION: n equals a,t,g, or c

<400> SEQUENCE: 63

```
agcttattgc aaagacaaat gtttgaagtg tttgttgaga tttcctgttg tncttcctga     60
ggcagncaca gcataagctc tttnaccctc tacttctcag cacataagct ttcttaccat    120
ctatcactgg agtcaggggt gaggggagga ccgcatgaca gttggttaat atacacttat    180
tttttggcaa aaacgttttc tctgggacca gaatgatctt gatactgaaa aaatttctag    240
tgctagatcc tctttctaag tgtgaaagga cttatctgga atgctccaga atgatcccaa    300
gtgttgagct gagagggacc tggcagcaga atctgattat tgaaaagtgg caattgttga    360
tttattgaag acagaataat aactcagcag aactgttatg ttgagctgaa cccgacctcc    420
ttcagccgaa tcatgcaaga atgcctgctg catggctgtt gctgctactt attaaggctt    480
ggtgttctgg gcacagtgca atgcatttct acatggttga tcctcacagc aaatgaacaa    540
cacaggctta aggaaacaag caactctcaa agtcctgcag tgagtagagc ttagctgttg    600
```

-continued

```
gtagtcaaca tgccacgcga ttcggragtt gagcctgtct ccagaggtta gagatgttca    660

gtttcctctt aaggttctta cgtagatttt tttcatgact ttatctacat cctccttaaa    720

tttacgtttt tagtccttac tggctcttga tatcaccagt tttgttgtta ttagtaattt    780

ctaactgccc taaatttgtc tgttttaaga ttcaagggat gatacctcag tctgttatct    840

ggaatatggt ttacaaatcc attttttctc ttcaaggctt tgaaaacatt gacattgtct    900

cctcctaaca tttttatttg tcttgcagac tcctaattta tttaatttat cgttaggaag    960

acgacttttc tgtcttttga tgattttagc tgcccttctc tagaccttgc tgattccatt   1020

atctttacca agaattgaaa gtgaaagtgg catttgtcat agaatgccat ggtcttattc   1080

caaagtatct taggatggaa caatacaagg cataatatgg ggtcagtgag gtttgttaca   1140

cgagtgaatg accaacaaca ctactgtctg ttcaaaccca gtctgaaggg tgaatcagac   1200

cgaccattgg ccgtgagggt ctggactgct cagtattatc tcaaggatat caagggttat   1260

tggaaactgt gtgatcaaag gggctccatg actttatgca gggattcagt agggagccaa   1320

gaaggttgag aatagttcag agaccagagt ctaagaccaa tcaagaagaa tggatcaatt   1380

agagatatga attctggtgc ttatattttt gtggagctgg ttgtgagata aaaggtcaag   1440

cctaccagac tgaaaagtgt atgtgaaagc tctttaaaaa aaaaaaaaaa aaactcgag    1499
```

<210> SEQ ID NO 64
<211> LENGTH: 655
<212> TYPE: DNA
<213> ORGANISM: Homo sapiens

<400> SEQUENCE: 64

```
ggcacgaggc aggaaccgct aaacgagaca gacactggcg actcagagcc ccggatgtgt     60

gggttccttt ctctgcagat catggggccc ttgattgtgc ttgtgggatt gtgtttcttc    120

gtggttgccc atgttaagaa gagaaacacg ctgaatgctg gccaggatgc ctctgagaga    180

gaagagggac agatccagat tatggagcct gtccaggtca ctgtaggtga ctcggtaata    240

atatttccac cccctccacc accttacttt cctgaatctt cagcttctgc ggtcgctgag    300

agtcctggaa ctaacagtct gcttccgaat gaaaaccccc cttcatatta cagtattttc    360

aactatggga ccccaacttc agagggtgca gcctctgaaa gagactgtga atctatatat    420

accatttctg ggacgaattc atcttctgag gcctcacaca ctccacatct tccatctgaa    480

ttgcctccta gatatgaaga aaaagaaaat gctgcagcta cattcttgcc tctatcttct    540

gagccttccc caccgtaaac tatggactct agttcagttt tatatgcaat ggatcactac    600

tccatcaatt tcttcaaaca aaaaaacaac agcaaaaaaa aaaaaaaaaa aaaaa         655
```

<210> SEQ ID NO 65
<211> LENGTH: 1450
<212> TYPE: DNA
<213> ORGANISM: Homo sapiens

<400> SEQUENCE: 65

```
ggcacgagcg gaagtgcaac tcgaacttgg tcggggcgcg gatcccgaga gggaaagtca     60

taacaaccgc acgagggagt tcgactggcg aactggaagg ccacgcctcc tcccgcctgc    120

cccctcagcc ctgtggctgg gggcagagct cagactgtct tctgaagatt gatgtctatt    180

tccttgagct ctttaatttt gttgccaatt tggataaaca tggcacaaat ccagcaggga    240

ggtccagatg aaaaagaaaa gactaccgca ctgaaagatt tattatctag gatagatttg    300

gatgaactaa tgaaaaaaga tgaaccgcct cttgattttc ctgataccct ggaaggattt    360
```

-continued

```
gaatatgctt ttaatgaaaa gggacagtta agacacataa aaactgggga accatttgtt    420
tttaactacc gggaagattt acacagatgg aaccagaaaa gatacgaggc tctaggagag    480
atcatcacga agtatgtata tgagctcctg gaaaaggatt gtaatttgaa aaaagtatct    540
attccagtag atgccactga gagtgaacca aagagtttta tctttatgag tgaggatgct    600
ttgacaaatc cacagaaact gatggtttta attcatggta gtggtgttgt cagggcaggg    660
cagtgggcta gaagacttat tataaatgaa gatctggaca gtggcacaca gataccgttt    720
attaaaagag ctgtggctga aggatatgga gtaatagtac taaatcccaa tgaaaactat    780
attgaagtag aaaagccgaa gatacacgta cagtcatcat ctgatagttc agatgaacca    840
gcagaaaaac gggaaagaaa agataaagtt tctaaagaaa caaagaagcg acgtgatttc    900
tatgagaagt atcgtaaccc ccaaagagaa aaagaaatga tgcaattgta tatcagagaa    960
aatggttctc ctgaagaaca tgcaatctat gtttgggatc atttcatagc tcaggctgct   1020
gctgagaatg tgtttttcgt tgctcacagc tatggaggac ttgcttttgt tgaactgcaa   1080
ctcatgatca aacaagctaa ttcagatgct gggaagtgct ttcgcttagc tatgtggaag   1140
aaccattgac tgtatacaac caacaagtgt atggtgcaac aggagatcca ttgaaaaccg   1200
tttataggac tgaacgacaa ccccaaatgc aagtgaccat gagcaactac aaataggtat   1260
acatatgcat ttgagctgaa cagactttct gacatataat ttagtcaaaa ttgctgtatt   1320
tcttcccctt aaatttatac ataatcagct tcttgtatgg acccaaattg gagaaatgta   1380
attcagtagt tggtgagaaa taaaggattg tgacctctgt gtaattatca ggaaaaaaaa   1440
aaaaaaaaaa                                                          1450
```

<210> SEQ ID NO 66
<211> LENGTH: 670
<212> TYPE: DNA
<213> ORGANISM: Homo sapiens

<400> SEQUENCE: 66

```
ggcacgagag gcgctaaggg gaacaccccc ttccccaggt cttttatttg tttaagttat     60
ttttgcacaa atgactcttt tatatttaat tcgatttcat tgcctccctt cttaaagcca    120
acaggctcag tttacaaacc tgtgagctac tgttggctgc tgccctcctt cccagtgaaa    180
ggtacaaagc aataagcatc atgcatcctc cccttacccc tccaacaccc ctctgcctct    240
ggctcaggtt gctcaaagca cagatcctct cttaccccgt ccccaggttt gaaacacata    300
gcctcatttc aaggtgtagc caggttcccc cgactttcct ctgggatata aaaaaggggg    360
taagggggca aagagagccc tctgggcctc tcctcccata cacactacac tgccccttct    420
ccccccatca aaacgctcag agacgttgtg atgatgcgac tgaggattat gcaacgtggt    480
ccaaccggag cggccagcat gaccagctgt ccaggggctg cctcctgcct tttcttttgt    540
aaagacaaga cccttgggag ttttaattct gttttgtact tgccctgtgg ggcctccact    600
gcttttctat gggagacact cttaatttaa cagatgagaa tattttgaaa aaaaaaaaaa    660
aaaaaaaaaa                                                           670
```

<210> SEQ ID NO 67
<211> LENGTH: 1692
<212> TYPE: DNA
<213> ORGANISM: Homo sapiens

<400> SEQUENCE: 67

-continued

```
tgcagtccta gctactgggg aggtggaggc tgcagtgagc cgagatcaca ccactgcact     60

acagcctggg cgacagagag agactctccc aaaacaaaca aacaaaaccc aaaaataaag    120

aagtcatctt gaaagaagtt tcaacatttg ccttttcatt ctgagattac agttttctat    180

aaacatctaa gagtgaagag tctgacgttt tttggtcaca gctgagccac tgcgtgaccc    240

ccgccccgcc ccacactcac tttgctctag gcaaagctgt actctgaaag ctggccccaa    300

tggggaggtt aggactgtgc ctgctcagaa gtctgtgggt gcctcagaga agggcaacaa    360

ccctaggctg gaccctagcc ttgagagtac ttcctactgc cagagcccsc agatyycttc    420

cggtggcagc agatactgcc agaagagcct gcggtgcaca caccagaatc cgggtacttg    480

gatgagaagg acacattact gatcaccttc ctccaggcaa ccctgtcagt taaggactac    540

agtcccgccc ccattatgta gatagggaaa cagaggcaaa gaagttagga aactcgccca    600

gaactctcag ctcatgaata aaaaagcaga actaaaaccc agtgctctcc ctggctgggc    660

aaacgtgtgg aagttgatgt gcctggttac tgtttgtgct tcgcttatca taaccagtga    720

cagcgtggtt agcactgttc gcctcaaggg cagctgtgag gattacttgg gattgtcctg    780

tggaaacact tcacatgcat attaactagg agaaaagcca ctggagaatg agctttatga    840

gctctatcaa tcaccacagc tagtctgacc taggggtaag caaaatggaa gacaggaaaa    900

agggaataca tttgctyagg acagcgtgag ggccacgtga gctgcttgat tggtagcgat    960

ttgtacaggg gctttatgga tcactaggtt ttaatttgca aggcctgaaa ctgtccttag   1020

cattctctga aacccacagt gccagtcgcc cttcacgcct cggccagcag aaagctcctc   1080

atgagtggat cctcttgaga acttcagagg ggtcaggtga cggtgactga gactgcctca   1140

gtgatcacgc tcggtgctat gagctgaaat ctgggccaag ggcacagtaa gttcaggcag   1200

ctagtatgtt taaaataact acttttcggg agctaagcca tgaggacgta aaggcattaa   1260

gaatgataca atggactttg gggactcagg ggaaagggtt ggggtgaggg ataaaagggt   1320

ccagtgtaca ctgcttgggt gatgggtgcc ccaaaatcct ggaaatcacc gctaaagaac   1380

ctcacgtaac caaacaccac ctgaacccca aaaacctact gaaactttta aaaattaaaa   1440

atacatacat aaaatagcta cttttactgc tgtcaacagc atgttcctga aaaatgttgg   1500

aattcaaact ttctggaggg cagctggtca agaaacttat tcacgtcagg agttttctaa   1560

aatttgtttt taatgcttat tggtacttct gcattagaag taactacaaa tgtcttatta   1620

aagtttccac tttaaatgca aaaaaaaaaa aaaaaaatga ccctcgaggg ggggcccggt   1680

acccaattcg cc                                                       1692
```

<210> SEQ ID NO 68
<211> LENGTH: 655
<212> TYPE: DNA
<213> ORGANISM: Homo sapiens

<400> SEQUENCE: 68

```
gatgtagagc agactgagct catccatcat gatttcttcg tgatattact gccaagcaga     60

ttataaggtg aagtcaatgt gacaaaagga aattcggcta aaagcttcct gaagcctttt    120

gatgctaagc agtccttctt ttgatattta atacccatgg acataaactt ctgccttaga    180

ggtcgccatg gagttttgtt ttgttttgtt ttgttttgtt tttgccatct gttaacagtc    240

ctgagtaccc atagagcctt ttactattta tcagcatyct agagtcgtca gtatggattg    300

tcaaaacttg cattkgtctc ttttttgttc agtgttgtgt gcatccacat ttyctttctt    360

ttttaaacaa ccctgcttat gtaacatcca cattttctga cttacctttc aaacctgcca    420
```

-continued

```
gaaagcagaa gtgatattta awacacttgg tatgttttat atatwgattc taatgataat    480

gtttrgtcta agatggacct gacaaggcca ggcatrgtgg ttcaacagca ctttgagagg    540

ctgaggcagg atgattgcct gagcctggga gttcaaggtt acagtgaact gtgatcacat    600

cctgccttct agcctgggtg acagagcaag accctgtctc aaaaaaaaaa aaaaa         655
```

<210> SEQ ID NO 69
<211> LENGTH: 1618
<212> TYPE: DNA
<213> ORGANISM: Homo sapiens

<400> SEQUENCE: 69

```
taacgcgcct gcaggtcgac actagtggat ccaaagaatt sggcacagta aaaaaaaaag     60

aaaaaaaaag aatactgcct cacatcaaat ggtctatgtt acttagtata tatgatcaag    120

taacatgcag tcatcatcaa aactgtatta caatgtttag aagagtttcc tattgacaaa    180

ataaataaaa tgtttctgct ttatgattaa ataaatccat cattgtttat gcatgattaa    240

gttgcaaaaa gtttcagagg ttataaaggt tttaaagatg cttctatatc ctttggtttt    300

gcttttatct ttgaaattgg atacaaaagc cacaatcttt gctgtgttgg aagatgtata    360

ggaatagaaa catgaaaccc acaaacataa aggtttacct tgaagtggta gactttttaa    420

aaatgagaac acttgaatta gaaatactga aagcttacca aaagtttgtc aaaccgggaa    480

tcaagaccta ttgtgtcgct catccttgac cccacatcta ctcactttcc aactcctatg    540

tagcaaatcc cctaaatacc tctcaaattt attcacttgt ctccatacct acagccatca    600

atcactctcg tcaaagtcaa tgctgtctat taactggttc ttaaaattgc tacattcttt    660

tctgtgcctc ggcttttact ccttactatc ctaaattcta tattcaggca gggtgattct    720

tgtattggag acaaagagag agcacataga ccaaggtgtt ttggaaacag tcggccctcc    780

ctatctgcag gttccacatc tgcagctcta accaactgca gatcaaaaat actgggaaga    840

agtatataaa aacaaaataa tacaaataag aaacaacaca gtataacaat gatttacata    900

gcatttacat tgtattagat ataagtactc tagaaatgat ttgaagtatt gtttgacact    960

tgaacaacat gagggttagg gatgccaatc tcccccgcac acagtcaaaa atctgtgttt   1020

aacttttgag ttcccaaaaa cttacctatt atccaattgt tgacaggaag ccttactgat   1080

aatacagtca attaacacat attttgcacg tcatatatat tatatactgt attcctacaa   1140

tgaagtaagc tagagaaaat gttaacaaaa ttataaagaa taaaacacat attttatata   1200

ctttttttaga gagagagttc tcactatctt tgcaaggctg gactcgaatt tctgggctca   1260

agcaatcctt ctgtctctgc ctcctgagta gctgggacta caggcacttg ctaccacacc   1320

cagctcctat atttattatt tattaagtgg aagtggatca tcttcatcct tctcatcttc   1380

aggtggagta ggctgaggag gagcagggag aagagggttg ggtgttgctg tctcaggggt   1440

ggcagaggca gaagaaagta taagtgaacc catgcagttc aaacccatat tgttcaagta   1500

tcagctgtaa acaggagggc gtgtataggt tatatgcaaa tattaaacca ctttatatga   1560

gggacttggg catccatgaa ttttggcatt tagaggttcc tggaaccaat ccctcgag     1618
```

<210> SEQ ID NO 70
<211> LENGTH: 1802
<212> TYPE: DNA
<213> ORGANISM: Homo sapiens
<220> FEATURE:
<221> NAME/KEY: SITE
<222> LOCATION: (1790)

-continued

<223> OTHER INFORMATION: n equals a,t,g, or c
<220> FEATURE:
<221> NAME/KEY: SITE
<222> LOCATION: (1792)
<223> OTHER INFORMATION: n equals a,t,g, or c
<220> FEATURE:
<221> NAME/KEY: SITE
<222> LOCATION: (1801)
<223> OTHER INFORMATION: n equals a,t,g, or c

<400> SEQUENCE: 70
gaattcggca cgagtctctc tcacttttga aatgcttatt attttaatga caataatgca 60
gagagagaga gtatttttga atagacttaa gttttccttc aactaatgtc tccttggagg 120
acagaaatac aactaaaccc tctgtcaacg tgggtatgta tttttttact ttctattttt 180
caattagttc ttttatgttt tttcttctag tcattgttaa agctaccaat ggaccaagat 240
atgttgtggg ttgtcgtcga caggtaatac tttatatttg tatagtgcct gatgattgac 300
aaagcagttt catgtaagtk attgtctcya attcttgagg cwagcaggtg gagcatttat 360
gcccataact cacaaggatg atttgttcag acatagctag ttattaacaa agcctgaatt 420
caamccatgg gctttgactc ctggcattcc gtactttcta ctgtattaca ttgtctcagt 480
cagatctgtt aatagccact tagaaataaa agtattttag aactggaaaa cagacatttt 540
attttaatgt catttttaaa gaggacttaa aagtgttaga tatcatcagt tacctgtgtt 600
tatatttaga cattcagaac tgttacttat ggactgtacc atggcctaag ttaattttgt 660
atgaggtcat ttagattagg gtagggcaag ttgaaataat tctaaatttt attttacagt 720
tatcaaagat gccaacaaat gacctcaagt cattcagtag tgtctgaaat caatttatgt 780
attattcttt aggaagtgtc cttagataat tcttttaaat tcattggaag agttttctct 840
gtttaattgt catttcaggt tcaggtttta aaacattcac agaacatggc tgtaagggag 900
aatttaatcc aggaactata aatctcctat taggattttg cctagtatat aagcggttga 960
cattttctaa gtcaaaatat tagataccta aactgacaag ggattttcat gtccctttca 1020
gggctctgtg gatgccgaaa gttggcattt ctaagatatt tcaggttgca tgaggacaag 1080
actgtatttg aagactaaaa aacattagaa aagccgaagt atatataagt tgagtatccc 1140
ttatccaaaa tgcttgagcc agaaatgtgt tttagatttt ggcttttttt ttttcaggtt 1200
ttagaatatt tgtgktgkac tggttgagca tycctaatta aaaaaaatca aaagtttgaa 1260
atgctccgat gagcattttc tttgagcatc atgtcagcat tcaaaaaatt tcacattgkg 1320
gagcattttg gattttcaga ttaagaatac tcagcctgka tttcctatag atgtaaacat 1380
tgaaatagct tcatattgat ttctcctctt attttttcaa gtaacctcac ttcttagccg 1440
ttttttcctt aattgttata ttaatcctag tgttttgcct atcttcctaa atttgaagct 1500
ctttgtaaaa tcctgtgaca agtggtcagt aatttatatg attccgaaat tgtattggca 1560
cgcagttttt taaactatta aaaagtaact tgggtcgggc ggggtggctc atgcctgtaa 1620
tcccagcact ttgggaggct gaggtgggca gatcacgagg tcaggagatc aagaccagcc 1680
tgaccaacat ggtgaaaccc cgtctttact aaaaaaaaaa aaaaaaaaaa aaaaaaaaaa 1740
aaaaaaaaaa aaactcgagg gggggcccgt acccaattcg ccctatagtn antatagtga 1800 nt 1802

<210> SEQ ID NO 71
<211> LENGTH: 1292
<212> TYPE: DNA
<213> ORGANISM: Homo sapiens -continued

<400> SEQUENCE: 71
ggatgataga tgatctgtaa atattttctc tcattccata ttcctctggc tccttttaag 60
atttttcttt atgtctggtt tcaaggaatt tgattttgtt gtgccctggt ggagtataag 120
ctttcttttg agtttttgc tcttgttgtt aagcttttgg agtttgtggg tttatacttt 180
tcatcagatt tggaacatct ttggctatta tttctccaaa tagtcacaca tcgctcctcg 240
gattccagtt acatatatat tattaggttc ttgaagttgt cccatacctt actgatgctc 300
tgctcttttt ctttggtctt atatttgggt ttcatttgga tagtttttat ttctgtgtct 360
ttacattcac tcgtctttcc ttctgctgtg tcttgactgc tgctagttcc atccaatgta 420
tttcatttat atatctataa tttgtggttt gatagaaatg cagtgatgta gcaggtatca 480
ataaatactg ccttaatttg ttgcgaaaat ataacagatt cctgttctgt atgttagcta 540
aaaaggtatg caaaccaccc tgtatgtcat attaacattt atgtcccttt gtttccatgt 600
caacttttag tttctctgcc aaaacctaca tatgtttttt ttatatgatt attctacatt 660
ttctgctgag agtggacatc tgcattagta gttctatgat atttgtttta taagttgcca 720
gaatggttgc tctgtttggc agactgcaga caaatattta tctatgattc gttgcatgat 780
atgaccatga ttttgctaca aaaaacttga aatagatttt aatattttct ttactattat 840
cagagagaga gctggattac ctgcaaaagt gtacttttgc ttattgctgt cattgataac 900
tcagtgccag ctgggcgtgg tcactggtat tacctccatg tgatcacttt ttgttcacta 960
atgttaattt aaaaaatttt aggctgggcg caggtggctc acacctgtaa tcccagcact 1020
ttgggaggcc gaggcagggg gatcatgagg tcaggagatc aagaccagcc tggccaacat 1080
ggtgaaaccc agtctctact gaaaatacaa aaattagcct ggcatggtgg taagcgcctg 1140
ttatgccagc tacttgggag gatgaggcag gagaatcgct tgaacctggg aggtggaggt 1200
tgcagtgagc caagattgca ccattgcact ccagcctggg caacaagagc aaaactctgt 1260
ctcaaaaaaa aaaaaaaaaa aaaaaaaaaa aa 1292

<210> SEQ ID NO 72
<211> LENGTH: 883
<212> TYPE: DNA
<213> ORGANISM: Homo sapiens
<220> FEATURE:
<221> NAME/KEY: SITE
<222> LOCATION: (8)
<223> OTHER INFORMATION: n equals a,t,g, or c
<220> FEATURE:
<221> NAME/KEY: SITE
<222> LOCATION: (28)
<223> OTHER INFORMATION: n equals a,t,g, or c
<220> FEATURE:
<221> NAME/KEY: SITE
<222> LOCATION: (30)
<223> OTHER INFORMATION: n equals a,t,g, or c
<220> FEATURE:
<221> NAME/KEY: SITE
<222> LOCATION: (47)
<223> OTHER INFORMATION: n equals a,t,g, or c
<220> FEATURE:
<221> NAME/KEY: SITE
<222> LOCATION: (873)
<223> OTHER INFORMATION: n equals a,t,g, or c

<400> SEQUENCE: 72
aaaatagnaa taactaaaag gcgaattnan ccctctagat gcatgcncga cacggccgcc 60
agtgtgatgg atatctgcag aattcggctt atcgtgaacc tggctttggt ggacctggga 120

-continued

```
ctggcactca ctctcccctt ttgggcagcc gagtcggcac tggactttca ctggcccttc    180

ggaggtgccc tctgcaagat ggttctgacg gccactgtcc tcaacgtcta tgccagcatc    240

ttcctcatca cagcgctgag cgttgctcgc tactgggtgg tggccatggc tgcggggcca    300

ggcacccacc tctcactctt ctgggcccga atagccaccc tggcagtgtg ggcggcagct    360

gccctggtga cggtgcccac agctgtcttc ggggtggagg gtgaggtgtg tggtgtgcgc    420

ctttgcctgc tgcgtttccc cagcaggtct tggctggggg cctaccagct gcagagggtg    480

gtgctggctt tcatggtgcc cttgggcgtc atcaccacca gctacctgct gctgctggcc    540

ttcctgcagc ggcggcaacg gcggcggcag gacagcaggg tcgtggcccg ctctgtccgc    600

atcctggtgg cttccttctt cctctgctgg tttcccaacc atgtggtcac tctctggggt    660

gtcctggtgc agtttgccct ggtgccctgg atcagtactt tctatactct ccagccgtat    720

gtcttccctg tcactacttg cttggcacac agcaatagct gtctcaaccc tattgcctat    780

gtcttaagcc gaattccagc acactggcgg ccgttactag tggatccgag ctcggtacca    840

agcttgatgc atagcttgag tattcatagt gcncctaaat agt                      883
```

```
<210> SEQ ID NO 73
<211> LENGTH: 785
<212> TYPE: DNA
<213> ORGANISM: Homo sapiens
<220> FEATURE:
<221> NAME/KEY: SITE
<222> LOCATION: (716)
<223> OTHER INFORMATION: n equals a,t,g, or c
<220> FEATURE:
<221> NAME/KEY: SITE
<222> LOCATION: (731)
<223> OTHER INFORMATION: n equals a,t,g, or c
<220> FEATURE:
<221> NAME/KEY: SITE
<222> LOCATION: (772)
<223> OTHER INFORMATION: n equals a,t,g, or c

<400> SEQUENCE: 73

ctgcaggaat tcggcacgag gttttatcat ccaggatatg gtcactctca gtggcatatt     60

ccatgtgcat ctgataagga tgtatgttct gctcttcctg ggtaaagtgt tataaattca    120

aattgttgat aatgttcagg tcatctatat ccttaatggt tttctccctg attcttttat    180

taactactga gagaagaata ttggcatgtc cacctataat tttgaattcg tctatttttc    240

tttcagatct gtctgttttg ccttaaacat tccttatctt tcagaataat taaaagtaaa    300

aaaacattgt tacttgtttt ttccatttct gatgttctcc attttgttgc atagatccaa    360

gtttctgagc ttttaccctg tgaatcatag tcattttaaa tttcttgtca tatgtgagag    420

tttagttctg attactgctt tgtcttttca gattgtgttt tattgtgtat tttcacattc    480

cttgtaattt tttatgttaa aaaaattgtg tatgtgcmaa gctgaacata ggacagaaga    540

cactgaagta aatgttttca tgcttggaaa tgagcaggcc tttcctcctc ctctctttag    600

tcgtgggytt gtgcttgttt agttgagttg ggtttgaagt ttgktcacct ttggctttgg    660

gtctcctaac ctgactttct gtgtttcctg tgcactgctc ccaagataga aactgnttct    720

gggctatctt ncagttggaa ttccttactt gattcttatc agcatgggtt angaagggaa    780

acatg                                                                785
```

```
<210> SEQ ID NO 74
<211> LENGTH: 2341
<212> TYPE: DNA
<213> ORGANISM: Homo sapiens
```

-continued

<220> FEATURE:
<221> NAME/KEY: SITE
<222> LOCATION: (161)
<223> OTHER INFORMATION: n equals a,t,g, or c
<220> FEATURE:
<221> NAME/KEY: SITE
<222> LOCATION: (163)
<223> OTHER INFORMATION: n equals a,t,g, or c
<220> FEATURE:
<221> NAME/KEY: SITE
<222> LOCATION: (170)
<223> OTHER INFORMATION: n equals a,t,g, or c
<220> FEATURE:
<221> NAME/KEY: SITE
<222> LOCATION: (1229)
<223> OTHER INFORMATION: n equals a,t,g, or c
<220> FEATURE:
<221> NAME/KEY: SITE
<222> LOCATION: (2243)
<223> OTHER INFORMATION: n equals a,t,g, or c
<220> FEATURE:
<221> NAME/KEY: SITE
<222> LOCATION: (2309)
<223> OTHER INFORMATION: n equals a,t,g, or c

<400> SEQUENCE: 74

```
gcccagttcc tcttgaaaag gcagagaatt tagacagaaa ttcaccaact gctttcttac     60
agaaagtaaa ccaatttctg cttccagaaa aatggagtaa atgtattttg ccctattcct    120
tctactaaga aaaactataa accctgaaca ttatatataa nanatatgan aactcagacc    180
tggagagacc aaggcagatg tggtagggac ttmataaatt gtatagtgat gaatcctcta    240
agttttcttt tctgctttat aatttgcaga cttttagctg aaaatgccat caacatagaa    300
atactaacag gcacatatga gaatttccca acaaaagcct attattttag gcaaaggtca    360
aggaaatagt ctaccaaggc agaaaacatt tcgacaataa ccactctact gtagtcaagt    420
accacagaaa acactattac ctcaagtgaa gagcttagat ctttagayct tcataccagc    480
caggctgtga caaggtgtcc caaccctcct ccagaatagt atctcagaat agcagaagtt    540
ggaactttca tccccaactt gtggtaataa gcccctcact ctccttccac accttgatat    600
gactggagag caaatgggga gctggatcta ctctaaaagc agcaatgaag aagcaccctc    660
ctttccatac caggtggtgc ttgtggaggc catgtgggaa acagtaacaa gtcacttctt    720
cctccgagac aggctatcag tggaggccca gtggtgaccc agaatccacc ctccagccag    780
cagtaatgag gaacctccgc tgcctaggtg tcaacagaga ttgagaggaa acctttattt    840
ctatcatcac ctggcagtaa tgcagtgtcc ctccctcact cccttgcctt gctggagtag    900
tgtctgagga agctagctaa gacagaaaag gtaaataagt tctagagtct cataatgcct    960
aaaatgtcct ggttcattta gaaatcattt ggtatacaaa gaaccaggaa aaatctcaac   1020
ttgaatgtaa aaggtaatta gaagattcca gaacaaaaat gacaaagatg ttggaattat   1080
tcagaaaata ttttaaagca gtcatcataa aaatgcttcc agtatattgs ttacaacata   1140
tatgaamcaa atttaaaaat tatctyagcc aaaaaattaa aatatwtgaa agaactgaat   1200
ggacatttta gaactgaaac ttacaatanc cacataaaaa attcatgaag gtaagcagga   1260
aaaaactata aacacagcct cagggacctg tagtattata actgaaggcc taatttttgt   1320
gttatcagag tcccagaagg agagaagaaa tgggcaactt tgagaaaggt ctcaaagact   1380
gaaaacttcc ttaatttggc aataggcaaa aacccacrga ttcctwaatt cargcaamcc   1440
caaaatctct tagcactgta tcagaatacc atagaatggg tggtttatwa aaacaaaaat   1500
gtgttgctca caatactgga ggctggaaga ccgtgatcag aatgccagca cagatgagtt   1560
```

-continued ctgctgaaga catttttttgg ctatagatgg acatcatctc attgtatcct cacatgttgg 1620
agaaaagaaa aagatatctc ttgtctcctt ctccctctct ctctctcttt ttttttttat 1680
aaggcctctg atctcaacrt gagggcccca mmctcatrac ktartctaac cctaattacc 1740
tcccaaaggc ctaacctcca aataacatca cattgaattt aggatgtcta catatgaatt 1800
ttgaggggac acaaactttc agtgcataaa actaaccaag acaaacacaa agaatccaaa 1860
ctaaggtata ccatggtaaa atatctgaaa attaaaagaa agaacaaatt ttgaaagcag 1920
ctagaggaaa tagctcatct ataggagaga aaacaataca aatggaagca ggaaacatca 1980
gaaatagatg aaagccatag aaaagtggca caacactgtc tatgtgatga aataaaataa 2040
ctttcaattc tggtttttat atctggtata tttgtctttt aggaatggaa gggctataaa 2100
gacatttgat gaaagaaagc tgagaggatt tgtcaccaga aggtctrcct tttaaarrgg 2160
ggctcaagar rrttctctat ccaggaaaaa aaaaagaaaa agtttaaaaa agaaacttta 2220
aaacaccaga tttaaagaaa acncagtgga aagggaaaaa tgagtggctt catcttcctt 2280
ttcctcttca gtttggtaga tttatttgnc cagctgaagt taaaattatg ccattatcag 2340
a 2341

<210> SEQ ID NO 75
<211> LENGTH: 1882
<212> TYPE: DNA
<213> ORGANISM: Homo sapiens
<220> FEATURE:
<221> NAME/KEY: SITE
<222> LOCATION: (755)
<223> OTHER INFORMATION: n equals a,t,g, or c
<220> FEATURE:
<221> NAME/KEY: SITE
<222> LOCATION: (1237)
<223> OTHER INFORMATION: n equals a,t,g, or c
<220> FEATURE:
<221> NAME/KEY: SITE
<222> LOCATION: (1866)
<223> OTHER INFORMATION: n equals a,t,g, or c

<400> SEQUENCE: 75
gcaagttttg tgtttggccc tcaataaact agtctctctg tacccctggc agggggtggg 60
aggagtcctg ggggagctcc cttccaaatc ttacagggtg gtctgtttct tctttggata 120
ataatgatgt aatggctagt ctcttgagaa cttgctgtgt tccatacatt gtactaagca 180
tttatttgga ttatctcatt aaatcttcac aatcacttta tttaacagat ggagaaatta 240
aggcacatgg aacctaagtt gttcaaggtc atggagccag taagtgttag agccaagtcg 300
tttggctcca gagcctgtgt tcttaactac tactttgtag tgtctttctt acatattagt 360
tgggcctgtg tattgctagt tgaattcctc ttcccagtgg caggccttca cgtgtttgac 420
catggttttc atgttctcca aacctcagtt ctctagattt gtactttggt aggtcatcat 480
tttccacaga tcctacctct ttaggtcaga aaatcttgcc agtttataaa gattctctgg 540
gactaactcc cacaaagcaa ggtcacaaga gatcaatgta caaatgaagc agttcagtga 600
gtttgtctac cattctccat aagtacatgg grgacamctg atgattggaa ggtttggttc 660
acctcatggg agctgtgata tctcactcac cacacagatc tgctcttctg agggaccatc 720
ttgccaattt ccagagagtt gcagggatat taaanttttg cacattaagc ttcctctttc 780
caagctgsac atgggscctg ctaccgkttg tgaamagtct tctagagtga tawaggttct 840
agctttctta gttaagatcg tattttctga taccactccc ttgtcacttt gcctgaaatg 900
agaaactccc aacctcaact gcttttctag tctcttccaa tgaatgcctt ccaaagggct 960

-continued

```
ggtgtcctcc agggtgtatt agttgttact aatttcatcc tccaaggctg atctgatttt   1020

caagatctgt agagagacct tagtatattg ccttgcctgt accaaatmca gtcattatgg   1080

cmcaggaaaa tctcaaatmc cttattggaa acccaggcaa atatttattt gaccttaatg   1140

aaatgaaaaa gacattggat gcatacattt aaagaaaacc caaaactttg gaatctttac   1200

caaggagggt atcttttgaa aaggacagkc tggaacnaag aacttgataa aatagaagta   1260

aaggttgaca cttttttttt tttttttga gatctatatc actctgtcgc ccgggctgga   1320

gtgtagtggc gtgatcttgg ctcactgaaa cctcggcctc ctgggtacag gtgattctca   1380

tgcctcagcc tcctgagtag ctggcactat gggcatgtgc caccatgccc agctaatttt   1440

kgtgtttttg gtggagacag ggttttaccg tgttggctag ctggtcctga cctcctggcc   1500

tcaagtgatc cacccgactt ggcctcccaa agtgaaagtc ggcattacta gccctgttca   1560

gcacatgaga cagggcactg gatggtgtct acctaatgat tttcaaccca ggggcccttg   1620

gcccaagcgt atcactggta taaagggcct ctgccagcta atgtgagggt gagtgtggct   1680

gttgtttcca tgagagaact cctgggagtt ctacactcag caaacgtttg ttgttggact   1740

atgaaggcgg acacagattt tatacgaatt tgtaatgcta acatctagca taagaattgg   1800

caaccataga aaatactacg tgtatatata tgtttatagt ctcaaaaaaa aaaaaaaaaa   1860

aaaaanaaaa aagggcggcc gc                                              1882
```

```
<210> SEQ ID NO 76
<211> LENGTH: 2892
<212> TYPE: DNA
<213> ORGANISM: Homo sapiens
<220> FEATURE:
<221> NAME/KEY: SITE
<222> LOCATION: (858)
<223> OTHER INFORMATION: n equals a,t,g, or c

<400> SEQUENCE: 76

agactctgag tccagctccg aagaggaaga ggaattcggt gtggttggaa atcgctctcg     60

ctttgccaag ggagactatt tacgatgctg caagatctgt tatccgctct gtggttttgt    120

catccttgct gcctgtgttg tggcctgtgt tggcttggtg tggatgcagg ttgctctcaa    180

ggaggatctg gatgccctca aggaaaaatt tcgaacaatg gaatctaatc agaaaagctc    240

attccaagaa atccccaaac ttaatgaaga actactcagc aagcaaaaac aacttgagaa    300

gattgaatct ggagagatgg gtttgaacaa agtctggata aacatcacag aaatgaataa    360

gcagatttct ctgttgactt ctgcagtgaa ccacctcaaa gccaatgtta agtcagctgc    420

agacttgatt agcctgccta ccactgtaga gggacttcag aagagtgtag cttccattgg    480

cmatacttta aacagcgtcc atcttgctgt ggaagcacta cagaaaactg tggatgaaca    540

caagaaaacg atggaattac tgcagagtga tatgaatcag cacttcttga aggagactcc    600

tggaagcaac cagatcattc cgtcaccttc agccacatca gaacttgaca ataaaaccca    660

cagtgagaat ttgaaacaga tgggtgatag atctgccact ctgaaaagac agtctttgga    720

tcaagtcacc aacagaacag atacagtaaa aatccaaagc ataaagaaag aaggatagtt    780

ccaaattctc caggtatccc aagcttaaga gagraactcc agcttgatcc agtgctctta    840

cmaacmaacc tgrgagcnac mggcctccag agaccgccga tgargagcaa gtagagagtt    900

cacatcaaag ccatcagcat tgccaaaatt ttcacagttt cttggagacc cagttgagaa    960

agctgcccaa ctaagaccta tctccctacc aggagtttct agcactgaag atcttcagga   1020
```

-continued

```
tttattccgc aagactggcc aggacgtgga tgggaagctg acctaccagg aaatctggac   1080
ctccctaggt tctgctatgc cagaaccaga gagcttgaga gcatttgatt ccgatggaga   1140
tggaagatac tcattcctgg agctaagggt agctttaggt atctagcttc atcaggcata   1200
ttttagaaat ggactgccta atatctattt acctaacaac aaaacaaccc ttacttaccc   1260
atcagtcctc tagtcctcca aactactgta gcagatactt tgccaccttt taacttgttt   1320
gaagaagcta tataaaagtt atttttttaa agaagaagac cattttactt atgatgttca   1380
gaaatctatg atttcctaca accagtaaga tcttacattt taaaattgcc agaaaaaaaa   1440
ttaaagccct ctttttttct ctttcctttt tttgaggggga ggagacctta tcttttaaag   1500
ctgggaaatg tatatagaga gagaataagc cacttttata tttcacttaa atttgcctta   1560
aattagctgc actttataga gactcagaaa atgtcttttc tttaaaagat aggccttttc   1620
tgtttgtaaa tatttaaatg aaagaaagca ttgtgcatat tgtgtggaaa gtaggaagaa   1680
tggttttgaa caggatatga acaaatgact tattaaaaat tgctgatctg gtgtaggtgg   1740
cagctgaaac tacatccatg tctccataag gyatccctca aaggcccagg cgctgccagg   1800
gggtttgtcc tggtagctgg aggaaccgat ttcagggagt agacactgga gacaatactg   1860
actccaggca tggctcatgg aagtaggatt ctggttcttt gttcctattc cctcagctaa   1920
tcccaacctg ggaatcagag aagtcttggg gatttttctc atttttagta ctatttcagg   1980
gtttatgagc ataaaaagtt atccattggg gagctccatt ttccctgctg agtgagctag   2040
attgccttcc ccacccaccc acttaagtct gtcttaaagc cgtagctggc tcccaccacc   2100
agtaccatct ccatttgaat ggcagggcta aattccccca gccattatct cacactgacc   2160
acccagagct ttagaagaga gctgtgcttc taattttgac ccagaaaacc ataccccttg   2220
agattttacc tagaggctaa ccaagagcct aatatgtttc tctgggggat gactaaagcc   2280
aaaaaggctg tgagatgaaa catgtgaaat aatattcagt ttccttacca ttaccagctc   2340
agaagtagct agaggctttc tacccaaagg atgccaaagt atagcagggc aggcctggag   2400
ctagggcctt cacatggtgg tagcaagttt ttcaaatcta atacaatcaa gtacaatact   2460
tcctttaaat gcttctgtgg acctggcatg aaagatccct agattgaaag gaataatacc   2520
tccatgtctc ctgtatgttg agtctagaat tgctgtgttg ttcttagaag cagtctttgg   2580
gcaacaactt gaaaggggaa aaaaaaacta caaaaactta actttggtat aggccaagtc   2640
agggagaaag tagagaaagc tgtcatgcca cagacttctt tagtggagat catttccttt   2700
ttaactttgt tcaggttgcc cttcaccatg gatacagtcc ggtaccctta aacatttaag   2760
ggctgttttt tttttcttta catgatgttc agcttggtat taaccaaact taaatttttt   2820
ttccagaagt attaaaattt agttaaagca aaaaaaaaaa aaaaaaaaaa aaaaaaaaaa   2880
aagggcggcc gc                                                       2892
```

<210> SEQ ID NO 77
<211> LENGTH: 1673
<212> TYPE: DNA
<213> ORGANISM: Homo sapiens

<400> SEQUENCE: 77

```
cggcacgagc tggaaatgaa atttgcccct gtttatatgt acctgtcttt tatttgcctc     60
tgtctttttt attgcaactc aatagacaca caccattgct ttgtctctga ttatttggca    120
tttgaatcgt caatgaggga agcttttaca gaacttttga tactaataaa aggtgagtca    180
aatgttttaa aaaagatgca gaatcatcat ttatgtcaga gctactgact cacacttaaa    240
```

-continued ttgcagtgtt agcactgaaa aagaaatgta tatggatggg aatatagatt gcaggccaat 300
taggacccct cttttgaagt tggaattgag ggatagctac tgttctcttc tatctttgag 360
ggttaggaga actttattca gtgttgaata actgtattcc tcctgtttat taatgtttgt 420
tgtgggggtc ttctattcag cacccatctc tgcctgtcct gctccccccgc ccccagagga 480 ggatataata agaggcatgg gacaggggct tataataata agacatggga ggggttgatt 540
acccagtgtc ttcaagtaac ttttacgaga gatttgaaat agccagcgat caatgcaaaa 600
tagcaatggc cttggcagaa tttgcacata catactcaat gtttacagtt taaactctgg 660
tgtcagacag ggtcatagtt accccgattg gatgcatccc atctctggtg cagaacctct 720
aaaacttggg aaatcattga aagtcatctg cttattaaaa aagcagattc tcagactcac 780
atcagactag gagaagtcct gagaaatcta aatttttagc acatgctttg gggggattctt 840 tacatcacgt gtgtttggga aactgtgctg attgatgtcc atggaaagca gcctcaggca 900
tggggagggg ctggaaaaga attatttagg tcagtttcgg gatcttagat tgtttcttgg 960
ctacactggc cactttttaa agtgtgctta gaaagagtat gacacctttt taattttcaa 1020
aaggacttgg gttcagtgta tgtccttatg ttaaagaaac agccctcttt gtagttactc 1080
tagaaatagg tagaatggca gaaagagcgc tggctgtctg tgtttgaggc ctgttttgta 1140
cttcatgtgg ccatgtggta tgggaacatc ctgggatttc tgtgagcctc tgtgaactca 1200
gattccccat ctggaaaaca ggagtaacaa cactggttgg aacctttatg gagtgtaaat 1260
aaagtgatag ctctttgtaa gcgacgaaga gccaggtcag tgtttaattt tattttctca 1320
gaaatagtac tagttattaa ggcctttaac aaaaaaaaat ctttgaaaag gctaatgggg 1380
gcctggtata gtgtgtcatg cctgtaagcc cagcattttg gcaggctaaa gggggggagga 1440 tcacttgagg ccaggagttt gagagcagcg tgggtaacat ggtgacatcc tgtctgtaca 1500
aaaaataaaa acattagctg aatgtggtgg catgcgccta tagtcccagc tactcggaag 1560
ctgaggtggg aagattgttt gagcccagga gggtgaggga agctataatt atgccactgt 1620
actccagcct gggcgacaga gtgagatcct gtcttaaaaa aaaaaaaaaa aaa 1673

<210> SEQ ID NO 78
<211> LENGTH: 1461
<212> TYPE: DNA
<213> ORGANISM: Homo sapiens

<400> SEQUENCE: 78
ccacgcgtcc ggagagttat ggagaatgct gattttgatt attatgatgc cagatactga 60
gaatatctta catgtatctt ctgagcagag cttctgttcc acaaagttaa atccatgctt 120
aatataattt ttgccaagta aattttagtc gattgcacct cagttgttga ttagtaaccc 180
atcggcagta gaaagatggc agtgtttttt ccaggctgtt tgttcctcta agtatctaga 240
cgaggccgag tcagccttat gggtctaaag ctgccaattt tcctgtggtt tctttatttc 300
tttatccctt tatccagctg ctacttactg ctattgccac atttgccctc tggctcatgg 360
gatagcatgc ttagcttccc ctgaggctac tgttaatgct tcctttttac tctgctggct 420
ggaaatgtac ttggcatcct tagtcttaaa cctctcctcc ctctttttc cacagacacc 480 aggcacttaa gtagcacttt cagcctgcac cagttatcag tagtagcttt caacccctca 540
tttctggtct ggtaactcag cacactgtcc caagagagct tgactaagcc aatttgcccc 600
ctcttccctt cttcctctgt ctgttcatct ttctttttc tttttcctac ccatccattt 660

-continued

```
ccttgactct ccttttattt ttctcttact ctctttaatc tcccaaatga tttttttctg    720

cttttagtat agcagatgcc ccagaattag gcagatactt gtaatacaaa ataaaacaat    780

agtaaatttt aaaattaaac atttgctcaa gattggatca actaaaaaac gagtttattt    840

tttatgactg gtctattcgc ccctttatgg ctataatgca gattttttgt attaaaagtg    900

tataggtttg tgtttttgtt ttttttgtgc ttttacataa agagttgtga agatcgtttt    960

tatgcaggcc tgctcattca agatgatctg tgatgtggga aaaaagtaaa atctttttct   1020

agctaatgtt ttacaaggaa aaggaaagct acttttattt ttatttattt attttttttac  1080

atacaatgat tcgaatacac agtttgagtt atttttcaaa ctaactttct ctgaatatgc   1140

tataaatgtt ggctgttcat ttttcaagta atggtttgta aacaactttt aggcattctt   1200

agctaactaa tatttatgac caatagttta ggacataaag attataccta tgaattgggg   1260

gatcaagaac agtaacagtg ctctgcaggc ctcgatcatt aactgccaac aaaatctaca   1320

ggacaattcc aaatgtctgc aaaagaaaaa catgaaaaat tcatactgat aattatagat   1380

cagaatcatt taaagccctt atctccttcc tcctctcatt tccctaatct taattctttc   1440

ctctggaaaa aaaaaaaaaa a                                              1461
```

<210> SEQ ID NO 79
<211> LENGTH: 1517
<212> TYPE: DNA
<213> ORGANISM: Homo sapiens
<220> FEATURE:
<221> NAME/KEY: SITE
<222> LOCATION: (1145)
<223> OTHER INFORMATION: n equals a,t,g, or c

<400> SEQUENCE: 79

```
aggagaaact ctaaaaactg cagatattat ttcatgctat atgttccatc ctctgatgag     60

aatgtgagga aagaaaattg tatcctgcat ggctgaaaat ggtcccctac aaaaatatca    120

tgttggacaa ctaatctgag atagtggtat ctctggaaag cagtttagca ctggtgagtt    180

tggactttca tggcaggctg ccttggttca tatcttttgg taatgatact tatcctctgt    240

raggcccatt tctttatttg tggaaatgaa gacaatagag tgcttagata taatttagaa    300

caatgtccgt cacatagtaa acacgtaata aacggtagct cttattgtta ttattattac    360

tattattacc ttgaagacag gggctctgtc ttgttcatca ttccatctcc agctcttagc    420

acagtccctg gcacaattca aacatgtatt tggatgaatg acaaatagct actgaatatt    480

tgccctgttc caagcattgt tagaggtaca tgggacaggg cagtgaacaa aacagacaaa    540

acctcctgct gtctcagagt tcacactcta atggggagac ccaggcaatg aggaaataat    600

taaaatatac aatgtgtctt atggcaataa atgacaaaga aaaataaagc agaggtgaga    660

aacagtggca gtgttttggt gatcatttgc tttgcaacaa gccactcccc aaagttagtg    720

gcctaaaaca atttaatcac agttcatgtt ctggctacaa caatacacat ccctctcatg    780

tgcaaaatac actcactcct ccctcagagc ctcgtaccat taagggttca ggttcaaagc    840

ttaagatctt atcctctgaa gtaggtttag ggacaaacaa gtcttctcag gtacttcttc    900

tggggacaca gagacttgtg aactaaaaga caagttacct accttccaac acaactgaca    960

tgcaatgggg atataggaaa agataatttc aataggcgct tctgtgcaaa agcgggggaa   1020

atgagagtca ctcagcagtc acggttcata ttaatctaaa atctagccag gcatatatcc   1080

caagtcttcc tgatgtgagg acaagaatta tttcttgatt agggctcact twwtctcttt   1140

gaggntggtt cgcctcagct tttggatttg tcctctgaat catccttcct tgtctataaa   1200
```

-continued

```
atgcatgtat atactcatac atacatagag agaaagagag agagagagag agagagactc   1260

tgtcacgcag gctggagtgc aatggtgtga tctcagctca ctgcaaccta caactcctgg   1320

gttcaagcaa ttctcctgtc tcagcctccc gagcacctgt agtccctgct actcaggagg   1380

ctgaggcagg agaattgctt gaatccgaga ggcagaggtt gtcagtgagc agagattaca   1440

ccactgcact ccagcttggg tgacagagca aggcttcatc tcaaaaaaag acaaaaaaaa   1500

aaaaaaaaaa ctcgtag                                                  1517
```

<210> SEQ ID NO 80
<211> LENGTH: 574
<212> TYPE: DNA
<213> ORGANISM: Homo sapiens

<400> SEQUENCE: 80

```
tagtagagcg cgtgtataga ggcagagagg agtgaagtcc acagttcctc tcctccaaga     60

gcctgccgac catgcccgcg ggcgtgccca tgtccaccta cctgaaaatg ttcgcagcca    120

gtctcctggc catgtgcgca ggggcagaag tggtgcacag gtactaccga ccggacctga    180

caatacctga aattccacca aagcgtggag aactcaaaac ggagcttttg ggactgaaag    240

aaagaaaaca caaacctcaa gtttctcaac aggaggaact taaataacta tgccaagaat    300

tctgtgaaca atataagtct taaatatgta tttcttaatt tattgcatca aactacttgt    360

ccttaagcac ttagtctaat gctaactgca agaggaggtg ctcagtggat gtttagccga    420

tacgttgaaa tttaattacg gtttgattga tatttcttga aaactgccaa agcacatatc    480

atcaaaccat ttcatgaata tggtttggaa gatgtttagt cttgaatata acgcgaaata    540

gaatatttgt aagtctacta taaaaaaaaa aaaa                                574
```

<210> SEQ ID NO 81
<211> LENGTH: 1455
<212> TYPE: DNA
<213> ORGANISM: Homo sapiens
<220> FEATURE:
<221> NAME/KEY: SITE
<222> LOCATION: (390)
<223> OTHER INFORMATION: n equals a,t,g, or c
<220> FEATURE:
<221> NAME/KEY: SITE
<222> LOCATION: (456)
<223> OTHER INFORMATION: n equals a,t,g, or c
<220> FEATURE:
<221> NAME/KEY: SITE
<222> LOCATION: (1100)
<223> OTHER INFORMATION: n equals a,t,g, or c
<220> FEATURE:
<221> NAME/KEY: SITE
<222> LOCATION: (1293)
<223> OTHER INFORMATION: n equals a,t,g, or c
<220> FEATURE:
<221> NAME/KEY: SITE
<222> LOCATION: (1409)
<223> OTHER INFORMATION: n equals a,t,g, or c

<400> SEQUENCE: 81

```
ggtccaccct cccccagggg cctccccagc ctccctctcc acctccctgc cccccggaga     60

tacctccaaa gccggtacgc ctgttcccag agttcggtga gtgctgcagc caggagatgg    120

ggctctgggt ggatggcctg ggatccctgg aatcaggcct ctggaaggta tgcaaggatc    180

acactccttt ctgtgcaagc ctgccaccag cccactgtgt ggccccgggc aggtcacagc    240

ctccctgagc gctattctct tcatcctcac aatggagaca gcacccacct ctctggcctc    300
```

-continued

```
ctgaccgtta agtgtggggc catggccggc tttgccagtt acccatggtc tgattttcca    360

tggtgttggg tggtttgctt ttctttttkn tttttttttt tgagacagag cgagagtctg    420

tctcaaaaaa aaagacaagt tgcagatgag ctgagntttg ggcagagcaa gcgggattct    480

gatggggggt ggatgttgcg ctcgtcagca ggcaatagtt agttggttga gggttttgat    540

camggggtag ctactgcctg ccccatttta tccagctctg tagttgctat agagttgcta    600

gaaccttggc acatcactta tcagttttgt cacctcagat ggcttcttca ctacttgggg    660

tgtctcctgg gtgtggggct ctccttcctg tggcctctgc tgactgcctg gcactggcac    720

acatgctctg gtgaggggag gaccaacggt ttttcccgtt tgttttctgc ttcctcgttt    780

aaccctcctc gtcttgtaag atgaatgtwc ttgtctctgt tcactatgca gatgaggact    840

ttgaggctca gagacgccac taacttgcct ggtccaagcc ttttgggcct ctcaggctgc    900

agccagcaat gctgcagtga agtttgcctg ggaggctgac cctaggagtc tgcaggcgtg    960

ttaggacccc cgatctagaa gacagcagag atgtaggcca gggaggacca ataccgagca   1020

tctgagggca ggcacacctc agactgacca gaatacaaat gaattcgagt cacttacaaa   1080

caaagtggca taaggccagn cacagtggcc catgcctata atcccagcac tttcggaggc   1140

cgaggtggga ggattgcttg aggccaacga tgtgagacca gcctgggcaa catagcaaga   1200

ccttgtctct acaaaaataa aaattcaaaa aagtggcatt taacacatac tttttttctt   1260

ttttttgaga cagarttttg ctctgtcccc cangctggag tgcaatggtg tgatctcggc   1320

tcactgcaac ctccacctcc caggagaact gcttgaacct gggaggcggt tgcagtgagc   1380

caagatcgca ccacttcact ccagcctgna caacggagca agactccatc taaaaaaaaa   1440

aaaaaaaaaa ctcga                                                     1455
```

```
<210> SEQ ID NO 82
<211> LENGTH: 1640
<212> TYPE: DNA
<213> ORGANISM: Homo sapiens
<220> FEATURE:
<221> NAME/KEY: SITE
<222> LOCATION: (687)
<223> OTHER INFORMATION: n equals a,t,g, or c
<220> FEATURE:
<221> NAME/KEY: SITE
<222> LOCATION: (764)
<223> OTHER INFORMATION: n equals a,t,g, or c

<400> SEQUENCE: 82

gtgagcactg gtttaagcac ctcatagact ggcatttctg cctcccacaa gataactgga     60

cctggcttag gaatctgaat agcagcatgc atggagtgct tctatgtgtc aagcactgtt    120

ttaagcacgt ttgaaataac tcacttcatt tgaaataact gagtctacat gatgactgta    180

aaaggttggt tctgttgtta cctgcatttt accgatgagg aaactgaagc cttcagaagt    240

gcagtcactt gtccagggcc acatagcagg ctgagatttg aaccgccagg ccttttgact    300

ccagagctta cactcttaac tccattcatc tgctaagtcc ttccctgtcc tcttgcaaga    360

tgccttaatc cagggattat caaacttttt cttaaaatca ggagaactca ttgcaaacca    420

attcatacct agattccaca gaatcaaaga tgcagccgag ttacccattg agctggagtg    480

ggggcgtara attgccctgt ttggcctcct tsctgacatt gctgttccta ctgcagcctc    540

tgatgcttcc ccttggaggc tcccagaccc agttgggcaa ccacagtgtt gtccgtctgc    600

ttctcccagt tcagaggctc ggctttgccg aagtccctcc actcgaagtg gcacagagtt    660

gaggtctctt ccaggcacac tggcgtnccc tcactgggct cctgtccctg ccttggtcaa    720
```

-continued

```
catcctggtg cgcactgggt gggtgactaa caacattttt gganttgtgg ctggagccca     780

ggtgactact ccaaatcacg gttttccatt ctgtgtgaga tggcctcatg cctttctatg     840

cctctgacag gcagttctct gaatttcgaa ggctcttgtc ttaagagact gtcagaagtc     900

cctttggcaa gggactgtgg gcaaaccgcc cagcggctgt ggtcaattcc tctctctgat     960

ggcagtagtg ctacctaggg ggccgcctgg gtgaaacggg ctttttttgca tacttccaaa    1020

ctggttccct gtagctaggg gaccaaacaa ttattgtctg aaccaagatg ctcctgagag    1080

tgaagagaat gtaaagtgct cagtcctgga cagatggtat atatgatcgc cgtaaataca    1140

gccagccctt gccagaagtg ggtctggaga aatggtgcgg gggggcgtga aaagggctta    1200

caacccgcag tcctgtgtct ctgctaggtg aattggtagc atcagtcctc actctgctta    1260

ttcagaccaa aaaattgtta agttcttccc accaccacgg agcacagact tgattaagat    1320

ccagaaaggt cagccgggtg cagtgacttg cgcctgtaat cccagcactt tgggaggccg    1380

aggcgggtgg ctcacttgag gtcaggagtt tgagaccagc ctggccaacc tggtaaaacc    1440

ctgtctctac taaaaataca aaaattakcc asgcatggtg gcccatgcca taatcccagc    1500

tactggcggg gctgaggcag gagaattgct tgaacccggg aggcgaaggt tgcagtgagc    1560

tgagatcgtg ccatgcactc cagcctgggg gacagagtga gactctgtct caaaaaaaaa    1620

aaaaaaaaaa aaaaactcga                                                1640
```

<210> SEQ ID NO 83
<211> LENGTH: 525
<212> TYPE: DNA
<213> ORGANISM: Homo sapiens

<400> SEQUENCE: 83

```
ggcacgagga gaactgatgg gggtggagag aagctccttg tgggaggaga gggaactacc      60

agcagagccc ctcctaccgc agacacagga tcggagacaa cctccaaccc cacctgcctc     120

ctgaagtgct gctgacatgc aactgcctta actttgccta cctggcctcc ttatgatccc     180

cctccggcgt ggtatggttg gggggcttct tttgctgctg gccacggcaa acaagctgct     240

tgctgcttcc ttcagagacc tcatggatgt tcttacatgc ccccgacccc ggtagatggc     300

tccctgttgt ttggggagcc tggaaggtgg ttatgccttt tggatgcagg agaggagcaa     360

gaaagagtgg agagggagaa tgggggagcc ggaccctgac ctccctgggt tctggttgga     420

gatgaaaaaa ttagaagcat caggtctaag atcagcttct cttggaagca gagcctgaga     480

caagatataa atgccagtca tttattaaaa aaaaaaaaaa aaaaa                     525
```

<210> SEQ ID NO 84
<211> LENGTH: 837
<212> TYPE: DNA
<213> ORGANISM: Homo sapiens
<220> FEATURE:
<221> NAME/KEY: SITE
<222> LOCATION: (717)
<223> OTHER INFORMATION: n equals a,t,g, or c

<400> SEQUENCE: 84

```
cactatagaa ggtacgcctg caggtaccgg tccggaattc ccgggtcgac ccacgcgtcc      60

gggtgggaga tgattggctc atggcggctg acgtcccccct tgctggtctc gtgatagtga     120

gtgagcgctc atgggatctg gttgtttaga agcatgcagc acctcctgct tcactctctc     180

tgtctctcct gctccaccat ggccagaaac gtgcctgctt ccccttcgcc ttctgccgtg     240
```

-continued

```
attgtcagtt tcytgaggsc tccccagcca tgcttcctgt acagcctgca raactgtgag    300

tcaattaaac ctcttttctt cataaattcc ccagtttcca gtagttcttt atagcagtgt    360

gaaaacagac taatggaccc ttctggttga aggaatgyag ccattctgct tgtttrasta    420

tktcctttct attcatctct atttccyggg aggtgtttat ccaagtgcaa taggagrtat    480

tggtgacygc asagtcccct cagtgttctg ctagtaaata gttgaaggtt gatcaktgat    540

ctycwgcrtt ttcagtctgg catggaaaag ccccyrtgya actggtaaag rtatcartaa    600

gcaccaggag gtatctaaat ccaccaggag ccataggcat cacgttgacg tccatttacc    660

agtcttccct ggcaagattc ttctgaattg tgctgccttg gccaaaagag gtatggnagg    720

ggctgggcrc agtggctyry gcctgtratc ccagcaggag ttcgagacca ggcaggagaa    780

tcactagcag agaatatgtc tccccaaccc ctctcaaaaa aaaaaaaggg cggccgc       837
```

```
<210> SEQ ID NO 85
<211> LENGTH: 1574
<212> TYPE: DNA
<213> ORGANISM: Homo sapiens
<220> FEATURE:
<221> NAME/KEY: SITE
<222> LOCATION: (19)
<223> OTHER INFORMATION: n equals a,t,g, or c
<220> FEATURE:
<221> NAME/KEY: SITE
<222> LOCATION: (873)
<223> OTHER INFORMATION: n equals a,t,g, or c

<400> SEQUENCE: 85

gtgatctttg taatatctnc tgttgtttct atgatatagg agctagggga agggggttgt     60

ttgccttctt caggacctga ctggacagat ggacctggct caagcaacta ctctggatgc    120

actttgctgt gtgggatgaa ctaaaagtgt ctgaattttg ctgataactt tataaaactc    180

actatggcat gcttccctcc tggtgggccc taggatggat gacactcaag atactacaga    240

tgtgggtgca ggcatgcaca cacacgatgg aatatggcca ttcctacaca ggtggggtag    300

agagtgggtc agcagcctgg cacctcacag aggtgggacc taagaggact catgattatg    360

cagagaattg gattgggtct ctgtcataga ttgagtaatc tcttccctta cctcaattcc    420

atctccaccc atctctacat ctgggcacag caacccagag atggccaaaa gcattcaagc    480

ctgggggaag atgtttgact attgctgctc ttcaccagaa cctcacacct ctcctgggac    540

tggaaccctt cagtgggtgt gtggccagtt ttggaggctg gaatgatggg ccagggtgta    600

ggattcattc tccatgtaaa gtttcctttc atcctgccta gccatcccca aggtttattt    660

ccagaagaaa ggaatatctc tacttggatc aattctggtc atttcaagag gatggaggcc    720

tcaagtgtgg gaacttcccc tactccctgg atgtgtgtac ctagcacact tccttctccc    780

accccttttt ccagttggat ttgtttttct gttctcttct gtcctgtctt atactgcaac    840

tgtgtctcct aggggacaga tggccttctt tgncatcttc actctccacc cccagagagg    900

agtcagagcc ataactcaat cactcagccc ctccaaagat agttgatgtg tgataatctc    960

ataatgttga gaaccctgat gagatacatt gtcttcctct ccctacaatg cctctggggc   1020

caaggcaccc attcttcttg ctatcctcca tccccccttga ggcttccact tttttttttt   1080

ttagacataa agctgggcat cagcaactgg cctgtggtga tgcaaagctg ctttgctctg   1140

tatctggctg gactgatctg tctcacaaga agccatgagg ccatagggag aagctccctc   1200

tccccttcat cttctgctcc aaaggtggta gcaagaggag tacccagtta ggggttggag   1260

cccccatata acatcttcct gtcagaagac tgatggatct ttttcattcc aaccatctcc   1320
```

-continued

```
ctttcccccg atgaatgcaa taaaactctg tgacaccagc aaccattgct ctttagaaat   1380

gggttttctg atcatatggc tgatgtgtta tgggcagtat ggatgtcttc atttgttgct   1440

tctgtttttc atcttttttg ttttattaat aaaaatttat gtatttgctc ctgttactat   1500

aataatacag ggaataaatt attcaatcca aaaaaaaaaa aaaaaaaaaa aaaaaaaaaa   1560

aaaaaaaact cgag                                                     1574
```

<210> SEQ ID NO 86
<211> LENGTH: 1628
<212> TYPE: DNA
<213> ORGANISM: Homo sapiens

<400> SEQUENCE: 86

```
tccctctctc ctgcctgtgc tcaaacaccc acagagaact ctggaaggag aagaaaaaca     60

tacctctctc cttccccggc ctttccccac acacactgag gttgagaagc tgggaataaa    120

cagcgtccaa cacttttaaa tggcggtggc agctccagac aagggagaag ggaaggactg    180

agagaagaaa ttattagact ttttagactg gctgaaccca gaacctttac attggttaca    240

aaatcatgcc tggaggtgaa aaattcaata gcattatacc aagtgtttgg gcaacggtgt    300

agagacaata gtagagacaa gctacagctt tagacagtgg tagagagaag ctacaacttt    360

agcttgtaga aacagctgtt gggtgttcag cagatgcagt ctaggtgcat gcaaacccac    420

tgtgtgcagc atgccttcac tctcacgaca agggagccag accttgtgtc tgcggctggc    480

tgaatattgc atggaatctg tggattcaca gaggcttctt ctcagctaag agggagtgtg    540

gctggatgca tttctctgtg gctcattcaa tttggggtat actcatacta ctgagtctct    600

atgaaggagt gataagctgg gtcttcaatt tccaaatgtt taccaaactc ctactatgtg    660

ccaagcacta ttcccactgc tttgagagct aacggtaaac aacaacagyg aaaaaacatg    720

taacatccca accagtgctt ctaaggattt aaaatatgct ggtacttatg actttattct    780

tacttctgta ttatagatat gtatatggct ttggggtatg tgtatatgta cacatatatg    840

cacacatata cacacacaca catatatata atcagctgtc catagcctac tcatctctga    900

taatttatat tttgtactca aatttctcga atacccctac caaatcattc tctcctcctt    960

accaatatta taatgtccct gacaataaca taacaaaccc agctctaaca cctacagatt   1020

tctttgagaa caaacaactt ctacatgcaa tttcttttct atactcacca actggttttc   1080

ttcaacctcc tgcccaccct gtccagctca ggacatcaac aaccctttat ggaaaccacc   1140

gaggtcagac tggatgcagt cagttggact gattcatcat gactagttca attaagagct   1200

gatcaccttc aaacagctct gactttggaa gcaattgatt tgactgcctc tttggtcaca   1260

tggccagatt tacccataat tttttgcaaa cttggatgca tctttagata cagagcaatg   1320

ctttggcatc tgggggaggg ggttgttcct ggtgctgtca cttgtaccca ctctcctgtt   1380

tcctctccaa ctatgagtca cattttccct caatatctcc tatcttactt tttgagtgat   1440

cagccctgac tttcaagtct aaatttctcc tccacgccaa aaacaaaaca aaaacagaaa   1500

aacaaaaaaa gctttttgct gtatcacacc acctaaagtt tggctagtga acatgagcag   1560

acctcttctg aatcccacac atcagccatg ctcttgcagc catgtagagg agctggaggt   1620

gggtgggc                                                            1628
```

<210> SEQ ID NO 87
<211> LENGTH: 1795
<212> TYPE: DNA

-continued

<213> ORGANISM: Homo sapiens

<400> SEQUENCE: 87

```
ggcacgagaa caaactataa actacttacc tgcatattgc tttactggga aaaatcttag     60
cagatgatac ttccttacat ttgtagagta gaatgtgttt tatgtctttt attagtatag    120
atgactggcc ctatatcatc taatagatag tccttttcat catggagatg aattattgtg    180
ggtccagagt tttgtatatg tctctaatcc tgctagggag tccaatcata cccttgtggt    240
cctatacttc agccacacag gctgcagctt tagtgacatc acacgtgtgg aaaccctctc    300
tagaggctca ccagatcaat atttctcctg aaccttcaat acattatgat agatggcaca    360
ctcagagtaa ttgtagttta ataaattctc ttcaataaat ggttctggaa aaacaatatc    420
tatatgcaga agaatagaag aagactgccc acttctaaca atatacaaaa atcaaatgaa    480
aattaaagaa ttaaatctaa gaccctgagc tatgaagcta ctacaagaaa actttgggaa    540
aaatcttcag gacattgacc tgggcaaaga ttttttgagt aatactccat aagtacaggc    600
aaccaaagca aaaaatgaac aaatgggatc acatcaagtt aaaaagcttc cacacaacaa    660
agaaaacaat caaagtgaag agacaaccca cagaatggga gaaaatattt gcaaactacc    720
catttgaatg ggattaataa tcagaatata tgaggagctc aaacaactct atagaaaaaa    780
atataataat ctgatcaaaa aatgggcaaa agatttgagt agacattcct caaaagaaga    840
catgcaaatg gtaaacaaac atattgcgaa gtactcaaca tcactgatca tcagagaaat    900
gcagatcaaa aactacaatg agatatcatc tcatctcaat taaaatggct tctttttcca    960
aaagagaggc aataactaat gctggtgaga atgggaagaa aaaaagaatc ctcatgcact   1020
gttggtggga atataaacta gtaaaaccac tatggagaac agtttggagt ttcctcaaaa   1080
aactaaaaat ggagctacta tataatccag caatttcacg cctgggtata tacccaaaag   1140
aaaataaatc catgtatcaa agaaatattt gcactttcat atttgttgta gcaatgttca   1200
caatagtcaa gatttggaag caacctgagt ccacaaacag ataaatgaat aaagaaaatg   1260
tactatacac aatggagtta ctattcagcc atgaaaaaga atgagatgct atcatttgca   1320
acaacataga tggaactgga agtcattgtg ttaagtgaaa taagccagaa acagaaagac   1380
aaacatcaca tgtcctcact tatttgtggg atctaaaaat cagaacactt gaactcatgg   1440
acatagagag tagaaggatg attaccagag gctgggaagg gtagtgggag gaaggtgggt   1500
gttggggtga aggatgtggg gatggttaat gggtaccaaa aattgaatga ataaggccta   1560
ctatttgata gcacaacagg ctgactacag ccaataatag tttaactaca ttttaaaata   1620
actaagagta taattggatt gtttgtaaca caaagataaa tgcttgaggg gatggatgtc   1680
tcattttcca ttatgtgatt attacacatt gcatgcctat ataaaacatc tcatatctca   1740
tgcaccccat caatataaac acctactgtg tatccacaaa aaaaaaaaaa aaaaa        1795
```

<210> SEQ ID NO 88
<211> LENGTH: 1864
<212> TYPE: DNA
<213> ORGANISM: Homo sapiens
<220> FEATURE:
<221> NAME/KEY: SITE
<222> LOCATION: (1844)
<223> OTHER INFORMATION: n equals a,t,g, or c

<400> SEQUENCE: 88

```
cccaagccag ccatttatta caagaagcaa caggttattg acattacatg tttgaaaatt     60
ccctttggtc tttagggaaa ataaacagga agccaagatt tggagccttt gtaataagga    120
```

-continued

```
cttcctgcag aaagtctttt ctttactata attgagtaat tcatatttag agtcacatgt    180
ccagtagcat ttctaatttt gagcattcac cttgctacct ttaaaaaaca tctgagtttt    240
aagtggcctt tttatcatca tacacatgtg catacaaaga agggacttgg cagtttaaaa    300
gccacatata ttcactttta ttgccctaaa tttacatgaa acagacatac tggcaaactc    360
acatattgct ggtgctaacc ttatatttca tagtgttggc atattcccct tttcttagat    420
tcttactccg aaatataggt acacatcctt tgctctgtgc agagggaatt acatcctttt    480
tcctctccta caaaaacatg ctttattaag tatccatcat tactttcctt tatgctcgct    540
caatatgcaa tgtgctgtta ttctaccatg taccttaaat aaaggatgat ggcaaagtta    600
tttaccatgt agaaaccatt ttctttctag aaacaatagc tcagcctcac tgtagcagct    660
ggcatgtgtg gtcaagtgga tagttgtact cttgcaagtt ggatttaata tcatatatac    720
tggaccttca gactgttaaa aatcaatgta accttttttt attgctatgg caagcaatta    780
gtatttcact gcacgtcttc catactaatg ttcatttcta aatcttatat gtaggcattt    840
gttagttcca atgatttcct cactaatata acacttttta atgggaatct ttccacctac    900
agccctggaa tgataatgct acagtaattc ttctgaattg actttttctt tcatcctgtc    960
agctttggac aatatcccaa ttatggcagg gaacaggtgg ggaactaaga tcagttacaa   1020
aaagttgtag atgtgtcaac tttgtatggc tgggatcact gtgcccaaac aaaacaggcg   1080
aaatacctca gttaaaattt ttccatcaaa gtctttaaaa gaagagtata ctgaagaaag   1140
ggcagtcata atacttactt ctaacagctt ctaaagggta catgtttaac atttcatttc   1200
aaaatcaccc caaatttgca ctaaatacca atgaagtgtt attttgcttt agtagtcttc   1260
tgagcaacaa actatgggga attctgkaaa amcatataaa aagtycaagm cttttttttt   1320
aaatgaatga ttactatgtt aaatgcaaac tttttttttt ttttatttaa acaaacatac   1380
acttctcctg gcaaggttat agatgattaa cctctgttca tagacttata tataaaacta   1440
gagggttttt tgtttacttt tttaattttt caagtgcaat tgtttcttac acagacatta   1500
ttactattaa attatcattt agccagttat ctgcaaatat atagtatgta ttgtctcttc   1560
ttgtgacgtt tagtttaatt gcttatttta aagcagaaam attagttaca agtgtcttac   1620
aatattttta ccaacagtaa agtagagact taatgaaaat accttagtgt gattttaata   1680
taatttgcat attttagttg tataaagttt taatgtaaaa tgtccattat tgaagggaaa   1740
agatctttca ataaaaaata cccacgaaaa aaaaaaaaaa aaaaagggcg gccgctctag   1800
aggatccaag cttacgtacg cgtgcatgcg acgtcatagc tctnaaaagg ggactccaga   1860
gctt                                                                1864
```

<210> SEQ ID NO 89
<211> LENGTH: 1983
<212> TYPE: DNA
<213> ORGANISM: Homo sapiens

<400> SEQUENCE: 89

```
gacgttgaag atgagaacaa gcagaagaaa caattggatt tctatgaaaa gaaaacagat     60
tggtgtacac ttacacaaat ttgtgcagat tatttgtcta gaaggaaagt catacaggtt    120
gggcagtctg gtcacaaaaa gggacagggg ttgagggggt tctggtgact gtgatgaagg    180
cctcactctc aggcctccgg tcccactgaa ggtcagatga aaggtagtct tccctggcgg    240
ttgctgctgc cactgaatgg gccctaactt tgtcgtcttg tgtttgaatc ttctgcagga    300
```

-continued

```
cacgttagcg tatgccacag ctttgttgaa tgaaaaagag caatcaggaa gcagtaatgg    360
gtcggagagt agtcctgcca atgagaacgg agacaggcat ctacagcagg tataacggtc    420
agcatgtcct tgtgtgcaaa gggcagcctt gctcttaagc tttccaaaaa gaatttccac    480
agctgaggga aaacaagatg cttcctctgg aatgtgagtc caaagagtta ccagcgctgc    540
cctctagtga tctcagctca gcatatgcac taaccgtgtg tttacagggc tgagtagtgc    600
tgcagtgtga agtgaatgga aggcctcgag gtgtttgtgg ctggccaccc tgatcagcct    660
gcaggtagtc ccgatgaagc cagggcacag ggggattcgt tccagcttgt tcactttatt    720
ctgccttgcc aggttactga aagtccctcg tttgctctca ccagccttcc tggaaatgtg    780
gactcttgaa agaaaagctc ccgtgctctt gaagtatacc tgcttgccag gggagtccaa    840
gaaaattttg acatgtattt ttaaaaaaag aaaaaaaaac agctttaata ccaatcatta    900
tagtagaaaa agaaaataaa tatgtattga acacccactg tgtgcaaaca ctgaactaag    960
tgtcagttaa tcattacgtc tttccaatag tctgtaactt tccttaacag cagtctcctc   1020
tgtggtccct tcacagtact tggtacagaa taggccccat taaatgaatg ttactgatgt   1080
agtaggtgtc attttttttt aagtgttatc tttcggatcc tcataagcac tatgtgaggc   1140
agctgtcacc ctgattttac agaaaggtaa ctgcagccca gcacagtgat gtgacttagc   1200
ccaaggtcac tccacacatt acctcatcac ctacttcatt tgcagagaaa ataaaagctg   1260
tcacaggaga gctcctgcgg ccactaattc ccaagcatct gcactgttct tgtstcctct   1320
cctgtgacag tgggaagttt gcctctgtcc acccaaagcc cctagcgctc atccccgccc   1380
accttggcag agctttgcgt tctaatgtgt atgtaactct tcaatatcca gaacgctyca   1440
ccctgccaga cccttcccag cgacgtctca gcacactggt ttctcttctg ccctgtcaaa   1500
gcctctcttc tgccctgtca aagcctctct tctccctgtt gcccctgcct tcttttctct   1560
tctttgcagc caaacttcga ctaattctct aaacttaact ttccccattt tcttatctct   1620
cactcgctct tcagcctctt ccctgctaac tccctcttct ctccaactca gcagttgggg   1680
tgacaggtgg cctgcagctt tcaggcctca tcttagccga ctgctcggca gcatctagcg   1740
ctcctggcgc tcttcccgtt tgaaacacta ttccagggct ttcctgacac ttctctctcg   1800
tagttttcct caaacccttc tggctgttcc ttctctgtct ccttcctagt actgcctctt   1860
ctggaccacc agtaaaggtt tgtggagtct ctaacctgta tcctcctgcc ctcactccat   1920
attctctccg cgtcgacgcg gccgcgaatt cccgggtcga cgagctcact agtcggcggc   1980
cgc                                                                 1983
```

<210> SEQ ID NO 90
<211> LENGTH: 1957
<212> TYPE: DNA
<213> ORGANISM: Homo sapiens
<220> FEATURE:
<221> NAME/KEY: SITE
<222> LOCATION: (349)
<223> OTHER INFORMATION: n equals a,t,g, or c

<400> SEQUENCE: 90

```
gtttctctgc aattatttgg ttcagtttta attttatctg taacaatgat agtaattgct     60
gtttcacttt ctctcttctg tgatgttgtt tcctctgaat gtatgagctg ctttactcct    120
aagtttgctg acattgttgc aaatgcttat cagaatgaat cctatatttt tatttaaaat    180
gatcgtgtca ttttcaatca ggcagcccat ccaaacatgc ggacctatta tttctgcact    240
gatacaggaa aggaaatgga gttgtggatg aaagccatgt tagatgctgc cctagtacag    300
```

-continued

```
acagaacctg tgaaaaggta aaggcttgta gaaaaaatga tggtgattnc cacttccatt    360
ttattccatg ccttgcaagt atttcactgt catagtmcat atcattttaa tagtcatggt    420
atgaaatcat tttttcctca gaaagcaagg atcaattcct gttctgaatt aaattaatac    480
acattttgtt agtttgcgat accacctaca tttttattcc acttttcttc tttttcttct    540
ttattcattt tcacctatcg gtgtactggg gtgaatccag aatcctaaca ttcaaactga    600
atgttctttc ttcttacaga attaccttta atttccggtg agtacgtttt taattgttac    660
cttaaagcta cacagatttt tatcctttga gatagtgttt ttaagattct aaatcttaga    720
agagagttta tttttatgaa gttaatttgt gtttttctgt aatagtgtgt tgatgtttct    780
aaagtgtgat gaattacagt aagaamcttt gatartttca ttttttcaac atttctgatt    840
aatttttatt gtttttgtaa tgaatgtctc cagaaaatag ttcgtcaagc atttagattg    900
tttccaaatc cacttcttgg tgaattgtac ctttttttata ttgaaactcc actactcaga    960
tyccttgata atatagataa gtgctgttaa aattgaccca tgtatttttc cctgcttgaa   1020
gatacgaatc attttaatat tcttcagtat agctagttag aggaaatctg attctcagac   1080
tacataaata caagtagtat aatgtgcttt ttaaaaaata tgtattcctg taattcgaag   1140
aaaaaattat gatgcaagtt aatttttctt ccagtcagtg acagctgagc acatatctta   1200
tgtaagaaag atgctaatgt gcatcttttt tccctcttct ttttttttccc tcttctcagg   1260
aaattaggga ttgttmcagt atacatctag tcctttgttt ttcttattct agtgtgcatt   1320
ttaataaagt cttggctttt tggctaaaag acttaggttg atgctgtgta tttgtgctat   1380
ttttgtaaat atcaagtcta aatcaagtta cccaatcact agtaattaga gctggggaaa   1440
aactgaaaag aaaagagggt ctaggatata gctctaggac atctattttt aagaaaaacc   1500
acttttgcca catgcatatt gcaggatgag agcagataga aggaaaatct gtttttggaa   1560
ttgcatgtgt aaaaattacc tgagtagcat aaagatgagg tggttagcac tgataacgag   1620
agaaaatgtg taggtgaaga gaattcattt aaaatcttca ggctgagcat ggtggctcac   1680
acctgtaatt ctagcacttt gggaggttga gggatcactt gagcccagga ttttgagatc   1740
agcctgggca acatgatgaa acaccatctg taccaaaaat acaaaaaatta gctgggcgta   1800
gtaccacact cttgtagtcc ctgctactcg ggaggctgaa gcatgaggat cacttgaatc   1860
aggaggttga ggctgctgtg agctgtgact gtgccactgc actccagcct ggacaacgga   1920
gtgagaccct gtcaaaaaaa aaaaaaaaaa aactcga                            1957
```

<210> SEQ ID NO 91
<211> LENGTH: 573
<212> TYPE: DNA
<213> ORGANISM: Homo sapiens

<400> SEQUENCE: 91

```
ggcacgagtg aatattaact gtgttatttt tatacacttt ttaagcctta actcgccatt     60
gatttaccag tttaacgttt cctggggttt ctttgcccat ggggttctct gcccccaccc    120
ccggcccttt gtttgacttg cgtcgtctga tactcagtat tgtagctttt tgtccgcatg    180
ttactccctg taaatacgct gttatacata ctgttaacac ccctttgctt tttctatggg    240
acctccaggc caccatattt agaactagtt accttattaa aaaagaaaaa acagtctgtt    300
ggcttctcag tctgcatctt ggaggcaggg aggtgagggc aggtgcccct cagacacttc    360
aggaaggtag tttgcattct atttaaaaaa gggagtgggg agcaaatgaa aatcaaatgt    420
```

-continued

```
ggggggaaaa cactaaaggg ggcaagaaac aaaggaatta caaaccctct gctctttgta    480

tttctctgtt gtgaagaata aactgtacct gcacccggaa aaaaaaaaaa aaaaaaaaaa    540

aaaaaaaaaa aaaaaaaaaa aaaaaaaaaa aaa                                 573
```

<210> SEQ ID NO 92
<211> LENGTH: 1212
<212> TYPE: DNA
<213> ORGANISM: Homo sapiens

<400> SEQUENCE: 92

```
gccctcccca gctagaatga acattctgcc aggcagggac caatatgttt tatctctgaa     60

tctctaggac agtgctaatc aaataataga ccatcagtaa tattcgaata catgtatgga    120

taagggattt gttccaggtc acatagctag ttgttgctaa tagaaaggac aagtatgtag    180

ataccagcca cagttttttt agtatctcta cgccctattg cctttccttt aactttaagc    240

ttggtcttac ccatattttc tgtagtttaa ccttgctttt gatccctcta aggggctgtt    300

ttatataaac tcatgatcat tgttcttttt tctctctctt tccttcccct ccttccttcc    360

cttcttctct cttcctacct ctgtctcttt ttctttcctt cccagtctcc ctcctctttc    420

tttttcact tgtaggcttc tgttaattaa tcaatatggt acttattaag cactgagtca    480

aatgtctaac actgtactgt atcctatgag aaatgaaata gaagcagatt gaagacatac    540

cattacttga ggaatttaat attttattag ccccttcttc tcaatggcct ttgtgctctt    600

ctggttctgg ttatctgtgt tcttttctgg ccttctgcct tgaccatttc ttttggcccc    660

tgccttggaa attagtacat aatttaccct cattttggct tcacatgatc cagctacagc    720

aagacccaaa taagaaaaga tgttacagcg acattgatga agttggtcta acacagaaac    780

tgaaagagtg agagagacag aagaaagaag catgaagtag ggaatgagga gtagagaatg    840

tcaccaacgg ggaattacat gtgaccaaaa aatcaaaaga ttatgactgg gtacatatga    900

aaaataggta caggccaggt gtagtggctc acacctgtaa tcccagcact tggggaagcc    960

gargtgggtg gattgcttga gcccaggagt ttgagaccag cctgggcaac atggtgaaac   1020

cccatctcta caaaaaatmc aaaaattagc csggcatggt ggcacacaac tgtagtctca   1080

gctactcagg aagctgaggt gggaagayca ttgagcccag raggcaragg ttgcagtgag   1140

ctgtgatcct gccactgsac tccagcctgg gtgacagggc aagaccctgt ytmaaaaaaa   1200

aaaaaaaaaa aa                                                       1212
```

<210> SEQ ID NO 93
<211> LENGTH: 1144
<212> TYPE: DNA
<213> ORGANISM: Homo sapiens
<220> FEATURE:
<221> NAME/KEY: SITE
<222> LOCATION: (849)
<223> OTHER INFORMATION: n equals a,t,g, or c
<220> FEATURE:
<221> NAME/KEY: SITE
<222> LOCATION: (865)
<223> OTHER INFORMATION: n equals a,t,g, or c
<220> FEATURE:
<221> NAME/KEY: SITE
<222> LOCATION: (1087)
<223> OTHER INFORMATION: n equals a,t,g, or c

<400> SEQUENCE: 93

```
aattcggcac gagggacagt cagctaacta ggcaagtcac aatcttatat agcataatca     60

tggaagtaac actccatcat ctttgctgtg ttctattggt tagaagcaag tcactaggct    120
```

-continued

```
agcccatact actgggagag gattacacaa gaacatgtgg gtagaaatgg gaataacttc    180
agctgtccaa caatcttaca ggtatatcct tcatcaatca ttagctataa gtaatattgg    240
gtttccatta gtcaaagatc tgtgtgtcag caagccagga cttcaatatt ttttaaagat    300
ggtctttcta gagaaaaata cagtaataat gggatgacag aaggccatgt gttttgtttt    360
gctttgtgtt gtgtcttggt tttcctctct atgactttgc ttgttaycag cttagaaaaa    420
actaacgcag gtggggtgat agcatggggc tgtatctcag tctctgtgca gacacaaact    480
ttttcctctc ctaccagtta ccaaacattg tttattgcct gtaagctctg gaatcccaga    540
aaactttagt tttaatcttt atcatcatca ttatcacata atttacatcc tagtttagat    600
ttggagcttg ttttagatta atackttaca gagtagtttt acatgaataa gcttaaacat    660
tttcccccga ttttagttct ctggcttacc agaaaaatga aaaacaacaa caacaaaatc    720
cccaaaactg agaacccagg aatgatagac aacaaacttg tgttttaatt ttcatgattc    780
tagttgttca acctgttttt ttgacactct gtatctgcat tcatttattc actaaaaaga    840
tgcttagtna attgtaagta tcatnttagg cactgtgaat tcattgataa gatattctct    900
ctctctctct ttttttcttt tgagatggag tctctgtctg ttgcccaggc tggagtacag    960
tggcatgatc tcgtcggctc actgcagcct ctgcctcccg ggttcaatcc attctcctgc   1020
ctcagctact ccagcggctg aggcagaaga attgcttgaa cctgggcagc ggaggttgca   1080
gtgagcnaag attacgccac tgcactccag tctttctcaa aaaaaaaaaa aaaaaaaact   1140
cgag                                                                1144
```

<210> SEQ ID NO 94
<211> LENGTH: 1274
<212> TYPE: DNA
<213> ORGANISM: Homo sapiens
<220> FEATURE:
<221> NAME/KEY: SITE
<222> LOCATION: (722)
<223> OTHER INFORMATION: n equals a,t,g, or c

<400> SEQUENCE: 94

```
agctgagtgt gcgagcgcca ggggttccag ctgcacgtcc caggctctcc agcgcgcggc     60
aggccggggc gggacgagga gagctgcggg gacaacgcct gtggctgggt ccggagtgcg    120
ggtgcggcgc gggacaagcg ggcagcatgc tcagggcggt cgggagccta ctgcgccttg    180
gccgcgggct aacagtccgc tgcggccccg gggcgcctct cgaggccacg cgacggcccg    240
caccggctct tccgccccgg ggtctcccct gctactccag cggcggggcc cccagcaatt    300
ctgggcccca aggtcacggg gagattcacc gagtccccac gcagcgcagg ccttcgcagt    360
tcgacaagaa aatcctgctg tggacagggc gtttcaaatc gatggaggag atcccgcctc    420
ggatcccgcc agaaatgata gacaccgcaa gaaacaaagc tcgagtgaaa gcttgttaca    480
taatgattgg actcacaatt atcgcctgct ttgctgtgat agtgtcagcc aaaagggctg    540
tagaacgaca tgaatcctta acaagttgga acttggcaaa gaaagctaag tgscgtgaag    600
aagctgcatt ggctgcacag gctaaagcta atgatattct aagtgacaaa gtgttcacct    660
gaataccatc cctgtcatca gcaacagtag aagatgggaa aaatagaata tttaccaaaa    720
tntctgccat ggttttattt tggtaacaag aagcacaatg tctttttttat ttttattttt    780
tagtaaactt ttactgaagt ataccatgca ttcaaaaagt ggacaaaact gtatacagtc    840
tgatagatat ttatgtcgtg aacacctgtg taaccactgc caaagtgaag atgtagaata    900
```

-continued

```
ttggcaacac ttcacagcct cattcctgcc ttttctcagc cattacctcc caaacatagc    960

agtttttctg agtttcatca cctttgattc attttgcctg tttttgaact ttatataaat   1020

ggatttatac attatgcact tgtgtgtgtg gattatttac ctgacagtta taaggttaat   1080

ccacaaattg tgtgtaccat tagttcatcc attgtcattg ctgtattctg ttgtataaac   1140

ataccacaat ttattttgat atttggcaca gtttctggcc actacatata atgctaaaat   1200

gagcacattg tatatgtcat taaaatgagg ttgaactaaa aaaaaaaaaa aaaaaaaaaa   1260

aaaaaaaact cgag                                                     1274
```

<210> SEQ ID NO 95
<211> LENGTH: 1780
<212> TYPE: DNA
<213> ORGANISM: Homo sapiens

<400> SEQUENCE: 95

```
tatttgggat tatactgaac ctatttgtcc aataacctga gttttcaaat aattttagtt     60

ctataagtac tataattata taaatattaa tgaattcaga ttagctgaaa ggaaaaaaag    120

tagaagcctg actacttggt gctaactact aaagattttg gcagaatcaa tgttggattt    180

ggctttcctg tcccttcccc atgccagccc cccagagtgt tctgccttgt gctgcctccc    240

ttcacckgga gtgccacacc cctctctctg ccagttcagc tcttcattct tcaaggcctg    300

accttgtctg acccttgtgc ctctaaaccc gtggccccac ctctcttggg cacgagctat    360

gtcaggtgat gtttgtgttt ttggttatgc ccatctccat agccagacca agcactctgg    420

aagccagggt tgggtgctta tttatctgtt tgccatgcag aaaatatctt gcacaaaatt    480

acctctgtta aggaatctga agctgaattt agtttggctg agtcagggtt gggttttttt    540

taaggggctg tggggtgaaa tgttgactgg aagccaccca caaacacaca cctgctggtt    600

aggaacccgg ctgtgggtgg ttctgagctg tttggcttca ttgacagttt ctgattgccc    660

tgagcaccag gtctcatctt gcatctcatc ctggcctgga gaacattcag tttccttcca    720

acccttccca cctttccccc actcccttgg aggaactgaa gttggggttg aggagagcca    780

gatggctgga gtgggtattt gaaggtcttt ctgtcacctg ttcagtgtgg tctgccccac    840

ccctgctgac caagactgac tgaaatgtaa aataatacag accatctcaa ctcagaaagc    900

tggcacattt ttgaaagccc aagtgtgggt aagtgcgtgg aacaacgata attcacactg    960

ctttatgagt agaaattgtg agaaatattg tgccaggcaa tttgcaaaat cttggaaggt   1020

tgtgtgcact taaccaccca gcaactactc ctggatgcat cctagagaag tgccatgtga   1080

acagagaatg attttaagac ttcactgaag tattgtttag gtagcaagat tgggaaaagc   1140

ctgcatttca tcagcagaag aatggataaa taaatgagtt gtttttggtc cttggaaagt   1200

gaatatgaaa gagttacgtc tcaacacaga tagatgaaaa attatgctga gaaagttggt   1260

gaagctacat acaaggtacc cttagtgtaa agttaagcat actgtgtacc tgtgggcacg   1320

ttacttcaac ttgtttttca ctttttctgt aaaatgggat agtagtggca atctcacagg   1380

gtgattgtgg gtggggggt ggtcaatgaa gtaatgcatg taaaatgctt agaatagtgt   1440

ctagcatgta agccttgtgg acatatagaa agtgttattg ttttgcacag taatctattt   1500

tctgtggatt caaataatat gaaatgagta taaaatcatg tattggaacg atgtgtgcaa   1560

gtcaccattc tgccttccta aggcaggaga cctgatggat ttgggggggg tacatggggc   1620

cttcagttgt gttttctttg tttttttcta aaaattgatg cagaggcatc acaatgttaa   1680

gattttaaca gggtagtgtg gtgggtactt tttaactgtt tgcttaaagt gtttcaaagt   1740
```

-continued aaaaatattt cttaaaaaaa aaaaaaaaaa aaaaaaaaaa 1780

<210> SEQ ID NO 96
<211> LENGTH: 1794
<212> TYPE: DNA
<213> ORGANISM: Homo sapiens
<220> FEATURE:
<221> NAME/KEY: SITE
<222> LOCATION: (457)
<223> OTHER INFORMATION: n equals a,t,g, or c

<400> SEQUENCE: 96
gaagcattta gtaggatttt aaagaaactt gagaactgtt acataaggtg atgaattggg 60
catagcatgt aaaattatat ttaagcaagg aaatgatctc tggtgtttta atattcaact 120
tgattgcttc ctcttgggtt ctgtgtttcc cactgtgtga cctgagctgt cagaaaacct 180
taagaatttt ctttgcatca tttttccatg cagtttgtgt acatgtctca tgtacctcgt 240
ggcagccact ggttttgttc atcaaatggt gggttgtggg atgctctcct gcagtctccc 300
tctaattaaa gaggttaaat tgccgtttgc tcagccttta gttcctttcc acagcttcct 360
aggctcttaa aaattagcac tatattcctt tcagattaaa aaaaaaacaa aaacaaaaac 420
ctgtttgctg tctttactgc tgtggtcttg tctagangca aatctgaaca aactgattga 480
aaggggtgtt tggtggctgg tgttctcttt gactaaagag gcttacatgt actgtggtac 540
agtctgctta cttaaaaggt gaggcttgaa ttaaaatmca gccagataka agccagactc 600
taatcaaatg aggtgattag atcaatgaat gaagagagga gaggagtcag gtgttgcctt 660
tccctggctg ttgaatagct gatgttccag attgccctac agtgttgtgt tagggcatcc 720
aggagggatm cttttcaggc ttaggtacac ctcagtcttt aaaatgagga attakgacac 780
attcatgtgt gtgtccctaa tctgctcctg agaagagaag tgcaatcagg gtcttatttt 840
gtgaccactg acttgcacac tgagacaaaa gggccatctg caagctgaaa atagtggatt 900
ccttaaaata aaacactatt cacatttgat ggtgtggtag ttttrakaaa atgttcaagt 960
gtcaagttca ttttcattta taatctgaga cagttttata agtcacctcc ctgggggtaa 1020
aaatgcatgt tctgtcctca tagtgagaca catcttctgc ttagagtcta gaaagctcta 1080
agaaagattt atgccatctg tgcagctggc atttttatag taaaattttt tttactttgc 1140
tccaagttta agttatctca tgacaaactt tcttgaaaga ggcattcact attattatag 1200
gaagtatact yctttattga aaaggagata atgtatcagg taacttatta aagtattttc 1260
tcaaagttta gtatctttag gaatacagtg cctcaataca atataaaata ttttgtaaat 1320
aatagaatga attcatttta gaatttaaat gatgctaata aaatagacca ttattctaaa 1380
agtttaacta atttagaatc aaccctggtt gaaaataagc cttaagctgt ttttttggaa 1440
gactttaaat cctttatggc taagagatga cagacagggc cgagtgcggt kgctcatgcc 1500
tgtaatccca gcactttggg aggccgaggc gggcggatca cgaggtcagg aaatcaagac 1560
catcctggct aacacggtga aaccctgtct ctactaaaaa atacaaaaaa aattagccgg 1620
gcgtggtggc gggcgcctgt agtcccagct actcaggagg ctgaagcagg agcatggtgt 1680
gaacccagga ggcagagctt gcagtgagct gagatcacac cactgcactc cagcctgggc 1740
aacagagcga gagagtgaga ctctgtctca aaaaaaaaaa aaaaaaaaac tcga 1794

<210> SEQ ID NO 97
<211> LENGTH: 2065
<212> TYPE: DNA

-continued

<213> ORGANISM: Homo sapiens

<400> SEQUENCE: 97
ggcacgagat taaaaggcct ttcaaaagaa tgggtttgaa aaactcagta ccctttaata 60
catgtacatt tctttccttt tttcatttaa tgtaacatgt ctgttgtaac tatgtttctt 120
aaatattatt ttaaggttat gtgttcttta attatggtca aatataattt ggtcaccaaa 180
aatgaaataa tagtttaaaa caagtagctg ttactaagtg tgctaaaaat actcatttta 240
taattaattt tagttttctt agtatattat tataaattgt gccctaagtc aggtacaaat 300
gtacacatca aaatgcccat attgtatcta tctgtagtcg tttaatgtga attatatgtg 360
aatttttttc aaaattttac taaccagaat tctgttatag gcacctaacc acgcagcatg 420
aggaaaacgg cacaacacaa tcttgaggtg ccttctgaat catcagatta aattatgctt 480
catatgtttt tgcttttact gtatttcttt aaaaactcta aatctttatt catgtgtcac 540
tggattaatt tatctgataa tgtgtctcac aagaatctgt tagatcgttt attcttcagt 600
tgtactttga atggtggggt ggaagtttca ggtgaacaat ggataacaaa aagcaagtta 660
tggaagattg tgaagaggat ggaaaaactg aatacaagat accaaaaatg aaaaaaagtg 720
tcccattttt aataactata ttctattatt ttataaatgt gtaataaagg ggtccctctt 780
tattggttgt tatcccctta atctttggtc tttttcagta attttaagtt ttctgggatt 840
ttttttggtt tataaaactt gtgtttagac tttatcttgc tatggagttt tcacacttct 900
atagcacata tcctagtatc tagtcatttc tgttttaata tgaatttcag taatttaatt 960
ttaatctggt gacatattaa tcgaaaataa ggagtaatgt atacctccac atgtcctttc 1020
tttttgtctt ctcttaaatt cacaatatcc agtaggagtg gttattcaat ttcttcgtgg 1080
ttttaatcat caaatgaagt tagagaagta tactaatccc agcaactatg actcatctag 1140
gcatgttaag accataaagt aattcaggaa actattttcc tgatttttaa ataactttta 1200
gtgttatgta acatctatcc ttctgtttta gacatgcatt tcacatatag ttgaattcta 1260
gattctaaga taattcattt tgggtaatac ttcagagtac tggatctaga atcaggcttc 1320
ctgaatttaa actcaggctc cccattaact gtgtgtctgt gagcccagtt tctcatctgt 1380
aaaatggggc aacagtggca ctcatcttaa agggttggat aataaaataa tgcatgtaag 1440
gccctaagca tagtgcctgg cacagaatta ctgctcaaat gttagctgtc gtattaatat 1500
tgcacttttg cacactgatg tacatttcct gttgaccagg ctcattcttt aagcattctc 1560
catgcttaaa ccagttccat aatccctagg cctgtactcc agggattgag actgaaagga 1620
tcatttatgc catgtttctc taaaagcatc attgctggaa gacttttgat aagtctgatg 1680
tgtctcaagc tattctcagg cctttttttgt agagtttaga aatgaagtat ttgaatcaat 1740
ttagtatctc ctttactatg tttctccttt taatctcagc caaccccccta cctgcaggta 1800 aacccagcat tcattaagag ctgggttggg gtactctatt ctgtatgcat cataatagct 1860
taacattatt tagtagctgt aacttacagg tttaatgcta gatgaggatg tctcaagccg 1920
tgagtgtgct tgtgtaaaaa tggtggcaac atcatctcgt tggtaggaat tttttacttg 1980
aattgttatt ttgggaaaat gttaacagat ttcttctgga taaagaaaat aaattggatg 2040
atgtataaaa aaaaaaaaaa aaaaa 2065

<210> SEQ ID NO 98
<211> LENGTH: 1154
<212> TYPE: DNA
<213> ORGANISM: Homo sapiens -continued

<400> SEQUENCE: 98

```
ggcacgaggt gccgtgtgtg tgtgcgtgtg taagtgtgca tgtgcataca tgtgcatgtc     60
tgtaggtgca cacatctgtg tgtgtgtgtg catgtgtgtg ctgcatgtct gtggggaggt    120
gtcctccgtg agagcgtgtg acagctggga tttgcactct tgcgtgctgc cccagagacc    180
acagcctggg caggccctga ccttctgtgc cccgtgcatc gagccggtct gctgcgggtg    240
cctgtggccg ccaatgggga actcgggtga gctggcagga gggtgtgccc agagccctgg    300
ctgctgctac tgccactcag cacagctggg ccaggctgtt gccccagagg gcgtcagacg    360
tgaactttgg gaacatcttt attctgtttt aaagtgagca caaattatta gacactttcc    420
ccaaaatcca tgtgtttggg gcgtcttccg gccatgccac acatctgtgt ttgcctggct    480
gtttctgcac cgagttccgt ccacagcccg ggtttctgtt gttttaagtc ttgagccctg    540
ggccgggggc cacttctcat tggtggctgg aggctcggcc aagtgagggg ctgcttctgg    600
ttggagaggg gagtttctgg aagggggttc cccatgtgtc tccagcgctt cctgcagtct    660
ggggaggggc ttggcaggag caggtctggt gagaaagccc tggccggggg tggaggctca    720
gtcctgggag tgggcggggc agctgggctc ggggtgttaa cagggtcctg cggggggact    780
ctgtgctgag tcaaaggagc cggaagctgg tgtgggccgg gtggggtggg gaaggtgggt    840
gcaggcaggg gaggggcttt ggactgaagg tgagacccag gcctgggcaa ggatgcggtg    900
tgcccagagc tggcagagtc atctgcctga agcctgactg tggcctgggt ggggtaagga    960
aggtttggag aggctttggg gcctgcggga aagggggctg tggagagaga ggctgaccga   1020
gggctgccga gaggaagacc agtgttgctg gagcctgtgg tggagagggg cttggtgggt   1080
gaaccctcca gggaaggcct ggggcagggc tcagaggacc tggaaggtgt gcagagttgt   1140
gtccagcagg agct                                                     1154
```

<210> SEQ ID NO 99
<211> LENGTH: 615
<212> TYPE: DNA
<213> ORGANISM: Homo sapiens

<400> SEQUENCE: 99

```
ccagggagac agcagcgtgg tcagagtggt aggagctggc catcggtgag agctgctcca     60
tgcctggctg ctgggtgcta gagcttgtgg accactggct tgcctcactg tggttggtgg    120
tggcggtgac agagtgtgca gcacgaccag agtggctttt ctggctttgc ccgcccagct    180
gctccatgcc aggaggagga ggagacacct agagcctgcg acaccatggc tcgsctcgct    240
gcagtgtagg ktctacccat gtaacagatg aggaaaccaa ggagcacagt tatttactaa    300
ctcgcacaag gttcgaggcc gagctcagac ctgtggagca gaagctgagt gcgctgcagt    360
ccccgctggc ccagargccc ttcttcgagg tgccctcacc sctgggcgcc gtggacctgt    420
acgagtaygc atgcggggay gaggacctgg agccgctgtg acgccgcccg cgagaaacgc    480
cgcrcggggc cgctccccac gtgccaccac cgggccaccg cggctcgtgt aaaaactgtt    540
gtggaaaatg agtgcgtttg tacggaatga taaactttta tttattcaca aaaaaaaaaa    600
aaaaaaaaaa aattc                                                     615
```

<210> SEQ ID NO 100
<211> LENGTH: 1624
<212> TYPE: DNA
<213> ORGANISM: Homo sapiens
<220> FEATURE:

-continued

<221> NAME/KEY: SITE
<222> LOCATION: (117)
<223> OTHER INFORMATION: n equals a,t,g, or c

<400> SEQUENCE: 100
atatgtttct gaatagatcc agttgaatag tctcattcaa tttgagactg ttgaacaact 60
gttgttttct cacatacatt taaagtcagg gcacatgcgt cactgcttat ttttcgnact 120
tgacatattc cctgcatttc catgtctgcc tgtcctttag ataaacagta aaagtttccc 180
atgtgccagt atttctcaaa tggtttacat cagaatcacc tggaggactt ttaagctaga 240
ttgtttggtc ccatcccagg gattctgaat caacaggttt gcgatgggtc cagatagttt 300
acttttccaa gtttactaac aagtttgcca agttccccca gtttattacc attagaccat 360
acctttttgt ccaatcattt aaamcaaatt tttatataat aagttttatt tgtatgtaat 420
aaattttatt atataaaaat aagttttaat atatattata taaaaagttt taataaatac 480
ctaatatatt atttaatatg ataaaactta tattaaatga aattttatgc tgtyctcttg 540
tcaatctgtc ttttgttatc ttgctggtgt gcctgtcatg tgagggactg caatctgata 600
tgcctatttt ccacagtcaa agcaattaca agagaattgt tacaattacc cagttatgtc 660
aagagatttt tttttaattc actaaggtag agataaggag aatgtattaa aataggatat 720
tttaattata aatgcatgac tggggagggg gtattgtttt tgaataaaat atgaggttat 780
ttgccatgac aaaaaaaaaa agaagtagga aaatcccatg gaaatttatg ttccttctaa 840
cttttaaaac tacctaaaaa atataattga tttaaattat atctcaatat tccccattct 900
tttatatccc cttaaatagg tacccatgaa gagattatga actacttgaa ggtggagact 960
gtacggtggt gtgttggagc tggcttgtaa tgtcttatga gtgacaatcg ttagtttgag 1020
gaattttgtg agacagttgt caaattgttg ctagcttgaa atctgcggca attggagtat 1080
ttacaccata gaaatgctat aagtgaagrc ctacctttcc cttaagagct agttgttaaa 1140
cctttaccag cataccactg gaccttgtct aaaatttctt tgtgttccca gtgtcttgcc 1200
cagtagatac aagataaata ttgccagaat cagatatcag gaagtagtaa gaaaaggagt 1260
taatatgcaa actaaatcac tcgctcaatt gaataattga gatcttctgt tcatttgttc 1320
cttggacctt aatcatttgc attttggaga aaatttttc tgctttaaaa gtctgtaatt 1380
tcagtttttg tgtcggggag agggaaaaac tatttgtctg tagttgcttt ttgtgacaaa 1440
gtgaataccc actgggctaa gtttcatatc taaagcttgt cactaagaat tttcattttt 1500
aggggtcaaa aacctatttt gaaaatagtg ttgtgtgaat gctgtaagtg ttgtacatgt 1560
ctctggtttc agaattaaaa gaattcagag ttaaaaaaaa aaaaaaaaaa aaaaaaaact 1620
cgta 1624

<210> SEQ ID NO 101
<211> LENGTH: 1756
<212> TYPE: DNA
<213> ORGANISM: Homo sapiens

<400> SEQUENCE: 101
ggcacgagtt ttcctctcac atatatattg ttttgtgtcc ctggctaaag tacaagcttt 60
ttgaaggcag aaaccatgtc tttggtttct tttgtatttc ccatagcacc ttttactgtg 120
agagtgggca cacagtatat gttgtggaat gacatcctga gtgatccctc cctggctggg 180
cctcagatta aattccctga aatggaacag tcctaaccaa cacaggacag gtattctcca 240
tctggcatgt tggttgctcc tttcaacctg ctatttgaaa tggctccctt caacatcttt 300

-continued

```
ctgttcccac agtggggctt gctatggcta atgctgtact tgctgtatgt gttccaggcg    360
agtctgcgga caccagaact gacctgggag cgagtgagat ctcaagttga ccagtgatat    420
ggcctgatgg caagaggata gtactgctgg cagaggtaag ctgagactgg caaaaatact    480
cccccacaac aggagagact gcaataccca ggtcccctcc tcctcatgtt ctcgaatact    540
ttcaactcct ctgttaagca caagtttgac tactttccca atggatttta cttctaattg    600
tgaaagatct tttcattcag caattaagaa actattttgg ttccccactt ttcaccaatt    660
atcctgtctc tccacgtcaa tccacaggtt gagttagata attattacta tagaaggaat    720
tcacagatag aaccagtgcc actttgagtg atgcatacaa agagataatg tcacttgtgg    780
gatgttttaa tcactaagca caaagtagat atgcccgact gtaaccagga ctatcttagg    840
caagttctgg gaatgtatgt ttttactgat agattccctg tttttgaagt ccattcccctt   900
gaattgagcc agatgagtat aggtacctac ctagatatca attgctcaat tgatatttcc    960
ccatcctagc tcctagctca cattgacact attgactttc attttattgg cttccatgtc   1020
agtgtttgac cacttttcct ttcttaaaag ctcctcttcc ctagtcctgg attcctgaca   1080
gctataatat tagatgcctt ctattcttac cttgaagctt tctcttcttc agagaaagat   1140
accaaaatat caaggaggat aataatactt ttctcaattt tgattttcag ttggtttttt   1200
ttcttttttt atattaaaga acctgaatat gaaaatgtaa aatatacatt gtctttatct   1260
aggggcccat aagttaggag tttttagtgt ccttactgtt tcttcacatt ttcctcactt   1320
tatctcatct tctcagatac ttcagggcat ttgtaaaggg actgaactat ttcttcacaa   1380
ggaaggagta tatatgagga ggagatgggc agattgccaa atatgcatta atagctttga   1440
tgtcagtctg ctgactgatg acttgtttct agctgcccta ggaggtccca cctggtaatt   1500
ttggtgacaa aagcaagtac catgggtgtt tttggctaga tggttgagca aaaaggtggt   1560
caggcttcat aggaaacaaa ataggaaagg gtggcattgg gggcaatttc tagttcttct   1620
actgtctgaa tcaccaactc aaaatacaag gctgacaatg ctgtctttga attcaggaga   1680
agcaaactga aggagaagca caaaaatcat cacagctatg gtgaaaccct gtctctacaa   1740
aaaaaaaaaa aaaaaa                                                   1756
```

<210> SEQ ID NO 102
<211> LENGTH: 1416
<212> TYPE: DNA
<213> ORGANISM: Homo sapiens

<400> SEQUENCE: 102

```
tacatagtta ttcttttttta ttttttactc aagttacatt taatatcttt atcacaggaa    60
ggctggcaat ataaaacttc ctatgtacga aaactcaaaa ataaccaaag tggcaagtga    120
ataattcctt tgagaagcaa aagaacagta caatgtttat taacacgttt cttcctgaat    180
tttcttcaat ttttttaaac acacaaaaag cttttctgta cttagattgc tgtttgctgt    240
ttttaatgtt gttaacatgc atattattgc atttatggat agtagtagat agtgtaatat    300
acatgaaacc aacatctagg gatggctgcc ttctgagtgc tttacagatg gcacgttctc    360
ttattatcca gcttaatcac agctcctcca actgataact tcacatcatc tgcagtattt    420
ccaatctgta aatctggttg gcacaagttg gttttagcgt atttggaacc gtattttaaa    480
tcactggaac tactttgcct taatgcccat gggctgtcag ctcccaaggg ctaagaccaa    540
gtttttctta actttgtgca tatagcgtgg gacctgccca gaacaggtac tcaacaattt    600
```

-continued

```
tgctgagcag aactgtcctc aatggagaaa agaaaggaga aaggctttac tgaagactgc    660

cccaaataca aacaaattcc attttaaatg gaatatatac actttagccc ccaaatgcag    720

accagtgcac gtctgtgtag tttccgacta gtcacctggt aatagatcat tcctgtcatt    780

cacaggctca gtcccagctc tatttttcag tatcttgaat caagttctct ctcctctaat    840

catggaagaa atagacccat aactagttat tttgggtaaa tgggagctat ttaaaaaatt    900

gatattttaa aagcttaaat gaaatgttaa tcaaatatga tttatgatta ttttctttct    960

atgagtattc tttaattgtg gaaggcagtt tcttaggaag ggaacaaggg ttctctttta   1020

caaccaaaag tttggtggtg gttttttttt cacaaaatta ttgagtttaa aaaaattgat   1080

ggttgttttg catttcacct agtagcttat tcaatggttt gtttttctgc taaatgttaa   1140

ccgtcaaaac ttgaattaat ttcttaattg ctatttctac ttcaggaatc ttaagaaaga   1200

tggcttaacc cagtcagaag ggacaagcat aattttcttc catggctatt taagtaagta   1260

ttaggagagc tttcacgacc atgctatagc ttcctagtga cgcagaattg gtaagacttg   1320

tgtgatatat acatgtgtga cttgttacat atcatagcaa ctgtgtagtg ggaaggatgt   1380

aaacagttcg atatcaagct tatcgatacc gtcgac                             1416
```

```
<210> SEQ ID NO 103
<211> LENGTH: 704
<212> TYPE: DNA
<213> ORGANISM: Homo sapiens
<220> FEATURE:
<221> NAME/KEY: SITE
<222> LOCATION: (287)
<223> OTHER INFORMATION: n equals a,t,g, or c

<400> SEQUENCE: 103

actgtgtctg tcttgtctct gatatttata tgccattatg tggcctctac tgccttagga     60

ttctaatgtt cccactaaga tcagctaact cagttccact acagtgttta ccaccatcat    120

ctctcgcaaa caaagacagc cacttcagag ctcctaggaa atagtggtgc tcccatcatc    180

attgcattcc ttaatsacat ggtgaaaatt aacaatggct aaggagcctt tgtgttttct    240

cctctacaat atgcccagga atttctggca ttttggccat cttattnata ggctattact    300

gaatttmagc ctmatcctmc caaattatta atgccaaaat attaactctt gattcttagg    360

tgagtgcacc catgccaata aatttgccat gatctaacct taaatgtatt ctcatatatg    420

ctgtccaagt ttctrctgat taaaatggca aggcctttag ttctcctaca taggttttct    480

ctctccagag aaggcctcaa ttctctgact aggctatgtt gggatataac tggaggcact    540

aataggtagt agggtaaatt ctttatttta ttatttttgg agacagggag ggtcttgctt    600

tgttcagact ggagtgcagt ggtgtgatca tggctcattg caactttgaa ctcctgggcg    660

acagagcaag actccatctc aaaaaaaaaa aaaaaaaaac tcga                    704
```

```
<210> SEQ ID NO 104
<211> LENGTH: 1259
<212> TYPE: DNA
<213> ORGANISM: Homo sapiens

<400> SEQUENCE: 104

gacggggacc agagcacgtt cctggctgca gaggccacaa gtcacgctgt ctctgagagc     60

cacggtggcc tcatctctct gccataaact tgccaattat cctgctgctg cctcattgac    120

ttcgcaccca ctcttccctc tggaacagag gacactctcg ccagctctcc ccatggcgga    180

tccttgtcta gggtcaggcc tctgctccaa agtcacccct ggggacacct tctctgacca    240
```

-continued

```
gcccctcatt cctatggcct catgctgttt ttatttcttc ctaggactta gcacgtatcc    300
tagaaattaa cctgctggta tatcctgttt cttgtctgtc tctttccagt ggaatgtcac    360
catcgcccag gtggggattt ttgtgtgttt tgttcactgc tgtacamcca gcccccagca    420
cagcgsctgt ccaggacaag tgcccagtaa acacttggga agcaatgcaa gcgtgcgtgc    480
atggataagt awttctttss cagatgaggg ggctaaggtt cagagaaggc cctgggggtc    540
tcagactcat agcccagtgc tctttctgct gacacgccct ggtctctggg gcagtttgtt    600
gcctgttcag caacaaagag ggtgtgcctc gttaggggtc ctgcgtgcga atcgcagtcc    660
ctgcgtgtct tggctggagg tmacmaccct ytctgctcca gggcctgtaa ttaccactta    720
ccctggtcaa tgggtccgag agattmccct tgtaggcagg gctgtggcca gggtgctcac    780
ctggccccca gsaggtccca tgggcactgt ctggccgggc ttcatggctg acattccagg    840
tacatttcta gccctgggct gccatgggca gagggtgggg agagggtcgt gggcttcagg    900
ctggacaaac cagtcagcct tcccagctgg gccgcctgac cacccacttc ctgtggggct    960
ccttgaggcc tggagggtgg agggggtctc tgttcaaccc ccacccatgc cctcttccct   1020
tctctccctc ggcaggtcyt cccagcagyt cctgcaaaca gacccccgac ccaagccctt   1080
ccttctgsct ccactgccac cactgctgct catctctgct ggcacagaag tctcttccct   1140
ggtcttccag aaatcccctc tccacactca gccagaggga gctattaaaa ctgtgggcca   1200
gcccacatca gtccacagca aaaaaaaaaa aaaaaaaaaa aaaaaaaaaa aaactcgag    1259
```

<210> SEQ ID NO 105
<211> LENGTH: 1804
<212> TYPE: DNA
<213> ORGANISM: Homo sapiens

<400> SEQUENCE: 105

```
ggcagagcag acgcgkctcc ttggagggag tgcggtcctc tagggaggca tcgggctcct     60
aggggcttct tggcgtgtgt ggtgggattg gggtccgccg gccatggcct tcactttcgc    120
tgcgttctgc tacatgctgt ctctggtgct gtgcgctgcg ctcatcttct tcgccatctg    180
gcacataatt gcctttgatg agttaaggac agattttaag agccccatag accagtgcaa    240
tcctgttcat gcgagggaac ggttgaggaa catcgagcgc atctgcttcc ttctgcgaaa    300
gctggtgctg ccagaatact ccatccatag cctcttctgc attatgttcc tgtgtgcgca    360
agagtggctc acgctggggc tgaatgtccc tctacttttc tatcacttct ggaggtattt    420
ccactgtcca gcagatagct cagaactagc ctacgaccca ccggtggtca tgaatgccga    480
cactttgagt tactgtcaga aggaggcckg gtgtaagctg gccttctatc tcctctcctt    540
cttctactac ctttactgca tgatctacac tttagtgagc tcttaacgca aagaccatgc    600
acatcatcag agactgagat gggagaggcc tgagacggag aggtgcattt ctgctggtga    660
ctggaggagg gaccagaatg aggatacgtg agaaatagac ccggcaggca gtcagactga    720
atgggagctg gaatcacgca gcagctggga gccgagttaa ccctgcgtgt ctgtgtcacc    780
ctgtttgtca atctttggca ttcgaattcc acacacgggg tcctagagcc cttctgagca    840
tcagtggtgt gggggagtag gtgacgaaac actagacctc tcctgagaga gaattgctgc    900
ttcctgaatc cacttcattg aacagcacct tgcaagttca aatgagttcc tgggagtgga    960
ggctggaagg ccacaaggtg cttgctaagg aacagaatga cccagagtca aggccaagtc   1020
tgcagggacc tgttgaaagc ctcgagaatg kcttggctgc ccaagactct tgktgccttt   1080
```

-continued

```
cttccaagcc atggccatgc cctttttctc aaatgggarg ggctggargg tgtgtgggat   1140

ttgtcttcag ctgcaaccag ccttgagcct gctgggctat tttcagctga ggaggggtga   1200

atataggaaa aatgcatttt tgaaacrttt gcaacatgat caaggtgtta gttctccacc   1260

acacaagttg tattcttctt ttgccacctc aaaccatcac agagtcttta aatgcaaatc   1320

aattggtcaa tgctagtcaa agctatgttc ttacaaaaac cccagacagc tcagagctca   1380

gaaaatcctg tggagtggct gctctgtacc gtgggcatcc ggcagccagg aagtgagaca   1440

acataattat aactttgttt tatgatgctg catcatttgt actgtttagg tcgacrtgag   1500

gacatcatct tatttagaat tttccgtttg gcattctctt ttgggtggga gttatgctgg   1560

gggttgtaaa taatgacaag gctgagattt ttatgatgtt taaattgggc acaatgattt   1620

tgaccttatt ccccaaactt cttttctttt ctactgttta acatacacag gctatttata   1680

cacgtcccca gctcccatct gaaacctgtg actcaggttt atgaatggtg tttgtgtagc   1740

aacacattgt gtgctatgtt tattaaaatg cagcgacaaa aaaaaraaaa aaaaaaaact   1800

cgag                                                                1804
```

<210> SEQ ID NO 106
<211> LENGTH: 971
<212> TYPE: DNA
<213> ORGANISM: Homo sapiens

<400> SEQUENCE: 106

```
ctagcccggg cggatccccc gggctgcagg cgccgaggct ggaggccgag ctctgcagag     60

ttacaattga gactgctaac ccctaccttt gaagggatca acggattgtt gttgaaacaa    120

catttagttc agaatccagt cagactctgg caacttttag gtggtacttt ctattttaac    180

acctcaaggt tgaagcagaa gaataaggag aaggataagt cgaaggggaa ggcgcctgaa    240

gaggacgaak aggagaggag acgccgtgag cgggacgacc agatgtaccg agagcggctg    300

cgcaccttgc tggtcatcgc ggttgtcatg agcctcctga atgctctcag caccagcgga    360

ggcagcattt cctggaacga ctttgtccac gagatgctgg ccaagggcga ggtgcagcgc    420

gtccaggtgg tgcctgagag cgacgtggtg gaagtctacc tgcaccctgg agccgtggtg    480

tttgggcggc ctcggctagc cttgatgtac cgaatgcagg ttgcaaatat tgacaagttt    540

gaagagaagc ttcgagcagc tgaagatgag ctgaatatcg aggccaagga caggatccca    600

gtttcctaca agcgaacagg attctttggg aaatgccctg tactctgtgg ggatgacggy    660

agtgggcctg gccatcctgt ggtatgtttt ccgtctggcc gggatgactg gaggcaccgc    720

cggcgatgga cgtccaggtc ccggctcctg tgctggaaag cgttgatggg gagcgtcggc    780

gctgaccaca ckcgggagct gcggaagccc agcggttcac acaggcctcc cttcaacgta    840

gtcatcccct ggtggtggaa gcaagacgac ggcccctgac gtgcagccac acacagaaaa    900

ggctgctgtg aaacatttta atgcttcgac tttttttttc ttccagcctg gagcaacaag    960

agcaaaactc c                                                         971
```

<210> SEQ ID NO 107
<211> LENGTH: 821
<212> TYPE: DNA
<213> ORGANISM: Homo sapiens

<400> SEQUENCE: 107

```
gttttgagtg tgtgaattac atatatgaac atctgaraaa atcctataag cagtttaatc     60

aactgttcca ctccactcca agtgagtcca taggcagaat tgagttatgg ggagagcggc    120
```

ctagtaataa ttggtttgcg taatacaaag ttctactggg tagtgatgtt gtagaagttc 180
atatagaatc agctgagctt tcagaaatgg tgaaagggtg gtaatagtca taacttagat 240
tgtaattttt ttcccatagg cttttaaaaa atattcatga ggttcttttt ttatttcaat 300
agtttttggg gaacaggtgg tttttggtta catgataagt tcttcagtgg tgatttctga 360
gattttggtg cacctgtcat gtgagcagta tgaactctac tttatgtgta gtcttatccc 420
tcatgtgtat gaactccacc ttatgtgtag tcttatccct cacccactcc tgcccttccc 480
cacaagtccc caaagtccat tatatgatct ttatgccttt acatcttcac agtttagctc 540
tcacacaact tattataatt tataagtaag ccagcattgg atatagttgt attccattat 600
taatttaaga aaccttatgc aagtaattat tagtcatcat cccaaaaaaa agggagaaca 660
gggttagatt cagaatactt tgataagagc taaatactat catgagtgct gtcagtctgt 720
agtaactttc cattggtatt ctatgtcttt taggcttaca gatacttttt acactcttac 780
aaaatgtgca caagaagaag ctgcagctca gagctcgtgc c 821

<210> SEQ ID NO 108
<211> LENGTH: 1576
<212> TYPE: DNA
<213> ORGANISM: Homo sapiens
<220> FEATURE:
<221> NAME/KEY: SITE
<222> LOCATION: (252)
<223> OTHER INFORMATION: n equals a,t,g, or c
<220> FEATURE:
<221> NAME/KEY: SITE
<222> LOCATION: (804)
<223> OTHER INFORMATION: n equals a,t,g, or c

<400> SEQUENCE: 108
ctgctgctgt gtccctggtg gctgtgtttt gattggtcaa tgggctgcat ccccctcatt 60
aagtccatca gcgactggag ggtaattgca cttgcagcac tctggttctg cctaattggc 120
ctgatatgcc aagccctgtg ctctgaagac ggccacaaga gaaggatcct tactctgggc 180
ctgggatttc tcgttatccc atttctcccc gcgagtaacc tgttcttccg agtgggcttc 240
gtggtcgcgg antgttcctc tacctcccca gcattgggta ctgtgtgctg ctgacttttg 300
gattcggagc cctgagcaaa cataccaaga aaaagaaact cattgccgct gtcgtgctgg 360
gaatcttatt catcaacacg ctgagatgtg tgctgcgcac ggcgagtggc ggagtgagga 420
acagcttttc agaagtgctc tgtctgtgtg tcccctcaat gytaaggttc actmcamcat 480
tggcaaaaac ctggctgata aaggcaacca gacagctgcc atcagatact accgggaagc 540
tgtaagatta aatcccaagt atgttcatgc catgaataat cttggaaata tcttaaaaga 600
aaggaatgag ctacaggaag ctgaggagct gctgtctttg gctgttcaaa tacagccaga 660
ctttgccgct gcgtggatga atctaggcat agtgcagaat agcctgaaaa cggtttgaag 720
cagcagagca aaakttaccg gacagcaatt aaacacagaa gggaaatacc cmgactgtta 780
ctacaacctc gggcgtctgg taancgcggg gtgccctgtg cctgtggaag gaaagatggg 840
ttattttyct tatttataat aaaatgacat agtgacaccc acctagccca tacattttat 900
aaagttcytt cacatgtttc tayctcattt gaaggtagct atttgattyc cttttgagta 960
attttttaaa gctctcatta gagagcagta cagtgtgaat tagtcaagtt taagaggtca 1020
cccacgcaaa aggttaaacc caggaataaa ttaacatgtt aaagtcccgt ccgccctgta 1080
aaacagcact ccaatgggta acttcctgat aaacatcagt ttctctgttt ttaaaacaag 1140

-continued

```
aattgagtaa gaacagagat taaagtaaca aatycgtagt atgatttctg agctcccttg   1200

ttctccttct tcaagggagc agagctcttc atctgcaggg agcatttccc ccaaaaaagg   1260

cagctttgga gggcacggga tttatttgaa agggctttga cattatttgg tggaaataga   1320

aaataacgtg ttctgtagta gctttatatt tttggttatt gacaggatgt ttacgaagat   1380

ctgattgctc ttgattttct tgacaaaaat aaaatgagac acacacatag caaaattctt   1440

taaacacgaa tggttgtctt ctccctataa tcaatcattt aatttggttt caagaaaaca   1500

aatacatatg ttcctaatat atttagatgt attcaataaa cattgttaat taaaaaaaaa   1560

aaaaaaaaaa ctcgag                                                   1576
```

<210> SEQ ID NO 109
<211> LENGTH: 1779
<212> TYPE: DNA
<213> ORGANISM: Homo sapiens

<400> SEQUENCE: 109

```
aggaatacat acgatccttg tctaccagga gtctaataga aagatggaca gcgtggaccc     60

tgccagcagc caggccatgg agctctctga tgtcaccctc attgagggtg tgggtaatga    120

ggtgatggtg gtggcaggtg tggtggtgct gattctagcc ttggtcctag cttggctctc    180

tacctacgta gcagacagcg gtagcaacca gctcctgggc gctattgtgt cagcaggcga    240

cacatccgtc ctccacctgg ggcatgtgga ccacctggtg gcaggccaag gcaaccccga    300

gccaactgaa ctcccccatc catcagagga caagcaggtg caggcagcag cagtccagag    360

gcccccctga gatctgagga tagcacctgc ctccctccca gccctggcct catcactgtg    420

cggctcaaat tcctcaatga taccgaggag ctggctgtgg ctaggccaga ggataccgtg    480

ggtgccctga agagcaaata cttccctgga caagaaagcc agatgaaact gatctaccag    540

ggccgcctgc tacaagaccc agcccgcaca ctgcgttctc tgaacattac cgacaactgt    600

gtgattcact gccaccgctc acccccaggg tcagctgttc caggcccctc agcctccttg    660

gcccccctcgg ccactgagcc acccagcctt ggtgtcaatg tgggcagcct catggtgcct    720

gtctttgtgg tgctgttggg tgtggtctgg tacttccgaa tcaattaccg ccaattcttc    780

acagcacctg ccactgtctc cctggtggga gtcaccgtct tcttcagctt cctagtattt    840

gggatgtatg gacgataagg acataggaag aaaatgaaag gcatggtctt tctcctttat    900

ggcctcccca cttttcctgg ccagagctgg gcccaagggc cggggaggga ggggtggaaa    960

ggatgtgatg gaaatctcct ccataggaca caggaggcaa gtatgcggcc tccccttctc   1020

atccacagga gtacagatgt ccctcccgtg cgagcacaac tcaggtagaa atgaggatgt   1080

catcttcctt cacttttagg gtcctctgaa ggagttcaaa gctgctggcc aagctcagtg   1140

gggagcctgg gctctgagat tccctcccac ctgtggttct gactcttccc agtgtcctgc   1200

atgtctgccc ccagcaccca gggctgcctg caagggcagc tcagcatggc cccagcacaa   1260

ctccgtaggg agcctggagt atccttccat ttctcagcca aatactcatc ttttgagact   1320

gaaatcacac tggcgggaat gaagattgtg ccagccttct cttatgggca cctagccgcc   1380

ttcaccttct tcctctaccc cttagcagga atagggtgtc ctcccttctt tcaaagcact   1440

ttgcttgcat tttattttat ttttttaaga gtccttcata gagctcagtc aggaagggga   1500

tggggcacca agccaagccc ccagcattgg gagcggccag gccacagctg ctgctcccgt   1560

agtcctcagg ctgtaagcaa gagacagcac tggcccttgg ccagcgtcct accctgccca   1620

actccaagga ctgggtatgg atygctgggc cctaggctct tgcttctggg gctattggag   1680
```

-continued ggtcagtgtc tgtgactgaa taaagttcca ttttgtggta aaaaaaaaaa aaaaaaaaaa 1740
aaaaaaaaaa aaaaaaaaaa aaaaaaaaaa agggcggcc 1779

<210> SEQ ID NO 110
<211> LENGTH: 1365
<212> TYPE: DNA
<213> ORGANISM: Homo sapiens

<400> SEQUENCE: 110
ggcacgaggg agaactgctt taattagcct aggtgaaaag tagtcctagc agtgtaaata 60
tgtataatta gagttttcta atttcactgt gagatctcta acttttgagt ggcaaacaga 120
tcaagtcttt tgctcataga cttttctgtg ggttattaa aatgcaaaag ctttattttt 180
tttaataatg ccatactcca ttagtgtcag atgatggtat ggaatttgtt cccttgcttt 240
cccccactgt tactgcttca gtttatagat tgccagcaga gttcagaaat agagcaggga 300
tttacccgtt ctttgcttgg acatcccatt ttcttttgtc cagacccatg ttggcaatca 360
tgtatgaact gtgttatact tctcagtgct ttcttttttc tttttgataa gatggatatc 420
aaaaatagtt gctgtgcaaa agttagtagt cttcttcaag aagaaaacca attctttttc 480
taataatatc ctgtgaaatt gcttcattca ttcatttatt tttaagccaa atgtcagcag 540
agtgctgctg cttttatcta gtaattttga tatgtaagta ttaatgcatt tttaaaagat 600
gtctacattg aaacatgttc ttcccagtgt cctgcttatg atgctttgtt cagatttttt 660
gtaagagacc agttagtaca ctgggggtgt atattgtgta catgtgtcat tttagttagg 720
cattgtaggc caaatgtgat tataaatgaa gttgatgaac attaattttg ttattagtga 780
gttttttgaa ttgtaaatgg atttccagtt taccttctgt tgtctacagc ttttttaatt 840
ttaaggtttg actaattgta tccatctcat tgtacagtgt tttagttgca agcagaaagt 900
agaatttggt ataaagcagg ttatttctat attgaaagga gtacagttga aattgtagat 960
ttaagattgt taaaatcatg acaattctaa cttgtctatt ctaacctatt gtgtacaatc 1020
tgatttttta aaattgtaaa catgtatgat cttggtttca tgtgtttttg aaagtgttat 1080
tgtttaaaaa atgaaaaaag catatctgct aaagagctgt cagttttcat tactgactct 1140
gtaaaataca ctgttctttg tgtactgtgt gttattttgc cagctgctgc attagccttc 1200
aaaagtattt ggaaacttaa gatgaactac atttcttgca aagtacattc ctttctgtgg 1260
tattttgtcc tgtaactgaa gtatagtaat tattttatgg aaatgttagc aattctgtac 1320
caactttgaa taaaatgaaa aatttataaa aaaaaaaaaa aaaaa 1365

<210> SEQ ID NO 111
<211> LENGTH: 1957
<212> TYPE: DNA
<213> ORGANISM: Homo sapiens

<400> SEQUENCE: 111
cctagctgtc cccctgagat gaagaaagag ctccctgttg acagctgcct gccccgctca 60
ctcgagcttc accctcagaa gatggatccc aagagacagc acattcagct cctgagcagc 120
ctgactgagt gcctgacggt ggaccccctc agtgccagcg tctggaggca gctgtaccct 180
aagcacctgt cacagtccag ccttctgctg gagcacttgc tcagctcctg ggagcagatt 240
cccaagaagg tacagaagtc tttgcaagaa accattcagt ccctcaagct taccaaccag 300
gagctgctga ggaagggtag cagtaacaac caggatgtcg tcacctgtga catggcctgc 360

-continued

```
aagggcctgt tgcagcaggt tcagggtcct cggctgccct ggacgcggct cctcctgttg    420

ctgctggtct tcgctgtagg cttcctgtgc catgacctcc ggtcacacag ctccttccag    480

gcctccctta ctggccggtt gcttcgatca tctggcttct tacctgctag ccaacaagcg    540

tgtgccaagc tctactccta cagtctgcaa ggctacagct ggctggggga gacactgccg    600

ctctggggct cccacctgct caccgtggtg cggcccagct tgcagctggc ctgggctcac    660

accaatgcca cagtcagctt cctttctgcc cactgtgcct ctcaccttgc gtggtttggt    720

gacagtctca ccagtctctc tcagaggcta cagatccagc tccccgattc cgtgaatcag    780

ctactccgct atctgagaga gctgcccctg cttttccacc agaatgtgct gctgccactg    840

tggcacctct tgcttgaggc cctggcctgg gcccaggagc actgccatga ggcatgcaga    900

ggtgaggtga cctgggactg catgaagaca cagctcagtg aggctgtcca ctggacctgg    960

ctttgcctac aggacattac agtggctttc ttggactggg cacttgccct gatatcccag   1020

cagtaggccc tgccttcctg gccactgatt tctgcatggg tagaccatcc aagactgcag   1080

cgggtagaag gtggcagttc ttcatgggag tctttttaac ttggtgcctg agttctctcc   1140

taggcaagtg gccagttgcc tccacctcag ttcttccatc tttggtgggg acagggccca   1200

gcagcatctc agcctcctac ccacaattcc actgaacact tttctggccc tactgcacat   1260

ggcccccagc ctccatcctt gtgctggtag cctctcacaa ctccgccctt gccctctgcc   1320

ttccacttcc ttccatctca tttctaaacc ccaaacagct catctctaaa aagatagaac   1380

tcccagcagg tggcttctgt gttcttctga caaatgattc ctgcttctcc agactttagc   1440

agcctcctgt tcccattctt ggtcacagct ctagccacag cagaaggaaa ggggcttcca   1500

gaagaatata gcaccgcatt gggaaacagc agcctcacct ccacctgaag cctgggtgtg   1560

gctgtcagtg gacatgggga gctggatgga aatgcctctc acttcaaaat gcccagcctg   1620

ccccaaatgc ctctaagccc ctccctgtcc cctcccttgt agtcctactt cttccaactt   1680

tccattcccc atcatgctgg gggtcttggt cacaaggctc agcttctctc cactgtccat   1740

ccctcctatc atctgtagag cagagcacag gcagttgtgt gccttgggcc cagggaaccc   1800

tccatcaacc tgagacagga ctcagtatat ggttcttggg tatgccctac caggtggaat   1860

aaaggacaca gatttgattt ctaaaaaaaa aaaaaaaaaa aaaaaaaaaa aaaaaaaaaa   1920

aaaaaaaaaa aaaaaaaaaa aaaaaaaaaa aaaaaaa                            1957
```

<210> SEQ ID NO 112
<211> LENGTH: 1135
<212> TYPE: DNA
<213> ORGANISM: Homo sapiens

<400> SEQUENCE: 112

```
acgagctgaa atcttggagg gaagaaaaca catcccaccc tgcctccggg aaggggcctc     60

tcctggacat gtctcctgca gctgctgctg agccagatgg ggaccagcag gacagacacg    120

tcagcaaact catcttctgc ttctttgtct tcggcgccgt cttgttgtgt gtgggagtcc    180

tgctctccat ctttgggttc caggcatgcc aatataagcc cctcccagac tgccccatgg    240

tgctcaaggt ggcggggctg catgtgccgt ggttgggctt ggggctgtga tcctggcccg    300

ctcccgggcg caacttcagc tccgtgcagg gctgcagaga ggtcagcaga tggaccccga    360

ccgagccttc atctgtggag agagccgcca gtttgcccag tgccttatct ttgggtttct    420

gttcttgaca agcggcatgc tcatcagcgt cctgggcatt tgggtccctg gatgtggctc    480

caactgggcg caggaaccgc taaacgagac agacactggc gactcagagc cccggatgtg    540
```

-continued

```
tgggttcctt tctctgcaga tcatggggcc cttgattgtg cttgtgggat tgtgtttctt    600
cgtggttgcc catgttaaga agagaaacac gctgaatgct ggccaggatg cctctgagag    660
agaagaggga cagatccaga ttatggagcc tgtccaggtc actgtaggtg actcggtaat    720
aatatttcca ccccctccac caccttactt tcctgaatct tcagcttctg cggtcgctga    780
gagtcctgga actaacagtc tgcttccgaa tgaaaacccc ccttcatatt acagtatttt    840
caactatggg accccaactt cagagggtgc agcctctgaa agagactgtg aatctatata    900
taccatttct gggacgaatt catcttctga ggcctcacac actccacatc ttccatctga    960
attgcctcct agatatgaag aaaaagaaaa tgctgcagct acattcttgc ctctatcttc   1020
tgagccttcc ccaccgtaaa ctatggactc tagttcagtt ttatatgcaa tggatcacta   1080
ttttatttaa ttttttttaa ataaaaaata caatagcaaa aaaaaaaaaa aaaaa        1135
```

<210> SEQ ID NO 113
<211> LENGTH: 1446
<212> TYPE: DNA
<213> ORGANISM: Homo sapiens

<400> SEQUENCE: 113

```
ggcacgagcg gaagtgcaac tcgaacttgg tcggggcgcg gatcccgaga gggaaagtca     60
taacaaccgc acgagggagt tcgactggcg aactggaagg ccacgcctcc tcccgcctgc    120
cccctcagcc ctgtggctgg ggcagagctc agactgtctt ctgaagattg atgtctattt    180
ccttgagctc tttaattttg ttgccaattt ggataaacat ggcacaaatc cagcagggag    240
gtccagatga aaaagaaaag actaccgcac tgaaagattt attatctagg atagatttgg    300
atgaactaat gaaaaaagat gaaccgcctc ttgatttcct gataccctgg aaggtttgaa    360
tatgctttta atgaaaaggg acagttaaga cacataaaaa ctggggaacc atttgttttt    420
aactaccggg aagatttaca cagatggaac cagaaaagat acgaggctct aggagagatc    480
atcacgaata tgtatatgag ctcctggaaa aggattgtaa tttgaaaaaa gtatctattc    540
cagtagatgc cactgagagt gaaccaaaga gttttatctt tatgagtgag gatgctttga    600
caaatccaca gaagctgatg gttttaattc atggtagtgg tgttgtcagg gcagggcagt    660
gggctagaag acttattata aatgaagatc tggacagtgg cacacagata ccgtttatta    720
aaagagctgt ggctgaagga tatggagtaa tagtactaaa tcccaatgaa aactatattg    780
aagtagaaaa gccgaagata cacgtacagt catcatctga tagttcagat gaaccagcag    840
aaaaacggga aagaaaagat aaagtttcta aagaaacaaa gaaccgacgt gatttctatg    900
agaactatcg taacccccaa agagaaaaag aaaggatgca attgtatatc agagaaaatg    960
gttctcctga agaacatgca atctatgttt gggatcattt catagctcag gctgctgctg   1020
agaatgtgtt tttcgttgct cacagctatg gaggacttgc ttttgttgaa ctgcaactca   1080
tgatcaaaca agctaattca gatgctggga agtgctttcg cttagctatg tggaagaacc   1140
attgactgta tacaaccaac aagtgtatgg tgcaacagga gatccattga aaaccgttta   1200
taggactgaa cgacaacccc aaatgcaagt gaccatgagc aactacaaat aggtatacat   1260
atgcatttga gctgaacaga ctttctgaca tataatttag tcaaaattgc tgtatttctt   1320
ccccttaaat ttatacataa tcagcttctt gtatggaccc aaattggaga aatgtaattc   1380
agtagttggt gagaaataaa ggattgtgac ctctgtgtaa ttatcaggaa aaaaaaaaaa   1440
aaaaaa                                                               1446
```

-continued

<210> SEQ ID NO 114
<211> LENGTH: 733
<212> TYPE: DNA
<213> ORGANISM: Homo sapiens

<400> SEQUENCE: 114
tgtgaccgat atctgcaraa ttcggcttat cgygaacctg gctttggygg acctgggact 60
ggcactcact ctcccctttt gggcagccga gtcggcactg gactttcact ggcccttcgg 120
aggtgccctc tgcaagatgg ttctgacggc cactgtcctc aacgtctatg ccagcatctt 180
cctcatcaca gcgctgagcg ttgctcgcta ctgggtggtg gccatggctg cggggccagg 240
cacccacctc tcactcttct gggcccgaat agccaccctg gcagtgtggg cggcggctgc 300
cctggtgacg gtgcccacag ctgtcttcgg ggtggargt gargtgtgtg gtgtgcgcct 360
ttgcctgctg cgtttcccca gcaggtactg gctgggggcc taccagctgc agagggtggt 420
gctggctttc atggtgccct tgggcgtcat caccaccagc tacctgctgc tgctggcctt 480
cctgcagcgg cggcaacggc ggcggcagga cagcagggtc gtggcccgct ctgtccgcat 540
cctggtggct tccttcttcc tctgctggtt tcccaaccat gtggtcactc tctggggtgt 600
cctggtgaag tttgacctgg tgccctggaa cagtactttc tatactatcc agacgtatgt 660
cttccctgtc actacttgct tggcacacag caatagctgc ctsaacccaw tagcytaygt 720
cttaagcmga att 733

<210> SEQ ID NO 115
<211> LENGTH: 1518
<212> TYPE: DNA
<213> ORGANISM: Homo sapiens
<220> FEATURE:
<221> NAME/KEY: SITE
<222> LOCATION: (1146)
<223> OTHER INFORMATION: n equals a,t,g, or c

<400> SEQUENCE: 115
aggagaaact ctaaaaactg cagatattat ttcatgctat atgttccatc ctctgatgag 60
aatgtgagga aagaaaattg tatcctgcat ggctgaaaat ggtcccctac aaaaatatca 120
tgttggacaa ctaatctgag atagtggtat ctctggaaag cagtttagca ctggtgagtt 180
tggactttca tggcaggctg ccttggttca tatcttttgg taatgatact tatcctctgt 240
raggcccatt tctttatttg tggaaatgaa gacaatagag tgcttagata taatttasca 300
acaatgtccg tcacatagta aacacgtaat aaacggtagc tcttattgtt attattatta 360
ctattattac cttgaagaca ggggctctgt cttgttcatc attccatctc cagctcttag 420
cacagtccct ggcacaattc aaacatgtat ttggatgaat gacaaatagc tactgaatat 480
ttgccctgtt ccaagcattg ttagaggtac atgggacagg gcagtgaaca aaacagacaa 540
aacctcctgc tgtctcagag ttcacactct aatggggaga cccaggcaat gaggaaataa 600
ttaaaatata caatgtgtct tatggcaata aatgacaaag aaaaataaag cagaggtgag 660
aaacagtggc agtgttttgg tgatcatttg ctttgcaaca agccactccc caaagttagt 720
ggcctaaaac aatttaatca cagttcatgt tctggctaca acaatacaca tccctctcat 780
gtgcaaaata cactcactcc tccctcagag cctcgtacca ttaagggttc aggttcaaag 840
cttaagatct tatcctctga agtaggttta gggacaaaca agtcttctca ggtacttctt 900
ctggggacac agagacttgt gaactaaaag acaagttacc taccttccaa cacaactgac 960
atgcaatggg gatataggaa aagataattt caataggcgc ttctgtgcaa aagcggggga 1020

-continued

```
aatgagagtc actcagcagt cacggttcat attaatctaa aatctagcca ggcatatatc   1080

ccaagtcttc ctgatgtgag gacaagaatt atttcttgat tagggctcac ttwwtctctt   1140

tgaggntggt tcgcctcagc ttttggattt gtcctctgaa tcatccttcc ttgtctataa   1200

aatgcatgta tatactcata catacataga gagaaagaga gagagagaga gagagagact   1260

ctgtcacgca ggctggagtg caatggtgtg atctcagctc actgcaacct acaactcctg   1320

ggttcaagca attctcctgt ctcagcctcc cgagcacctg tagtccctgc tactcaggag   1380

gctgaggcag gagaattgct tgaatccgag aggcagaggt tgtcagtgag cagagattac   1440

accactgcac tccagcttgg gtgacagagc aaggcttcat ctcaaaaaaa gacaaaaaaa   1500

aaaaaaaaaa actcgtag                                                 1518
```

<210> SEQ ID NO 116
<211> LENGTH: 1054
<212> TYPE: DNA
<213> ORGANISM: Homo sapiens

<400> SEQUENCE: 116

```
ggcacgagtg tgtgtgtgtg tgtgtgtgtg tgtctgtctg tgtgtctgtg tatgtgtatt     60

tctggctgtc tgttccattg ctctatatgt ctgtttttta tgctggtacc atactgtttt    120

gattactgtt tagtaatgta ttttgaaatc aagacatgtg ggtacctcct gctttgttct    180

ccttgtcaag attattccag gtcttttgtt gcttcttcat agacgaatta actgctgatt    240

tatgaacttg aatattctga tttctttgac agttagttct cattgtaaat tgataaatta    300

tcactctggt tttatacatc agtttttagc tatggctaat aacagtcttt cctcacaatt    360

catatttagc atgttggcaa aatcatattt tggaacctgc aagacatagt ctctggtcta    420

tagtaaatca agctgctagg ttgtagtctg acaacttgtg taatatttta gctctggatg    480

atattaattt ttaagattat taaattttat ttttcagtgt tttacattga cagcaaaatt    540

gagtgggaag tacatactaa tttttctgta tcttagaatt tctttgggat cattttaact    600

attttaatgt tttaaatttt attgtgaatc tttttaagga aggctgagct gttgctacaa    660

ctgtaaaata aatattctta aagcaggcag tgatgatcaa aatcttgcca tttgaccatt    720

aagctgctag aatatgagag tgataattta ggaatgagtt gattaaagaa aataacaaag    780

tagtttacta aggaattaat aatagcaaat aaaaggttta acaaacaaca ataaatattc    840

tgttgatatt gcaccttaac tttccatcat catcttggga gctgactttt ttgctgattt    900

cattccgata agataagttc atttgaccac gtgattatta tttaatacat ctactgataa    960

ctctataata gaaagtggca gattttagat aaagggtttg tgatttttaa ggttgatatt   1020

aacaggtagt atcataaaaa aaaaaaaaaa aaaa                               1054
```

<210> SEQ ID NO 117
<211> LENGTH: 921
<212> TYPE: DNA
<213> ORGANISM: Homo sapiens

<400> SEQUENCE: 117

```
ggcacgagac gccgtgagcg ggacgaccag atgtaccgag agcggctgcg caccttgctg     60

gtcatcgcgg ttgtcatgag cctcctgaat gctctcagca ccagcggagg cagcatttcc    120

tggaacgact ttgtccacga gatgctggcc aagggcgagg tgcagcgcgt ccaggtggtg    180

cctgagagcg acgtggtgga agtctacctg caccctggag ccgtggtgtt tgggcggcct    240
```

-continued

```
cggctagcct tgatgtaccg aatgcagttg caaatattga caagtttgaa gagaagcttc    300

gagcagctga agatgagctg aatatcgagg ccaaggacag gatcccagtt tcctacaagc    360

gaacaggatt ctttgggaaa tgccctgtac tctgtgggga tgacggtagt gggcctggcc    420

atcctgtggt atgttttccg tctggccggg atgactggag gcaccgccgg cgatggacgt    480

ccatgtcccg gctcctgtgc tggaaagcgt tgatggggag cgtcggcgct gaccacacgc    540

gggagctgcg gaagcccagc ggttcacaca ggcctccctt caacgtagtc atcccctggt    600

ggtggaagca agacgacggc ccctgacgtg cagccacaca cagaaaaggc tgctgtgaac    660

attttatgct tcgacttttt ttttcttcag agacagggtg tcgttctgtc gcccaggctg    720

gagtgcagtg ccaccatcat agctcactgc agcctccacc tcctaggctc aagcttccta    780

agtagttggg actcaaggct tgagtcacca tgccaggctc tgttttttca gtctgtgaaa    840

aataaagtca tcagcatgtg aaaaaaaaaa aaaaaaaaaa aaaaaaaaaa aaaaaaaaaa    900

aaaaaaaaaa aaaaaaaaaa a                                              921
```

```
<210> SEQ ID NO 118
<211> LENGTH: 243
<212> TYPE: PRT
<213> ORGANISM: Homo sapiens

<400> SEQUENCE: 118

Met Gly Thr Leu Pro Trp Leu Leu Ala Phe Phe Ile Leu Gly Leu Gln
  1               5                  10                  15

Ala Trp Asp Thr Pro Thr Ile Val Ser Arg Lys Glu Trp Gly Ala Arg
             20                  25                  30

Pro Leu Ala Cys Arg Ala Leu Leu Thr Leu Pro Val Ala Tyr Ile Ile
         35                  40                  45

Thr Asp Gln Leu Pro Gly Met Gln Cys Gln Gln Gln Ser Val Cys Ser
     50                  55                  60

Gln Met Leu Arg Gly Leu Gln Ser His Ser Val Tyr Thr Ile Gly Trp
 65                  70                  75                  80

Cys Asp Val Ala Tyr Asn Phe Leu Val Gly Asp Asp Gly Arg Val Tyr
                 85                  90                  95

Glu Gly Val Gly Trp Asn Ile Gln Gly Leu His Thr Gln Gly Tyr Asn
            100                 105                 110

Asn Ile Ser Leu Gly Ile Ala Phe Phe Gly Asn Lys Ile Ser Ser Ser
        115                 120                 125

Pro Ser Pro Ala Ala Leu Ser Ala Ala Glu Gly Leu Ile Ser Tyr Ala
    130                 135                 140

Ile Gln Lys Gly His Leu Ser Pro Arg Tyr Ile Gln Pro Leu Leu Leu
145                 150                 155                 160

Lys Glu Glu Thr Cys Leu Asp Pro Gln His Pro Val Met Pro Arg Lys
                165                 170                 175

Val Cys Pro Asn Ile Ile Lys Arg Ser Ala Trp Glu Ala Arg Glu Thr
            180                 185                 190

His Cys Pro Lys Met Asn Leu Pro Ala Lys Tyr Val Ile Ile Ile His
        195                 200                 205

Thr Ala Gly Thr Ser Cys Thr Val Ser Thr Asp Cys Gln Thr Val Val
    210                 215                 220

Arg Asn Ile Gln Ser Phe His Met Asp Thr Arg Asn Phe Cys Asp Ile
225                 230                 235                 240

Gly Tyr Gln
```

-continued

<210> SEQ ID NO 119
<211> LENGTH: 41
<212> TYPE: PRT
<213> ORGANISM: Homo sapiens

<400> SEQUENCE: 119

```
Met Lys Arg Arg Glu Met Thr Gln Phe Leu Leu Ser Leu Val Ala Leu
  1               5                  10                  15

Asn Cys Cys Ser Ile Ser Leu Gly Arg Leu Thr Tyr Pro Gly Gly Phe
             20                  25                  30

His Leu Lys Leu Asp Pro Leu Glu Leu
         35                  40
```

<210> SEQ ID NO 120
<211> LENGTH: 526
<212> TYPE: PRT
<213> ORGANISM: Homo sapiens
<220> FEATURE:
<221> NAME/KEY: SITE
<222> LOCATION: (466)
<223> OTHER INFORMATION: Xaa equals any of the naturally occurring
      L-amino acids

<400> SEQUENCE: 120

```
Met Ala Ala Leu Thr Ile Ala Thr Gly Thr Gly Asn Trp Phe Ser Ala
  1               5                  10                  15

Leu Ala Leu Gly Val Thr Leu Leu Lys Cys Leu Leu Ile Pro Thr Tyr
             20                  25                  30

His Ser Thr Asp Phe Glu Val His Arg Asn Trp Leu Ala Ile Thr His
         35                  40                  45

Ser Leu Pro Ile Ser Gln Trp Tyr Tyr Glu Ala Thr Ser Glu Trp Thr
     50                  55                  60

Leu Asp Tyr Pro Pro Phe Phe Ala Trp Phe Glu Tyr Ile Leu Ser His
 65                  70                  75                  80

Val Ala Lys Tyr Phe Asp Gln Glu Met Leu Asn Val His Asn Leu Asn
                 85                  90                  95

Tyr Ser Ser Ser Arg Thr Leu Leu Phe Gln Arg Phe Ser Val Ile Phe
            100                 105                 110

Met Asp Val Leu Phe Val Tyr Ala Val Arg Glu Cys Cys Lys Cys Ile
        115                 120                 125

Asp Gly Lys Lys Val Gly Lys Glu Leu Thr Glu Lys Pro Lys Phe Ile
    130                 135                 140

Leu Ser Val Leu Leu Leu Trp Asn Phe Gly Leu Leu Ile Val Asp His
145                 150                 155                 160

Ile His Phe Gln Tyr Asn Gly Phe Leu Phe Gly Leu Met Leu Leu Ser
                165                 170                 175

Ile Ala Arg Leu Phe Gln Lys Arg His Met Glu Gly Ala Phe Leu Phe
            180                 185                 190

Ala Val Leu Leu His Phe Lys His Ile Tyr Leu Tyr Val Ala Pro Ala
        195                 200                 205

Tyr Gly Val Tyr Leu Leu Arg Ser Tyr Cys Phe Thr Ala Asn Lys Pro
    210                 215                 220

Asp Gly Ser Ile Arg Trp Lys Ser Phe Ser Phe Val Arg Val Ile Ser
225                 230                 235                 240

Leu Gly Leu Val Val Phe Leu Val Ser Ala Leu Ser Leu Gly Pro Phe
                245                 250                 255

Leu Ala Leu Asn Gln Leu Pro Gln Val Phe Ser Arg Leu Phe Pro Phe
```

-continued

```
            260                 265                 270

Lys Arg Gly Leu Cys His Ala Tyr Trp Ala Pro Asn Phe Trp Ala Leu
        275                 280                 285

Tyr Asn Ala Leu Asp Lys Val Leu Ser Val Ile Gly Leu Lys Leu Lys
    290                 295                 300

Phe Leu Asp Pro Asn Asn Ile Pro Lys Ala Ser Met Thr Ser Gly Leu
305                 310                 315                 320

Val Gln Gln Phe Gln His Thr Val Leu Pro Ser Val Thr Pro Leu Ala
                325                 330                 335

Thr Leu Ile Cys Thr Leu Ile Ala Ile Leu Pro Ser Ile Phe Cys Leu
            340                 345                 350

Trp Phe Lys Pro Gln Gly Pro Arg Gly Phe Leu Arg Cys Leu Thr Leu
        355                 360                 365

Cys Ala Leu Ser Ser Phe Met Phe Gly Trp His Val His Glu Lys Ala
    370                 375                 380

Ile Leu Leu Ala Ile Leu Pro Met Ser Leu Leu Ser Val Gly Lys Ala
385                 390                 395                 400

Gly Asp Ala Ser Ile Phe Leu Ile Leu Thr Thr Thr Gly His Tyr Ser
                405                 410                 415

Leu Phe Pro Leu Leu Phe Thr Ala Pro Glu Leu Pro Ile Lys Ile Leu
            420                 425                 430

Leu Met Leu Leu Phe Thr Ile Tyr Ser Ile Ser Ser Leu Lys Thr Leu
        435                 440                 445

Phe Arg Lys Glu Lys Pro Leu Phe Asn Trp Met Glu Thr Phe Tyr Leu
    450                 455                 460

Leu Xaa Leu Gly Pro Leu Glu Val Cys Cys Glu Phe Val Phe Pro Phe
465                 470                 475                 480

Thr Ser Trp Lys Val Lys Tyr Pro Phe Ile Pro Leu Leu Leu Thr Ser
                485                 490                 495

Val Tyr Cys Ala Val Gly Ile Thr Tyr Ala Trp Phe Lys Leu Tyr Val
            500                 505                 510

Ser Val Leu Ile Asp Ser Ala Ile Gly Lys Thr Lys Lys Gln
        515                 520                 525
```

```
<210> SEQ ID NO 121
<211> LENGTH: 354
<212> TYPE: PRT
<213> ORGANISM: Homo sapiens
<220> FEATURE:
<221> NAME/KEY: SITE
<222> LOCATION: (98)
<223> OTHER INFORMATION: Xaa equals any of the naturally occurring
      L-amino acids
<220> FEATURE:
<221> NAME/KEY: SITE
<222> LOCATION: (100)
<223> OTHER INFORMATION: Xaa equals any of the naturally occurring
      L-amino acids
<220> FEATURE:
<221> NAME/KEY: SITE
<222> LOCATION: (109)
<223> OTHER INFORMATION: Xaa equals any of the naturally occurring
      L-amino acids
<220> FEATURE:
<221> NAME/KEY: SITE
<222> LOCATION: (123)
<223> OTHER INFORMATION: Xaa equals any of the naturally occurring
      L-amino acids
<220> FEATURE:
<221> NAME/KEY: SITE
<222> LOCATION: (129)
<223> OTHER INFORMATION: Xaa equals any of the naturally occurring
```

-continued

L-amino acids
<220> FEATURE:
<221> NAME/KEY: SITE
<222> LOCATION: (131)
<223> OTHER INFORMATION: Xaa equals any of the naturally occurring L-amino acids
<220> FEATURE:
<221> NAME/KEY: SITE
<222> LOCATION: (159)
<223> OTHER INFORMATION: Xaa equals any of the naturally occurring L-amino acids
<220> FEATURE:
<221> NAME/KEY: SITE
<222> LOCATION: (169)
<223> OTHER INFORMATION: Xaa equals any of the naturally occurring L-amino acids
<220> FEATURE:
<221> NAME/KEY: SITE
<222> LOCATION: (171)
<223> OTHER INFORMATION: Xaa equals any of the naturally occurring L-amino acids
<220> FEATURE:
<221> NAME/KEY: SITE
<222> LOCATION: (172)
<223> OTHER INFORMATION: Xaa equals any of the naturally occurring L-amino acids
<220> FEATURE:
<221> NAME/KEY: SITE
<222> LOCATION: (175)
<223> OTHER INFORMATION: Xaa equals any of the naturally occurring L-amino acids
<220> FEATURE:
<221> NAME/KEY: SITE
<222> LOCATION: (183)
<223> OTHER INFORMATION: Xaa equals any of the naturally occurring L-amino acids
<220> FEATURE:
<221> NAME/KEY: SITE
<222> LOCATION: (188)
<223> OTHER INFORMATION: Xaa equals any of the naturally occurring L-amino acids
<220> FEATURE:
<221> NAME/KEY: SITE
<222> LOCATION: (189)
<223> OTHER INFORMATION: Xaa equals any of the naturally occurring L-amino acids
<220> FEATURE:
<221> NAME/KEY: SITE
<222> LOCATION: (225)
<223> OTHER INFORMATION: Xaa equals any of the naturally occurring L-amino acids
<220> FEATURE:
<221> NAME/KEY: SITE
<222> LOCATION: (229)
<223> OTHER INFORMATION: Xaa equals any of the naturally occurring L-amino acids
<220> FEATURE:
<221> NAME/KEY: SITE
<222> LOCATION: (231)
<223> OTHER INFORMATION: Xaa equals any of the naturally occurring L-amino acids

<400> SEQUENCE: 121

```
Met Glu Asp Gly Val Leu Lys Glu Gly Phe Leu Val Lys Arg Gly His
  1               5                  10                  15

Ile Val His Asn Trp Lys Ala Arg Trp Phe Ile Leu Arg Gln Asn Thr
             20                  25                  30

Leu Val Tyr Tyr Lys Leu Glu Gly Gly Arg Arg Val Thr Pro Pro Lys
         35                  40                  45

Gly Arg Ile Leu Leu Asp Gly Cys Thr Ile Thr Cys Pro Cys Leu Glu
     50                  55                  60

Tyr Glu Asn Arg Pro Leu Leu Ile Lys Leu Lys Thr Gln Thr Ser Thr
 65                  70                  75                  80
```

-continued

```
Glu Tyr Phe Leu Glu Ala Cys Ser Arg Glu Glu Ala Gly Cys Leu Gly
                 85                  90                  95

Leu Xaa Arg Xaa Pro Gly Leu Phe Met Gln Gly Ser Xaa Gly Lys Val
            100                 105                 110

Gln Gln Leu His Ser Leu Arg Asn Ser Phe Xaa Leu Pro Pro His Ile
        115                 120                 125

Xaa Leu Xaa Arg Ile Val Asp Lys Met His Asp Ser Asn Thr Gly Ile
    130                 135                 140

Arg Ser Ser Pro Asn Met Glu Gln Arg Ser Thr Tyr Lys Lys Xaa Phe
145                 150                 155                 160

Leu Gly Ser Ser Leu Val Asp Trp Xaa Ile Xaa Xaa Ser Phe Xaa Gly
                165                 170                 175

Ser Arg Leu Glu Ala Val Xaa Leu Ala Ser Met Xaa Xaa Glu Glu Asn
            180                 185                 190

Phe Leu Arg Ser Val Ala Val Arg Cys Met Gly Gly Ile Arg Ser Gly
        195                 200                 205

Asp Leu Ala Glu Gln Phe Leu Asp Asp Ser Thr Ala Leu Tyr Thr Phe
    210                 215                 220

Xaa Glu Ser Tyr Xaa Lys Xaa Ile Ser Pro Lys Glu Glu Ile Ser Leu
225                 230                 235                 240

Ser Thr Val Glu Leu Ser Gly Thr Val Val Lys Gln Gly Tyr Leu Ala
                245                 250                 255

Lys Gln Gly His Lys Arg Lys Asn Trp Lys Val Arg Arg Phe Val Leu
            260                 265                 270

Arg Lys Asp Pro Ala Phe Leu His Tyr Tyr Asp Pro Ser Lys Glu Glu
        275                 280                 285

Asn Arg Pro Val Gly Gly Phe Ser Leu Arg Gly Ser Leu Val Ser Ala
    290                 295                 300

Leu Glu Asp Asn Gly Val Pro Thr Gly Val Lys Gly Asn Val Gln Gly
305                 310                 315                 320

Asn Leu Phe Lys Val Ile Thr Lys Asp Asp Thr His Tyr Tyr Ile Gln
                325                 330                 335

Ala Ser Ser Lys Ala Glu Arg Ala Glu Trp Ile Glu Ala Ile Lys Lys
            340                 345                 350

Leu Thr


<210> SEQ ID NO 122
<211> LENGTH: 63
<212> TYPE: PRT
<213> ORGANISM: Homo sapiens

<400> SEQUENCE: 122

Met Trp Lys Arg Val Cys Val Cys Val Phe Leu Tyr Ile Ala Trp Val
  1               5                  10                  15

Gln Leu Trp Met Cys Ala Lys Glu Cys Glu Cys Val Cys Val Cys Val
            20                  25                  30

Lys Gly Ser Val Leu Glu Pro Thr Ser Val Cys Cys Glu Ser Gly Lys
         35                  40                  45

Arg Val Gly Glu Gly Arg Glu Met Leu Thr Leu Val Gly Ala Gly
     50                  55                  60


<210> SEQ ID NO 123
<211> LENGTH: 309
<212> TYPE: PRT
<213> ORGANISM: Homo sapiens
<220> FEATURE:
```

-continued

<221> NAME/KEY: SITE
<222> LOCATION: (129)
<223> OTHER INFORMATION: Xaa equals any of the naturally occurring
      L-amino acids
<220> FEATURE:
<221> NAME/KEY: SITE
<222> LOCATION: (178)
<223> OTHER INFORMATION: Xaa equals any of the naturally occurring
      L-amino acids
<220> FEATURE:
<221> NAME/KEY: SITE
<222> LOCATION: (187)
<223> OTHER INFORMATION: Xaa equals any of the naturally occurring
      L-amino acids
<220> FEATURE:
<221> NAME/KEY: SITE
<222> LOCATION: (262)
<223> OTHER INFORMATION: Xaa equals any of the naturally occurring
      L-amino acids
<220> FEATURE:
<221> NAME/KEY: SITE
<222> LOCATION: (308)
<223> OTHER INFORMATION: Xaa equals any of the naturally occurring
      L-amino acids

<400> SEQUENCE: 123

```
Met Phe Thr Ile Lys Leu Leu Leu Phe Ile Val Pro Leu Val Ile Ser
  1               5                  10                  15

Ser Arg Ile Asp Gln Asp Asn Ser Ser Phe Asp Ser Leu Ser Pro Glu
             20                  25                  30

Pro Lys Ser Arg Phe Ala Met Leu Asp Asp Val Lys Ile Leu Ala Asn
         35                  40                  45

Gly Leu Leu Gln Leu Gly His Gly Leu Lys Asp Phe Val His Lys Thr
     50                  55                  60

Lys Gly Gln Ile Asn Asp Ile Phe Gln Lys Leu Asn Ile Phe Asp Gln
 65                  70                  75                  80

Ser Phe Tyr Asp Leu Ser Leu Gln Thr Ser Glu Ile Lys Glu Glu Glu
                 85                  90                  95

Lys Glu Leu Arg Arg Thr Thr Tyr Lys Leu Gln Val Lys Asn Glu Glu
            100                 105                 110

Val Lys Asn Met Ser Leu Glu Leu Asn Ser Lys Leu Glu Ser Leu Leu
        115                 120                 125

Xaa Glu Lys Ile Leu Leu Gln Gln Lys Val Lys Tyr Leu Glu Glu Gln
    130                 135                 140

Leu Thr Asn Leu Ile Gln Asn Gln Pro Glu Thr Pro Glu His Pro Glu
145                 150                 155                 160

Val Thr Ser Leu Lys Thr Phe Val Glu Lys Gln Asp Asn Ser Ile Lys
                165                 170                 175

Asp Xaa Leu Gln Thr Val Glu Asp Gln Tyr Xaa Gln Leu Asn Gln Gln
            180                 185                 190

His Ser Gln Ile Lys Glu Ile Glu Asn Gln Leu Arg Arg Thr Ser Ile
        195                 200                 205

Gln Glu Pro Thr Glu Ile Ser Leu Ser Ser Lys Pro Arg Ala Pro Arg
    210                 215                 220

Thr Thr Pro Phe Leu Gln Leu Asn Glu Ile Arg Asn Val Lys His Asp
225                 230                 235                 240

Gly Ile Pro Ala Glu Cys Thr Thr Ile Tyr Asn Arg Gly Glu His Thr
                245                 250                 255

Ser Gly Met Tyr Ala Xaa Arg Pro Ser Asn Ser Gln Val Phe His Val
            260                 265                 270

Tyr Cys Asp Val Ile Ser Gly Ser Pro Trp Thr Leu Ile Gln His Arg
```

-continued

```
        275                 280                 285

Ile Asp Gly Ser Gln Asn Phe Asn Glu Thr Trp Glu Asn Tyr Lys Tyr
    290                 295                 300

Gly Phe Gly Xaa Ala
305


<210> SEQ ID NO 124
<211> LENGTH: 211
<212> TYPE: PRT
<213> ORGANISM: Homo sapiens
<220> FEATURE:
<221> NAME/KEY: SITE
<222> LOCATION: (99)
<223> OTHER INFORMATION: Xaa equals any of the naturally occurring
      L-amino acids

<400> SEQUENCE: 124

Met Ala Asn Ala Gly Leu Gln Leu Leu Gly Phe Ile Leu Ala Phe Leu
  1               5                  10                  15

Gly Trp Ile Gly Ala Ile Val Ser Thr Ala Leu Pro Gln Trp Arg Ile
             20                  25                  30

Tyr Ser Tyr Ala Gly Asp Asn Ile Val Thr Ala Gln Ala Met Tyr Glu
         35                  40                  45

Gly Leu Trp Met Ser Cys Val Ser Gln Ser Thr Gly Gln Ile Gln Cys
     50                  55                  60

Lys Val Phe Asp Ser Leu Leu Asn Leu Ser Ser Thr Leu Gln Ala Thr
 65                  70                  75                  80

Arg Ala Leu Met Val Val Gly Ile Leu Leu Gly Val Ile Ala Ile Phe
                 85                  90                  95

Val Ala Xaa Val Gly Met Lys Cys Met Lys Cys Leu Glu Asp Asp Glu
            100                 105                 110

Val Gln Lys Met Arg Met Ala Val Ile Gly Gly Ala Ile Phe Leu Leu
        115                 120                 125

Ala Gly Leu Ala Ile Leu Val Ala Thr Ala Trp Tyr Gly Asn Arg Ile
    130                 135                 140

Val Gln Glu Phe Tyr Asp Pro Met Thr Pro Val Asn Ala Arg Tyr Glu
145                 150                 155                 160

Phe Gly Gln Ala Leu Phe Thr Gly Trp Ala Ala Ala Ser Leu Cys Leu
                165                 170                 175

Leu Gly Gly Ala Leu Leu Cys Cys Ser Cys Pro Arg Lys Thr Thr Ser
            180                 185                 190

Tyr Pro Thr Pro Arg Pro Tyr Pro Lys Pro Ala Pro Ser Ser Gly Lys
        195                 200                 205

Asp Tyr Val
    210


<210> SEQ ID NO 125
<211> LENGTH: 50
<212> TYPE: PRT
<213> ORGANISM: Homo sapiens

<400> SEQUENCE: 125

Met Ala Pro Leu Trp Thr Leu Arg Pro Val Leu Val Trp Thr Thr Pro
  1               5                  10                  15

Thr Ser Met Gly Glu Val Ser Pro Trp Leu Thr Ser Thr Val Met Ala
             20                  25                  30

Lys Trp Thr Ser Ser Met Ala Thr Gly Met Ala Pro Thr Ala Ser Ile
         35                  40                  45
```

-continued

```
Cys Arg
     50


<210> SEQ ID NO 126
<211> LENGTH: 262
<212> TYPE: PRT
<213> ORGANISM: Homo sapiens

<400> SEQUENCE: 126

Met Leu Phe Ser Ala Leu Leu Leu Glu Val Ile Trp Ile Leu Ala Ala
  1               5                  10                  15

Asp Gly Gly Gln His Trp Thr Tyr Glu Gly Pro His Gly Gln Asp His
             20                  25                  30

Trp Pro Ala Ser Tyr Pro Glu Cys Gly Asn Asn Ala Gln Ser Pro Ile
         35                  40                  45

Asp Ile Gln Thr Asp Ser Val Thr Phe Asp Pro Asp Leu Pro Ala Leu
     50                  55                  60

Gln Pro His Gly Tyr Asp Gln Pro Gly Thr Glu Pro Leu Asp Leu His
 65                  70                  75                  80

Asn Asn Gly His Thr Val Gln Leu Ser Leu Pro Ser Thr Leu Tyr Leu
                 85                  90                  95

Gly Gly Leu Pro Arg Lys Tyr Val Ala Ala Gln Leu His Leu His Trp
            100                 105                 110

Gly Gln Lys Gly Ser Pro Gly Gly Ser Glu His Gln Ile Asn Ser Glu
        115                 120                 125

Ala Thr Phe Ala Glu Leu His Ile Val His Tyr Asp Ser Asp Ser Tyr
    130                 135                 140

Asp Ser Leu Ser Glu Ala Ala Glu Arg Pro Gln Gly Leu Ala Val Leu
145                 150                 155                 160

Gly Ile Leu Ile Glu Leu Glu Lys Leu Gln Gly Thr Leu Phe Ser Thr
                165                 170                 175

Glu Glu Glu Pro Ser Lys Leu Leu Val Gln Asn Tyr Arg Ala Leu Gln
            180                 185                 190

Pro Leu Asn Gln Arg Met Val Phe Ala Ser Phe Ile Gln Ala Gly Ser
        195                 200                 205

Ser Tyr Thr Thr Gly Glu Met Leu Ser Leu Gly Val Gly Ile Leu Val
    210                 215                 220

Gly Cys Leu Cys Leu Leu Leu Ala Val Tyr Phe Ile Ala Arg Lys Ile
225                 230                 235                 240

Arg Lys Lys Arg Leu Glu Asn Arg Lys Ser Val Val Phe Thr Ser Ala
                245                 250                 255

Gln Ala Thr Thr Glu Ala
            260


<210> SEQ ID NO 127
<211> LENGTH: 270
<212> TYPE: PRT
<213> ORGANISM: Homo sapiens
<220> FEATURE:
<221> NAME/KEY: SITE
<222> LOCATION: (27)
<223> OTHER INFORMATION: Xaa equals any of the naturally occurring
      L-amino acids

<400> SEQUENCE: 127

Met His Tyr Tyr Arg Tyr Ser Asn Ala Lys Val Ser Cys Trp Tyr Lys
  1               5                  10                  15
```

-continued

```
Tyr Leu Leu Phe Ser Tyr Asn Ile Ile Phe Xaa Leu Ala Gly Val Val
            20                  25                  30

Phe Leu Gly Val Gly Leu Trp Ala Trp Ser Glu Lys Gly Val Leu Ser
        35                  40                  45

Asp Leu Thr Lys Val Thr Arg Met His Gly Ile Asp Pro Val Val Leu
    50                  55                  60

Val Leu Met Val Gly Val Val Met Phe Thr Leu Gly Phe Ala Gly Cys
65                  70                  75                  80

Val Gly Ala Leu Arg Glu Asn Ile Cys Leu Leu Asn Phe Phe Cys Gly
                85                  90                  95

Thr Ile Val Leu Ile Phe Phe Leu Glu Leu Ala Val Ala Val Leu Ala
            100                 105                 110

Phe Leu Phe Gln Asp Trp Val Arg Asp Arg Phe Arg Glu Phe Phe Glu
        115                 120                 125

Ser Asn Ile Lys Ser Tyr Arg Asp Asp Ile Asp Leu Gln Asn Leu Ile
    130                 135                 140

Asp Ser Leu Gln Lys Ala Asn Gln Cys Cys Gly Ala Tyr Gly Pro Glu
145                 150                 155                 160

Asp Trp Asp Leu Asn Val Tyr Phe Asn Cys Ser Gly Ala Ser Tyr Ser
                165                 170                 175

Arg Glu Lys Cys Gly Val Pro Phe Ser Cys Cys Val Pro Asp Pro Ala
            180                 185                 190

Gln Lys Val Val Asn Thr Gln Cys Gly Tyr Asp Val Arg Ile Gln Leu
        195                 200                 205

Lys Ser Lys Trp Asp Glu Ser Ile Phe Thr Lys Gly Cys Ile Gln Ala
    210                 215                 220

Leu Glu Ser Trp Leu Pro Arg Asn Ile Tyr Ile Val Ala Gly Val Phe
225                 230                 235                 240

Ile Ala Ile Ser Leu Leu Gln Ile Phe Gly Ile Phe Leu Ala Arg Thr
                245                 250                 255

Leu Ile Ser Asp Ile Glu Ala Val Lys Ala Gly His His Phe
            260                 265                 270


<210> SEQ ID NO 128
<211> LENGTH: 91
<212> TYPE: PRT
<213> ORGANISM: Homo sapiens

<400> SEQUENCE: 128

Met Leu Arg Cys Gly Gly Arg Gly Leu Leu Leu Gly Leu Ala Val Ala
  1               5                  10                  15

Ala Ala Ala Val Met Ala Ala Arg Leu Met Gly Trp Trp Gly Pro Arg
            20                  25                  30

Ala Gly Phe Arg Leu Phe Ile Pro Glu Glu Leu Ser Arg Tyr Arg Gly
        35                  40                  45

Gly Pro Gly Asp Pro Gly Leu Tyr Leu Ala Leu Leu Gly Arg Val Tyr
    50                  55                  60

Asp Val Ser Ser Gly Arg Ser Thr Thr Ser Leu Gly Pro Thr Ile Ala
65                  70                  75                  80

Ala Ser Gln Ala Glu Thr His Pro Glu Leu Ser
                85                  90


<210> SEQ ID NO 129
<211> LENGTH: 222
<212> TYPE: PRT
<213> ORGANISM: Homo sapiens
```

-continued

<220> FEATURE:
<221> NAME/KEY: SITE
<222> LOCATION: (120)
<223> OTHER INFORMATION: Xaa equals any of the naturally occurring L-amino acids

<400> SEQUENCE: 129

```
Met Leu Trp Leu Leu Phe Phe Leu Val Thr Ala Ile His Ala Glu Leu
  1               5                  10                  15

Cys Gln Pro Gly Ala Glu Asn Ala Phe Lys Val Arg Leu Ser Ile Arg
             20                  25                  30

Thr Ala Leu Gly Asp Lys Ala Tyr Ala Trp Asp Thr Asn Glu Glu Tyr
         35                  40                  45

Leu Phe Lys Ala Met Val Ala Phe Ser Met Arg Lys Val Pro Asn Arg
     50                  55                  60

Glu Ala Thr Glu Ile Ser His Val Leu Leu Cys Asn Val Thr Gln Arg
 65                  70                  75                  80

Val Ser Phe Trp Phe Val Val Thr Asp Pro Ser Lys Asn His Thr Leu
                 85                  90                  95

Pro Ala Val Glu Val Gln Ser Ala Ile Arg Met Asn Lys Asn Arg Ile
            100                 105                 110

Asn Asn Ala Phe Phe Leu Asn Xaa Gln Thr Leu Glu Phe Leu Lys Ile
        115                 120                 125

Pro Ser Thr Leu Ala Pro Pro Met Asp Pro Ser Val Pro Ile Trp Ile
    130                 135                 140

Ile Ile Phe Gly Val Ile Phe Cys Ile Ile Ile Val Ala Ile Ala Leu
145                 150                 155                 160

Leu Ile Leu Ser Gly Ile Trp Gln Arg Arg Arg Lys Asn Lys Glu Pro
                165                 170                 175

Ser Glu Val Asp Asp Ala Glu Asp Lys Cys Glu Asn Met Ile Thr Ile
            180                 185                 190

Glu Asn Gly Ile Pro Ser Asp Pro Leu Asp Met Lys Gly Gly His Ile
        195                 200                 205

Asn Asp Ala Phe Met Thr Glu Asp Glu Arg Leu Thr Pro Leu
    210                 215                 220
```

<210> SEQ ID NO 130
<211> LENGTH: 760
<212> TYPE: PRT
<213> ORGANISM: Homo sapiens
<220> FEATURE:
<221> NAME/KEY: SITE
<222> LOCATION: (267)
<223> OTHER INFORMATION: Xaa equals any of the naturally occurring L-amino acids
<220> FEATURE:
<221> NAME/KEY: SITE
<222> LOCATION: (315)
<223> OTHER INFORMATION: Xaa equals any of the naturally occurring L-amino acids
<220> FEATURE:
<221> NAME/KEY: SITE
<222> LOCATION: (438)
<223> OTHER INFORMATION: Xaa equals any of the naturally occurring L-amino acids

<400> SEQUENCE: 130

```
Met Ile Pro Asn Gln His Asn Ala Gly Ala Gly Ser His Gln Pro Ala
  1               5                  10                  15

Val Phe Arg Met Ala Val Leu Asp Thr Asp Leu Asp His Ile Leu Pro
             20                  25                  30
```

-continued

```
Ser Ser Val Leu Pro Pro Phe Trp Ala Lys Leu Val Val Gly Ser Val
        35                  40                  45

Ala Ile Val Cys Phe Ala Arg Ser Tyr Asp Gly Asp Phe Val Phe Asp
    50                  55                  60

Asp Ser Glu Ala Ile Val Asn Asn Lys Asp Leu Gln Ala Glu Thr Pro
65                  70                  75                  80

Leu Gly Asp Leu Trp His His Asp Phe Trp Gly Ser Arg Leu Ser Ser
                85                  90                  95

Asn Thr Ser His Lys Ser Tyr Arg Pro Leu Thr Val Leu Thr Phe Arg
            100                 105                 110

Ile Asn Tyr Tyr Leu Ser Gly Gly Phe His Pro Val Gly Phe His Val
        115                 120                 125

Val Asn Ile Leu Leu His Ser Gly Ile Ser Val Leu Met Val Asp Val
    130                 135                 140

Phe Ser Val Leu Phe Gly Gly Leu Gln Tyr Thr Ser Lys Gly Arg Arg
145                 150                 155                 160

Leu His Leu Ala Pro Arg Ala Ser Leu Leu Ala Ala Leu Leu Phe Ala
                165                 170                 175

Val His Pro Val His Thr Glu Cys Val Ala Gly Val Val Gly Arg Ala
            180                 185                 190

Asp Leu Leu Cys Ala Leu Phe Phe Leu Leu Ser Phe Leu Gly Tyr Cys
        195                 200                 205

Lys Ala Phe Arg Glu Ser Asn Lys Glu Gly Ala His Ser Ser Thr Phe
    210                 215                 220

Trp Val Leu Leu Ser Ile Phe Leu Gly Ala Val Ala Met Leu Cys Lys
225                 230                 235                 240

Glu Gln Gly Ile Thr Val Leu Gly Leu Asn Ala Val Phe Asp Ile Leu
                245                 250                 255

Val Ile Gly Lys Phe Asn Val Leu Glu Ile Xaa Gln Lys Val Leu His
            260                 265                 270

Lys Asp Lys Ser Leu Glu Asn Leu Gly Met Leu Arg Asn Gly Gly Leu
        275                 280                 285

Leu Phe Arg Met Thr Leu Leu Thr Ser Gly Gly Ala Gly Met Leu Tyr
    290                 295                 300

Val Arg Trp Arg Ile Met Gly Thr Gly Pro Xaa Ala Phe Thr Glu Val
305                 310                 315                 320

Asp Asn Pro Ala Ser Phe Ala Asp Ser Met Leu Val Arg Ala Val Asn
                325                 330                 335

Tyr Asn Tyr Tyr Tyr Ser Leu Asn Ala Trp Leu Leu Leu Cys Pro Trp
            340                 345                 350

Trp Leu Cys Phe Asp Trp Ser Met Gly Cys Ile Pro Leu Ile Lys Ser
        355                 360                 365

Ile Ser Asp Trp Arg Val Ile Ala Leu Ala Ala Leu Trp Phe Cys Leu
    370                 375                 380

Ile Gly Leu Ile Cys Gln Ala Leu Cys Ser Glu Asp Gly His Lys Arg
385                 390                 395                 400

Arg Ile Leu Thr Leu Gly Leu Gly Phe Leu Val Ile Pro Phe Leu Pro
                405                 410                 415

Ala Ser Asn Leu Phe Phe Arg Val Gly Phe Val Val Ala Glu Arg Val
            420                 425                 430

Leu Tyr Leu Pro Ser Xaa Gly Tyr Cys Val Leu Leu Thr Phe Gly Phe
        435                 440                 445

Gly Ala Leu Ser Lys His Thr Lys Lys Lys Lys Leu Ile Ala Ala Val
```

-continued

```
    450                 455                 460

Val Leu Gly Ile Leu Phe Ile Asn Thr Leu Arg Cys Val Leu Arg Ser
465                 470                 475                 480

Gly Glu Trp Arg Ser Glu Glu Gln Leu Phe Arg Ser Ala Leu Ser Val
                485                 490                 495

Cys Pro Leu Asn Ala Lys Val His Tyr Asn Ile Gly Lys Asn Leu Ala
            500                 505                 510

Asp Lys Gly Asn Gln Thr Ala Ala Ile Arg Tyr Tyr Arg Glu Ala Val
        515                 520                 525

Arg Leu Asn Pro Lys Tyr Val His Ala Met Asn Asn Leu Gly Asn Ile
    530                 535                 540

Leu Lys Glu Arg Asn Glu Leu Gln Glu Ala Glu Glu Leu Leu Ser Leu
545                 550                 555                 560

Ala Val Gln Ile Gln Pro Asp Phe Ala Ala Ala Trp Met Asn Leu Gly
                565                 570                 575

Ile Val Gln Asn Ser Leu Lys Arg Phe Glu Ala Ala Glu Gln Ser Tyr
            580                 585                 590

Arg Thr Ala Ile Lys His Arg Arg Lys Tyr Pro Asp Cys Tyr Tyr Asn
        595                 600                 605

Leu Gly Arg Leu Tyr Ala Asp Leu Asn Arg His Val Asp Ala Leu Asn
    610                 615                 620

Ala Trp Arg Asn Ala Thr Val Leu Lys Pro Glu His Ser Leu Ala Trp
625                 630                 635                 640

Asn Asn Met Ile Ile Leu Leu Asp Asn Thr Gly Asn Leu Ala Gln Ala
                645                 650                 655

Glu Ala Val Gly Arg Glu Ala Leu Glu Leu Ile Pro Asn Asp His Ser
            660                 665                 670

Leu Met Phe Ser Leu Ala Asn Val Leu Gly Lys Ser Gln Lys Tyr Lys
        675                 680                 685

Glu Ser Glu Ala Leu Phe Leu Lys Ala Ile Lys Ala Asn Pro Asn Ala
    690                 695                 700

Ala Ser Tyr His Gly Asn Leu Ala Val Leu Tyr His Arg Trp Gly His
705                 710                 715                 720

Leu Asp Leu Ala Lys Lys His Tyr Glu Ile Ser Leu Gln Leu Asp Pro
                725                 730                 735

Thr Ala Ser Gly Thr Lys Glu Asn Tyr Gly Leu Leu Arg Arg Lys Leu
            740                 745                 750

Glu Leu Met Gln Lys Lys Ala Val
        755                 760


<210> SEQ ID NO 131
<211> LENGTH: 201
<212> TYPE: PRT
<213> ORGANISM: Homo sapiens

<400> SEQUENCE: 131

Met Phe Phe Leu Gly Ala Val Leu Cys Leu Ser Phe Ser Trp Leu Phe
  1               5                  10                  15

His Thr Val Tyr Cys His Ser Glu Lys Val Ser Arg Thr Phe Ser Lys
             20                  25                  30

Leu Asp Tyr Ser Gly Ile Ala Leu Leu Ile Met Gly Ser Phe Val Pro
         35                  40                  45

Trp Leu Tyr Tyr Ser Phe Tyr Cys Ser Pro Gln Pro Arg Leu Ile Tyr
     50                  55                  60
```

-continued

```
Leu Ser Ile Val Cys Val Leu Gly Ile Ser Ala Ile Ile Val Ala Gln
 65                  70                  75                  80

Trp Asp Arg Phe Ala Thr Pro Lys His Arg Gln Thr Arg Ala Gly Val
                85                  90                  95

Phe Leu Gly Leu Gly Leu Ser Gly Val Val Pro Thr Met His Phe Thr
            100                 105                 110

Ile Ala Glu Gly Phe Val Lys Ala Thr Thr Val Gly Gln Met Gly Trp
        115                 120                 125

Phe Phe Leu Met Ala Val Met Tyr Ile Thr Gly Ala Gly Leu Tyr Ala
    130                 135                 140

Ala Arg Ile Pro Glu Arg Phe Phe Pro Gly Lys Phe Asp Ile Trp Phe
145                 150                 155                 160

Gln Ser His Gln Ile Phe His Val Leu Val Val Ala Ala Ala Phe Val
                165                 170                 175

His Phe Tyr Gly Val Ser Asn Leu Gln Glu Phe Arg Tyr Gly Leu Glu
            180                 185                 190

Gly Gly Cys Thr Asp Asp Thr Leu Leu
        195                 200


<210> SEQ ID NO 132
<211> LENGTH: 46
<212> TYPE: PRT
<213> ORGANISM: Homo sapiens

<400> SEQUENCE: 132

Met Gly Arg Gln Ala Leu Leu Leu Leu Ala Leu Cys Ala Thr Gly Ala
  1               5                  10                  15

Gln Gly Leu Tyr Phe His Ile Gly Glu Thr Glu Lys Arg Cys Phe Ile
             20                  25                  30

Glu Glu Ile Pro Asp Glu Thr Met Val Ile Gly Gln Ala Gly
         35                  40                  45


<210> SEQ ID NO 133
<211> LENGTH: 305
<212> TYPE: PRT
<213> ORGANISM: Homo sapiens
<220> FEATURE:
<221> NAME/KEY: SITE
<222> LOCATION: (11)
<223> OTHER INFORMATION: Xaa equals any of the naturally occurring
      L-amino acids

<400> SEQUENCE: 133

Met Ala Leu Cys Ala Leu Thr Arg Ala Leu Xaa Ser Leu Asn Leu Ala
  1               5                  10                  15

Pro Pro Thr Val Ala Ala Pro Ala Pro Ser Leu Phe Pro Ala Ala Gln
             20                  25                  30

Met Met Asn Asn Gly Leu Leu Gln Gln Pro Ser Ala Leu Met Leu Leu
         35                  40                  45

Pro Cys Arg Pro Val Leu Thr Ser Val Ala Leu Asn Ala Asn Phe Val
     50                  55                  60

Ser Trp Lys Ser Arg Thr Lys Tyr Thr Ile Thr Pro Val Lys Met Arg
 65                  70                  75                  80

Lys Ser Gly Gly Arg Asp His Thr Gly Arg Ile Arg Val His Gly Ile
                85                  90                  95

Gly Gly Gly His Lys Gln Arg Tyr Arg Met Ile Asp Phe Leu Arg Phe
            100                 105                 110

Arg Pro Glu Glu Thr Lys Ser Gly Pro Phe Glu Glu Lys Val Ile Gln
```

-continued

```
        115                 120                 125

Val Arg Tyr Asp Pro Cys Arg Ser Ala Asp Ile Ala Leu Val Ala Gly
    130                 135                 140

Gly Ser Arg Lys Arg Trp Ile Ile Ala Thr Glu Asn Met Gln Ala Gly
145                 150                 155                 160

Asp Thr Ile Leu Asn Ser Asn His Ile Gly Arg Met Ala Val Ala Ala
                165                 170                 175

Arg Glu Gly Asp Ala His Pro Leu Gly Ala Leu Pro Val Gly Thr Leu
            180                 185                 190

Ile Asn Asn Val Glu Ser Glu Pro Gly Arg Gly Ala Gln Tyr Ile Arg
        195                 200                 205

Ala Ala Gly Thr Cys Gly Val Leu Leu Arg Lys Val Asn Gly Thr Ala
    210                 215                 220

Ile Ile Gln Leu Pro Ser Lys Arg Gln Met Gln Val Leu Glu Thr Cys
225                 230                 235                 240

Val Ala Thr Val Gly Arg Val Ser Asn Val Asp His Asn Lys Arg Val
                245                 250                 255

Ile Gly Lys Ala Gly Arg Asn Arg Trp Leu Gly Lys Arg Pro Asn Ser
            260                 265                 270

Gly Arg Trp His Arg Lys Gly Gly Trp Ala Gly Arg Lys Ile Arg Pro
        275                 280                 285

Leu Pro Pro Met Lys Ser Tyr Val Lys Leu Pro Ser Ala Ser Ala Gln
    290                 295                 300

Ser
305


<210> SEQ ID NO 134
<211> LENGTH: 81
<212> TYPE: PRT
<213> ORGANISM: Homo sapiens

<400> SEQUENCE: 134

Met Asn Gln Leu Met Phe Gln Asp Leu Leu Cys Cys Leu Cys Leu Phe
  1               5                  10                  15

Val Ile Gly Leu Ile Ser Leu Leu Arg Lys Thr Tyr Ser Cys Val Asn
            20                  25                  30

Leu Cys Lys Val Met Leu Pro Val Lys Lys Tyr Ser Thr Val Ser Thr
        35                  40                  45

Val Leu Cys Arg Asn Met Lys Leu Asn Gly Lys Asn Val Leu Met Phe
     50                  55                  60

Val Val Met Leu Leu Gly Gln Trp Met Gly Lys Leu Pro Lys Leu Ser
 65                  70                  75                  80

Pro


<210> SEQ ID NO 135
<211> LENGTH: 242
<212> TYPE: PRT
<213> ORGANISM: Homo sapiens
<220> FEATURE:
<221> NAME/KEY: SITE
<222> LOCATION: (88)
<223> OTHER INFORMATION: Xaa equals any of the naturally occurring
      L-amino acids
<220> FEATURE:
<221> NAME/KEY: SITE
<222> LOCATION: (139)
<223> OTHER INFORMATION: Xaa equals any of the naturally occurring
      L-amino acids
```

-continued

<400> SEQUENCE: 135

```
Met Glu Gln Ala Arg Lys Ser Ser Thr Val Ser Leu Leu Ile Thr Val
  1               5                  10                  15

Leu Phe Ala Val Ala Phe Ser Val Leu Leu Leu Ser Cys Lys Asp His
             20                  25                  30

Val Gly Tyr Ile Phe Thr Thr Asp Arg Asp Ile Ile Asn Leu Val Ala
         35                  40                  45

Gln Val Val Pro Ile Tyr Ala Val Ser His Leu Phe Glu Ala Leu Ala
     50                  55                  60

Cys Thr Ser Gly Gly Val Leu Arg Gly Ser Gly Asn Gln Lys Val Gly
 65                  70                  75                  80

Ala Ile Val Asn Thr Ile Gly Xaa Tyr Val Val Gly Leu Pro Ile Gly
                 85                  90                  95

Ile Ala Leu Met Phe Ala Thr Thr Leu Gly Val Met Gly Leu Trp Ser
            100                 105                 110

Gly Ile Ile Ile Cys Thr Val Phe Gln Ala Val Cys Phe Leu Gly Phe
        115                 120                 125

Ile Ile Gln Leu Asn Trp Lys Lys Ala Cys Xaa Gln Ala Gln Val His
    130                 135                 140

Ala Asn Leu Lys Val Asn Asn Val Pro Arg Ser Gly Asn Ser Ala Leu
145                 150                 155                 160

Pro Gln Asp Pro Leu His Pro Gly Cys Pro Glu Asn Leu Glu Gly Ile
                165                 170                 175

Leu Thr Asn Asp Val Gly Lys Thr Gly Glu Pro Gln Ser Asp Gln Gln
            180                 185                 190

Met Arg Gln Glu Glu Pro Leu Pro Glu His Pro Gln Asp Gly Ala Lys
        195                 200                 205

Leu Ser Arg Lys Gln Leu Val Leu Arg Arg Gly Leu Leu Leu Leu Gly
    210                 215                 220

Val Phe Leu Ile Leu Leu Val Gly Ile Leu Val Arg Phe Tyr Val Arg
225                 230                 235                 240

Ile Gln
```

<210> SEQ ID NO 136
<211> LENGTH: 285
<212> TYPE: PRT
<213> ORGANISM: Homo sapiens

<400> SEQUENCE: 136

```
Met Val Val Ala Gly Val Val Val Leu Ile Leu Ala Leu Val Leu Ala
  1               5                  10                  15

Trp Leu Ser Thr Tyr Val Ala Asp Ser Gly Ser Asn Gln Leu Leu Gly
             20                  25                  30

Ala Ile Val Ser Ala Gly Asp Thr Ser Val Leu His Leu Gly His Val
         35                  40                  45

Asp His Leu Val Ala Gly Gln Gly Asn Pro Glu Pro Thr Glu Leu Pro
     50                  55                  60

His Pro Ser Glu Gly Asn Asp Glu Lys Ala Glu Glu Ala Gly Glu Gly
 65                  70                  75                  80

Arg Gly Asp Ser Thr Gly Glu Ala Gly Ala Gly Gly Gly Val Glu Pro
                 85                  90                  95

Ser Leu Glu His Leu Leu Asp Ile Gln Gly Leu Pro Lys Arg Gln Ala
            100                 105                 110

Gly Ala Gly Ser Ser Ser Pro Glu Ala Pro Leu Arg Ser Glu Asp Ser
```

-continued

```
        115                 120                 125

Thr Cys Leu Pro Pro Ser Pro Gly Leu Ile Thr Val Arg Leu Lys Phe
    130                 135                 140

Leu Asn Asp Thr Glu Glu Leu Ala Val Ala Arg Pro Glu Asp Thr Val
145                 150                 155                 160

Gly Ala Leu Lys Ser Lys Tyr Phe Pro Gly Gln Glu Ser Gln Met Lys
                165                 170                 175

Leu Ile Tyr Gln Gly Arg Leu Leu Gln Asp Pro Ala Arg Thr Leu Arg
            180                 185                 190

Ser Leu Asn Ile Thr Asp Asn Cys Val Ile His Cys His Arg Ser Pro
        195                 200                 205

Pro Gly Ser Ala Val Pro Gly Pro Ser Ala Ser Leu Ala Pro Ser Ala
    210                 215                 220

Thr Glu Pro Pro Ser Leu Gly Val Asn Val Gly Ser Leu Met Val Pro
225                 230                 235                 240

Val Phe Val Val Leu Leu Gly Val Val Trp Tyr Phe Arg Ile Asn Tyr
                245                 250                 255

Arg Gln Phe Phe Thr Ala Pro Ala Thr Val Ser Leu Val Gly Val Thr
            260                 265                 270

Val Phe Phe Ser Phe Leu Val Phe Gly Met Tyr Gly Arg
        275                 280                 285


<210> SEQ ID NO 137
<211> LENGTH: 157
<212> TYPE: PRT
<213> ORGANISM: Homo sapiens
<220> FEATURE:
<221> NAME/KEY: SITE
<222> LOCATION: (114)
<223> OTHER INFORMATION: Xaa equals any of the naturally occurring
      L-amino acids
<220> FEATURE:
<221> NAME/KEY: SITE
<222> LOCATION: (119)
<223> OTHER INFORMATION: Xaa equals any of the naturally occurring
      L-amino acids
<220> FEATURE:
<221> NAME/KEY: SITE
<222> LOCATION: (120)
<223> OTHER INFORMATION: Xaa equals any of the naturally occurring
      L-amino acids
<220> FEATURE:
<221> NAME/KEY: SITE
<222> LOCATION: (121)
<223> OTHER INFORMATION: Xaa equals any of the naturally occurring
      L-amino acids

<400> SEQUENCE: 137

Met Asp Ala Met Ile Leu Leu Asn Val Leu Ala Leu Thr Arg Leu Ala
  1               5                  10                  15

Lys Ala Ala Ala Thr Asn Phe Val Ala Gln Gly Arg Gly Thr Ile Ile
             20                  25                  30

Asn Ile Gly Ser Ile Val Ala Leu Ala Pro Lys Val Leu Asn Gly Val
         35                  40                  45

Tyr Gly Gly Thr Lys Ala Phe Val Gln Ala Phe Ser Glu Ser Leu Gln
     50                  55                  60

His Glu Leu Ser Asp Lys Gly Val Val Val Gln Val Val Leu Pro Gly
 65                  70                  75                  80

Ala Thr Ala Thr Glu Phe Trp Asp Ile Ala Gly Leu Pro Val Lys Gln
                 85                  90                  95

Pro Ala Gly Ser His Gly Asp Asp His Arg Lys Pro Gly Gly Arg Arg
```

-continued

```
        100                 105                 110

Pro Xaa Arg Pro Cys Pro Xaa Xaa Xaa Val Thr Ile Pro Ser Leu Pro
        115                 120                 125

Asp Ser Ala Asp Trp Asp Thr Thr Asn Ala Arg Gly Trp Pro Trp Val
    130                 135                 140

Arg Thr Cys Arg Thr Val Asn Pro Pro Leu Val Met Gly
145                 150                 155
```

<210> SEQ ID NO 138
<211> LENGTH: 308
<212> TYPE: PRT
<213> ORGANISM: Homo sapiens
<220> FEATURE:
<221> NAME/KEY: SITE
<222> LOCATION: (87)
<223> OTHER INFORMATION: Xaa equals any of the naturally occurring L-amino acids
<220> FEATURE:
<221> NAME/KEY: SITE
<222> LOCATION: (185)
<223> OTHER INFORMATION: Xaa equals any of the naturally occurring L-amino acids

<400> SEQUENCE: 138

```
Met Pro Val Pro Trp Phe Leu Leu Ser Leu Ala Leu Gly Arg Ser Pro
  1               5                  10                  15

Val Val Leu Ser Leu Glu Arg Leu Val Gly Pro Gln Asp Ala Thr His
             20                  25                  30

Cys Ser Pro Gly Leu Ser Cys Arg Leu Trp Asp Ser Asp Ile Leu Cys
         35                  40                  45

Leu Pro Gly Asp Ile Val Pro Ala Pro Gly Pro Val Leu Ala Pro Thr
     50                  55                  60

His Leu Gln Thr Glu Leu Val Leu Arg Cys Gln Lys Glu Thr Asp Cys
 65                  70                  75                  80

Asp Leu Cys Leu Arg Val Xaa Val His Leu Ala Val His Gly His Trp
                 85                  90                  95

Glu Glu Pro Glu Asp Glu Glu Lys Phe Gly Gly Ala Ala Asp Leu Gly
            100                 105                 110

Val Glu Glu Pro Arg Asn Ala Ser Leu Gln Ala Gln Val Val Leu Ser
        115                 120                 125

Phe Gln Ala Tyr Pro Thr Ala Arg Cys Val Leu Leu Glu Val Gln Val
    130                 135                 140

Pro Ala Ala Leu Val Gln Phe Gly Gln Ser Val Gly Ser Val Val Tyr
145                 150                 155                 160

Asp Cys Phe Glu Ala Ala Leu Gly Ser Glu Val Arg Ile Trp Ser Tyr
                165                 170                 175

Thr Gln Pro Arg Tyr Glu Lys Glu Xaa Asn His Thr Gln Gln Leu Pro
            180                 185                 190

Asp Cys Arg Gly Leu Glu Val Trp Asn Ser Ile Pro Ser Cys Trp Ala
        195                 200                 205

Leu Pro Trp Leu Asn Val Ser Ala Asp Gly Asp Asn Val His Leu Val
    210                 215                 220

Leu Asn Val Ser Glu Glu Gln His Phe Gly Leu Ser Leu Tyr Trp Asn
225                 230                 235                 240

Gln Val Gln Gly Pro Pro Lys Pro Arg Trp His Lys Asn Leu Thr Gly
                245                 250                 255

Pro Gln Ile Ile Thr Leu Asn His Thr Asp Leu Val Pro Cys Leu Cys
            260                 265                 270
```

-continued

```
Ile Gln Val Trp Pro Leu Glu Pro Asp Ser Val Arg Arg Thr Ser Ala
        275                 280                 285

Pro Ser Gly Arg Thr Pro Ala His Thr Arg Thr Ser Gly Lys Pro Pro
    290                 295                 300

Asp Cys Asp Cys
305
```

<210> SEQ ID NO 139
<211> LENGTH: 508
<212> TYPE: PRT
<213> ORGANISM: Homo sapiens

<400> SEQUENCE: 139

```
Met Asp Pro Lys Leu Gly Arg Met Ala Ala Ser Leu Leu Ala Val Leu
  1               5                  10                  15

Leu Leu Leu Leu Leu Glu Arg Gly Met Phe Ser Ser Pro Ser Pro Pro
             20                  25                  30

Pro Ala Leu Leu Glu Lys Val Phe Gln Tyr Ile Asp Leu His Gln Asp
         35                  40                  45

Glu Phe Val Gln Thr Leu Lys Glu Trp Val Ala Ile Glu Ser Asp Ser
     50                  55                  60

Val Gln Pro Val Pro Arg Phe Arg Gln Glu Leu Phe Arg Met Met Ala
 65                  70                  75                  80

Val Ala Ala Asp Thr Leu Gln Arg Leu Gly Ala Arg Val Ala Ser Val
                 85                  90                  95

Asp Met Gly Pro Gln Gln Leu Pro Asp Gly Gln Ser Leu Pro Ile Pro
            100                 105                 110

Pro Val Ile Leu Ala Glu Leu Gly Ser Asp Pro Thr Lys Gly Thr Val
        115                 120                 125

Cys Phe Tyr Gly His Leu Asp Val Gln Pro Ala Asp Arg Gly Asp Gly
    130                 135                 140

Trp Leu Thr Asp Pro Tyr Val Leu Thr Glu Val Asp Gly Lys Leu Tyr
145                 150                 155                 160

Gly Arg Gly Ala Thr Asp Asn Lys Gly Pro Val Leu Ala Trp Ile Asn
                165                 170                 175

Ala Val Ser Ala Phe Arg Ala Leu Glu Gln Asp Leu Pro Val Asn Ile
            180                 185                 190

Lys Phe Ile Ile Glu Gly Met Glu Glu Ala Gly Ser Val Ala Leu Glu
        195                 200                 205

Glu Leu Val Glu Lys Glu Lys Asp Arg Phe Phe Ser Gly Val Asp Tyr
    210                 215                 220

Ile Val Ile Ser Asp Asn Leu Trp Ile Ser Gln Arg Lys Pro Ala Ile
225                 230                 235                 240

Thr Tyr Gly Thr Arg Gly Asn Ser Tyr Phe Met Val Glu Val Lys Cys
                245                 250                 255

Arg Asp Gln Asp Phe His Ser Gly Thr Phe Gly Gly Ile Leu His Glu
            260                 265                 270

Pro Met Ala Asp Leu Val Ala Leu Leu Gly Ser Leu Val Asp Ser Ser
        275                 280                 285

Gly His Ile Leu Val Pro Gly Ile Tyr Asp Glu Val Val Pro Leu Thr
    290                 295                 300

Glu Glu Glu Ile Asn Thr Tyr Lys Ala Ile His Leu Asp Leu Glu Glu
305                 310                 315                 320

Tyr Arg Asn Ser Ser Arg Val Glu Lys Phe Leu Phe Asp Thr Lys Glu
```

-continued

```
                325                 330                 335

Glu Ile Leu Met His Leu Trp Arg Tyr Pro Ser Leu Ser Ile His Gly
            340                 345                 350

Ile Glu Gly Ala Phe Asp Glu Pro Gly Thr Lys Thr Val Ile Pro Gly
        355                 360                 365

Arg Val Ile Gly Lys Phe Ser Ile Arg Leu Val Pro His Met Asn Val
    370                 375                 380

Ser Ala Val Glu Lys Gln Val Thr Arg His Leu Glu Asp Val Phe Ser
385                 390                 395                 400

Lys Arg Asn Ser Ser Asn Lys Met Val Val Ser Met Thr Leu Gly Leu
                405                 410                 415

His Pro Trp Ile Ala Asn Ile Asp Asp Thr Gln Tyr Leu Ala Ala Lys
            420                 425                 430

Arg Ala Ile Arg Thr Val Phe Gly Thr Glu Pro Asp Met Ile Arg Asp
        435                 440                 445

Gly Ser Thr Ile Pro Ile Ala Lys Met Phe Gln Glu Ile Val His Lys
    450                 455                 460

Ser Val Val Leu Ile Pro Leu Gly Ala Val Asp Asp Gly Glu His Ser
465                 470                 475                 480

Gln Asn Glu Lys Ile Asn Arg Trp Asn Tyr Ile Glu Gly Thr Lys Leu
                485                 490                 495

Phe Ala Ala Phe Phe Leu Glu Met Ala Gln Leu His
            500                 505


<210> SEQ ID NO 140
<211> LENGTH: 506
<212> TYPE: PRT
<213> ORGANISM: Homo sapiens
<220> FEATURE:
<221> NAME/KEY: SITE
<222> LOCATION: (65)
<223> OTHER INFORMATION: Xaa equals any of the naturally occurring
      L-amino acids
<220> FEATURE:
<221> NAME/KEY: SITE
<222> LOCATION: (112)
<223> OTHER INFORMATION: Xaa equals any of the naturally occurring
      L-amino acids
<220> FEATURE:
<221> NAME/KEY: SITE
<222> LOCATION: (423)
<223> OTHER INFORMATION: Xaa equals any of the naturally occurring
      L-amino acids
<220> FEATURE:
<221> NAME/KEY: SITE
<222> LOCATION: (425)
<223> OTHER INFORMATION: Xaa equals any of the naturally occurring
      L-amino acids

<400> SEQUENCE: 140

Met Gly Met Arg Arg His Ser Leu Met Leu Leu Pro Trp Trp Leu Gly
  1               5                  10                  15

Ala Ala Gly Arg Lys Glu Cys His Arg Glu Gln Leu Val Ala Ala Val
             20                  25                  30

Glu Val Thr Glu Gln Glu Thr Lys Val Pro Lys Lys Thr Val Ile Ile
         35                  40                  45

Glu Glu Thr Ile Thr Thr Val Val Lys Ser Pro Arg Gly Gln Arg Arg
     50                  55                  60

Xaa Pro Ser Lys Ser Pro Ser Arg Ser Pro Ser Arg Cys Ser Ala Ser
 65                  70                  75                  80

Pro Leu Arg Pro Gly Leu Leu Ala Pro Asp Leu Leu Tyr Leu Pro Gly
```

-continued

```
                85                  90                  95

Ala Gly Gln Pro Arg Arg Pro Glu Ala Glu Pro Gly Gln Lys Pro Xaa
            100                 105                 110

Val Pro Thr Leu Tyr Val Thr Glu Ala Glu Ala His Ser Pro Ala Leu
        115                 120                 125

Pro Gly Leu Ser Gly Pro Gln Pro Lys Trp Val Glu Val Glu Glu Thr
    130                 135                 140

Ile Glu Val Arg Val Lys Lys Met Gly Pro Gln Gly Val Ser Pro Thr
145                 150                 155                 160

Thr Glu Val Pro Arg Ser Ser Ser Gly His Leu Phe Thr Leu Pro Gly
                165                 170                 175

Ala Thr Pro Gly Gly Asp Pro Asn Ser Asn Asn Ser Asn Asn Lys Leu
            180                 185                 190

Leu Ala Gln Glu Ala Trp Ala Gln Gly Thr Ala Met Val Gly Val Arg
        195                 200                 205

Glu Pro Leu Val Phe Arg Val Asp Ala Arg Gly Ser Val Asp Trp Ala
    210                 215                 220

Ala Ser Gly Met Gly Ser Leu Glu Glu Glu Gly Thr Met Glu Glu Ala
225                 230                 235                 240

Gly Glu Glu Glu Gly Glu Asp Gly Asp Ala Phe Val Thr Glu Glu Ser
                245                 250                 255

Gln Asp Thr His Ser Leu Gly Asp Arg Asp Pro Lys Ile Leu Thr His
            260                 265                 270

Asn Gly Arg Met Leu Thr Leu Ala Asp Leu Glu Asp Tyr Val Pro Gly
        275                 280                 285

Glu Gly Glu Thr Phe His Cys Gly Gly Pro Gly Pro Gly Ala Pro Asp
    290                 295                 300

Asp Pro Pro Cys Glu Val Ser Val Ile Gln Arg Glu Ile Gly Glu Pro
305                 310                 315                 320

Thr Val Gly Ser Leu Cys Cys Ser Ala Trp Gly Met His Trp Val Pro
                325                 330                 335

Glu Ala Leu Ser Ala Ser Leu Gly Leu Ser Pro Val Gly Arg His His
            340                 345                 350

Arg Asp Pro Arg Ser Val Ala Leu Arg Ala Pro Pro Ser Ser Cys Gly
        355                 360                 365

Arg Pro Arg Leu Gly Leu Trp Ala Val Leu Pro Gly Arg Ser Leu Ser
    370                 375                 380

Ala Pro Ala Ser Gly Val Leu Arg Thr Val Ala Arg Ala Ala Ser Pro
385                 390                 395                 400

Gln Ser Phe Pro Pro Arg Pro Ser Thr Ser Gly Gln Trp Gly Arg Arg
                405                 410                 415

Ser Pro Phe Thr Ser Val Xaa Gly Xaa Gly Pro Ser Tyr Leu Thr Gln
            420                 425                 430

Leu Gln Pro Gly Gly Leu Gly Gly Ala Cys Asn Val Gly Met Thr Gly
        435                 440                 445

Ser Lys Thr Ser Ala Leu Gly Cys Phe Leu Ser Ala Trp Gln Glu Pro
    450                 455                 460

Gln Asp Cys Gly Arg Arg Met Trp Pro Trp Ala Phe Val Leu Phe Pro
465                 470                 475                 480

His Gly Pro Gly Pro Ser Leu Leu Ala Pro Ala Thr Ala Ala Arg Pro
                485                 490                 495

Asp Met Ala Leu Pro Leu Leu Gln Ser Trp
            500                 505
```

-continued

<210> SEQ ID NO 141
<211> LENGTH: 48
<212> TYPE: PRT
<213> ORGANISM: Homo sapiens

<400> SEQUENCE: 141

```
Met Arg Leu Leu Leu Leu Leu Leu Val Ala Ala Ser Ala Met Val Arg
  1               5                  10                  15

Ser Glu Ala Ser Ala Asn Leu Gly Gly Val Pro Ser Lys Arg Leu Lys
             20                  25                  30

Met Gln Tyr Ala Thr Gly Pro Leu Leu Lys Phe Gln Ile Cys Val Ser
         35                  40                  45
```

<210> SEQ ID NO 142
<211> LENGTH: 130
<212> TYPE: PRT
<213> ORGANISM: Homo sapiens
<220> FEATURE:
<221> NAME/KEY: SITE
<222> LOCATION: (64)
<223> OTHER INFORMATION: Xaa equals any of the naturally occurring L-amino acids
<220> FEATURE:
<221> NAME/KEY: SITE
<222> LOCATION: (65)
<223> OTHER INFORMATION: Xaa equals any of the naturally occurring L-amino acids

<400> SEQUENCE: 142

```
Met Leu Met Pro Val His Phe Leu Leu Leu Leu Leu Leu Leu Leu Gly
  1               5                  10                  15

Gly Pro Arg Thr Gly Leu Pro His Lys Phe Tyr Lys Ala Lys Pro Ile
             20                  25                  30

Phe Ser Cys Leu Asn Thr Ala Leu Ser Glu Ala Glu Lys Gly Gln Trp
         35                  40                  45

Glu Asp Ala Ser Leu Leu Ser Lys Arg Ser Phe His Tyr Leu Arg Xaa
     50                  55                  60

Xaa Thr Pro Leu Arg Glu Arg Arg Arg Arg Ala Lys Arg Lys Arg Leu
 65                  70                  75                  80

Ser Pro Ser Leu Gly Pro Gly Val Glu Pro Glu Ala Pro Gly Thr Asp
                 85                  90                  95

Thr Cys Pro Lys His Ser Pro Gly Glu Ser His Ala Arg Thr Arg Pro
            100                 105                 110

Arg Val Pro Thr Ala Pro Ser Ser Pro Cys Pro Ser Thr Ser Pro Pro
        115                 120                 125

Thr Ser
    130
```

<210> SEQ ID NO 143
<211> LENGTH: 43
<212> TYPE: PRT
<213> ORGANISM: Homo sapiens
<220> FEATURE:
<221> NAME/KEY: SITE
<222> LOCATION: (25)
<223> OTHER INFORMATION: Xaa equals any of the naturally occurring L-amino acids
<220> FEATURE:
<221> NAME/KEY: SITE
<222> LOCATION: (29)
<223> OTHER INFORMATION: Xaa equals any of the naturally occurring L-amino acids -continued

<400> SEQUENCE: 143

```
Met Ala Phe Leu Gln Ser Ala Ser Tyr Val Met Val Ile Leu Cys Ala
  1               5                  10                  15

Cys Val Ile Ile Ile Gly Ile Leu Xaa Tyr Ala Phe Xaa Phe Glu Thr
             20                  25                  30

Leu Ser Pro Lys Lys Arg Arg Asp Ile Glu Ile
         35                  40
```

<210> SEQ ID NO 144
<211> LENGTH: 91
<212> TYPE: PRT
<213> ORGANISM: Homo sapiens

<400> SEQUENCE: 144

```
Met Gln Leu Ile Glu Ser Arg Phe His Phe Arg Cys Val Trp Ile Leu
  1               5                  10                  15

His Leu Leu Ala Leu Phe Ser Thr Trp Pro Pro Lys Asp Pro Glu Gly
             20                  25                  30

Ser Pro Pro Ser Ala Thr Ser Ser Pro Leu Thr Pro His Leu Ser Leu
         35                  40                  45

Thr Leu Pro Phe Lys Gln Ala Pro Val Ser Asn Val Ser Ser Ala Ile
     50                  55                  60

His Val Met Leu Asp Lys Ser Val Ser Leu Ser Glu Ile Gln Phe Ser
 65                  70                  75                  80

His Met Pro Asn Gly Lys Arg Ala Ser Thr Leu
                 85                  90
```

<210> SEQ ID NO 145
<211> LENGTH: 266
<212> TYPE: PRT
<213> ORGANISM: Homo sapiens

<400> SEQUENCE: 145

```
Met Glu Leu Leu Thr Ala Leu Leu Arg Leu Phe Leu Ser Arg Pro Ala
  1               5                  10                  15

Glu Cys Gln Asp Met Leu Gly Arg Leu Leu Tyr Tyr Cys Ile Glu Glu
             20                  25                  30

Glu Lys Asp Met Ala Val Arg Asp Arg Gly Leu Phe Tyr Tyr Arg Leu
         35                  40                  45

Leu Leu Val Gly Ile Asp Glu Val Lys Arg Ile Leu Cys Ser Pro Lys
     50                  55                  60

Ser Asp Pro Thr Leu Gly Leu Leu Glu Asp Pro Ala Glu Arg Pro Val
 65                  70                  75                  80

Asn Ser Trp Ala Ser Asp Phe Asn Thr Leu Val Pro Val Tyr Gly Lys
                 85                  90                  95

Ala His Trp Ala Thr Ile Ser Lys Cys Gln Gly Ala Glu Arg Cys Asp
            100                 105                 110

Pro Glu Leu Pro Lys Thr Ser Ser Phe Ala Ala Ser Gly Pro Leu Ile
        115                 120                 125

Pro Glu Glu Asn Lys Glu Arg Val Gln Glu Leu Pro Asp Ser Gly Ala
    130                 135                 140

Leu Met Leu Val Pro Asn Arg Gln Leu Thr Ala Asp Tyr Phe Glu Lys
145                 150                 155                 160

Thr Trp Leu Ser Leu Lys Val Ala His Gln Gln Val Leu Pro Trp Arg
                165                 170                 175

Gly Glu Phe His Pro Asp Thr Leu Gln Met Ala Leu Gln Val Val Asn
```

-continued

```
            180                 185                 190

Ile Gln Thr Ile Ala Met Ser Arg Ala Gly Ser Arg Pro Trp Lys Ala
        195                 200                 205

Tyr Leu Ser Ala Gln Asp Asp Thr Gly Cys Leu Phe Leu Thr Glu Leu
    210                 215                 220

Leu Leu Glu Pro Gly Asn Ser Glu Met Gln Ile Ser Val Lys Gln Asn
225                 230                 235                 240

Glu Ala Arg Thr Glu Thr Leu Asn Ser Phe Ile Ser Val Leu Glu Thr
                245                 250                 255

Val Ile Gly Thr Ile Glu Glu Ile Lys Ser
            260                 265


<210> SEQ ID NO 146
<211> LENGTH: 434
<212> TYPE: PRT
<213> ORGANISM: Homo sapiens

<400> SEQUENCE: 146

Met Ala Pro Glu Gly Leu Val Pro Ala Val Leu Trp Gly Leu Ser Leu
  1               5                  10                  15

Phe Leu Asn Leu Pro Gly Pro Ile Trp Leu Gln Pro Ser Pro Pro Pro
             20                  25                  30

Gln Ser Ser Pro Pro Pro Gln Pro His Pro Cys His Thr Cys Arg Gly
         35                  40                  45

Leu Val Asp Ser Phe Asn Lys Gly Leu Glu Arg Thr Ile Arg Asp Asn
     50                  55                  60

Phe Gly Gly Gly Asn Thr Ala Trp Glu Glu Glu Asn Leu Ser Lys Tyr
 65                  70                  75                  80

Lys Asp Ser Glu Thr Arg Leu Val Glu Val Leu Glu Gly Val Cys Ser
                 85                  90                  95

Lys Ser Asp Phe Glu Cys His Arg Leu Leu Glu Leu Ser Glu Glu Leu
            100                 105                 110

Val Glu Ser Trp Trp Phe His Lys Gln Gln Glu Ala Pro Asp Leu Phe
        115                 120                 125

Gln Trp Leu Cys Ser Asp Ser Leu Lys Leu Cys Cys Pro Ala Gly Thr
    130                 135                 140

Phe Gly Pro Ser Cys Leu Pro Cys Pro Gly Gly Thr Glu Arg Pro Cys
145                 150                 155                 160

Gly Gly Tyr Gly Gln Cys Glu Gly Glu Gly Thr Arg Gly Gly Ser Gly
                165                 170                 175

His Cys Asp Cys Gln Ala Gly Tyr Gly Gly Glu Ala Cys Gly Gln Cys
            180                 185                 190

Gly Leu Gly Tyr Phe Glu Ala Glu Arg Asn Ala Ser His Leu Val Cys
        195                 200                 205

Ser Ala Cys Phe Gly Pro Cys Ala Arg Cys Ser Gly Pro Glu Glu Ser
    210                 215                 220

Asn Cys Leu Gln Cys Lys Lys Gly Trp Ala Leu His His Leu Lys Cys
225                 230                 235                 240

Val Asp Ile Asp Glu Cys Gly Thr Glu Gly Ala Asn Cys Gly Ala Asp
                245                 250                 255

Gln Phe Cys Val Asn Thr Glu Gly Ser Tyr Glu Cys Arg Asp Cys Ala
            260                 265                 270

Lys Ala Cys Leu Gly Cys Met Gly Ala Gly Pro Gly Arg Cys Lys Lys
        275                 280                 285
```

-continued

```
Cys Ser Pro Gly Tyr Gln Gln Val Gly Ser Lys Cys Leu Asp Val Asp
    290                 295                 300

Glu Cys Glu Thr Glu Val Cys Pro Gly Glu Asn Lys Gln Cys Glu Asn
305                 310                 315                 320

Thr Glu Gly Gly Tyr Arg Cys Ile Cys Ala Glu Gly Tyr Lys Gln Met
                325                 330                 335

Glu Gly Ile Cys Val Lys Glu Gln Ile Pro Gly Ala Phe Pro Ile Leu
            340                 345                 350

Thr Asp Leu Thr Pro Glu Thr Thr Arg Arg Trp Lys Leu Gly Ser His
        355                 360                 365

Pro His Ser Thr Tyr Val Lys Met Lys Met Gln Arg Asp Glu Ala Thr
    370                 375                 380

Phe Pro Gly Leu Tyr Gly Lys Gln Val Ala Lys Leu Gly Ser Gln Ser
385                 390                 395                 400

Arg Gln Ser Asp Arg Gly Thr Arg Leu Ile His Val Ile Asn Ala Leu
                405                 410                 415

Pro Pro Thr Cys Pro Pro Gln Lys Lys Lys Lys Lys Lys Lys Lys Gly
            420                 425                 430

Gly Arg


<210> SEQ ID NO 147
<211> LENGTH: 236
<212> TYPE: PRT
<213> ORGANISM: Homo sapiens
<220> FEATURE:
<221> NAME/KEY: SITE
<222> LOCATION: (55)
<223> OTHER INFORMATION: Xaa equals any of the naturally occurring
      L-amino acids

<400> SEQUENCE: 147

Met Ile Ser Leu Pro Gly Pro Leu Val Thr Asn Leu Leu Arg Phe Leu
  1               5                  10                  15

Phe Leu Gly Leu Ser Ala Leu Ala Pro Pro Ser Arg Ala Gln Leu Gln
            20                  25                  30

Leu His Leu Pro Ala Asn Arg Leu Gln Ala Val Glu Gly Gly Glu Val
        35                  40                  45

Val Leu Pro Ala Trp Tyr Xaa Leu His Gly Glu Val Ser Ser Ser Gln
     50                  55                  60

Pro Trp Glu Val Pro Phe Val Met Trp Phe Phe Lys Gln Lys Glu Lys
 65                  70                  75                  80

Glu Asp Gln Val Leu Ser Tyr Ile Asn Gly Val Thr Thr Ser Lys Pro
                 85                  90                  95

Gly Val Ser Leu Val Tyr Ser Met Pro Ser Arg Asn Leu Ser Leu Arg
            100                 105                 110

Leu Glu Gly Leu Gln Glu Lys Asp Ser Gly Pro Tyr Ser Cys Ser Val
        115                 120                 125

Asn Val Gln Asp Lys Gln Gly Lys Ser Arg Gly His Ser Ile Lys Thr
    130                 135                 140

Leu Glu Leu Asn Val Leu Val Pro Pro Ala Pro Pro Ser Cys Arg Leu
145                 150                 155                 160

Gln Gly Val Pro His Val Gly Ala Asn Val Thr Leu Ser Cys Gln Ser
                165                 170                 175

Pro Arg Ser Lys Pro Ala Val Gln Tyr Gln Trp Asp Arg Gln Leu Pro
            180                 185                 190

Ser Phe Gln Thr Phe Phe Ala Pro Ala Leu Asp Val Ile Arg Gly Ser
```

-continued

```
        195                 200                 205

Leu Ser Leu Thr Asn Leu Ser Ser Ser Met Ala Gly Val Tyr Val Cys
    210                 215                 220

Lys Ala His Asn Glu Val Gly Thr Ala Asn Val Met
225                 230                 235


<210> SEQ ID NO 148
<211> LENGTH: 99
<212> TYPE: PRT
<213> ORGANISM: Homo sapiens
<220> FEATURE:
<221> NAME/KEY: SITE
<222> LOCATION: (78)
<223> OTHER INFORMATION: Xaa equals any of the naturally occurring
      L-amino acids

<400> SEQUENCE: 148

Met Thr Trp Gly Thr Trp Leu Val His Thr Phe Leu Cys Ser Val Ala
  1               5                  10                  15

Ser Ala Lys Thr Leu Lys Ser Val Arg Lys Tyr Leu Ser Leu Cys Ser
             20                  25                  30

Pro Ile Gly Ser Ser Phe Val Val Ser Glu Gly Ser Tyr Leu Asp Ile
         35                  40                  45

Ser Asp Trp Leu Asn Pro Ala Lys Leu Ser Leu Tyr Tyr Gln Ile Asn
     50                  55                  60

Ala Thr Ser Pro Trp Val Arg Asp Leu Cys Gly Gln Arg Xaa Thr Asp
 65                  70                  75                  80

Ala Cys Glu Gln Leu Cys Asp Pro Glu Thr Gly Glu Pro Trp Glu Pro
                 85                  90                  95

Gly Trp Gly


<210> SEQ ID NO 149
<211> LENGTH: 69
<212> TYPE: PRT
<213> ORGANISM: Homo sapiens
<220> FEATURE:
<221> NAME/KEY: SITE
<222> LOCATION: (56)
<223> OTHER INFORMATION: Xaa equals any of the naturally occurring
      L-amino acids

<400> SEQUENCE: 149

Met Tyr Lys Ala Phe Leu Leu Ala Leu Thr Thr Val Phe Tyr Leu Gly
  1               5                  10                  15

Ile Leu Asn Ser His Phe His Gly Cys Val Leu Cys Asn Thr Asn Val
             20                  25                  30

Phe Lys Trp Tyr Ser His Pro Val Gly Gln Leu Ser Lys Arg Cys Leu
         35                  40                  45

Asp Ala Ser Lys Leu Ala Tyr Xaa Lys Phe Thr Ser Ile Lys Tyr Gln
     50                  55                  60

Cys Asn Tyr Ser Thr
 65


<210> SEQ ID NO 150
<211> LENGTH: 61
<212> TYPE: PRT
<213> ORGANISM: Homo sapiens

<400> SEQUENCE: 150

Met His Glu Cys Gln Ser Phe Pro Leu Cys Val His Leu Arg Leu Val
  1               5                  10                  15
```

-continued

```
Leu Leu Leu Ser Phe Lys Thr Gln Val His Glu Phe His Glu Val Phe
            20                  25                  30

Pro His Tyr Ser His Phe Asn Phe Pro Ser Leu Asn Asn Tyr Asp Ile
        35                  40                  45

Asn Leu Leu Leu Asn His Glu Leu Trp His Thr Thr Pro
    50                  55                  60


<210> SEQ ID NO 151
<211> LENGTH: 88
<212> TYPE: PRT
<213> ORGANISM: Homo sapiens
<220> FEATURE:
<221> NAME/KEY: SITE
<222> LOCATION: (73)
<223> OTHER INFORMATION: Xaa equals any of the naturally occurring
      L-amino acids

<400> SEQUENCE: 151

Met Asn Leu Val Gly Phe Cys Leu Phe Ile Cys Leu Leu Leu Met Leu
  1               5                  10                  15

Leu Leu Leu Leu Leu Phe Ser Lys Phe Ser Ile Val Glu Lys Tyr Ala
            20                  25                  30

Ala Pro Glu Glu Met Ile Gly His Ser Pro Ala Trp Cys Trp Thr Leu
        35                  40                  45

Ser Ser Leu Ala Gln Pro Ser Pro Asp Leu Ser Val Tyr Leu Thr Leu
    50                  55                  60

Val Phe Tyr Ile Leu Gln Arg Gln Xaa Gln Asn Asn Pro Asn Leu Thr
 65                  70                  75                  80

Gln Ile Pro Gly Ile His Leu Ile
                 85


<210> SEQ ID NO 152
<211> LENGTH: 78
<212> TYPE: PRT
<213> ORGANISM: Homo sapiens
<220> FEATURE:
<221> NAME/KEY: SITE
<222> LOCATION: (40)
<223> OTHER INFORMATION: Xaa equals any of the naturally occurring
      L-amino acids
<220> FEATURE:
<221> NAME/KEY: SITE
<222> LOCATION: (46)
<223> OTHER INFORMATION: Xaa equals any of the naturally occurring
      L-amino acids
<220> FEATURE:
<221> NAME/KEY: SITE
<222> LOCATION: (60)
<223> OTHER INFORMATION: Xaa equals any of the naturally occurring
      L-amino acids

<400> SEQUENCE: 152

Met Met Gly Asn Asp Leu Leu His Leu Val Phe Leu Gln Leu Ser Leu
  1               5                  10                  15

Gly Val Ala Ser Gly Gly Trp Ile Leu Trp Pro Leu Arg Arg Leu Gly
            20                  25                  30

Gly Ala His Thr Ser Lys Asp Xaa Asn Lys Asn Gly His Xaa Val His
        35                  40                  45

Cys Leu Val Ile Thr Asn Glu Pro Leu Val Ser Xaa Lys Lys Ile Gly
    50                  55                  60

Leu Ser Ser Pro His Thr Cys Pro Ser Thr Leu Gln Gln Phe
 65                  70                  75
```

-continued

<210> SEQ ID NO 153
<211> LENGTH: 123
<212> TYPE: PRT
<213> ORGANISM: Homo sapiens

<400> SEQUENCE: 153

Met Met Val Trp Asn Leu Phe Pro Cys Phe Pro Pro Leu Leu Leu Leu
1 5 10 15

Gln Phe Ile Asp Cys Gln Gln Ser Ser Glu Ile Glu Gln Gly Phe Thr
20 25 30

Arg Ser Leu Leu Gly His Pro Ile Phe Phe Cys Pro Asp Pro Cys Trp
35 40 45

Gln Ser Cys Met Asn Cys Val Ile Leu Ser Val Leu Ser Phe Phe Phe
50 55 60

Leu Ile Arg Trp Ile Ser Lys Ile Val Ala Val Gln Lys Leu Glu Ser
65 70 75 80

Ser Ser Arg Arg Lys Pro Ile Leu Phe Leu Ile Ile Ser Cys Glu Ile
85 90 95

Ala Ser Phe Ile His Leu Phe Leu Ser Gln Met Ser Ala Glu Cys Cys
100 105 110

Cys Phe Tyr Leu Val Ile Leu Ile Cys Lys Tyr
115 120

<210> SEQ ID NO 154
<211> LENGTH: 68
<212> TYPE: PRT
<213> ORGANISM: Homo sapiens

<400> SEQUENCE: 154

Met Tyr Leu Gly Ser Arg Ile Val Lys Ala Leu Phe Phe Leu Leu Phe
1 5 10 15

Cys Ile Phe His Ile Trp Tyr Asn Glu His Val Leu Arg Thr Val Leu
20 25 30

Asp Leu Arg Lys Tyr Ala Asn Thr Val Gln Ile Val Leu Ala Ser Pro
35 40 45

Met Pro Ser Ser Ser Ile Ala Asn Val Ser Thr Leu Val Trp Cys Val
50 55 60

Cys Cys Asn Gly
65

<210> SEQ ID NO 155
<211> LENGTH: 43
<212> TYPE: PRT
<213> ORGANISM: Homo sapiens

<400> SEQUENCE: 155

Met Lys Cys Thr Glu Lys Cys Val Val Val Phe Phe Thr Phe Val Leu
1 5 10 15

Tyr Met Tyr Val Tyr Trp Val Leu Trp Ala Val Glu Ala Lys Leu Thr
20 25 30

Ser His Val Ala His Glu Met Leu Val Ser Cys
35 40

<210> SEQ ID NO 156
<211> LENGTH: 63
<212> TYPE: PRT
<213> ORGANISM: Homo sapiens

<400> SEQUENCE: 156

-continued

Met Phe Ile Leu Leu Ile Val Phe Val Phe Ser Lys Ser Lys Gln Val
1 5 10 15

Leu Ser Ile Cys Leu Lys Ile Phe Lys Val Glu Ile Asn Ser Ile Ser
20 25 30

Phe Cys Lys Asn Lys Lys Tyr Lys Asp Leu Pro Tyr Ala Phe Ala Ser
35 40 45

Glu Lys Thr Gly Arg Thr Tyr Ser Asn Val Asn Asn Asp Tyr Leu
50 55 60

<210> SEQ ID NO 157
<211> LENGTH: 61
<212> TYPE: PRT
<213> ORGANISM: Homo sapiens

<400> SEQUENCE: 157

Met Ile Val Tyr Trp Met Ile Trp Ala Leu Arg Ser Pro Leu Thr Thr
1 5 10 15

Ala Gln Asn Ile His Ser Ser Thr Ala Leu Thr Glu Phe Ala Lys Cys
20 25 30

Ile Lys Glu Val Thr Trp Arg Val Arg Ser Tyr Glu Thr Ile Cys Arg
35 40 45

Lys Trp Gly Lys Lys Gly His Met Ala Gln Leu Lys Leu
50 55 60

<210> SEQ ID NO 158
<211> LENGTH: 82
<212> TYPE: PRT
<213> ORGANISM: Homo sapiens

<400> SEQUENCE: 158

Met Arg Phe Phe Leu Glu Cys Val Leu Leu Ile Cys Phe Arg Ala Met
1 5 10 15

Ser Ala Ile Tyr Thr His Thr Ser Ile Gly Asn Ala Gln Lys Leu Phe
20 25 30

Thr Asp Gly Ser Ala Phe Arg Arg Val Arg Glu Pro Leu Pro Lys Glu
35 40 45

Gly Lys Ser Trp Pro Gln Leu Glu Gln Ala Cys Leu Gly Pro Cys Ser
50 55 60

Val Phe Gln Leu Gln Thr Ala Cys Ile Ile Pro Ser Cys Tyr Ser Ser
65 70 75 80

Phe Thr

<210> SEQ ID NO 159
<211> LENGTH: 46
<212> TYPE: PRT
<213> ORGANISM: Homo sapiens

<400> SEQUENCE: 159

Met Cys Cys Ala Ser His Pro Cys Gln Arg Glu Gly Trp Leu Cys Val
1 5 10 15

Ile Phe Thr Val Phe Leu Lys Val Thr Val Cys Val Phe Thr Phe Val
20 25 30

Gln Ile Thr Gly Ser Lys Ala Ala Asn Ser Ala Ile Thr Cys
35 40 45

<210> SEQ ID NO 160
<211> LENGTH: 187
<212> TYPE: PRT

-continued

<213> ORGANISM: Homo sapiens

<400> SEQUENCE: 160

```
Met Ala Cys Lys Gly Leu Leu Gln Gln Val Gln Gly Pro Arg Leu Pro
  1               5                  10                  15

Trp Thr Arg Leu Leu Leu Leu Leu Leu Val Phe Ala Val Gly Phe Leu
             20                  25                  30

Cys His Asp Leu Pro Val Thr Gln Leu Leu Pro Gly Trp Leu Gly Glu
         35                  40                  45

Thr Leu Pro Leu Trp Gly Ser His Leu Leu Thr Val Val Arg Pro Ser
     50                  55                  60

Leu Gln Leu Ala Trp Ala His Thr Asn Ala Thr Val Ser Phe Leu Ser
 65                  70                  75                  80

Ala His Cys Ala Ser His Leu Ala Trp Phe Gly Asp Ser Leu Thr Ser
                 85                  90                  95

Leu Ser Gln Arg Leu Gln Ile Gln Leu Pro Asp Ser Val Asn Gln Leu
            100                 105                 110

Leu Arg Tyr Leu Arg Glu Leu Pro Leu Leu Phe His Gln Asn Val Leu
        115                 120                 125

Leu Pro Leu Trp His Leu Leu Leu Glu Ala Leu Ala Trp Ala Gln Glu
    130                 135                 140

His Cys His Glu Ala Cys Arg Gly Glu Val Thr Trp Asp Cys Met Lys
145                 150                 155                 160

Thr Gln Leu Ser Glu Ala Val His Trp Thr Trp Leu Cys Tyr Arg Thr
                165                 170                 175

Leu Gln Trp Leu Ser Trp Thr Gly His Leu Pro
            180                 185
```

<210> SEQ ID NO 161
<211> LENGTH: 113
<212> TYPE: PRT
<213> ORGANISM: Homo sapiens

<400> SEQUENCE: 161

```
Met Ile Phe Ser Met Pro Gln Gln Gly Ser Ser Trp Phe Leu Ser Ala
  1               5                  10                  15

Phe Leu Ser Trp Pro Leu Ala Leu Ala Pro Ala Leu Thr Pro Thr Pro
             20                  25                  30

Ala Pro Ala Arg Ala Pro Gly Ala Pro Arg Ala Ala Gly Ala Pro Gly
         35                  40                  45

Arg Val Ala Ala Gly Arg Gly Thr Cys Ala Gly Ala Leu Ala Pro Gly
     50                  55                  60

Gln Glu Ala Trp Ser Ala Val Trp Glu Pro Gly Leu Phe Ile Trp Val
 65                  70                  75                  80

Glu His Pro Leu Gly Cys Gln Gly His Gly Leu Asp Arg Phe Pro Leu
                 85                  90                  95

Pro Thr Ala Leu Pro Leu Gln Gly Gly His Ala Ala Cys Cys Pro Gln
            100                 105                 110

Leu
```

<210> SEQ ID NO 162
<211> LENGTH: 292
<212> TYPE: PRT
<213> ORGANISM: Homo sapiens

<400> SEQUENCE: 162

-continued

```
Met Gly Ile Gln Thr Ser Pro Val Leu Leu Ala Ser Leu Gly Val Gly
  1               5                  10                  15

Leu Val Thr Leu Leu Gly Leu Ala Val Gly Ser Tyr Leu Val Arg Arg
             20                  25                  30

Ser Arg Arg Pro Gln Val Thr Leu Leu Asp Pro Asn Glu Lys Tyr Leu
         35                  40                  45

Leu Arg Leu Leu Asp Lys Thr Thr Val Ser His His Thr Leu Gly Leu
     50                  55                  60

Pro Val Gly Lys His Ile Tyr Leu Ser Thr Arg Ile Asp Gly Ser Leu
 65                  70                  75                  80

Val Ile Arg Pro Tyr Thr Pro Val Thr Ser Asp Glu Asp Gln Gly Tyr
                 85                  90                  95

Val Asp Leu Val Ile Lys Val Tyr Leu Lys Gly Val His Pro Lys Phe
            100                 105                 110

Pro Glu Gly Gly Lys Met Ser Gln Tyr Leu Asp Ser Leu Lys Val Gly
        115                 120                 125

Asp Val Val Glu Phe Arg Gly Pro Ser Gly Leu Leu Thr Tyr Thr Gly
    130                 135                 140

Lys Gly His Phe Asn Ile Gln Pro Asn Lys Lys Ser Pro Pro Glu Pro
145                 150                 155                 160

Arg Val Ala Lys Lys Leu Gly Met Ile Ala Gly Gly Thr Gly Ile Thr
                165                 170                 175

Pro Met Leu Gln Leu Ile Arg Ala Ile Leu Lys Val Pro Glu Asp Pro
            180                 185                 190

Thr Gln Cys Phe Leu Leu Phe Ala Asn Gln Thr Glu Lys Asp Ile Ile
        195                 200                 205

Leu Arg Glu Asp Leu Glu Glu Leu Gln Ala Arg Tyr Pro Asn Arg Phe
    210                 215                 220

Lys Leu Trp Phe Thr Leu Asp His Pro Pro Lys Asp Trp Ala Tyr Ser
225                 230                 235                 240

Lys Gly Phe Val Thr Ala Asp Met Ile Arg Glu His Leu Pro Ala Pro
                245                 250                 255

Gly Asp Asp Val Leu Val Leu Leu Cys Gly Pro Pro Pro Met Val Gln
            260                 265                 270

Leu Ala Cys His Pro Asn Leu Asp Lys Leu Gly Tyr Ser Gln Lys Met
        275                 280                 285

Arg Phe Thr Tyr
    290
```

<210> SEQ ID NO 163
<211> LENGTH: 86
<212> TYPE: PRT
<213> ORGANISM: Homo sapiens

<400> SEQUENCE: 163

```
Met Val Met Val Phe Phe Leu Thr Phe Ser Gly Ser His Gly Cys Val
  1               5                  10                  15

Pro Thr Ser Gln Pro Trp Lys Asp Ala Glu Asp Gln Val Gly Cys Val
             20                  25                  30

His Ala Val Ala Trp Val Asn Ser Ala Leu Tyr Thr Val Leu Cys Pro
         35                  40                  45

Phe Leu Gly Lys Pro Lys Cys Ser Phe Ser Phe Asp Arg Asn Glu Ser
     50                  55                  60

Glu Asp Leu Asn Lys Gln Glu Val Lys Cys Arg Ala Val Pro Val Ser
 65                  70                  75                  80
```

-continued

```
Val Ser Ser Ser Met Leu
                85


<210> SEQ ID NO 164
<211> LENGTH: 106
<212> TYPE: PRT
<213> ORGANISM: Homo sapiens

<400> SEQUENCE: 164

Met Leu Ala Thr Met Val Val Gln Ile Leu Arg Leu Arg Pro His Thr
  1               5                  10                  15

Gln Lys Trp Ser His Val Leu Thr Leu Leu Gly Leu Ser Leu Val Leu
             20                  25                  30

Gly Leu Pro Trp Ala Leu Ile Phe Phe Ser Phe Ala Ser Gly Thr Phe
         35                  40                  45

Gln Leu Val Val Leu Tyr Leu Phe Ser Ile Ile Thr Ser Phe Gln Gly
     50                  55                  60

Phe Leu Ile Phe Ile Trp Tyr Trp Ser Met Arg Leu Gln Ala Arg Gly
 65                  70                  75                  80

Gly Pro Ser Pro Leu Lys Ser Asn Ser Asp Ser Ala Arg Leu Pro Ile
                85                  90                  95

Ser Ser Gly Ser Thr Ser Ser Ser Arg Ile
            100                 105


<210> SEQ ID NO 165
<211> LENGTH: 58
<212> TYPE: PRT
<213> ORGANISM: Homo sapiens

<400> SEQUENCE: 165

Met Ala Trp Arg Val Trp Cys Leu Trp Gly Ile Pro Pro Leu Phe Cys
  1               5                  10                  15

Ser Pro Gly Thr Leu Ser Cys Val Cys Val Ser Phe Leu Ser Pro Gly
             20                  25                  30

Asn Gly Met Ala Ser Glu His His Pro Arg Ser Ile Phe Pro Leu Gln
         35                  40                  45

Asn Asp Val Ser Ser His Val Cys Phe Cys
     50                  55


<210> SEQ ID NO 166
<211> LENGTH: 40
<212> TYPE: PRT
<213> ORGANISM: Homo sapiens

<400> SEQUENCE: 166

Met Arg Ser Asp Cys Val Leu Ile Trp Gln Leu Val Gly Val Leu Leu
  1               5                  10                  15

Ala Ser Gly Leu Ser Gly Asp Arg Ala Pro Leu Ile Val Leu Thr Ala
             20                  25                  30

Cys Asp Lys Ala Trp Ala Thr Val
         35                  40


<210> SEQ ID NO 167
<211> LENGTH: 65
<212> TYPE: PRT
<213> ORGANISM: Homo sapiens
<220> FEATURE:
<221> NAME/KEY: SITE
<222> LOCATION: (29)
<223> OTHER INFORMATION: Xaa equals any of the naturally occurring
```

-continued

```
      L-amino acids
<220> FEATURE:
<221> NAME/KEY: SITE
<222> LOCATION: (35)
<223> OTHER INFORMATION: Xaa equals any of the naturally occurring
      L-amino acids
<220> FEATURE:
<221> NAME/KEY: SITE
<222> LOCATION: (63)
<223> OTHER INFORMATION: Xaa equals any of the naturally occurring
      L-amino acids
<220> FEATURE:
<221> NAME/KEY: SITE
<222> LOCATION: (64)
<223> OTHER INFORMATION: Xaa equals any of the naturally occurring
      L-amino acids

<400> SEQUENCE: 167

Met Trp Ala Cys Trp Gly Met Leu Gly Cys Ile Pro Leu Phe Val Pro
  1               5                  10                  15

Trp Val Pro Val Leu Gly Lys His Phe Ser Gly Cys Xaa Tyr Leu Cys
             20                  25                  30

Gly Arg Xaa Pro Cys Trp Ile Ala Phe Ile Cys Val Arg Thr Pro Cys
         35                  40                  45

Gly Pro Thr Thr Ala Pro Thr Ala Thr Leu Lys Trp Ser Pro Xaa Xaa
     50                  55                  60

Thr
 65


<210> SEQ ID NO 168
<211> LENGTH: 46
<212> TYPE: PRT
<213> ORGANISM: Homo sapiens

<400> SEQUENCE: 168

Met Arg Tyr Trp Thr Asp Met Arg Arg Asn Tyr Arg Val Thr Tyr Gln
  1               5                  10                  15

Val Val Leu Leu Phe Leu Cys Phe Ser Leu Leu Thr Glu Cys Lys Thr
             20                  25                  30

Phe Glu Pro Arg Ser Glu Arg Ser Leu Phe Ser Tyr Pro Leu
         35                  40                  45


<210> SEQ ID NO 169
<211> LENGTH: 140
<212> TYPE: PRT
<213> ORGANISM: Homo sapiens

<400> SEQUENCE: 169

Met Phe Ala Gly Leu Phe Phe Leu Phe Phe Val Arg Phe Gly Ile Gly
  1               5                  10                  15

Arg Gln Leu Leu Ile Lys Phe Pro Trp Phe Phe Ser Phe Gly Tyr Phe
             20                  25                  30

Ser Lys Gln Gly Pro Thr Gln Lys Gln Ile Asp Ala Ala Ser Phe Thr
         35                  40                  45

Leu Thr Phe Phe Gly Gln Gly Tyr Ser Gln Gly Thr Gly Thr Asp Lys
     50                  55                  60

Asn Lys Pro Asn Ile Lys Ile Cys Thr Gln Val Lys Gly Pro Glu Ala
 65                  70                  75                  80

Gly Tyr Val Ala Thr Pro Ile Ala Met Val Gln Ala Ala Met Thr Leu
                 85                  90                  95

Leu Ser Asp Ala Ser His Leu Pro Lys Ala Gly Gly Val Phe Thr Pro
            100                 105                 110
```

```
Gly Ala Ala Phe Ser Lys Thr Lys Leu Ile Asp Arg Leu Asn Lys His
        115                 120                 125

Gly Ile Glu Phe Ser Val Ile Ser Ser Ser Glu Val
    130                 135                 140


<210> SEQ ID NO 170
<211> LENGTH: 53
<212> TYPE: PRT
<213> ORGANISM: Homo sapiens

<400> SEQUENCE: 170

Met Gln Glu Cys Leu Leu His Gly Cys Cys Cys Tyr Leu Leu Arg Leu
  1               5                  10                  15

Gly Val Leu Gly Thr Val Gln Cys Ile Ser Thr Trp Leu Ile Leu Thr
             20                  25                  30

Ala Asn Glu Gln His Arg Leu Lys Glu Thr Ser Asn Ser Gln Ser Pro
         35                  40                  45

Ala Val Ser Arg Ala
     50


<210> SEQ ID NO 171
<211> LENGTH: 167
<212> TYPE: PRT
<213> ORGANISM: Homo sapiens

<400> SEQUENCE: 171

Met Cys Gly Phe Leu Ser Leu Gln Ile Met Gly Pro Leu Ile Val Leu
  1               5                  10                  15

Val Gly Leu Cys Phe Phe Val Val Ala His Val Lys Lys Arg Asn Thr
             20                  25                  30

Leu Asn Ala Gly Gln Asp Ala Ser Glu Arg Glu Glu Gly Gln Ile Gln
         35                  40                  45

Ile Met Glu Pro Val Gln Val Thr Val Gly Asp Ser Val Ile Ile Phe
     50                  55                  60

Pro Pro Pro Pro Pro Pro Tyr Phe Pro Glu Ser Ser Ala Ser Ala Val
 65                  70                  75                  80

Ala Glu Ser Pro Gly Thr Asn Ser Leu Leu Pro Asn Glu Asn Pro Pro
                 85                  90                  95

Ser Tyr Tyr Ser Ile Phe Asn Tyr Gly Thr Pro Thr Ser Glu Gly Ala
            100                 105                 110

Ala Ser Glu Arg Asp Cys Glu Ser Ile Tyr Thr Ile Ser Gly Thr Asn
        115                 120                 125

Ser Ser Ser Glu Ala Ser His Thr Pro His Leu Pro Ser Glu Leu Pro
    130                 135                 140

Pro Arg Tyr Glu Glu Lys Glu Asn Ala Ala Ala Thr Phe Leu Pro Leu
145                 150                 155                 160

Ser Ser Glu Pro Ser Pro Pro
                165


<210> SEQ ID NO 172
<211> LENGTH: 325
<212> TYPE: PRT
<213> ORGANISM: Homo sapiens

<400> SEQUENCE: 172

Met Ser Ile Ser Leu Ser Ser Leu Ile Leu Leu Pro Ile Trp Ile Asn
  1               5                  10                  15
```

-continued

```
Met Ala Gln Ile Gln Gln Gly Gly Pro Asp Glu Lys Glu Lys Thr Thr
            20                  25                  30

Ala Leu Lys Asp Leu Leu Ser Arg Ile Asp Leu Asp Glu Leu Met Lys
        35                  40                  45

Lys Asp Glu Pro Pro Leu Asp Phe Pro Asp Thr Leu Glu Gly Phe Glu
    50                  55                  60

Tyr Ala Phe Asn Glu Lys Gly Gln Leu Arg His Ile Lys Thr Gly Glu
 65                 70                  75                  80

Pro Phe Val Phe Asn Tyr Arg Glu Asp Leu His Arg Trp Asn Gln Lys
                85                  90                  95

Arg Tyr Glu Ala Leu Gly Glu Ile Ile Thr Lys Tyr Val Tyr Glu Leu
            100                 105                 110

Leu Glu Lys Asp Cys Asn Leu Lys Lys Val Ser Ile Pro Val Asp Ala
        115                 120                 125

Thr Glu Ser Glu Pro Lys Ser Phe Ile Phe Met Ser Glu Asp Ala Leu
    130                 135                 140

Thr Asn Pro Gln Lys Leu Met Val Leu Ile His Gly Ser Gly Val Val
145                 150                 155                 160

Arg Ala Gly Gln Trp Ala Arg Arg Leu Ile Ile Asn Glu Asp Leu Asp
                165                 170                 175

Ser Gly Thr Gln Ile Pro Phe Ile Lys Arg Ala Val Ala Glu Gly Tyr
            180                 185                 190

Gly Val Ile Val Leu Asn Pro Asn Glu Asn Tyr Ile Glu Val Glu Lys
        195                 200                 205

Pro Lys Ile His Val Gln Ser Ser Ser Asp Ser Ser Asp Glu Pro Ala
    210                 215                 220

Glu Lys Arg Glu Arg Lys Asp Lys Val Ser Lys Glu Thr Lys Lys Arg
225                 230                 235                 240

Arg Asp Phe Tyr Glu Lys Tyr Arg Asn Pro Gln Arg Glu Lys Glu Met
                245                 250                 255

Met Gln Leu Tyr Ile Arg Glu Asn Gly Ser Pro Glu Glu His Ala Ile
            260                 265                 270

Tyr Val Trp Asp His Phe Ile Ala Gln Ala Ala Ala Glu Asn Val Phe
        275                 280                 285

Phe Val Ala His Ser Tyr Gly Gly Leu Ala Phe Val Glu Leu Gln Leu
    290                 295                 300

Met Ile Lys Gln Ala Asn Ser Asp Ala Gly Lys Cys Phe Arg Leu Ala
305                 310                 315                 320

Met Trp Lys Asn His
                325
```

<210> SEQ ID NO 173
<211> LENGTH: 113
<212> TYPE: PRT
<213> ORGANISM: Homo sapiens

<400> SEQUENCE: 173

```
Met His Pro Pro Leu Thr Pro Pro Thr Pro Leu Cys Leu Trp Leu Arg
  1               5                  10                  15

Leu Leu Lys Ala Gln Ile Leu Ser Tyr Pro Val Pro Arg Phe Glu Thr
            20                  25                  30

His Ser Leu Ile Ser Arg Cys Ser Gln Val Pro Pro Thr Phe Leu Trp
        35                  40                  45

Asp Ile Lys Lys Gly Val Arg Gly Gln Arg Glu Pro Ser Gly Pro Leu
    50                  55                  60
```

-continued

```
Leu Pro Tyr Thr Leu His Cys Pro Phe Ser Pro His Gln Asn Ala Gln
 65                  70                  75                  80

Arg Arg Cys Asp Asp Ala Thr Glu Asp Tyr Ala Thr Trp Ser Asn Arg
                 85                  90                  95

Ser Gly Gln His Asp Gln Leu Ser Arg Gly Cys Leu Leu Pro Phe Leu
            100                 105                 110

Leu
```

```
<210> SEQ ID NO 174
<211> LENGTH: 61
<212> TYPE: PRT
<213> ORGANISM: Homo sapiens
<220> FEATURE:
<221> NAME/KEY: SITE
<222> LOCATION: (37)
<223> OTHER INFORMATION: Xaa equals any of the naturally occurring
      L-amino acids
<220> FEATURE:
<221> NAME/KEY: SITE
<222> LOCATION: (39)
<223> OTHER INFORMATION: Xaa equals any of the naturally occurring
      L-amino acids

<400> SEQUENCE: 174

Met Gly Arg Leu Gly Leu Cys Leu Leu Arg Ser Leu Trp Val Pro Gln
  1               5                  10                  15

Arg Arg Ala Thr Thr Leu Gly Trp Thr Leu Ala Leu Arg Val Leu Pro
             20                  25                  30

Thr Ala Arg Ala Xaa Arg Xaa Leu Pro Val Ala Ala Asp Thr Ala Arg
         35                  40                  45

Arg Ala Cys Gly Ala His Thr Arg Ile Arg Val Leu Gly
     50                  55                  60
```

```
<210> SEQ ID NO 175
<211> LENGTH: 41
<212> TYPE: PRT
<213> ORGANISM: Homo sapiens
<220> FEATURE:
<221> NAME/KEY: SITE
<222> LOCATION: (41)
<223> OTHER INFORMATION: Xaa equals any of the naturally occurring
      L-amino acids

<400> SEQUENCE: 175

Met Asp Ile Asn Phe Cys Leu Arg Gly Arg His Gly Val Leu Phe Cys
  1               5                  10                  15

Phe Val Leu Phe Cys Phe Cys His Leu Leu Thr Val Leu Ser Thr His
             20                  25                  30

Arg Ala Phe Tyr Tyr Leu Ser Ala Xaa
         35                  40
```

```
<210> SEQ ID NO 176
<211> LENGTH: 42
<212> TYPE: PRT
<213> ORGANISM: Homo sapiens

<400> SEQUENCE: 176

Met Ile Lys Leu Gln Lys Val Ser Glu Val Ile Lys Val Leu Lys Met
  1               5                  10                  15

Leu Leu Tyr Pro Leu Val Leu Leu Leu Ser Leu Lys Leu Asp Thr Lys
             20                  25                  30

Ala Thr Ile Phe Ala Val Leu Glu Asp Val
```

-continued

```
        35                  40


<210> SEQ ID NO 177
<211> LENGTH: 47
<212> TYPE: PRT
<213> ORGANISM: Homo sapiens

<400> SEQUENCE: 177

Met Tyr Phe Phe Thr Phe Tyr Phe Ser Ile Ser Ser Phe Met Phe Phe
  1               5                  10                  15

Leu Leu Val Ile Val Lys Ala Thr Asn Gly Pro Arg Tyr Val Val Gly
            20                  25                  30

Cys Arg Arg Gln Val Ile Leu Tyr Ile Cys Ile Val Pro Asp Asp
        35                  40                  45


<210> SEQ ID NO 178
<211> LENGTH: 50
<212> TYPE: PRT
<213> ORGANISM: Homo sapiens

<400> SEQUENCE: 178

Met Ser Gly Phe Lys Glu Phe Asp Phe Val Val Pro Trp Trp Ser Ile
  1               5                  10                  15

Ser Phe Leu Leu Ser Phe Leu Leu Leu Leu Leu Ser Phe Trp Ser Leu
            20                  25                  30

Trp Val Tyr Thr Phe His Gln Ile Trp Asn Ile Phe Gly Tyr Tyr Phe
        35                  40                  45

Ser Lys
     50


<210> SEQ ID NO 179
<211> LENGTH: 227
<212> TYPE: PRT
<213> ORGANISM: Homo sapiens

<400> SEQUENCE: 179

Met Val Leu Thr Ala Thr Val Leu Asn Val Tyr Ala Ser Ile Phe Leu
  1               5                  10                  15

Ile Thr Ala Leu Ser Val Ala Arg Tyr Trp Val Val Ala Met Ala Ala
            20                  25                  30

Gly Pro Gly Thr His Leu Ser Leu Phe Trp Ala Arg Ile Ala Thr Leu
        35                  40                  45

Ala Val Trp Ala Ala Ala Ala Leu Val Thr Val Pro Thr Ala Val Phe
     50                  55                  60

Gly Val Glu Gly Glu Val Cys Gly Val Arg Leu Cys Leu Leu Arg Phe
 65                  70                  75                  80

Pro Ser Arg Ser Trp Leu Gly Ala Tyr Gln Leu Gln Arg Val Val Leu
                 85                  90                  95

Ala Phe Met Val Pro Leu Gly Val Ile Thr Thr Ser Tyr Leu Leu Leu
            100                 105                 110

Leu Ala Phe Leu Gln Arg Arg Gln Arg Arg Arg Gln Asp Ser Arg Val
        115                 120                 125

Val Ala Arg Ser Val Arg Ile Leu Val Ala Ser Phe Phe Leu Cys Trp
    130                 135                 140

Phe Pro Asn His Val Val Thr Leu Trp Gly Val Leu Val Gln Phe Ala
145                 150                 155                 160

Leu Val Pro Trp Ile Ser Thr Phe Tyr Thr Leu Gln Pro Tyr Val Phe
                165                 170                 175
```

-continued

```
Pro Val Thr Thr Cys Leu Ala His Ser Asn Ser Cys Leu Asn Pro Ile
            180                 185                 190

Ala Tyr Val Leu Ser Arg Ile Pro Ala His Trp Arg Pro Leu Leu Val
        195                 200                 205

Asp Pro Ser Ser Val Pro Ser Leu Met His Ser Leu Ser Ile His Ser
    210                 215                 220

Ala Pro Lys
225


<210> SEQ ID NO 180
<211> LENGTH: 44
<212> TYPE: PRT
<213> ORGANISM: Homo sapiens

<400> SEQUENCE: 180

Met Phe Arg Ser Ser Ile Ser Leu Met Val Phe Ser Leu Ile Leu Leu
  1               5                  10                  15

Leu Thr Thr Glu Arg Arg Ile Leu Ala Cys Pro Pro Ile Ile Leu Asn
             20                  25                  30

Ser Ser Ile Phe Leu Ser Asp Leu Ser Val Leu Pro
         35                  40


<210> SEQ ID NO 181
<211> LENGTH: 46
<212> TYPE: PRT
<213> ORGANISM: Homo sapiens

<400> SEQUENCE: 181

Met Asn Pro Leu Ser Phe Leu Phe Cys Phe Ile Ile Cys Arg Leu Leu
  1               5                  10                  15

Ala Glu Asn Ala Ile Asn Ile Glu Ile Leu Thr Gly Thr Tyr Glu Asn
             20                  25                  30

Phe Pro Thr Lys Ala Tyr Tyr Phe Arg Gln Arg Ser Arg Lys
         35                  40                  45


<210> SEQ ID NO 182
<211> LENGTH: 41
<212> TYPE: PRT
<213> ORGANISM: Homo sapiens

<400> SEQUENCE: 182

Met Ala Ser Leu Leu Arg Thr Cys Cys Val Pro Tyr Ile Val Leu Ser
  1               5                  10                  15

Ile Tyr Leu Asp Tyr Leu Ile Lys Ser Ser Gln Ser Leu Tyr Leu Thr
             20                  25                  30

Asp Gly Glu Ile Lys Ala His Gly Thr
         35                  40


<210> SEQ ID NO 183
<211> LENGTH: 47
<212> TYPE: PRT
<213> ORGANISM: Homo sapiens

<400> SEQUENCE: 183

Met Leu Gln Asp Leu Leu Ser Ala Leu Trp Phe Cys His Pro Cys Cys
  1               5                  10                  15

Leu Cys Cys Gly Leu Cys Trp Leu Gly Val Asp Ala Gly Cys Ser Gln
             20                  25                  30

Gly Gly Ser Gly Cys Pro Gln Gly Lys Ile Ser Asn Asn Gly Ile
```

-continued

```
        35                  40                  45


<210> SEQ ID NO 184
<211> LENGTH: 70
<212> TYPE: PRT
<213> ORGANISM: Homo sapiens

<400> SEQUENCE: 184

Met Lys Phe Ala Pro Val Tyr Met Tyr Leu Ser Phe Ile Cys Leu Cys
  1               5                  10                  15

Leu Phe Tyr Cys Asn Ser Ile Asp Thr His His Cys Phe Val Ser Asp
             20                  25                  30

Tyr Leu Ala Phe Glu Ser Ser Met Arg Glu Ala Phe Thr Glu Leu Leu
         35                  40                  45

Ile Leu Ile Lys Gly Glu Ser Asn Val Leu Lys Lys Met Gln Asn His
     50                  55                  60

His Leu Cys Gln Ser Tyr
 65                  70


<210> SEQ ID NO 185
<211> LENGTH: 41
<212> TYPE: PRT
<213> ORGANISM: Homo sapiens

<400> SEQUENCE: 185

Met Gly Leu Lys Leu Pro Ile Phe Leu Trp Phe Leu Tyr Phe Phe Ile
  1               5                  10                  15

Pro Leu Ser Ser Cys Tyr Leu Leu Leu Leu Pro His Leu Pro Ser Gly
             20                  25                  30

Ser Trp Asp Ser Met Leu Ser Phe Pro
         35                  40


<210> SEQ ID NO 186
<211> LENGTH: 92
<212> TYPE: PRT
<213> ORGANISM: Homo sapiens
<220> FEATURE:
<221> NAME/KEY: SITE
<222> LOCATION: (18)
<223> OTHER INFORMATION: Xaa equals any of the naturally occurring
      L-amino acids

<400> SEQUENCE: 186

Met Ala Gly Cys Leu Gly Ser Tyr Leu Leu Val Met Ile Leu Ile Leu
  1               5                  10                  15

Cys Xaa Ala His Phe Phe Ile Cys Gly Asn Glu Asp Asn Arg Val Leu
             20                  25                  30

Arg Tyr Asn Leu Glu Gln Cys Pro Ser His Ser Lys His Val Ile Asn
         35                  40                  45

Gly Ser Ser Tyr Cys Tyr Tyr Tyr Tyr Tyr Tyr Tyr Leu Glu Asp Arg
     50                  55                  60

Gly Ser Val Leu Phe Ile Ile Pro Ser Pro Ala Leu Ser Thr Val Pro
 65                  70                  75                  80

Gly Thr Ile Gln Thr Cys Ile Trp Met Asn Asp Lys
                 85                  90


<210> SEQ ID NO 187
<211> LENGTH: 71
<212> TYPE: PRT
<213> ORGANISM: Homo sapiens
```

-continued

<400> SEQUENCE: 187

Met Pro Ala Gly Val Pro Met Ser Thr Tyr Leu Lys Met Phe Ala Ala
1 5 10 15

Ser Leu Leu Ala Met Cys Ala Gly Ala Glu Val Val His Arg Tyr Tyr
20 25 30

Arg Pro Asp Leu Thr Ile Pro Glu Ile Pro Pro Lys Arg Gly Glu Leu
35 40 45

Lys Thr Glu Leu Leu Gly Leu Lys Glu Arg Lys His Lys Pro Gln Val
50 55 60

Ser Gln Gln Glu Glu Leu Lys
65 70

<210> SEQ ID NO 188
<211> LENGTH: 66
<212> TYPE: PRT
<213> ORGANISM: Homo sapiens
<220> FEATURE:
<221> NAME/KEY: SITE
<222> LOCATION: (23)
<223> OTHER INFORMATION: Xaa equals any of the naturally occurring
L-amino acids
<220> FEATURE:
<221> NAME/KEY: SITE
<222> LOCATION: (45)
<223> OTHER INFORMATION: Xaa equals any of the naturally occurring
L-amino acids

<400> SEQUENCE: 188

Met Ala Gly Phe Ala Ser Tyr Pro Trp Ser Asp Phe Pro Trp Cys Trp
1 5 10 15

Val Val Cys Phe Ser Phe Xaa Phe Phe Phe Leu Arg Gln Ser Glu Ser
20 25 30

Leu Ser Gln Lys Lys Arg Gln Val Ala Asp Glu Leu Xaa Phe Gly Gln
35 40 45

Ser Lys Arg Asp Ser Asp Gly Gly Trp Met Leu Arg Ser Ser Ala Gly
50 55 60

Asn Ser
65

<210> SEQ ID NO 189
<211> LENGTH: 70
<212> TYPE: PRT
<213> ORGANISM: Homo sapiens
<220> FEATURE:
<221> NAME/KEY: SITE
<222> LOCATION: (14)
<223> OTHER INFORMATION: Xaa equals any of the naturally occurring
L-amino acids
<220> FEATURE:
<221> NAME/KEY: SITE
<222> LOCATION: (21)
<223> OTHER INFORMATION: Xaa equals any of the naturally occurring
L-amino acids

<400> SEQUENCE: 189

Met Gln Pro Ser Tyr Pro Leu Ser Trp Ser Gly Gly Val Xaa Leu Pro
1 5 10 15

Cys Leu Ala Ser Xaa Leu Thr Leu Leu Phe Leu Leu Gln Pro Leu Met
20 25 30

Leu Pro Leu Gly Gly Ser Gln Thr Gln Leu Gly Asn His Ser Val Val
35 40 45

Arg Leu Leu Leu Pro Val Gln Arg Leu Gly Phe Ala Glu Val Pro Pro
50 55 60

-continued

```
Leu Glu Val Ala Gln Ser
 65                 70


<210> SEQ ID NO 190
<211> LENGTH: 40
<212> TYPE: PRT
<213> ORGANISM: Homo sapiens

<400> SEQUENCE: 190

Met Ile Pro Leu Arg Arg Gly Met Val Gly Gly Leu Leu Leu Leu Leu
  1               5                  10                  15

Ala Thr Ala Asn Lys Leu Leu Ala Ala Ser Phe Arg Asp Leu Met Asp
             20                  25                  30

Val Leu Thr Cys Pro Arg Pro Arg
         35                  40


<210> SEQ ID NO 191
<211> LENGTH: 66
<212> TYPE: PRT
<213> ORGANISM: Homo sapiens
<220> FEATURE:
<221> NAME/KEY: SITE
<222> LOCATION: (36)
<223> OTHER INFORMATION: Xaa equals any of the naturally occurring
      L-amino acids

<400> SEQUENCE: 191

Met Gln His Leu Leu Leu His Ser Leu Cys Leu Ser Cys Ser Thr Met
  1               5                  10                  15

Ala Arg Asn Val Pro Ala Ser Pro Ser Pro Ser Ala Val Ile Val Ser
             20                  25                  30

Phe Leu Arg Xaa Pro Gln Pro Cys Phe Leu Tyr Ser Leu Gln Asn Cys
         35                  40                  45

Glu Ser Ile Lys Pro Leu Phe Phe Ile Asn Ser Pro Val Ser Ser Ser
     50                  55                  60

Ser Leu
 65


<210> SEQ ID NO 192
<211> LENGTH: 66
<212> TYPE: PRT
<213> ORGANISM: Homo sapiens

<400> SEQUENCE: 192

Met Leu Pro Ser Trp Trp Ala Leu Gly Trp Met Thr Leu Lys Ile Leu
  1               5                  10                  15

Gln Met Trp Val Gln Ala Cys Thr His Thr Met Glu Tyr Gly His Ser
             20                  25                  30

Tyr Thr Gly Gly Val Glu Ser Gly Ser Ala Ala Trp His Leu Thr Glu
         35                  40                  45

Val Gly Pro Lys Arg Thr His Asp Tyr Ala Glu Asn Trp Ile Gly Ser
     50                  55                  60

Leu Ser
 65


<210> SEQ ID NO 193
<211> LENGTH: 48
<212> TYPE: PRT
<213> ORGANISM: Homo sapiens

<400> SEQUENCE: 193
```

```
Met His Phe Ser Val Ala His Ser Ile Trp Gly Ile Leu Ile Leu Leu
  1               5                  10                  15

Ser Leu Tyr Glu Gly Val Ile Ser Trp Val Phe Asn Phe Gln Met Phe
             20                  25                  30

Thr Lys Leu Leu Leu Cys Ala Lys His Tyr Ser His Cys Phe Glu Ser
         35                  40                  45


<210> SEQ ID NO 194
<211> LENGTH: 66
<212> TYPE: PRT
<213> ORGANISM: Homo sapiens

<400> SEQUENCE: 194

Met Ser Leu Ile Leu Leu Gly Ser Pro Ile Ile Pro Leu Trp Ser Tyr
  1               5                  10                  15

Thr Ser Ala Thr Gln Ala Ala Ala Leu Val Thr Ser His Val Trp Lys
             20                  25                  30

Pro Ser Leu Glu Ala His Gln Ile Asn Ile Ser Pro Glu Pro Ser Ile
         35                  40                  45

His Tyr Asp Arg Trp His Thr Gln Ser Asn Cys Ser Leu Ile Asn Ser
     50                  55                  60

Leu Gln
 65


<210> SEQ ID NO 195
<211> LENGTH: 57
<212> TYPE: PRT
<213> ORGANISM: Homo sapiens

<400> SEQUENCE: 195

Met Lys Gln Thr Tyr Trp Gln Thr His Ile Leu Leu Val Leu Thr Leu
  1               5                  10                  15

Tyr Phe Ile Val Leu Ala Tyr Ser Pro Phe Leu Arg Phe Leu Leu Arg
             20                  25                  30

Asn Ile Gly Thr His Pro Leu Leu Cys Ala Glu Gly Ile Thr Ser Phe
         35                  40                  45

Phe Leu Ser Tyr Lys Asn Met Leu Tyr
     50                  55


<210> SEQ ID NO 196
<211> LENGTH: 52
<212> TYPE: PRT
<213> ORGANISM: Homo sapiens

<400> SEQUENCE: 196

Met Gly Pro Asn Phe Val Val Leu Cys Leu Asn Leu Leu Gln Asp Thr
  1               5                  10                  15

Leu Ala Tyr Ala Thr Ala Leu Leu Asn Glu Lys Glu Gln Ser Gly Ser
             20                  25                  30

Ser Asn Gly Ser Glu Ser Ser Pro Ala Asn Glu Asn Gly Asp Arg His
         35                  40                  45

Leu Gln Gln Val
     50


<210> SEQ ID NO 197
<211> LENGTH: 43
<212> TYPE: PRT
<213> ORGANISM: Homo sapiens
```

-continued

<400> SEQUENCE: 197

```
Met Ile Val Ile Ala Val Ser Leu Ser Leu Phe Cys Asp Val Val Ser
  1               5                  10                  15

Ser Glu Cys Met Ser Cys Phe Thr Pro Lys Phe Ala Asp Ile Val Ala
             20                  25                  30

Asn Ala Tyr Gln Asn Glu Ser Tyr Ile Phe Ile
         35                  40
```

<210> SEQ ID NO 198
<211> LENGTH: 52
<212> TYPE: PRT
<213> ORGANISM: Homo sapiens

<400> SEQUENCE: 198

```
Met Leu Leu Pro Val Asn Thr Leu Leu Tyr Ile Leu Leu Thr Pro Leu
  1               5                  10                  15

Cys Phe Phe Tyr Gly Thr Ser Arg Pro Pro Tyr Leu Glu Leu Val Thr
             20                  25                  30

Leu Leu Lys Lys Lys Lys Gln Ser Val Gly Phe Ser Val Cys Ile Leu
         35                  40                  45

Glu Ala Gly Arg
     50
```

<210> SEQ ID NO 199
<211> LENGTH: 40
<212> TYPE: PRT
<213> ORGANISM: Homo sapiens

<400> SEQUENCE: 199

```
Met Ile Ile Val Leu Phe Ser Leu Ser Phe Leu Pro Leu Leu Pro Ser
  1               5                  10                  15

Leu Leu Leu Ser Ser Tyr Leu Cys Leu Phe Phe Phe Pro Ser Gln Ser
             20                  25                  30

Pro Ser Ser Phe Phe Phe His Leu
         35                  40
```

<210> SEQ ID NO 200
<211> LENGTH: 71
<212> TYPE: PRT
<213> ORGANISM: Homo sapiens
<220> FEATURE:
<221> NAME/KEY: SITE
<222> LOCATION: (25)
<223> OTHER INFORMATION: Xaa equals any of the naturally occurring L-amino acids

<400> SEQUENCE: 200

```
Met Thr Glu Gly His Val Phe Cys Phe Ala Leu Cys Cys Val Leu Val
  1               5                  10                  15

Phe Leu Ser Met Thr Leu Leu Val Xaa Ser Leu Glu Lys Thr Asn Ala
             20                  25                  30

Gly Gly Val Ile Ala Trp Gly Cys Ile Ser Val Ser Val Gln Thr Gln
         35                  40                  45

Thr Phe Ser Ser Pro Thr Ser Tyr Gln Thr Leu Phe Ile Ala Cys Lys
     50                  55                  60

Leu Trp Asn Pro Arg Lys Leu
 65                  70
```

<210> SEQ ID NO 201
<211> LENGTH: 59

-continued

```
<212> TYPE: PRT
<213> ORGANISM: Homo sapiens
<220> FEATURE:
<221> NAME/KEY: SITE
<222> LOCATION: (37)
<223> OTHER INFORMATION: Xaa equals any of the naturally occurring
      L-amino acids

<400> SEQUENCE: 201

Met Ile Gly Leu Thr Ile Ile Ala Cys Phe Ala Val Ile Val Ser Ala
  1               5                  10                  15

Lys Arg Ala Val Glu Arg His Glu Ser Leu Thr Ser Trp Asn Leu Ala
             20                  25                  30

Lys Lys Ala Lys Xaa Arg Glu Glu Ala Ala Leu Ala Ala Gln Ala Lys
         35                  40                  45

Ala Asn Asp Ile Leu Ser Asp Lys Val Phe Thr
     50                  55


<210> SEQ ID NO 202
<211> LENGTH: 80
<212> TYPE: PRT
<213> ORGANISM: Homo sapiens

<400> SEQUENCE: 202

Met Leu Thr Gly Ser His Pro Gln Thr His Thr Cys Trp Leu Gly Thr
  1               5                  10                  15

Arg Leu Trp Val Val Leu Ser Cys Leu Ala Ser Leu Thr Val Ser Asp
             20                  25                  30

Cys Pro Glu His Gln Val Ser Ser Cys Ile Ser Ser Trp Pro Gly Glu
         35                  40                  45

His Ser Val Ser Phe Gln Pro Phe Pro Pro Phe Pro His Ser Leu Gly
     50                  55                  60

Gly Thr Glu Val Gly Val Glu Glu Ser Gln Met Ala Gly Val Gly Ile
 65                  70                  75                  80


<210> SEQ ID NO 203
<211> LENGTH: 70
<212> TYPE: PRT
<213> ORGANISM: Homo sapiens

<400> SEQUENCE: 203

Met Ile Ser Gly Val Leu Ile Phe Asn Leu Ile Ala Ser Ser Trp Val
  1               5                  10                  15

Leu Cys Phe Pro Leu Cys Asp Leu Ser Cys Gln Lys Thr Leu Arg Ile
             20                  25                  30

Phe Phe Ala Ser Phe Phe His Ala Val Cys Val His Val Ser Cys Thr
         35                  40                  45

Ser Trp Gln Pro Leu Val Leu Phe Ile Lys Trp Trp Val Val Gly Cys
     50                  55                  60

Ser Pro Ala Val Ser Leu
 65                  70


<210> SEQ ID NO 204
<211> LENGTH: 78
<212> TYPE: PRT
<213> ORGANISM: Homo sapiens

<400> SEQUENCE: 204

Met Leu His Met Phe Leu Leu Leu Leu Tyr Phe Phe Lys Asn Ser Lys
  1               5                  10                  15
```

-continued

```
Ser Leu Phe Met Cys His Trp Ile Asn Leu Ser Asp Asn Val Ser His
            20                  25                  30

Lys Asn Leu Leu Asp Arg Leu Phe Phe Ser Cys Thr Leu Asn Gly Gly
        35                  40                  45

Val Glu Val Ser Gly Glu Gln Trp Ile Thr Lys Ser Lys Leu Trp Lys
    50                  55                  60

Ile Val Lys Arg Met Glu Lys Leu Asn Thr Arg Tyr Gln Lys
65                  70                  75


<210> SEQ ID NO 205
<211> LENGTH: 115
<212> TYPE: PRT
<213> ORGANISM: Homo sapiens

<400> SEQUENCE: 205

Met Cys Met Ser Val Gly Ala His Ile Cys Val Cys Val Cys Met Cys
  1               5                  10                  15

Val Leu His Val Cys Gly Glu Val Ser Ser Val Arg Ala Cys Asp Ser
            20                  25                  30

Trp Asp Leu His Ser Cys Val Leu Pro Gln Arg Pro Gln Pro Gly Gln
        35                  40                  45

Ala Leu Thr Phe Cys Ala Pro Cys Ile Glu Pro Val Cys Cys Gly Cys
    50                  55                  60

Leu Trp Pro Pro Met Gly Asn Ser Gly Glu Leu Ala Gly Gly Cys Ala
65                  70                  75                  80

Gln Ser Pro Gly Cys Cys Tyr Cys His Ser Ala Gln Leu Gly Gln Ala
                85                  90                  95

Val Ala Pro Glu Gly Val Arg Arg Glu Leu Trp Glu His Leu Tyr Ser
            100                 105                 110

Val Leu Lys
        115


<210> SEQ ID NO 206
<211> LENGTH: 50
<212> TYPE: PRT
<213> ORGANISM: Homo sapiens

<400> SEQUENCE: 206

Met Pro Gly Cys Trp Val Leu Glu Leu Val Asp His Trp Leu Ala Ser
  1               5                  10                  15

Leu Trp Leu Val Val Ala Val Thr Glu Cys Ala Ala Arg Pro Glu Trp
            20                  25                  30

Leu Phe Trp Leu Cys Pro Pro Ser Cys Ser Met Pro Gly Gly Gly Gly
        35                  40                  45

Asp Thr
    50


<210> SEQ ID NO 207
<211> LENGTH: 57
<212> TYPE: PRT
<213> ORGANISM: Homo sapiens

<400> SEQUENCE: 207

Met Lys Phe Tyr Ala Val Leu Leu Ser Ile Cys Leu Leu Leu Ser Cys
  1               5                  10                  15

Trp Cys Ala Cys His Val Arg Asp Cys Asn Leu Ile Cys Leu Phe Ser
            20                  25                  30

Thr Val Lys Ala Ile Thr Arg Glu Leu Leu Gln Leu Pro Ser Tyr Val
```

-continued

```
        35                  40                  45

Lys Arg Phe Phe Phe Asn Ser Leu Arg
    50                  55


<210> SEQ ID NO 208
<211> LENGTH: 56
<212> TYPE: PRT
<213> ORGANISM: Homo sapiens

<400> SEQUENCE: 208

Met Leu Val Ala Pro Phe Asn Leu Leu Phe Glu Met Ala Pro Phe Asn
  1               5                  10                  15

Ile Phe Leu Phe Pro Gln Trp Gly Leu Leu Trp Leu Met Leu Tyr Leu
             20                  25                  30

Leu Tyr Val Phe Gln Ala Ser Leu Arg Thr Pro Glu Leu Thr Trp Glu
        35                  40                  45

Arg Val Arg Ser Gln Val Asp Gln
    50                  55


<210> SEQ ID NO 209
<211> LENGTH: 49
<212> TYPE: PRT
<213> ORGANISM: Homo sapiens

<400> SEQUENCE: 209

Met Leu Leu Thr Cys Ile Leu Leu His Leu Trp Ile Val Val Asp Ser
  1               5                  10                  15

Val Ile Tyr Met Lys Pro Thr Ser Arg Asp Gly Cys Leu Leu Ser Ala
             20                  25                  30

Leu Gln Met Ala Arg Ser Leu Ile Ile Gln Leu Asn His Ser Ser Ser
        35                  40                  45

Asn


<210> SEQ ID NO 210
<211> LENGTH: 44
<212> TYPE: PRT
<213> ORGANISM: Homo sapiens

<400> SEQUENCE: 210

Met Pro Leu Cys Gly Leu Tyr Cys Leu Arg Ile Leu Met Phe Pro Leu
  1               5                  10                  15

Arg Ser Ala Asn Ser Val Pro Leu Gln Cys Leu Pro Pro Ser Ser Leu
             20                  25                  30

Ala Asn Lys Asp Ser His Phe Arg Ala Pro Arg Lys
        35                  40


<210> SEQ ID NO 211
<211> LENGTH: 44
<212> TYPE: PRT
<213> ORGANISM: Homo sapiens
<220> FEATURE:
<221> NAME/KEY: SITE
<222> LOCATION: (18)
<223> OTHER INFORMATION: Xaa equals any of the naturally occurring
      L-amino acids
<220> FEATURE:
<221> NAME/KEY: SITE
<222> LOCATION: (25)
<223> OTHER INFORMATION: Xaa equals any of the naturally occurring
      L-amino acids

<400> SEQUENCE: 211
```

-continued

```
Met Ser Pro Ser Pro Arg Trp Gly Phe Leu Cys Val Leu Phe Thr Ala
  1               5                  10                  15

Val Xaa Pro Ala Pro Ser Thr Ala Xaa Val Gln Asp Lys Cys Pro Val
             20                  25                  30

Asn Thr Trp Glu Ala Met Gln Ala Cys Val His Gly
         35                  40
```

<210> SEQ ID NO 212
<211> LENGTH: 160
<212> TYPE: PRT
<213> ORGANISM: Homo sapiens
<220> FEATURE:
<221> NAME/KEY: SITE
<222> LOCATION: (136)
<223> OTHER INFORMATION: Xaa equals any of the naturally occurring L-amino acids

<400> SEQUENCE: 212

```
Met Ala Phe Thr Phe Ala Ala Phe Cys Tyr Met Leu Ser Leu Val Leu
  1               5                  10                  15

Cys Ala Ala Leu Ile Phe Phe Ala Ile Trp His Ile Ile Ala Phe Asp
             20                  25                  30

Glu Leu Arg Thr Asp Phe Lys Ser Pro Ile Asp Gln Cys Asn Pro Val
         35                  40                  45

His Ala Arg Glu Arg Leu Arg Asn Ile Glu Arg Ile Cys Phe Leu Leu
     50                  55                  60

Arg Lys Leu Val Leu Pro Glu Tyr Ser Ile His Ser Leu Phe Cys Ile
 65                  70                  75                  80

Met Phe Leu Cys Ala Gln Glu Trp Leu Thr Leu Gly Leu Asn Val Pro
                 85                  90                  95

Leu Leu Phe Tyr His Phe Trp Arg Tyr Phe His Cys Pro Ala Asp Ser
            100                 105                 110

Ser Glu Leu Ala Tyr Asp Pro Pro Val Val Met Asn Ala Asp Thr Leu
        115                 120                 125

Ser Tyr Cys Gln Lys Glu Ala Xaa Cys Lys Leu Ala Phe Tyr Leu Leu
    130                 135                 140

Ser Phe Phe Tyr Tyr Leu Tyr Cys Met Ile Tyr Thr Leu Val Ser Ser
145                 150                 155                 160
```

<210> SEQ ID NO 213
<211> LENGTH: 198
<212> TYPE: PRT
<213> ORGANISM: Homo sapiens

<400> SEQUENCE: 213

```
Met Tyr Arg Glu Arg Leu Arg Thr Leu Leu Val Ile Ala Val Val Met
  1               5                  10                  15

Ser Leu Leu Asn Ala Leu Ser Thr Ser Gly Gly Ser Ile Ser Trp Asn
             20                  25                  30

Asp Phe Val His Glu Met Leu Ala Lys Gly Glu Val Gln Arg Val Gln
         35                  40                  45

Val Val Pro Glu Ser Asp Val Val Glu Val Tyr Leu His Pro Gly Ala
     50                  55                  60

Val Val Phe Gly Arg Pro Arg Leu Ala Leu Met Tyr Arg Met Gln Val
 65                  70                  75                  80

Ala Asn Ile Asp Lys Phe Glu Glu Lys Leu Arg Ala Ala Glu Asp Glu
                 85                  90                  95

Leu Asn Ile Glu Ala Lys Asp Arg Ile Pro Val Ser Tyr Lys Arg Thr
```

-continued

```
            100                 105                 110

Gly Phe Phe Gly Lys Cys Pro Val Leu Cys Gly Asp Asp Gly Ser Gly
        115                 120                 125

Pro Gly His Pro Val Val Cys Phe Pro Ser Gly Arg Asp Asp Trp Arg
    130                 135                 140

His Arg Arg Arg Trp Thr Ser Arg Ser Arg Leu Leu Cys Trp Lys Ala
145                 150                 155                 160

Leu Met Gly Ser Val Gly Ala Asp His Thr Arg Glu Leu Arg Lys Pro
                165                 170                 175

Ser Gly Ser His Arg Pro Pro Phe Asn Val Val Ile Pro Trp Trp Trp
            180                 185                 190

Lys Gln Asp Asp Gly Pro
        195


<210> SEQ ID NO 214
<211> LENGTH: 59
<212> TYPE: PRT
<213> ORGANISM: Homo sapiens

<400> SEQUENCE: 214

Met Asn Ser Thr Leu Cys Val Val Leu Ser Leu Met Cys Met Asn Ser
  1               5                  10                  15

Thr Leu Cys Val Val Leu Ser Leu Thr His Ser Cys Pro Ser Pro Gln
            20                  25                  30

Val Pro Lys Val His Tyr Met Ile Phe Met Pro Leu His Leu His Ser
        35                  40                  45

Leu Ala Leu Thr Gln Leu Ile Ile Ile Tyr Lys
     50                  55


<210> SEQ ID NO 215
<211> LENGTH: 84
<212> TYPE: PRT
<213> ORGANISM: Homo sapiens
<220> FEATURE:
<221> NAME/KEY: SITE
<222> LOCATION: (71)
<223> OTHER INFORMATION: Xaa equals any of the naturally occurring
      L-amino acids

<400> SEQUENCE: 215

Met Gly Cys Ile Pro Leu Ile Lys Ser Ile Ser Asp Trp Arg Val Ile
  1               5                  10                  15

Ala Leu Ala Ala Leu Trp Phe Cys Leu Ile Gly Leu Ile Cys Gln Ala
            20                  25                  30

Leu Cys Ser Glu Asp Gly His Lys Arg Arg Ile Leu Thr Leu Gly Leu
        35                  40                  45

Gly Phe Leu Val Ile Pro Phe Leu Pro Ala Ser Asn Leu Phe Phe Arg
     50                  55                  60

Val Gly Phe Val Val Ala Xaa Cys Ser Ser Thr Ser Pro Ala Leu Gly
 65                  70                  75                  80

Thr Val Cys Cys


<210> SEQ ID NO 216
<211> LENGTH: 81
<212> TYPE: PRT
<213> ORGANISM: Homo sapiens

<400> SEQUENCE: 216

Met Val Val Ala Gly Val Val Val Leu Ile Leu Ala Leu Val Leu Ala
```

-continued

```
  1               5                  10                  15

Trp Leu Ser Thr Tyr Val Ala Asp Ser Gly Ser Asn Gln Leu Leu Gly
            20                  25                  30

Ala Ile Val Ser Ala Gly Asp Thr Ser Val Leu His Leu Gly His Val
        35                  40                  45

Asp His Leu Val Ala Gly Gln Gly Asn Pro Glu Pro Thr Glu Leu Pro
    50                  55                  60

His Pro Ser Glu Asp Lys Gln Val Gln Ala Ala Ala Val Gln Arg Pro
 65                  70                  75                  80

Pro


<210> SEQ ID NO 217
<211> LENGTH: 90
<212> TYPE: PRT
<213> ORGANISM: Homo sapiens

<400> SEQUENCE: 217

Met Met Val Trp Asn Leu Phe Pro Cys Phe Pro Pro Leu Leu Leu Leu
  1               5                  10                  15

Gln Phe Ile Asp Cys Gln Gln Ser Ser Glu Ile Glu Gln Gly Phe Thr
            20                  25                  30

Arg Ser Leu Leu Gly His Pro Ile Phe Phe Cys Pro Asp Pro Cys Trp
        35                  40                  45

Gln Ser Cys Met Asn Cys Val Ile Leu Leu Ser Ala Phe Phe Phe Leu
    50                  55                  60

Phe Asp Lys Met Asp Ile Lys Asn Ser Cys Cys Ala Lys Val Ser Ser
 65                  70                  75                  80

Leu Leu Gln Glu Glu Asn Gln Phe Phe Phe
                 85                  90


<210> SEQ ID NO 218
<211> LENGTH: 335
<212> TYPE: PRT
<213> ORGANISM: Homo sapiens

<400> SEQUENCE: 218

Met Lys Lys Glu Leu Pro Val Asp Ser Cys Leu Pro Arg Ser Leu Glu
  1               5                  10                  15

Leu His Pro Gln Lys Met Asp Pro Lys Arg Gln His Ile Gln Leu Leu
            20                  25                  30

Ser Ser Leu Thr Glu Cys Leu Thr Val Asp Pro Leu Ser Ala Ser Val
        35                  40                  45

Trp Arg Gln Leu Tyr Pro Lys His Leu Ser Gln Ser Ser Leu Leu Leu
    50                  55                  60

Glu His Leu Leu Ser Ser Trp Glu Gln Ile Pro Lys Lys Val Gln Lys
 65                  70                  75                  80

Ser Leu Gln Glu Thr Ile Gln Ser Leu Lys Leu Thr Asn Gln Glu Leu
                 85                  90                  95

Leu Arg Lys Gly Ser Ser Asn Asn Gln Asp Val Val Thr Cys Asp Met
            100                 105                 110

Ala Cys Lys Gly Leu Leu Gln Gln Val Gln Gly Pro Arg Leu Pro Trp
        115                 120                 125

Thr Arg Leu Leu Leu Leu Leu Leu Val Phe Ala Val Gly Phe Leu Cys
    130                 135                 140

His Asp Leu Arg Ser His Ser Ser Phe Gln Ala Ser Leu Thr Gly Arg
145                 150                 155                 160
```

-continued

```
Leu Leu Arg Ser Ser Gly Phe Leu Pro Ala Ser Gln Gln Ala Cys Ala
                165                 170                 175

Lys Leu Tyr Ser Tyr Ser Leu Gln Gly Tyr Ser Trp Leu Gly Glu Thr
            180                 185                 190

Leu Pro Leu Trp Gly Ser His Leu Leu Thr Val Val Arg Pro Ser Leu
        195                 200                 205

Gln Leu Ala Trp Ala His Thr Asn Ala Thr Val Ser Phe Leu Ser Ala
    210                 215                 220

His Cys Ala Ser His Leu Ala Trp Phe Gly Asp Ser Leu Thr Ser Leu
225                 230                 235                 240

Ser Gln Arg Leu Gln Ile Gln Leu Pro Asp Ser Val Asn Gln Leu Leu
                245                 250                 255

Arg Tyr Leu Arg Glu Leu Pro Leu Leu Phe His Gln Asn Val Leu Leu
            260                 265                 270

Pro Leu Trp His Leu Leu Leu Glu Ala Leu Ala Trp Ala Gln Glu His
        275                 280                 285

Cys His Glu Ala Cys Arg Gly Glu Val Thr Trp Asp Cys Met Lys Thr
    290                 295                 300

Gln Leu Ser Glu Ala Val His Trp Thr Trp Leu Cys Leu Gln Asp Ile
305                 310                 315                 320

Thr Val Ala Phe Leu Asp Trp Ala Leu Ala Leu Ile Ser Gln Gln
                325                 330                 335


<210> SEQ ID NO 219
<211> LENGTH: 229
<212> TYPE: PRT
<213> ORGANISM: Homo sapiens

<400> SEQUENCE: 219

Met Asp Pro Asp Arg Ala Phe Ile Cys Gly Glu Ser Arg Gln Phe Ala
  1               5                  10                  15

Gln Cys Leu Ile Phe Gly Phe Leu Phe Leu Thr Ser Gly Met Leu Ile
             20                  25                  30

Ser Val Leu Gly Ile Trp Val Pro Gly Cys Gly Ser Asn Trp Ala Gln
         35                  40                  45

Glu Pro Leu Asn Glu Thr Asp Thr Gly Asp Ser Glu Pro Arg Met Cys
     50                  55                  60

Gly Phe Leu Ser Leu Gln Ile Met Gly Pro Leu Ile Val Leu Val Gly
 65                  70                  75                  80

Leu Cys Phe Phe Val Val Ala His Val Lys Lys Arg Asn Thr Leu Asn
                 85                  90                  95

Ala Gly Gln Asp Ala Ser Glu Arg Glu Glu Gly Gln Ile Gln Ile Met
            100                 105                 110

Glu Pro Val Gln Val Thr Val Gly Asp Ser Val Ile Ile Phe Pro Pro
        115                 120                 125

Pro Pro Pro Pro Tyr Phe Pro Glu Ser Ser Ala Ser Ala Val Ala Glu
    130                 135                 140

Ser Pro Gly Thr Asn Ser Leu Leu Pro Asn Glu Asn Pro Pro Ser Tyr
145                 150                 155                 160

Tyr Ser Ile Phe Asn Tyr Gly Thr Pro Thr Ser Glu Gly Ala Ala Ser
                165                 170                 175

Glu Arg Asp Cys Glu Ser Ile Tyr Thr Ile Ser Gly Thr Asn Ser Ser
            180                 185                 190

Ser Glu Ala Ser His Thr Pro His Leu Pro Ser Glu Leu Pro Pro Arg
```

```
        195                 200                 205

Tyr Glu Glu Lys Glu Asn Ala Ala Ala Thr Phe Leu Pro Leu Ser Ser
    210                 215                 220

Glu Pro Ser Pro Pro
225


<210> SEQ ID NO 220
<211> LENGTH: 62
<212> TYPE: PRT
<213> ORGANISM: Homo sapiens

<400> SEQUENCE: 220

Met Ser Ile Ser Leu Ser Ser Leu Ile Leu Leu Pro Ile Trp Ile Asn
  1               5                  10                  15

Met Ala Gln Ile Gln Gln Gly Gly Pro Asp Glu Lys Glu Lys Thr Thr
             20                  25                  30

Ala Leu Lys Asp Leu Leu Ser Arg Ile Asp Leu Asp Glu Leu Met Lys
         35                  40                  45

Lys Asp Glu Pro Pro Leu Asp Phe Leu Ile Pro Trp Lys Val
     50                  55                  60


<210> SEQ ID NO 221
<211> LENGTH: 170
<212> TYPE: PRT
<213> ORGANISM: Homo sapiens
<220> FEATURE:
<221> NAME/KEY: SITE
<222> LOCATION: (163)
<223> OTHER INFORMATION: Xaa equals any of the naturally occurring
      L-amino acids

<400> SEQUENCE: 221

Met Ala Ala Gly Pro Gly Thr His Leu Ser Leu Phe Trp Ala Arg Ile
  1               5                  10                  15

Ala Thr Leu Ala Val Trp Ala Ala Ala Ala Leu Val Thr Val Pro Thr
             20                  25                  30

Ala Val Phe Gly Val Glu Gly Glu Val Cys Gly Val Arg Leu Cys Leu
         35                  40                  45

Leu Arg Phe Pro Ser Arg Tyr Trp Leu Gly Ala Tyr Gln Leu Gln Arg
     50                  55                  60

Val Val Leu Ala Phe Met Val Pro Leu Gly Val Ile Thr Thr Ser Tyr
 65                  70                  75                  80

Leu Leu Leu Leu Ala Phe Leu Gln Arg Arg Gln Arg Arg Arg Gln Asp
                 85                  90                  95

Ser Arg Val Val Ala Arg Ser Val Arg Ile Leu Val Ala Ser Phe Phe
            100                 105                 110

Leu Cys Trp Phe Pro Asn His Val Val Thr Leu Trp Gly Val Leu Val
        115                 120                 125

Lys Phe Asp Leu Val Pro Trp Asn Ser Thr Phe Tyr Thr Ile Gln Thr
    130                 135                 140

Tyr Val Phe Pro Val Thr Thr Cys Leu Ala His Ser Asn Ser Cys Leu
145                 150                 155                 160

Asn Pro Xaa Ala Tyr Val Leu Ser Arg Ile
                165                 170


<210> SEQ ID NO 222
<211> LENGTH: 42
<212> TYPE: PRT
<213> ORGANISM: Homo sapiens
```

-continued

```
<220> FEATURE:
<221> NAME/KEY: SITE
<222> LOCATION: (18)
<223> OTHER INFORMATION: Xaa equals any of the naturally occurring
      L-amino acids
<220> FEATURE:
<221> NAME/KEY: SITE
<222> LOCATION: (37)
<223> OTHER INFORMATION: Xaa equals any of the naturally occurring
      L-amino acids

<400> SEQUENCE: 222

Met Ala Gly Cys Leu Gly Ser Tyr Leu Leu Val Met Ile Leu Ile Leu
  1               5                  10                  15

Cys Xaa Ala His Phe Phe Ile Cys Gly Asn Glu Asp Asn Arg Val Leu
             20                  25                  30

Arg Tyr Asn Leu Xaa Thr Met Ser Val Thr
         35                  40


<210> SEQ ID NO 223
<211> LENGTH: 56
<212> TYPE: PRT
<213> ORGANISM: Homo sapiens

<400> SEQUENCE: 223

Met Cys Ile Ser Gly Cys Leu Phe His Cys Ser Ile Cys Leu Phe Phe
  1               5                  10                  15

Met Leu Val Pro Tyr Cys Phe Asp Tyr Cys Leu Val Met Tyr Phe Glu
             20                  25                  30

Ile Lys Thr Cys Gly Tyr Leu Leu Leu Cys Ser Pro Cys Gln Asp Tyr
         35                  40                  45

Ser Arg Ser Phe Val Ala Ser Ser
     50                  55


<210> SEQ ID NO 224
<211> LENGTH: 96
<212> TYPE: PRT
<213> ORGANISM: Homo sapiens

<400> SEQUENCE: 224

Met Tyr Arg Glu Arg Leu Arg Thr Leu Leu Val Ile Ala Val Val Met
  1               5                  10                  15

Ser Leu Leu Asn Ala Leu Ser Thr Ser Gly Gly Ser Ile Ser Trp Asn
             20                  25                  30

Asp Phe Val His Glu Met Leu Ala Lys Gly Glu Val Gln Arg Val Gln
         35                  40                  45

Val Val Pro Glu Ser Asp Val Val Glu Val Tyr Leu His Pro Gly Ala
     50                  55                  60

Val Val Phe Gly Arg Pro Arg Leu Ala Leu Met Tyr Arg Met Gln Leu
 65                  70                  75                  80

Gln Ile Leu Thr Ser Leu Lys Arg Ser Phe Glu Gln Leu Lys Met Ser
                 85                  90                  95


<210> SEQ ID NO 225
<211> LENGTH: 22
<212> TYPE: PRT
<213> ORGANISM: Homo sapiens

<400> SEQUENCE: 225

Trp Ala Gly Thr Gln Glu Pro Thr Gly Leu Pro Ser Thr Leu Ser Arg
  1               5                  10                  15
```

```
Ser Glu Ser Trp Asp His
            20


<210> SEQ ID NO 226
<211> LENGTH: 171
<212> TYPE: PRT
<213> ORGANISM: Homo sapiens

<400> SEQUENCE: 226

Glu Ile Ile His Asn Leu Pro Thr Ser Arg Met Ala Ala Arg Thr Lys
  1               5                  10                  15

Lys Lys Asn Asp Ile Ile Asn Ile Lys Val Pro Ala Asp Cys Asn Thr
            20                  25                  30

Arg Met Ser Tyr Tyr Tyr Lys Gly Ser Gly Lys Arg Gly Glu Met Glu
        35                  40                  45

Ser Trp Leu Val Met Ser Ser Trp Ser Ile Leu Asp Phe Glu Phe Leu
     50                  55                  60

Glu Ala Arg Pro Gln Leu Phe Asn Leu Val Tyr Thr Glu His Ser Thr
 65                  70                  75                  80

Tyr Ser Gly Arg His Tyr Thr Arg Glu Arg Gly Gly Phe Met Val Phe
                 85                  90                  95

Lys Asn Ser Tyr Ser Gln Leu Leu Leu Lys Arg Lys Asp Ser Leu Cys
            100                 105                 110

Ala Phe Ile Gln Pro Met Ala Leu Asn Ile Ile His Val Pro Met Ser
        115                 120                 125

Ser Lys Cys Ile Phe Pro Ala Gln Ser Gly Pro Ser Thr Phe Arg Ser
    130                 135                 140

Leu Trp Trp Cys Pro His Pro Ile Ser Lys Cys Gln Leu Gly Leu Tyr
145                 150                 155                 160

Ser Ser Gln Ile Arg Asp Ile Pro Tyr Leu Ala
                165                 170


<210> SEQ ID NO 227
<211> LENGTH: 35
<212> TYPE: PRT
<213> ORGANISM: Homo sapiens

<400> SEQUENCE: 227

Glu Ile Ile His Asn Leu Pro Thr Ser Arg Met Ala Ala Arg Thr Lys
  1               5                  10                  15

Lys Lys Asn Asp Ile Ile Asn Ile Lys Val Pro Ala Asp Cys Asn Thr
            20                  25                  30

Arg Met Ser
        35


<210> SEQ ID NO 228
<211> LENGTH: 36
<212> TYPE: PRT
<213> ORGANISM: Homo sapiens

<400> SEQUENCE: 228

Tyr Tyr Tyr Lys Gly Ser Gly Lys Arg Gly Glu Met Glu Ser Trp Leu
  1               5                  10                  15

Val Met Ser Ser Trp Ser Ile Leu Asp Phe Glu Phe Leu Glu Ala Arg
            20                  25                  30

Pro Gln Leu Phe
        35
```

-continued

<210> SEQ ID NO 229
<211> LENGTH: 36
<212> TYPE: PRT
<213> ORGANISM: Homo sapiens

<400> SEQUENCE: 229

```
Asn Leu Val Tyr Thr Glu His Ser Thr Tyr Ser Gly Arg His Tyr Thr
  1               5                  10                  15

Arg Glu Arg Gly Gly Phe Met Val Phe Lys Asn Ser Tyr Ser Gln Leu
             20                  25                  30

Leu Leu Lys Arg
         35
```

<210> SEQ ID NO 230
<211> LENGTH: 35
<212> TYPE: PRT
<213> ORGANISM: Homo sapiens

<400> SEQUENCE: 230

```
Lys Asp Ser Leu Cys Ala Phe Ile Gln Pro Met Ala Leu Asn Ile Ile
  1               5                  10                  15

His Val Pro Met Ser Ser Lys Cys Ile Phe Pro Ala Gln Ser Gly Pro
             20                  25                  30

Ser Thr Phe
         35
```

<210> SEQ ID NO 231
<211> LENGTH: 29
<212> TYPE: PRT
<213> ORGANISM: Homo sapiens

<400> SEQUENCE: 231

```
Arg Ser Leu Trp Trp Cys Pro His Pro Ile Ser Lys Cys Gln Leu Gly
  1               5                  10                  15

Leu Tyr Ser Ser Gln Ile Arg Asp Ile Pro Tyr Leu Ala
             20                  25
```

<210> SEQ ID NO 232
<211> LENGTH: 533
<212> TYPE: PRT
<213> ORGANISM: Homo sapiens
<220> FEATURE:
<221> NAME/KEY: SITE
<222> LOCATION: (473)
<223> OTHER INFORMATION: Xaa equals any of the naturally occurring
      L-amino acids

<400> SEQUENCE: 232

```
Glu Ala Cys Gly Ala Ala Ala Met Ala Ala Leu Thr Ile Ala Thr Gly
  1               5                  10                  15

Thr Gly Asn Trp Phe Ser Ala Leu Ala Leu Gly Val Thr Leu Leu Lys
             20                  25                  30

Cys Leu Leu Ile Pro Thr Tyr His Ser Thr Asp Phe Glu Val His Arg
         35                  40                  45

Asn Trp Leu Ala Ile Thr His Ser Leu Pro Ile Ser Gln Trp Tyr Tyr
     50                  55                  60

Glu Ala Thr Ser Glu Trp Thr Leu Asp Tyr Pro Pro Phe Phe Ala Trp
 65                  70                  75                  80

Phe Glu Tyr Ile Leu Ser His Val Ala Lys Tyr Phe Asp Gln Glu Met
                 85                  90                  95

Leu Asn Val His Asn Leu Asn Tyr Ser Ser Ser Arg Thr Leu Leu Phe
```

-continued

```
            100                 105                 110

Gln Arg Phe Ser Val Ile Phe Met Asp Val Leu Phe Val Tyr Ala Val
        115                 120                 125

Arg Glu Cys Cys Lys Cys Ile Asp Gly Lys Lys Val Gly Lys Glu Leu
    130                 135                 140

Thr Glu Lys Pro Lys Phe Ile Leu Ser Val Leu Leu Leu Trp Asn Phe
145                 150                 155                 160

Gly Leu Leu Ile Val Asp His Ile His Phe Gln Tyr Asn Gly Phe Leu
                165                 170                 175

Phe Gly Leu Met Leu Leu Ser Ile Ala Arg Leu Phe Gln Lys Arg His
            180                 185                 190

Met Glu Gly Ala Phe Leu Phe Ala Val Leu Leu His Phe Lys His Ile
        195                 200                 205

Tyr Leu Tyr Val Ala Pro Ala Tyr Gly Val Tyr Leu Leu Arg Ser Tyr
    210                 215                 220

Cys Phe Thr Ala Asn Lys Pro Asp Gly Ser Ile Arg Trp Lys Ser Phe
225                 230                 235                 240

Ser Phe Val Arg Val Ile Ser Leu Gly Leu Val Val Phe Leu Val Ser
                245                 250                 255

Ala Leu Ser Leu Gly Pro Phe Leu Ala Leu Asn Gln Leu Pro Gln Val
            260                 265                 270

Phe Ser Arg Leu Phe Pro Phe Lys Arg Gly Leu Cys His Ala Tyr Trp
        275                 280                 285

Ala Pro Asn Phe Trp Ala Leu Tyr Asn Ala Leu Asp Lys Val Leu Ser
    290                 295                 300

Val Ile Gly Leu Lys Leu Lys Phe Leu Asp Pro Asn Asn Ile Pro Lys
305                 310                 315                 320

Ala Ser Met Thr Ser Gly Leu Val Gln Gln Phe Gln His Thr Val Leu
                325                 330                 335

Pro Ser Val Thr Pro Leu Ala Thr Leu Ile Cys Thr Leu Ile Ala Ile
            340                 345                 350

Leu Pro Ser Ile Phe Cys Leu Trp Phe Lys Pro Gln Gly Pro Arg Gly
        355                 360                 365

Phe Leu Arg Cys Leu Thr Leu Cys Ala Leu Ser Ser Phe Met Phe Gly
    370                 375                 380

Trp His Val His Glu Lys Ala Ile Leu Leu Ala Ile Leu Pro Met Ser
385                 390                 395                 400

Leu Leu Ser Val Gly Lys Ala Gly Asp Ala Ser Ile Phe Leu Ile Leu
                405                 410                 415

Thr Thr Thr Gly His Tyr Ser Leu Phe Pro Leu Leu Phe Thr Ala Pro
            420                 425                 430

Glu Leu Pro Ile Lys Ile Leu Leu Met Leu Leu Phe Thr Ile Tyr Ser
        435                 440                 445

Ile Ser Ser Leu Lys Thr Leu Phe Arg Lys Glu Lys Pro Leu Phe Asn
    450                 455                 460

Trp Met Glu Thr Phe Tyr Leu Leu Xaa Leu Gly Pro Leu Glu Val Cys
465                 470                 475                 480

Cys Glu Phe Val Phe Pro Phe Thr Ser Trp Lys Val Lys Tyr Pro Phe
                485                 490                 495

Ile Pro Leu Leu Leu Thr Ser Val Tyr Cys Ala Val Gly Ile Thr Tyr
            500                 505                 510

Ala Trp Phe Lys Leu Tyr Val Ser Val Leu Ile Asp Ser Ala Ile Gly
        515                 520                 525
```

-continued

```
Lys Thr Lys Lys Gln
    530


<210> SEQ ID NO 233
<211> LENGTH: 460
<212> TYPE: PRT
<213> ORGANISM: Homo sapiens

<400> SEQUENCE: 233

Met Phe Thr Ile Lys Leu Leu Leu Phe Ile Val Pro Leu Val Ile Ser
  1               5                  10                  15

Ser Arg Ile Asp Gln Asp Asn Ser Ser Phe Asp Ser Leu Ser Pro Glu
             20                  25                  30

Pro Lys Ser Arg Phe Ala Met Leu Asp Asp Val Lys Ile Leu Ala Asn
         35                  40                  45

Gly Leu Leu Gln Leu Gly His Gly Leu Lys Asp Phe Val His Lys Thr
     50                  55                  60

Lys Gly Gln Ile Asn Asp Ile Phe Gln Lys Leu Asn Ile Phe Asp Gln
 65                  70                  75                  80

Ser Phe Tyr Asp Leu Ser Leu Gln Thr Ser Glu Ile Lys Glu Glu Glu
                 85                  90                  95

Lys Glu Leu Arg Arg Thr Thr Tyr Lys Leu Gln Val Lys Asn Glu Glu
            100                 105                 110

Val Lys Asn Met Ser Leu Glu Leu Asn Ser Lys Leu Glu Ser Leu Leu
        115                 120                 125

Glu Glu Lys Ile Leu Leu Gln Gln Lys Val Lys Tyr Leu Glu Glu Gln
    130                 135                 140

Leu Thr Asn Leu Ile Gln Asn Gln Pro Glu Thr Pro Glu His Pro Glu
145                 150                 155                 160

Val Thr Ser Leu Lys Thr Phe Val Glu Lys Gln Asp Asn Ser Ile Lys
                165                 170                 175

Asp Leu Leu Gln Thr Val Glu Asp Gln Tyr Lys Gln Leu Asn Gln Gln
            180                 185                 190

His Ser Gln Ile Lys Glu Ile Glu Asn Gln Leu Arg Arg Thr Ser Ile
        195                 200                 205

Gln Glu Pro Thr Glu Ile Ser Leu Ser Ser Lys Pro Arg Ala Pro Arg
    210                 215                 220

Thr Thr Pro Phe Leu Gln Leu Asn Glu Ile Arg Asn Val Lys His Asp
225                 230                 235                 240

Gly Ile Pro Ala Glu Cys Thr Thr Ile Tyr Asn Arg Gly Glu His Thr
                245                 250                 255

Ser Gly Met Tyr Ala Ile Arg Pro Ser Asn Ser Gln Val Phe His Val
            260                 265                 270

Tyr Cys Asp Val Ile Ser Gly Ser Pro Trp Thr Leu Ile Gln His Arg
        275                 280                 285

Ile Asp Gly Ser Gln Asn Phe Asn Glu Thr Trp Glu Asn Tyr Lys Tyr
    290                 295                 300

Gly Phe Gly Arg Leu Asp Gly Glu Phe Trp Leu Gly Leu Glu Lys Ile
305                 310                 315                 320

Tyr Ser Ile Val Lys Gln Ser Asn Tyr Val Leu Arg Ile Glu Leu Glu
                325                 330                 335

Asp Trp Lys Asp Asn Lys His Tyr Ile Glu Tyr Ser Phe Tyr Leu Gly
            340                 345                 350

Asn His Glu Thr Asn Tyr Thr Leu His Leu Val Ala Ile Thr Gly Asn
```

355 360 365

Val Pro Asn Ala Ile Pro Glu Asn Lys Asp Leu Val Phe Ser Thr Trp
370 375 380

Asp His Lys Ala Lys Gly His Phe Asn Cys Pro Glu Gly Tyr Ser Gly
385 390 395 400

Gly Trp Trp Trp His Asp Glu Cys Gly Glu Asn Asn Leu Asn Gly Lys
405 410 415

Tyr Asn Lys Pro Arg Ala Lys Ser Lys Pro Glu Arg Arg Arg Gly Leu
420 425 430

Ser Trp Lys Ser Gln Asn Gly Arg Leu Tyr Ser Ile Lys Ser Thr Lys
435 440 445

Met Leu Ile His Pro Thr Asp Ser Glu Ser Phe Glu
450 455 460

<210> SEQ ID NO 234
<211> LENGTH: 37
<212> TYPE: PRT
<213> ORGANISM: Homo sapiens

<400> SEQUENCE: 234

Met Phe Thr Ile Lys Leu Leu Leu Phe Ile Val Pro Leu Val Ile Ser
1 5 10 15

Ser Arg Ile Asp Gln Asp Asn Ser Ser Phe Asp Ser Leu Ser Pro Glu
20 25 30

Pro Lys Ser Arg Phe
35

<210> SEQ ID NO 235
<211> LENGTH: 34
<212> TYPE: PRT
<213> ORGANISM: Homo sapiens

<400> SEQUENCE: 235

Ala Met Leu Asp Asp Val Lys Ile Leu Ala Asn Gly Leu Leu Gln Leu
1 5 10 15

Gly His Gly Leu Lys Asp Phe Val His Lys Thr Lys Gly Gln Ile Asn
20 25 30

Asp Ile

<210> SEQ ID NO 236
<211> LENGTH: 35
<212> TYPE: PRT
<213> ORGANISM: Homo sapiens

<400> SEQUENCE: 236

Phe Gln Lys Leu Asn Ile Phe Asp Gln Ser Phe Tyr Asp Leu Ser Leu
1 5 10 15

Gln Thr Ser Glu Ile Lys Glu Glu Glu Lys Glu Leu Arg Arg Thr Thr
20 25 30

Tyr Lys Leu
35

<210> SEQ ID NO 237
<211> LENGTH: 36
<212> TYPE: PRT
<213> ORGANISM: Homo sapiens

<400> SEQUENCE: 237

Gln Val Lys Asn Glu Glu Val Lys Asn Met Ser Leu Glu Leu Asn Ser

-continued

```
  1               5                  10                  15

Lys Leu Glu Ser Leu Leu Glu Glu Lys Ile Leu Leu Gln Gln Lys Val
             20                  25                  30

Lys Tyr Leu Glu
         35


<210> SEQ ID NO 238
<211> LENGTH: 36
<212> TYPE: PRT
<213> ORGANISM: Homo sapiens

<400> SEQUENCE: 238

Glu Gln Leu Thr Asn Leu Ile Gln Asn Gln Pro Glu Thr Pro Glu His
  1               5                  10                  15

Pro Glu Val Thr Ser Leu Lys Thr Phe Val Glu Lys Gln Asp Asn Ser
             20                  25                  30

Ile Lys Asp Leu
         35


<210> SEQ ID NO 239
<211> LENGTH: 35
<212> TYPE: PRT
<213> ORGANISM: Homo sapiens

<400> SEQUENCE: 239

Leu Gln Thr Val Glu Asp Gln Tyr Lys Gln Leu Asn Gln Gln His Ser
  1               5                  10                  15

Gln Ile Lys Glu Ile Glu Asn Gln Leu Arg Arg Thr Ser Ile Gln Glu
             20                  25                  30

Pro Thr Glu
         35


<210> SEQ ID NO 240
<211> LENGTH: 35
<212> TYPE: PRT
<213> ORGANISM: Homo sapiens

<400> SEQUENCE: 240

Ile Ser Leu Ser Ser Lys Pro Arg Ala Pro Arg Thr Thr Pro Phe Leu
  1               5                  10                  15

Gln Leu Asn Glu Ile Arg Asn Val Lys His Asp Gly Ile Pro Ala Glu
             20                  25                  30

Cys Thr Thr
         35


<210> SEQ ID NO 241
<211> LENGTH: 36
<212> TYPE: PRT
<213> ORGANISM: Homo sapiens

<400> SEQUENCE: 241

Ile Tyr Asn Arg Gly Glu His Thr Ser Gly Met Tyr Ala Ile Arg Pro
  1               5                  10                  15

Ser Asn Ser Gln Val Phe His Val Tyr Cys Asp Val Ile Ser Gly Ser
             20                  25                  30

Pro Trp Thr Leu
         35


<210> SEQ ID NO 242
<211> LENGTH: 36
```

-continued

<212> TYPE: PRT
<213> ORGANISM: Homo sapiens

<400> SEQUENCE: 242

Ile Gln His Arg Ile Asp Gly Ser Gln Asn Phe Asn Glu Thr Trp Glu
1 5 10 15

Asn Tyr Lys Tyr Gly Phe Gly Arg Leu Asp Gly Glu Phe Trp Leu Gly
20 25 30

Leu Glu Lys Ile
35

<210> SEQ ID NO 243
<211> LENGTH: 35
<212> TYPE: PRT
<213> ORGANISM: Homo sapiens

<400> SEQUENCE: 243

Tyr Ser Ile Val Lys Gln Ser Asn Tyr Val Leu Arg Ile Glu Leu Glu
1 5 10 15

Asp Trp Lys Asp Asn Lys His Tyr Ile Glu Tyr Ser Phe Tyr Leu Gly
20 25 30

Asn His Glu
35

<210> SEQ ID NO 244
<211> LENGTH: 35
<212> TYPE: PRT
<213> ORGANISM: Homo sapiens

<400> SEQUENCE: 244

Thr Asn Tyr Thr Leu His Leu Val Ala Ile Thr Gly Asn Val Pro Asn
1 5 10 15

Ala Ile Pro Glu Asn Lys Asp Leu Val Phe Ser Thr Trp Asp His Lys
20 25 30

Ala Lys Gly
35

<210> SEQ ID NO 245
<211> LENGTH: 36
<212> TYPE: PRT
<213> ORGANISM: Homo sapiens

<400> SEQUENCE: 245

His Phe Asn Cys Pro Glu Gly Tyr Ser Gly Gly Trp Trp Trp His Asp
1 5 10 15

Glu Cys Gly Glu Asn Asn Leu Asn Gly Lys Tyr Asn Lys Pro Arg Ala
20 25 30

Lys Ser Lys Pro
35

<210> SEQ ID NO 246
<211> LENGTH: 34
<212> TYPE: PRT
<213> ORGANISM: Homo sapiens

<400> SEQUENCE: 246

Glu Arg Arg Arg Gly Leu Ser Trp Lys Ser Gln Asn Gly Arg Leu Tyr
1 5 10 15

Ser Ile Lys Ser Thr Lys Met Leu Ile His Pro Thr Asp Ser Glu Ser
20 25 30

-continued

Phe Glu

<210> SEQ ID NO 247
<211> LENGTH: 36
<212> TYPE: PRT
<213> ORGANISM: Homo sapiens

<400> SEQUENCE: 247

Leu Pro Pro Arg Gly Pro Ala Thr Phe Gly Ser Pro Gly Cys Pro Pro
1 5 10 15

Ala Asn Ser Pro Pro Ser Ala Pro Ala Thr Pro Glu Pro Ala Arg Ala
20 25 30

Pro Glu Arg Val
35

<210> SEQ ID NO 248
<211> LENGTH: 44
<212> TYPE: PRT
<213> ORGANISM: Homo sapiens

<400> SEQUENCE: 248

Gly Thr Arg Ala Gly Val Ser Lys Tyr Thr Gly Gly Arg Gly Val Thr
1 5 10 15

Trp Ala Pro Ser Ser Ala Ala Val Pro Arg Ile Ser Ser Ala Thr Met
20 25 30

Arg Met Gly Leu Thr Ser Phe Ser Thr Thr Gly Ala
35 40

<210> SEQ ID NO 249
<211> LENGTH: 306
<212> TYPE: PRT
<213> ORGANISM: Homo sapiens
<220> FEATURE:
<221> NAME/KEY: SITE
<222> LOCATION: (293)
<223> OTHER INFORMATION: Xaa equals any of the naturally occurring
L-amino acids

<400> SEQUENCE: 249

Trp Gln Ser Gly His Arg Leu Trp Gln Leu Glu Trp Pro Pro Pro Pro
1 5 10 15

Leu Ser Ala Asp Glu His Pro Trp Glu Gly Pro Leu Pro Gly Thr Ser
20 25 30

Pro Ser Pro Lys Phe Ser Met Pro Ser Pro Val Pro His Gly His His
35 40 45

Arg Pro Thr Leu Thr Met Thr Arg Ser Trp Arg Ile Phe Phe Asn Asn
50 55 60

Ile Ala Tyr Arg Ser Ser Ser Ala Asn Arg Leu Phe Arg Val Ile Arg
65 70 75 80

Arg Glu His Gly Asp Pro Leu Ile Glu Glu Leu Asn Pro Gly Asp Ala
85 90 95

Leu Glu Pro Glu Gly Arg Gly Thr Gly Gly Val Val Thr Asp Phe Asp
100 105 110

Gly Asp Gly Met Leu Asp Leu Ile Leu Ser His Gly Glu Ser Met Ala
115 120 125

Gln Pro Leu Ser Val Phe Arg Gly Asn Gln Gly Phe Asn Asn Asn Trp
130 135 140

Leu Arg Val Val Pro Arg Thr Arg Phe Gly Ala Phe Ala Arg Gly Ala
145 150 155 160

-continued

```
Lys Val Val Leu Tyr Thr Lys Lys Ser Gly Ala His Leu Arg Ile Ile
                165                 170                 175

Asp Gly Gly Ser Gly Tyr Leu Cys Glu Met Glu Pro Val Ala His Phe
            180                 185                 190

Gly Leu Gly Lys Asp Glu Ala Ser Ser Val Glu Val Thr Trp Pro Asp
        195                 200                 205

Gly Lys Met Val Ser Arg Asn Val Ala Ser Gly Glu Met Asn Ser Val
    210                 215                 220

Leu Glu Ile Leu Tyr Pro Arg Asp Glu Asp Thr Leu Gln Asp Pro Ala
225                 230                 235                 240

Pro Leu Glu Cys Gly Gln Gly Phe Ser Gln Gln Glu Asn Gly His Cys
                245                 250                 255

Met Asp Thr Asn Glu Cys Ile Gln Phe Pro Phe Val Cys Pro Arg Asp
            260                 265                 270

Lys Pro Val Cys Val Asn Thr Tyr Gly Ser Tyr Arg Cys Arg Thr Asn
        275                 280                 285

Lys Lys Cys Ser Xaa Gly Leu Arg Val Pro Thr Arg Met Ala His Thr
    290                 295                 300

Gly Leu
305


<210> SEQ ID NO 250
<211> LENGTH: 36
<212> TYPE: PRT
<213> ORGANISM: Homo sapiens

<400> SEQUENCE: 250

Trp Gln Ser Gly His Arg Leu Trp Gln Leu Glu Trp Pro Pro Pro Pro
  1               5                  10                  15

Leu Ser Ala Asp Glu His Pro Trp Glu Gly Pro Leu Pro Gly Thr Ser
             20                  25                  30

Pro Ser Pro Lys
         35


<210> SEQ ID NO 251
<211> LENGTH: 35
<212> TYPE: PRT
<213> ORGANISM: Homo sapiens

<400> SEQUENCE: 251

Phe Ser Met Pro Ser Pro Val Pro His Gly His His Arg Pro Thr Leu
  1               5                  10                  15

Thr Met Thr Arg Ser Trp Arg Ile Phe Phe Asn Asn Ile Ala Tyr Arg
             20                  25                  30

Ser Ser Ser
         35


<210> SEQ ID NO 252
<211> LENGTH: 37
<212> TYPE: PRT
<213> ORGANISM: Homo sapiens

<400> SEQUENCE: 252

Ala Asn Arg Leu Phe Arg Val Ile Arg Arg Glu His Gly Asp Pro Leu
  1               5                  10                  15

Ile Glu Glu Leu Asn Pro Gly Asp Ala Leu Glu Pro Glu Gly Arg Gly
             20                  25                  30

Thr Gly Gly Val Val
```

35

<210> SEQ ID NO 253
<211> LENGTH: 34
<212> TYPE: PRT
<213> ORGANISM: Homo sapiens

<400> SEQUENCE: 253

Thr Asp Phe Asp Gly Asp Gly Met Leu Asp Leu Ile Leu Ser His Gly
1 5 10 15

Glu Ser Met Ala Gln Pro Leu Ser Val Phe Arg Gly Asn Gln Gly Phe
20 25 30

Asn Asn

<210> SEQ ID NO 254
<211> LENGTH: 35
<212> TYPE: PRT
<213> ORGANISM: Homo sapiens

<400> SEQUENCE: 254

Asn Trp Leu Arg Val Val Pro Arg Thr Arg Phe Gly Ala Phe Ala Arg
1 5 10 15

Gly Ala Lys Val Val Leu Tyr Thr Lys Lys Ser Gly Ala His Leu Arg
20 25 30

Ile Ile Asp
35

<210> SEQ ID NO 255
<211> LENGTH: 36
<212> TYPE: PRT
<213> ORGANISM: Homo sapiens

<400> SEQUENCE: 255

Gly Gly Ser Gly Tyr Leu Cys Glu Met Glu Pro Val Ala His Phe Gly
1 5 10 15

Leu Gly Lys Asp Glu Ala Ser Ser Val Glu Val Thr Trp Pro Asp Gly
20 25 30

Lys Met Val Ser
35

<210> SEQ ID NO 256
<211> LENGTH: 35
<212> TYPE: PRT
<213> ORGANISM: Homo sapiens

<400> SEQUENCE: 256

Arg Asn Val Ala Ser Gly Glu Met Asn Ser Val Leu Glu Ile Leu Tyr
1 5 10 15

Pro Arg Asp Glu Asp Thr Leu Gln Asp Pro Ala Pro Leu Glu Cys Gly
20 25 30

Gln Gly Phe
35

<210> SEQ ID NO 257
<211> LENGTH: 36
<212> TYPE: PRT
<213> ORGANISM: Homo sapiens

<400> SEQUENCE: 257

Ser Gln Gln Glu Asn Gly His Cys Met Asp Thr Asn Glu Cys Ile Gln
1 5 10 15

-continued

```
Phe Pro Phe Val Cys Pro Arg Asp Lys Pro Val Cys Val Asn Thr Tyr
             20                  25                  30

Gly Ser Tyr Arg
         35


<210> SEQ ID NO 258
<211> LENGTH: 22
<212> TYPE: PRT
<213> ORGANISM: Homo sapiens
<220> FEATURE:
<221> NAME/KEY: SITE
<222> LOCATION: (9)
<223> OTHER INFORMATION: Xaa equals any of the naturally occurring
      L-amino acids

<400> SEQUENCE: 258

Cys Arg Thr Asn Lys Lys Cys Ser Xaa Gly Leu Arg Val Pro Thr Arg
  1               5                  10                  15

Met Ala His Thr Gly Leu
             20


<210> SEQ ID NO 259
<211> LENGTH: 9
<212> TYPE: PRT
<213> ORGANISM: Homo sapiens

<400> SEQUENCE: 259

Gln Ser Pro Ile Asp Ile Gln Thr Asp
  1               5


<210> SEQ ID NO 260
<211> LENGTH: 18
<212> TYPE: PRT
<213> ORGANISM: Homo sapiens

<400> SEQUENCE: 260

Leu His Asn Asn Gly His Thr Val Gln Leu Ser Leu Pro Ser Thr Leu
  1               5                  10                  15

Tyr Leu


<210> SEQ ID NO 261
<211> LENGTH: 11
<212> TYPE: PRT
<213> ORGANISM: Homo sapiens

<400> SEQUENCE: 261

Tyr Val Ala Ala Gln Leu His Leu His Trp Gly
  1               5                  10


<210> SEQ ID NO 262
<211> LENGTH: 11
<212> TYPE: PRT
<213> ORGANISM: Homo sapiens

<400> SEQUENCE: 262

Ala Glu Leu His Ile Val His Tyr Asp Ser Asp
  1               5                  10


<210> SEQ ID NO 263
<211> LENGTH: 16
<212> TYPE: PRT
<213> ORGANISM: Homo sapiens

<400> SEQUENCE: 263
```

-continued

```
Gly Gln His Trp Thr Tyr Glu Gly Pro His Gly Gln Asp His Trp Pro
  1               5                  10                  15


<210> SEQ ID NO 264
<211> LENGTH: 14
<212> TYPE: PRT
<213> ORGANISM: Homo sapiens

<400> SEQUENCE: 264

Gln Ser Pro Ile Asp Ile Gln Thr Asp Ser Val Thr Phe Asp
  1               5                  10


<210> SEQ ID NO 265
<211> LENGTH: 15
<212> TYPE: PRT
<213> ORGANISM: Homo sapiens

<400> SEQUENCE: 265

Leu His Asn Asn Gly His Thr Val Gln Leu Ser Leu Pro Ser Thr
  1               5                  10                  15


<210> SEQ ID NO 266
<211> LENGTH: 12
<212> TYPE: PRT
<213> ORGANISM: Homo sapiens

<400> SEQUENCE: 266

Lys Tyr Val Ala Ala Gln Leu His Leu His Trp Gly
  1               5                  10


<210> SEQ ID NO 267
<211> LENGTH: 13
<212> TYPE: PRT
<213> ORGANISM: Homo sapiens

<400> SEQUENCE: 267

Ala Glu Leu His Ile Val His Tyr Asp Ser Asp Ser Tyr
  1               5                  10


<210> SEQ ID NO 268
<211> LENGTH: 1667
<212> TYPE: DNA
<213> ORGANISM: Homo sapiens

<400> SEQUENCE: 268

ggccgcgccg ccgctgccgc cgccgcgcgc gattctgctt ctcagaagat gcactattat     60

agatactcta acgccaaggt cagctgctgg tacaagtacc tccttttcag ctacaacatc    120

atcttctgat tggctggagt tgtcttcctt ggagtcgggc tgtgggcatg gagcgaaaag    180

ggtgtgctgt ccgacctcac caaagtgacc cggatgcatg gaatcgaccc tgtggtgctg    240

gtcctgatgg tgggcgtggt gatgttcacc ctggggttcg ccggctgcgt gggggctctg    300

cgggagaata tctgcttgct caactttttc tgtggcacca tcgtgctcat cttcttcctg    360

gagctggctg tggccgtgct ggccttcctg ttccaggact gggtgaggga ccggttccgg    420

gagttcttcg agagcaacat caagtcctac cgggacgata tcgatctgca aaacctcatc    480

gactcccttc agaaagctaa ccagtgctgt ggcgcatatg gccctgaaag actgggacct    540

cagacgtcta cttcaattgc agcggtgcca gctacagccg agagaatgcg ggtccccctt    600

ctcctgctgc gtgccagatc ctgcgcaaaa agttgtgaac acacagtgtg gatatgatgt    660

caggattcag ctgaagagca agtgggatga gtccatcttc acgaaaggct gcatccaggc    720
```

-continued

```
gctggaaagc tggctcccgc ggaacattta cattgtggct ggcgtcttca tcgccatctc    780

gctgttgcag atatttggca tcttcctggc aaggacgctg atctcagaca tcgaggcagt    840

gaaggccggc catcacttct gaggagcaga gttgagggag ccgagctgag ccacgctggg    900

aggccagagc ctttctctgc catcagccct acgtccagag ggagaggagc cgacaccccc    960

agagccagtg ccccatctta agcatcagcg tgacgtgacc tctctgtttc tgcttgctgg   1020

tgctgaagac caagggtccc ccttgttacc tgcccaaact tgtgactgca tccctctgga   1080

gtctacccag agacagagaa tgtgtcttta tgtgggagtg gtgactctga aagacagaga   1140

gggctcctgt ggctgccagg agggcttgac tcagaccccc tgcagctcaa gcatgtctgc   1200

aggacacctg gtccccctct cccagtggca tcccaaacat ctgctttggg tccatcccac   1260

atctgtgggt gggcccgtgg gtaagaaggg aaccccacag gcgtggaaca gggcatcctc   1320

tctcccatcc aagcaaagcc agcatggggg cctgcccgta acgggaggcg gacgtggccc   1380

cgctgggcct ctgagtgcca gcgcagtctg ctgggacatg cacatatcag gggttgtttg   1440

caggatcctc agccatgttc aagtgaagta agcctgagcc agtgcgtgga ctggtgccac   1500

gggagtgcct tgtccactgt ccccctgtgt ccaccagcta ttctcctggc gccggaactg   1560

cctctggtct tgatagcatt aagccctgat tggccggtgg cgcggtgggc atggttcttc   1620

actgagagcc ggctctcctt ttcttaaagt gtgtaaatag tttattt                 1667


<210> SEQ ID NO 269
<211> LENGTH: 270
<212> TYPE: PRT
<213> ORGANISM: Homo sapiens

<400> SEQUENCE: 269

Met His Tyr Tyr Arg Tyr Ser Asn Ala Lys Val Ser Cys Trp Tyr Lys
  1               5                  10                  15

Tyr Leu Leu Phe Ser Tyr Asn Ile Ile Phe Trp Leu Ala Gly Val Val
            20                  25                  30

Phe Leu Gly Val Gly Leu Trp Ala Trp Ser Glu Lys Gly Val Leu Ser
        35                  40                  45

Asp Leu Thr Lys Val Thr Arg Met His Gly Ile Asp Pro Val Val Leu
    50                  55                  60

Val Leu Met Val Gly Val Val Met Phe Thr Leu Gly Phe Ala Gly Cys
 65                  70                  75                  80

Val Gly Ala Leu Arg Glu Asn Ile Cys Leu Leu Asn Phe Phe Cys Gly
                 85                  90                  95

Thr Ile Val Leu Ile Phe Phe Leu Glu Leu Ala Val Ala Val Leu Ala
            100                 105                 110

Phe Leu Phe Gln Asp Trp Val Arg Asp Arg Phe Arg Glu Phe Phe Glu
        115                 120                 125

Ser Asn Ile Lys Ser Tyr Arg Asp Asp Ile Asp Leu Gln Asn Leu Ile
    130                 135                 140

Asp Ser Leu Gln Lys Ala Asn Gln Cys Cys Gly Ala Tyr Gly Pro Glu
145                 150                 155                 160

Asp Trp Asp Leu Asn Val Tyr Phe Asn Cys Ser Gly Ala Ser Tyr Ser
                165                 170                 175

Arg Glu Lys Cys Gly Val Pro Phe Ser Cys Cys Val Pro Asp Pro Ala
            180                 185                 190

Gln Lys Val Val Asn Thr Gln Cys Gly Tyr Asp Val Arg Ile Gln Leu
        195                 200                 205
```

-continued

```
Lys Ser Lys Trp Asp Glu Ser Ile Phe Thr Lys Gly Cys Ile Gln Ala
    210                 215                 220

Leu Glu Ser Trp Leu Pro Arg Asn Ile Tyr Ile Val Ala Gly Val Phe
225                 230                 235                 240

Ile Ala Ile Ser Leu Leu Gln Ile Phe Gly Ile Phe Leu Ala Arg Thr
                245                 250                 255

Leu Ile Ser Asp Ile Glu Ala Val Lys Ala Gly His His Phe
            260                 265                 270


<210> SEQ ID NO 270
<211> LENGTH: 277
<212> TYPE: PRT
<213> ORGANISM: Homo sapiens

<400> SEQUENCE: 270

Ser Gly Asn Leu Gly Ser Ala Asp Gly Trp Ala Tyr Ile Asp Val Glu
  1               5                  10                  15

Val Arg Arg Pro Trp Ala Phe Val Gly Pro Gly Cys Ser Arg Ser Ser
             20                  25                  30

Gly Asn Gly Ser Thr Ala Tyr Gly Leu Val Gly Ser Pro Arg Trp Leu
         35                  40                  45

Ser Pro Phe His Thr Gly Gly Ala Val Ser Leu Pro Arg Arg Pro Arg
     50                  55                  60

Gly Pro Gly Pro Val Leu Gly Val Ala Arg Pro Cys Leu Arg Cys Val
 65                  70                  75                  80

Leu Arg Pro Glu His Tyr Glu Pro Gly Ser His Tyr Ser Gly Phe Ala
                 85                  90                  95

Gly Arg Asp Ala Ser Arg Ala Phe Val Thr Gly Asp Cys Ser Glu Ala
            100                 105                 110

Gly Leu Val Asp Asp Val Ser Asp Leu Ser Ala Ala Glu Met Leu Thr
        115                 120                 125

Leu His Asn Trp Leu Ser Phe Tyr Glu Lys Asn Tyr Val Cys Val Gly
    130                 135                 140

Arg Val Thr Gly Arg Phe Tyr Gly Glu Asp Gly Leu Pro Thr Pro Ala
145                 150                 155                 160

Leu Thr Gln Val Glu Ala Ala Ile Thr Arg Gly Leu Glu Ala Asn Lys
                165                 170                 175

Leu Gln Leu Gln Glu Lys Gln Thr Phe Pro Pro Cys Asn Ala Glu Trp
            180                 185                 190

Ser Ser Ala Arg Gly Ser Arg Leu Trp Cys Ser Gln Lys Ser Gly Gly
        195                 200                 205

Val Ser Arg Asp Trp Ile Gly Val Pro Arg Lys Leu Tyr Lys Pro Gly
    210                 215                 220

Ala Lys Glu Pro Arg Cys Val Cys Val Arg Thr Thr Gly Pro Pro Ser
225                 230                 235                 240

Gly Gln Met Pro Asp Asn Pro Pro His Arg Asn Arg Gly Asp Leu Asp
                245                 250                 255

His Pro Asn Leu Ala Glu Tyr Thr Gly Cys Pro Pro Leu Ala Ile Thr
            260                 265                 270

Cys Ser Phe Pro Leu
        275


<210> SEQ ID NO 271
<211> LENGTH: 36
<212> TYPE: PRT
```

-continued

<213> ORGANISM: Homo sapiens

<400> SEQUENCE: 271

Ser Gly Asn Leu Gly Ser Ala Asp Gly Trp Ala Tyr Ile Asp Val Glu
1               5                   10                  15

Val Arg Arg Pro Trp Ala Phe Val Gly Pro Gly Cys Ser Arg Ser Ser
            20                  25                  30

Gly Asn Gly Ser
        35

<210> SEQ ID NO 272
<211> LENGTH: 36
<212> TYPE: PRT
<213> ORGANISM: Homo sapiens

<400> SEQUENCE: 272

Thr Ala Tyr Gly Leu Val Gly Ser Pro Arg Trp Leu Ser Pro Phe His
1               5                   10                  15

Thr Gly Gly Ala Val Ser Leu Pro Arg Arg Pro Arg Gly Pro Gly Pro
            20                  25                  30

Val Leu Gly Val
        35

<210> SEQ ID NO 273
<211> LENGTH: 36
<212> TYPE: PRT
<213> ORGANISM: Homo sapiens

<400> SEQUENCE: 273

Ala Arg Pro Cys Leu Arg Cys Val Leu Arg Pro Glu His Tyr Glu Pro
1               5                   10                  15

Gly Ser His Tyr Ser Gly Phe Ala Gly Arg Asp Ala Ser Arg Ala Phe
            20                  25                  30

Val Thr Gly Asp
        35

<210> SEQ ID NO 274
<211> LENGTH: 36
<212> TYPE: PRT
<213> ORGANISM: Homo sapiens

<400> SEQUENCE: 274

Cys Ser Glu Ala Gly Leu Val Asp Asp Val Ser Asp Leu Ser Ala Ala
1               5                   10                  15

Glu Met Leu Thr Leu His Asn Trp Leu Ser Phe Tyr Glu Lys Asn Tyr
            20                  25                  30

Val Cys Val Gly
        35

<210> SEQ ID NO 275
<211> LENGTH: 36
<212> TYPE: PRT
<213> ORGANISM: Homo sapiens

<400> SEQUENCE: 275

Arg Val Thr Gly Arg Phe Tyr Gly Glu Asp Gly Leu Pro Thr Pro Ala
1               5                   10                  15

Leu Thr Gln Val Glu Ala Ala Ile Thr Arg Gly Leu Glu Ala Asn Lys
            20                  25                  30

Leu Gln Leu Gln

-continued

35

<210> SEQ ID NO 276
<211> LENGTH: 36
<212> TYPE: PRT
<213> ORGANISM: Homo sapiens

<400> SEQUENCE: 276

Glu Lys Gln Thr Phe Pro Pro Cys Asn Ala Glu Trp Ser Ser Ala Arg
1 5 10 15

Gly Ser Arg Leu Trp Cys Ser Gln Lys Ser Gly Gly Val Ser Arg Asp
20 25 30

Trp Ile Gly Val
35

<210> SEQ ID NO 277
<211> LENGTH: 29
<212> TYPE: PRT
<213> ORGANISM: Homo sapiens

<400> SEQUENCE: 277

Pro Arg Lys Leu Tyr Lys Pro Gly Ala Lys Glu Pro Arg Cys Val Cys
1 5 10 15

Val Arg Thr Thr Gly Pro Pro Ser Gly Gln Met Pro Asp
20 25

<210> SEQ ID NO 278
<211> LENGTH: 32
<212> TYPE: PRT
<213> ORGANISM: Homo sapiens

<400> SEQUENCE: 278

Asn Pro Pro His Arg Asn Arg Gly Asp Leu Asp His Pro Asn Leu Ala
1 5 10 15

Glu Tyr Thr Gly Cys Pro Pro Leu Ala Ile Thr Cys Ser Phe Pro Leu
20 25 30

<210> SEQ ID NO 279
<211> LENGTH: 171
<212> TYPE: PRT
<213> ORGANISM: Homo sapiens

<400> SEQUENCE: 279

Ser Gln Leu Leu Pro Gly Ser Val Pro Gly Trp Ala Ala His Pro Leu
1 5 10 15

Arg Arg Thr Val Leu Ser Pro Ser Gln His Thr His Asn Ser Ser His
20 25 30

Arg Met Lys Ala Asn Cys Glu Val Ser Ala Ser Gln Arg Leu Thr Gly
35 40 45

Arg Ile Arg His Pro Arg Gly Leu Leu Gln Asn Ser Pro Arg Ser Arg
50 55 60

Lys Leu Trp Met Arg Leu Gly Leu Arg Ser Arg Tyr Ser Gly Thr Gln
65 70 75 80

Ala Arg Ser Ala Pro Ala Gly Gly His Ile Val Asp Thr Ala Glu Gln
85 90 95

Arg Gln Val Gln Ala Arg Val Pro Trp Ala Ala Ala Val Ala Arg Gln
100 105 110

Leu Leu Arg Tyr Glu Lys Ala Lys Ala Ser Ala Gly Thr Pro Pro Ala
115 120 125

-continued

```
His Lys Pro Cys Cys His Tyr Arg Cys Cys Gly Tyr Ser Gln Ala Gln
    130                 135                 140

Gln Lys Pro Thr Ala Ser Ala Pro Gln His Leu Tyr Arg Pro Thr Arg
145                 150                 155                 160

Pro His Phe Arg Gly Cys Arg Ser Ile Ser Val
                165                 170


<210> SEQ ID NO 280
<211> LENGTH: 13
<212> TYPE: PRT
<213> ORGANISM: Homo sapiens

<400> SEQUENCE: 280

Leu Leu Leu Cys Pro Trp Trp Leu Cys Phe Asp Trp Ser
  1               5                  10


<210> SEQ ID NO 281
<211> LENGTH: 270
<212> TYPE: PRT
<213> ORGANISM: Homo sapiens

<400> SEQUENCE: 281

Met Gly Cys Ile Pro Leu Ile Lys Ser Ile Ser Asp Trp Arg Val Ile
  1               5                  10                  15

Ala Leu Ala Ala Leu Trp Phe Cys Leu Ile Gly Leu Ile Cys Gln Ala
            20                  25                  30

Leu Cys Ser Glu Asp Gly His Lys Arg Arg Ile Leu Thr Leu Gly Leu
        35                  40                  45

Gly Phe Leu Val Ile Pro Phe Leu Pro Ala Ser Asn Leu Phe Phe Arg
     50                  55                  60

Val Gly Phe Val Val Ala Glu Cys Val Leu Tyr Leu Pro Ser Ile Gly
 65                  70                  75                  80

Tyr Cys Val Leu Leu Thr Phe Gly Phe Gly Ala Leu Ser Lys His Thr
                 85                  90                  95

Lys Lys Lys Lys Leu Ile Ala Ala Val Val Leu Gly Ile Leu Phe Ile
            100                 105                 110

Asn Thr Leu Arg Cys Val Leu Arg Thr Ala Lys Trp Arg Ser Glu Glu
        115                 120                 125

Gln Leu Phe Arg Ser Ala Leu Ser Val Cys Pro Leu Asn Ala Lys Val
    130                 135                 140

His Tyr Asn Ile Gly Lys Asn Leu Ala Asp Lys Gly Asn Gln Thr Ala
145                 150                 155                 160

Ala Ile Arg Tyr Tyr Arg Glu Ala Val Arg Leu Asn Pro Lys Tyr Val
                165                 170                 175

His Ala Met Asn Asn Leu Gly Asn Ile Leu Lys Glu Arg Asn Glu Leu
            180                 185                 190

Gln Glu Ala Glu Glu Leu Leu Ser Leu Ala Val Gln Ile Gln Pro Asp
        195                 200                 205

Phe Ala Ala Ala Trp Met Asn Leu Gly Ile Val Gln Asn Ser Leu Lys
    210                 215                 220

Arg Phe Glu Thr Ala Glu Gln Asn Tyr Arg Thr Ala Ile Lys His Arg
225                 230                 235                 240

Arg Lys Tyr Pro Asp Cys Tyr Tyr Asn Leu Gly Arg Leu Val Arg Thr
                245                 250                 255

Gly Cys Pro Val Pro Val Glu Gly Lys Met Gly Tyr Phe Ser
            260                 265                 270
```

-continued

<210> SEQ ID NO 282
<211> LENGTH: 38
<212> TYPE: PRT
<213> ORGANISM: Homo sapiens

<400> SEQUENCE: 282

```
Met Gly Cys Ile Pro Leu Ile Lys Ser Ile Ser Asp Trp Arg Val Ile
  1               5                  10                  15

Ala Leu Ala Ala Leu Trp Phe Cys Leu Ile Gly Leu Ile Cys Gln Ala
             20                  25                  30

Leu Cys Ser Glu Asp Gly
         35
```

<210> SEQ ID NO 283
<211> LENGTH: 38
<212> TYPE: PRT
<213> ORGANISM: Homo sapiens

<400> SEQUENCE: 283

```
His Lys Arg Arg Ile Leu Thr Leu Gly Leu Gly Phe Leu Val Ile Pro
  1               5                  10                  15

Phe Leu Pro Ala Ser Asn Leu Phe Phe Arg Val Gly Phe Val Val Ala
             20                  25                  30

Glu Cys Val Leu Tyr Leu
         35
```

<210> SEQ ID NO 284
<211> LENGTH: 38
<212> TYPE: PRT
<213> ORGANISM: Homo sapiens

<400> SEQUENCE: 284

```
Pro Ser Ile Gly Tyr Cys Val Leu Leu Thr Phe Gly Phe Gly Ala Leu
  1               5                  10                  15

Ser Lys His Thr Lys Lys Lys Lys Leu Ile Ala Ala Val Val Leu Gly
             20                  25                  30

Ile Leu Phe Ile Asn Thr
         35
```

<210> SEQ ID NO 285
<211> LENGTH: 38
<212> TYPE: PRT
<213> ORGANISM: Homo sapiens

<400> SEQUENCE: 285

```
Leu Arg Cys Val Leu Arg Thr Ala Lys Trp Arg Ser Glu Glu Gln Leu
  1               5                  10                  15

Phe Arg Ser Ala Leu Ser Val Cys Pro Leu Asn Ala Lys Val His Tyr
             20                  25                  30

Asn Ile Gly Lys Asn Leu
         35
```

<210> SEQ ID NO 286
<211> LENGTH: 38
<212> TYPE: PRT
<213> ORGANISM: Homo sapiens

<400> SEQUENCE: 286

```
Ala Asp Lys Gly Asn Gln Thr Ala Ala Ile Arg Tyr Tyr Arg Glu Ala
  1               5                  10                  15
```

-continued

Val Arg Leu Asn Pro Lys Tyr Val His Ala Met Asn Asn Leu Gly Asn
20 25 30

Ile Leu Lys Glu Arg Asn
35

<210> SEQ ID NO 287
<211> LENGTH: 38
<212> TYPE: PRT
<213> ORGANISM: Homo sapiens

<400> SEQUENCE: 287

Glu Leu Gln Glu Ala Glu Glu Leu Leu Ser Leu Ala Val Gln Ile Gln
1 5 10 15

Pro Asp Phe Ala Ala Ala Trp Met Asn Leu Gly Ile Val Gln Asn Ser
20 25 30

Leu Lys Arg Phe Glu Thr
35

<210> SEQ ID NO 288
<211> LENGTH: 42
<212> TYPE: PRT
<213> ORGANISM: Homo sapiens

<400> SEQUENCE: 288

Ala Glu Gln Asn Tyr Arg Thr Ala Ile Lys His Arg Arg Lys Tyr Pro
1 5 10 15

Asp Cys Tyr Tyr Asn Leu Gly Arg Leu Val Arg Thr Gly Cys Pro Val
20 25 30

Pro Val Glu Gly Lys Met Gly Tyr Phe Ser
35 40

<210> SEQ ID NO 289
<211> LENGTH: 16
<212> TYPE: PRT
<213> ORGANISM: Homo sapiens

<400> SEQUENCE: 289

Leu Ile Lys Ser Ile Ser Asp Trp Arg Val Ile Ala Leu Ala Ala Leu
1 5 10 15

<210> SEQ ID NO 290
<211> LENGTH: 15
<212> TYPE: PRT
<213> ORGANISM: Homo sapiens

<400> SEQUENCE: 290

Arg Asp Asn Asp Tyr Leu Leu His Gly His Arg Pro Pro Met Phe
1 5 10 15

<210> SEQ ID NO 291
<211> LENGTH: 24
<212> TYPE: PRT
<213> ORGANISM: Homo sapiens

<400> SEQUENCE: 291

Ser Phe Arg Ala Cys Phe Lys Ser Ile Phe Arg Ile His Thr Glu Thr
1 5 10 15

Gly Asn Ile Trp Thr His Leu Leu
20

<210> SEQ ID NO 292
<211> LENGTH: 29

-continued

<212> TYPE: PRT
<213> ORGANISM: Homo sapiens

<400> SEQUENCE: 292

Gly Phe Val Leu Phe Leu Phe Leu Gly Ile Leu Thr Met Leu Arg Pro
1 5 10 15

Asn Met Tyr Phe Met Ala Pro Leu Gln Glu Lys Val Val
20 25

<210> SEQ ID NO 293
<211> LENGTH: 457
<212> TYPE: PRT
<213> ORGANISM: Homo sapiens

<400> SEQUENCE: 293

Thr Gly Pro Glu Phe Pro Gly Ser Asn Ser Thr Val Ala Arg Arg Ile
1 5 10 15

Lys Asp Leu Ala Ala Asp Ile Glu Glu Glu Leu Val Cys Arg Leu Lys
20 25 30

Ile Cys Asp Gly Phe Ser Leu Gln Leu Asp Glu Ser Ala Asp Val Ser
35 40 45

Gly Leu Ala Val Leu Leu Val Phe Val Arg Tyr Arg Phe Asn Lys Ser
50 55 60

Ile Glu Glu Asp Leu Leu Leu Cys Glu Ser Leu Gln Ser Asn Ala Thr
65 70 75 80

Gly Glu Glu Ile Phe Asn Cys Ile Asn Ser Phe Met Gln Lys His Glu
85 90 95

Ile Glu Trp Glu Lys Cys Val Asp Val Cys Ser Asp Ala Ser Arg Ala
100 105 110

Val Asp Gly Lys Ile Ala Glu Ala Val Thr Leu Ile Lys Tyr Val Ala
115 120 125

Pro Glu Ser Thr Ser Ser His Cys Leu Leu Tyr Arg His Ala Leu Ala
130 135 140

Val Lys Ile Met Pro Thr Ser Leu Lys Asn Val Leu Asp Gln Ala Val
145 150 155 160

Gln Ile Ile Asn Tyr Ile Lys Ala Arg Pro His Gln Ser Arg Leu Leu
165 170 175

Lys Ile Leu Cys Glu Glu Met Gly Ala Gln His Thr Ala Leu Leu Leu
180 185 190

Asn Thr Glu Val Arg Trp Leu Ser Arg Gly Lys Val Leu Val Arg Leu
195 200 205

Phe Glu Leu Arg Arg Glu Leu Leu Val Phe Met Asp Ser Ala Phe Arg
210 215 220

Leu Ser Asp Cys Leu Thr Asn Ser Ser Trp Leu Leu Arg Leu Ala Tyr
225 230 235 240

Leu Ala Asp Ile Phe Thr Lys Leu Asn Glu Val Asn Leu Ser Met Gln
245 250 255

Gly Lys Asn Val Thr Val Phe Thr Val Phe Asp Lys Met Ser Ser Leu
260 265 270

Leu Arg Lys Leu Glu Phe Trp Ala Ser Ser Val Glu Glu Glu Asn Phe
275 280 285

Asp Cys Phe Pro Thr Leu Ser Asp Phe Leu Thr Glu Ile Asn Ser Thr
290 295 300

Val Asp Lys Asp Ile Cys Ser Ala Ile Val Gln His Leu Arg Gly Leu
305 310 315 320

-continued

```
Arg Ala Thr Leu Leu Lys Tyr Phe Pro Val Thr Asn Asp Asn Asn Ala
                325                 330                 335

Trp Val Arg Asn Pro Phe Thr Val Thr Val Lys Pro Ala Ser Leu Val
            340                 345                 350

Ala Arg Asp Tyr Glu Ser Leu Ile Asp Leu Thr Ser Asp Ser Gln Val
        355                 360                 365

Lys Gln Asn Phe Ser Glu Leu Ser Leu Asn Asp Phe Trp Ser Ser Leu
    370                 375                 380

Ile Gln Glu Tyr Pro Ser Ile Ala Arg Arg Ala Val Arg Val Leu Leu
385                 390                 395                 400

Pro Phe Ala Thr Met His Leu Cys Glu Thr Gly Phe Ser Tyr Tyr Ala
                405                 410                 415

Ala Thr Lys Thr Lys Tyr Arg Lys Arg Leu Asp Ala Ala Pro His Met
            420                 425                 430

Arg Ile Arg Leu Ser Asn Ile Thr Pro Asn Ile Lys Arg Ile Cys Asp
        435                 440                 445

Lys Lys Thr Gln Lys His Cys Ser His
    450                 455
```

<210> SEQ ID NO 294
<211> LENGTH: 31
<212> TYPE: PRT
<213> ORGANISM: Homo sapiens

<400> SEQUENCE: 294

```
Asp Ile Glu Glu Glu Leu Val Cys Arg Leu Lys Ile Cys Asp Gly Phe
  1               5                  10                  15

Ser Leu Gln Leu Asp Glu Ser Ala Asp Val Ser Gly Leu Ala Val
             20                  25                  30
```

<210> SEQ ID NO 295
<211> LENGTH: 36
<212> TYPE: PRT
<213> ORGANISM: Homo sapiens

<400> SEQUENCE: 295

```
Asn Ser Phe Met Gln Lys His Glu Ile Glu Trp Glu Lys Cys Val Asp
  1               5                  10                  15

Val Cys Ser Asp Ala Ser Arg Ala Val Asp Gly Lys Ile Ala Glu Ala
             20                  25                  30

Val Thr Leu Ile
         35
```

<210> SEQ ID NO 296
<211> LENGTH: 36
<212> TYPE: PRT
<213> ORGANISM: Homo sapiens

<400> SEQUENCE: 296

```
Leu Asp Gln Ala Val Gln Ile Ile Asn Tyr Ile Lys Ala Arg Pro His
  1               5                  10                  15

Gln Ser Arg Leu Leu Lys Ile Leu Cys Glu Glu Met Gly Ala Gln His
             20                  25                  30

Thr Ala Leu Leu
         35
```

<210> SEQ ID NO 297
<211> LENGTH: 49
<212> TYPE: PRT

<213> ORGANISM: Homo sapiens

<400> SEQUENCE: 297

Ser Ala Phe Arg Leu Ser Asp Cys Leu Thr Asn Ser Ser Trp Leu Leu
1 5 10 15

Arg Leu Ala Tyr Leu Ala Asp Ile Phe Thr Lys Leu Asn Glu Val Asn
20 25 30

Leu Ser Met Gln Gly Lys Asn Val Thr Val Phe Thr Val Phe Asp Lys
35 40 45

Met

<210> SEQ ID NO 298
<211> LENGTH: 32
<212> TYPE: PRT
<213> ORGANISM: Homo sapiens

<400> SEQUENCE: 298

Ser Asp Phe Leu Thr Glu Ile Asn Ser Thr Val Asp Lys Asp Ile Cys
1 5 10 15

Ser Ala Ile Val Gln His Leu Arg Gly Leu Arg Ala Thr Leu Leu Lys
20 25 30

<210> SEQ ID NO 299
<211> LENGTH: 38
<212> TYPE: PRT
<213> ORGANISM: Homo sapiens

<400> SEQUENCE: 299

Ser Asp Ser Gln Val Lys Gln Asn Phe Ser Glu Leu Ser Leu Asn Asp
1 5 10 15

Phe Trp Ser Ser Leu Ile Gln Glu Tyr Pro Ser Ile Ala Arg Arg Ala
20 25 30

Val Arg Val Leu Leu Pro
35

<210> SEQ ID NO 300
<211> LENGTH: 325
<212> TYPE: PRT
<213> ORGANISM: Homo sapiens
<220> FEATURE:
<221> NAME/KEY: SITE
<222> LOCATION: (171)
<223> OTHER INFORMATION: Xaa equals any of the naturally occurring L-amino acids
<220> FEATURE:
<221> NAME/KEY: SITE
<222> LOCATION: (222)
<223> OTHER INFORMATION: Xaa equals any of the naturally occurring L-amino acids

<400> SEQUENCE: 300

Asp Pro Arg Val Arg Glu Cys Leu Gln Asp Trp Ala Ser Phe Leu Arg
1 5 10 15

Leu Ala Ile Pro Ser Met Leu Met Leu Cys Met Glu Trp Trp Ala Tyr
20 25 30

Glu Val Gly Ser Phe Leu Ser Gly Ile Leu Gly Met Val Glu Leu Gly
35 40 45

Ala Gln Ser Ile Val Tyr Glu Leu Ala Ile Ile Val Tyr Met Val Pro
50 55 60

Ala Gly Phe Ser Val Ala Ala Ser Val Arg Val Gly Asn Ala Leu Gly
65 70 75 80

-continued

```
Ala Gly Asp Met Glu Gln Ala Arg Lys Ser Ser Thr Val Ser Leu Leu
                85                  90                  95

Ile Thr Val Leu Phe Ala Val Ala Phe Ser Val Leu Leu Leu Ser Cys
            100                 105                 110

Lys Asp His Val Gly Tyr Ile Phe Thr Thr Asp Arg Asp Ile Ile Asn
        115                 120                 125

Leu Val Ala Gln Val Val Pro Ile Tyr Ala Val Ser His Leu Phe Glu
    130                 135                 140

Ala Leu Ala Cys Thr Ser Gly Gly Val Leu Arg Gly Ser Gly Asn Gln
145                 150                 155                 160

Lys Val Gly Ala Ile Val Asn Thr Ile Gly Xaa Tyr Val Val Gly Leu
                165                 170                 175

Pro Ile Gly Ile Ala Leu Met Phe Ala Thr Thr Leu Gly Val Met Gly
            180                 185                 190

Leu Trp Ser Gly Ile Ile Ile Cys Thr Val Phe Gln Ala Val Cys Phe
        195                 200                 205

Leu Gly Phe Ile Ile Gln Leu Asn Trp Lys Lys Ala Cys Xaa Gln Ala
    210                 215                 220

Gln Val His Ala Asn Leu Lys Val Asn Asn Val Pro Arg Ser Gly Asn
225                 230                 235                 240

Ser Ala Leu Pro Gln Asp Pro Leu His Pro Gly Cys Pro Glu Asn Leu
                245                 250                 255

Glu Gly Ile Leu Thr Asn Asp Val Gly Lys Thr Gly Glu Pro Gln Ser
            260                 265                 270

Asp Gln Gln Met Arg Gln Glu Glu Pro Leu Pro Glu His Pro Gln Asp
        275                 280                 285

Gly Ala Lys Leu Ser Arg Lys Gln Leu Val Leu Arg Arg Gly Leu Leu
    290                 295                 300

Leu Leu Gly Val Phe Leu Ile Leu Leu Val Gly Ile Leu Val Arg Phe
305                 310                 315                 320

Tyr Val Arg Ile Gln
                325


<210> SEQ ID NO 301
<211> LENGTH: 328
<212> TYPE: PRT
<213> ORGANISM: Homo sapiens

<400> SEQUENCE: 301

Gly Thr Arg Ile His Thr Ile Leu Val Tyr Gln Glu Ser Asn Arg Lys
  1               5                  10                  15

Met Asp Ser Val Asp Pro Ala Ser Ser Gln Ala Met Glu Leu Ser Asp
            20                  25                  30

Val Thr Leu Ile Glu Gly Val Gly Asn Glu Val Met Val Val Ala Gly
        35                  40                  45

Val Val Val Leu Ile Leu Ala Leu Val Leu Ala Trp Leu Ser Thr Tyr
     50                  55                  60

Val Ala Asp Ser Gly Ser Asn Gln Leu Leu Gly Ala Ile Val Ser Ala
 65                  70                  75                  80

Gly Asp Thr Ser Val Leu His Leu Gly His Val Asp His Leu Val Ala
                85                  90                  95

Gly Gln Gly Asn Pro Glu Pro Thr Glu Leu Pro His Pro Ser Glu Gly
            100                 105                 110

Asn Asp Glu Lys Ala Glu Glu Ala Gly Glu Gly Arg Gly Asp Ser Thr
        115                 120                 125
```

-continued

```
Gly Glu Ala Gly Ala Gly Gly Gly Val Glu Pro Ser Leu Glu His Leu
    130                 135                 140

Leu Asp Ile Gln Gly Leu Pro Lys Arg Gln Ala Gly Ala Gly Ser Ser
145                 150                 155                 160

Ser Pro Glu Ala Pro Leu Arg Ser Glu Asp Ser Thr Cys Leu Pro Pro
                165                 170                 175

Ser Pro Gly Leu Ile Thr Val Arg Leu Lys Phe Leu Asn Asp Thr Glu
            180                 185                 190

Glu Leu Ala Val Ala Arg Pro Glu Asp Thr Val Gly Ala Leu Lys Ser
        195                 200                 205

Lys Tyr Phe Pro Gly Gln Glu Ser Gln Met Lys Leu Ile Tyr Gln Gly
    210                 215                 220

Arg Leu Leu Gln Asp Pro Ala Arg Thr Leu Arg Ser Leu Asn Ile Thr
225                 230                 235                 240

Asp Asn Cys Val Ile His Cys His Arg Ser Pro Pro Gly Ser Ala Val
                245                 250                 255

Pro Gly Pro Ser Ala Ser Leu Ala Pro Ser Ala Thr Glu Pro Pro Ser
            260                 265                 270

Leu Gly Val Asn Val Gly Ser Leu Met Val Pro Val Phe Val Val Leu
        275                 280                 285

Leu Gly Val Val Trp Tyr Phe Arg Ile Asn Tyr Arg Gln Phe Phe Thr
    290                 295                 300

Ala Pro Ala Thr Val Ser Leu Val Gly Val Thr Val Phe Phe Ser Phe
305                 310                 315                 320

Leu Val Phe Gly Met Tyr Gly Arg
                325


<210> SEQ ID NO 302
<211> LENGTH: 26
<212> TYPE: PRT
<213> ORGANISM: Homo sapiens

<400> SEQUENCE: 302

Asp Ser Arg Ile Ser Leu Leu Val Asn Asn Ala Gly Val Gly Ala Thr
  1               5                  10                  15

Ala Ser Leu Leu Glu Ser Asp Ala Asp Lys
             20                  25


<210> SEQ ID NO 303
<211> LENGTH: 159
<212> TYPE: PRT
<213> ORGANISM: Homo sapiens
<220> FEATURE:
<221> NAME/KEY: SITE
<222> LOCATION: (110)
<223> OTHER INFORMATION: Xaa equals any of the naturally occurring
      L-amino acids

<400> SEQUENCE: 303

Met Asp Ala Met Ile Leu Leu Asn Val Leu Ala Leu Thr Arg Leu Ala
  1               5                  10                  15

Lys Ala Ala Ala Thr Asn Phe Val Ala Gln Gly Arg Gly Thr Ile Ile
             20                  25                  30

Asn Ile Gly Ser Ile Val Ala Leu Ala Pro Lys Val Leu Asn Gly Val
         35                  40                  45

Tyr Gly Gly Thr Lys Ala Phe Val Gln Ala Phe Ser Glu Ser Leu Gln
     50                  55                  60
```

-continued

```
His Glu Leu Ser Asp Lys Gly Val Val Val Gln Val Val Leu Pro Gly
 65                  70                  75                  80

Ala Thr Ala Thr Glu Phe Trp Asp Ile Ala Gly Leu Pro Val Asn Asn
                 85                  90                  95

Leu Pro Glu Ala Met Val Met Thr Thr Glu Asn Leu Val Xaa Ala Ala
            100                 105                 110

Leu Ala Gly Leu Ala Gln Gly Glu Ala Val Thr Ile Pro Ser Leu Pro
        115                 120                 125

Asp Ser Ala Asp Trp Asp Thr Tyr Glu Arg Ala Arg Leu Ala Leu Gly
    130                 135                 140

Pro Asn Leu Ser His Arg Glu Pro Ala Ala Arg Tyr Gly Leu Lys
145                 150                 155


<210> SEQ ID NO 304
<211> LENGTH: 146
<212> TYPE: PRT
<213> ORGANISM: Homo sapiens

<400> SEQUENCE: 304

Gly Thr Pro Ala Gly Thr Gly Pro Glu Phe Pro Gly Arg Pro Thr Arg
  1               5                  10                  15

Pro Ser Arg Thr Glu Ser Ala Gln Thr Thr Gln His Ser Pro Leu Arg
             20                  25                  30

Pro Leu Trp Arg Leu Lys Arg Asp Ser Ser Pro Cys His Pro Gln Thr
         35                  40                  45

Arg Ala Asp Trp Gly Val Cys Pro Pro Trp Gly Gly Ala Ala Gln Gly
     50                  55                  60

Leu Arg Pro Gly Cys His Leu Ala Pro Arg Arg Cys Leu Cys Pro Gly
 65                  70                  75                  80

Ser Cys Cys Pro Trp His Trp Ala Glu Ala Gln Trp Ser Phe Leu Trp
                 85                  90                  95

Arg Gly Leu Trp Gly Leu Arg Thr Leu Pro Thr Ala Leu Arg Ala Ser
            100                 105                 110

Pro Ala Ala Ser Gly Thr Val Thr Tyr Ser Ala Cys Leu Gly Thr Ser
        115                 120                 125

Cys Leu Leu Arg Ala Pro Cys Trp Arg Leu Arg Thr Cys Arg Gln Ser
    130                 135                 140

Trp Cys
145


<210> SEQ ID NO 305
<211> LENGTH: 28
<212> TYPE: PRT
<213> ORGANISM: Homo sapiens

<400> SEQUENCE: 305

Gly Thr Pro Ala Gly Thr Gly Pro Glu Phe Pro Gly Arg Pro Thr Arg
  1               5                  10                  15

Pro Ser Arg Thr Glu Ser Ala Gln Thr Thr Gln His
             20                  25


<210> SEQ ID NO 306
<211> LENGTH: 30
<212> TYPE: PRT
<213> ORGANISM: Homo sapiens

<400> SEQUENCE: 306

Ser Pro Leu Arg Pro Leu Trp Arg Leu Lys Arg Asp Ser Ser Pro Cys
```

-continued

```
  1               5                   10                  15

His Pro Gln Thr Arg Ala Asp Trp Gly Val Cys Pro Pro Trp
             20                  25                  30


<210> SEQ ID NO 307
<211> LENGTH: 30
<212> TYPE: PRT
<213> ORGANISM: Homo sapiens

<400> SEQUENCE: 307

Gly Gly Ala Ala Gln Gly Leu Arg Pro Gly Cys His Leu Ala Pro Arg
  1               5                   10                  15

Arg Cys Leu Cys Pro Gly Ser Cys Cys Pro Trp His Trp Ala
             20                  25                  30


<210> SEQ ID NO 308
<211> LENGTH: 30
<212> TYPE: PRT
<213> ORGANISM: Homo sapiens

<400> SEQUENCE: 308

Glu Ala Gln Trp Ser Phe Leu Trp Arg Gly Leu Trp Gly Leu Arg Thr
  1               5                   10                  15

Leu Pro Thr Ala Leu Arg Ala Ser Pro Ala Ala Ser Gly Thr
             20                  25                  30


<210> SEQ ID NO 309
<211> LENGTH: 28
<212> TYPE: PRT
<213> ORGANISM: Homo sapiens

<400> SEQUENCE: 309

Val Thr Tyr Ser Ala Cys Leu Gly Thr Ser Cys Leu Leu Arg Ala Pro
  1               5                   10                  15

Cys Trp Arg Leu Arg Thr Cys Arg Gln Ser Trp Cys
             20                  25


<210> SEQ ID NO 310
<211> LENGTH: 507
<212> TYPE: PRT
<213> ORGANISM: Homo sapiens

<400> SEQUENCE: 310

Met Pro Val Pro Trp Phe Leu Leu Ser Leu Ala Leu Gly Arg Ser Pro
  1               5                   10                  15

Val Val Leu Ser Leu Glu Arg Leu Val Gly Pro Gln Asp Ala Thr His
             20                  25                  30

Cys Ser Pro Gly Leu Ser Cys Arg Leu Trp Asp Ser Asp Ile Leu Cys
         35                  40                  45

Leu Pro Gly Asp Ile Val Pro Ala Pro Gly Pro Val Leu Ala Pro Thr
     50                  55                  60

His Leu Gln Thr Glu Leu Val Leu Arg Cys Gln Lys Glu Thr Asp Cys
 65                  70                  75                  80

Asp Leu Cys Leu Arg Val Ala Val His Leu Ala Val His Gly His Trp
                 85                  90                  95

Glu Glu Pro Glu Asp Glu Glu Lys Phe Gly Gly Ala Ala Asp Leu Gly
            100                 105                 110

Val Glu Glu Pro Arg Asn Ala Ser Leu Gln Ala Gln Val Val Leu Ser
        115                 120                 125
```

-continued

```
Phe Gln Ala Tyr Pro Thr Ala Arg Cys Val Leu Leu Glu Val Gln Val
    130                 135                 140

Pro Ala Ala Leu Val Gln Phe Gly Gln Ser Val Gly Ser Val Val Tyr
145                 150                 155                 160

Asp Cys Phe Glu Ala Ala Leu Gly Ser Glu Val Arg Ile Trp Ser Tyr
                165                 170                 175

Thr Gln Pro Arg Tyr Glu Lys Glu Leu Asn His Thr Gln Gln Leu Pro
            180                 185                 190

Asp Cys Arg Gly Leu Glu Val Trp Asn Ser Ile Pro Ser Cys Trp Ala
        195                 200                 205

Leu Pro Trp Leu Asn Val Ser Ala Asp Gly Asp Asn Val His Leu Val
    210                 215                 220

Leu Asn Val Ser Glu Glu Gln His Phe Gly Leu Ser Leu Tyr Trp Asn
225                 230                 235                 240

Gln Val Gln Gly Pro Pro Lys Pro Arg Trp His Lys Asn Leu Thr Gly
                245                 250                 255

Pro Gln Ile Ile Thr Leu Asn His Thr Asp Leu Val Pro Cys Leu Cys
            260                 265                 270

Ile Gln Val Trp Pro Leu Glu Pro Asp Ser Val Arg Thr Asn Ile Cys
        275                 280                 285

Pro Phe Arg Glu Asp Pro Arg Ala His Gln Asn Leu Trp Gln Ala Ala
    290                 295                 300

Arg Leu Arg Leu Leu Thr Leu Gln Ser Trp Leu Leu Asp Ala Pro Cys
305                 310                 315                 320

Ser Leu Pro Ala Glu Ala Ala Leu Cys Trp Arg Ala Pro Gly Gly Asp
                325                 330                 335

Pro Cys Gln Pro Leu Val Pro Pro Leu Ser Trp Glu Asn Val Thr Val
            340                 345                 350

Asp Lys Val Leu Glu Phe Pro Leu Leu Lys Gly His Pro Asn Leu Cys
        355                 360                 365

Val Gln Val Asn Ser Ser Glu Lys Leu Gln Leu Gln Glu Cys Leu Trp
    370                 375                 380

Ala Asp Ser Leu Gly Pro Leu Lys Asp Asp Val Leu Leu Leu Glu Thr
385                 390                 395                 400

Arg Gly Pro Gln Asp Asn Arg Ser Leu Cys Ala Leu Glu Pro Ser Gly
                405                 410                 415

Cys Thr Ser Leu Pro Ser Lys Ala Ser Thr Arg Ala Ala Arg Leu Gly
            420                 425                 430

Glu Tyr Leu Leu Gln Asp Leu Gln Ser Gly Gln Cys Leu Gln Leu Trp
        435                 440                 445

Asp Asp Asp Leu Gly Ala Leu Trp Ala Cys Pro Met Asp Lys Tyr Ile
    450                 455                 460

His Lys Arg Trp Ala Leu Val Trp Leu Ala Cys Leu Leu Phe Arg Arg
465                 470                 475                 480

Ala Leu Ser Leu Ile Leu Leu Leu Lys Lys Asp His Ala Lys Gly Trp
                485                 490                 495

Leu Arg Leu Leu Lys Gln Asp Val Arg Ser Gly
            500                 505
```

<210> SEQ ID NO 311
<211> LENGTH: 11
<212> TYPE: PRT
<213> ORGANISM: Homo sapiens

<400> SEQUENCE: 311

-continued

```
Pro Pro Arg Pro Ser Thr Ser Gly Gln Trp Gly
  1               5                  10


<210> SEQ ID NO 312
<211> LENGTH: 11
<212> TYPE: PRT
<213> ORGANISM: Homo sapiens

<400> SEQUENCE: 312

Arg Arg Ser Pro Phe Thr Ser Ala Gln Thr Gly
  1               5                  10


<210> SEQ ID NO 313
<211> LENGTH: 23
<212> TYPE: PRT
<213> ORGANISM: Homo sapiens

<400> SEQUENCE: 313

Gly Thr Gly Trp Asp Phe Gly Leu Ala Ala Val Cys Leu Arg Ala Ala
  1               5                  10                  15

Glu Val Ala Gly Ser Phe Lys
             20


<210> SEQ ID NO 314
<211> LENGTH: 146
<212> TYPE: PRT
<213> ORGANISM: Homo sapiens

<400> SEQUENCE: 314

Gly Tyr Arg Arg Val Phe Glu Glu Tyr Met Arg Val Ile Ser Gln Arg
  1               5                  10                  15

Tyr Pro Asp Ile Arg Ile Glu Gly Glu Asn Tyr Leu Pro Gln Pro Ile
             20                  25                  30

Tyr Arg His Ile Ala Ser Phe Leu Ser Val Phe Lys Leu Val Leu Ile
         35                  40                  45

Gly Leu Ile Ile Val Gly Lys Asp Pro Phe Ala Phe Phe Gly Met Gln
     50                  55                  60

Ala Pro Ser Ile Trp Gln Trp Gly Gln Glu Asn Lys Val Tyr Ala Cys
 65                  70                  75                  80

Met Met Val Phe Phe Leu Ser Asn Met Ile Glu Asn Gln Cys Met Ser
                 85                  90                  95

Thr Gly Ala Phe Glu Ile Thr Leu Asn Asp Val Pro Val Trp Ser Lys
            100                 105                 110

Leu Glu Ser Gly His Leu Pro Ser Met Gln Gln Leu Val Gln Ile Leu
        115                 120                 125

Asp Asn Glu Met Lys Leu Asn Val His Met Asp Ser Ile Pro His His
    130                 135                 140

Arg Ser
145


<210> SEQ ID NO 315
<211> LENGTH: 34
<212> TYPE: PRT
<213> ORGANISM: Homo sapiens

<400> SEQUENCE: 315

Gly Tyr Arg Arg Val Phe Glu Glu Tyr Met Arg Val Ile Ser Gln Arg
  1               5                  10                  15

Tyr Pro Asp Ile Arg Ile Glu Gly Glu Asn Tyr Leu Pro Gln Pro Ile
```

-continued

```
            20                  25                  30

Tyr Arg


<210> SEQ ID NO 316
<211> LENGTH: 34
<212> TYPE: PRT
<213> ORGANISM: Homo sapiens

<400> SEQUENCE: 316

His Ile Ala Ser Phe Leu Ser Val Phe Lys Leu Val Leu Ile Gly Leu
  1               5                  10                  15

Ile Ile Val Gly Lys Asp Pro Phe Ala Phe Phe Gly Met Gln Ala Pro
             20                  25                  30

Ser Ile


<210> SEQ ID NO 317
<211> LENGTH: 34
<212> TYPE: PRT
<213> ORGANISM: Homo sapiens

<400> SEQUENCE: 317

Trp Gln Trp Gly Gln Glu Asn Lys Val Tyr Ala Cys Met Met Val Phe
  1               5                  10                  15

Phe Leu Ser Asn Met Ile Glu Asn Gln Cys Met Ser Thr Gly Ala Phe
             20                  25                  30

Glu Ile


<210> SEQ ID NO 318
<211> LENGTH: 36
<212> TYPE: PRT
<213> ORGANISM: Homo sapiens

<400> SEQUENCE: 318

Thr Leu Asn Asp Val Pro Val Trp Ser Lys Leu Glu Ser Gly His Leu
  1               5                  10                  15

Pro Ser Met Gln Gln Leu Val Gln Ile Leu Asp Asn Glu Met Lys Leu
             20                  25                  30

Asn Val His Met
         35


<210> SEQ ID NO 319
<211> LENGTH: 8
<212> TYPE: PRT
<213> ORGANISM: Homo sapiens

<400> SEQUENCE: 319

Asp Ser Ile Pro His His Arg Ser
  1               5


<210> SEQ ID NO 320
<211> LENGTH: 30
<212> TYPE: PRT
<213> ORGANISM: Homo sapiens

<400> SEQUENCE: 320

Gly Arg Ala Arg Gly Arg Pro Pro Gly Pro Glu Ala Ala Pro Ala Ser
  1               5                  10                  15

Leu Ser Val Ser Leu Arg Arg Glu Val His Ser Arg Gly Glu
             20                  25                  30
```

-continued

<210> SEQ ID NO 321
<211> LENGTH: 333
<212> TYPE: PRT
<213> ORGANISM: Homo sapiens
<220> FEATURE:
<221> NAME/KEY: SITE
<222> LOCATION: (15)
<223> OTHER INFORMATION: Xaa equals any of the naturally occurring L-amino acids
<220> FEATURE:
<221> NAME/KEY: SITE
<222> LOCATION: (16)
<223> OTHER INFORMATION: Xaa equals any of the naturally occurring L-amino acids
<220> FEATURE:
<221> NAME/KEY: SITE
<222> LOCATION: (20)
<223> OTHER INFORMATION: Xaa equals any of the naturally occurring L-amino acids

<400> SEQUENCE: 321

```
Gln Thr Pro Phe Thr Cys Thr Leu Ile His Arg His Ala Cys Xaa Xaa
  1               5                  10                  15

Pro Val Arg Xaa Ser Arg Val Asp Pro Arg Val Arg Gly Lys Gln Ala
             20                  25                  30

Leu Ile Trp Leu Leu Gly Val His Gly Glu Arg Ile Pro Asn Ala Pro
         35                  40                  45

Tyr Val Leu Glu Asp Phe Val Glu Asn Val Lys Ser Glu Thr Phe Pro
     50                  55                  60

Ala Val Lys Met Glu Leu Leu Thr Ala Leu Leu Arg Leu Phe Leu Ser
 65                  70                  75                  80

Arg Pro Ala Glu Cys Gln Asp Met Leu Gly Arg Leu Leu Tyr Tyr Cys
                 85                  90                  95

Ile Glu Glu Glu Lys Asp Met Ala Val Arg Asp Arg Gly Leu Phe Tyr
            100                 105                 110

Tyr Arg Leu Leu Leu Val Gly Ile Asp Glu Val Lys Arg Ile Leu Cys
        115                 120                 125

Ser Pro Lys Ser Asp Pro Thr Leu Gly Leu Leu Glu Asp Pro Ala Glu
    130                 135                 140

Arg Pro Val Asn Ser Trp Ala Ser Asp Phe Asn Thr Leu Val Pro Val
145                 150                 155                 160

Tyr Gly Lys Ala His Trp Ala Thr Ile Ser Lys Cys Gln Gly Ala Glu
                165                 170                 175

Arg Cys Asp Pro Glu Leu Pro Lys Thr Ser Ser Phe Ala Ala Ser Gly
            180                 185                 190

Pro Leu Ile Pro Glu Glu Asn Lys Glu Arg Val Gln Glu Leu Pro Asp
        195                 200                 205

Ser Gly Ala Leu Met Leu Val Pro Asn Arg Gln Leu Thr Ala Asp Tyr
    210                 215                 220

Phe Glu Lys Thr Trp Leu Ser Leu Lys Val Ala His Gln Gln Val Leu
225                 230                 235                 240

Pro Trp Arg Gly Glu Phe His Pro Asp Thr Leu Gln Met Ala Leu Gln
                245                 250                 255

Val Val Asn Ile Gln Thr Ile Ala Met Ser Arg Ala Gly Ser Arg Pro
            260                 265                 270

Trp Lys Ala Tyr Leu Ser Ala Gln Asp Asp Thr Gly Cys Leu Phe Leu
        275                 280                 285

Thr Glu Leu Leu Leu Glu Pro Gly Asn Ser Glu Met Gln Ile Ser Val
    290                 295                 300
```

-continued

```
Lys Gln Asn Glu Ala Arg Thr Glu Thr Leu Asn Ser Phe Ile Ser Val
305                 310                 315                 320

Leu Glu Thr Val Ile Gly Thr Ile Glu Glu Ile Lys Ser
                325                 330


<210> SEQ ID NO 322
<211> LENGTH: 12
<212> TYPE: PRT
<213> ORGANISM: Homo sapiens

<400> SEQUENCE: 322

Cys Glu Asn Thr Glu Gly Gly Tyr Arg Cys Ile Cys
  1               5                  10


<210> SEQ ID NO 323
<211> LENGTH: 12
<212> TYPE: PRT
<213> ORGANISM: Homo sapiens

<400> SEQUENCE: 323

Cys Asp Cys Gln Ala Gly Tyr Gly Gly Glu Ala Cys
  1               5                  10


<210> SEQ ID NO 324
<211> LENGTH: 14
<212> TYPE: PRT
<213> ORGANISM: Homo sapiens

<400> SEQUENCE: 324

Cys Ile Cys Ala Glu Gly Tyr Lys Gln Met Glu Gly Ile Cys
  1               5                  10


<210> SEQ ID NO 325
<211> LENGTH: 27
<212> TYPE: PRT
<213> ORGANISM: Homo sapiens

<400> SEQUENCE: 325

Asp Ile Asp Glu Cys Gly Thr Glu Gly Ala Asn Cys Gly Ala Asp Gln
  1               5                  10                  15

Phe Cys Val Asn Thr Glu Gly Ser Tyr Glu Cys
             20                  25


<210> SEQ ID NO 326
<211> LENGTH: 26
<212> TYPE: PRT
<213> ORGANISM: Homo sapiens

<400> SEQUENCE: 326

Asp Val Asp Glu Cys Glu Thr Glu Val Cys Pro Gly Glu Asn Lys Gln
  1               5                  10                  15

Cys Glu Asn Thr Glu Gly Gly Tyr Arg Cys
             20                  25


<210> SEQ ID NO 327
<211> LENGTH: 34
<212> TYPE: PRT
<213> ORGANISM: Homo sapiens

<400> SEQUENCE: 327

Cys Asp Cys Gln Ala Gly Tyr Gly Gly Glu Ala Cys Gly Gln Cys Gly
  1               5                  10                  15

Leu Gly Tyr Phe Glu Ala Glu Arg Asn Ala Ser His Leu Val Cys Ser
```

-continued

```
            20                  25                  30

Ala Cys


<210> SEQ ID NO 328
<211> LENGTH: 389
<212> TYPE: PRT
<213> ORGANISM: Homo sapiens

<400> SEQUENCE: 328

Met Ile Ser Leu Pro Gly Pro Leu Val Thr Asn Leu Leu Arg Phe Leu
  1               5                  10                  15

Phe Leu Gly Leu Ser Ala Leu Ala Pro Pro Ser Arg Ala Gln Leu Gln
            20                  25                  30

Leu His Leu Pro Ala Asn Arg Leu Gln Ala Val Glu Gly Gly Glu Val
        35                  40                  45

Val Leu Pro Ala Trp Tyr Thr Leu His Gly Glu Val Ser Ser Ser Gln
    50                  55                  60

Pro Trp Glu Val Pro Phe Val Met Trp Phe Phe Lys Gln Lys Glu Lys
 65                  70                  75                  80

Glu Asp Gln Val Leu Ser Tyr Ile Asn Gly Val Thr Thr Ser Lys Pro
                 85                  90                  95

Gly Val Ser Leu Val Tyr Ser Met Pro Ser Arg Asn Leu Ser Leu Arg
            100                 105                 110

Leu Glu Gly Leu Gln Glu Lys Asp Ser Gly Pro Tyr Ser Cys Ser Val
        115                 120                 125

Asn Val Gln Asn Lys Gln Gly Lys Ser Arg Gly His Ser Ile Lys Thr
    130                 135                 140

Leu Glu Leu Asn Val Leu Val Pro Pro Ala Pro Pro Ser Cys Arg Leu
145                 150                 155                 160

Gln Gly Val Pro His Val Gly Ala Asn Val Thr Leu Ser Cys Gln Ser
                165                 170                 175

Pro Arg Ser Lys Pro Ala Val Gln Tyr Gln Trp Asp Arg Gln Leu Pro
            180                 185                 190

Ser Phe Gln Thr Phe Phe Ala Pro Ala Leu Asp Val Ile Arg Gly Ser
        195                 200                 205

Leu Ser Leu Thr Asn Leu Ser Ser Ser Met Ala Gly Val Tyr Val Cys
    210                 215                 220

Lys Ala His Asn Glu Val Gly Thr Ala Gln Cys Asn Val Thr Leu Glu
225                 230                 235                 240

Val Ser Thr Gly Pro Gly Ala Ala Val Val Ala Gly Ala Val Val Gly
                245                 250                 255

Thr Leu Val Gly Leu Gly Leu Leu Ala Gly Leu Val Leu Leu Tyr His
            260                 265                 270

Arg Arg Gly Lys Ala Leu Glu Glu Pro Ala Asn Asp Ile Lys Glu Asp
        275                 280                 285

Ala Ile Ala Pro Arg Thr Leu Pro Trp Pro Lys Ser Ser Asp Thr Ile
    290                 295                 300

Ser Lys Asn Gly Thr Leu Ser Ser Val Thr Ser Ala Arg Ala Leu Arg
305                 310                 315                 320

Pro Pro His Gly Pro Pro Arg Pro Gly Ala Leu Thr Pro Thr Pro Ser
                325                 330                 335

Leu Ser Ser Gln Ala Leu Pro Ser Pro Arg Leu Pro Thr Thr Asp Gly
            340                 345                 350

Ala His Pro Gln Pro Ile Ser Pro Ile Pro Gly Gly Val Ser Ser Ser
```

-continued

```
        355                 360                 365

Gly Leu Ser Arg Met Gly Ala Val Pro Val Met Val Pro Ala Gln Ser
    370                 375                 380

Gln Ala Gly Ser Leu
385


<210> SEQ ID NO 329
<211> LENGTH: 35
<212> TYPE: PRT
<213> ORGANISM: Homo sapiens

<400> SEQUENCE: 329

Met Ile Ser Leu Pro Gly Pro Leu Val Thr Asn Leu Leu Arg Phe Leu
  1               5                  10                  15

Phe Leu Gly Leu Ser Ala Leu Ala Pro Pro Ser Arg Ala Gln Leu Gln
             20                  25                  30

Leu His Leu
         35


<210> SEQ ID NO 330
<211> LENGTH: 35
<212> TYPE: PRT
<213> ORGANISM: Homo sapiens

<400> SEQUENCE: 330

Pro Ala Asn Arg Leu Gln Ala Val Glu Gly Gly Glu Val Val Leu Pro
  1               5                  10                  15

Ala Trp Tyr Thr Leu His Gly Glu Val Ser Ser Ser Gln Pro Trp Glu
             20                  25                  30

Val Pro Phe
         35


<210> SEQ ID NO 331
<211> LENGTH: 35
<212> TYPE: PRT
<213> ORGANISM: Homo sapiens

<400> SEQUENCE: 331

Val Met Trp Phe Phe Lys Gln Lys Glu Lys Glu Asp Gln Val Leu Ser
  1               5                  10                  15

Tyr Ile Asn Gly Val Thr Thr Ser Lys Pro Gly Val Ser Leu Val Tyr
             20                  25                  30

Ser Met Pro
         35


<210> SEQ ID NO 332
<211> LENGTH: 35
<212> TYPE: PRT
<213> ORGANISM: Homo sapiens

<400> SEQUENCE: 332

Ser Arg Asn Leu Ser Leu Arg Leu Glu Gly Leu Gln Glu Lys Asp Ser
  1               5                  10                  15

Gly Pro Tyr Ser Cys Ser Val Asn Val Gln Asn Lys Gln Gly Lys Ser
             20                  25                  30

Arg Gly His
         35


<210> SEQ ID NO 333
<211> LENGTH: 35
```

-continued

<212> TYPE: PRT
<213> ORGANISM: Homo sapiens

<400> SEQUENCE: 333

Ser Ile Lys Thr Leu Glu Leu Asn Val Leu Val Pro Pro Ala Pro Pro
1 5 10 15

Ser Cys Arg Leu Gln Gly Val Pro His Val Gly Ala Asn Val Thr Leu
20 25 30

Ser Cys Gln
35

<210> SEQ ID NO 334
<211> LENGTH: 35
<212> TYPE: PRT
<213> ORGANISM: Homo sapiens

<400> SEQUENCE: 334

Ser Pro Arg Ser Lys Pro Ala Val Gln Tyr Gln Trp Asp Arg Gln Leu
1 5 10 15

Pro Ser Phe Gln Thr Phe Phe Ala Pro Ala Leu Asp Val Ile Arg Gly
20 25 30

Ser Leu Ser
35

<210> SEQ ID NO 335
<211> LENGTH: 35
<212> TYPE: PRT
<213> ORGANISM: Homo sapiens

<400> SEQUENCE: 335

Leu Thr Asn Leu Ser Ser Ser Met Ala Gly Val Tyr Val Cys Lys Ala
1 5 10 15

His Asn Glu Val Gly Thr Ala Gln Cys Asn Val Thr Leu Glu Val Ser
20 25 30

Thr Gly Pro
35

<210> SEQ ID NO 336
<211> LENGTH: 35
<212> TYPE: PRT
<213> ORGANISM: Homo sapiens

<400> SEQUENCE: 336

Gly Ala Ala Val Val Ala Gly Ala Val Val Gly Thr Leu Val Gly Leu
1 5 10 15

Gly Leu Leu Ala Gly Leu Val Leu Leu Tyr His Arg Arg Gly Lys Ala
20 25 30

Leu Glu Glu
35

<210> SEQ ID NO 337
<211> LENGTH: 35
<212> TYPE: PRT
<213> ORGANISM: Homo sapiens

<400> SEQUENCE: 337

Pro Ala Asn Asp Ile Lys Glu Asp Ala Ile Ala Pro Arg Thr Leu Pro
1 5 10 15

Trp Pro Lys Ser Ser Asp Thr Ile Ser Lys Asn Gly Thr Leu Ser Ser
20 25 30

Val Thr Ser
35

<210> SEQ ID NO 338
<211> LENGTH: 35
<212> TYPE: PRT
<213> ORGANISM: Homo sapiens

<400> SEQUENCE: 338

Ala Arg Ala Leu Arg Pro Pro His Gly Pro Pro Arg Pro Gly Ala Leu
1 5 10 15

Thr Pro Thr Pro Ser Leu Ser Ser Gln Ala Leu Pro Ser Pro Arg Leu
20 25 30

Pro Thr Thr
35

<210> SEQ ID NO 339
<211> LENGTH: 39
<212> TYPE: PRT
<213> ORGANISM: Homo sapiens

<400> SEQUENCE: 339

Asp Gly Ala His Pro Gln Pro Ile Ser Pro Ile Pro Gly Gly Val Ser
1 5 10 15

Ser Ser Gly Leu Ser Arg Met Gly Ala Val Pro Val Met Val Pro Ala
20 25 30

Gln Ser Gln Ala Gly Ser Leu
35

<210> SEQ ID NO 340
<211> LENGTH: 36
<212> TYPE: PRT
<213> ORGANISM: Homo sapiens

<400> SEQUENCE: 340

Leu Ser Leu Thr Asn Leu Ser Ser Ser Met Ala Gly Val Tyr Val Cys
1 5 10 15

Lys Ala His Asn Glu Val Gly Thr Ala Gln Cys Asn Val Thr Leu Glu
20 25 30

Val Ser Thr Gly
35

<210> SEQ ID NO 341
<211> LENGTH: 27
<212> TYPE: PRT
<213> ORGANISM: Homo sapiens

<400> SEQUENCE: 341

Gly Ser Ser Phe Val Val Ser Glu Gly Ser Tyr Leu Asp Ile Ser Asp
1 5 10 15

Trp Leu Asn Pro Ala Lys Leu Ser Leu Tyr Tyr
20 25

<210> SEQ ID NO 342
<211> LENGTH: 12
<212> TYPE: PRT
<213> ORGANISM: Homo sapiens

<400> SEQUENCE: 342

Leu Asp Ile Ser Asp Trp Leu Asn Pro Ala Lys Leu
1 5 10

<210> SEQ ID NO 343
<211> LENGTH: 11
<212> TYPE: PRT
<213> ORGANISM: Homo sapiens

<400> SEQUENCE: 343

Ser Asp Trp Leu Asn Pro Ala Lys Leu Ser Leu
1               5                   10

<210> SEQ ID NO 344
<211> LENGTH: 13
<212> TYPE: PRT
<213> ORGANISM: Homo sapiens

<400> SEQUENCE: 344

Asp Ala Cys Glu Gln Leu Cys Asp Pro Glu Thr Gly Glu
1               5                   10

<210> SEQ ID NO 345
<211> LENGTH: 21
<212> TYPE: PRT
<213> ORGANISM: Homo sapiens

<400> SEQUENCE: 345

Glu Gly Lys Ile Lys Ile Cys Glu Lys Lys Ala Ile Lys Val Ile Leu
1               5                   10                  15

His Thr Cys Asn Ser
            20

<210> SEQ ID NO 346
<211> LENGTH: 23
<212> TYPE: PRT
<213> ORGANISM: Homo sapiens

<400> SEQUENCE: 346

Asn Ser Ala Arg Val Glu Phe Phe Ile Pro Pro Leu Arg Ile Thr Gln
1               5                   10                  15

Lys Val Arg Ser Thr Lys Ser
            20

<210> SEQ ID NO 347
<211> LENGTH: 123
<212> TYPE: PRT
<213> ORGANISM: Homo sapiens

<400> SEQUENCE: 347

Met Met Val Trp Asn Leu Phe Pro Cys Phe Pro Pro Leu Leu Leu Leu
1               5                   10                  15

Gln Phe Ile Asp Cys Gln Gln Ser Ser Glu Ile Glu Gln Gly Phe Thr
            20                  25                  30

Arg Ser Leu Leu Gly His Pro Ile Phe Phe Cys Pro Asp Pro Cys Trp
        35                  40                  45

Gln Ser Cys Met Asn Cys Val Ile Leu Ser Val Leu Ser Phe Phe Phe
    50                  55                  60

Leu Ile Arg Trp Ile Ser Lys Ile Val Ala Val Gln Lys Leu Glu Ser
65                  70                  75                  80

Ser Ser Arg Arg Lys Pro Ile Leu Phe Leu Ile Ile Ser Cys Glu Ile
                85                  90                  95

Ala Ser Phe Ile His Leu Phe Leu Ser Gln Met Ser Ala Glu Cys Cys
            100                 105                 110

-continued

```
Cys Phe Tyr Leu Val Ile Leu Ile Cys Lys Tyr
        115                 120


<210> SEQ ID NO 348
<211> LENGTH: 28
<212> TYPE: PRT
<213> ORGANISM: Homo sapiens

<400> SEQUENCE: 348

Met Met Val Trp Asn Leu Phe Pro Cys Phe Pro Pro Leu Leu Leu Leu
  1               5                  10                  15

Gln Phe Ile Asp Cys Gln Gln Ser Ser Glu Ile Glu
             20                  25


<210> SEQ ID NO 349
<211> LENGTH: 28
<212> TYPE: PRT
<213> ORGANISM: Homo sapiens

<400> SEQUENCE: 349

Gln Gly Phe Thr Arg Ser Leu Leu Gly His Pro Ile Phe Phe Cys Pro
  1               5                  10                  15

Asp Pro Cys Trp Gln Ser Cys Met Asn Cys Val Ile
             20                  25


<210> SEQ ID NO 350
<211> LENGTH: 35
<212> TYPE: PRT
<213> ORGANISM: Homo sapiens

<400> SEQUENCE: 350

Leu Ser Val Leu Ser Phe Phe Phe Leu Ile Arg Trp Ile Ser Lys Ile
  1               5                  10                  15

Val Ala Val Gln Lys Leu Glu Ser Ser Ser Arg Arg Lys Pro Ile Leu
             20                  25                  30

Phe Leu Ile
         35


<210> SEQ ID NO 351
<211> LENGTH: 32
<212> TYPE: PRT
<213> ORGANISM: Homo sapiens

<400> SEQUENCE: 351

Ile Ser Cys Glu Ile Ala Ser Phe Ile His Leu Phe Leu Ser Gln Met
  1               5                  10                  15

Ser Ala Glu Cys Cys Cys Phe Tyr Leu Val Ile Leu Ile Cys Lys Tyr
             20                  25                  30


<210> SEQ ID NO 352
<211> LENGTH: 59
<212> TYPE: PRT
<213> ORGANISM: Homo sapiens

<400> SEQUENCE: 352

Lys Val Asp Thr Pro Arg Arg His Phe Cys Pro Glu Ile Ser Phe Phe
  1               5                  10                  15

Leu Thr Pro Leu Pro Gln Ser Ala Arg Asn Ser Thr Val Arg Asn Ala
             20                  25                  30

Leu Ser Gly Leu Lys Asn Leu Thr Pro Ala Met Ile Ser Thr Val Ser
         35                  40                  45
```

-continued

```
Lys Gln Asp Thr Ser Lys Leu Gly Glu Glu Glu
     50                  55


<210> SEQ ID NO 353
<211> LENGTH: 26
<212> TYPE: PRT
<213> ORGANISM: Homo sapiens

<400> SEQUENCE: 353

Pro Thr Arg Pro Pro Thr Arg Pro Leu Ser Phe Thr Phe Thr Lys Gln
  1               5                  10                  15

Thr Ser Ser Thr Cys Leu Ser Leu His Phe
             20                  25


<210> SEQ ID NO 354
<211> LENGTH: 50
<212> TYPE: PRT
<213> ORGANISM: Homo sapiens

<400> SEQUENCE: 354

Leu Glu Cys Val Leu Leu Ile Cys Phe Arg Ala Met Ser Ala Ile Tyr
  1               5                  10                  15

Thr His Thr Ser Ile Gly Asn Ala Gln Lys Leu Phe Thr Asp Gly Ser
             20                  25                  30

Ala Phe Arg Arg Val Arg Glu Pro Leu Pro Lys Glu Gly Lys Ser Trp
         35                  40                  45

Pro Gln
     50


<210> SEQ ID NO 355
<211> LENGTH: 22
<212> TYPE: PRT
<213> ORGANISM: Homo sapiens

<400> SEQUENCE: 355

Lys Gln Asn Leu Thr Asn Leu Asp Val Pro Val Gln Tyr His Val Ala
  1               5                  10                  15

Leu Ser Asp Lys Val Lys
             20


<210> SEQ ID NO 356
<211> LENGTH: 117
<212> TYPE: PRT
<213> ORGANISM: Homo sapiens
<220> FEATURE:
<221> NAME/KEY: SITE
<222> LOCATION: (71)
<223> OTHER INFORMATION: Xaa equals any of the naturally occurring
      L-amino acids

<400> SEQUENCE: 356

Pro Ser Cys Pro Pro Glu Met Lys Lys Glu Leu Pro Val Asp Ser Cys
  1               5                  10                  15

Leu Pro Arg Ser Leu Glu Leu His Pro Gln Lys Met Asp Pro Lys Arg
             20                  25                  30

Gln His Ile Gln Leu Leu Ser Ser Leu Thr Glu Cys Leu Thr Val Asp
         35                  40                  45

Pro Leu Ser Ala Ser Val Trp Arg Gln Leu Tyr Pro Lys His Leu Ser
     50                  55                  60

Gln Ser Ser Leu Leu Leu Xaa His Leu Leu Ser Ser Trp Glu Gln Ile
 65                  70                  75                  80
```

-continued

```
Pro Lys Lys Val Gln Lys Ser Leu Gln Glu Thr Ile Gln Ser Leu Lys
                85                  90                  95

Leu Thr Asn Gln Glu Leu Leu Arg Lys Gly Ser Ser Asn Asn Gln Asp
            100                 105                 110

Val Val Thr Cys Asp
        115
```

<210> SEQ ID NO 357
<211> LENGTH: 103
<212> TYPE: PRT
<213> ORGANISM: Homo sapiens

<400> SEQUENCE: 357

```
Lys Ala Pro Tyr Ser Trp Leu Ala Asp Ser Trp Pro His Pro Ser Arg
  1               5                  10                  15

Ser Pro Ser Ala Gln Glu Pro Arg Gly Ser Cys Cys Pro Ser Asn Pro
             20                  25                  30

Asp Pro Asp Asp Arg Tyr Tyr Asn Glu Ala Gly Ile Ser Leu Tyr Leu
         35                  40                  45

Ala Gln Thr Ala Arg Gly Thr Ala Ala Pro Gly Glu Gly Pro Val Tyr
     50                  55                  60

Ser Thr Ile Asp Pro Ala Gly Glu Glu Leu Gln Thr Phe His Gly Gly
 65                  70                  75                  80

Phe Pro Gln His Pro Ser Gly Asp Leu Gly Pro Trp Ser Gln Tyr Ala
                 85                  90                  95

Pro Pro Glu Trp Ser Gln Gly
            100
```

<210> SEQ ID NO 358
<211> LENGTH: 43
<212> TYPE: PRT
<213> ORGANISM: Homo sapiens

<400> SEQUENCE: 358

```
Leu Gln Gln Thr Met Gln Ala Met Leu His Phe Gly Gly Arg Leu Ala
  1               5                  10                  15

Gln Ser Leu Arg Gly Thr Ser Lys Glu Ala Ala Ser Asp Pro Ser Asp
             20                  25                  30

Ser Pro Asn Leu Pro Thr Pro Gly Ser Trp Trp
         35                  40
```

<210> SEQ ID NO 359
<211> LENGTH: 45
<212> TYPE: PRT
<213> ORGANISM: Homo sapiens

<400> SEQUENCE: 359

```
Glu Gln Leu Thr Gln Ala Ser Arg Val Tyr Ala Ser Gly Gly Thr Glu
  1               5                  10                  15

Gly Phe Pro Leu Ser Arg Trp Ala Pro Gly Arg His Gly Thr Ala Ala
             20                  25                  30

Glu Glu Gly Ala Gln Glu Arg Pro Leu Pro Thr Asp Glu
         35                  40                  45
```

<210> SEQ ID NO 360
<211> LENGTH: 45
<212> TYPE: PRT
<213> ORGANISM: Homo sapiens

<400> SEQUENCE: 360

-continued

```
Met Ala Pro Gly Arg Gly Leu Trp Leu Gly Arg Leu Phe Gly Val Pro
  1               5                  10                  15

Gly Gly Pro Ala Glu Asn Glu Asn Gly Ala Leu Lys Ser Arg Arg Pro
             20                  25                  30

Ser Ser Trp Leu Pro Pro Thr Val Ser Val Leu Ala Leu
         35                  40                  45


<210> SEQ ID NO 361
<211> LENGTH: 44
<212> TYPE: PRT
<213> ORGANISM: Homo sapiens

<400> SEQUENCE: 361

Val Lys Arg Gly Ala Pro Pro Glu Met Pro Ser Pro Gln Glu Leu Glu
  1               5                  10                  15

Ala Ser Ala Pro Arg Met Val Gln Thr His Arg Ala Val Arg Ala Leu
             20                  25                  30

Cys Asp His Thr Ala Ala Arg Pro Asp Gln Leu Ser
         35                  40


<210> SEQ ID NO 362
<211> LENGTH: 38
<212> TYPE: PRT
<213> ORGANISM: Homo sapiens

<400> SEQUENCE: 362

Phe Arg Arg Gly Glu Val Leu Arg Val Ile Thr Thr Val Asp Glu Asp
  1               5                  10                  15

Trp Leu Arg Cys Gly Arg Asp Gly Met Glu Gly Leu Val Pro Val Gly
             20                  25                  30

Tyr Thr Ser Leu Val Leu
         35


<210> SEQ ID NO 363
<211> LENGTH: 215
<212> TYPE: PRT
<213> ORGANISM: Homo sapiens

<400> SEQUENCE: 363

Leu Gln Gln Thr Met Gln Ala Met Leu His Phe Gly Gly Arg Leu Ala
  1               5                  10                  15

Gln Ser Leu Arg Gly Thr Ser Lys Glu Ala Ala Ser Asp Pro Ser Asp
             20                  25                  30

Ser Pro Asn Leu Pro Thr Pro Gly Ser Trp Trp Glu Gln Leu Thr Gln
         35                  40                  45

Ala Ser Arg Val Tyr Ala Ser Gly Gly Thr Glu Gly Phe Pro Leu Ser
     50                  55                  60

Arg Trp Ala Pro Gly Arg His Gly Thr Ala Ala Glu Glu Gly Ala Gln
 65                  70                  75                  80

Glu Arg Pro Leu Pro Thr Asp Glu Met Ala Pro Gly Arg Gly Leu Trp
                 85                  90                  95

Leu Gly Arg Leu Phe Gly Val Pro Gly Gly Pro Ala Glu Asn Glu Asn
            100                 105                 110

Gly Ala Leu Lys Ser Arg Arg Pro Ser Ser Trp Leu Pro Pro Thr Val
        115                 120                 125

Ser Val Leu Ala Leu Val Lys Arg Gly Ala Pro Pro Glu Met Pro Ser
    130                 135                 140
```

-continued

```
Pro Gln Glu Leu Glu Ala Ser Ala Pro Arg Met Val Gln Thr His Arg
145                 150                 155                 160

Ala Val Arg Ala Leu Cys Asp His Thr Ala Ala Arg Pro Asp Gln Leu
                165                 170                 175

Ser Phe Arg Arg Gly Glu Val Leu Arg Val Ile Thr Thr Val Asp Glu
            180                 185                 190

Asp Trp Leu Arg Cys Gly Arg Asp Gly Met Glu Gly Leu Val Pro Val
        195                 200                 205

Gly Tyr Thr Ser Leu Val Leu
    210                 215


<210> SEQ ID NO 364
<211> LENGTH: 72
<212> TYPE: PRT
<213> ORGANISM: Homo sapiens
<220> FEATURE:
<221> NAME/KEY: SITE
<222> LOCATION: (7)
<223> OTHER INFORMATION: Xaa equals any of the naturally occurring
      L-amino acids

<400> SEQUENCE: 364

Ala Arg Ala Cys Pro Arg Xaa Gly Ala Ala Val Glu Lys Leu Gly Gly
  1               5                  10                  15

Lys Pro Val Gln Pro Asp Ser Lys Pro Thr Cys Cys Ser Gln Val Lys
            20                  25                  30

Ala Glu Gly Leu Ile Phe Ala Gly Leu Thr Gly Leu Lys Leu Leu Pro
        35                  40                  45

Ser Ser Leu Gln Arg Ala Val Phe Val Arg Gln Cys Leu Gly Phe Trp
     50                  55                  60

Asn Asp Gly Ser Arg Ala Leu Gln
 65                  70


<210> SEQ ID NO 365
<211> LENGTH: 136
<212> TYPE: PRT
<213> ORGANISM: Homo sapiens
<220> FEATURE:
<221> NAME/KEY: SITE
<222> LOCATION: (130)
<223> OTHER INFORMATION: Xaa equals any of the naturally occurring
      L-amino acids

<400> SEQUENCE: 365

Met Ser Pro Asn Leu Asn Ala Thr His Thr Ser Ala Gln Thr Pro Gly
  1               5                  10                  15

Phe Met Glu Arg Lys Thr Thr His Thr Val Ala Gln Ala Leu Ser His
            20                  25                  30

Ala Val Arg Thr Ile Arg Gly Ala Arg Ser Pro Leu Arg Pro Asp Ala
        35                  40                  45

Ser Arg Thr Pro Thr Ser Cys Gln Met Ser Thr Gln Ser Leu Leu Ile
     50                  55                  60

Cys Lys Ala Arg Leu Pro Ser Phe Gln Asn Pro Arg His Cys Leu Thr
 65                  70                  75                  80

Lys Thr Ala Leu Cys Lys Glu Leu Gly Ser Asn Leu Ser Pro Val Arg
                 85                  90                  95

Pro Ala Lys Ile Ser Pro Ser Ala Leu Thr Cys Glu Gln His Val Gly
            100                 105                 110

Leu Glu Ser Gly Trp Thr Gly Phe Pro Pro Ser Phe Ser Thr Ala Ala
        115                 120                 125
```

-continued

```
Pro Xaa Leu Gly Gln Ala Arg Ala
    130                135


<210> SEQ ID NO 366
<211> LENGTH: 31
<212> TYPE: PRT
<213> ORGANISM: Homo sapiens

<400> SEQUENCE: 366

Phe Gln Ser Val Tyr His Met Lys Leu Gln Ser Ser Asn Leu Pro Ala
  1             5                  10                  15

Ser Val Tyr Gly Asn Asn Leu Asn Cys Ile Asn Ser Ser Ser Ser
             20                 25                  30


<210> SEQ ID NO 367
<211> LENGTH: 241
<212> TYPE: PRT
<213> ORGANISM: Homo sapiens

<400> SEQUENCE: 367

Gly Leu Ser Ile His Asp Gly Thr Trp Lys Ser Ala Ile Tyr Gly Phe
  1             5                  10                  15

Gly Asp Gln Ser Asn Leu Arg Lys Leu Arg Asn Val Ser Asn Leu Lys
             20                 25                  30

Pro Val Pro Leu Ile Gly Pro Lys Leu Lys Arg Arg Trp Pro Ile Ser
         35                 40                  45

Tyr Cys Arg Glu Leu Lys Gly Tyr Ser Ile Pro Phe Met Gly Ser Asp
     50                 55                  60

Val Ser Val Val Arg Arg Thr Gln Arg Tyr Leu Tyr Glu Asn Leu Glu
 65                 70                  75                  80

Glu Ser Pro Val Gln Tyr Ala Ala Tyr Val Thr Val Gly Gly Ile Thr
                 85                 90                  95

Ser Val Ile Lys Leu Met Phe Ala Gly Leu Phe Phe Leu Phe Phe Val
            100                105                 110

Arg Phe Gly Ile Gly Arg Gln Leu Leu Ile Lys Phe Pro Trp Phe Phe
        115                120                 125

Ser Phe Gly Tyr Phe Ser Lys Gln Gly Pro Thr Gln Lys Gln Ile Asp
    130                135                 140

Ala Ala Ser Phe Thr Leu Thr Phe Phe Gly Gln Gly Tyr Ser Gln Gly
145                150                 155                 160

Thr Gly Thr Asp Lys Asn Lys Pro Asn Ile Lys Ile Cys Thr Gln Val
                165                170                 175

Lys Gly Pro Glu Ala Gly Tyr Val Ala Thr Pro Ile Ala Met Val Gln
            180                185                 190

Ala Ala Met Thr Leu Leu Ser Asp Ala Ser His Leu Pro Lys Ala Gly
        195                200                 205

Gly Val Phe Thr Pro Gly Ala Ala Phe Ser Lys Thr Lys Leu Ile Asp
    210                215                 220

Arg Leu Asn Lys His Gly Ile Glu Phe Ser Val Ile Ser Ser Ser Glu
225                230                 235                 240

Val


<210> SEQ ID NO 368
<211> LENGTH: 62
<212> TYPE: PRT
<213> ORGANISM: Homo sapiens
```

-continued

<400> SEQUENCE: 368

```
Met Asp Pro Asp Arg Ala Phe Ile Cys Gly Glu Ser Arg Gln Phe Ala
  1               5                  10                  15

Gln Cys Leu Ile Phe Gly Phe Leu Phe Leu Thr Ser Gly Met Leu Ile
             20                  25                  30

Ser Val Leu Gly Ile Trp Val Pro Gly Cys Gly Ser Asn Trp Ala Gln
         35                  40                  45

Glu Pro Leu Asn Glu Thr Asp Thr Gly Asp Ser Glu Pro Arg
     50                  55                  60
```

<210> SEQ ID NO 369
<211> LENGTH: 229
<212> TYPE: PRT
<213> ORGANISM: Homo sapiens

<400> SEQUENCE: 369

```
Met Asp Pro Asp Arg Ala Phe Ile Cys Gly Glu Ser Arg Gln Phe Ala
  1               5                  10                  15

Gln Cys Leu Ile Phe Gly Phe Leu Phe Leu Thr Ser Gly Met Leu Ile
             20                  25                  30

Ser Val Leu Gly Ile Trp Val Pro Gly Cys Gly Ser Asn Trp Ala Gln
         35                  40                  45

Glu Pro Leu Asn Glu Thr Asp Thr Gly Asp Ser Glu Pro Arg Met Cys
     50                  55                  60

Gly Phe Leu Ser Leu Gln Ile Met Gly Pro Leu Ile Val Leu Val Gly
 65                  70                  75                  80

Leu Cys Phe Phe Val Val Ala His Val Lys Lys Arg Asn Thr Leu Asn
                 85                  90                  95

Ala Gly Gln Asp Ala Ser Glu Arg Glu Glu Gly Gln Ile Gln Ile Met
            100                 105                 110

Glu Pro Val Gln Val Thr Val Gly Asp Ser Val Ile Ile Phe Pro Pro
        115                 120                 125

Pro Pro Pro Pro Tyr Phe Pro Glu Ser Ser Ala Ser Ala Val Ala Glu
    130                 135                 140

Ser Pro Gly Thr Asn Ser Leu Leu Pro Asn Glu Asn Pro Pro Ser Tyr
145                 150                 155                 160

Tyr Ser Ile Phe Asn Tyr Gly Thr Pro Thr Ser Glu Gly Ala Ala Ser
                165                 170                 175

Glu Arg Asp Cys Glu Ser Ile Tyr Thr Ile Ser Gly Thr Asn Ser Ser
            180                 185                 190

Ser Glu Ala Ser His Thr Pro His Leu Pro Ser Glu Leu Pro Pro Arg
        195                 200                 205

Tyr Glu Glu Lys Glu Asn Ala Ala Ala Thr Phe Leu Pro Leu Ser Ser
    210                 215                 220

Glu Pro Ser Pro Pro
225
```

<210> SEQ ID NO 370
<211> LENGTH: 37
<212> TYPE: PRT
<213> ORGANISM: Homo sapiens

<400> SEQUENCE: 370

```
Phe Asp Phe Ile Ala Ser Leu Leu Lys Ala Asn Arg Leu Ser Leu Gln
  1               5                  10                  15

Thr Cys Glu Leu Leu Leu Ala Ala Ala Leu Leu Pro Ser Glu Arg Tyr
```

-continued

```
            20                  25                  30

Lys Ala Ile Ser Ile
        35


<210> SEQ ID NO 371
<211> LENGTH: 63
<212> TYPE: PRT
<213> ORGANISM: Homo sapiens

<400> SEQUENCE: 371

Met Asn Lys Lys Ala Glu Leu Lys Pro Ser Ala Leu Pro Gly Trp Ala
  1               5                  10                  15

Asn Val Trp Lys Leu Met Cys Leu Val Thr Val Cys Ala Ser Leu Ile
            20                  25                  30

Ile Thr Ser Asp Ser Val Val Ser Thr Val Arg Leu Lys Gly Ser Cys
        35                  40                  45

Glu Asp Tyr Leu Gly Leu Ser Cys Gly Asn Thr Ser His Ala Tyr
     50                  55                  60


<210> SEQ ID NO 372
<211> LENGTH: 434
<212> TYPE: PRT
<213> ORGANISM: Homo sapiens

<400> SEQUENCE: 372

Met Ser Ala Asp Gly Ala Glu Ala Asp Gly Ser Thr Gln Val Thr Val
  1               5                  10                  15

Glu Glu Pro Val Gln Gln Pro Ser Val Val Asp Arg Val Ala Ser Met
            20                  25                  30

Pro Leu Ile Ser Ser Thr Cys Asp Met Val Ser Ala Ala Tyr Ala Ser
        35                  40                  45

Thr Lys Glu Ser Tyr Pro His Val Lys Thr Val Cys Asp Ala Ala Glu
     50                  55                  60

Lys Gly Val Arg Thr Leu Thr Ala Ala Ala Val Ser Gly Ala Gln Pro
 65                  70                  75                  80

Ile Leu Ser Lys Leu Glu Pro Gln Ile Ala Ser Ala Ser Glu Tyr Ala
                 85                  90                  95

His Arg Gly Leu Asp Lys Leu Glu Glu Asn Leu Pro Ile Leu Gln Gln
            100                 105                 110

Pro Thr Glu Lys Val Leu Ala Asp Thr Lys Glu Leu Val Ser Ser Lys
        115                 120                 125

Val Ser Gly Ala Gln Glu Met Val Ser Ser Ala Lys Asp Thr Val Ala
    130                 135                 140

Thr Gln Leu Ser Glu Ala Val Asp Ala Thr Arg Gly Ala Val Gln Ser
145                 150                 155                 160

Gly Val Asp Lys Thr Lys Ser Val Val Thr Gly Gly Val Gln Ser Val
                165                 170                 175

Met Gly Ser Arg Leu Gly Gln Met Val Leu Ser Gly Val Asp Thr Val
            180                 185                 190

Leu Gly Lys Ser Glu Glu Trp Ala Asp Asn His Leu Pro Leu Thr Asp
        195                 200                 205

Ala Glu Leu Ala Arg Ile Ala Thr Ser Leu Asp Gly Phe Asp Val Ala
    210                 215                 220

Ser Val Gln Gln Gln Arg Gln Glu Gln Ser Tyr Phe Val Arg Leu Gly
225                 230                 235                 240

Ser Leu Ser Glu Arg Leu Arg Gln His Ala Tyr Glu His Ser Leu Gly
```

-continued

```
                245                 250                 255

Lys Leu Arg Ala Thr Lys Gln Arg Ala Gln Glu Ala Leu Leu Gln Leu
            260                 265                 270

Ser Gln Ala Leu Ser Leu Met Glu Thr Val Lys Gln Gly Val Asp Gln
        275                 280                 285

Lys Leu Val Glu Gly Gln Glu Lys Leu His Gln Met Trp Leu Ser Trp
    290                 295                 300

Asn Gln Lys Gln Leu Gln Gly Pro Glu Lys Glu Pro Pro Lys Pro Glu
305                 310                 315                 320

Gln Val Glu Ser Arg Ala Leu Thr Met Phe Arg Asp Ile Ala Gln Gln
                325                 330                 335

Leu Gln Ala Thr Cys Thr Ser Leu Gly Ser Ser Ile Gln Gly Leu Pro
            340                 345                 350

Thr Asn Val Lys Asp Gln Val Gln Gln Ala Arg Arg Gln Val Glu Asp
        355                 360                 365

Leu Gln Ala Thr Phe Ser Ser Ile His Ser Phe Gln Asp Leu Ser Ser
    370                 375                 380

Ser Ile Leu Ala Gln Ser Arg Glu Arg Val Ala Ser Ala Arg Glu Ala
385                 390                 395                 400

Leu Asp His Met Val Glu Tyr Val Ala Gln Asn Thr Pro Val Thr Trp
                405                 410                 415

Leu Val Gly Pro Phe Ala Pro Gly Ile Thr Glu Lys Ala Pro Glu Glu
            420                 425                 430

Lys Lys


<210> SEQ ID NO 373
<211> LENGTH: 66
<212> TYPE: PRT
<213> ORGANISM: Homo sapiens

<400> SEQUENCE: 373

Met Leu Cys Lys Ser Leu Leu Tyr Cys Val Val Ser Tyr Leu Tyr Tyr
  1               5                  10                  15

Phe Val Phe Ile Tyr Phe Phe Pro Val Phe Leu Ile Cys Ser Trp Leu
             20                  25                  30

Glu Leu Gln Met Trp Asn Leu Gln Ile Gly Arg Ala Asp Cys Phe Gln
         35                  40                  45

Asn Thr Leu Val Tyr Val Leu Ser Leu Cys Leu Gln Tyr Lys Asn His
     50                  55                  60

Pro Ala
 65


<210> SEQ ID NO 374
<211> LENGTH: 25
<212> TYPE: PRT
<213> ORGANISM: Homo sapiens

<400> SEQUENCE: 374

Ile Asp Leu Ser Phe Pro Ser Thr Asn Val Ser Leu Glu Asp Arg Asn
  1               5                  10                  15

Thr Thr Lys Pro Ser Val Asn Val Gly
             20                  25


<210> SEQ ID NO 375
<211> LENGTH: 12
<212> TYPE: PRT
<213> ORGANISM: Homo sapiens
```

-continued

<400> SEQUENCE: 375

Val Ala His Ala Cys Asn Pro Ser Thr Leu Gly Gly
1 5 10

<210> SEQ ID NO 376
<211> LENGTH: 17
<212> TYPE: PRT
<213> ORGANISM: Homo sapiens

<400> SEQUENCE: 376

Gly Gly Gln Ile Thr Arg Ser Gly Asp Gln Asp Gln Pro Asp Gln His
1 5 10 15

Gly

<210> SEQ ID NO 377
<211> LENGTH: 12
<212> TYPE: PRT
<213> ORGANISM: Homo sapiens

<400> SEQUENCE: 377

Gly Phe Thr Met Leu Val Arg Leu Val Leu Ile Ser
1 5 10

<210> SEQ ID NO 378
<211> LENGTH: 28
<212> TYPE: PRT
<213> ORGANISM: Homo sapiens

<400> SEQUENCE: 378

Pro Arg Asp Leu Pro Thr Ser Ala Ser Gln Ser Ala Gly Ile Thr Gly
1 5 10 15

Met Ser His Pro Ala Arg Pro Lys Leu Leu Phe Asn
20 25

<210> SEQ ID NO 379
<211> LENGTH: 46
<212> TYPE: PRT
<213> ORGANISM: Homo sapiens

<400> SEQUENCE: 379

Pro Phe Trp Ala Ala Glu Ser Ala Leu Asp Phe His Trp Pro Phe Gly
1 5 10 15

Gly Ala Leu Cys Lys Met Val Leu Thr Ala Thr Val Leu Asn Val Tyr
20 25 30

Ala Ser Ile Phe Leu Ile Thr Ala Leu Ser Val Ala Arg Tyr
35 40 45

<210> SEQ ID NO 380
<211> LENGTH: 12
<212> TYPE: PRT
<213> ORGANISM: Homo sapiens

<400> SEQUENCE: 380

Thr His Ala Asp Lys Asn Gln Val Arg Asn Ser Asn
1 5 10

<210> SEQ ID NO 381
<211> LENGTH: 15
<212> TYPE: PRT
<213> ORGANISM: Homo sapiens

<400> SEQUENCE: 381

-continued

Gln Phe Leu Ser Trp Glu Gln Cys Thr Gly Asn Thr Glu Ser Gln
1 5 10 15

<210> SEQ ID NO 382
<211> LENGTH: 13
<212> TYPE: PRT
<213> ORGANISM: Homo sapiens
<220> FEATURE:
<221> NAME/KEY: SITE
<222> LOCATION: (9)
<223> OTHER INFORMATION: Xaa equals any of the naturally occurring L-amino acids

<400> SEQUENCE: 382

Val Arg Arg Pro Lys Ala Lys Gly Xaa Gln Thr Ser Asn
1 5 10

<210> SEQ ID NO 383
<211> LENGTH: 19
<212> TYPE: PRT
<213> ORGANISM: Homo sapiens

<400> SEQUENCE: 383

Pro Thr Gln Leu Asn Lys His Lys Pro Thr Thr Lys Glu Arg Arg Arg
1 5 10 15

Lys Gly Leu

<210> SEQ ID NO 384
<211> LENGTH: 9
<212> TYPE: PRT
<213> ORGANISM: Homo sapiens

<400> SEQUENCE: 384

Leu Ile Ser Lys His Glu Asn Ile Tyr
1 5

<210> SEQ ID NO 385
<211> LENGTH: 27
<212> TYPE: PRT
<213> ORGANISM: Homo sapiens
<220> FEATURE:
<221> NAME/KEY: SITE
<222> LOCATION: (5)
<223> OTHER INFORMATION: Xaa equals any of the naturally occurring L-amino acids
<220> FEATURE:
<221> NAME/KEY: SITE
<222> LOCATION: (6)
<223> OTHER INFORMATION: Xaa equals any of the naturally occurring L-amino acids
<220> FEATURE:
<221> NAME/KEY: SITE
<222> LOCATION: (8)
<223> OTHER INFORMATION: Xaa equals any of the naturally occurring L-amino acids
<220> FEATURE:
<221> NAME/KEY: SITE
<222> LOCATION: (22)
<223> OTHER INFORMATION: Xaa equals any of the naturally occurring L-amino acids

<400> SEQUENCE: 385

Thr Leu Tyr Ile Xaa Xaa Met Xaa Thr Gln Thr Trp Arg Asp Gln Gly
1 5 10 15

Arg Cys Gly Arg Asp Xaa Ile Asn Cys Ile Val
20 25

-continued

<210> SEQ ID NO 386
<211> LENGTH: 33
<212> TYPE: PRT
<213> ORGANISM: Homo sapiens

<400> SEQUENCE: 386

```
Ser Leu Cys Thr Pro Gly Arg Gly Trp Glu Glu Ser Trp Gly Ser Ser
  1               5                  10                  15

Leu Pro Asn Leu Thr Gly Trp Ser Val Ser Ser Leu Asp Asn Asn Asp
             20                  25                  30

Val
```

<210> SEQ ID NO 387
<211> LENGTH: 204
<212> TYPE: PRT
<213> ORGANISM: Homo sapiens
<220> FEATURE:
<221> NAME/KEY: SITE
<222> LOCATION: (107)
<223> OTHER INFORMATION: Xaa equals any of the naturally occurring
      L-amino acids

<400> SEQUENCE: 387

```
Met Gln Val Ala Leu Lys Glu Asp Leu Asp Ala Leu Lys Glu Lys Phe
  1               5                  10                  15

Arg Thr Met Glu Ser Asn Gln Lys Ser Ser Phe Gln Glu Ile Pro Lys
             20                  25                  30

Leu Asn Glu Glu Leu Leu Ser Lys Gln Lys Gln Leu Glu Lys Ile Glu
         35                  40                  45

Ser Gly Glu Met Gly Leu Asn Lys Val Trp Ile Asn Ile Thr Glu Met
     50                  55                  60

Asn Lys Gln Ile Ser Leu Leu Thr Ser Ala Val Asn His Leu Lys Ala
 65                  70                  75                  80

Asn Val Lys Ser Ala Ala Asp Leu Ile Ser Leu Pro Thr Thr Val Glu
                 85                  90                  95

Gly Leu Gln Lys Ser Val Ala Ser Ile Gly Xaa Thr Leu Asn Ser Val
            100                 105                 110

His Leu Ala Val Glu Ala Leu Gln Lys Thr Val Asp Glu His Lys Lys
        115                 120                 125

Thr Met Glu Leu Leu Gln Ser Asp Met Asn Gln His Phe Leu Lys Glu
    130                 135                 140

Thr Pro Gly Ser Asn Gln Ile Ile Pro Ser Pro Ser Ala Thr Ser Glu
145                 150                 155                 160

Leu Asp Asn Lys Thr His Ser Glu Asn Leu Lys Gln Met Gly Asp Arg
                165                 170                 175

Ser Ala Thr Leu Lys Arg Gln Ser Leu Asp Gln Val Thr Asn Arg Thr
            180                 185                 190

Asp Thr Val Lys Ile Gln Ser Ile Lys Lys Glu Gly
        195                 200
```

<210> SEQ ID NO 388
<211> LENGTH: 43
<212> TYPE: PRT
<213> ORGANISM: Homo sapiens

<400> SEQUENCE: 388

```
Met Gln Val Ala Leu Lys Glu Asp Leu Asp Ala Leu Lys Glu Lys Phe
  1               5                  10                  15

Arg Thr Met Glu Ser Asn Gln Lys Ser Ser Phe Gln Glu Ile Pro Lys
```

-continued

```
            20                  25                  30

Leu Asn Glu Glu Leu Leu Ser Lys Gln Lys Gln
        35                  40


<210> SEQ ID NO 389
<211> LENGTH: 43
<212> TYPE: PRT
<213> ORGANISM: Homo sapiens

<400> SEQUENCE: 389

Leu Glu Lys Ile Glu Ser Gly Glu Met Gly Leu Asn Lys Val Trp Ile
  1               5                  10                  15

Asn Ile Thr Glu Met Asn Lys Gln Ile Ser Leu Leu Thr Ser Ala Val
            20                  25                  30

Asn His Leu Lys Ala Asn Val Lys Ser Ala Ala
        35                  40


<210> SEQ ID NO 390
<211> LENGTH: 43
<212> TYPE: PRT
<213> ORGANISM: Homo sapiens
<220> FEATURE:
<221> NAME/KEY: SITE
<222> LOCATION: (21)
<223> OTHER INFORMATION: Xaa equals any of the naturally occurring
      L-amino acids

<400> SEQUENCE: 390

Asp Leu Ile Ser Leu Pro Thr Thr Val Glu Gly Leu Gln Lys Ser Val
  1               5                  10                  15

Ala Ser Ile Gly Xaa Thr Leu Asn Ser Val His Leu Ala Val Glu Ala
            20                  25                  30

Leu Gln Lys Thr Val Asp Glu His Lys Lys Thr
        35                  40


<210> SEQ ID NO 391
<211> LENGTH: 43
<212> TYPE: PRT
<213> ORGANISM: Homo sapiens

<400> SEQUENCE: 391

Met Glu Leu Leu Gln Ser Asp Met Asn Gln His Phe Leu Lys Glu Thr
  1               5                  10                  15

Pro Gly Ser Asn Gln Ile Ile Pro Ser Pro Ser Ala Thr Ser Glu Leu
            20                  25                  30

Asp Asn Lys Thr His Ser Glu Asn Leu Lys Gln
        35                  40


<210> SEQ ID NO 392
<211> LENGTH: 32
<212> TYPE: PRT
<213> ORGANISM: Homo sapiens

<400> SEQUENCE: 392

Met Gly Asp Arg Ser Ala Thr Leu Lys Arg Gln Ser Leu Asp Gln Val
  1               5                  10                  15

Thr Asn Arg Thr Asp Thr Val Lys Ile Gln Ser Ile Lys Lys Glu Gly
            20                  25                  30


<210> SEQ ID NO 393
<211> LENGTH: 258
<212> TYPE: PRT
```

-continued

```
<213> ORGANISM: Homo sapiens
<220> FEATURE:
<221> NAME/KEY: SITE
<222> LOCATION: (161)
<223> OTHER INFORMATION: Xaa equals any of the naturally occurring
      L-amino acids

<400> SEQUENCE: 393

Asp Ser Glu Ser Ser Ser Glu Glu Glu Glu Glu Phe Gly Val Val Gly
  1               5                  10                  15

Asn Arg Ser Arg Phe Ala Lys Gly Asp Tyr Leu Arg Cys Cys Lys Ile
             20                  25                  30

Cys Tyr Pro Leu Cys Gly Phe Val Ile Leu Ala Ala Cys Val Val Ala
         35                  40                  45

Cys Val Gly Leu Val Trp Met Gln Val Ala Leu Lys Glu Asp Leu Asp
     50                  55                  60

Ala Leu Lys Glu Lys Phe Arg Thr Met Glu Ser Asn Gln Lys Ser Ser
 65                  70                  75                  80

Phe Gln Glu Ile Pro Lys Leu Asn Glu Glu Leu Leu Ser Lys Gln Lys
                 85                  90                  95

Gln Leu Glu Lys Ile Glu Ser Gly Glu Met Gly Leu Asn Lys Val Trp
            100                 105                 110

Ile Asn Ile Thr Glu Met Asn Lys Gln Ile Ser Leu Leu Thr Ser Ala
        115                 120                 125

Val Asn His Leu Lys Ala Asn Val Lys Ser Ala Ala Asp Leu Ile Ser
    130                 135                 140

Leu Pro Thr Thr Val Glu Gly Leu Gln Lys Ser Val Ala Ser Ile Gly
145                 150                 155                 160

Xaa Thr Leu Asn Ser Val His Leu Ala Val Glu Ala Leu Gln Lys Thr
                165                 170                 175

Val Asp Glu His Lys Lys Thr Met Glu Leu Leu Gln Ser Asp Met Asn
            180                 185                 190

Gln His Phe Leu Lys Glu Thr Pro Gly Ser Asn Gln Ile Ile Pro Ser
        195                 200                 205

Pro Ser Ala Thr Ser Glu Leu Asp Asn Lys Thr His Ser Glu Asn Leu
    210                 215                 220

Lys Gln Met Gly Asp Arg Ser Ala Thr Leu Lys Arg Gln Ser Leu Asp
225                 230                 235                 240

Gln Val Thr Asn Arg Thr Asp Thr Val Lys Ile Gln Ser Ile Lys Lys
                245                 250                 255

Glu Gly


<210> SEQ ID NO 394
<211> LENGTH: 12
<212> TYPE: PRT
<213> ORGANISM: Homo sapiens

<400> SEQUENCE: 394

Ser Pro Gln Phe Leu Ser Ser Lys Ser Leu Pro Thr
  1               5                  10


<210> SEQ ID NO 395
<211> LENGTH: 107
<212> TYPE: PRT
<213> ORGANISM: Homo sapiens

<400> SEQUENCE: 395

Gly Pro Pro Ser Pro Arg Gly Leu Pro Ser Leu Pro Leu His Leu Pro
```

-continued

```
  1               5                   10                  15

Ala Pro Arg Arg Tyr Leu Gln Ser Arg Tyr Ala Cys Ser Gln Ser Ser
             20                  25                  30

Val Ser Ala Ala Ala Arg Arg Trp Gly Ser Gly Trp Met Ala Trp Asp
         35                  40                  45

Pro Trp Asn Gln Ala Ser Gly Arg Tyr Ala Arg Ile Thr Leu Leu Ser
     50                  55                  60

Val Gln Ala Cys His Gln Pro Thr Val Trp Pro Arg Ala Gly His Ser
 65                  70                  75                  80

Leu Pro Glu Arg Tyr Ser Leu His Pro His Asn Gly Asp Ser Thr His
                 85                  90                  95

Leu Ser Gly Leu Leu Thr Val Lys Cys Gly Ala
            100                 105


<210> SEQ ID NO 396
<211> LENGTH: 37
<212> TYPE: PRT
<213> ORGANISM: Homo sapiens

<400> SEQUENCE: 396

Gly Pro Pro Ser Pro Arg Gly Leu Pro Ser Leu Pro Leu His Leu Pro
  1               5                   10                  15

Ala Pro Arg Arg Tyr Leu Gln Ser Arg Tyr Ala Cys Ser Gln Ser Ser
             20                  25                  30

Val Ser Ala Ala Ala
         35


<210> SEQ ID NO 397
<211> LENGTH: 33
<212> TYPE: PRT
<213> ORGANISM: Homo sapiens

<400> SEQUENCE: 397

Arg Arg Trp Gly Ser Gly Trp Met Ala Trp Asp Pro Trp Asn Gln Ala
  1               5                   10                  15

Ser Gly Arg Tyr Ala Arg Ile Thr Leu Leu Ser Val Gln Ala Cys His
             20                  25                  30

Gln


<210> SEQ ID NO 398
<211> LENGTH: 37
<212> TYPE: PRT
<213> ORGANISM: Homo sapiens

<400> SEQUENCE: 398

Pro Thr Val Trp Pro Arg Ala Gly His Ser Leu Pro Glu Arg Tyr Ser
  1               5                   10                  15

Leu His Pro His Asn Gly Asp Ser Thr His Leu Ser Gly Leu Leu Thr
             20                  25                  30

Val Lys Cys Gly Ala
         35


<210> SEQ ID NO 399
<211> LENGTH: 173
<212> TYPE: PRT
<213> ORGANISM: Homo sapiens
<220> FEATURE:
<221> NAME/KEY: SITE
<222> LOCATION: (130)
<223> OTHER INFORMATION: Xaa equals any of the naturally occurring
```

```
      L-amino acids
<220> FEATURE:
<221> NAME/KEY: SITE
<222> LOCATION: (152)
<223> OTHER INFORMATION: Xaa equals any of the naturally occurring
      L-amino acids

<400> SEQUENCE: 399

Gly Pro Pro Ser Pro Arg Gly Leu Pro Ser Leu Pro Leu His Leu Pro
  1               5                  10                  15

Ala Pro Arg Arg Tyr Leu Gln Ser Arg Tyr Ala Cys Ser Gln Ser Ser
             20                  25                  30

Val Ser Ala Ala Ala Arg Arg Trp Gly Ser Gly Trp Met Ala Trp Asp
         35                  40                  45

Pro Trp Asn Gln Ala Ser Gly Arg Tyr Ala Arg Ile Thr Leu Leu Ser
     50                  55                  60

Val Gln Ala Cys His Gln Pro Thr Val Trp Pro Arg Ala Gly His Ser
 65                  70                  75                  80

Leu Pro Glu Arg Tyr Ser Leu His Pro His Asn Gly Asp Ser Thr His
                 85                  90                  95

Leu Ser Gly Leu Leu Thr Val Lys Cys Gly Ala Met Ala Gly Phe Ala
            100                 105                 110

Ser Tyr Pro Trp Ser Asp Phe Pro Trp Cys Trp Val Val Cys Phe Ser
        115                 120                 125

Phe Xaa Phe Phe Phe Leu Arg Gln Ser Glu Ser Leu Ser Gln Lys Lys
    130                 135                 140

Arg Gln Val Ala Asp Glu Leu Xaa Phe Gly Gln Ser Lys Arg Asp Ser
145                 150                 155                 160

Asp Gly Gly Trp Met Leu Arg Ser Ser Ala Gly Asn Ser
                165                 170


<210> SEQ ID NO 400
<211> LENGTH: 119
<212> TYPE: PRT
<213> ORGANISM: Homo sapiens
<220> FEATURE:
<221> NAME/KEY: SITE
<222> LOCATION: (46)
<223> OTHER INFORMATION: Xaa equals any of the naturally occurring
      L-amino acids
<220> FEATURE:
<221> NAME/KEY: SITE
<222> LOCATION: (52)
<223> OTHER INFORMATION: Xaa equals any of the naturally occurring
      L-amino acids
<220> FEATURE:
<221> NAME/KEY: SITE
<222> LOCATION: (110)
<223> OTHER INFORMATION: Xaa equals any of the naturally occurring
      L-amino acids

<400> SEQUENCE: 400

Met Glu Ser Cys Ser Val Val Gln Ala Gly Val Lys Trp Cys Asp Leu
  1               5                  10                  15

Gly Ser Leu Gln Pro Pro Pro Arg Phe Lys Gln Phe Ser Trp Glu Val
             20                  25                  30

Glu Val Ala Val Ser Arg Asp His Thr Ile Ala Leu Gln Xaa Gly Gly
         35                  40                  45

Gln Ser Lys Xaa Leu Ser Gln Lys Lys Glu Lys Lys Tyr Val Leu Asn
     50                  55                  60

Ala Thr Phe Leu Asn Phe Tyr Phe Cys Arg Asp Lys Val Leu Leu Cys
 65                  70                  75                  80
```

-continued

```
Cys Pro Gly Trp Ser His Ile Val Gly Leu Lys Gln Ser Ser His Leu
                 85                  90                  95

Gly Leu Arg Lys Cys Trp Asp Tyr Arg His Gly Pro Leu Xaa Leu Ala
            100                 105                 110

Leu Cys His Phe Val Cys Lys
        115


<210> SEQ ID NO 401
<211> LENGTH: 18
<212> TYPE: PRT
<213> ORGANISM: Homo sapiens

<400> SEQUENCE: 401

Asn Gln Glu Asn Ser Leu Gln Thr Asn Ser Tyr Leu Asp Ser Thr Glu
  1               5                  10                  15

Ser Lys


<210> SEQ ID NO 402
<211> LENGTH: 31
<212> TYPE: PRT
<213> ORGANISM: Homo sapiens
<220> FEATURE:
<221> NAME/KEY: SITE
<222> LOCATION: (17)
<223> OTHER INFORMATION: Xaa equals any of the naturally occurring
      L-amino acids
<220> FEATURE:
<221> NAME/KEY: SITE
<222> LOCATION: (19)
<223> OTHER INFORMATION: Xaa equals any of the naturally occurring
      L-amino acids
<220> FEATURE:
<221> NAME/KEY: SITE
<222> LOCATION: (30)
<223> OTHER INFORMATION: Xaa equals any of the naturally occurring
      L-amino acids

<400> SEQUENCE: 402

Gln Lys Arg Ala Cys Phe Pro Phe Ala Phe Cys Arg Asp Cys Gln Phe
  1               5                  10                  15

Xaa Glu Xaa Ser Pro Ala Met Leu Pro Val Gln Pro Ala Xaa Leu
             20                  25                  30


<210> SEQ ID NO 403
<211> LENGTH: 11
<212> TYPE: PRT
<213> ORGANISM: Homo sapiens

<400> SEQUENCE: 403

Val Ser Ala His Gly Ile Trp Leu Phe Arg Ser
  1               5                  10


<210> SEQ ID NO 404
<211> LENGTH: 49
<212> TYPE: PRT
<213> ORGANISM: Homo sapiens
<220> FEATURE:
<221> NAME/KEY: SITE
<222> LOCATION: (35)
<223> OTHER INFORMATION: Xaa equals any of the naturally occurring
      L-amino acids
<220> FEATURE:
<221> NAME/KEY: SITE
<222> LOCATION: (37)
<223> OTHER INFORMATION: Xaa equals any of the naturally occurring
      L-amino acids
<220> FEATURE:
```

-continued

<221> NAME/KEY: SITE
<222> LOCATION: (48)
<223> OTHER INFORMATION: Xaa equals any of the naturally occurring
      L-amino acids

<400> SEQUENCE: 404

```
Lys His Ala Ala Pro Pro Ala Ser Leu Ser Leu Ser Leu Leu Leu His
  1               5                  10                  15

His Gly Gln Lys Arg Ala Cys Phe Pro Phe Ala Phe Cys Arg Asp Cys
             20                  25                  30

Gln Phe Xaa Glu Xaa Ser Pro Ala Met Leu Pro Val Gln Pro Ala Xaa
         35                  40                  45

Leu
```

<210> SEQ ID NO 405
<211> LENGTH: 101
<212> TYPE: PRT
<213> ORGANISM: Homo sapiens

<400> SEQUENCE: 405

```
Met Cys Asp Asn Leu Ile Met Leu Arg Thr Leu Met Arg Tyr Ile Val
  1               5                  10                  15

Phe Leu Ser Leu Gln Cys Leu Trp Gly Gln Gly Thr His Ser Ser Cys
             20                  25                  30

Tyr Pro Pro Ser Pro Leu Arg Leu Pro Leu Phe Phe Phe Leu Asp Ile
         35                  40                  45

Lys Leu Gly Ile Ser Asn Trp Pro Val Val Met Gln Ser Cys Phe Ala
     50                  55                  60

Leu Tyr Leu Ala Gly Leu Ile Cys Leu Thr Arg Ser His Glu Ala Ile
 65                  70                  75                  80

Gly Arg Ser Ser Leu Ser Pro Ser Ser Ser Ala Pro Lys Val Val Ala
                 85                  90                  95

Arg Gly Val Pro Ser
            100
```

<210> SEQ ID NO 406
<211> LENGTH: 138
<212> TYPE: PRT
<213> ORGANISM: Homo sapiens

<400> SEQUENCE: 406

```
Met Leu Val Leu Met Thr Leu Phe Leu Leu Leu Tyr Tyr Arg Tyr Val
  1               5                  10                  15

Tyr Gly Phe Gly Val Cys Val Tyr Val His Ile Tyr Ala His Ile Tyr
             20                  25                  30

Thr His Thr His Ile Tyr Asn Gln Leu Ser Ile Ala Tyr Ser Ser Leu
         35                  40                  45

Ile Ile Tyr Ile Leu Tyr Ser Asn Phe Ser Asn Thr Pro Thr Lys Ser
     50                  55                  60

Phe Ser Pro Pro Tyr Gln Tyr Tyr Asn Val Pro Asp Asn Asn Ile Thr
 65                  70                  75                  80

Asn Pro Ala Leu Thr Pro Thr Asp Phe Phe Glu Asn Lys Gln Leu Leu
                 85                  90                  95

His Ala Ile Ser Phe Leu Tyr Ser Pro Thr Gly Phe Leu Gln Pro Pro
            100                 105                 110

Ala His Pro Val Gln Leu Arg Thr Ser Thr Thr Leu Tyr Gly Asn His
        115                 120                 125
```

-continued

```
Arg Gly Gln Thr Gly Cys Ser Gln Leu Asp
    130                 135


<210> SEQ ID NO 407
<211> LENGTH: 67
<212> TYPE: PRT
<213> ORGANISM: Homo sapiens

<400> SEQUENCE: 407

Ser Asn Thr Pro Thr Lys Ser Phe Ser Pro Pro Tyr Gln Tyr Tyr Asn
  1               5                  10                  15

Val Pro Asp Asn Asn Ile Thr Asn Pro Ala Leu Thr Pro Thr Asp Phe
             20                  25                  30

Phe Glu Asn Lys Gln Leu Leu His Ala Ile Ser Phe Leu Tyr Ser Pro
         35                  40                  45

Thr Gly Phe Leu Gln Pro Pro Ala His Pro Val Gln Leu Arg Thr Ser
     50                  55                  60

Thr Thr Leu
 65


<210> SEQ ID NO 408
<211> LENGTH: 12
<212> TYPE: PRT
<213> ORGANISM: Homo sapiens

<400> SEQUENCE: 408

Met Glu Met Asn Tyr Cys Gly Ser Arg Val Leu Tyr
  1               5                  10


<210> SEQ ID NO 409
<211> LENGTH: 61
<212> TYPE: PRT
<213> ORGANISM: Homo sapiens

<400> SEQUENCE: 409

Leu Gly Ser Pro Ile Ile Pro Leu Trp Ser Tyr Thr Ser Ala Thr Gln
  1               5                  10                  15

Ala Ala Ala Leu Val Thr Ser His Val Trp Lys Pro Ser Leu Glu Ala
             20                  25                  30

His Gln Ile Asn Ile Ser Pro Glu Pro Ser Ile His Tyr Asp Arg Trp
         35                  40                  45

His Thr Gln Ser Asn Cys Ser Leu Ile Asn Ser Leu Gln
     50                  55                  60


<210> SEQ ID NO 410
<211> LENGTH: 12
<212> TYPE: PRT
<213> ORGANISM: Homo sapiens

<400> SEQUENCE: 410

Ile Pro Glu Glu Ala Ser Cys Phe Pro Ser Ala Val
  1               5                  10


<210> SEQ ID NO 411
<211> LENGTH: 17
<212> TYPE: PRT
<213> ORGANISM: Homo sapiens

<400> SEQUENCE: 411

Glu Ile Leu Phe Gly Lys Leu Lys Ser Lys Ala Ala Leu Cys Thr Gln
  1               5                  10                  15
```

-continued

Gly

<210> SEQ ID NO 412
<211> LENGTH: 19
<212> TYPE: PRT
<213> ORGANISM: Homo sapiens

<400> SEQUENCE: 412

His Ala Asp Arg Tyr Thr Cys Cys Arg Cys Leu Ser Pro Phe Ser Leu
1 5 10 15

Ala Gly Leu

<210> SEQ ID NO 413
<211> LENGTH: 15
<212> TYPE: PRT
<213> ORGANISM: Homo sapiens

<400> SEQUENCE: 413

Leu Ser Asp Pro Leu Leu Leu Pro Asp Cys Ser Phe Ser Phe Asn
1 5 10 15

<210> SEQ ID NO 414
<211> LENGTH: 25
<212> TYPE: PRT
<213> ORGANISM: Homo sapiens

<400> SEQUENCE: 414

Lys Ala Val Ala Tyr Ala Asn Val Ser Cys Arg Arg Phe Lys His Lys
1 5 10 15

Thr Thr Lys Leu Gly Pro Ile Gln Trp
20 25

<210> SEQ ID NO 415
<211> LENGTH: 26
<212> TYPE: PRT
<213> ORGANISM: Homo sapiens

<400> SEQUENCE: 415

Pro Ser Ser Gln Ser Pro Glu Pro Pro Gln Pro Leu Ser Leu Phe Val
1 5 10 15

Thr Arg Leu Pro Asn Leu Tyr Asp Phe Pro
20 25

<210> SEQ ID NO 416
<211> LENGTH: 19
<212> TYPE: PRT
<213> ORGANISM: Homo sapiens

<400> SEQUENCE: 416

Ser Arg Gln Ile Ile Cys Thr Asn Leu Cys Lys Cys Thr Pro Ile Cys
1 5 10 15

Phe Leu Phe

<210> SEQ ID NO 417
<211> LENGTH: 15
<212> TYPE: PRT
<213> ORGANISM: Homo sapiens

<400> SEQUENCE: 417

Lys Gly Ser Leu Pro Trp Arg Leu Leu Leu Pro Leu Asn Gly Pro
1 5 10 15

-continued

<210> SEQ ID NO 418
<211> LENGTH: 19
<212> TYPE: PRT
<213> ORGANISM: Homo sapiens

<400> SEQUENCE: 418

Leu Cys Arg Leu Val Phe Glu Ser Ser Ala Gly His Val Ser Val Cys
1 5 10 15

His Ser Phe

<210> SEQ ID NO 419
<211> LENGTH: 11
<212> TYPE: PRT
<213> ORGANISM: Homo sapiens

<400> SEQUENCE: 419

Met Leu Leu Pro Val Asn Thr Leu Leu Tyr Ile
1 5 10

<210> SEQ ID NO 420
<211> LENGTH: 14
<212> TYPE: PRT
<213> ORGANISM: Homo sapiens

<400> SEQUENCE: 420

Leu Leu Thr Pro Leu Cys Phe Phe Tyr Gly Thr Ser Arg Pro
1 5 10

<210> SEQ ID NO 421
<211> LENGTH: 7
<212> TYPE: PRT
<213> ORGANISM: Homo sapiens

<400> SEQUENCE: 421

Pro Tyr Leu Glu Leu Val Thr
1 5

<210> SEQ ID NO 422
<211> LENGTH: 13
<212> TYPE: PRT
<213> ORGANISM: Homo sapiens

<400> SEQUENCE: 422

Leu Leu Lys Lys Lys Lys Gln Ser Val Gly Phe Ser Val
1 5 10

<210> SEQ ID NO 423
<211> LENGTH: 7
<212> TYPE: PRT
<213> ORGANISM: Homo sapiens

<400> SEQUENCE: 423

Cys Ile Leu Glu Ala Gly Arg
1 5

<210> SEQ ID NO 424
<211> LENGTH: 11
<212> TYPE: PRT
<213> ORGANISM: Homo sapiens

<400> SEQUENCE: 424

Met Gly Phe Ser Ala Pro Thr Pro Gly Pro Leu
1 5 10

-continued

<210> SEQ ID NO 425
<211> LENGTH: 11
<212> TYPE: PRT
<213> ORGANISM: Homo sapiens

<400> SEQUENCE: 425

Phe Asp Leu Arg Arg Leu Ile Leu Ser Ile Val
1 5 10

<210> SEQ ID NO 426
<211> LENGTH: 17
<212> TYPE: PRT
<213> ORGANISM: Homo sapiens

<400> SEQUENCE: 426

Ala Phe Cys Pro His Val Thr Pro Cys Lys Tyr Ala Val Ile His Thr
1 5 10 15

Val

<210> SEQ ID NO 427
<211> LENGTH: 11
<212> TYPE: PRT
<213> ORGANISM: Homo sapiens

<400> SEQUENCE: 427

Asn Thr Pro Leu Leu Phe Leu Trp Asp Leu Gln
1 5 10

<210> SEQ ID NO 428
<211> LENGTH: 17
<212> TYPE: PRT
<213> ORGANISM: Homo sapiens

<400> SEQUENCE: 428

Ala Thr Ile Phe Arg Thr Ser Tyr Leu Ile Lys Lys Glu Lys Thr Val
1 5 10 15

Cys

<210> SEQ ID NO 429
<211> LENGTH: 17
<212> TYPE: PRT
<213> ORGANISM: Homo sapiens

<400> SEQUENCE: 429

Trp Leu Leu Ser Leu His Leu Gly Gly Arg Glu Val Arg Ala Gly Ala
1 5 10 15

Pro

<210> SEQ ID NO 430
<211> LENGTH: 11
<212> TYPE: PRT
<213> ORGANISM: Homo sapiens

<400> SEQUENCE: 430

Gln Thr Leu Gln Glu Gly Ser Leu His Ser Ile
1 5 10

<210> SEQ ID NO 431
<211> LENGTH: 95
<212> TYPE: PRT
<213> ORGANISM: Homo sapiens

<400> SEQUENCE: 431

-continued

```
Met Gly Phe Ser Ala Pro Thr Pro Gly Pro Leu Phe Asp Leu Arg Arg
  1               5                  10                  15

Leu Ile Leu Ser Ile Val Ala Phe Cys Pro His Val Thr Pro Cys Lys
             20                  25                  30

Tyr Ala Val Ile His Thr Val Asn Thr Pro Leu Leu Phe Leu Trp Asp
         35                  40                  45

Leu Gln Ala Thr Ile Phe Arg Thr Ser Tyr Leu Ile Lys Lys Glu Lys
     50                  55                  60

Thr Val Cys Trp Leu Leu Ser Leu His Leu Gly Gly Arg Glu Val Arg
 65                  70                  75                  80

Ala Gly Ala Pro Gln Thr Leu Gln Glu Gly Ser Leu His Ser Ile
                 85                  90                  95


<210> SEQ ID NO 432
<211> LENGTH: 33
<212> TYPE: PRT
<213> ORGANISM: Homo sapiens

<400> SEQUENCE: 432

Tyr Trp Val Ser Ile Ser Gln Arg Ser Val Cys Gln Gln Ala Arg Thr
  1               5                  10                  15

Ser Ile Phe Phe Lys Asp Gly Leu Ser Arg Glu Lys Tyr Ser Asn Asn
             20                  25                  30

Gly


<210> SEQ ID NO 433
<211> LENGTH: 160
<212> TYPE: PRT
<213> ORGANISM: Homo sapiens

<400> SEQUENCE: 433

Leu Ser Val Arg Ala Pro Gly Val Pro Ala Ala Arg Pro Arg Leu Ser
  1               5                  10                  15

Ser Ala Arg Gln Ala Gly Ala Gly Arg Gly Glu Leu Arg Gly Gln Arg
             20                  25                  30

Leu Trp Leu Gly Pro Glu Cys Gly Cys Gly Ala Gly Gln Ala Gly Ser
         35                  40                  45

Met Leu Arg Ala Val Gly Ser Leu Leu Arg Leu Gly Arg Gly Leu Thr
     50                  55                  60

Val Arg Cys Gly Pro Gly Ala Pro Leu Glu Ala Thr Arg Arg Pro Ala
 65                  70                  75                  80

Pro Ala Leu Pro Pro Arg Gly Leu Pro Cys Tyr Ser Ser Gly Gly Ala
                 85                  90                  95

Pro Ser Asn Ser Gly Pro Gln Gly His Gly Glu Ile His Arg Val Pro
            100                 105                 110

Thr Gln Arg Arg Pro Ser Gln Phe Asp Lys Lys Ile Leu Leu Trp Thr
        115                 120                 125

Gly Arg Phe Lys Ser Met Glu Glu Ile Pro Pro Arg Ile Pro Pro Glu
    130                 135                 140

Met Ile Asp Thr Ala Arg Asn Lys Ala Arg Val Lys Ala Cys Tyr Ile
145                 150                 155                 160


<210> SEQ ID NO 434
<211> LENGTH: 36
<212> TYPE: PRT
<213> ORGANISM: Homo sapiens

<400> SEQUENCE: 434
```

-continued

```
Leu Ser Val Arg Ala Pro Gly Val Pro Ala Ala Arg Pro Arg Leu Ser
  1               5                  10                  15

Ser Ala Arg Gln Ala Gly Ala Gly Arg Gly Glu Leu Arg Gly Gln Arg
             20                  25                  30

Leu Trp Leu Gly
         35


<210> SEQ ID NO 435
<211> LENGTH: 34
<212> TYPE: PRT
<213> ORGANISM: Homo sapiens

<400> SEQUENCE: 435

Pro Glu Cys Gly Cys Gly Ala Gly Gln Ala Gly Ser Met Leu Arg Ala
  1               5                  10                  15

Val Gly Ser Leu Leu Arg Leu Gly Arg Gly Leu Thr Val Arg Cys Gly
             20                  25                  30

Pro Gly


<210> SEQ ID NO 436
<211> LENGTH: 34
<212> TYPE: PRT
<213> ORGANISM: Homo sapiens

<400> SEQUENCE: 436

Ala Pro Leu Glu Ala Thr Arg Arg Pro Ala Pro Ala Leu Pro Pro Arg
  1               5                  10                  15

Gly Leu Pro Cys Tyr Ser Ser Gly Gly Ala Pro Ser Asn Ser Gly Pro
             20                  25                  30

Gln Gly


<210> SEQ ID NO 437
<211> LENGTH: 27
<212> TYPE: PRT
<213> ORGANISM: Homo sapiens

<400> SEQUENCE: 437

His Gly Glu Ile His Arg Val Pro Thr Gln Arg Arg Pro Ser Gln Phe
  1               5                  10                  15

Asp Lys Lys Ile Leu Leu Trp Thr Gly Arg Phe
             20                  25


<210> SEQ ID NO 438
<211> LENGTH: 29
<212> TYPE: PRT
<213> ORGANISM: Homo sapiens

<400> SEQUENCE: 438

Lys Ser Met Glu Glu Ile Pro Pro Arg Ile Pro Pro Glu Met Ile Asp
  1               5                  10                  15

Thr Ala Arg Asn Lys Ala Arg Val Lys Ala Cys Tyr Ile
             20                  25


<210> SEQ ID NO 439
<211> LENGTH: 57
<212> TYPE: PRT
<213> ORGANISM: Homo sapiens

<400> SEQUENCE: 439

Cys Ser Pro Gly Gln Asp Glu Met Gln Asp Glu Thr Trp Cys Ser Gly
```

-continued

```
  1               5                  10                  15

Gln Ser Glu Thr Val Asn Glu Ala Lys Gln Leu Arg Thr Thr His Ser
             20                  25                  30

Arg Val Pro Asn Gln Gln Val Cys Val Cys Gly Trp Leu Pro Val Asn
         35                  40                  45

Ile Ser Pro His Ser Pro Leu Lys Lys
     50                  55


<210> SEQ ID NO 440
<211> LENGTH: 147
<212> TYPE: PRT
<213> ORGANISM: Homo sapiens

<400> SEQUENCE: 440

Met Ser Gly Asp Val Cys Val Phe Gly Tyr Ala His Leu His Ser Gln
  1               5                  10                  15

Thr Lys His Ser Gly Ser Gln Gly Trp Val Leu Ile Tyr Leu Phe Ala
             20                  25                  30

Met Gln Lys Ile Ser Cys Thr Lys Leu Pro Leu Leu Arg Asn Leu Lys
         35                  40                  45

Leu Asn Leu Val Trp Leu Ser Gln Gly Trp Val Phe Phe Lys Gly Leu
     50                  55                  60

Trp Gly Glu Met Leu Thr Gly Ser His Pro Gln Thr His Thr Cys Trp
 65                  70                  75                  80

Leu Gly Thr Arg Leu Trp Val Val Leu Ser Cys Leu Ala Ser Leu Thr
                 85                  90                  95

Val Ser Asp Cys Pro Glu His Gln Val Ser Ser Cys Ile Ser Ser Trp
            100                 105                 110

Pro Gly Glu His Ser Val Ser Phe Gln Pro Phe Pro Pro Phe Pro His
        115                 120                 125

Ser Leu Gly Gly Thr Glu Val Gly Val Glu Glu Ser Gln Met Ala Gly
    130                 135                 140

Val Gly Ile
145


<210> SEQ ID NO 441
<211> LENGTH: 15
<212> TYPE: PRT
<213> ORGANISM: Homo sapiens

<400> SEQUENCE: 441

Leu Asn Ile Leu Ile Ser Leu Thr Val Ser Ser His Cys Lys Leu
  1               5                  10                  15


<210> SEQ ID NO 442
<211> LENGTH: 13
<212> TYPE: PRT
<213> ORGANISM: Homo sapiens

<400> SEQUENCE: 442

Ile Asn Tyr His Ser Gly Phe Ile His Gln Phe Leu Ala
  1               5                  10


<210> SEQ ID NO 443
<211> LENGTH: 11
<212> TYPE: PRT
<213> ORGANISM: Homo sapiens

<400> SEQUENCE: 443
```

-continued

```
Met Ala Asn Asn Ser Leu Ser Ser Gln Phe Ile
  1               5                  10


<210> SEQ ID NO 444
<211> LENGTH: 65
<212> TYPE: PRT
<213> ORGANISM: Homo sapiens

<400> SEQUENCE: 444

Ile Ser Gly Val Leu Ile Phe Asn Leu Ile Ala Ser Ser Trp Val Leu
  1               5                  10                  15

Cys Phe Pro Leu Cys Asp Leu Ser Cys Gln Lys Thr Leu Arg Ile Phe
             20                  25                  30

Phe Ala Ser Phe Phe His Ala Val Cys Val His Val Ser Cys Thr Ser
         35                  40                  45

Trp Gln Pro Leu Val Leu Phe Ile Lys Trp Trp Val Val Gly Cys Ser
     50                  55                  60

Pro
 65


<210> SEQ ID NO 445
<211> LENGTH: 23
<212> TYPE: PRT
<213> ORGANISM: Homo sapiens

<400> SEQUENCE: 445

Cys Asp Leu Ser Cys Gln Lys Thr Leu Arg Ile Phe Phe Ala Ser Phe
  1               5                  10                  15

Phe His Ala Val Cys Val His
             20


<210> SEQ ID NO 446
<211> LENGTH: 9
<212> TYPE: PRT
<213> ORGANISM: Homo sapiens

<400> SEQUENCE: 446

Glu Leu Ala Ile Gly Glu Ser Cys Ser
  1               5


<210> SEQ ID NO 447
<211> LENGTH: 17
<212> TYPE: PRT
<213> ORGANISM: Homo sapiens

<400> SEQUENCE: 447

Pro Val Ile Trp Pro Asp Gly Lys Arg Ile Val Leu Leu Ala Glu Val
  1               5                  10                  15

Ser


<210> SEQ ID NO 448
<211> LENGTH: 27
<212> TYPE: PRT
<213> ORGANISM: Homo sapiens

<400> SEQUENCE: 448

Phe Tyr Tyr Phe Trp Arg Gln Gly Gly Ser Cys Phe Val Gln Thr Gly
  1               5                  10                  15

Val Gln Trp Cys Asp His Gly Ser Leu Gln Leu
             20                  25
```

-continued

<210> SEQ ID NO 449
<211> LENGTH: 10
<212> TYPE: PRT
<213> ORGANISM: Homo sapiens

<400> SEQUENCE: 449

```
Thr Pro Gly Arg Gln Ser Lys Thr Pro Ser
  1               5                  10
```

<210> SEQ ID NO 450
<211> LENGTH: 34
<212> TYPE: PRT
<213> ORGANISM: Homo sapiens

<400> SEQUENCE: 450

```
Tyr Phe Ile Ile Phe Gly Asp Arg Glu Gly Leu Ala Leu Phe Arg Leu
  1               5                  10                  15

Glu Cys Ser Gly Val Ile Met Ala His Cys Asn Phe Glu Leu Leu Gly
             20                  25                  30

Asp Arg
```

<210> SEQ ID NO 451
<211> LENGTH: 10
<212> TYPE: PRT
<213> ORGANISM: Homo sapiens

<400> SEQUENCE: 451

```
Cys Phe Leu Ser Val Ser Phe Gln Trp Asn
  1               5                  10
```

<210> SEQ ID NO 452
<211> LENGTH: 17
<212> TYPE: PRT
<213> ORGANISM: Homo sapiens

<400> SEQUENCE: 452

```
Val Thr Ile Ala Gln Val Gly Ile Phe Val Cys Phe Val His Cys Cys
  1               5                  10                  15

Thr
```

<210> SEQ ID NO 453
<211> LENGTH: 17
<212> TYPE: PRT
<213> ORGANISM: Homo sapiens

<400> SEQUENCE: 453

```
Pro Gly Gln Val Pro Ser Lys His Leu Gly Ser Asn Ala Ser Val Arg
  1               5                  10                  15

Ala
```

<210> SEQ ID NO 454
<211> LENGTH: 22
<212> TYPE: PRT
<213> ORGANISM: Homo sapiens

<400> SEQUENCE: 454

```
Asp Glu Gly Ala Lys Val Gln Arg Arg Pro Trp Gly Ser Gln Thr His
  1               5                  10                  15

Ser Pro Val Leu Phe Leu
             20
```

<210> SEQ ID NO 455

-continued

<211> LENGTH: 18
<212> TYPE: PRT
<213> ORGANISM: Homo sapiens

<400> SEQUENCE: 455

Leu Thr Arg Pro Gly Leu Trp Gly Ser Leu Leu Pro Val Gln Gln Gln
1 5 10 15

Arg Gly

<210> SEQ ID NO 456
<211> LENGTH: 15
<212> TYPE: PRT
<213> ORGANISM: Homo sapiens

<400> SEQUENCE: 456

Cys Ala Ser Leu Gly Val Leu Arg Ala Asn Arg Ser Pro Cys Val
1 5 10 15

<210> SEQ ID NO 457
<211> LENGTH: 18
<212> TYPE: PRT
<213> ORGANISM: Homo sapiens

<400> SEQUENCE: 457

Ser Trp Leu Glu Val Thr Thr Leu Ser Ala Pro Gly Pro Val Ile Thr
1 5 10 15

Thr Tyr

<210> SEQ ID NO 458
<211> LENGTH: 18
<212> TYPE: PRT
<213> ORGANISM: Homo sapiens
<220> FEATURE:
<221> NAME/KEY: SITE
<222> LOCATION: (9)
<223> OTHER INFORMATION: Xaa equals any of the naturally occurring
L-amino acids

<400> SEQUENCE: 458

Pro Gly Gln Trp Val Arg Glu Ile Xaa Leu Val Gly Arg Ala Val Ala
1 5 10 15

Arg Val

<210> SEQ ID NO 459
<211> LENGTH: 16
<212> TYPE: PRT
<213> ORGANISM: Homo sapiens
<220> FEATURE:
<221> NAME/KEY: SITE
<222> LOCATION: (6)
<223> OTHER INFORMATION: Xaa equals any of the naturally occurring
L-amino acids

<400> SEQUENCE: 459

Leu Thr Trp Pro Pro Xaa Gly Pro Met Gly Thr Val Trp Pro Gly Phe
1 5 10 15

<210> SEQ ID NO 460
<211> LENGTH: 17
<212> TYPE: PRT
<213> ORGANISM: Homo sapiens

<400> SEQUENCE: 460

Met Ala Asp Ile Pro Gly Thr Phe Leu Ala Leu Gly Cys His Gly Gln
1 5 10 15

Arg

<210> SEQ ID NO 461
<211> LENGTH: 15
<212> TYPE: PRT
<213> ORGANISM: Homo sapiens

<400> SEQUENCE: 461

Val Gly Arg Gly Ser Trp Ala Ser Gly Trp Thr Asn Gln Ser Ala
1 5 10 15

<210> SEQ ID NO 462
<211> LENGTH: 16
<212> TYPE: PRT
<213> ORGANISM: Homo sapiens

<400> SEQUENCE: 462

Pro Asp His Pro Leu Pro Val Gly Leu Leu Glu Ala Trp Arg Val Glu
1 5 10 15

<210> SEQ ID NO 463
<211> LENGTH: 142
<212> TYPE: PRT
<213> ORGANISM: Homo sapiens
<220> FEATURE:
<221> NAME/KEY: SITE
<222> LOCATION: (72)
<223> OTHER INFORMATION: Xaa equals any of the naturally occurring
L-amino acids
<220> FEATURE:
<221> NAME/KEY: SITE
<222> LOCATION: (87)
<223> OTHER INFORMATION: Xaa equals any of the naturally occurring
L-amino acids

<400> SEQUENCE: 463

Trp Gly Ser Gln Thr His Ser Pro Val Leu Phe Leu Leu Thr Arg Pro
1 5 10 15

Gly Leu Trp Gly Ser Leu Leu Pro Val Gln Gln Gln Arg Gly Cys Ala
20 25 30

Ser Leu Gly Val Leu Arg Ala Asn Arg Ser Pro Cys Val Ser Trp Leu
35 40 45

Glu Val Thr Thr Leu Ser Ala Pro Gly Pro Val Ile Thr Thr Tyr Pro
50 55 60

Gly Gln Trp Val Arg Glu Ile Xaa Leu Val Gly Arg Ala Val Ala Arg
65 70 75 80

Val Leu Thr Trp Pro Pro Xaa Gly Pro Met Gly Thr Val Trp Pro Gly
85 90 95

Phe Met Ala Asp Ile Pro Gly Thr Phe Leu Ala Leu Gly Cys His Gly
100 105 110

Gln Arg Val Gly Arg Gly Ser Trp Ala Ser Gly Trp Thr Asn Gln Xaa
115 120 125

Ser Ala Phe Pro Ala Gly Pro Pro Asp His Pro Leu Pro Val
130 135 140

<210> SEQ ID NO 464
<211> LENGTH: 94
<212> TYPE: PRT
<213> ORGANISM: Homo sapiens
<220> FEATURE:
<221> NAME/KEY: SITE
<222> LOCATION: (84)
<223> OTHER INFORMATION: Xaa equals any of the naturally occurring -continued

```
      L-amino acids

<400> SEQUENCE: 464

Leu Ala Arg Ala Asp Pro Pro Gly Cys Arg Arg Arg Gly Trp Arg Pro
  1               5                  10                  15

Ser Ser Ala Glu Leu Gln Leu Arg Leu Leu Thr Pro Thr Phe Glu Gly
             20                  25                  30

Ile Asn Gly Leu Leu Leu Lys Gln His Leu Val Gln Asn Pro Val Arg
         35                  40                  45

Leu Trp Gln Leu Leu Gly Gly Thr Phe Tyr Phe Asn Thr Ser Arg Leu
     50                  55                  60

Lys Gln Lys Asn Lys Glu Lys Asp Lys Ser Lys Gly Lys Ala Pro Glu
 65                  70                  75                  80

Glu Asp Glu Xaa Glu Arg Arg Arg Arg Glu Arg Asp Asp Gln
                 85                  90


<210> SEQ ID NO 465
<211> LENGTH: 12
<212> TYPE: PRT
<213> ORGANISM: Homo sapiens

<400> SEQUENCE: 465

Phe Leu Arg Phe Trp Cys Thr Cys His Val Ser Ser
  1               5                  10
```

ANTIBODIES TO HHPEN62 POLYPEPTIDE

CROSS-REFERENCE TO RELATED APPLICATIONS

This application is a continuation of U.S. patent application Ser. No. 09/948,783, filed Sep. 10, 2001 now abandoned, which claims benefit under 35 U.S.C. § 119(e) of U.S. Provisional Patent Application No. 60/231,846 filed Sep. 11, 2000; U.S. patent application Ser. No. 09/948,783 is a continuation-in-part of U.S. patent application Ser. No. 09/892,877 filed Jun. 28, 2001 now abandoned, which is a continuation application of U.S. patent application Ser. No. 09/437,658 filed Nov. 10, 1999 now abandoned, which is a continuation-in-part of International Patent Application No. PCT/US99/09847, filed May 6, 1999, which claims benefit under 35 U.S.C. § 119(e) based on the following U.S. Provisional Applications: No. 60/085,093, filed on May 12, 1998; No. 60/085,094, filed on May 12, 1998; No. 60/085,105, filed on May 12, 1998; No. 60/085,180, filed on May 12, 1998; No. 60/085,927, filed on May 18, 1998; No. 60/085,906, filed on May 18, 1998; No. 60/085,920, filed on May 18, 1998; No. 60/085,924, filed on May 18, 1998; No. 60/085,922, filed on May 18, 1998; No. 60/085,923, filed on May 18, 1998; No. 60/085,921, filed on May 18, 1998; No. 60/085,925, filed on May 18, 1998; and, No. 60/085,928, filed on May 18, 1998. Each of the above referenced patents and/or patent applications is hereby incorporated by reference in its entirety.

FIELD OF THE INVENTION

This invention relates to newly identified polynucleotides, polypeptides encoded by these polynucleotides, antibodies that bind these polypeptides, uses of such polynucleotides, polypeptides, and antibodies, and their production.

BACKGROUND OF THE INVENTION

Unlike bacterium, which exist as a single compartment surrounded by a membrane, human cells and other eucaryotes are subdivided by membranes into many functionally distinct compartments. Each membrane-bounded compartment, or organelle, contains different proteins essential for the function of the organelle. The cell uses "sorting signals," which are amino acid motifs located within the protein, to target proteins to particular cellular organelles.

One type of sorting signal, called a signal sequence, a signal peptide, or a leader sequence, directs a class of proteins to an organelle called the endoplasmic reticulum (ER). The ER separates the membrane-bounded proteins from all other types of proteins. Once localized to the ER, both groups of proteins can be further directed to another organelle called the Golgi apparatus. Here, the Golgi distributes the proteins to vesicles, including secretory vesicles, the cell membrane, lysosomes, and the other organelles.

Proteins targeted to the ER by a signal sequence can be released into the extracellular space as a secreted protein. For example, vesicles containing secreted proteins can fuse with the cell membrane and release their contents into the extracellular space—a process called exocytosis. Exocytosis can occur constitutively or after receipt of a triggering signal. In the latter case, the proteins are stored in secretory vesicles (or secretory granules) until exocytosis is triggered. Similarly, proteins residing on the cell membrane can also be secreted into the extracellular space by proteolytic cleavage of a "linker" holding the protein to the membrane.

Despite the great progress made in recent years, only a small number of genes encoding human secreted proteins have been identified. These secreted proteins include the commercially valuable human insulin, interferon, Factor VIII, human growth hormone, tissue plasminogen activator, and erythropoeitin. Thus, in light of the pervasive role of secreted proteins in human physiology, a need exists for identifying and characterizing novel human secreted proteins and the genes that encode them. This knowledge will allow one to detect, to treat, and to prevent medical diseases, disorders, and/or conditions by using secreted proteins or the genes that encode them.

SUMMARY OF THE INVENTION

The present invention relates to novel polynucleotides and the encoded polypeptides. Moreover, the present invention relates to vectors, host cells, antibodies, and recombinant and synthetic methods for producing the polypeptides and polynucleotides. Also provided are diagnostic methods for detecting diseases, disorders, and/or conditions related to the polypeptides and polynucleotides, and therapeutic methods for treating such diseases, disorders, and/or conditions. The invention further relates to screening methods for identifying binding partners of the polypeptides.

DETAILED DESCRIPTION

Definitions

The following definitions are provided to facilitate understanding of certain terms used throughout this specification.

In the present invention, "isolated" refers to material removed from its original environment (e.g., the natural environment if it is naturally occurring), and thus is altered "by the hand of man" from its natural state. For example, an isolated polynucleotide could be part of a vector or a composition of matter, or could be contained within a cell, and still be "isolated" because that vector, composition of matter, or particular cell is not the original environment of the polynucleotide. The term "isolated" does not refer to genomic or cDNA libraries, whole cell total or mRNA preparations, genomic DNA preparations (including those separated by electrophoresis and transferred onto blots), sheared whole cell genomic DNA preparations or other compositions where the art demonstrates no distinguishing features of the polynucleotide/sequences of the present invention.

In the present invention, a "secreted" protein refers to those proteins capable of being directed to the ER, secretory vesicles, or the extracellular space as a result of a signal sequence, as well as those proteins released into the extracellular space without necessarily containing a signal sequence. If the secreted protein is released into the extracellular space, the secreted protein can undergo extracellular processing to produce a "mature" protein. Release into the extracellular space can occur by many mechanisms, including exocytosis and proteolytic cleavage.

In specific embodiments, the polynucleotides of the invention are at least 15, at least 30, at least 50, at least 100, at least 125, at least 500, or at least 1000 continuous nucleotides but are less than or equal to 300 kb, 200 kb, 100 kb, 50 kb, 15 kb, 10 kb, 7.5 kb, 5 kb, 2.5 kb, 2.0 kb, or 1 kb, in length. In a further embodiment, polynucleotides of the invention comprise a portion of the coding sequences, as disclosed herein, but do not comprise all or a portion of any intron. In another embodiment, the polynucleotides comprising coding sequences do not contain coding sequences of a genomic flanking gene (i.e., 5' or 3' to the gene of interest in the genome). In other embodiments, the polynucleotides of the invention do not contain the coding sequence of more than 1000, 500, 250, 100, 50, 25, 20, 15, 10, 5, 4, 3, 2, or 1 genomic flanking gene(s).

As used herein, a "polynucleotide" refers to a molecule having a nucleic acid sequence contained in SEQ ID NO:X or the cDNA contained within the clone deposited with the ATCC. For example, the polynucleotide can contain the nucleotide sequence of the full length cDNA sequence, including the 5' and 3' untranslated sequences, the coding region, with or without the signal sequence, the secreted protein coding region, as well as fragments, epitopes, domains, and variants of the nucleic acid sequence. Moreover, as used herein, a "polypeptide" refers to a molecule having the translated amino acid sequence generated from the polynucleotide as broadly defined.

In the present invention, the full length sequence identified as SEQ ID NO:X was often generated by overlapping sequences contained in multiple clones (contig analysis). A representative clone containing all or most of the sequence for SEQ ID NO:X was deposited with the American Type Culture Collection ("ATCC"). As shown in Table 1, each clone is identified by a cDNA Clone ID (Identifier) and the ATCC Deposit Number. The ATCC is located at 10801 University Boulevard, Manassas, Va. 20110-2209, USA. The ATCC deposit was made pursuant to the terms of the Budapest Treaty on the international recognition of the deposit of microorganisms for purposes of patent procedure.

A "polynucleotide" of the present invention also includes those polynucleotides capable of hybridizing, under stringent hybridization conditions, to sequences contained in SEQ ID NO:X, the complement thereof, or the cDNA within the clone deposited with the ATCC. "Stringent hybridization conditions" refers to an overnight incubation at 42 degree C. in a solution comprising 50% formamide, 5×SSC (750 mM NaCl, 75 mM trisodium citrate), 50 mM sodium phosphate (pH 7.6), 5× Denhardt's solution, 10% dextran sulfate, and 20 μg/ml denatured, sheared salmon sperm DNA, followed by washing the filters in 0.1×SSC at about 65 degree C.

Also contemplated are nucleic acid molecules that hybridize to the polynucleotides of the present invention at lower stringency hybridization conditions. Changes in the stringency of hybridization and signal detection are primarily accomplished through the manipulation of formamide concentration (lower percentages of formamide result in lowered stringency); salt conditions, or temperature. For example, lower stringency conditions include an overnight incubation at 37 degree C. in a solution comprising 6×SSPE (20×SSPE=3M NaCl; 0.2M $NaH_2PO_4$; 0.02M EDTA, pH 7.4), 0.5% SDS, 30% formamide, 100 ug/ml salmon sperm blocking DNA; followed by washes at 50 degree C. with 1×SSPE, 0.1% SDS. In addition, to achieve even lower stringency, washes performed following stringent hybridization can be done at higher salt concentrations (e.g. 5×SSC).

Note that variations in the above conditions may be accomplished through the inclusion and/or substitution of alternate blocking reagents used to suppress background in hybridization experiments. Typical blocking reagents include Denhardt's reagent, BLOTTO, heparin, denatured salmon sperm DNA, and commercially available proprietary formulations. The inclusion of specific blocking reagents may require modification of the hybridization conditions described above, due to problems with compatibility.

Of course, a polynucleotide which hybridizes only to polyA+ sequences (such as any 3' terminal polyA+ tract of a cDNA shown in the sequence listing), or to a complementary stretch of T (or U) residues, would not be included in the definition of "polynucleotide," since such a polynucleotide would hybridize to any nucleic acid molecule containing a poly (A) stretch or the complement thereof (e.g., practically any double-stranded cDNA clone generated using oligo dT as a primer).

The polynucleotide of the present invention can be composed of any polyribonucleotide or polydeoxribonucleotide, which may be unmodified RNA or DNA or modified RNA or DNA. For example, polynucleotides can be composed of single- and double-stranded DNA, DNA that is a mixture of single- and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions. In addition, the polynucleotide can be composed of triple-stranded regions comprising RNA or DNA or both RNA and DNA. A polynucleotide may also contain one or more modified bases or DNA or RNA backbones modified for stability or for other reasons. "Modified" bases include, for example, tritylated bases and unusual bases such as inosine. A variety of modifications can be made to DNA and RNA; thus, "polynucleotide" embraces chemically, enzymatically, or metabolically modified forms.

The polypeptide of the present invention can be composed of amino acids joined to each other by peptide bonds or modified peptide bonds, i.e., peptide isosteres, and may contain amino acids other than the 20 gene-encoded amino acids. The polypeptides may be modified by either natural processes, such as posttranslational processing, or by chemical modification techniques which are well known in the art. Such modifications are well described in basic texts and in more detailed monographs, as well as in a voluminous research literature. Modifications can occur anywhere in a polypeptide, including the peptide backbone, the amino acid side-chains and the amino or carboxyl termini. It will be appreciated that the same type of modification may be present in the same or varying degrees at several sites in a given polypeptide. Also, a given polypeptide may contain many types of modifications. Polypeptides may be branched, for example, as a result of ubiquitination, and they may be cyclic, with or without branching. Cyclic, branched, and branched cyclic polypeptides may result from posttranslation natural processes or may be made by synthetic methods. Modifications include acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cysteine, formation of pyroglutamate, formylation, gamma-carboxylation, glycosylation, GPI anchor formation, hydroxylation, iodination, methylation, myristoylation, oxidation, pegylation, proteolytic processing, phosphorylation, prenylation, racemization, selenoylation, sulfation, transfer-RNA mediated addition of amino acids to proteins such as arginylation, and ubiquitination. (See, for instance, PROTEINS—STRUCTURE AND MOLECULAR PROPERTIES, 2nd Ed., T. E. Creighton, W. H. Freeman and Company, New York (1993); POSTTRANSLATIONAL COVALENT MODIFICATION OF PROTEINS, B. C. Johnson, Ed., Academic Press, New York, pgs. 1-12 (1983); Seifter et al., Meth Enzymol 182:626-646 (1990); Rattan et al., Ann NY Acad Sci 663:48-62 (1992).)

"SEQ ID NO:X" refers to a polynucleotide sequence while "SEQ ID NO:Y" refers to a polypeptide sequence, both sequences identified by an integer specified in Table 1.

"A polypeptide having biological activity" refers to polypeptides exhibiting activity similar, but not necessarily identical to, an activity of a polypeptide of the present invention, including mature forms, as measured in a particular biological assay, with or without dose dependency. In the case where dose dependency does exist, it need not be identical to that of the polypeptide, but rather substantially similar to the dose-dependence in a given activity as compared to the polypeptide of the present invention (i.e., the candidate polypeptide will exhibit greater activity or not more than about 25-fold less and, preferably, not more than about tenfold less activity, and most preferably, not more than about three-fold less activity relative to the polypeptide of the present invention.)

Polynucleotides and Polypeptides of the Invention

Features of Protein Encoded by Gene No: 1

In specific embodiments, polypeptides of the invention comprise, or alternatively consist of, the following amino acid sequence: WAGTQEPTGLPSTLSRSESWDH (SEQ ID NO: 225). Moreover, fragments and variants of these polypeptides (such as, for example, fragments as described herein, polypeptides at least 80%, 85%, 90%, 95%, 96%, 97%, 98%, 99%, or 100% identical to these polypeptides, or polypeptides encoded by a polynucleotide which hybridizes, under stringent conditions, to the polynucleotide encoding these polypeptides) are encompassed by the invention. Antibodies that bind polypeptides of the invention and polynucleotides encoding these polypeptides are also encompassed by the invention.

The translation product of this gene shares sequence homology with tag-7 which is thought to be important in tumor metastasis and is itself a secretory protein (see, Kiselev S L, et al., J Biol Chem. 273:18633 (1998) and Genetika. 1996 May; 32(5): 621-628. (Russian)), and a family of peptidoglycan recognition proteins involved in the innate immune response to peptidoglycan in species as diverse as insects and humans (see, Kang, D. et. al., PNAS 95:10078 (1998)).

This gene is expressed primarily in keratinocytes.

Polynucleotides and polypeptides of the invention would be useful as reagents for differential identification of the tissue(s) or cell type(s) present in a biological sample and for diagnosis of diseases and conditions which include, but are not limited to, dermatological disorders, especially skin cancers such as melanoma. Similarly, polypeptides and antibodies directed to these polypeptides would be useful in providing immunological probes for differential identification of the tissue(s) or cell type(s). For a number of disorders of the above tissues or cells, particularly of the integumentary system, expression of this gene at significantly higher or lower levels may be routinely detected in certain tissues or cell types (e.g., skin, cancerous and wounded tissues) or bodily fluids (e.g., sweat, lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder. Preferred polypeptides of the present invention comprise, or alternatively consist of one, two, or all three of the immunogenic epitopes shown in SEQ ID NO: 118 as residues: Ser-25 to Ala-31, Gln-146 to Ser-151, His-231 to Asn-236. Polynucleotides encoding said polypeptides are encompassed by the invention, as are antibodies that bind one or more of these peptides.

The tissue distribution in keratinocytes and homology to tag-7 indicates that polynucleotides and polypeptides corresponding to this gene would be useful for detection, treatment, and/or prevention of dermatological disorders, especially skin cancers like melanoma, and integumentary tumors (e.g., keratoses, Bowen's disease, basal cell carcinoma, squamous cell carcinoma, malignant melanoma, Paget's disease, mycosis fungoides, and Kaposi's sarcoma). Tag-7 was discovered when gene expression was compared in a metastatic (VMR-Liv) neoplastic cell line and a related nonmetastatic (VMR-O) neoplastic cell line by means of the differential display method. A fragment of cDNA corresponding to the tag-7 gene, differentially expressed in the metastatic cell line, was isolated. The full-length tag-7 cDNA was gened and its nucleotide sequence was determined. The gene sequence claimed in this patent application has significant homology to tag-7 and on that basis is expected to share significant biological activities with tag-7. Such activities can be assayed as set forth herein and by assays known in the art. Additionally, the homology to a conserved peptidoglycan recognition protein family involved in innate immunity, indicates that polynucleotides and polypeptides corresponding to this gene would be useful for the treatment, diagnosis, and/or prevention of various skin disorders including congenital disorders (e.g., nevi, moles, freckles, Mongolian spots, hemangiomas, port-wine syndrome), injuries and inflammation of the skin (e.g., wounds, rashes, prickly heat disorder, psoriasis, dermatitis), atherosclerosis, uticaria, eczema, photosensitivity, autoimmune disorders (e.g., lupus erythematosus, vitiligo, dermatomyositis, morphea, scleroderma, pemphigoid, and pemphigus), keloids, striae, erythema, petechiae, purpura, and xanthelasma. Moreover, such disorders may predispose increased susceptibility to viral and bacterial infections of the skin (e.g., cold sores, warts, chickenpox, molluscum contagiosum, herpes zoster, boils, cellulitis, erysipelas, impetigo, tinea, althlete's foot, and ringworm). Furthermore, the protein may also be used to determine biological activity, to raise antibodies, as tissue markers, to isolate cognate ligands or receptors, to identify agents that modulate their interactions, in addition to its use as a nutritional supplement. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:11 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a-b, where a is any integer between 1 to 1177 of SEQ ID NO:11, b is an integer of 15 to 1191, where both a and b correspond to the positions of nucleotide residues shown in SEQ ID NO:11, and where b is greater than or equal to a +14.

Features of Protein Encoded by Gene No: 2

The translation product of this gene shares weak sequence homology with FGF Receptor Ligand-2 which is thought to be important in activating FGF receptor in mediating cell proliferative functions.

In specific embodiments, polypeptides of the invention comprise, or alternatively consist of, an amino acid sequence selected from the group: EIIHNLPTSRMAARTKKKNDIINIKVPADCNTRMSYYYKGSGKRGEMESWLV MSS- WSILDFEFLEARPQLFNLVYTEHSTYSG-RHYTRERGGFMVFKNSYSQLLL KRKDSLCAFIQPMALNIIHVPMSSKCIF-PAQSGPSTFRSLWWCPHPISKCQLGL YSSQIRDIPYLA (SEQ ID NO: 226), EIIHNLPTSRMAARTKKKNDIINI-KVPADCNTRMS (SEQ ID NO: 227), YYYKGSGKRGE-MESWLVMSSWSILDFEFLEARPQLF (SEQ ID NO: 228), NLVYTEHSTYSGRHYTRERGGFMVFKN-SYSQLLLKR (SEQ ID NO: 229), KDSLCAFIQPMALNII-HVPMSSKCIFPAQSGPSTF (SEQ ID NO: 230), and/or RSLWWCPHPISKCQLGLYSSQIRDIPYLA (SEQ ID NO: 231). Moreover, fragments and variants of these polypeptides (such as, for example, fragments as described herein, polypeptides at least 80%, 85%, 90%, 95%, 96%, 97%, 98%, 99%, or 100% identical to these polypeptides, or polypeptides encoded by a polynucleotide which hybridizes, under stringent conditions, to the polynucleotide encoding these polypeptides) are encompassed by the invention. Antibodies that bind polypeptides of the invention and polynucleotides encoding these polypeptides are also encompassed by the invention. This gene is expressed primarily in neutrophils.

Polynucleotides and polypeptides of the invention would be useful as reagents for differential identification of the tissue(s) or cell type(s) present in a biological sample and for diagnosis of diseases and conditions which include, but are not limited to, abnormal immune reactions or disorders. Similarly, polypeptides and antibodies directed to these polypeptides would be useful in providing immunological probes for differential identification of the tissue(s) or cell type(s). For a number of disorders of the above tissues or cells, particularly of the immune system tissue and connective tissues, expression of this gene at significantly higher or lower levels may be routinely detected in certain tissues or cell types (e.g., immune, cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder. Preferred polypeptides of the present invention comprise, or alternatively consist of the immunogenic epitopes shown in SEQ ID NO: 119 as residues: Met-1 to Met-6. Polynucleotides encoding said polypeptides are encompassed by the invention, as are antibodies that bind one or more of these peptides.

The tissue distribution and homology to FGF Receptor Ligand-2 indicates that polynucleotides and polypeptides corresponding to this gene would be useful for detection, treatment, and/or prevention of immune disorders, especially those that are mediated by neutrophil functions. They can be utilized in the treatment of neural and immune disorders, or to stimulate proliferation of vertebrate cells, raise antibodies, and to screen for antagonists useful for inhibiting tumor growth. Moreover, the expression of this gene product indicates a role in regulating the proliferation, survival, differentiation, and/or activation of hematopoietic cell lineages, including blood stem cells. This gene product may be involved in the regulation of cytokine production, antigen presentation, or other processes that may also suggest a usefulness in the treatment of cancer (e.g., by boosting immune responses). Representative uses are described in the “Immune Activity” and “Infectious Disease” sections below, in Example 11, 13, 14, 16, 18, 19, 20, and 27, and elsewhere herein. Since the gene is expressed in cells of lymphoid origin, the natural gene product may be involved in immune functions. Therefore it may be also used as an agent for immunological disorders including arthritis, asthma, immunodeficiency diseases such as AIDS, leukemia, rheumatoid arthritis, granulomatous disease, inflammatory bowel disease, sepsis, acne, neutropenia, neutrophilia, psoriasis, hypersensitivities, such as T-cell mediated cytotoxicity; immune reactions to transplanted organs and tissues, such as host-versus-graft and graft-versus-host diseases, or autoimmunity disorders, such as autoimmune infertility, lense tissue injury, demyelination, systemic lupus erythematosis, drug induced hemolytic anemia, rheumatoid arthritis, Sjogren’s disease, scleroderma and tissues. In addition, this gene product may have commercial utility in the expansion of stem cells and committed progenitors of various blood lineages, and in the differentiation and/or proliferation of various cell types. Furthermore, the protein may also be used to determine biological activity, raise antibodies, as tissue markers, to isolate cognate ligands or receptors, to identify agents that modulate their interactions, in addition to its use as a nutritional supplement. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:12 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a-b, where a is any integer between 1 to 1237 of SEQ ID NO:12, b is an integer of 15 to 1251, where both a and b correspond to the positions of nucleotide residues shown in SEQ ID NO:12, and where b is greater than or equal to a +14.

Features of Protein Encoded by Gene No: 3

The translation product of this gene shares sequence homology with glycosyl transferase, which is thought to be important in glycosylation of proteins (see, e.g., Genbank Accession No. g2996578). Based on the sequence similarity, the translation product of this clone is expected to share at least some biological activities with glycosyltransferase proteins. Such activities are known in the art.

The polypeptide of this gene has been determined to have transmembrane domains at about amino acid positions 238-254, 338-354, 143-159, 13-29, 429-445, 384-400, 489-505, 462-478, 102-118, and 189-205 of the amino acid sequence referenced in Table 1 for this gene. Based upon these characteristics, it is believed that the protein product of this gene shares structural features to type IIIa membrane proteins.

The gene encoding the disclosed cDNA is believed to reside on chromosome 11. Accordingly, polynucleotides related to this invention would be useful as a marker in linkage analysis for chromosome 11.

In specific embodiments, polypeptides of the invention comprise, or alternatively consist of, an amino acid sequence selected from the group: EACGAAAMAALTIATGTGN-WFSALALGVTLLKCLLIPTYHSTDFEVHRNWL AITH-SLPISQWYYEATSEWTLDYPPFFAWFEY-ILSHVAKYFDQEMLNVHNLN YSSSRTLLFQRFSVIFMDVLFVYAVREC-CKCIDGKKVGKELTEKPKFILSVLLL WNFGLLIVDHI-HFQYNGFLFGLMLLSIARLFQKRHMEGA-FLFAVLLHFKHIYL YVAPAYGVYLLRSYCFTANKPDGSIR-WKSFSFVRVISLGLVVFLVSALSLGPF LALNQLPQVF-SRLFPFKRGLCHAYWAPNFWALYNALD-KVLSVIGLKLKFLDP NNIPKASMTSGLVQQFQHTVLPSVT-PLATLICTLIAILPSIFCLWFKPQGPRGFL RCLTL-CALSSFMFGWHVHEKAILLAILPMSLLS-VGKAGDASIFLILTTTGHYSL FPLLFTAPELPIKILLMLLFTIYSISS-LKTLFRKEKPLFNWMETFYLLXLGPLEVC CEFVF-PFTSW KVKYPFIPLLLTSVYCAVGITYAWFKLY-VSVLIDSAIGKTKKQ (SEQ ID NO: 232). Moreover, fragments and variants of these polypeptides (such as, for example, fragments as described herein, polypeptides at least 80%, 85%, 90%, 95%, 96%, 97%, 98%, 99%, or 100% identical to these polypeptides, or polypeptides encoded by a polynucleotide which hybridizes, under stringent conditions, to the polynucleotide encoding these polypeptides) are encompassed by the invention. Antibodies that bind polypeptides of the invention and polynucleotides encoding these polypeptides are also encompassed by the invention.

This gene is expressed primarily in osteoclastoma cells, B-cells, macrophage, tonsils, ovarian cancer tissue, melanocytes, haemopoietic cells and colon tissue, and, to a lesser extent, in several other tissues and organs.

Polynucleotides and polypeptides of the invention would be useful as reagents for differential identification of the tissue(s) or cell type(s) present in a biological sample and for diagnosis of diseases and conditions which include, but are not limited to, disorders of the skin, blood, skeletal system and cancer. Similarly, polypeptides and antibodies directed to these polypeptides would be useful in providing immunological probes for differential identification of the tissue(s) or cell type(s). For a number of disorders of the above tissues or cells, particularly of the haemopoietic system, epithelium and skeletal system, expression of this gene at significantly higher or lower levels may be routinely detected in certain tissues or cell types (e.g., immune, musculo-skeletal, cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder. Preferred polypeptides of the present invention comprise, or alternatively consist of one, two, three, four or all five of the immunogenic epitopes shown in SEQ ID NO: 120 as residues: Glu-136 to Pro-141, Ala-221 to Ser-227, Asp-307 to Pro-312, Lys-355 to Gly-361, Phe-449 to Pro-454. Polynucleotides encoding said polypeptides are encompassed by the invention, as are antibodies that bind one or more of these peptides.

The tissue distribution in musculo-skeletal and immune tissues, and the homology to glycosyl transferase protein, indicates that polynucleotides and polypeptides corresponding to this gene would be useful for the treatment, prevention, detection and/or diagnosis of disorders of the haemopoietic, skeletal and epithelial systems, and cancers thereof, as well as disorders associated with incorrect post-translational modification of proteins (i.e. glycosylation). The tissue distribution in immune cells (e.g., B-cells and macrophage) indicates polynucleotides and polypeptides corresponding to this gene would be useful for the diagnosis detection, prevention and/or treatment of a variety of immune system disorders. Representative uses are described in the "Immune Activity" and "Infectious Disease" sections below, in Example 11, 13, 14, 16, 18, 19, 20, and 27, and elsewhere herein. Briefly, the expression indicates a role in regulating the proliferation; survival; differentiation; and/or activation of hematopoietic cell lineages, including blood stem cells. Involvement in the regulation of cytokine production, antigen presentation, or other processes indicates a usefulness for treatment of cancer (e.g. by boosting immune responses). Expression in cells of lymphoid origin, indicates the natural gene product would be involved in immune functions. Therefore it would also be useful as an agent for immunological disorders including arthritis, asthma, immunodeficiency diseases such as AIDS, leukemia, rheumatoid arthritis, granulomatous disease, inflammatory bowel disease, sepsis, acne, neutropenia, neutrophilia, psoriasis, hypersensitivities, such as T-cell mediated cytotoxicity; immune reactions to transplanted organs and tissues, such as host-versus-graft and graft-versus-host diseases, or autoimmunity disorders, such as autoimmune infertility, lense tissue injury, demyelination, systemic lupus erythematosis, drug induced hemolytic anemia, rheumatoid arthritis, Sjogren's disease, and scleroderma. Moreover, the protein may represent a secreted factor that influences the differentiation or behavior of other blood cells, or that recruits hematopoietic cells to sites of injury. Thus, this gene product is thought to be useful in the expansion of stem cells and committed progenitors of various blood lineages, and in the differentiation and/or proliferation of various cell types. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:13 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a-b, where a is any integer between 1 to 1720 of SEQ ID NO:13, b is an integer of 15 to 1734, where both a and b correspond to the positions of nucleotide residues shown in SEQ ID NO:13, and where b is greater than or equal to a +14.

Features of Protein Encoded by Gene No: 4

The translation product of this gene shares sequence homology with human pleckstrin protein which is thought to be important in platelet formation or activity (see, e.g., Genbank Accession No. g35518 and Tyers, M., et al., Nature 333 (6172), 470-473 (1988); all references available through this accession are hereby incorporated herein by reference). Therefore, it is likely that this gene also has activity in platelets.

This gene is expressed primarily in keratinocytes, and, to a lesser extent, in spleen and bone marrow.

Polynucleotides and polypeptides of the invention would be useful as reagents for differential identification of the tissue(s) or cell type(s) present in a biological sample and for diagnosis of the following diseases and conditions which include, but are not limited to, immune and clotting disorders. Similarly, polypeptides and antibodies directed to these polypeptides would be useful in providing immunological probes for differential identification of the tissue(s) or cell type(s). For a number of disorders of the above tissues or cells, particularly of the immune and blood clotting systems, expression of this gene at significantly higher or lower levels may be routinely detected in certain tissues or cell types (e.g., immune, blood clotting, cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder. Preferred polypeptides of the present invention comprise, or alternatively consist of one or both of the immunogenic epitopes shown in SEQ ID NO: 121 as residues: Leu-38 to Gly-49, Lys-75 to Thr-80. Polynucleotides encoding said polypeptides are encompassed by the invention, as are antibodies that bind one or more of these peptides.

The tissue distribution in keratinocytes, spleen and bone marrow, and the homology to pleckstrin indicates that polynucleotides and polypeptides corresponding to this gene would be useful for the study, diagnosis, detection, prevention and/or treatment of immune system and clotting disorders. Furthermore, since this protein is 50% identical to the Pleckstrin protein, it is an excellent candidate for a protein kinase C substrate. Identification of this protein as a target of protein kinase C, and the exploration of its role in protein kinase C mediated responses, such as inflammation, may lead to a better understanding of the inflammatory response. Furthermore, the protein may also be used to determine biological activity, to raise antibodies, as tissue markers, to isolate cognate ligands or receptors, to identify agents that modulate their interactions, in addition to its use as a nutritional supplement. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:14 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a-b, where a is any integer between 1 to 1526 of SEQ ID NO:14, b is an integer of 15 to 1540, where both a and b correspond to the positions of nucleotide residues shown in SEQ ID NO:14, and where b is greater than or equal to a +14.

Features of Protein Encoded by Gene No: 5

The gene encoding the disclosed cDNA is thought to reside on chromosome 17. Accordingly, polynucleotides related to this invention would be useful as a marker in linkage analysis for chromosome 17.

This gene is expressed primarily in infant liver/spleen tissues, T cells, bone marrow stromal cells, and thymus tissue, and, to a lesser extent, in brain and tonsils tissues.

Polynucleotides and polypeptides of the invention would be useful as reagents for differential identification of the tissue(s) or cell type(s) present in a biological sample and for diagnosis of diseases and conditions which include, but are not limited to, various immune system disorders and/or diseases. Similarly, polypeptides and antibodies directed to these polypeptides would be useful in providing immunological probes for differential identification of the tissue(s) or cell type(s). For a number of disorders of the above tissues or cells, particularly of the immune system, expression of this gene at significantly higher or lower levels may be routinely detected in certain tissues or cell types (e.g., immune, cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder. Preferred polypeptides of the present invention comprise, or alternatively consist of the immunogenic epitopes shown in SEQ ID NO: 122 as residues: Ser-46 to Arg-54. Polynucleotides encoding said polypeptides are encompassed by the invention, as are antibodies that bind one or more of these peptides.

The tissue distribution in liver/spleen tissues, T-cells, bone marrow stromal cells, and thymus tissue indicates that polynucleotides and polypeptides corresponding to this gene would be useful for the diagnosis, detection, prevention and/or treatment of a variety of cancers, most notably cancers of the immune system. Representative uses are described in the Immune Activity and Infectious Disease sections below, in Example 11, 13, 14, 16, 18, 19, 20, and 27, and elsewhere herein. Briefly, the expression of this gene product in a variety of cells of the immune system indicates that polynucleotides and polypeptides corresponding to this gene may be players in the progression of these diseases, and may be a beneficial target for inhibitors as therapeutics. Furthermore, the tissue distribution indicates that polynucleotides and polypeptides corresponding to this gene would be useful for the treatment and/or diagnosis of hematopoietic related disorders such as anemia, pancytopenia, leukopenia, thrombocytopenia or leukemia, since stromal cells are important in the production of cells of hematopoietic lineages. The uses include bone marrow cell ex vivo culture, bone marrow transplantation, bone marrow reconstitution, radiotherapy or chemotherapy of neoplasia. The gene product may also be involved in lymphopoiesis, therefore, it can be used in immune disorders such as infection, inflammation, allergy, immunodeficiency etc. In addition, this gene product may have commercial utility in the expansion of stem cells and committed progenitors of various blood lineages, and in the differentiation and/or proliferation of various cell types. Furthermore, the protein may also be used to determine biological activity, to raise antibodies, as tissue markers, to isolate cognate ligands or receptors, to identify agents that modulate their interactions, in addition to its use as a nutritional supplement. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:15 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a-b, where a is any integer between 1 to 1544 of SEQ ID NO:15, b is an integer of 15 to 1558, where both a and b correspond to the positions of nucleotide residues shown in SEQ ID NO:15, and where b is greater than or equal to a +14.

Features of Protein Encoded by Gene No: 6

The translation product of this gene shares sequence homology with angiopoietin-2, an anti-angiogenic factor. See, for example, Maisonpierre, et al., Angiopoietin-2, a natural antagonist for Tie2 that disrupts in vivo angiogenesis. Science. (1997) 277(5322): 55-60, incorporated herein by reference in its entirety. Based on the sequence similarity, the translation product of this gene is expected to share certain biological activities with Angiopoietin-2 as may be assessed by assays known in the art and described herein.

In specific embodiments, polypeptides of the invention comprise, or alternatively consist of, an amino acid sequence selected from the group: MFTIKLLLFIVPLVISS-RIDQDNSSFDSLSPEPKSRFAMLD-DVKILANGLLQLGH GLKDFVHKTKGQIN-DIFQKLNIFDQSFYDLSLQTSEIKEEEKELRRTTYKLQVK NEEVKNMSLELNSKLE-SLLEEKILLQQKVKYLEEQLTNLIQNQPETPEHPEVTS LKTFVEKQDNSIKDLLQTVEDQYKQLN-QQHSQIKEIENQLRRTSIQEPTEISLSS KPRAPRTTP-FLQLNEIRNVKHDGIPAECTTIYNRGE-HTSGMYAIRPSNSQVFHV YCDVISGSPWTLIQHRIDGSQNFNET-WENYKYGFGRLDGEFWLGLEKIYSIVK QSNYVLRI-ELEDWKDNKHYIEYSFYLGNHETNY-TLHLVAITGNVPNAIPENK DLVFSTWDHKAKGHFNCPEGYSGGWWWH-DECGENNLNGKYNKPRAKSKP ERRRGLSWKSQN-GRLYSIKSTKMLIHPTDSESFE (SEQ ID NO: 233), MFT-IKLLLFIVPLVISSRIDQDNSSFDSLSPEPKSRF (SEQ ID NO: 234), AMLDDVKILANGLLQLGHGLKDFVHKT-KGQINDI (SEQ ID NO: 235), FQKLNIFDQSFYDLSLQT-SEIKEEEKELRRTTYKL (SEQ ID NO: 236), QVKNEEVKNMSLELNSKLESLLEEKILLQQKVKYLE (SEQ ID NO: 237), EQLTNLIQNQPETPEHPEVTSLKT-FVEKQDNSIKDL (SEQ ID NO: 238), LQTVEDQYKQL-NQQHSQIKEIENQLRRTSIQEPTE (SEQ ID NO: 239), ISLSSKPRAPRTTPFLQLNEIRNVKHDGIPAECTT (SEQ ID NO: 240), IYNRGEHTSGMYAIRPSNSQVFHVYCD-VISGSPWTL (SEQ ID NO: 241), IQHRIDGSQNFNET-WENYKYGFGRLDGEFWLGLEKI (SEQ ID NO: 242), YSIVKQSNYVLRIELEDWKDNKHYIEYSFYLGNHE (SEQ ID NO: 243), TNYTLHLVAITGNVPNAIPEN-KDLVFSTWDHKAKG (SEQ ID NO: 244), HFNCP-EGYSGGWWWHDECGENNLNGKYNKPRAKSKP (SEQ ID NO: 245), and/or ERRRGLSWKSQNGRLYSIK-STKMLIHPTDSESFE (SEQ ID NO: 246). Moreover, fragments and variants of these polypeptides (such as, for example, fragments as described herein, polypeptides at least 80%, 85%, 90%, 95%, 96%, 97%, 98%, 99%, or 100% identical to these polypeptides, or polypeptides encoded by a polynucleotide which hybridizes, under stringent conditions, to the polynucleotide encoding these polypeptides) are encompassed by the invention. Antibodies that bind polypeptides of the invention and polynucleotides encoding these polypeptides are also encompassed by the invention.

The gene encoding the disclosed cDNA is believed to reside on chromosome 1. Accordingly, polynucleotides related to this invention would be useful as a marker in linkage analysis for chromosome 1.

This gene is expressed primarily in liver.

Polynucleotides and polypeptides of the invention would be useful as reagents for differential identification of the tissue(s) or cell type(s) present in a biological sample and for diagnosis of diseases and conditions which include, but are not limited to, angiogenesis and neovascularisation associated with tumour development. Similarly, polypeptides and antibodies directed to these polypeptides would be useful in providing immunological probes for differential identification of the tissue(s) or cell type(s). For a number of disorders of the above tissues or cells, particularly of the vascular system, expression of this gene at significantly higher or lower levels may be routinely detected in certain tissues or cell types (e.g., vascular, liver, cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder. Preferred polypeptides of the present invention comprise, or alternatively consist of one, two, three or all four of the immunogenic epitopes shown in SEQ ID NO: 123 as residues: Arg-18 to Asp-27, Leu-29 to Arg-36, Ser-90 to Tyr-104, Val-108 to Lys-114. Polynucleotides encoding said polypeptides are encompassed by the invention, as are antibodies that bind one or more of these peptides.

The tissue distribution primarily in liver and homology to angiopoietin-2 indicates that polynucleotides and polypeptides corresponding to this gene would be useful for the treatment, prevention, diagnosis and/or detection of disorders associated with angiogenesis including the inhibition of angiogenesis and neovascularisation associated with tumour development; the promotion of neovascularisation and wound healing; the treatment of ischaemia; thromboembolytic disease; atherosclerosis; inflammation; and diabetes. Moreover, polynucleotides and polypeptides corresponding to this gene may be useful for treating disorders and/or disease states that include, but are not limited to, solid tumors, blood born tumors such as leukemias, tumor metastasis, Kaposi's sarcoma, benign tumors, for example hemangiomas, acoustic neuromas, neurofibromas, trachomas, and pyogenic granulomas, rheumatoid arthritis, psoriasis, ocular angiogenic diseases, for example, diabetic retinopathy, retinopathy of prematurity, macular degeneration, corneal graft rejection, neovascular glaucoma, retrolental fibroplasia, rubeosis, retinoblastoma, and uvietis, delayed wound healing, endometriosis, vascluogenesis, granulations, hypertrophic scars (keloids), nonunion fractures, scleroderma, trachoma, vascular adhesions, myocardial angiogenesis, coronary collaterals, cerebral collaterals, arteriovenous malformations, ischemic limb angiogenesis, Osler-Webber Syndrome, plaque neovascularization, telangiectasia, hemophiliac joints, angiofibroma fibromuscular dysplasia, wound granulation, Crohn's disease, atherosclerosis, birth control agent by preventing vascularization required for embryo implantation controlling menstruation, diseases that have angiogenesis as a pathologic consequence such as cat scratch disease (*Rochele minalia quintosa*), ulcers (*Helicobacter pylori*), Bartonellosis and bacillary angiomatosis. Furthermore, the protein may also be used to determine biological activity, to raise antibodies, as tissue markers, to isolate cognate ligands or receptors, to identify agents that modulate their interactions, in addition to its use as a nutritional supplement. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:16 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a-b, where a is any integer between 1 to 1622 of SEQ ID NO:16, b is an integer of 15 to 1636, where both a and b correspond to the positions of nucleotide residues shown in SEQ ID NO:16, and where b is greater than or equal to a +14.

Features of Protein Encoded by Gene No: 7

In specific embodiments, polypeptides of the invention comprise, or alternatively consist of, the following amino acid sequence: LPPRGPATFGSPGCPPANSPPSAPAT-PEPARAPERV (SEQ ID NO: 247). Moreover, fragments and variants of these polypeptides (such as, for example, fragments as described herein, polypeptides at least 80%, 85%, 90%, 95%, 96%, 97%, 98%, 99%, or 100% identical to these polypeptides, or polypeptides encoded by a polynucleotide which hybridizes, under stringent conditions, to the polynucleotide encoding these polypeptides) are encompassed by the invention. Antibodies that bind polypeptides of the invention and polynucleotides encoding these polypeptides are also encompassed by the invention.

When tested against fibroblast cell lines, supernatants removed from cells containing this gene activated the EGR1 assay. Thus, it is likely that this gene activates fibroblast cells through a signal transduction pathway. Early growth response 1 (EGR1) is a promoter associated with certain genes that induces various tissues and cell types upon activation, leading the cells to undergo differentiation and proliferation. The translation product of this gene shares sequence homology with murine claudin-1 and other murine and human members of the claudin family of integral membrane proteins which are structurally similar and contain four transmembrane domains (see, e.g., Genbank Acc. Nos. gi|3335182 (AF072127) and/or gi|4128015|gn1|PID|e1363658; all references available through these accessions are hereby incorporated in their entirety by reference herein). Three integral membrane proteins, claudin-1, -2, and occludin, are known to be components of tight junction (TJ) strands. FLAG-tagged claudin-1 and -2 protein have been demonstrated using immunofluorescence microscopy to be highly concentrated at cell contact sites as planes through a homophilic interaction. It is believed that claudin-1 and -2 are mainly responsible for TJ strand formation, and occludin is an accessory protein in some function of TJ strands (see, e.g., J. Cell Biol 143:391-401 (1998), which is hereby incorporated by reference herein).

This gene is expressed primarily in wound healing tissues, and various carcinoma tissues, and, to a lesser extent, in some other tissues.

Polynucleotides and polypeptides of the invention would be useful as reagents for differential identification of the tissue(s) or cell type(s) present in a biological sample and for diagnosis of diseases and conditions which include, but are not limited to, tumorigenesis. Similarly, polypeptides and antibodies directed to these polypeptides would be useful in providing immunological probes for differential identification of the tissue(s) or cell type(s). For a number of disorders of the above tissues or cells, particularly of wounded tissues, and cancerous tissues, expression of this gene at significantly higher or lower levels may be routinely detected in certain tissues or cell types (e.g., cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

The tissue distribution in healing wound tissue and various carcinomas indicates that polynucleotides and polypeptides corresponding to this gene would be useful for detection, diagnosis, treatment, and/or prevention of wounds and tumors. Representative uses are described elsewhere herein. Additionally, the homology of the translation product of this gene to claudin-1, a integral membrane protein involved in tight junction formation, and the biological activity of supernatants from cells expressing this gene on fibroblast cells in EGR assays indicate that polynucleotides and polypeptides corresponding to this gene would be useful for the detection, diagnosis, treatment, and/or prevention of cancer and other proliferative disorders. Expression within cellular sources marked by proliferating cells (e.g., healing wound and various carcinomas) and the homology of the translation product of this gene to a family of claudin proteins indicates that this protein may play a role in the regulation of cellular division and tight junction formation. Furthermore, the protein may also be used to determine biological activity, to raise antibodies, as tissue markers, to isolate cognate ligands or receptors, to identify agents that modulate their interactions, in addition to its use as a nutritional supplement. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:17 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a-b, where a is any integer between 1 to 1242 of SEQ ID NO:17, b is an integer of 15 to 1256, where both a and b correspond to the positions of nucleotide residues shown in SEQ ID NO:17, and where b is greater than or equal to a +14.

Features of Protein Encoded by Gene No: 8

The translation product of this gene shares sequence homology with fibulin which is thought to be important in cellular adhesion and extracellular matrix organization.

In specific embodiments, polypeptides of the invention comprise, or alternatively consist of, an amino acid sequence selected from the group: GTRAGVSKYTGGRGVT-WAPSSAAVPRISSATMRMGLTSFSTTGA (SEQ ID NO: 248), WQSGHRLWQLEWPPPPLSADEHPWEG-PLPGTSPSPKFSMPSPVPHGHHRPTL TMTRSWRIFFN-NIAYRSSSANRLFRVIRREHGDPLIEEL-NPGDALEPEGRGTGG VVTDFDGDGMLDLILSHGESMAQPLSV-FRGNQGFNNNWLRVVPRTRFGAFA RGAKVVLYT-KKSGAHLRIIDGGSGYLCEMEPVAHF-GLGKDEASSVEVTWPD GKMVSRNVASGEMNSVLEILYPRD-EDTLQDPAPLECGQGFSQQENGHCMDT NECIQF-PFVCPRDKPVCVNTYGSYRCRTNKKC-SXGLRVPTRMAHTGL (SEQ ID NO: 249), WQSGHRLWQLEWPPPPLSADEHPWEGPLPGTSPSPK (SEQ ID NO: 250), FSMPSPVPHGHHRPTLTMTR-SWRIFFNNIAYRSSS (SEQ ID NO: 251), ANRLFRVIR-REHGDPLIEELNPGDALEPEGRGTGGVV (SEQ ID NO: 252), TDFDGDGMLDLILSHGESMAQPLSV-FRGNQGFNN (SEQ ID NO: 253), NWLRVVPRTRFGA-FARGAKVVLYTKKSGAHLRIID (SEQ ID NO: 254), GGSGYLCEMEPVAHFGLGKDEASS-VEVTWPDGKMVS (SEQ ID NO: 255), RNVASGEMNS-VLEILYPRDEDTLQDPAPLECGQGF (SEQ ID NO: 256), SQQENGHCMDTNECIQFPFVCPRDKPVCVNTYGSYR (SEQ ID NO: 257), and/or CRTNKKCSXGLRVPTR-MAHTGL (SEQ ID NO: 258). Moreover, fragments and variants of these polypeptides (such as, for example, fragments as described herein, polypeptides at least 80%, 85%, 90%, 95%, 96%, 97%, 98%, 99%, or 100% identical to these polypeptides, or polypeptides encoded by a polynucleotide which hybridizes, under stringent conditions, to the polynucleotide encoding these polypeptides) are encompassed by the invention. Antibodies that bind polypeptides of the invention and polynucleotides encoding these polypeptides are also encompassed by the invention.

The gene encoding the disclosed cDNA is believed to reside on chromosome 10. Accordingly, polynucleotides related to this invention would be useful as a marker in linkage analysis for chromosome 10.

This gene is expressed primarily in brain, kidney, Gessler Wilms tumor, and synovial sarcoma.

Polynucleotides and polypeptides of the invention would be useful as reagents for differential identification of the tissue(s) or cell type(s) present in a biological sample and for diagnosis of diseases and conditions which include, but are not limited to, thrombosis, atherosclerosis, neoplasia, schizophrenia, Alzheimer's disease, Parkinson's disease, Huntington's disease, transmissible spongiform encephalopathies (TSE), Creutzfeldt-Jakob disease (CJD), specific brain tumors, aphasia, mania, depression and dementia. Similarly, polypeptides and antibodies directed to these polypeptides would be useful to provide immunological probes for differential identification of the tissue(s) or cell type(s). For a number of disorders of the above tissues or cells, particularly of the central nervous and cardiovascular systems, expression of this gene at significantly higher or lower levels may be routinely detected in certain tissues or cell types (e.g., brain, cancerous and wounded tissues) or bodily fluids (e.g., lymph, serum, plasma, urine, synovial fluid or cerebrospinal fluid) or another tissue or cell sample taken from an individual having such a disorder, relative to the standard gene expression level, i.e., the expression level in healthy tissue or bodily fluid from an individual not having the disorder.

Based on the sequence similarity, the translation product of this clone is expected to share at least some biological activities with fibulin proteins. Such activities are known in the art, some of which are described elsewhere herein. Fibulin itself, can be used to manipulate adhesion of cells to fibronectin, collagen, laminin, and possibly also other proteins. The tissue distribution in brain and the homology to fibulin indicates that polynucleotides and polypeptides corresponding to this gene would be useful for the treatment, prevention, detection and/or diagnosis of developmental, degenerative and/or neoplastic conditions (such as cancer) with mechanisms contingent on the regulation of cellular adhesion and extracellular matrix organization. Thrombosis, atherosclerosis and restenosis may be potential cardiovascular targets for application. In addition, polynucleotides and polypeptides corresponding to this gene would be useful for the detection, treatment, and/or prevention of neurodegenerative disease states, behavioral disorders, or inflammatory conditions. Representative uses are described in the "Regeneration" and "Hyperproliferative Disorders" sections below, in Example 11, 15, and 18, and elsewhere herein. Briefly, the uses include, but are not limited to the detection, treatment, and/or prevention of Alzheimer's Disease, Parkinson's Disease, Huntington's Disease, Tourette Syndrome, meningitis, encephalitis, demyelinating diseases, peripheral neuropathies, neoplasia, trauma, congenital malformations, spinal cord injuries, ischemia and infarction, aneurysms, hemorrhages, schizophrenia, mania, dementia, paranoia, obsessive compulsive disorder, depression, panic disorder, learning disabilities, ALS, psychoses, autism, and altered behaviors, including disorders in feeding, sleep patterns, balance, and perception. In addition, elevated expression of this gene product in regions of the brain indicates it plays a role in normal neural function. Furthermore, the protein may also be used to determine biological activity, to raise antibodies, as tissue markers, to isolate cognate ligands or receptors, to identify agents that modulate their interactions, in addition to its use as a nutritional supplement. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:18 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a-b, where a is any integer between 1 to 1129 of SEQ ID NO:18, b is an integer of 15 to 1143, where both a and b correspond to the positions of nucleotide residues shown in SEQ ID NO:18, and where b is greater than or equal to a +14.

Features of Protein Encoded by Gene No: 9

The translation product of this gene shares sequence homology with carbonic anhydrase VI, which is thought to be important in protein degradation and pH regulation (see, e.g., GenBank Accession No.: BAA78709.1 and Mori K, et al., J Biol Chem. 274:15701-5 (1999); EMBL locus BTCARANVI (accession X96503); and Jiang et al., Biochem. J. 318:291-296 (1996) which are hereby incorporated herein in their entireties, by reference). Based on this homology, it is likely that this gene would have activity similar to carbonic anhydrase.

In specific embodiments, polypeptides of the invention comprise, or alternatively consist of, an amino acid sequence selected from the group: QSPIDIQTD (SEQ ID NO: 259), LHNNGHTVQLSLPSTLYL (SEQ ID NO: 260), YVAAQLHLHWG (SEQ ID NO: 261), AELHIVHYDSD (SEQ ID NO: 262), GQHWTYEGPHGQDHWP (SEQ ID NO: 263), QSPIDIQTDSVTFD (SEQ ID NO: 264), LHNNGHTVQLSLPST (SEQ ID NO: 265), KYVAAQLHLHWG (SEQ ID NO: 266), and/or AEL-HIVHYDSDSY (SEQ ID NO: 267). Moreover, fragments and variants of these polypeptides (such as, for example, fragments as described herein, polypeptides at least 80%, 85%, 90%, 95%, 96%, 97%, 98%, 99%, or 100% identical to these polypeptides, or polypeptides encoded by a polynucleotide which hybridizes, under stringent conditions, to the polynucleotide encoding these polypeptides) are encompassed by the invention. Antibodies that bind polypeptides of the invention and polynucleotides encoding these polypeptides are also encompassed by the invention.

The gene encoding the disclosed cDNA is thought to reside on chromosome 1. Accordingly, polynucleotides related to this invention would be useful as a marker in linkage analysis for chromosome 1.

This gene is expressed primarily in fetal tissues and brain tissue, and, to a lesser extent, in melanocytes, wilms tumor and retinal tissues.

Polynucleotides and polypeptides of the invention would be useful as reagents for differential identification of the tissue(s) or cell type(s) present in a biological sample and for diagnosis of diseases and conditions which include, but are not limited to, glaucoma and alkalosis resulting from disease of the kidney. Similarly, polypeptides and antibodies directed to these polypeptides would be useful in providing immunological probes for differential identification of the tissue(s) or cell type(s). For a number of disorders of the above tissues or cells, particularly of the systems regulating ionic balance and pH in the fluids of the body, expression of this gene at significantly higher or lower levels may be routinely detected in certain tissues or cell types (e.g., metabolic, regulatory, renal, cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder. Preferred polypeptides of the present invention comprise, or alternatively consist of one, two, three, four, five, six or all seven of the immunogenic epitopes shown in SEQ ID NO: 126 as residues: Tyr-24 to His-32, Pro-38 to Ala-44, Pro-66 to Glu-75, His-111 to Gly-116, Tyr-139 to Ser-146, Thr-176 to Ser-181, Lys-239 to Lys-249. Polynucleotides encoding said polypeptides are encompassed by the invention, as are antibodies that bind one or more of these peptides.

The tissue distribution and homology to secreted carbonic anhydrase indicates that polynucleotides and polypeptides corresponding to this gene would be useful for developing drugs that modulate ionic balance in the serum and in the retina, and may be used for treating diseases such as glaucoma or alkalosis secondary to renal disease. Representative uses are described elsewhere herein. Furthermore, this protein may play a role in the regulation of cellular division, and may show utility in the diagnosis, treatment, and/or prevention of developmental diseases and disorders, including cancer, and other proliferative conditions. Representative uses are described in the "Hyperproliferative Disorders" and "Regeneration" sections below and elsewhere herein. Briefly, developmental tissues rely on decisions involving cell differentiation and/or apoptosis in pattern formation. Dysregulation of apoptosis can result in inappropriate suppression of cell death, as occurs in the development of some cancers, or in failure to control the extent of cell death, as is believed to occur in acquired immunodeficiency and certain neurodegenerative disorders, such as spinal muscular atrophy (SMA). Alternatively, this gene product may be involved in the pattern of cellular proliferation that accompanies early embryogenesis. Thus, aberrant expression of this gene product in tissues—particularly adult tissues—may correlate with patterns of abnormal cellular proliferation, such as found in various cancers. Because of potential roles in proliferation and differentiation, polynucleotides and polypeptides corresponding to this gene may have applications in the adult for tissue regeneration and the treatment of cancers. It may also act as a morphogen to control cell and tissue type specification. Therefore, the polynucleotides and polypeptides of the present invention would be useful in treating, detecting, and/or preventing said disorders and conditions, in addition to other types of degenerative conditions. Thus this protein may modulate apoptosis or tissue differentiation and would be useful in the detection, treatment, and/or prevention of degenerative or proliferative conditions and diseases. Polynucleotides and polypeptides corresponding to this gene would be useful in modulating the immune response to aberrant polypeptides, as may exist in proliferating and cancerous cells and tissues. Polynucleotides and polypeptides of the invention can also be used to gain new insight into the regulation of cellular growth and proliferation. Furthermore, the protein may also be used to determine biological activity, to raise antibodies, as tissue markers, to isolate cognate ligands or receptors, to identify agents that modulate their interactions, in addition to its use as a nutritional supplement. Protein, as well as, antibodies directed against the protein may show utility as a tumor marker and/or immunotherapy targets for the above listed tissues. The protein may also be used to determine biological activity, to raise antibodies, as tissue markers, to isolate cognate ligands or receptors, to identify agents that modulate their interactions, in addition to its use as a nutritional supplement. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:19 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a-b, where a is any integer between 1 to 1523 of SEQ ID NO:19, b is an integer of 15 to 1537, where both a and b correspond to the positions of nucleotide residues shown in SEQ ID NO:19, and where b is greater than or equal to a +14.

Features of Protein Encoded by Gene No: 10

The translation product of this gene shares sequence homology with murine CD63/ME491 which is thought to be important in activation of macrophage and platelet population (marker of); CD37 (Genbank Acc. No. gi|29794, all references available through this accession are hereby incorporated in their entirety by reference herein), a human leukocyte marker; and several members of the tetraspanin protein family (see, e.g., Genbank Acc. No. gi|3152703 (AF065389) and gi|2995865 (AF053455), all references available through these accessions are hereby incorporated in their entirety by reference herein), which are expressed in a wide variety of species and regulate cell adhesion, migration, proliferation and differentiation.

This translation product of this gene appears to contain four transmembrane domains starting from about amino acid positions 24 to about 40, from about 98 to about 114, from about position 62 to about 78, from about position 235 to about 251. Further, this polypeptide is likely to be a Type IIIa membrane protein (Ncyt Cexo) as identified using the PSORT analysis tool. The transmembrane 4 superfamily (TM4SF) which has at least 16 members is the second biggest subfamily among CD antigen superfamilies and activation antigens of T-cells. All TM4SF members contain four putative transmembrane domains, two extracellular loops, and two short cytoplasmic tails. They are variously expressed on immature, early, mature, activated lymphocytes, monocytes, macrophages, granulocytes, platelets, eosinophils, basophils, certain leukemic and lymphoma cells, and a variety of other cells and tissues. CD9 cell surface protein is expressed by both hematopoietic and neural cells, and may play a role in intercellular signaling in the immune and nervous system. CD63 is a 53-Kd lysosomal membrane glycoprotein that has been identified as a platelet activation molecule; it plays an important role in cell adhesion of platelets and endothelial cells. Increased mRNA for CD63 antigen was found in atherosclerotic lesions of Watanabe heritable hyperlipidemic rabbits, suggesting a potential role of CD63 in progression of atherosclerosis. CD63 is also a mast cell marker. This gene also shares close homology with C33 antigen (CD82); CD82 was originally identified as the target of several mAbs inhibitory to syncytium formation induced by human T-cell leukemia virus type I (HTLV-I), the etiological agent of adult T-cell leukemia. Therefore, this gene could be a target for the development of a drug for this leukemia. CD81 is the target of an antiproliferative antibody. A diverse group of human cell lines, including hematolymphoid, neuroectodermal, and mesenchymal cells, express the CD81 protein. Many of the lymphoid cell lines, in particular those derived from large cell lymphomas, were susceptible to the antiproliferative effects of the antibody. CD81 may therefore play an important role in the regulation of lymphoma cell growth. CD9, CD20, CD37, CD63, CD81 and CD82 have been implicated in the regulation of cell growth, adhesion, and signal transduction of B, T lymphocytes and some other non-lymphoid cells. They associate with CD2, CD21, CD4, CD8, MHC Class II molecules, integrins, and function as co-receptor for T, B and other lymphoid cells. Some TM4SF are leukocyte antigens, highly expressed in activated leukocytes, lymphocytes, and are highly specific surface markers for lymphoblastic leukemia, lymphoma, melanoma, and neuroblastoma. CD9 has been show to be involved in cell motility and tumor metastasis. These antigen could be a valuable immunogen or target to implement active and passive immunotherapy in patients with cancer. Others have been shown to be involved in inhibition of prostate cancer metastasis.

In specific embodiments, polynucleotides of the invention comprise, or alternatively consist of, the following nucleotide sequence: GGCCGCGCCGCCGCTGCCGCCGC-CGCGCGCGATTCTGCTTCTCAGAAGAT GCACTAT-TATAGATACTCTAACGCCAAGGTCAGCTGCTGGTA AAGTACC TCCTTTTCAGCTACAACATCATCTTCT-GATTGGCTGGAGTTGTCTTCCTTGG AGTCGGGCT-GTGGGCATGGAGCGAAAAGGGTGTGCT-GTCCGACCTCACCA AAGTGACCCGGATGCATGGAATCGAC-CCTGTGGTGCTGGTCCTGATGGTG GGCGTGGTGAT-GTTCACCCTGGGGTTCGCCGGCT-GCGTGGGGGCTCTGCG GGAGAATATCTGCTTGCT-CAACTTTTTCTGTGGCACCATCGTGCTCATCTT CTTCCTGGAGCTGGCTGTGGCCGTGCTG-GCCTTCCTGTTCCAGGACTGGGT GAGGGACCGGT-TCCGGGAGTTCTTCGAGAGCAACAT-CAAGTCCTACCGGG ACGATATCGATCTGCAAAACCTCATC-GACTCCCTTCAGAAAGCTAACCAG TGCTGTGGCG-CATATGGCCCTGAAAGACTGGGACCTCA-GACGTCTACTTC AATTGCAGCGGTGCCAGCTACAGC-CGAGAGAATGCGGGGTCCCCTTCTCC TGCTGCGT-GCCAGATCCTGCGCAAAAAGTTGTGAA-CACACAGTGTGGATA TGATGTCAGGATTCAGCTGAAGAG-CAAGTGGGATGAGTCCATCTTCACGA AAGGCTG-CATCCAGGCGCTGGAAAGCTGGCTC-CCGCGGAACATTTACATT GTGGCTGGCGTCTTCATCGC-CATCTCGCTGTTGCAGATATTTGGCATCTTC CTG-GCAAGGACGCTGATCTCAGACATCGAG-GCAGTGAAGGCCGGCCATCA CTTCTGAGGAGCAGAGTTGAGGGAGC-CGAGCTGAGCCACGCTGGGAGGC CAGAGC-CTTTCTCTGCCATCAGCCCTACGTCCA-GAGGGAGAGGAGCCGAC ACCCCCAGAGCCAGTGCCCCATCTTAAG-CATCAGCGTGACGTGACCTCTC TGTTTCTGCT-TGCTGGTGCTGAAGACCAAGGGTC-CCCCTTGTTACCTGCCC AAACTTGTGACTGCATCCCTCTGGAGTC-TACCCAGAGACAGAGAATGTGT CTTTATGTGG-GAGTGGTGACTCTGAAAGACA-GAGAGGGCTCCTGTGGCTG CCAGGAGGGCTTGACTCAGACCCCCTG-CAGCTCAAGCATGTCTGCAGGAC ACCTGGTC-CCCCTCTCCCAGTGGCATCCCAAA-CATCTGCTTTGGGTCCATC CCACATCTGTGGGTGGGCCCGTGGGTAA-GAAGGGAACCCCACAGGCGTG GAACAGGGCATC-CTCTCTCCCATCCAAGCAAAGCCAG-CATGGGGGCCTGC CCGTAACGGGAGGCGGACGTGGC-CCCGCTGGGCCTCTGAGTGCCAGCGCA GTCT-GCTGGGACATGCACATATCAGGGGT-TGTTTGCAGGATCCTCAGCCA TGTTCAAGTGAAGTAAGCCTGAGCCAGT-GCGTGGACTGGTGCCACGGGAG TGCCTTGTC-CACTGTCCCCCTGTGTCCACCAGCTAT-TCTCCTGGCGCCGGA ACTGCCTCTGGTCTTGATAGCATTAAGC-CCTGATTGGCCGGTGGCGCGGTG GGCATGGTTCT-TCACTGAGAGCCGGCTCTCCTTTTCT-TAAAGTGTGTAAAT AGTTTATTT (SEQ ID NO:268). In specific embodiments, polypeptides of the invention comprise, or alternatively consist of, the following amino acid sequence: MHYYRYSNAKVSCWYKYLLFSYNIIFW-LAGVVFLGVGLWAWSEKGVLSDL TKVTRMHGID-PVVLVLMVGVVMFTLGFAGCVGALRENI-CLLNFFCGTIVLIFF LELAVAVLAFLFQDWVRDRFREF-FESNIKSYRDDIDLQNLIDSLQKANQCCGA YGPED-WDLNVYFNCSGASYSREKCGVPFSCCVP-DPAQKVVNTQCGYDVRIQ LKSKWDESIFTKGCIQALESWL-PRNIYIVAGVFIAISLLQIFGIFLARTLISDIEAV KAGHHF (SEQ ID NO: 269) Moreover, fragments and variants of these polypeptides (such as, for example, fragments as described herein, polypeptides at least 80%, 85%, 90%, 95%, 96%, 97%, 98%, 99%, or 100% identical to these polypeptides, or polypeptides encoded by a polynucleotide which hybridizes, under stringent conditions, to the polynucleotide encoding these polypeptides) are encompassed by the invention. Antibodies that bind polypeptides of the invention and polynucleotides encoding these polypeptides are also encompassed by the invention.

This gene maps to chromosome 10, and therefore would be useful in linkage analysis as a marker for chromosome 10.

This gene is expressed primarily in infant and human brain and, to a lesser extent, in pancreas islet cell tumor, Wilm's tumor, uterine cancer, and B cell lymphomas.

Polynucleotides and polypeptides of the invention would be useful as reagents for differential identification of the tissue(s) or cell type(s) present in a biological sample and for diagnosis of diseases and conditions: cancers and central nervous system disorders. Similarly, polypeptides and antibodies directed to those polypeptides would be useful to provide immunological probes for differential identification of the tissue(s) or cell type(s). For a number of disorders of the above tissues or cells, particularly of the, immune, metabolic and central nervous system, expression of this gene at significantly higher or lower levels may be detected in certain tissues or cell types (e.g., CNS, cancerous and wounded tissues) or bodily fluids (e.g., lymph, bile, serum, plasma, urine, synovial fluid or spinal fluid) taken from an individual having such a disorder, relative to the standard gene expression level, i.e., the expression level in healthy tissue from an individual not having the disorder. Preferred polypeptides of the present invention comprise, or alternatively consist of the immunogenic epitopes shown in SEQ ID NO: 127 as residues: Met-1 to Ala-9. Polynucleotides encoding said polypeptides are encompassed by the invention, as are antibodies that bind one or more of these peptides.

The tissue distribution in infant and human brain, and various tumors, and homology to murine CD63/ME491, human CD37, and tetraspanins indicates that polynucleotides and/or polypeptides corresponding to this gene would be useful for the study, detection, treatment, and/or prevention of central nervous system diseases and cancers. Moreover, the expression within embryonic tissue and other cellular sources marked by proliferating cells, and its homology indicates that polynucleotides and/or polypeptides of the invention may play a role in the regulation of cellular division, and may show utility in the diagnosis, treatment, and/or prevention of developmental diseases and disorders, cancer, and other proliferative conditions. Representative uses are described in the "Hyperproliferative Disorders" and "Regeneration" sections below and elsewhere herein. Briefly, developmental tissues rely on decisions involving cell differentiation and/or apoptosis in pattern formation. Dysregulation of apoptosis can result in inappropriate suppression of cell death, as occurs in the development of some cancers, or in failure to control the extent of cell death, as is believed to occur in acquired immunodeficiency and certain neurodegenerative disorders, such as spinal muscular atrophy (SMA). Because of potential roles in proliferation and differentiation, this gene product may have applications in the adult for tissue regeneration and the treatment of cancers. It may also act as a morphogen to control cell and tissue type specification. Therefore, the polynucleotides and polypeptides of the present invention would be useful in treating, detecting, and/or preventing said disorders and conditions, in addition to other types of degenerative conditions. Thus this protein may modulate apoptosis or tissue differentiation and would be useful in the detection, treatment, and/or prevention of degenerative or proliferative conditions and diseases. The polynucleotides and/or polypeptides of the invention would be useful in modulating the immune response to aberrant polypeptides, as may exist in proliferating and cancerous cells and tissues. The protein can also be used to gain new insight into the regulation of cellular growth and proliferation. Furthermore, the protein may also be used to determine biological activity, to raise antibodies, as tissue markers, to isolate cognate ligands or receptors, to identify agents that modulate their interactions, in addition to its use as a nutritional supplement. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:20 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a-b, where a is any integer between 1 to 2658 of SEQ ID NO:20, b is an integer of 15 to 2672, where both a and b correspond to the positions of nucleotide residues shown in SEQ ID NO:20, and where b is greater than or equal to a +14.

Features of Protein Encoded by Gene No: 11

In specific embodiments, polypeptides of the invention comprise, or alternatively consist of, an amino acid sequence selected from the group: SQLLPGSVPGWAAHPLRRTVLSPSQHTHNSSHRMKANCEVSASQRLTGRIRH PRGLLQNSPRSRKLWMRLGLRSRYSGTQARSAPAGGHIVDTAEQRQVQARV PWAAAVARQLLRYEKAKASAGTPPAHKPCCHYRCCGYSQAQQKPTASAPQ HLYRPTRPHFRGCRSISV (SEQ ID NO: 279), SGNLGSADGWAYIDVEVRRPWAFVGPGCSRSSGNGSTAYGLVGSPRWLSPF HTGGAVSLPRRPRGPGPVLGVARPCLRCVLRPEHYEPGSHYSGFAGRDASRA FVTGDCSEAGLVDDVSDLSAAEMLTLHNWLSFYEKNYVCVGRVTGRFYGED GLPTPALTQVEAAITRGLEANKLQLQEKQTFPPCNAEWSSARGSRLWCSQKS GGVSRDWIGVPRKLYKPGAKEPRCVCVRTTGPPSGQMPDNPPHRNRGDLDH PNLAEYTGCPPLAITCSFPL (SEQ ID NO: 270), SGNLGSADGWAYIDVEVRRPWAFVGPGCSRSSGNGS (SEQ ID NO: 271), TAYGLVGSPRWLSPFHTGGAVSLPRRPRGPGPVLGV (SEQ ID NO: 272), ARPCLRCVLRPEHYEPGSHYSGFAGRDASRAFVTGD (SEQ ID NO: 273), CSEAGLVDDVSDLSAAEMLTLHNWLSFYEKNYVCVG (SEQ ID NO: 274), RVTGRFYGEDGLPTPALTQVEAAITRGLEANKLQLQ (SEQ ID NO: 275), EKQTFPPCNAEWSSARGSRLWCSQKSGGVSRDWIGV (SEQ ID NO: 276), PRKLYKPGAKEPRCVCVRTTGPPSGQMPD (SEQ ID NO: 277), and/or NPPHRNRGDLDHPNLAEYTGCPPLAITCSFPL (SEQ ID NO: 278). Moreover, fragments and variants of these polypeptides (such as, for example, fragments as described herein, polypeptides at least 80%, 85%, 90%, 95%, 96%, 97%, 98%, 99%, or 100% identical to these polypeptides, or polypeptides encoded by a polynucleotide which hybridizes, under stringent conditions, to the polynucleotide encoding these polypeptides) are encompassed by the invention. Antibodies that bind polypeptides of the invention and polynucleotides encoding these polypeptides are also encompassed by the invention.

The translation product of this gene shares sequence homology to several steroid receptor proteins (see, e.g., Genbank Acc. Nos. g1|PID|e314174, gn1|PID|e1154367 (AJ002030), and/or gn1|PID|e257707); all references available through these accessions are hereby incorporated by reference herein). Based on the sequence similarity, the translation product of this clone is expected to share at least some biological activities with steroid receptor binding proteins. Such activities are known in the art, some of which are described elsewhere herein.

This gene is expressed primarily in brain, fetal tissue, immune cells (e.g., T-cells), breasts and, to a lesser extent, in variety of other tissues and cell types.

Polynucleotides and polypeptides of the invention would be useful as reagents for differential identification of the tissue(s) or cell type(s) present in a biological sample and for diagnosis of diseases and conditions which include, but are not limited to, developmental, degenerative and behavioral diseases of the brain such as schizophrenia, Alzheimer's disease, Parkinson's disease, Huntington's disease, transmissible spongiform encephalopathies (TSE), Creutzfeldt-Jakob disease (CJD), specific brain tumors, aphasia, mania, depression, dementia, paranoia, addictive behavior and sleep disorders. Similarly, polypeptides and antibodies directed to these polypeptides would be useful in providing immunological probes for differential identification of the tissue(s) or cell type(s). For a number of disorders of the above tissues or cells, particularly of the brain, expression of this gene at significantly higher or lower levels may be routinely detected in certain tissues or cell types (e.g., immune, cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder. Preferred polypeptides of the present invention comprise, or alternatively consist of one, two or all three of the immunogenic epitopes shown in SEQ ID NO: 128 as residues: Glu-42 to Pro-53, Ser-67 to Thr-73, Ala-84 to Leu-90. Polynucleotides encoding said polypeptides are encompassed by the invention, as are antibodies that bind one or more of these peptides.

The tissue distribution in brain and the homology to steroid receptor proteins indicates polynucleotides and polypeptides corresponding to this gene would be useful for the detection, treatment, and/or prevention of neurodegenerative disease states, behavioral disorders, or inflammatory conditions. Representative uses are described in the "Regeneration" and "Hyperproliferative Disorders" sections below, in Example 11, 15, and 18, and elsewhere herein. Briefly, the uses include, but are not limited to the detection, treatment, and/or prevention of Alzheimer's Disease, Parkinson's Disease, Huntington's Disease, Tourette Syndrome, meningitis, transmissible spongiform encephalopathy (TSE), Creutzfeldt-Jakob disease (CJD), aphasia, specific brain tumors, encephalitis, demyelinating diseases, peripheral neuropathies, neoplasia, trauma, congenital malformations, spinal cord injuries, ischemia and infarction, aneurysms, hemorrhages, schizophrenia, mania, dementia, paranoia, obsessive compulsive disorder, depression, panic disorder, learning disabilities, ALS, psychoses, autism, and altered behaviors, including disorders in feeding, sleep patterns, balance, and perception. In addition, elevated expression of this gene product in regions of the brain indicates it plays a role in normal neural function. Potentially, this gene product is involved in synapse formation, neurotransmission, learning, cognition, homeostasis, or neuronal differentiation or survival. The tissue distribution in T-cells indicates that polynucleotides and polypeptides corresponding to this gene would be useful for the diagnosis, detection, prevention, and/or treatment of a variety of immune system disorders. Representative uses are described in the "Immune Activity" and "Infectious Disease" sections below, in Example 11, 13, 14, 16, 18, 19, 20, and 27, and elsewhere herein. Briefly, the expression indicates a role in regulating the proliferation; survival; differentiation; and/or activation of hematopoietic cell lineages, including blood stem cells. Involvement in the regulation of cytokine production, antigen presentation, or other processes indicates a usefulness for treatment of cancer (e.g., by boosting immune responses). Expression in cells of lymphoid origin, indicates the natural gene product would be involved in immune functions. Therefore it would also be useful as an agent for immunological disorders including arthritis, asthma, immunodeficiency diseases such as AIDS, leukemia, rheumatoid arthritis, granulomatous disease, inflammatory bowel disease, sepsis, acne, neutropenia, neutrophilia, psoriasis, hypersensitivities, such as T-cell mediated cytotoxicity; immune reactions to transplanted organs and tissues, such as host-versus-graft and graft-versus-host diseases, or autoimmunity disorders, such as autoimmune infertility, lense tissue injury, demyelination, systemic lupus erythematosis, drug induced hemolytic anemia, rheumatoid arthritis, Sjogren's disease, and scleroderma. Moreover, the protein may represent a secreted factor that influences the differentiation or behavior of other blood cells, or that recruits hematopoietic cells to sites of injury. Thus, this gene product is thought to be useful in the expansion of stem cells and committed progenitors of various blood lineages, and in the differentiation and/or proliferation of various cell types. Furthermore, the protein may also be used to determine biological activity, to raise antibodies, as tissue markers, to isolate cognate ligands or receptors, to identify agents that modulate their interactions, in addition to its use as a nutritional supplement. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:21 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a-b, where a is any integer between 1 to 1494 of SEQ ID NO:21, b is an integer of 15 to 1508, where both a and b correspond to the positions of nucleotide residues shown in SEQ ID NO:21, and where b is greater than or equal to a +14.

Features of Protein Encoded by Gene No: 12

The polypeptide of this gene has been determined to have a transmembrane domain at about amino acid position 144-160 of the amino acid sequence referenced in Table 1 for this gene. Moreover, a cytoplasmic tail encompassing amino acids 161-222 of this protein has also been determined. Based upon these characteristics, it is believed that the protein product of this gene shares structural features to type Ia membrane proteins.

This gene is expressed primarily in kidney and gall bladder tissues, fetal tissue, and testes tissue.

Polynucleotides and polypeptides of the invention would be useful as reagents for differential identification of the tissue(s) or cell type(s) present in a biological sample and for diagnosis of diseases and conditions which include, but are not limited to, renal disorders, metabolic diseases, and disorders of the reproductive and developing organs. Similarly, polypeptides and antibodies directed to these polypeptides would be useful in providing immunological probes for differential identification of the tissue(s) or cell type(s). For a number of disorders of the above tissues or cells, particularly of the renal, metabolic, developing, and reproductive systems, expression of this gene at significantly higher or lower levels may be routinely detected in certain tissues or cell types (e.g., renal, metabolic, reproductive, cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder. Preferred polypeptides of the present invention comprise, or alternatively consist of the immunogenic epitopes shown in SEQ ID NO: 129 as residues: Lys-60 to Ala-66. Polynucleotides encoding said polypeptides are encompassed by the invention, as are antibodies that bind one or more of these peptides.

The tissue distribution in kidney and gall bladder tissues, testicular tissue, and fetal tissues, indicates that polynucleotides and polypeptides corresponding to this gene would be useful for treatment, prevention, detection and/or diagnosis of disorders of the renal system, reproductive system, metabolic system and developing systems. Furthermore, the tissue distribution in kidney indicates that polynucleotides and polypeptides corresponding to this gene would be useful in the treatment, prevention, diagnosis and/or detection of kidney diseases including renal failure, nephritus, renal tubular acidosis, proteinuria, pyuria, edema, pyelonephritis, hydronephritis, nephrotic syndrome, crush syndrome, glomerulonephritis, hematuria, renal colic and kidney stones, in addition to Wilm's Tumor Disease, and congenital kidney abnormalities such as horseshoe kidney, polycystic kidney, and Falconi's syndrome. Alternatively, the tissue distribution indicates that polynucleotides and polypeptides corresponding to this gene would be useful for the treatment and diagnosis of conditions concerning proper testicular function (e.g., endocrine function, sperm maturation), as well as cancer. Therefore, this gene product would be useful in the treatment of male infertility and/or impotence. This gene product is also useful in assays designed to identify binding agents, as such agents (antagonists) would be useful as male contraceptive agents. Similarly, the protein is believed to be useful in the treatment and/or diagnosis of testicular cancer. The testes are also a site of active gene expression of transcripts that may be expressed, particularly at low levels, in other tissues of the body. Therefore, this gene product may be expressed in other specific tissues or organs where it may play related functional roles in other processes, such as hematopoiesis, inflammation, bone formation, and kidney function, to name a few possible target indications. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:22 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a-b, where a is any integer between 1 to 1433 of SEQ ID NO:22, b is an integer of 15 to 1447, where both a and b correspond to the positions of nucleotide residues shown in SEQ ID NO:22, and where b is greater than or equal to a +14.

Features of Protein Encoded by Gene No: 13

The translation product of this gene shares weak homology with O-linked GlcNAc transferases (see, e.g., Genbank Acc. No. gi|2266994) which are important for a variety of cellular functions, including, but not limited to, stability of secreted proteins and proper function. Based on the sequence similarity, the translation product of this clone is expected to share at least some biological activities with glycosylation enzyme proteins. Such activities are known in the art, (see, e.g., G Lubas W A, et al., J Biol Chem. 272:9316-24 (1997); all references available through this citation are hereby incorporated herein by reference) and some of which are described elsewhere herein.

In specific embodiments, polypeptides of the invention comprise, or alternatively consist of, an amino acid sequence selected from the group: LLLCPWWLCFDWS (SEQ ID NO: 280), MGCIPLIKSISDWRVIALAALWFCLIGLICQALCSEDGHKRRILTLGLGFLVIPF LPASNLFFRVGFVVAECVLYLPSIGYCVLLTFGFGALSKHTKKKKLIAAVVLG ILFINTLRCVLRTAKWRSEEQLFRSALSVCPLNAKVHYNIGKNLADKGNQTA AIRYYREAVRLNPKYVHAMNNLGNILKERNELQEAEELLSLAVQIQPDFAAA WMNLGIVQNSLKRFETAEQNYRTAIKHRRKYPDCYYNLGRLVRTGCPVPVE GKMGYFS (SEQ ID NO: 281), MGCIPLIKSISDWRVIALAALWFCLIGLICQALCSEDG (SEQ ID NO: 282), HKRRILTLGLGFLVIPFLPASNLFFRVGFVVAECVLYL (SEQ ID NO: 283), PSIGYCVLLTFGFGALSKHTKKKKLIAAVVLGILFINT (SEQ ID NO: 284), LRCVLRTAKWRSEEQLFRSALSVCPLNAKVHYNIGKNL (SEQ ID NO: 285), ADKGNQTAAIRYYREAVRLNPKYVHAMNNLGNILKERN (SEQ ID NO: 286), ELQEAEELLSLAVQIQPDFAAAWMNLGIVQNSLKRFET (SEQ ID NO: 287), and/or AEQNYRTAIKHRRKYPDCYYNLGRLVRTGCPVPVEGKMGYFS (SEQ ID NO: 288). Moreover, fragments and variants of these polypeptides (such as, for example, fragments as described herein, polypeptides at least 80%, 85%, 90%, 95%, 96%, 97%, 98%, 99%, or 100% identical to these polypeptides, or polypeptides encoded by a polynucleotide which hybridizes, under stringent conditions, to the polynucleotide encoding these polypeptides) are encompassed by the invention. Antibodies that bind polypeptides of the invention and polynucleotides encoding these polypeptides are also encompassed by the invention.

The polypeptide encoded by this gene has been determined to have transmembrane domains at about amino acid position 38 to about 54, at about 136 to about 152, at about 161 to about 177, at about 192 to about 208, at about 223 to about 239, at about 243 to about 259, at about 374 to about 390, at about 402 to about 418, at about 432 to about 448, and at about 461 to about 477 of the amino acid sequence referenced in Table 7 for this gene. Based upon these characteristics, it is believed that the protein product of this gene shares structural features to type IIIa membrane proteins.

Included in this invention as preferred domains are Aldo/keto reductase family putative active site signatures, which were identified using the ProSite analysis tool (Swiss Institute of Bioinformatics). The aldo-keto reductase family groups together a number of structurally and functionally related NADPH-dependent oxidoreductases as well as some other proteins. Three consensus patterns specific to this family of proteins were developed. The third pattern, located in the C-terminal, is centered on a lysine residue whose chemical modification, in aldose and aldehyde reductases, affect the catalytic efficiency. The consensus pattern is as follows: [LIVM]-[PAIV]-[KR]-[ST]-x(4)-R-x(2)-[GS-TAEQK]-[NSL]-x(2)-[LIVMFA] [K is a putative active site residue]. In specific embodiments, polypeptides of the invention comprise, or alternatively consist of, the following amino acid sequence: LIKSISDWRVIALAAL (SEQ ID NO: 289). Moreover, fragments and variants of these polypeptides (such as, for example, fragments as described herein, polypeptides at least 80%, 85%, 90%, 95%, 96%, 97%, 98%, 99%, or 100% identical to these polypeptides, or polypeptides encoded by a polynucleotide which hybridizes, under stringent conditions, to the polynucleotide encoding these polypeptides) are encompassed by the invention. Antibodies that bind polypeptides of the invention and polynucleotides encoding these polypeptides are also encompassed by the invention. Further preferred are polypeptides comprising the Aldo/keto reductase family putative active site signature above, and at least 5, 10, 15, 20, 25, 30, 50, or 75 additional contiguous amino acid residues of the amino acid sequence referenced in Table 7 for this gene. The additional contiguous amino acid residues may be N-terminal or C-terminal to the Aldo/keto reductase family putative active site signatures. Alternatively, the additional contiguous amino acid residues may be both N-terminal and C-terminal to the Aldo/keto reductase family putative active site signatures, wherein the total N- and C-terminal contiguous amino acid residues equal the specified number.

FIGS. 1A-G show the nucleotide (SEQ ID NO:23) and deduced amino acid sequence (SEQ ID NO: 130) corresponding to this gene.

FIG. 2 shows an analysis of the amino acid sequence (SEQ ID NO: 130). Alpha, beta, turn and coil regions; hydrophilicity and hydrophobicity; amphipathic regions; flexible regions; antigenic index and surface probability are shown, and all were generated using the default settings of the recited computer algorithyms. In the "Antigenic Index or Jameson-Wolf" graph, the positive peaks indicate locations of the highly antigenic regions of the protein, i.e., regions from which epitope-bearing peptides of the invention can be obtained. Polypeptides comprising, or alternatively consisting of, domains defined by these graphs are contemplated by the present invention, as are polynucleotides encoding these polypeptides.

The data presented in FIG. 2 are also represented in tabular form in Table 3. The columns are labeled with the headings "Res", "Position", and Roman Numerals I-XIV. The column headings refer to the following features of the amino acid sequence presented in FIG. 2, and Table 3: "Res": amino acid residue of SEQ ID NO: 130 and FIGS. 1A-G; "Position": position of the corresponding residue within SEQ ID NO: 130 and FIGS. 1A-G; I: Alpha, Regions—Garnier-Robson; II: Alpha, Regions—Chou-Fasman; III: Beta, Regions—Garnier-Robson; IV: Beta, Regions—Chou-Fasman; V: Turn, Regions—Garnier-Robson; VI: Turn, Regions—Chou-Fasman; VII: Coil, Regions—Garnier-Robson; VIII: Hydrophilicity Plot—Kyte-Doolittle; IX: Hydrophobicity Plot—Hopp-Woods; X: Alpha, Amphipathic Regions—Eisenberg; XI: Beta, Amphipathic Regions—Eisenberg; XII: Flexible Regions—Karplus-Schulz; XIII: Antigenic Index—Jameson-Wolf; and XIV: Surface Probability Plot—Emini.

Preferred embodiments of the invention in this regard include fragments that comprise, or alternatively consisting of, one or more of the following regions: alpha-helix and alpha-helix forming regions ("alpha-regions"), beta-sheet and beta-sheet forming regions ("beta-regions"), turn and turn-forming regions ("turn-regions"), coil and coil-forming regions ("coil-regions"), hydrophilic regions, hydrophobic regions, alpha amphipathic regions, beta amphipathic regions, flexible regions, surface-forming regions and high antigenic index regions. The data representing the structural or functional attributes of the protein set forth in FIG. 2 and/or Table 3, as described above, was generated using the various modules and algorithms of the DNA*STAR set on default parameters. In a preferred embodiment, the data presented in columns VIII, IX, XIII, and XIV of Table 3 can be used to determine regions of the protein which exhibit a high degree of potential for antigenicity. Regions of high antigenicity are determined from the data presented in columns VIII, IX, XIII, and/or XIV by choosing values which represent regions of the polypeptide which are likely to be exposed on the surface of the polypeptide in an environment in which antigen recognition may occur in the process of initiation of an immune response.

Certain preferred regions in these regards are set out in FIG. 2, but may, as shown in Table 3, be represented or identified by using tabular representations of the data presented in FIG. 2. The DNA*STAR computer algorithm used to generate FIG. 2 (set on the original default parameters) was used to present the data in FIG. 2 in a tabular format (See Table 3). The tabular format of the data in FIG. 2 is used to easily determine specific boundaries of a preferred region.

The present invention is further directed to fragments of the polynucleotide sequences described herein. By a fragment of, for example, the polynucleotide sequence of a deposited cDNA or the nucleotide sequence shown in SEQ ID NO:23, is intended polynucleotide fragments at least about 15 nt, and more preferably at least about 20 nt, at least about 25 nt, still more preferably at least about 30 nt, at least about 35 nt, and even more preferably, at least about 40 nt in length, at least about 45 nt in length, at least about 50 nt in length, at least about 60 nt in length, at least about 70 nt in length, at least about 80 nt in length, at least about 90 nt in length, at least about 100 nt in length, at least about 125 nt in length, at least about 150 nt in length, at least about 175 nt in length, which are useful as diagnostic probes and primers as discussed herein. Of course, larger fragments 200-1500 nt in length are also useful according to the present invention, as are fragments corresponding to most, if not all, of the nucleotide sequence of a deposited cDNA or as shown in SEQ ID NO:23. By a fragment at least 20 nt in length, for example, is intended fragments which include 20 or more contiguous bases from the nucleotide sequence of a deposited cDNA or the nucleotide sequence as shown in SEQ ID NO:23. In this context "about" includes the particularly recited size, an sizes larger or smaller by several (5, 4, 3, 2, or 1) nucleotides, at either terminus or at both termini. Representative examples of polynucleotide fragments of the invention include, for example, fragments that comprise, or alternatively, consist of, a sequence from about nucleotide 1 to about 50, from about 51 to about 100, from about 101 to about 150, from about 151 to about 200, from about 201 to about 250, from about 251 to about 300, from about 301 to about 350, from about 351 to about 400, from about 401 to about 450, from about 451 to about 500, and from about 501 to about 550, and from about 551 to about 600, from about 601 to about 650, from about 651 to about 700, from about 701 to about 750, from about 751 to about 800, from about 801 to about 850, from about 851 to about 900, from about 901 to about 950, from about 951 to about 1000, from about 1001 to about 1050, from about 1051 to about 1100, from about 1101 to about 1150 from about 1151 to about 1200, from about 1201 to about 1250, from about 1251 to about 1300, from about 1301 to about 1350, from about 1351 to about 1400, from about 1401 to about 1450, from about 1451 to about 1500, from about 1501 to about 1550, from about 1551 to about 1600, from about 1601 to about 1650, from about 1651 to about 1700, from about 1701 to about 1750, from about 1751 to about 1800, from about 1801 to about 1850, from about 1851 to about 1900, from about 1901 to about 1950, from about 1951 to about 2000, from about 2001 to about 2050, from about 2051 to about 2100, from about 2101 to about 2150 from about 2151 to about 2200, from about 2201 to about 2250, from about 2251 to about 2300, from about 2301 to about 2350, from about 2351 to about 2400, from about 2401 to about 2450, from about 2451 to about 2500, 2501 to about 2550, from about 2551 to about 2600, from about 2601 to about 2650, from about 2651 to about 2700, from about 2701 to about 2750, from about 2751 to about 2800, from about 2801 to about 2850, from about 2851 to about 2900, from about 2901 to about 2950, from about 2951 to about 3000, from about 3001 to about 3050, from about 3051 to about 3100, from about 3101 to about 3150 from about 3151 to about 3200, from about 3201 to about 3250, from about 3251 to about 3300, from about 3301 to about 3350, from about 3351 to about 3400, from about 3401 to about 3450, from about 3451 to about 3500, 3501 to about 3550, from about 3551 to about 3600, from about 3601 to about 3650, from about 3651 to about 3700, from about 3701 to about 3750, from about 3751 to about 3800, from about 3801 to about 3850, and from about 3851 to 3886 of SEQ ID NO:23, or the complementary strand thereto, or the cDNA contained in a deposited clone. In this context "about" includes the particularly recited ranges, and ranges larger or smaller by several (5, 4, 3, 2, or 1) nucleotides, at either terminus or at both termini. In additional embodiments, the polynucleotides of the invention encode functional attributes of the corresponding protein.

Preferred polypeptide fragments of the invention comprise, or alternatively consist of, the secreted protein having a continuous series of deleted residues from the amino or the carboxy terminus, or both. Particularly, N-terminal deletions of the polypeptide can be described by the general formula m-760 where m is an integer from 2 to 755, where m corresponds to the position of the amino acid residue identified in SEQ ID NO:130. More in particular, the invention provides polynucleotides encoding polypeptides comprising, or alternatively consisting of, an amino acid sequence selected from the group: I-2 to V-760; P-3 to V-760; N-4 to V-760; Q-5 to V-760; H-6 to V-760; N-7 to V-760; A-8 to V-760; G-9 to V-760; A-10 to V-760; G-11 to V-760; S-12 to V-760; H-13 to V-760; Q-14 to V-760; P-15 to V-760; A-16 to V-760; V-17 to V-760; F-18 to V-760; R-19 to V-760; M-20 to V-760; A-21 to V-760; V-22 to V-760; L-23 to V-760; D-24 to V-760; T-25 to V-760; D-26 to V-760; L-27 to V-760; D-28 to V-760; H-29 to V-760; I-30 to V-760; L-31 to V-760; P-32 to V-760; S-33 to V-760; S-34 to V-760; V-35 to V-760; L-36 to V-760; P-37 to V-760; P-38 to V-760; F-39 to V-760; W-40 to V-760; A-41 to V-760; K-42 to V-760; L-43 to V-760; V-44 to V-760; V-45 to V-760; G-46 to V-760; S-47 to V-760; V-48 to V-760; A-49 to V-760; I-50 to V-760; V-51 to V-760; C-52 to V-760; F-53 to V-760; A-54 to V-760; R-55 to V-760; S-56 to V-760; Y-57 to V-760; D-58 to V-760; G-59 to V-760; D-60 to V-760; F-61 to V-760; V-62 to V-760; F-63 to V-760; D-64 to V-760; D-65 to V-760; S-66 to V-760; E-67 to V-760; A-68 to V-760; I-69 to V-760; V-70 to V-760; N-71 to V-760; N-72 to V-760; K-73 to V-760; D-74 to V-760; L-75 to V-760; Q-76 to V-760; A-77 to V-760; E-78 to V-760; T-79 to V-760; P-80 to V-760; L-81 to V-760; G-82 to V-760; D-83 to V-760; L-84 to V-760; W-85 to V-760; H-86 to V-760; H-87 to V-760; D-88 to V-760; F-89 to V-760; W-90 to V-760; G-91 to V-760; S-92 to V-760; R-93 to V-760; L-94 to V-760; S-95 to V-760; S-96 to V-760; N-97 to V-760; T-98 to V-760; S-99 to V-760; H-100 to V-760; K-01 to V-760; S-102 to V-760; Y-103 to V-760; R-104 to V-760; P-105 to V-760; L-106 to V-760; T-107 to V-760; V-108 to V-760; L-109 to V-760; T-110 to V-760; F-111 to V-760; R-112 to V-760; I-113 to V-760; N-114 to V-760; Y-115 to V-760; Y-116 to V-760; L-117 to V-760; S-118 to V-760; G-119 to V-760; G-120 to V-760; F-121 to V-760; H-122 to V-760; P-123 to V-760; V-124 to V-760; G-125 to V-760; F-126 to V-760; H-127 to V-760; V-128 to V-760; V-129 to V-760; N-130 to V-760; 1-131 to V-760; L-132 to V-760; L-133 to V-760; H-134 to V-760; S-135 to V-760; G-136 to V-760; I-137 to V-760; S-138 to V-760; V-139 to V-760; L-140 to V-760; M-141 to V-760; V-142 to V-760; D-143 to V-760; V-144 to V-760; F-145 to V-760; S-146 to V-760; V-147 to V-760; L-148 to V-760; F-149 to V-760; G-150 to V-760; G-151 to V-760; L-152 to V-760; Q-153 to V-760; Y-154 to V-760; T-155 to V-760; S-156 to V-760; K-157 to V-760; G-158 to V-760; R-159 to V-760; R-160 to V-760; L-161 to V-760; H-162 to V-760; L-163 to V-760; A-164 to V-760; P-165 to V-760; R-166 to V-760; A-167 to V-760; S-168 to V-760; L-169 to V-760; L-170 to V-760; A-171 to V-760; A-172 to V-760; L-173 to V-760; L-174 to V-760; F-175 to V-760; A-176 to V-760; V-177 to V-760; H-178 to V-760; P-179 to V-760; V-180 to V-760; H-181 to V-760; T-182 to V-760; E-183 to V-760; C-184 to V-760; V-185 to V-760; A-186 to V-760; G-187 to V-760; V-188 to V-760; V-189 to V-760; G-190 to V-760; R-191 to V-760; A-192 to V-760; D-193 to V-760; L-194 to V-760; L-195 to V-760; C-196 to V-760; A-197 to V-760; L-198 to V-760; F-199 to V-760; F-200 to V-760; L-201 to V-760; L-202 to V-760; S-203 to V-760; F-204 to V-760; L-205 to V-760; G-206 to V-760; Y-207 to V-760; C-208 to V-760; K-209 to V-760; A-210 to V-760; F-211 to V-760; R-212 to V-760; E-213 to V-760; S-214 to V-760; N-215 to V-760; K-216 to V-760; E-217 to V-760; G-218 to V-760; A-219 to V-760; H-220 to V-760; S-221 to V-760; S-222 to V-760; T-223 to V-760; F-224 to V-760; W-225 to V-760; V-226 to V-760; L-227 to V-760; L-228 to V-760; S-229 to V-760; 1-230 to V-760; F-231 to V-760; L-232 to V-760; G-233 to V-760; A-234 to V-760; V-235 to V-760; A-236 to V-760; M-237 to V-760; L-238 to V-760; C-239 to V-760; K-240 to V-760; E-241 to V-760; Q-242 to V-760; G-243 to V-760; 1-244 to V-760; T-245 to V-760; V-246 to V-760; L-247 to V-760; G-248 to V-760; L-249 to V-760; N-250 to V-760; A-251 to V-760; V-252 to V-760; F-253 to V-760; D-254 to V-760; I-255 to V-760; L-256 to V-760; V-257 to V-760; I-258 to V-760; G-259 to V-760; K-260 to V-760; F-261 to V-760; N-262 to V-760; V-263 to V-760; L-264 to V-760; E-265 to V-760; I-266 to V-760; X-267 to V-760; Q-268 to V-760; K-269 to V-760; V-270 to V-760; L-271 to V-760; H-272 to V-760; K-273 to V-760; D-274 to V-760; K-275 to V-760; S-276 to V-760; L-277 to V-760; E-278 to V-760; N-279 to V-760; L-280 to V-760; G-281 to V-760; M-282 to V-760; L-283 to V-760; R-284 to V-760; N-285 to V-760; G-286 to V-760; G-287 to V-760; L-288 to V-760; L-289 to V-760; F-290 to V-760; R-291 to V-760; M-292 to V-760; T-293 to V-760; L-294 to V-760; L-295 to V-760; T-296 to V-760; S-297 to V-760; G-298 to V-760; G-299 to V-760; A-300 to V-760; G-301 to V-760; M-302 to V-760; L-303 to V-760; Y-304 to V-760; V-305 to V-760; R-306 to V-760; W-307 to V-760; R-308 to V-760; I-309 to V-760; M-310 to V-760; G-311 to V-760; T-312 to V-760; G-313 to V-760; P-314 to V-760; X-315 to V-760; A-316 to V-760; F-317 to V-760; T-318 to V-760; E-319 to V-760; V-320 to V-760; D-321 to V-760; N-322 to V-760; P-323 to V-760; A-324 to V-760; S-325 to V-760; F-326 to V-760; A-327 to V-760; D-328 to V-760; S-329 to V-760; M-330 to V-760; L-331 to V-760; V-332 to V-760; R-333 to V-760; A-334 to V-760; V-335 to V-760; N-336 to V-760; Y-337 to V-760; N-338 to V-760; Y-339 to V-760; Y-340 to V-760; Y-341 to V-760; S-342 to V-760; L-343 to V-760; N-344 to V-760; A-345 to V-760; W-346 to V-760; L-347 to V-760; L-348 to V-760; L-349 to V-760; C-350 to V-760; P-351 to V-760; W-352 to V-760; W-353 to V-760; L-354 to V-760; C-355 to V-760; F-356 to V-760; D-357 to V-760; W-358 to V-760; S-359 to V-760; M-360 to V-760; G-361 to V-760; C-362 to V-760; I-363 to V-760; P-364 to V-760; L-365 to V-760; I-366 to V-760; K-367 to V-760; S-368 to V-760; I-369 to V-760; S-370 to V-760; D-371 to V-760; W-372 to V-760; R-373 to V-760; V-374 to V-760; I-375 to V-760; A-376 to V-760; L-377 to V-760; A-378 to V-760; A-379 to V-760; L-380 to V-760; W-381 to V-760; F-382 to V-760; C-383 to V-760; L-384 to V-760; I-385 to V-760; G-386 to V-760; L-387 to V-760; I-388 to V-760; C-389 to V-760; Q-390 to V-760; A-391 to V-760; L-392 to V-760; C-393 to V-760; S-394 to V-760; E-395 to V-760; D-396 to V-760; G-397 to V-760; H-398 to V-760; K-399 to V-760; R-400 to V-760; R-401 to V-760; 1-402 to V-760; L-403 to V-760; T-404 to V-760; L-405 to V-760; G-406 to V-760; L-407 to V-760; G-408 to V-760; F-409 to V-760; L-410 to V-760; V-411 to V-760; I-412 to V-760; P-413 to V-760; F-414 to V-760; L-415 to V-760; P-416 to V-760; A-417 to V-760; S-418 to V-760; N-419 to V-760; L-420 to V-760; F-421 to V-760; F-422 to V-760; R-423 to V-760; V-424 to V-760; G-425 to V-760; F-426 to V-760; V-427 to V-760; V-428 to V-760; A-429 to V-760; E-430 to V-760; R-431 to V-760; V-432 to V-760; L-433 to V-760; Y-434 to V-760; L-435 to V-760; P-436 to V-760; S-437 to V-760; X-438 to V-760; G-439 to V-760; Y-440 to V-760; C-441 to V-760; V-442 to V-760; L-443 to V-760; L-444 to V-760; T-445 to V-760; F-446 to V-760; G-447 to V-760; F-448 to V-760; G-449 to V-760; A-450 to V-760; L-451 to V-760; S-452 to V-760; K-453 to V-760; H-454 to V-760; T-455 to V-760; K-456 to V-760; K-457 to V-760; K-458 to V-760; K-459 to V-760; L-460 to V-760; I-461 to V-760; A-462 to V-760; A-463 to V-760; V-464 to V-760; V-465 to V-760; L-466 to V-760; G-467 to V-760; I-468 to V-760; L-469 to V-760; F-470 to V-760; I-471 to V-760; N-472 to V-760; T-473 to V-760; L-474 to V-760; R-475 to V-760; C-476 to V-760; V-477 to V-760; L-478 to V-760; R-479 to V-760; S-480 to V-760; G-481 to V-760; E-482 to V-760; W-483 to V-760; R-484 to V-760; S-485 to V-760; E-486 to V-760; E-487 to V-760; Q-488 to V-760; L-489 to V-760; F-490 to V-760; R-491 to V-760; S-492 to V-760; A-493 to V-760; L-494 to V-760; S-495 to V-760; V-496 to V-760; C-497 to V-760; P-498 to V-760; L-499 to V-760; N-500 to V-760; A-501 to V-760; K-502 to V-760; V-503 to V-760; H-504 to V-760; Y-505 to V-760; N-506 to V-760; I-507 to V-760; G-508 to V-760; K-509 to V-760; N-510 to V-760; L-511 to V-760; A-512 to V-760; D-513 to V-760; K-514 to V-760; G-515 to V-760; N-516 to V-760; Q-517 to V-760; T-518 to V-760; A-519 to V-760; A-520 to V-760; I-521 to V-760; R-522 to V-760; Y-523 to V-760; Y-524 to V-760; R-525 to V-760; E-526 to V-760; A-527 to V-760; V-528 to V-760; R-529 to V-760; L-530 to V-760; N-531 to V-760; P-532 to V-760; K-533 to V-760; Y-534 to V-760; V-535 to V-760; H-536 to V-760; A-537 to V-760; M-538 to V-760; N-539 to V-760; N-540 to V-760; L-541 to V-760; G-542 to V-760; N-543 to V-760; 1-544 to V-760; L-545 to V-760; K-546 to V-760; E-547 to V-760; R-548 to V-760; N-549 to V-760; E-550 to V-760; L-551 to V-760; Q-552 to V-760; E-553 to V-760; A-554 to V-760; E-555 to V-760; E-556 to V-760; L-557 to V-760; L-558 to V-760; S-559 to V-760; L-560 to V-760; A-561 to V-760; V-562 to V-760; Q-563 to V-760; S-564 to V-760; Q-565 to V-760; P-566 to V-760; D-567 to V-760; F-568 to V-760; A-569 to V-760; A-570 to V-760; A-571 to V-760; W-572 to V-760; M-573 to V-760; N-574 to V-760; L-575 to V-760; G-576 to V-760; W-577 to V-760; V-578 to V-760; Q-579 to V-760; N-580 to V-760; S-581 to V-760; L-582 to V-760; K-583 to V-760; R-584 to V-760; F-585 to V-760; E-586 to V-760; A-587 to V-760; A-588 to V-760; E-589 to V-760; Q-590 to V-760; S-591 to V-760; Y-592 to V-760; R-593 to V-760; T-594 to V-760; A-595 to V-760; S-596 to V-760; K-597 to V-760; H-598 to V-760; R-599 to V-760; R-600 to V-760; K-601 to V-760; Y-602 to V-760; P-603 to V-760; D-604 to V-760; C-605 to V-760; Y-606 to V-760; Y-607 to V-760; N-608 to V-760; L-609 to V-760; G-610 to V-760; R-611 to V-760; L-612 to V-760; Y-613 to V-760; A-614 to V-760; D-615 to V-760; L-616 to V-760; N-617 to V-760; R-618 to V-760; H-619 to V-760; V-620 to V-760; D-621 to V-760; A-622 to V-760; L-623 to V-760; N-624 to V-760; A-625 to V-760; W-626 to V-760; R-627 to V-760; N-628 to V-760; A-629 to V-760; T-630 to V-760; V-631 to V-760; L-632 to V-760; K-633 to V-760; P-634 to V-760; E-635 to V-760; H-636 to V-760; S-637 to V-760; L-638 to V-760; A-639 to V-760; W-640 to V-760; N-641 to V-760; N-642 to V-760; M-643 to V-760; A-644 to V-760; W-645 to V-760; L-646 to V-760; L-647 to V-760; D-648 to V-760; N-649 to V-760; T-650 to V-760; G-651 to V-760; N-652 to V-760; L-653 to V-760; A-654 to V-760; Q-655 to V-760; A-656 to V-760; E-657 to V-760; A-658 to V-760; V-659 to V-760; G-660 to V-760; R-661 to V-760; E-662 to V-760; A-663 to V-760; L-664 to V-760; E-665 to V-760; L-666 to V-760; E-667 to V-760; P-668 to V-760; N-669 to V-760; D-670 to V-760; H-671 to V-760; S-672 to V-760; L-673 to V-760; M-674 to V-760; F-675 to V-760; S-676 to V-760; L-677 to V-760; A-678 to V-760; N-679 to V-760; V-680 to V-760; L-681 to V-760; G-682 to V-760; K-683 to V-760; S-684 to V-760; Q-685 to V-760; K-686 to V-760; Y-687 to V-760; K-688 to V-760; E-689 to V-760; S-690 to V-760; E-691 to V-760; A-692 to V-760; L-693 to V-760; F-694 to V-760; L-695 to V-760; K-696 to V-760; A-697 to V-760; L-698 to V-760; K-699 to V-760; A-700 to V-760; N-701 to V-760; P-702 to V-760; N-703 to V-760; A-704 to V-760; A-705 to V-760; S-706 to V-760; Y-707 to V-760; H-708 to V-760; G-709 to V-760; N-710 to V-760; L-711 to V-760; A-712 to V-760; V-713 to V-760; L-714 to V-760; Y-715 to V-760; H-716 to V-760; R-717 to V-760; W-718 to V-760; G-719 to V-760; H-720 to V-760; L-721 to V-760; D-722 to V-760; L-723 to V-760; A-724 to V-760; K-725 to V-760; K-726 to V-760; H-727 to V-760; Y-728 to V-760; E-729 to V-760; 1-730 to V-760; S-731 to V-760; L-732 to V-760; Q-733 to V-760; L-734 to V-760; D-735 to V-760; P-736 to V-760; T-737 to V-760; A-738 to V-760; S-739 to V-760; G-740 to V-760; T-741 to V-760; K-742 to V-760; E-743 to V-760; N-744 to V-760; Y-745 to V-760; G-746 to V-760; L-747 to V-760; L-748 to V-760; R-749 to V-760; R-750 to V-760; K-751 to V-760; L-752 to V-760; E-753 to V-760; L-754 to V-760; and M-755 to V-760 of SEQ ID NO:130. Polypeptides encoded by these polynucleotides are also encompassed by the invention.

Also as mentioned above, even if deletion of one or more amino acids from the C-terminus of a protein results in modification of loss of one or more biological functions of the protein, other functional activities (e.g., biological activities, ability to multimerize, ability to bind ligand, ability to generate antibodies, ability to bind antibodies) may still be retained. For example the ability of the shortened polypeptide to induce and/or bind to antibodies which recognize the complete or mature forms of the polypeptide generally will be retained when less than the majority of the residues of the complete or mature polypeptide are removed from the C-terminus. Whether a particular polypeptide lacking C-terminal residues of a complete polypeptide retains such immunologic activities can readily be determined by routine methods described herein and otherwise known in the art. It is not unlikely that a polypeptide with a large number of deleted C-terminal amino acid residues may retain some biological or immunogenic activities. In fact, peptides composed of as few as six amino acid residues may often evoke an immune response.

Accordingly, the present invention further provides polypeptides having one or more residues deleted from the carboxy terminus of the amino acid sequence of the polypeptide shown in FIGS. 1A-G (SEQ ID NO:130), as described by the general formula 1-n, where n is an integer from 6 to 759, where n corresponds to the position of the amino acid residue identified in SEQ ID NO:130. More in particular, the invention provides polynucleotides encoding polypeptides comprising, or alternatively consisting of, an amino acid sequence selected from the group: M-1 to A-759; M-1 to K-758; M-1 to K-757; M-1 to Q-756; M-1 to M-755; M-1 to L-754; M-1 to E-753; M-1 to L-752; M-1 to K-751; M-1 to R-750; M-1 to R-749; M-1 to L-748; M-1 to L-747; M-1 to G-746; M-1 to Y-745; M-1 to N-744; M-1 to E-743; M-1 to K-742; M-1 to T-741; M-1 to G-740; M-1 to S-739; M-1 to A-738; M-1 to T-737; M-1 to P-736; M-1 to D-735; M-1 to L-734; M-1 to Q-733; M-1 to L-732; M-1 to S-731; M-1 to I-730; M-1 to E-729; M-1 to Y-728; M-1 to H-727; M-1 to K-726; M-1 to K-725; M-1 to A-724; M-1 to L-723; M-1 to D-722; M-1 to L-721; M-1 to H-720; M-1 to G-719; M-1 to W-718; M-1 to R-717; M-1 to H-716; M-1 to Y-715; M-1 to L-714; M-1 to V-713; M-1 to A-712; M-1 to L-711; M-1 to N-710; M-1 to G-709; M-1 to H-708; M-1 to Y-707; M-1 to S-706; M-1 to A-705; M-1 to A-704; M-1 to N-703; M-1 to P-702; M-1 to N-701; M-1 to A-700; M-1 to K-699; M-1 to 1-698; M-1 to A-697; M-1 to K-696; M-1 to L-695; M-1 to F-694; M-1 to L-693; M-1 to A-692; M-1 to E-691; M-1 to S-690; M-1 to E-689; M-1 to K-688; M-1 to Y-687; M-1 to K-686; M-1 to Q-685; M-1 to S-684; M-1 to K-683; M-1 to G-682; M-1 to L-681; M-1 to V-680; M-1 to N-679; M-1 to A-678; M-1 to L-677; M-1 to S-676; M-1 to F-675; M-1 to M-674; M-1 to L-673; M-1 to S-672; M-1 to H-671; M-1 to D-670; M-1 to N-669; M-1 to P-668; M-1 to I-667; M-1 to L-666; M-1 to E-665; M-1 to L-664; M-1 to A-663; M-1 to E-662; M-1 to R-661; M-1 to G-660; M-1 to V-659; M-1 to A-658; M-1 to E-657; M-1 to A-656; M-1 to Q-655; M-1 to A-654; M-1 to L-653; M-1 to N-652; M-1 to G-651; M-1 to T-650; M-1 to N-649; M-1 to D-648; M-1 to L-647; M-1 to L-646; M-1 to I-645; M-1 to 1-644; M-1 to M-643; M-1 to N-642; M-1 to N-641; M-1 to W-640; M-1 to A-639; M-1 to L-638; M-1 to S-637; M-1 to H-636; M-1 to E-635; M-1 to P-634; M-1 to K-633; M-1 to L-632; M-1 to V-631; M-1 to T-630; M-1 to A-629; M-1 to N-628; M-1 to R-627; M-1 to W-626; M-1 to A-625; M-1 to N-624; M-1 to L-623; M-1 to A-622; M-1 to D-621; M-1 to V-620; M-1 to H-619; M-1 to R-618; M-1 to N-617; M-1 to L-616; M-1 to D-615; M-1 to A-614; M-1 to Y-613; M-1 to L-612; M-1 to R-611; M-1 to G-610; M-1 to L-609; M-1 to N-608; M-1 to Y-607; M-1 to Y-606; M-1 to C-605; M-1 to D-604; M-1 to P-603; M-1 to Y-602; M-1 to K-601; M-1 to R-600; M-1 to R-599; M-1 to H-598; M-1 to K-597; M-1 to I-596; M-1 to A-595; M-1 to T-594; M-1 to R-593; M-1 to Y-592; M-1 to S-591; M-1 to Q-590; M-1 to E-589; M-1 to A-588; M-1 to A-587; M-1 to E-586; M-1 to F-585; M-1 to R-584; M-1 to K-583; M-1 to L-582; M-1 to S-581; M-1 to N-580; M-1 to Q-579; M-1 to V-578; M-1 to I-577; M-1 to G-576; M-1 to L-575; M-1 to N-574; M-1 to M-573; M-1 to W-572; M-1 to A-571; M-1 to A-570; M-1 to A-569; M-1 to F-568; M-1 to D-567; M-1 to P-566; M-1 to Q-565; M-1 to 1-564; M-1 to Q-563; M-1 to V-562; M-1 to A-561; M-1 to L-560; M-1 to S-559; M-1 to L-558; M-1 to L-557; M-1 to E-556; M-1 to E-555; M-1 to A-554; M-1 to E-553; M-1 to Q-552; M-1 to L-551; M-1 to E-550; M-1 to N-549; M-1 to R-548; M-1 to E-547; M-1 to K-546; M-1 to L-545; M-1 to I-544; M-1 to N-543; M-1 to G-542; M-1 to L-541; M-1 to N-540; M-1 to N-539; M-1 to M-538; M-1 to A-537; M-1 to H-536; M-1 to V-535; M-1 to Y-534; M-1 to K-533; M-1 to P-532; M-1 to N-531; M-1 to L-530; M-1 to R-529; M-1 to V-528; M-1 to A-527; M-1 to E-526; M-1 to R-525; M-1 to Y-524; M-1 to Y-523; M-1 to R-522; M-1 to 1-521; M-1 to A-520; M-1 to A-519; M-1 to T-518; M-1 to Q-517; M-1 to N-516; M-1 to G-515; M-1 to K-514; M-1 to D-513; M-1 to A-512; M-1 to L-511; M-1 to N-510; M-1 to K-509; M-1 to G-508; M-1 to I-507; M-1 to N-506; M-1 to Y-505; M-1 to H-504; M-1 to V-503; M-1 to K-502; M-1 to A-501; M-1 to N-500; M-1 to L-499; M-1 to P-498; M-1 to C-497; M-1 to V-496; M-1 to S-495; M-1 to L-494; M-1 to A-493; M-1 to S-492; M-1 to R-491; M-1 to F-490; M-1 to L-489; M-1 to Q-488; M-1 to E-487; M-1 to E-486; M-1 to S-485; M-1 to R-484; M-1 to W-483; M-1 to E-482; M-1 to G-481; M-1 to S-480; M-1 to R-479; M-1 to L-478; M-1 to V-477; M-1 to C-476; M-1 to R-475; M-1 to L-474; M-1 to T-473; M-1 to N-472; M-1 to 1-471; M-1 to F-470; M-1 to L-469; M-1 to I-468; M-1 to G-467; M-1 to L-466; M-1 to V-465; M-1 to V-464; M-1 to A-463; M-1 to A-462; M-1 to I-461; M-1 to L-460; M-1 to K-459; M-1 to K-458; M-1 to K-457; M-1 to K-456; M-1 to T-455; M-1 to H-454; M-1 to K-453; M-1 to S-452; M-1 to L-451; M-1 to A-450; M-1 to G-449; M-1 to F-448; M-1 to G-447; M-1 to F-446; M-1 to T-445; M-1 to L-444; M-1 to L-443; M-1 to V-442; M-1 to C-441; M-1 to Y-440; M-1 to G-439; M-1 to X-438; M-1 to S-437; M-1 to P-436; M-1 to L-435; M-1 to Y-434; M-1 to L-433; M-1 to V-432; M-1 to R-431; M-1 to E-430; M-1 to A-429; M-1 to V-428; M-1 to V-427; M-1 to F-426; M-1 to G-425; M-1 to V-424; M-1 to R-423; M-1 to F-422; M-1 to F-421; M-1 to L-420; M-1 to N-419; M-1 to S-418; M-1 to A-417; M-1 to P-416; M-1 to L-415; M-1 to F-414; M-1 to P-413; M-1 to I-412; M-1 to V-411; M-1 to L-410; M-1 to F-409; M-1 to G-408; M-1 to L-407; M-1 to G-406; M-1 to L-405; M-1 to T-404; M-1 to L-403; M-1 to I-402; M-1 to R-401; M-1 to R-400; M-1 to K-399; M-1 to H-398; M-1 to G-397; M-1 to D-396; M-1 to E-395; M-1 to S-394; M-1 to C-393; M-1 to L-392; M-1 to A-391; M-1 to Q-390; M-1 to C-389; M-1 to 1-388; M-1 to L-387; M-1 to G-386; M-1 to I-385; M-1 to L-384; M-1 to C-383; M-1 to F-382; M-1 to W-381; M-1 to L-380; M-1 to A-379; M-1 to A-378; M-1 to L-377; M-1 to A-376; M-1 to 1-375; M-1 to V-374; M-1 to R-373; M-1 to W-372; M-1 to D-371; M-1 to S-370; M-1 to 1-369; M-1 to S-368; M-1 to K-367; M-1 to I-366; M-1 to L-365; M-1 to P-364; M-1 to 1-363; M-1 to C-362; M-1 to G-361; M-1 to M-360; M-1 to S-359; M-1 to W-358; M-1 to D-357; M-1 to F-356; M-1 to C-355; M-1 to L-354; M-1 to W-353; M-1 to W-352; M-1 to P-351; M-1 to C-350; M-1 to L-349; M-1 to L-348; M-1 to L-347; M-1 to W-346; M-1 to A-345; M-1 to N-344; M-1 to L-343; M-1 to S-342; M-1 to Y-341; M-1 to Y-340; M-1 to Y-339; M-1 to N-338; M-1 to Y-337; M-1 to N-336; M-1 to V-335; M-1 to A-334; M-1 to R-333; M-1 to V-332; M-1 to L-331; M-1 to M-330; M-1 to S-329; M-1 to D-328; M-1 to A-327; M-1 to F-326; M-1 to S-325; M-1 to A-324; M-1 to P-323; M-1 to N-322; M-1 to D-321; M-1 to V-320; M-1 to E-319;

M-1 to T-318; M-1 to F-317; M-1 to A-316; M-1 to X-315; M-1 to P-314; M-1 to G-313; M-1 to T-312; M-1 to G-311; M-1 to M-310; M-1 to I-309; M-1 to R-308; M-1 to W-307; M-1 to R-306; M-1 to V-305; M-1 to Y-304; M-1 to L-303; M-1 to M-302; M-1 to G-301; M-1 to A-300; M-1 to G-299; M-1 to G-298; M-1 to S-297; M-1 to T-296; M-1 to L-295; M-1 to L-294; M-1 to T-293; M-1 to M-292; M-1 to R-291; M-1 to F-290; M-1 to L-289; M-1 to L-288; M-1 to G-287; M-1 to G-286; M-1 to N-285; M-1 to R-284; M-1 to L-283; M-1 to M-282; M-1 to G-281; M-1 to L-280; M-1 to N-279; M-1 to E-278; M-1 to L-277; M-1 to S-276; M-1 to K-275; M-1 to D-274; M-1 to K-273; M-1 to H-272; M-1 to L-271; M-1 to V-270; M-1 to K-269; M-1 to Q-268; M-1 to X-267; M-1 to I-266; M-1 to E-265; M-1 to L-264; M-1 to V-263; M-1 to N-262; M-1 to F-261; M-1 to K-260; M-1 to G-259; M-1 to 1-258; M-1 to V-257; M-1 to L-256; M-1 to I-255; M-1 to D-254; M-1 to F-253; M-1 to V-252; M-1 to A-251; M-1 to N-250; M-1 to L-249; M-1 to G-248; M-1 to L-247; M-1 to V-246; M-1 to T-245; M-1 to I-244; M-1 to G-243; M-1 to Q-242; M-1 to E-241; M-1 to K-240; M-1 to C-239; M-1 to L-238; M-1 to M-237; M-1 to A-236; M-1 to V-235; M-1 to A-234; M-1 to G-233; M-1 to L-232; M-1 to F-231; M-1 to 1-230; M-1 to S-229; M-1 to L-228; M-1 to L-227; M-1 to V-226; M-1 to W-225; M-1 to F-224; M-1 to T-223; M-1 to S-222; M-1 to S-221; M-1 to H-220; M-1 to A-219; M-1 to G-218; M-1 to E-217; M-1 to K-216; M-1 to N-215; M-1 to S-214; M-1 to E-213; M-1 to R-212; M-1 to F-211; M-1 to A-210; M-1 to K-209; M-1 to C-208; M-1 to Y-207; M-1 to G-206; M-1 to L-205; M-1 to F-204; M-1 to S-203; M-1 to L-202; M-1 to L-201; M-1 to F-200; M-1 to F-199; M-1 to L-198; M-1 to A-197; M-1 to C-196; M-1 to L-195; M-1 to L-194; M-1 to D-193; M-1 to A-192; M-1 to R-191; M-1 to G-190; M-1 to V-189; M-1 to V-188; M-1 to G-187; M-1 to A-186; M-1 to V-185; M-1 to C-184; M-1 to E-183; M-1 to T-182; M-1 to H-181; M-1 to V-180; M-1 to P-179; M-1 to H-178; M-1 to V-177; M-1 to A-176; M-1 to F-175; M-1 to L-174; M-1 to L-173; M-1 to A-172; M-1 to A-171; M-1 to L-170; M-1 to L-169; M-1 to S-168; M-1 to A-167; M-1 to R-166; M-1 to P-165; M-1 to A-164; M-1 to L-163; M-1 to H-162; M-1 to L-161; M-1 to R-160; M-1 to R-159; M-1 to G-158; M-1 to K-157; M-1 to S-156; M-1 to T-155; M-1 to Y-154; M-1 to Q-153; M-1 to L-152; M-1 to G-151; M-1 to G-150; M-1 to F-149; M-1 to L-148; M-1 to V-147; M-1 to S-146; M-1 to F-145; M-1 to V-144; M-1 to D-143; M-1 to V-142; M-1 to M-141; M-1 to L-140; M-1 to V-139; M-1 to S-138; M-1 to 1-137; M-1 to G-136; M-1 to S-135; M-1 to H-134; M-1 to L-133; M-1 to L-132; M-1 to 1-131; M-1 to N-130; M-1 to V-129; M-1 to V-128; M-1 to H-127; M-1 to F-126; M-1 to G-125; M-1 to V-124; M-1 to P-123; M-1 to H-122; M-1 to F-121; M-1 to G-120; M-1 to G-119; M-1 to S-118; M-1 to L-117; M-1 to Y-116; M-1 to Y-115; M-1 to N-114; M-1 to I-113; M-1 to R-112; M-1 to F-1; M-1 to T-110; M-1 to L-109; M-1 to V-108; M-1 to T-107; M-1 to L-106; M-1 to P-105; M-1 to R-104; M-1 to Y-103; M-1 to S-102; M-1 to K-101; M-1 to H-100; M-1 to S-99; M-1 to T-98; M-1 to N-97; M-1 to S-96; M-1 to S-95; M-1 to L-94; M-1 to R-93; M-1 to S-92; M-1 to G-91; M-1 to W-90; M-1 to F-89; M-1 to D-88; M-1 to H-87; M-1 to H-86; M-1 to W-85; M-1 to L-84; M-1 to D-83; M-1 to G-82; M-1 to L-81; M-1 to P-80; M-1 to T-79; M-1 to E-78; M-1 to A-77; M-1 to Q-76; M-1 to L-75; M-1 to D-74; M-1 to K-73; M-1 to N-72; M-1 to N-71; M-1 to V-70; M-1 to I-69; M-1 to A-68; M-1 to E-67; M-1 to S-66; M-1 to D-65; M-1 to D-64; M-1 to F-63; M-1 to V-62; M-1 to F-61; M-1 to D-60; M-1 to G-59; M-1 to D-58; M-1 to Y-57; M-1 to S-56; M-1 to R-55; M-1 to A-54; M-1 to F-53; M-1 to C-52; M-1 to V-51; M-1 to 1-50; M-1 to A-49; M-1 to V-48; M-1 to S-47; M-1 to G-46; M-1 to V-45; M-1 to V-44; M-1 to L-43; M-1 to K-42; M-1 to A-41; M-1 to W-40; M-1 to F-39; M-1 to P-38; M-1 to P-37; M-1 to L-36; M-1 to V-35; M-1 to S-34; M-1 to S-33; M-1 to P-32; M-1 to L-31; M-1 to I-30; M-1 to H-29; M-1 to D-28; M-1 to L-27; M-1 to D-26; M-1 to T-25; M-1 to D-24; M-1 to L-23; M-1 to V-22; M-1 to A-21; M-1 to M-20; M-1 to R-19; M-1 to F-18; M-1 to V-17; M-1 to A-16; M-1 to P-15; M-1 to Q-14; M-1 to H-13; M-1 to S-12; M-1 to G-11; M-1 to A-10; M-1 to G-9; M-1 to A-8; M-1 to N-7; and M-1 to H-6 of SEQ ID NO: 130. Polypeptides encoded by these polynucleotides are also encompassed by the invention.

In addition, any of the above listed N- or C-terminal deletions can be combined to produce a N- and C-terminal deleted polypeptide. The invention also provides polypeptides comprising, or alternatively consisting of, one or more amino acids deleted from both the amino and the carboxyl termini, which may be described generally as having residues m-n of SEQ ID NO:130, where n and m are integers as described above. Polynucleotides encoding these polypeptides are also encompassed by the invention.

The present invention is also directed to proteins containing polypeptides at least 80%, 85%, 90%, 92%, 93%, 94%, 95%, 96%, 97%, 98% or 99% identical to a polypeptide sequence set forth herein as m-n. In preferred embodiments, the application is directed to proteins containing polypeptides at least 80%, 85%, 90%, 95%, 96%, 97%, 98% or 99% identical to polypeptides having the amino acid sequence of the specific N- and C-terminal deletions recited herein. Polynucleotides encoding these polypeptides are also encompassed by the invention.

Also included are polynucleotide sequences encoding a polypeptide consisting of a portion of the complete amino acid sequence encoded by a cDNA clone contained in ATCC Deposit No. 209745, where this portion excludes any integer of amino acid residues from 1 to about 755 amino acids from the amino terminus of the complete amino acid sequence encoded by a cDNA clone contained in ATCC Deposit No. 209745, or any integer of amino acid residues from 6 to about 759 amino acids from the carboxy terminus, or any combination of the above amino terminal and carboxy terminal deletions, of the complete amino acid sequence encoded by the cDNA clone contained in ATCC Deposit No. 209745. Polypeptides encoded by these polynucleotides also are encompassed by the invention.

As described herein or otherwise known in the art, the polynucleotides of the invention have uses that include, but are not limited to, serving as probes or primers in chromosome identification, chromosome mapping, and linkage analysis.

This gene is expressed primarily in ovarian cancer tissues and substantia nigra and, to a lesser extent, in amygdala and brain, striatum.

Polynucleotides and polypeptides of the invention would be useful as reagents for differential identification of the tissue(s) or cell type(s) present in a biological sample and for diagnosis of diseases and conditions which include, but are not limited to, neurodegenerative disorders and/or disorders of the reproductive system, including, but not limited to ovarian cancer. Similarly, polypeptides and antibodies directed to these polypeptides would be useful in providing immunological probes for differential identification of the tissue(s) or cell type(s). For a number of disorders of the above tissues or cells, particularly of the central nervous system and brain and/or reproductive system, expression of this gene at significantly higher or lower levels may be routinely detected in certain tissues or cell types (e.g., CNS, neural, nervous, neuronal, reproductive, ovarian, cancerous and wounded tissues) or bodily fluids (e.g., lymph, serum, plasma, urine, vaginal pool, synovial fluid and spinal fluid) or another tissue or cell sample taken from an individual having such a disorder, relative to the standard gene expression level, i.e., the expression level in healthy tissue or bodily fluid from an individual not having the disorder. Preferred polypeptides of the present invention comprise, or alternatively consist of one, two or all three of the immunogenic epitopes shown in SEQ ID NO: 130 as residues: Arg-93 to Arg-104, Tyr-154 to Arg-159, Arg-212 to His-220. Polynucleotides encoding said polypeptides are encompassed by the invention, as are antibodies that bind one or more of these peptides.

The tissue distribution in substantia nigra and, to a lesser extent, in amygdala and brain, striatum, indicates that polynucleotides and polypeptides corresponding to this gene would be useful for the detection, treatment, and/or prevention of neurodegenerative disease states, behavioral disorders, or inflammatory conditions. Representative uses are described in the "Regeneration" and "Hyperproliferative Disorders" sections below, in Example 11, 15, and 18, and elsewhere herein. Briefly, the uses include, but are not limited to the detection, treatment, and/or prevention of Alzheimer's Disease, Parkinson's Disease, Huntington's Disease, Tourette Syndrome, meningitis, encephalitis, demyelinating diseases, peripheral neuropathies, neoplasia, trauma, congenital malformations, spinal cord injuries, ischemia and infarction, aneurysms, hemorrhages, schizophrenia, mania, dementia, paranoia, obsessive compulsive disorder, depression, panic disorder, learning disabilities, ALS, psychoses, autism, and altered behaviors, including disorders in feeding, sleep patterns, balance, and perception. In addition, elevated expression of this gene product in regions of the brain indicates it plays a role in normal neural function. Potentially, this gene product is involved in synapse formation, neurotransmission, learning, cognition, homeostasis, or neuronal differentiation or survival.

The tissue distribution in reproductive and developing tissues indicates that polynucleotides and/or polypeptides corresponding to this gene would be useful for the treatment, prevention, detection, and/or diagnosis of disorders of reproductive system organs, including cancers, disorders affecting fertility, and/or developmental disorders. Specifically, expression in ovarian cancer tissue, indicates that polynucleotides and/or polypeptides corresponding to this gene, agonists, and/or antagonists thereof (including, but not limited to antibodies or fragments thereof, that bind polypeptides of the invention) would be useful for the treatment, prevention, detection and diagnosis of conditions concerning proper ovarian function (e.g., egg maturation, endocrine function), as well as cancer. The expression in ovarian tissue may indicate that polynucleotides and/or polypeptides corresponding to this gene, agonists, and/or antagonists thereof (including, but not limited to antibodies or fragments thereof, that bind polypeptides of the invention) can be used to treat, prevent, detect and/or diagnose disorders of the ovary, including inflammatory disorders, such as oophoritis (e.g., caused by viral or bacterial infection), ovarian cysts, amenorrhea, infertility, hirsutism, and ovarian cancer (including, but not limited to, primary and secondary cancerous growth, endometrioid carcinoma of the ovary, ovarian papillary serous adenocarcinoma, ovarian mucinous adenocarcinoma, Ovarian Krukenberg tumor).

Moreover, the predicted membrane localization indicates that polynucleotides and/or polypeptides corresponding to this gene would be a good target for antagonists, particularly small molecules or antibodies, which block functional activity (such as, for example, binding of the receptor by its cognate ligand(s); transport function; signalling function). Accordingly, preferred are antibodies and or small molecules which specifically bind an extracellular portion of the translation product of this gene. The extracellular regions can be ascertained from the information regarding the transmembrane domains as set out above. Also provided is a kit for detecting cancer. In one embodiment, the kit would be useful for detecting ovarian cancer. Such a kit comprises in one embodiment an antibody specific for the translation product of this gene bound to a solid support. Also provided is a method of detecting cancer (for example, ovarian cancer) in an individual which comprises a step of contacting an antibody specific for the translation product of this gene to a bodily fluid from the individual, preferably serum, and ascertaining whether antibody binds to an antigen found in the bodily fluid. Preferably the antibody is bound to a solid support and the bodily fluid is serum. The above embodiments, as well as other treatments and diagnostic tests (kits and methods), are more particularly described elsewhere herein. Furthermore, the protein may also be used to determine biological activity, to raise antibodies, as tissue markers, to isolate cognate ligands or receptors, to identify agents that modulate their interactions, in addition to its use as a nutritional supplement. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:23 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a-b, where a is any integer between 1 to 3872 of SEQ ID NO:23, b is an integer of 15 to 3886, where both a and b correspond to the positions of nucleotide residues shown in SEQ ID NO:23, and where b is greater than or equal to a +14.

Features of Protein Encoded by Gene No: 14

In specific embodiments, polypeptides of the invention comprise, or alternatively consist of, an amino acid sequence selected from the group: RDNDYLLHGHRPPMF (SEQ ID NO:290), SFRACFKSIFRIHTETGNIWTHLL (SEQ ID NO:291), and/or GFVLFLFLGILTMLRPNMYFMAPLQEKVV (SEQ ID NO:292). Moreover, fragments and variants of these polypeptides (such as, for example, fragments as described herein, polypeptides at least 80%, 85%, 90%, 95%, 96%, 97%, 98%, 99%, or 100% identical to these polypeptides, or polypeptides encoded by a polynucleotide which hybridizes, under stringent conditions, to the polynucleotide encoding these polypeptides) are encompassed by the invention. Antibodies that bind polypeptides of the invention and polynucleotides encoding these polypeptides are also encompassed by the invention.

The gene encoding the disclosed cDNA is thought to reside on chromosome 1. Accordingly, polynucleotides related to this invention would be useful as a marker in linkage analysis for chromosome 1.

This gene is expressed primarily in bone marrow, fetal liver and spleen tissues, several types of leukocytes including neutrophils, and T-cells, placental tissue, and brain tissue.

Polynucleotides and polypeptides of the invention would be useful as reagents for differential identification of the tissue(s) or cell type(s) present in a biological sample and for diagnosis of diseases and conditions which include, but are not limited to, diseases and/or disorders of the immune system and central nervous system including AIDS, Lupus, hemotological cancers, mood disorders, and dementia. Similarly, polypeptides and antibodies directed to these polypeptides would be useful in providing immunological probes for differential identification of the tissue(s) or cell type(s). For a number of disorders of the above tissues or cells, particularly of the immune system and central nervous system, expression of this gene at significantly higher or lower levels may be routinely detected in certain tissues or cell types (e.g., immune, neural, cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder. Preferred polypeptides of the present invention comprise, or alternatively consist of one, two or all three of the immunogenic epitopes shown in SEQ ID NO: 131 as residues: Glu-24 to Tyr-35, Arg-83 to Thr-92, Pro-148 to Gly-154. Polynucleotides encoding said polypeptides are encompassed by the invention, as are antibodies that bind one or more of these peptides.

The tissue distribution indicates that polynucleotides and polypeptides corresponding to this gene would be useful for the detection, treatment, and/or prevention of a variety of immune system disorders. Representative uses are described in the 'Immune Activity' and 'Infectious Disease' sections below, in Example 11, 13, 14, 16, 18, 19, 20, and 27, and elsewhere herein. Briefly, the expression of this gene product in fetal liver and spleen tissues, and several types of leukocytes, indicates a role in the regulation of the proliferation; survival; differentiation; and/or activation of potentially all hematopoietic cell lineages, including blood stem cells. Polynucleotides and polypeptides of the invention may be involved in the regulation of cytokine production, antigen presentation, or other processes that may also suggest a usefulness in the treatment of cancer (e.g., by boosting immune responses). Since the gene is expressed in cells of lymphoid origin, polynucleotides and polypeptides of the invention, as well as, antibodies directed against the protein may show utility as a tumor marker and/or immunotherapy targets for the above listed tissues. Therefore it may be also used as an agent for immunological disorders including arthritis, asthma, immune deficiency diseases such as AIDS, leukemia, rheumatoid arthritis, inflammatory bowel disease, sepsis, acne, and psoriasis. In addition, polynucleotides and polypeptides of the invention may have commercial utility in the expansion of stem cells and committed progenitors of various blood lineages, and in the differentiation and/or proliferation of various cell types. Alternatively, the tissue distribution indicates that polynucleotides and polypeptides corresponding to this gene would be useful for the detection, diagnosis, prevention and/or treatment of neurodegenerative disease states and behavioural disorders such as Alzheimer's Disease, Parkinson's Disease, Huntington's Disease, Tourette Syndrome, schizophrenia, mania, dementia, paranoia, obsessive compulsive disorder, panic disorder, learning disabilities, ALS, psychoses, autism, and altered behaviors, including disorders in feeding, sleep patterns, balance, and perception. In addition, the gene or gene product may also play a role in the treatment and/or detection of developmental disorders associated with the developing embryo, or sexually-linked disorders. Furthermore, the protein may also be used to determine biological activity, to raise antibodies, as tissue markers, to isolate cognate ligands or receptors, to identify agents that modulate their interactions, in addition to its use as a nutritional supplement. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:24 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a-b, where a is any integer between 1 to 1569 of SEQ ID NO:24, b is an integer of 15 to 1583, where both a and b correspond to the positions of nucleotide residues shown in SEQ ID NO:24, and where b is greater than or equal to a +14.

Features of Protein Encoded by Gene No: 15

The translation product of this gene shares sequence homology with gp25L, which is thought to be important in protein processing.

This gene is expressed primarily in stimulated synovium, cerebellum, immune cells (e.g., T-cells), and placental tissues, and, to a lesser extent, in several other tissues and organs.

Polynucleotides and polypeptides of the invention would be useful as reagents for differential identification of the tissue(s) or cell type(s) present in a biological sample and for diagnosis of diseases and conditions which include, but are not limited to, inflammation, disorders of developing systems, central nervous system, and musculo-skeletal system. Similarly, polypeptides and antibodies directed to these polypeptides would be useful in providing immunological probes for differential identification of the tissue(s) or cell type(s). For a number of disorders of the above tissues or cells, particularly of the immune, central nervous system, musculo-skeletal, and developing systems, expression of this gene at significantly higher or lower levels may be routinely detected in certain tissues or cell types (e.g., immune, neural, musculo-skeletal, cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

The tissue distribution and homology to gp25L indicates that polynucleotides and polypeptides corresponding to this gene would be useful for treatment, prevention, detection and/or diagnosis of disorders of immune, central nervous system, musculo-skeletal, and developing systems. In addition, the expression of this gene product in synovium indicates a role in the detection and treatment of disorders and conditions affecting the skeletal system, in particular osteoporosis as well as disorders afflicting connective tissues (e.g., arthritis, trauma, tendonitis, chrondomalacia and inflammation), such as in the diagnosis or treatment of various autoimmune disorders such as rheumatoid arthritis, lupus, scleroderma, and dermatomyositis as well as dwarfism, spinal deformation, and specific joint abnormalities as well as chondrodysplasias (i.e., spondyloepiphyseal dysplasia congenita, familial arthritis, Atelosteogenesis type II, metaphyseal chondrodysplasia type Schmid). The tissue distribution and homology to gp25L indicates that the polynucleotides and polypeptides of the invention would be useful for treatment, prevention, detection and/or diagnosis of disorders associated with expression of Gp25L-H, e.g. Cushing's disease, cystic fibrosis, diabetes mellitus, diabetes insipidus, glucose-galactose malabsorption syndrome, hypercholesterolemia, hyper and hypoglycemia, Grave's disease, goiter, inflammation and autoimmune disorders including Addison's disease, adult respiratory distress syndrome, allergies (including hay fever and hives), anemia, asthma, atherosclerosis, bronchitis, cholecystitis, Crohn's disease, ulcerative colitis, atopic dermatitis, dermatomyositis, diabetes mellitus, emphysema, atrophic gastritis, glomerulonephritis, gout, hypereosinophilia, irritable bowel syndrome, lupus erythematosus, multiple sclerosis, myasthenia gravis, myocardial or pericardial inflammation, osteoarthritis, osteoporosis, pancreatitis, polymyositis, rheumatoid arthritis, scleroderma, Sjogren's syndrome and autoimmune thyroiditis, complications of cancer, hemodialysis, extracorporeal circulation; viral, bacterial, fungal, parasitic, protozoal and helminthic infections and trauma. The tissue distribution in T-cells indicates that polynucleotides and polypeptides of the invention would be useful for the diagnosis, detection, prevention and/or treatment of a variety of immune system disorders. Representative uses are described in the "Immune Activity" and "Infectious Disease" sections below, in Example 11, 13, 14, 16, 18, 19, 20, and 27, and elsewhere herein. Briefly, the expression indicates a role in regulating the proliferation; survival; differentiation; and/or activation of hematopoietic cell lineages, including blood stem cells. Involvement in the regulation of cytokine production, antigen presentation, or other processes indicates a usefulness for treatment of cancer (e.g. by boosting immune responses). Expression in cells of lymphoid origin, indicates the natural gene product would be involved in immune functions. Therefore it would also be useful as an agent for immunological disorders including arthritis, asthma, immunodeficiency diseases such as AIDS, leukemia, rheumatoid arthritis, granulomatous disease, inflammatory bowel disease, sepsis, acne, neutropenia, neutrophilia, psoriasis, hypersensitivities, such as T-cell mediated cytotoxicity; immune reactions to transplanted organs and tissues, such as host-versus-graft and graft-versus-host diseases, or autoimmunity disorders, such as autoimmune infertility, lense tissue injury, demyelination, systemic lupus erythematosis, drug induced hemolytic anemia, rheumatoid arthritis, Sjogren's disease, and scleroderma. Moreover, the protein may represent a secreted factor that influences the differentiation or behavior of other blood cells, or that recruits hematopoietic cells to sites of injury. Thus, this gene product is thought to be useful in the expansion of stem cells and committed progenitors of various blood lineages, and in the differentiation and/or proliferation of various cell types. Furthermore, the protein may also be used to determine biological activity, raise antibodies, as tissue markers, to isolate cognate ligands or receptors, to identify agents that modulate their interactions, in addition to its use as a nutritional supplement. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:25 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a-b, where a is any integer between 1 to 1655 of SEQ ID NO:25, b is an integer of 15 to 1669, where both a and b correspond to the positions of nucleotide residues shown in SEQ ID NO:25, and where b is greater than or equal to a +14.

Features of Protein Encoded by Gene No: 16

The translation product of this gene shares sequence homology with ribosomal proteins (see, e.g., Genbank accession number g|437926 and PID|d1011606; all references available through these accessions are hereby incorporated in their entirety by reference herein). Based on the sequence similarity, the translation product of this clone is expected to share at least some biological activities with ribosomal proteins.

This gene is expressed primarily in immune and hematopoietic cells, fetal tissue, adipose tissue, uterine cancer tissue, ovary tumor, breast and brain tissues, and, to a lesser extent, in several other tissues.

Polynucleotides and polypeptides of the invention would be useful as reagents for differential identification of the tissue(s) or cell type(s) present in a biological sample and for diagnosis of diseases and conditions which include, but are not limited to, immune and hematopoietic disorders, disorders of the central nervous system and reproductive organs. Similarly, polypeptides and antibodies directed to these polypeptides would be useful in providing immunological probes for differential identification of the tissue(s) or cell type(s). For a number of disorders of the above tissues or cells, particularly of the immune system, hematopoietic, central nervous system and reproductive system, expression of this gene at significantly higher or lower levels may be routinely detected in certain tissues or cell types (e.g., immune, reproductive, neural, cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

The tissue distribution in breast, brain, and immune tissues indicates that polynucleotides and polypeptides corresponding to this gene would be useful for the treatment, prevention, detection and/or diagnosis of disorders of the immune, hematopoietic, central nervous and reproductive systems. Moreover, the expression within fetal tissues and other cellular sources marked by proliferating cells indicates that polynucleotides and polypeptides of the invention may play a role in the regulation of cellular division, and may show utility in the diagnosis, treatment, and/or prevention of developmental diseases and disorders, including cancer, and other proliferative conditions. Representative uses are described in the "Hyperproliferative Disorders" and "Regeneration" sections below and elsewhere herein. Briefly, developmental tissues rely on decisions involving cell differentiation and/or apoptosis in pattern formation. Dysregulation of apoptosis can result in inappropriate suppression of cell death, as occurs in the development of some cancers, or in failure to control the extent of cell death, as is believed to occur in acquired immunodeficiency and certain degenerative disorders, such as spinal muscular atrophy (SMA). Alternatively, this gene product may be involved in the pattern of cellular proliferation that accompanies early embryogenesis. Thus, aberrant expression of this gene product in tissues—particularly adult tissues—may correlate with patterns of abnormal cellular proliferation, such as found in various cancers. Because of potential roles in proliferation and differentiation, polynucleotides and polypeptides of the invention may have applications in the adult for tissue regeneration and the treatment of cancers. It may also act as a morphogen to control cell and tissue type specification. Therefore, the polynucleotides and polypeptides of the present invention would be useful in treating, detecting, and/or preventing said disorders and conditions, in addition to other types of degenerative conditions. Thus this protein may modulate apoptosis or tissue differentiation and would be useful in the detection, treatment, and/or prevention of degenerative or proliferative conditions and diseases. The protein would be useful in modulating the immune response to aberrant polypeptides, as may exist in proliferating and cancerous cells and tissues. The protein can also be used to gain new insight into the regulation of cellular growth and proliferation. Furthermore, the protein may also be used to determine biological activity, raise antibodies, as tissue markers, to isolate cognate ligands or receptors, to identify agents that modulate their interactions, in addition to its use as a nutritional supplement. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:26 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a-b, where a is any integer between 1 to 1039 of SEQ ID NO:26, b is an integer of 15 to 1053, where both a and b correspond to the positions of nucleotide residues shown in SEQ ID NO:26, and where b is greater than or equal to a +14.

Features of Protein Encoded by Gene No: 17

The gene encoding the disclosed cDNA is believed to reside on chromosome 11. Accordingly, polynucleotides related to this invention would be useful as a marker in linkage analysis for chromosome 11.

In specific embodiments, polypeptides of the invention comprise, or alternatively consist of, an amino acid sequence selected from the group: TGPEFPGSNSTVARRIKDLAADIEEELVCRLKICDGFSLQLDESADVSGLAVLL VFVRYRFNKSIEEDLLLCESLQSNATGEEIFNCINSFMQKHEIEWEKCVDVCSD ASRAVDGKIAEAVTLIKYVAPESTSSHCLLYRHALAVKIMPTSLKNVLDQAV QIINYIKARPHQSRLLKILCEEMGAQHTALLLNTEVRWLSRGKVLVRLFELRR ELLVFMDSAFRLSDCLTNSSWLLRLAYLADIFTKLNEVNLSMQGKNVTVFTV FDKMSSLLRKLEFWASSVEEENFDCFPTLSDFLTEINSTVDKDICSAIVQHLRG LRATLLKYFPVTNDNNAWVRNPFTVTVKPASLVARDYESLIDLTSDSQVKQN FSELSLNDFWSSLIQEYPSIARRAVRVLLPFATMHLCETGFSYYAATKTKYRK RLDAAPHMRIRLSNITPNIKICDKKTQKHCSH (SEQ ID NO:293), DIEEELVCRLKICDGFSLQLDESADVSGLAV (SEQ ID NO:294), NSFMQKHEIEWEKCVDVCSDASRAVDGKIAEAVTLI (SEQ ID NO:295), LDQAVQIINYIKARPHQSRLLKILCEEMGAQHTALL (SEQ ID NO:296), SAFRLSDCLTNSSWLLRLAYLADIFTKLNEVNLSMQGKNVTVFTVFDKM (SEQ ID NO:297), SDFLTEINSTVDKDICSAIVQHLRGLRATLLK (SEQ ID NO:298), and/or SDSQVKQNFSELSLNDFWSSLIQEYPSIARRAVRVLLP (SEQ ID NO:299). Moreover, fragments and variants of these polypeptides (such as, for example, fragments as described herein, polypeptides at least 80%, 85%, 90%, 95%, 96%, 97%, 98%, 99%, or 100% identical to these polypeptides, or polypeptides encoded by a polynucleotide which hybridizes, under stringent conditions, to the polynucleotide encoding these polypeptides) are encompassed by the invention. Antibodies that bind polypeptides of the invention and polynucleotides encoding these polypeptides are also encompassed by the invention.

This gene is expressed primarily in spleen from a chronic lymphocytic leukemia patient, and hodgkin's lymphoma, and, to a lesser extent, in pancreatic islet cell tumors and activated T cells.

Polynucleotides and polypeptides of the invention would be useful as reagents for differential identification of the tissue(s) or cell type(s) present in a biological sample and for diagnosis of diseases and conditions which include, but are not limited to, chronic lymphocytic leukemia; hodgkin's lymphoma; pancreatic islet cell cancer; cancer in general; hematopoietic disorders; immune dysfunction. Similarly, polypeptides and antibodies directed to these polypeptides would be useful in providing immunological probes for differential identification of the tissue(s) or cell type(s). For a number of disorders of the above tissues or cells, particularly of the immune system and pancreas, expression of this gene at significantly higher or lower levels may be routinely detected in certain tissues or cell types (e.g., hematopoietic, cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

The tissue distribution in spleen from a chronic lymphocytic leukemia patient, and hodgkin's lymphoma, pancreatic islet cell tumors, and activated T-cells indicates that polynucleotides and/or polypeptides corresponding to this gene would be useful in the treatment, prevention, detection and/or diagnosis of a variety of immune system disorders. Representative uses are described in the "Immune Activity" and "Infectious Disease" sections below, in Example 11, 13, 14, 16, 18, 19, 20, and 27, and elsewhere herein. Briefly, the protein product of this gene would be useful for the diagnosis and/or treatment of a variety of cancers, including CLL; Hodgkin's lymphoma; and pancreatic cancer. Expression of this gene product in a variety of cancers indicates that it may be a bad player and may likely be a target for inhibitors as therapeutics. Alternately, this gene product may be expressed in both normal and abnormal hematopoietic tissues, where it may play necessary roles in the proliferation; survival; differentiation; or activation of hematopoietic cell lineages. Likewise, expression in pancreatic islet cell tumors may simply reflect a necessary role that this protein plays in normal pancreatic function. Furthermore, the protein may also be used to determine biological activity, to raise antibodies, as tissue markers, to isolate cognate ligands or receptors, to identify agents that modulate their interactions, in addition to its use as a nutritional supplement.

Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:27 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a-b, where a is any integer between 1 to 1463 of SEQ ID NO:27, b is an integer of 15 to 1477, where both a and b correspond to the positions of nucleotide residues shown in SEQ ID NO:27, and where b is greater than or equal to a +14.

Features of Protein Encoded by Gene No: 18

When tested against U937 Myeloid cell lines, supernatants removed from cells containing this gene activated the GAS assay. Thus, it is likely that this gene activates myeloid cells, and to a lesser extent other cells, through the Jak-STAT signal transduction pathway. The gamma activating sequence (GAS) is a promoter element found upstream of many genes which are involved in the Jak-STAT pathway. The Jak-STAT pathway is a large, signal transduction pathway involved in the differentiation and proliferation of cells. Therefore, activation of the Jak-STAT pathway, reflected by the binding of the GAS element, can be used to indicate proteins involved in the proliferation and differentiation of cells.

The polypeptide of this gene has been determined to have transmembrane domains at about amino acid positions 219 to about 235, at about 114 to about 130, at about 86 to about 102, and at about 43 to about 59 of the amino acid sequence referenced in Table 1 for this gene. Based upon these characteristics, it is believed that the protein product of this gene shares structural features to type IIIa membrane proteins.

The gene encoding the disclosed cDNA is believed to reside on chromosome 17. Accordingly, polynucleotides related to this invention would be useful as a marker in linkage analysis for chromosome 17.

In specific embodiments, polypeptides of the invention comprise, or alternatively consist of, the following amino acid sequence: DPRVRECLQDWASFLRLAIPSMLMLCMEWWAYEVGSFLSGILGMVELGAQS IVYELAIIVYMVPAGFSVAASVRVGNALGAGDMEQARKSSTVSLLITVLFAV AFSVLLLSCKDHVGYIFTTDRDIINLVAQVVPIYAVSHLFEALACTSGGVLRGS GNQKVGAIVNTIGXYVVGLPIGIALMFATTLGVMGLWSGIIICTVFQAVCFLG FIIQLNWKKACXQAQVHANLKVNNVPRSGNSALPQDPLHPGCPENLEGILTN DVGKTGEPQSDQQMRQEEPLPEHPQDGAKLSRKQLVLRRGLLLLGVFLILLV GILVRFYVRIQ (SEQ ID NO:300). Moreover, fragments and variants of these polypeptides (such as, for example, fragments as described herein, polypeptides at least 80%, 85%, 90%, 95%, 96%, 97%, 98%, 99%, or 100% identical to these polypeptides, or polypeptides encoded by a polynucleotide which hybridizes, under stringent conditions, to the polynucleotide encoding these polypeptides) are encompassed by the invention. Antibodies that bind polypeptides of the invention and polynucleotides encoding these polypeptides are also encompassed by the invention.

This gene is expressed primarily in endometrial tumor tissue, cartilage tissue, fetal tissue, immune tissue (B-cells and macrophages), and to a lesser extent in several other tissues and organs.

Polynucleotides and polypeptides of the invention would be useful as reagents for differential identification of the tissue(s) or cell type(s) present in a biological sample and for diagnosis of diseases and conditions which include, but are not limited to, tumors and disorders of the musculo-skeletal system. Similarly, polypeptides and antibodies directed to these polypeptides would be useful in providing immunological probes for differential identification of the tissue(s) or cell type(s). For a number of disorders of the above tissues or cells, particularly of the musculo-skeletal system, expression of this gene at significantly higher or lower levels may be routinely detected in certain tissues or cell types (e.g., musculo-skeletal, immune, cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder. Preferred polypeptides of the present invention comprise, or alternatively consist of the immunogenic epitopes shown in SEQ ID NO: 135 as residues: Met-1 to Ser-8. Polynucleotides encoding said polypeptides are encompassed by the invention, as are antibodies that bind one or more of these peptides.

The tissue distribution in musculo-skeletal tissues and biological activity in the GAS assay, indicates that polynucleotides and polypeptides corresponding to this gene would be useful for the treatment, prevention, detection and/or diagnosis of disorders of the musculo-skeletal system, and cancers thereof. The tissue distribution in immune cells (e.g., B-cells and macrophages) and biological activity in the GAS assay indicates that polynucleotides and polypeptides corresponding to this gene would be useful for the diagnosis and treatment of a variety of immune system disorders. Representative uses are described in the "Immune Activity" and "Infectious Disease" sections below, in Example 11, 13, 14, 16, 18, 19, 20, and 27, and elsewhere herein. Briefly, the expression indicates a role in regulating the proliferation; survival; differentiation; and/or activation of hematopoietic cell lineages, including blood stem cells. Involvement in the regulation of cytokine production, antigen presentation, or other processes indicates a usefulness for treatment of cancer (e.g., by boosting immune responses). Expression in cells of lymphoid origin, indicates the natural gene product would be involved in immune functions. Therefore it would also be useful as an agent for immunological disorders including arthritis, asthma, immunodeficiency diseases such as AIDS, leukemia, rheumatoid arthritis, granulomatous disease, inflammatory bowel disease, sepsis, acne, neutropenia, neutrophilia, psoriasis, hypersensitivities, such as T-cell mediated cytotoxicity; immune reactions to transplanted organs and tissues, such as host-versus-graft and graft-versus-host diseases, or autoimmunity disorders, such as autoimmune infertility, lense tissue injury, demyelination, systemic lupus erythematosis, drug induced hemolytic anemia, rheumatoid arthritis, Sjogren's disease, and scleroderma. Moreover, the protein may represent a secreted factor that influences the differentiation or behavior of other blood cells, or that recruits hematopoietic cells to sites of injury. Thus, this gene product is thought to be useful in the expansion of stem cells and committed progenitors of various blood lineages, and in the differentiation and/or proliferation of various cell types. In addition, the expression of this gene product in cartilage tissue indicates a role in the detection and treatment of disorders and conditions affecting the skeletal system, in particular osteoporosis as well as disorders afflicting connective tissues (e.g., arthritis, trauma, tendonitis, chrondomalacia and inflammation), such as in the diagnosis or treatment of various autoimmune disorders such as rheumatoid arthritis, lupus, scleroderma, and dermatomyositis as well as dwarfism, spinal deformation, and specific joint abnormalities as well as chondrodysplasias (i.e., spondyloepiphyseal dysplasia congenita, familial arthritis, Atelosteogenesis type II, metaphyseal chondrodysplasia type Schmid). Furthermore, the protein may also be used to determine biological activity, to raise antibodies, as tissue markers, to isolate cognate ligands or receptors, to identify agents that modulate their interactions, in addition to its use as a nutritional supplement. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:28 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a-b, where a is any integer between 1 to 2490 of SEQ ID NO:28, b is an integer of 15 to 2504, where both a and b correspond to the positions of nucleotide residues shown in SEQ ID NO:28, and where b is greater than or equal to a +14.

Features of Protein Encoded by Gene No: 19

The gene encoding the disclosed cDNA is thought to reside on chromosome 17. Accordingly, polynucleotides related to this invention would be useful as a marker in linkage analysis for chromosome 17.

In specific embodiments, polypeptides of the invention comprise, or alternatively consist of, the following amino acid sequence: GTRIHTILVYQESNRKMDSVDPASSQAMELSDVTLIEGVGNEVMVVAGVVVL ILALVLAWLSTYVADSGSNQLLGAIVSAGDTSVLHLGHVDHLVAGQGNPEPT ELPHPSEGNDEKAEEAGEGRGDSTGEAGAGGGVEPSLEHLLDIQGLPKRQAG AGSSSPEAPLRSEDSTCLPPSPGLITVRLKFLNDTEELAVARPEDTVGALKSKY FPGQESQMKLIYQGRLLQDPARTLRSLNITDNCVIHCHRSPPGSAVPGPSASLA PSATEPPSLGVNVGSLMVPVFVVLLGVVWYFRINYRQFFTAPATVSLVGVTV FFSFLVFGMYGR (SEQ ID NO: 301). Moreover, fragments and variants of these polypeptides (such as, for example, fragments as described herein, polypeptides at least 80%, 85%, 90%, 95%, 96%, 97%, 98%, 99%, or 100% identical to these polypeptides, or polypeptides encoded by a polynucleotide which hybridizes, under stringent conditions, to the polynucleotide encoding these polypeptides) are encompassed by the invention. Antibodies that bind polypeptides of the invention and polynucleotides encoding these polypeptides are also encompassed by the invention.

The polypeptide of this gene has been determined to have transmembrane domains at about amino acid positions 234 to about 250 and at about 266 to about 282 of the amino acid sequence referenced in Table 1 for this gene. Based upon these characteristics, it is believed that the protein product of this gene shares structural features to type IIIa membrane proteins.

This gene is expressed primarily in breast and cerebellum tissues, ovary cancer tissue, B-cells, tonsils, as well as in cells of the hematopoietic system, and, to a lesser extent, in several other organs and tissues.

Polynucleotides and polypeptides of the invention would be useful as reagents for differential identification of the tissue(s) or cell type(s) present in a biological sample and for diagnosis of diseases and conditions which include, but are not limited to, disorders of the brain, reproductive system and hematopoietic system. Similarly, polypeptides and antibodies directed to these polypeptides would be useful in providing immunological probes for differential identification of the tissue(s) or cell type(s). For a number of disorders of the above tissues or cells, particularly of the immune and hematopoietic system, central nervous system and reproductive system, expression of this gene at significantly higher or lower levels may be routinely detected in certain tissues or cell types (e.g., immune, neural, reproductive, cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder. Preferred polypeptides of the present invention comprise, or alternatively consist of one, two, three or all four of the immunogenic epitopes shown in SEQ ID NO: 136 as residues: Gly-56 to Gly-86, Leu-107 to Ala-112, Ala-121 to Thr-129, Lys-164 to Gln-174. Polynucleotides encoding said polypeptides are encompassed by the invention, as are antibodies that bind one or more of these peptides.

The tissue distribution in immune, reproductive, and neural tissues indicates that polynucleotides and polypeptides corresponding to this gene would be useful for the treatment, prevention, detection and/or diagnosis of disorders of the immune and haemopoietic system, the central nervous system, and the reproductive system. Furthermore, the expression in the breast tissue may indicate its uses in breast neoplasia and breast cancers, such as fibroadenoma, pipillary carcinoma, ductal carcinoma, Paget's disease, medullary carcinoma, mucinous carcinoma, tubular carcinoma, secretory carcinoma and apocrine carcinoma, as well as juvenile hypertrophy and gynecomastia, mastitis and abscess, duct ectasia, fat necrosis and fibrocystic diseases. Alternatively, the tissue distribution in cerebellum tissue indicates that polynucleotides and polypeptides corresponding to this gene would be useful for the detection, treatment, prevention and/or diagnosis of neurodegenerative disease states and behavioural disorders such as Alzheimer's Disease, Parkinson's Disease, Huntington's Disease, Tourette Syndrome, schizophrenia, mania, dementia, paranoia, obsessive compulsive disorder, panic disorder, learning disabilities, ALS, psychoses, autism, and altered behaviors, including disorders in feeding, sleep patterns, balance, and perception. In addition, the gene or gene product may also play a role in the treatment and/or detection of developmental disorders associated with the developing embryo, or sexually-linked disorders. In addition, the tissue distribution in immune system cells and tissues indicates that polynucleotides and polypeptides corresponding to this gene would be useful for the detection, diagnosis, prevention and/or treatment of immune system disorders. Representative uses are described in the "Immune Activity" and "Infectious Disease" sections below, in Example 11, 13, 14, 16, 18, 19, 20, and 27, and elsewhere herein. This gene product may be involved in the regulation of cytokine production, antigen presentation, or other processes that may also suggest a usefulness in the treatment of cancer (e.g., by boosting immune responses). Since the gene is expressed in cells of lymphoid origin, the gene or protein, as well as, antibodies directed against the protein may show utility as a tumor marker and/or immunotherapy targets for the above listed tissues. Therefore it may be also used as an agent for immunological disorders including arthritis, asthma, immune deficiency diseases such as AIDS, leukemia, rheumatoid arthritis, inflammatory bowel disease, sepsis, acne, and psoriasis. In addition, this gene product may have commercial utility in the expansion of stem cells and committed progenitors of various blood lineages, and in the differentiation and/or proliferation of various cell types. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:29 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a-b, where a is any integer between 1 to 1852 of SEQ ID NO:29, b is an integer of 15 to 1866, where both a and b correspond to the positions of nucleotide residues shown in SEQ ID NO:29, and where b is greater than or equal to a +14.

Features of Protein Encoded by Gene No: 20

The translation product of this gene shares weak sequence homology with dehydrogenase enzymes (see, e.g., gn1|PID|e1316908, all references available through this accession are hereby incorporated in their entirety by reference herein) which are thought to be important in a variety of enzymatic conversions, including the biosynthesis of clavulanic acid from a precursor clavulanic acid aldehyde. The obtained clavulanic acid is in turn a key ingredient in antibiotics.

In specific embodiments, polypeptides of the invention comprise, or alternatively consist of, an amino acid sequence selected from the group: DSRISLLVNNAGVGATASLLESDADK (SEQ ID NO:302) and/or MDAMILLNVLALTRLAKAAATNFVAQGRGTIINIGSIVALAPKVLNGVYGGT KAFVQAFSESLQHELSDKGVVVQVVLPGATATEFWDIAGLPVNNLPEAMVM TTENLVXAALAGLAQGEAVTIPSLPDSADWDTYERARLALGPNLSHREPAAR YGLK (SEQ ID NO:303). Moreover, fragments and variants of these polypeptides (such as, for example, fragments as described herein, polypeptides at least 80%, 85%, 90%, 95%, 96%, 97%, 98%, 99%, or 100% identical to these polypeptides, or polypeptides encoded by a polynucleotide which hybridizes, under stringent conditions, to the polynucleotide encoding these polypeptides) are encompassed by the invention. Antibodies that bind polypeptides of the invention and polynucleotides encoding these polypeptides are also encompassed by the invention.

This gene is expressed primarily in CD34 positive hematopoietic cells.

Polynucleotides and polypeptides of the invention would be useful as reagents for differential identification of the tissue(s) or cell type(s) present in a biological sample and for diagnosis of diseases and conditions which include, but are not limited to, hematopoietic diseases and/or disorders; impaired immune function; lymphomas and leukemias. Similarly, polypeptides and antibodies directed to these polypeptides would be useful in providing immunological probes for differential identification of the tissue(s) or cell type(s). For a number of disorders of the above tissues or cells, particularly of the immune system, expression of this gene at significantly higher or lower levels may be routinely detected in certain tissues or cell types (e.g., hematopoietic, cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder. Preferred polypeptides of the present invention comprise, or alternatively consist of, the immunogenic epitopes shown in SEQ ID NO: 137 as residues: Pro-97 to Pro-113. Polynucleotides encoding said polypeptides are encompassed by the invention, as are antibodies that bind one or more of these peptides.

The tissue distribution in CD34 positive hematopoietic cells indicates that polynucleotides and polypeptides corresponding to this gene would be useful for the diagnosis, detection, prevention and/or treatment of a variety of hematopoietic disorders. Expression of this gene product specifically in CD34 positive cells indicates that it plays a role in early events of hematopoiesis, including proliferation; survival; differentiation; and activation of early stem and committed progenitor cells. Polynucleotides and polypeptides corresponding to this gene would be useful for the treatment and diagnosis of hematopoietic related disorders such as anemia, pancytopenia, leukopenia, thrombocytopenia or leukemia since stromal cells are important in the production of cells of hematopoietic lineages. Representative uses are described in the "Immune Activity" and "Infectious Disease" sections below, in Example 11, 13, 14, 16, 18, 19, 20, and 27, and elsewhere herein. Briefly, the uses include bone marrow cell ex-vivo culture, bone marrow transplantation, bone marrow reconstitution, radiotherapy or chemotherapy of neoplasia. The gene product may also be involved in lymphopoiesis, therefore, it can be used in immune disorders such as infection, inflammation, allergy, immunodeficiency etc. In addition, this gene product may have commercial utility in the expansion of stem cells and committed progenitors of various blood lineages, and in the differentiation and/or proliferation of various cell types. Furthermore, the protein may also be used to determine biological activity, to raise antibodies, as tissue markers, to isolate cognate ligands or receptors, to identify agents that modulate their interactions, in addition to its use as a nutritional supplement. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:30 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a-b, where a is any integer between 1 to 1487 of SEQ ID NO:30, b is an integer of 15 to 1501, where both a and b correspond to the positions of nucleotide residues shown in SEQ ID NO:30, and where b is greater than or equal to a +14.

Features of Protein Encoded by Gene No: 21

In specific embodiments, polypeptides of the invention comprise, or alternatively consist of, an amino acid sequence selected from the group: GTPAGTGPEFPGRPTRPSRTE-SAQTTQHSPLRPLWRLKRDSSPCHPQTRADWG VCP-PWGGAAQGLRPGCHLAPRRCLCPGSCCP-WHWAEAQWSFLWRGLWGLR TLPTALRASPAASGTVTYSACLGTSCLLRAPCWRLRT CRQSWC (SEQ ID NO:304), GTPAGTGPEFPGRP-TRPSRTESAQTTQH (SEQ ID NO:305), SPLRPLWR-LKRDSSPCHPQTRADWGVCPPW (SEQ ID NO:306), GGAAQGLRPGCHLAPRRCLCPGSCCPWHWA (SEQ ID NO:307), EAQWSFLWRGLWGLRTLPTAL-RASPAASGT (SEQ ID NO:308), VTYSACLGTSCLL-RAPCWRLRTCRQSWC (SEQ ID NO:309), and/or MPVP-WFLLSLALGRSPVVLSLERLVGPQDATHCSPGLSCRL WDILCLPGDI VPAPGPVLAPTHLQTELVLRCQKETD-CDLCLRVAVHLAVHGHWEEPEDEEK FGGAADLGVEEPRNASLQAQVVLSFQAY-PTARCVLLEVQVPAALVQFGQSV GSVVYD-CFEAALGSEVRIWSYTQPRYEKEL-NHTQQLPDCRGLEVWNSIPSCW ALPWLNVSADGDNVHLVLNVSEEQHF-GLSLYWNQVQGPPKPRWHKNLTGP QIITLNHTDLVP-CLCIQVWPLEPDSVRTNICPFRED-PRAHQNLWQAARLRLLT LQSWLLDAPCSLPAEAALCWRAPGGDPC-QPLVPPLSWENVTVDKVLEFPLLK GHPNLCVQVNS-SEKLQLQECLWADSLGPLKDDV-LLLETRGPQDNRSLCALEP SGCTSLPSKASTRAARLGEYLLQDLQS-GQCLQLWDDDLGALWACPMDKYIH KRWALVWLA-CLLFRRALSLILLLKKDHAKGWLRLLKQDVRSG (SEQ ID NO:310). Moreover, fragments and variants of these polypeptides (such as, for example, fragments as described herein, polypeptides at least 80%, 85%, 90%, 95%, 96%, 97%, 98%, 99%, or 100% identical to these polypeptides, or polypeptides encoded by a polynucleotide which hybridizes, under stringent conditions, to the polynucleotide encoding these polypeptides) are encompassed by the invention. Antibodies that bind polypeptides of the invention and polynucleotides encoding these polypeptides are also encompassed by the invention.

The gene encoding the disclosed cDNA is believed to reside on chromosome 3. Accordingly, polynucleotides related to this invention would be useful as a marker in linkage analysis for chromosome 3.

This gene is expressed primarily in osteoarthritis, breast cancer, and uterine cancer, and, to a lesser extent, in brain.

Polynucleotides and polypeptides of the invention would be useful as reagents for differential identification of the tissue(s) or cell type(s) present in a biological sample and for diagnosis of diseases and conditions which include, but are not limited to, cancer, particularly breast and uterine cancer; and neurological diseases and/or disorders. Similarly, polypeptides and antibodies directed to these polypeptides would be useful in providing immunological probes for differential identification of the tissue(s) or cell type(s). For a number of disorders of the above tissues or cells, particularly of the breast, lymph node, and CNS, expression of this gene at significantly higher or lower levels may be routinely detected in certain tissues or cell types (e.g., reproductive, breast, skeletal, joint, neural, and cancerous and wounded tissues) or bodily fluids (e.g., lymph, serum, plasma, amniotic fluid, urine, synovial fluid and spinal fluid) or another tissue or cell sample taken from an individual having such a disorder, relative to the standard gene expression level, i.e., the expression level in healthy tissue or bodily fluid from an individual not having the disorder. Preferred polypeptides of the present invention comprise, or alternatively consist of the immunogenic epitopes shown in SEQ ID NO: 138 as residues: Gln-75 to Cys-80. Polynucleotides encoding said polypeptides are encompassed by the invention, as are antibodies that bind one or more of these peptides.

The tissue distribution in breast and uterine cancer indicates that polynucleotides and/or polypeptides corresponding to this gene would be useful for the diagnosis, detection, prevention and/or treatment of a variety of cancers, particularly breast cancer and uterine cancer. Expression of this gene in brain also indicates that it may play a role in neurological function, and that its absence may lead to disorders such as Alzheimer's and/or Parkinson's disease. Expression of this gene product at elevated levels within cancerous tissue indicates that it may be a player in the progression of the disease, perhaps by driving proliferation or blocking differentiation or apoptosis. Therefore, beneficial therapeutics may be developed based upon attempts to block this gene product. Representative uses are described in the "Hyperproliferative Disorders" and "Regeneration" sections below and elsewhere herein. Briefly, developmental tissues rely on decisions involving cell differentiation and/or apoptosis in pattern formation. Dysregulation of apoptosis can result in inappropriate suppression of cell death, as occurs in the development of some cancers, or in failure to control the extent of cell death, as is believed to occur in acquired immunodeficiency and certain neurodegenerative disorders, such as spinal muscular atrophy (SMA). Because of potential roles in proliferation and differentiation, polynucleotides and/or polypeptides corresponding to this gene may have applications in the adult for tissue regeneration and the treatment of cancers. It may also act as a morphogen to control cell and tissue type specification. Therefore, the polynucleotides and polypeptides of the present invention would be useful in treating, detecting, and/or preventing said disorders and conditions, in addition to other types of degenerative conditions. Thus this protein may modulate apoptosis or tissue differentiation and would be useful in the detection, treatment, and/or prevention of degenerative or proliferative conditions and diseases. The protein would be useful in modulating the immune response to aberrant polypeptides, as may exist in proliferating and cancerous cells and tissues. The protein can also be used to gain new insight into the regulation of cellular growth and proliferation. Furthermore, the protein may also be used to determine biological activity, to raise antibodies, as tissue markers, to isolate cognate ligands or receptors, to identify agents that modulate their interactions, in addition to its use as a nutritional supplement. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:31 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a-b, where a is any integer between 1 to 1738 of SEQ ID NO:31, b is an integer of 15 to 1752, where both a and b correspond to the positions of nucleotide residues shown in SEQ ID NO:31, and where b is greater than or equal to a +14.

Features of Protein Encoded by Gene No: 22

This gene shares sequence homology with a yeast hypothetical 52.9 KD protein CDC26-YMR31 intergenic region (see, e.g. Genbank Accession No. gp|D506171YSCCHRVI_114; all references available through this accession are hereby incorporated in their entirety by reference herein).

This gene has been mapped to chromosome 18q22-23, and therefore can be used in linkage analysis as a marker for 18q22-23.

This gene is expressed primarily in whole brain tissue, as well as brain specific tissues such as hypothalamus, frontal cortex, cerebellum, amygdala, and hippocampus tissues, as well as other brain specific tissues.

Polynucleotides and polypeptides of the invention would be useful as reagents for differential identification of the tissue(s) or cell type(s) present in a biological sample and for diagnosis of diseases and conditions which include, but are not limited to, schizophrenia, developmental disorders, and abnormal mental states. Similarly, polypeptides and antibodies directed to these polypeptides would be useful in providing immunological probes for differential identification of the tissue(s) or cell type(s). For a number of disorders of the above tissues or cells, particularly of the central nervous system, expression of this gene at significantly higher or lower levels may be routinely detected in certain tissues or cell types (e.g., neural, brain, cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder. Preferred polypeptides of the present invention comprise, or alternatively consist of one, two, three, four, five, six, seven, eight, nine or all ten of the immunogenic epitopes shown in SEQ ID NO: 139 as residues: Met-98 to Gln-107, Gly-120 to Gly-126, Pro-138 to Trp-145, Leu-159 to Gly-169, Val-211 to Arg-217, Cys-256 to His-262, Glu-320 to Val-327, Phe-399 to Asn-406, Asp-444 to Ser-450, Asp-475 to Trp-488. Polynucleotides encoding said polypeptides are encompassed by the invention, as are antibodies that bind one or more of these peptides.

The tissue distribution in whole brain tissue and brain specific tissues indicates that polynucleotides and polypeptides corresponding to this gene would be useful for treating, preventing, detecting and/or diagnosing neural and neurodegenerative disorders. Furthermore, the tissue distribution indicates that polynucleotides and polypeptides corresponding to this gene would be useful for the detection, diagnosis, prevention and/or treatment of neurodegenerative disease states and behavioural disorders such as Alzheimer's Disease, Parkinson's Disease, Huntington's Disease, Tourette Syndrome, schizophrenia, mania, dementia, paranoia, obsessive compulsive disorder, panic disorder, learning disabilities, ALS, psychoses, autism, and altered behaviors, including disorders in feeding, sleep patterns, balance, and perception. In addition, the gene or gene product may also play a role in the treatment and/or detection of developmental disorders associated with the developing embryo, or sexually-linked disorders. Elevated expression of this gene product within the frontal cortex of the brain indicates that it may be involved in neuronal survival; synapse formation; conductance; neural differentiation, etc. Such involvement may impact many processes, such as learning and cognition. Additionally, the amygdala processes sensory information and relays this to other areas of the brain including the endocrine and autonomic domains of the hypothalamus and the brain stem. Thus, polynucleotides and polypeptides corresponding to this gene may also be useful for the detection and/or treatment of neural disorders that impact processes mediated by the amygdala. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:32 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a-b, where a is any integer between 1 to 2138 of SEQ ID NO:32, b is an integer of 15 to 2152, where both a and b correspond to the positions of nucleotide residues shown in SEQ ID NO:32, and where b is greater than or equal to a +14.

Features of Protein Encoded by Gene No: 23

In specific embodiments, polypeptides of the invention comprise, or alternatively consist of, an amino acid sequence selected from the group: PPRPSTSGQWG (SEQ ID NO:311) and/or RRSPFTSAQTG (SEQ ID NO:312). Moreover, fragments and variants of these polypeptides (such as, for example, fragments as described herein, polypeptides at least 80%, 85%, 90%, 95%, 96%, 97%, 98%, 99%, or 100% identical to these polypeptides, or polypeptides encoded by a polynucleotide which hybridizes, under stringent conditions, to the polynucleotide encoding these polypeptides) are encompassed by the invention. Antibodies that bind polypeptides of the invention and polynucleotides encoding these polypeptides are also encompassed by the invention.

The gene encoding the disclosed cDNA is thought to reside on chromosome 1. Accordingly, polynucleotides related to this invention would be useful as a marker in linkage analysis for chromosome 1.

When tested against SKNMC cell lines, supernatants removed from cells containing this gene activated the NFkB promoter element. Thus, it is likely that this gene activates neuroblastoma cells through the NFkB signal transduction pathway. NF-kB (Nuclear Factor kB) is a transcription factor activated by a wide variety of agents, leading to cell activation, differentiation, or apoptosis. Reporter constructs utilizing the NF-kB promoter element are used to screen supernatants for such activity.

This gene is expressed primarily in breast and soleus tissues, and, to a lesser extent, in several cell types, including T-cells.

Polynucleotides and polypeptides of the invention would be useful as reagents for differential identification of the tissue(s) or cell type(s) present in a biological sample and for diagnosis of diseases and conditions which include, but are not limited to, breast cancer, and musculo-skeletal diseases and/or disorders. Similarly, polypeptides and antibodies directed to these polypeptides would be useful in providing immunological probes for differential identification of the tissue(s) or cell type(s). For a number of disorders of the above tissues or cells, particularly of the lactation system and breast, as well as the musculo-skeletal system, expression of this gene at significantly higher or lower levels may be routinely detected in certain tissues or cell types (e.g., musculo-skeletal, breast, cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder. Preferred polypeptides of the present invention comprise, or alternatively consist of one or both of the immunogenic epitopes shown in SEQ ID NO: 140 as residues: Thr-35 to Lys-43, Pro-59 to Arg-64. Polynucleotides encoding said polypeptides are encompassed by the invention, as are antibodies that bind one or more of these peptides.

The tissue distribution in soleus tissue indicates that the protein product of this gene would be useful for the detection, treatment, and/or prevention of conditions and pathologies of the cardiovascular system, such as heart disease, restenosis, atherosclerosis, stoke, angina, thrombosis, and wound healing. Representative uses are described elsewhere herein. Likewise, expression in breast tissue indicates that polynucleotides and/or polypeptides of the invention would be useful for diagnosis, treatment and/or prevention of breast neoplasia and breast cancers, such as fibroadenoma, pipillary carcinoma, ductal carcinoma, Paget's disease, medullary carcinoma, mucinous carcinoma, tubular carcinoma, secretory carcinoma and apocrine carcinoma, as well as juvenile hypertrophy and gynecomastia, mastitis and abscess, duct ectasia, fat necrosis and fibrocystic diseases. Furthermore, the protein may also be used to determine biological activity, to raise antibodies, as tissue markers, to isolate cognate ligands or receptors, to identify agents that modulate their interactions, in addition to its use as a nutritional supplement. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:33 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a-b, where a is any integer between 1 to 1743 of SEQ ID NO:33, b is an integer of 15 to 1757, where both a and b correspond to the positions of nucleotide residues shown in SEQ ID NO:33, and where b is greater than or equal to a +14.

Features of Protein Encoded by Gene No: 24

The gene encoding the disclosed cDNA is believed to reside on chromosome 3. Accordingly, polynucleotides related to this invention would be useful as a marker in linkage analysis for chromosome 3.

In specific embodiments, polypeptides of the invention comprise, or alternatively consist of, an amino acid sequence selected from the group: GTGWDFGLAAVCLRAAEVAGSFK (SEQ ID NO:313), GYRRVFEEYMRVISQRYPDRIEGENYLPQPIYRHIASFLSVFKLVLIGLIIVGK DPFAFFGMQAPSIWQWGQENKVYACMMVFFLSNMIENQCMSTGAFEITLND VPVWSKLESGHLPSMQQLVQILDNEMKLNVHMDSIPHHRS (SEQ ID NO:314), GYRRVFEEYMRVISQRYPDIRIEGENYLPQPIYR (SEQ ID NO:315), HIASFLSVFKLVLIGLIIVGKDPFAFFGMQAPSI (SEQ ID NO:316), WQWGQENKVYACMMVFFLSNMIENQCMSTGAFEI (SEQ ID NO:317), TLNDVPVWSKLESGHLPSMQQLVQILDNEMKLNVHM (SEQ ID NO:318), and/or DSIPHHRS (SEQ ID NO: 298). Moreover, fragments and variants of these polypeptides (such as, for example, fragments as described herein, polypeptides at least 80%, 85%, 90%, 95%, 96%, 97%, 98%, 99%, or 100% identical to these polypeptides, or polypeptides encoded by a polynucleotide which hybridizes, under stringent conditions, to the polynucleotide encoding these polypeptides) are encompassed by the invention. Antibodies that bind polypeptides of the invention and polynucleotides encoding these polypeptides are also encompassed by the invention.

This gene is expressed primarily in fast-growing tissues such as early development stage tissues, cancerous tissues, and hematopoietic tissues, and, to a lesser extent, in some other tissues.

Polynucleotides and polypeptides of the invention would be useful as reagents for differential identification of the tissue(s) or cell type(s) present in a biological sample and for diagnosis of diseases and conditions which include, but are not limited to, growth disorders, tumorigenesis, and immune and inflammatory disorders. Similarly, polypeptides and antibodies directed to these polypeptides would be useful in providing immunological probes for differential identification of the tissue(s) or cell type(s). For a number of disorders of the above tissues or cells, particularly of the fast-growing tissues such as early development stage tissues, cancer tissues, and hematopoietic tissues, expression of this gene at significantly higher or lower levels may be routinely detected in certain tissues or cell types (e.g., cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

The tissue distribution in fast-growing tissues such as early development stage tissues, cancerous tissues, and hematopoietic tissues, indicates that polynucleotides and polypeptides corresponding to this gene would be useful for detection, treatment, and/or prevention of growth disorders, tumorigenesis, and immune and inflammatory disorders. Similarly, the tissue distribution indicates that polynucleotides and polypeptides corresponding to this gene would be useful for the detection, treatment, and/or prevention of cancer and other proliferative disorders. Expression in cellular sources marked by proliferating cells indicates that this protein may play a role in the regulation of cellular division. Additionally, the expression in hematopoietic cells and tissues indicates that polynucleotides and polypeptides corresponding to this gene may play a role in the proliferation, differentiation, and/or survival of hematopoietic cell lineages. In such an event, polynucleotides and polypeptides corresponding to this gene may be useful in the treatment of lymphoproliferative disorders, and in the maintenance and differentiation of various hematopoietic lineages from early hematopoietic stem and committed progenitor cells. Moreover, the expression within embryonic tissue and other cellular sources marked by proliferating cells indicates that polynucleotides and polypeptides corresponding to this gene may play a role in the regulation of cellular division, and may show utility in the diagnosis, treatment, and/or prevention of developmental diseases and disorders, including cancer, and other proliferative conditions. Representative uses are described in the "Hyperproliferative Disorders" and "Regeneration" sections below and elsewhere herein. Briefly, developmental tissues rely on decisions involving cell differentiation and/or apoptosis in pattern formation. Dysregulation of apoptosis can result in inappropriate suppression of cell death, as occurs in the development of some cancers, or in failure to control the extent of cell death, as is believed to occur in acquired immunodeficiency and certain degenerative disorders, such as spinal muscular atrophy (SMA). Alternatively, this gene product may be involved in the pattern of cellular proliferation that accompanies early embryogenesis. Thus, aberrant expression of this gene product in tissues—particularly adult tissues—may correlate with patterns of abnormal cellular proliferation, such as found in various cancers. Because of potential roles in proliferation and differentiation, this gene product may have applications in the adult for tissue regeneration and the treatment of cancers. It may also act as a morphogen to control cell and tissue type specification. Therefore, the polynucleotides and polypeptides of the present invention would be useful in treating, detecting, and/or preventing said disorders and conditions, in addition to other types of degenerative conditions. Thus this protein may modulate apoptosis or tissue differentiation and would be useful in the detection, treatment, and/or prevention of degenerative or proliferative conditions and diseases. The protein would be useful in modulating the immune response to aberrant polypeptides, as may exist in proliferating and cancerous cells and tissues. The protein can also be used to gain new insight into the regulation of cellular growth and proliferation. Furthermore, the protein may also be used to determine biological activity, to raise antibodies, as tissue markers, to isolate cognate ligands or receptors, to identify agents that modulate their interactions, in addition to its use as a nutritional supplement. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:34 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a-b, where a is any integer between 1 to 1452 of SEQ ID NO:34, b is an integer of 15 to 1466, where both a and b correspond to the positions of nucleotide residues shown in SEQ ID NO:34, and where b is greater than or equal to a +14.

Features of Protein Encoded by Gene No: 25

In specific embodiments, polypeptides of the invention comprise, or alternatively consist of, the following amino acid sequence: GRARGRPPGPEAAPASLSVSLRREVHSRGE (SEQ ID NO: 320). Moreover, fragments and variants of these polypeptides (such as, for example, fragments as described herein, polypeptides at least 80%, 85%, 90%, 95%, 96%, 97%, 98%, 99%, or 100% identical to these polypeptides, or polypeptides encoded by a polynucleotide which hybridizes, under stringent conditions, to the polynucleotide encoding these polypeptides) are encompassed by the invention. Antibodies that bind polypeptides of the invention and polynucleotides encoding these polypeptides are also encompassed by the invention.

The polypeptide of this gene has been determined to have a transmembrane domain at about amino acid position 2 to about 18 of the amino acid sequence referenced in Table 1 for this gene. Moreover, a cytoplasmic tail encompassing amino acids 19 to 130 of this protein has also been determined. Based upon these characteristics, it is believed that the protein product of this gene shares structural features to type Ib membrane proteins.

This gene is expressed primarily in olfactory epithelium and prostate.

Polynucleotides and polypeptides of the invention would be useful as reagents for differential identification of the tissue(s) or cell type(s) present in a biological sample and for diagnosis of diseases and conditions which include, but are not limited to, olfactory and prostate disorders and prostate cancer. Similarly, polypeptides and antibodies directed to these polypeptides would be useful in providing immunological probes for differential identification of the tissue(s) or cell type(s). For a number of disorders of the above tissues or cells, particularly of the olfactory system, expression of this gene at significantly higher or lower levels may be routinely detected in certain tissues or cell types (e.g., olfactory, cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder. Preferred polypeptides of the present invention comprise, or alternatively consist of one or both of the immunogenic epitopes shown in SEQ ID NO: 142 as residues: His-24 to Ala-29, Glu-42 to Glu-49. Polynucleotides encoding said polypeptides are encompassed by the invention, as are antibodies that bind one or more of these peptides.

The tissue distribution primarily in the olfactory epithelium indicates a role for polynucleotides and polypeptides corresponding to this gene in the treatment, prevention, detection and/or diagnosis of olfactory and sensory disorders, including loss of the sense of smell. The expression in the prostate tissue indicates that polynucleotides and/or polypeptides of the invention would be useful for diagnosis, treatment and/or prevention of the disorders of the prostate, including inflammatory disorders, such as chronic prostatitis, granulomatous prostatitis and malacoplakia, prostatic hyperplasia and prostate neoplastic disorders, including adenocarcinoma, transitional cell carcinomas, ductal carcinomas, squamous cell carcinomas, or as hormones or factors with systemic or reproductive functions. Furthermore, the protein may also be used to determine biological activity, raise antibodies, as tissue markers, to isolate cognate ligands or receptors, to identify agents that modulate their interactions, in addition to its use as a nutritional supplement. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:35 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a-b, where a is any integer between 1 to 512 of SEQ ID NO:35, b is an integer of 15 to 526, where both a and b correspond to the positions of nucleotide residues shown in SEQ ID NO:35, and where b is greater than or equal to a +14.

Features of Protein Encoded by Gene No: 26

The gene encoding the disclosed cDNA is believed to reside on chromosome 14. Accordingly, polynucleotides related to this invention would be useful as a marker in linkage analysis for chromosome 14.

This gene is expressed primarily in 8 week embryo.

Polynucleotides and polypeptides of the invention would be useful as reagents for differential identification of the tissue(s) or cell type(s) present in a biological sample and for diagnosis of diseases and conditions which include, but are not limited to, developmental disorders. Similarly, polypeptides and antibodies directed to these polypeptides would be useful in providing immunological probes for differential identification of the tissue(s) or cell type(s). For a number of disorders of the above tissues or cells, particularly during fetal development, expression of this gene at significantly higher or lower levels may be routinely detected in certain tissues or cell types (e.g., embryonic, cancerous and wounded tissues) or bodily fluids (e.g., lymph, amniotic fluid, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

The expression of this gene primarily in the embryo, indicates a key role for polynucleotides and polypeptides corresponding to this gene in embryo development and further indicates its usefulness in the treatment and/or detection of embryonic developmental defects. Moreover, the expression within embryonic tissue and other cellular sources marked by proliferating cells indicates that polynucleotides and polypeptides corresponding to this gene may play a role in the regulation of cellular division, and may show utility in the diagnosis, treatment, and/or prevention of developmental diseases and disorders, including cancer, and other proliferative conditions. Representative uses are described in the "Hyperproliferative Disorders" and "Regeneration" sections below and elsewhere herein. Briefly, developmental tissues rely on decisions involving cell differentiation and/or apoptosis in pattern formation. Dysregulation of apoptosis can result in inappropriate suppression of cell death, as occurs in the development of some cancers, or in failure to control the extent of cell death, as is believed to occur in acquired immunodeficiency and certain degenerative disorders, such as spinal muscular atrophy (SMA). Alternatively, polynucleotides and polypeptides corresponding to this gene may be involved in the pattern of cellular proliferation that accompanies early embryogenesis. Thus, aberrant expression of this gene product in tissues—particularly adult tissues—may correlate with patterns of abnormal cellular proliferation, such as found in various cancers. Because of potential roles in proliferation and differentiation, polynucleotides and polypeptides corresponding to this gene may have applications in the adult for tissue regeneration and the treatment of cancers. It may also act as a morphogen to control cell and tissue type specification. Therefore, the polynucleotides and polypeptides of the present invention would be useful in treating, detecting, and/or preventing said disorders and conditions, in addition to other types of degenerative conditions. Thus this protein may modulate apoptosis or tissue differentiation and would be useful in the detection, treatment, and/or prevention of degenerative or proliferative conditions and diseases. The polynucleotides and polypeptides corresponding to this gene would be useful in modulating the immune response to aberrant polypeptides, as may exist in proliferating and cancerous cells and tissues. The protein can also be used to gain new insight into the regulation of cellular growth and proliferation. Furthermore, the protein may also be used to determine biological activity, to raise antibodies, as tissue markers, to isolate cognate ligands or receptors, to identify agents that modulate their interactions, in addition to its use as a nutritional supplement. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:36 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a-b, where a is any integer between 1 to 2398 of SEQ ID NO:36, b is an integer of 15 to 2412, where both a and b correspond to the positions of nucleotide residues shown in SEQ ID NO:36, and where b is greater than or equal to a +14.

Features of Protein Encoded by Gene No: 27

This gene is expressed primarily in neutrophils.

Polynucleotides and polypeptides of the invention would be useful as reagents for differential identification of the tissue(s) or cell type(s) present in a biological sample and for diagnosis of diseases and conditions which include, but are not limited to, disorders affecting the immune system. Similarly, polypeptides and antibodies directed to these polypeptides would be useful in providing immunological probes for differential identification of the tissue(s) or cell type(s). For a number of disorders of the above tissues or cells, particularly of the immune system, expression of this gene at significantly higher or lower levels may be routinely detected in certain tissues or cell types (e.g., immune, cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder. Preferred polypeptides of the present invention comprise, or alternatively consist of one or both of the immunogenic epitopes shown in SEQ ID NO: 144 as residues: Trp-25 to Thr-38, Pro-83 to Ala-88. Polynucleotides encoding said polypeptides are encompassed by the invention, as are antibodies that bind one or more of these peptides.

The tissue distribution in neutrophils indicates that polynucleotides and polypeptides corresponding to this gene would be useful for the diagnosis, detection, prevention and/or treatment of immune system disorders, especially those affecting neutrophils. Furthermore, polynucleotides and polypeptides corresponding to this gene may be involved in the regulation of cytokine production, antigen presentation, or other processes that may also suggest a usefulness in the treatment of cancer (e.g. by boosting immune responses). Since the gene is expressed in cells of lymphoid origin, the gene or protein, as well as, antibodies directed against the protein may show utility as a tumor marker and/or immunotherapy targets for the above listed tissues. Therefore it may be also used as an agent for immunological disorders including arthritis, asthma, immune deficiency diseases such as AIDS, leukemia, rheumatoid arthritis, inflammatory bowel disease, sepsis, acne, and psoriasis. In addition, polynucleotides and polypeptides corresponding to this gene may have commercial utility in the expansion of stem cells and committed progenitors of various blood lineages, and in the differentiation and/or proliferation of various cell types. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:37 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a-b, where a is any integer between 1 to 1260 of SEQ ID NO:37, b is an integer of 15 to 1274, where both a and b correspond to the positions of nucleotide residues shown in SEQ ID NO:37, and where b is greater than or equal to a +14.

Features of Protein Encoded by Gene No: 28

The translation product of this gene shares sequence homology with protein complexes related to clathrin adaptors (see, e.g., AAD43327 (AF155157) which are thought to play a role in signal-mediated trafficking of integral membrane proteins in mammalian cells (see, e.g., Le Borgne and Hoflack, Curr Opin Cell Biol 10:499-503 (1998); all references available through this accession and reference are hereby incorporated by reference herein.) Based on the sequence similarity, the translation product of this clone is expected to share at least some biological activities with protein complexes related to clathrin adaptors. Such activities are known in the art, some of which are described elsewhere herein.

The gene encoding the disclosed cDNA is thought to reside on chromosome 1. Accordingly, polynucleotides related to this invention would be useful as a marker in linkage analysis for chromosome 1.

In specific embodiments, polypeptides of the invention comprise, or alternatively consist of, the following amino acid sequence: QTPFTCTLIHRHACXXPVRXSRVD-PRVRGKQALIWLLGVHGERIPNAPYVLE DFVENVK-SETFPAVKMELLTALLRLFLSRPAECQD-MLGRLLYYCIEEEKDMA VRDRGLFYYRLLLVGIDEVKRILCSPKS-DPTLGLLEDPAERPVNSWASDFNTL VPVYGKAH-WATISKCQGAERCDPELPKTSSFAASG-PLIPEENKERVQELPDSG ALMLVPNRQLTADYFEKTWLSLK-VAHQQVLPWRGEFHPDTLQMALQVVNI QTIAM-SRAGSRPWKAYLSAQDDTGCLFL-TELLLEPGNSEMQISVKQNEARTE TLNSFISVLETVIGTIEEIKS (SEQ ID NO: 321) Moreover, fragments and variants of these polypeptides (such as, for example, fragments as described herein, polypeptides at least 80%, 85%, 90%, 95%, 96%, 97%, 98%, 99%, or 100% identical to these polypeptides, or polypeptides encoded by a polynucleotide which hybridizes, under stringent conditions, to the polynucleotide encoding these polypeptides) are encompassed by the invention. Antibodies that bind polypeptides of the invention and polynucleotides encoding these polypeptides are also encompassed by the invention.

This gene is expressed primarily in fetal liver, immune cells (e.g., eosinophils and T-cells), colon tumor, and brain tissue, and, to a lesser extent, in various other fetal and transformed cell types.

Polynucleotides and polypeptides of the invention would be useful as reagents for differential identification of the tissue(s) or cell type(s) present in a biological sample and for diagnosis of diseases and conditions which include, but are not limited to, immune, developmental and neurological conditions. Similarly, polypeptides and antibodies directed to these polypeptides would be useful in providing immunological probes for differential identification of the tissue(s) or cell type(s). For a number of disorders of the above tissues or cells, particularly of the developing, immune and central nervous systems, expression of this gene at significantly higher or lower levels may be routinely detected in certain tissues or cell types (e.g., immune, developing, neural, cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder. Preferred polypeptides of the present invention comprise, or alternatively consist of one, two, three, four, five or all six of the immunogenic epitopes shown in SEQ ID NO: 145 as residues: Pro-75 to Asn-81, Gln-106 to Cys-111, Glu-130 to Asp-141, Arg-176 to Asp-182, Ala-201 to Trp-206, Lys-238 to Thr-246. Polynucleotides encoding said polypeptides are encompassed by the invention, as are antibodies that bind one or more of these peptides.

The tissue distribution in fetal liver and brain tissues indicates that polynucleotides and polypeptides corresponding to this gene would be useful for the study, detection, diagnosis, prevention and/or treatment of growth disorders and neoplasias of the immune and central nervous systems. The tissue distribution indicates polynucleotides and polypeptides corresponding to this gene would be useful for the detection, treatment, and/or prevention of neurodegenerative disease states, behavioral disorders, or inflammatory conditions. Representative uses are described in the "Regeneration" and "Hyperproliferative Disorders" sections below, in Example 11, 15, and 18, and elsewhere herein. Briefly, the uses include, but are not limited to the detection, treatment, and/or prevention of Alzheimer's Disease, Parkinson's Disease, Huntington's Disease, Tourette Syndrome, meningitis, encephalitis, demyelinating diseases, peripheral neuropathies, neoplasia, trauma, congenital malformations, spinal cord injuries, ischemia and infarction, aneurysms, hemorrhages, schizophrenia, mania, dementia, paranoia, obsessive compulsive disorder, depression, panic disorder, learning disabilities, ALS, psychoses, autism, and altered behaviors, including disorders in feeding, sleep patterns, balance, and perception. In addition, elevated expression of this gene product in regions of the brain indicates it plays a role in normal neural function. Potentially, this gene product is involved in synapse formation, neurotransmission, learning, cognition, homeostasis, or neuronal differentiation or survival. In addition, the gene or gene product may also play a role in the treatment and/or detection of developmental disorders associated with the developing embryo, or sexually-linked disorders. Alternatively, expression of this gene product in fetal liver/spleen tissue indicates a role in the regulation of the proliferation; survival; differentiation; and/or activation of potentially all hematopoietic cell lineages, including blood stem cells. Polynucleotides and polypeptides of the invention may be involved in the regulation of cytokine production, antigen presentation, or other processes that may also suggest a usefulness in the treatment of cancer (e.g., by boosting immune responses). Since the gene is expressed in cells of lymphoid origin, the gene or protein, as well as, antibodies directed against the protein may show utility as a tumor marker and/or immunotherapy targets for the above listed tissues. Therefore it may be also used as an agent for immunological disorders including arthritis, asthma, immune deficiency diseases such as AIDS, leukemia, rheumatoid arthritis, inflammatory bowel disease, sepsis, acne, and psoriasis. In addition, this gene product may have commercial utility in the expansion of stem cells and committed progenitors of various blood lineages, and in the differentiation and/or proliferation of various cell types. Furthermore, the protein may also be used to determine biological activity, to raise antibodies, as tissue markers, to isolate cognate ligands or receptors, to identify agents that modulate their interactions, in addition to its use as a nutritional supplement. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:38 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a-b, where a is any integer between 1 to 1022 of SEQ ID NO:38, b is an integer of 15 to 1036, where both a and b correspond to the positions of nucleotide residues shown in SEQ ID NO:38, and where b is greater than or equal to a +14.

Features of Protein Encoded by Gene No: 29

This gene shares sequence homology to fibulin (see, e.g., GeneSeq Accession No. R11148 and R11149; all references available through these accessions are hereby incorporated in their entirety by reference herein). Fibulin binds to the cytoplasmic domain of the beta-1 subunit of integrin adhesion receptors in a cation-dependent, EDTA-reversible manner. Thus, polynucleotides and polypeptides of the invention may be used to manipulate adhesion of cells to fibronectin, collagen, laminin, and possibly also other proteins.

When tested against both U937 Myeloid cell lines and Jurkat T-cell cell lines, supernatants removed from cells containing this gene activated the GAS assay. Thus, it is likely that this gene activates both T-cells and myeloid cells, and to a lesser extent other tissues and cell types, through the Jak-STAT signal transduction pathway. The gamma activating sequence (GAS) is a promoter element found upstream of many genes which are involved in the Jak-STAT pathway. The Jak-STAT pathway is a large, signal transduction pathway involved in the differentiation and proliferation of cells. Therefore, activation of the Jak-STAT pathway, reflected by the binding of the GAS element, can be used to indicate proteins involved in the proliferation and differentiation of cells.

In specific embodiments, polypeptides of the invention comprise, or alternatively consist of, the following amino acid sequence: CENTEGGYRCIC (SEQ ID NO:322). Moreover, fragments and variants of these polypeptides (such as, for example, fragments as described herein, polypeptides at least 80%, 85%, 90%, 95%, 96%, 97%, 98%, 99%, or 100% identical to these polypeptides, or polypeptides encoded by a polynucleotide which hybridizes, under stringent conditions, to the polynucleotide encoding these polypeptides) are encompassed by the invention. Antibodies that bind polypeptides of the invention and polynucleotides encoding these polypeptides are also encompassed by the invention. This sequence contains an aspartic acid and asparagine hydroxylation site of the consensus sequence: C.[DN].{4}[FY].C.C (D or N is the hydroxylation site). Post-translational hydroxylation of aspartic acid or asparagine to form erythro-beta-hydroxyaspartic acid or erythro-beta-hydroxyasparagine has been identified in a number of proteins with domains homologous to epidermal growth factor (EGF) (see, e.g., Stenflo J., et al., J. Biol. Chem. 263:21-24 (1988)). Examples of such proteins are the blood coagulation protein factors VII, IX and X, proteins C, S, and Z, the LDL receptor, thrombomodulin, etc. Based on sequence comparisons of the EGF-homology region that contains hydroxylated Asp or Asn, a consensus sequence has been identified that seems to be required by the hydroxylase(s). All references are hereby incorporated in their entirety herein by reference.

In specific embodiments, polypeptides of the invention comprise, or alternatively consist of, an amino acid sequence selected from the group: CDCQAGYGGEAC (SEQ ID NO: 323) and/or CICAEGYKQMEGIC (SEQ ID NO: 324). Moreover, fragments and variants of these polypeptides (such as, for example, fragments as described herein, polypeptides at least 80%, 85%, 90%, 95%, 96%, 97%, 98%, 99%, or 100% identical to these polypeptides, or polypeptides encoded by a polynucleotide which hybridizes, under stringent conditions, to the polynucleotide encoding these polypeptides) are encompassed by the invention. Antibodies that bind polypeptides of the invention and polynucleotides encoding these polypeptides are also encompassed by the invention. These sequences contain EGF-like domain signatures (consensus sequence: C.C.{5}G.{2}C or C.C.{2}[GP][FYW].{4,8}C). A sequence of about thirty to forty amino-acid residues long found in the sequence of epidermal growth factor (EGF) has been shown to be present, in a more or less conserved form, in a large number of other, mostly animal proteins. The functional significance of EGF domains in what appear to be unrelated proteins is not yet clear. However, a common feature is that these repeats are found in the extracellular domain of membrane-bound proteins or in proteins known to be secreted. For further information see, e.g., Davis C. G., New Biol. 2:410-419 (1990), Blomquist M. C., et al., Proc. Natl. Acad. Sci. U.S.A. 81:7363-7367 (1984), Barker W. C., et al., Protein Nucl. Acid Enz. 29:54-68 (1986), Doolittle R. F., et al., Nature 307:558-560 (1984), Appella E., et al., FEBS Lett. 231:1-4 (1988), Campbell I. D., et al., Curr. Opin. Struct.

Biol. 3:385-392 (1993), and/or Tamkun J. W., et al., Cell 46:271-282 (1986). All references are hereby incorporated in their entirety herein by reference.

In specific embodiments, polypeptides of the invention comprise, or alternatively consist of, an amino acid sequence selected from the group: DIDECGTEGANCGADQFCVN-TEGSYEC (SEQ ID NO: 325) and/or DVDECETEVCP-GENKQCENTEGGYRC (SEQ ID NO: 326). Moreover, fragments and variants of these polypeptides (such as, for example, fragments as described herein, polypeptides at least 80%, 85%, 90%, 95%, 96%, 97%, 98%, 99%, or 100% identical to these polypeptides, or polypeptides encoded by a polynucleotide which hybridizes, under stringent conditions, to the polynucleotide encoding these polypeptides) are encompassed by the invention. Antibodies that bind polypeptides of the invention and polynucleotides encoding these polypeptides are also encompassed by the invention. These sequences contain Calcium-binding EGF-like domain pattern signatures (consensus sequence: [DEQN].[DEQN] {2}C.{3,14}C.{3,7}C.[DN].{4}[FY].C). A sequence of about forty amino-acid residues long found in the sequence of epidermal growth factor (EGF) has been shown to be present in a large number of membrane-bound and extracellular, mostly animal proteins. Many of these proteins require calcium for their biological function and a calcium-binding site has been found to be located at the N-terminus of some EGF-like domains. Calcium-binding may be crucial for numerous protein-protein interactions. Some proteins that are known or that are predicted to contain calcium-binding EGF-like domains include: Bone morphogenic protein 1 (BMP-1), Calcium-dependent serine proteinase (CASP), Cartilage oligomeric matrix protein COMP, Coagulation factors VII, IX, and X, Fibrillin 1 and fibrillin 2, and Leucocyte antigen. For references see: New Biol. 2:410-419 (1990), Blomquist M. C., et al., Proc. Natl. Acad. Sci. U.S.A. 81:7363-7367 (1984), Barker W. C., et al., Protein Nucl. Acid Enz. 29:54-68 (1986), Doolittle R. F., et al., Nature 307:558-560 (1984), Appella E., et al., FEBS Lett. 231:1-4 (1988) Campbell I. D., et al., Curr. Opin. Struct. Biol. 3:385-392 (1993), Rao Z., et al., Cell 82:131-141 (1995), et al., J. Biol. Chem. 267:19642-19649 (1992). All references are hereby incorporated in their entirety herein by reference.

In specific embodiments, polypeptides of the invention comprise, or alternatively consist of, the following amino acid sequence: CDCQAGYGGEACGQCGLGYFEAER-NASHLVCSAC (SEQ ID NO: 327). Moreover, fragments and variants of these polypeptides (such as, for example, fragments as described herein, polypeptides at least 80%, 85%, 90%, 95%, 96%, 97%, 98%, 99%, or 100% identical to these polypeptides, or polypeptides encoded by a polynucleotide which hybridizes, under stringent conditions, to the polynucleotide encoding these polypeptides) are encompassed by the invention. Antibodies that bind polypeptides of the invention and polynucleotides encoding these polypeptides are also encompassed by the invention. This sequence contains a Laminin-type EGF-like (LE) domain signature (consensus sequence: C-x(1,2)-C-x(5)-G-x(2)-C-x(2)-C-x(3,4)-[FYW]-x(3,15)-C). Laminins (see, e.g., Beck K., et al., FASEB J. 4:148-160 (1990)) are the major noncollagenous components of basement membranes that mediate cell adhesion, growth migration, and differentiation. They are composed of distinct but related alpha, beta and gamma chains. The three chains form a cross-shaped molecule that consist of a long arm and three short globular arms. The long arm consist of a coiled coil structure contributed by all three chains and cross-linked by interchain disulfide bonds. Beside different types of globular domains each subunit contains, in its first half, consecutive repeats of about 60 amino acids in length that include eight conserved cysteines (see, e.g., Engel J., FEBS Lett. 251:1-7 (1989)). The tertiary structure (see, e.g, Stetefeld J., et al., J. Mol. Biol. 257:644-657 (1996) Baumgartner R., et al., J. Mol. Biol. 257:658-668 (1996)) of this domain is remotely similar in its N-terminal to that of the EGF-like module. It is known as a 'LE' or 'laminin-type EGF-like' domain. The number of copies of the LE domain in the different forms of laminins is highly variable; from 3 up to 22 copies have been found. All references are hereby incorporated in their entirety herein by reference.

The gene encoding the disclosed cDNA is thought to reside on chromosome 3. Accordingly, polynucleotides related to this invention would be useful as a marker in linkage analysis for chromosome 3.

This gene is expressed primarily in cerebellum tissue, and, to a lesser extent, in multiple tissues and cell types including prostate, liver, T-cells, kidney, and lung tissues, as well as musculo-skeletal tissues such as endothelial tissue, healing groin wound tissue, fetal heart tissue, and osteosarcoma tissue.

Polynucleotides and polypeptides of the invention would be useful as reagents for differential identification of the tissue(s) or cell type(s) present in a biological sample and for diagnosis of diseases and conditions which include, but are not limited to, diseases and/or disorders of the central nervous system, including dementia, mood disorders, both unipolar and bipolar depression, and Alzheimer's disease, as well as disorders of the musculo-skeletal, renal, and pulmonary systems. Similarly, polypeptides and antibodies directed to these polypeptides would be useful in providing immunological probes for differential identification of the tissue(s) or cell type(s). For a number of disorders of the above tissues or cells, particularly of the central nervous system, renal, pulmonary system, and musculo-skeletal system, expression of this gene at significantly higher or lower levels may be routinely detected in certain tissues or cell types (e.g., neural, musculo-skeletal, cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder. Preferred polypeptides of the present invention comprise, or alternatively consist of one, two, three, four, five, six, seven, eight, nine ten, eleven, twelve, thirteen, fourteen, or all fifteen of the immunogenic epitopes shown in SEQ ID NO: 146 as residues: Pro-28 to Thr-45, Arg-59 to Gly-67, Ala-71 to Glu-84, Lys-120 to Asp-126, Pro-159 to Gly-164, Glu-167 to Gly-186, Arg-217 to Asn-225, Glu-245 to Ala-255, Gly-282 to Gly-297, Pro-312 to Gly-324, Thr-356 to Lys-364, Gly-366 to Thr-372, Lys-377 to Ala-383, Gly-397 to Thr-407, Thr-419 to Gly-433. Polynucleotides encoding said polypeptides are encompassed by the invention, as are antibodies that bind one or more of these peptides.

The tissue distribution indicates that polynucleotides and polypeptides corresponding to this gene would be useful for the diagnosis, detection, prevention and/or treatment of a variety of cancers, most notably cancers of the central nervous system, pulmonary, and renal systems, as well as the disorders of the central nervous system listed above. Representative uses are described in the "Hyperproliferative Diseases", "Chemotaxis" and "Binding Activity" sections below, in Examples 11, 12, 13, 14, 15, 16, 18, 19, and 20, and elsewhere herein. Briefly, the expression of this gene product in a variety of systems indicates that polynucleotides and polypeptides corresponding to this gene may be a player in the progression of these diseases, and may be a beneficial target for inhibitors as therapeutics. Alternatively, the tissue distribution in musculo-skeletal tissues, as the homology to fibulin, indicates that polynucleotides and polypeptides corresponding to this gene would be useful for the detection, diagnosis, prevention and/or treatment of disorders involving the vasculature. Elevated expression of this gene product by endothelial cells indicates that it may play vital roles in the regulation of endothelial cell function; secretion; proliferation; or angiogenesis. Alternately, this may represent a gene product expressed by the endothelium and transported to distant sites of action on a variety of target organs. Furthermore, the protein may also be used to determine biological activity, to raise antibodies, as tissue markers, to isolate cognate ligands or receptors, to identify agents that modulate their interactions, in addition to its use as a nutritional supplement. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:39 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a-b, where a is any integer between 1 to 1365 of SEQ ID NO:39, b is an integer of 15 to 1379, where both a and b correspond to the positions of nucleotide residues shown in SEQ ID NO:39, and where b is greater than or equal to a +14.

Features of Protein Encoded by Gene No: 30

The translation product of this gene shares sequence homology with coxsackie and adenovirus receptor in mouse. Particularly, this gene shares sequence homology with a human A33 antigen, which is a transmembrane protein and a novel member of the immunoglobulin superfamily. (see, e.g., Proc. Natl. Acad. Sci. U.S.A. 94, 469-474 (1997); see also, Accession No. 1814277; all references available through the accession and reference are hereby incorporated herein by reference.) Therefore, this gene likely has activity similar to the human A33 antigen.

In specific embodiments, polypeptides of the invention comprise, or alternatively consist of, an amino acid sequence selected from the group: MISLPGPLVTNLLRFLFLGLSALAPPSRAQLQLHLPANRLQAVEGGEVVLPAW YTLHGEVSSSQPWEVPFVMWFFKQKEKEDQVLSYINGVTTSKPGVSLVYSMP SRNLSLRLEGLQEKDSGPYSCSVNVQNKQGKSRGHSIKTLELNVLVPPAPPSC RLQGVPHVGANVTLSCQSPRSKPAVQYQWDRQLPSFQTFFAPALDVIRGSLS LTNLSSSMAGVYVCKAHNEVGTAQCNVTLEVSTGPGAAVVAGAVVGTLVG LGLLAGLVLLYHRRGKALEEPANDIKEDAIAPRTLPWPKSSDTISKNGTLSSV TSARALRPPHGPPRPGALTPTPSLSSQALPSPRLPTTDGAHPQPISPIPGGVSSSG LSRMGAVPVMVPAQSQAGSL (SEQ ID NO:328), MISLPGPLVTNLLRFLFLGLSALAPPSRAQLQLHL (SEQ ID NO:329), PANRLQAVEGGEVVLPAWYTLHGEVSSSQPWEVPF (SEQ ID NO:330), VMWFFKQKEKEDQVLSYINGVTTSKPGVSLVYSMP (SEQ ID NO:331), SRNLSLRLEGLQEKDSGPYSCSVNVQNKQGKSRGH (SEQ ID NO:332), SIKTLELNVLVPPAPPSCRLQGVPHVGANVTLSCQ (SEQ ID NO:333), SPRSKPAVQYQWDRQLPSFQTFFAPALDVIRGSLS (SEQ ID NO:334), LTNLSSSMAGVYVCKAHNEVGTAQCNVTLEVSTGP (SEQ ID NO:335), GAAVVAGAVVGTLVGLGLLAGLVLLYHRRGKALEE (SEQ ID NO:336), PANDIKEDAIAPRTLPWPKSSDTISKNGTLSSVTS (SEQ ID NO:337), ARALRPPHGPPRPGALTPTPSLSSQALPSPRLPTT (SEQ ID NO:338), and/or DGAHPQPISPIPGGVSSSGLSRMGAVPVMVPAQSQAGSL (SEQ ID NO:339). Moreover, fragments and variants of these polypeptides (such as, for example, fragments as described herein, polypeptides at least 80%, 85%, 90%, 95%, 96%, 97%, 98%, 99%, or 100% identical to these polypeptides, or polypeptides encoded by a polynucleotide which hybridizes, under stringent conditions, to the polynucleotide encoding these polypeptides) are encompassed by the invention. Antibodies that bind polypeptides of the invention and polynucleotides encoding these polypeptides are also encompassed by the invention.

The translated product of this gene also shares some homology with a mouse basement membrane proteoglycan (see, e.g., GenBank Accession AAA39911.1 and Noonan, D. M., et al., J. Biol. Chem. 266, 22939-22947 (1991); all references available through this citation are hereby incorporated herein by reference). Based on the sequence similarity, the translation product of this clone is expected to share at least some biological activities with extracellular basement membrane proteoglcans. Such activities are known in the art, some of which are described elsewhere herein.

In specific embodiments, polypeptides of the invention comprise, or alternatively consist of, the following amino acid sequence: LSLTNLSSSMAGVYVCKAHNEVGTAQCNVTLEVSTG (SEQ ID NO: 340). Moreover, fragments and variants of these polypeptides (such as, for example, fragments as described herein, polypeptides at least 80%, 85%, 90%, 95%, 96%, 97%, 98%, 99%, or 100% identical to these polypeptides, or polypeptides encoded by a polynucleotide which hybridizes, under stringent conditions, to the polynucleotide encoding these polypeptides) are encompassed by the invention. Antibodies that bind polypeptides of the invention and polynucleotides encoding these polypeptides are also encompassed by the invention.

Contact of cells with supernatant expressing the product of this gene has been shown to increase the permeability of the plasma membrane of THP-1 cell lines to calcium. Thus it is likely that the product of this gene is involved in a signal transduction pathway that is initiated when the product binds a receptor on the surface of the plasma membrane of both monocytes, and to a lesser extent, other immune and hematopoietic cells. Thus, polynucleotides and polypeptides have uses which include, but are not limited to, activating monocytes. Binding of a ligand to a receptor is known to alter intracellular levels of small molecules, such as calcium, potassium and sodium, as well as alter pH and membrane potential. Alterations in small molecule concentration can be measured to identify supernatants which bind to receptors of a particular cell.

This gene is expressed in various tissues including placenta, brain, heart, muscle, adipocytes, and liver.

Polynucleotides and polypeptides of the invention would be useful as reagents for differential identification of the tissue(s) or cell type(s) present in a biological sample and for diagnosis of diseases and conditions: viral diseases, and immune diseases and/or disorders. Similarly, polypeptides and antibodies directed to those polypeptides would be useful to provide immunological probes for differential identification of the tissue(s) or cell type(s). For a number of disorders of the above tissues or cells, particularly of the immune system and central nervous system, expression of this gene at significantly higher or lower levels may be routinely detected in certain tissues or cell types (e.g., CNS, reproductive, vascular, cancerous and wounded tissues) or bodily fluids (e.g., lymph, amniotic fluid, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

The tissue distribution in various tissues including placenta, brain, heart, muscle, adipocytes, and liver, and the homology to A33 antigen indicates that polynucleotides and polypeptides corresponding to this gene would be useful for the diagnosis, detection, prevention and/or treatment of a variety of cancers, most notably cancers of the immune system, as well as viral infections. Expression of this gene product indicates that polynucleotides and polypeptides corresponding to this gene may be a player in the progression of these diseases, and may be a beneficial target for inhibitors as therapeutics. Representative uses are described in the "Chemotaxis" and "Binding Activity" sections below, in Examples 11, 12, 13, 14, 15, 16, 18, 19, and 20, and elsewhere herein. Furthermore, the protein may also be used to determine biological activity, to raise antibodies, as tissue markers, to isolate cognate ligands or receptors, to identify agents that modulate their interactions, in addition to its use as a nutritional supplement. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:40 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a-b, where a is any integer between 1 to 1918 of SEQ ID NO:40, b is an integer of 15 to 1932, where both a and b correspond to the positions of nucleotide residues shown in SEQ ID NO:40, and where b is greater than or equal to a +14.

Features of Protein Encoded by Gene No: 31

In specific embodiments, polypeptides of the invention comprise, or alternatively consist of, an amino acid sequence selected from the group:GSSFVVSEGSYLDISDWLNPAKLSLYY (SEQ ID NO:341), LDISDWLNPAKL (SEQ ID NO:342), SDWLNPAKLSL (SEQ ID NO:343), and/or DACEQLCDPETGE (SEQ ID NO:344). Moreover, fragments and variants of these polypeptides (such as, for example, fragments as described herein, polypeptides at least 80%, 85%, 90%, 95%, 96%, 97%, 98%, 99%, or 100% identical to these polypeptides, or polypeptides encoded by a polynucleotide which hybridizes, under stringent conditions, to the polynucleotide encoding these polypeptides) are encompassed by the invention. Antibodies that bind polypeptides of the invention and polynucleotides encoding these polypeptides are also encompassed by the invention.

This gene is expressed primarily in human ovary and adrenal gland tissues.

Polynucleotides and polypeptides of the invention would be useful as reagents for differential identification of the tissue(s) or cell type(s) present in a biological sample and for diagnosis of diseases and conditions which include, but are not limited to, reproductive diseases and/or disorders, particularly ovarian cancer. Similarly, polypeptides and antibodies directed to these polypeptides would be useful in providing immunological probes for differential identification of the tissue(s) or cell type(s). For a number of disorders of the above tissues or cells, particularly of the reproductive system, expression of this gene at significantly higher or lower levels may be routinely detected in certain tissues or cell types (e.g., reproductive, and cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

The tissue distribution in ovary tissue indicates that polynucleotides and polypeptides corresponding to this gene would be useful for diagnosing and/or treating reproductive system disorders including ovarian cancer, as well as cancers of other tissues where expression has been observed. Representative uses are described in the "Hyperproliferative Disorders" and "Regeneration" sections below and elsewhere herein. Expression in ovarian tissue, indicates that polynucleotides and polypeptides corresponding to this gene would be useful for the treatment, prevention, detection and diagnosis of conditions concerning proper ovarian function (e.g., egg maturation, endocrine function), as well as cancer. The expression in ovarian tissue may indicate the gene or its products can be used to treat, prevent, detect and/or diagnose disorders of the ovary, including inflammatory disorders, such as oophoritis (e.g., caused by viral or bacterial infection), ovarian cysts, amenorrhea, infertility, hirsutism, and ovarian cancer (including, but not limited to, primary and secondary cancerous growth, endometrioid carcinoma of the ovary, ovarian papillary serous adenocarcinoma, ovarian mucinous adenocarcinoma, Ovarian Krukenberg tumor). Furthermore, the protein may also be used to determine biological activity, to raise antibodies, as tissue markers, to isolate cognate ligands or receptors, to identify agents that modulate their interactions, in addition to its use as a nutritional supplement. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:41 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a-b, where a is any integer between 1 to 1416 of SEQ ID NO:41, b is an integer of 15 to 1430, where both a and b correspond to the positions of nucleotide residues shown in SEQ ID NO:41, and where b is greater than or equal to a +14.

Features of Protein Encoded by Gene No: 32

This gene is expressed primarily in thymus and stromal cells.

Polynucleotides and polypeptides of the invention would be useful as reagents for differential identification of the tissue(s) or cell type(s) present in a biological sample and for diagnosis of diseases and conditions which include, but are not limited to, aberrant immune responses, such as either chronic or acute inflammation. Similarly, polypeptides and antibodies directed to these polypeptides would be useful in providing immunological probes for differential identification of the tissue(s) or cell type(s). For a number of disorders of the above tissues or cells, particularly of the immune system, expression of this gene at significantly higher or lower levels may be routinely detected in certain tissues or cell types (e.g., immune, cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

The tissue distribution in thymus stromal cells indicates that polynucleotides and polypeptides corresponding to this gene would be useful for diagnosing, detecting, preventing and/or treating disorders of the immune system, particularly those involving a pathological inflammatory response. Representative uses are described in the "Immune Activity" and "Infectious Disease" sections below, in Example 11, 13, 14, 16, 18, 19, 20, and 27, and elsewhere herein. Furthermore, the gene product may also be involved in lymphopoiesis, therefore, it can be used in immune disorders such as infection, inflammation, allergy, immunodeficiency etc. In addition, polynucleotides and polypeptides corresponding to this gene may have commercial utility in the expansion of stem cells and committed progenitors of various blood lineages, and in the differentiation and/or proliferation of various cell types. Furthermore, the protein may also be used to determine biological activity, to raise antibodies, as tissue markers, to isolate cognate ligands or receptors, to identify agents that modulate their interactions, in addition to its use as a nutritional supplement. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:42 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a-b, where a is any integer between 1 to 1393 of SEQ ID NO:42, b is an integer of 15 to 1407, where both a and b correspond to the positions of nucleotide residues shown in SEQ ID NO:42, and where b is greater than or equal to a +14.

Features of Protein Encoded by Gene No: 33

In specific embodiments, polypeptides of the invention comprise, or alternatively consist of, the following amino acid sequence: EGKIKICEKKAIKVILHTCNS (SEQ ID NO: 345). Moreover, fragments and variants of these polypeptides (such as, for example, fragments as described herein, polypeptides at least 80%, 85%, 90%, 95%, 96%, 97%, 98%, 99%, or 100% identical to these polypeptides, or polypeptides encoded by a polynucleotide which hybridizes, under stringent conditions, to the polynucleotide encoding these polypeptides) are encompassed by the invention. Antibodies that bind polypeptides of the invention and polynucleotides encoding these polypeptides are also encompassed by the invention.

This gene is expressed primarily in frontal cortex.

Polynucleotides and polypeptides of the invention would be useful as reagents for differential identification of the tissue(s) or cell type(s) present in a biological sample and for diagnosis of diseases and conditions which include, but are not limited to, central nervous system (CNS) diseases and/or disorders. Similarly, polypeptides and antibodies directed to these polypeptides would be useful in providing immunological probes for differential identification of the tissue(s) or cell type(s). For a number of disorders of the above tissues or cells, particularly of the CNS, expression of this gene at significantly higher or lower levels may be routinely detected in certain tissues or cell types (e.g., brain, cancerous and wounded tissues) or bodily fluids (e.g., lymph, serum, plasma, urine, synovial fluid or cerebrospinal fluid) or another tissue or cell sample taken from an individual having such a disorder, relative to the standard gene expression level, i.e., the expression level in healthy tissue or bodily fluid from an individual not having the disorder. Preferred polypeptides of the present invention comprise, or alternatively consist of the immunogenic epitopes shown in SEQ ID NO: 150 as residues: Pro-41 to Asp-47. Polynucleotides encoding said polypeptides are encompassed by the invention, as are antibodies that bind one or more of these peptides.

The tissue distribution in frontal cortex indicates that polynucleotides and polypeptides corresponding to this gene would be useful for detection, treatment, and/or prevention of CNS disorders including disorders of the brain and nervous system. Representative uses are described in the "Regeneration" and "Hyperproliferative Disorders" sections below, in Example 11, 15, and 18, and elsewhere herein. Elevated expression of this gene product within the frontal cortex of the brain indicates that it may be involved in neuronal survival, synapse formation, conductance, neural differentiation, etc. Such involvement may impact many processes, such as learning and cognition. It may also be useful in the treatment of such neurodegenerative disorders as schizophrenia, ALS, or Alzheimer's. Furthermore, the protein may also be used to determine biological activity, to raise antibodies, as tissue markers, to isolate cognate ligands or receptors, to identify agents that modulate their interactions, in addition to its use as a nutritional supplement. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:43 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a-b, where a is any integer between 1 to 936 of SEQ ID NO:43, b is an integer of 15 to 950, where both a and b correspond to the positions of nucleotide residues shown in SEQ ID NO:43, and where b is greater than or equal to a +14.

Features of Protein Encoded by Gene No: 34

This gene is expressed primarily in adipose tissue, human embryo, and neutrophils.

Polynucleotides and polypeptides of the invention would be useful as reagents for differential identification of the tissue(s) or cell type(s) present in a biological sample and for diagnosis of diseases and conditions which include, but are not limited to, obesity, Nasu-Hakola disease, cardiovascular disease, non-insulin-dependent diabetes mellitus. Similarly, polypeptides and antibodies directed to these polypeptides would be useful in providing immunological probes for differential identification of the tissue(s) or cell type(s). For a number of disorders of the above tissues or cells, particularly of the adipose, expression of this gene at significantly higher or lower levels may be routinely detected in certain tissues or cell types (e.g., adipose, cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

The tissue distribution in adipose indicates that polynucleotides and polypeptides corresponding to this gene would be useful for the treatment, prevention, detection and diagnosis of metabolic disorders related to lipids and adipose tissue, such as obesity, Nasu-Hakola disease (membranous lipodystrophy), cardiovascular disease, lipidemia, non-insulin-dependent diabetes mellitus, stroke and carcinoma. The tissue distribution in neutrophils indicates polynucleotides and polypeptides corresponding to this gene would be useful for the diagnosis and treatment of a variety of immune system disorders. Representative uses are described in the "Immune Activity" and "Infectious Disease" sections below, in Example 11, 13, 14, 16, 18, 19, 20, and 27, and elsewhere herein. Briefly, the expression indicates a role in regulating the proliferation; survival; differentiation; and/or activation of hematopoietic cell lineages, including blood stem cells. Involvement in the regulation of cytokine production, antigen presentation, or other processes indicates a usefulness for treatment of cancer (e.g., by boosting immune responses). Expression in cells of lymphoid origin, indicates the natural gene product would be involved in immune functions. Therefore it would also be useful as an agent for immunological disorders including arthritis, asthma, immunodeficiency diseases such as AIDS, leukemia, rheumatoid arthritis, granulomatous disease, inflammatory bowel disease, sepsis, acne, neutropenia, neutrophilia, psoriasis, hypersensitivities, such as T-cell mediated cytotoxicity; immune reactions to transplanted organs and tissues, such as host-versus-graft and graft-versus-host diseases, or autoimmunity disorders, such as autoimmune infertility, lense tissue injury, demyelination, systemic lupus erythematosis, drug induced hemolytic anemia, rheumatoid arthritis, Sjogren's disease, and scleroderma. Moreover, the protein may represent a secreted factor that influences the differentiation or behavior of other blood cells, or that recruits hematopoietic cells to sites of injury. Thus, polynucleotides and polypeptides corresponding to this gene are thought to be useful in the expansion of stem cells and committed progenitors of various blood lineages, and in the differentiation and/or proliferation of various cell types. Moreover, the expression within embryonic tissue and other cellular sources marked by proliferating cells indicates that polynucleotides and polypeptides corresponding to this gene may play a role in the regulation of cellular division, and may show utility in the diagnosis, treatment, and/or prevention of developmental diseases and disorders, including cancer, and other proliferative conditions. Representative uses are described in the "Hyperproliferative Disorders" and "Regeneration" sections below and elsewhere herein. Briefly, developmental tissues rely on decisions involving cell differentiation and/or apoptosis in pattern formation. Dysregulation of apoptosis can result in inappropriate suppression of cell death, as occurs in the development of some cancers, or in failure to control the extent of cell death, as is believed to occur in acquired immunodeficiency and certain degenerative disorders, such as spinal muscular atrophy (SMA). Alternatively, this gene product may be involved in the pattern of cellular proliferation that accompanies early embryogenesis. Thus, aberrant expression of this gene product in tissues—particularly adult tissues—may correlate with patterns of abnormal cellular proliferation, such as found in various cancers. Because of potential roles in proliferation and differentiation, this gene product may have applications in the adult for tissue regeneration and the treatment of cancers. It may also act as a morphogen to control cell and tissue type specification. Therefore, the polynucleotides and polypeptides of the present invention would be useful in treating, detecting, and/or preventing said disorders and conditions, in addition to other types of degenerative conditions. Thus polynucleotides and polypeptides corresponding to this gene may modulate apoptosis or tissue differentiation and would be useful in the detection, treatment, and/or prevention of degenerative or proliferative conditions and diseases. The polynucleotides and polypeptides corresponding to this gene would be useful in modulating the immune response to aberrant polypeptides, as may exist in proliferating and cancerous cells and tissues. The protein can also be used to gain new insight into the regulation of cellular growth and proliferation. Furthermore, the protein may also be used to determine biological activity, to raise antibodies, as tissue markers, to isolate cognate ligands or receptors, to identify agents that modulate their interactions, in addition to its use as a nutritional supplement. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:44 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a-b, where a is any integer between 1 to 990 of SEQ ID NO:44, b is an integer of 15 to 1004, where both a and b correspond to the positions of nucleotide residues shown in SEQ ID NO:44, and where b is greater than or equal to a +14.

Features of Protein Encoded by Gene No: 35

In specific embodiments, polypeptides of the invention comprise, or alternatively consist of, the following amino acid sequence: NSARVEFFIPPLRITQKVRSTKS (SEQ ID NO:346). Moreover, fragments and variants of these polypeptides (such as, for example, fragments as described herein, polypeptides at least 80%, 85%, 90%, 95%, 96%, 97%, 98%, 99%, or 100% identical to these polypeptides, or polypeptides encoded by a polynucleotide which hybridizes, under stringent conditions, to the polynucleotide encoding these polypeptides) are encompassed by the invention. Antibodies that bind polypeptides of the invention and polynucleotides encoding these polypeptides are also encompassed by the invention.

This gene is apparently expressed primarily in IL-1- and LPS-induced neutrophils.

Polynucleotides and polypeptides of the invention would be useful as reagents for differential identification of the tissue(s) or cell type(s) present in a biological sample and for diagnosis of diseases and conditions which include, but are not limited to, abnormal immune reactions or disorders including, but not limited to, chronic or cyclic neutropenia, neutrophilia, and neutrocytosis. Similarly, polypeptides and antibodies directed to these polypeptides would be useful in providing immunological probes for differential identification of the tissue(s) or cell type(s). For a number of disorders of the above tissues or cells, particularly of the immune system, expression of this gene at significantly higher or lower levels may be routinely detected in certain tissues or cell types (e.g., immune, cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

The tissue distribution in neutrophils indicates that polynucleotides and polypeptides corresponding to this gene would be useful for detection, treatment, and/or prevention of immune disorders or abnormal reactions mediated by neutrophils, including infection, inflammation, allergy, immunodeficiency, chronic or cyclic neutropenia, neutrophilia, and neutrocytosis, and the like. Representative uses are described in the "Immune Activity" and "Infectious Disease" sections below, in Example 11, 13, 14, 16, 18, 19, 20, and 27, and elsewhere herein. Moreover, the expression of this gene product indicates a role in regulating the proliferation, survival, differentiation, and/or activation of hematopoietic cell lineages, including blood stem cells. Polynucleotides and polypeptides corresponding to this gene may be involved in the regulation of cytokine production, antigen presentation, or other processes that may also suggest a usefulness in the treatment of cancer (e.g., by boosting immune responses). Since the gene is expressed in cells of lymphoid origin, the natural gene product may be involved in immune functions. Therefore it may be also used as an agent for immunological disorders including arthritis, asthma, immunodeficiency diseases such as AIDS, leukemia, rheumatoid arthritis, granulomatous disease, inflammatory bowel disease, sepsis, acne, neutropenia, neutrophilia, psoriasis, hypersensitivities, such as T-cell mediated cytotoxicity, immune reactions to transplanted organs and tissues, such as host-versus-graft and graft-versus-host diseases, or autoimmunity disorders, such as autoimmune infertility, lense tissue injury, demyelination, systemic lupus erythematosis, drug induced hemolytic anemia, rheumatoid arthritis, Sjogren's disease, scleroderma and tissues. In addition, polynucleotides and polypeptides corresponding to this gene may have commercial utility in the expansion of stem cells and committed progenitors of various blood lineages, and in the differentiation and/or proliferation of various cell types. Furthermore, the protein may also be used to determine biological activity, raise antibodies, as tissue markers, to isolate cognate ligands or receptors, to identify agents that modulate their interactions, in addition to its use as a nutritional supplement. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:45 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a-b, where a is any integer between 1 to 1667 of SEQ ID NO:45, b is an integer of 15 to 1681, where both a and b correspond to the positions of nucleotide residues shown in SEQ ID NO:45, and where b is greater than or equal to a +14.

Features of Protein Encoded by Gene No: 36

The translated ORF of the contig has homology with the human, porcine, and bovine INS10 double-chain insulin precursor, especially around a region containing multiple cysteine residues.

In specific embodiments, polypeptides of the invention comprise, or alternatively consist of, an amino acid sequence selected from the group: MMVWNLFPCFPPLLLLQFIDCQQSSEIEQGFTRSLLGHPIFFCPDPCWQSCMN CVILSVLSFFFLIRWISKIVAVQK-LESSSRRKPILFLIISCEIASFIHLFLSQMSAEC CCFYLVILICKY (SEQ ID NO:347), MMVWNLFPCFP-PLLLLQFIDCQQSSEIE (SEQ ID NO:348), QGFTRSLLGHPIFFCPDPCWQSCMNCVI (SEQ ID NO:349), LSVLSFFFLIRWISKIVAVQKLESSSR-RKPILFLI (SEQ ID NO:350), and/or ISCEIAS-FIHLFLSQMSAECCCFYLVILICKY (SEQ ID NO:351). Moreover, fragments and variants of these polypeptides (such as, for example, fragments as described herein, polypeptides at least 80%, 85%, 90%, 95%, 96%, 97%, 98%, 99%, or 100% identical to these polypeptides, or polypeptides encoded by a polynucleotide which hybridizes, under stringent conditions, to the polynucleotide encoding these polypeptides) are encompassed by the invention. Antibodies that bind polypeptides of the invention and polynucleotides encoding these polypeptides are also encompassed by the invention.

The polypeptide of this gene has been determined to have a transmembrane domain at about amino acid position 50 to about 66 of the amino acid sequence referenced in Table 1 for this gene. Moreover, a cytoplasmic tail encompassing amino acids 67 to 90 of this protein has also been determined. Based upon these characteristics, it is believed that the protein product of this gene shares structural features to type Ia membrane proteins.

The gene encoding the disclosed cDNA is believed to reside on chromosome 21. Accordingly, polynucleotides related to this invention would be useful as a marker in linkage analysis for chromosome 21.

This gene is expressed primarily in cells and tissues isolated from a 15 days post-incision healing abdomen wound and, to a lesser extent, in many immune tissues (e.g., T-cells and B-cells) and connective tissues/cells with proliferative capacity, such as osteoclastoma, ovarian cancer, B-cell lymphoma and hepatocellular tumor.

Polynucleotides and polypeptides of the invention would be useful as reagents for differential identification of the tissue(s) or cell type(s) present in a biological sample and for diagnosis of diseases and conditions which include, but are not limited to, wound healing, diabetes mellitus, and cancers of the bone and connective tissues, lymphomas, and cancers of the liver. Similarly, polypeptides and antibodies directed to these polypeptides would be useful in providing immunological probes for differential identification of the tissue(s) or cell type(s). For a number of disorders of the above tissues or cells, particularly those of the cells and tissues involved in healing tissue damages and regeneration, diabetes mellitis, and many cancers including, but not limited to ovarian cancer, breast cancer, colon cancer, cardiac tumors, pancreatic cancer, melanoma, retinoblastoma, glioblastoma, lung cancer, intestinal cancer, testicular cancer, stomach cancer, neuroblastoma, myxoma, myoma, lymphoma, endothelioma, osteoblastoma, osteoclastoma, osteosarcoma, chondrosarcoma, adenoma, and the like, expression of this gene at significantly higher or lower levels may be routinely detected in certain tissues or cell types (e.g., cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder. Preferred polypeptides of the present invention comprise, or alternatively consist of one, or both of the immunogenic epitopes shown in SEQ ID NO: 153 as residues: Gln-22 to Phe-31, Leu-78 to Lys-85. Polynucleotides encoding said polypeptides are encompassed by the invention, as are antibodies that bind one or more of these peptides.

The tissue distribution in healing wound and regenerating tissues/cells indicates that polynucleotides and polypeptides corresponding to this gene would be useful for detection, treatment, and/or prevention of tissue damages, trauma, necrosis, and tissue regeneration. In addition, since this gene exhibits homology with an insulin precursor, polynucleotides and polypeptides corresponding to this gene can be used to regulate the metabolism of glucose or other sugars, the synthesis of proteins, and the formation and storage of neutral lipids. The tissue distribution in immune tissues (e.g., T-cells and B-cells) indicates that polynucleotides and polypeptides corresponding to this gene would be useful for the diagnosis and treatment of a variety of immune system disorders. Representative uses are described in the "Immune Activity" and "Infectious Disease" sections below, in Example 11, 13, 14, 16, 18, 19, 20, and 27, and elsewhere herein. Briefly, the expression indicates a role in regulating the proliferation; survival; differentiation; and/or activation of hematopoietic cell lineages, including blood stem cells. Involvement in the regulation of cytokine production, antigen presentation, or other processes indicates a usefulness for treatment of cancer (e.g., by boosting immune responses). Expression in cells of lymphoid origin, indicates the natural gene product would be involved in immune functions. Therefore polynucleotides and polypeptides corresponding to this gene would also be useful as an agent for immunological disorders including arthritis, asthma, immunodeficiency diseases such as AIDS, leukemia, rheumatoid arthritis, granulomatous disease, inflammatory bowel disease, sepsis, acne, neutropenia, neutrophilia, psoriasis, hypersensitivities, such as T-cell mediated cytotoxicity; immune reactions to transplanted organs and tissues, such as host-versus-graft and graft-versus-host diseases, or autoimmunity disorders, such as autoimmune infertility, lense tissue injury, demyelination, systemic lupus erythematosis, drug induced hemolytic anemia, rheumatoid arthritis, Sjogren's disease, and scleroderma. Moreover, the protein may represent a secreted factor that influences the differentiation or behavior of other blood cells, or that recruits hematopoietic cells to sites of injury. Thus, polynucleotides and polypeptides corresponding to this gene are thought to be useful in the expansion of stem cells and committed progenitors of various blood lineages, and in the differentiation and/or proliferation of various cell types. Furthermore, the protein may also be used to determine biological activity, raise antibodies, as tissue markers, to isolate cognate ligands or receptors, to identify agents that modulate their interactions, in addition to its use as a nutritional supplement. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:46 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a-b, where a is any integer between 1 to 1347 of SEQ ID NO:46, b is an integer of 15 to 1361, where both a and b correspond to the positions of nucleotide residues shown in SEQ ID NO:46, and where b is greater than or equal to a +14.

Features of Protein Encoded by Gene No: 37

In specific embodiments, polypeptides of the invention comprise, or alternatively consist of, the following amino acid sequence: KVDTPRRHFCPEISFFLTPLPQSARNSTVRNALSGLKNLTPAMISTVSKQDTSK LGEEE (SEQ ID NO:352). Moreover, fragments and variants of these polypeptides (such as, for example, fragments as described herein, polypeptides at least 80%, 85%, 90%, 95%, 96%, 97%, 98%, 99%, or 100% identical to these polypeptides, or polypeptides encoded by a polynucleotide which hybridizes, under stringent conditions, to the polynucleotide encoding these polypeptides) are encompassed by the invention. Antibodies that bind polypeptides of the invention and polynucleotides encoding these polypeptides are also encompassed by the invention.

When tested against U937 Myeloid cell lines, supernatants removed from cells containing this gene activated the GAS assay. Thus, it is likely that this gene activates myeloid cells through the Jak-STAT signal transduction pathway. The gamma activating sequence (GAS) is a promoter element found upstream of many genes which are involved in the Jak-STAT pathway. The Jak-STAT pathway is a large, signal transduction pathway involved in the differentiation and proliferation of cells. Therefore, activation of the Jak-STAT pathway, reflected by the binding of the GAS element, can be used to indicate proteins involved in the proliferation and differentiation of cells.

The polypeptide of this gene has been determined to have a transmembrane domain at about amino acid position 7 to about 23 of the amino acid sequence referenced in Table 1 for this gene. Moreover, a cytoplasmic tail encompassing amino acids 24 to 105 of this protein has also been determined. Based upon these characteristics, it is believed that the protein product of this gene shares structural features to type Ia membrane proteins.

This gene is expressed primarily in B-cell lymphoma.

Polynucleotides and polypeptides of the invention would be useful as reagents for differential identification of the tissue(s) or cell type(s) present in a biological sample and for diagnosis of diseases and conditions which include, but are not limited to, B-cell lymphoma, immunodeficient or autoimmune conditions. Similarly, polypeptides and antibodies directed to these polypeptides would be useful in providing immunological probes for differential identification of the tissue(s) or cell type(s). For a number of disorders of the above tissues or cells, particularly of the immune system, expression of this gene at significantly higher or lower levels may be routinely detected in certain tissues or cell types (e.g., immune, cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

The tissue distribution indicates that polynucleotides and polypeptides corresponding to this gene would be useful for the detection, treatment, and/or prevention of B-cell lymphomas, as well as other immune disorders including: leukemias, auto-immunities, immunodeficiencies (e.g., AIDS), immuno-suppressive conditions (transplantation) and hematopoietic disorders, such as anemia, pancytopenia, leukopenia, thrombocytopenia or leukemia, since stromal cells are important in the production of cells of hematopoietic lineages. In addition, polynucleotides and polypeptides corresponding to this gene may be applicable in conditions of general microbial infection, inflammation or cancer. Representative uses are described in the "Immune Activity" and "Infectious Disease" sections below, in Example 11, 13, 14, 16, 18, 19, 20, and 27, and elsewhere herein. The uses include bone marrow cell ex vivo culture, bone marrow transplantation, bone marrow reconstitution, radiotherapy or chemotherapy of neoplasia. The polynucleotides and polypeptides corresponding to this gene may also be involved in lymphopoiesis, therefore, it can be used in immune disorders such as infection, inflammation, allergy, immunodeficiency etc. In addition, the biological activity of supernatants from cells expressing this gene in the GAS assay indicates that this gene product may have commercial utility in the expansion of stem cells and committed progenitors of various blood lineages, and in the differentiation and/or proliferation of various cell types. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:47 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a-b, where a is any integer between 1 to 1123 of SEQ ID NO:47, b is an integer of 15 to 1137, where both a and b correspond to the positions of nucleotide residues shown in SEQ ID NO:47, and where b is greater than or equal to a +14.

Features of Protein Encoded by Gene No: 38

The polypeptide of this gene has been determined to have a transmembrane domain at about amino acid position 8 to about 24 of the amino acid sequence referenced in Table 1 for this gene. Moreover, a cytoplasmic tail encompassing amino acids 1 to 7 of this protein has also been determined. Based upon these characteristics, it is believed that the protein product of this gene shares structural features to type II membrane proteins.

The gene encoding the disclosed cDNA is thought to reside on chromosome 10. Accordingly, polynucleotides related to this invention would be useful as a marker in linkage analysis for chromosome 10.

This gene is expressed primarily in infant brain, testes, brain, osteoblasts, and caudate nucleus tissues, and, to a lesser extent, in various other normal and transformed cell types, including smooth muscle and adult heart tissues, and T-cell lymphoma.

Polynucleotides and polypeptides of the invention would be useful as reagents for differential identification of the tissue(s) or cell type(s) present in a biological sample and for diagnosis of diseases and conditions which include, but are not limited to, neurological and growth defects. Similarly, polypeptides and antibodies directed to these polypeptides would be useful in providing immunological probes for differential identification of the tissue(s) or cell type(s). For a number of disorders of the above tissues or cells, particularly of the developing nervous system, expression of this gene at significantly higher or lower levels may be routinely detected in certain tissues or cell types (e.g., immune, neural, cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

The tissue distribution in infant brain tissue indicates that polynucleotides and polypeptides corresponding to this gene would be useful for the study, detection and/or treatment of infant and general nervous system disorders and neoplasias. The tissue distribution indicates polynucleotides and polypeptides corresponding to this gene would be useful for the detection, treatment, and/or prevention of neurodegenerative disease states, behavioral disorders, or inflammatory conditions. Representative uses are described in the "Regeneration" and "Hyperproliferative Disorders" sections below, in Example 11, 15, and 18, and elsewhere herein. Briefly, the uses include, but are not limited to the detection, treatment, and/or prevention of Alzheimer's Disease, Parkinson's Disease, Huntington's Disease, Tourette Syndrome, meningitis, encephalitis, demyelinating diseases, peripheral neuropathies, neoplasia, trauma, congenital malformations, spinal cord injuries, ischemia and infarction, aneurysms, hemorrhages, schizophrenia, mania, dementia, paranoia, obsessive compulsive disorder, depression, panic disorder, learning disabilities, ALS, psychoses, autism, and altered behaviors, including disorders in feeding, sleep patterns, balance, and perception. In addition, elevated expression of this gene product in regions of the brain indicates it plays a role in normal neural function. Potentially, this gene product is involved in synapse formation, neurotransmission, learning, cognition, homeostasis, or neuronal differentiation or survival. In addition, the gene or gene product may also play a role in the treatment and/or detection of developmental disorders associated with the developing embryo, or sexually-linked disorders. Moreover, the tissue distribution in immune cells (e.g., T-cells) indicates that polynucleotides and polypeptides corresponding to this gene would be useful for the diagnosis, detection, prevention and/or treatment of a variety of immune system disorders. Representative uses are described in the "Immune Activity" and "Infectious Disease" sections below, in Example 11, 13, 14, 16, 18, 19, 20, and 27, and elsewhere herein. Briefly, the expression indicates a role in regulating the proliferation; survival; differentiation; and/or activation of hematopoietic cell lineages, including blood stem cells. Involvement in the regulation of cytokine production, antigen presentation, or other processes indicates a usefulness for treatment of cancer (e.g., by boosting immune responses). Expression in cells of lymphoid origin, indicates the natural gene product would be involved in immune functions. Therefore it would also be useful as an agent for immunological disorders including arthritis, asthma, immunodeficiency diseases such as AIDS, leukemia, rheumatoid arthritis, granulomatous disease, inflammatory bowel disease, sepsis, acne, neutropenia, neutrophilia, psoriasis, hypersensitivities, such as T-cell mediated cytotoxicity; immune reactions to transplanted organs and tissues, such as host-versus-graft and graft-versus-host diseases, or autoimmunity disorders, such as autoimmune infertility, lense tissue injury, demyelination, systemic lupus erythematosis, drug induced hemolytic anemia, rheumatoid arthritis, Sjogren's disease, and scleroderma. Moreover, the protein may represent a secreted factor that influences the differentiation or behavior of other blood cells, or that recruits hematopoietic cells to sites of injury. Thus, this gene product is thought to be useful in the expansion of stem cells and committed progenitors of various blood lineages, and in the differentiation and/or proliferation of various cell types. Furthermore, the protein may also be used to determine biological activity, to raise antibodies, as tissue markers, to isolate cognate ligands or receptors, to identify agents that modulate their interactions, in addition to its use as a nutritional supplement. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:48 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a-b, where a is any integer between 1 to 2749 of SEQ ID NO:48, b is an integer of 15 to 2763, where both a and b correspond to the positions of nucleotide residues shown in SEQ ID NO:48, and where b is greater than or equal to a +14.

Features of Protein Encoded by Gene No: 39

The translated product of this gene shares some homology with a *Caenorhabditis elegans* gene product containing zinc finger-like motifs (see, e.g., Genbank Accession No.: AAA91223 and Wilson, R., et al., Nature 368, 32-38 (1994)). Similarly, the translated product of this gene also shares some homology with transcriptional regulatory proteins from *Saccharomyces cerevisiae* (see, e.g., GenBank Accessions Nos.: CAA92346.1, BAA04890.1, and AAA34471.1). All references available through the above listed accessions and citations are hereby incorporated herein by reference. Based on the sequence similarity, the translation product of this clone is expected to share at least some biological activities with transcriptional regulatory proteins. Such activities are known in the art, some of which are described elsewhere herein.

This gene is expressed primarily in epithelial-TNFalpha and INF induced cells and brain frontal cortex.

Polynucleotides and polypeptides of the invention would be useful as reagents for differential identification of the tissue(s) or cell type(s) present in a biological sample and for diagnosis of diseases and conditions which include, but are not limited to, neurodegenerative diseases and/or disorders. Similarly, polypeptides and antibodies directed to these polypeptides would be useful in providing immunological probes for differential identification of the tissue(s) or cell type(s). For a number of disorders of the above tissues or cells, particularly of the central nervous system, expression of this gene at significantly higher or lower levels may be routinely detected in certain tissues or cell types (e.g., CNS, cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder. Preferred polypeptides of the present invention comprise, or alternatively consist of one or both of the immunogenic epitopes shown in SEQ ID NO: 156 as residues: Lys-35 to Asp-41, Glu-49 to Leu-63. Polynucleotides encoding said polypeptides are encompassed by the invention, as are antibodies that bind one or more of these peptides.

The tissue distribution in the brain indicates that polynucleotides and polypeptides corresponding to this gene would be useful for detection, treatment, and/or prevention of neurodegenerative disorders, especially those involving the frontal cortex. Representative uses are described in the "Regeneration" and "Hyperproliferative Disorders" sections below, in Example 11, 15, and 18, and elsewhere herein. Briefly, the elevated expression of this gene product within the frontal cortex of the brain indicates that it may be involved in neuronal survival; synapse formation; conductance; neural differentiation, etc. Such involvement may impact many processes, such as learning and cognition. Polynucleotides and polypeptides corresponding to this gene may also be useful in the treatment of such neurodegenerative disorders as schizophrenia; ALS; or Alzheimer's. Furthermore, the protein may also be used to determine biological activity, to raise antibodies, as tissue markers, to isolate cognate ligands or receptors, to identify agents that modulate their interactions, in addition to its use as a nutritional supplement. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:49 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a-b, where a is any integer between 1 to 1334 of SEQ ID NO:49, b is an integer of 15 to 1348, where both a and b correspond to the positions of nucleotide residues shown in SEQ ID NO:49, and where b is greater than or equal to a +14.

Features of Protein Encoded by Gene No: 40

In specific embodiments, polypeptides of the invention comprise, or alternatively consist of, the following amino acid sequence: PTRPPTRPLSFTFTKQTSSTCLSLHF (SEQ ID NO:353). Moreover, fragments and variants of these polypeptides (such as, for example, fragments as described herein, polypeptides at least 80%, 85%, 90%, 95%, 96%, 97%, 98%, 99%, or 100% identical to these polypeptides, or polypeptides encoded by a polynucleotide which hybridizes, under stringent conditions, to the polynucleotide encoding these polypeptides) are encompassed by the invention. Antibodies that bind polypeptides of the invention and polynucleotides encoding these polypeptides are also encompassed by the invention.

The gene encoding the disclosed cDNA is believed to reside on chromosome 18. Accordingly, polynucleotides related to this invention would be useful as a marker in linkage analysis for chromosome 18.

This gene is expressed primarily in infant brain, frontal cortex, and, to a lesser extent, in melanocytes.

Polynucleotides and polypeptides of the invention would be useful as reagents for differential identification of the tissue(s) or cell type(s) present in a biological sample and for diagnosis of diseases and conditions which include, but are not limited to, neurodegenerative diseases and/or disorders. Similarly, polypeptides and antibodies directed to these polypeptides would be useful in providing immunological probes for differential identification of the tissue(s) or cell type(s). For a number of disorders of the above tissues or cells, particularly of the central nervous system, expression of this gene at significantly higher or lower levels may be routinely detected in certain tissues or cell types (e.g., CNS, cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder. Preferred polypeptides of the present invention comprise, or alternatively consist of one or both of the immunogenic epitopes shown in SEQ ID NO: 157 as residues: Val-40 to Cys-47, Lys-49 to Gly-54. Polynucleotides encoding said polypeptides are encompassed by the invention, as are antibodies that bind one or more of these peptides.

The tissue distribution indicates that polynucleotides and polypeptides corresponding to this gene would be useful for the detection, treatment, and/or prevention of neurodegenerative disorders especially those involving the frontal cortex. Moreover, polynucleotides and polypeptides corresponding to this gene would be useful for the detection, treatment, and/or prevention of neurodegenerative disease states, behavioral disorders, or inflammatory conditions. Representative uses are described in the “Regeneration” and “Hyperproliferative Disorders” sections below, in Example 11, 15, and 18, and elsewhere herein. Briefly, the uses include, but are not limited to the detection, treatment, and/or prevention of Alzheimer’s Disease, Parkinson’s Disease, Huntington’s Disease, Tourette Syndrome, meningitis, encephalitis, demyelinating diseases, peripheral neuropathies, neoplasia, trauma, congenital malformations, spinal cord injuries, ischemia and infarction, aneurysms, hemorrhages, schizophrenia, mania, dementia, paranoia, obsessive compulsive disorder, depression, panic disorder, learning disabilities, ALS, psychoses, autism, and altered behaviors, including disorders in feeding, sleep patterns, balance, and perception. In addition, elevated expression of this gene product in regions of the brain indicates it plays a role in normal neural function. Potentially, polynucleotides and polypeptides corresponding to this gene are involved in synapse formation, neurotransmission, learning, cognition, homeostasis, or neuronal differentiation or survival. Furthermore, the protein may also be used to determine biological activity, to raise antibodies, as tissue markers, to isolate cognate ligands or receptors, to identify agents that modulate their interactions, in addition to its use as a nutritional supplement. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:50 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a-b, where a is any integer between 1 to 1250 of SEQ ID NO:50, b is an integer of 15 to 1264, where both a and b correspond to the positions of nucleotide residues shown in SEQ ID NO:50, and where b is greater than or equal to a +14.

Features of Protein Encoded by Gene No: 41

This gene shows structural homology with the duck insulin precursor which is thought to be important in metabolic homeostasis. (see, e.g., Genbank Accession No. pir|A01600|IPDK insulin precursor; all references available through this accession number are hereby incorporated in their entirety by reference herein).

In specific embodiments, polypeptides of the invention comprise, or alternatively consist of, the following amino acid sequence: LECVLLICFRAMSAIYTHTSIGNAQKLFTDGSAFRRVREPLPKEGKSWPQ (SEQ ID NO: 354). Moreover, fragments and variants of these polypeptides (such as, for example, fragments as described herein, polypeptides at least 80%, 85%, 90%, 95%, 96%, 97%, 98%, 99%, or 100% identical to these polypeptides, or polypeptides encoded by a polynucleotide which hybridizes, under stringent conditions, to the polynucleotide encoding these polypeptides) are encompassed by the invention. Antibodies that bind polypeptides of the invention and polynucleotides encoding these polypeptides are also encompassed by the invention.

This gene is expressed primarily in eosinophil-IL5 induced cells, and, to a lesser extent, in B cell lymphoma, breast lymph node, and CD34 depleted buffy coat (cord blood).

Polynucleotides and polypeptides of the invention would be useful as reagents for differential identification of the tissue(s) or cell type(s) present in a biological sample and for diagnosis of diseases and conditions which include, but are not limited to, immune diseases and/or disorders. Similarly, polypeptides and antibodies directed to these polypeptides would be useful in providing immunological probes for differential identification of the tissue(s) or cell type(s). For a number of disorders of the above tissues or cells, particularly of the immune system, expression of this gene at significantly higher or lower levels may be routinely detected in certain tissues or cell types (e.g., immune, hematopoietic, and cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder. Preferred polypeptides of the present invention comprise immunogenic epitopes shown in SEQ ID NO: 158 as residues: Arg-39 to Glu-56. Polynucleotides encoding said polypeptides are encompassed by the invention, as are antibodies that bind one or more of these peptides.

The tissue distribution in hematopoietic tissues indicates that polynucleotides and polypeptides corresponding to this gene would be useful for detection, treatment, and/or prevention of immune disorders especially those involving eosinophils and B-cells. Polynucleotides and polypeptides corresponding to this gene would be useful for the detection, treatment, and/or prevention of a variety of immune system disorders. Representative uses are described in the "Immune Activity" and "Infectious Disease" sections below, in Example 11, 13, 14, 16, 18, 19, 20, and 27, and elsewhere herein. Briefly, the expression of this gene product indicates a role in regulating the proliferation; survival; differentiation; and/or activation of hematopoietic cell lineages, including blood stem cells. Polynucleotides and polypeptides corresponding to this gene may be involved in the regulation of cytokine production, antigen presentation, or other processes suggesting a usefulness in the treatment of cancer (e.g., by boosting immune responses). Since the gene is expressed in cells of lymphoid origin, the natural gene product may be involved in immune functions. Therefore polynucleotides and polypeptides of the invention may be also used as an agent for immunological disorders including arthritis, asthma, immunodeficiency diseases such as AIDS, leukemia, rheumatoid arthritis, granulomatous disease, inflammatory bowel disease, sepsis, acne, neutropenia, neutrophilia, psoriasis, hypersensitivities, such as T-cell mediated cytotoxicity; immune reactions to transplanted organs and tissues, such as host-versus-graft and graft-versus-host diseases, or autoimmunity disorders, such as autoimmune infertility, lense tissue injury, demyelination, systemic lupus erythematosis, drug induced hemolytic anemia, rheumatoid arthritis, Sjogren's disease, scleroderma and tissues. Moreover, the protein may represent a secreted factor that influences the differentiation or behavior of other blood cells, or that recruits hematopoietic cells to sites of injury. In addition, polynucleotides and polypeptides corresponding to this gene may have commercial utility in the expansion of stem cells and committed progenitors of various blood lineages, and in the differentiation and/or proliferation of various cell types. Furthermore, the protein may also be used to determine biological activity, raise antibodies, as tissue markers, to isolate cognate ligands or receptors, to identify agents that modulate their interactions, in addition to its use as a nutritional supplement. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:51 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a-b, where a is any integer between 1 to 1646 of SEQ ID NO:51, b is an integer of 15 to 1660, where both a and b correspond to the positions of nucleotide residues shown in SEQ ID NO:51, and where b is greater than or equal to a +14.

Features of Protein Encoded by Gene No: 42

In specific embodiments, polypeptides of the invention comprise, or alternatively consist of, the following amino acid sequence: KQNLTNLDVPVQYHVALSDKVK (SEQ ID NO: 355). Moreover, fragments and variants of these polypeptides (such as, for example, fragments as described herein, polypeptides at least 80%, 85%, 90%, 95%, 96%, 97%, 98%, 99%, or 100% identical to these polypeptides, or polypeptides encoded by a polynucleotide which hybridizes, under stringent conditions, to the polynucleotide encoding these polypeptides) are encompassed by the invention. Antibodies that bind polypeptides of the invention and polynucleotides encoding these polypeptides are also encompassed by the invention.

This gene is expressed primarily in pineal gland and, to a lesser extent, in multiple sclerosis cells.

Polynucleotides and polypeptides of the invention would be useful as reagents for differential identification of the tissue(s) or cell type(s) present in a biological sample and for diagnosis of diseases and conditions which include, but are not limited to, insomnia, multiple sclerosis, and other neurodegenerative diseases and/or disorders. Similarly, polypeptides and antibodies directed to these polypeptides would be useful in providing immunological probes for differential identification of the tissue(s) or cell type(s). For a number of disorders of the above tissues or cells, particularly of the central nervous system and endocrine system, expression of this gene at significantly higher or lower levels may be routinely detected in certain tissues or cell types (e.g., CNS, cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder. Preferred polypeptides of the present invention comprise, or alternatively consist of the immunogenic epitopes shown in SEQ ID NO: 159 as residues: Pro-7 to Gly-12. Polynucleotides encoding said polypeptides are encompassed by the invention, as are antibodies that bind one or more of these peptides.

The tissue distribution primarily in pineal gland and, to a lesser extent, in multiple sclerosis cells indicates that polynucleotides and polypeptides corresponding to this gene would be useful for treatment of insomnia and jet lag through agonist or antagonist interaction with pineal gland receptors to allow regulation of melatonin production. Representative uses are described elsewhere herein. This gene may also be useful in the treatment of multiple sclerosis. Furthermore, the protein may also be used to determine biological activity, to raise antibodies, as tissue markers, to isolate cognate ligands or receptors, to identify agents that modulate their interactions, in addition to its use as a nutritional supplement. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:52 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a-b, where a is any integer between 1 to 1664 of SEQ ID NO:52, b is an integer of 15 to 1678, where both a and b correspond to the positions of nucleotide residues shown in SEQ ID NO:52, and where b is greater than or equal to a +14.

Features of Protein Encoded by Gene No: 43

The gene encoding the disclosed cDNA is believed to reside on chromosome 2. Accordingly, polynucleotides related to this invention would be useful as a marker in linkage analysis for chromosome 2.

In specific embodiments, polypeptides of the invention comprise, or alternatively consist of, the following amino acid sequence: PSCPPEMKKELPVDSCLPRSLELHPQK-MDPKRQHIQLLSSLTECLTVDPLSASV WRQLYP-KHLSQSSLLLXHLLSSWEQIPKKVQK-SLQETIQSLKLTNQELLRKGS SNNQDVVTCD (SEQ ID NO: 356). Moreover, fragments and variants of these polypeptides (such as, for example, fragments as described herein, polypeptides at least 80%, 85%, 90%, 95%, 96%, 97%, 98%, 99%, or 100% identical to these polypeptides, or polypeptides encoded by a polynucleotide which hybridizes, under stringent conditions, to the polynucleotide encoding these polypeptides) are encompassed by the invention. Antibodies that bind polypeptides of the invention and polynucleotides encoding these polypeptides are also encompassed by the invention.

When tested against Jurket and U937 cell lines, supernatants removed from cells containing this gene activated the NFkB promoter element. Thus, it is likely that this gene activates T-cells and myeloid cells through the NFkB signal transduction pathway. NF-kB (Nuclear Factor kB) is a transcription factor activated by a wide variety of agents, leading to cell activation, differentiation, or apoptosis. Reporter constructs utilizing the NF-kB promoter element are used to screen supernatants for such activity.

This gene is expressed primarily in ovary tumors and breast cancer and, to a lesser extent, in normal lung and colon tumors.

Polynucleotides and polypeptides of the invention would be useful as reagents for differential identification of the tissue(s) or cell type(s) present in a biological sample and for diagnosis of diseases and conditions which include, but are not limited to, cancer, particularly of the ovary and breast; and colon. Similarly, polypeptides and antibodies directed to these polypeptides would be useful in providing immunological probes for differential identification of the tissue(s) or cell type(s). For a number of disorders of the above tissues or cells, particularly of the colon, breast, or female reproductive system, expression of this gene at significantly higher or lower levels may be routinely detected in certain tissues or cell types (e.g., reproductive, gastrointestinal, and cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

The tissue distribution primarily in ovary tumors and breast cancer and, to a lesser extent, in normal lung and colon tumors indicates that polynucleotides and polypeptides corresponding to this gene would be useful for the diagnosis and/or treatment of a variety of cancers, most notably cancers of the ovary, breast, or colon. Representative uses are described in the "Hyperproliferative Disorders" and "Regeneration" sections below and elsewhere herein. Briefly, the expression of polynucleotides and polypeptides corresponding to this gene in a variety of cancers indicates that it may be a player in the progression of the disease, and may be a beneficial target for inhibitors as therapeutics. Similarly, expression in ovarian tissue, indicates that polynucleotides and polypeptides corresponding to this gene would be useful for the treatment, prevention, detection and diagnosis of conditions concerning proper ovarian function (e.g., egg maturation, endocrine function), as well as cancer. The expression in ovarian tissue may indicate the gene or its products can be used to treat, prevent, detect and/or diagnose disorders of the ovary, including inflammatory disorders, such as oophoritis (e.g., caused by viral or bacterial infection), ovarian cysts, amenorrhea, infertility, hirsutism, and ovarian cancer (including, but not limited to, primary and secondary cancerous growth, endometrioid carcinoma of the ovary, ovarian papillary serous adenocarcinoma, ovarian mucinous adenocarcinoma, Ovarian Krukenberg tumor). Likewise, expression in breast tissue indicates that polynucleotides and/or polypeptides of the invention would be useful for diagnosis, treatment and/or prevention of breast neoplasia and breast cancers, such as fibroadenoma, pipillary carcinoma, ductal carcinoma, Paget's disease, medullary carcinoma, mucinous carcinoma, tubular carcinoma, secretory carcinoma and apocrine carcinoma, as well as juvenile hypertrophy and gynecomastia, mastitis and abscess, duct ectasia, fat necrosis and fibrocystic diseases. The tissue distribution in colon and colon cancer indicates that polynucleotides and polypeptides corresponding to this gene would be useful for diagnosis, treatment, prevention and/or detection of tumors, especially of the intestine, such as, carcinoid tumors, lymphomas, non-neoplastic polyps, adenomas, familial syndromes, colorectal carcinogenesis, colorectal carcinoma, cancer of the colon, cancer of the rectum and carcinoid tumors, as well as cancers in other tissues where expression has been indicated. The expression in the colon tissue may indicate that polynucleotides and polypeptides of the invention can be used to treat, detect, prevent and/or diagnose disorders of the colon, including inflammatory disorders such as, congenital abnormalities, such as atresia and stenosis, Meckel diverticulum, congenital aganglionic megacolon-Hirschsprung disease; enterocolitis, such as diarrhea and dysentary, infectious enterocolitis, including viral gastroenteritis, bacterial enterocolitis, necrotizing enterocolitis, antibiotic-associated colitis (pseudomembranous colitis), and collagenous and lymphocytic colitis, miscellaneous intestinal inflammatory disorders, including parasites and protozoa, amoebic colitis, acquired immunodeficiency syndrome, transplantation, drug-induced intestinal injury, radiation enterocolitis, neutropenic colitis, diverticular colon disease (DCD), inflammatory colonic disease, idiopathic inflammatory bowel disease, such as Crohn's disease (CD), non-inflammatory bowel disease (non-IBD) colonic inflammation; ulcerative disorders such as, ulcerative colitis (UC); eosinophilic colitis; noncancerous tumors, such as, polyps in the colon, adenomas, leiomyomas, lipomas, and angiomas. Furthermore, the protein may also be used to determine biological activity, to raise antibodies, as tissue markers, to isolate cognate ligands or receptors, to identify agents that modulate their interactions, in addition to its use as a nutritional supplement. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:53 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a-b, where a is any integer between 1 to 1846 of SEQ ID NO:53, b is an integer of 15 to 1860, where both a and b correspond to the positions of nucleotide residues shown in SEQ ID NO:53, and where b is greater than or equal to a +14.

Features of Protein Encoded by Gene No: 44

In an alternative reading frame, this gene shares sequence homology with a murine testosterone induced transcript (see, e.g., Geneseq Accession No. 758299; all references available through this accession are hereby incorporated by reference herein.). This same region also shares sequence homology with a human cancer suppressor transfer factor protein (see, e.g., Geneseq Accession No. R86875; all references available through this accession are hereby incorporated by reference herein.).

The gene encoding the disclosed cDNA is thought to reside on chromosome 11. Accordingly, polynucleotides related to this invention would be useful as a marker in linkage analysis for chromosome 11.

In specific embodiments, polypeptides of the invention comprise, or alternatively consist of, the following amino acid sequence: KAPYSWLADSWPHPSRSPSAQEPRG-SCCPSNPDPDDRYYNEAGISLYLAQTA RGTAAPGEG-PVYSTIDPAGEELQTFHGGFPQHPS-GDLGPWSQYAPPEWSQG (SEQ ID NO: 357). Moreover, fragments and variants of these polypeptides (such as, for example, fragments as described herein, polypeptides at least 80%, 85%, 90%, 95%, 96%, 97%, 98%, 99%, or 100% identical to these polypeptides, or polypeptides encoded by a polynucleotide which hybridizes, under stringent conditions, to the polynucleotide encoding these polypeptides) are encompassed by the invention. Antibodies that bind polypeptides of the invention and polynucleotides encoding these polypeptides are also encompassed by the invention.

This gene is expressed primarily in various embryonic/fetal tissues, particularly fetal brain tissue.

Polynucleotides and polypeptides of the invention would be useful as reagents for differential identification of the tissue(s) or cell type(s) present in a biological sample and for diagnosis of diseases and conditions which include, but are not limited to, congenital birth defects, particularly of the central nervous system, and cancers, such as MEN. Similarly, polypeptides and antibodies directed to these polypeptides would be useful in providing immunological probes for differential identification of the tissue(s) or cell type(s). For a number of disorders of the above tissues or cells, particularly of the central nervous system, expression of this gene at significantly higher or lower levels may be routinely detected in certain tissues or cell types (e.g., neural, developing, cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

The tissue distribution in fetal and embryonic tissues indicates that polynucleotides and polypeptides corresponding to this gene would be useful for the diagnosis, detection, prevention and/or treatment of a variety of cancers, most notably cancers of the central nervous system, such as MEN, as well as the disorders of the central nervous system listed above. Representative uses are described in the "Hyperproliferative Disorders" and "Regeneration" sections below and elsewhere herein. Briefly, the expression within embryonic tissue and other cellular sources marked by proliferating cells indicates that polynucleotides and polypeptides of the invention may play a role in the regulation of cellular division, and may show utility in the detection, treatment, and/or prevention of cancer and other proliferative disorders. Similarly, embryonic development also involves decisions involving cell differentiation and/or apoptosis in pattern formation. Thus, polynucleotides and polypeptides of the invention may also be involved in apoptosis or tissue differentiation and could again be useful in cancer therapy. Expression of polynucleotides and polypeptides corresponding to this gene in a variety of systems indicates that this gene may be a player in the progression of these diseases, and may be a beneficial target for inhibitors as therapeutics. Furthermore, the protein may also be used to determine biological activity, to raise antibodies, as tissue markers, to isolate cognate ligands or receptors, to identify agents that modulate their interactions, in addition to its use as a nutritional supplement. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:54 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a-b, where a is any integer between 1 to 1649 of SEQ ID NO:54, b is an integer of 15 to 1663, where both a and b correspond to the positions of nucleotide residues shown in SEQ ID NO:54, and where b is greater than or equal to a +14.

Features of Protein Encoded by Gene No: 45

The gene encoding the disclosed cDNA is thought to reside on chromosome 1. Accordingly, polynucleotides related to this invention would be useful as a marker in linkage analysis for chromosome 1.

This gene is highly homologous to bovine cytochrome b-5 reductase (see e.g., GENBANK: locus BOVCYB5R, accession M83104; Strittmatter et al., J. Biol. Chem. 267:2519-2523 (1992); the references available through the accession number and the captioned reference are hereby incorporated herein by reference). Based on this homology, it is likely that this gene would have activity similar to NADH-cytochrome b5 reductase.

This gene is expressed primarily in liver and lung tissues.

Polynucleotides and polypeptides of the invention would be useful as reagents for differential identification of the tissue(s) or cell type(s) present in a biological sample and for diagnosis of diseases and conditions which include, but are not limited to, diseases and/or disorders of the liver and lung including chronic liver failure, bronchitis, emphysema, and chronic lung failure. Similarly, polypeptides and antibodies directed to these polypeptides would be useful in providing immunological probes for differential identification of the tissue(s) or cell type(s). For a number of disorders of the above tissues or cells, particularly of the hepatic and pulmonary systems, expression of this gene at significantly higher or lower levels may be routinely detected in certain tissues or cell types (e.g., hepatic, pulmonary, cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder. Preferred polypeptides of the present invention comprise, or alternatively consist of one, two, three, four, five or all six of the immunogenic epitopes shown in SEQ ID NO: 162 as residues: Arg-31 to Gln-37, Val-88 to Gly-95, Pro-110 to Gln-120, Gln-151 to Ala-163, Asp-231 to Trp-237, Pro-277 to Lys-287. Polynucleotides encoding said polypeptides are encompassed by the invention, as are antibodies that bind one or more of these peptides.

The tissue distribution in liver tissue indicates that polynucleotides and polypeptides corresponding to this gene would be useful for the detection and treatment of liver disorders and cancers (e.g., hepatoblastoma, jaundice, hepatitis, liver metabolic diseases and conditions that are attributable to the differentiation of hepatocyte progenitor cells). Representative uses are described in the "Hyperproliferative Disorders", "Infectious Disease", and "Binding Activity" sections below, in Example 11, and 27, and elsewhere herein. Alternatively, the tissue distribution indicates that polynucleotides and polypeptides corresponding to this gene would be useful for the detection and treatment of disorders associated with developing lungs, particularly in premature infants where the lungs are the last tissues to develop. The tissue distribution indicates that polynucleotides and polypeptides corresponding to this gene would be useful for the diagnosis and intervention of lung tumors, since the gene may be involved in the regulation of cell division, particularly since it is expressed in fetal tissue. Furthermore, the protein may also be used to determine biological activity, to raise antibodies, as tissue markers, to isolate cognate ligands or receptors, to identify agents that modulate their interactions, in addition to its use as a nutritional supplement. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:55 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a-b, where a is any integer between 1 to 1618 of SEQ ID NO:55, b is an integer of 15 to 1632, where both a and b correspond to the positions of nucleotide residues shown in SEQ ID NO:55, and where b is greater than or equal to a +14.

Features of Protein Encoded by Gene No: 46

This gene is expressed primarily in tonsil tissue and neutrophils, and, to a lesser extent, in testes tissue, brain and cerebellum tissues.

Polynucleotides and polypeptides of the invention would be useful as reagents for differential identification of the tissue(s) or cell type(s) present in a biological sample and for diagnosis of diseases and conditions which include, but are not limited to, diseases and/or disorders of the tonsils, immune system disorders, reproductive disorders, and neural disorders. Similarly, polypeptides and antibodies directed to these polypeptides would be useful in providing immunological probes for differential identification of the tissue(s) or cell type(s). For a number of disorders of the above tissues or cells, particularly of the tonsils, and the immune, reproductive, and neural systems, expression of this gene at significantly higher or lower levels may be routinely detected in certain tissues or cell types (e.g., immune, neural, reproductive, tonsils, cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder. Preferred polypeptides of the present invention comprise, or alternatively consist of one or both of the immunogenic epitopes shown in SEQ ID NO: 163 as residues: Pro-17 to Glu-26, Asp-60 to Val-72. Polynucleotides encoding said polypeptides are encompassed by the invention, as are antibodies that bind one or more of these peptides.

The tissue distribution indicates that polynucleotides and polypeptides corresponding to this gene would be useful for the detection, treatment, and/or prevention of a variety of immune system disorders. Representative uses are described in the "Immune Activity" and "Infectious Disease" sections below, in Example 11, 13, 14, 16, 18, 19, 20, and 27, and elsewhere herein. Briefly, the expression of polynucleotides and polypeptides corresponding to this gene in tonsils as well as neutrophils indicates a role in the regulation of the proliferation; survival; differentiation; and/or activation of potentially all hematopoietic cell lineages, including blood stem cells. Polynucleotides and polypeptides corresponding to this gene may be involved in the regulation of cytokine production, antigen presentation, or other processes that may also suggest a usefulness in the treatment of cancer (e.g., by boosting immune responses). Since the gene is expressed in cells of lymphoid origin, the gene or protein, as well as, antibodies directed against the protein may show utility as a tumor marker and/or immunotherapy targets for the above listed tissues. Therefore it may be also used as an agent for immunological disorders including arthritis, asthma, immune deficiency diseases such as AIDS, leukemia, rheumatoid arthritis, inflammatory bowel disease, sepsis, acne, and psoriasis. In addition, polynucleotides and polypeptides corresponding to this gene may have commercial utility in the expansion of stem cells and committed progenitors of various blood lineages, and in the differentiation and/or proliferation of various cell types. Alternatively, the tissue distribution indicates that polynucleotides and polypeptides corresponding to this gene would be useful for the treatment and/or diagnosis of conditions concerning proper testicular function (e.g. endocrine function, sperm maturation), as well as cancer. Therefore, polynucleotides and polypeptides corresponding to this gene would be useful in the treatment of male infertility and/or impotence. Polynucleotides and polypeptides corresponding to this gene is also useful in assays designed to identify binding agents, as such agents (antagonists) would be useful as male contraceptive agents. Similarly, the protein is believed to be useful in the treatment and/or diagnosis of testicular cancer. The testes are also a site of active gene expression of transcripts that may be expressed, particularly at low levels, in other tissues of the body. Therefore, polynucleotides and polypeptides corresponding to this gene may be expressed in other specific tissues or organs where it may play related functional roles in other processes, such as hematopoiesis, inflammation, bone formation, and kidney function, to name a few possible target indications. The tissue distribution in brain and cerebellum tissues indicates that polynucleotides and polypeptides corresponding to this gene would be useful for the detection/treatment of neurodegenerative disease states and behavioural disorders such as Alzheimers Disease, Parkinsons Disease, Huntingtons Disease, Tourette Syndrome, schizophrenia, mania, dementia, paranoia, obsessive compulsive disorder, panic disorder, learning disabilities, ALS, psychoses, autism, and altered behaviors, including disorders in feeding, sleep patterns, balance, and perception. In addition, the gene or gene product may also play a role in the treatment and/or detection of developmental disorders associated with the developing embryo, or sexually-linked disorders. Furthermore, the protein may also be used to determine biological activity, to raise antibodies, as tissue markers, to isolate cognate ligands or receptors, to identify agents that modulate their interactions, in addition to its use as a nutritional supplement. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:56 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a-b, where a is any integer between 1 to 2219 of SEQ ID NO:56, b is an integer of 15 to 2233, where both a and b correspond to the positions of nucleotide residues shown in SEQ ID NO:56, and where b is greater than or equal to a +14.

Features of Protein Encoded by Gene No: 47

The translation product of this gene shares sequence homology with seven trans-membrane receptors and plectin, which is thought to be important in muscular dystrophy and multiple other diseases.

The gene encoding the disclosed cDNA is thought to reside on chromosome 16. Accordingly, polynucleotides related to this invention would be useful as a marker in linkage analysis for chromosome 16.

This gene is expressed primarily in brain, fetal organs and placental tissue, and, to a lesser extent, in several other organs and tissues.

Polynucleotides and polypeptides of the invention would be useful as reagents for differential identification of the tissue(s) or cell type(s) present in a biological sample and for diagnosis of diseases and conditions which include, but are not limited to, diseases and/or disorders of the central nervous system, fetal and developing organs. Similarly, polypeptides and antibodies directed to these polypeptides would be useful in providing immunological probes for differential identification of the tissue(s) or cell type(s). For a number of disorders of the above tissues or cells, particularly of the central nervous system, developing and fetal systems, expression of this gene at significantly higher or lower levels may be routinely detected in certain tissues or cell types (e.g., neural, developing, cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder. Preferred polypeptides of the present invention comprise, or alternatively consist of one, two or all three of the immunogenic epitopes shown in SEQ ID NO: 164 as residues: Arg-13 to Trp-19, Leu-76 to Ala-92, Ser-100 to Arg-105. Polynucleotides encoding said polypeptides are encompassed by the invention, as are antibodies that bind one or more of these peptides.

The tissue distribution and homology to plectin and seven transmembrane receptors indicates that polynucleotides and polypeptides corresponding to this gene would be useful for the treatment and/or diagnosis of disorders of the central nervous system, as well as developing and fetal systems. Moreover, the expression within fetal tissue indicates this protein may play a role in the regulation of cellular division, and may show utility in the diagnosis, treatment, and/or prevention of developmental diseases and disorders, cancer, and other proliferative conditions. Representative uses are described in the "Hyperproliferative Disorders" and "Regeneration" sections below and elsewhere herein. Briefly, developmental tissues rely on decisions involving cell differentiation and/or apoptosis in pattern formation. Dysregulation of apoptosis can result in inappropriate suppression of cell death, as occurs in the development of some cancers, or in failure to control the extent of cell death, as is believed to occur in acquired immunodeficiency and certain neurodegenerative disorders, such as spinal muscular atrophy (SMA). Because of potential roles in proliferation and differentiation, polynucleotides and polypeptides corresponding to this gene may have applications in the adult for tissue regeneration and the treatment of cancers. It may also act as a morphogen to control cell and tissue type specification. Therefore, the polynucleotides and polypeptides of the present invention would be useful in treating, detecting, and/or preventing said disorders and conditions, in addition to other types of degenerative conditions. Thus, polynucleotides and polypeptides corresponding to this gene may modulate apoptosis or tissue differentiation and would be useful in the detection, treatment, and/or prevention of degenerative or proliferative conditions and diseases. The polynucleotides and polypeptides corresponding to this gene would be useful in modulating the immune response to aberrant polypeptides, as may exist in proliferating and cancerous cells and tissues. The protein can also be used to gain new insight into the regulation of cellular growth and proliferation. Furthermore, the protein may also be used to determine biological activity, to raise antibodies, as tissue markers, to isolate cognate ligands or receptors, to identify agents that modulate their interactions, in addition to its use as a nutritional supplement. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:57 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a-b, where a is any integer between 1 to 1949 of SEQ ID NO:57, b is an integer of 15 to 1963, where both a and b correspond to the positions of nucleotide residues shown in SEQ ID NO:57, and where b is greater than or equal to a +14.

Features of Protein Encoded by Gene No: 48

In specific embodiments, polypeptides of the invention comprise, or alternatively consist of, an amino acid sequence selected from the group: LQQTMQAMLHFGGRLAQSL-RGTSKEAASDPSDSPNLPTPGSWW (SEQ ID NO: 358), EQLTQASRVYASGGTEGFPLSR-WAPGRHGTAAEEGAQERPLPTDE (SEQ ID NO: 359), MAPGRGLWLGRLFGVPGGPAENENGALK-SRRPSSWLPPTVSVLAL (SEQ ID NO: 360), VKRGAPPEMPSPQELEASAPRM-VQTHRAVRALCDHTAARPDQLS (SEQ ID NO: 361), FRRGEVLRVITTVDEDWLRCGRDG-MEGLVPVGYTSLVL (SEQ ID NO: 362), and/or LQQT-MQAMLHFGGRLAQSLRGTSKEAASDPSD-SPNLPTPGSWWEQLTQASR VYASGGTEGFPLSRWAPGRHGTAAEE-GAQERPLPTDEMAPGRGLWLGRLFG VPGGPAENEN-GALKSRRPSSWLPPTVSVLA-LVKRGAPPEMPSPQELEASAPR MVQTHRAVRALCDHTAARPDQLSFRR-GEVLRVITTVDEDWLRCGRDGMEG LVPVGYTSLVL (SEQ ID NO: 363). Moreover, fragments and variants of these polypeptides (such as, for example, fragments as described herein, polypeptides at least 80%, 85%, 90%, 95%, 96%, 97%, 98%, 99%, or 100% identical to these polypeptides, or polypeptides encoded by a polynucleotide which hybridizes, under stringent conditions, to the polynucleotide encoding these polypeptides) are encompassed by the invention. Antibodies that bind polypeptides of the invention and polynucleotides encoding these polypeptides are also encompassed by the invention.

A portion of the translation product of this gene shares sequence homology with SH3 domain of human SH3P17 protein (see, e.g., Genseq accession number W34234; all references available through this accession are hereby incorporated by reference herein) which is thought to be important in cell growth, malignancy, and/or signal transduction processes. Therefore, it is likely that the translation product of this gene shares at least some biological activity with polypeptides/proteins possessing SH domains.

This gene is expressed primarily in synovium, synovial sarcoma, and chondrosarcoma tissues, and, to a lesser extent, in endometrial stromal cells.

Polynucleotides and polypeptides of the invention would be useful as reagents for differential identification of the tissue(s) or cell type(s) present in a biological sample and for diagnosis of diseases and conditions which include, but are not limited to, skeletal and reproductive disorders. Similarly, polypeptides and antibodies directed to these polypeptides would be useful in providing immunological probes for differential identification of the tissue(s) or cell type(s). For a number of disorders of the above tissues or cells, particularly of the skeletal and reproductive systems, expression of this gene at significantly higher or lower levels may be routinely detected in certain tissues or cell types (e.g., skeletal, reproductive, cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

The tissue distribution in skeletal tissues indicates that polynucleotides and polypeptides corresponding to this gene would be useful for the detection, diagnosis, prevention and/or treatment of disorders and conditions affecting the skeletal system, in particular osteoporosis as well as disorders afflicting connective tissues (e.g., arthritis, trauma, tendonitis, chrondomalacia and inflammation). The polynucleotides and polypeptides of the invention would be useful in the diagnosis or treatment of various autoimmune disorders such as rheumatoid arthritis, lupus, scleroderma, and dermatomyositis as well as dwarfism, spinal deformation, and specific joint abnormalities as well as chondrodysplasias (i.e., spondyloepiphyseal dysplasia congenita, familial arthritis, Atelosteogenesis type II, metaphyseal chondrodysplasia type Schmid). Alternatively, the tissue distribution in endometrium indicates that polynucleotides and polypeptides corresponding to this gene would be useful for treating female infertility. The polynucleotides and polypeptides of the invention are likely involved in preparation of the endometrium of implantation and could be administered either topically or orally. Alternatively, this gene could be transfected in gene-replacement treatments into the cells of the endometrium and the protein products could be produced. Similarly, these treatments could be performed during artificial insemination for the purpose of increasing the likelihood of implantation and development of a healthy embryo. In both cases this gene or its gene product could be administered at later stages of pregnancy to promote healthy development of the endometrium. Furthermore, the protein may also be used to determine biological activity, to raise antibodies, as tissue markers, to isolate cognate ligands or receptors, to identify agents that modulate their interactions, in addition to its use as a nutritional supplement. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:58 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a-b, where a is any integer between 1 to 1253 of SEQ ID NO:58, b is an integer of 15 to 1267, where both a and b correspond to the positions of nucleotide residues shown in SEQ ID NO:58, and where b is greater than or equal to a +14.

Features of Protein Encoded by Gene No: 49

The gene encoding the disclosed cDNA is believed to reside on chromosome 7. Accordingly, polynucleotides related to this invention would be useful as a marker in linkage analysis for chromosome 7.

In specific embodiments, polypeptides of the invention comprise, or alternatively consist of, an amino acid sequence selected from the group: ARACPRXGAAVEKLGGK-PVQPDSKPTCCSQVKAEGLIFAGLTGLKLLPSSLQ RAVFVRQCLGFWNDGSRALQ (SEQ ID NO:364) and MSPNLNATHTSAQTPGFMERKTTHTVA-QALSHAVRTIRGARSPLRPDASRTP TSCQMSTQSL-LICKARLPSFQNPRHCLTKTALCKELG-SNLSPVRPAKISPSALT CEQHVGLESGWTGFPPSFSTAAPXLGQARA (SEQ ID NO: 365). Moreover, fragments and variants of these polypeptides (such as, for example, fragments as described herein, polypeptides at least 80%, 85%, 90%, 95%, 96%, 97%, 98%, 99%, or 100% identical to these polypeptides, or polypeptides encoded by a polynucleotide which hybridizes, under stringent conditions, to the polynucleotide encoding these polypeptides) are encompassed by the invention. Antibodies that bind polypeptides of the invention and polynucleotides encoding these polypeptides are also encompassed by the invention.

This gene is expressed primarily in hypothalamus, hepatocellular tumor, ovarian cancer reexcision and, to a lesser extent, in other tissues.

Polynucleotides and polypeptides of the invention would be useful as reagents for differential identification of the tissue(s) or cell type(s) present in a biological sample and for diagnosis of diseases and conditions which include, but are not limited to, obesity, metabolic disorders, and hepatocellular tumors. Similarly, polypeptides and antibodies directed to these polypeptides would be useful in providing immunological probes for differential identification of the tissue(s) or cell type(s). For a number of disorders of the above tissues or cells, particularly of the, endocrine system, hypothalamus and hepatocellular tumor, expression of this gene at significantly higher or lower levels may be routinely detected in certain tissues or cell types (e.g., hypothalamus, cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

The tissue distribution in hypothalamus and hepatocellular tumors indicates that the protein products of this gene would be useful for detection, treatment, and/or prevention of obesity, metabolic disorders, and hepatocellular tumors. Similarly, the tissue distribution indicates that polynucleotides and polypeptides corresponding to this gene would be useful for the detection, treatment, and/or prevention of various endocrine disorders and cancers, particularly Addison's disease, Cushing's Syndrome, and disorders and/or cancers of the pancreas (e.g., diabetes mellitus), adrenal cortex, ovaries, pituitary (e.g., hyper-, hypopituitarism), thyroid (e.g., hyper-, hypothyroidism), parathyroid (e.g., hyper-, hypoparathyroidism), hypothalamus, and testes. Furthermore, the protein may also be used to determine biological activity, to raise antibodies, as tissue markers, to isolate cognate ligands or receptors, to identify agents that modulate their interactions, in addition to its use as a nutritional supplement. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:59 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a-b, where a is any integer between 1 to 1281 of SEQ ID NO:59, b is an integer of 15 to 1295, where both a and b correspond to the positions of nucleotide residues shown in SEQ ID NO:59, and where b is greater than or equal to a +14.

Features of Protein Encoded by Gene No: 50

In specific embodiments, polypeptides of the invention comprise, or alternatively consist of, the following amino acid sequence: FQSVYHMKLQSSNLPASVYGNNLNCINSSSS (SEQ ID NO: 366). Moreover, fragments and variants of these polypeptides (such as, for example, fragments as described herein, polypeptides at least 80%, 85%, 90%, 95%, 96%, 97%, 98%, 99%, or 100% identical to these polypeptides, or polypeptides encoded by a polynucleotide which hybridizes, under stringent conditions, to the polynucleotide encoding these polypeptides) are encompassed by the invention. Antibodies that bind polypeptides of the invention and polynucleotides encoding these polypeptides are also encompassed by the invention.

This gene is expressed primarily in brain, placenta, immune cells (e.g., B-cells and macrophage), fetal tissue and breast.

Polynucleotides and polypeptides of the invention would be useful as reagents for differential identification of the tissue(s) or cell type(s) present in a biological sample and for diagnosis of diseases and conditions which include, but are not limited to, reproductive, neurological and behavioural disorders. Similarly, polypeptides and antibodies directed to these polypeptides would be useful in providing immunological probes for differential identification of the tissue(s) or cell type(s). For a number of disorders of the above tissues or cells, particularly of the CNS, immune and female reproductive systems, expression of this gene at significantly higher or lower levels may be routinely detected in certain tissues or cell types (e.g., immune, reproductive, CNS, cancerous and wounded tissues) or bodily fluids (e.g., lymph, breast milk, amniotic fluid, serum, plasma, urine, synovial fluid or cerebrospinal fluid) or another tissue or cell sample taken from an individual having such a disorder, relative to the standard gene expression level, i.e., the expression level in healthy tissue or bodily fluid from an individual not having the disorder.

The tissue distribution in brain indicates the protein product of this clone would be useful for the detection, treatment, and/or prevention of neurodegenerative disease states, behavioral disorders, or inflammatory conditions. Representative uses are described in the "Regeneration" and "Hyperproliferative Disorders" sections below, in Example 11, 15, and 18, and elsewhere herein. Briefly, the uses include, but are not limited to the detection, treatment, and/or prevention of Alzheimer's Disease, Parkinson's Disease, Huntington's Disease, Tourette Syndrome, meningitis, encephalitis, demyelinating diseases, peripheral neuropathies, neoplasia, trauma, congenital malformations, spinal cord injuries, ischemia and infarction, aneurysms, hemorrhages, schizophrenia, mania, dementia, paranoia, obsessive compulsive disorder, depression, panic disorder, learning disabilities, ALS, psychoses, autism, and altered behaviors, including disorders in feeding, sleep patterns, balance, and perception. In addition, elevated expression of Polynucleotides and polypeptides corresponding to this gene in regions of the brain indicates it plays a role in normal neural function. Potentially, polynucleotides and polypeptides corresponding to this gene would be involved in synapse formation, neurotransmission, learning, cognition, homeostasis, or neuronal differentiation or survival. The tissue distribution in B-cells and macrophage indicates that polynucleotides and polypeptides corresponding to this gene would be useful for the diagnosis and treatment of a variety of immune system disorders. Representative uses are described in the "Immune Activity" and "Infectious Disease" sections below, in Example 11, 13, 14, 16, 18, 19, 20, and 27, and elsewhere herein. Briefly, the expression indicates a role in regulating the proliferation; survival; differentiation; and/or activation of hematopoietic cell lineages, including blood stem cells. Involvement in the regulation of cytokine production, antigen presentation, or other processes indicates a usefulness for treatment of cancer (e.g., by boosting immune responses). Expression in cells of lymphoid origin, indicates the natural gene product would be involved in immune functions. Therefore it would also be useful as an agent for immunological disorders including arthritis, asthma, immunodeficiency diseases such as AIDS, leukemia, rheumatoid arthritis, granulomatous disease, inflammatory bowel disease, sepsis, acne, neutropenia, neutrophilia, psoriasis, hypersensitivities, such as T-cell mediated cytotoxicity; immune reactions to transplanted organs and tissues, such as host-versus-graft and graft-versus-host diseases, or autoimmunity disorders, such as autoimmune infertility, lense tissue injury, demyelination, systemic lupus erythematosis, drug induced hemolytic anemia, rheumatoid arthritis, Sjogren's disease, and scleroderma. Moreover, the protein may represent a secreted factor that influences the differentiation or behavior of other blood cells, or that recruits hematopoietic cells to sites of injury. Thus, polynucleotides and polypeptides corresponding to this gene is thought to be useful in the expansion of stem cells and committed progenitors of various blood lineages, and in the differentiation and/or proliferation of various cell types. In addition, expression in breast and placenta indicates a role in the detection and/or treatment of female infertility and/or pregnancy disorders. In addition, the gene or gene product may also play a role in the treatment and/or detection of developmental disorders associated with the developing embryo, or sexually-linked disorders. Moreover, the expression within fetal tissue and other cellular sources marked by proliferating cells indicates this protein may play a role in the regulation of cellular division, and may show utility in the diagnosis, treatment, and/or prevention of developmental diseases and disorders, including cancer, and other proliferative conditions. Representative uses are described in the "Hyperproliferative Disorders" and "Regeneration" sections below and elsewhere herein. Briefly, developmental tissues rely on decisions involving cell differentiation and/or apoptosis in pattern formation. Dysregulation of apoptosis can result in inappropriate suppression of cell death, as occurs in the development of some cancers, or in failure to control the extent of cell death, as is believed to occur in acquired immunodeficiency and certain degenerative disorders, such as spinal muscular atrophy (SMA). Alternatively, polynucleotides and polypeptides corresponding to this gene may be involved in the pattern of cellular proliferation that accompanies early embryogenesis. Thus, aberrant expression of polynucleotides and polypeptides corresponding to this gene in tissues—particularly adult tissues—may correlate with patterns of abnormal cellular proliferation, such as found in various cancers. Because of potential roles in proliferation and differentiation, polynucleotides and polypeptides corresponding to this gene may have applications in the adult for tissue regeneration and the treatment of cancers. It may also act as a morphogen to control cell and tissue type specification. Therefore, the polynucleotides and polypeptides of the present invention would be useful in treating, detecting, and/or preventing said disorders and conditions, in addition to other types of degenerative conditions. Thus this protein may modulate apoptosis or tissue differentiation and would be useful in the detection, treatment, and/or prevention of degenerative or proliferative conditions and diseases. The protein would be useful in modulating the immune response to aberrant polypeptides, as may exist in proliferating and cancerous cells and tissues. The protein can also be used to gain new insight into the regulation of cellular growth and proliferation. Furthermore, the protein may also be used to determine biological activity, raise antibodies, as tissue markers, to isolate cognate ligands or receptors, to identify agents that modulate their interactions, in addition to its use as a nutritional supplement. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:60 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a-b, where a is any integer between 1 to 901 of SEQ ID NO:60, b is an integer of 15 to 915, where both a and b correspond to the positions of nucleotide residues shown in SEQ ID NO:60, and where b is greater than or equal to a +14.

Features of Protein Encoded by Gene No: 51

This gene is expressed primarily in adipocytes.

Polynucleotides and polypeptides of the invention would be useful as reagents for differential identification of the tissue(s) or cell type(s) present in a biological sample and for diagnosis of diseases and conditions which include, but are not limited to, obesity, Nasu-Hakola disease, cardiovascular disease, non-insulin-dependent diabetes mellitus. Similarly, polypeptides and antibodies directed to these polypeptides would be useful in providing immunological probes for differential identification of the tissue(s) or cell type(s). For a number of disorders of the above tissues or cells, particularly of the adipose, expression of this gene at significantly higher or lower levels may be routinely detected in certain tissues or cell types (e.g., endocrine, cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder. Preferred polypeptides of the present invention comprise, or alternatively consist of one or both of the immunogenic epitopes shown in SEQ ID NO: 168 as residues: Asp-6 to Arg-12, Lys-31 to Leu-41. Polynucleotides encoding said polypeptides are encompassed by the invention, as are antibodies that bind one or more of these peptides.

The tissue distribution in adipose tissue indicates that polynucleotides and polypeptides corresponding to this gene would be useful for the treatment and diagnosis of endocrine and metabolic disorders related to lipids and adipose tissue, such as obesity, Nasu-Hakola disease (membranous lipodystrophy), cardiovascular disease, lipidemia, non-insulin-dependent diabetes mellitus, stroke and carcinoma. Furthermore, polynucleotides and polypeptides corresponding to this gene may show utility in ameliorating conditions which occur secondary to aberrant fatty-acid metabolism (e.g., aberrant myelin sheath development), either directly or indirectly. Furthermore, the protein may also be used to determine biological activity, raise antibodies, as tissue markers, to isolate cognate ligands or receptors, to identify agents that modulate their interactions, in addition to its use as a nutritional supplement. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:61 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a-b, where a is any integer between 1 to 1431 of SEQ ID NO:61, b is an integer of 15 to 1445, where both a and b correspond to the positions of nucleotide residues shown in SEQ ID NO:61, and where b is greater than or equal to a +14.

Features of Protein Encoded by Gene No: 52

The gene encoding the disclosed cDNA is thought to reside on chromosome 1. Accordingly, polynucleotides related to this invention would be useful as a marker in linkage analysis for chromosome 1.

In specific embodiments, polypeptides of the invention comprise, or alternatively consist of, the following amino acid sequence: GLSIHDGTWKSAI YGFGDQSNLRKLRNVSNLKPVPLIGPKLKRRWPISYCRELKGYSIPFMGSDVS VVRRTQRYLYENLEESPVQYAAYVTVGGITSVIKLMFAGLFFLFFVRFG IRQ LLIKFPWFFSFGYFSKQGPTQKQIDAASFTLTFFGQGYSQGTGTDKNKPNIKIC TQVKGPEAGYVATPIAMVQAAMTLLSDASHLPKAGGVFTPGAAFSKTKLI DRLNKHGIEFSVISSSEV (SEQ ID NO: 367) Moreover, fragments and variants of these polypeptides (such as, for example, fragments as described herein, polypeptides at least 80%, 85%, 90%, 95%, 96%, 97%, 98%, 99%, or 100% identical to these polypeptides, or polypeptides encoded by a polynucleotide which hybridizes, under stringent conditions, to the polynucleotide encoding these polypeptides) are encompassed by the invention. Antibodies that bind polypeptides of the invention and polynucleotides encoding these polypeptides are also encompassed by the invention.

This gene is expressed primarily in testes, endometrial tumor tissue, prostate cancer tissue, immune tissue (e.g., bone marrow and T-cells) and placenta tissue, and, to a lesser extent, in several other tissues and organs.

Polynucleotides and polypeptides of the invention would be useful as reagents for differential identification of the tissue(s) or cell type(s) present in a biological sample and for diagnosis of diseases and conditions which include, but are not limited to, reproductive diseases and disorders, cancers and hematopoietic disorders. Similarly, polypeptides and antibodies directed to these polypeptides would be useful in providing immunological probes for differential identification of the tissue(s) or cell type(s). For a number of disorders of the above tissues or cells, particularly of the hematopoietic and reproductive system, expression of this gene at significantly higher or lower levels may be routinely detected in certain tissues or cell types (e.g., immune, reproductive, cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder. Preferred polypeptides of the present invention comprise, or alternatively consist of one or both of the immunogenic epitopes shown in SEQ ID NO: 169 as residues: Phe-32 to Gln-41, Gln-54 to Asn-68. Polynucleotides encoding said polypeptides are encompassed by the invention, as are antibodies that bind one or more of these peptides.

The tissue distribution in testes tissue and bone marrow indicates that polynucleotides and polypeptides corresponding to this gene would be useful for the treatment and/or diagnosis of disorders of the hematopoietic and reproductive systems, and cancers thereof. The tissue distribution in bone marrow and T-cells indicates the protein product of this clone would be useful for the diagnosis and treatment of a variety of immune system disorders. Representative uses are described in the "Immune Activity" and "Infectious Disease" sections below, in Example 11, 13, 14, 16, 18, 19, 20, and 27, and elsewhere herein. Briefly, the expression indicates a role in regulating the proliferation; survival; differentiation; and/or activation of hematopoietic cell lineages, including blood stem cells. Involvement in the regulation of cytokine production, antigen presentation, or other processes indicates a usefulness for treatment of cancer (e.g. by boosting immune responses). Expression in cells of lymphoid origin, indicates the natural gene product would be involved in immune functions. Therefore it would also be useful as an agent for immunological disorders including arthritis, asthma, immunodeficiency diseases such as AIDS, leukemia, rheumatoid arthritis, granulomatous disease, inflammatory bowel disease, sepsis, acne, neutropenia, neutrophilia, psoriasis, hypersensitivities, such as T-cell mediated cytotoxicity; immune reactions to transplanted organs and tissues, such as host-versus-graft and graft-versus-host diseases, or autoimmunity disorders, such as autoimmune infertility, lense tissue injury, demyelination, systemic lupus erythematosis, drug induced hemolytic anemia, rheumatoid arthritis, Sjogren's disease, and scleroderma. Moreover, the protein may represent a secreted factor that influences the differentiation or behavior of other blood cells, or that recruits hematopoietic cells to sites of injury. Thus, polynucleotides and polypeptides corresponding to this gene is thought to be useful in the expansion of stem cells and committed progenitors of various blood lineages, and in the differentiation and/or proliferation of various cell types. The tissue distribution indicates that polynucleotides and polypeptides corresponding to this gene would be useful for the treatment and diagnosis of conditions concerning proper testicular function (e.g., endocrine function, sperm maturation), as well as cancer. Therefore, polynucleotides and polypeptides corresponding to this gene would be useful in the treatment of male infertility and/or impotence. Polynucleotides and polypeptides corresponding to this gene is also useful in assays designed to identify binding agents, as such agents (antagonists) would be useful as male contraceptive agents. Similarly, the protein is believed to be useful in the treatment and/or diagnosis of testicular cancer. The testes are also a site of active gene expression of transcripts that may be expressed, particularly at low levels, in other tissues of the body. Therefore, polynucleotides and polypeptides corresponding to this gene may be expressed in other specific tissues or organs where it may play related functional roles in other processes, such as hematopoiesis, inflammation, bone formation, and kidney function, to name a few possible target indications. Furthermore, the protein may also be used to determine biological activity, to raise antibodies, as tissue markers, to isolate cognate ligands or receptors, to identify agents that modulate their interactions, in addition to its use as a nutritional supplement. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:62 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a-b, where a is any integer between 1 to 1086 of SEQ ID NO:62, b is an integer of 15 to 1100, where both a and b correspond to the positions of nucleotide residues shown in SEQ ID NO:62, and where b is greater than or equal to a +14.

Features of Protein Encoded by Gene No: 53

The translation product of this gene has homology with metallothionine proteins from several organisms.

This gene is expressed primarily in ovarian cancer, fetal tissue (e.g., liver, spleen, and heart), testes, embryo, colon, T-cells, neutrophils, tonsils, B-cell lymphoma, and to a lesser extent in many other tissues.

Polynucleotides and polypeptides of the invention would be useful as reagents for differential identification of the tissue(s) or cell type(s) present in a biological sample and for diagnosis of diseases and conditions which include, but are not limited to, reproductive defects, and lymphoid and ovarian cancers. Similarly, polypeptides and antibodies directed to these polypeptides would be useful in providing immunological probes for differential identification of the tissue(s) or cell type(s). For a number of disorders of the above tissues or cells, particularly of the immune and female reproductive systems, and of lymphoid and ovarian cancers, expression of this gene at significantly higher or lower levels may be routinely detected in certain tissues or cell types (e.g., immune, reproductive, cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder. Preferred polypeptides of the present invention comprise, or alternatively consist of the immunogenic epitopes shown in SEQ ID NO: 170 as residues: Leu-39 to Ser-47. Polynucleotides encoding said polypeptides are encompassed by the invention, as are antibodies that bind one or more of these peptides.

The tissue distribution in ovarian cancer, tonsils, and B-cell lymphoma indicates that polynucleotides and polypeptides corresponding to this gene would be useful for the study, detection and/or treatment of female reproductive disorders, gonadal and general lymphoid neoplasias, and cancers thereof. The tissue distribution in immune cells (e.g., neutrophils and T-cells) indicates the protein product of this clone would be useful for the diagnosis and treatment of a variety of immune system disorders. Representative uses are described in the "Immune Activity" and "Infectious Disease" sections below, in Example 11, 13, 14, 16, 18, 19, 20, and 27, and elsewhere herein. Briefly, the expression indicates a role in regulating the proliferation; survival; differentiation; and/or activation of hematopoietic cell lineages, including blood stem cells. Involvement in the regulation of cytokine production, antigen presentation, or other processes indicates a usefulness for treatment of cancer (e.g. by boosting immune responses). Expression in cells of lymphoid origin, indicates the natural gene product would be involved in immune functions. Therefore it would also be useful as an agent for immunological disorders including arthritis, asthma, immunodeficiency diseases such as AIDS, leukemia, rheumatoid arthritis, granulomatous disease, inflammatory bowel disease, sepsis, acne, neutropenia, neutrophilia, psoriasis, hypersensitivities, such as T-cell mediated cytotoxicity; immune reactions to transplanted organs and tissues, such as host-versus-graft and graft-versus-host diseases, or autoimmunity disorders, such as autoimmune infertility, lense tissue injury, demyelination, systemic lupus erythematosis, drug induced hemolytic anemia, rheumatoid arthritis, Sjogren's disease, and scleroderma. Moreover, the protein may represent a secreted factor that influences the differentiation or behavior of other blood cells, or that recruits hematopoietic cells to sites of injury. Thus, polynucleotides and polypeptides corresponding to this gene is thought to be useful in the expansion of stem cells and committed progenitors of various blood lineages, and in the differentiation and/or proliferation of various cell types. Expression of polynucleotides and polypeptides corresponding to this gene in tonsils indicates a role in the regulation of the proliferation; survival; differentiation; and/or activation of potentially all hematopoietic cell lineages, including blood stem cells. Polynucleotides and polypeptides corresponding to this gene may be involved in the regulation of cytokine production, antigen presentation, or other processes that may also suggest a usefulness in the treatment of cancer (e.g., by boosting immune responses). Since the gene is expressed in cells of lymphoid origin, the gene or protein, as well as, antibodies directed against the protein may show utility as a tumor marker and/or immunotherapy targets for the above listed tissues. Therefore it may be also used as an agent for immunological disorders including arthritis, asthma, immune deficiency diseases such as AIDS, leukemia, rheumatoid arthritis, inflammatory bowel disease, sepsis, acne, and psoriasis. In addition, polynucleotides and polypeptides corresponding to this gene may have commercial utility in the expansion of stem cells and committed progenitors of various blood lineages, and in the differentiation and/or proliferation of various cell types. Furthermore, the protein may also be used to determine biological activity, raise antibodies, as tissue markers, to isolate cognate ligands or receptors, to identify agents that modulate their interactions, in addition to its use as a nutritional supplement. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:63 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a-b, where a is any integer between 1 to 1485 of SEQ ID NO:63, b is an integer of 15 to 1499, where both a and b correspond to the positions of nucleotide residues shown in SEQ ID NO:63, and where b is greater than or equal to a +14.

Features of Protein Encoded by Gene No: 54

In specific embodiments, polypeptides of the invention comprise, or alternatively consist of, an amino acid sequence selected from the group: MDPDRAFICGESRQFAQCLIFGFLFLTSGMLISVLGIWVPGCGSNWAQEPLNE TDTGDSEPRMCGFLSLQIMGPLIV- LVGLCFFVVAHVKKRNTLNAGQDASERE EGQIQIMEPVQVTVGDSVIIFPPPPPPY-FPESSASAVAESPGTNSLLPNENPPSY YSIFNYGTPT-SEGAASERDCESIYTISGTNSSSEASHT-PHLPSELPPRYEEKENA AATFLPLSSEPSPP (SEQ ID NO: 369), and/or MDPDRAFICGESRQFAQCLIFG-FLFLTSGMLISVLGIWVPGCGSNWAQEPLNE TDTGD-SEPR (SEQ ID NO: 368). Moreover, fragments and variants of these polypeptides (such as, for example, fragments as described herein, polypeptides at least 80%, 85%, 90%, 95%, 96%, 97%, 98%, 99%, or 100% identical to these polypeptides, or polypeptides encoded by a polynucleotide which hybridizes, under stringent conditions, to the polynucleotide encoding these polypeptides) are encompassed by the invention. Antibodies that bind polypeptides of the invention and polynucleotides encoding these polypeptides are also encompassed by the invention.

This gene is expressed primarily in adult kidney and pulmonary tissues, as well as in osteoblasts.

Polynucleotides and polypeptides of the invention would be useful as reagents for differential identification of the tissue(s) or cell type(s) present in a biological sample and for diagnosis of diseases and conditions which include, but are not limited to, metabolic, endocrine and skeletal disorders. Similarly, polypeptides and antibodies directed to these polypeptides would be useful in providing immunological probes for differential identification of the tissue(s) or cell type(s). For a number of disorders of the above tissues or cells, particularly of the endocrine, skeletal, metabolic and developmental systems, expression of this gene at significantly higher or lower levels may be routinely detected in certain tissues or cell types (e.g., endocrine, skeletal, cancerous and wounded tissues) or bodily fluids (e.g., sputum, lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder. Preferred polypeptides of the present invention comprise, or alternatively consist of one, two, three, four, five or all six of the immunogenic epitopes shown in SEQ ID NO: 171 as residues: Ala-35 to Gly-45, Pro-67 to Pro-73, Pro-91 to Ser-97, Thr-127 to Leu-139, Leu-143 to Asn-152, Ser-162 to Pro-167. Polynucleotides encoding said polypeptides are encompassed by the invention, as are antibodies that bind one or more of these peptides.

The tissue distribution in kidney tissue and osteoblasts indicates that polynucleotides and polypeptides corresponding to this gene would be useful for the study, diagnosis and/or treatment of various endocrine and skeletal disorders. Furthermore, elevated levels of expression of polynucleotides and polypeptides corresponding to this gene in osteoblasts indicates that it may play a role in the survival, proliferation, and/or growth of osteoblasts. Therefore, it may be useful in influencing bone mass in such conditions as osteoporosis. Alternatively, the tissue distribution in kidney indicates that this gene or gene product would be useful in the treatment and/or detection of kidney diseases including renal failure, nephritus, renal tubular acidosis, proteinuria, pyuria, edema, pyelonephritis, hydronephritis, nephrotic syndrome, crush syndrome, glomerulonephritis, hematuria, renal colic and kidney stones, in addition to Wilm's Tumor Disease, and congenital kidney abnormalities such as horseshoe kidney, polycystic kidney, and Falconi's syndrome. Furthermore, the protein may also be used to determine biological activity, to raise antibodies, as tissue markers, to isolate cognate ligands or receptors, to identify agents that modulate their interactions, in addition to its use as a nutritional supplement. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:64 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a-b, where a is any integer between 1 to 641 of SEQ ID NO:64, b is an integer of 15 to 655, where both a and b correspond to the positions of nucleotide residues shown in SEQ ID NO:64, and where b is greater than or equal to a +14.

Features of Protein Encoded by Gene No: 55

This gene is expressed primarily in neutrophils and embryonic tissues.

Polynucleotides and polypeptides of the invention would be useful as reagents for differential identification of the tissue(s) or cell type(s) present in a biological sample and for diagnosis of diseases and conditions which include, but are not limited to, immune system disorders and cancers, and developmental disorders. Similarly, polypeptides and antibodies directed to these polypeptides would be useful in providing immunological probes for differential identification of the tissue(s) or cell type(s). For a number of disorders of the above tissues or cells, particularly of the immune and developing systems, expression of this gene at significantly higher or lower levels may be routinely detected in certain tissues or cell types (e.g., immune, developing, cancerous and wounded tissues) or bodily fluids (e.g., lymph, amniotic fluid, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder. Preferred polypeptides of the present invention comprise, or alternatively consist of one, two, three, four, five, six, seven or all eight of the immunogenic epitopes shown in SEQ ID NO: 172 as residues: Gln-21 to Ala-33, Lys-48 to Leu-54, His-91 to Arg-97, Ala-143 to Gln-148, Glu-173 to Thr-179, Ser-215 to Lys-254, Arg-262 to Glu-269, Ala-309 to Gly-314. Polynucleotides encoding said polypeptides are encompassed by the invention, as are antibodies that bind one or more of these peptides.

The tissue distribution in neutrophils and embryonic tissues indicates that polynucleotides and polypeptides corresponding to this gene would be useful for the diagnosis, study and/or treatment of various developmental and immune system disorders and cancers thereof, as well as cancers of other tissues where expression of this gene has been observed. Furthermore, expression within embryonic tissue and other cellular sources marked by proliferating cells indicates that this protein may play a role in the regulation of cellular division, and may show utility in the detection, treatment, and/or prevention of cancer and other proliferative disorders. Similarly, embryonic development also involves decisions involving cell differentiation and/or apoptosis in pattern formation. Thus, this protein may also be involved in apoptosis or tissue differentiation and could again be useful in cancer therapy. Alternatively, expression of polynucleotides and polypeptides corresponding to this gene in neutrophils also strongly indicates a role for this protein in immune function and immune surveillance. Furthermore, the protein may also be used to determine biological activity, to raise antibodies, as tissue markers, to isolate cognate ligands or receptors, to identify agents that modulate their interactions, in addition to its use as a nutritional supplement. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:65 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a-b, where a is any integer between 1 to 1436 of SEQ ID NO:65, b is an integer of 15 to 1450, where both a and b correspond to the positions of nucleotide residues shown in SEQ ID NO:65, and where b is greater than or equal to a +14.

Features of Protein Encoded by Gene No: 56

In specific embodiments, polypeptides of the invention comprise, or alternatively consist of, the following amino acid sequence: FDFIASLLKANRLSLQTCELL-LAAALLPSERYKAISI (SEQ ID NO: 370). Moreover, fragments and variants of these polypeptides (such as, for example, fragments as described herein, polypeptides at least 80%, 85%, 90%, 95%, 96%, 97%, 98%, 99%, or 100% identical to these polypeptides, or polypeptides encoded by a polynucleotide which hybridizes, under stringent conditions, to the polynucleotide encoding these polypeptides) are encompassed by the invention. Antibodies that bind polypeptides of the invention and polynucleotides encoding these polypeptides are also encompassed by the invention.

This gene is expressed primarily in fetal liver, spleen and, to a lesser extent, in breast.

Polynucleotides and polypeptides of the invention would be useful as reagents for differential identification of the tissue(s) or cell type(s) present in a biological sample and for diagnosis of diseases and conditions which include, but are not limited to, immune and haemopoietic diseases and/or disorders, in addition to, fetal development. Similarly, polypeptides and antibodies directed to these polypeptides would be useful in providing immunological probes for differential identification of the tissue(s) or cell type(s). For a number of disorders of the above tissues or cells, particularly of the circulatory system, expression of this gene at significantly higher or lower levels may be routinely detected in certain tissues or cell types (e.g., hematopoietic, developmental, and cancerous and wounded tissues) or bodily fluids (e.g., lymph, amniotic fluid, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder. Preferred polypeptides of the present invention comprise, or alternatively consist of one or both of the immunogenic epitopes shown in SEQ ID NO: 173 as residues: Ile-50 to Ser-61, Pro-75 to Ser-104. Polynucleotides encoding said polypeptides are encompassed by the invention, as are antibodies that bind one or more of these peptides.

The tissue distribution in fetal liver and spleen indicates that polynucleotides and polypeptides corresponding to this gene would be useful for detection, treatment, and/or prevention of haemopoietic disorders involving stem cell production and maturation. Similarly, polynucleotides and polypeptides corresponding to this gene would be useful for the treatment and diagnosis of hematopoietic related disorders such as anemia, pancytopenia, leukopenia, thrombocytopenia or leukemia since stromal cells are important in the production of cells of hematopoietic lineages. Representative uses are described in the “Immune Activity” and “Infectious Disease” sections below, in Example 11, 13, 14, 16, 18, 19, 20, and 27, and elsewhere herein. Briefly, the uses include bone marrow cell ex-vivo culture, bone marrow transplantation, bone marrow reconstitution, radiotherapy or chemotherapy of neoplasia. The gene product may also be involved in lymphopoiesis, therefore, it can be used in immune disorders such as infection, inflammation, allergy, immunodeficiency etc. In addition, polynucleotides and polypeptides corresponding to this gene may have commercial utility in the expansion of stem cells and committed progenitors of various blood lineages, and in the differentiation and/or proliferation of various cell types. Furthermore, the protein may also be used to determine biological activity, to raise antibodies, as tissue markers, to isolate cognate ligands or receptors, to identify agents that modulate their interactions, in addition to its use as a nutritional supplement. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:66 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a-b, where a is any integer between 1 to 656 of SEQ ID NO:66, b is an integer of 15 to 670, where both a and b correspond to the positions of nucleotide residues shown in SEQ ID NO:66, and where b is greater than or equal to a +14.

Features of Protein Encoded by Gene No: 57

In specific embodiments, polypeptides of the invention comprise, or alternatively consist of, the following amino acid sequence: MNKKAELKPSALPGWANVWKLM-CLVTVCASLIITSDSVVSTVRLKGSCEDY LGLSCGNT-SHAY (SEQ ID NO: 371). Moreover, fragments and variants of these polypeptides (such as, for example, fragments as described herein, polypeptides at least 80%, 85%, 90%, 95%, 96%, 97%, 98%, 99%, or 100% identical to these polypeptides, or polypeptides encoded by a polynucleotide which hybridizes, under stringent conditions, to the polynucleotide encoding these polypeptides) are encompassed by the invention. Antibodies that bind polypeptides of the invention and polynucleotides encoding these polypeptides are also encompassed by the invention.

This gene is expressed primarily in adult pulmonary cells.

Polynucleotides and polypeptides of the invention would be useful as reagents for differential identification of the tissue(s) or cell type(s) present in a biological sample and for diagnosis of diseases and conditions which include, but are not limited to, emphysema and other pulmonary diseases and/or disorders. Similarly, polypeptides and antibodies directed to these polypeptides would be useful in providing immunological probes for differential identification of the tissue(s) or cell type(s). For a number of disorders of the above tissues or cells, particularly of the pulmonary system, expression of this gene at significantly higher or lower levels may be routinely detected in certain tissues or cell types (e.g., lung, cardiovascular, and cancerous and wounded tissues) or bodily fluids (e.g., lymph, sputum, pulmonary surfactant, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

The tissue distribution in adult pulmonary cells indicates that polynucleotides and polypeptides corresponding to this gene would be useful for detection, treatment, and/or prevention of disorders of the pulmonary systems, especially emphysema, asthma, and other similar dysfunctions. Representative uses are described elsewhere herein. Furthermore, the protein may also be used to determine biological activity, to raise antibodies, as tissue markers, to isolate cognate ligands or receptors, to identify agents that modulate their interactions, in addition to its use as a nutritional supplement. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:67 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a-b, where a is any integer between 1 to 1678 of SEQ ID NO:67, b is an integer of 15 to 1692, where both a and b correspond to the positions of nucleotide residues shown in SEQ ID NO:67, and where b is greater than or equal to a +14.

Features of Protein Encoded by Gene No: 58

In specific embodiments, polypeptides of the invention comprise, or alternatively consist of, the following amino acid sequence: MSADGAEADGSTQVTVEEPVQQPSVVDRVASMPLISSTCDMVSAAYASTKE SYPHVKTVCDAAEKGVRTLTAAAVSGAQPILSKLEPQIASASEYAHRGLDKL EENLPILQQPTEKVLADTKELVSSKVSGAQEMVSSAKDTVATQLSEAVDATR GAVQSGVDKTKSVVTGGVQSVMGSRLGQMVLSGVDTVLGKSEEWADNHLP LTDAELARIATSLDGFDVASVQQQRQEQSYFVRLGSLSERLRQHAYEHSLGK LRATKQRAQEALLQLSQALSLMETVKQGVDQKLVEGQEKLHQMWLSWNQ KQLQGPEKEPPKPEQVESRALTMFRDIAQQLQATCTSLGSSIQGLPTNVKDQV QQARRQVEDLQATFSSIHSFQDLSSSILAQSRERVASAREALDHMVEYVAQN TPVTWLVGPFAPGITEKAPEEKK (SEQ ID NO: 372) which shares homology with a human adipocyte differentiation-related protein (see GenBank Accession CAA65989 and Heid, H. W., et al., Biochem. J. 320, 1025-1030 (1996); all references available through this accession and citation are hereby incorporated herein by reference). Moreover, fragments and variants of these polypeptides (such as, for example, fragments as described herein, polypeptides at least 80%, 85%, 90%, 95%, 96%, 97%, 98%, 99%, or 100% identical to these polypeptides, or polypeptides encoded by a polynucleotide which hybridizes, under stringent conditions, to the polynucleotide encoding these polypeptides) are encompassed by the invention. Antibodies that bind polypeptides of the invention and polynucleotides encoding these polypeptides are also encompassed by the invention. This gene is expressed primarily in hypothalamus (schizophrenic), and, to a lesser extent, in cerebellum.

Polynucleotides and polypeptides of the invention would be useful as reagents for differential identification of the tissue(s) or cell type(s) present in a biological sample and for diagnosis of diseases and conditions which include, but are not limited to, schizophenia and hypothalic diseases and/or diseases. Similarly, polypeptides and antibodies directed to these polypeptides would be useful in providing immunological probes for differential identification of the tissue(s) or cell type(s). For a number of disorders of the above tissues or cells, particularly of the central nervous system, expression of this gene at significantly higher or lower levels may be routinely detected in certain tissues or cell types (e.g., CNS, cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

The tissue distribution in hypothalamus (schizophrenic) and, to a lesser extent, in cerebellum indicates that polynucleotides and polypeptides corresponding to this gene would be useful for detection, treatment, and/or prevention of neurological disorders, especially schizophenia, neurodegenerative disease states, behavioral disorders, or inflammatory conditions. Representative uses are described in the "Regeneration" and "Hyperproliferative Disorders" sections below, in Example 11, 15, and 18, and elsewhere herein. Briefly, the uses include, but are not limited to the detection, treatment, and/or prevention of Alzheimer's Disease, Parkinson's Disease, Huntington's Disease, Tourette Syndrome, meningitis, encephalitis, demyelinating diseases, peripheral neuropathies, neoplasia, trauma, congenital malformations, spinal cord injuries, ischemia and infarction, aneurysms, hemorrhages, schizophrenia, mania, dementia, paranoia, obsessive compulsive disorder, depression, panic disorder, learning disabilities, ALS, psychoses, autism, and altered behaviors, including disorders in feeding, sleep patterns, balance, and perception. In addition, elevated expression of this gene product in regions of the brain indicates it plays a role in normal neural function. Potentially, polynucleotides and polypeptides corresponding to this gene are involved in synapse formation, neurotransmission, learning, cognition, homeostasis, or neuronal differentiation or survival. Furthermore, the protein may also be used to determine biological activity, to raise antibodies, as tissue markers, to isolate cognate ligands or receptors, to identify agents that modulate their interactions, in addition to its use as a nutritional supplement. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:68 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a-b, where a is any integer between 1 to 641 of SEQ ID NO:68, b is an integer of 15 to 655, where both a and b correspond to the positions of nucleotide residues shown in SEQ ID NO:68, and where b is greater than or equal to a +14.

Features of Protein Encoded by Gene No: 5

In specific embodiments, polypeptides of the invention comprise, or alternatively consist of, the following amino acid sequence: MLCKSLLYCVVSYLYYFVFIYFFPV-FLICSWLELQMWNLQIGRADCFQNTLV YVLSLCLQYKNHPA (SEQ ID NO: 373). Moreover, fragments and variants of these polypeptides (such as, for example, fragments as described herein, polypeptides at least 80%, 85%, 90%, 95%, 96%, 97%, 98%, 99%, or 100% identical to these polypeptides, or polypeptides encoded by a polynucleotide which hybridizes, under stringent conditions, to the polynucleotide encoding these polypeptides) are encompassed by the invention. Antibodies that bind polypeptides of the invention and polynucleotides encoding these polypeptides are also encompassed by the invention.

This gene is expressed primarily in CD34 positive hematopoietic cells.

Polynucleotides and polypeptides of the invention would be useful as reagents for differential identification of the tissue(s) or cell type(s) present in a biological sample and for diagnosis of diseases and conditions which include, but are not limited to, hematopoietic diseases and/or disorders; impaired immune function; susceptibility to infections; lymphomas and leukemias. Similarly, polypeptides and antibodies directed to these polypeptides would be useful in providing immunological probes for differential identification of the tissue(s) or cell type(s). For a number of disorders of the above tissues or cells, particularly of the immune system, expression of this gene at significantly higher or lower levels may be routinely detected in certain tissues or cell types (e.g., hematopoitic, immune, cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

The tissue distribution in CD34 positive cells indicates that polynucleotides and polypeptides corresponding to this gene would be useful for the diagnosis, detection, prevention and/or treatment of a variety of hematopoietic disorders. Expression of this gene product particularly in CD34 positive cells indicates that polynucleotides and polypeptides of the invention may play a role in the proliferation; survival; differentiation; and/or activation of early stem and committed progenitor cells within the hematopoietic system. Thus, polynucleotides and polypeptides of the invention may be useful in determining the numbers and proportions of different hematopoietic cell lineages both in vitro and in vivo. Additionally, the tissue distribution indicates polynucleotides and polypeptides corresponding to this gene would be useful for the treatment and diagnosis of hematopoietic related disorders such as anemia, pancytopenia, leukopenia, thrombocytopenia or leukemia since stromal cells are important in the production of cells of hematopoietic lineages. Representative uses are described in the “Immune Activity” and “Infectious Disease” sections below, in Example 11, 13, 14, 16, 18, 19, 20, and 27, and elsewhere herein. Briefly, the uses include bone marrow cell ex-vivo culture, bone marrow transplantation, bone marrow reconstitution, radiotherapy or chemotherapy of neoplasia. The gene product may also be involved in lymphopoiesis, therefore, it can be used in immune disorders such as infection, inflammation, allergy, immunodeficiency etc. In addition, polynucleotides and polypeptides of the invention may have commercial utility in the expansion of stem cells and committed progenitors of various blood lineages, and in the differentiation and/or proliferation of various cell types. Furthermore, the protein may also be used to determine biological activity, to raise antibodies, as tissue markers, to isolate cognate ligands or receptors, to identify agents that modulate their interactions, in addition to its use as a nutritional supplement. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:69 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a-b, where a is any integer between 1 to 1604 of SEQ ID NO:69, b is an integer of 15 to 1618, where both a and b correspond to the positions of nucleotide residues shown in SEQ ID NO:69, and where b is greater than or equal to a +14.

Features of Protein Encoded by Gene No: 60

In specific embodiments, polypeptides of the invention comprise, or alternatively consist of, an amino acid sequence selected from the group: IDLSFPSTNVSLEDRNTTKPS-VNVG (SEQ ID NO: 374), VAHACNPSTLGG (SEQ ID NO: 375), GGQITRSGDQDQPDQHG (SEQ ID NO: 376), GFTMLVRLVLIS (SEQ ID NO: 377), and PRDLPT-SASQSAGITGMSHPARPKLLFN (SEQ ID NO: 378). Moreover, fragments and variants of these polypeptides (such as, for example, fragments as described herein, polypeptides at least 80%, 85%, 90%, 95%, 96%, 97%, 98%, 99%, or 100% identical to these polypeptides, or polypeptides encoded by a polynucleotide which hybridizes, under stringent conditions, to the polynucleotide encoding these polypeptides) are encompassed by the invention. Antibodies that bind polypeptides of the invention and polynucleotides encoding these polypeptides are also encompassed by the invention.

This gene is expressed primarily in dermatofibrosarcoma protuberance and 12 week old early human embryos.

Polynucleotides and polypeptides of the invention would be useful as reagents for differential identification of the tissue(s) or cell type(s) present in a biological sample and for diagnosis of diseases and conditions which include, but are not limited to, dermatofibrosarcoma; cancer; abnormal cell proliferation; embryological/developmental defects; inhibition of apoptosis; and hematopoietic diseases and/or disorders. Similarly, polypeptides and antibodies directed to these polypeptides would be useful in providing immunological probes for differential identification of the tissue(s) or cell type(s). For a number of disorders of the above tissues or cells, particularly of the skin and epithelium, expression of this gene at significantly higher or lower levels may be routinely detected in certain tissues or cell types (e.g., integumentary, reproductive, developmental, and cancerous and wounded tissues) or bodily fluids (e.g., lymph, serum, plasma, amniotic fluid, urine, synovial fluid and spinal fluid) or another tissue or cell sample taken from an individual having such a disorder, relative to the standard gene expression level, i.e., the expression level in healthy tissue or bodily fluid from an individual not having the disorder.

The tissue distribution indicates that polynucleotides and polypeptides corresponding to this gene would be useful for the diagnosis and/or treatment of abnormal cellular proliferation, such as cancer. Expression of this gene in dermatofibrosarcoma and 12 week early stage embryos indicates that polynucleotides and polypeptides of the invention are involved in cellular proliferation and/or a block in differentiation. Polynucleotides and polypeptides of the invention may drive cellular proliferation directly, or may play a role in inhibiting apoptosis or interfering with differentiation events. Similarly, polynucleotides and polypeptides of the invention would be useful for the treatment, diagnosis, and/or prevention of various skin disorders. Representative uses are described in the “Biological Activity”, “Hyperproliferative Disorders”, “Infectious Disease”, and “Regeneration” sections below, in Example 11, 19, and 20, and elsewhere herein. Briefly, the protein would be useful in detecting, treating, and/or preventing congenital disorders (i.e. nevi, moles, freckles, Mongolian spots, hemangiomas, port-wine syndrome), integumentary tumors (i.e., keratoses, Bowen’s disease, basal cell carcinoma, squamous cell carcinoma, malignant melanoma, Paget’s disease, mycosis fungoides, and Kaposi’s sarcoma), injuries and inflammation of the skin (i.e., wounds, rashes, prickly heat disorder, psoriasis, dermatitis), atherosclerosis, uticaria, eczema, photosensitivity, autoimmune disorders (i.e., lupus erythematosus, vitiligo, dermatomyositis, morphea, scleroderma, pemphigoid, and pemphigus), keloids, striae, erythema, petechiae, purpura, and xanthelasma. In addition, such disorders may predispose increased susceptibility to viral and bacterial infections of the skin (i.e., cold sores, warts, chickenpox, molluscum contagiosum, herpes zoster, boils, cellulitis, erysipelas, impetigo, tinea, althlete’s foot, and ringworm). Moreover, polynucleotides and polypeptides corresponding to this gene may also be useful for the treatment or diagnosis of various connective tissue disorders (i.e., arthritis, trauma, tendonitis, chrondomalacia and inflammation, etc.), autoimmune disorders (i.e., rheumatoid arthritis, lupus, scleroderma, dermatomyositis, etc.), dwarfism, spinal deformation, joint abnormalities, and chondrodysplasias (i.e., spondyloepiphyseal dysplasia congenita, familial osteoarthritis, Atelosteogenesis type II, metaphyseal chondrodysplasia type Schmid). Furthermore, the protein may also be used to determine biological activity, to raise antibodies, as tissue markers, to isolate cognate ligands or receptors, to identify agents that modulate their interactions, in addition to its use as a nutritional supplement. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:70 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a-b, where a is any integer between 1 to 1788 of SEQ ID NO:70, b is an integer of 15 to 1802, where both a and b correspond to the positions of nucleotide residues shown in SEQ ID NO:70, and where b is greater than or equal to a +14.

Features of Protein Encoded by Gene No: 61

This gene is expressed primarily in neutrophils.

Polynucleotides and polypeptides of the invention would be useful as reagents for differential identification of the tissue(s) or cell type(s) present in a biological sample and for diagnosis of diseases and conditions which include, but are not limited to, disorders affecting the immune system. Similarly, polypeptides and antibodies directed to these polypeptides would be useful in providing immunological probes for differential identification of the tissue(s) or cell type(s). For a number of disorders of the above tissues or cells, particularly of the immune system expression of this gene at significantly higher or lower levels may be routinely detected in certain tissues or cell types (e.g., immune, cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue from an individual not having the disorder.

The tissue distribution in neutrophils indicates that polynucleotides and polypeptides corresponding to this gene would be useful for the diagnosis, detection, prevention and/or treatment of immune system disorders, especially those affecting neutrophils. Representative uses are described in the “Immune Activity” and “Infectious Disease” sections below, in Example 11, 13, 14, 16, 18, 19, 20, and 27, and elsewhere herein. Briefly, this gene product may be involved in the regulation of cytokine production, antigen presentation, or other processes that may also suggest a usefulness in the treatment of cancer (e.g., by boosting immune responses). Since the gene is expressed in cells of lymphoid origin, the gene or protein, as well as, antibodies directed against the protein may show utility as a tumor marker and/or immunotherapy targets for the above listed tissues. Therefore it may be also used as an agent for immunological disorders including arthritis, asthma, immune deficiency diseases such as AIDS, leukemia, rheumatoid arthritis, inflammatory bowel disease, sepsis, acne, and psoriasis. In addition, this gene product may have commercial utility in the expansion of stem cells and committed progenitors of various blood lineages, and in the differentiation and/or proliferation of various cell types. Furthermore, the protein may also be used to determine biological activity, to raise antibodies, as tissue markers, to isolate cognate ligands or receptors, to identify agents that modulate their interactions, in addition to its use as a nutritional supplement. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:71 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a-b, where a is any integer between 1 to 1278 of SEQ ID NO:71, b is an integer of 15 to 1292, where both a and b correspond to the positions of nucleotide residues shown in SEQ ID NO:71, and where b is greater than or equal to a +14.

Features of Protein Encoded by Gene No: 62

The translation product of this gene shares sequence homology with angiotensin II receptor which is thought to be important in ligand binding for blood pressure regulation. (see, e.g., GenBank Accession No. gi|387891, gi|1763532, and/or gi|349736; all references available through these accessions are hereby incorporated herein by reference). In specific embodiments, polypeptides of the invention comprise, or alternatively consist of, the following amino acid sequence (portion of extracellular domain): PFWAAE-SALDFHWPFGGALCKMVLTATVLNVYAS-IFLITALSVARY (SEQ ID NO: 379). Moreover, fragments and variants of these polypeptides (such as, for example, fragments as described herein, polypeptides at least 80%, 85%, 90%, 95%, 96%, 97%, 98%, 99%, or 100% identical to these polypeptides, or polypeptides encoded by a polynucleotide which hybridizes, under stringent conditions, to the polynucleotide encoding these polypeptides) are encompassed by the invention. Antibodies that bind polypeptides of the invention and polynucleotides encoding these polypeptides are also encompassed by the invention.

This gene is expressed primarily in 7TM-pbfd and PCMIX libraries (tissue types unknown).

Polynucleotides and polypeptides of the invention would be useful as reagents for differential identification of the tissue(s) or cell type(s) present in a biological sample and for diagnosis of diseases and conditions which include, but are not limited to, blood pressure regulatory diseases and/or disorders. Similarly, polypeptides and antibodies directed to these polypeptides would be useful in providing immunological probes for differential identification of the tissue(s) or cell type(s). For a number of disorders of the above tissues or cells, particularly of the vascular system, expression of this gene at significantly higher or lower levels may be routinely detected in certain tissues or cell types (e.g., cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder. Preferred polypeptides of the present invention comprise, or alternatively consist of the immunogenic epitopes shown in SEQ ID NO: 179 as residues: Gln-117 to Ser-126. Polynucleotides encoding said polypeptides are encompassed by the invention, as are antibodies that bind one or more of these peptides.

The tissue distribution and homology to angiotensin II receptor indicates that polynucleotides and polypeptides corresponding to this gene would be useful for the study, detection, treatment, and/or prevention of vascular diseases such as blood pressure regulatory disorders. Representative uses are described elsewhere herein. In particular, the extracellular region of the receptor can be used as a soluble antagonist. Moreover, polynucleotides and polypeptides of the invention would be useful in the detection, treatment, and/or prevention of a variety of vascular disorders and conditions, which include, but are not limited to miscrovascular disease, vascular leak syndrome, aneurysm, stroke, embolism, thrombosis, coronary artery disease, arteriosclerosis, and/or atherosclerosis. Furthermore, the protein may also be used to determine biological activity, to raise antibodies, as tissue markers, to isolate cognate ligands or receptors, to identify agents that modulate their interactions, in addition to its use as a nutritional supplement. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:72 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a-b, where a is any integer between 1 to 869 of SEQ ID NO:72, b is an integer of 15 to 883, where both a and b correspond to the positions of nucleotide residues shown in SEQ ID NO:72, and where b is greater than or equal to a +14.

Features of Protein Encoded by Gene No: 63

In specific embodiments, polypeptides of the invention comprise, or alternatively consist of, an amino acid sequence selected from the group: THADKNQVRNSN (SEQ ID NO: 380), QFLSWEQCTGNTESQ (SEQ ID NO: 381), VRRP-KAKGXQTSN (SEQ ID NO: 382), PTQLNKHKPTTKER-RRKGL (SEQ ID NO: 383), and/or LISKHENIY (SEQ ID NO: 384). Moreover, fragments and variants of these polypeptides (such as, for example, fragments as described herein, polypeptides at least 80%, 85%, 90%, 95%, 96%, 97%, 98%, 99%, or 100% identical to these polypeptides, or polypeptides encoded by a polynucleotide which hybridizes, under stringent conditions, to the polynucleotide encoding these polypeptides) are encompassed by the invention. Antibodies that bind polypeptides of the invention and polynucleotides encoding these polypeptides are also encompassed by the invention.

This gene is expressed primarily in neutrophils.

Polynucleotides and polypeptides of the invention would be useful as reagents for differential identification of the tissue(s) or cell type(s) present in a biological sample and for diagnosis of diseases and conditions which include, but are not limited to, diseases and/or disorders affecting the immune system. Similarly, polypeptides and antibodies directed to these polypeptides would be useful in providing immunological probes for differential identification of the tissue(s) or cell type(s). For a number of disorders of the above tissues or cells, particularly of the immune system, expression of this gene at significantly higher or lower levels may be routinely detected in certain tissues or cell types (e.g., immune, cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

The tissue distribution in neutrophils indicates that polynucleotides and polypeptides corresponding to this gene would be useful for the diagnosis and/or treatment of immune system disorders, especially those affecting neutrophils. Representative uses are described in the "Immune Activity" and "Infectious Disease" sections below, in Example 11, 13, 14, 16, 18, 19, 20, and 27, and elsewhere herein. Briefly, polynucleotides and polypeptides of the invention may be involved in the regulation of cytokine production, antigen presentation, or other processes that may also suggest a usefulness in the treatment of cancer (e.g., by boosting immune responses). Since the gene is expressed in cells of lymphoid origin, the gene or protein, as well as, antibodies directed against the protein may show utility as a tumor marker and/or immunotherapy targets for the above listed tissues. Therefore polynucleotides and polypeptides of the invention may be also used as an agent for immunological disorders including arthritis, asthma, immune deficiency diseases such as AIDS, leukemia, rheumatoid arthritis, inflammatory bowel disease, sepsis, acne, and psoriasis. In addition, polynucleotides and polypeptides of the invention may have commercial utility in the expansion of stem cells and committed progenitors of various blood lineages, and in the differentiation and/or proliferation of various cell types. Furthermore, the protein may also be used to determine biological activity, to raise antibodies, as tissue markers, to isolate cognate ligands or receptors, to identify agents that modulate their interactions, in addition to its use as a nutritional supplement. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:73 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a-b, where a is any integer between 1 to 771 of SEQ ID NO:73, b is an integer of 15 to 785, where both a and b correspond to the positions of nucleotide residues shown in SEQ ID NO:73, and where b is greater than or equal to a +14.

Features of Protein Encoded by Gene No: 64

In specific embodiments, polypeptides of the invention comprise, or alternatively consist of, the following amino acid sequence: TLYIXXMXTQTWRDQGRCGRDXINCIV (SEQ ID NO: 385). Moreover, fragments and variants of these polypeptides (such as, for example, fragments as described herein, polypeptides at least 80%, 85%, 90%, 95%, 96%, 97%, 98%, 99%, or 100% identical to these polypeptides, or polypeptides encoded by a polynucleotide which hybridizes, under stringent conditions, to the polynucleotide encoding these polypeptides) are encompassed by the invention. Antibodies that bind polypeptides of the invention and polynucleotides encoding these polypeptides are also encompassed by the invention.

This gene is expressed primarily in brain tissue from a manic depressive, in some cancer tissues such as ovarian cancer, and in spleen from a patient with chronic lymphocytic leukemia and, to a lesser extent, in other tissues.

Polynucleotides and polypeptides of the invention would be useful as reagents for differential identification of the tissue(s) or cell type(s) present in a biological sample and for diagnosis of diseases and conditions which include, but are not limited to, brain disorders (e.g., manic depression), and tumorigenesis. Similarly, polypeptides and antibodies directed to these polypeptides would be useful in providing immunological probes for differential identification of the tissue(s) or cell type(s). For a number of disorders of the above tissues or cells, particularly of the central nervous system (CNS), reproductive system, and immune system, expression of this gene at significantly higher or lower levels may be routinely detected in certain tissues or cell types (e.g., brain, reproductive, immune, cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder. Preferred polypeptides of the present invention comprise, or alternatively consist of one or both of the immunogenic epitopes shown in SEQ ID NO: 181 as residues: Thr-29 to Ala-37, Arg-41 to Lys-46. Polynucleotides encoding said polypeptides are encompassed by the invention, as are antibodies that bind one or more of these peptides.

The tissue distribution primarily in brain tissue from a manic depressive indicates that polynucleotides and polypeptides corresponding to this gene would be useful for diagnosing and treating manic depression and tumorigenesis. The tissue distribution in brain also indicates that polynucleotides and polypeptides corresponding to this gene would be useful for the detection, treatment, and/or prevention of neurodegenerative disease states, behavioral disorders, or inflammatory conditions. Representative uses are described in the "Regeneration" and "Hyperproliferative Disorders" sections below, in Example 11, 15, and 18, and elsewhere herein. Briefly, the uses include, but are not limited to the detection, treatment, and/or prevention of Alzheimer's Disease, Parkinson's Disease, Huntington's Disease, Tourette Syndrome, meningitis, encephalitis, demyelinating diseases, peripheral neuropathies, neoplasia, trauma, congenital malformations, spinal cord injuries, ischemia and infarction, aneurysms, hemorrhages, schizophrenia, mania, dementia, paranoia, obsessive compulsive disorder, depression, panic disorder, learning disabilities, ALS, psychoses, autism, and altered behaviors, including disorders in feeding, sleep patterns, balance, and perception. In addition, elevated expression of this gene product in regions of the brain indicates that polynucleotides and polypeptides corresponding to this gene may play a role in normal neural function. Potentially, polynucleotides and polypeptides corresponding to this gene are involved in synapse formation, neurotransmission, learning, cognition, homeostasis, or neuronal differentiation or survival. Furthermore, the protein may also be used to determine biological activity, to raise antibodies, as tissue markers, to isolate cognate ligands or receptors, to identify agents that modulate their interactions, in addition to its use as a nutritional supplement. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:74 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a-b, where a is any integer between 1 to 2327 of SEQ ID NO:74, b is an integer of 15 to 2341, where both a and b correspond to the positions of nucleotide residues shown in SEQ ID NO:74, and where b is greater than or equal to a +14.

Features of Protein Encoded by Gene No: 65

In specific embodiments, polypeptides of the invention comprise, or alternatively consist of, the following amino acid sequence: SLCTPGRGWEESWGSSLPNLTGWS-VSSLDNNDV (SEQ ID NO: 386). Moreover, fragments and variants of these polypeptides (such as, for example, fragments as described herein, polypeptides at least 80%, 85%, 90%, 95%, 96%, 97%, 98%, 99%, or 100% identical to these polypeptides, or polypeptides encoded by a polynucleotide which hybridizes, under stringent conditions, to the polynucleotide encoding these polypeptides) are encompassed by the invention. Antibodies that bind polypeptides of the invention and polynucleotides encoding these polypeptides are also encompassed by the invention.

This gene is expressed primarily in metastic melanoma spleen, rhabdomyosarcoma, and IL-1 induced neutrophils and, to a lesser extent, in other tissues.

Polynucleotides and polypeptides of the invention would be useful as reagents for differential identification of the tissue(s) or cell type(s) present in a biological sample and for diagnosis of diseases and conditions which include, but are not limited to, tumorigenesis, metastasis and inflammatory disorders. Similarly, polypeptides and antibodies directed to these polypeptides would be useful in providing immunological probes for differential identification of the tissue(s) or cell type(s). For a number of disorders of the above tissues or cells, particularly of the skin, connective tissue and immune system, expression of this gene at significantly higher or lower levels may be routinely detected in certain tissues or cell types (e.g., skin, cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

The tissue distribution in metastic melanoma spleen, rhabdomyosarcoma, and IL-1 induced neutrophils indicates that polynucleotides and polypeptides corresponding to this gene would be useful for detection, treatment, and/or prevention of certain tumors such as melanoma, rhabdomyosarcoma and inflammatory disorders. Similarly, the tissue distribution indicates that polynucleotides and polypeptides corresponding to this gene would be useful for the treatment, diagnosis, and/or prevention of various skin disorders including congenital disorders (e.g., nevi, moles, freckles, Mongolian spots, hemangiomas, port-wine syndrome), integumentary tumors (e.g., keratoses, Bowen's disease, basal cell carcinoma, squamous cell carcinoma, malignant melanoma, Paget's disease, mycosis fungoides, and Kaposi's sarcoma), injuries and inflammation of the skin (e.g., wounds, rashes, prickly heat disorder, psoriasis, dermatitis), atherosclerosis, uticaria, eczema, photosensitivity, autoimmune disorders (e.g., lupus erythematosus, vitiligo, dermatomyositis, morphea, scleroderma, pemphigoid, and pemphigus), keloids, striae, erythema, petechiae, purpura, and xanthelasma. Moreover, such disorders may predispose increased susceptibility to viral and bacterial infections of the skin (e.g., cold sores, warts, chickenpox, molluscum contagiosum, herpes zoster, boils, cellulitis, erysipelas, impetigo, tinea, althlete's foot, and ringworm). The tissue distribution in neutrophils indicates that polynucleotides and polypeptides corresponding to this gene would be useful for the diagnosis and treatment of a variety of immune system disorders. Representative uses are described in the "Immune Activity" and "Infectious Disease" sections below, in Example 11, 13, 14, 16, 18, 19, 20, and 27, and elsewhere herein. Briefly, the expression indicates a role in regulating the proliferation; survival; differentiation; and/or activation of hematopoietic cell lineages, including blood stem cells. Involvement in the regulation of cytokine production, antigen presentation, or other processes indicates a usefulness for treatment of cancer (e.g., by boosting immune responses). Expression in cells of lymphoid origin, indicates the natural gene product would be involved in immune functions. Therefore polynucleotides and polypeptides of the invention would also be useful as an agent for immunological disorders including arthritis, asthma, immunodeficiency diseases such as AIDS, leukemia, rheumatoid arthritis, granulomatous disease, inflammatory bowel disease, sepsis, acne, neutropenia, neutrophilia, psoriasis, hypersensitivities, such as T-cell mediated cytotoxicity; immune reactions to transplanted organs and tissues, such as host-versus-graft and graft-versus-host diseases, or autoimmunity disorders, such as autoimmune infertility, lense tissue injury, demyelination, systemic lupus erythematosis, drug induced hemolytic anemia, rheumatoid arthritis, Sjogren's disease, and scleroderma. Moreover, the protein may represent a secreted factor that influences the differentiation or behavior of other blood cells, or that recruits hematopoietic cells to sites of injury. Thus, this gene product is thought to be useful in the expansion of stem cells and committed progenitors of various blood lineages, and in the differentiation and/or proliferation of various cell types. Furthermore, the protein may also be used to determine biological activity, to raise antibodies, as tissue markers, to isolate cognate ligands or receptors, to identify agents that modulate their interactions, in addition to its use as a nutritional supplement. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:75 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a-b, where a is any integer between 1 to 1868 of SEQ ID NO:75, b is an integer of 15 to 1882, where both a and b correspond to the positions of nucleotide residues shown in SEQ ID NO:75, and where b is greater than or equal to a +14.

Features of Protein Encoded by Gene No: 66

In specific embodiments, polypeptides of the invention comprise, or alternatively consist of, an amino acid sequence selected from the group: DSESSSEEEEEFGVVGNRSR-FAKGDYLRCCKICYPLCGFVILAACVVACVGLV WMQVALKEDLDALKEKFRTMESNQKSS-FQEIPKLNEELLSKQKQLEKIESGE MGLNKVWIN-ITEMNKQISLLTSAVNHLKANVK-SAADLISLPTTVEGLQKSVA SIGXTLNSVHLAVEALQKTVDEHKKT-MELLQSDMNQHFLKETPGSNQIIPSPS ATSELDNKTHSENLKQMGDRS-ATLKRQSLDQVTNRTDTVKIQSIKKEG (SEQ ID NO:393), MQVALKEDLDALKEKFRTMESNQKSS-FQEIPKLNEELLSKQKQLEKIESGEM GLNKVWIN-ITEMNKQISLLTSAVNHLKANVK-SAADLISLPTTVEGLQKSVASI GXTLNSVHLAVEALQKTVDEHKKT- MELLQSDMNQHFLKETPGSNQIIPSPSATSELDNKTHSENLKQMGDRSATLKRQSLDQVTNRTDTVKIQSIKKEG (SEQ ID NO:387), MQVALKEDLDALKEKFRTMESNQKSSFQEIPKLNEELLSKQKQ (SEQ ID NO:388), LEKIESGEMGLNKVWINITEMNKQISLLTSAVNHLKANVKSAA (SEQ ID NO:389), DLISLPTTVEGLQKSVASIGXTLNSVHLAVEALQKTVDEHKKT (SEQ ID NO:390), MELLQSDMNQHFLKETPGSNQIIPSPSATSELDNKTHSENLKQ (SEQ ID NO:391), and/or MGDRSATLKRQSLDQVTNRTDTVKIQSIKKEG (SEQ ID NO: 392). Moreover, fragments and variants of these polypeptides (such as, for example, fragments as described herein, polypeptides at least 80%, 85%, 90%, 95%, 96%, 97%, 98%, 99%, or 100% identical to these polypeptides, or polypeptides encoded by a polynucleotide which hybridizes, under stringent conditions, to the polynucleotide encoding these polypeptides) are encompassed by the invention. Antibodies that bind polypeptides of the invention and polynucleotides encoding these polypeptides are also encompassed by the invention.

The gene encoding the disclosed cDNA is believed to reside on chromosome 1. Accordingly, polynucleotides related to this invention would be useful as a marker in linkage analysis for chromosome 1.

This gene is expressed primarily in fetal, placental and infant brain tissues, and, to a lesser extent, in many normal and neoplastic cell types.

Polynucleotides and polypeptides of the invention would be useful as reagents for differential identification of the tissue(s) or cell type(s) present in a biological sample and for diagnosis of diseases and conditions which include, but are not limited to, developmental disorders, cancer and general growth disorders. Similarly, polypeptides and antibodies directed to these polypeptides would be useful in providing immunological probes for differential identification of the tissue(s) or cell type(s). For a number of disorders of the above tissues or cells, particularly of the reproductive, developing, and nervous systems, expression of this gene at significantly higher or lower levels may be routinely detected in certain tissues or cell types (e.g., reproductive, developmental, neural, cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder. Preferred polypeptides of the present invention comprise, or alternatively consist of the immunogenic epitopes shown in SEQ ID NO: 183 as residues: Cys-30 to Asn-44. Polynucleotides encoding said polypeptides are encompassed by the invention, as are antibodies that bind one or more of these peptides.

The tissue distribution in infant brain and embryonic tissues indicates that polynucleotides and polypeptides corresponding to this gene would be useful for the study, detection and/or treatment of growth and neoplastic disorders. Furthermore, the tissue distribution indicates that polynucleotides and polypeptides corresponding to this gene would be useful for the detection, treatment, and/or prevention of cancer and other proliferative disorders. Expression within embryonic tissue and other cellular sources marked by proliferating cells indicates that polynucleotides and polypeptides of the invention may play a role in the regulation of cellular division. Embryonic development also involves decisions involving cell differentiation and/or apoptosis in pattern formation. Thus polynucleotides and polypeptides of the invention may also be involved in apoptosis or tissue differentiation and could again be useful in cancer therapy. Alternatively, the tissue distribution in brain indicates polynucleotides and polypeptides corresponding to this gene would be useful for the detection, treatment, and/or prevention of neurodegenerative disease states, behavioral disorders, or inflammatory conditions. Representative uses are described in the "Regeneration" and "Hyperproliferative Disorders" sections below, in Example 11, 15, and 18, and elsewhere herein. Briefly, the uses include, but are not limited to, the detection, treatment, and/or prevention of Alzheimer's Disease, Parkinson's Disease, Huntington's Disease, Tourette Syndrome, meningitis, encephalitis, demyelinating diseases, peripheral neuropathies, neoplasia, trauma, congenital malformations, spinal cord injuries, ischemia and infarction, aneurysms, hemorrhages, schizophrenia, mania, dementia, paranoia, obsessive compulsive disorder, depression, panic disorder, learning disabilities, ALS, psychoses, autism, and altered behaviors, including disorders in feeding, sleep patterns, balance, and perception. In addition, elevated expression of this gene product in regions of the brain indicates it plays a role in normal neural function. Potentially, polynucleotides and polypeptides of the invention are involved in synapse formation, neurotransmission, learning, cognition, homeostasis, or neuronal differentiation or survival. In addition, the gene or gene product may also play a role in the treatment and/or detection of developmental disorders associated with the developing embryo, or sexually-linked disorders. Furthermore, the protein may also be used to determine biological activity, to raise antibodies, as tissue markers, to isolate cognate ligands or receptors, to identify agents that modulate their interactions, in addition to its use as a nutritional supplement. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:76 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a-b, where a is any integer between 1 to 2878 of SEQ ID NO:76, b is an integer of 15 to 2892, where both a and b correspond to the positions of nucleotide residues shown in SEQ ID NO:76, and where b is greater than or equal to a +14.

Features of Protein Encoded by Gene No: 67

This gene is apparently exclusively in fetal heart tissue.

Polynucleotides and polypeptides of the invention would be useful as reagents for differential identification of the tissue(s) or cell type(s) present in a biological sample and for diagnosis of diseases and conditions which include, but are not limited to, cardiovascular and growth defects. Similarly, polypeptides and antibodies directed to these polypeptides would be useful in providing immunological probes for differential identification of the tissue(s) or cell type(s). For a number of disorders of the above tissues or cells, particularly of the developing cardiovascular system, expression of this gene at significantly higher or lower levels may be routinely detected in certain tissues or cell types (e.g., cardiovascular, heart, cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

The tissue distribution in fetal heart tissue indicates that polynucleotides and polypeptides corresponding to this gene would be useful for the study, detection and/or treatment of disorders and growth defects of heart development and function. Furthermore, the tissue distribution in fetal heart tissue indicates that polynucleotides and polypeptides corresponding to this gene would be useful for the detection, treatment, and/or prevention of conditions and pathologies of the cardiovascular system, such as heart disease, restenosis, atherosclerosis, stroke, angina, thrombosis, and wound healing. Furthermore, the protein may also be used to determine biological activity, to raise antibodies, as tissue markers, to isolate cognate ligands or receptors, to identify agents that modulate their interactions, in addition to its use as a nutritional supplement. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:77 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a-b, where a is any integer between 1 to 1659 of SEQ ID NO:77, b is an integer of 15 to 1673, where both a and b correspond to the positions of nucleotide residues shown in SEQ ID NO:77, and where b is greater than or equal to a +14.

Features of Protein Encoded by Gene No: 68

This gene is expressed primarily in pancreas islet cell tumor tissue.

Polynucleotides and polypeptides of the invention would be useful as reagents for differential identification of the tissue(s) or cell type(s) present in a biological sample and for diagnosis of diseases and conditions which include, but are not limited to, digestive and metabolic defects and tumors, particularly tumors of the pancreas. Similarly, polypeptides and antibodies directed to these polypeptides would be useful in providing immunological probes for differential identification of the tissue(s) or cell type(s). For a number of disorders of the above tissues or cells, particularly of the endocrine system, expression of this gene at significantly higher or lower levels may be routinely detected in certain tissues or cell types (e.g., endocrine, pancreas, cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

The tissue distribution in pancreas islet cell tumor tissue indicates that polynucleotides and polypeptides corresponding to this gene would be useful for the study, detection and/or treatment of hormonal and neoplastic disorders of endocrine organs and metabolism. Additionally, the tissue distribution indicates polynucleotides and polypeptides corresponding to this gene would be useful for the detection, treatment, and/or prevention of various endocrine disorders and cancers. Representative uses are described in the "Biological Activity", "Hyperproliferative Disorders", and "Binding Activity" sections below, in Example 11, 17, 18, 19, 20 and 27, and elsewhere herein. Briefly, the protein can be used for the detection, treatment, and/or prevention of the Addison's disease, Cushing's Syndrome, and disorders and/or cancers of the pancreas (e.g., diabetes mellitus), adrenal cortex, ovaries, pituitary (e.g., hyper-, hypopituitarism), thyroid (e.g., hyper-, hypothyroidism), parathyroid (e.g., hyper-, hypoparathyroidism), hypothalamus, and testes. Furthermore, the protein may also be used to determine biological activity, to raise antibodies, as tissue markers, to isolate cognate ligands or receptors, to identify agents that modulate their interactions, in addition to its use as a nutritional supplement. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:78 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a-b, where a is any integer between 1 to 1447 of SEQ ID NO:78, b is an integer of 15 to 1461, where both a and b correspond to the positions of nucleotide residues shown in SEQ ID NO:78, and where b is greater than or equal to a +14.

Features of Protein Encoded by Gene No: 69

This gene is expressed primarily in tonsils.

Polynucleotides and polypeptides of the invention would be useful as reagents for differential identification of the tissue(s) or cell type(s) present in a biological sample and for diagnosis of diseases and conditions which include, but are not limited to, diseases and/or disorders of the tonsils, and disorders of the immune system. Similarly, polypeptides and antibodies directed to these polypeptides would be useful in providing immunological probes for differential identification of the tissue(s) or cell type(s). For a number of disorders of the above tissues or cells, particularly of the tonsils, and the immune system, expression of this gene at significantly higher or lower levels may be routinely detected in certain tissues or cell types (e.g., tonsils, immune, cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

The tissue distribution indicates that polynucleotides and polypeptides corresponding to this gene would be useful for the detection, treatment, and/or prevention of a variety of immune system disorders. Expression of this gene product in tonsils indicates a role in the regulation of the proliferation; survival; differentiation; and/or activation of potentially all hematopoietic cell lineages, including blood stem cells. Representative uses are described in the "Immune Activity" and "Infectious Disease" sections below, in Example 11, 13, 14, 16, 18, 19, 20, and 27, and elsewhere herein. Briefly, polynucleotides and polypeptides of the invention may be involved in the regulation of cytokine production, antigen presentation, or other processes that may also suggest a usefulness in the treatment of cancer (e.g., by boosting immune responses). Since the gene is expressed in cells of lymphoid origin, the gene or protein, as well as, antibodies directed against the protein may show utility as a tumor marker and/or immunotherapy targets for the above listed tissues. Therefore polynucleotides and polypeptides of the invention may be also used as an agent for immunological disorders including arthritis, asthma, immune deficiency diseases such as AIDS, leukemia, rheumatoid arthritis, inflammatory bowel disease, sepsis, acne, and psoriasis. In addition, polynucleotides and polypeptides of the invention may have commercial utility in the expansion of stem cells and committed progenitors of various blood lineages, and in the differentiation and/or proliferation of various cell types. Furthermore, the protein may also be used to determine biological activity, to raise antibodies, as tissue markers, to isolate cognate ligands or receptors, to identify agents that modulate their interactions, in addition to its use as a nutritional supplement. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:79 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a-b, where a is any integer between 1 to 1503 of SEQ ID NO:79, b is an integer of 15 to 1517, where both a and b correspond to the positions of nucleotide residues shown in SEQ ID NO:79, and where b is greater than or equal to a +14.

Features of Protein Encoded by Gene No: 70

In specific embodiments, polypeptides of the invention comprise, or alternatively consist of, the following amino acid sequence: SPQFLSSKSLPT (SEQ ID NO:394). Moreover, fragments and variants of these polypeptides (such as, for example, fragments as described herein, polypeptides at least 80%, 85%, 90%, 95%, 96%, 97%, 98%, 99%, or 100% identical to these polypeptides, or polypeptides encoded by a polynucleotide which hybridizes, under stringent conditions, to the polynucleotide encoding these polypeptides) are encompassed by the invention. Antibodies that bind polypeptides of the invention and polynucleotides encoding these polypeptides are also encompassed by the invention.

This gene is expressed primarily in infant brain and spinal cord.

Polynucleotides and polypeptides of the invention would be useful as reagents for differential identification of the tissue(s) or cell type(s) present in a biological sample and for diagnosis of diseases and conditions which include, but are not limited to, congenital brain disorders, including various forms of mental retardation, spina bifida, epilepsy, and various mood disorders, including bipolar and unipolar depression. Similarly, polypeptides and antibodies directed to these polypeptides would be useful in providing immunological probes for differential identification of the tissue(s) or cell type(s). For a number of disorders of the above tissues or cells, particularly of the central nervous system, expression of this gene at significantly higher or lower levels may be routinely detected in certain tissues or cell types (e.g., brain, CNS, cancerous and wounded tissues) or bodily fluids (e.g., lymph, amniotic fluid, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder. Preferred polypeptides of the present invention comprise, or alternatively consist of one or both of the immunogenic epitopes shown in SEQ ID NO: 187 as residues: Pro-42 to Lys-49, Lys-56 to Lys-71. Polynucleotides encoding said polypeptides are encompassed by the invention, as are antibodies that bind one or more of these peptides.

The tissue distribution in infant brain and spinal cord indicates that polynucleotides and polypeptides corresponding to this gene would be useful for the diagnosis, detection, prevention and/or treatment of disorders of the brain and nervous system, including congenital brain disorders, including various forms of mental retardation, spina bifida, epilepsy, and various mood disorders, including bipolar and unipolar depression. Additionally, polynucleotides and polypeptides corresponding to this gene may have cytostatic, thrombotic and/or osteopathic activity. It may also be useful in the treatment of such neurodegenerative disorders as schizophrenia; ALS; or Alzheimer's. The tissue distribution in brain further indicates that polynucleotides and polypeptides corresponding to this gene would be useful for the detection, treatment, and/or prevention of neurodegenerative disease states, behavioral disorders, or inflammatory conditions. Representative uses are described in the "Regeneration" and "Hyperproliferative Disorders" sections below, in Example 11, 15, and 18, and elsewhere herein. Briefly, the uses include, but are not limited to the detection, treatment, and/or prevention of Alzheimer's Disease, Parkinson's Disease, Huntington's Disease, Tourette Syndrome, meningitis, encephalitis, demyelinating diseases, peripheral neuropathies, neoplasia, trauma, congenital malformations, spinal cord injuries, ischemia and infarction, aneurysms, hemorrhages, schizophrenia, mania, dementia, paranoia, obsessive compulsive disorder, depression, panic disorder, learning disabilities, ALS, psychoses, autism, and altered behaviors, including disorders in feeding, sleep patterns, balance, and perception. In addition, elevated expression of this gene product in regions of the brain indicates that polynucleotides and polypeptides corresponding to this gene may play a role in normal neural function. Potentially, polynucleotides and polypeptides corresponding to this gene are involved in synapse formation, neurotransmission, learning, cognition, homeostasis, or neuronal differentiation or survival. Furthermore, the protein may also be used to determine biological activity, to raise antibodies, as tissue markers, to isolate cognate ligands or receptors, to identify agents that modulate their interactions, in addition to its use as a nutritional supplement. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:80 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a-b, where a is any integer between 1 to 560 of SEQ ID NO:80, b is an integer of 15 to 574, where both a and b correspond to the positions of nucleotide residues shown in SEQ ID NO:80, and where b is greater than or equal to a +14.

Features of Protein Encoded by Gene No: 71

In specific embodiments, polypeptides of the invention comprise, or alternatively consist of, an amino acid sequence selected from the group: GPPSPRGLPSLPLHLPAPRRYLQSRYACSQSSVSAAARRWGSGWMAWDPWN QASGRYARITLLSVQACHQ PTVWPRAGHSLPERYSLHPHNGDSTHLSGLLTVKCGA (SEQ ID NO: 395), GPPSPRGLPSLPLHLPAPRRYLQSRYACSQSSVSAAA (SEQ ID NO:396), RRWGSGWMAWDPWNQASGRYARITLLSVQACHQ (SEQ ID NO:397), GPPSPRGLPSLPLHLPAPRRYLQSRYACSQSSVSAAARRWGSGWMAWDPWN QASGRYARITLLSVQACHQPTVWPRAGHSLPERYSLHPHNGDSTHLSGLLTV KCGAMAGFASYPWSDFPWCWVVCFSFXFFFLRQSESLSQKKRQVADELXFG QSKRDSDGGWMLRSSAGNS (SEQ ID NO:399), MESCSVVQAGVKWCDLGSLQPPPRFKQFSWEVEVAVSRDHTIALQXGGQSK XLSQKKEKKYVLNATFLNFYFCRDKVLLCCPGWSHIVGLKQSSHLGLRKCW DYRHGPLXLALCHFVCK (SEQ ID NO:400), and/or PTVWPRAGHSLPERYSLHPHNGDSTHLSGLLTVKCGA (SEQ ID NO:392). Moreover, fragments and variants of these polypeptides (such as, for example, fragments as described herein, polypeptides at least 80%, 85%, 90%, 95%, 96%, 97%, 98%, 99%, or 100% identical to these polypeptides, or polypeptides encoded by a polynucleotide which hybridizes, under stringent conditions, to the polynucleotide encoding these polypeptides) are encompassed by the invention. Antibodies that bind polypeptides of the invention and polynucleotides encoding these polypeptides are also encompassed by the invention.

This gene is expressed primarily in neutrophils.

Polynucleotides and polypeptides of the invention would be useful as reagents for differential identification of the tissue(s) or cell type(s) present in a biological sample and for diagnosis of diseases and conditions which include, but are not limited to, infection, inflammation and other immune reactions or disorders. Similarly, polypeptides and antibodies directed to these polypeptides would be useful in providing immunological probes for differential identification of the tissue(s) or cell type(s). For a number of disorders of the above tissues or cells, particularly of the immune system, expression of this gene at significantly higher or lower levels may be routinely detected in certain tissues or cell types (e.g., immune, cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

The tissue distribution in neutrophils indicates that polynucleotides and polypeptides corresponding to this gene would be useful for detection, treatment, and/or prevention of immune disorders, such as infection, inflammation, allergy and immunodeficiency. Therefore, polynucleotides and polypeptides corresponding to this gene may have clinical relevance in the treatment of impaired immunity, in the correction of autoimmunity, in immune modulation, in the treatment of allergy, and in the regulation of inflammation. It may also play a role in influencing differentiation of specific hematopoietic lineages, and may even affect the hematopoietic stem cell. The tissue distribution in neutophils also indicates that polynucleotides and polypeptides corresponding to this gene may be useful for the diagnosis and treatment of a variety of immune system disorders. Representative uses are described in the “Immune Activity” and “Infectious Disease” sections below, in Example 11, 13, 14, 16, 18, 19, 20, and 27, and elsewhere herein. Briefly, the expression indicates a role in regulating the proliferation; survival; differentiation; and/or activation of hematopoietic cell lineages, including blood stem cells. Involvement in the regulation of cytokine production, antigen presentation, or other processes indicates a usefulness for treatment of cancer (e.g., by boosting immune responses). Expression in cells of lymphoid origin, indicates the natural gene product would be involved in immune functions. Therefore polynucleotides and polypeptides corresponding to this gene would also be useful as an agent for immunological disorders including arthritis, asthma, immunodeficiency diseases such as AIDS, leukemia, rheumatoid arthritis, granulomatous disease, inflammatory bowel disease, sepsis, acne, neutropenia, neutrophilia, psoriasis, hypersensitivities, such as T-cell mediated cytotoxicity; immune reactions to transplanted organs and tissues, such as host-versus-graft and graft-versus-host diseases, or autoimmunity disorders, such as autoimmune infertility, lense tissue injury, demyelination, systemic lupus erythematosis, drug induced hemolytic anemia, rheumatoid arthritis, Sjogren’s disease, and scleroderma. Moreover, the protein may represent a secreted factor that influences the differentiation or behavior of other blood cells, or that recruits hematopoietic cells to sites of injury. Thus, this gene product is thought to be useful in the expansion of stem cells and committed progenitors of various blood lineages, and in the differentiation and/or proliferation of various cell types. Furthermore, the protein may also be used to determine biological activity, raise antibodies, as tissue markers, to isolate cognate ligands or receptors, to identify agents that modulate their interactions, in addition to its use as a nutritional supplement. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:81 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a-b, where a is any integer between 1 to 1441 of SEQ ID NO:81, b is an integer of 15 to 1455, where both a and b correspond to the positions of nucleotide residues shown in SEQ ID NO:81, and where b is greater than or equal to a +14.

Features of Protein Encoded by Gene No: 72

In specific embodiments, polypeptides of the invention comprise, or alternatively consist of, the following amino acid sequence: NQENSLQTN SYLDSTESK (SEQ ID NO: 401). Moreover, fragments and variants of these polypeptides (such as, for example, fragments as described herein, polypeptides at least 80%, 85%, 90%, 95%, 96%, 97%, 98%, 99%, or 100% identical to these polypeptides, or polypeptides encoded by a polynucleotide which hybridizes, under stringent conditions, to the polynucleotide encoding these polypeptides) are encompassed by the invention. Antibodies that bind polypeptides of the invention and polynucleotides encoding these polypeptides are also encompassed by the invention.

The polypeptide of this gene has been determined to have a transmembrane domain at about amino acid position 12 to about 28 of the amino acid sequence referenced in Table 1 for this gene. Moreover, a cytoplasmic tail encompassing about amino acids 29 to about 70 of this protein has also been determined. Based upon these characteristics, it is believed that polynucleotides and polypeptides corresponding to this gene shares structural features to type Ib membrane proteins.

This gene is expressed primarily in neutrophils, activated T-cells, tonsils, and fetal heart.

Polynucleotides and polypeptides of the invention would be useful as reagents for differential identification of the tissue(s) or cell type(s) present in a biological sample and for diagnosis of diseases and conditions which include, but are not limited to, immune system disorders. Similarly, polypeptides and antibodies directed to these polypeptides would be useful in providing immunological probes for differential identification of the tissue(s) or cell type(s). For a number of disorders of the above tissues or cells, particularly of the immune system, expression of this gene at significantly higher or lower levels may be routinely detected in certain tissues or cell types (e.g., immune, cardiovascular, cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

The tissue distribution neutrophils and T-cells indicates that polynucleotides and polypeptides corresponding to this gene would be useful for diagnosis and treatment of immune related disorders including, infection, inflammation, allergy, tissue/organ transplantation, immunodeficiency, etc. Representative uses are described in the "Immune Activity" and "Infectious Disease" sections below, in Example 11, 13, 14, 16, 18, 19, 20, and 27, and elsewhere herein. Briefly, the expression indicates a role in regulating the proliferation; survival; differentiation; and/or activation of hematopoietic cell lineages, including blood stem cells. Involvement in the regulation of cytokine production, antigen presentation, or other processes indicates a usefulness for treatment of cancer (e.g., by boosting immune responses). Polynucleotides and polypeptides corresponding to this gene may have clinical relevance in the treatment of impaired immunity, in the correction of autoimmunity, in immune modulation, in the treatment of allergy, and in the regulation of inflammation. It may also play a role in influencing differentiation of specific hematopoietic lineages, and may even affect the hematopoietic stem cell. Furthermore, the protein may also be used to determine biological activity, raise antibodies, as tissue markers, to isolate cognate ligands or receptors, to identify agents that modulate their interactions, in addition to its use as a nutritional supplement. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:82 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a-b, where a is any integer between 1 to 1626 of SEQ ID NO:82, b is an integer of 15 to 1640, where both a and b correspond to the positions of nucleotide residues shown in SEQ ID NO:82, and where b is greater than or equal to a +14.

Features of Protein Encoded by Gene No: 73

This gene is expressed primarily in hemangioperiocytoma, placental tissue, and breast and endometrial tumor tissues, and, to a lesser extent, in various other normal and transformed cell types.

Polynucleotides and polypeptides of the invention would be useful as reagents for differential identification of the tissue(s) or cell type(s) present in a biological sample and for diagnosis of diseases and conditions which include, but are not limited to, defects and tumors of female reproductive organs. Similarly, polypeptides and antibodies directed to these polypeptides would be useful in providing immunological probes for differential identification of the tissue(s) or cell type(s). For a number of disorders of the above tissues or cells, particularly of the reproductive system, expression of this gene at significantly higher or lower levels may be routinely detected in certain tissues or cell types (e.g., reproductive, cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

The tissue distribution in endometrial tumor tissue and placental tissue indicates that polynucleotides and polypeptides corresponding to this gene would be useful for the study, detection and/or treatment of reproductive system disorders and neoplasias, as well as cancers of other tissues where expression of this gene has been observed. Furthermore, the protein may also be used to determine biological activity, to raise antibodies, as tissue markers, to isolate cognate ligands or receptors, to identify agents that modulate their interactions, in addition to its use as a nutritional supplement. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:83 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a-b, where a is any integer between 1 to 511 of SEQ ID NO:83, b is an integer of 15 to 525, where both a and b correspond to the positions of nucleotide residues shown in SEQ ID NO:83, and where b is greater than or equal to a +14.

Features of Protein Encoded by Gene No: 74

In an alternative reading frame, this gene shares homology with a DNA mismatch repair proteins, including PMS 4, and PMS 1 (See Accession No. R95251, gn1|PID|d1008095 and pir|JC2399|JC2399).

In specific embodiments, polypeptides of the invention comprise, or alternatively consist of, an amino acid sequence selected from the group: QKRACFPFAFCRDCQFXEXSPAMLPVQPAXL (SEQ ID NO: 402); VSAHGIWLFRS (SEQ ID NO: 403); and/or KHAAPPASLSLSLLLHHGQKRACFPFAFCRDCQFXEXSPAMLPVQPAXL (SEQ ID NO: 404). Moreover, fragments and variants of these polypeptides (such as, for example, fragments as described herein, polypeptides at least 80%, 85%, 90%, 95%, 96%, 97%, 98%, 99%, or 100% identical to these polypeptides, or polypeptides encoded by a polynucleotide which hybridizes, under stringent conditions, to the polynucleotide encoding these polypeptides) are encompassed by the invention. Antibodies that bind polypeptides of the invention and polynucleotides encoding these polypeptides are also encompassed by the invention. This gene is expressed primarily in hematopoietic cells and tissues, such as monocytes, primary dendritic cells, and thymus; and, to a lesser extent, in brain Polynucleotides and polypeptides of the invention would be useful as reagents for differential identification of the tissue(s) or cell type(s) present in a biological sample and for diagnosis of diseases and conditions which include, but are not limited to, hematopoietic diseases and/or disorders; immune dysfunction; susceptibility to infection; impaired immune surveillance; neurological disorders, and cancers which may result from increased genetic instability. Similarly, polypeptides and antibodies directed to these polypeptides would be useful in providing immunological probes for differential identification of the tissue(s) or cell type(s). For a number of disorders of the above tissues or cells, particularly of the immune system, CNS, and solid tissues, expression of this gene at significantly higher or lower levels may be routinely detected in certain tissues or cell types (e.g., hematopoietic, cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

The tissue distribution primarily in hematopoietic cells and tissues and the homology to DNA mismatch repair proteins indicates that polynucleotides and polypeptides corresponding to this gene would be useful for the diagnosis and/or treatment of a variety of disorders, especially cancer. Representative uses are described in the "Immune Activity" and "Infectious Disease" sections below, in Example 11, 13, 14, 16, 18, 19, 20, and 27, and elsewhere herein. Briefly, the expression of this gene product in a number of hematopoietic cells and tissues indicates that polynucleotides and polypeptides of the invention may play a role in the proliferation; differentiation; survival; and/or activation of a variety of hematopoietic lineages, particularly the monocyte/macrophage pathway. Expression of this gene product in a variety of brain tissues also indicates that polynucleotides and polypeptides of the invention may play a role in normal neuronal function or in establishment of neural connectivity. Therefore, polynucleotides and polypeptides of the invention may be useful in the treatment of neurological disorders, such as Alzheimer's or Parkinson's. Furthermore, the protein may also be used to determine biological activity, to raise antibodies, as tissue markers, to isolate cognate ligands or receptors, to identify agents that modulate their interactions, in addition to its use as a nutritional supplement. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:84 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a-b, where a is any integer between 1 to 823 of SEQ ID NO:84, b is an integer of 15 to 837, where both a and b correspond to the positions of nucleotide residues shown in SEQ ID NO:84, and where b is greater than or equal to a +14.

Features of Protein Encoded by Gene No: 75

In specific embodiments, polypeptides of the invention comprise, or alternatively consist of, the following amino acid sequence: MCDNLIMLRTLMRYIVFLSLQCLWGQGTHSSCYPPSPLRLPLFFFLDIKLGISN WPVVMQSCFALYLAGLICLTRSHEAIGRSSLSPSSSAPKVVARGVPS (SEQ ID NO: 405). Moreover, fragments and variants of these polypeptides (such as, for example, fragments as described herein, polypeptides at least 80%, 85%, 90%, 95%, 96%, 97%, 98%, 99%, or 100% identical to these polypeptides, or polypeptides encoded by a polynucleotide which hybridizes, under stringent conditions, to the polynucleotide encoding these polypeptides) are encompassed by the invention. Antibodies that bind polypeptides of the invention and polynucleotides encoding these polypeptides are also encompassed by the invention.

This gene is expressed primarily in T-cell lymphoma, endometrial tumors, and infant brain cells.

Polynucleotides and polypeptides of the invention would be useful as reagents for differential identification of the tissue(s) or cell type(s) present in a biological sample and for diagnosis of diseases and conditions which include, but are not limited to, T-cell lymphoma, endometrial tumor, and neurodegenerative or developmental diseases and/or disorders. Similarly, polypeptides and antibodies directed to these polypeptides would be useful in providing immunological probes for differential identification of the tissue(s) or cell type(s). For a number of disorders of the above tissues or cells, particularly of the immune, central nervous system, and reproductive systems, expression of this gene at significantly higher or lower levels may be routinely detected in certain tissues or cell types (e.g., neural, immune, reproductive, cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder. Preferred polypeptides of the present invention comprise, or alternatively consist of one or both of the immunogenic epitopes shown in SEQ ID NO: 192 as residues: Glu-28 to Tyr-33, Gly-50 to Tyr-57. Polynucleotides encoding said polypeptides are encompassed by the invention, as are antibodies that bind one or more of these peptides.

The tissue distribution indicates that polynucleotides and polypeptides corresponding to this gene would be useful for detecting, diagnosing, preventing and/or treating T-cell lymphoma, endometrial tumors, neurodegenerative or developmental disorders. The tissue distribution in infant brain cells indicates that polynucleotides and polypeptides corresponding to this gene would be useful for the detection/treatment of neurodegenerative disease states and behavioural disorders. Representative uses are described in the "Regeneration" and "Hyperproliferative Disorders" sections below, in Example 11, 15, and 18, and elsewhere herein. Briefly, the uses include, but are not limited to the detection, treatment, and/or prevention of Alzheimer's Disease, Parkinson's Disease, Huntington's Disease, Tourette Syndrome, schizophrenia, mania, dementia, paranoia, obsessive compulsive disorder, panic disorder, learning disabilities, ALS, psychoses, autism, and altered behaviors, including disorders in feeding, sleep patterns, balance, and perception. In addition, polynucleotides and polypeptides of the invention may also play a role in the treatment and/or detection of developmental disorders associated with the developing embryo, or sexually-linked disorders. Furthermore, the protein may also be used to determine biological activity, to raise antibodies, as tissue markers, to isolate cognate ligands or receptors, to identify agents that modulate their interactions, in addition to its use as a nutritional supplement. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:85 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a-b, where a is any integer between 1 to 1560 of SEQ ID NO:85, b is an integer of 15 to 1574, where both a and b correspond to the positions of nucleotide residues shown in SEQ ID NO:85, and where b is greater than or equal to a +14.

Features of Protein Encoded by Gene No: 76

A translated product of this gene shares some homology with *C. elegans* UNC-53 protein variant 7A and 8A which would be useful to promote neuronal regeneration, revascularisation or wound healing (see, e.g., GenSeq Accession W20057 and W20056; all references available through these accessions are hereby incorporated herein by reference).

In specific embodiments, polypeptides of the invention comprise, or alternatively consist of, an amino acid sequence selected from the group: MLVLMTLFLLLYYRYVYGFGVCVYVHIYAHIYTHTHIYNQLSIAYSSLIIYILY SNFSNTPTKSFSPPYQYYNVPDNNITNPALTPTDFFENKQLLHAISFLYSPTGFL QPPAHPVQLRTSTTLYGNHRGQTGCSQLD (SEQ ID NO:406), and SNTPTKSFSPPYQYYNVPDNNITNPALTPTDFFENKQLLHAISFLYSPTGFLQPP AHPVQLRTSTTL (SEQ ID NO: 407). Moreover, fragments and variants of these polypeptides (such as, for example, fragments as described herein, polypeptides at least 80%, 85%, 90%, 95%, 96%, 97%, 98%, 99%, or 100% identical to these polypeptides, or polypeptides encoded by a polynucleotide which hybridizes, under stringent conditions, to the polynucleotide encoding these polypeptides) are encompassed by the invention. Antibodies that bind polypeptides of the invention and polynucleotides encoding these polypeptides are also encompassed by the invention.

This gene is expressed primarily in cancer cells, particular from hepatocellular carcinoma.

Homology to proteins that promote wound healing and revascularization indicate that polynucleotides and polypeptides corresponding to this gene would be useful in the detection, treatment, and/or prevention of a variety of vascular disorders and conditions, which include, but are not limited to miscrovascular disease, vascular leak syndrome, aneurysm, stroke, embolism, thrombosis, coronary artery disease, arteriosclerosis, and/or atherosclerosis. Moreover, homology to proteins involved in neuronal regeneration indicates that polynucleotides and polypeptides corresponding to this gene would be useful for the detection, treatment, and/or prevention of neurodegenerative disease states, behavioral disorders, or inflammatory conditions. Representative uses are described in the "Regeneration" and "Hyperproliferative Disorders" sections below, in Example 11, 15, and 18, and elsewhere herein. Briefly, the uses include, but are not limited to the detection, treatment, and/or prevention of Alzheimer's Disease, Parkinson's Disease, Huntington's Disease, Tourette Syndrome, meningitis, encephalitis, demyelinating diseases, peripheral neuropathies, neoplasia, trauma, congenital malformations, spinal cord injuries, ischemia and infarction, aneurysms, hemorrhages, schizophrenia, mania, dementia, paranoia, obsessive compulsive disorder, depression, panic disorder, learning disabilities, ALS, psychoses, autism, and altered behaviors, including disorders in feeding, sleep patterns, balance, and perception. In addition, elevated expression of this gene product in regions of the brain indicates it plays a role in normal neural function. Potentially, polynucleotides and polypeptides corresponding to this gene are involved in synapse formation, neurotransmission, learning, cognition, homeostasis, or neuronal differentiation or survival. Polynucleotides and polypeptides of the invention would be useful as reagents for differential identification of the tissue(s) or cell type(s) present in a biological sample and for diagnosis of diseases and conditions which include, but are not limited to, central and peripheral nervous system tissues, wounded and healing tissues, cardiovascular system tissues, ocular tissues (particularly retina), hepatocellular carcinoma and other similar cancer, particularly of the liver. Similarly, polypeptides and antibodies directed to these polypeptides would be useful in providing immunological probes for differential identification of the tissue(s) or cell type(s). For a number of disorders of the above tissues or cells, particularly of the hepatic system, expression of this gene at significantly higher or lower levels may be routinely detected in certain tissues or cell types (e.g., hepatic, cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

The tissue distribution in tissues of cancerous origins, such as hepatocellular carcinoma tissue, indicates that polynucleotides and polypeptides corresponding to this gene would be useful for the diagnosis and/or treatment of a variety of cancers, most notably cancers of the liver, such as hepatocellular carcinoma. Expression of this gene product in a variety of cancers indicates that polynucleotides and polypeptides corresponding to this gene may be a player in the progression of these diseases, and may be a beneficial target for inhibitors as therapeutics. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:86 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a-b, where a is any integer between 1 to 1614 of SEQ ID NO:86, b is an integer of 15 to 1628, where both a and b correspond to the positions of nucleotide residues shown in SEQ ID NO:86, and where b is greater than or equal to a +14.

Features of Protein Encoded by Gene No: 77

In specific embodiments, polypeptides of the invention comprise, or alternatively consist of, an amino acid sequence selected from the group: MEMNYCGSRVLY (SEQ ID NO: 408) and/or MEMNYCGSRVLYMSLILLGSPIIPLWSYTSATQAAALVTSHVWKPSLEAHQIN ISPEPSIHYDRWHTQSNCSLINSLQ (SEQ ID NO:409). Moreover, fragments and variants of these polypeptides (such as, for example, fragments as described herein, polypeptides at least 80%, 85%, 90%, 95%, 96%, 97%, 98%, 99%, or 100% identical to these polypeptides, or polypeptides encoded by a polynucleotide which hybridizes, under stringent conditions, to the polynucleotide encoding these polypeptides) are encompassed by the invention. Antibodies that bind polypeptides of the invention and polynucleotides encoding these polypeptides are also encompassed by the invention.

This gene is expressed primarily in T-cell lymphoma, and, to a lesser extent, in hepatocellular tumor tissue.

Polynucleotides and polypeptides of the invention would be useful as reagents for differential identification of the tissue(s) or cell type(s) present in a biological sample and for diagnosis of diseases and conditions which include, but are not limited to, T-cell lymphoma, hepatocellular tumors, and cancers. Similarly, polypeptides and antibodies directed to these polypeptides would be useful in providing immunological probes for differential identification of the tissue(s) or cell type(s). For a number of disorders of the above tissues or cells, particularly of the immune and hepatic systems, expression of this gene at significantly higher or lower levels may be routinely detected in certain tissues or cell types (e.g., immune, hepatic, cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder. Preferred polypeptides of the present invention comprise, or alternatively consist of the immunogenic epitopes shown in SEQ ID NO: 194 as residues: Pro-46 to Asn-58. Polynucleotides encoding said polypeptides are encompassed by the invention, as are antibodies that bind one or more of these peptides.

The tissue distribution in T-cell lymphoma and hepatocellular tumor tissue indicates that polynucleotides and polypeptides corresponding to this gene would be useful for the detection, diagnosis, prevention and/or treatment of T-cell lymphomas and hepatocellular tumors, as well as cancers of other tissues where expression of this gene has been observed. Representative uses are described in the "Immune Activity" and "Infectious Disease" sections below, in Example 11, 13, 14, 16, 18, 19, 20, and 27, and elsewhere herein. Furthermore, the protein may also be used to determine biological activity, to raise antibodies, as tissue markers, to isolate cognate ligands or receptors, to identify agents that modulate their interactions, in addition to its use as a nutritional supplement. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:87 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a-b, where a is any integer between 1 to 1781 of SEQ ID NO:87, b is an integer of 15 to 1795, where both a and b correspond to the positions of nucleotide residues shown in SEQ ID NO:87, and where b is greater than or equal to a +14.

Features of Protein Encoded by Gene No: 78

This gene is expressed primarily in brain tissue, and, to a lesser extent, in ntera2 cell lines, melanocytes, normal colon, and T-helper cells.

Polynucleotides and polypeptides of the invention would be useful as reagents for differential identification of the tissue(s) or cell type(s) present in a biological sample and for diagnosis of diseases and conditions which include, but are not limited to, neurodegenerative diseases and/or conditions. Similarly, polypeptides and antibodies directed to these polypeptides would be useful in providing immunological probes for differential identification of the tissue(s) or cell type(s). For a number of disorders of the above tissues or cells, particularly of the nervous system, expression of this gene at significantly higher or lower levels may be routinely detected in certain tissues or cell types (e.g., neural, immune, hematopoietic, gastrointestinal, and cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder. Preferred polypeptides of the present invention comprise, or alternatively consist of the immunogenic epitopes shown in SEQ ID NO: 195 as residues: Met-1 to Trp-6. Polynucleotides encoding said polypeptides are encompassed by the invention, as are antibodies that bind one or more of these peptides.

The tissue distribution in brain tissue indicates that polynucleotides and polypeptides corresponding to this gene would be useful for detecting and/or treating neurodegenerative diseases of the central nervous system. Representative uses are described in the "Regeneration" and "Hyperproliferative Disorders" sections below, in Example 11, 15, and 18, and elsewhere herein. Briefly, the tissue distribution indicates that polynucleotides and polypeptides corresponding to this gene would be useful for the detection, diagnosis, prevention, and/or treatment of neurodegenerative disease states and behavioural disorders such as Alzheimer's Disease, Parkinson's Disease, Huntington's Disease, Tourette Syndrome, schizophrenia, mania, dementia, paranoia, obsessive compulsive disorder, panic disorder, learning disabilities, ALS, psychoses, autism, and altered behaviors, including disorders in feeding, sleep patterns, balance, and perception. In addition, the gene or gene product may also play a role in the treatment and/or detection of developmental disorders associated with the developing embryo, or sexually-linked disorders. Furthermore, the protein may also be used to determine biological activity, to raise antibodies, as tissue markers, to isolate cognate ligands or receptors, to identify agents that modulate their interactions, in addition to its use as a nutritional supplement. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:88 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a-b, where a is any integer between 1 to 1850 of SEQ ID NO: 88, b is an integer of 15 to 1864, where both a and b correspond to the positions of nucleotide residues shown in SEQ ID NO:88, and where b is greater than or equal to a +14.

Features of Protein Encoded by Gene No: 79

The gene encoding the disclosed cDNA is thought to reside on chromosome 1. Accordingly, polynucleotides related to this invention would be useful as a marker in linkage analysis for chromosome 1.

In specific embodiments, polypeptides of the invention comprise, or alternatively consist of, an amino acid sequence selected from the group: IPEEASCFPSAV (SEQ ID NO: 410), EILFGKLKSKAALCTQG (SEQ ID NO: 411), HADRYTCCRCLSPFSLAGL (SEQ ID NO: 412), LSDPLLLPDCSFSFN (SEQ ID NO: 413), KAVAYANVSCRRFKHKTTKLGPIQW (SEQ ID NO: 414), PSSQSPEPPQPLSLFVTRLPNLYDFP (SEQ ID NO: 415), and/or SRQIICTNLCKCTPICFLF (SEQ ID NO: 416). Moreover, fragments and variants of these polypeptides (such as, for example, fragments as described herein, polypeptides at least 80%, 85%, 90%, 95%, 96%, 97%, 98%, 99%, or 100% identical to these polypeptides, or polypeptides encoded by a polynucleotide which hybridizes, under stringent conditions, to the polynucleotide encoding these polypeptides) are encompassed by the invention. Antibodies that bind polypeptides of the invention and polynucleotides encoding these polypeptides are also encompassed by the invention.

Translated products of this gene share some homology with a Factor VIIa protein (see, e.g., GenSeq Accession No. R13788; all references available through this accession are hereby incorporated herein by reference). In specific embodiments, polypeptides of the invention comprise, or alternatively consist of, an amino acid sequence selected from the group: KGSLPWRLLLPLNGP (SEQ ID NO: 417) and LCRLVFESSAGHVSVCHSF (SEQ ID NO: 418). Moreover, fragments and variants of these polypeptides (such as, for example, fragments as described herein, polypeptides at least 80%, 85%, 90%, 95%, 96%, 97%, 98%, 99%, or 100% identical to these polypeptides, or polypeptides encoded by a polynucleotide which hybridizes, under stringent conditions, to the polynucleotide encoding these polypeptides) are encompassed by the invention. Antibodies that bind polypeptides of the invention and polynucleotides encoding these polypeptides are also encompassed by the invention.

This gene is expressed primarily in breast tissue, fetal liver and adult hepatoma tissues, and, to a lesser extent, in merkel cells and osteoblasts.

Polynucleotides and polypeptides of the invention would be useful as reagents for differential identification of the tissue(s) or cell type(s) present in a biological sample and for diagnosis of diseases and conditions which include, but are not limited to, circulatory disorders (particularly coagulatory disorders), cancers of the liver or breast. Similarly, polypeptides and antibodies directed to these polypeptides would be useful in providing immunological probes for differential identification of the tissue(s) or cell type(s). For a number of disorders of the above tissues or cells, particularly of the circulatory system or glandular systems, expression of this gene at significantly higher or lower levels may be routinely detected in certain tissues or cell types (e.g., breast, liver, cancerous and wounded tissues) or bodily fluids (e.g., lymph, breast milk, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder. Preferred polypeptides of the present invention comprise, or alternatively consist of the immunogenic epitopes shown in SEQ ID NO: 196 as residues: Asn-25 to Gln-50. Polynucleotides encoding said polypeptides are encompassed by the invention, as are antibodies that bind one or more of these peptides.

The tissue distribution in breast and hepatoma tissues indicates that polynucleotides and polypeptides corresponding to this gene would be useful for diagnosing and/or treating tumors of the breast or liver. Furthermore, the expression in the breast tissue may indicate its uses in breast neoplasia and breast cancers, such as fibroadenoma, pipillary carcinoma, ductal carcinoma, Paget's disease, medullary carcinoma, mucinous carcinoma, tubular carcinoma, secretory carcinoma and apocrine carcinoma, as well as juvenile hypertrophy and gynecomastia, mastitis and abscess, duct ectasia, fat necrosis and fibrocystic diseases. Alternatively, the tissue distribution indicates that polynucleotides and polypeptides corresponding to this gene would be useful for the detection and treatment of liver disorders and cancers (e.g., hepatoblastoma, jaundice, hepatitis, liver metabolic diseases and conditions that are attributable to the differentiation of hepatocyte progenitor cells). Protein, as well as, antibodies directed against the protein may show utility as a tumor marker and immunotherapy targets for the above listed tumors and tissues.

Many polynucleotide sequences, such as EST sequences, are publicly available and accessible through sequence databases. Some of these sequences are related to SEQ ID NO:89 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a-b, where a is any integer between 1 to 1969 of SEQ ID NO:89, b is an integer of 15 to 1983, where both a and b correspond to the positions of nucleotide residues shown in SEQ ID NO:89, and where b is greater than or equal to a +14.

Features of Protein Encoded by Gene No: 80

This gene is expressed primarily in thymus and brain tissues.

Polynucleotides and polypeptides of the invention would be useful as reagents for differential identification of the tissue(s) or cell type(s) present in a biological sample and for diagnosis of diseases and conditions which include, but are not limited to, diseases and/or disorders of the immune system and diseases of the brain, including various types of mood disorders. Similarly, polypeptides and antibodies directed to these polypeptides would be useful in providing immunological probes for differential identification of the tissue(s) or cell type(s). For a number of disorders of the above tissues or cells, particularly of the immune system and central nervous system, expression of this gene at significantly higher or lower levels may be routinely detected in certain tissues or cell types (e.g., immune, neural, cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

The tissue distribution indicates that polynucleotides and polypeptides corresponding to this gene would be useful for the detection, treatment, and/or prevention of a variety of immune system disorders. Representative uses are described in the "Immune Activity" and "Infectious Disease" sections below, in Example 11, 13, 14, 16, 18, 19, 20, and 27, and elsewhere herein. Briefly, the expression of this gene product in thymus indicates a role in the regulation of the proliferation; survival; differentiation; and/or activation of potentially all hematopoietic cell lineages, including blood stem cells. Polynucleotides and polypeptides corresponding to this gene may be involved in the regulation of cytokine production, antigen presentation, or other processes that may also suggest a usefulness in the treatment of cancer (e.g., by boosting immune responses). Since the gene is expressed in cells of lymphoid origin, the gene or protein, as well as, antibodies directed against the protein may show utility as a tumor marker and/or immunotherapy targets for the above listed tissues. Therefore polynucleotides and polypeptides of the invention may be also used as an agent for immunological disorders including arthritis, asthma, immune deficiency diseases such as AIDS, leukemia, rheumatoid arthritis, inflammatory bowel disease, sepsis, acne, and psoriasis. In addition, polynucleotides and polypeptides of the invention may have commercial utility in the expansion of stem cells and committed progenitors of various blood lineages, and in the differentiation and/or proliferation of various cell types. Alternatively, the tissue distribution in brain tissue indicates that polynucleotides and polypeptides corresponding to this gene would be useful for the detection, diagnosis, prevention and/or treatment of neurodegenerative disease states and behavioural disorders such as Alzheimer's Disease, Parkinson's Disease, Huntington's Disease, Tourette Syndrome, schizophrenia, mania, dementia, paranoia, obsessive compulsive disorder, panic disorder, learning disabilities, ALS, psychoses, autism, and altered behaviors, including disorders in feeding, sleep patterns, balance, and perception. In addition, the gene or gene product may also play a role in the treatment and/or detection of developmental disorders associated with the developing embryo, or sexually-linked disorders. Furthermore, the protein may also be used to determine biological activity, to raise antibodies, as tissue markers, to isolate cognate ligands or receptors, to identify agents that modulate their interactions, in addition to its use as a nutritional supplement. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:90 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a-b, where a is any integer between 1 to 1943 of SEQ ID NO:90, b is an integer of 15 to 1957, where both a and b correspond to the positions of nucleotide residues shown in SEQ ID NO:90, and where b is greater than or equal to a +14.

Features of Protein Encoded by Gene No: 81

In specific embodiments, polypeptides of the invention comprise, or alternatively consist of, an amino acid sequence selected from the group: MLLPVNTLLYI (SEQ ID NO: 419), LLTPLCFFYGTSRP (SEQ ID NO: 420), PYLELVT (SEQ ID NO: 421), LLKKKKQSVGFSV (SEQ ID NO: 422), CILEAGR (SEQ ID NO: 423), MGFSAPTPGPL (SEQ ID NO: 424), FDLRRLILSIV (SEQ ID NO: 425), AFCPHVTPCKYAVIHTV (SEQ ID NO: 426), NTPLLFLWDLQ (SEQ ID NO: 427), ATIFRTSYLIKKEKTVC (SEQ ID NO: 428), WLLSLHLGGREVRAGAP (SEQ ID NO: 429), QTLQEGSLHSI (SEQ ID NO: 430), and/or MGFSAPTPGPLFDLRRLILSIVAFCPHVTPCKYAVIHTVNTPLLFLWDLQATIF RTSYLIKKEKTVCWLLSLHLGGREVRAGAPQTLQEGSLHSI (SEQ ID NO: 431). Moreover, fragments and variants of these polypeptides (such as, for example, fragments as described herein, polypeptides at least 80%, 85%, 90%, 95%, 96%, 97%, 98%, 99%, or 100% identical to these polypeptides, or polypeptides encoded by a polynucleotide which hybridizes, under stringent conditions, to the polynucleotide encoding these polypeptides) are encompassed by the invention. Antibodies that bind polypeptides of the invention and polynucleotides encoding these polypeptides are also encompassed by the invention.

This gene is expressed primarily in brain and breast tissues, and, to a lesser extent, in several other cell and tissue types including colon and liver tissues.

Polynucleotides and polypeptides of the invention would be useful as reagents for differential identification of the tissue(s) or cell type(s) present in a biological sample and for diagnosis of diseases and conditions which include, but are not limited to, breast and brain cancers, mood disorders, dementia, and Alzheimer's disease. Similarly, polypeptides and antibodies directed to these polypeptides would be useful in providing immunological probes for differential identification of the tissue(s) or cell type(s). For a number of disorders of the above tissues or cells, particularly of the central nervous and lactations systems, expression of this gene at significantly higher or lower levels may be routinely detected in certain tissues or cell types (e.g., neural, reproductive, cancerous and wounded tissues) or bodily fluids (e.g., lymph, breast milk, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder. Preferred polypeptides of the present invention comprise, or alternatively consist of the immunogenic epitopes shown in SEQ ID NO: 198 as residues: Gly-21 to Tyr-27. Polynucleotides encoding said polypeptides are encompassed by the invention, as are antibodies that bind one or more of these peptides.

The expression in breast tissue indicates that polynucleotides and/or polypeptides of the invention would be useful for diagnosis, treatment and/or prevention of breast neoplasia and breast cancers, such as fibroadenoma, pipillary carcinoma, ductal carcinoma, Paget's disease, medullary carcinoma, mucinous carcinoma, tubular carcinoma, secretory carcinoma and apocrine carcinoma, as well as juvenile hypertrophy and gynecomastia, mastitis and abscess, duct ectasia, fat necrosis and fibrocystic diseases. Representative uses are described in the "Regeneration" and "Hyperproliferative Disorders" sections below, in Example 11, 15, and 18, and elsewhere herein. Alternatively, the tissue distribution of this gene in brain tissue indicates that polynucleotides and polypeptides of the invention would be useful for the detection and/or treatment of brain cancers and neural disorders, such as Alzheimer's Disease, Parkinson's Disease, Huntington's Disease, Tourette Syndrome, schizophrenia, mania, dementia, paranoia, obsessive compulsive disorder, panic disorder, learning disabilities, ALS, psychoses, autism, and altered behaviors, including disorders in feeding, sleep patterns, balance, and perception. In addition, the gene or gene product may also play a role in the treatment and/or detection of developmental disorders associated with the developing embryo, or sexually-linked disorders. Furthermore, the protein may also be used to determine biological activity, to raise antibodies, as tissue markers, to isolate cognate ligands or receptors, to identify agents that modulate their interactions, in addition to its use as a nutritional supplement. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:91 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a-b, where a is any integer between 1 to 559 of SEQ ID NO:91, b is an integer of 15 to 573, where both a and b correspond to the positions of nucleotide residues shown in SEQ ID NO:91, and where b is greater than or equal to a +14.

Features of Protein Encoded by Gene No: 82

The gene encoding the disclosed cDNA is believed to reside on chromosome 1. Accordingly, polynucleotides related to this invention would be useful as a marker in linkage analysis for chromosome 1.

This gene is expressed primarily in liver and, to a lesser extent, in other tissues.

Polynucleotides and polypeptides of the invention would be useful as reagents for differential identification of the tissue(s) or cell type(s) present in a biological sample and for diagnosis of diseases and conditions which include, but are not limited to, liver/hepatocyte disorders. Similarly, polypeptides and antibodies directed to these polypeptides would be useful in providing immunological probes for differential identification of the tissue(s) or cell type(s). For a number of disorders of the above tissues or cells, particularly of the liver, expression of this gene at significantly higher or lower levels may be routinely detected in certain tissues or cell types (e.g., liver, cancerous and wounded tissues) or bodily fluids (e.g., lymph, bile, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

The tissue distribution in liver indicates that polynucleotides and polypeptides corresponding to this gene would be useful for detection, treatment, and/or prevention of liver (hepatocyte) disorders and cancers (e.g., hepatoblastoma, jaundice, hepatitis, liver metabolic diseases and conditions that are attributable to the differentiation of hepatocyte progenitor cells). Furthermore, the protein may also be used to determine biological activity, to raise antibodies, as tissue markers, to isolate cognate ligands or receptors, to identify agents that modulate their interactions, in addition to its use as a nutritional supplement. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:92 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a-b, where a is any integer between 1 to 1198 of SEQ ID NO:92, b is an integer of 15 to 1212, where both a and b correspond to the positions of nucleotide residues shown in SEQ ID NO:92, and where b is greater than or equal to a +14.

Features of Protein Encoded by Gene No: 83

In specific embodiments, polypeptides of the invention comprise, or alternatively consist of, the following amino acid sequence: YWVSISQRSVCQQARTSIFFKDG-LSREKYSNNG (SEQ ID NO: 432). Moreover, fragments and variants of these polypeptides (such as, for example, fragments as described herein, polypeptides at least 80%, 85%, 90%, 95%, 96%, 97%, 98%, 99%, or 100% identical to these polypeptides, or polypeptides encoded by a polynucleotide which hybridizes, under stringent conditions, to the polynucleotide encoding these polypeptides) are encompassed by the invention. Antibodies that bind polypeptides of the invention and polynucleotides encoding these polypeptides are also encompassed by the invention.

This gene is expressed primarily in T cells.

Polynucleotides and polypeptides of the invention would be useful as reagents for differential identification of the tissue(s) or cell type(s) present in a biological sample and for diagnosis of diseases and conditions which include, but are not limited to, immune disorders, including AIDS and various other diseases in which the immune system is suppressed. Similarly, polypeptides and antibodies directed to these polypeptides would be useful in providing immunological probes for differential identification of the tissue(s) or cell type(s). For a number of disorders of the above tissues or cells, particularly of the immune system, expression of this gene at significantly higher or lower levels may be routinely detected in certain tissues or cell types (e.g., immune, cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

The tissue distribution in T cells indicates that the polypeptides or polynucleotides would be useful for treatment, prophylaxis, and diagnosis of immune and autoimmune diseases, such as lupus, transplant rejection, allergic reactions, arthritis, asthma, immunodeficiency diseases, leukemia, and AIDS. Representative uses are described in the "Immune Activity" and "Infectious Disease" sections below, in Example 11, 13, 14, 16, 18, 19, 20, and 27, and elsewhere herein. Briefly, the expression indicates a role in regulating the proliferation; survival; differentiation; and/or activation of hematopoietic cell lineages, including blood stem cells. Involvement in the regulation of cytokine production, antigen presentation, or other processes indicates a usefulness for treatment of cancer (e.g., by boosting immune responses). Expression in cells of lymphoid origin, indicates the natural gene product would be involved in immune functions. Therefore polynucleotides and polypeptides of the invention would also be useful as an agent for immunological disorders including arthritis, asthma, immunodeficiency diseases such as AIDS, leukemia, rheumatoid arthritis, granulomatous disease, inflammatory bowel disease, sepsis, acne, neutropenia, neutrophilia, psoriasis, hypersensitivities, such as T-cell mediated cytotoxicity; immune reactions to transplanted organs and tissues, such as host-versus-graft and graft-versus-host diseases, or autoimmunity disorders, such as autoimmune infertility, lense tissue injury, demyelination, systemic lupus erythematosis, drug induced hemolytic anemia, rheumatoid arthritis, Sjogren's disease, and scleroderma. Moreover, the protein may represent a secreted factor that influences the differentiation or behavior of other blood cells, or that recruits hematopoietic cells to sites of injury. Thus, polynucleotides and polypeptides of the invention are thought to be useful in the expansion of stem cells and committed progenitors of various blood lineages, and in the differentiation and/or proliferation of various cell types. The polypeptides or polynucleotides of the present invention would also be useful in the treatment, prophlaxis, and detection of thymus disorders, such as Grave's Disease, lymphocytic thyroiditis, hyperthyroidism, and hypothyroidism. Similarly, elevated levels of expression of this gene product in T cell lineages indicates that it may play an active role in normal T cell function and in the regulation of the immune response. For example, this gene product may be involved in T cell activation, in the activation or control of differentiation of other hematopoietic cell lineages, in antigen recognition, or in T cell proliferation. Furthermore, the protein may also be used to determine biological activity, raise antibodies, as tissue markers, to isolate cognate ligands or receptors, to identify agents that modulate their interactions, in addition to its use as a nutritional supplement. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:93 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a-b, where a is any integer between 1 to 1130 of SEQ ID NO:93, b is an integer of 15 to 1144, where both a and b correspond to the positions of nucleotide residues shown in SEQ ID NO:93, and where b is greater than or equal to a +14.

Features of Protein Encoded by Gene No: 84

The translation product of this gene shares sequence homology with a protein which was found to accumulate during growth-factor-induced proliferation and transformation of normal rat fibroblasts (see, e.g., Glaichenhaus, N., and Cuzin, F., Cell 50:1081 (1987); and Genbank Acc. No. gi|207250; all references available through this accession and reference are hereby incorporated by reference herein.)

In specific embodiments, polypeptides of the invention comprise, or alternatively consist of, an amino acid sequence selected from the group: LSVRAPGVPAARPRLSSARQAGAGRGELRGQRLWLGPECGCGAGQAGSMLR AVGSLLRLGRGLTVRCGPGAPLEATRR-PAPALPPRGLPCYSSGGAPSNSGPQG HGEIHRVPTQRRPSQFDKKILLWTGRFKSMEEIP-PRIPPEMIDTARNKARVKAC YI (SEQ ID NO:433), LSVRAPGVPAARPRLSSARQAGAGRGELRGQRLWLG (SEQ ID NO:434), PECGCGAGQAGSMLRAVGSLLR-LGRGLTVRCGPG (SEQ ID NO:435), APLEATRRPA-PALPPRGLPCYSSGGAPSNSGPQG (SEQ ID NO:436), HGEIHRVPTQRRPSQFDKKILLWTGRF (SEQ ID NO:437), and/or KSMEEIPPRIPPEMIDTARNKARVKA-CYI (SEQ ID NO:438). Moreover, fragments and variants of these polypeptides (such as, for example, fragments as described herein, polypeptides at least 80%, 85%, 90%, 95%, 96%, 97%, 98%, 99%, or 100% identical to these polypeptides, or polypeptides encoded by a polynucleotide which hybridizes, under stringent conditions, to the polynucleotide encoding these polypeptides) are encompassed by the invention. Antibodies that bind polypeptides of the invention and polynucleotides encoding these polypeptides are also encompassed by the invention.

The polypeptide of this gene has been determined to have a transmembrane domain at about amino acid position 4 to about 20 of the amino acid sequence referenced in Table 1 for this gene. Moreover, a cytoplasmic tail encompassing amino acids 1 to 3 of this protein has also been determined. Based upon these characteristics, it is believed that polynucleotides and polypeptides corresponding to this gene shares structural features to type II membrane proteins.

This gene is expressed primarily in placenta.

Polynucleotides and polypeptides of the invention would be useful as reagents for differential identification of the tissue(s) or cell type(s) present in a biological sample and for diagnosis of diseases and conditions which include, but are not limited to, developmental anomalies or fetal deficiencies, cancers or neoplastic conditions. Similarly, polypeptides and antibodies directed to these polypeptides would be useful in providing immunological probes for differential identification of the tissue(s) or cell type(s). For a number of disorders of the above tissues or cells, particularly of the developing embryo, expression of this gene at significantly higher or lower levels may be routinely detected in certain tissues or cell types (e.g., embryonic, placental, cancerous and wounded tissues) or bodily fluids (e.g., lymph, amniotic fluid, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

The tissue distribution and homology to a protein which was found to accumulate during proliferation and transformation of normal fibroblasts indicates that polynucleotides and polypeptides corresponding to this gene would be useful for the treatment and diagnosis of developmental anomalies or fetal deficiencies, neoplasms and cancers. Additionally, the tissue distribution in placenta indicates that polynucleotides and polypeptides corresponding to this gene would be useful for the diagnosis and/or treatment of disorders of the placenta. Specific expression within the placenta indicates that polynucleotides and polypeptides of the invention may play a role in the proper establishment and maintenance of placental function. Alternately, polynucleotides and polypeptides of the invention may be produced by the placenta and then transported to the embryo, where it may play a crucial role in the development and/or survival of the developing embryo or fetus. Expression of this gene product in a vascular-rich tissue such as the placenta also indicates that polynucleotides and polypeptides of the invention may be produced more generally in endothelial cells or within the circulation. In such instances, it may play more generalized roles in vascular function, such as in angiogenesis. Polynucleotides and polypeptides of the invention may also be produced in the vasculature and have effects on other cells within the circulation, such as hematopoietic cells. It may serve to promote the proliferation, survival, activation, and/or differentiation of hematopoietic cells, as well as other cells throughout the body. Protein, as well as, antibodies directed against the protein may show utility as a tumor marker and/or immunotherapy targets for the above listed tissues. Furthermore, the protein may also be used to determine biological activity, to raise antibodies, as tissue markers, to isolate cognate ligands or receptors, to identify agents that modulate their interactions, in addition to its use as a nutritional supplement. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:94 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a-b, where a is any integer between 1 to 1260 of SEQ ID NO:94, b is an integer of 15 to 1274, where both a and b correspond to the positions of nucleotide residues shown in SEQ ID NO:94, and where b is greater than or equal to a +14.

Features of Protein Encoded by Gene No: 85

The translated product of this gene shares some homology with a novel alpha-neurotoxin from the king cobra (*Ophiophagus hannah*) venom (see, e.g., Genbank Accession No. JC1474 and P80965; all references available through these accessions are hereby incorporated herein by reference). Based on the sequence similarity, the translation product of this clone is expected to share at least some biological activities with neurotransmitter proteins.

In specific embodiments, polypeptides of the invention comprise, or alternatively consist of, an amino acid sequence selected from the group: CSPGQDEMQDETWCSGQSETVNEAKQLRTTHSRVPNQQVCVCGWLPVNISPHSPLKK (SEQ ID NO: 439) and/or MSGDVCVFGYAHLHSQTKHSGSQGWVLIYLFAMQKISCTKLPLLRNLKLNL VWLSQGWVFFKGLWGEMLTGSHPQTHTCWLGTRLWVVLSCLASLTVSDCP EHQVSSCISSWPGEHSVSFQPFPPFPHSLGGTEVGVEESQMAGVGI (SEQ ID NO: 440). Moreover, fragments and variants of these polypeptides (such as, for example, fragments as described herein, polypeptides at least 80%, 85%, 90%, 95%, 96%, 97%, 98%, 99%, or 100% identical to these polypeptides, or polypeptides encoded by a polynucleotide which hybridizes, under stringent conditions, to the polynucleotide encoding these polypeptides) are encompassed by the invention. Antibodies that bind polypeptides of the invention and polynucleotides encoding these polypeptides are also encompassed by the invention.

The gene encoding the disclosed cDNA is thought to reside on chromosome 3. Accordingly, polynucleotides related to this invention would be useful as a marker in linkage analysis for chromosome 3.

This gene is expressed primarily in T-cell lymphoma and synovial sarcoma tissues, and, to a lesser extent, in fetal liver/spleen tissue and synovial fibroblasts.

Polynucleotides and polypeptides of the invention would be useful as reagents for differential identification of the tissue(s) or cell type(s) present in a biological sample and for diagnosis of diseases and conditions which include, but are not limited to, T-Cell lymphoma and synovial sarcoma. Similarly, polypeptides and antibodies directed to these polypeptides would be useful in providing immunological probes for differential identification of the tissue(s) or cell type(s). For a number of disorders of the above tissues or cells, particularly of the immune system, expression of this gene at significantly higher or lower levels may be routinely detected in certain tissues or cell types (e.g., immune, hematopoietic, and cancerous and wounded tissues) or bodily fluids (e.g., lymph, serum, plasma, urine, synovial fluid or spinal fluid) or another tissue or cell sample taken from an individual having such a disorder, relative to the standard gene expression level, i.e., the expression level in healthy tissue or bodily fluid from an individual not having the disorder. Preferred polypeptides of the present invention comprise, or alternatively consist of one or both of the immunogenic epitopes shown in SEQ ID NO: 202 as residues: Gly-4 to His-10, Asp-32 to Val-38. Polynucleotides encoding said polypeptides are encompassed by the invention, as are antibodies that bind one or more of these peptides.

The tissue distribution in T-cell lymphoma and synovial sarcoma tissues indicates that polynucleotides and polypeptides corresponding to this gene would be useful for the detection, diagnosis, prevention and/or treatment of T-cell lymphomas and synovial sarcomas, as well as cancers of other tissues where expression of this gene has been observed. Representative uses are described in the "Immune Activity" and "Infectious Disease" sections below, in Example 11, 13, 14, 16, 18, 19, 20, and 27, and elsewhere herein. Furthermore, the protein may also be used to determine biological activity, to raise antibodies, as tissue markers, to isolate cognate ligands or receptors, to identify agents that modulate their interactions, in addition to its use as a nutritional supplement. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:95 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a-b, where a is any integer between 1 to 1766 of SEQ ID NO:95, b is an integer of 15 to 1780, where both a and b correspond to the positions of nucleotide residues shown in SEQ ID NO:95, and where b is greater than or equal to a +14.

Features of Protein Encoded by Gene No: 86

In specific embodiments, polypeptides of the invention comprise, or alternatively consist of, an amino acid sequence selected from the group: LNILISLTVSSHCKL (SEQ ID NO: 441), INYHSGFIHQFLA (SEQ ID NO: 442), and/or MANNSLSSQFI (SEQ ID NO: 443). Moreover, fragments and variants of these polypeptides (such as, for example, fragments as described herein, polypeptides at least 80%, 85%, 90%, 95%, 96%, 97%, 98%, 99%, or 100% identical to these polypeptides, or polypeptides encoded by a polynucleotide which hybridizes, under stringent conditions, to the polynucleotide encoding these polypeptides) are encompassed by the invention. Antibodies that bind polypeptides of the invention and polynucleotides encoding these polypeptides are also encompassed by the invention.

The translated product of this gene shares some homology with Integrin Beta 5 subunit protein (see, e.g., GenBank Accession No. Q64657; all references available through this accession are hereby incorporated herein by reference).

In specific embodiments, polypeptides of the invention comprise, or alternatively consist of, the following amino acid sequence: ISGVLIFNLIASSWVLCFPLCDLSCQKTLRIFFASFFHAVCVHVSCTSWQPLVLF IKWWVVGCSP (SEQ ID NO: 444). Moreover, fragments and variants of these polypeptides (such as, for example, fragments as described herein, polypeptides at least 80%, 85%, 90%, 95%, 96%, 97%, 98%, 99%, or 100% identical to these polypeptides, or polypeptides encoded by a polynucleotide which hybridizes, under stringent conditions, to the polynucleotide encoding these polypeptides) are encompassed by the invention. Antibodies that bind polypeptides of the invention and polynucleotides encoding these polypeptides are also encompassed by the invention.

The translated product of this gene also contains a Zinc finger (C2H2 type) domain consistent with the consensus pattern: C.{2,4}C.{3}[LIVMFYWC].{8}H.{3,5}H (identified using the ProSite analysis tool (Swiss Institute of Bioinformatics)). Accordingly, in specific embodiments, polypeptides of the invention comprise, or alternatively consist of, the following amino acid sequence: CDLSCQKTLRIFFASFFHAVCVH (SEQ ID NO: 445). Moreover, fragments and variants of these polypeptides (such as, for example, fragments as described herein, polypeptides at least 80%, 85%, 90%, 95%, 96%, 97%, 98%, 99%, or 100% identical to these polypeptides, or polypeptides encoded by a polynucleotide which hybridizes, under stringent conditions, to the polynucleotide encoding these polypeptides) are encompassed by the invention. Antibodies that bind polypeptides of the invention and polynucleotides encoding these polypeptides are also encompassed by the invention.

This gene is expressed primarily in thymus tissue.

Polynucleotides and polypeptides of the invention would be useful as reagents for differential identification of the tissue(s) or cell type(s) present in a biological sample and for diagnosis of diseases and conditions which include, but are not limited to, diseases and/or disorders of the immune system. Similarly, polypeptides and antibodies directed to these polypeptides would be useful in providing immunological probes for differential identification of the tissue(s) or cell type(s). For a number of disorders of the above tissues or cells, particularly of the immune system, expression of this gene at significantly higher or lower levels may be routinely detected in certain tissues or cell types (e.g., immune, cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

The tissue distribution indicates that polynucleotides and polypeptides corresponding to this gene would be useful for the detection, treatment, and/or prevention of a variety of immune system disorders. Representative uses are described in the "Immune Activity" and "Infectious Disease" sections below, in Example 11, 13, 14, 16, 18, 19, 20, and 27, and elsewhere herein. Briefly, the expression of this gene product in thymus indicates a role in the regulation of the proliferation; survival; differentiation; and/or activation of potentially all hematopoietic cell lineages, including blood stem cells. Polynucleotides and polypeptides corresponding to this gene may be involved in the regulation of cytokine production, antigen presentation, or other processes that may also suggest a usefulness in the treatment of cancer (e.g., by boosting immune responses). Since the gene is expressed in cells of lymphoid origin, the gene or protein, as well as, antibodies directed against the protein may show utility as a tumor marker and/or immunotherapy targets for the above listed tissues. Therefore polynucleotides and polypeptides of the invention may be also used as an agent for immunological disorders including arthritis, asthma, immune deficiency diseases such as AIDS, leukemia, rheumatoid arthritis, inflammatory bowel disease, sepsis, acne, and psoriasis. In addition, polynucleotides and polypeptides of the invention may have commercial utility in the expansion of stem cells and committed progenitors of various blood lineages, and in the differentiation and/or proliferation of various cell types. Furthermore, the protein may also be used to determine biological activity, to raise antibodies, as tissue markers, to isolate cognate ligands or receptors, to identify agents that modulate their interactions, in addition to its use as a nutritional supplement. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:96 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a-b, where a is any integer between 1 to 1780 of SEQ ID NO:96, b is an integer of 15 to 1794, where both a and b correspond to the positions of nucleotide residues shown in SEQ ID NO:96, and where b is greater than or equal to a +14.

Features of Protein Encoded by Gene No: 87

The gene encoding the disclosed cDNA is believed to reside on chromosome 10. Accordingly, polynucleotides related to this invention would be useful as a marker in linkage analysis for chromosome 10.

This gene is expressed primarily in brain, kidney, testes, colon cancer, parathyroid tumor, immune cells (e.g., T-cells) and to a lesser extent, in many other tissues.

Polynucleotides and polypeptides of the invention would be useful as reagents for differential identification of the tissue(s) or cell type(s) present in a biological sample and for diagnosis of diseases and conditions which include, but are not limited to, kidney diseases and various diseases of the brain including mood disorders. Similarly, polypeptides and antibodies directed to these polypeptides would be useful in providing immunological probes for differential identification of the tissue(s) or cell type(s). For a number of disorders of the above tissues or cells, particularly of the brain and renal systems, expression of this gene at significantly higher or lower levels may be routinely detected in certain tissues or cell types (e.g., kidney, CNS, immune, cancerous and wounded tissues) or bodily fluids (e.g., lymph, serum, plasma, urine, synovial fluid or cerebrospinal fluid) or another tissue or cell sample taken from an individual having such a disorder, relative to the standard gene expression level, i.e., the expression level in healthy tissue or bodily fluid from an individual not having the disorder. Preferred polypeptides of the present invention comprise, or alternatively consist of the immunogenic epitopes shown in SEQ ID NO: 204 as residues: Arg-68 to Lys-78. Polynucleotides encoding said polypeptides are encompassed by the invention, as are antibodies that bind one or more of these peptides.

The tissue distribution in kidney indicates that polynucleotides and polypeptides corresponding to this gene would be useful in the treatment, prevention, diagnosis and/or detection of kidney diseases including renal failure, nephritis, renal tubular acidosis, proteinuria, pyuria, edema, pyelonephritis, hydronephritis, nephrotic syndrome, crush syndrome, glomerulonephritis, hematuria, renal colic and kidney stones, in addition to Wilm's Tumor Disease, and congenital kidney abnormalities such as horseshoe kidney, polycystic kidney, and Falconi's syndrome. The tissue distribution in brain indicates that polynucleotides and polypeptides corresponding to this gene would be useful for the detection, treatment, and/or prevention of neurodegenerative disease states, behavioral disorders, or inflammatory conditions. Representative uses are described in the "Regeneration" and "Hyperproliferative Disorders" sections below, in Example 11, 15, and 18, and elsewhere herein. Briefly, the uses include, but are not limited to the detection, treatment, and/or prevention of Alzheimer's Disease, Parkinson's Disease, Huntington's Disease, Tourette Syndrome, meningitis, encephalitis, demyelinating diseases, peripheral neuropathies, neoplasia, trauma, congenital malformations, spinal cord injuries, ischemia and infarction, aneurysms, hemorrhages, schizophrenia, mania, dementia, paranoia, obsessive compulsive disorder, depression, panic disorder, learning disabilities, ALS, psychoses, autism, and altered behaviors, including disorders in feeding, sleep patterns, balance, and perception. In addition, elevated expression of this gene product in regions of the brain indicates it plays a role in normal neural function. Potentially, this gene product is involved in synapse formation, neurotransmission, learning, cognition, homeostasis, or neuronal differentiation or survival. The tissue distribution in testes, kidney, and other tissues associates with the endocrine system indicates that polynucleotides and polypeptides corresponding to this gene would be useful for the detection, treatment, and/or prevention of various endocrine disorders and cancers. Representative uses are described in the "Biological Activity", "Hyperproliferative Disorders", and "Binding Activity" sections below, in Example 11, 17, 18, 19, 20 and 27, and elsewhere herein. Briefly, the protein can be used for the detection, treatment, and/or prevention of Addison's disease, Cushing's Syndrome, and disorders and/or cancers of the pancrease (e.g., diabetes mellitus), adrenal cortex, ovaries, pituitary (e.g., hyper-, hypopituitarism), thyroid (e.g., hyper-, hypothyroidism), parathyroid (e.g., hyper-, hypoparathyroidism), hypothalamus, and testes. The tissue distribution in immune cells (e.g., T-cells) indicates that polynucleotides and polypeptides corresponding to this gene would be useful for the diagnosis and treatment of a variety of immune system disorders. Representative uses are described in the "Immune Activity" and "Infectious Disease" sections below, in Example 11, 13, 14, 16, 18, 19, 20, and 27, and elsewhere herein. Briefly, the expression indicates a role in regulating the proliferation; survival; differentiation; and/or activation of hematopoietic cell lineages, including blood stem cells. Involvement in the regulation of cytokine production, antigen presentation, or other processes indicates a usefulness for treatment of cancer (e.g. by boosting immune responses). Expression in cells of lymphoid origin, indicates the natural gene product would be involved in immune functions. Therefore it would also be useful as an agent for immunological disorders including arthritis, asthma, immunodeficiency diseases such as AIDS, leukemia, rheumatoid arthritis, granulomatous disease, inflammatory bowel disease, sepsis, acne, neutropenia, neutrophilia, psoriasis, hypersensitivities, such as T-cell mediated cytotoxicity; immune reactions to transplanted organs and tissues, such as host-versus-graft and graft-versus-host diseases, or autoimmunity disorders, such as autoimmune infertility, lense tissue injury, demyelination, systemic lupus erythematosis, drug induced hemolytic anemia, rheumatoid arthritis, Sjogren's disease, and scleroderma. Moreover, the protein may represent a secreted factor that influences the differentiation or behavior of other blood cells, or that recruits hematopoietic cells to sites of injury. Thus, this gene product is thought to be useful in the expansion of stem cells and committed progenitors of various blood lineages, and in the differentiation and/or proliferation of various cell types. Furthermore, the protein may also be used to determine biological activity, to raise antibodies, as tissue markers, to isolate cognate ligands or receptors, to identify agents that modulate their interactions, in addition to its use as a nutritional supplement. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:97 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a-b, where a is any integer between 1 to 2051 of SEQ ID NO:97, b is an integer of 15 to 2065, where both a and b correspond to the positions of nucleotide residues shown in SEQ ID NO:97, and where b is greater than or equal to a +14.

Features of Protein Encoded by Gene No: 88

It has been discovered that this gene is expressed primarily in neutrophils.

Polynucleotides and polypeptides of the invention would be useful as reagents for differential identification of the tissue(s) or cell type(s) present in a biological sample and for diagnosis of diseases and conditions which include, but are not limited to, immune and inflammatory disorders. Similarly, polypeptides and antibodies directed to these polypeptides would be useful in providing immunological probes for differential identification of the tissue(s) or cell type(s). For a number of disorders of the above tissues or cells, particularly of the immune and inflammatory systems, expression of this gene at significantly higher or lower levels may be routinely detected in certain tissues or cell types (e.g., immune, cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder. Preferred polypeptides of the present invention comprise, or alternatively consist of the immunogenic epitopes shown in SEQ ID NO: 205 as residues: Pro-41 to Gln-48. Polynucleotides encoding said polypeptides are encompassed by the invention, as are antibodies that bind one or more of these peptides.

The tissue distribution in neutrophils indicates that polynucleotides and polypeptides corresponding to this gene would be useful for the study, diagnosis, detection prevention and/or treatment of immune and inflammatory diseases. Representative uses are described in the "Immune Activity" and "Infectious Disease" sections below, in Example 11, 13, 14, 16, 18, 19, 20, and 27, and elsewhere herein. Briefly, the expression of this gene product indicates a role in regulating the proliferation; survival; differentiation; and/or activation of hematopoietic cell lineages, including blood stem cells. Furthermore, polynucleotides and polypeptides of the invention may be involved in the regulation of cytokine production, antigen presentation, or other processes that may also suggest a usefulness in the treatment of cancer (e.g., by boosting immune responses). Since the gene is expressed in cells of lymphoid origin, the gene or protein, as well as, antibodies directed against the protein may show utility as a tumor marker and/or immunotherapy targets for the above listed tissues. Therefore polynucleotides and polypeptides of the invention may be also used as an agent for immunological disorders including arthritis, asthma, immune deficiency diseases such as AIDS, leukemia, rheumatoid arthritis, inflammatory bowel disease, sepsis, acne, and psoriasis. In addition, this gene product may have commercial utility in the expansion of stem cells and committed progenitors of various blood lineages, and in the differentiation and/or proliferation of various cell types. Furthermore, the protein may also be used to determine biological activity, to raise antibodies, as tissue markers, to isolate cognate ligands or receptors, to identify agents that modulate their interactions, in addition to its use as a nutritional supplement. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:98 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a-b, where a is any integer between 1 to 1140 of SEQ ID NO:98, b is an integer of 15 to 1154, where both a and b correspond to the positions of nucleotide residues shown in SEQ ID NO:98, and where b is greater than or equal to a +14.

Features of Protein Encoded by Gene No: 89

In specific embodiments, polypeptides of the invention comprise, or alternatively consist of, the following amino acid sequence: ELAIGESCS (SEQ ID NO: 446). Moreover, fragments and variants of these polypeptides (such as, for example, fragments as described herein, polypeptides at least 80%, 85%, 90%, 95%, 96%, 97%, 98%, 99%, or 100% identical to these polypeptides, or polypeptides encoded by a polynucleotide which hybridizes, under stringent conditions, to the polynucleotide encoding these polypeptides) are encompassed by the invention. Antibodies that bind polypeptides of the invention and polynucleotides encoding these polypeptides are also encompassed by the invention.

The translation product of this gene shares sequence homology with NY-REN-8 antigen (see, e.g., Genbank accession number AF155098 (AD42864); all references available through this accession are hereby incorporated by reference herein) which is an antigen recognized by autologous antibody in patients with renal-cell carcinoma and may be important in cancer diagnosis, therapy, and/or prevention. Based on the sequence similarity, the translation product of this clone is expected to share at least some biological activities with NY-REN-8 antigen and other related antigens.

This gene is expressed primarily in brain, testes, and fetal tissue.

Polynucleotides and polypeptides of the invention would be useful as reagents for differential identification of the tissue(s) or cell type(s) present in a biological sample and for diagnosis of diseases and conditions which include, but are not limited to, developmental, degenerative and behavioral diseases of the brain such as schizophrenia, Alzheimer's disease, Parkinson's disease, Huntington's disease, transmissible spongiform encephalopathies (TSE), Creutzfeldt-Jakob disease (CJD), specific brain tumors, aphasia, mania, depression, dementia, paranoia, addictive behavior and sleep disorders. Similarly, polypeptides and antibodies directed to these polypeptides would be useful in providing immunological probes for differential identification of the tissue(s) or cell type(s). For a number of disorders of the above tissues or cells, particularly of the brain, expression of this gene at significantly higher or lower levels may be routinely detected in certain tissues or cell types (e.g., CNS, endocrine, cancerous and wounded tissues) or bodily fluids (e.g., lymph, serum, plasma, urine, synovial fluid or cerebrospinal fluid) or another tissue or cell sample taken from an individual having such a disorder, relative to the standard gene expression level, i.e., the expression level in healthy tissue or bodily fluid from an individual not having the disorder. Preferred polypeptides of the present invention comprise, or alternatively consist of the immunogenic epitopes shown in SEQ ID NO: 206 as residues: Gly-45 to Thr-50. Polynucleotides encoding said polypeptides are encompassed by the invention, as are antibodies that bind one or more of these peptides.

The tissue distribution in brain indicates polynucleotides and polypeptides corresponding to this gene would be useful for the detection, treatment, and/or prevention of neurodegenerative disease states, behavioral disorders, or inflammatory conditions. Representative uses are described in the "Regeneration" and "Hyperproliferative Disorders" sections below, in Example 11, 15, and 18, and elsewhere herein. Briefly, the uses include, but are not limited to the detection, treatment, and/or prevention of Alzheimer's Disease, Parkinson's Disease, Huntington's Disease, Tourette Syndrome, meningitis, encephalitis, demyelinating diseases, peripheral neuropathies, neoplasia, trauma, congenital malformations, spinal cord injuries, ischemia and infarction, aneurysms, hemorrhages, schizophrenia, mania, dementia, paranoia, obsessive compulsive disorder, depression, panic disorder, learning disabilities, ALS, psychoses, autism, and altered behaviors, including disorders in feeding, sleep patterns, balance, and perception. In addition, elevated expression of this gene product in regions of the brain indicates that polynucleotides and polypeptides of the invention may play a role in normal neural function. Potentially, polynucleotides and polypeptides of the invention are involved in synapse formation, neurotransmission, learning, cognition, homeostasis, or neuronal differentiation or survival. Moreover, the expression within fetal tissue and other cellular sources marked by proliferating cells indicates that polynucleotides and polypeptides of the invention may play a role in the regulation of cellular division, and may show utility in the diagnosis, treatment, and/or prevention of developmental diseases and disorders, including cancer, and other proliferative conditions. Representative uses are described in the "Hyperproliferative Disorders" and "Regeneration" sections below and elsewhere herein. Briefly, developmental tissues rely on decisions involving cell differentiation and/or apoptosis in pattern formation. Dysregulation of apoptosis can result in inappropriate suppression of cell death, as occurs in the development of some cancers, or in failure to control the extent of cell death, as is believed to occur in acquired immunodeficiency and certain degenerative disorders, such as spinal muscular atrophy (SMA). Alternatively, polynucleotides and polypeptides of the invention may be involved in the pattern of cellular proliferation that accompanies early embryogenesis. Thus, aberrant expression of this gene product in tissues—particularly adult tissues—may correlate with patterns of abnormal cellular proliferation, such as found in various cancers. Because of potential roles in proliferation and differentiation, polynucleotides and polypeptides of the invention may have applications in the adult for tissue regeneration and the treatment of cancers. It may also act as a morphogen to control cell and tissue type specification. Therefore, the polynucleotides and polypeptides of the present invention would be useful in treating, detecting, and/or preventing said disorders and conditions, in addition to other types of degenerative conditions. Thus polynucleotides and polypeptides of the invention may modulate apoptosis or tissue differentiation and would be useful in the detection, treatment, and/or prevention of degenerative or proliferative conditions and diseases. Polynucleotides and polypeptides of the invention would be useful in modulating the immune response to aberrant polypeptides, as may exist in proliferating and cancerous cells and tissues. The protein can also be used to gain new insight into the regulation of cellular growth and proliferation. Furthermore, the protein may also be used to determine biological activity, to raise antibodies, as tissue markers, to isolate cognate ligands or receptors, to identify agents that modulate their interactions, in addition to its use as a nutritional supplement. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:99 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a-b, where a is any integer between 1 to 601 of SEQ ID NO:99, b is an integer of 15 to 615, where both a and b correspond to the positions of nucleotide residues shown in SEQ ID NO:99, and where b is greater than or equal to a +14.

Features of Protein Encoded by Gene No: 90

The gene encoding the disclosed cDNA is believed to reside on chromosome 3. Accordingly, polynucleotides related to this invention would be useful as a marker in linkage analysis for chromosome 3.

This gene is expressed primarily in brain tissue, kidney, tonsils, bone marrow, colon, testes, ovary tumor, and to a lesser extent many other tissues.

Polynucleotides and polypeptides of the invention would be useful as reagents for differential identification of the tissue(s) or cell type(s) present in a biological sample and for diagnosis of diseases and conditions which include, but are not limited to, neurological and behavioural disorders. Similarly, polypeptides and antibodies directed to these polypeptides would be useful in providing immunological probes for differential identification of the tissue(s) or cell type(s). For a number of disorders of the above tissues or cells, particularly of the central nervous system, expression of this gene at significantly higher or lower levels may be routinely detected in certain tissues or cell types (e.g., CNS, cancerous and wounded tissues) or bodily fluids (e.g., lymph, serum, plasma, urine, synovial fluid or cerebrospinal fluid) or another tissue or cell sample taken from an individual having such a disorder, relative to the standard gene expression level, i.e., the expression level in healthy tissue or bodily fluid from an individual not having the disorder.

The tissue distribution in brain indicates that polynucleotides and polypeptides corresponding to this gene would be useful for the detection, treatment, and/or prevention of neurodegenerative disease states, behavioral disorders, or inflammatory conditions. Representative uses are described in the "Regeneration" and "Hyperproliferative Disorders" sections below, in Example 11, 15, and 18, and elsewhere herein. Briefly, the uses include, but are not limited to the detection, treatment, and/or prevention of Alzheimer's Disease, Parkinson's Disease, Huntington's Disease, Tourette Syndrome, meningitis, encephalitis, demyelinating diseases, peripheral neuropathies, neoplasia, trauma, congenital malformations, spinal cord injuries, ischemia and infarction, aneurysms, hemorrhages, schizophrenia, mania, dementia, paranoia, obsessive compulsive disorder, depression, panic disorder, learning disabilities, ALS, psychoses, autism, and altered behaviors, including disorders in feeding, sleep patterns, balance, and perception. In addition, elevated expression of this gene product in regions of the brain indicates it plays a role in normal neural function. Potentially, polynucleotides and polypeptides of the invention are involved in synapse formation, neurotransmission, learning, cognition, homeostasis, or neuronal differentiation or survival. The tissue distribution in bone marrow and other immune tissues indicates that polynucleotides and polypeptides corresponding to this gene would be useful for the diagnosis and treatment of a variety of immune system disorders. Representative uses are described in the "Immune Activity" and "Infectious Disease" sections below, in Example 11, 13, 14, 16, 18, 19, 20, and 27, and elsewhere herein. Briefly, the expression indicates a role in regulating the proliferation; survival; differentiation; and/or activation of hematopoietic cell lineages, including blood stem cells. Involvement in the regulation of cytokine production, antigen presentation, or other processes indicates a usefulness for treatment of cancer (e.g., by boosting immune responses). Expression in cells of lymphoid origin, indicates the natural gene product would be involved in immune functions. Therefore polynucleotides and polypeptides of the invention would also be useful as an agent for immunological disorders including arthritis, asthma, immunodeficiency diseases such as AIDS, leukemia, rheumatoid arthritis, granulomatous disease, inflammatory bowel disease, sepsis, acne, neutropenia, neutrophilia, psoriasis, hypersensitivities, such as T-cell mediated cytotoxicity; immune reactions to transplanted organs and tissues, such as host-versus-graft and graft-versus-host diseases, or autoimmunity disorders, such as autoimmune infertility, lense tissue injury, demyelination, systemic lupus erythematosis, drug induced hemolytic anemia, rheumatoid arthritis, Sjogren's disease, and scleroderma. Moreover, the protein may represent a secreted factor that influences the differentiation or behavior of other blood cells, or that recruits hematopoietic cells to sites of injury. Thus, this gene product is thought to be useful in the expansion of stem cells and committed progenitors of various blood lineages, and in the differentiation and/or proliferation of various cell types. Furthermore, the protein may also be used to determine biological activity, to raise antibodies, as tissue markers, to isolate cognate ligands or receptors, to identify agents that modulate their interactions, in addition to its use as a nutritional supplement. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:100 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a-b, where a is any integer between 1 to 1610 of SEQ ID NO:100, b is an integer of 15 to 1624, where both a and b correspond to the positions of nucleotide residues shown in SEQ ID NO:100, and where b is greater than or equal to a +14.

Features of Protein Encoded by Gene No: 91

In specific embodiments, polypeptides of the invention comprise, or alternatively consist of, the following amino acid sequence: PVIWPDGKRIVLLAEVS (SEQ ID NO: 447). Moreover, fragments and variants of these polypeptides (such as, for example, fragments as described herein, polypeptides at least 80%, 85%, 90%, 95%, 96%, 97%, 98%, 99%, or 100% identical to these polypeptides, or polypeptides encoded by a polynucleotide which hybridizes, under stringent conditions, to the polynucleotide encoding these polypeptides) are encompassed by the invention. Antibodies that bind polypeptides of the invention and polynucleotides encoding these polypeptides are also encompassed by the invention.

This gene is expressed primarily in adrenal gland tumor.

Polynucleotides and polypeptides of the invention would be useful as reagents for differential identification of the tissue(s) or cell type(s) present in a biological sample and for diagnosis of diseases and conditions which include, but are not limited to, adrenal gland cancer. Similarly, polypeptides and antibodies directed to these polypeptides would be useful in providing immunological probes for differential identification of the tissue(s) or cell type(s). For a number of disorders of the above tissues or cells, particularly of the adrenal system, expression of this gene at significantly higher or lower levels may be routinely detected in certain tissues or cell types (e.g., adrenal gland, cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder. Preferred polypeptides of the present invention comprise, or alternatively consist of the immunogenic epitopes shown in SEQ ID NO: 208 as residues: Arg-49 to Gln-56. Polynucleotides encoding said polypeptides are encompassed by the invention, as are antibodies that bind one or more of these peptides.

The tissue distribution in adrenal gland indicates that polynucleotides and polypeptides corresponding to this gene would be useful for the diagnosis, detection, prevention and/or treatment of disorders involving the adrenal gland. Expression of this gene product in adrenal gland tumor indicates that polynucleotides and polypeptides of the invention may play a role in the proliferation of cells of the adrenal gland, or potentially in the proliferation of cells in general. In such an event, it may play a role in determining the course and severity of cancer. Alternatively, polynucleotides and polypeptides of the invention may play a role in the normal function of adrenal glands, such as in the production of corticosteroids, androgens, or epinephrines. Thus polynucleotides and polypeptides of the invention may play a role in general homeostasis, as well as in disorders involving the androgen hormones. Furthermore, the protein may also be used to determine biological activity, to raise antibodies, as tissue markers, to isolate cognate ligands or receptors, to identify agents that modulate their interactions, in addition to its use as a nutritional supplement. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:101 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a-b, where a is any integer between 1 to 1742 of SEQ ID NO:101, b is an integer of 15 to 1756, where both a and b correspond to the positions of nucleotide residues shown in SEQ ID NO:101, and where b is greater than or equal to a +14.

Features of Protein Encoded by Gene No: 92

The gene encoding the disclosed cDNA is thought to reside on chromosome 2. Accordingly, polynucleotides related to this invention would be useful as a marker in linkage analysis for chromosome 2.

This gene is expressed in multiple tissues, including the thymus, and cell types, including B cells and monocytes.

Polynucleotides and polypeptides of the invention would be useful as reagents for differential identification of the tissue(s) or cell type(s) present in a biological sample and for diagnosis of diseases and conditions which include, but are not limited to, disorders and/or disorders afflicting the immune system, such as AIDS and autoimmune diseases.

Similarly, polypeptides and antibodies directed to these polypeptides would be useful in providing immunological probes for differential identification of the tissue(s) or cell type(s). For a number of disorders of the above tissues or cells, particularly of the immune system, expression of this gene at significantly higher or lower levels may be routinely detected in certain tissues or cell types (e.g., immune, cancerous and wounded tissues) or bodily fluids (e.g., lymph, serum, plasma, urine, synovial fluid and spinal fluid) taken from an individual having such a disorder, relative to the standard gene expression level, i.e., the expression level in healthy tissue or bodily fluid from an individual not having the disorder.

The tissue distribution in immune system tissues and cells indicates that polynucleotides and polypeptides corresponding to this gene would be useful for the diagnosis, detection, prevention and/or treatment of disorders affecting the immune system, especially autoimmune diseases and AIDS. Representative uses are described in the "Immune Activity" and "Infectious Disease" sections below, in Example 11, 13, 14, 16, 18, 19, 20, and 27, and elsewhere herein. Briefly, polynucleotides and polypeptides of the invention may be involved in the regulation of cytokine production, antigen presentation, or other processes that may also suggest a usefulness in the treatment of cancer (e.g., by boosting immune responses). Since the gene is expressed in cells of lymphoid origin, the gene or protein, as well as, antibodies directed against the protein may show utility as a tumor marker and/or immunotherapy targets for the above listed tissues. Therefore polynucleotides and polypeptides of the invention may be also used as an agent for immunological disorders including arthritis, asthma, immune deficiency diseases such as AIDS, leukemia, rheumatoid arthritis, inflammatory bowel disease, sepsis, acne, and psoriasis. In addition, this gene product may have commercial utility in the expansion of stem cells and committed progenitors of various blood lineages, and in the differentiation and/or proliferation of various cell types. Furthermore, the protein may also be used to determine biological activity, to raise antibodies, as tissue markers, to isolate cognate ligands or receptors, to identify agents that modulate their interactions, in addition to its use as a nutritional supplement. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:102 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a-b, where a is any integer between 1 to 1402 of SEQ ID NO:102, b is an integer of 15 to 1416, where both a and b correspond to the positions of nucleotide residues shown in SEQ ID NO:102, and where b is greater than or equal to a +14.

Features of Protein Encoded by Gene No: 93

The translated product of this gene shares some homology with an X-linked retinopathy protein (see, e.g., Genbank Accession No. AAB26149.1 and Wong, P., et al., Genomics 15(3):467-71 (1993); all references available through this accession and citation are hereby incorporated herein by reference).

In specific embodiments, polypeptides of the invention comprise, or alternatively consist of, an amino acid sequence selected from the group: FYYFWRQGGSCFVQTGVQWCDHGSLQL (SEQ ID NO: 448) and TPGRQSKTPS (SEQ ID NO: 449). Moreover, fragments and variants of these polypeptides (such as, for example, fragments as described herein, polypeptides at least 80%, 85%, 90%, 95%, 96%, 97%, 98%, 99%, or 100% identical to these polypeptides, or polypeptides encoded by a polynucleotide which hybridizes, under stringent conditions, to the polynucleotide encoding these polypeptides) are encompassed by the invention. Antibodies that bind polypeptides of the invention and polynucleotides encoding these polypeptides are also encompassed by the invention.

The translated product of this gene also shares some homology with a Human histiocyte-secreted factor (HSF) protein (see, e.g., GenSeq Accession No. R96800; all references available through this accession are hereby incorporated herein by reference).

In specific embodiments, polypeptides of the invention comprise, or alternatively consist of, the following amino acid sequence: YFIIFGDREGLALFRLECSGVIMAHCNFELLGDR (SEQ ID NO: 450). Moreover, fragments and variants of these polypeptides (such as, for example, fragments as described herein, polypeptides at least 80%, 85%, 90%, 95%, 96%, 97%, 98%, 99%, or 100% identical to these polypeptides, or polypeptides encoded by a polynucleotide which hybridizes, under stringent conditions, to the polynucleotide encoding these polypeptides) are encompassed by the invention. Antibodies that bind polypeptides of the invention and polynucleotides encoding these polypeptides are also encompassed by the invention.

This gene is expressed primarily in fetal lung tissue.

Polynucleotides and polypeptides of the invention would be useful as reagents for differential identification of the tissue(s) or cell type(s) present in a biological sample and for diagnosis of diseases and conditions which include, but are not limited to ocular, immune, and lung diseases and/or disorders. Similarly, polypeptides and antibodies directed to these polypeptides would be useful in providing immunological probes for differential identification of the tissue(s) or cell type(s). For a number of disorders of the above tissues or cells, particularly of the eye (especially retina), immune system, and lung, expression of this gene at significantly higher or lower levels may be routinely detected in certain tissues or cell types (e.g., retina, blood, pulmonary, cancerous and wounded tissues) or bodily fluids (e.g., lymph, serum, plasma, urine, sputum, pulmonary surfactant, synovial fluid and spinal fluid) or another tissue or cell sample taken from an individual having such a disorder, relative to the standard gene expression level, i.e., the expression level in healthy tissue or bodily fluid from an individual not having the disorder. Preferred polypeptides of the present invention comprise, or alternatively consist of the immunogenic epitopes shown in SEQ ID NO: 210 as residues: Leu-32 to His-38. Polynucleotides encoding said polypeptides are encompassed by the invention, as are antibodies that bind one or more of these peptides.

The tissue distribution in fetal lung tissue indicates that polynucleotides and polypeptides corresponding to this gene would be useful for the detection, diagnosis, prevention and/or treatment of lung diseases and/or disorders. Representative uses are described elsewhere herein. Furthermore, the tissue distribution indicates that polynucleotides and polypeptides corresponding to this gene would be useful for the detection and treatment of disorders associated with developing lungs, particularly in premature infants where the lungs are the last tissues to develop. The tissue distribution indicates that polynucleotides and polypeptides corresponding to this gene would be useful for the diagnosis and intervention of lung tumors, since the gene may be involved in the regulation of cell division, particularly since it is expressed in fetal tissue. Furthermore, the protein may also be used to determine biological activity, to raise antibodies, as tissue markers, to isolate cognate ligands or receptors, to identify agents that modulate their interactions, in addition to its use as a nutritional supplement. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:103 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a-b, where a is any integer between 1 to 690 of SEQ ID NO:103, b is an integer of 15 to 704, where both a and b correspond to the positions of nucleotide residues shown in SEQ ID NO:103, and where b is greater than or equal to a +14.

Features of Protein Encoded by Gene No: 94

The translated product of this gene shares some homology with peripheral benzodiazepine receptor interacting protein (see Genbank Accession No. AAD11957.1; all references available through this accession are hereby incorporated herein by reference).

In specific embodiments, polypeptides of the invention comprise, or alternatively consist of, an amino acid sequence selected from the group: CFLSVSFQWN (SEQ ID NO: 451), VTIAQVGIFVCFVHCCT (SEQ ID NO: 452), PGQVPSKHLGSNASVRA (SEQ ID NO: 453), DEGAKVQRRPWGSQTHSPVLFL (SEQ ID NO: 454), LTRPGLWGSLLPVQQQRG (SEQ ID NO: 455), CASLGVLRANRSPCV (SEQ ID NO: 456), SWLEVTTLSAPGPVITTY (SEQ ID NO: 457), PGQWVREIXLVGRAVARV (SEQ ID NO: 458), LTWPPXGPMGTVWPGF (SEQ ID NO: 459), MADIPGTFLALGCHGQR (SEQ ID NO: 460), VGRGSWASGWTNQSA (SEQ ID NO: 461), PDHPLPVGLLEAWRVE (SEQ ID NO: 462) and/or WGSQTHSPVLFLLTRPGLWGSLLPVQQQRGCASLGVLRANRSPCVSWLEVTT LSAPGPVITTYPGQWVREIXLVGRAVARVLTWPPXGPMGTVWPGFMADIPGT FLALGCHGQRVGRGSWASGWTNQ-SAFPAGPPDHPLPV (SEQ ID NO: 463). Moreover, fragments and variants of these polypeptides (such as, for example, fragments as described herein, polypeptides at least 80%, 85%, 90%, 95%, 96%, 97%, 98%, 99%, or 100% identical to these polypeptides, or polypeptides encoded by a polynucleotide which hybridizes, under stringent conditions, to the polynucleotide encoding these polypeptides) are encompassed by the invention. Antibodies that bind polypeptides of the invention and polynucleotides encoding these polypeptides are also encompassed by the invention.

This gene is expressed primarily neutrophils and eosinophils, and, to a lesser extent, in bone marrow and fetal liver/spleen tissue.

Polynucleotides and polypeptides of the invention would be useful as reagents for differential identification of the tissue(s) or cell type(s) present in a biological sample and for diagnosis of diseases and conditions which include, but are not limited to, asthma and diseases and/or disorders afflicting the immune system. Similarly, polypeptides and antibodies directed to these polypeptides would be useful in providing immunological probes for differential identification of the tissue(s) or cell type(s). For a number of disorders of the above tissues or cells, particularly of the immune system, expression of this gene at significantly higher or lower levels may be routinely detected in certain tissues or cell types (e.g., immune, cancerous and wounded tissues) or bodily fluids (e.g., lymph, serum, plasma, urine, synovial fluid and spinal fluid) taken from an individual having such a disorder, relative to the standard gene expression level, i.e., the expression level in healthy tissue or bodily fluid from an individual not having the disorder. Preferred polypeptides of the present invention comprise, or alternatively consist of the immunogenic epitopes shown in SEQ ID NO: 211 as residues: Ser-2 to Trp-7. Polynucleotides encoding said polypeptides are encompassed by the invention, as are antibodies that bind one or more of these peptides.

The tissue distribution in immune system cells and tissues indicates that polynucleotides and polypeptides corresponding to this gene would be useful for the diagnosis, detection, prevention and/or treatment of asthma or other disorders affecting the immune system. Representative uses are described in the "Immune Activity" and "Infectious Disease" sections below, in Example 11, 13, 14, 16, 18, 19, 20, and 27, and elsewhere herein. Briefly, polynucleotides and polypeptides of the invention may be involved in the regulation of cytokine production, antigen presentation, or other processes that may also suggest a usefulness in the treatment of cancer (e.g., by boosting immune responses). Since the gene is expressed in cells of lymphoid origin, the gene or protein, as well as, antibodies directed against the protein may show utility as a tumor marker and/or immunotherapy targets for the above listed tissues. Therefore polynucleotides and polypeptides of the invention may be also used as an agent for immunological disorders including arthritis, asthma, immune deficiency diseases such as AIDS, leukemia, rheumatoid arthritis, inflammatory bowel disease, sepsis, acne, and psoriasis. In addition, polynucleotides and polypeptides of the invention may have commercial utility in the expansion of stem cells and committed progenitors of various blood lineages, and in the differentiation and/or proliferation of various cell types. Furthermore, the protein may also be used to determine biological activity, to raise antibodies, as tissue markers, to isolate cognate ligands or receptors, to identify agents that modulate their interactions, in addition to its use as a nutritional supplement. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:104 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a-b, where a is any integer between 1 to 1245 of SEQ ID NO:104, b is an integer of 15 to 1259, where both a and b correspond to the positions of nucleotide residues shown in SEQ ID NO:104, and where b is greater than or equal to a +14.

Features of Protein Encoded by Gene No: 95

This gene shares sequence homology to the rat cornichon-like protein (see, e.g., Genbank Accession No. 2317276), the murine cornichon protein (see, e.g., Genbank Accession No. gi|2460430), and the human cornichon protein (see, e.g., Genbank Accession No. gi|4063709). All references available through these accessions are hereby incorporated by reference herein. The *Drosophila* cornichon gene is thought to be involved in signaling processes necessary for both anterior-posterior and dorsal-ventral pattern formation in *Drosophila*. Thus, it is likely that this gene plays a similar role in human development.

The gene encoding the disclosed cDNA is thought to reside on chromosome 1. Accordingly, polynucleotides related to this invention would be useful as a marker in linkage analysis for chromosome 1.

This gene is expressed primarily in endometrial tumor tissue and infant brain tissue, and, to a lesser extent, in frontal cortex tissue.

Polynucleotides and polypeptides of the invention would be useful as reagents for differential identification of the tissue(s) or cell type(s) present in a biological sample and for diagnosis of diseases and conditions which include, but are not limited to, endometrial tumor, and neural and developmental diseases and/or disorders. Similarly, polypeptides and antibodies directed to these polypeptides would be useful in providing immunological probes for differential identification of the tissue(s) or cell type(s). For a number of disorders of the above tissues or cells, particularly of the neural and reproductive organs, expression of this gene at significantly higher or lower levels may be routinely detected in certain tissues or cell types (e.g., neural, reproductive, cancerous and wounded tissues) or bodily fluids (e.g., lymph, serum, plasma, urine, amniotic fluid, synovial fluid and spinal fluid) or another tissue or cell sample taken from an individual having such a disorder, relative to the standard gene expression level, i.e., the expression level in healthy tissue or bodily fluid from an individual not having the disorder. Preferred polypeptides of the present invention comprise, or alternatively consist of the immunogenic epitopes shown in SEQ ID NO: 212 as residues: Glu-33 to Phe-38. Polynucleotides encoding said polypeptides are encompassed by the invention, as are antibodies that bind one or more of these peptides.

The tissue distribution in infant brain tissue and frontal cortex tissue, and the homology to cornichon proteins, indicates that polynucleotides and polypeptides corresponding to this gene would be useful for detecting, diagnosing, preventing and/or treating neural and developmental disorders. The tissue distribution indicates that polynucleotides and polypeptides corresponding to this gene would be useful for the detection, diagnosis, prevention and/or treatment of neurodegenerative disease states and behavioural disorders such as Alzheimer's Disease, Parkinson's Disease, Huntington's Disease, Tourette Syndrome, schizophrenia, mania, dementia, paranoia, obsessive compulsive disorder, panic disorder, learning disabilities, ALS, psychoses, autism, and altered behaviors, including disorders in feeding, sleep patterns, balance, and perception. In addition, polynucleotides and polypeptides of the invention may also play a role in the treatment and/or detection of developmental disorders associated with the developing embryo, or sexually-linked disorders. Representative uses are described in the "Regeneration" and "Hyperproliferative Disorders" sections below, in Example 11, 15, and 18, and elsewhere herein. Briefly, the elevated expression of this gene product within the frontal cortex of the brain indicates that polynucleotides and polypeptides of the invention may be involved in neuronal survival; synapse formation; conductance; neural differentiation, etc. Such involvement may impact many processes, such as learning and cognition. Alternatively, the tissue distribution in endometrial tumor tissue indicates that polynucleotides and polypeptides of the invention would be useful for the detection and/or treatment of endometrial tumors and/or reproductive disorders, as well as tumors of other tissues where expression of this gene has been observed. Furthermore, the protein may also be used to determine biological activity, to raise antibodies, as tissue markers, to isolate cognate ligands or receptors, to identify agents that modulate their interactions, in addition to its use as a nutritional supplement. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:105 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a-b, where a is any integer between 1 to 1790 of SEQ ID NO:105, b is an integer of 15 to 1804, where both a and b correspond to the positions of nucleotide residues shown in SEQ ID NO:105, and where b is greater than or equal to a +14.

Features of Protein Encoded by Gene No: 96

The translation product of this gene shares significant sequence homology with a protein which was recently sequenced by another group, which was named paraplegin by this group (see, e.g., Genbank Accession No. g3273089).

The gene encoding the disclosed cDNA is thought to reside on chromosome 16. Accordingly, polynucleotides related to this invention would be useful as a marker in linkage analysis for chromosome 16.

In specific embodiments, polypeptides of the invention comprise, or alternatively consist of, the following amino acid sequence: LARADPPGCRRRGWRPSSAELQLR-LLTPTFEGINGLLLKQHLVQNPVRLWQL LGGTFY-FNTSRLKQKNKE KDKSKGKAPEEDEXER-RRRERDDQ (SEQ ID NO: 464). Moreover, fragments and variants of these polypeptides (such as, for example, fragments as described herein, polypeptides at least 80%, 85%, 90%, 95%, 96%, 97%, 98%, 99%, or 100% identical to these polypeptides, or polypeptides encoded by a polynucleotide which hybridizes, under stringent conditions, to the polynucleotide encoding these polypeptides) are encompassed by the invention. Antibodies that bind polypeptides of the invention and polynucleotides encoding these polypeptides are also encompassed by the invention.

When tested against Jurkat T-cell cell lines, supernatants removed from cells containing this gene activated the GAS assay. Thus, it is likely that this gene activates T-cells, and to a lesser extent other immune cells, through the Jak-STAT signal transduction pathway. The gamma activating sequence (GAS) is a promoter element found upstream of many genes which are involved in the Jak-STAT pathway. The Jak-STAT pathway is a large, signal transduction pathway involved in the differentiation and proliferation of cells. Therefore, activation of the Jak-STAT pathway, reflected by the binding of the GAS element, can be used to indicate proteins involved in the proliferation and differentiation of cells.

This gene is expressed primarily in Jurkat T-cells, Macrophage, T-Cell Lymphoma, tonsils, and salivary glands.

Polynucleotides and polypeptides of the invention would be useful as reagents for differential identification of the tissue(s) or cell type(s) present in a biological sample and for diagnosis of diseases and conditions which include, but are not limited to, T-Cell lymphomas. Similarly, polypeptides and antibodies directed to these polypeptides would be useful in providing immunological probes for differential identification of the tissue(s) or cell type(s). For a number of disorders of the above tissues or cells, particularly of the immune system, expression of this gene at significantly higher or lower levels may be routinely detected in certain tissues or cell types (e.g., immune, hematopoietic, and cancerous and wounded tissues) or bodily fluids (e.g., lymph, serum, plasma, urine, synovial fluid or spinal fluid) or another tissue or cell sample taken from an individual having such a disorder, relative to the standard gene expression level, i.e., the expression level in healthy tissue or bodily fluid from an individual not having the disorder. Preferred polypeptides of the present invention comprise, or alternatively consist of one, two, three, four, five, six or all seven of the immunogenic epitopes shown in SEQ ID NO: 213 as residues: Met-1 to Leu-6, Asp-84 to Lys-89, Asp-124 to Gly-130, Ser-138 to Trp-143, His-145 to Ser-153, Thr-170 to Pro-183, Trp-191 to Pro-198. Polynucleotides encoding said polypeptides are encompassed by the invention, as are antibodies that bind one or more of these peptides.

The tissue distribution in immune tissues and T-cells, in conjunction with the detected GAS biological activity data, indicates that polynucleotides and polypeptides corresponding to this gene would be useful for the detection and/or treatment of T-cell lymphomas. Representative uses are described in the "Immune Activity" and "Infectious Disease" sections below, in Example 11, 13, 14, 16, 18, 19, 20, and 27, and elsewhere herein. Briefly, the expression of this gene product in T cell lymphoma indicates that polynucleotides and polypeptides of the invention may play a role in the proliferation of the lymphoid cell lineages, and may be involved in normal antigen recognition and activation of T cells during the immune process. Furthermore, the protein may also be used to determine biological activity, to raise antibodies, as tissue markers, to isolate cognate ligands or receptors, to identify agents that modulate their interactions, in addition to its use as a nutritional supplement. Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:106 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a-b, where a is any integer between 1 to 957 of SEQ ID NO:106, b is an integer of 15 to 971, where both a and b correspond to the positions of nucleotide residues shown in SEQ ID NO:106, and where b is greater than or equal to a +14.

Features of Protein Encoded by Gene No: 97

In specific embodiments, polypeptides of the invention comprise, or alternatively consist of, the following amino acid sequence: FLRFWCTCHVSS (SEQ ID NO: 465). Moreover, fragments and variants of these polypeptides (such as, for example, fragments as described herein, polypeptides at least 80%, 85%, 90%, 95%, 96%, 97%, 98%, 99%, or 100% identical to these polypeptides, or polypeptides encoded by a polynucleotide which hybridizes, under stringent conditions, to the polynucleotide encoding these polypeptides) are encompassed by the invention. Antibodies that bind polypeptides of the invention and polynucleotides encoding these polypeptides are also encompassed by the invention.

This gene is expressed primarily in bladder, dermal endothelial cells, retina, and dendritic cells.

Polynucleotides and polypeptides of the invention would be useful as reagents for differential identification of the tissue(s) or cell type(s) present in a biological sample and for diagnosis of diseases and conditions which include, but are not limited to, diseases of the bladder, including bladder cancer. Similarly, polypeptides and antibodies directed to these polypeptides would be useful in providing immunological probes for differential identification of the tissue(s) or cell type(s). For a number of disorders of the above tissues or cells, particularly of the urinary system, expression of this gene at significantly higher or lower levels may be routinely detected in certain tissues or cell types (e.g., bladder, cancerous and wounded tissues) or bodily fluids (e.g., lymph, serum, plasma, urine, synovial fluid and spinal fluid) or another tissue or cell sample taken from an individual having such a disorder, relative to the standard gene expression level, i.e., the expression level in healthy tissue or bodily fluid from an individual not having the disorder.

The tissue distribution in bladder indicates that the polynucleotides and polypeptides corresponding to this gene would be useful for treatment, prevention, detection and/or diagnosis of urinary tract disorders (e.g., cystitis, urinary tract calcui, incontinance) and bladder tumors or cancers. The tissue distribution in endothelial cells indicates that polynucleotides and polypeptides corresponding to this gene would be useful for the diagnosis, detection, prevention and/or treatment of disorders involving the vasculature and/or dermal tissue. Elevated expression of this gene product by endothelial cells indicates that it may play vital roles in the regulation of endothelial cell function; secretion; proliferation; or angiogenesis. Alternately, this may represent a gene product expressed by the endothelium and transported to distant sites of action on a variety of target organs. Expression of this gene product by hematopoietic cells also indicates involvement in the proliferation; survival; activation; or differentiation of all blood cell lineages. The tissue distribution in retina indicates that polynucleotides and polypeptides corresponding to this gene would be useful for the treatment, prevention, diagnosis and/or detection of eye disorders including blindness, color blindness, impaired vision, short and long sightedness, retinitis pigmentosa, retinitis proliferans, and retinoblastoma, retinochoroiditis, retinopathy and retinoschisis. Furthermore, the protein may also be used to determine biological activity, to raise antibodies, as tissue markers, to isolate cognate ligands or receptors, to identify agents that modulate their interactions, in addition to its use as a nutritional supplement.

Protein, as well as, antibodies directed against the protein may show utility as a tumor marker and/or immunotherapy targets for the above listed tissues.

Many polynucleotide sequences, such as EST sequences, are publicly available and accessible through sequence databases. Some of these sequences are related to SEQ ID NO:107 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a-b, where a is any integer between 1 to 807 of SEQ ID NO:107, b is an integer of 15 to 821, where both a and b correspond to the positions of nucleotide residues shown in SEQ ID NO:107, and where b is greater than or equal to a +1.

| Gene No. | cDNA Clone ID | ATCC Deposit Nr and Date | Vector | NT SEQ ID NO: X | Total NT Seq. | 5' NT of Clone Seq. | 3' NT of Clone Seq. | 5' NT of Start Codon | 5' NT of First AA of Signal Pep | AA SEQ ID NO: Y | First AA of Sig Pep | Last AA of Sig Pep | First AA of Secreted Portion | Last AA of ORF |
|---|---|---|---|---|---|---|---|---|---|---|---|---|---|---|
| 1 | HKABZ65 | 209683 Mar. 20, 1998 | pCMVSport 2.0 | 11 | 1191 | 1 | 1191 | 69 | 69 | 118 | 1 | 17 | 18 | 243 |
| 2 | HNGIC80 | 209683 Mar. 20, 1998 | Uni-ZAP XR | 12 | 1251 | 1 | 1251 | 24 | 24 | 119 | 1 | 24 | 25 | 41 |
| 3 | HDPUG50 | 209745 Apr. 7, 1998 | pCMVSport 3.0 | 13 | 1734 | 1 | 1734 | 22 | 22 | 120 | 1 | 34 | 35 | 526 |
| 4 | HAEAB66 | 209745 Apr. 7, 1998 | pBluescript SK- | 14 | 1540 | 914 | 1537 | 105 | 105 | 121 | 1 | 30 | 31 | 354 |
| 5 | HHEPF59 | 209746 Apr. 7, 1998 | pCMVSport 3.0 | 15 | 1558 | 1 | 1558 | 38 | 38 | 122 | 1 | 21 | 22 | 63 |
| 6 | HE9BK23 | 209683 Mar. 20, 1998 | Uni-ZAP XR | 16 | 1636 | 1 | 1636 | 39 | 39 | 123 | 1 | 21 | 22 | 309 |
| 7 | HCYBI36 | 209683 Mar. 20, 1998 | pBluescript SK- | 17 | 1256 | 148 | 1256 | 235 | 235 | 124 | 1 | 23 | 24 | 211 |
| 8 | HSSDX51 | 209683 Mar. 20, 1998 | Uni-ZAP XR | 18 | 1143 | 1 | 1143 | 133 | 133 | 125 | 1 | 20 | 21 | 50 |
| 9 | HSDAJ46 | 209746 Apr. 7, 1998 | Uni-ZAP XR | 19 | 1537 | 92 | 1537 | 299 | 299 | 126 | 1 | 18 | 19 | 262 |
| 10 | HRACG45 | 209745 Apr. 7, 1998 | pCMVSport 3.0 | 20 | 2672 | 222 | 2672 | 178 | 178 | 127 | 1 | 42 | 43 | 270 |
| 11 | HAPPW30 | 209683 Mar. 20, 1998 | Uni-ZAP XR | 21 | 1508 | 14 | 1501 | 54 | 54 | 128 | 1 | 22 | 23 | 91 |
| 12 | HE2ES51 | 209745 Apr. 7, 1998 | Uni-ZAP XR | 22 | 1447 | 1 | 1447 | 77 | 77 | 129 | 1 | 14 | 15 | 222 |
| 13 | HAGGJ80 | 209745 Apr. 7, 1998 | Uni-ZAP XR | 23 | 3886 | 1289 | 3886 | 251 | 251 | 130 | 1 | 56 | 57 | 760 |
| 13 | HAGGJ80 | 209745 Apr. 7, 1998 | Uni-ZAP XR | 108 | 1576 | 1 | 1576 | 40 | 40 | 215 | 1 | 34 | 35 | 84 |
| 14 | HTXDW56 | 209746 Apr. 7, 1998 | Uni-ZAP XR | 24 | 1583 | 1 | 1583 | 217 | 217 | 131 | 1 | 22 | 23 | 201 |
| 15 | HEEAG23 | 209745 Apr. 7, 1998 | Uni-ZAP XR | 25 | 1669 | 25 | 1280 | 57 | 57 | 132 | 1 | 18 | 19 | 46 |
| 16 | HDPKI93 | 209745 Apr. 7, 1998 | pCMVSport 3.0 | 26 | 1053 | 1 | 1053 | 46 | 46 | 133 | 1 | 21 | 22 | 305 |
| 17 | HDLAC10 | 209745 Apr. 7, 1998 | pCMVSport 2.0 | 27 | 1477 | 1 | 1477 | 132 | 132 | 134 | 1 | 29 | 30 | 81 |
| 18 | HDPOH06 | 209745 Apr. 7, 1998 | pCMVSport 3.0 | 28 | 2504 | 1 | 2504 | 252 | 252 | 135 | 1 | 29 | 30 | 242 |
| 19 | HCE4G61 | 209745 Apr. 7, 1998 | Uni-ZAP XR | 29 | 1866 | 1 | 1866 | 130 | 130 | 136 | 1 | 23 | 24 | 285 |
| 19 | HCE4G61 | 209745 Apr. 7, 1998 | Uni-ZAP XR | 109 | 1779 | 1 | 1720 | 125 | 125 | 216 | 1 | 20 | 21 | 81 |
| 20 | HCWUI13 | 209745 Apr. 7, 1998 | ZAP Express | 30 | 1501 | 1 | 1501 | 80 | 80 | 137 | 1 | 18 | 19 | 157 |
| 21 | HDPSP01 | 209745 Apr. 7, 1998 | pCMVSport 3.0 | 31 | 1752 | 1 | 1752 | 227 | 227 | 138 | 1 | 20 | 21 | 308 |
| 22 | HHPEN62 | 209746 Apr. 7, 1998 | Uni-ZAP XR | 32 | 2152 | 141 | 2152 | 183 | 183 | 139 | 1 | 27 | 28 | 508 |
| 23 | HUKBT29 | 209746 Apr. 7, 1998 | Lambda ZAP II | 33 | 1757 | 56 | 1757 | 74 | 74 | 140 | 1 | 19 | 20 | 506 |
| 24 | HMAJR50 | 209683 Mar. 20, 1998 | Uni-ZAP XR | 34 | 1466 | 32 | 1466 | 70 | 70 | 141 | 1 | 21 | 22 | 48 |
| 25 | HBIMB51 | 209683 Mar. 20, 1998 | pCMVSport 3.0 | 35 | 526 | 1 | 526 | 93 | 93 | 142 | 1 | 21 | 22 | 130 |
| 26 | HE8DX88 | 209683 Mar. 20, 1998 | Uni-ZAP XR | 36 | 2412 | 1 | 2412 | 256 | 256 | 143 | 1 | 29 | 30 | 43 |
| 27 | HNGHT03 | 209746 Apr. 7, 1998 | Uni-ZAP XR | 37 | 1274 | 65 | 1274 | 305 | 305 | 144 | 1 | 24 | 25 | 91 |
| 28 | HWABU17 | 209745 Apr. 7, 1998 | pCMVSport 3.0 | 38 | 1036 | 1 | 1036 | 202 | 202 | 145 | 1 | 18 | 19 | 266 |

-continued

| Gene No. | cDNA Clone ID | ATCC Deposit Nr and Date | Vector | NT SEQ ID NO: X | Total NT Seq. | 5' NT of Clone Seq. | 3' NT of Clone Seq. | 5' NT of Start Codon | 5' NT of First AA of Signal Pep | AA SEQ ID NO: Y | First AA of Sig Pep | Last AA of Sig Pep | First AA of Secreted Portion | Last AA of ORF |
|---|---|---|---|---|---|---|---|---|---|---|---|---|---|---|
| 29 | HDTAT90 | 209746 Apr. 7, 1998 | pCMVSport 2.0 | 39 | 1379 | 8 | 1379 | 78 | 78 | 146 | 1 | 26 | 27 | 434 |
| 30 | HHFGR93 | 209746 Apr. 7, 1998 | Uni-ZAP XR | 40 | 1932 | 1 | 1836 | 130 | 130 | 147 | 1 | 29 | 30 | 236 |
| 31 | HOVCB25 | 209746 Apr. 7, 1998 | pSport1 | 41 | 1430 | 1 | 1430 | 150 | 150 | 148 | 1 | 18 | 19 | 99 |
| 32 | HSYAV66 | 209746 Apr. 7, 1998 | pCMVSport 3.0 | 42 | 1407 | 1 | 1407 | 186 | 186 | 149 | 1 | 28 | 29 | 69 |
| 33 | HFPCT29 | 209683 Mar. 20, 1998 | Uni-ZAP XR | 43 | 950 | 1 | 950 | 268 | 268 | 150 | 1 | 26 | 27 | 61 |
| 34 | HAWAT25 | 209683 Mar. 20, 1998 | pBluescript SK- | 44 | 1004 | 56 | 1004 | 149 | 149 | 151 | 1 | 32 | 33 | 88 |
| 35 | HNHFR04 | 209683 Mar. 20, 1998 | Uni-ZAP XR | 45 | 1681 | 1 | 1681 | 71 | 71 | 152 | 1 | 21 | 22 | 78 |
| 36 | HOSFT61 | 209683 Mar. 20, 1998 | Uni-ZAP XR | 46 | 1361 | 1 | 1361 | 210 | 210 | 153 | 1 | 21 | 22 | 123 |
| 36 | HOSFT61 | 209683 Mar. 20, 1998 | Uni-ZAP XR | 110 | 1365 | 1 | 1365 | 211 | 211 | 217 | 1 | 21 | 22 | 90 |
| 37 | HBJIO81 | 209683 Mar. 20, 1998 | Uni-ZAP XR | 47 | 1137 | 1 | 1137 | 220 | 220 | 154 | 1 | 23 | 24 | 68 |
| 38 | HADCL55 | 209745 Apr. 7, 1998 | pSport1 | 48 | 2763 | 15 | 2763 | 60 | 60 | 155 | 1 | 29 | 30 | 43 |
| 39 | HAIBO81 | 209745 Apr. 7, 1998 | Uni-ZAP XR | 49 | 1348 | 1 | 1348 | 250 | 250 | 156 | 1 | 18 | 19 | 63 |
| 40 | HBBBC37 | 209745 Apr. 7, 1998 | pCMVSport 1 | 50 | 1264 | 1 | 1264 | 81 | 81 | 157 | 1 | 17 | 18 | 61 |
| 41 | HBJMX85 | 209745 Apr. 7, 1998 | Uni-ZAP XR | 51 | 1660 | 39 | 1660 | 45 | 45 | 158 | 1 | 18 | 19 | 82 |
| 42 | HCEES66 | 209745 Apr. 7, 1998 | Uni-ZAP XR | 52 | 1678 | 1 | 1678 | 178 | 178 | 159 | 1 | 39 | 40 | 46 |
| 43 | HCEMP62 | 209745 Apr. 7, 1998 | Uni-ZAP XR | 53 | 1860 | 269 | 1726 | 352 | 352 | 160 | 1 | 30 | 31 | 187 |
| 43 | HCEMP62 | 209745 Apr. 7, 1998 | Uni-ZAP XR | 111 | 1957 | 582 | 1823 | 19 | 19 | 218 | 1 | 33 | 34 | 335 |
| 44 | HE2FB90 | 209746 Apr. 7, 1998 | Uni-ZAP XR | 54 | 1663 | 1 | 1663 | 205 | 205 | 161 | 1 | 27 | 28 | 113 |
| 45 | HTHDJ94 | 209746 Apr. 7, 1998 | Uni-ZAP XR | 55 | 1632 | 20 | 1632 | 66 | 66 | 162 | 1 | 26 | 27 | 292 |
| 46 | HTOHJ89 | 209746 Apr. 7, 1998 | Uni-ZAP XR | 56 | 2233 | 1 | 2233 | 42 | 42 | 163 | 1 | 17 | 18 | 86 |
| 47 | HUSHB62 | 209745 Apr. 7, 1998 | Lambda ZAP II | 57 | 1963 | 1 | 1760 | 130 | 130 | 164 | 1 | 49 | 50 | 106 |
| 48 | HSXAG02 | 209683 Mar. 20, 1998 | Uni-ZAP XR | 58 | 1267 | 411 | 1243 | 600 | 600 | 165 | 1 | 22 | 23 | 58 |
| 49 | HHTLH52 | 209683 Mar. 20, 1998 | ZAP Express | 59 | 1295 | 1 | 1295 | 218 | 218 | 166 | 1 | 22 | 23 | 40 |
| 50 | HCFMS95 | 209683 Mar. 20, 1998 | pSport1 | 60 | 915 | 1 | 915 | 123 | 123 | 167 | 1 | 22 | 23 | 65 |
| 51 | HOUCT90 | 209683 Mar. 20, 1998 | Uni-ZAP XR | 61 | 1445 | 1 | 1445 | 74 | 74 | 168 | 1 | 30 | 31 | 46 |
| 52 | HCFLR78 | 209745 Apr. 7, 1998 | pSport1 | 62 | 1100 | 224 | 1100 | 475 | 475 | 169 | 1 | 16 | 17 | 140 |
| 53 | HTOHT18 | 209745 Apr. 7, 1998 | Uni-ZAP XR | 63 | 1499 | 267 | 1499 | 433 | 433 | 170 | 1 | 24 | 25 | 53 |
| 54 | HKPMB11 | 209745 Apr. 7, 1998 | pBluescript | 64 | 655 | 1 | 655 | 55 | 55 | 171 | 1 | 25 | 26 | 167 |
| 54 | HKPMB11 | 209745 Apr. 7, 1998 | pBluescript | 112 | 1135 | 490 | 1135 | 350 | 350 | 219 | 1 | 30 | 31 | 229 |
| 55 | HNFHS38 | 209745 Apr. 7, 1998 | Uni-ZAP XR | 65 | 1450 | 1 | 1450 | 172 | 172 | 172 | 1 | 18 | 19 | 325 |
| 55 | HNFHS38 | 209745 Apr. 7, 1998 | Uni-ZAP XR | 113 | 1446 | 1 | 1446 | 171 | 171 | 220 | 1 | 18 | 19 | 62 |
| 56 | HAIBU10 | 209745 Apr. 7, 1998 | Uni-ZAP XR | 66 | 670 | 1 | 669 | 201 | 201 | 173 | 1 | 20 | 21 | 113 |
| 57 | HAPOK30 | 209745 Apr. 7, 1998 | Uni-ZAP XR | 67 | 1692 | 1 | 1692 | 300 | 300 | 174 | 1 | 19 | 20 | 61 |
| 58 | HCEEM18 | 209745 Apr. 7, 1998 | Uni-ZAP XR | 68 | 655 | 18 | 655 | 157 | 157 | 175 | 1 | 30 | 31 | 41 |
| 59 | HCWUA22 | 209745 Apr. 7, 1998 | ZAP Express | 69 | 1618 | 48 | 1618 | 233 | 233 | 176 | 1 | 33 | 34 | 42 |
| 60 | HDSAG91 | 209745 Apr. 7, 1998 | Uni-ZAP XR | 70 | 1802 | 1 | 1802 | 156 | 156 | 177 | 1 | 23 | 24 | 47 |

-continued

| Gene No. | cDNA Clone ID | ATCC Deposit Nr and Date | Vector | NT SEQ ID NO: X | Total NT Seq. | 5' NT of Clone Seq. | 3' NT of Clone Seq. | 5' NT of Start Codon | 5' NT of First AA of Signal Pep | AA SEQ ID NO: Y | First AA of Sig Pep | Last AA of Sig Pep | First AA of Secreted Portion | Last AA of ORF |
|---|---|---|---|---|---|---|---|---|---|---|---|---|---|---|
| 61 | HNEDJ35 | 209746 Apr. 7, 1998 | Uni-ZAP XR | 71 | 1292 | 1 | 1292 | 71 | 71 | 178 | 1 | 36 | 37 | 50 |
| 62 | H7TBA62 | 209745 Apr. 7, 1998 | PCRII | 72 | 883 | 1 | 807 | 199 | 199 | 179 | 1 | 65 | 66 | 227 |
| 62 | H7TBA62 | 209745 Apr. 7, 1998 | PCRII | 114 | 733 | 9 | 718 | 224 | 224 | 221 | 1 | 36 | 37 | 170 |
| 63 | HNGIO50 | 209746 Apr. 7, 1998 | Uni-ZAP XR | 73 | 785 | 1 | 785 | 132 | 132 | 180 | 1 | 27 | 28 | 44 |
| 64 | HMIAW81 | 209683 Mar. 20, 1998 | Uni-ZAP XR | 74 | 2341 | 1 | 2215 | 229 | 229 | 181 | 1 | 17 | 18 | 46 |
| 65 | HMMCJ60 | 209683 Mar. 20, 1998 | pSport1 | 75 | 1882 | 1 | 1882 | 132 | 132 | 182 | 1 | 16 | 17 | 41 |
| 66 | HDPIO09 | 209745 Apr. 7, 1998 | pCMVSport 3.0 | 76 | 2892 | 17 | 2892 | 85 | 85 | 183 | 1 | 36 | 37 | 47 |
| 67 | HHFHH34 | 209745 Apr. 7, 1998 | Uni-ZAP XR | 77 | 1673 | 1 | 1673 | 16 | 16 | 184 | 1 | 22 | 23 | 70 |
| 68 | HISCL83 | 209745 Apr. 7, 1998 | pSport1 | 78 | 1461 | 1 | 1461 | 259 | 259 | 185 | 1 | 21 | 22 | 41 |
| 69 | HTOAI70 | 209746 Apr. 7, 1998 | Uni-ZAP XR | 79 | 1517 | 1 | 1517 | 190 | 190 | 186 | 1 | 19 | 20 | 92 |
| 69 | HTOAI70 | 209746 Apr. 7, 1998 | Uni-ZAP XR | 115 | 1518 | 1 | 1518 | 190 | 190 | 222 | 1 | 19 | 20 | 42 |
| 70 | HSDER95 | 209683 Mar. 20, 1998 | Uni-ZAP XR | 80 | 574 | 1 | 574 | 72 | 72 | 187 | 1 | 25 | 26 | 71 |
| 71 | HNECL25 | 209683 Mar. 20, 1998 | Uni-ZAP XR | 81 | 1455 | 1 | 1455 | 322 | 322 | 188 | 1 | 32 | 33 | 66 |
| 72 | HNFGZ45 | 209683 Mar. 20, 1998 | Uni-ZAP XR | 82 | 1640 | 1 | 1640 | 450 | 450 | 189 | 1 | 38 | 39 | 70 |
| 73 | HHGCU49 | 209745 Apr. 7, 1998 | Lambda ZAP II | 83 | 525 | 1 | 525 | 173 | 173 | 190 | 1 | 23 | 24 | 40 |
| 74 | HDPND68 | 209745 Apr. 7, 1998 | pCMVSport 3.0 | 84 | 837 | 1 | 837 | 154 | 154 | 191 | 1 | 17 | 18 | 66 |
| 75 | HETDT81 | 209746 Apr. 7, 1998 | Uni-ZAP XR | 85 | 1574 | 1 | 1574 | 189 | 189 | 192 | 1 | 25 | 26 | 66 |
| 76 | HHLBA14 | 209746 Apr. 7, 1998 | pBluescript SK- | 86 | 1628 | 353 | 1627 | 546 | 546 | 193 | 1 | 24 | 25 | 48 |
| 77 | HLTBU43 | 209746 Apr. 7, 1998 | Uni-ZAP XR | 87 | 1795 | 1 | 1795 | 198 | 198 | 194 | 1 | 19 | 20 | 66 |
| 78 | HNTSJ84 | 209746 Apr. 7, 1998 | pSport1 | 88 | 1864 | 239 | 1864 | 336 | 336 | 195 | 1 | 22 | 23 | 57 |
| 79 | HOHCG16 | 209746 Apr. 7, 1998 | pCMVSport 2.0 | 89 | 1983 | 1 | 1983 | 257 | 257 | 196 | 1 | 18 | 19 | 52 |
| 80 | HTHCB31 | 209746 Apr. 7, 1998 | Uni-ZAP XR | 90 | 1957 | 1 | 1957 | 46 | 46 | 197 | 1 | 17 | 18 | 43 |
| 81 | HUKAM16 | 209746 Apr. 7, 1998 | Lambda ZAP II | 91 | 573 | 1 | 573 | 178 | 178 | 198 | 1 | 23 | 24 | 52 |
| 82 | HLDOJ66 | 209683 Mar. 20, 1998 | pCMVSport 3.0 | 92 | 1212 | 1 | 1212 | 313 | 313 | 199 | 1 | 20 | 21 | 40 |
| 83 | HTXKF10 | 209683 Mar. 20, 1998 | Uni-ZAP XR | 93 | 1144 | 1 | 1144 | 334 | 334 | 200 | 1 | 32 | 33 | 71 |
| 84 | HPMAI22 | 209683 Mar. 20, 1998 | Uni-ZAP XR | 94 | 1274 | 334 | 1274 | 483 | 483 | 201 | 1 | 16 | 17 | 59 |
| 85 | HL2AG57 | 209746 Apr. 7, 1998 | Uni-ZAP XR | 95 | 1780 | 349 | 1780 | 560 | 560 | 202 | 1 | 31 | 32 | 80 |
| 86 | HTHBH29 | 209746 Apr. 7, 1998 | Uni-ZAP XR | 96 | 1794 | 1223 | 1431 | 93 | 93 | 203 | 1 | 30 | 31 | 70 |
| 86 | HTHBH29 | 209746 Apr. 7, 1998 | Uni-ZAP XR | 116 | 1054 | 1 | 1054 | 52 | 52 | 223 | 1 | 24 | 25 | 56 |
| 87 | HUSAM59 | 209683 Mar. 20, 1998 | Lambda ZAP II | 97 | 2065 | 1 | 2065 | 475 | 475 | 204 | 1 | 17 | 18 | 78 |
| 88 | HNGGR26 | 209745 Apr. 7, 1998 | Uni-ZAP XR | 98 | 1154 | 1 | 1154 | 50 | 50 | 205 | 1 | 27 | 28 | 115 |
| 89 | HTLCX30 | 209683 Mar. 20, 1998 | Uni-ZAP XR | 99 | 615 | 1 | 459 | 60 | 60 | 206 | 1 | 28 | 29 | 50 |
| 90 | HCEBC87 | 209683 Mar. 20, 1998 | Uni-ZAP XR | 100 | 1624 | 243 | 1624 | 517 | 517 | 207 | 1 | 23 | 24 | 57 |
| 91 | HATCB92 | 209683 Mar. 20, 1998 | Uni-ZAP XR | 101 | 1756 | 1 | 1756 | 247 | 247 | 208 | 1 | 40 | 41 | 56 |
| 92 | HMSCX69 | 209746 Apr. 7, 1998 | Uni-ZAP XR | 102 | 1416 | 207 | 1416 | 246 | 246 | 209 | 1 | 16 | 17 | 49 |
| 93 | HLHAL68 | 209746 Apr. 7, 1998 | Uni-ZAP XR | 103 | 704 | 1 | 704 | 30 | 30 | 210 | 1 | 21 | 22 | 44 |

-continued

| Gene No. | cDNA Clone ID | ATCC Deposit Nr and Date | Vector | NT SEQ ID NO: X | Total NT Seq. | 5' NT of Clone Seq. | 3' NT of Clone Seq. | 5' NT of Start Codon | 5' NT of First AA of Signal Pep | AA SEQ ID NO: Y | First AA of Sig Pep | Last AA of Sig Pep | First AA of Secreted Portion | Last AA of ORF |
|---|---|---|---|---|---|---|---|---|---|---|---|---|---|---|
| 94 | HEOMR73 | 209746 Apr. 7, 1998 | pSport1 | 104 | 1259 | 644 | 1259 | 354 | 354 | 211 | 1 | 24 | 25 | 44 |
| 95 | HETIB83 | 209746 Apr. 7, 1998 | Uni-ZAP XR | 105 | 1804 | 1 | 1804 | 104 | 104 | 212 | 1 | 30 | 31 | 160 |
| 96 | HJPDD28 | 209746 Apr. 7, 1998 | Uni-ZAP XR | 106 | 971 | 260 | 971 | 283 | 283 | 213 | 1 | 21 | 22 | 198 |
| 96 | HJPDD28 | 209746 Apr. 7, 1998 | Uni-ZAP XR | 117 | 921 | 1 | 921 | 31 | 31 | 224 | 1 | 21 | 22 | 96 |
| 97 | HBAMB15 | 209683 Mar. 20, 1998 | pSport1 | 107 | 821 | 330 | 821 | 390 | 390 | 214 | 1 | 19 | 20 | 59 |

Table 1 summarizes the information corresponding to each "Gene No." described above. The nucleotide sequence identified as "NT SEQ ID NO:X" was assembled from partially homologous ("overlapping") sequences obtained from the "cDNA clone ID" identified in Table 1 and, in some cases, from additional related DNA clones. The overlapping sequences were assembled into a single contiguous sequence of high redundancy (usually three to five overlapping sequences at each nucleotide position), resulting in a final sequence identified as SEQ ID NO:X.

The cDNA Clone ID was deposited on the date and given the corresponding deposit number listed in "ATCC Deposit No:Z and Date." Some of the deposits contain multiple different clones corresponding to the same gene. "Vector" refers to the type of vector contained in the cDNA Clone ID.

"Total NT Seq." refers to the total number of nucleotides in the contig identified by "Gene No." The deposited clone may contain all or most of these sequences, reflected by the nucleotide position indicated as "5' NT of Clone Seq." and the "3' NT of Clone Seq." of SEQ ID NO:X. The nucleotide position of SEQ ID NO:X of the putative start codon (methionine) is identified as "5' NT of Start Codon." Similarly, the nucleotide position of SEQ ID NO:X of the predicted signal sequence is identified as "5' NT of First AA of Signal Pep."

The translated amino acid sequence, beginning with the methionine, is identified as "AA SEQ ID NO:Y," although other reading frames can also be easily translated using known molecular biology techniques. The polypeptides produced by these alternative open reading frames are specifically contemplated by the present invention.

The first and last amino acid position of SEQ ID NO:Y of the predicted signal peptide is identified as "First AA of Sig Pep" and "Last AA of Sig Pep." The predicted first amino acid position of SEQ ID NO:Y of the secreted portion is identified as "Predicted First AA of Secreted Portion." Finally, the amino acid position of SEQ ID NO:Y of the last amino acid in the open reading frame is identified as "Last AA of ORF."

SEQ ID NO:X (where X may be any of the polynucleotide sequences disclosed in the sequence listing) and the translated SEQ ID NO:Y (where Y may be any of the polypeptide sequences disclosed in the sequence listing) are sufficiently accurate and otherwise suitable for a variety of uses well known in the art and described further below. For instance, SEQ ID NO:X is useful for designing nucleic acid hybridization probes that will detect nucleic acid sequences contained in SEQ ID NO:X or the cDNA contained in the deposited clone. These probes will also hybridize to nucleic acid molecules in biological samples, thereby enabling a variety of forensic and diagnostic methods of the invention. Similarly, polypeptides identified from SEQ ID NO:Y may be used, for example, to generate antibodies which bind specifically to proteins containing the polypeptides and the secreted proteins encoded by the cDNA clones identified in Table 1.

Nevertheless, DNA sequences generated by sequencing reactions can contain sequencing errors. The errors exist as misidentified nucleotides, or as insertions or deletions of nucleotides in the generated DNA sequence. The erroneously inserted or deleted nucleotides cause frame shifts in the reading frames of the predicted amino acid sequence. In these cases, the predicted amino acid sequence diverges from the actual amino acid sequence, even though the generated DNA sequence may be greater than 99.9% identical to the actual DNA sequence (for example, one base insertion or deletion in an open reading frame of over 1000 bases).

Accordingly, for those applications requiring precision in the nucleotide sequence or the amino acid sequence, the present invention provides not only the generated nucleotide sequence identified as SEQ ID NO:X and the predicted translated amino acid sequence identified as SEQ ID NO:Y, but also a sample of plasmid DNA containing a human cDNA of the invention deposited with the ATCC, as set forth in Table 1. The nucleotide sequence of each deposited clone can readily be determined by sequencing the deposited clone in accordance with known methods. The predicted amino acid sequence can then be verified from such deposits. Moreover, the amino acid sequence of the protein encoded by a particular clone can also be directly determined by peptide sequencing or by expressing the protein in a suitable host cell containing the deposited human cDNA, collecting the protein, and determining its sequence.

The present invention also relates to the genes corresponding to SEQ ID NO:X, SEQ ID NO:Y, or the deposited clone. The corresponding gene can be isolated in accordance with known methods using the sequence information disclosed herein. Such methods include preparing probes or primers from the disclosed sequence and identifying or amplifying the corresponding gene from appropriate sources of genomic material.

Also provided in the present invention are allelic variants, orthologs, and/or species homologs. Procedures known in the art can be used to obtain full-length genes, allelic variants, splice variants, full-length coding portions, orthologs, and/or species homologs of genes corresponding to SEQ ID NO:X, SEQ ID NO:Y, or a deposited clone, using information from the sequences disclosed herein or the clones deposited with the ATCC. For example, allelic variants and/or species homologs may be isolated and identified by making suitable probes or primers from the sequences provided herein and screening a suitable nucleic acid source for allelic variants and/or the desired homologue.

Table 2 summarizes the expression profile of polynucleotides corresponding to the clones disclosed in Table 1. The first column provides a unique clone identifier, "Clone ID", for a cDNA clone related to each contig sequence disclosed in Table 1. Column 2, "Library Code" shows the expression profile of tissue and/or cell line libraries which express the polynucleotides of the invention. Each Library Code in column 2 represents a tissue/cell source identifier code corresponding to the Library Code and Library description provided in Table 4. Expression of these polynucleotides was not observed in the other tissues and/or cell libraries tested. One of skill in the art could routinely use this information to identify tissues which show a predominant expression pattern of the corresponding polynucleotide of the invention or to identify polynucleotides which show predominant and/or specific tissue expression.

Table 3, column 1, provides a nucleotide sequence identifier, "SEQ ID NO:X," that matches a nucleotide SEQ ID NO:X disclosed in Table 1, column 5. Table 3, column 2, provides the chromosomal location, "Cytologic Band or Chromosome," of polynucleotides corresponding to SEQ ID NO:X. Chromosomal location was determined by finding exact matches to EST and cDNA sequences contained in the NCBI (National Center for Biotechnology Information) UniGene database. Given a presumptive chromosomal location, disease locus association was determined by comparison with the Morbid Map, derived from Online Mendelian Inheritance in Man (Online Mendelian Inheritance in Man, OMIM™. McKusick-Nathans Institute for Genetic Medicine, Johns Hopkins University (Baltimore, Md.) and National Center for Biotechnology Information, National Library of Medicine (Bethesda, Md.) 2000. World Wide Web URL: http://www.ncbi.nlm.nih.gov/omim/). If the putative chromosomal location of the Query overlapped with the chromosomal location of a Morbid Map entry, the OMIM reference identification number of the morbid map entry is provided in Table 3, column 3, labelled "OMIM ID." A key to the OMIM reference identification numbers is provided in Table 5.

Table 4 provides a key to the Library Code disclosed in Table 2. Column 1 provides the Library Code disclosed in Table 2, column 2. Column 2 provides a description of the tissue or cell source from which the corresponding library was derived.

Table 5 provides a key to the OMIM reference identification numbers disclosed in Table 3, column 3. OMIM reference identification numbers (Column 1) were derived from Online Mendelian Inheritance in Man (Online Mendelian Inheritance in Man, OMIM. McKusick-Nathans Institute for Genetic Medicine, Johns Hopkins University (Baltimore, Md.) and National Center for Biotechnology Information, National Library of Medicine, (Bethesda, Md.) 2000. World Wide Web URL: http://www.ncbi.nlm.nih.gov/omim/). Column 2 provides diseases associated with the cytologic band disclosed in Table 3, column 2, as determined using the Morbid Map database.

TABLE 2

| Clone ID | Library Codes |
|---|---|
| HKABZ65 | H0494 |
| HNGIC80 | S0052 |
| HDPUG50 | H0013 H0038 H0046 H0083 H0144 H0212 H0438 H0457 H0488 H0494 H0497 H0521 H0543 H0545 H0580 H0581 H0583 H0591 H0597 H0599 H0616 H0627 H0659 H0661 H0665 H0672 H0673 H0674 H0682 H0685 L0055 L0163 L0362 L0517 L0545 L0659 L0662 L0740 L0747 L0748 L0758 L0759 L0763 L0766 L0767 L0770 L0771 L0776 L0777 L0779 L0782 S0010 S0026 S0142 S0214 S0344 S0360 S0390 S0420 S0434 |
| HAEAB66 | H0266 H0494 H0646 H0676 L0383 L0517 L0596 L0659 L0662 L0747 L0748 L0749 L0750 L0752 L0755 L0758 L0761 L0764 L0771 L0774 L0777 L0783 L0789 L0792 L0800 L0803 L0804 L0806 L0809 S0116 S0356 S0358 S0402 T0048 T0109 |
| HHEPF59 | H0038 H0063 H0254 H0255 H0264 H0318 H0333 H0389 H0392 H0413 H0422 H0428 H0445 H0449 H0483 H0521 H0542 H0543 H0556 H0583 H0606 H0615 H0648 H0664 H0673 H0702 L0157 L0382 L0439 L0447 L0471 L0595 L0646 L0650 L0655 L0659 L0662 L0665 L0666 L0748 L0756 L0761 L0764 L0766 L0768 L0769 L0779 L0782 L0789 L0791 L0803 L0809 S0027 S0028 S0049 S0212 S0418 |
| HE9BK23 | H0014 H0098 H0144 H0355 H0393 H0509 H0510 H0574 H0632 L0581 L0748 L0775 L0790 L0803 L0804 |
| HCYBI36 | H0014 H0031 H0123 H0156 H0170 H0171 H0188 H0264 H0295 H0341 H0428 H0431 H0435 H0445 H0479 H0494 H0509 H0520 H0521 H0529 H0530 H0543 H0547 H0551 H0574 H0575 H0586 H0587 H0592 H0596 H0620 H0633 H0638 H0648 H0658 H0661 H0670 H0672 H0674 H0684 H0690 L0021 L0157 L0362 L0448 L0451 L0483 L0525 L0589 L0602 L0637 L0646 L0648 L0649 L0653 L0655 L0657 L0662 L0664 L0665 L0717 L0731 L0740 L0747 L0748 L0749 L0752 L0754 L0755 L0758 L0759 L0761 L0763 L0764 L0766 L0770 L0774 L0775 L0776 L0777 L0779 L0780 L0803 L0804 L0806 L0809 S0003 S0014 S0052 S0122 S0132 S0194 S0212 S0242 S0352 S0358 S0374 S0378 S0388 S0422 S0450 S3014 T0002 T0010 T0023 T0040 T0114 |
| HSSDX51 | H0050 H0052 H0069 H0135 H0391 H0575 H0652 H0690 L0021 L0438 L0439 L0554 L0599 L0653 L0665 L0717 L0774 L0775 S0038 S0049 S0222 S0312 S0334 S0338 T0006 T0082 |

TABLE 2-continued

| Clone ID | Library Codes |
| --- | --- |
| HSDAJ46 | H0009 H0052 H0144 H0352 H0392 L0593 L0595 L0598 L0608 L0740 L0741 L0745 L0746 L0748 L0749 L0759 L0769 L0770 L0777 L0783 L0809 S0031 |
| HRACG45 | H0009 H0030 H0036 H0059 H0555 L0599 S0358 |
| HAPPW30 | H0009 H0012 H0038 H0052 H0103 H0135 H0169 H0188 H0208 H0213 H0266 H0292 H0388 H0412 H0424 H0521 H0538 H0539 H0545 H0547 H0575 H0616 H0653 H0663 H0672 L0163 L0591 L0599 L0638 L0665 L0731 L0742 L0747 L0748 L0752 L0753 L0755 L0757 L0758 L0759 L0764 L0767 L0769 L0770 L0772 L0774 L0775 L0776 L0777 L0779 L0786 L0809 S0010 S0027 S0045 S0049 S0392 S0474 T0040 T0041 T0042 |
| HE2ES51 | H0015 H0038 H0170 H0356 H0622 L0774 L0803 S0015 S0438 |
| HAGGJ80 | H0040 H0144 H0327 H0422 H0427 H0539 H0542 H0547 H0551 H0561 H0581 H0648 H0658 H0659 H0672 H0684 L0157 L0352 L0362 L0438 L0471 L0519 L0591 L0659 L0662 L0663 L0665 L0731 L0756 L0758 L0759 L0764 L0766 L0774 L0775 L0777 L0779 L0783 S0003 S0028 S0036 S0051 S0150 S0152 S0342 S0346 S0358 S0360 S0374 |
| HTXDW56 | H0009 H0024 H0031 H0038 H0039 H0040 H0042 H0046 H0051 H0061 H0069 H0083 H0100 H0123 H0144 H0156 H0208 H0251 H0264 H0265 H0266 H0271 H0295 H0327 H0351 H0370 H0393 H0427 H0431 H0435 H0436 H0457 H0484 H0485 H0494 H0519 H0521 H0522 H0529 H0542 H0543 H0545 H0547 H0551 H0556 H0561 H0580 H0581 H0586 H0616 H0617 H0622 H0624 H0635 H0642 H0644 H0656 H0658 H0660 H0661 H0667 H0687 H0688 H0696 L0021 L0040 L0373 L0439 L0515 L0565 L0591 L0595 L0596 L0598 L0605 L0626 L0636 L0637 L0638 L0653 L0655 L0659 L0662 L0663 L0664 L0665 L0666 L0731 L0740 L0742 L0744 L0745 L0747 L0748 L0749 L0750 L0751 L0752 L0754 L0755 L0756 L0757 L0758 L0759 L0761 L0763 L0764 L0766 L0770 L0771 L0776 L0789 L0794 L0803 L0804 L0805 L0806 L0809 S0002 S0003 S0010 S0026 S0027 S0040 S0042 S0044 S0045 S0114 S0116 S0132 S0134 S0192 S0212 S0278 S0316 S0328 S0330 S0356 S0358 S0360 S0374 S0376 S0378 S0380 S0412 S0414 S0426 S0462 S0474 T0082 |
| HEEAG23 | H0038 H0052 H0123 H0144 H0194 H0255 H0286 H0328 H0375 H0436 H0484 H0521 H0542 H0549 H0556 H0624 L0748 L0789 S0027 S0030 S0126 S0196 S0222 S0278 S0300 S0358 S0420 |
| HDPKI93 | H0024 H0039 H0052 H0059 H0087 H0135 H0144 H0255 H0264 H0265 H0295 H0341 H0393 H0478 H0494 H0510 H0521 H0522 H0539 H0543 H0549 H0574 H0597 H0598 H0616 H0677 L0565 L0588 L0596 L0665 L0738 L0743 L0747 L0749 L0751 L0769 S0126 S0146 S0206 S0210 S0356 S0360 |
| HDLAC10 | H0031 H0170 H0320 H0373 H0422 H0445 H0485 H0494 H0519 H0539 H0543 H055O H0555 H0581 H0586 H0650 H0657 H0658 H0672 H0690 L0374 L0438 L0599 L0606 L0635 L0638 L0655 L0665 L0666 L0667 L0743 L0745 L0759 L0761 L0764 L0766 L0777 L0779 L0803 L0804 S0134 S0212 S0218 S0358 S0360 T0067 |
| HDPOH06 | H0046 H0087 H0318 H0431 H0521 H0522 L0599 L0608 L0662 L0663 L0666 L0731 L0748 L0749 L0774 L0775 L0777 L0783 L0803 S0318 S0344 |
| HCWUI13 | H0589 |
| HDPSP01 | H0052 H0059 H0100 H0123 H0135 H0370 H0392 H0427 H0478 H0494 H0521 H0545 H0550 H0551 H0555 H0586 H0617 H0618 H0620 H0684 L0665 L0666 L0731 L0743 L0745 L0747 L0750 L0751 L0752 L0755 L0759 L0764 L0769 L0771 L0774 L0775 L0777 L0780 L0783 L0792 L0804 L0805 L0806 L0809 S0051 S0132 S0314 S0328 S0418 S3014 |
| HHPEN62 | H0046 H0051 H0052 H0100 H0261 H0305 H0327 H0438 L0635 L0741 L0769 L0770 L0803 S0010 S0036 S0051 S0112 S0260 S0282 S0346 |
| HUKBT29 | H0002 H0051 H0059 H0116 H0149 H0255 H0522 H0543 H0555 H0599 L0366 L0460 L0485 L0604 L0747 L0777 L0803 S0330 S0364 S0366 S0428 S0430 S0446 |
| HMAJR50 | H0013 H0014 H0031 H0032 H0038 H0040 H0046 H0051 H0052 H0056 H0059 H0069 H0090 H0123 H0130 H0134 H0144 H0170 H0250 H0267 H0316 H0327 H0328 H0341 H0357 H0402 H0412 H0416 H0421 H0423 H0436 H0441 H0445 H0497 H0519 H0520 H0521 H0529 H0542 H0543 H0546 H0547 H0549 H0551 H0553 H0556 H0560 H0574 H0587 H0598 H0615 H0619 H0623 H0625 H0632 H0638 H0640 H0641 H0644 H0650 H0657 H0695 L0387 L0438 L0439 L0471 L0586 L0588 L0593 L0598 L0607 L0637 L0642 L0646 L0648 L0655 L0659 L0662 L0663 L0664 L0665 L0666 L0667 L0731 L0738 L0740 L0747 L0748 L0750 L0752 L0754 L0755 L0756 L0757 L0758 L0759 L0767 L0770 L0771 L0775 L0776 L0779 L0806 S0003 S0013 S0026 S0028 S0036 S0053 S0116 S0126 S0132 S0144 S0152 S0196 S0210 S0222 S0260 S0278 S0348 S0352 S0354 S0356 S0358 S0360 S0374 S0378 S0380 S0418 S0452 S0474 T0006 T0082 |
| HBIMB51 | H0593 S0152 |
| HE8DX88 | H0013 |
| HNGHT03 | S0052 |

TABLE 2-continued

| Clone ID | Library Codes |
|---|---|
| HWABU17 | H0024 H0052 H0208 H0422 H0457 H0581 H0624 S0002 S0031 S0344 S0360 S0364 T0041 |
| HDTAT90 | H0052 H0224 H0252 H0280 H0486 H0539 H0592 H0616 S0045 S0150 |
| HHFGR93 | H0024 H0030 H0040 H0042 H0046 H0050 H0051 H0056 H0124 H0144 H0265 H0305 H0328 H0361 H0413 H0422 H0427 H0441 H0485 H0506 H0519 H0543 H0553 H0555 H0556 H0569 H0575 H0586 H0599 H0616 H0619 H0644 L0363 L0471 L0599 L0603 L0605 L0644 L0659 L0662 L0665 L0666 L0731 L0747 L0748 L0749 L0750 L0751 L0754 L0755 L0764 L0769 L0770 L0775 L0779 L0783 L0794 L0800 L0803 L0804 L0806 S0038 S0045 S0046 S0146 S0280 S0358 S3012 |
| HOVCB25 | H0428 |
| HSYAV66 | H0036 H0551 |
| HFPCT29 | S0222 |
| HAWAT25 | H0100 H0135 H0171 H0263 H0670 L0774 L0803 S0216 T0060 |
| HNHFR04 | S0053 S0428 |
| HOSFT61 | H0170 H0328 H0331 H0428 H0519 H0521 H0529 H0542 H0546 H0576 H0583 H0587 H0601 H0615 H0624 H0658 H0660 H0683 L0367 L0438 L0439 L0471 L0731 L0754 L0759 L0791 S0003 S0026 S0114 S0194 S0212 S0214 S0222 S0420 T0041 |
| HBJIO81 | H0318 L0766 |
| HADCL55 | H0013 H0031 H0038 H0144 H0253 H0266 H0310 H0424 H0427 H0497 H0519 H0521 H0522 H0539 H0545 H0549 H0553 H0555 H0581 H0591 H0599 H0618 H0633 H0661 H0664 L0021 L0142 L0438 L0439 L0649 L0659 L0662 L0664 L0665 L0740 L0745 L0747 L0748 L0758 L0759 L0769 L0779 L0790 S0010 S0126 S0144 S0218 S0360 S0390 S0418 S0422 S0426 S0452 S3014 |
| HAIBO81 | S0001 S0132 |
| HBBBC37 | H0013 H0014 H0038 H0069 H0096 H0100 H0201 H0264 H0374 H0486 H0494 H0543 H0551 H0587 H0687 L0021 L0105 L0369 L0438 L0439 L0471 L0485 L0591 L0598 L0599 L0659 L0717 L0740 L0743 L0748 L0749 L0751 L0752 L0755 L0756 L0758 L0768 L0769 L0770 L0771 L0774 L0775 L0776 L0777 L0779 L0792 L0794 L0803 L0804 L0805 L0806 S0001 S0003 S0122 S0222 S0260 S0330 S0346 S0388 S0468 T0023 T0039 T0042 |
| HBJMX85 | H0254 H0255 H10306 H0318 H0327 H0402 H0421 H0436 H0445 H0457 H0486 H0506 H0543 H0555 H0556 H0583 S0007 S0114 S0140 S0218 S0348 S0358 |
| HCEES66 | H0052 L0753 L0756 |
| HCEMP62 | H0024 H0030 H0040 H0041 H0046 H0052 H0063 H0123 H0135 H0165 H0179 H018 H0188 H0208 H0264 H0266 H0286 H0290 H0318 H0370 H0402 H0411 H0428 H0436 H0445 H0484 H0489 H0506 H0509 H0521 H0522 H0543 H0547 H0551 H0553 H0556 H0561 H0575 H0581 H0583 H0586 H0587 H0593 H0596 H0600 H0617 H0620 H0622 H0667 H0668 H0672 H0702 H0707 L0372 L0517 L0521 L0565 L0599 L0637 L0657 L0662 L0663 L0664 L0665 L0666 L0717 L0731 L0744 L0747 L0748 L0749 L0751 L0754 L0757 L0759 L0761 L0763 L0764 L0766 L0768 L0769 L0770 L0776 L0777 L0803 S0001 S0002 S0037 S0044 S0049 S0150 S0212 S0216 S0250 S0278 S0354 S0358 S0360 S0364 S0380 S0426 S0446 S0458 53012 T0039 |
| HE2FB90 | H0012 H0050 H0130 H0171 H0318 H0333 H0428 H0539 H0549 H0571 H0624 H0662 L0439 L0639 L0665 L0750 L0755 L0756 L0764 L0769 L0772 L0792 L0794 S0046 |
| HTHDJ94 | H0009 H0013 H0039 H0042 H0046 H0052 H0063 H0123 H0124 H0135 H0144 H0150 H0156 H0163 H0170 H0200 H0264 H0295 H0423 H0445 H0486 H0494 H0519 H0520 H0521 H0543 H0544 H0545 H0553 H0556 H0561 H0575 H0581 H0593 H0599 H0600 H0606 H0644 H0645 H0652 H0658 H0662 H0673 H0674 L0005 LO055 L0143 L0369 L0438 L0439 L0485 L0519 L0520 L0526 L0536 L0549 L0637 L0659 L0731 L0740 L0748 L0750 L0752 L0753 L0755 L0757 L0758 L0759 L0763 L0764 L0766 L0768 L0770 L0774 L0776 L0777 L0779 L0783 L0803 L0806 L0809 S0002 S0010 S0027 S0032 S0132 S0358 S0364 S0434 S0466 S0474 S3012 |
| HTOHJ89 | H0264 |
| HUSHB62 | H0012 H0013 H0030 H0031 H0032 H0038 H0039 H0044 H0046 H0052 H0056 H0059 H0070 H0083 H0090 H0100 H0122 H0123 H0124 H0134 H0135 H0144 H0150 H0156 H0194 H0201 H0220 H0231 H0253 H0255 H0261 H0264 H0266 H0271 H0306 H0351 H0352 H0356 H0370 H0375 H0393 H0402 H0412 H0413 H0422 H0423 H0424 H0427 H0429 H0431 H0435 H0436 H0437 H0438 H0441 H0445 H0478 H0483 H0484 H0486 H0494 H0506 H0S10 H0518 H0521 H0529 H0539 H0542 H0543 H0545 H0549 H0551 H0553 H0555 H0556 H0561 H0575 H0580 H0581 H0583 H0586 H0587 H0591 H0593 H0599 H0615 H0616 H0617 H0618 H0620 H0622 H0623 H0626 H0634 H0635 H0641 H0644 H0646 H0650 H0656 H0657 H0661 H0662 H0664 H0665 H0670 H0672 H0673 H0679 H0682 H0685 H0687 H0691 H0696 H0702 H0707 L0041 L0142 L0143 L0157 L0352 L0362 L0372 L0375 L0378 L0388 L0438 L0439 L0493 L0498 L0511 L0515 L0517 L0518 L0529 L0540 L0553 L0560 L0564 L0596 |

TABLE 2-continued

| Clone ID | Library Codes |
|---|---|
| | L0599 L0600 L0603 L0608 L0612 L0635 L0638 L0641 L0644 L0645 L0646 L0650 L0651 L0656 L0657 L0658 L0659 L0662 L0663 L0664 L0665 L0666 L0667 L0697 L0731 L0740 L0741 L0742 L0743 L0744 L0745 L0747 L0748 L0749 L0750 L0751 L0752 L0754 L0758 L0759 L0761 L0762 L0763 L0766 L0767 L0768 L0769 L0770 L0771 L0774 L0775 L0777 L0779 L0783 L0786 L0789 L0791 L0794 L0796 L0803 L0804 L0806 L0809 S0007 S0010 S0011 S0027 S0028 S0031 S0032 S0037 S0038 S0040 S0045 S0046 S0049 S00S3 S0116 S0126 S0132 S0140 S0144 S0192 S0194 S0212 S0222 S0260 S0278 S0280 S0282 S0350 S03S4 S03S6 S03S8 S0360 S0376 S0378 S0384 S0390 S0418 S0426 S0428 S3012 S3014 S6024 T0002 T0049 T0067 |
| HSXAG02 | H0013 H0014 H0024 H0031 H0032 H0038 H0039 H0040 H0046 H0050 H0051 H0052 H0056 H0O57 H0081 H0085 H0086 H0087 H0100 H0105 H0116 H0123 H0124 H0135 H0144 H0150 H0163 H0171 H0178 H0181 H0188 H0196 H0208 H0242 H0251 H0252 H0253 H0264 H0266 H0268 H0269 H0274 H0284 H0286 H0290 H0292 H0294 H0309 H0316 H0318 H0333 H0343 H0352 H0381 H0392 H0411 H0412 H0413 H0427 H0428 H0437 H0484 H0485 H0486 H0506 H0519 H0520 H0539 H0544 H0545 H0546 H0547 H0549 H0550 H0551 H0553 H0575 H0586 H0587 H0590 H0592 H0594 H0597 H0598 H0599 H0600 H0602 H0617 H0619 H0620 H0622 H0623 H0624 H0626 H0628 H0631 H0647 H0648 H0653 H0659 H0660 H0664 H0665 H0667 H0673 H0677 H0684 H0687 H0688 H0689 H0690 H0691 H0696 L0005 L0021 L0053 L0361 L0364 L0372 L0375 L0378 L0384 L0426 L0438 L0439 L0471 L0493 L0517 L0521 L0523 L0542 L0565 L0588 L0592 L0596 L0597 L0598 L0629 L0637 L0645 L0646 L0648 L0649 L0651 L0653 L0654 L0656 L0657 L0659 L0662 L0663 L0664 L0665 L0666 L0717 L0731 L0740 L0742 L0743 L0744 L0747 L0748 L0749 L0750 L0751 L0754 L0755 L0757 L0758 L0759 L0762 L0763 L0764 L0768 L0769 L0770 L0771 L0772 L0774 L0775 L0776 L0777 L0779 L0780 L0783 L0796 L0800 L0803 L0806 L0807 S0001 S0011 S0022 S0026 S0027 S0028 S0036 S0037 S0038 S0040 S0044 S0045 S0046 S0116 S0126 S0192 S0194 S0196 S0208 S0210 S0212 S0242 S0250 50294 S0328 S0330 50332 S0342 S0352 S0354 S0356 S0358 S0360 S0364 S0374 S0376 S0388 S0418 S0420 S0432 S0446 S3012 S3014 T0003 T0004 T0040 T0049 |
| HHTLH52 | H0615 S6014 |
| HCFMS95 | H0061 H0068 H0090 H0170 H0255 H0265 H0266 H0309 H0413 H0423 H0457 H0486 H0494 H0521 H0539 H0549 H0551 H0575 H0581 H0618 H0637 H0638 H0648 H0657 H0658 H0659 H0670 H0682 H0689 LO055 L0363 L0369 L0438 L0439 L0593 L0601 L0638 L0645 L0651 L0655 L0657 L0659 L0663 L0664 L0666 L0731 L0740 L0743 L0744 L0746 L0748 L0749 L0751 L0752 L0754 L0758 L0761 L0764 L0767 L0768 L0769 L0771 L0774 L0775 L0776 L0779 L0803 L0806 L0809 S0002 S0045 S0134 S0142 S0196 S0250 S0354 S0358 S0360 S0376 S0378 S0426 T0008 T0049 T0060 |
| HOUCT90 | S0040 |
| HCFLR78 | H0009 H0013 H0032 H0038 H0039 H0040 H0042 H0046 H0050 H0051 H0068 H0083 H0090 H0100 H0144 H0169 H0170 H0196 H0250 H0252 H0265 H0284 H0286 H0294 H0327 H0331 H0333 H0341 H0351 H0355 H0400 H0403 H0423 H0428 H0458 H0509 H0510 H0521 H0539 H0542 H0543 H0547 H0556 H0560 H0561 H0574 H0575 H0581 H0593 H0596 H0616 H0617 H0619 H0622 H0623 H0624 H0644 H0645 H0656 H0658 H0690 L0362 L0366 L0369 L0411 L0438 L0439 L0530 L0595 L0599 L0606 L0651 L0654 L0657 L0659 L0662 L0663 L0666 L0731 L0740 L0747 L0748 L0749 L0750 L0752 L0754 L0755 L0757 L0758 L0759 L0763 L0764 L0766 L0769 L0770 L0771 L0772 L0774 L0775 L0776 L0777 L0791 L0792 L0796 L0809 S0003 S0007 S0010 S0013 S0026 S0027 S0028 S0038 S0040 S0044 S0046 S0051 S0126 S0134 S0142 S0144 S0152 S0192 S0194 S0212 S0222 S0242 S0250 S0278 S0330 S0342 S0344 S0354 S0358 S0360 S0366 S0374 S0376 S0380 S0392 S0420 S0462 T0006 T0048 T0110 |
| HTOHT18 | H0013 H0014 H0038 H0081 H0090 H0144 H0251 H0252 H0264 H0265 H0290 H0318 H0328 H0352 H0370 H0413 H0435 H0484 H0494 H0497 H0521 H0522 H0543 H0545 H0574 H0581 H0597 H0616 H0619 H0624 H0657 H0665 H0667 H0668 L0363 L0364 L0375 L0439 L0588 L0601 L0664 L0666 L0717 L0747 L0748 L0749 L0750 L0758 L0762 L0764 L0766 L0769 L0771 L0776 L0777 L0779 L0794 L0800 L0804 L0805 L0806 S0045 S0050 S0140 S0210 S0354 S0358 S0420 T0002 T0042 T0049 |
| HKPMB11 | H0453 H0575 L0803 S0126 S0210 |
| HNFHS38 | H0013 H0271 S0152 S0342 |
| HAIBU10 | H0087 H0135 H0166 H0171 H0188 H0213 H0252 H0263 H0333 H0343 H0427 H0457 H0545 H0556 H0580 H0587 H0594 H0624 H0634 H0660 H0666 H0674 H0689 L0021 L0471 L0615 L0637 L0644 L0653 L0659 L0663 L0665 L0717 L0731 L0743 L0748 L0750 L0753 L0754 L0757 |

TABLE 2-continued

| Clone ID | Library Codes |
|---|---|
| | L0758 L0759 L0761 L0762 L0763 L0764 L0766 L0769 L0770 L0775 L0776 L0779 L0790 L0791 L0794 L0800 L0803 L0804 L0805 L0809 S0013 S0116 S0132 S0134 S0144 S0354 S0358 S0450 |
| HAPOK30 | H0575 H0592 H0670 L0352 L0439 L0517 L0600 L0608 L0663 L0740 L0747 L0752 L0755 L0756 L0759 L0763 L0764 L0766 L0768 L0770 L0777 L0785 L0794 L0803 L0809 S0010 S0222 S0328 |
| HCEEM18 | H0012 H0014 H0023 H0024 H0031 H0036 H0051 H0052 H0069 H0081 H0111 H0123 H0124 H0179 H0253 H0266 H0271 H0294 H0305 H0309 H0327 H0333 H0341 H0370 H0429 H0449 H0486 H0494 H0506 H0510 H0521 H0539 H0543 H0544 H0550 H0551 H0575 H0581 H0586 H0599 H0616 H0620 H0623 H0628 H0635 H0644 H0653 H0657 H0665 H0683 L0382 L0471 L0565 L0601 L0604 L0651 L0664 L0745 L0750 L0752 L0754 L0757 L0758 L0759 L0766 L0769 L0779 L0789 L0794 L0800 L0803 S0002 S0022 S0027 S0028 S0037 S0040 S0044 S0045 S0046 S0051 S0126 S0142 S0144 S0152 S0212 S0220 S0278 S0344 S0356 S0358 S0360 S0420 S0424 S3014 T0010 T0040 T0041 T0042 T0049 |
| HCWUA22 | H0305 H0589 |
| HDSAG91 | H0329 H0635 L0766 |
| HNEDJ35 | H0179 H0435 |
| H7TBA62 | S0198 S0228 S0252 S0264 S0268 S0270 S0274 |
| HNGIO50 | S0052 |
| HMIAW81 | H0046 H0328 H0445 L0519 S6028 |
| HMMCJ60 | H0124 H0444 S0053 |
| HDPIO09 | H0006 H0013 H0014 H0031 H0032 H0039 H0040 H0051 H0052 H0059 H0090 H0196 H0252 H0265 H0266 H0294 H0309 H0328 H0373 H0375 H0421 H0422 H0423 H0427 H0428 H0431 H0445 H0486 H0488 H0497 H0510 H0521 H0529 H0542 H0547 H0550 H0553 H0556 H0561 H0574 H0580 H0591 H0596 H0622 H0623 H0624 H0628 H0634 H0637 H0641 H0644 H0648 H0658 H0659 H0661 H0676 H0684 H0687 L0439 L0481 L0485 L0512 L0517 L0563 L0638 L0646 L0651 L0659 L0661 L0662 L0663 L0664 L0665 L0666 L0682 L0697 L0731 L0740 L0745 L0747 L0748 L0749 L0750 L0751 L0752 L0754 L0755 L0756 L0757 L0758 L0759 L0763 L0764 L0766 L0768 L0769 L0770 L0774 L0775 L0776 L0777 L0779 L0780 L0783 L0789 L0809 S0001 S0002 S0003 S0010 S0027 S0028 S0038 S0046 S0051 S0114 S0116 S0142 S0218 S0222 S0276 S0294 S0328 S0330 S0346 S03S4 S0356 S0374 T0042 |
| HHFHH34 | H0O50 H0520 |
| HISCL83 | H0539 |
| HTOAI70 | H0264 |
| HSDER95 | H0009 H0321 H0362 H0427 H0547 H0658 H0690 L0438 L0588 L0592 L0598 L0740 L0749 L0756 L0759 L0766 L0769 L0773 L0775 L0776 L0791 L0803 L0804 S0031 S0136 S0176 S0328 S0374 |
| HNECL25 | H0179 |
| HNFGZ45 | H0179 H0264 H0271 H0422 H0619 S0358 |
| HHGCU49 | H0013 H0086 H0087 H0100 H0123 H0124 H0150 H0163 H0181 H0288 H0333 H0422 H0544 H0545 H0546 H0547 H0550 H0553 H0619 H0628 H0644 H06S8 H066S L0384 L0521 L0565 L0603 L0605 L0623 L0655 L0656 L0659 L0743 L0744 L0751 L0754 L0757 L0771 L0777 L0794 L0803 L0809 S0027 S0028 S0037 S0052 S0206 S0212 S0360 |
| HDPND68 | H0063 H0144 H0264 H0305 H0316 H0402 H0427 H0431 H0517 H0522 H0690 L0021 L0378 L0381 L0527 L0534 L0539 L0562 L0589 L0665 L0745 L0748 L0751 L0766 L0770 SQOOl S0002 S0038 S0052 |
| HETDT81 | H0038 H0046 H0090 H0253 H0539 H0617 L0439 L0455 L0646 L0649 L0658 L0659 L0662 L0750 L0754 L0764 L0766 L0771 L0777 L0780 L0789 L0803 S0142 S0344 S0358 |
| HHLBA14 | H0013 H0264 H0427 H0547 L0438 L0439 S0010 S0222 T0041 T0091 |
| HLTBU43 | H0090 |
| HNTSJ84 | H0013 H0428 H0542 H0547 H0622 L0636 L0662 L0717 L0740 L0749 L0766 L0769 L0779 L0789 S0007 S0242 S0282 S0354 |
| HOHCG16 | H0411 H0509 H0538 L0439 L0532 L0743 L0744 L0748 L0749 S0250 |
| HTHCB31 | H0063 H0170 L0589 S0001 |
| HUKAM16 | H0028 H0059 H0081 H0135 H0194 H0231 H0255 H0264 H0352 H0423 H0483 H0521 H0529 H0542 H0547 H0553 H0587 H0616 H0628 H0662 H0663 H0687 L0439 L0471 L0526 L0605 L0639 L0664 L0665 L0743 L0744 L0745 L0747 L0748 L0759 L0769 L0774 L0776 L0777 L0809 S0002 S0007 S0036 S0212 S0330 S0360 S0378 S0418 S0428 T0010 |
| HLDOJ66 | H0510 |
| HTXKF10 | H0556 |
| HPMAI22 | H0031 H0662 L0600 L0657 L0755 L0756 L0767 L0768 L0779 L0794 |
| HL2AG57 | H0013 H0090 H0131 H0135 H0264 H0341 H0359 H0519 H0689 L0439 L0637 L0640 L0647 L0659 L0665 L0764 L0768 L0779 S0212 |
| HTHBH29 | H0063 H0100 H0520 |
| HUSAM59 | H0032 H0052 H0068 H0083 H0090 H0156 H0170 H0171 H0212 H0266 H0268 H0309 H0392 H0411 H0422 H0423 H0435 H0441 H0445 H0494 H0519 H0529 H0543 H0547 H0561 H0574 H0591 H0596 H0628 H0633 H0656 H0657 H0658 H0667 H0686 H0696 L0438 L0439 L0471 L0519 L0521 L0581 L0598 L0601 L0649 L0653 L0659 L0662 L0664 L0665 |

TABLE 2-continued

| Clone ID | Library Codes |
|---|---|
|  | L0666 L0717 L0740 L0742 L0745 L0747 L0750 L0752 L0753 L0754 L0755 L0756 L0758 L0764 L0766 L0768 L0770 L0773 L0775 L0777 L0779 L0780 L0782 L0783 L0789 L0794 L0803 L0804 L0809 S0011 S0022 S0042 S0051 S0192 S0242 S0358 S0360 S0374 S0380 S0402 S0424 S0474 56028 T0069 T0114 |
| HNGGR26 | S0052 |
| HTLCX30 | H0253 L0758 L0794 |
| HCEBC87 | H0052 H0163 H0171 H0351 H0411 H0415 H0592 H0694 L0439 L0465 L0520 L0592 L0650 L0657 L0666 L0745 L0748 L0751 L0752 L0755 L0756 L0758 L0766 L0777 L0779 L0783 L0788 L0803 L0805 S0010 S0136 S0358 |
| HATCB92 | H0156 |
| HMSCX69 | H0063 H0100 H0139 H0144 H0264 H0318 H0327 H0331 H0538 H0650 H0656 L0381 L0438 L0606 L0638 L0740 L0749 L0750 L0754 L0756 L0759 L0761 L0766 L0769 L0770 L0774 L0777 L0779 L0792 S0002 S0053 T0010 |
| HLHAL68 | H0024 |
| HEOMR73 | H0179 H0271 H0457 H0695 L0748 |
| HETIB83 | H0046 H0134 H0306 H0318 H0396 H0402 H0429 H0445 H0560 H0581 H0638 H0650 H0656 H0657 H0689 L0438 L0439 L0655 L0740 L0761 L0766 L0777 L0789 L0794 S0002 S0038 S0050 S0278 S0344 |
| HJPDD28 | H0002 H0014 H0015 H0024 H0031 H0036 H0040 H0046 H0052 H0083 H0090 H0169 H0204 H0214 H0264 H0265 H0266 H0352 H0370 H0393 H0421 H0431 H0435 H0448 H0494 H0583 H0620 H0635 H0642 H0653 H0656 H0658 L0021 L0364 L0372 L0374 L0462 L0588 L0596 L0599 L0622 L0644 L0647 L0659 L0663 L0665 L0666 L0731 L0740 L0747 L0750 L0751 L0752 L0753 L0754 L0758 L0759 L0765 L0766 L0769 L0771 L0772 L0773 L0783 L0806 S0038 S0040 S0142 S0280 S0356 S0358 S0366 S0442 S3014 S6028 |
| HBAMB15 | H0328 H0410 H0530 L0455 L0740 |

TABLE 3

| SEQ ID NO: X | Cytologic Band or Chromosome: | OMIM Reference(s): |
|---|---|---|
| 19 | 1q21 | 104770 107670 110700 135940 145001 146790 152445 159001 174000 179755 182860 191315 230800 266200 600897 601105 601412 601652 602491 |
| 21 | 9q33-q34.1 | 103000 114350 120900 131195 146150 185000 189980 223900 253800 268900 600184 602575 |
| 57 | 16q13 | 114835 132700 172490 600968 |
| 66 | 12 |  |

TABLE 4

| Library Code | Library Description |
|---|---|
|  | BL29 Burkitt's lymphoma, Pascalis Sideras |
| H0002 | Human Adult Heart |
| H0006 | Human Frontal Lobe of Brain |
| H0009 | Human Fetal Brain |
| H0012 | Human Fetal Kidney |
| H0013 | Human 8 Week Whole Embryo |
| H0014 | Human Gall Bladder |
| H0015 | Human Gall Bladder, fraction II |
| H0023 | Human Fetal Lung |
| H0024 | Human Fetal Lung III |
| H0028 | Human Old Ovary |
| H0030 | Human Placenta |
| H0031 | Human Placenta |
| H0032 | Human Prostate |
| H0036 | Human Adult Small Intestine |
| H0038 | Human Testes |
| H0039 | Human Pancreas Tumor |
| H0040 | Human Testes Tumor |
| H0041 | Human Fetal Bone |
| H0042 | Human Adult Pulmonary |
| H0044 | Human Cornea |

TABLE 4-continued

| Library Code | Library Description |
|---|---|
| H0046 | Human Endometrial Tumor |
| H0050 | Human Fetal Heart |
| H0051 | Human Hippocampus |
| H0052 | Human Cerebellum |
| H0056 | Human Umbilical Vein, Endo. remake |
| H0057 | Human Fetal Spleen |
| H0059 | Human Uterine Cancer |
| H0061 | Human Macrophage |
| H0063 | Human Thymus |
| H0068 | Human Skin Tumor |
| H0069 | Human Activated T-Cells |
| H0070 | Human Pancreas |
| H0081 | Human Fetal Epithelium (Skin) |
| H0083 | HUMAN JURKAT MEMBRANE BOUND POLYSOMES |
| H0085 | Human Colon |
| H0086 | Human epithelioid sarcoma |
| H0087 | Human Thymus |
| H0090 | Human T-Cell Lymphoma |
| H0096 | Human Parotid Cancer |
| H0098 | Human Adult Liver, subtracted |
| H0100 | Human Whole Six Week Old Embryo |
| H0103 | Human Fetal Brain, subtracted |
| H0105 | Human Fetal Heart, subtracted |
| H0111 | Human Placenta, subtracted |
| H0116 | Human Thymus Tumor, subtracted |
| H0122 | Human Adult Skeletal Muscle |
| H0123 | Human Fetal Dura Mater |
| H0124 | Human Rhabdomyosarcoma |
| H0130 | LNCAP untreated |
| H0131 | LNCAP + 0.3 nM R1881 |
| H0134 | Raji Cells, cyclohexamide treated |
| H0135 | Human Synovial Sarcoma |
| H0139 | Activated T-Cells, 4 hrs. |
| H0144 | Nine Week Old Early Stage Human |
| H0149 | 7 Week Old Early Stage Human, subtracted |
| H0150 | Human Epididymus |
| H0156 | Human Adrenal Gland Tumor |
| H0163 | Human Synovium |

TABLE 4-continued

| Library Code | Library Description |
|---|---|
| H0165 | Human Prostate Cancer, Stage B2 |
| H0166 | Human Prostate Cancer, Stage B2 fraction |
| H0169 | Human Prostate Cancer, Stage C fraction |
| H0170 | 12 Week Old Early Stage Human |
| H0171 | 12 Week Old Early Stage Human, II |
| H0178 | Human Fetal Brain |
| H0179 | Human Neutrophil |
| H0181 | Human Primary Breast Cancer |
| H0188 | Human Normal Breast |
| H0194 | Human Cerebellum, subtracted |
| H0196 | Human Cardiomyopathy, subtracted |
| H0200 | Human Greater Omentum, fract II remake, |
| H0201 | Human Hippocampus, subtracted |
| H0204 | Human Colon Cancer, subtracted |
| H0208 | Early Stage Human Lung, subtracted |
| H0212 | Human Prostate, subtracted |
| H0213 | Human Pituitary, subtracted |
| H0214 | Raji cells, cyclohexamide treated, subtracted |
| H0220 | Activated T-Cells, 4 hrs, subtracted |
| H0224 | Activated T-Cells, 12 hrs, subtracted |
| H0231 | Human Colon, subtraction |
| H0242 | Human Fetal Heart, Differential (Fetal-Specific) |
| H0250 | Human Activated Monocytes |
| H0251 | Human Chondrosarcoma |
| H0252 | Human Osteosarcoma |
| H0253 | Human adult testis, large inserts |
| H0254 | breast lymph node CDNA library |
| H0255 | breast lymph node CDNA library |
| H0261 | H. cerebellum, Enzyme subtracted |
| H0263 | human colon cancer |
| H0264 | human tonsils |
| H0265 | Activated T-Cell (12 hs)/Thiouridine labelledEco |
| H0266 | Human Microvascular Endothelial Cells, fract. A |
| H0267 | Human Microvascular Endothelial Cells, fract. B |
| H0268 | Human Umbilical Vein Endothelial Cells, fract. A |
| H0269 | Human Umbilical Vein Endothelial Cells, fract. B |
| H0271 | Human Neutrophil, Activated |
| H0274 | Human Adult Spleen, fractionII |
| H0280 | K562 + PMA (36 hrs) |
| H0284 | Human OB MG63 control fraction I |
| H0286 | Human OB MG63 treated (10 nM E2) fraction I |
| H0288 | Human OB HOS control fraction I |
| H0290 | Human OB HOS treated (1 nM E2) fraction I |
| H0292 | Human OB HOS treated (10 nM E2) fraction I |
| H0294 | Amniotic Cells - TNF induced |
| H0295 | Amniotic Cells - Primary Culture |
| H0305 | CD34 positive cells (Cord Blood) |
| H0306 | CD34 depleted Buffy Coat (Cord Blood) |
| H0309 | Human Chronic Synovitis |
| H0310 | human caudate nucleus |
| H0316 | HUMAN STOMACH |
| H0318 | HUMAN B CELL LYMPHOMA |
| H0320 | Human frontal cortex |
| H0321 | HUMAN SCHWANOMA |
| H0327 | human corpus colosum |
| H0328 | human ovarian cancer |
| H0329 | Dermatofibrosarcoma Protuberance |
| H0331 | Hepatocellular Tumor |
| H0333 | Hemangiopericytoma |
| H0341 | Bone Marrow Cell Line (RS4, 11) |
| H0343 | stomach cancer (human) |
| H0351 | Glioblastoma |
| H0352 | wilm's tumor |
| H0355 | Human Liver |
| H0356 | Human Kidney |
| H0357 | H. Normalized Fetal Liver, II |
| H0359 | KMH2 cell line |
| H0361 | Human rejected kidney |
| H0362 | HeLa cell line |
| H0366 | L428 cell line |
| H0370 | H. Lymph node breast Cancer |
| H0373 | Human Heart |
| H0374 | Human Brain |
| H0375 | Human Lung |
| H0381 | Bone Cancer |
| H0388 | Human Rejected Kidney, 704 re-excision |
| H0389 | H. Brain, X-Chromosome hybridization |

TABLE 4-continued

| Library Code | Library Description |
|---|---|
| H0391 | H. Meniingima, M6 |
| H0392 | H. Meningima, M1 |
| H0393 | Fetal Liver, subtraction II |
| H0396 | L1 Cell line |
| H0400 | Human Striatum Depression, re-rescue |
| H0402 | CD34 depleted Buffy Coat (Cord Blood), re-excision |
| H0403 | H. Umbilical Vein Endothelial Cells, IL4 induced |
| H0410 | H. Male bladder, adult |
| H0411 | H Female Bladder, Adult |
| H0412 | Human umbilical vein endothelial cells, IL-4 induced |
| H0413 | Human Umbilical Vein Endothelial Cells, uninduced |
| H0415 | H. Ovarian Tumor, II, OV5232 |
| H0416 | Human Neutrophils, Activated, re-excision |
| H0421 | Human Bone Marrow, re-excision |
| H0422 | T-Cell PHA 16 hrs |
| H0423 | T-Cell PHA 24 hrs |
| H0424 | Human Pituitary, subt IX |
| H0427 | Human Adipose |
| H0428 | Human Ovary |
| H0429 | K562 + PMA (36 hrs), re-excision |
| H0431 | H. Kidney Medulla, re-excision |
| H0435 | Ovarian Tumor Oct. 3, 1995 |
| H0436 | Resting T-Cell Library, II |
| H0437 | H Umbilical Vein Endothelial Cells, frac A, re-excision |
| H0438 | H. Whole Brain #2, re-excision |
| H0441 | H. Kidney Cortex, subtracted |
| H0444 | Spleen metastic melanoma |
| H0445 | Spleen, Chronic lymphocytic leukemia |
| H0448 | Salivary gland, subtracted |
| H0449 | CD34 + cell, I |
| H0453 | H. Kidney Pyramid, subtracted |
| H0457 | Human Eosinophils |
| H0458 | CD34 + cell, I, frac II |
| H0478 | Salivary Gland, Lib 2 |
| H0479 | Salivary Gland, Lib 3 |
| H0483 | Breast Cancer cell line, MDA 36 |
| H0484 | Breast Cancer Cell line, angiogenic |
| H0485 | Hodgkin's Lymphoma I |
| H0486 | Hodgkin's Lymphoma II |
| H0488 | Human Tonsils, Lib 2 |
| H0489 | Crohn's Disease |
| H0494 | Keratinocyte |
| H0497 | HEL cell line |
| H0506 | Ulcerative Colitis |
| H0509 | Liver, Hepatoma |
| H0510 | Human Liver, normal |
| H0517 | Nasal polyps |
| H0518 | pBMC stimulated w/poly I/C |
| H0519 | NTERA2, control |
| H0520 | NTERA2 + retinoic acid, 14 days |
| H0521 | Primary Dendritic Cells, lib 1 |
| H0522 | Primary Dendritic cells, frac 2 |
| H0529 | Myoloid Progenitor Cell Line |
| H0530 | Human Dermal Endothelial Cells, untreated |
| H0538 | Merkel Cells |
| H0539 | Pancreas Islet Cell Tumor |
| H0542 | T Cell helper I |
| H0543 | T cell helper II |
| H0544 | Human endometrial stromal cells |
| H0545 | Human endometrial stromal cells-treated with progesterone |
| H0546 | Human endometrial stromal cells-treated with estradiol |
| H0547 | NTERA2 teratocarcinoma cell line + retinoic acid (14 days) |
| H0549 | H. Epididiymus, caput & corpus |
| H0550 | H. Epididiymus, cauda |
| H0551 | Human Thymus Stromal Cells |
| H0553 | Human Placenta |
| H0555 | Rejected Kidney, lib 4 |
| H0556 | Activated T-cell(12 h)/Thiouridine-re-excision |
| H0560 | KMH2 |
| H0561 | L428 |
| H0569 | Human Fetal Brain, normalized CO |
| H0571 | Human Fetal Brain, normalized C500HE |
| H0574 | Hepatocellular Tumor, re-excision |
| H0575 | Human Adult Pulmonary, re-excision |
| H0576 | Resting T-Cell, re-excision |
| H0580 | Dendritic cells, pooled |
| H0581 | Human Bone Marrow, treated |

TABLE 4-continued

| Library Code | Library Description |
|---|---|
| H0583 | B Cell lymphoma |
| H0586 | Healing groin wound, 6.5 hours post incision |
| H0587 | Healing groin wound, 7.5 hours post incision |
| H0589 | CD34 positive cells (cord blood), re-ex |
| H0590 | Human adult small intestine, re-excision |
| H0591 | Human T-cell lymphoma, re-excision |
| H0592 | Healing groin wound - zero hr post-incision (control) |
| H0593 | Olfactory epithelium, nasalcavity |
| H0594 | Human Lung Cancer, re-excision |
| H0596 | Human Colon Cancer, re-excision |
| H0597 | Human Colon, re-excision |
| H0598 | Human Stomach, re-excision |
| H0599 | Human Adult Heart, re-excision |
| H0600 | Healing Abdomen wound, 70 & 90 min post incision |
| H0601 | Healing Abdomen Wound, 15 days post incision |
| H0602 | Healing Abdomen Wound, 21 & 29 days post incision |
| H0606 | Human Primary Breast Cancer, re-excision |
| H0615 | Human Ovarian Cancer Reexcision |
| H0616 | Human Testes, Reexcision |
| H0617 | Human Primary Breast Cancer Reexcision |
| H0618 | Human Adult Testes, Large Inserts, Reexcision |
| H0619 | Fetal Heart |
| H0620 | Human Fetal Kidney, Reexcision |
| H0622 | Human Pancreas Tumor, Reexcision |
| H0623 | Human Umbilical Vein, Reexcision |
| H0624 | 12 Week Early Stage Human II, Reexcision |
| H0625 | Ku 812F Basophils Line |
| H0626 | Saos2 Cells, Untreated |
| H0627 | Saos2 Cells, Vitamin D3 Treated |
| H0628 | Human Pre-Differentiated Adipocytes |
| H0631 | Saos2, Dexamethosome Treated |
| H0632 | Hepatocellular Tumor, re-excision |
| H0633 | Lung Carcinoma A549 TNFalpha activated |
| H0634 | Human Testes Tumor, re-excision |
| H0635 | Human Activated T-Cells, re-excision |
| H0637 | Dendritic Cells From CD34 Cells |
| H0638 | CD40 activated monocyte dendridic cells |
| H0640 | Ficolled Human Stromal Cells, Untreated |
| H0641 | LPS activated derived dendritic cells |
| H0642 | Hep G2 Cells, lambda library |
| H0644 | Human Placenta (re-excision) |
| H0645 | Fetal Heart, re-excision |
| H0646 | Lung, Cancer (4005313 A3): Invasive Poorly Differentiated Lung Adenocarcinoma, |
| H0647 | Lung, Cancer (4005163 B7): Invasive, Poorly Diff. Adenocarcinoma, Metastatic |
| H0648 | Ovary, Cancer: (4004562 B6) Papillary Serous Cystic Neoplasm, Low Malignant Pot |
| H0650 | B-Cells |
| H0652 | Lung, Normal: (4005313 B1) |
| H0653 | Stromal Cells |
| H0656 | B-cells (unstimulated) |
| H0657 | B-cells (stimulated) |
| H0658 | Ovary, Cancer (9809C332): Poorly differentiated adenocarcinoma |
| H0659 | Ovary, Cancer (15395A1F): Grade II Papillary Carcinoma |
| H0660 | Ovary, Cancer: (15799A1F) Poorly differentiated carcinoma |
| H0661 | Breast, Cancer: (4004943 A5) |
| H0662 | Breast, Normal: (4005522B2) |
| H0663 | Breast, Cancer: (4005522 A2) |
| H0664 | Breast, Cancer: (9806C012R) |
| H0665 | Stromal cells 3.88 |
| H0666 | Ovary, Cancer: (4004332 A2) |
| H0667 | Stromal cells (HBM3.18) |
| H0668 | stromal cell clone 2.5 |
| H0670 | Ovary, Cancer (4004650 A3): Well-Differentiated Micropapillary Serous Carcinoma |
| H0672 | Ovary, Cancer: (4004576 A8) |
| H0673 | Human Prostate Cancer, Stage B2, re-excision |
| H0674 | Human Prostate Cancer, Stage C, re-excission |
| H0676 | Colon, Cancer: (9808C064R)-total RNA |
| H0677 | TNFR degenerate oligo |
| H0679 | screened clones from Tonsil library |
| H0682 | Ovarian cancer, Serous Papillary Adenocarcinoma |
| H0683 | Ovarian cancer, Serous Papillary Adenocarcinoma |
| H0684 | Ovarian cancer, Serous Papillary Adenocarcinoma |

TABLE 4-continued

| Library Code | Library Description |
|---|---|
| H0685 | Adenocarcinoma of Ovary, Human Cell Line, # OVCAR-3 |
| H0686 | Adenocarcinoma of Ovary, Human Cell Line |
| H0687 | Human normal ovary (#9610G215) |
| H0688 | Human Ovarian Cancer (#9807G017) |
| H0689 | Ovarian Cancer |
| H0690 | Ovarian Cancer, #9702G001 |
| H0691 | Normal Ovary, #9710G208 |
| H0694 | Prostate cancer (adenocarcinoma) |
| H0695 | mononucleocytes from patient |
| H0696 | Prostate Adenocarcinoma |
| H0702 | NK15 (IL2 treated for 48 hours) |
| H0707 | Stomach Cancer (S007635) |
| L0005 | Clontech human aorta polyA + mRNA (#6572) |
| L0017 | Human (J. Swensen) |
| L0021 | Human adult (K. Okubo) |
| L0040 | Human colon mucosa |
| L0041 | Human epidermal keratinocyte |
| L0053 | Human pancreatic tumor |
| L0055 | Human promyelocyte |
| L0103 | DKFZphamy1 |
| L0105 | Human aorta polyA + (TFujiwara) |
| L0142 | Human placenta cDNA (TFujiwara) |
| L0143 | Human placenta polyA + (TFujiwara) |
| L0157 | Human fetal brain (TFujiwara) |
| L0163 | Human heart cDNA (YNakamura) |
| L0352 | Normalized infant brain, Bento Soares |
| L0361 | Stratagene ovary (#937217) |
| L0362 | Stratagene ovarian cancer (#937219) |
| L0363 | NCI_CGAP_GC2 |
| L0364 | NCI_CGAP_GC5 |
| L0366 | Stratagene schizo brain S11 |
| L0367 | NCI_CGAP_Sch1 |
| L0369 | NCI_CGAP_AA1 |
| L0372 | NCI_CGAP_Col2 |
| L0373 | NCI_CGAP_Co11 |
| L0374 | NCI_CGAP_Co2 |
| L0375 | NCI_CGAP_Kid6 |
| L0378 | NCI_CGAP_Lu1 |
| L0381 | NCI_CGAP_HN4 |
| L0382 | NCI_CGAP_Pr25 |
| L0383 | NCI_CGAP_Pr24 |
| L0384 | NCI_CGAP_Pr23 |
| L0387 | NCI_CGAP_GCB0 |
| L0388 | NCI_CGAP_HN6 |
| L0411 | 1-NIB |
| L0426 | b4HB3MA-Cot51.5-HAP-Ft |
| L0438 | normalized infant brain cDNA |
| L0439 | Soares infant brain 1NIB |
| L0447 | NHB3MK |
| L0448 | 3HFLSK20 |
| L0451 | N3HFLSK20 |
| L0455 | Human retina cDNA randomly primed sublibrary |
| L0460 | Adult heart, Lambda gt11 |
| L0462 | WATM1 |
| L0465 | TEST1, Human adult Testis tissue |
| L0471 | Human fetal heart, Lambda ZAP Express |
| L0481 | CD34 + DIRECTIONAL |
| L0483 | Human pancreatic islet |
| L0485 | STRATAGENE Human skeletal muscle cDNA library, cat. #936215. |
| L0493 | NCI_CGAP_Ov26 |
| L0498 | NCI_CGAP_HSC3 |
| L0511 | NCI_CGAP_Ov34 |
| L0512 | NCI_CGAP_Ov36 |
| L0515 | NCI_CGAP_Ov32 |
| L0517 | NCI_CGAP_Pr1 |
| L0518 | NCI_CGAP_Pr2 |
| L0519 | NCI_CGAP_Pr3 |
| L0520 | NCI_CGAP_Alv1 |
| L0521 | NCI_CGAP_Ewl |
| L0523 | NCI_CGAP_Lip2 |
| L0525 | NCI_CGAP_Li2 |
| L0526 | NCI_CGAP_Pr12 |
| L0527 | NCI_CGAP_Ov2 |
| L0529 | NCI_CGAP_Pr6 |
| L0530 | NCI_CGAP_Pr8 |
| L0532 | NCI_CGAP_Thy1 |

TABLE 4-continued

| Library Code | Library Description |
|---|---|
| L0534 | Chromosome 7 Fetal Brain cDNA Library |
| L0536 | NCI_CGAP_Br4 |
| L0539 | Chromosome 7 Placental cDNA Library |
| L0540 | NCI_CGAP_Pr10 |
| L0542 | NCI_CGAP_Pr11 |
| L0545 | NCI_CGAP_Pr4.1 |
| L0549 | NCI_CGAP_HN10 |
| L0553 | NCI_CGAP_Co22 |
| L0554 | NCI_CGAP_Li8 |
| L0560 | NCI_CGAP_HN12 |
| L0562 | Chromosome 7 HeLa cDNA Library |
| L0563 | Human Bone Marrow Stromal Fibroblast |
| L0564 | Jia bone marrow stoma |
| L0565 | Normal Human Trabecular Bone Cells |
| L0581 | Stratagene liver (#937224) |
| L0586 | HTCDL1 |
| L0588 | Stratagene endothelial cell 937223 |
| L0589 | Stratagene fetal retina 937202 |
| L0591 | Stratagene HeLa cell s3 937216 |
| L0592 | Statagene hNT neuron (#937233) |
| L0593 | Stratagene neuroepithelium (#937231) |
| L0595 | Stratagene NT2 neuronal precursor 937230 |
| L0596 | Stratagene colon (#937204) |
| L0597 | Stratagene corneal stoma (#937222) |
| L0598 | Morton Fetal Cochlea |
| L0599 | Stratagene lung (#937210) |
| L0600 | Weizmann Olfactory Epithelium |
| L0601 | Stratagene pancreas (#937208) |
| L0602 | Pancreatic Islet |
| L0603 | Stratagene placenta (#937225) |
| L0604 | Stratagene muscle 937209 |
| L0605 | Stratagene fetal spleen (#937205) |
| L0606 | NCI_CGAP_Lym5 |
| L0607 | NCI_CGAP_Lym6 |
| L0608 | Statagene lung carcinoma 937218 |
| L0612 | Schiller oligodendroglioma |
| L0615 | 22 week old human fetal liver cDNA library |
| L0622 | HM1 |
| L0623 | HM3 |
| L0626 | NCI_CGAP_GC1 |
| L0629 | NCI_CGAP_Me13 |
| L0635 | NCI_CGAP_PNS1 |
| L0636 | NCI_CGAP_Pit1 |
| L0637 | NCI_CGAP_Brn3 |
| L0638 | NCI_CGAP_Brn35 |
| L0639 | NCI_CGAP_Brn52 |
| L0640 | NCI_CGAP_Br18 |
| L0641 | NCI_CGAP_Co17 |
| L0642 | NCI_CGAP_Co18 |
| L0644 | NCI_CGAP_Co20 |
| L0645 | NCI_CGAP_Co21 |
| L0646 | NCI_GGAP_Co14 |
| L0647 | NCI_CGAP_Sar4 |
| L0648 | NCI_CGAP_Eso2 |
| L0649 | NCI_CGAP_GU1 |
| L0650 | NCI_CGAP_Kid13 |
| L0651 | NCI_CGAP_Kid8 |
| L0653 | NCI_CGAP_Lu28 |
| L0654 | NCI_CGAP_Lu31 |
| L0655 | NCI_CGAP_Lym12 |
| L0656 | NCI_CGAP_Ov38 |
| L0657 | NCI_CGAP_Ov23 |
| L0658 | NCI_CGAP_Ov35 |
| L0659 | NCI_CGAP_Pan1 |
| L0661 | NGI_CGAP_Mel15 |
| L0662 | NCI_CGAP_Gas4 |
| L0663 | NCI_CGAP_Ut2 |
| L0664 | NCI_CGAP_Ut3 |
| L0665 | NCI_CGAP_Ut4 |
| L0666 | NCI_CGAP_Ut1 |
| L0667 | NCI_CGAP_CML1 |
| L0682 | Stanley Frontal NB pool 2 |
| L0697 | Testis 1 |
| L0717 | Gessler Wilms tumor |
| L0731 | Soares_pregnant_uterus_NbHPU |
| L0738 | Human colorectal cancer |
| L0740 | Soares melanocyte 2NbHM |

TABLE 4-continued

| Library Code | Library Description |
|---|---|
| L0741 | Soares adult brain N2b4HB55Y |
| L0742 | Soares adult brain N2b5HB55Y |
| L0743 | Soares breast 2NbHBst |
| L0744 | Soares breast 3NbHBst |
| L0745 | Soares retina N2b4HR |
| L0746 | Soares retina N2b5HR |
| L0747 | Soares_fetal_heart_NbHH19W |
| L0748 | Soares fetal liver spleen 1NFLS |
| L0749 | Soares_fetal_liver_spleen_1NFLS_S1 |
| L0750 | Soares_fetal_lung_NbHL19W |
| L0751 | Soares ovary tumor NbHOT |
| L0752 | Soares_parathyroid_tumor_NbHPA |
| L0753 | Soares_pineal_gland_N3HPG |
| L0754 | Soares placenta Nb2HP |
| L0755 | Soares_placenta_8to9weeks_2NbHP8to9W |
| L0756 | Soares_multiple_sclerosis_2NbHMSP |
| L0757 | Soares_senescent_fibroblasts_NbHSF |
| L0758 | Soares_testis_NHT |
| L0759 | Soares_total_fetus_Nb2HF8_9w |
| L0761 | NCI_CGAP_CLL1 |
| L0762 | NCI_CGAP_Br1.1 |
| L0763 | NCI_CGAP_Br2 |
| L0764 | NCI_CGAP_Co3 |
| L0765 | NCI_CGAP_Co4 |
| L0766 | NCI_CGAP_GCB1 |
| L0767 | NCI_CGAP_GC3 |
| L0768 | NCI_CGAP_GC4 |
| L0769 | NCI_CGAP_Brn25 |
| L0770 | NCI_CGAP_Brn23 |
| L0771 | NCI_CGAP_Co8 |
| L0772 | NCI_CGAP_Co10 |
| L0773 | NCI_CGAP_Co9 |
| L0774 | NCI_CGAP_Kid3 |
| L0775 | NCI_CGAP_Kid5 |
| L0776 | NCI_CGAP_Lu5 |
| L0777 | Soares_NhHMPu_S1 |
| L0779 | Soares_NFL_T_GBC_S1 |
| L0780 | Soares_NSF_F8_9W_OT_PA_P_S1 |
| L0782 | NCI_CGAP_Pr21 |
| L0783 | NCI_CGAP_Pr22 |
| L0785 | Barstead spleen HPLRB2 |
| L0786 | Soares_NbHFB |
| L0788 | NCI_CGAP_Sub2 |
| L0789 | NCI_CGAP_Sub3 |
| L0790 | NCI_CGAP_Sub4 |
| L0791 | NCI_CGAP_Sub5 |
| L0792 | NCI_CGAP_Sub6 |
| L0794 | NCI_CGAP_GC6 |
| L0796 | NCI_CGAP_Brn50 |
| L0800 | NCI_CGAP_Co16 |
| L0803 | NCI_CGAP_Kid11 |
| L0804 | NCI_CGAP_Kid12 |
| L0805 | NCI_CGAP_Lu24 |
| L0806 | NCI_CGAP_Lu19 |
| L0807 | NCI_CGAP_Ov18 |
| L0809 | NCI_CGAP_Pr28 |
| S0001 | Brain frontal cortex |
| S0002 | Monocyte activated |
| S0003 | Human Osteoclastoma |
| S0007 | Early Stage Human Brain |
| S0010 | Human Amygdala |
| S0011 | STROMAL-OSTEOCLASTOMA |
| S0013 | Prostate |
| S0014 | Kidney Cortex |
| S0015 | Kidney medulla |
| S0022 | Human Osteoclastoma Stromal Cells - unamplified |
| S0026 | Stromal cell TF274 |
| S0027 | Smooth muscle, serum treated |
| S0028 | Smooth muscle, control |
| S0029 | brain stem |
| S0030 | Brain pons |
| S0031 | Spinal cord |
| S0032 | Smooth muscle-ILb induced |
| S0036 | Human Substantia Nigra |
| S0037 | Smooth muscle, IL1b induced |
| S0038 | Human Whole Brain #2 - Oligo dT > 1.5 Kb |
| S0040 | Adipocytes |

TABLE 4-continued

| Library Code | Library Description |
|---|---|
| S0042 | Testes |
| S0044 | Prostate BPH |
| S0045 | Endothelial cells-control |
| S0046 | Endothelial-induced |
| S0049 | Human Brain, Striatum |
| S0050 | Human Frontal Cortex, Schizophrenia |
| S0051 | Human Hypothalmus, Schizophrenia |
| S0052 | neutrophils control |
| S0053 | Neutrophils IL-1 and LPS induced |
| S0112 | Hypothalamus |
| S0114 | Anergic T-cell |
| S0116 | Bone marrow |
| S0122 | Osteoclastoma-normalized A |
| S0126 | Osteoblasts |
| S0132 | Epithelial-TNFa and INF induced |
| S0134 | Apoptotic T-cell |
| S0136 | PERM TF274 |
| S0140 | eosinophil-IL5 induced |
| S0142 | Macrophage-oxLDL |
| S0144 | Macrophage (GM-CSF treated) |
| S0146 | prostate-edited |
| S0150 | LNCAP prostate cell line |
| S0152 | PC3 Prostate cell line |
| S0176 | Prostate, normal, subtraction I |
| S0192 | Synovial Fibroblasts (control) |
| S0194 | Synovial hypoxia |
| S0196 | Synovial IL-1/TNF stimulated |
| S0198 | 7TM-pbfd |
| S0206 | Smooth Muscle- HASTE normalized |
| S0208 | Messangial cell, frac 1 |
| S0210 | Messangial cell, frac 2 |
| S0212 | Bone Marrow Stromal Cell, untreated |
| S0214 | Human Osteoclastoma, re-excision |
| S0216 | Neutrophils IL-1 and LPS induced |
| S0218 | Apoptotic T-cell, re-excision |
| S0220 | H. hypothalamus, frac A, re-excision |
| S0222 | H. Frontal cortex, epileptic, re-excision |
| S0228 | PSMIX |
| S0242 | Synovial Fibroblasts (Il1/TNF), subt |
| S0250 | Human Osteoblasts II |
| S0252 | 7TM-PIMIX |
| S0260 | Spinal Cord, re-excision |
| S0264 | PPMIX |
| S0268 | PRMIX |
| S0270 | PTMIX |
| S0274 | PCMIX |
| S0276 | Synovial hypoxia-RSF subtracted |
| S0278 | H Macrophage (GM-CSF treated), re-excision |
| S0280 | Human Adipose Tissue, re-excision |
| S0282 | Brain Frontal Cortex, re-excision |
| S0294 | Larynx tumor |
| S0300 | Frontal lobe, dementia, re-excision |
| S0312 | Human osteoarthritic, fraction II |
| S0314 | Human osteoarthritis, fraction I |
| S0316 | Human Normal Cartilage, Fraction I |
| S0318 | Human Normal Cartilage Fraction II |
| S0328 | Palate carcinoma |
| S0330 | Palate normal |
| S0332 | Pharynx carcinoma |
| S0334 | Human Normal Cartilage Fraction III |
| S0338 | Human Osteoarthritic Cartilage Fraction III |
| S0342 | Adipocytes, re-excision |
| S0344 | Macrophage-oxLDL, re-excision |
| S0346 | Human Amygdala, re-excision |
| S0348 | Cheek Carcinoma |
| S0350 | Pharynx Carcinoma |
| S0352 | Larynx Carcinoma |
| S0354 | Colon Normal II |
| S0356 | Colon Carcinoma |
| S0358 | Colon Normal III |
| S0360 | Colon Tumor II |
| S0364 | Human Quadriceps |
| S0366 | Human Soleus |
| S0374 | Normal colon |
| S0376 | Colon Tumor |
| S0378 | Pancreas normal PCA4 No |
| S0380 | Pancreas Tumor PCA4 Tu |

TABLE 4-continued

| Library Code | Library Description |
|---|---|
| S0384 | Tongue carcinoma |
| S0388 | Human Hypothalamus, schizophrenia, re-excision |
| S0390 | Smooth muscle, control, re-excision |
| S0392 | Salivary Gland |
| S0402 | Adrenal Gland, normal |
| S0412 | Temporal cortex-Alzheizmer, subtracted |
| S0414 | Hippocampus, Alzheimer Subtracted |
| S0418 | CHME Cell Line, treated 5 hrs |
| S0420 | CHME Cell Line, untreated |
| S0422 | Mo7e Cell Line GM-CSF treated (1 ng/ml) |
| S0424 | TF-1 Cell Line GM-CSF Treated |
| S0426 | Monocyte activated, re-excision |
| S0428 | Neutrophils control, re-excision |
| S0430 | Aryepiglottis Normal |
| S0432 | Sinus piniformis Tumour |
| S0434 | Stomach Normal |
| S0438 | Liver Normal Met5No |
| S0442 | Colon Normal |
| S0446 | Tongue Tumour |
| S0450 | Larynx Tumour |
| S0452 | Thymus |
| S0456 | Tongue Normal |
| S0458 | Thyroid Normal (SDCA2 No) |
| S0462 | Thyroid Thyroiditis |
| S0466 | Larynx Tumor |
| S0468 | Ea.hy.926 cell line |
| S0474 | Human blood platelets |
| S3012 | Smooth Muscle Serum Treated, Norm |
| S3014 | Smooth muscle, serum induced, re-exc |
| S6014 | H. hypothalamus, frac A |
| S6024 | Alzheimers, spongy change |
| S6028 | Human Manic Depression Tissue |
| T0002 | Activated T-cells |
| T0003 | Human Fetal Lung |
| T0004 | Human White Fat |
| T0006 | Human Pineal Gland |
| T0008 | Colorectal Tumor |
| T0010 | Human Infant Brain |
| T0023 | Human Pancreatic Carcinoma |
| T0039 | HSA 172 Cells |
| T0040 | HSC172 cells |
| T0041 | Jurkat T-cell G1 phase |
| T0042 | Jurkat T-Cell, S phase |
| T0048 | Human Aortic Endothelium |
| T0049 | Aorta endothelial cells + TNF-a |
| T0060 | Human White Adipose |
| T0067 | Human Thyroid |
| T0069 | Human Uterus, normal |
| T0082 | Human Adult Retina |
| T0091 | Liver, hepatocellular carcinoma |
| T0109 | Human (HCC) cell line liver (mouse) metastasis, remake |
| T0110 | Human colon carcinoma (HCC) cell line, remake |
| T0114 | Human (Caco-2) cell line, adenocarcinoma, colon, remake |

TABLE 5

| OMIM ID | OMIM Description |
|---|---|
| 103000 | Hemolytic anemia due to adenylate kinase deficiency (3) |
| 104770 | ?Amyloidosis, secondary, susceptibility to (1) |
| 107670 | Apolipoprotein A-II deficiency (3) |
| 110700 | Vivax malaria, susceptibility to (1) |
| 114350 | Leukemia, acute myeloid (2) |
| 114835 | Monocyte carboxyesterase deficiency (1) (?) |
| 120900 | C5 deficiency (1) |
| 131195 | Hereditary hemorrhagic telangiectasia-1, 187300 (3) |
| 132700 | Cylindromatosis (2) |
| 135940 | Ichthyosis vulgaris, 146700 (1) (?) |
| 145001 | Hyperparathyroidism-jaw tumor syndrome (2) |
| 146150 | Hypomelanosis of Ito (2) (?) |
| 146790 | Lupus nephritis, susceptibility to (3) |
| 152445 | Erythrokeratoderma, progressive symmetric, 602036 (3) |
| | Vohwinkel syndrome, 124500 (3) |
| 159001 | Muscular dystrophy, limb-girdle, type 1B (2) |

TABLE 5-continued

| OMIM ID | OMIM Description |
|---|---|
| 172490 | Phosphorylase kinase deficiency of liver and muscle, 261750 (2) (?) |
| 174000 | Medullary cystic kidney disease, AD (2) |
| 179755 | Renal cell carcinoma, papillary, 1 (2) |
| 182860 | Elliptocytosis-2 (3) |
| | Pyropoikilocytosis (3) |
| | Spherocytosis, recessive (3) |
| 185000 | Stomatocytosis I (1) (?) |
| 189980 | Leukemia, chronic myeloid (3) |
| 191315 | Insensitivity to pain, congenital, with anhidrosis, 256800 (3) |
| 223900 | Dysautonomia, familial (2) |
| 230800 | Gaucher disease (3) |
| | Gaucher disease with cardiovascular calcification (3) |
| 253800 | Fukuyama type congenital muscular dystrophy (2) |
| | Walker-Warburg syndrome, 236670 (2) (?) |
| 266200 | Anemia, hemolytic, due to PK deficiency (3) |
| 268900 | [Sarcosinemia] (2) |
| 600184 | Carnitine acetyltransferase deficiency (1) (?) |
| 600897 | Cataract, zonular pulverulent-1, 116200 (3) |
| 600968 | Gitelman syndrome, 263800 (3) |
| 601105 | Pycnodysostosis, 265800 (3) |
| 601412 | Deafness, autosomal dominant 7 (2) |
| 601652 | Glaucoma 1A, primary open angle, juvenile-onset, 137750 (3) |
| 602491 | Hyperlipidemia, familial combined, 1 (2) |
| 602575 | Nail-patella syndrome with open-angle glaucoma, 137750 (3) |
| | Nail-patella syndrome, 161200 (3) |

The polypeptides of the invention can be prepared in any suitable manner. Such polypeptides include isolated naturally occurring polypeptides, recombinantly produced polypeptides, synthetically produced polypeptides, or polypeptides produced by a combination of these methods. Means for preparing such polypeptides are well understood in the art.

The polypeptides may be in the form of the secreted protein, including the mature form, or may be a part of a larger protein, such as a fusion protein (see below). It is often advantageous to include an additional amino acid sequence which contains secretory or leader sequences, pro-sequences, sequences which aid in purification, such as multiple histidine residues, or an additional sequence for stability during recombinant production.

The polypeptides of the present invention are preferably provided in an isolated form, and preferably are substantially purified. A recombinantly produced version of a polypeptide, including the secreted polypeptide, can be substantially purified using techniques described herein or otherwise known in the art, such as, for example, by the one-step method described in Smith and Johnson, Gene 67:31-40 (1988). Polypeptides of the invention also can be purified from natural, synthetic or recombinant sources using techniques described herein or otherwise known in the art, such as, for example, antibodies of the invention raised against the secreted protein.

The present invention provides a polynucleotide comprising, or alternatively consisting of, the nucleic acid sequence of SEQ ID NO:X, and/or a cDNA contained in ATCC deposit Z. The present invention also provides a polypeptide comprising, or alternatively, consisting of, the polypeptide sequence of SEQ ID NO:Y and/or a polypeptide encoded by the cDNA contained in ATCC deposit Z. Polynucleotides encoding a polypeptide comprising, or alternatively consisting of the polypeptide sequence of SEQ ID NO:Y and/or a polypeptide sequence encoded by the cDNA contained in ATCC deposit Z are also encompassed by the invention.

Signal Sequences

The present invention also encompasses mature forms of the polypeptide having the polypeptide sequence of SEQ ID NO:Y and/or the polypeptide sequence encoded by the cDNA in a deposited clone. Polynucleotides encoding the mature forms (such as, for example, the polynucleotide sequence in SEQ ID NO:X and/or the polynucleotide sequence contained in the cDNA of a deposited clone) are also encompassed by the invention. According to the signal hypothesis, proteins secreted by mammalian cells have a signal or secretary leader sequence which is cleaved from the mature protein once export of the growing protein chain across the rough endoplasmic reticulum has been initiated. Most mammalian cells and even insect cells cleave secreted proteins with the same specificity. However, in some cases, cleavage of a secreted protein is not entirely uniform, which results in two or more mature species of the protein. Further, it has long been known that cleavage specificity of a secreted protein is ultimately determined by the primary structure of the complete protein, that is, it is inherent in the amino acid sequence of the polypeptide.

Methods for predicting whether a protein has a signal sequence, as well as the cleavage point for that sequence, are available. For instance, the method of McGeoch, Virus Res. 3:271-286 (1985), uses the information from a short N-terminal charged region and a subsequent uncharged region of the complete (uncleaved) protein. The method of von Heinje, Nucleic Acids Res. 14:4683-4690 (1986) uses the information from the residues surrounding the cleavage site, typically residues −13 to +2, where +1 indicates the amino terminus of the secreted protein. The accuracy of predicting the cleavage points of known mammalian secretory proteins for each of these methods is in the range of 75-80%. (von Heinje, supra.) However, the two methods do not always produce the same predicted cleavage point(s) for a given protein.

In the present case, the deduced amino acid sequence of the secreted polypeptide was analyzed by a computer program called SignalP (Henrik Nielsen et al., Protein Engineering 10:1-6 (1997)), which predicts the cellular location of a protein based on the amino acid sequence. As part of this computational prediction of localization, the methods of McGeoch and von Heinje are incorporated. The analysis of the amino acid sequences of the secreted proteins described herein by this program provided the results shown in Table 1.

As one of ordinary skill would appreciate, however, cleavage sites sometimes vary from organism to organism and cannot be predicted with absolute certainty. Accordingly, the present invention provides secreted polypeptides having a sequence shown in SEQ ID NO:Y which have an N-terminus beginning within 5 residues (i.e., + or −5 residues) of the predicted cleavage point. Similarly, it is also recognized that in some cases, cleavage of the signal sequence from a secreted protein is not entirely uniform, resulting in more than one secreted species. These polypeptides, and the polynucleotides encoding such polypeptides, are contemplated by the present invention.

Moreover, the signal sequence identified by the above analysis may not necessarily predict the naturally occurring signal sequence. For example, the naturally occurring signal sequence may be further upstream from the predicted signal sequence. However, it is likely that the predicted signal sequence will be capable of directing the secreted protein to the ER. Nonetheless, the present invention provides the mature protein produced by expression of the polynucleotide sequence of SEQ ID NO:X and/or the polynucleotide sequence contained in the cDNA of a deposited clone, in a mammalian cell (e.g., COS cells, as described below). These polypeptides, and the polynucleotides encoding such polypeptides, are contemplated by the present invention.

Polynucleotide and Polypeptide Variants

The present invention is directed to variants of the polynucleotide sequence disclosed in SEQ ID NO:X, the complementary strand thereto, and/or the cDNA sequence contained in a deposited clone.

The present invention also encompasses variants of the polypeptide sequence disclosed in SEQ ID NO:Y and/or encoded by a deposited clone.

"Variant" refers to a polynucleotide or polypeptide differing from the polynucleotide or polypeptide of the present invention, but retaining essential properties thereof. Generally, variants are overall closely similar, and, in many regions, identical to the polynucleotide or polypeptide of the present invention.

The present invention is also directed to nucleic acid molecules which comprise, or alternatively consist of, a nucleotide sequence which is at least 80%, 85%, 90%, 95%, 96%, 97%, 98% or 99% identical to, for example, the nucleotide coding sequence in SEQ ID NO:X or the complementary strand thereto, the nucleotide coding sequence contained in a deposited cDNA clone or the complementary strand thereto, a nucleotide sequence encoding the polypeptide of SEQ ID NO:Y, a nucleotide sequence encoding the polypeptide encoded by the cDNA contained in a deposited clone, and/or polynucleotide fragments of any of these nucleic acid molecules (e.g., those fragments described herein). Polynucleotides which hybridize to these nucleic acid molecules under stringent hybridization conditions or lower stringency conditions are also encompassed by the invention, as are polypeptides encoded by these polynucleotides.

The present invention is also directed to polypeptides which comprise, or alternatively consist of, an amino acid sequence which is at least 80%, 85%, 90%, 95%, 96%, 97%, 98%, 99% identical to, for example, the polypeptide sequence shown in SEQ ID NO:Y, the polypeptide sequence encoded by the cDNA contained in a deposited clone, and/or polypeptide fragments of any of these polypeptides (e.g., those fragments described herein).

By a nucleic acid having a nucleotide sequence at least, for example, 95% "identical" to a reference nucleotide sequence of the present invention, it is intended that the nucleotide sequence of the nucleic acid is identical to the reference sequence except that the nucleotide sequence may include up to five point mutations per each 100 nucleotides of the reference nucleotide sequence encoding the polypeptide. In other words, to obtain a nucleic acid having a nucleotide sequence at least 95% identical to a reference nucleotide sequence, up to 5% of the nucleotides in the reference sequence may be deleted or substituted with another nucleotide, or a number of nucleotides up to 5% of the total nucleotides in the reference sequence may be inserted into the reference sequence. The query sequence may be an entire sequence shown in Table 1, the ORF (open reading frame), or any fragment specified as described herein.

As a practical matter, whether any particular nucleic acid molecule or polypeptide is at least 80%, 85%, 90%, 95%, 96%, 97%, 98% or 99% identical to a nucleotide sequence of the presence invention can be determined conventionally using known computer programs. A preferred method for determining the best overall match between a query sequence (a sequence of the present invention) and a subject sequence, also referred to as a global sequence alignment, can be determined using the FASTDB computer program based on the algorithm of Brutlag et al. (Comp. App. Biosci. 6:237-245 (1990)). In a sequence alignment the query and subject sequences are both DNA sequences. An RNA sequence can be compared by converting U's to T's. The result of said global sequence alignment is in percent identity. Preferred parameters used in a FASTDB alignment of DNA sequences to calculate percent identiy are: Matrix=Unitary, k-tuple=4, Mismatch Penalty=1, Joining Penalty=30, Randomization Group Length=0, Cutoff Score=1, Gap Penalty=5, Gap Size Penalty 0.05, Window Size=500 or the length of the subject nucleotide sequence, whichever is shorter.

If the subject sequence is shorter than the query sequence because of 5' or 3' deletions, not because of internal deletions, a manual correction must be made to the results. This is because the FASTDB program does not account for 5' and 3' truncations of the subject sequence when calculating percent identity. For subject sequences truncated at the 5' or 3' ends, relative to the query sequence, the percent identity is corrected by calculating the number of bases of the query sequence that are 5' and 3' of the subject sequence, which are not matched/aligned, as a percent of the total bases of the query sequence. Whether a nucleotide is matched/aligned is determined by results of the FASTDB sequence alignment. This percentage is then subtracted from the percent identity, calculated by the above FASTDB program using the specified parameters, to arrive at a final percent identity score. This corrected score is what is used for the purposes of the present invention. Only bases outside the 5' and 3' bases of the subject sequence, as displayed by the FASTDB alignment, which are not matched/aligned with the query sequence, are calculated for the purposes of manually adjusting the percent identity score.

For example, a 90 base subject sequence is aligned to a 100 base query sequence to determine percent identity. The deletions occur at the 5' end of the subject sequence and therefore, the FASTDB alignment does not show a matched/alignment of the first 10 bases at 5' end. The 10 unpaired bases represent 10% of the sequence (number of bases at the 5' and 3' ends not matched/total number of bases in the query sequence) so 10% is subtracted from the percent identity score calculated by the FASTDB program. If the remaining 90 bases were perfectly matched the final percent identity would be 90%. In another example, a 90 base subject sequence is compared with a 100 base query sequence. This time the deletions are internal deletions so that there are no bases on the 5' or 3' of the subject sequence which are not matched/aligned with the query. In this case the percent identity calculated by FASTDB is not manually corrected. Once again, only bases 5' and 3' of the subject sequence which are not matched/aligned with the query sequence are manually corrected for. No other manual corrections are to made for the purposes of the present invention.

By a polypeptide having an amino acid sequence at least, for example, 95% "identical" to a query amino acid sequence of the present invention, it is intended that the amino acid sequence of the subject polypeptide is identical to the query sequence except that the subject polypeptide sequence may include up to five amino acid alterations per each 100 amino acids of the query amino acid sequence. In other words, to obtain a polypeptide having an amino acid sequence at least 95% identical to a query amino acid sequence, up to 5% of the amino acid residues in the subject sequence may be inserted, deleted, (indels) or substituted with another amino acid. These alterations of the reference sequence may occur at the amino or carboxy terminal positions of the reference amino acid sequence or anywhere between those terminal positions, interspersed either individually among residues in the reference sequence or in one or more contiguous groups within the reference sequence.

As a practical matter, whether any particular polypeptide is at least 80%, 85%, 90%, 95%, 96%, 97%, 98% or 99% identical to, for instance, an amino acid sequences shown in Table 1 (SEQ ID NO:Y) or to the amino acid sequence encoded by cDNA contained in a deposited clone can be determined conventionally using known computer programs. A preferred method for determining the best overall match between a query sequence (a sequence of the present invention) and a subject sequence, also referred to as a global sequence alignment, can be determined using the FASTDB computer program based on the algorithm of Brutlag et al. (Comp. App. Biosci. 6:237-245 (1990)). In a sequence alignment the query and subject sequences are either both nucleotide sequences or both amino acid sequences. The result of said global sequence alignment is in percent identity. Preferred parameters used in a FASTDB amino acid alignment are: Matrix=PAM 0, k-tuple=2, Mismatch Penalty=1, Joining Penalty=20, Randomization Group Length=0, Cutoff Score=1, Window Size=sequence length, Gap Penalty=5, Gap Size Penalty=0.05, Window Size=500 or the length of the subject amino acid sequence, whichever is shorter.

If the subject sequence is shorter than the query sequence due to N- or C-terminal deletions, not because of internal deletions, a manual correction must be made to the results. This is because the FASTDB program does not account for N- and C-terminal truncations of the subject sequence when calculating global percent identity. For subject sequences truncated at the N- and C-termini, relative to the query sequence, the percent identity is corrected by calculating the number of residues of the query sequence that are N- and C-terminal of the subject sequence, which are not matched/aligned with a corresponding subject residue, as a percent of the total bases of the query sequence. Whether a residue is matched/aligned is determined by results of the FASTDB sequence alignment. This percentage is then subtracted from the percent identity, calculated by the above FASTDB program using the specified parameters, to arrive at a final percent identity score. This final percent identity score is what is used for the purposes of the present invention. Only residues to the N- and C-termini of the subject sequence, which are not matched/aligned with the query sequence, are considered for the purposes of manually adjusting the percent identity score. That is, only query residue positions outside the farthest N- and C-terminal residues of the subject sequence.

For example, a 90 amino acid residue subject sequence is aligned with a 100 residue query sequence to determine percent identity. The deletion occurs at the N-terminus of the subject sequence and therefore, the FASTDB alignment does not show a matching/alignment of the first 10 residues at the N-terminus. The 10 unpaired residues represent 10% of the sequence (number of residues at the N- and C-termini not matched/total number of residues in the query sequence) so 10% is subtracted from the percent identity score calculated by the FASTDB program. If the remaining 90 residues were perfectly matched the final percent identity would be 90%. In another example, a 90 residue subject sequence is compared with a 100 residue query sequence. This time the deletions are internal deletions so there are no residues at the N- or C-termini of the subject sequence which are not matched/aligned with the query. In this case the percent identity calculated by FASTDB is not manually corrected. Once again, only residue positions outside the N- and C-terminal ends of the subject sequence, as displayed in the FASTDB alignment, which are not matched/aligned with the query sequence are manually corrected for. No other manual corrections are to made for the purposes of the present invention.

The variants may contain alterations in the coding regions, non-coding regions, or both. Especially preferred are polynucleotide variants containing alterations which produce silent substitutions, additions, or deletions, but do not alter the properties or activities of the encoded polypeptide. Nucleotide variants produced by silent substitutions due to the degeneracy of the genetic code are preferred. Moreover, variants in which 5-10, 1-5, or 1-2 amino acids are substituted, deleted, or added in any combination are also preferred. Polynucleotide variants can be produced for a variety of reasons, e.g., to optimize codon expression for a particular host (change codons in the human mRNA to those preferred by a bacterial host such as *E. coli*).

Naturally occurring variants are called "allelic variants," and refer to one of several alternate forms of a gene occupying a given locus on a chromosome of an organism. (Genes II, Lewin, B., ed., John Wiley & Sons, New York (1985).) These allelic variants can vary at either the polynucleotide and/or polypeptide level and are included in the present invention. Alternatively, non-naturally occurring variants may be produced by mutagenesis techniques or by direct synthesis.

Using known methods of protein engineering and recombinant DNA technology, variants may be generated to improve or alter the characteristics of the polypeptides of the present invention. For instance, one or more amino acids can be deleted from the N-terminus or C-terminus of the secreted protein without substantial loss of biological function. The authors of Ron et al., J. Biol. Chem. 268: 2984-2988 (1993), reported variant KGF proteins having heparin binding activity even after deleting 3, 8, or 27 amino-terminal amino acid residues. Similarly, Interferon gamma exhibited up to ten times higher activity after deleting 8-10 amino acid residues from the carboxy terminus of this protein. (Dobeli et al., J. Biotechnology 7:199-216 (1988).)

Moreover, ample evidence demonstrates that variants often retain a biological activity similar to that of the naturally occurring protein. For example, Gayle and coworkers (J. Biol. Chem 268:22105-22111 (1993)) conducted extensive mutational analysis of human cytokine IL-1a. They used random mutagenesis to generate over 3,500 individual IL-1a mutants that averaged 2.5 amino acid changes per variant over the entire length of the molecule. Multiple mutations were examined at every possible amino acid position. The investigators found that "[m]ost of the molecule could be altered with little effect on either [binding or biological activity]." (See, Abstract.) In fact, only 23 unique amino acid sequences, out of more than 3,500 nucleotide sequences examined, produced a protein that significantly differed in activity from wild-type.

Furthermore, even if deleting one or more amino acids from the N-terminus or C-terminus of a polypeptide results in modification or loss of one or more biological functions, other biological activities may still be retained. For example, the ability of a deletion variant to induce and/or to bind antibodies which recognize the secreted form will likely be retained when less than the majority of the residues of the secreted form are removed from the N-terminus or C-terminus. Whether a particular polypeptide lacking N- or C-terminal residues of a protein retains such immunogenic activities can readily be determined by routine methods described herein and otherwise known in the art.

Thus, the invention further includes polypeptide variants which show substantial biological activity. Such variants include deletions, insertions, inversions, repeats, and substitutions selected according to general rules known in the art so as have little effect on activity. For example, guidance concerning how to make phenotypically silent amino acid substitutions is provided in Bowie et al., Science 247:1306-1310 (1990), wherein the authors indicate that there are two main strategies for studying the tolerance of an amino acid sequence to change.

The first strategy exploits the tolerance of amino acid substitutions by natural selection during the process of evolution. By comparing amino acid sequences in different species, conserved amino acids can be identified. These conserved amino acids are likely important for protein function. In contrast, the amino acid positions where substitutions have been tolerated by natural selection indicates that these positions are not critical for protein function. Thus, positions tolerating amino acid substitution could be modified while still maintaining biological activity of the protein.

The second strategy uses genetic engineering to introduce amino acid changes at specific positions of a cloned gene to identify regions critical for protein function. For example, site directed mutagenesis or alanine-scanning mutagenesis (introduction of single alanine mutations at every residue in the molecule) can be used. (Cunningham and Wells, Science 244:1081-1085 (1989).) The resulting mutant molecules can then be tested for biological activity.

As the authors state, these two strategies have revealed that proteins are surprisingly tolerant of amino acid substitutions. The authors further indicate which amino acid changes are likely to be permissive at certain amino acid positions in the protein. For example, most buried (within the tertiary structure of the protein) amino acid residues require nonpolar side chains, whereas few features of surface side chains are generally conserved. Moreover, tolerated conservative amino acid substitutions involve replacement of the aliphatic or hydrophobic amino acids Ala, Val, Leu and Ile; replacement of the hydroxyl residues Ser and Thr; replacement of the acidic residues Asp and Glu; replacement of the amide residues Asn and Gln, replacement of the basic residues Lys, Arg, and His; replacement of the aromatic residues Phe, Tyr, and Trp, and replacement of the small-sized amino acids Ala, Ser, Thr, Met, and Gly.

Besides conservative amino acid substitution, variants of the present invention include (i) substitutions with one or more of the non-conserved amino acid residues, where the substituted amino acid residues may or may not be one encoded by the genetic code, or (ii) substitution with one or more of amino acid residues having a substituent group, or (iii) fusion of the mature polypeptide with another compound, such as a compound to increase the stability and/or solubility of the polypeptide (for example, polyethylene glycol), or (iv) fusion of the polypeptide with additional amino acids, such as, for example, an IgG Fc fusion region peptide, or leader or secretory sequence, or a sequence facilitating purification. Such variant polypeptides are deemed to be within the scope of those skilled in the art from the teachings herein.

For example, polypeptide variants containing amino acid substitutions of charged amino acids with other charged or neutral amino acids may produce proteins with improved characteristics, such as less aggregation. Aggregation of pharmaceutical formulations both reduces activity and increases clearance due to the aggregate's immunogenic activity. (Pinckard et al., Clin. Exp. Immunol. 2:331-340 (1967); Robbins et al., Diabetes 36: 838-845 (1987); Cleland et al., Crit. Rev. Therapeutic Drug Carrier Systems 10:307-377 (1993).)

A further embodiment of the invention relates to a polypeptide which comprises the amino acid sequence of the present invention having an amino acid sequence which contains at least one amino acid substitution, but not more than 50 amino acid substitutions, even more preferably, not more than 40 amino acid substitutions, still more preferably, not more than 30 amino acid substitutions, and still even more preferably, not more than 20 amino acid substitutions. Of course, in order of ever-increasing preference, it is highly preferable for a peptide or polypeptide to have an amino acid sequence which comprises the amino acid sequence of the present invention, which contains at least one, but not more than 10, 9, 8, 7, 6, 5, 4, 3, 2 or 1 amino acid substitutions. In specific embodiments, the number of additions, substitutions, and/or deletions in the amino acid sequence of the present invention or fragments thereof (e.g., the mature form and/or other fragments described herein), is 1-5, 5-10, 5-25, 5-50, 10-50 or 50-150, conservative amino acid substitutions are preferable.

Polynucleotide and Polypeptide Fragments

The present invention is also directed to polynucleotide fragments of the polynucleotides of the invention.

In the present invention, a "polynucleotide fragment" refers to a short polynucleotide having a nucleic acid sequence which: is a portion of that contained in a deposited clone, or encoding the polypeptide encoded by the cDNA in a deposited clone; is a portion of that shown in SEQ ID NO:X or the complementary strand thereto, or is a portion of a polynucleotide sequence encoding the polypeptide of SEQ ID NO:Y. The nucleotide fragments of the invention are preferably at least about 15 nt, and more preferably at least about 20 nt, still more preferably at least about 30 nt, and even more preferably, at least about 40 nt, at least about 50 nt, at least about 75 nt, or at least about 150 nt in length. A fragment "at least 20 nt in length," for example, is intended to include 20 or more contiguous bases from the cDNA sequence contained in a deposited clone or the nucleotide sequence shown in SEQ ID NO:X. In this context "about" includes the particularly recited value, a value larger or smaller by several (5, 4, 3, 2, or 1) nucleotides, at either terminus or at both termini. These nucleotide fragments have uses that include, but are not limited to, as diagnostic probes and primers as discussed herein. Of course, larger fragments (e.g., 50, 150, 500, 600, 2000 nucleotides) are preferred.

Moreover, representative examples of polynucleotide fragments of the invention, include, for example, fragments comprising, or alternatively consisting of, a sequence from about nucleotide number 1-50, 51-100, 101-150, 151-200, 201-250, 251-300, 301-350, 351-400, 401-450, 451-500, 501-550, 551-600, 651-700, 701-750, 751-800, 800-850, 851-900, 901-950, 951-1000, 1001-1050, 1051-1100, 1101-1150, 1151-1200, 1201-1250, 1251-1300, 1301-1350, 1351-1400, 1401-1450, 1451-1500, 1501-1550, 1551-1600, 1601-1650, 1651-1700, 1701-1750, 1751-1800, 1801-1850, 1851-1900, 1901-1950, 1951-2000, or 2001 to the end of SEQ ID NO:X, or the complementary strand thereto, or the cDNA contained in a deposited clone. In this context "about" includes the particularly recited ranges, and ranges larger or smaller by several (5, 4, 3, 2, or 1) nucleotides, at either terminus or at both termini. Preferably, these fragments encode a polypeptide which has biological activity. More preferably, these polynucleotides can be used as probes or primers as discussed herein. Polynucleotides which hybridize to these nucleic acid molecules under stringent hybridization conditions or lower stringency conditions are also encompassed by the invention, as are polypeptides encoded by these polynucleotides.

In the present invention, a “polypeptide fragment” refers to an amino acid sequence which is a portion of that contained in SEQ ID NO:Y or encoded by the cDNA contained in a deposited clone. Protein (polypeptide) fragments may be “free-standing,” or comprised within a larger polypeptide of which the fragment forms a part or region, most preferably as a single continuous region. Representative examples of polypeptide fragments of the invention, include, for example, fragments comprising, or alternatively consisting of, from about amino acid number 1-20, 21-40, 41-60, 61-80, 81-100, 102-120, 121-140, 141-160, or 161 to the end of the coding region. Moreover, polypeptide fragments can be about 20, 30, 40, 50, 60, 70, 80, 90, 100, 110, 120, 130, 140, or 150 amino acids in length. In this context “about” includes the particularly recited ranges or values, and ranges or values larger or smaller by several (5, 4, 3, 2, or 1) amino acids, at either extreme or at both extremes. Polynucleotides encoding these polypeptides are also encompassed by the invention.

Preferred polypeptide fragments include the secreted protein as well as the mature form. Further preferred polypeptide fragments include the secreted protein or the mature form having a continuous series of deleted residues from the amino or the carboxy terminus, or both. For example, any number of amino acids, ranging from 1-60, can be deleted from the amino terminus of either the secreted polypeptide or the mature form. Similarly, any number of amino acids, ranging from 1-30, can be deleted from the carboxy terminus of the secreted protein or mature form. Furthermore, any combination of the above amino and carboxy terminus deletions are preferred. Similarly, polynucleotides encoding these polypeptide fragments are also preferred.

Also preferred are polypeptide and polynucleotide fragments characterized by structural or functional domains, such as fragments that comprise alpha-helix and alpha-helix forming regions, beta-sheet and beta-sheet-forming regions, turn and turn-forming regions, coil and coil-forming regions, hydrophilic regions, hydrophobic regions, alpha amphipathic regions, beta amphipathic regions, flexible regions, surface-forming regions, substrate binding region, and high antigenic index regions. Polypeptide fragments of SEQ ID NO:Y falling within conserved domains are specifically contemplated by the present invention. Moreover, polynucleotides encoding these domains are also contemplated.

Other preferred polypeptide fragments are biologically active fragments. Biologically active fragments are those exhibiting activity similar, but not necessarily identical, to an activity of the polypeptide of the present invention. The biological activity of the fragments may include an improved desired activity, or a decreased undesirable activity. Polynucleotides encoding these polypeptide fragments are also encompassed by the invention.

Preferably, the polynucleotide fragments of the invention encode a polypeptide which demonstrates a functional activity. By a polypeptide demonstrating a “functional activity” is meant, a polypeptide capable of displaying one or more known functional activities associated with a full-length (complete) polypeptide of invention protein. Such functional activities include, but are not limited to, biological activity, antigenicity [ability to bind (or compete with a polypeptide of the invention for binding) to an antibody to the polypeptide of the invention], immunogenicity (ability to generate antibody which binds to a polypeptide of the invention), ability to form multimers with polypeptides of the invention, and ability to bind to a receptor or ligand for a polypeptide of the invention.

The functional activity of polypeptides of the invention, and fragments, variants derivatives, and analogs thereof, can be assayed by various methods.

For example, in one embodiment where one is assaying for the ability to bind or compete with full-length polypeptide of the invention for binding to an antibody of the polypeptide of the invention, various immunoassays known in the art can be used, including but not limited to, competitive and non-competitive assay systems using techniques such as radioimmunoassays, ELISA (enzyme linked immunosorbent assay), “sandwich” immunoassays, immunoradiometric assays, gel diffusion precipitation reactions, immunodiffusion assays, in situ immunoassays (using colloidal gold, enzyme or radioisotope labels, for example), western blots, precipitation reactions, agglutination assays (e.g., gel agglutination assays, hemagglutination assays), complement fixation assays, immunofluorescence assays, protein A assays, and immunoelectrophoresis assays, etc. In one embodiment, antibody binding is detected by detecting a label on the primary antibody. In another embodiment, the primary antibody is detected by detecting binding of a secondary antibody or reagent to the primary antibody. In a further embodiment, the secondary antibody is labeled. Many means are known in the art for detecting binding in an immunoassay and are within the scope of the present invention.

In another embodiment, where a ligand for a polypeptide of the invention identified, or the ability of a polypeptide fragment, variant or derivative of the invention to multimerize is being evaluated, binding can be assayed, e.g., by means well-known in the art, such as, for example, reducing and non-reducing gel chromatography, protein affinity chromatography, and affinity blotting. See generally, Phizicky, E., et al., 1995, Microbiol. Rev. 59:94-123. In another embodiment, physiological correlates of binding of a polypeptide of the invention to its substrates (signal transduction) can be assayed.

In addition, assays described herein (see Examples) and otherwise known in the art may routinely be applied to measure the ability of polypeptides of the invention and fragments, variants derivatives and analogs thereof to elicit related biological activity related to that of the polypeptide of the invention (either in vitro or in vivo). Other methods will be known to the skilled artisan and are within the scope of the invention.

Epitopes and Antibodies

The present invention encompasses polypeptides comprising, or alternatively consisting of, an epitope of the polypeptide having an amino acid sequence of SEQ ID NO:Y, or an epitope of the polypeptide sequence encoded by a polynucleotide sequence contained in ATCC deposit No. Z or encoded by a polynucleotide that hybridizes to the complement of the sequence of SEQ ID NO:X or contained in ATCC deposit No. Z under stringent hybridization conditions or lower stringency hybridization conditions as defined supra. The present invention further encompasses polynucleotide sequences encoding an epitope of a polypeptide sequence of the invention (such as, for example, the sequence disclosed in SEQ ID NO:X), polynucleotide sequences of the complementary strand of a polynucleotide sequence encoding an epitope of the invention, and polynucleotide sequences which hybridize to the complementary strand under stringent hybridization conditions or lower stringency hybridization conditions defined supra.

The term "epitopes," as used herein, refers to portions of a polypeptide having antigenic or immunogenic activity in an animal, preferably a mammal, and most preferably in a human. In a preferred embodiment, the present invention encompasses a polypeptide comprising an epitope, as well as the polynucleotide encoding this polypeptide. An "immunogenic epitope," as used herein, is defined as a portion of a protein that elicits an antibody response in an animal, as determined by any method known in the art, for example, by the methods for generating antibodies described infra. (See, for example, Geysen et al., Proc. Natl. Acad. Sci. USA 81:3998-4002 (1983)). The term "antigenic epitope," as used herein, is defined as a portion of a protein to which an antibody can immunospecifically bind its antigen as determined by any method well known in the art, for example, by the immunoassays described herein. Immunospecific binding excludes non-specific binding but does not necessarily exclude cross-reactivity with other antigens. Antigenic epitopes need not necessarily be immunogenic.

Fragments which function as epitopes may be produced by any conventional means. (See, e.g., Houghten, Proc. Natl. Acad. Sci. USA 82:5131-5135 (1985), further described in U.S. Pat. No. 4,631,211).

In the present invention, antigenic epitopes preferably contain a sequence of at least 4, at least 5, at least 6, at least 7, more preferably at least 8, at least 9, at least 10, at least 11, at least 12, at least 13, at least 14, at least 15, at least 20, at least 25, at least 30, at least 40, at least 50, and, most preferably, between about 15 to about 30 amino acids. Preferred polypeptides comprising immunogenic or antigenic epitopes are at least 10, 15, 20, 25, 30, 35, 40, 45, 50, 55, 60, 65, 70, 75, 80, 85, 90, 95, or 100 amino acid residues in length. Additional non-exclusive preferred antigenic epitopes include the antigenic epitopes disclosed herein, as well as portions thereof. Antigenic epitopes are useful, for example, to raise antibodies, including monoclonal antibodies, that specifically bind the epitope. Preferred antigenic epitopes include the antigenic epitopes disclosed herein, as well as any combination of two, three, four, five or more of these antigenic epitopes. Antigenic epitopes can be used as the target molecules in immunoassays. (See, for instance, Wilson et al., Cell 37:767-778 (1984); Sutcliffe et al., Science 219:660-666 (1983)).

Similarly, immunogenic epitopes can be used, for example, to induce antibodies according to methods well known in the art. (See, for instance, Sutcliffe et al., supra; Wilson et al., supra; Chow et al., Proc. Natl. Acad. Sci. USA 82:910-914; and Bittle et al., J. Gen. Virol. 66:2347-2354 (1985). Preferred immunogenic epitopes include the immunogenic epitopes disclosed herein, as well as any combination of two, three, four, five or more of these immunogenic epitopes. The polypeptides comprising one or more immunogenic epitopes may be presented for eliciting an antibody response together with a carrier protein, such as an albumin, to an animal system (such as rabbit or mouse), or, if the polypeptide is of sufficient length (at least about 25 amino acids), the polypeptide may be presented without a carrier. However, immunogenic epitopes comprising as few as 8 to 10 amino acids have been shown to be sufficient to raise antibodies capable of binding to, at the very least, linear epitopes in a denatured polypeptide (e.g., in Western blotting).

Epitope-bearing polypeptides of the present invention may be used to induce antibodies according to methods well known in the art including, but not limited to, in vivo immunization, in vitro immunization, and phage display methods. See, e.g., Sutcliffe et al., supra; Wilson et al., supra, and Bittle et al., J. Gen. Virol., 66:2347-2354 (1985). If in vivo immunization is used, animals may be immunized with free peptide; however, anti-peptide antibody titer may be boosted by coupling the peptide to a macromolecular carrier, such as keyhole limpet hemacyanin (KLH) or tetanus toxoid. For instance, peptides containing cysteine residues may be coupled to a carrier using a linker such as maleimidobenzoyl-N-hydroxysuccinimide ester (MBS), while other peptides may be coupled to carriers using a more general linking agent such as glutaraldehyde. Animals such as rabbits, rats and mice are immunized with either free or carrier-coupled peptides, for instance, by intraperitoneal and/or intradermal injection of emulsions containing about 100 μg of peptide or carrier protein and Freund's adjuvant or any other adjuvant known for stimulating an immune response. Several booster injections may be needed, for instance, at intervals of about two weeks, to provide a useful titer of anti-peptide antibody which can be detected, for example, by ELISA assay using free peptide adsorbed to a solid surface. The titer of anti-peptide antibodies in serum from an immunized animal may be increased by selection of anti-peptide antibodies, for instance, by adsorption to the peptide on a solid support and elution of the selected antibodies according to methods well known in the art.

As one of skill in the art will appreciate, and as discussed above, the polypeptides of the present invention comprising an immunogenic or antigenic epitope can be fused to other polypeptide sequences. For example, the polypeptides of the present invention may be fused with the constant domain of immunoglobulins (IgA, IgE, IgG, IgM), or portions thereof (CH1, CH2, CH3, or any combination thereof and portions thereof) resulting in chimeric polypeptides. Such fusion proteins may facilitate purification and may increase half-life in vivo. This has been shown for chimeric proteins consisting of the first two domains of the human CD4-polypeptide and various domains of the constant regions of the heavy or light chains of mammalian immunoglobulins. See, e.g., EP 394,827; Traunecker et al., Nature, 331:84-86 (1988). Enhanced delivery of an antigen across the epithelial barrier to the immune system has been demonstrated for antigens (e.g., insulin) conjugated to an FcRn binding partner such as IgG or Fc fragments (see, e.g., PCT Publications WO 96/22024 and WO 99/04813). IgG Fusion proteins that have a disulfide-linked dimeric structure due to the IgG portion desulfide bonds have also been found to be more efficient in binding and neutralizing other molecules than monomeric polypeptides or fragments thereof alone. See, e.g., Fountoulakis et al., J. Biochem., 270:3958-3964 (1995). Nucleic acids encoding the above epitopes can also be recombined with a gene of interest as an epitope tag (e.g., the hemagglutinin ("HA") tag or flag tag) to aid in detection and purification of the expressed polypeptide. For example, a system described by Janknecht et al. allows for the ready purification of non-denatured fusion proteins expressed in human cell lines (Janknecht et al., 1991, Proc. Natl. Acad. Sci. USA 88:8972-897). In this system, the gene of interest is subcloned into a vaccinia recombination plasmid such that the open reading frame of the gene is translationally fused to an amino-terminal tag consisting of six histidine residues. The tag serves as a matrix binding domain for the fusion protein. Extracts from cells infected with the recombinant vaccinia virus are loaded onto Ni2+ nitriloacetic acid-agarose column and histidine-tagged proteins can be selectively eluted with imidazole-containing buffers.

Additional fusion proteins of the invention may be generated through the techniques of gene-shuffling, motif-shuffling, exon-shuffling, and/or codon-shuffling (collectively referred to as "DNA shuffling"). DNA shuffling may be employed to modulate the activities of polypeptides of the invention, such methods can be used to generate polypeptides with altered activity, as well as agonists and antagonists of the polypeptides. See, generally, U.S. Pat. Nos. 5,605,793; 5,811,238; 5,830,721; 5,834,252; and 5,837,458, and Patten et al., Curr. Opinion Biotechnol. 8:724-33 (1997); Harayama, Trends Biotechnol. 16(2):76-82 (1998); Hansson, et al., J. Mol. Biol. 287:265-76 (1999); and Lorenzo and Blasco, Biotechniques 24(2):308-13 (1998) (each of these patents and publications are hereby incorporated by reference in its entirety). In one embodiment, alteration of polynucleotides corresponding to SEQ ID NO:X and the polypeptides encoded by these polynucleotides may be achieved by DNA shuffling. DNA shuffling involves the assembly of two or more DNA segments by homologous or site-specific recombination to generate variation in the polynucleotide sequence. In another embodiment, polynucleotides of the invention, or the encoded polypeptides, may be altered by being subjected to random mutagenesis by error-prone PCR, random nucleotide insertion or other methods prior to recombination. In another embodiment, one or more components, motifs, sections, parts, domains, fragments, etc., of a polynucleotide encoding a polypeptide of the invention may be recombined with one or more components, motifs, sections, parts, domains, fragments, etc. of one or more heterologous molecules.

Antibodies

Further polypeptides of the invention relate to antibodies and T-cell antigen receptors (TCR) which immunospecifically bind a polypeptide, polypeptide fragment, or variant of SEQ ID NO:Y, and/or an epitope, of the present invention (as determined by immunoassays well known in the art for assaying specific antibody-antigen binding). Antibodies of the invention include, but are not limited to, polyclonal, monoclonal, multispecific, human, humanized or chimeric antibodies, single chain antibodies, Fab fragments, F(ab') fragments, fragments produced by a Fab expression library, anti-idiotypic (anti-Id) antibodies (including, e.g., anti-Id antibodies to antibodies of the invention), and epitope-binding fragments of any of the above. The term "antibody," as used herein, refers to immunoglobulin molecules and immunologically active portions of immunoglobulin molecules, i.e., molecules that contain an antigen binding site that immunospecifically binds an antigen. The immunoglobulin molecules of the invention can be of any type (e.g., IgG, IgE, IgM, IgD, IgA and IgY), class (e.g., IgG1, IgG2, IgG3, IgG4, IgA1 and IgA2) or subclass of immunoglobulin molecule.

Most preferably the antibodies are human antigen-binding antibody fragments of the present invention and include, but are not limited to, Fab, Fab' and F(ab')2, Fd, single-chain Fvs (scFv), single-chain antibodies, disulfide-linked Fvs (sdFv) and fragments comprising either a VL or VH domain. Antigen-binding antibody fragments, including single-chain antibodies, may comprise the variable region(s) alone or in combination with the entirety or a portion of the following: hinge region, CH1, CH2, and CH3 domains. Also included in the invention are antigen-binding fragments also comprising any combination of variable region(s) with a hinge region, CH1, CH2, and CH3 domains. The antibodies of the invention may be from any animal origin including birds and mammals. Preferably, the antibodies are human, murine (e.g., mouse and rat), donkey, ship rabbit, goat, guinea pig, camel, horse, or chicken. As used herein, "human" antibodies include antibodies having the amino acid sequence of a human immunoglobulin and include antibodies isolated from human immunoglobulin libraries or from animals transgenic for one or more human immunoglobulin and that do not express endogenous immunoglobulins, as described infra and, for example in, U.S. Pat. No. 5,939,598 by Kucherlapati et al.

The antibodies of the present invention may be monospecific, bispecific, trispecific or of greater multispecificity. Multispecific antibodies may be specific for different epitopes of a polypeptide of the present invention or may be specific for both a polypeptide of the present invention as well as for a heterologous epitope, such as a heterologous polypeptide or solid support material. See, e.g., PCT publications WO 93/17715; WO 92/08802; WO 91/00360; WO 92/05793; Tutt, et al., J. Immunol. 147:60-69 (1991); U.S. Pat. Nos. 4,474,893; 4,714,681; 4,925,648; 5,573,920; 5,601,819; Kostelny et al., J. Immunol. 148:1547-1553 (1992).

Antibodies of the present invention may be described or specified in terms of the epitope(s) or portion(s) of a polypeptide of the present invention which they recognize or specifically bind. The epitope(s) or polypeptide portion(s) may be specified as described herein, e.g., by N-terminal and C-terminal positions, by size in contiguous amino acid residues, or listed in the Tables and Figures. Antibodies which specifically bind any epitope or polypeptide of the present invention may also be excluded. Therefore, the present invention includes antibodies that specifically bind polypeptides of the present invention, and allows for the exclusion of the same.

Antibodies of the present invention may also be described or specified in terms of their cross-reactivity. Antibodies that do not bind any other analog, ortholog, or homolog of a polypeptide of the present invention are included. Antibodies that bind polypeptides with at least 95%, at least 90%, at least 85%, at least 80%, at least 75%, at least 70%, at least 65%, at least 60%, at least 55%, and at least 50% identity (as calculated using methods known in the art and described herein) to a polypeptide of the present invention are also included in the present invention. In specific embodiments, antibodies of the present invention cross-react with murine, rat and/or rabbit homologs of human proteins and the corresponding epitopes thereof. Antibodies that do not bind polypeptides with less than 95%, less than 90%, less than 85%, less than 80%, less than 75%, less than 70%, less than 65%, less than 60%, less than 55%, and less than 50% identity (as calculated using methods known in the art and described herein) to a polypeptide of the present invention are also included in the present invention. In a specific embodiment, the above-described cross-reactivity is with respect to any single specific antigenic or immunogenic polypeptide, or combination(s) of 2, 3, 4, 5, or more of the specific antigenic and/or immunogenic polypeptides disclosed herein. Further included in the present invention are antibodies which bind polypeptides encoded by polynucleotides which hybridize to a polynucleotide of the present invention under stringent hybridization conditions (as described herein). Antibodies of the present invention may also be described or specified in terms of their binding affinity to a polypeptide of the invention. Preferred binding affinities include those with a dissociation constant or Kd less than $5\times10^{-2}$ M, $10^{-2}$ M, $5\times10^{-3}$ M, $10^{-3}$ M, $5\times10^{-4}$ M, $10^{-4}$ M, $5\times10^{-5}$ M, $10^{-5}$ M, $5\times10^{-6}$ M, $10^{-6}$M, $5\times10^{-7}$ M, $10^{7}$ M, $5\times10^{-8}$ M, $10^{-8}$ M, $5\times10^{-9}$ M, $10^{-9}$ M, $5\times10^{-10}$ M, $10^{-10}$ M, $5\times10^{-11}$ M, $10^{-11}$ M, $5\times10^{-12}$ M, $10^{-12}$ M, $5\times10^{-13}$ M, $10^{-13}$ M, $5\times10^{-14}$ M, $10^{-14}$ M, $5\times10^{-15}$ M, or $10^{-15}$ M.

The invention also provides antibodies that competitively inhibit binding of an antibody to an epitope of the invention as determined by any method known in the art for determining competitive binding, for example, the immunoassays described herein. In preferred embodiments, the antibody competitively inhibits binding to the epitope by at least 95%, at least 90%, at least 85%, at least 80%, at least 75%, at least 70%, at least 60%, or at least 50%.

Antibodies of the present invention may act as agonists or antagonists of the polypeptides of the present invention. For example, the present invention includes antibodies which disrupt the receptor/ligand interactions with the polypeptides of the invention either partially or fully. Preferrably, antibodies of the present invention bind an antigenic epitope disclosed herein, or a portion thereof. The invention features both receptor-specific antibodies and ligand-specific antibodies. The invention also features receptor-specific antibodies which do not prevent ligand binding but prevent receptor activation. Receptor activation (i.e., signaling) may be determined by techniques described herein or otherwise known in the art. For example, receptor activation can be determined by detecting the phosphorylation (e.g., tyrosine or serine/threonine) of the receptor or its substrate by immunoprecipitation followed by western blot analysis (for example, as described supra). In specific embodiments, antibodies are provided that inhibit ligand activity or receptor activity by at least 95%, at least 90%, at least 85%, at least 80%, at least 75%, at least 70%, at least 60%, or at least 50% of the activity in absence of the antibody.

The invention also features receptor-specific antibodies which both prevent ligand binding and receptor activation as well as antibodies that recognize the receptor-ligand complex, and, preferably, do not specifically recognize the unbound receptor or the unbound ligand. Likewise, included in the invention are neutralizing antibodies which bind the ligand and prevent binding of the ligand to the receptor, as well as antibodies which bind the ligand, thereby preventing receptor activation, but do not prevent the ligand from binding the receptor. Further included in the invention are antibodies which activate the receptor. These antibodies may act as receptor agonists, i.e., potentiate or activate either all or a subset of the biological activities of the ligand-mediated receptor activation, for example, by inducing dimerization of the receptor. The antibodies may be specified as agonists, antagonists or inverse agonists for biological activities comprising the specific biological activities of the peptides of the invention disclosed herein. The above antibody agonists can be made using methods known in the art. See, e.g., PCT publication WO 96/40281; U.S. Pat. No. 5,811,097; Deng et al., Blood 92(6):1981-1988 (1998); Chen et al., Cancer Res. 58(16):3668-3678 (1998); Harrop et al., J. Immunol. 161 (4):1786-1794 (1998); Zhu et al., Cancer Res. 58(15):3209-3214 (1998); Yoon et al., J. Immunol. 160(7):3170-3179 (1998); Prat et al., J. Cell. Sci. 111 (Pt2):237-247 (1998); Pitard et al., J. Immunol. Methods 205(2):177-190 (1997); Liautard et al., Cytokine 9(4):233-241 (1997); Carlson et al., J. Biol. Chem. 272(17):11295-11301 (1997); Taryman et al., Neuron 14(4):755-762 (1995); Muller et al., Structure 6(9): 1153-1167 (1998); Bartunek et al., Cytokine 8(1):14-20 (1996) (which are all incorporated by reference herein in their entireties).

Antibodies of the present invention may be used, for example, but not limited to, to purify, detect, and target the polypeptides of the present invention, including both in vitro and in vivo diagnostic and therapeutic methods. For example, the antibodies have use in immunoassays for qualitatively and quantitatively measuring levels of the polypeptides of the present invention in biological samples. See, e.g., Harlow et al., Antibodies: A Laboratory Manual, (Cold Spring Harbor Laboratory Press, 2nd ed. 1988) (incorporated by reference herein in its entirety).

As discussed in more detail below, the antibodies of the present invention may be used either alone or in combination with other compositions. The antibodies may further be recombinantly fused to a heterologous polypeptide at the N- or C-terminus or chemically conjugated (including covalently and non-covalently conjugations) to polypeptides or other compositions. For example, antibodies of the present invention may be recombinantly fused or conjugated to molecules useful as labels in detection assays and effector molecules such as heterologous polypeptides, drugs, radionuclides, or toxins. See, e.g., PCT publications WO 92/08495; WO 91/14438; WO 89/12624; U.S. Pat. No. 5,314,995; and EP 396,387.

The antibodies of the invention include derivatives that are modified, i.e, by the covalent attachment of any type of molecule to the antibody such that covalent attachment does not prevent the antibody from generating an anti-idiotypic response. For example, but not by way of limitation, the antibody derivatives include antibodies that have been modified, e.g., by glycosylation, acetylation, pegylation, phosphylation, amidation, derivatization by known protecting/blocking groups, proteolytic cleavage, linkage to a cellular ligand or other protein, etc. Any of numerous chemical modifications may be carried out by known techniques, including, but not limited to specific chemical cleavage, acetylation, formylation, metabolic synthesis of tunicamycin, etc. Additionally, the derivative may contain one or more non-classical amino acids.

The antibodies of the present invention may be generated by any suitable method known in the art. Polyclonal antibodies to an antigen-of-interest can be produced by various procedures well known in the art. For example, a polypeptide of the invention can be administered to various host animals including, but not limited to, rabbits, mice, rats, etc. to induce the production of sera containing polyclonal antibodies specific for the antigen. Various adjuvants may be used to increase the immunological response, depending on the host species, and include but are not limited to, Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (bacille Calmette-Guerin) and *corynebacterium parvum*. Such adjuvants are also well known in the art.

Monoclonal antibodies can be prepared using a wide variety of techniques known in the art including the use of hybridoma, recombinant, and phage display technologies, or a combination thereof. For example, monoclonal antibodies can be produced using hybridoma techniques including those known in the art and taught, for example, in Harlow et al., Antibodies: A Laboratory Manual, (Cold Spring Harbor Laboratory Press, 2nd ed. 1988); Hammerling, et al., in: Monoclonal Antibodies and T-Cell Hybridomas 563-681 (Elsevier, N.Y., 1981) (said references incorporated by reference in their entireties). The term "monoclonal antibody" as used herein is not limited to antibodies produced through hybridoma technology. The term "monoclonal antibody" refers to an antibody that is derived from a single clone, including any eukaryotic, prokaryotic, or phage clone, and not the method by which it is produced.

Methods for producing and screening for specific antibodies using hybridoma technology are routine and well known in the art and are discussed in detail in the Examples (e.g., Example 16). In a non-limiting example, mice can be immunized with a polypeptide of the invention or a cell expressing such peptide. Once an immune response is detected, e.g., antibodies specific for the antigen are detected in the mouse serum, the mouse spleen is harvested and splenocytes isolated. The splenocytes are then fused by well known techniques to any suitable myeloma cells, for example cells from cell line SP20 available from the ATCC. Hybridomas are selected and cloned by limited dilution. The hybridoma clones are then assayed by methods known in the art for cells that secrete antibodies capable of binding a polypeptide of the invention. Ascites fluid, which generally contains high levels of antibodies, can be generated by immunizing mice with positive hybridoma clones.

Accordingly, the present invention provides methods of generating monoclonal antibodies as well as antibodies produced by the method comprising culturing a hybridoma cell secreting an antibody of the invention wherein, preferably, the hybridoma is generated by fusing splenocytes isolated from a mouse immunized with an antigen of the invention with myeloma cells and then screening the hybridomas resulting from the fusion for hybridoma clones that secrete an antibody able to bind a polypeptide of the invention.

Antibody fragments which recognize specific epitopes may be generated by known techniques. For example, Fab and F(ab')2 fragments of the invention may be produced by proteolytic cleavage of immunoglobulin molecules, using enzymes such as papain (to produce Fab fragments) or pepsin (to produce F(ab')2 fragments). F(ab')2 fragments contain the variable region, the light chain constant region and the CH1 domain of the heavy chain.

For example, the antibodies of the present invention can also be generated using various phage display methods known in the art. In phage display methods, functional antibody domains are displayed on the surface of phage particles which carry the polynucleotide sequences encoding them. In a particular embodiment, such phage can be utilized to display antigen binding domains expressed from a repertoire or combinatorial antibody library (e.g., human or murine). Phage expressing an antigen binding domain that binds the antigen of interest can be selected or identified with antigen, e.g., using labeled antigen or antigen bound or captured to a solid surface or bead. Phage used in these methods are typically filamentous phage including fd and M13 binding domains expressed from phage with Fab, Fv or disulfide stabilized Fv antibody domains recombinantly fused to either the phage gene III or gene VIII protein. Examples of phage display methods that can be used to make the antibodies of the present invention include those disclosed in Brinkman et al., J. Immunol. Methods 182:41-50 (1995); Ames et al., J. Immunol. Methods 184:177-186 (1995); Kettleborough et al., Eur. J. Immunol. 24:952-958 (1994); Persic et al., Gene 187 9-18 (1997); Burton et al., Advances in Immunology 57:191-280 (1994); PCT application No. PCT/GB91/01134; PCT publications WO 90/02809; WO 91/10737; WO 92/01047; WO 92/18619; WO 93/11236; WO 95/15982; WO 95/20401; and U.S. Pat. Nos. 5,698,426; 5,223,409; 5,403,484; 5,580,717; 5,427,908; 5,750,753; 5,821,047; 5,571,698; 5,427,908; 5,516,637; 5,780,225; 5,658,727; 5,733,743 and 5,969,108; each of which is incorporated herein by reference in its entirety.

As described in the above references, after phage selection, the antibody coding regions from the phage can be isolated and used to generate whole antibodies, including human antibodies, or any other desired antigen binding fragment, and expressed in any desired host, including mammalian cells, insect cells, plant cells, yeast, and bacteria, e.g., as described in detail below. For example, techniques to recombinantly produce Fab, Fab' and F(ab')2 fragments can also be employed using methods known in the art such as those disclosed in PCT publication WO 92/22324; Mullinax et al., BioTechniques 12(6):864-869 (1992); and Sawai et al., AJRI 34:26-34 (1995); and Better et al., Science 240:1041-1043 (1988) (said references incorporated by reference in their entireties).

Examples of techniques which can be used to produce single-chain Fvs and antibodies include those described in U.S. Pat. Nos. 4,946,778 and 5,258,498; Huston et al., Methods in Enzymology 203:46-88 (1991); Shu et al., PNAS 90:7995-7999 (1993); and Skerra et al., Science 240:1038-1040 (1988). For some uses, including in vivo use of antibodies in humans and in vitro detection assays, it may be preferable to use chimeric, humanized, or human antibodies. A chimeric antibody is a molecule in which different portions of the antibody are derived from different animal species, such as antibodies having a variable region derived from a murine monoclonal antibody and a human immunoglobulin constant region. Methods for producing chimeric antibodies are known in the art. See e.g., Morrison, Science 229:1202 (1985); Oi et al., BioTechniques 4:214 (1986); Gillies et al., (1989) J. Immunol. Methods 125:191-202; U.S. Pat. Nos. 5,807,715; 4,816,567; and 4,816,397, which are incorporated herein by reference in their entirety. Humanized antibodies are antibody molecules from non-human species antibody that binds the desired antigen having one or more complementarity determining regions (CDRs) from the non-human species and a framework regions from a human immunoglobulin molecule. Often, framework residues in the human framework regions will be substituted with the corresponding residue from the CDR donor antibody to alter, preferably improve, antigen binding. These framework substitutions are identified by methods well known in the art, e.g., by modeling of the interactions of the CDR and framework residues to identify framework residues important for antigen binding and sequence comparison to identify unusual framework residues at particular positions. (See, e.g., Queen et al., U.S. Pat. No. 5,585,089; Riechmann et al., Nature 332:323 (1988), which are incorporated herein by reference in their entireties.) Antibodies can be humanized using a variety of techniques known in the art including, for example, CDR-grafting (EP 239,400; PCT publication WO 91/09967; U.S. Pat. Nos. 5,225,539; 5,530,101; and 5,585,089), veneering or resurfacing (EP 592,106; EP 519,596; Padlan, Molecular Immunology 28(4/5):489-498 (1991); Studnicka et al., Protein Engineering 7(6):805-814 (1994); Roguska. et al., PNAS 91:969-973 (1994)), and chain shuffling (U.S. Pat. No. 5,565,332).

Completely human antibodies are particularly desirable for therapeutic treatment of human patients. Human antibodies can be made by a variety of methods known in the art including phage display methods described above using antibody libraries derived from human immunoglobulin sequences. See also, U.S. Pat. Nos. 4,444,887 and 4,716,111; and PCT publications WO 98/46645, WO 98/50433, WO 98/24893, WO 98/16654, WO 96/34096, WO 96/33735, and WO 91/10741; each of which is incorporated herein by reference in its entirety.

Human antibodies can also be produced using transgenic mice which are incapable of expressing functional endogenous immunoglobulins, but which can express human immunoglobulin genes. For example, the human heavy and light chain immunoglobulin gene complexes may be introduced randomly or by homologous recombination into mouse embryonic stem cells. Alternatively, the human variable region, constant region, and diversity region may be introduced into mouse embryonic stem cells in addition to the human heavy and light chain genes. The mouse heavy and light chain immunoglobulin genes may be rendered non-functional separately or simultaneously with the introduction of human immunoglobulin loci by homologous recombination. In particular, homozygous deletion of the JH region prevents endogenous antibody production. The modified embryonic stem cells are expanded and microinjected into blastocysts to produce chimeric mice. The chimeric mice are then bred to produce homozygous offspring which express human antibodies. The transgenic mice are immunized in the normal fashion with a selected antigen, e.g., all or a portion of a polypeptide of the invention. Monoclonal antibodies directed against the antigen can be obtained from the immunized, transgenic mice using conventional hybridoma technology. The human immunoglobulin transgenes harbored by the transgenic mice rearrange during B cell differentiation, and subsequently undergo class switching and somatic mutation. Thus, using such a technique, it is possible to produce therapeutically useful IgG, IgA, IgM and IgE antibodies. For an overview of this technology for producing human antibodies, see Lonberg and Huszar, Int. Rev. Immunol. 13:65-93 (1995). For a detailed discussion of this technology for producing human antibodies and human monoclonal antibodies and protocols for producing such antibodies, see, e.g., PCT publications WO 98/24893; WO 92/01047; WO 96/34096; WO 96/33735; European Patent No. 0 598 877; U.S. Pat. Nos. 5,413,923; 5,625,126; 5,633,425; 5,569,825; 5,661,016; 5,545,806; 5,814,318; 5,885,793; 5,916,771; and 5,939,598, which are incorporated by reference herein in their entirety. In addition, companies such as Abgenix, Inc. (Freemont, Calif.) and Genpharm (San Jose, Calif.) can be engaged to provide human antibodies directed against a selected antigen using technology similar to that described above.

Completely human antibodies which recognize a selected epitope can be generated using a technique referred to as "guided selection." In this approach a selected non-human monoclonal antibody, e.g., a mouse antibody, is used to guide the selection of a completely human antibody recognizing the same epitope. (Jespers et al., Bio/technology 12:899-903 (1988)).

Further, antibodies to the polypeptides of the invention can, in turn, be utilized to generate anti-idiotype antibodies that "mimic" polypeptides of the invention using techniques well known to those skilled in the art. (See, e.g., Greenspan & Bona, FASEB J. 7(5):437-444; (1989) and Nissinoff, J. Immunol. 147(8):2429-2438 (1991)). For example, antibodies which bind to and competitively inhibit polypeptide multimerization and/or binding of a polypeptide of the invention to a ligand can be used to generate anti-idiotypes that "mimic" the polypeptide multimerization and/or binding domain and, as a consequence, bind to and neutralize polypeptide and/or its ligand. Such neutralizing anti-idiotypes or Fab fragments of such anti-idiotypes can be used in therapeutic regimens to neutralize polypeptide ligand. For example, such anti-idiotypic antibodies can be used to bind a polypeptide of the invention and/or to bind its ligands/receptors, and thereby block its biological activity.

Polynucleotides Encoding Antibodies

The invention further provides polynucleotides comprising a nucleotide sequence encoding an antibody of the invention and fragments thereof. The invention also encompasses polynucleotides that hybridize under stringent or lower stringency hybridization conditions, e.g., as defined supra, to polynucleotides that encode an antibody, preferably, that specifically binds to a polypeptide of the invention, preferably, an antibody that binds to a polypeptide having the amino acid sequence of SEQ ID NO:Y.

The polynucleotides may be obtained, and the nucleotide sequence of the polynucleotides determined, by any method known in the art. For example, if the nucleotide sequence of the antibody is known, a polynucleotide encoding the antibody may be assembled from chemically synthesized oligonucleotides (e.g., as described in Kutmeier et al., BioTechniques 17:242 (1994)), which, briefly, involves the synthesis of overlapping oligonucleotides containing portions of the sequence encoding the antibody, annealing and ligating of those oligonucleotides, and then amplification of the ligated oligonucleotides by PCR.

Alternatively, a polynucleotide encoding an antibody may be generated from nucleic acid from a suitable source. If a clone containing a nucleic acid encoding a particular antibody is not available, but the sequence of the antibody molecule is known, a nucleic acid encoding the immunoglobulin may be chemically synthesized or obtained from a suitable source (e.g., an antibody cDNA library, or a cDNA library generated from, or nucleic acid, preferably poly A+ RNA, isolated from, any tissue or cells expressing the antibody, such as hybridoma cells selected to express an antibody of the invention) by PCR amplification using synthetic primers hybridizable to the 3' and 5' ends of the sequence or by cloning using an oligonucleotide probe specific for the particular gene sequence to identify, e.g., a cDNA clone from a cDNA library that encodes the antibody. Amplified nucleic acids generated by PCR may then be cloned into replicable cloning vectors using any method well known in the art.

Once the nucleotide sequence and corresponding amino acid sequence of the antibody is determined, the nucleotide sequence of the antibody may be manipulated using methods well known in the art for the manipulation of nucleotide sequences, e.g., recombinant DNA techniques, site directed mutagenesis, PCR, etc. (see, for example, the techniques described in Sambrook et al., 1990, Molecular Cloning, A Laboratory Manual, 2d Ed., Cold Spring Harbor Laboratory, Cold Spring Harbor, N.Y. and Ausubel et al., eds., 1998, Current Protocols in Molecular Biology, John Wiley & Sons, NY, which are both incorporated by reference herein in their entireties), to generate antibodies having a different amino acid sequence, for example to create amino acid substitutions, deletions, and/or insertions.

In a specific embodiment, the amino acid sequence of the heavy and/or light chain variable domains may be inspected to identify the sequences of the complementarity determining regions (CDRs) by methods that are well know in the art, e.g., by comparison to known amino acid sequences of other heavy and light chain variable regions to determine the regions of sequence hypervariability. Using routine recombinant DNA techniques, one or more of the CDRs may be inserted within framework regions, e.g., into human framework regions to humanize a non-human antibody, as described supra. The framework regions may be naturally occurring or consensus framework regions, and preferably human framework regions (see, e.g., Chothia et al., J. Mol. Biol. 278: 457-479 (1998) for a listing of human framework regions). Preferably, the polynucleotide generated by the combination of the framework regions and CDRs encodes an antibody that specifically binds a polypeptide of the invention. Preferably, as discussed supra, one or more amino acid substitutions may be made within the framework regions, and, preferably, the amino acid substitutions improve binding of the antibody to its antigen. Additionally, such methods may be used to make amino acid substitutions or deletions of one or more variable region cysteine residues participating in an intrachain disulfide bond to generate antibody molecules lacking one or more intrachain disulfide bonds. Other alterations to the polynucleotide are encompassed by the present invention and within the skill of the art.

In addition, techniques developed for the production of "chimeric antibodies" (Morrison et al., Proc. Natl. Acad. Sci. 81:851-855 (1984); Neuberger et al., Nature 312:604-608 (1984); Takeda et al., Nature 314:452-454 (1985)) by splicing genes from a mouse antibody molecule of appropriate antigen specificity together with genes from a human antibody molecule of appropriate biological activity can be used. As described supra, a chimeric antibody is a molecule in which different portions are derived from different animal species, such as those having a variable region derived from a murine mAb and a human immunoglobulin constant region, e.g., humanized antibodies.

Alternatively, techniques described for the production of single chain antibodies (U.S. Pat. No. 4,946,778; Bird, Science 242:423-42 (1988); Huston et al., Proc. Natl. Acad. Sci. USA 85:5879-5883 (1988); and Ward et al., Nature 334:544-54 (1989)) can be adapted to produce single chain antibodies. Single chain antibodies are formed by linking the heavy and light chain fragments of the Fv region via an amino acid bridge, resulting in a single chain polypeptide. Techniques for the assembly of functional Fv fragments in *E. coli* may also be used (Skerra et al., Science 242:1038-1041 (1988)).

Methods of Producing Antibodies

The antibodies of the invention can be produced by any method known in the art for the synthesis of antibodies, in particular, by chemical synthesis or preferably, by recombinant expression techniques.

Recombinant expression of an antibody of the invention, or fragment, derivative or analog thereof, (e.g., a heavy or light chain of an antibody of the invention or a single chain antibody of the invention), requires construction of an expression vector containing a polynucleotide that encodes the antibody. Once a polynucleotide encoding an antibody molecule or a heavy or light chain of an antibody, or portion thereof (preferably containing the heavy or light chain variable domain), of the invention has been obtained, the vector for the production of the antibody molecule may be produced by recombinant DNA technology using techniques well known in the art. Thus, methods for preparing a protein by expressing a polynucleotide containing an antibody encoding nucleotide sequence are described herein. Methods which are well known to those skilled in the art can be used to construct expression vectors containing antibody coding sequences and appropriate transcriptional and translational control signals. These methods include, for example, in vitro recombinant DNA techniques, synthetic techniques, and in vivo genetic recombination. The invention, thus, provides replicable vectors comprising a nucleotide sequence encoding an antibody molecule of the invention, or a heavy or light chain thereof, or a heavy or light chain variable domain, operably linked to a promoter. Such vectors may include the nucleotide sequence encoding the constant region of the antibody molecule (see, e.g., PCT Publication WO 86/05807; PCT Publication WO 89/01036; and U.S. Pat. No. 5,122,464) and the variable domain of the antibody may be cloned into such a vector for expression of the entire heavy or light chain.

The expression vector is transferred to a host cell by conventional techniques and the transfected cells are then cultured by conventional techniques to produce an antibody of the invention. Thus, the invention includes host cells containing a polynucleotide encoding an antibody of the invention, or a heavy or light chain thereof, or a single chain antibody of the invention, operably linked to a heterologous promoter. In preferred embodiments for the expression of double-chained antibodies, vectors encoding both the heavy and light chains may be co-expressed in the host cell for expression of the entire immunoglobulin molecule, as detailed below.

A variety of host-expression vector systems may be utilized to express the antibody molecules of the invention. Such host-expression systems represent vehicles by which the coding sequences of interest may be produced and subsequently purified, but also represent cells which may, when transformed or transfected with the appropriate nucleotide coding sequences, express an antibody molecule of the invention in situ. These include but are not limited to microorganisms such as bacteria (e.g., *E. coli, B. subtilis*) transformed with recombinant bacteriophage DNA, plasmid DNA or cosmid DNA expression vectors containing antibody coding sequences; yeast (e.g., *Saccharomyces, Pichia*) transformed with recombinant yeast expression vectors containing antibody coding sequences; insect cell systems infected with recombinant virus expression vectors (e.g., baculovirus) containing antibody coding sequences; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing antibody coding sequences; or mammalian cell systems (e.g., COS, CHO, BHK, 293, 3T3 cells) harboring recombinant expression constructs containing promoters derived from the genome of mammalian cells (e.g., metallothionein promoter) or from mammalian viruses (e.g., the adenovirus late promoter; the vaccinia virus 7.5K promoter). Preferably, bacterial cells such as *Escherichia coli*, and more preferably, eukaryotic cells, especially for the expression of whole recombinant antibody molecule, are used for the expression of a recombinant antibody molecule. For example, mammalian cells such as Chinese hamster ovary cells (CHO), in conjunction with a vector such as the major intermediate early gene promoter element from human cytomegalovirus is an effective expression system for antibodies (Foecking et al., Gene 45:101 (1986); Cockett et al., Bio/Technology 8:2 (1990)).

In bacterial systems, a number of expression vectors may be advantageously selected depending upon the use intended for the antibody molecule being expressed. For example, when a large quantity of such a protein is to be produced, for the generation of pharmaceutical compositions of an antibody molecule, vectors which direct the expression of high levels of fusion protein products that are readily purified may be desirable. Such vectors include, but are not limited, to the *E. coli* expression vector pUR278 (Ruther et al., EMBO J. 2:1791 (1983)), in which the antibody coding sequence may be ligated individually into the vector in frame with the lac Z coding region so that a fusion protein is produced; pIN vectors (Inouye & Inouye, Nucleic Acids Res. 13:3101-3109 (1985); Van Heeke & Schuster, J. Biol. Chem. 24:5503-5509 (1989)); and the like. pGEX vectors may also be used to express foreign polypeptides as fusion proteins with glutathione S-transferase (GST). In general, such fusion proteins are soluble and can easily be purified from lysed cells by adsorption and binding to matrix glutathione-agarose beads followed by elution in the presence of free glutathione. The pGEX vectors are designed to include thrombin or factor Xa protease cleavage sites so that the cloned target gene product can be released from the GST moiety.

In an insect system, *Autographa californica* nuclear polyhedrosis virus (AcNPV) is used as a vector to express foreign genes. The virus grows in *Spodoptera frugiperda* cells. The antibody coding sequence may be cloned individually into non-essential regions (for example the polyhedrin gene) of the virus and placed under control of an AcNPV promoter (for example the polyhedrin promoter).

In mammalian host cells, a number of viral-based expression systems may be utilized. In cases where an adenovirus is used as an expression vector, the antibody coding sequence of interest may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing the antibody molecule in infected hosts. (e.g., see Logan & Shenk, Proc. Natl. Acad. Sci. USA 81:355-359 (1984)). Specific initiation signals may also be required for efficient translation of inserted antibody coding sequences. These signals include the ATG initiation codon and adjacent sequences. Furthermore, the initiation codon must be in phase with the reading frame of the desired coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators, etc. (see Bittner et al., Methods in Enzymol. 153:51-544 (1987)).

In addition, a host cell strain may be chosen which modulates the expression of the inserted sequences, or modifies and processes the gene product in the specific fashion desired. Such modifications (e.g., glycosylation) and processing (e.g., cleavage) of protein products may be important for the function of the protein. Different host cells have characteristic and specific mechanisms for the post-translational processing and modification of proteins and gene products. Appropriate cell lines or host systems can be chosen to ensure the correct modification and processing of the foreign protein expressed. To this end, eukaryotic host cells which possess the cellular machinery for proper processing of the primary transcript, glycosylation, and phosphorylation of the gene product may be used. Such mammalian host cells include but are not limited to CHO, VERY, BHK, Hela, COS, MDCK, 293, 3T3, W138, and in particular, breast cancer cell lines such as, for example, BT483, Hs578T, HTB2, BT20 and T47D, and normal mammary gland cell line such as, for example, CRL7030 and Hs578Bst.

For long-term, high-yield production of recombinant proteins, stable expression is preferred. For example, cell lines which stably express the antibody molecule may be engineered. Rather than using expression vectors which contain viral origins of replication, host cells can be transformed with DNA controlled by appropriate expression control elements (e.g., promoter, enhancer, sequences, transcription terminators, polyadenylation sites, etc.), and a selectable marker. Following the introduction of the foreign DNA, engineered cells may be allowed to grow for 1-2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines. This method may advantageously be used to engineer cell lines which express the antibody molecule. Such engineered cell lines may be particularly useful in screening and evaluation of compounds that interact directly or indirectly with the antibody molecule.

A number of selection systems may be used, including but not limited to the herpes simplex virus thymidine kinase (Wigler et al., Cell 11:223 (1977)), hypoxanthine-guanine phosphoribosyltransferase (Szybalska & Szybalski, Proc. Natl. Acad. Sci. USA 48:202 (1992)), and adenine phosphoribosyltransferase (Lowy et al., Cell 22:817 (1980)) genes can be employed in tk-, hgprt- or aprt-cells, respectively. Also, antimetabolite resistance can be used as the basis of selection for the following genes: dhfr, which confers resistance to methotrexate (Wigler et al., Natl. Acad. Sci. USA 77:357 (1980); O'Hare et al., Proc. Natl. Acad. Sci. USA 78:1527 (1981)); gpt, which confers resistance to mycophenolic acid (Mulligan & Berg, Proc. Natl. Acad. Sci. USA 78:2072 (1981)); neo, which confers resistance to the aminoglycoside G-418 Clinical Pharmacy 12:488-505; Wu and Wu, Biotherapy 3:87-95 (1991); Tolstoshev, Ann. Rev. Pharmacol. Toxicol. 32:573-596 (1993); Mulligan, Science 260:926-932 (1993); and Morgan and Anderson, Ann. Rev. Biochem. 62:191-217 (1993); May, 1993, TIB TECH 11(5):155-215); and hygro, which confers resistance to hygromycin (Santerre et al., Gene 30:147 (1984)). Methods commonly known in the art of recombinant DNA technology may be routinely applied to select the desired recombinant clone, and such methods are described, for example, in Ausubel et al. (eds.), Current Protocols in Molecular Biology, John Wiley & Sons, NY (1993); Kriegler, Gene Transfer and Expression, A Laboratory Manual, Stockton Press, NY (1990); and in Chapters 12 and 13, Dracopoli et al. (eds), Current Protocols in Human Genetics, John Wiley & Sons, NY (1994); Colberre-Garapin et al., J. Mol. Biol. 150:1 (1981), which are incorporated by reference herein in their entireties.

The expression levels of an antibody molecule can be increased by vector amplification (for a review, see Bebbington and Hentschel, The use of vectors based on gene amplification for the expression of cloned genes in mammalian cells in DNA cloning, Vol. 3. (Academic Press, New York, 1987)). When a marker in the vector system expressing antibody is amplifiable, increase in the level of inhibitor present in culture of host cell will increase the number of copies of the marker gene. Since the amplified region is associated with the antibody gene, production of the antibody will also increase (Crouse et al., Mol. Cell. Biol. 3:257 (1983)).

The host cell may be co-transfected with two expression vectors of the invention, the first vector encoding a heavy chain derived polypeptide and the second vector encoding a light chain derived polypeptide. The two vectors may contain identical selectable markers which enable equal expression of heavy and light chain polypeptides. Alternatively, a single vector may be used which encodes, and is capable of expressing, both heavy and light chain polypeptides. In such situations, the light chain should be placed before the heavy chain to avoid an excess of toxic free heavy chain (Proudfoot, Nature 322:52 (1986); Kohler, Proc. Natl. Acad. Sci.

USA 77:2197 (1980)). The coding sequences for the heavy and light chains may comprise cDNA or genomic DNA.

Once an antibody molecule of the invention has been produced by an animal, chemically synthesized, or recombinantly expressed, it may be purified by any method known in the art for purification of an immunoglobulin molecule, for example, by chromatography (e.g., ion exchange, affinity, particularly by affinity for the specific antigen after Protein A, and sizing column chromatography), centrifugation, differential solubility, or by any other standard technique for the purification of proteins. In addition, the antibodies of the present invention or fragments thereof can be fused to heterologous polypeptide sequences described herein or otherwise known in the art, to facilitate purification.

The present invention encompasses antibodies recombinantly fused or chemically conjugated (including both covalently and non-covalently conjugations) to a polypeptide (or portion thereof, preferably at least 10, 20, 30, 40, 50, 60, 70, 80, 90 or 100 amino acids of the polypeptide) of the present invention to generate fusion proteins. The fusion does not necessarily need to be direct, but may occur through linker sequences. The antibodies may be specific for antigens other than polypeptides (or portion thereof, preferably at least 10, 20, 30, 40, 50, 60, 70, 80, 90 or 100 amino acids of the polypeptide) of the present invention. For example, antibodies may be used to target the polypeptides of the present invention to particular cell types, either in vitro or in vivo, by fusing or conjugating the polypeptides of the present invention to antibodies specific for particular cell surface receptors. Antibodies fused or conjugated to the polypeptides of the present invention may also be used in in vitro immunoassays and purification methods using methods known in the art. See e.g., Harbor et al., supra, and PCT publication WO 93/21232; EP 439,095; Naramura et al., Immunol. Lett. 39:91-99 (1994); U.S. Pat. No. 5,474,981; Gillies et al., PNAS 89:1428-1432 (1992); Fell et al., J. Immunol. 146:2446-2452 (1991), which are incorporated by reference in their entireties.

The present invention further includes compositions comprising the polypeptides of the present invention fused or conjugated to antibody domains other than the variable regions. For example, the polypeptides of the present invention may be fused or conjugated to an antibody Fc region, or portion thereof. The antibody portion fused to a polypeptide of the present invention may comprise the constant region, hinge region, CH1 domain, CH2 domain, and CH3 domain or any combination of whole domains or portions thereof. The polypeptides may also be fused or conjugated to the above antibody portions to form multimers. For example, Fc portions fused to the polypeptides of the present invention can form dimers through disulfide bonding between the Fc portions. Higher multimeric forms can be made by fusing the polypeptides to portions of IgA and IgM. Methods for fusing or conjugating the polypeptides of the present invention to antibody portions are known in the art. See, e.g., U.S. Pat. Nos. 5,336,603; 5,622,929; 5,359,046; 5,349,053; 5,447,851; 5,112,946; EP 307,434; EP 367,166; PCT publications WO 96/04388; WO 91/06570; Ashkenazi et al., Proc. Natl. Acad. Sci. USA 88:10535-10539 (1991); Zheng et al., J. Immunol. 154:5590-5600 (1995); and Vil et al., Proc. Natl. Acad. Sci. USA 89:11337-11341 (1992) (said references incorporated by reference in their entireties).

As discussed, supra, the polypeptides corresponding to a polypeptide, polypeptide fragment, or a variant of SEQ ID NO:Y may be fused or conjugated to the above antibody portions to increase the in vivo half life of the polypeptides or for use in immunoassays using methods known in the art. Further, the polypeptides corresponding to SEQ ID NO:Y may be fused or conjugated to the above antibody portions to facilitate purification. One reported example describes chimeric proteins consisting of the first two domains of the human CD4-polypeptide and various domains of the constant regions of the heavy or light chains of mammalian immunoglobulins. (EP 394,827; Traunecker et al., Nature 331:84-86 (1988). The polypeptides of the present invention fused or conjugated to an antibody having disulfide-linked dimeric structures (due to the IgG) may also be more efficient in binding and neutralizing other molecules, than the monomeric secreted protein or protein fragment alone. (Fountoulakis et al., J. Biochem. 270:3958-3964 (1995)). In many cases, the Fc part in a fusion protein is beneficial in therapy and diagnosis, and thus can result in, for example, improved pharmacokinetic properties. (EP A 232,262). Alternatively, deleting the Fc part after the fusion protein has been expressed, detected, and purified, would be desired. For example, the Fc portion may hinder therapy and diagnosis if the fusion protein is used as an antigen for immunizations. In drug discovery, for example, human proteins, such as hIL-5, have been fused with Fc portions for the purpose of high-throughput screening assays to identify antagonists of hIL-5. (See, Bennett et al., J. Molecular Recognition 8:52-58 (1995); Johanson et al., J. Biol. Chem. 270:9459-9471 (1995).

Moreover, the antibodies or fragments thereof of the present invention can be fused to marker sequences, such as a peptide to facilitate purification. In preferred embodiments, the marker amino acid sequence is a hexa-histidine peptide, such as the tag provided in a pQE vector (QIAGEN, Inc., 9259 Eton Avenue, Chatsworth, Calif., 91311), among others, many of which are commercially available. As described in Gentz et al., Proc. Natl. Acad. Sci. USA 86:821-824 (1989), for instance, hexa-histidine provides for convenient purification of the fusion protein. Other peptide tags useful for purification include, but are not limited to, the "HA" tag, which corresponds to an epitope derived from the influenza hemagglutinin protein (Wilson et al., Cell 37:767 (1984)) and the "flag" tag.

The present invention further encompasses antibodies or fragments thereof conjugated to a diagnostic or therapeutic agent. The antibodies can be used diagnostically to, for example, monitor the development or progression of a tumor as part of a clinical testing procedure to, e.g., determine the efficacy of a given treatment regimen. Detection can be facilitated by coupling the antibody to a detectable substance. Examples of detectable substances include various enzymes, prosthetic groups, fluorescent materials, luminescent materials, bioluminescent materials, radioactive materials, positron emitting metals using various positron emission tomographies, and nonradioactive paramagnetic metal ions. The detectable substance may be coupled or conjugated either directly to the antibody (or fragment thereof) or indirectly, through an intermediate (such as, for example, a linker known in the art) using techniques known in the art. See, for example, U.S. Pat. No. 4,741,900 for metal ions which can be conjugated to antibodies for use as diagnostics according to the present invention. Examples of suitable enzymes include horseradish peroxidase, alkaline phosphatase, beta-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin; and examples of suitable radioactive material include 125I, 131I, 111In or 99Tc.

Further, an antibody or fragment thereof may be conjugated to a therapeutic moiety such as a cytotoxin, e.g., a cytostatic or cytocidal agent, a therapeutic agent or a radioactive metal ion, e.g., alpha-emitters such as, for example, 213Bi. A cytotoxin or cytotoxic agent includes any agent that is detrimental to cells. Examples include paclitaxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. Therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine).

The conjugates of the invention can be used for modifying a given biological response, the therapeutic agent or drug moiety is not to be construed as limited to classical chemical therapeutic agents. For example, the drug moiety may be a protein or polypeptide possessing a desired biological activity. Such proteins may include, for example, a toxin such as abrin, ricin A, pseudomonas exotoxin, or diphtheria toxin; a protein such as tumor necrosis factor, a-interferon, β-interferon, nerve growth factor, platelet derived growth factor, tissue plasminogen activator, an apoptotic agent, e.g., TNF-alpha, TNF-beta, AIM I (See, International Publication No. WO 97/33899), AIM II (See, International Publication No. WO 97/34911), Fas Ligand (Takahashi et al., *Int. Immunol.,* 6:1567-1574 (1994)), VEGI (See, International Publication No. WO 99/23105), a thrombotic agent or an anti-angiogenic agent, e.g., angiostatin or endostatin; or, biological response modifiers such as, for example, lymphokines, interleukin-1 ("IL-1"), interleukin-2 ("IL-2"), interleukin-6 ("IL-6"), granulocyte macrophage colony stimulating factor ("GM-CSF"), granulocyte colony stimulating factor ("G-CSF"), or other growth factors.

Antibodies may also be attached to solid supports, which are particularly useful for immunoassays or purification of the target antigen. Such solid supports include, but are not limited to, glass, cellulose, polyacrylamide, nylon, polystyrene, polyvinyl chloride or polypropylene.

Techniques for conjugating such therapeutic moiety to antibodies are well known, see, e.g., Arnon et al., "Monoclonal Antibodies For Immunotargeting Of Drugs In Cancer Therapy", in Monoclonal Antibodies And Cancer Therapy, Reisfeld et al. (eds.), pp. 243-56 (Alan R. Liss, Inc. 1985); Hellstrom et al., "Antibodies For Drug Delivery", in Controlled Drug Delivery (2nd Ed.), Robinson et al. (eds.), pp. 623-53 (Marcel Dekker, Inc. 1987); Thorpe, "Antibody Carriers Of Cytotoxic Agents In Cancer Therapy: A Review", in Monoclonal Antibodies '84: Biological And Clinical Applications, Pinchera et al. (eds.), pp. 475-506 (1985); "Analysis, Results, And Future Prospective Of The Therapeutic Use Of Radiolabeled Antibody In Cancer Therapy", in Monoclonal Antibodies For Cancer Detection And Therapy, Baldwin et al. (eds.), pp. 303-16 (Academic Press 1985), and Thorpe et al., "The Preparation And Cytotoxic Properties Of Antibody-Toxin Conjugates", Immunol. Rev. 62:119-58 (1982).

Alternatively, an antibody can be conjugated to a second antibody to form an antibody heteroconjugate as described by Segal in U.S. Pat. No. 4,676,980, which is incorporated herein by reference in its entirety.

An antibody, with or without a therapeutic moiety conjugated to it, administered alone or in combination with cytotoxic factor(s) and/or cytokine(s) can be used as a therapeutic.

Immunophenotyping

The antibodies of the invention may be utilized for immunophenotyping of cell lines and biological samples. The translation product of the gene of the present invention may be useful as a cell specific marker, or more specifically as a cellular marker that is differentially expressed at various stages of differentiation and/or maturation of particular cell types. Monoclonal antibodies directed against a specific epitope, or combination of epitopes, will allow for the screening of cellular populations expressing the marker. Various techniques can be utilized using monoclonal antibodies to screen for cellular populations expressing the marker(s), and include magnetic separation using antibody-coated magnetic beads, "panning" with antibody attached to a solid matrix (i.e., plate), and flow cytometry (See, e.g., U.S. Pat. No. 5,985,660; and Morrison et al., *Cell,* 96:737-49 (1999)).

These techniques allow for the screening of particular populations of cells, such as might be found with hematological malignancies (i.e. minimal residual disease (MRD) in acute leukemic patients) and "non-self" cells in transplantations to prevent Graft-versus-Host Disease (GVHD). Alternatively, these techniques allow for the screening of hematopoietic stem and progenitor cells capable of undergoing proliferation and/or differentiation, as might be found in human umbilical cord blood.

Assays for Antibody Binding

The antibodies of the invention may be assayed for immunospecific binding by any method known in the art. The immunoassays which can be used include but are not limited to competitive and non-competitive assay systems using techniques such as western blots, radioimmunoassays, ELISA (enzyme linked immunosorbent assay), "sandwich" immunoassays, immunoprecipitation assays, precipitin reactions, gel diffusion precipitin reactions, immunodiffusion assays, agglutination assays, complement-fixation assays, immunoradiometric assays, fluorescent immunoassays, protein A immunoassays, to name but a few. Such assays are routine and well known in the art (see, e.g., Ausubel et al, eds, 1994, Current Protocols in Molecular Biology, Vol. 1, John Wiley & Sons, Inc., New York, which is incorporated by reference herein in its entirety). Exemplary immunoassays are described briefly below (but are not intended by way of limitation).

Immunoprecipitation protocols generally comprise lysing a population of cells in a lysis buffer such as RIPA buffer (1% NP-40 or Triton X-100, 1% sodium deoxycholate, 0.1% SDS, 0.15 M NaCl, 0.01 M sodium phosphate at pH 7.2, 1% Trasylol) supplemented with protein phosphatase and/or protease inhibitors (e.g., EDTA, PMSF, aprotinin, sodium vanadate), adding the antibody of interest to the cell lysate, incubating for a period of time (e.g., 1-4 hours) at 4° C., adding protein A and/or protein G sepharose beads to the cell lysate, incubating for about an hour or more at 4° C., washing the beads in lysis buffer and resuspending the beads in SDS/sample buffer. The ability of the antibody of interest to immunoprecipitate a particular antigen can be assessed by, e.g., western blot analysis. One of skill in the art would be knowledgeable as to the parameters that can be modified to increase the binding of the antibody to an antigen and decrease the background (e.g., pre-clearing the cell lysate with sepharose beads). For further discussion regarding immunoprecipitation protocols see, e.g., Ausubel et al, eds, 1994, Current Protocols in Molecular Biology, Vol. 1, John Wiley & Sons, Inc., New York at 10.16.1.

Western blot analysis generally comprises preparing protein samples, electrophoresis of the protein samples in a polyacrylamide gel (e.g., 8%-20% SDS-PAGE depending on the molecular weight of the antigen), transferring the protein sample from the polyacrylamide gel to a membrane such as nitrocellulose, PVDF or nylon, blocking the membrane in blocking solution (e.g., PBS with 3% BSA or non-fat milk), washing the membrane in washing buffer (e.g., PBS-Tween 20), blocking the membrane with primary antibody (the antibody of interest) diluted in blocking buffer, washing the membrane in washing buffer, blocking the membrane with a secondary antibody (which recognizes the primary antibody, e.g., an anti-human antibody) conjugated to an enzymatic substrate (e.g., horseradish peroxidase or alkaline phosphatase) or radioactive molecule (e.g., 32P or 125I) diluted in blocking buffer, washing the membrane in wash buffer, and detecting the presence of the antigen. One of skill in the art would be knowledgeable as to the parameters that can be modified to increase the signal detected and to reduce the background noise. For further discussion regarding western blot protocols see, e.g., Ausubel et al, eds, 1994, Current Protocols in Molecular Biology, Vol. 1, John Wiley & Sons, Inc., New York at 10.8.1.

ELISAs comprise preparing antigen, coating the well of a 96 well microtiter plate with the antigen, adding the antibody of interest conjugated to a detectable compound such as an enzymatic substrate (e.g., horseradish peroxidase or alkaline phosphatase) to the well and incubating for a period of time, and detecting the presence of the antigen. In ELISAs the antibody of interest does not have to be conjugated to a detectable compound; instead, a second antibody (which recognizes the antibody of interest) conjugated to a detectable compound may be added to the well. Further, instead of coating the well with the antigen, the antibody may be coated to the well. In this case, a second antibody conjugated to a detectable compound may be added following the addition of the antigen of interest to the coated well. One of skill in the art would be knowledgeable as to the parameters that can be modified to increase the signal detected as well as other variations of ELISAs known in the art. For further discussion regarding ELISAs see, e.g., Ausubel et al, eds, 1994, Current Protocols in Molecular Biology, Vol. 1, John Wiley & Sons, Inc., New York at 11.2.1.

The binding affinity of an antibody to an antigen and the off-rate of an antibody-antigen interaction can be determined by competitive binding assays. One example of a competitive binding assay is a radioimmunoassay comprising the incubation of labeled antigen (e.g., 3H or 125I) with the antibody of interest in the presence of increasing amounts of unlabeled antigen, and the detection of the antibody bound to the labeled antigen. The affinity of the antibody of interest for a particular antigen and the binding off-rates can be determined from the data by scatchard plot analysis. Competition with a second antibody can also be determined using radioimmunoassays. In this case, the antigen is incubated with antibody of interest conjugated to a labeled compound (e.g., 3H or 125I) in the presence of increasing amounts of an unlabeled second antibody.

Therapeutic Uses

The present invention is further directed to antibody-based therapies which involve administering antibodies of the invention to an animal, preferably a mammal, and most preferably a human, patient for treating one or more of the disclosed diseases, disorders, or conditions. Therapeutic compounds of the invention include, but are not limited to, antibodies of the invention (including fragments, analogs and derivatives thereof as described herein) and nucleic acids encoding antibodies of the invention (including fragments, analogs and derivatives thereof and anti-idiotypic antibodies as described herein). The antibodies of the invention can be used to treat, inhibit or prevent diseases, disorders or conditions associated with aberrant expression and/or activity of a polypeptide of the invention, including, but not limited to, any one or more of the diseases, disorders, or conditions described herein. The treatment and/or prevention of diseases, disorders, or conditions associated with aberrant expression and/or activity of a polypeptide of the invention includes, but is not limited to, alleviating symptoms associated with those diseases, disorders or conditions. Antibodies of the invention may be provided in pharmaceutically acceptable compositions as known in the art or as described herein.

A summary of the ways in which the antibodies of the present invention may be used therapeutically includes binding polynucleotides or polypeptides of the present invention locally or systemically in the body or by direct cytotoxicity of the antibody, e.g. as mediated by complement (CDC) or by effector cells (ADCC). Some of these approaches are described in more detail below. Armed with the teachings provided herein, one of ordinary skill in the art will know how to use the antibodies of the present invention for diagnostic, monitoring or therapeutic purposes without undue experimentation.

The antibodies of this invention may be advantageously utilized in combination with other monoclonal or chimeric antibodies, or with lymphokines or hematopoietic growth factors (such as, e.g., IL-2, IL-3 and IL-7), for example, which serve to increase the number or activity of effector cells which interact with the antibodies.

The antibodies of the invention may be administered alone or in combination with other types of treatments (e.g., radiation therapy, chemotherapy, hormonal therapy, immunotherapy and anti-tumor agents). Generally, administration of products of a species origin or species reactivity (in the case of antibodies) that is the same species as that of the patient is preferred. Thus, in a preferred embodiment, human antibodies, fragments derivatives, analogs, or nucleic acids, are administered to a human patient for therapy or prophylaxis.

It is preferred to use high affinity and/or potent in vivo inhibiting and/or neutralizing antibodies against polypeptides or polynucleotides of the present invention, fragments or regions thereof, for both immunoassays directed to and therapy of disorders related to polynucleotides or polypeptides, including fragments thereof, of the present invention. Such antibodies, fragments, or regions, will preferably have an affinity for polynucleotides or polypeptides of the invention, including fragments thereof. Preferred binding affinities include those with a dissociation constant or Kd less than $5\times10^{-2}$ M, $10^{-2}$ M, $5\times10^{-3}$ M, $10^{-3}$ M, $5\times10^{-4}$ M, $10^{-4}$ M, $5\times10^{-5}$ M, $10^{-5}$ M, $5\times10^{-6}$ M, $10^{-6}$ M, $5\times10^{-7}$ M, $10^{-7}$ M, $5\times10^{-8}$ M, $10^{-8}$ M, $5\times10^{-9}$ M, $10^{-9}$ M, $5\times10^{-10}$ M, $10^{-10}$ M, $5\times10^{-11}$ M, $10^{-11}$ M, $5\times10^{-12}$ M, $10^{-12}$ M, $5\times10^{-13}$ M, $10^{-13}$ M, $5\times10^{-14}$ M, $10^{-14}$ M, $5\times10^{-15}$ M, and $10^{-15}$ M.

Gene Therapy

In a specific embodiment, nucleic acids comprising sequences encoding antibodies or functional derivatives thereof, are administered to treat, inhibit or prevent a disease or disorder associated with aberrant expression and/or activity of a polypeptide of the invention, by way of gene therapy. Gene therapy refers to therapy performed by the administration to a subject of an expressed or expressible nucleic acid. In this embodiment of the invention, the nucleic acids produce their encoded protein that mediates a therapeutic effect.

Any of the methods for gene therapy available in the art can be used according to the present invention. Exemplary methods are described below.

For general reviews of the methods of gene therapy, see Goldspiel et al., Clinical Pharmacy 12:488-505 (1993); Wu and Wu, Biotherapy 3:87-95 (1991); Tolstoshev, Ann. Rev. Pharmacol. Toxicol. 32:573-596 (1993); Mulligan, Science 260:926-932 (1993); and Morgan and Anderson, Ann. Rev. Biochem. 62:191-217 (1993); May, TIBTECH 11(5):155-215 (1993). Methods commonly known in the art of recombinant DNA technology which can be used are described in Ausubel et al. (eds.), Current Protocols in Molecular Biology, John Wiley & Sons, NY (1993); and Kriegler, Gene Transfer and Expression, A Laboratory Manual, Stockton Press, NY (1990).

In a preferred aspect, the compound comprises nucleic acid sequences encoding an antibody, said nucleic acid sequences being part of expression vectors that express the antibody or fragments or chimeric proteins or heavy or light chains thereof in a suitable host. In particular, such nucleic acid sequences have promoters operably linked to the antibody coding region, said promoter being inducible or constitutive, and, optionally, tissue-specific. In another particular embodiment, nucleic acid molecules are used in which the antibody coding sequences and any other desired sequences are flanked by regions that promote homologous recombination at a desired site in the genome, thus providing for intrachromosomal expression of the antibody encoding nucleic acids (Koller and Smithies, Proc. Natl. Acad. Sci. USA 86:8932-8935 (1989); Zijlstra et al., Nature 342:435-438 (1989). In specific embodiments, the expressed antibody molecule is a single chain antibody; alternatively, the nucleic acid sequences include sequences encoding both the heavy and light chains, or fragments thereof, of the antibody.

Delivery of the nucleic acids into a patient may be either direct, in which case the patient is directly exposed to the nucleic acid or nucleic acid-carrying vectors, or indirect, in which case, cells are first transformed with the nucleic acids in vitro, then transplanted into the patient. These two approaches are known, respectively, as in vivo or ex vivo gene therapy.

In a specific embodiment, the nucleic acid sequences are directly administered in vivo, where it is expressed to produce the encoded product. This can be accomplished by any of numerous methods known in the art, e.g., by constructing them as part of an appropriate nucleic acid expression vector and administering it so that they become intracellular, e.g., by infection using defective or attenuated retrovirals or other viral vectors (see U.S. Pat. No. 4,980,286), or by direct injection of naked DNA, or by use of microparticle bombardment (e.g., a gene gun; Biolistic, Dupont), or coating with lipids or cell-surface receptors or transfecting agents, encapsulation in liposomes, microparticles, or microcapsules, or by administering them in linkage to a peptide which is known to enter the nucleus, by administering it in linkage to a ligand subject to receptor-mediated endocytosis (see, e.g., Wu and Wu, J. Biol. Chem. 262:4429-4432 (1987)) (which can be used to target cell types specifically expressing the receptors), etc. In another embodiment, nucleic acid-ligand complexes can be formed in which the ligand comprises a fusogenic viral peptide to disrupt endosomes, allowing the nucleic acid to avoid lysosomal degradation. In yet another embodiment, the nucleic acid can be targeted in vivo for cell specific uptake and expression, by targeting a specific receptor (see, e.g., PCT Publications WO 92/06180; WO 92/22635; WO92/20316; WO93/14188, WO 93/20221). Alternatively, the nucleic acid can be introduced intracellularly and incorporated within host cell DNA for expression, by homologous recombination (Koller and Smithies, Proc. Natl. Acad. Sci. USA 86:8932-8935 (1989); Zijlstra et al., Nature 342:435-438 (1989)).

In a specific embodiment, viral vectors that contains nucleic acid sequences encoding an antibody of the invention are used. For example, a retroviral vector can be used (see Miller et al., Meth. Enzymol. 217:581-599 (1993)). These retroviral vectors contain the components necessary for the correct packaging of the viral genome and integration into the host cell DNA. The nucleic acid sequences encoding the antibody to be used in gene therapy are cloned into one or more vectors, which facilitates delivery of the gene into a patient. More detail about retroviral vectors can be found in Boesen et al., Biotherapy 6:291-302 (1994), which describes the use of a retroviral vector to deliver the mdr1 gene to hematopoietic stem cells in order to make the stem cells more resistant to chemotherapy. Other references illustrating the use of retroviral vectors in gene therapy are: Clowes et al., J. Clin. Invest. 93:644-651 (1994); Kiem et al., Blood 83:1467-1473 (1994); Salmons and Gunzberg, Human Gene Therapy 4:129-141 (1993); and Grossman and Wilson, Curr. Opin. in Genetics and Devel. 3:110-114 (1993).

Adenoviruses are other viral vectors that can be used in gene therapy. Adenoviruses are especially attractive vehicles for delivering genes to respiratory epithelia. Adenoviruses naturally infect respiratory epithelia where they cause a mild disease. Other targets for adenovirus-based delivery systems are liver, the central nervous system, endothelial cells, and muscle. Adenoviruses have the advantage of being capable of infecting non-dividing cells. Kozarsky and Wilson, Current Opinion in Genetics and Development 3:499-503 (1993) present a review of adenovirus-based gene therapy. Bout et al., Human Gene Therapy 5:3-10 (1994) demonstrated the use of adenovirus vectors to transfer genes to the respiratory epithelia of rhesus monkeys. Other instances of the use of adenoviruses in gene therapy can be found in Rosenfeld et al., Science 252:431-434 (1991); Rosenfeld et al., Cell 68:143-155 (1992); Mastrangeli et al., J. Clin. Invest. 91:225-234 (1993); PCT Publication WO94/12649; and Wang, et al., Gene Therapy 2:775-783 (1995). In a preferred embodiment, adenovirus vectors are used.

Adeno-associated virus (AAV) has also been proposed for use in gene therapy (Walsh et al., Proc. Soc. Exp. Biol. Med. 204:289-300 (1993); U.S. Pat. No. 5,436,146).

Another approach to gene therapy involves transferring a gene to cells in tissue culture by such methods as electroporation, lipofection, calcium phosphate mediated transfection, or viral infection. Usually, the method of transfer includes the transfer of a selectable marker to the cells. The cells are then placed under selection to isolate those cells that have taken up and are expressing the transferred gene. Those cells are then delivered to a patient.

In this embodiment, the nucleic acid is introduced into a cell prior to administration in vivo of the resulting recombinant cell. Such introduction can be carried out by any method known in the art, including but not limited to transfection, electroporation, microinjection, infection with a viral or bacteriophage vector containing the nucleic acid sequences, cell fusion, chromosome-mediated gene transfer, microcell-mediated gene transfer, spheroplast fusion, etc. Numerous techniques are known in the art for the introduction of foreign genes into cells (see, e.g., Loeffler and Behr, Meth. Enzymol. 217:599-618 (1993); Cohen et al., Meth. Enzymol. 217:618-644 (1993); Cline, Pharmac. Ther. 29:69-92m (1985) and may be used in accordance with the present invention, provided that the necessary developmental and physiological functions of the recipient cells are not disrupted. The technique should provide for the stable transfer of the nucleic acid to the cell, so that the nucleic acid is expressible by the cell and preferably heritable and expressible by its cell progeny.

The resulting recombinant cells can be delivered to a patient by various methods known in the art. Recombinant blood cells (e.g., hematopoietic stem or progenitor cells) are preferably administered intravenously. The amount of cells envisioned for use depends on the desired effect, patient state, etc., and can be determined by one skilled in the art.

Cells into which a nucleic acid can be introduced for purposes of gene therapy encompass any desired, available cell type, and include but are not limited to epithelial cells, endothelial cells, keratinocytes, fibroblasts, muscle cells, hepatocytes; blood cells such as Tlymphocytes, Blymphocytes, monocytes, macrophages, neutrophils, eosinophils, megakaryocytes, granulocytes; various stem or progenitor cells, in particular hematopoietic stem or progenitor cells, e.g., as obtained from bone marrow, umbilical cord blood, peripheral blood, fetal liver, etc.

In a preferred embodiment, the cell used for gene therapy is autologous to the patient.

In an embodiment in which recombinant cells are used in gene therapy, nucleic acid sequences encoding an antibody are introduced into the cells such that they are expressible by the cells or their progeny, and the recombinant cells are then administered in vivo for therapeutic effect. In a specific embodiment, stem or progenitor cells are used. Any stem and/or progenitor cells which can be isolated and maintained in vitro can potentially be used in accordance with this embodiment of the present invention (see e.g. PCT Publication WO 94/08598; Stemple and Anderson, Cell 71:973-985 (1992); Rheinwald, Meth. Cell Bio. 21A:229 (1980); and Pittelkow and Scott, Mayo Clinic Proc. 61:771 (1986)).

In a specific embodiment, the nucleic acid to be introduced for purposes of gene therapy comprises an inducible promoter operably linked to the coding region, such that expression of the nucleic acid is controllable by controlling the presence or absence of the appropriate inducer of transcription. Demonstration of Therapeutic or Prophylactic Activity The compounds or pharmaceutical compositions of the invention are preferably tested in vitro, and then in vivo for the desired therapeutic or prophylactic activity, prior to use in humans. For example, in vitro assays to demonstrate the therapeutic or prophylactic utility of a compound or pharmaceutical composition include, the effect of a compound on a cell line or a patient tissue sample. The effect of the compound or composition on the cell line and/or tissue sample can be determined utilizing techniques known to those of skill in the art including, but not limited to, rosette formation assays and cell lysis assays. In accordance with the invention, in vitro assays which can be used to determine whether administration of a specific compound is indicated, include in vitro cell culture assays in which a patient tissue sample is grown in culture, and exposed to or otherwise administered a compound, and the effect of such compound upon the tissue sample is observed.

Therapeutic/Prophylactic Administration and Composition

The invention provides methods of treatment, inhibition and prophylaxis by administration to a subject of an effective amount of a compound or pharmaceutical composition of the invention, preferably an antibody of the invention. In a preferred aspect, the compound is substantially purified (e.g., substantially free from substances that limit its effect or produce undesired side-effects). The subject is preferably an animal, including but not limited to animals such as cows, pigs, horses, chickens, cats, dogs, etc., and is preferably a mammal, and most preferably human.

Formulations and methods of administration that can be employed when the compound comprises a nucleic acid or an immunoglobulin are described above; additional appropriate formulations and routes of administration can be selected from among those described herein below.

Various delivery systems are known and can be used to administer a compound of the invention, e.g., encapsulation in liposomes, microparticles, microcapsules, recombinant cells capable of expressing the compound, receptor-mediated endocytosis (see, e.g., Wu and Wu, J. Biol. Chem. 262:4429-4432 (1987)), construction of a nucleic acid as part of a retroviral or other vector, etc. Methods of introduction include but are not limited to intradermal, intramuscular, intraperitoneal, intravenous, subcutaneous, intranasal, epidural, and oral routes. The compounds or compositions may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local. In addition, it may be desirable to introduce the pharmaceutical compounds or compositions of the invention into the central nervous system by any suitable route, including intraventricular and intrathecal injection; intraventricular injection may be facilitated by an intraventricular catheter, for example, attached to a reservoir, such as an Ommaya reservoir. Pulmonary administration can also be employed, e.g., by use of an inhaler or nebulizer, and formulation with an aerosolizing agent.

In a specific embodiment, it may be desirable to administer the pharmaceutical compounds or compositions of the invention locally to the area in need of treatment; this may be achieved by, for example, and not by way of limitation, local infusion during surgery, topical application, e.g., in conjunction with a wound dressing after surgery, by injection, by means of a catheter, by means of a suppository, or by means of an implant, said implant being of a porous, non-porous, or gelatinous material, including membranes, such as sialastic membranes, or fibers. Preferably, when administering a protein, including an antibody, of the invention, care must be taken to use materials to which the protein does not absorb.

In another embodiment, the compound or composition can be delivered in a vesicle, in particular a liposome (see Langer, Science 249:1527-1533 (1990); Treat et al., in Liposomes in the Therapy of Infectious Disease and Cancer, Lopez-Berestein and Fidler (eds.), Liss, New York, pp. 353-365 (1989); Lopez-Berestein, ibid., pp. 317-327; see generally ibid.)

In yet another embodiment, the compound or composition can be delivered in a controlled release system. In one embodiment, a pump may be used (see Langer, supra; Sefton, CRC Crit. Ref. Biomed. Eng. 14:201 (1987); Buchwald et al., Surgery 88:507 (1980); Saudek et al., N. Engl. J. Med. 321:574 (1989)). In another embodiment, polymeric materials can be used (see Medical Applications of Controlled Release, Langer and Wise (eds.), CRC Pres., Boca Raton, Fla. (1974); Controlled Drug Bioavailability, Drug Product Design and Performance, Smolen and Ball (eds.), Wiley, New York (1984); Ranger and Peppas, J., Macromol. Sci. Rev. Macromol. Chem. 23:61 (1983); see also Levy et al., Science 228:190 (1985); During et al., Ann. Neurol. 25:351 (1989); Howard et al., J. Neurosurg. 71:105 (1989)). In yet another embodiment, a controlled release system can be placed in proximity of the therapeutic target, i.e., the brain, thus requiring only a fraction of the systemic dose (see, e.g., Goodson, in Medical Applications of Controlled Release, supra, vol. 2, pp. 115-138 (1984)).

Other controlled release systems are discussed in the review by Langer (Science 249:1527-1533 (1990)).

In a specific embodiment where the compound of the invention is a nucleic acid encoding a protein, the nucleic acid can be administered in vivo to promote expression of its encoded protein, by constructing it as part of an appropriate nucleic acid expression vector and administering it so that it becomes intracellular, e.g., by use of a retroviral vector (see U.S. Pat. No. 4,980,286), or by direct injection, or by use of microparticle bombardment (e.g., a gene gun; Biolistic, Dupont), or coating with lipids or cell-surface receptors or transfecting agents, or by administering it in linkage to a homeobox-like peptide which is known to enter the nucleus (see e.g., Joliot et al., Proc. Natl. Acad. Sci. USA 88:1864-1868 (1991)), etc. Alternatively, a nucleic acid can be introduced intracellularly and incorporated within host cell DNA for expression, by homologous recombination.

The present invention also provides pharmaceutical compositions. Such compositions comprise a therapeutically effective amount of a compound, and a pharmaceutically acceptable carrier. In a specific embodiment, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in "Remington's Pharmaceutical Sciences" by E. W. Martin. Such compositions will contain a therapeutically effective amount of the compound, preferably in purified form, together with a suitable amount of carrier so as to provide the form for proper administration to the patient. The formulation should suit the mode of administration.

In a preferred embodiment, the composition is formulated in accordance with routine procedures as a pharmaceutical composition adapted for intravenous administration to human beings. Typically, compositions for intravenous administration are solutions in sterile isotonic aqueous buffer. Where necessary, the composition may also include a solubilizing agent and a local anesthetic such as lignocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The compounds of the invention can be formulated as neutral or salt forms. Pharmaceutically acceptable salts include those formed with anions such as those derived from hydrochloric, phosphoric, acetic, oxalic, tartaric acids, etc., and those formed with cations such as those derived from sodium, potassium, ammonium, calcium, ferric hydroxides, isopropylamine, triethylamine, 2-ethylamino ethanol, histidine, procaine, etc.

The amount of the compound of the invention which will be effective in the treatment, inhibition and prevention of a disease or disorder associated with aberrant expression and/or activity of a polypeptide of the invention can be determined by standard clinical techniques. In addition, in vitro assays may optionally be employed to help identify optimal dosage ranges. The precise dose to be employed in the formulation will also depend on the route of administration, and the seriousness of the disease or disorder, and should be decided according to the judgment of the practitioner and each patient's circumstances. Effective doses may be extrapolated from dose-response curves derived from in vitro or animal model test systems.

For antibodies, the dosage administered to a patient is typically 0.1 mg/kg to 100 mg/kg of the patient's body weight. Preferably, the dosage administered to a patient is between 0.1 mg/kg and 20 mg/kg of the patient's body weight, more preferably 1 mg/kg to 10 mg/kg of the patient's body weight. Generally, human antibodies have a longer half-life within the human body than antibodies from other species due to the immune response to the foreign polypeptides. Thus, lower dosages of human antibodies and less frequent administration is often possible. Further, the dosage and frequency of administration of antibodies of the invention may be reduced by enhancing uptake and tissue penetration (e.g., into the brain) of the antibodies by modifications such as, for example, lipidation.

The invention also provides a pharmaceutical pack or kit comprising one or more containers filled with one or more of the ingredients of the pharmaceutical compositions of the invention. Optionally associated with such container(s) can be a notice in the form prescribed by a governmental agency regulating the manufacture, use or sale of pharmaceuticals or biological products, which notice reflects approval by the agency of manufacture, use or sale for human administration.

Diagnosis and Imaging

Labeled antibodies, and derivatives and analogs thereof, which specifically bind to a polypeptide of interest can be used for diagnostic purposes to detect, diagnose, or monitor diseases, disorders, and/or conditions associated with the aberrant expression and/or activity of a polypeptide of the invention. The invention provides for the detection of aberrant expression of a polypeptide of interest, comprising (a) assaying the expression of the polypeptide of interest in cells or body fluid of an individual using one or more antibodies specific to the polypeptide interest and (b) comparing the level of gene expression with a standard gene expression level, whereby an increase or decrease in the assayed polypeptide gene expression level compared to the standard expression level is indicative of aberrant expression.

The invention provides a diagnostic assay for diagnosing a disorder, comprising (a) assaying the expression of the polypeptide of interest in cells or body fluid of an individual using one or more antibodies specific to the polypeptide interest and (b) comparing the level of gene expression with a standard gene expression level, whereby an increase or decrease in the assayed polypeptide gene expression level compared to the standard expression level is indicative of a particular disorder. With respect to cancer, the presence of a relatively high amount of transcript in biopsied tissue from an individual may indicate a predisposition for the development of the disease, or may provide a means for detecting the disease prior to the appearance of actual clinical symptoms. A more definitive diagnosis of this type may allow health professionals to employ preventative measures or aggressive treatment earlier thereby preventing the development or further progression of the cancer.

Antibodies of the invention can be used to assay protein levels in a biological sample using classical immunohistological methods known to those of skill in the art (e.g., see Jalkanen, et al., J. Cell. Biol. 101:976-985 (1985); Jalkanen, et al., J. Cell. Biol. 105:3087-3096 (1987)). Other antibody-based methods useful for detecting protein gene expression include immunoassays, such as the enzyme linked immunosorbent assay (ELISA) and the radioimmunoassay (RIA). Suitable antibody assay labels are known in the art and include enzyme labels, such as, glucose oxidase; radioisotopes, such as iodine (125I, 121I), carbon (14C), sulfur (35S), tritium (3H), indium (112In), and technetium (99Tc); luminescent labels, such as luminol; and fluorescent labels, such as fluorescein and rhodamine, and biotin.

One aspect of the invention is the detection and diagnosis of a disease or disorder associated with aberrant expression of a polypeptide of interest in an animal, preferably a mammal and most preferably a human. In one embodiment, diagnosis comprises: a) administering (for example, parenterally, subcutaneously, or intraperitoneally) to a subject an effective amount of a labeled molecule which specifically binds to the polypeptide of interest; b) waiting for a time interval following the administering for permitting the labeled molecule to preferentially concentrate at sites in the subject where the polypeptide is expressed (and for unbound labeled molecule to be cleared to background level); c) determining background level; and d) detecting the labeled molecule in the subject, such that detection of labeled molecule above the background level indicates that the subject has a particular disease or disorder associated with aberrant expression of the polypeptide of interest. Background level can be determined by various methods including, comparing the amount of labeled molecule detected to a standard value previously determined for a particular system.

It will be understood in the art that the size of the subject and the imaging system used will determine the quantity of imaging moiety needed to produce diagnostic images. In the case of a radioisotope moiety, for a human subject, the quantity of radioactivity injected will normally range from about 5 to 20 millicuries of 99mTc. The labeled antibody or antibody fragment will then preferentially accumulate at the location of cells which contain the specific protein. In vivo tumor imaging is described in S. W. Burchiel et al., "Immunopharmacokinetics of Radiolabeled Antibodies and Their Fragments." (Chapter 13 in Tumor Imaging: The Radiochemical Detection of Cancer, S. W. Burchiel and B. A. Rhodes, eds., Masson Publishing Inc. (1982).

Depending on several variables, including the type of label used and the mode of administration, the time interval following the administration for permitting the labeled molecule to preferentially concentrate at sites in the subject and for unbound labeled molecule to be cleared to background level is 6 to 48 hours or 6 to 24 hours or 6 to 12 hours. In another embodiment the time interval following administration is 5 to 20 days or 5 to 10 days.

In an embodiment, monitoring of the disease or disorder is carried out by repeating the method for diagnosing the disease or disease, for example, one month after initial diagnosis, six months after initial diagnosis, one year after initial diagnosis, etc.

Presence of the labeled molecule can be detected in the patient using methods known in the art for in vivo scanning. These methods depend upon the type of label used. Skilled artisans will be able to determine the appropriate method for detecting a particular label. Methods and devices that may be used in the diagnostic methods of the invention include, but are not limited to, computed tomography (CT), whole body scan such as position emission tomography (PET), magnetic resonance imaging (MRI), and sonography.

In a specific embodiment, the molecule is labeled with a radioisotope and is detected in the patient using a radiation responsive surgical instrument (Thurston et al., U.S. Pat. No. 5,441,050). In another embodiment, the molecule is labeled with a fluorescent compound and is detected in the patient using a fluorescence responsive scanning instrument. In another embodiment, the molecule is labeled with a positron emitting metal and is detected in the patent using positron emission-tomography. In yet another embodiment, the molecule is labeled with a paramagnetic label and is detected in a patient using magnetic resonance imaging (MRI).

Kits

The present invention provides kits that can be used in the above methods. In one embodiment, a kit comprises an antibody of the invention, preferably a purified antibody, in one or more containers. In a specific embodiment, the kits of the present invention contain a substantially isolated polypeptide comprising an epitope which is specifically immunoreactive with an antibody included in the kit. Preferably, the kits of the present invention further comprise a control antibody which does not react with the polypeptide of interest. In another specific embodiment, the kits of the present invention contain a means for detecting the binding of an antibody to a polypeptide of interest (e.g., the antibody may be conjugated to a detectable substrate such as a fluorescent compound, an enzymatic substrate, a radioactive compound or a luminescent compound, or a second antibody which recognizes the first antibody may be conjugated to a detectable substrate).

In another specific embodiment of the present invention, the kit is a diagnostic kit for use in screening serum containing antibodies specific against proliferative and/or cancerous polynucleotides and polypeptides. Such a kit may include a control antibody that does not react with the polypeptide of interest. Such a kit may include a substantially isolated polypeptide antigen comprising an epitope which is specifically immunoreactive with at least one anti-polypeptide antigen antibody. Further, such a kit includes means for detecting the binding of said antibody to the antigen (e.g., the antibody may be conjugated to a fluorescent compound such as fluorescein or rhodamine which can be detected by flow cytometry). In specific embodiments, the kit may include a recombinantly produced or chemically synthesized polypeptide antigen. The polypeptide antigen of the kit may also be attached to a solid support.

In a more specific embodiment the detecting means of the above-described kit includes a solid support to which said polypeptide antigen is attached. Such a kit may also include a non-attached reporter-labeled anti-human antibody. In this embodiment, binding of the antibody to the polypeptide antigen can be detected by binding of the said reporter-labeled antibody.

In an additional embodiment, the invention includes a diagnostic kit for use in screening serum containing antigens of the polypeptide of the invention. The diagnostic kit includes a substantially isolated antibody specifically immunoreactive with polypeptide or polynucleotide antigens, and means for detecting the binding of the polynucleotide or polypeptide antigen to the antibody. In one embodiment, the antibody is attached to a solid support. In a specific embodiment, the antibody may be a monoclonal antibody. The detecting means of the kit may include a second, labeled monoclonal antibody. Alternatively, or in addition, the detecting means may include a labeled, competing antigen.

In one diagnostic configuration, test serum is reacted with a solid phase reagent having a surface-bound antigen obtained by the methods of the present invention. After binding with specific antigen antibody to the reagent and removing unbound serum components by washing, the reagent is reacted with reporter-labeled anti-human antibody to bind reporter to the reagent in proportion to the amount of bound anti-antigen antibody on the solid support. The reagent is again washed to remove unbound labeled antibody, and the amount of reporter associated with the reagent is determined. Typically, the reporter is an enzyme which is detected by incubating the solid phase in the presence of a suitable fluorometric, luminescent or calorimetric substrate (Sigma, St. Louis, Mo.).

The solid surface reagent in the above assay is prepared by known techniques for attaching protein material to solid support material, such as polymeric beads, dip sticks, 96-well plate or filter material. These attachment methods generally include non-specific adsorption of the protein to the support or covalent attachment of the protein, typically through a free amine group, to a chemically reactive group on the solid support, such as an activated carboxyl, hydroxyl, or aldehyde group. Alternatively, streptavidin coated plates can be used in conjunction with biotinylated antigen(s).

Thus, the invention provides an assay system or kit for carrying out this diagnostic method. The kit generally includes a support with surface-bound recombinant antigens, and a reporter-labeled anti-human antibody for detecting surface-bound anti-antigen antibody.

Fusion Proteins

Any polypeptide of the present invention can be used to generate fusion proteins. For example, the polypeptide of the present invention, when fused to a second protein, can be used as an antigenic tag. Antibodies raised against the polypeptide of the present invention can be used to indirectly detect the second protein by binding to the polypeptide. Moreover, because secreted proteins target cellular locations based on trafficking signals, the polypeptides of the present invention can be used as targeting molecules once fused to other proteins.

Examples of domains that can be fused to polypeptides of the present invention include not only heterologous signal sequences, but also other heterologous functional regions. The fusion does not necessarily need to be direct, but may occur through linker sequences.

Moreover, fusion proteins may also be engineered to improve characteristics of the polypeptide of the present invention. For instance, a region of additional amino acids, particularly charged amino acids, may be added to the N-terminus of the polypeptide to improve stability and persistence during purification from the host cell or subsequent handling and storage. Also, peptide moieties may be added to the polypeptide to facilitate purification. Such regions may be removed prior to final preparation of the polypeptide. The addition of peptide moieties to facilitate handling of polypeptides are familiar and routine techniques in the art.

Moreover, polypeptides of the present invention, including fragments, and specifically epitopes, can be combined with parts of the constant domain of immunoglobulins (IgA, IgE, IgG, IgM) or portions thereof (CH1, CH2, CH3, and any combination thereof, including both entire domains and portions thereof), resulting in chimeric polypeptides. These fusion proteins facilitate purification and show an increased half-life in vivo. One reported example describes chimeric proteins consisting of the first two domains of the human CD4-polypeptide and various domains of the constant regions of the heavy or light chains of mammalian immunoglobulins. (EP A 394,827; Traunecker et al., Nature 331: 84-86 (1988).) Fusion proteins having disulfide-linked dimeric structures (due to the IgG) can also be more efficient in binding and neutralizing other molecules, than the monomeric secreted protein or protein fragment alone. (Fountoulakis et al., J. Biochem. 270:3958-3964 (1995).)

Similarly, EP-A-O 464 533 (Canadian counterpart 2045869) discloses fusion proteins comprising various portions of constant region of immunoglobulin molecules together with another human protein or part thereof. In many cases, the Fc part in a fusion protein is beneficial in therapy and diagnosis, and thus can result in, for example, improved pharmacokinetic properties. (EP-A 0232 262.) Alternatively, deleting the Fc part after the fusion protein has been expressed, detected, and purified, would be desired. For example, the Fc portion may hinder therapy and diagnosis if the fusion protein is used as an antigen for immunizations. In drug discovery, for example, human proteins, such as hIL-5, have been fused with Fc portions for the purpose of high-throughput screening assays to identify antagonists of hIL-5. (See, D. Bennett et al., J. Molecular Recognition 8:52-58 (1995); K. Johanson et al., J. Biol. Chem. 270:9459-9471 (1995).)

Moreover, the polypeptides of the present invention can be fused to marker sequences, such as a peptide which facilitates purification of the fused polypeptide. In preferred embodiments, the marker amino acid sequence is a hexa-histidine peptide, such as the tag provided in a pQE vector (QIAGEN, Inc., 9259 Eton Avenue, Chatsworth, Calif., 91311), among others, many of which are commercially available. As described in Gentz et al., Proc. Natl. Acad. Sci. USA 86:821-824 (1989), for instance, hexa-histidine provides for convenient purification of the fusion protein. Another peptide tag useful for purification, the "HA" tag, corresponds to an epitope derived from the influenza hemagglutinin protein. (Wilson et al., Cell 37:767 (1984).)

Thus, any of these above fusions can be engineered using the polynucleotides or the polypeptides of the present invention.

Vectors, Host Cells, and Protein Production

The present invention also relates to vectors containing the polynucleotide of the present invention, host cells, and the production of polypeptides by recombinant techniques. The vector may be, for example, a phage, plasmid, viral, or retroviral vector. Retroviral vectors may be replication competent or replication defective. In the latter case, viral propagation generally will occur only in complementing host cells.

The polynucleotides may be joined to a vector containing a selectable marker for propagation in a host. Generally, a plasmid vector is introduced in a precipitate, such as a calcium phosphate precipitate, or in a complex with a charged lipid. If the vector is a virus, it may be packaged in vitro using an appropriate packaging cell line and then transduced into host cells.

The polynucleotide insert should be operatively linked to an appropriate promoter, such as the phage lambda PL promoter, the *E. coli* lac, trp, phoA and tac promoters, the SV40 early and late promoters and promoters of retroviral LTRs, to name a few. Other suitable promoters will be known to the skilled artisan. The expression constructs will further contain sites for transcription initiation, termination, and, in the transcribed region, a ribosome binding site for translation. The coding portion of the transcripts expressed by the constructs will preferably include a translation initiating codon at the beginning and a termination codon (UAA, UGA or UAG) appropriately positioned at the end of the polypeptide to be translated.

As indicated, the expression vectors will preferably include at least one selectable marker. Such markers include dihydrofolate reductase, G418 or neomycin resistance for eukaryotic cell culture and tetracycline, kanamycin or ampicillin resistance genes for culturing in *E. coli* and other bacteria. Representative examples of appropriate hosts include, but are not limited to, bacterial cells, such as *E. coli*, *Streptomyces* and *Salmonella typhimurium* cells; fungal cells, such as yeast cells (e.g., *Saccharomyces cerevisiae* or *Pichia pastoris* (ATCC Accession No. 201178)); insect cells such as *Drosophila* S2 and *Spodoptera* Sf9 cells; animal cells such as CHO, COS, 293, and Bowes melanoma cells; and plant cells. Appropriate culture mediums and conditions for the above-described host cells are known in the art.

Among vectors preferred for use in bacteria include pQE70, pQE60 and pQE-9, available from QIAGEN, Inc.; pBluescript vectors, Phagescript vectors, pNH8A, pNH16a, pNH18A, pNH46A, available from Stratagene Cloning Systems, Inc.; and ptrc99a, pKK223-3, pKK233-3, pDR540, pRIT5 available from Pharmacia Biotech, Inc. Among preferred eukaryotic vectors are pWLNEO, pSV2CAT, pOG44, pXT1 and pSG available from Stratagene; and pSVK3, pBPV, pMSG and pSVL available from Pharmacia. Preferred expression vectors for use in yeast systems include, but are not limited to pYES2, pYD1, pTEF1/Zeo, pYES2/GS, pPICZ, pGAPZ, pGAPZalph, pPIC9, pPIC3.5, pHIL-D2, pHIL-S1, pPIC3.5K, pPIC9K, and PAO815 (all available from Invitrogen, Carlbad, Calif.). Other suitable vectors will be readily apparent to the skilled artisan.

Introduction of the construct into the host cell can be effected by calcium phosphate transfection, DEAE-dextran mediated transfection, cationic lipid-mediated transfection, electroporation, transduction, infection, or other methods. Such methods are described in many standard laboratory manuals, such as Davis et al., Basic Methods In Molecular Biology (1986). It is specifically contemplated that the polypeptides of the present invention may in fact be expressed by a host cell lacking a recombinant vector.

A polypeptide of this invention can be recovered and purified from recombinant cell cultures by well-known methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Most preferably, high performance liquid chromatography ("HPLC") is employed for purification.

Polypeptides of the present invention, and preferably the secreted form, can also be recovered from: products purified from natural sources, including bodily fluids, tissues and cells, whether directly isolated or cultured; products of chemical synthetic procedures; and products produced by recombinant techniques from a prokaryotic or eukaryotic host, including, for example, bacterial, yeast, higher plant, insect, and mammalian cells. Depending upon the host employed in a recombinant production procedure, the polypeptides of the present invention may be glycosylated or may be non-glycosylated. In addition, polypeptides of the invention may also include an initial modified methionine residue, in some cases as a result of host-mediated processes. Thus, it is well known in the art that the N-terminal methionine encoded by the translation initiation codon generally is removed with high efficiency from any protein after translation in all eukaryotic cells. While the N-terminal methionine on most proteins also is efficiently removed in most prokaryotes, for some proteins, this prokaryotic removal process is inefficient, depending on the nature of the amino acid to which the N-terminal methionine is covalently linked.

In one embodiment, the yeast *Pichia pastoris* is used to express the polypeptide of the present invention in a eukaryotic system. *Pichia pastoris* is a methylotrophic yeast which can metabolize methanol as its sole carbon source. A main step in the methanol metabolization pathway is the oxidation of methanol to formaldehyde using $O_2$. This reaction is catalyzed by the enzyme alcohol oxidase. In order to metabolize methanol as its sole carbon source, *Pichia pastoris* must generate high levels of alcohol oxidase due, in part, to the relatively low affinity of alcohol oxidase for $O_2$. Consequently, in a growth medium depending on methanol as a main carbon source, the promoter region of one of the two alcohol oxidase genes (AOX1) is highly active. In the presence of methanol, alcohol oxidase produced from the AOX1 gene comprises up to approximately 30% of the total soluble protein in *Pichia pastoris*. See, Ellis, S. B., et al., *Mol. Cell. Biol.* 5:1111-21 (1985); Koutz, P. J, et al., *Yeast* 5:167-77 (1989); Tschopp, J. F., et al., *Nucl. Acids Res.* 15:3859-76 (1987). Thus, a heterologous coding sequence, such as, for example, a polynucleotide of the present invention, under the transcriptional regulation of all or part of the AOX1 regulatory sequence is expressed at exceptionally high levels in *Pichia* yeast grown in the presence of methanol.

In one example, the plasmid vector pPIC9K is used to express DNA encoding a polypeptide of the invention, as set forth herein, in a Pichea yeast system essentially as described in "*Pichia* Protocols: Methods in Molecular Biology," D. R. Higgins and J. Cregg, eds. The Humana Press, Totowa, N.J., 1998. This expression vector allows expression and secretion of a protein of the invention by virtue of the strong AOX1 promoter linked to the *Pichia pastoris* alkaline phosphatase (PHO) secretory signal peptide (i.e., leader) located upstream of a multiple cloning site.

Many other yeast vectors could be used in place of pPIC9K, such as, pYES2, pYD1, pTEF1/Zeo, pYES2/GS, pPICZ, pGAPZ, pGAPZalpha, pPIC9, pPIC3.5, pHIL-D2, pHIL-S1, pPIC3.5K, and PAO815, as one skilled in the art would readily appreciate, as long as the proposed expression construct provides appropriately located signals for transcription, translation, secretion (if desired), and the like, including an in-frame AUG as required.

In another embodiment, high-level expression of a heterologous coding sequence, such as, for example, a polynucleotide of the present invention, may be achieved by cloning the heterologous polynucleotide of the invention into an expression vector such as, for example, pGAPZ or pGAPZalpha, and growing the yeast culture in the absence of methanol.

In addition to encompassing host cells containing the vector constructs discussed herein, the invention also encompasses primary, secondary, and immortalized host cells of vertebrate origin, particularly mammalian origin, that have been engineered to delete or replace endogenous genetic material (e.g., coding sequence), and/or to include genetic material (e.g., heterologous polynucleotide sequences) that is operably associated with the polynucleotides of the invention, and which activates, alters, and/or amplifies endogenous polynucleotides. For example, techniques known in the art may be used to operably associate heterologous control regions (e.g., promoter and/or enhancer) and endogenous polynucleotide sequences via homologous recombination, resulting in the formation of a new transcription unit (see, e.g., U.S. Pat. No. 5,641,670, issued Jun. 24, 1997; U.S. Pat. No. 5,733,761, issued Mar. 31, 1998; International Publication No. WO 96/29411, published Sep. 26, 1996; International Publication No. WO 94/12650, published Aug. 4, 1994; Koller et al., Proc. Natl. Acad. Sci. USA 86:8932-8935 (1989); and Zijlstra et al., Nature 342:435-438 (1989), the disclosures of each of which are incorporated by reference in their entireties).

In addition, polypeptides of the invention can be chemically synthesized using techniques known in the art (e.g., see Creighton, 1983, Proteins: Structures and Molecular Principles, W.H. Freeman & Co., N.Y., and Hunkapiller et al., *Nature,* 310:105-111 (1984)). For example, a polypeptide corresponding to a fragment of a polypeptide sequence of the invention can be synthesized by use of a peptide synthesizer. Furthermore, if desired, nonclassical amino acids or chemical amino acid analogs can be introduced as a substitution or addition into the polypeptide sequence. Non-classical amino acids include, but are not limited to, to the D-isomers of the common amino acids, 2,4-diaminobutyric acid, a-amino isobutyric acid, 4-aminobutyric acid, Abu, 2-amino butyric acid, g-Abu, e-Ahx, 6-amino hexanoic acid, Aib, 2-amino isobutyric acid, 3-amino propionic acid, ornithine, norleucine, norvaline, hydroxyproline, sarcosine, citrulline, homocitrulline, cysteic acid, t-butylglycine, t-butylalanine, phenylglycine, cyclohexylalanine, b-alanine, fluoro-amino acids, designer amino acids such as b-methyl amino acids, Ca-methyl amino acids, Na-methyl amino acids, and amino acid analogs in general. Furthermore, the amino acid can be D (dextrorotary) or L (levorotary).

The invention encompasses polypeptides which are differentially modified during or after translation, e.g., by glycosylation, acetylation, phosphorylation, amidation, derivatization by known protecting/blocking groups, proteolytic cleavage, linkage to an antibody molecule or other cellular ligand, etc. Any of numerous chemical modifications may be carried out by known techniques, including but not limited, to specific chemical cleavage by cyanogen bromide, trypsin, chymotrypsin, papain, V8 protease, $NaBH_4$; acetylation, formylation, oxidation, reduction; metabolic synthesis in the presence of tunicamycin; etc.

Additional post-translational modifications encompassed by the invention include, for example, e.g., N-linked or O-linked carbohydrate chains, processing of N-terminal or C-terminal ends), attachment of chemical moieties to the amino acid backbone, chemical modifications of N-linked or O-linked carbohydrate chains, and addition or deletion of an N-terminal methionine residue as a result of procaryotic host cell expression. The polypeptides may also be modified with a detectable label, such as an enzymatic, fluorescent, isotopic or affinity label to allow for detection and isolation of the protein.

Also provided by the invention are chemically modified derivatives of the polypeptides of the invention which may provide additional advantages such as increased solubility, stability and circulating time of the polypeptide, or decreased immunogenicity (see U.S. Pat. No. 4,179,337). The chemical moieties for derivitization may be selected from water soluble polymers such as polyethylene glycol, ethylene glycol/propylene glycol copolymers, carboxymethylcellulose, dextran, polyvinyl alcohol and the like. The polypeptides may be modified at random positions within the molecule, or at predetermined positions within the molecule and may include one, two, three or more attached chemical moieties.

The polymer may be of any molecular weight, and may be branched or unbranched. For polyethylene glycol, the preferred molecular weight is between about 1 kDa and about 100 kDa (the term "about" indicating that in preparations of polyethylene glycol, some molecules will weigh more, some less, than the stated molecular weight) for ease in handling and manufacturing. Other sizes may be used, depending on the desired therapeutic profile (e.g., the duration of sustained release desired, the effects, if any on biological activity, the ease in handling, the degree or lack of antigenicity and other known effects of the polyethylene glycol to a therapeutic protein or analog).

The polyethylene glycol molecules (or other chemical moieties) should be attached to the protein with consideration of effects on functional or antigenic domains of the protein. There are a number of attachment methods available to those skilled in the art, e.g., EP 0 401 384, herein incorporated by reference (coupling PEG to G-CSF), see also Malik et al., Exp. Hematol. 20:1028-1035 (1992) (reporting pegylation of GM-CSF using tresyl chloride). For example, polyethylene glycol may be covalently bound through amino acid residues via a reactive group, such as, a free amino or carboxyl group. Reactive groups are those to which an activated polyethylene glycol molecule may be bound. The amino acid residues having a free amino group may include lysine residues and the N-terminal amino acid residues; those having a free carboxyl group may include aspartic acid residues glutamic acid residues and the C-terminal amino acid residue. Sulfhydryl groups may also be used as a reactive group for attaching the polyethylene glycol molecules. Preferred for therapeutic purposes is attachment at an amino group, such as attachment at the N-terminus or lysine group.

One may specifically desire proteins chemically modified at the N-terminus. Using polyethylene glycol as an illustration of the present composition, one may select from a variety of polyethylene glycol molecules (by molecular weight, branching, etc.), the proportion of polyethylene glycol molecules to protein (polypeptide) molecules in the reaction mix, the type of pegylation reaction to be performed, and the method of obtaining the selected N-terminally pegylated protein. The method of obtaining the N-terminally pegylated preparation (i.e., separating this moiety from other monopegylated moieties if necessary) may be by purification of the N-terminally pegylated material from a population of pegylated protein molecules. Selective proteins chemically modified at the N-terminus modification may be accomplished by reductive alkylation which exploits differential reactivity of different types of primary amino groups (lysine versus the N-terminal) available for derivatization in a particular protein. Under the appropriate reaction conditions, substantially selective derivatization of the protein at the N-terminus with a carbonyl group containing polymer is achieved.

The polypeptides of the invention may be in monomers or multimers (i.e., dimers, trimers, tetramers and higher multimers). Accordingly, the present invention relates to monomers and multimers of the polypeptides of the invention, their preparation, and compositions (preferably, Therapeutics) containing them. In specific embodiments, the polypeptides of the invention are monomers, dimers, trimers or tetramers. In additional embodiments, the multimers of the invention are at least dimers, at least trimers, or at least tetramers.

Multimers encompassed by the invention may be homomers or heteromers. As used herein, the term homomer, refers to a multimer containing only polypeptides corresponding to the amino acid sequence of SEQ ID NO:Y or encoded by the cDNA contained in a deposited clone (including fragments, variants, splice variants, and fusion proteins, corresponding to these polypeptides as described herein). These homomers may contain polypeptides having identical or different amino acid sequences. In a specific embodiment, a homomer of the invention is a multimer containing only polypeptides having an identical amino acid sequence. In another specific embodiment, a homomer of the invention is a multimer containing polypeptides having different amino acid sequences. In specific embodiments, the multimer of the invention is a homodimer (e.g., containing polypeptides having identical or different amino acid sequences) or a homotrimer (e.g., containing polypeptides having identical and/or different amino acid sequences). In additional embodiments, the homomeric multimer of the invention is at least a homodimer, at least a homotrimer, or at least a homotetramer.

As used herein, the term heteromer refers to a multimer containing one or more heterologous polypeptides (i.e., polypeptides of different proteins) in addition to the polypeptides of the invention. In a specific embodiment, the multimer of the invention is a heterodimer, a heterotrimer, or a heterotetramer. In additional embodiments, the heteromeric multimer of the invention is at least a heterodimer, at least a heterotrimer, or at least a heterotetramer.

Multimers of the invention may be the result of hydrophobic, hydrophilic, ionic and/or covalent associations and/or may be indirectly linked, by for example, liposome formation. Thus, in one embodiment, multimers of the invention, such as, for example, homodimers or homotrimers, are formed when polypeptides of the invention contact one another in solution. In another embodiment, heteromultimers of the invention, such as, for example, heterotrimers or heterotetramers, are formed when polypeptides of the invention contact antibodies to the polypeptides of the invention (including antibodies to the heterologous polypeptide sequence in a fusion protein of the invention) in solution. In other embodiments, multimers of the invention are formed by covalent associations with and/or between the polypeptides of the invention. Such covalent associations may involve one or more amino acid residues contained in the polypeptide sequence (e.g., that recited in the sequence listing, or contained in the polypeptide encoded by a deposited clone). In one instance, the covalent associations are cross-linking between cysteine residues located within the polypeptide sequences which interact in the native (i.e., naturally occurring) polypeptide. In another instance, the covalent associations are the consequence of chemical or recombinant manipulation. Alternatively, such covalent associations may involve one or more amino acid residues contained in the heterologous polypeptide sequence in a fusion protein of the invention.

In one example, covalent associations are between the heterologous sequence contained in a fusion protein of the invention (see, e.g., U.S. Pat. No. 5,478,925). In a specific example, the covalent associations are between the heterologous sequence contained in an Fc fusion protein of the invention (as described herein). In another specific example, covalent associations of fusion proteins of the invention are between heterologous polypeptide sequence from another protein that is capable of forming covalently associated multimers, such as for example, oseteoprotegerin (see, e.g., International Publication NO: WO 98/49305, the contents of which are herein incorporated by reference in its entirety). In another embodiment, two or more polypeptides of the invention are joined through peptide linkers. Examples include those peptide linkers described in U.S. Pat. No. 5,073,627 (hereby incorporated by reference). Proteins comprising multiple polypeptides of the invention separated by peptide linkers may be produced using conventional recombinant DNA technology.

Another method for preparing multimer polypeptides of the invention involves use of polypeptides of the invention fused to a leucine zipper or isoleucine zipper polypeptide sequence. Leucine zipper and isoleucine zipper domains are polypeptides that promote multimerization of the proteins in which they are found. Leucine zippers were originally identified in several DNA-binding proteins (Landschulz et al., Science 240:1759, (1988)), and have since been found in a variety of different proteins. Among the known leucine zippers are naturally occurring peptides and derivatives thereof that dimerize or trimerize. Examples of leucine zipper domains suitable for producing soluble multimeric proteins of the invention are those described in PCT application WO 94/10308, hereby incorporated by reference. Recombinant fusion proteins comprising a polypeptide of the invention fused to a polypeptide sequence that dimerizes or trimerizes in solution are expressed in suitable host cells, and the resulting soluble multimeric fusion protein is recovered from the culture supernatant using techniques known in the art.

Trimeric polypeptides of the invention may offer the advantage of enhanced biological activity. Preferred leucine zipper moieties and isoleucine moieties are those that preferentially form trimers. One example is a leucine zipper derived from lung surfactant protein D (SPD), as described in Hoppe et al. (FEBS Letters 344:191, (1994)) and in U.S. patent application Ser. No. 08/446,922, hereby incorporated by reference. Other peptides derived from naturally occurring trimeric proteins may be employed in preparing trimeric polypeptides of the invention.

In another example, proteins of the invention are associated by interactions between Flag® polypeptide sequence contained in fusion proteins of the invention containing Flag® polypeptide sequence. In a further embodiment, associations proteins of the invention are associated by interactions between heterologous polypeptide sequence contained in Flag® fusion proteins of the invention and anti-Flag® antibody.

The multimers of the invention may be generated using chemical techniques known in the art. For example, polypeptides desired to be contained in the multimers of the invention may be chemically cross-linked using linker molecules and linker molecule length optimization techniques known in the art (see, e.g., U.S. Pat. No. 5,478,925, which is herein incorporated by reference in its entirety). Additionally, multimers of the invention may be generated using techniques known in the art to form one or more inter-molecule cross-links between the cysteine residues located within the sequence of the polypeptides desired to be contained in the multimer (see, e.g., U.S. Pat. No. 5,478,925, which is herein incorporated by reference in its entirety). Further, polypeptides of the invention may be routinely modified by the addition of cysteine or biotin to the C terminus or N-terminus of the polypeptide and techniques known in the art may be applied to generate multimers containing one or more of these modified polypeptides (see, e.g., U.S. Pat. No. 5,478,925, which is herein incorporated by reference in its entirety). Additionally, techniques known in the art may be applied to generate liposomes containing the polypeptide components desired to be contained in the multimer of the invention (see, e.g., U.S. Pat. No. 5,478,925, which is herein incorporated by reference in its entirety).

Alternatively, multimers of the invention may be generated using genetic engineering techniques known in the art. In one embodiment, polypeptides contained in multimers of the invention are produced recombinantly using fusion protein technology described herein or otherwise known in the art (see, e.g., U.S. Pat. No. 5,478,925, which is herein incorporated by reference in its entirety). In a specific embodiment, polynucleotides coding for a homodimer of the invention are generated by ligating a polynucleotide sequence encoding a polypeptide of the invention to a sequence encoding a linker polypeptide and then further to a synthetic polynucleotide encoding the translated product of the polypeptide in the reverse orientation from the original C-terminus to the N-terminus (lacking the leader sequence) (see, e.g., U.S. Pat. No. 5,478,925, which is herein incorporated by reference in its entirety). In another embodiment, recombinant techniques described herein or otherwise known in the art are applied to generate recombinant polypeptides of the invention which contain a transmembrane domain (or hyrophobic or signal peptide) and which can be incorporated by membrane reconstitution techniques into liposomes (see, e.g., U.S. Pat. No. 5,478,925, which is herein incorporated by reference in its entirety).

Uses of the Polynucleotides

Each of the polynucleotides identified herein can be used in numerous ways as reagents. The following description should be considered exemplary and utilizes known techniques.

The polynucleotides of the present invention are useful for chromosome identification. There exists an ongoing need to identify new chromosome markers, since few chromosome marking reagents, based on actual sequence data (repeat polymorphisms), are presently available. Each polynucleotide of the present invention can be used as a chromosome marker.

Briefly, sequences can be mapped to chromosomes by preparing PCR primers (preferably 15-25 bp) from the sequences shown in SEQ ID NO:X. Primers can be selected using computer analysis so that primers do not span more than one predicted exon in the genomic DNA. These primers are then used for PCR screening of somatic cell hybrids containing individual human chromosomes. Only those hybrids containing the human gene corresponding to the SEQ ID NO:X will yield an amplified fragment.

Similarly, somatic hybrids provide a rapid method of PCR mapping the polynucleotides to particular chromosomes. Three or more clones can be assigned per day using a single thermal cycler. Moreover, sublocalization of the polynucleotides can be achieved with panels of specific chromosome fragments. Other gene mapping strategies that can be used include in situ hybridization, prescreening with labeled flow-sorted chromosomes, and preselection by hybridization to construct chromosome specific-cDNA libraries.

Precise chromosomal location of the polynucleotides can also be achieved using fluorescence in situ hybridization (FISH) of a metaphase chromosomal spread. This technique uses polynucleotides as short as 500 or 600 bases; however, polynucleotides 2,000-4,000 bp are preferred. For a review of this technique, see Verma et al., "Human Chromosomes: a Manual of Basic Techniques," Pergamon Press, New York (1988).

For chromosome mapping, the polynucleotides can be used individually (to mark a single chromosome or a single site on that chromosome) or in panels (for marking multiple sites and/or multiple chromosomes). Preferred polynucleotides correspond to the noncoding regions of the cDNAs because the coding sequences are more likely conserved within gene families, thus increasing the chance of cross hybridization during chromosomal mapping.

Once a polynucleotide has been mapped to a precise chromosomal location, the physical position of the polynucleotide can be used in linkage analysis. Linkage analysis establishes coinheritance between a chromosomal location and presentation of a particular disease. (Disease mapping data are found, for example, in V. McKusick, Mendelian Inheritance in Man (available on line through Johns Hopkins University Welch Medical Library).) Assuming 1 megabase mapping resolution and one gene per 20 kb, a cDNA precisely localized to a chromosomal region associated with the disease could be one of 50-500 potential causative genes.

Thus, once coinheritance is established, differences in the polynucleotide and the corresponding gene between affected and unaffected individuals can be examined. First, visible structural alterations in the chromosomes, such as deletions or translocations, are examined in chromosome spreads or by PCR. If no structural alterations exist, the presence of point mutations are ascertained. Mutations observed in some or all affected individuals, but not in normal individuals, indicates that the mutation may cause the disease. However, complete sequencing of the polypeptide and the corresponding gene from several normal individuals is required to distinguish the mutation from a polymorphism. If a new polymorphism is identified, this polymorphic polypeptide can be used for further linkage analysis.

Furthermore, increased or decreased expression of the gene in affected individuals as compared to unaffected individuals can be assessed using polynucleotides of the present invention. Any of these alterations (altered expression, chromosomal rearrangement, or mutation) can be used as a diagnostic or prognostic marker.

Thus, the invention also provides a diagnostic method useful during diagnosis of a disorder, involving measuring the expression level of polynucleotides of the present invention in cells or body fluid from an individual and comparing the measured gene expression level with a standard level of polynucleotide expression level, whereby an increase or decrease in the gene expression level compared to the standard is indicative of a disorder.

In still another embodiment, the invention includes a kit for analyzing samples for the presence of proliferative and/or cancerous polynucleotides derived from a test subject. In a general embodiment, the kit includes at least one polynucleotide probe containing a nucleotide sequence that will specifically hybridize with a polynucleotide of the present invention and a suitable container. In a specific embodiment, the kit includes two polynucleotide probes defining an internal region of the polynucleotide of the present invention, where each probe has one strand containing a 31'mer-end internal to the region. In a further embodiment, the probes may be useful as primers for polymerase chain reaction amplification.

Where a diagnosis of a disorder, has already been made according to conventional methods, the present invention is useful as a prognostic indicator, whereby patients exhibiting enhanced or depressed polynucleotide of the present invention expression will experience a worse clinical outcome relative to patients expressing the gene at a level nearer the standard level.

By "measuring the expression level of polynucleotide of the present invention" is intended qualitatively or quantitatively measuring or estimating the level of the polypeptide of the present invention or the level of the mRNA encoding the polypeptide in a first biological sample either directly (e.g., by determining or estimating absolute protein level or mRNA level) or relatively (e.g., by comparing to the polypeptide level or mRNA level in a second biological sample). Preferably, the polypeptide level or mRNA level in the first biological sample is measured or estimated and compared to a standard polypeptide level or mRNA level, the standard being taken from a second biological sample obtained from an individual not having the disorder or being determined by averaging levels from a population of individuals not having a disorder. As will be appreciated in the art, once a standard polypeptide level or mRNA level is known, it can be used repeatedly as a standard for comparison.

By "biological sample" is intended any biological sample obtained from an individual, body fluid, cell line, tissue culture, or other source which contains the polypeptide of the present invention or mRNA. As indicated, biological samples include body fluids (such as semen, lymph, sera, plasma, urine, synovial fluid and spinal fluid) which contain the polypeptide of the present invention, and other tissue sources found to express the polypeptide of the present invention. Methods for obtaining tissue biopsies and body fluids from mammals are well known in the art. Where the biological sample is to include mRNA, a tissue biopsy is the preferred source.

The method(s) provided above may preferrably be applied in a diagnostic method and/or kits in which polynucleotides and/or polypeptides are attached to a solid support. In one exemplary method, the support may be a "gene chip" or a "biological chip" as described in U.S. Pat. Nos. 5,837,832, 5,874,219, and 5,856,174. Further, such a gene chip with polynucleotides of the present invention attached may be used to identify polymorphisms between the polynucleotide sequences, with polynucleotides isolated from a test subject. The knowledge of such polymorphisms (i.e. their location, as well as, their existence) would be beneficial in identifying disease loci for many disorders, including cancerous diseases and conditions. Such a method is described in U.S. Pat. Nos. 5,858,659 and 5,856,104. The US patents referenced supra are hereby incorporated by reference in their entirety herein.

The present invention encompasses polynucleotides of the present invention that are chemically synthesized, or reproduced as peptide nucleic acids (PNA), or according to other methods known in the art. The use of PNAs would serve as the preferred form if the polynucleotides are incorporated onto a solid support, or gene chip. For the purposes of the present invention, a peptide nucleic acid (PNA) is a polyamide type of DNA analog and the monomeric units for adenine, guanine, thymine and cytosine are available commercially (Perceptive Biosystems). Certain components of DNA, such as phosphorus, phosphorus oxides, or deoxyribose derivatives, are not present in PNAs. As disclosed by P. E. Nielsen, M. Egholm, R. H. Berg and O. Buchardt, Science 254, 1497 (1991); and M. Egholm, O. Buchardt, L. Christensen, C. Behrens, S. M. Freier, D. A. Driver, R. H. Berg, S. K. Kim, B. Norden, and P. E. Nielsen, Nature 365, 666 (1993), PNAs bind specifically and tightly to complementary DNA strands and are not degraded by nucleases. In fact, PNA binds more strongly to DNA than DNA itself does. This is probably because there is no electrostatic repulsion between the two strands, and also the polyamide backbone is more flexible. Because of this, PNA/DNA duplexes bind under a wider range of stringency conditions than DNA/DNA duplexes, making it easier to perform multiplex hybridization. Smaller probes can be used than with DNA due to the strong binding. In addition, it is more likely that single base mismatches can be determined with PNA/DNA hybridization because a single mismatch in a PNA/DNA 15-mer lowers the melting point (T.sub.m) by 8°-20° C., vs. 4°-16° C. for the DNA/DNA 15-mer duplex. Also, the absence of charge groups in PNA means that hybridization can be done at low ionic strengths and reduce possible interference by salt during the analysis.

The present invention is useful for detecting cancer in mammals. In particular the invention is useful during diagnosis of pathological cell proliferative neoplasias which include, but are not limited to: acute myelogenous leukemias including acute monocytic leukemia, acute myeloblastic leukemia, acute promyelocytic leukemia, acute myelomonocytic leukemia, acute erythroleukemia, acute megakaryocytic leukemia, and acute undifferentiated leukemia, etc.; and chronic myelogenous leukemias including chronic myelomonocytic leukemia, chronic granulocytic leukemia, etc. Preferred mammals include monkeys, apes, cats, dogs, cows, pigs, horses, rabbits and humans. Particularly preferred are humans.

Pathological cell proliferative diseases, disorders, and/or conditions are often associated with inappropriate activation of proto-oncogenes. (Gelmann, E. P. et al., "The Etiology of Acute Leukemia: Molecular Genetics and Viral Oncology," in Neoplastic Diseases of the Blood, Vol 1., Wiernik, P. H. et al. eds., 161-182 (1985)). Neoplasias are now believed to result from the qualitative alteration of a normal cellular gene product, or from the quantitative modification of gene expression by insertion into the chromosome of a viral sequence, by chromosomal translocation of a gene to a more actively transcribed region, or by some other mechanism. (Gelmann et al., supra) It is likely that mutated or altered expression of specific genes is involved in the pathogenesis of some leukemias, among other tissues and cell types. (Gelmann et al., supra) Indeed, the human counterparts of the oncogenes involved in some animal neoplasias have been amplified or translocated in some cases of human leukemia and carcinoma. (Gelmann et al., supra)

For example, c-myc expression is highly amplified in the non-lymphocytic leukemia cell line HL-60. When HL-60 cells are chemically induced to stop proliferation, the level of c-myc is found to be downregulated. (International Publication Number WO 91/15580) However, it has been shown that exposure of HL-60 cells to a DNA construct that is complementary to the 5' end of c-myc or c-myb blocks translation of the corresponding mRNAs which downregulates expression of the c-myc or c-myb proteins and causes arrest of cell proliferation and differentiation of the treated cells. (International Publication Number WO 91/15580; Wickstrom et al., Proc. Natl. Acad. Sci. 85:1028 (1988); Anfossi et al., Proc. Natl. Acad. Sci. 86:3379 (1989)). However, the skilled artisan would appreciate the present invention's usefulness would not be limited to treatment of proliferative diseases, disorders, and/or conditions of hematopoietic cells and tissues, in light of the numerous cells and cell types of varying origins which are known to exhibit proliferative phenotypes.

In addition to the foregoing, a polynucleotide can be used to control gene expression through triple helix formation or antisense DNA or RNA. Antisense techniques are discussed, for example, in Okano, J. Neurochem. 56: 560 (1991); "Oligodeoxynucleotides as Antisense Inhibitors of Gene Expression, CRC Press, Boca Raton, Fla. (1988). Triple helix formation is discussed in, for instance Lee et al., Nucleic Acids Research 6: 3073 (1979); Cooney et al., Science 241: 456 (1988); and Dervan et al., Science 251: 1360 (1991). Both methods rely on binding of the polynucleotide to a complementary DNA or RNA. For these techniques, preferred polynucleotides are usually oligonucleotides 20 to 40 bases in length and complementary to either the region of the gene involved in transcription (triple helix—see Lee et al., Nucl. Acids Res. 6:3073 (1979); Cooney et al., Science 241:456 (1988); and Dervan et al., Science 251:1360 (1991)) or to the mRNA itself (antisense—Okano, J. Neurochem. 56:560 (1991); Oligodeoxynucleotides as Antisense Inhibitors of Gene Expression, CRC Press, Boca Raton, Fla. (1988).) Triple helix formation optimally results in a shut-off of RNA transcription from DNA, while antisense RNA hybridization blocks translation of an mRNA molecule into polypeptide. Both techniques are effective in model systems, and the information disclosed herein can be used to design antisense or triple helix polynucleotides in an effort to treat or prevent disease.

Polynucleotides of the present invention are also useful in gene therapy. One goal of gene therapy is to insert a normal gene into an organism having a defective gene, in an effort to correct the genetic defect. The polynucleotides disclosed in the present invention offer a means of targeting such genetic defects in a highly accurate manner. Another goal is to insert a new gene that was not present in the host genome, thereby producing a new trait in the host cell.

The polynucleotides are also useful for identifying individuals from minute biological samples. The United States military, for example, is considering the use of restriction fragment length polymorphism (RFLP) for identification of its personnel. In this technique, an individual's genomic DNA is digested with one or more restriction enzymes, and probed on a Southern blot to yield unique bands for identifying personnel. This method does not suffer from the current limitations of "Dog Tags" which can be lost, switched, or stolen, making positive identification difficult. The polynucleotides of the present invention can be used as additional DNA markers for RFLP.

The polynucleotides of the present invention can also be used as an alternative to RFLP, by determining the actual base-by-base DNA sequence of selected portions of an individual's genome. These sequences can be used to prepare PCR primers for amplifying and isolating such selected DNA, which can then be sequenced. Using this technique, individuals can be identified because each individual will have a unique set of DNA sequences. Once an unique ID database is established for an individual, positive identification of that individual, living or dead, can be made from extremely small tissue samples.

Forensic biology also benefits from using DNA-based identification techniques as disclosed herein. DNA sequences taken from very small biological samples such as tissues, e.g., hair or skin, or body fluids, e.g., blood, saliva, semen, synovial fluid, amniotic fluid, breast milk, lymph, pulmonary sputum or surfactant, urine, fecal matter, etc., can be amplified using PCR. In one prior art technique, gene sequences amplified from polymorphic loci, such as DQa class II HLA gene, are used in forensic biology to identify individuals. (Erlich, H., PCR Technology, Freeman and Co. (1992).) Once these specific polymorphic loci are amplified, they are digested with one or more restriction enzymes, yielding an identifying set of bands on a Southern blot probed with DNA corresponding to the DQa class II HLA gene. Similarly, polynucleotides of the present invention can be used as polymorphic markers for forensic purposes.

There is also a need for reagents capable of identifying the source of a particular tissue. Such need arises, for example, in forensics when presented with tissue of unknown origin. Appropriate reagents can comprise, for example, DNA probes or primers specific to particular tissue prepared from the sequences of the present invention. Panels of such reagents can identify tissue by species and/or by organ type. In a similar fashion, these reagents can be used to screen tissue cultures for contamination.

In the very least, the polynucleotides of the present invention can be used as molecular weight markers on Southern gels, as diagnostic probes for the presence of a specific mRNA in a particular cell type, as a probe to "subtract-out" known sequences in the process of discovering novel polynucleotides, for selecting and making oligomers for attachment to a "gene chip" or other support, to raise anti-DNA antibodies using DNA immunization techniques, and as an antigen to elicit an immune response.

Uses of the Polypeptides

Each of the polypeptides identified herein can be used in numerous ways. The following description should be considered exemplary and utilizes known techniques.

A polypeptide of the present invention can be used to assay protein levels in a biological sample using antibody-based techniques. For example, protein expression in tissues can be studied with classical immunohistological methods.

(Jalkanen, M., et al., J. Cell. Biol. 101:976-985 (1985); Jalkanen, M., et al., J. Cell. Biol. 105:3087-3096 (1987).) Other antibody-based methods useful for detecting protein gene expression include immunoassays, such as the enzyme linked immunosorbent assay (ELISA) and the radioimmunoassay (RIA). Suitable antibody assay labels are known in the art and include enzyme labels, such as, glucose oxidase, and radioisotopes, such as iodine (1251, 1211), carbon (14C), sulfur (35S), tritium (3H), indium (112In), and technetium (99mTc), and fluorescent labels, such as fluorescein and rhodamine, and biotin.

In addition to assaying secreted protein levels in a biological sample, proteins can also be detected in vivo by imaging. Antibody labels or markers for in vivo imaging of protein include those detectable by X-radiography, NMR or ESR. For X-radiography, suitable labels include radioisotopes such as barium or cesium, which emit detectable radiation but are not overtly harmful to the subject. Suitable markers for NMR and ESR include those with a detectable characteristic spin, such as deuterium, which may be incorporated into the antibody by labeling of nutrients for the relevant hybridoma.

A protein-specific antibody or antibody fragment which has been labeled with an appropriate detectable imaging moiety, such as a radioisotope (for example, 131I, 112In, 99mTc), a radio-opaque substance, or a material detectable by nuclear magnetic resonance, is introduced (for example, parenterally, subcutaneously, or intraperitoneally) into the mammal. It will be understood in the art that the size of the subject and the imaging system used will determine the quantity of imaging moiety needed to produce diagnostic images. In the case of a radioisotope moiety, for a human subject, the quantity of radioactivity injected will normally range from about 5 to 20 millicuries of 99mTc. The labeled antibody or antibody fragment will then preferentially accumulate at the location of cells which contain the specific protein. In vivo tumor imaging is described in S. W. Burchiel et al., "Immunopharmacokinetics of Radiolabeled Antibodies and Their Fragments." (Chapter 13 in Tumor Imaging: The Radiochemical Detection of Cancer, S. W. Burchiel and B. A. Rhodes, eds., Masson Publishing Inc. (1982).)

Thus, the invention provides a diagnostic method of a disorder, which involves (a) assaying the expression of a polypeptide of the present invention in cells or body fluid of an individual; (b) comparing the level of gene expression with a standard gene expression level, whereby an increase or decrease in the assayed polypeptide gene expression level compared to the standard expression level is indicative of a disorder. With respect to cancer, the presence of a relatively high amount of transcript in biopsied tissue from an individual may indicate a predisposition for the development of the disease, or may provide a means for detecting the disease prior to the appearance of actual clinical symptoms. A more definitive diagnosis of this type may allow health professionals to employ preventative measures or aggressive treatment earlier thereby preventing the development or further progression of the cancer.

Moreover, polypeptides of the present invention can be used to treat, prevent, and/or diagnose disease. For example, patients can be administered a polypeptide of the present invention in an effort to replace absent or decreased levels of the polypeptide (e.g., insulin), to supplement absent or decreased levels of a different polypeptide (e.g., hemoglobin S for hemoglobin B, SOD, catalase, DNA repair proteins), to inhibit the activity of a polypeptide (e.g., an oncogene or tumor suppressor), to activate the activity of a polypeptide (e.g., by binding to a receptor), to reduce the activity of a membrane bound receptor by competing with it for free ligand (e.g., soluble TNF receptors used in reducing inflammation), or to bring about a desired response (e.g., blood vessel growth inhibition, enhancement of the immune response to proliferative cells or tissues).

Similarly, antibodies directed to a polypeptide of the present invention can also be used to treat, prevent, and/or diagnose disease. For example, administration of an antibody directed to a polypeptide of the present invention can bind and reduce overproduction of the polypeptide. Similarly, administration of an antibody can activate the polypeptide, such as by binding to a polypeptide bound to a membrane (receptor).

At the very least, the polypeptides of the present invention can be used as molecular weight markers on SDS-PAGE gels or on molecular sieve gel filtration columns using methods well known to those of skill in the art. Polypeptides can also be used to raise antibodies, which in turn are used to measure protein expression from a recombinant cell, as a way of assessing transformation of the host cell. Moreover, the polypeptides of the present invention can be used to test the following biological activities.

Gene Therapy Methods

Another aspect of the present invention is to gene therapy methods for treating or preventing disorders, diseases and conditions. The gene therapy methods relate to the introduction of nucleic acid (DNA, RNA and antisense DNA or RNA) sequences into an animal to achieve expression of a polypeptide of the present invention. This method requires a polynucleotide which codes for a polypeptide of the invention that operatively linked to a promoter and any other genetic elements necessary for the expression of the polypeptide by the target tissue. Such gene therapy and delivery techniques are known in the art, see, for example, WO90/11092, which is herein incorporated by reference.

Thus, for example, cells from a patient may be engineered with a polynucleotide (DNA or RNA) comprising a promoter operably linked to a polynucleotide of the invention ex vivo, with the engineered cells then being provided to a patient to be treated with the polypeptide. Such methods are well-known in the art. For example, see Belldegrun et al., J. Natl. Cancer Inst., 85:207-216 (1993); Ferrantini et al., Cancer Research, 53:107-1112 (1993); Ferrantini et al., J. Immunology 153: 4604-4615 (1994); Kaido, T., et al., Int. J. Cancer 60: 221-229 (1995); Ogura et al., Cancer Research 50: 5102-5106 (1990); Santodonato, et al., Human Gene Therapy 7:1-10 (1996); Santodonato, et al., Gene Therapy 4:1246-1255 (1997); and Zhang, et al., Cancer Gene Therapy 3: 31-38 (1996)), which are herein incorporated by reference. In one embodiment, the cells which are engineered are arterial cells. The arterial cells may be reintroduced into the patient through direct injection to the artery, the tissues surrounding the artery, or through catheter injection.

As discussed in more detail below, the polynucleotide constructs can be delivered by any method that delivers injectable materials to the cells of an animal, such as, injection into the interstitial space of tissues (heart, muscle, skin, lung, liver, and the like). The polynucleotide constructs may be delivered in a pharmaceutically acceptable liquid or aqueous carrier.

In one embodiment, the polynucleotide of the invention is delivered as a naked polynucleotide. The term "naked" polynucleotide, DNA or RNA refers to sequences that are free from any delivery vehicle that acts to assist, promote or facilitate entry into the cell, including viral sequences, viral particles, liposome formulations, lipofectin or precipitating agents and the like. However, the polynucleotides of the invention can also be delivered in liposome formulations and lipofectin formulations and the like can be prepared by methods well known to those skilled in the art. Such methods are described, for example, in U.S. Pat. Nos. 5,593,972, 5,589,466, and 5,580,859, which are herein incorporated by reference.

The polynucleotide vector constructs of the invention used in the gene therapy method are preferably constructs that will not integrate into the host genome nor will they contain sequences that allow for replication. Appropriate vectors include pWLNEO, pSV2CAT, pOG44, pXT1 and pSG available from Stratagene; pSVK3, pBPV, pMSG and pSVL available from Pharmacia; and pEF1/V5, pcDNA3.1, and pRc/CMV2 available from Invitrogen. Other suitable vectors will be readily apparent to the skilled artisan.

Any strong promoter known to those skilled in the art can be used for driving the expression of polynucleotide sequence of the invention. Suitable promoters include adenoviral promoters, such as the adenoviral major late promoter; or heterologous promoters, such as the cytomegalovirus (CMV) promoter; the respiratory syncytial virus (RSV) promoter; inducible promoters, such as the MMT promoter, the metallothionein promoter; heat shock promoters; the albumin promoter; the ApoAI promoter; human globin promoters; viral thymidine kinase promoters, such as the Herpes Simplex thymidine kinase promoter; retroviral LTRs; the b-actin promoter; and human growth hormone promoters. The promoter also may be the native promoter for the polynucleotides of the invention.

Unlike other gene therapy techniques, one major advantage of introducing naked nucleic acid sequences into target cells is the transitory nature of the polynucleotide synthesis in the cells. Studies have shown that non-replicating DNA sequences can be introduced into cells to provide production of the desired polypeptide for periods of up to six months.

The polynucleotide construct of the invention can be delivered to the interstitial space of tissues within the an animal, including of muscle, skin, brain, lung, liver, spleen, bone marrow, thymus, heart, lymph, blood, bone, cartilage, pancreas, kidney, gall bladder, stomach, intestine, testis, ovary, uterus, rectum, nervous system, eye, gland, and connective tissue. Interstitial space of the tissues comprises the intercellular, fluid, mucopolysaccharide matrix among the reticular fibers of organ tissues, elastic fibers in the walls of vessels or chambers, collagen fibers of fibrous tissues, or that same matrix within connective tissue ensheathing muscle cells or in the lacunae of bone. It is similarly the space occupied by the plasma of the circulation and the lymph fluid of the lymphatic channels. Delivery to the interstitial space of muscle tissue is preferred for the reasons discussed below. They may be conveniently delivered by injection into the tissues comprising these cells. They are preferably delivered to and expressed in persistent, non-dividing cells which are differentiated, although delivery and expression may be achieved in non-differentiated or less completely differentiated cells, such as, for example, stem cells of blood or skin fibroblasts. In vivo muscle cells are particularly competent in their ability to take up and express polynucleotides.

For the naked nucleic acid sequence injection, an effective dosage amount of DNA or RNA will be in the range of from about 0.05 mg/kg body weight to about 50 mg/kg body weight. Preferably the dosage will be from about 0.005 mg/kg to about 20 mg/kg and more preferably from about 0.05 mg/kg to about 5 mg/kg. Of course, as the artisan of ordinary skill will appreciate, this dosage will vary according to the tissue site of injection. The appropriate and effective dosage of nucleic acid sequence can readily be determined by those of ordinary skill in the art and may depend on the condition being treated and the route of administration.

The preferred route of administration is by the parenteral route of injection into the interstitial space of tissues. However, other parenteral routes may also be used, such as, inhalation of an aerosol formulation particularly for delivery to lungs or bronchial tissues, throat or mucous membranes of the nose. In addition, naked DNA constructs can be delivered to arteries during angioplasty by the catheter used in the procedure.

The naked polynucleotides are delivered by any method known in the art, including, but not limited to, direct needle injection at the delivery site, intravenous injection, topical administration, catheter infusion, and so-called "gene guns". These delivery methods are known in the art.

The constructs may also be delivered with delivery vehicles such as viral sequences, viral particles, liposome formulations, lipofectin, precipitating agents, etc. Such methods of delivery are known in the art.

In certain embodiments, the polynucleotide constructs of the invention are complexed in a liposome preparation. Liposomal preparations for use in the instant invention include cationic (positively charged), anionic (negatively charged) and neutral preparations. However, cationic liposomes are particularly preferred because a tight charge complex can be formed between the cationic liposome and the polyanionic nucleic acid. Cationic liposomes have been shown to mediate intracellular delivery of plasmid DNA (Felgner et al., Proc. Natl. Acad. Sci. USA, 84:7413-7416 (1987), which is herein incorporated by reference); mRNA (Malone et al., Proc. Natl. Acad. Sci. USA, 86:6077-6081 (1989), which is herein incorporated by reference); and purified transcription factors (Debs et al., J. Biol. Chem., 265:10189-10192 (1990), which is herein incorporated by reference), in functional form.

Cationic liposomes are readily available. For example, N[1-2,3-dioleyloxy)propyl]-N,N,N-triethylammonium (DOTMA) liposomes are particularly useful and are available under the trademark Lipofectin, from GIBCO BRL, Grand Island, N.Y. (See, also, Felgner et al., Proc. Natl. Acad. Sci. USA, 84:7413-7416 (1987), which is herein incorporated by reference). Other commercially available liposomes include transfectace (DDAB/DOPE) and DOTAP/DOPE (Boehringer).

Other cationic liposomes can be prepared from readily available materials using techniques well known in the art. See, e.g. PCT Publication NO: WO 90/11092 (which is herein incorporated by reference) for a description of the synthesis of DOTAP (1,2-bis(oleoyloxy)-3-(trimethylammonio)propane) liposomes. Preparation of DOTMA liposomes is explained in the literature, see, e.g., Felgner et al., Proc. Natl. Acad. Sci. USA, 84:7413-7417, which is herein incorporated by reference. Similar methods can be used to prepare liposomes from other cationic lipid materials.

Similarly, anionic and neutral liposomes are readily available, such as from Avanti Polar Lipids (Birmingham, Ala.), or can be easily prepared using readily available materials. Such materials include phosphatidyl, choline, cholesterol, phosphatidyl ethanolamine, dioleoylphosphatidyl choline (DOPC), dioleoylphosphatidyl glycerol (DOPG), dioleoylphoshatidyl ethanolamine (DOPE), among others. These materials can also be mixed with the DOTMA and DOTAP starting materials in appropriate ratios. Methods for making liposomes using these materials are well known in the art.

For example, commercially dioleoylphosphatidyl choline (DOPC), dioleoylphosphatidyl glycerol (DOPG), and dioleoylphosphatidyl ethanolamine (DOPE) can be used in various combinations to make conventional liposomes, with or without the addition of cholesterol. Thus, for example, DOPG/DOPC vesicles can be prepared by drying 50 mg each of DOPG and DOPC under a stream of nitrogen gas into a sonication vial. The sample is placed under a vacuum pump overnight and is hydrated the following day with deionized water. The sample is then sonicated for 2 hours in a capped vial, using a Heat Systems model 350 sonicator equipped with an inverted cup (bath type) probe at the maximum setting while the bath is circulated at 15EC. Alternatively, negatively charged vesicles can be prepared without sonication to produce multilamellar vesicles or by extrusion through nucleopore membranes to produce unilamellar vesicles of discrete size. Other methods are known and available to those of skill in the art.

The liposomes can comprise multilamellar vesicles (MLVs), small unilamellar vesicles (SUVs), or large unilamellar vesicles (LUVs), with SUVs being preferred. The various liposome-nucleic acid complexes are prepared using methods well known in the art. See, e.g., Straubinger et al., Methods of Immunology, 101:512-527 (1983), which is herein incorporated by reference. For example, MLVs containing nucleic acid can be prepared by depositing a thin film of phospholipid on the walls of a glass tube and subsequently hydrating with a solution of the material to be encapsulated. SUVs are prepared by extended sonication of MLVs to produce a homogeneous population of unilamellar liposomes. The material to be entrapped is added to a suspension of preformed MLVs and then sonicated. When using liposomes containing cationic lipids, the dried lipid film is resuspended in an appropriate solution such as sterile water or an isotonic buffer solution such as 10 mM Tris/NaCl, sonicated, and then the preformed liposomes are mixed directly with the DNA. The liposome and DNA form a very stable complex due to binding of the positively charged liposomes to the cationic DNA. SUVs find use with small nucleic acid fragments. LUVs are prepared by a number of methods, well known in the art. Commonly used methods include $Ca^{2+}$-EDTA chelation (Papahadjopoulos et al., Biochim. Biophys. Acta, 394:483 (1975); Wilson et al., Cell, 17:77 (1979)); ether injection (Deamer et al., Biochim. Biophys. Acta, 443:629 (1976); Ostro et al., Biochem. Biophys. Res. Commun., 76:836 (1977); Fraley et al., Proc. Natl. Acad. Sci. USA, 76:3348 (1979)); detergent dialysis (Enoch et al., Proc. Natl. Acad. Sci. USA, 76:145 (1979)); and reverse-phase evaporation (REV) (Fraley et al., J. Biol. Chem., 255:10431 (1980); Szoka et al., Proc. Natl. Acad. Sci. USA, 75:145 (1978); Schaefer-Ridder et al., Science, 215:166 (1982)), which are herein incorporated by reference.

Generally, the ratio of DNA to liposomes will be from about 10:1 to about 1:10. Preferably, the ration will be from about 5:1 to about 1:5. More preferably, the ration will be about 3:1 to about 1:3. Still more preferably, the ratio will be about 1:1.

U.S. Pat. No. 5,676,954 (which is herein incorporated by reference) reports on the injection of genetic material, complexed with cationic liposomes carriers, into mice. U.S. Pat. Nos. 4,897,355, 4,946,787, 5,049,386, 5,459,127, 5,589,466, 5,693,622, 5,580,859, 5,703,055, and international publication NO: WO 94/9469 (which are herein incorporated by reference) provide cationic lipids for use in transfecting DNA into cells and mammals. U.S. Pat. Nos. 5,589,466, 5,693,622, 5,580,859, 5,703,055, and international publication NO: WO 94/9469 (which are herein incorporated by reference) provide methods for delivering DNA-cationic lipid complexes to mammals.

In certain embodiments, cells are engineered, ex vivo or in vivo, using a retroviral particle containing RNA which comprises a sequence encoding polypeptides of the invention. Retroviruses from which the retroviral plasmid vectors may be derived include, but are not limited to, Moloney Murine Leukemia Virus, spleen necrosis virus, Rous sarcoma Virus, Harvey Sarcoma Virus, avian leukosis virus, gibbon ape leukemia virus, human immunodeficiency virus, Myeloproliferative Sarcoma Virus, and mammary tumor virus.

The retroviral plasmid vector is employed to transduce packaging cell lines to form producer cell lines. Examples of packaging cells which may be transfected include, but are not limited to, the PE501, PA317, R-2, R-AM, PA12, T19-14X, VT-19-17-H2, RCRE, RCRIP, GP+E-86, GP+envAm12, and DAN cell lines as described in Miller, Human Gene Therapy, 1:5-14 (1990), which is incorporated herein by reference in its entirety. The vector may transduce the packaging cells through any means known in the art. Such means include, but are not limited to, electroporation, the use of liposomes, and $CaPO_4$ precipitation. In one alternative, the retroviral plasmid vector may be encapsulated into a liposome, or coupled to a lipid, and then administered to a host.

The producer cell line generates infectious retroviral vector particles which include polynucleotide encoding polypeptides of the invention. Such retroviral vector particles then may be employed, to transduce eukaryotic cells, either in vitro or in vivo. The transduced eukaryotic cells will express polypeptides of the invention.

In certain other embodiments, cells are engineered, ex vivo or in vivo, with polynucleotides of the invention contained in an adenovirus vector. Adenovirus can be manipulated such that it encodes and expresses polypeptides of the invention, and at the same time is inactivated in terms of its ability to replicate in a normal lytic viral life cycle. Adenovirus expression is achieved without integration of the viral DNA into the host cell chromosome, thereby alleviating concerns about insertional mutagenesis. Furthermore, adenoviruses have been used as live enteric vaccines for many years with an excellent safety profile (Schwartzet al., Am. Rev. Respir. Dis., 109:233-238 (1974)). Finally, adenovirus mediated gene transfer has been demonstrated in a number of instances including transfer of alpha-1-antitrypsin and CFTR to the lungs of cotton rats (Rosenfeld et al., Science, 252:431-434 (1991); Rosenfeld et al., Cell, 68:143-155 (1992)). Furthermore, extensive studies to attempt to establish adenovirus as a causative agent in human cancer were uniformly negative (Green et al. Proc. Natl. Acad. Sci. USA, 76:6606 (1979)).

Suitable adenoviral vectors useful in the present invention are described, for example, in Kozarsky and Wilson, Curr. Opin. Genet. Devel., 3:499-503 (1993); Rosenfeld et al., Cell, 68:143-155 (1992); Engelhardt et al., Human Genet. Ther., 4:759-769 (1993); Yang et al., Nature Genet., 7:362-369 (1994); Wilson et al., Nature, 365:691-692 (1993); and U.S. Pat. No. 5,652,224, which are herein incorporated by reference. For example, the adenovirus vector Ad2 is useful and can be grown in human 293 cells. These cells contain the E1 region of adenovirus and constitutively express E1a and E1b, which complement the defective adenoviruses by providing the products of the genes deleted from the vector. In addition to Ad2, other varieties of adenovirus (e.g., Ad3, Ad5, and Ad7) are also useful in the present invention.

Preferably, the adenoviruses used in the present invention are replication deficient. Replication deficient adenoviruses require the aid of a helper virus and/or packaging cell line to form infectious particles. The resulting virus is capable of infecting cells and can express a polynucleotide of interest which is operably linked to a promoter, but cannot replicate in most cells. Replication deficient adenoviruses may be deleted in one or more of all or a portion of the following genes: E1a, E1b, E3, E4, E2a, or L1 through L5.

In certain other embodiments, the cells are engineered, ex vivo or in vivo, using an adeno-associated virus (AAV). AAVs are naturally occurring defective viruses that require helper viruses to produce infectious particles (Muzyczka, Curr. Topics in Microbiol. Immunol., 158:97 (1992)). It is also one of the few viruses that may integrate its DNA into non-dividing cells. Vectors containing as little as 300 base pairs of AAV can be packaged and can integrate, but space for exogenous DNA is limited to about 4.5 kb. Methods for producing and using such AAVs are known in the art. See, for example, U.S. Pat. Nos. 5,139,941, 5,173,414, 5,354,678, 5,436,146, 5,474,935, 5,478,745, and 5,589,377.

For example, an appropriate AAV vector for use in the present invention will include all the sequences necessary for DNA replication, encapsidation, and host-cell integration. The polynucleotide construct containing polynucleotides of the invention is inserted into the AAV vector using standard cloning methods, such as those found in Sambrook et al., Molecular Cloning: A Laboratory Manual, Cold Spring Harbor Press (1989). The recombinant AAV vector is then transfected into packaging cells which are infected with a helper virus, using any standard technique, including lipofection, electroporation, calcium phosphate precipitation, etc. Appropriate helper viruses include adenoviruses, cytomegaloviruses, vaccinia viruses, or herpes viruses. Once the packaging cells are transfected and infected, they will produce infectious AAV viral particles which contain the polynucleotide construct of the invention. These viral particles are then used to transduce eukaryotic cells, either ex vivo or in vivo. The transduced cells will contain the polynucleotide construct integrated into its genome, and will express the desired gene product.

Another method of gene therapy involves operably associating heterologous control regions and endogenous polynucleotide sequences (e.g. encoding the polypeptide sequence of interest) via homologous recombination (see, e.g., U.S. Pat. No. 5,641,670, issued Jun. 24, 1997; International Publication NO: WO 96/29411, published Sep. 26, 1996; International Publication NO: WO 94/12650, published Aug. 4, 1994; Koller et al., Proc. Natl. Acad. Sci. USA, 86:8932-8935 (1989); and Zijlstra et al., Nature, 342:435-438 (1989). This method involves the activation of a gene which is present in the target cells, but which is not normally expressed in the cells, or is expressed at a lower level than desired.

Polynucleotide constructs are made, using standard techniques known in the art, which contain the promoter with targeting sequences flanking the promoter. Suitable promoters are described herein. The targeting sequence is sufficiently complementary to an endogenous sequence to permit homologous recombination of the promoter-targeting sequence with the endogenous sequence. The targeting sequence will be sufficiently near the 5' end of the desired endogenous polynucleotide sequence so the promoter will be operably linked to the endogenous sequence upon homologous recombination.

The promoter and the targeting sequences can be amplified using PCR. Preferably, the amplified promoter contains distinct restriction enzyme sites on the 5' and 3' ends. Preferably, the 3' end of the first targeting sequence contains the same restriction enzyme site as the 5' end of the amplified promoter and the 5' end of the second targeting sequence contains the same restriction site as the 3' end of the amplified promoter. The amplified promoter and targeting sequences are digested and ligated together.

The promoter-targeting sequence construct is delivered to the cells, either as naked polynucleotide, or in conjunction with transfection-facilitating agents, such as liposomes, viral sequences, viral particles, whole viruses, lipofection, precipitating agents, etc., described in more detail above. The P promoter-targeting sequence can be delivered by any method, included direct needle injection, intravenous injection, topical administration, catheter infusion, particle accelerators, etc. The methods are described in more detail below.

The promoter-targeting sequence construct is taken up by cells. Homologous recombination between the construct and the endogenous sequence takes place, such that an endogenous sequence is placed under the control of the promoter. The promoter then drives the expression of the endogenous sequence.

The polynucleotides encoding polypeptides of the present invention may be administered along with other polynucleotides encoding other angiongenic proteins. Angiogenic proteins include, but are not limited to, acidic and basic fibroblast growth factors, VEGF-1, VEGF-2 (VEGF-C), VEGF-3 (VEGF-B), epidermal growth factor alpha and beta, platelet-derived endothelial cell growth factor, platelet-derived growth factor, tumor necrosis factor alpha, hepatocyte growth factor, insulin like growth factor, colony stimulating factor, macrophage colony stimulating factor, granulocyte/macrophage colony stimulating factor, and nitric oxide synthase.

Preferably, the polynucleotide encoding a polypeptide of the invention contains a secretory signal sequence that facilitates secretion of the protein. Typically, the signal sequence is positioned in the coding region of the polynucleotide to be expressed towards or at the 5' end of the coding region. The signal sequence may be homologous or heterologous to the polynucleotide of interest and may be homologous or heterologous to the cells to be transfected. Additionally, the signal sequence may be chemically synthesized using methods known in the art.

Any mode of administration of any of the above-described polynucleotides constructs can be used so long as the mode results in the expression of one or more molecules in an amount sufficient to provide a therapeutic effect. This includes direct needle injection, systemic injection, catheter infusion, biolistic injectors, particle accelerators (i.e., “gene guns”), gelfoam sponge depots, other commercially available depot materials, osmotic pumps (e.g., Alza minipumps), oral or suppositorial solid (tablet or pill) pharmaceutical formulations, and decanting or topical applications during surgery. For example, direct injection of naked calcium phosphate-precipitated plasmid into rat liver and rat spleen or a protein-coated plasmid into the portal vein has resulted in gene expression of the foreign gene in the rat livers. (Kaneda et al., Science, 243:375 (1989)).

A preferred method of local administration is by direct injection. Preferably, a recombinant molecule of the present invention complexed with a delivery vehicle is administered by direct injection into or locally within the area of arteries. Administration of a composition locally within the area of arteries refers to injecting the composition centimeters and preferably, millimeters within arteries.

Another method of local administration is to contact a polynucleotide construct of the present invention in or around a surgical wound. For example, a patient can undergo surgery and the polynucleotide construct can be coated on the surface of tissue inside the wound or the construct can be injected into areas of tissue inside the wound.

Therapeutic compositions useful in systemic administration, include recombinant molecules of the present invention complexed to a targeted delivery vehicle of the present invention. Suitable delivery vehicles for use with systemic administration comprise liposomes comprising ligands for targeting the vehicle to a particular site.

Preferred methods of systemic administration, include intravenous injection, aerosol, oral and percutaneous (topical) delivery. Intravenous injections can be performed using methods standard in the art. Aerosol delivery can also be performed using methods standard in the art (see, for example, Stribling et al., Proc. Natl. Acad. Sci. USA, 189:11277-11281 (1992), which is incorporated herein by reference). Oral delivery can be performed by complexing a polynucleotide construct of the present invention to a carrier capable of withstanding degradation by digestive enzymes in the gut of an animal. Examples of such carriers, include plastic capsules or tablets, such as those known in the art. Topical delivery can be performed by mixing a polynucleotide construct of the present invention with a lipophilic reagent (e.g., DMSO) that is capable of passing into the skin.

Determining an effective amount of substance to be delivered can depend upon a number of factors including, for example, the chemical structure and biological activity of the substance, the age and weight of the animal, the precise condition requiring treatment and its severity, and the route of administration. The frequency of treatments depends upon a number of factors, such as the amount of polynucleotide constructs administered per dose, as well as the health and history of the subject. The precise amount, number of doses, and timing of doses will be determined by the attending physician or veterinarian. Therapeutic compositions of the present invention can be administered to any animal, preferably to mammals and birds. Preferred mammals include humans, dogs, cats, mice, rats, rabbits sheep, cattle, horses and pigs, with humans being particularly Biological Activities The polynucleotides or polypeptides, or agonists or antagonists of the present invention can be used in assays to test for one or more biological activities. If these polynucleotides and polypeptides do exhibit activity in a particular assay, it is likely that these molecules may be involved in the diseases associated with the biological activity. Thus, the polynucleotides or polypeptides, or agonists or antagonists could be used to treat the associated disease.

Immune Activity

Polynucleotides, polypeptides, antibodies, and/or agonists or antagonists of the present invention may be useful in treating, preventing, and/or diagnosing diseases, disorders, and/or conditions of the immune system, by, for example, activating or inhibiting the proliferation, differentiation, or mobilization (chemotaxis) of immune cells. Immune cells develop through a process called hematopoiesis, producing myeloid (platelets, red blood cells, neutrophils, and macrophages) and lymphoid (B and T lymphocytes) cells from pluripotent stem cells. The etiology of these immune diseases, disorders, and/or conditions may be genetic, somatic, such as cancer and some autoimmune diseases, acquired (e.g., by chemotherapy or toxins), or infectious. Moreover, polynucleotides, polypeptides, antibodies, and/or agonists or antagonists of the present invention can be used as a marker or detector of a particular immune system disease or disorder.

Polynucleotides, polypeptides, antibodies, and/or agonists or antagonists of the present invention may be useful in treating, preventing, and/or diagnosing diseases, disorders, and/or conditions of hematopoietic cells. Polynucleotides, polypeptides, antibodies, and/or agonists or antagonists of the present invention could be used to increase differentiation and proliferation of hematopoietic cells, including the pluripotent stem cells, in an effort to treat or prevent those diseases, disorders, and/or conditions associated with a decrease in certain (or many) types hematopoietic cells. Examples of immunologic deficiency syndromes include, but are not limited to: blood protein diseases, disorders, and/or conditions (e.g., agammaglobulinemia, dysgammaglobulinemia), ataxia telangiectasia, common variable immunodeficiency, Digeorge Syndrome, HIV infection, HTLV-BLV infection, leukocyte adhesion deficiency syndrome, lymphopenia, phagocyte bactericidal dysfunction, severe combined immunodeficiency (SCIDs), Wiskott-Aldrich Disorder, anemia, thrombocytopenia, or hemoglobinuria.

Moreover, polynucleotides, polypeptides, antibodies, and/or agonists or antagonists of the present invention could also be used to modulate hemostatic (the stopping of bleeding) or thrombolytic activity (clot formation). For example, by increasing hemostatic or thrombolytic activity, polynucleotides or polypeptides, and/or agonists or antagonists of the present invention could be used to treat or prevent blood coagulation diseases, disorders, and/or conditions (e.g., afibrinogenemia, factor deficiencies), blood platelet diseases, disorders, and/or conditions (e.g., thrombocytopenia), or wounds resulting from trauma, surgery, or other causes. Alternatively, polynucleotides, polypeptides, antibodies, and/or agonists or antagonists of the present invention that can decrease hemostatic or thrombolytic activity could be used to inhibit or dissolve clotting. These molecules could be important in the treatment or prevention of heart attacks (infarction), strokes, or scarring.

The polynucleotides, polypeptides, antibodies, and/or agonists or antagonists of the present invention may be useful in treating, preventing, and/or diagnosing autoimmune disorders. Many autoimmune disorders result from inappropriate recognition of self as foreign material by immune cells. This inappropriate recognition results in an immune response leading to the destruction of the host tissue. Therefore, the administration of polynucleotides and polypeptides of the invention that can inhibit an immune response, particularly the proliferation, differentiation, or chemotaxis of T-cells, may be an effective therapy in preventing autoimmune disorders.

Autoimmune diseases or disorders that may be treated, prevented, and/or diagnosed by polynucleotides, polypeptides, antibodies, and/or agonists or antagonists of the present invention include, but are not limited to, one or more of the following: autoimmune hemolytic anemia, autoimmune neonatal thrombocytopenia, idiopathic thrombocytopenia purpura, autoimmunocytopenia, hemolytic anemia, antiphospholipid syndrome, dermatitis, allergic encephalomyelitis, myocarditis, relapsing polychondritis, rheumatic heart disease, glomerulonephritis (e.g, IgA nephropathy), Multiple Sclerosis, Neuritis, Uveitis Ophthalmia, Polyendocrinopathies, Purpura (e.g., Henloch-Scoenlein purpura), Reiter's Disease, Stiff-Man Syndrome, Autoimmune Pulmonary Inflammation, Autism, Guillain-Barre Syndrome, insulin dependent diabetes mellitis, and autoimmune inflammatory eye, autoimmune thyroiditis, hypothyroidism (i.e., Hashimoto's thyroiditis, systemic lupus erhythematosus, Goodpasture's syndrome, Pemphigus, Receptor autoimmunities such as, for example, (a) Graves' Disease, (b) Myasthenia Gravis, and (c) insulin resistance, autoimmune hemolytic anemia, autoimmune thrombocytopenic purpura, rheumatoid arthritis, schleroderma with anti-collagen antibodies, mixed connective tissue disease, polymyositis/dermatomyositis, pernicious anemia, idiopathic Addison's disease, infertility, glomerulonephritis such as primary glomerulonephritis and IgA nephropathy, bullous pemphigoid, Sjogren's syndrome, diabetes millitus, and adrenergic drug resistance (including adrenergic drug resistance with asthma or cystic fibrosis), chronic active hepatitis, primary biliary cirrhosis, other endocrine gland failure, vitiligo, vasculitis, post-MI, cardiotomy syndrome, urticaria, atopic dermatitis, asthma, inflammatory myopathies, and other inflammatory, granulamatous, degenerative, and atrophic disorders.

Additional autoimmune disorders (that are probable) that may be treated, prevented, and/or diagnosed with the compositions of the invention include, but are not limited to, rheumatoid arthritis (often characterized, e.g., by immune complexes in joints), scleroderma with anti-collagen antibodies (often characterized, e.g., by nucleolar and other nuclear antibodies), mixed connective tissue disease (often characterized, e.g., by antibodies to extractable nuclear antigens (e.g., ribonucleoprotein)), polymyositis (often characterized, e.g., by nonhistone ANA), pernicious anemia (often characterized, e.g., by antiparietal cell, microsomes, and intrinsic factor antibodies), idiopathic Addison's disease (often characterized, e.g., by humoral and cell-mediated adrenal cytotoxicity, infertility (often characterized, e.g., by antispermatozoal antibodies), glomerulonephritis (often characterized, e.g., by glomerular basement membrane antibodies or immune complexes), bullous pemphigoid (often characterized, e.g., by IgG and complement in basement membrane), Sjogren's syndrome (often characterized, e.g., by multiple tissue antibodies, and/or a specific nonhistone ANA (SS-B)), diabetes millitus (often characterized, e.g., by cell-mediated and humoral islet cell antibodies), and adrenergic drug resistance (including adrenergic drug resistance with asthma or cystic fibrosis) (often characterized, e.g., by beta-adrenergic receptor antibodies).

Additional autoimmune disorders (that are possible) that may be treated, prevented, and/or diagnosed with the compositions of the invention include, but are not limited to, chronic active hepatitis (often characterized, e.g., by smooth muscle antibodies), primary biliary cirrhosis (often characterized, e.g., by mitchondrial antibodies), other endocrine gland failure (often characterized, e.g., by specific tissue antibodies in some cases), vitiligo (often characterized, e.g., by melanocyte antibodies), vasculitis (often characterized, e.g., by Ig and complement in vessel walls and/or low serum complement), post-MI (often characterized, e.g., by myocardial antibodies), cardiotomy syndrome (often characterized, e.g., by myocardial antibodies), urticaria (often characterized, e.g., by IgG and IgM antibodies to IgE), atopic dermatitis (often characterized, e.g., by IgG and IgM antibodies to IgE), asthma (often characterized, e.g., by IgG and IgM antibodies to IgE), and many other inflammatory, granulamatous, degenerative, and atrophic disorders.

In a preferred embodiment, the autoimmune diseases and disorders and/or conditions associated with the diseases and disorders recited above are treated, prevented, and/or diagnosed using for example, antagonists or agonists, polypeptides or polynucleotides, or antibodies of the present invention.

In a preferred embodiment polynucleotides, polypeptides, antibodies, and/or agonists or antagonists of the present invention could be used as an agent to boost immunoresponsiveness among B cell and/or T cell immunodeficient individuals.

B cell immunodeficiencies that may be ameliorated or treated by administering the polypeptides or polynucleotides of the invention, and/or agonists thereof, include, but are not limited to, severe combined immunodeficiency (SCID)-X linked, SCID-autosomal, adenosine deaminase deficiency (ADA deficiency), X-linked agammaglobulinemia (XLA), Bruton's disease, congenital agammaglobulinemia, X-linked infantile agammaglobulinemia, acquired agammaglobulinemia, adult onset agammaglobulinemia, late-onset agammaglobulinemia, dysgammaglobulinemia, hypogammaglobulinemia, transient hypogammaglobulinemia of infancy, unspecified hypogammaglobulinemia, agammaglobulinemia, common variable immunodeficiency (CVI) (acquired), Wiskott-Aldrich Syndrome (WAS), X-linked immunodeficiency with hyper IgM, non X-linked immunodeficiency with hyper IgM, selective IgA deficiency, IgG subclass deficiency (with or without IgA deficiency), antibody deficiency with normal or elevated Igs, immunodeficiency with thymoma, Ig heavy chain deletions, kappa chain deficiency, B cell lymphoproliferative disorder (BLPD), selective IgM immunodeficiency, recessive agammaglobulinemia (Swiss type), reticular dysgenesis, neonatal neutropenia, severe congenital leukopenia, thymic alymophoplasia-aplasia or dysplasia with immunodeficiency, ataxia-telangiectasia, short limbed dwarfism, X-linked lymphoproliferative syndrome (XLP), Nezelof syndrome-combined immunodeficiency with Igs, purine nucleoside phosphorylase deficiency (PNP), MHC Class II deficiency (Bare Lymphocyte Syndrome) and severe combined immunodeficiency.

T cell deficiencies that may be ameliorated or treated by administering the polypeptides or polynucleotides of the invention, and/or agonists thereof include, but are not limited to, for example, DiGeorge anomaly, thymic hypoplasia, third and fourth pharyngeal pouch syndrome, 22q11.2 deletion, chronic mucocutaneous candidiasis, natural killer cell deficiency (NK), idiopathic CD4+ T-lymphocytopenia, immunodeficiency with predominant T cell defect (unspecified), and unspecified immunodeficiency of cell mediated immunity. In specific embodiments, DiGeorge anomaly or conditions associated with DiGeorge anomaly are ameliorated or treated by, for example, administering the polypeptides or polynucleotides of the invention, or antagonists or agonists thereof.

Other immunodeficiencies that may be ameliorated or treated by administering polypeptides or polynucleotides of the invention, and/or agonists thereof, include, but are not limited to, severe combined immunodeficiency (SCID; e.g., X-linked SCID, autosomal SCID, and adenosine deaminase deficiency), ataxia-telangiectasia, Wiskott-Aldrich syndrome, short-limber dwarfism, X-linked lymphoproliferative syndrome (XLP), Nezelof syndrome (e.g., purine nucleoside phosphorylase deficiency), MHC Class II deficiency. In specific embodiments, ataxia-telangiectasia or conditions associated with ataxia-telangiectasia are ameliorated or treated by administering the polypeptides or polynucleotides of the invention, and/or agonists thereof.

In a specific preferred embodiment, rheumatoid arthritis is treated, prevented, and/or diagnosed using polynucleotides, polypeptides, antibodies, and/or agonists or antagonists of the present invention. In another specific preferred embodiment, systemic lupus erythemosus is treated, prevented, and/or diagnosed using polynucleotides, polypeptides, antibodies, and/or agonists or antagonists of the present invention. In another specific preferred embodiment, idiopathic thrombocytopenia purpura is treated, prevented, and/or diagnosed using polynucleotides, polypeptides, antibodies, and/or agonists or antagonists of the present invention. In another specific preferred embodiment IgA nephropathy is treated, prevented, and/or diagnosed using polynucleotides, polypeptides, antibodies, and/or agonists or antagonists of the present invention. In a preferred embodiment, the autoimmune diseases and disorders and/or conditions associated with the diseases and disorders recited above are treated, prevented, and/or diagnosed using antibodies against the protein of the invention.

Similarly, allergic reactions and conditions, such as asthma (particularly allergic asthma) or other respiratory problems, may also be treated, prevented, and/or diagnosed using polypeptides, antibodies, or polynucleotides of the invention, and/or agonists or antagonists thereof. Moreover, these molecules can be used to treat, prevent, and/or diagnose anaphylaxis, hypersensitivity to an antigenic molecule, or blood group incompatibility.

Moreover, inflammatory conditions may also be treated, diagnosed, and/or prevented with polynucleotides, polypeptides, antibodies, and/or agonists or antagonists of the present invention. Such inflammatory conditions include, but are not limited to, for example, respiratory disorders (such as, e.g., asthma and allergy); gastrointestinal disorders (such as, e.g., inflammatory bowel disease); cancers (such as, e.g., gastric, ovarian, lung, bladder, liver, and breast); CNS disorders (such as, e.g., multiple sclerosis, blood-brain barrier permeability, ischemic brain injury and/or stroke, traumatic brain injury, neurodegenerative disorders (such as, e.g., Parkinson's disease and Alzheimer's disease), AIDS-related dementia, and prion disease); cardiovascular disorders (such as, e.g., atherosclerosis, myocarditis, cardiovascular disease, and cardiopulmonary bypass complications); as well as many additional diseases, conditions, and disorders that are characterized by inflammation (such as, e.g., chronic hepatitis (B and C), rheumatoid arthritis, gout, trauma, septic shock, pancreatitis, sarcoidosis, dermatitis, renal ischemia-reperfusion injury, Grave's disease, systemic lupus erythematosis, diabetes mellitus (i.e., type 1 diabetes), and allogenic transplant rejection).

In specific embodiments, polypeptides, antibodies, or polynucleotides of the invention, and/or agonists or antagonists thereof, are useful to treat, diagnose, and/or prevent transplantation rejections, graft-versus-host disease, autoimmune and inflammatory diseases (e.g., immune complex-induced vasculitis, glomerulonephritis, hemolytic anemia, myasthenia gravis, type II collagen-induced arthritis, experimental allergic and hyperacute xenograft rejection, rheumatoid arthritis, and systemic lupus erythematosus (SLE). Organ rejection occurs by host immune cell destruction of the transplanted tissue through an immune response. Similarly, an immune response is also involved in GVHD, but, in this case, the foreign transplanted immune cells destroy the host tissues. Polypeptides, antibodies, or polynucleotides of the invention, and/or agonists or antagonists thereof, that inhibit an immune response, particularly the activation, proliferation, differentiation, or chemotaxis of T-cells, may be an effective therapy in preventing organ rejection or GVHD.

Similarly, polynucleotides, polypeptides, antibodies, and/or agonists or antagonists of the present invention may also be used to modulate and/or diagnose inflammation. For example, since polypeptides, antibodies, or polynucleotides of the invention, and/or agonists or antagonists of the invention may inhibit the activation, proliferation and/or differentiation of cells involved in an inflammatory response, these molecules can be used to treat, diagnose, or prognose, inflammatory conditions, both chronic and acute conditions, including, but not limited to, inflammation associated with infection (e.g., septic shock, sepsis, or systemic inflammatory response syndrome (SIRS)), ischemia-reperfusion injury, endotoxin lethality, arthritis, complement-mediated hyperacute rejection, nephritis, cytokine or chemokine induced lung injury, inflammatory bowel disease, Crohn's disease, and resulting from over production of cytokines (e.g., TNF or IL-1.).

Polypeptides, antibodies, polynucleotides and/or agonists or antagonists of the invention can be used to treat, detect, and/or prevent infectious agents. For example, by increasing the immune response, particularly increasing the proliferation activation and/or differentiation of B and/or T cells, infectious diseases may be treated, detected, and/or prevented. The immune response may be increased by either enhancing an existing immune response, or by initiating a new immune response. Alternatively, polynucleotides, polypeptides, antibodies, and/or agonists or antagonists of the present invention may also directly inhibit the infectious agent (refer to section of application listing infectious agents, etc), without necessarily eliciting an immune response.

Additional preferred embodiments of the invention include, but are not limited to, the use of polypeptides, antibodies, polynucleotides and/or agonists or antagonists in the following applications:

Administration to an animal (e.g., mouse, rat, rabbit, hamster, guinea pig, pigs, micro-pig, chicken, camel, goat, horse, cow, sheep, dog, cat, non-human primate, and human, most preferably human) to boost the immune system to produce increased quantities of one or more antibodies (e.g., IgG, IgA, IgM, and IgE), to induce higher affinity antibody production (e.g., IgG, IgA, IgM, and IgE), and/or to increase an immune response.

Administration to an animal (including, but not limited to, those listed above, and also including transgenic animals) incapable of producing functional endogenous antibody molecules or having an otherwise compromised endogenous immune system, but which is capable of producing human immunoglobulin molecules by means of a reconstituted or partially reconstituted immune system from another animal (see, e.g., published PCT Application Nos. WO98/24893, WO/9634096, WO/9633735, and WO/9110741.

A vaccine adjuvant that enhances immune responsiveness to specific antigen.

An adjuvant to enhance tumor-specific immune responses.

An adjuvant to enhance anti-viral immune responses. Anti-viral immune responses that may be enhanced using the compositions of the invention as an adjuvant, include virus and virus associated diseases or symptoms described herein or otherwise known in the art. In specific embodiments, the compositions of the invention are used as an adjuvant to enhance an immune response to a virus, disease, or symptom selected from the group consisting of: AIDS, meningitis, Dengue, EBV, and hepatitis (e.g., hepatitis B). In another specific embodiment, the compositions of the invention are used as an adjuvant to enhance an immune response to a virus, disease, or symptom selected from the group consisting of: HIV/AIDS, Respiratory syncytial virus, Dengue, Rotavirus, Japanese B encephalitis, Influenza A and B, Parainfluenza, Measles, Cytomegalovirus, Rabies, Junin, Chikungunya, Rift Valley fever, Herpes simplex, and yellow fever.

An adjuvant to enhance anti-bacterial or anti-fungal immune responses. Anti-bacterial or anti-fungal immune responses that may be enhanced using the compositions of the invention as an adjuvant, include bacteria or fungus and bacteria or fungus associated diseases or symptoms described herein or otherwise known in the art. In specific embodiments, the compositions of the invention are used as an adjuvant to enhance an immune response to a bacteria or fungus, disease, or symptom selected from the group consisting of: tetanus, Diphtheria, botulism, and meningitis type B. In another specific embodiment, the compositions of the invention are used as an adjuvant to enhance an immune response to a bacteria or fungus, disease, or symptom selected from the group consisting of: *Vibrio cholerae, Mycobacterium leprae, Salmonella typhi, Salmonella paratyphi, Meisseria meningitidis, Streptococcus pneumoniae*, Group B *streptococcus, Shigella* spp., Enterotoxigenic *Escherichia coli*, Enterohemorrhagic *E. coli, Borrelia burgdorferi*, and *Plasmodium* (malaria).

An adjuvant to enhance anti-parasitic immune responses. Anti-parasitic immune responses that may be enhanced using the compositions of the invention as an adjuvant, include parasite and parasite associated diseases or symptoms described herein or otherwise known in the art. In specific embodiments, the compositions of the invention are used as an adjuvant to enhance an immune response to a parasite. In another specific embodiment, the compositions of the invention are used as an adjuvant to enhance an immune response to *Plasmodium* (malaria).

As a stimulator of B cell responsiveness to pathogens.

As an activator of T cells.

As an agent that elevates the immune status of an individual prior to their receipt of immunosuppressive therapies.

As an agent to induce higher affinity antibodies.

As an agent to increase serum immunoglobulin concentrations.

As an agent to accelerate recovery of immunocompromised individuals.

As an agent to boost immunoresponsiveness among aged populations.

As an immune system enhancer prior to, during, or after bone marrow transplant and/or other transplants (e.g., allogeneic or xenogeneic organ transplantation). With respect to transplantation, compositions of the invention may be administered prior to, concomitant with, and/or after transplantation. In a specific embodiment, compositions of the invention are administered after transplantation, prior to the beginning of recovery of T-cell populations. In another specific embodiment, compositions of the invention are first administered after transplantation after the beginning of recovery of T cell populations, but prior to full recovery of B cell populations.

As an agent to boost immunoresponsiveness among individuals having an acquired loss of B cell function. Conditions resulting in an acquired loss of B cell function that may be ameliorated or treated by administering the polypeptides, antibodies, polynucleotides and/or agonists or antagonists thereof, include, but are not limited to, HIV Infection, AIDS, bone marrow transplant, and B cell chronic lymphocytic leukemia (CLL).

As an agent to boost immunoresponsiveness among individuals having a temporary immune deficiency. Conditions resulting in a temporary immune deficiency that may be ameliorated or treated by administering the polypeptides, antibodies, polynucleotides and/or agonists or antagonists thereof, include, but are not limited to, recovery from viral infections (e.g., influenza), conditions associated with malnutrition, recovery from infectious mononucleosis, or conditions associated with stress, recovery from measles, recovery from blood transfusion, recovery from surgery.

As a regulator of antigen presentation by monocytes, dendritic cells, and/or B-cells. In one embodiment, polynucleotides, polypeptides, antibodies, and/or agonists or antagonists of the present invention enhance antigen presentation or antagonizes antigen presentation in vitro or in vivo. Moreover, in related embodiments, said enhancement or antagonization of antigen presentation may be useful as an anti-tumor treatment or to modulate the immune system.

As an agent to direct an individuals immune system towards development of a humoral response (i.e. TH2) as opposed to a TH1 cellular response.

As a means to induce tumor proliferation and thus make it more susceptible to anti-neoplastic agents. For example, multiple myeloma is a slowly dividing disease and is thus refractory to virtually all anti-neoplastic regimens. If these cells were forced to proliferate more rapidly their susceptibility profile would likely change.

As a stimulator of B cell production in pathologies such as AIDS, chronic lymphocyte disorder and/or Common Variable Immunodeficiency.

As a therapy for generation and/or regeneration of lymphoid tissues following surgery, trauma or genetic defect.

As a gene-based therapy for genetically inherited disorders resulting in immuno-incompetence such as observed among SCID patients.

As an antigen for the generation of antibodies to inhibit or enhance immune mediated responses against polypeptides of the invention.

As a means of activating T cells.

As a means of activating monocytes/macrophages to defend against parasitic diseases that effect monocytes such as Leshmania.

As pretreatment of bone marrow samples prior to transplant. Such treatment would increase B cell representation and thus accelerate recover.

As a means of regulating secreted cytokines that are elicited by polypeptides of the invention.

Additionally, polypeptides or polynucleotides of the invention, and/or agonists thereof, may be used to treat or prevent IgE-mediated allergic reactions. Such allergic reactions include, but are not limited to, asthma, rhinitis, and eczema.

All of the above described applications as they may apply to veterinary medicine.

Antagonists of the invention include, for example, binding and/or inhibitory antibodies, antisense nucleic acids, or ribozymes. These would be expected to reverse many of the activities of the ligand described above as well as find clinical or practical application as:

A means of blocking various aspects of immune responses to foreign agents or self. Examples include autoimmune disorders such as lupus, and arthritis, as well as immunoresponsiveness to skin allergies, inflammation, bowel disease, injury and pathogens.

A therapy for preventing the B cell proliferation and Ig secretion associated with autoimmune diseases such as idiopathic thrombocytopenic purpura, systemic lupus erythramatosus and MS.

An inhibitor of B and/or T cell migration in endothelial cells. This activity disrupts tissue architecture or cognate responses and is useful, for example in disrupting immune responses, and blocking sepsis.

An inhibitor of graft versus host disease or transplant rejection.

A therapy for B cell and/or T cell malignancies such as ALL, Hodgkins disease, non-Hodgkins lymphoma, Chronic lymphocyte leukemia, plasmacytomas, multiple myeloma, Burkitt's lymphoma, and EBV-transformed diseases.

A therapy for chronic hypergammaglobulinemeia evident in such diseases as monoclonalgammopathy of undetermined significance (MGUS), Waldenstrom's disease, related idiopathic monoclonalgammopathies, and plasmacytomas.

A therapy for decreasing cellular proliferation of Large B-cell Lymphomas.

A means of decreasing the involvement of B cells and Ig associated with Chronic Myelogenous Leukemia.

An immunosuppressive agent(s).

Polynucleotides, polypeptides, antibodies, and/or agonists or antagonists of the present invention may be used to modulate IgE concentrations in vitro or in vivo.

In another embodiment, administration of polypeptides, antibodies, polynucleotides and/or agonists or antagonists of the invention, may be used to treat or prevent IgE-mediated allergic reactions including, but not limited to, asthma, rhinitis, and eczema.

The agonists and antagonists may be employed in a composition with a pharmaceutically acceptable carrier, e.g., as described herein.

The agonists or antagonists may be employed for instance to inhibit polypeptide chemotaxis and activation of macrophages and their precursors, and of neutrophils, basophils, B lymphocytes and some T-cell subsets, e.g., activated and CD8 cytotoxic T cells and natural killer cells, in certain auto-immune and chronic inflammatory and infective diseases. Examples of autoimmune diseases are described herein and include multiple sclerosis, and insulin-dependent diabetes. The antagonists or agonists may also be employed to treat infectious diseases including silicosis, sarcoidosis, idiopathic pulmonary fibrosis by, for example, preventing the recruitment and activation of mononuclear phagocytes. They may also be employed to treat idiopathic hypereosinophilic syndrome by, for example, preventing eosinophil production and migration. The antagonists or agonists or may also be employed for treating atherosclerosis, for example, by preventing monocyte infiltration in the artery wall.

Antibodies against polypeptides of the invention may be employed to treat ARDS.

Agonists and/or antagonists of the invention also have uses in stimulating wound and tissue repair, stimulating angiogenesis, stimulating the repair of vascular or lymphatic diseases or disorders. Additionally, agonists and antagonists of the invention may be used to stimulate the regeneration of mucosal surfaces.

In a specific embodiment, polynucleotides or polypeptides, and/or agonists thereof are used to treat or prevent a disorder characterized by primary or acquired immunodeficiency, deficient serum immunoglobulin production, recurrent infections, and/or immune system dysfunction. Moreover, polynucleotides or polypeptides, and/or agonists thereof may be used to treat or prevent infections of the joints, bones, skin, and/or parotid glands, blood-borne infections (e.g., sepsis, meningitis, septic arthritis, and/or osteomyelitis), autoimmune diseases (e.g., those disclosed herein), inflammatory disorders, and malignancies, and/or any disease or disorder or condition associated with these infections, diseases, disorders and/or malignancies) including, but not limited to, CVID, other primary immune deficiencies, HIV disease, CLL, recurrent bronchitis, sinusitis, otitis media, conjunctivitis, pneumonia, hepatitis, meningitis, herpes zoster (e.g., severe herpes zoster), and/or *pneumocystis carnii.*

In another embodiment, polynucleotides, polypeptides, antibodies, and/or agonists or antagonists of the present invention are used to treat, and/or diagnose an individual having common variable immunodeficiency disease ("CVID"; also known as "acquired agammaglobulinemia" and "acquired hypogammaglobulinemia") or a subset of this disease.

In a specific embodiment, polynucleotides, polypeptides, antibodies, and/or agonists or antagonists of the present invention may be used to treat, diagnose, and/or prevent (1) cancers or neoplasms and (2) autoimmune cell or tissue-related cancers or neoplasms. In a preferred embodiment, polynucleotides, polypeptides, antibodies, and/or agonists or antagonists of the present invention conjugated to a toxin or a radioactive isotope, as described herein, may be used to treat, diagnose, and/or prevent acute myelogeneous leukemia. In a further preferred embodiment, polynucleotides, polypeptides, antibodies, and/or agonists or antagonists of the present invention conjugated to a toxin or a radioactive isotope, as described herein, may be used to treat, diagnose, and/or prevent, chronic myelogeneous leukemia, multiple myeloma, non-Hodgkins lymphoma, and/or Hodgkins disease.

In another specific embodiment, polynucleotides or polypeptides, and/or agonists or antagonists of the invention may be used to treat, diagnose, prognose, and/or prevent selective IgA deficiency, myeloperoxidase deficiency, C2 deficiency, ataxia-telangiectasia, DiGeorge anomaly, common variable immunodeficiency (CVI), X-linked agammaglobulinemia, severe combined immunodeficiency (SCID), chronic granulomatous disease (CGD), and Wiskott-Aldrich syndrome.

Examples of autoimmune disorders that can be treated or detected are described above and also include, but are not limited to: Addison's Disease, hemolytic anemia, antiphospholipid syndrome, rheumatoid arthritis, dermatitis, allergic encephalomyelitis, glomerulonephritis, Goodpasture's Syndrome, Graves' Disease, Multiple Sclerosis, Myasthenia Gravis, Neuritis, Ophthalmia, Bullous Pemphigoid, Pemphigus, Polyendocrinopathies, Purpura, Reiter's Disease, Stiff-Man Syndrome, Autoimmune Thyroiditis, Systemic Lupus Erythematosus, Autoimmune Pulmonary Inflammation, Guillain-Barre Syndrome, insulin dependent diabetes mellitis, and autoimmune inflammatory eye disease.

In a preferred embodiment, the autoimmune diseases and disorders and/or conditions associated with the diseases and disorders recited above are treated, prognosed, prevented, and/or diagnosed using antibodies against the polypeptide of the invention.

As an agent to boost immunoresponsiveness among B cell immunodeficient individuals, such as, for example, an individual who has undergone a partial or complete splenectomy.

Additionally, polynucleotides, polypeptides, and/or antagonists of the invention may affect apoptosis, and therefore, would be useful in treating a number of diseases associated with increased cell survival or the inhibition of apoptosis. For example, diseases associated with increased cell survival or the inhibition of apoptosis that could be treated or detected by polynucleotides, polypeptides, and/or antagonists of the invention, include cancers (such as follicular lymphomas, carcinomas with p53 mutations, and hormone-dependent tumors, including, but not limited to colon cancer, cardiac tumors, pancreatic cancer, melanoma, retinoblastoma, glioblastoma, lung cancer, intestinal cancer, testicular cancer, stomach cancer, neuroblastoma, myxoma, myoma, lymphoma, endothelioma, osteoblastoma, osteoclastoma, osteosarcoma, chondrosarcoma, adenoma, breast cancer, prostate cancer, Kaposi's sarcoma and ovarian cancer); autoimmune disorders (such as, multiple sclerosis, Sjogren's syndrome, Hashimoto's thyroiditis, biliary cirrhosis, Behcet's disease, Crohn's disease, polymyositis, systemic lupus erythematosus and immune-related glomerulonephritis and rheumatoid arthritis) and viral infections (such as herpes viruses, pox viruses and adenoviruses), inflammation, graft v. host disease, acute graft rejection, and chronic graft rejection. In preferred embodiments, polynucleotides, polypeptides, and/or antagonists of the invention are used to inhibit growth, progression, and/or metastisis of cancers, in particular those listed above.

Additional diseases or conditions associated with increased cell survival that could be treated or detected by polynucleotides, polypeptides, and/or antagonists of the invention, include, but are not limited to, progression, and/or metastases of malignancies and related disorders such as leukemia (including acute leukemias (e.g., acute lymphocytic leukemia, acute myelocytic leukemia (including myeloblastic, promyelocytic, myelomonocytic, monocytic, and erythroleukemia)) and chronic leukemias (e.g., chronic myelocytic (granulocytic) leukemia and chronic lymphocytic leukemia)), polycythemia vera, lymphomas (e.g., Hodgkin's disease and non-Hodgkin's disease), multiple myeloma, Waldenstrom's macroglobulinemia, heavy chain disease, and solid tumors including, but not limited to, sarcomas and carcinomas such as fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilm's tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, menangioma, melanoma, neuroblastoma, and retinoblastoma.

Diseases associated with increased apoptosis that could be treated or detected by polynucleotides, polypeptides, and/or antagonists of the invention, include AIDS; neurodegenerative disorders (such as Alzheimer's disease, Parkinson's disease, Amyotrophic lateral sclerosis, Retinitis pigmentosa, Cerebellar degeneration and brain tumor or prior associated disease); autoimmune disorders (such as, multiple sclerosis, Sjogren's syndrome, Hashimoto's thyroiditis, biliary cirrhosis, Behcet's disease, Crohn's disease, polymyositis, systemic lupus erythematosus and immune-related glomerulonephritis and rheumatoid arthritis) myelodysplastic syndromes (such as aplastic anemia), graft v. host disease, ischemic injury (such as that caused by myocardial infarction, stroke and reperfusion injury), liver injury (e.g., hepatitis related liver injury, ischemia/reperfusion injury, cholestosis (bile duct injury) and liver cancer); toxin-induced liver disease (such as that caused by alcohol), septic shock, cachexia and anorexia.

Hyperproliferative diseases and/or disorders that could be detected and/or treated by polynucleotides, polypeptides, and/or antagonists of the invention, include, but are not limited to neoplasms located in the: liver, abdomen, bone, breast, digestive system, pancreas, peritoneum, endocrine glands (adrenal, parathyroid, pituitary, testicles, ovary, thymus, thyroid), eye, head and neck, nervous (central and peripheral), lymphatic system, pelvic, skin, soft tissue, spleen, thoracic, and urogenital.

Similarly, other hyperproliferative disorders can also be treated or detected by polynucleotides, polypeptides, and/or antagonists of the invention. Examples of such hyperproliferative disorders include, but are not limited to: hypergammaglobulinemia, lymphoproliferative disorders, paraproteinemias, purpura, sarcoidosis, Sezary Syndrome, Waldenstron's Macroglobulinemia, Gaucher's Disease, histiocytosis, and any other hyperproliferative disease, besides neoplasia, located in an organ system listed above.

Hyperproliferative Disorders

A polynucleotides or polypeptides, or agonists or antagonists of the invention can be used to treat, prevent, and/or diagnose hyperproliferative diseases, disorders, and/or conditions, including neoplasms. A polynucleotides or polypeptides, or agonists or antagonists of the present invention may inhibit the proliferation of the disorder through direct or indirect interactions. Alternatively, a polynucleotides or polypeptides, or agonists or antagonists of the present invention may proliferate other cells which can inhibit the hyperproliferative disorder.

For example, by increasing an immune response, particularly increasing antigenic qualities of the hyperproliferative disorder or by proliferating, differentiating, or mobilizing T-cells, hyperproliferative diseases, disorders, and/or conditions can be treated, prevented, and/or diagnosed. This immune response may be increased by either enhancing an existing immune response, or by initiating a new immune response. Alternatively, decreasing an immune response may also be a method of treating, preventing, and/or diagnosing hyperproliferative diseases, disorders, and/or conditions, such as a chemotherapeutic agent.

Examples of hyperproliferative diseases, disorders, and/or conditions that can be treated, prevented, and/or diagnosed by polynucleotides or polypeptides, or agonists or antagonists of the present invention include, but are not limited to neoplasms located in the: colon, abdomen, bone, breast, digestive system, liver, pancreas, peritoneum, endocrine glands (adrenal, parathyroid, pituitary, testicles, ovary, thymus, thyroid), eye, head and neck, nervous (central and peripheral), lymphatic system, pelvic, skin, soft tissue, spleen, thoracic, and urogenital.

Similarly, other hyperproliferative diseases, disorders, and/or conditions can also be treated, prevented, and/or diagnosed by a polynucleotides or polypeptides, or agonists or antagonists of the present invention. Examples of such hyperproliferative diseases, disorders, and/or conditions include, but are not limited to: hypergammaglobulinemia, lymphoproliferative diseases, disorders, and/or conditions, paraproteinemias, purpura, sarcoidosis, Sezary Syndrome, Waldenstron's Macroglobulinemia, Gaucher's Disease, histiocytosis, and any other hyperproliferative disease, besides neoplasia, located in an organ system listed above.

One preferred embodiment utilizes polynucleotides of the present invention to inhibit aberrant cellular division, by gene therapy using the present invention, and/or protein fusions or fragments thereof.

Thus, the present invention provides a method for treating or preventing cell proliferative diseases, disorders, and/or conditions by inserting into an abnormally proliferating cell a polynucleotide of the present invention, wherein said polynucleotide represses said expression.

Another embodiment of the present invention provides a method of treating or preventing cell-proliferative diseases, disorders, and/or conditions in individuals comprising administration of one or more active gene copies of the present invention to an abnormally proliferating cell or cells. In a preferred embodiment, polynucleotides of the present invention is a DNA construct comprising a recombinant expression vector effective in expressing a DNA sequence encoding said polynucleotides. In another preferred embodiment of the present invention, the DNA construct encoding the poynucleotides of the present invention is inserted into cells to be treated utilizing a retrovirus, or more preferrably an adenoviral vector (See G J. Nabel, et. al., PNAS 1999 96: 324-326, which is hereby incorporated by reference). In a most preferred embodiment, the viral vector is defective and will not transform non-proliferating cells, only proliferating cells. Moreover, in a preferred embodiment, the polynucleotides of the present invention inserted into proliferating cells either alone, or in combination with or fused to other polynucleotides, can then be modulated via an external stimulus (i.e. magnetic, specific small molecule, chemical, or drug administration, etc.), which acts upon the promoter upstream of said polynucleotides to induce expression of the encoded protein product. As such the beneficial therapeutic affect of the present invention may be expressly modulated (i.e. to increase, decrease, or inhibit expression of the present invention) based upon said external stimulus.

Polynucleotides of the present invention may be useful in repressing expression of oncogenic genes or antigens. By "repressing expression of the oncogenic genes" is intended the suppression of the transcription of the gene, the degradation of the gene transcript (pre-message RNA), the inhibition of splicing, the destruction of the messenger RNA, the prevention of the post-translational modifications of the protein, the destruction of the protein, or the inhibition of the normal function of the protein.

For local administration to abnormally proliferating cells, polynucleotides of the present invention may be administered by any method known to those of skill in the art including, but not limited to transfection, electroporation, microinjection of cells, or in vehicles such as liposomes, lipofectin, or as naked polynucleotides, or any other method described throughout the specification. The polynucleotide of the present invention may be delivered by known gene delivery systems such as, but not limited to, retroviral vectors (Gilboa, J. Virology 44:845 (1982); Hocke, Nature 320:275 (1986); Wilson, et al., Proc. Natl. Acad. Sci. U.S.A. 85:3014), vaccinia virus system (Chakrabarty et al., Mol. Cell Biol. 5:3403 (1985) or other efficient DNA delivery systems (Yates et al., Nature 313:812 (1985)) known to those skilled in the art. These references are exemplary only and are hereby incorporated by reference. In order to specifically deliver or transfect cells which are abnormally proliferating and spare non-dividing cells, it is preferable to utilize a retrovirus, or adenoviral (as described in the art and elsewhere herein) delivery system known to those of skill in the art. Since host DNA replication is required for retroviral DNA to integrate and the retrovirus will be unable to self replicate due to the lack of the retrovirus genes needed for its life cycle. Utilizing such a retroviral delivery system for polynucleotides of the present invention will target said gene and constructs to abnormally proliferating cells and will spare the non-dividing normal cells.

The polynucleotides of the present invention may be delivered directly to cell proliferative disorder/disease sites in internal organs, body cavities and the like by use of imaging devices used to guide an injecting needle directly to the disease site. The polynucleotides of the present invention may also be administered to disease sites at the time of surgical intervention.

By "cell proliferative disease" is meant any human or animal disease or disorder, affecting any one or any combination of organs, cavities, or body parts, which is characterized by single or multiple local abnormal proliferations of cells, groups of cells, or tissues, whether benign or malignant.

Any amount of the polynucleotides of the present invention may be administered as long as it has a biologically inhibiting effect on the proliferation of the treated cells. Moreover, it is possible to administer more than one of the polynucleotide of the present invention simultaneously to the same site. By "biologically inhibiting" is meant partial or total growth inhibition as well as decreases in the rate of proliferation or growth of the cells. The biologically inhibitory dose may be determined by assessing the effects of the polynucleotides of the present invention on target malignant or abnormally proliferating cell growth in tissue culture, tumor growth in animals and cell cultures, or any other method known to one of ordinary skill in the art.

The present invention is further directed to antibody-based therapies which involve administering of anti-polypeptides and anti-polynucleotide antibodies to a mammalian, preferably human, patient for treating, preventing, and/or diagnosing one or more of the described diseases, disorders, and/or conditions. Methods for producing anti-polypeptides and anti-polynucleotide antibodies polyclonal and monoclonal antibodies are described in detail elsewhere herein. Such antibodies may be provided in pharmaceutically acceptable compositions as known in the art or as described herein.

A summary of the ways in which the antibodies of the present invention may be used therapeutically includes binding polynucleotides or polypeptides of the present invention locally or systemically in the body or by direct cytotoxicity of the antibody, e.g. as mediated by complement (CDC) or by effector cells (ADCC). Some of these approaches are described in more detail below. Armed with the teachings provided herein, one of ordinary skill in the art will know how to use the antibodies of the present invention for diagnostic, monitoring or therapeutic purposes without undue experimentation.

In particular, the antibodies, fragments and derivatives of the present invention are useful for treating, preventing, and/or diagnosing a subject having or developing cell proliferative and/or differentiation diseases, disorders, and/or conditions as described herein. Such treatment comprises administering a single or multiple doses of the antibody, or a fragment, derivative, or a conjugate thereof.

The antibodies of this invention may be advantageously utilized in combination with other monoclonal or chimeric antibodies, or with lymphokines or hematopoietic growth factors, for example, which serve to increase the number or activity of effector cells which interact with the antibodies.

It is preferred to use high affinity and/or potent in vivo inhibiting and/or neutralizing antibodies against polypeptides or polynucleotides of the present invention, fragments or regions thereof, for both immunoassays directed to and therapy of diseases, disorders, and/or conditions related to polynucleotides or polypeptides, including fragments thereof, of the present invention. Such antibodies, fragments, or regions, will preferably have an affinity for polynucleotides or polypeptides, including fragments thereof. Preferred binding affinities include those with a dissociation constant or Kd less than $5\times10^{-6}$M, $10^{-6}$M, $5\times10^{-7}$M, $10^{-7}$M, $5\times10^{-8}$M, $10^{-8}$M, $5\times10^{-9}$M, $10^{-9}$M, $5\times10^{-10}$M, $10^{-10}$M, $5\times10^{-11}$ M, $10^{-11}$M, $5\times10^{-12}$M, $10^{-12}$M, $5\times10^{-13}$ M, $10^{-13}$M, $5\times10^{-14}$M, $10^{-14}$M, $5\times10^{-15}$M, and $10^{-15}$M.

Moreover, polypeptides of the present invention are useful in inhibiting the angiogenesis of proliferative cells or tissues, either alone, as a protein fusion, or in combination with other polypeptides directly or indirectly, as described elsewhere herein. In a most preferred embodiment, said anti-angiogenesis effect may be achieved indirectly, for example, through the inhibition of hematopoietic, tumor-specific cells, such as tumor-associated macrophages (See Joseph I B, et al. J Natl Cancer Inst, 90(21):1648-53 (1998), which is hereby incorporated by reference). Antibodies directed to polypeptides or polynucleotides of the present invention may also result in inhibition of angiogenesis directly, or indirectly (See Witte L, et al., Cancer Metastasis Rev. 17(2):155-61 (1998), which is hereby incorporated by reference)).

Polypeptides, including protein fusions, of the present invention, or fragments thereof may be useful in inhibiting proliferative cells or tissues through the induction of apoptosis. Said polypeptides may act either directly, or indirectly to induce apoptosis of proliferative cells and tissues, for example in the activation of a death-domain receptor, such as tumor necrosis factor (TNF) receptor-1, CD95 (Fas/APO-1), TNF-receptor-related apoptosis-mediated protein (TRAMP) and TNF-related apoptosis-inducing ligand (TRAIL) receptor-1 and -2 (See Schulze-Osthoff K, et. al., Eur J Biochem 254(3):439-59 (1998), which is hereby incorporated by reference). Moreover, in another preferred embodiment of the present invention, said polypeptides may induce apoptosis through other mechanisms, such as in the activation of other proteins which will activate apoptosis, or through stimulating the expression of said proteins, either alone or in combination with small molecule drugs or adjuviants, such as apoptonin, galectins, thioredoxins, anti-inflammatory proteins (See for example, Mutat Res 400(1-2):447-55 (1998), Med Hypotheses .50(5):423-33 (1998), Chem Biol Interact. April 24; 111-112:23-34 (1998), J Mol Med. 76(6):402-12 (1998), int J Tissue React; 20(1):3-15 (1998), which are all hereby incorporated by reference).

Polypeptides, including protein fusions to, or fragments thereof, of the present invention are useful in inhibiting the metastasis of proliferative cells or tissues. Inhibition may occur as a direct result of administering polypeptides, or antibodies directed to said polypeptides as described elsewhere herein, or indirectly, such as activating the expression of proteins known to inhibit metastasis, for example alpha 4 integrins, (See, e.g., Curr Top Microbiol Immunol 1998; 231:125-41, which is hereby incorporated by reference). Such therapeutic affects of the present invention may be achieved either alone, or in combination with small molecule drugs or adjuvants.

In another embodiment, the invention provides a method of delivering compositions containing the polypeptides of the invention (e.g., compositions containing polypeptides or polypeptide antibodies associated with heterologous polypeptides, heterologous nucleic acids, toxins, or prodrugs) to targeted cells expressing the polypeptide of the present invention. Polypeptides or polypeptide antibodies of the invention may be associated with heterologous polypeptides, heterologous nucleic acids, toxins, or prodrugs via hydrophobic, hydrophilic, ionic and/or covalent interactions.

Polypeptides, protein fusions to, or fragments thereof, of the present invention are useful in enhancing the immunogenicity and/or antigenicity of proliferating cells or tissues, either directly, such as would occur if the polypeptides of the present invention 'vaccinated' the immune response to respond to proliferative antigens and immunogens, or indirectly, such as in activating the expression of proteins known to enhance the immune response (e.g. chemokines), to said antigens and immunogens.

Cardiovascular Disorders

Polynucleotides or polypeptides, or agonists or antagonists of the invention may be used to treat, prevent, and/or diagnose cardiovascular diseases, disorders, and/or conditions, including peripheral artery disease, such as limb ischemia.

Cardiovascular diseases, disorders, and/or conditions include cardiovascular abnormalities, such as arterio-arterial fistula, arteriovenous fistula, cerebral arteriovenous malformations, congenital heart defects, pulmonary atresia, and Scimitar Syndrome. Congenital heart defects include aortic coarctation, cor triatriatum, coronary vessel anomalies, crisscross heart, dextrocardia, patent ductus arteriosus, Ebstein's anomaly, Eisenmenger complex, hypoplastic left heart syndrome, levocardia, tetralogy of fallot, transposition of great vessels, double outlet right ventricle, tricuspid atresia, persistent truncus arteriosus, and heart septal defects, such as aortopulmonary septal defect, endocardial cushion defects, Lutembacher's Syndrome, trilogy of Fallot, ventricular heart septal defects.

Cardiovascular diseases, disorders, and/or conditions also include heart disease, such as arrhythmias, carcinoid heart disease, high cardiac output, low cardiac output, cardiac tamponade, endocarditis (including bacterial), heart aneurysm, cardiac arrest, congestive heart failure, congestive cardiomyopathy, paroxysmal dyspnea, cardiac edema, heart hypertrophy, congestive cardiomyopathy, left ventricular hypertrophy, right ventricular hypertrophy, post-infarction heart rupture, ventricular septal rupture, heart valve diseases, myocardial diseases, myocardial ischemia, pericardial effusion, pericarditis (including constrictive and tuberculous), pneumopericardium, postpericardiotomy syndrome, pulmonary heart disease, rheumatic heart disease, ventricular dysfunction, hyperemia, cardiovascular pregnancy complications, Scimitar Syndrome, cardiovascular syphilis, and cardiovascular tuberculosis.

Arrhythmias include sinus arrhythmia, atrial fibrillation, atrial flutter, bradycardia, extrasystole, Adams-Stokes Syndrome, bundle-branch block, sinoatrial block, long QT syndrome, parasystole, Lown-Ganong-Levine Syndrome, Mahaim-type pre-excitation syndrome, Wolff-Parkinson-White syndrome, sick sinus syndrome, tachycardias, and ventricular fibrillation. Tachycardias include paroxysmal tachycardia, supraventricular tachycardia, accelerated idioventricular rhythm, atrioventricular nodal reentry tachycardia, ectopic atrial tachycardia, ectopic junctional tachycardia, sinoatrial nodal reentry tachycardia, sinus tachycardia, Torsades de Pointes, and ventricular tachycardia.

Heart valve disease include aortic valve insufficiency, aortic valve stenosis, hear murmurs, aortic valve prolapse, mitral valve prolapse, tricuspid valve prolapse, mitral valve insufficiency, mitral valve stenosis, pulmonary atresia, pulmonary valve insufficiency, pulmonary valve stenosis, tricuspid atresia, tricuspid valve insufficiency, and tricuspid valve stenosis.

Myocardial diseases include alcoholic cardiomyopathy, congestive cardiomyopathy, hypertrophic cardiomyopathy, aortic subvalvular stenosis, pulmonary subvalvular stenosis, restrictive cardiomyopathy, Chagas cardiomyopathy, endocardial fibroelastosis, endomyocardial fibrosis, Kearns Syndrome, myocardial reperfusion injury, and myocarditis.

Myocardial ischemias include coronary disease, such as angina pectoris, coronary aneurysm, coronary arteriosclerosis, coronary thrombosis, coronary vasospasm, myocardial infarction and myocardial stunning.

Cardiovascular diseases also include vascular diseases such as aneurysms, angiodysplasia, angiomatosis, bacillary angiomatosis, Hippel-Lindau Disease, Klippel-Trenaunay-Weber Syndrome, Sturge-Weber Syndrome, angioneurotic edema, aortic diseases, Takayasu's Arteritis, aortitis, Leriche's Syndrome, arterial occlusive diseases, arteritis, enarteritis, polyarteritis nodosa, cerebrovascular diseases, disorders, and/or conditions, diabetic angiopathies, diabetic retinopathy, embolisms, thrombosis, erythromelalgia, hemorrhoids, hepatic veno-occlusive disease, hypertension, hypotension, ischemia, peripheral vascular diseases, phlebitis, pulmonary veno-occlusive disease, Raynaud's disease, CREST syndrome, retinal vein occlusion, Scimitar syndrome, superior vena cava syndrome, telangiectasia, atacia telangiectasia, hereditary hemorrhagic telangiectasia, varicocele, varicose veins, varicose ulcer, vasculitis, and venous insufficiency.

Aneurysms include dissecting aneurysms, false aneurysms, infected aneurysms, ruptured aneurysms, aortic aneurysms, cerebral aneurysms, coronary aneurysms, heart aneurysms, and iliac aneurysms.

Arterial occlusive diseases include arteriosclerosis, intermittent claudication, carotid stenosis, fibromuscular dysplasias, mesenteric vascular occlusion, Moyamoya disease, renal artery obstruction, retinal artery occlusion, and thromboangiitis obliterans.

Cerebrovascular diseases, disorders, and/or conditions include carotid artery diseases, cerebral amyloid angiopathy, cerebral aneurysm, cerebral anoxia, cerebral arteriosclerosis, cerebral arteriovenous malformation, cerebral artery diseases, cerebral embolism and thrombosis, carotid artery thrombosis, sinus thrombosis, Wallenberg's syndrome, cerebral hemorrhage, epidural hematoma, subdural hematoma, subaraxhnoid hemorrhage, cerebral infarction, cerebral ischemia (including transient), subclavian steal syndrome, periventricular leukomalacia, vascular headache, cluster headache, migraine, and vertebrobasilar insufficiency.

Embolisms include air embolisms, amniotic fluid embolisms, cholesterol embolisms, blue toe syndrome, fat embolisms, pulmonary embolisms, and thromoboembolisms. Thrombosis include coronary thrombosis, hepatic vein thrombosis, retinal vein occlusion, carotid artery thrombosis, sinus thrombosis, Wallenberg's syndrome, and thrombophlebitis.

Ischemia includes cerebral ischemia, ischemic colitis, compartment syndromes, anterior compartment syndrome, myocardial ischemia, reperfusion injuries, and peripheral limb ischemia. Vasculitis includes aortitis, arteritis, Behcet's Syndrome, Churg-Strauss Syndrome, mucocutaneous lymph node syndrome, thromboangiitis obliterans, hypersensitivity vasculitis, Schoenlein-Henoch purpura, allergic cutaneous vasculitis, and Wegener's granulomatosis.

Polynucleotides or polypeptides, or agonists or antagonists of the invention, are especially effective for the treatment of critical limb ischemia and coronary disease.

Polypeptides may be administered using any method known in the art, including, but not limited to, direct needle injection at the delivery site, intravenous injection, topical administration, catheter infusion, biolistic injectors, particle accelerators, gelfoam sponge depots, other commercially available depot materials, osmotic pumps, oral or suppositorial solid pharmaceutical formulations, decanting or topical applications during surgery, aerosol delivery. Such methods are known in the art. Polypeptides of the invention may be administered as part of a Therapeutic, described in more detail below. Methods of delivering polynucleotides of the invention are described in more detail herein.

Anti-Angiogenesis Activity

The naturally occurring balance between endogenous stimulators and inhibitors of angiogenesis is one in which inhibitory influences predominate. Rastinejad et al., *Cell* 56:345-355 (1989). In those rare instances in which neovascularization occurs under normal physiological conditions, such as wound healing, organ regeneration, embryonic development, and female reproductive processes, angiogenesis is stringently regulated and spatially and temporally delimited. Under conditions of pathological angiogenesis such as that characterizing solid tumor growth, these regulatory controls fail. Unregulated angiogenesis becomes pathologic and sustains progression of many neoplastic and non-neoplastic diseases. A number of serious diseases are dominated by abnormal neovascularization including solid tumor growth and metastases, arthritis, some types of eye diseases, disorders, and/or conditions, and psoriasis. See, e.g., reviews by Moses et al., *Biotech.* 9:630-634 (1991); Folkman et al., *N. Engl. J. Med.,* 333:1757-1763 (1995); Auerbach et al., *J. Microvasc. Res.* 29:401-411 (1985); Folkman, Advances in Cancer Research, eds. Klein and Weinhouse, Academic Press, New York, pp. 175-203 (1985); Patz, *Am. J. Opthalmol.* 94:715-743 (1982); and Folkman et al., Science 221:719-725 (1983). In a number of pathological conditions, the process of angiogenesis contributes to the disease state. For example, significant data have accumulated which suggest that the growth of solid tumors is dependent on angiogenesis. Folkman and Klagsbrun, *Science* 235:442-447 (1987).

The present invention provides for treatment of diseases, disorders, and/or conditions associated with neovascularization by administration of the polynucleotides and/or polypeptides of the invention, as well as agonists or antagonists of the present invention. Malignant and metastatic conditions which can be treated with the polynucleotides and polypeptides, or agonists or antagonists of the invention include, but are not limited to, malignancies, solid tumors, and cancers described herein and otherwise known in the art (for a review of such disorders, see Fishman et al., Medicine, 2d Ed., J. B. Lippincott Co., Philadelphia (1985)). Thus, the present invention provides a method of treating, preventing, and/or diagnosing an angiogenesis-related disease and/or disorder, comprising administering to an individual in need thereof a therapeutically effective amount of a polynucleotide, polypeptide, antagonist and/or agonist of the invention. For example, polynucleotides, polypeptides, antagonists and/or agonists may be utilized in a variety of additional methods in order to therapeutically treator prevent a cancer or tumor. Cancers which may be treated, prevented, and/or diagnosed with polynucleotides, polypeptides, antagonists and/or agonists include, but are not limited to solid tumors, including prostate, lung, breast, ovarian, stomach, pancreas, larynx, esophagus, testes, liver, parotid, biliary tract, colon, rectum, cervix, uterus, endometrium, kidney, bladder, thyroid cancer; primary tumors and metastases; melanomas; glioblastoma; Kaposi's sarcoma; leiomyosarcoma; non-small cell lung cancer; colorectal cancer; advanced malignancies; and blood born tumors such as leukemias. For example, polynucleotides, polypeptides, antagonists and/or agonists may be delivered topically, in order to treat or prevent cancers such as skin cancer, head and neck tumors, breast tumors, and Kaposi's sarcoma.

Within yet other aspects, polynucleotides, polypeptides, antagonists and/or agonists may be utilized to treat superficial forms of bladder cancer by, for example, intravesical administration. Polynucleotides, polypeptides, antagonists and/or agonists may be delivered directly into the tumor, or near the tumor site, via injection or a catheter. Of course, as the artisan of ordinary skill will appreciate, the appropriate mode of administration will vary according to the cancer to be treated. Other modes of delivery are discussed herein.

Polynucleotides, polypeptides, antagonists and/or agonists may be useful in treating, preventing, and/or diagnosing other diseases, disorders, and/or conditions, besides cancers, which involve angiogenesis. These diseases, disorders, and/or conditions include, but are not limited to: benign tumors, for example hemangiomas, acoustic neuromas, neurofibromas, trachomas, and pyogenic granulomas; artheroscleric plaques; ocular angiogenic diseases, for example, diabetic retinopathy, retinopathy of prematurity, macular degeneration, corneal graft rejection, neovascular glaucoma, retrolental fibroplasia, rubeosis, retinoblastoma, uvietis and Pterygia (abnormal blood vessel growth) of the eye; rheumatoid arthritis; psoriasis; delayed wound healing; endometriosis; vasculogenesis; granulations; hypertrophic scars (keloids); nonunion fractures; scleroderma; trachoma; vascular adhesions; myocardial angiogenesis; coronary collaterals; cerebral collaterals; arteriovenous malformations; ischemic limb angiogenesis; Osler-Webber Syndrome; plaque neovascularization; telangiectasia; hemophiliac joints; angiofibroma; fibromuscular dysplasia; wound granulation; Crohn's disease; and atherosclerosis.

For example, within one aspect of the present invention methods are provided for treating, preventing, and/or diagnosing hypertrophic scars and keloids, comprising the step of administering a polynucleotide, polypeptide, antagonist and/or agonist of the invention to a hypertrophic scar or keloid.

Within one embodiment of the present invention polynucleotides, polypeptides, antagonists and/or agonists are directly injected into a hypertrophic scar or keloid, in order to prevent the progression of these lesions. This therapy is of particular value in the prophylactic treatment of conditions which are known to result in the development of hypertrophic scars and keloids (e.g., burns), and is preferably initiated after the proliferative phase has had time to progress (approximately 14 days after the initial injury), but before hypertrophic scar or keloid development. As noted above, the present invention also provides methods for treating, preventing, and/or diagnosing neovascular diseases of the eye, including for example, corneal neovascularization, neovascular glaucoma, proliferative diabetic retinopathy, retrolental fibroplasia and macular degeneration.

Moreover, Ocular diseases, disorders, and/or conditions associated with neovascularization which can be treated, prevented, and/or diagnosed with the polynucleotides and polypeptides of the present invention (including agonists and/or antagonists) include, but are not limited to: neovascular glaucoma, diabetic retinopathy, retinoblastoma, retrolental fibroplasia, uveitis, retinopathy of prematurity macular degeneration, corneal graft neovascularization, as well as other eye inflammatory diseases, ocular tumors and diseases associated with choroidal or iris neovascularization. See, e.g., reviews by Waltman et al., *Am. J. Ophthal.* 85:704-710 (1978) and Gartner et al., *Surv. Ophthal.* 22:291-312 (1978).

Thus, within one aspect of the present invention methods are provided for treating or preventing neovascular diseases of the eye such as corneal neovascularization (including corneal graft neovascularization), comprising the step of administering to a patient a therapeutically effective amount of a compound (as described above) to the cornea, such that the formation of blood vessels is inhibited. Briefly, the cornea is a tissue which normally lacks blood vessels. In certain pathological conditions however, capillaries may extend into the cornea from the pericorneal vascular plexus of the limbus. When the cornea becomes vascularized, it also becomes clouded, resulting in a decline in the patient's visual acuity. Visual loss may become complete if the cornea completely opacitates. A wide variety of diseases, disorders, and/or conditions can result in corneal neovascularization, including for example, corneal infections (e.g., trachoma, herpes simplex keratitis, leishmaniasis and onchocerciasis), immunological processes (e.g., graft rejection and Stevens-Johnson's syndrome), alkali burns, trauma, inflammation (of any cause), toxic and nutritional deficiency states, and as a complication of wearing contact lenses.

Within particularly preferred embodiments of the invention, may be prepared for topical administration in saline (combined with any of the preservatives and antimicrobial agents commonly used in ocular preparations), and administered in eyedrop form. The solution or suspension may be prepared in its pure form and administered several times daily. Alternatively, anti-angiogenic compositions, prepared as described above, may also be administered directly to the cornea. Within preferred embodiments, the anti-angiogenic composition is prepared with a muco-adhesive polymer which binds to cornea. Within further embodiments, the anti-angiogenic factors or anti-angiogenic compositions may be utilized as an adjunct to conventional steroid therapy. Topical therapy may also be useful prophylactically in corneal lesions which are known to have a high probability of inducing an angiogenic response (such as chemical burns). In these instances the treatment, likely in combination with steroids, may be instituted immediately to help prevent subsequent complications.

Within other embodiments, the compounds described above may be injected directly into the corneal stroma by an ophthalmologist under microscopic guidance. The preferred site of injection may vary with the morphology of the individual lesion, but the goal of the administration would be to place the composition at the advancing front of the vasculature (i.e., interspersed between the blood vessels and the normal cornea). In most cases this would involve perilimbic corneal injection to "protect" the cornea from the advancing blood vessels. This method may also be utilized shortly after a corneal insult in order to prophylactically prevent corneal neovascularization. In this situation the material could be injected in the perilimbic cornea interspersed between the corneal lesion and its undesired potential limbic blood supply. Such methods may also be utilized in a similar fashion to prevent capillary invasion of transplanted corneas. In a sustained-release form injections might only be required 2-3 times per year. A steroid could also be added to the injection solution to reduce inflammation resulting from the injection itself.

Within another aspect of the present invention, methods are provided for treating or preventing neovascular glaucoma, comprising the step of administering to a patient a therapeutically effective amount of a polynucleotide, polypeptide, antagonist and/or agonist to the eye, such that the formation of blood vessels is inhibited. In one embodiment, the compound may be administered topically to the eye in order to treat or prevent early forms of neovascular glaucoma. Within other embodiments, the compound may be implanted by injection into the region of the anterior chamber angle. Within other embodiments, the compound may also be placed in any location such that the compound is continuously released into the aqueous humor. Within another aspect of the present invention, methods are provided for treating or preventing proliferative diabetic retinopathy, comprising the step of administering to a patient a therapeutically effective amount of a polynucleotide, polypeptide, antagonist and/or agonist to the eyes, such that the formation of blood vessels is inhibited.

Within particularly preferred embodiments of the invention, proliferative diabetic retinopathy may be treated by injection into the aqueous humor or the vitreous, in order to increase the local concentration of the polynucleotide, polypeptide, antagonist and/or agonist in the retina. Preferably, this treatment should be initiated prior to the acquisition of severe disease requiring photocoagulation.

Within another aspect of the present invention, methods are provided for treating or preventing retrolental fibroplasia, comprising the step of administering to a patient a therapeutically effective amount of a polynucleotide, polypeptide, antagonist and/or agonist to the eye, such that the formation of blood vessels is inhibited. The compound may be administered topically, via intravitreous injection and/or via intraocular implants.

Additionally, diseases, disorders, and/or conditions which can be treated, prevented, and/or diagnosed with the polynucleotides, polypeptides, agonists and/or agonists include, but are not limited to, hemangioma, arthritis, psoriasis, angiofibroma, atherosclerotic plaques, delayed wound healing, granulations, hemophilic joints, hypertrophic scars, nonunion fractures, Osler-Weber syndrome, pyogenic granuloma, scleroderma, trachoma, and vascular adhesions.

Moreover, diseases, disorders, and/or conditions and/or states, which can be treated, prevented, and/or diagnosed with the polynucleotides, polypeptides, agonists and/or agonists include, but are not limited to, solid tumors, blood born tumors such as leukemias, tumor metastasis, Kaposi's sarcoma, benign tumors, for example hemangiomas, acoustic neuromas, neurofibromas, trachomas, and pyogenic granulomas, rheumatoid arthritis, psoriasis, ocular angiogenic diseases, for example, diabetic retinopathy, retinopathy of prematurity, macular degeneration, corneal graft rejection, neovascular glaucoma, retrolental fibroplasia, rubeosis, retinoblastoma, and uvietis, delayed wound healing, endometriosis, vascluogenesis, granulations, hypertrophic scars (keloids), nonunion fractures, scleroderma, trachoma, vascular adhesions, myocardial angiogenesis, coronary collaterals, cerebral collaterals, arteriovenous malformations, ischemic limb angiogenesis, Osler-Webber Syndrome, plaque neovascularization, telangiectasia, hemophiliac joints, angiofibroma fibromuscular dysplasia, wound granulation, Crohn's disease, atherosclerosis, birth control agent by preventing vascularization required for embryo implantation controlling menstruation, diseases that have angiogenesis as a pathologic consequence such as cat scratch disease (*Rochele minalia quintosa*), ulcers (*Helicobacter pylori*), Bartonellosis and bacillary angiomatosis.

In one aspect of the birth control method, an amount of the compound sufficient to block embryo implantation is administered before or after intercourse and fertilization have occurred, thus providing an effective method of birth control, possibly a "morning after" method. Polynucleotides, polypeptides, agonists and/or agonists may also be used in controlling menstruation or administered as either a peritoneal lavage fluid or for peritoneal implantation in the treatment of endometriosis.

Polynucleotides, polypeptides, agonists and/or agonists of the present invention may be incorporated into surgical sutures in order to prevent stitch granulomas.

Polynucleotides, polypeptides, agonists and/or agonists may be utilized in a wide variety of surgical procedures. For example, within one aspect of the present invention a compositions (in the form of, for example, a spray or film) may be utilized to coat or spray an area prior to removal of a tumor, in order to isolate normal surrounding tissues from malignant tissue, and/or to prevent the spread of disease to surrounding tissues. Within other aspects of the present invention, compositions (e.g., in the form of a spray) may be delivered via endoscopic procedures in order to coat tumors, or inhibit angiogenesis in a desired locale. Within yet other aspects of the present invention, surgical meshes which have been coated with anti-angiogenic compositions of the present invention may be utilized in any procedure wherein a surgical mesh might be utilized. For example, within one embodiment of the invention a surgical mesh laden with an anti-angiogenic composition may be utilized during abdominal cancer resection surgery (e.g., subsequent to colon resection) in order to provide support to the structure, and to release an amount of the anti-angiogenic factor.

Within further aspects of the present invention, methods are provided for treating tumor excision sites, comprising administering a polynucleotide, polypeptide, agonist and/or agonist to the resection margins of a tumor subsequent to excision, such that the local recurrence of cancer and the formation of new blood vessels at the site is inhibited. Within one embodiment of the invention, the anti-angiogenic compound is administered directly to the tumor excision site (e.g., applied by swabbing, brushing or otherwise coating the resection margins of the tumor with the anti-angiogenic compound). Alternatively, the anti-angiogenic compounds may be incorporated into known surgical pastes prior to administration. Within particularly preferred embodiments of the invention, the anti-angiogenic compounds are applied after hepatic resections for malignancy, and after neurosurgical operations.

Within one aspect of the present invention, polynucleotides, polypeptides, agonists and/or agonists may be administered to the resection margin of a wide variety of tumors, including for example, breast, colon, brain and hepatic tumors. For example, within one embodiment of the invention, anti-angiogenic compounds may be administered to the site of a neurological tumor subsequent to excision, such that the formation of new blood vessels at the site are inhibited.

The polynucleotides, polypeptides, agonists and/or agonists of the present invention may also be administered along with other anti-angiogenic factors. Representative examples of other anti-angiogenic factors include: Anti-Invasive Factor, retinoic acid and derivatives thereof, paclitaxel, Suramin, Tissue Inhibitor of Metalloproteinase-1, Tissue Inhibitor of Metalloproteinase-2, Plasminogen Activator Inhibitor-1, Plasminogen Activator Inhibitor-2, and various forms of the lighter "d group" transition metals.

Lighter "d group" transition metals include, for example, vanadium, molybdenum, tungsten, titanium, niobium, and tantalum species. Such transition metal species may form transition metal complexes. Suitable complexes of the above-mentioned transition metal species include oxo transition metal complexes.

Representative examples of vanadium complexes include oxo vanadium complexes such as vanadate and vanadyl complexes. Suitable vanadate complexes include metavanadate and orthovanadate complexes such as, for example, ammonium metavanadate, sodium metavanadate, and sodium orthovanadate. Suitable vanadyl complexes include, for example, vanadyl acetylacetonate and vanadyl sulfate including vanadyl sulfate hydrates such as vanadyl sulfate mono- and trihydrates.

Representative examples of tungsten and molybdenum complexes also include oxo complexes. Suitable oxo tungsten complexes include tungstate and tungsten oxide complexes. Suitable tungstate complexes include ammonium tungstate, calcium tungstate, sodium tungstate dihydrate, and tungstic acid. Suitable tungsten oxides include tungsten (IV) oxide and tungsten (VI) oxide. Suitable oxo molybdenum complexes include molybdate, molybdenum oxide, and molybdenyl complexes. Suitable molybdate complexes include ammonium molybdate and its hydrates, sodium molybdate and its hydrates, and potassium molybdate and its hydrates. Suitable molybdenum oxides include molybdenum (VI) oxide, molybdenum (VI) oxide, and molybdic acid. Suitable molybdenyl complexes include, for example, molybdenyl acetylacetonate. Other suitable tungsten and molybdenum complexes include hydroxo derivatives derived from, for example, glycerol, tartaric acid, and sugars.

A wide variety of other anti-angiogenic factors may also be utilized within the context of the present invention. Representative examples include platelet factor 4; protamine sulphate; sulphated chitin derivatives (prepared from queen crab shells), (Murata et al., Cancer Res. 51:22-26, 1991); Sulphated Polysaccharide Peptidoglycan Complex (SP-PG) (the function of this compound may be enhanced by the presence of steroids such as estrogen, and tamoxifen citrate); Staurosporine; modulators of matrix metabolism, including for example, proline analogs, cishydroxyproline, d,L-3,4-dehydroproline, Thiaproline, alpha,alpha-dipyridyl, aminopropionitrile fumarate; 4-propyl-5-(4-pyridinyl)-2(3H)-oxazolone; Methotrexate; Mitoxantrone; Heparin; Interferons; 2 Macroglobulin-serum; ChIMP-3 (Pavloff et al., J. Bio. Chem. 267:17321-17326, 1992); Chymostatin (Tomkinson et al., Biochem J. 286:475-480, 1992); Cyclodextrin Tetradecasulfate; Eponemycin; Camptothecin; Fumagillin (Ingber et al., Nature 348:555-557, 1990); Gold Sodium Thiomalate ("GST"; Matsubara and Ziff, J. Clin. Invest. 79:1440-1446, 1987); anticollagenase-serum; alpha2-antiplasmin (Holmes et al., J. Biol. Chem. 262(4):1659-1664, 1987); Bisantrene (National Cancer Institute); Lobenzarit disodium (N-(2)-carboxyphenyl-4-chloroanthronilic acid disodium or "CCA"; Takeuchi et al., Agents Actions 36:312-316, 1992); Thalidomide; Angostatic steroid; AGM-1470; carboxynaminolmidazole; and metalloproteinase inhibitors such as BB94.

Diseases at the Cellular Level

Diseases associated with increased cell survival or the inhibition of apoptosis that could be treated, prevented, and/or diagnosed by the polynucleotides or polypeptides and/or antagonists or agonists of the invention, include cancers (such as follicular lymphomas, carcinomas with p53 mutations, and hormone-dependent tumors, including, but not limited to colon cancer, cardiac tumors, pancreatic cancer, melanoma, retinoblastoma, glioblastoma, lung cancer, intestinal cancer, testicular cancer, stomach cancer, neuroblastoma, myxoma, myoma, lymphoma, endothelioma, osteoblastoma, osteoclastoma, osteosarcoma, chondrosarcoma, adenoma, breast cancer, prostate cancer, Kaposi's sarcoma and ovarian cancer); autoimmune diseases, disorders, and/or conditions (such as, multiple sclerosis, Sjogren's syndrome, Hashimoto's thyroiditis, biliary cirrhosis, Behcet's disease, Crohn's disease, polymyositis, systemic lupus erythematosus and immune-related glomerulonephritis and rheumatoid arthritis) and viral infections (such as herpes viruses, pox viruses and adenoviruses), inflammation, graft v. host disease, acute graft rejection, and chronic graft rejection. In preferred embodiments, the polynucleotides or polypeptides, and/or agonists or antagonists of the invention are used to inhibit growth, progression, and/or metasis of cancers, in particular those listed above.

Additional diseases or conditions associated with increased cell survival that could be treated, prevented or diagnosed by the polynucleotides or polypeptides, or agonists or antagonists of the invention, include, but are not limited to, progression, and/or metastases of malignancies and related disorders such as leukemia (including acute leukemias (e.g., acute lymphocytic leukemia, acute myelocytic leukemia (including myeloblastic, promyelocytic, myelomonocytic, monocytic, and erythroleukemia)) and chronic leukemias (e.g., chronic myelocytic (granulocytic) leukemia and chronic lymphocytic leukemia)), polycythemia vera, lymphomas (e.g., Hodgkin's disease and non-Hodgkin's disease), multiple myeloma, Waldenstrom's macroglobulinemia, heavy chain disease, and solid tumors including, but not limited to, sarcomas and carcinomas such as fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilm's tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, menangioma, melanoma, neuroblastoma, and retinoblastoma.

Diseases associated with increased apoptosis that could be treated, prevented, and/or diagnosed by the polynucleotides or polypeptides, and/or agonists or antagonists of the invention, include AIDS; neurodegenerative diseases, disorders, and/or conditions (such as Alzheimer's disease, Parkinson's disease, Amyotrophic lateral sclerosis, Retinitis pigmentosa, Cerebellar degeneration and brain tumor or prior associated disease); autoimmune diseases, disorders, and/or conditions (such as, multiple sclerosis, Sjogren's syndrome, Hashimoto's thyroiditis, biliary cirrhosis, Behcet's disease, Crohn's disease, polymyositis, systemic lupus erythematosus and immune-related glomerulonephritis and rheumatoid arthritis) myelodysplastic syndromes (such as aplastic anemia), graft v. host disease, ischemic injury (such as that caused by myocardial infarction, stroke and reperfusion injury), liver injury (e.g., hepatitis related liver injury, ischemia/reperfusion injury, cholestosis (bile duct injury) and liver cancer); toxin-induced liver disease (such as that caused by alcohol), septic shock, cachexia and anorexia.

Wound Healing and Epithelial Cell Proliferation

In accordance with yet a further aspect of the present invention, there is provided a process for utilizing the polynucleotides or polypeptides, and/or agonists or antagonists of the invention, for therapeutic purposes, for example, to stimulate epithelial cell proliferation and basal keratinocytes for the purpose of wound healing, and to stimulate hair follicle production and healing of dermal wounds. Polynucleotides or polypeptides, as well as agonists or antagonists of the invention, may be clinically useful in stimulating wound healing including surgical wounds, excisional wounds, deep wounds involving damage of the dermis and epidermis, eye tissue wounds, dental tissue wounds, oral cavity wounds, diabetic ulcers, dermal ulcers, cubitus ulcers, arterial ulcers, venous stasis ulcers, burns resulting from heat exposure or chemicals, and other abnormal wound healing conditions such as uremia, malnutrition, vitamin deficiencies and complications associated with systemic treatment with steroids, radiation therapy and antineoplastic drugs and antimetabolites. Polynucleotides or polypeptides, and/or agonists or antagonists of the invention, could be used to promote dermal reestablishment subsequent to dermal loss.

The polynucleotides or polypeptides, and/or agonists or antagonists of the invention, could be used to increase the adherence of skin grafts to a wound bed and to stimulate re-epithelialization from the wound bed. The following are a non-exhaustive list of grafts that polynucleotides or polypeptides, agonists or antagonists of the invention, could be used to increase adherence to a wound bed: autografts, artificial skin, allografts, autodermic graft, autoepdermic grafts, avacular grafts, Blair-Brown grafts, bone graft, brephoplastic grafts, cutis graft, delayed graft, dermic graft, epidermic graft, fascia graft, full thickness graft, heterologous graft, xenograft, homologous graft, hyperplastic graft, lamellar graft, mesh graft, mucosal graft, Ollier-Thiersch graft, omenpal graft, patch graft, pedicle graft, penetrating graft, split skin graft, thick split graft. The polynucleotides or polypeptides, and/or agonists or antagonists of the invention, can be used to promote skin strength and to improve the appearance of aged skin.

It is believed that the polynucleotides or polypeptides, and/or agonists or antagonists of the invention, will also produce changes in hepatocyte proliferation, and epithelial cell proliferation in the lung, breast, pancreas, stomach, small intestine, and large intestine. The polynucleotides or polypeptides, and/or agonists or antagonists of the invention, could promote proliferation of epithelial cells such as sebocytes, hair follicles, hepatocytes, type II pneumocytes, mucin-producing goblet cells, and other epithelial cells and their progenitors contained within the skin, lung, liver, and gastrointestinal tract. The polynucleotides or polypeptides, and/or agonists or antagonists of the invention, may promote proliferation of endothelial cells, keratinocytes, and basal keratinocytes.

The polynucleotides or polypeptides, and/or agonists or antagonists of the invention, could also be used to reduce the side effects of gut toxicity that result from radiation, chemotherapy treatments or viral infections. The polynucleotides or polypeptides, and/or agonists or antagonists of the invention, may have a cytoprotective effect on the small intestine mucosa. The polynucleotides or polypeptides, and/or agonists or antagonists of the invention, may also stimulate healing of mucositis (mouth ulcers) that result from chemotherapy and viral infections.

The polynucleotides or polypeptides, and/or agonists or antagonists of the invention, could further be used in full regeneration of skin in full and partial thickness skin defects, including burns, (i.e., repopulation of hair follicles, sweat glands, and sebaceous glands), treatment of other skin defects such as psoriasis. The polynucleotides or polypeptides, and/or agonists or antagonists of the invention, could be used to treat epidermolysis bullosa, a defect in adherence of the epidermis to the underlying dermis which results in frequent, open and painful blisters by accelerating reepithelialization of these lesions. The polynucleotides or polypeptides, and/or agonists or antagonists of the invention, could also be used to treat gastric and doudenal ulcers and help heal by scar formation of the mucosal lining and regeneration of glandular mucosa and duodenal mucosal lining more rapidly. Inflammatory bowel diseases, such as Crohn's disease and ulcerative colitis, are diseases which result in destruction of the mucosal surface of the small or large intestine, respectively. Thus, the polynucleotides or polypeptides, and/or agonists or antagonists of the invention, could be used to promote the resurfacing of the mucosal surface to aid more rapid healing and to prevent progression of inflammatory bowel disease. Treatment with the polynucleotides or polypeptides, and/or agonists or antagonists of the invention, is expected to have a significant effect on the production of mucus throughout the gastrointestinal tract and could be used to protect the intestinal mucosa from injurious substances that are ingested or following surgery. The polynucleotides or polypeptides, and/or agonists or antagonists of the invention, could be used to treat diseases associate with the under expression of the polynucleotides of the invention.

Moreover, the polynucleotides or polypeptides, and/or agonists or antagonists of the invention, could be used to prevent and heal damage to the lungs due to various pathological states. A growth factor such as the polynucleotides or polypeptides, and/or agonists or antagonists of the invention, which could stimulate proliferation and differentiation and promote the repair of alveoli and brochiolar epithelium to prevent or treat acute or chronic lung damage. For example, emphysema, which results in the progressive loss of aveoli, and inhalation injuries, i.e., resulting from smoke inhalation and burns, that cause necrosis of the bronchiolar epithelium and alveoli could be effectively treated, prevented, and/or diagnosed using the polynucleotides or polypeptides, and/or agonists or antagonists of the invention. Also, the polynucleotides or polypeptides, and/or agonists or antagonists of the invention, could be used to stimulate the proliferation of and differentiation of type II pneumocytes, which may help treat or prevent disease such as hyaline membrane diseases, such as infant respiratory distress syndrome and bronchopulmonary displasia, in premature infants.

The polynucleotides or polypeptides, and/or agonists or antagonists of the invention, could stimulate the proliferation and differentiation of hepatocytes and, thus, could be used to alleviate or treat liver diseases and pathologies such as fulminant liver failure caused by cirrhosis, liver damage caused by viral hepatitis and toxic substances (i.e., acetaminophen, carbon tetraholoride and other hepatotoxins known in the art).

In addition, the polynucleotides or polypeptides, and/or agonists or antagonists of the invention, could be used treat or prevent the onset of diabetes mellitus. In patients with newly diagnosed Types I and II diabetes, where some islet cell function remains, the polynucleotides or polypeptides, and/or agonists or antagonists of the invention, could be used to maintain the islet function so as to alleviate, delay or prevent permanent manifestation of the disease. Also, the polynucleotides or polypeptides, and/or agonists or antagonists of the invention, could be used as an auxiliary in islet cell transplantation to improve or promote islet cell function.

Neurological Diseases

Nervous system diseases, disorders, and/or conditions, which can be treated, prevented, and/or diagnosed with the compositions of the invention (e.g., polypeptides, polynucleotides, and/or agonists or antagonists), include, but are not limited to, nervous system injuries, and diseases, disorders, and/or conditions which result in either a disconnection of axons, a diminution or degeneration of neurons, or demyelination. Nervous system lesions which may be treated, prevented, and/or diagnosed in a patient (including human and non-human mammalian patients) according to the invention, include but are not limited to, the following lesions of either the central (including spinal cord, brain) or peripheral nervous systems: (1) ischemic lesions, in which a lack of oxygen in a portion of the nervous system results in neuronal injury or death, including cerebral infarction or ischemia, or spinal cord infarction or ischemia; (2) traumatic lesions, including lesions caused by physical injury or associated with surgery, for example, lesions which sever a portion of the nervous system, or compression injuries; (3) malignant lesions, in which a portion of the nervous system is destroyed or injured by malignant tissue which is either a nervous system associated malignancy or a malignancy derived from non-nervous system tissue; (4) infectious lesions, in which a portion of the nervous system is destroyed or injured as a result of infection, for example, by an abscess or associated with infection by human immunodeficiency virus, herpes zoster, or herpes simplex virus or with Lyme disease, tuberculosis, syphilis; (5) degenerative lesions, in which a portion of the nervous system is destroyed or injured as a result of a degenerative process including but not limited to degeneration associated with Parkinson's disease, Alzheimer's disease, Huntington's chorea, or amyotrophic lateral sclerosis (ALS); (6) lesions associated with nutritional diseases, disorders, and/or conditions, in which a portion of the nervous system is destroyed or injured by a nutritional disorder or disorder of metabolism including but not limited to, vitamin B12 deficiency, folic acid deficiency, Wernicke disease, tobacco-alcohol amblyopia, Marchiafava-Bignami disease (primary degeneration of the corpus callosum), and alcoholic cerebellar degeneration; (7) neurological lesions associated with systemic diseases including, but not limited to, diabetes (diabetic neuropathy, Bell's palsy), systemic lupus erythematosus, carcinoma, or sarcoidosis; (8) lesions caused by toxic substances including alcohol, lead, or particular neurotoxins; and (9) demyelinated lesions in which a portion of the nervous system is destroyed or injured by a demyelinating disease including, but not limited to, multiple sclerosis, human immunodeficiency virus-associated myelopathy, transverse myelopathy or various etiologies, progressive multifocal leukoencephalopathy, and central pontine myelinolysis.

In a preferred embodiment, the polypeptides, polynucleotides, or agonists or antagonists of the invention are used to protect neural cells from the damaging effects of cerebral hypoxia. According to this embodiment, the compositions of the invention are used to treat, prevent, and/or diagnose neural cell injury associated with cerebral hypoxia. In one aspect of this embodiment, the polypeptides, polynucleotides, or agonists or antagonists of the invention are used to treat, prevent, and/or diagnose neural cell injury associated with cerebral ischemia. In another aspect of this embodiment, the polypeptides, polynucleotides, or agonists or antagonists of the invention are used to treat, prevent, and/or diagnose neural cell injury associated with cerebral infarction. In another aspect of this embodiment, the polypeptides, polynucleotides, or agonists or antagonists of the invention are used to treat, prevent, and/or diagnose or prevent neural cell injury associated with a stroke. In a further aspect of this embodiment, the polypeptides, polynucleotides, or agonists or antagonists of the invention are used to treat, prevent, and/or diagnose neural cell injury associated with a heart attack.

The compositions of the invention which are useful for treating or preventing a nervous system disorder may be selected by testing for biological activity in promoting the survival or differentiation of neurons. For example, and not by way of limitation, compositions of the invention which elicit any of the following effects may be useful according to the invention: (1) increased survival time of neurons in culture; (2) increased sprouting of neurons in culture or in vivo; (3) increased production of a neuron-associated molecule in culture or in vivo, e.g., choline acetyltransferase or acetylcholinesterase with respect to motor neurons; or (4) decreased symptoms of neuron dysfunction in vivo. Such effects may be measured by any method known in the art. In preferred, non-limiting embodiments, increased survival of neurons may routinely be measured using a method set forth herein or otherwise known in the art, such as, for example, the method set forth in Arakawa et al. (J. Neurosci. 10:3507-3515 (1990)); increased sprouting of neurons may be detected by methods known in the art, such as, for example, the methods set forth in Pestronk et al. (Exp. Neurol. 70:65-82 (1980)) or Brown et al. (Ann. Rev. Neurosci. 4:17-42 (1981)); increased production of neuron-associated molecules may be measured by bioassay, enzymatic assay, antibody binding, Northern blot assay, etc., using techniques known in the art and depending on the molecule to be measured; and motor neuron dysfunction may be measured by assessing the physical manifestation of motor neuron disorder, e.g., weakness, motor neuron conduction velocity, or functional disability.

In specific embodiments, motor neuron diseases, disorders, and/or conditions that may be treated, prevented, and/or diagnosed according to the invention include, but are not limited to, diseases, disorders, and/or conditions such as infarction, infection, exposure to toxin, trauma, surgical damage, degenerative disease or malignancy that may affect motor neurons as well as other components of the nervous system, as well as diseases, disorders, and/or conditions that selectively affect neurons such as amyotrophic lateral sclerosis, and including, but not limited to, progressive spinal muscular atrophy, progressive bulbar palsy, primary lateral sclerosis, infantile and juvenile muscular atrophy, progressive bulbar paralysis of childhood (Fazio-Londe syndrome), poliomyelitis and the post polio syndrome, and Hereditary Motorsensory Neuropathy (Charcot-Marie-Tooth Disease).

Infectious Disease

A polypeptide or polynucleotide and/or agonist or antagonist of the present invention can be used to treat, prevent, and/or diagnose infectious agents. For example, by increasing the immune response, particularly increasing the proliferation and differentiation of B and/or T cells, infectious diseases may be treated, prevented, and/or diagnosed. The immune response may be increased by either enhancing an existing immune response, or by initiating a new immune response. Alternatively, polypeptide or polynucleotide and/or agonist or antagonist of the present invention may also directly inhibit the infectious agent, without necessarily eliciting an immune response.

Viruses are one example of an infectious agent that can cause disease or symptoms that can be treated, prevented, and/or diagnosed by a polynucleotide or polypeptide and/or agonist or antagonist of the present invention. Examples of viruses, include, but are not limited to Examples of viruses, include, but are not limited to the following DNA and RNA viruses and viral families: Arbovirus, Adenoviridae, Arenaviridae, Arterivirus, Bimaviridae, Bunyaviridae, Caliciviridae, Circoviridae, Coronaviridae, Dengue, EBV, HIV, Flaviviridae, Hepadnaviridae (Hepatitis), Herpesviridae (such as, Cytomegalovirus, Herpes Simplex, Herpes Zoster), Mononegavirus (e.g., Paramyxoviridae, Morbillivirus, Rhabdoviridae), Orthomyxoviridae (e.g., Influenza A, Influenza B, and parainfluenza), Papiloma virus, Papovaviridae, Parvoviridae, Picomaviridae, Poxyiridae (such as Smallpox or Vaccinia), Reoviridae (e.g., Rotavirus), Retroviridae (HTLV-I, HTLV-II, Lentivirus), and Togaviridae (e.g., Rubivirus). Viruses falling within these families can cause a variety of diseases or symptoms, including, but not limited to: arthritis, bronchiollitis, respiratory syncytial virus, encephalitis, eye infections (e.g., conjunctivitis, keratitis), chronic fatigue syndrome, hepatitis (A, B, C, E, Chronic Active, Delta), Japanese B encephalitis, Junin, Chikungunya, Rift Valley fever, yellow fever, meningitis, opportunistic infections (e.g., AIDS), pneumonia, Burkitt's Lymphoma, chickenpox, hemorrhagic fever, Measles, Mumps, Parainfluenza, Rabies, the common cold, Polio, leukemia, Rubella, sexually transmitted diseases, skin diseases (e.g., Kaposi's, warts), and viremia. polynucleotides or polypeptides, or agonists or antagonists of the invention, can be used to treat, prevent, and/or diagnose any of these symptoms or diseases. In specific embodiments, polynucleotides, polypeptides, or agonists or antagonists of the invention are used to treat, prevent, and/or diagnose: meningitis, Dengue, EBV, and/or hepatitis (e.g., hepatitis B). In an additional specific embodiment polynucleotides, polypeptides, or agonists or antagonists of the invention are used to treat patients nonresponsive to one or more other commercially available hepatitis vaccines. In a further specific embodiment polynucleotides, polypeptides, or agonists or antagonists of the invention are used to treat, prevent, and/or diagnose AIDS.

Similarly, bacterial or fungal agents that can cause disease or symptoms and that can be treated, prevented, and/or diagnosed by a polynucleotide or polypeptide and/or agonist or antagonist of the present invention include, but not limited to, include, but not limited to, the following Gram-Negative and Gram-positive bacteria and bacterial families and fungi: Actinomycetales (e.g., *Corynebacterium, Mycobacterium, Norcardia*), *Cryptococcus neoformans*, Aspergillosis, Bacillaceae (e.g., Anthrax, *Clostridium*), Bacteroidaceae, Blastomycosis, *Bordetella, Borrelia* (e.g., *Borrelia burgdorferi*), Brucellosis, Candidiasis, *Campylobacter*, Coccidioidomycosis, Cryptococcosis, Dermatocycoses, *E. coli* (e.g., Enterotoxigenic *E. coli* and Enterohemorrhagic *E. coli*), Enterobacteriaceae (*Klebsiella, Salmonella* (e.g., *Salmonella typhi*, and *Salmonella paratyphi*), *Serratia, Yersinia*), *Erysipelothrix, Helicobacter*, Legionellosis, Leptospirosis, *Listeria*, Mycoplasmatales, *Mycobacterium leprae, Vibrio cholerae*, Neisseriaceae (e.g., *Acinetobacter*, Gonorrhea, Menigococcal), Meisseria *meningitidis*, Pasteurellacea Infections (e.g., *Actinobacillus, Heamophilus* (e.g., *Heamophilus influenza* type B), *Pasteurella*), *Pseudomonas*, Rickettsiaceae, Chlamydiaceae, Syphilis, *Shigella* spp., Staphylococcal, Meningiococcal, Pneumococcal and Streptococcal (e.g., *Streptococcus pneumoniae* and Group B *Streptococcus*). These bacterial or fungal families can cause the following diseases or symptoms, including, but not limited to: bacteremia, endocarditis, eye infections (conjunctivitis, tuberculosis, uveitis), gingivitis, opportunistic infections (e.g., AIDS related infections), paronychia, prosthesis-related infections, Reiter's Disease, respiratory tract infections, such as Whooping Cough or Empyema, sepsis, Lyme Disease, Cat-Scratch Disease, Dysentery, Paratyphoid Fever, food poisoning, Typhoid, pneumonia, Gonorrhea, meningitis (e.g., mengitis types A and B), *Chlamydia*, Syphilis, Diphtheria, Leprosy, Paratuberculosis, Tuberculosis, Lupus, Botulism, gangrene, tetanus, impetigo, Rheumatic Fever, Scarlet Fever, sexually transmitted diseases, skin diseases (e.g., cellulitis, dermatocycoses), toxemia, urinary tract infections, wound infections. Polynucleotides or polypeptides, agonists or antagonists of the invention, can be used to treat, prevent, and/or diagnose any of these symptoms or diseases. In specific embodiments, polynucleotides, polypeptides, agonists or antagonists of the invention are used to treat, prevent, and/or diagnose: tetanus, Diptheria, botulism, and/or meningitis type B.

Moreover, parasitic agents causing disease or symptoms that can be treated, prevented, and/or diagnosed by a polynucleotide or polypeptide and/or agonist or antagonist of the present invention include, but not limited to, the following families or class: Amebiasis, Babesiosis, Coccidiosis, Cryptosporidiosis, Dientamoebiasis, Dourine, Ectoparasitic, Giardiasis, Hehninthiasis, Leishmaniasis, Theileriasis, Toxoplasmosis, Trypanosomiasis, and Trichomonas and Sporozoans (e.g., *Plasmodium virax, Plasmodium falciparium, Plasmodium malariae* and *Plasmodium ovale*). These parasites can cause a variety of diseases or symptoms, including, but not limited to: Scabies, Trombiculiasis, eye infections, intestinal disease (e.g., dysentery, giardiasis), liver disease, lung disease, opportunistic infections (e.g., AIDS related), malaria, pregnancy complications, and toxoplasmosis. polynucleotides or polypeptides, or agonists or antagonists of the invention, can be used totreat, prevent, and/or diagnose any of these symptoms or diseases. In specific embodiments, polynucleotides, polypeptides, or agonists or antagonists of the invention are used to treat, prevent, and/or diagnose malaria.

Preferably, treatment or prevention using a polypeptide or polynucleotide and/or agonist or antagonist of the present invention could either be by administering an effective amount of a polypeptide to the patient, or by removing cells from the patient, supplying the cells with a polynucleotide of the present invention, and returning the engineered cells to the patient (ex vivo therapy). Moreover, the polypeptide or polynucleotide of the present invention can be used as an antigen in a vaccine to raise an immune response against infectious disease.

Regeneration

A polynucleotide or polypeptide and/or agonist or antagonist of the present invention can be used to differentiate, proliferate, and attract cells, leading to the regeneration of tissues. (See, Science 276:59-87 (1997).) The regeneration of tissues could be used to repair, replace, or protect tissue damaged by congenital defects, trauma (wounds, burns, incisions, or ulcers), age, disease (e.g. osteoporosis, osteocarthritis, periodontal disease, liver failure), surgery, including cosmetic plastic surgery, fibrosis, reperfusion injury, or systemic cytokine damage.

Tissues that could be regenerated using the present invention include organs (e.g., pancreas, liver, intestine, kidney, skin, endothelium), muscle (smooth, skeletal or cardiac), vasculature (including vascular and lymphatics), nervous, hematopoietic, and skeletal (bone, cartilage, tendon, and ligament) tissue. Preferably, regeneration occurs without or decreased scarring. Regeneration also may include angiogenesis.

Moreover, a polynucleotide or polypeptide and/or agonist or antagonist of the present invention may increase regeneration of tissues difficult to heal. For example, increased tendon/ligament regeneration would quicken recovery time after damage. A polynucleotide or polypeptide and/or agonist or antagonist of the present invention could also be used prophylactically in an effort to avoid damage. Specific diseases that could be treated, prevented, and/or diagnosed include of tendinitis, carpal tunnel syndrome, and other tendon or ligament defects. A further example of tissue regeneration of non-healing wounds includes pressure ulcers, ulcers associated with vascular insufficiency, surgical, and traumatic wounds.

Similarly, nerve and brain tissue could also be regenerated by using a polynucleotide or polypeptide and/or agonist or antagonist of the present invention to proliferate and differentiate nerve cells. Diseases that could be treated, prevented, and/or diagnosed using this method include central and peripheral nervous system diseases, neuropathies, or mechanical and traumatic diseases, disorders, and/or conditions (e.g., spinal cord disorders, head trauma, cerebrovascular disease, and stoke). Specifically, diseases associated with peripheral nerve injuries, peripheral neuropathy (e.g., resulting from chemotherapy or other medical therapies), localized neuropathies, and central nervous system diseases (e.g., Alzheimer's disease, Parkinson's disease, Huntington's disease, amyotrophic lateral sclerosis, and Shy-Drager syndrome), could all be treated, prevented, and/or diagnosed using the polynucleotide or polypeptide and/or agonist or antagonist of the present invention.

Chemotaxis

A polynucleotide or polypeptide and/or agonist or antagonist of the present invention may have chemotaxis activity. A chemotaxic molecule attracts or mobilizes cells (e.g., monocytes, fibroblasts, neutrophils, T-cells, mast cells, eosinophils, epithelial and/or endothelial cells) to a particular site in the body, such as inflammation, infection, or site of hyperproliferation. The mobilized cells can then fight off and/or heal the particular trauma or abnormality.

A polynucleotide or polypeptide and/or agonist or antagonist of the present invention may increase chemotaxic activity of particular cells. These chemotactic molecules can then be used to treat, prevent, and/or diagnose inflammation, infection, hyperproliferative diseases, disorders, and/or conditions, or any immune system disorder by increasing the number of cells targeted to a particular location in the body. For example, chemotaxic molecules can be used to treat, prevent, and/or diagnose wounds and other trauma to tissues by attracting immune cells to the injured location. Chemotactic molecules of the present invention can also attract fibroblasts, which can be used to treat, prevent, and/or diagnose wounds.

It is also contemplated that a polynucleotide or polypeptide and/or agonist or antagonist of the present invention may inhibit chemotactic activity. These molecules could also be used totreat, prevent, and/or diagnose diseases, disorders, and/or conditions. Thus, a polynucleotide or polypeptide and/or agonist or antagonist of the present invention could be used as an inhibitor of chemotaxis.

Binding Activity

A polypeptide of the present invention may be used to screen for molecules that bind to the polypeptide or for molecules to which the polypeptide binds. The binding of the polypeptide and the molecule may activate (agonist), increase, inhibit (antagonist), or decrease activity of the polypeptide or the molecule bound. Examples of such molecules include antibodies, oligonucleotides, proteins (e.g., receptors), or small molecules.

Preferably, the molecule is closely related to the natural ligand of the polypeptide, e.g., a fragment of the ligand, or a natural substrate, a ligand, a structural or functional mimetic. (See, Coligan et al., Current Protocols in Immunology 1(2):Chapter 5 (1991).) Similarly, the molecule can be closely related to the natural receptor to which the polypeptide binds, or at least, a fragment of the receptor capable of being bound by the polypeptide (e.g., active site). In either case, the molecule can be rationally designed using known techniques.

Preferably, the screening for these molecules involves producing appropriate cells which express the polypeptide, either as a secreted protein or on the cell membrane. Preferred cells include cells from mammals, yeast, *Drosophila*, or *E. coli*. Cells expressing the polypeptide (or cell membrane containing the expressed polypeptide) are then preferably contacted with a test compound potentially containing the molecule to observe binding, stimulation, or inhibition of activity of either the polypeptide or the molecule.

The assay may simply test binding of a candidate compound to the polypeptide, wherein binding is detected by a label, or in an assay involving competition with a labeled competitor. Further, the assay may test whether the candidate compound results in a signal generated by binding to the polypeptide.

Alternatively, the assay can be carried out using cell-free preparations, polypeptide/molecule affixed to a solid support, chemical libraries, or natural product mixtures. The assay may also simply comprise the steps of mixing a candidate compound with a solution containing a polypeptide, measuring polypeptide/molecule activity or binding, and comparing the polypeptide/molecule activity or binding to a standard.

Preferably, an ELISA assay can measure polypeptide level or activity in a sample (e.g., biological sample) using a monoclonal or polyclonal antibody. The antibody can measure polypeptide level or activity by either binding, directly or indirectly, to the polypeptide or by competing with the polypeptide for a substrate.

Additionally, the receptor to which a polypeptide of the invention binds can be identified by numerous methods known to those of skill in the art, for example, ligand panning and FACS sorting (Coligan, et al., Current Protocols in Immun., 1(2), Chapter 5, (1991)). For example, expression cloning is employed wherein polyadenylated RNA is prepared from a cell responsive to the polypeptides, for example, NIH3T3 cells which are known to contain multiple receptors for the FGF family proteins, and SC-3 cells, and a cDNA library created from this RNA is divided into pools and used to transfect COS cells or other cells that are not responsive to the polypeptides. Transfected cells which are grown on glass slides are exposed to the polypeptide of the present invention, after they have been labelled. The polypeptides can be labeled by a variety of means including iodination or inclusion of a recognition site for a site-specific protein kinase.

Following fixation and incubation, the slides are subjected to auto-radiographic analysis. Positive pools are identified and sub-pools are prepared and re-transfected using an iterative sub-pooling and re-screening process, eventually yielding a single clones that encodes the putative receptor.

As an alternative approach for receptor identification, the labeled polypeptides can be photoaffinity linked with cell membrane or extract preparations that express the receptor molecule. Cross-linked material is resolved by PAGE analysis and exposed to X-ray film. The labeled complex containing the receptors of the polypeptides can be excised, resolved into peptide fragments, and subjected to protein microsequencing. The amino acid sequence obtained from microsequencing would be used to design a set of degenerate oligonucleotide probes to screen a cDNA library to identify the genes encoding the putative receptors.

Moreover, the techniques of gene-shuffling, motif-shuffling, exon-shuffling, and/or codon-shuffling (collectively referred to as "DNA shuffling") may be employed to modulate the activities of polypeptides of the invention thereby effectively generating agonists and antagonists of polypeptides of the invention. See generally, U.S. Pat. Nos. 5,605,793, 5,811,238, 5,830,721, 5,834,252, and 5,837,458, and Patten, P. A., et al., Curr. Opinion Biotechnol. 8:724-33 (1997); Harayama, S. Trends Biotechnol. 16(2):76-82 (1998); Hansson, L. O., et al., J. Mol. Biol. 287:265-76 (1999); and Lorenzo, M. M. and Blasco, R. Biotechniques 24(2):308-13 (1998) (each of these patents and publications are hereby incorporated by reference). In one embodiment, alteration of polynucleotides and corresponding polypeptides of the invention may be achieved by DNA shuffling. DNA shuffling involves the assembly of two or more DNA segments into a desired polynucleotide sequence of the invention molecule by homologous, or site-specific, recombination. In another embodiment, polynucleotides and corresponding polypeptides of the invention may be altered by being subjected to random mutagenesis by error-prone PCR, random nucleotide insertion or other methods prior to recombination. In another embodiment, one or more components, motifs, sections, parts, domains, fragments, etc., of the polypeptides of the invention may be recombined with one or more components, motifs, sections, parts, domains, fragments, etc. of one or more heterologous molecules. In preferred embodiments, the heterologous molecules are family members. In further preferred embodiments, the heterologous molecule is a growth factor such as, for example, platelet-derived growth factor (PDGF), insulin-like growth factor (IGF-I), transforming growth factor (TGF)-alpha, epidermal growth factor (EGF), fibroblast growth factor (FGF), TGF-beta, bone morphogenetic protein (BMP)-2, BMP-4, BMP-5, BMP-6, BMP-7, activins A and B, decapentaplegic(dpp), 60A, OP-2, dorsalin, growth differentiation factors (GDFs), nodal, MIS, inhibin-alpha, TGF-beta1, TGF-beta2, TGF-beta3, TGF-beta5, and glial-derived neurotrophic factor (GDNF).

Other preferred fragments are biologically active fragments of the polypeptides of the invention. Biologically active fragments are those exhibiting activity similar, but not necessarily identical, to an activity of the polypeptide. The biological activity of the fragments may include an improved desired activity, or a decreased undesirable activity.

Additionally, this invention provides a method of screening compounds to identify those which modulate the action of the polypeptide of the present invention. An example of such an assay comprises combining a mammalian fibroblast cell, a the polypeptide of the present invention, the compound to be screened and 3[H] thymidine under cell culture conditions where the fibroblast cell would normally proliferate. A control assay may be performed in the absence of the compound to be screened and compared to the amount of fibroblast proliferation in the presence of the compound to determine if the compound stimulates proliferation by determining the uptake of 3[H] thymidine in each case. The amount of fibroblast cell proliferation is measured by liquid scintillation chromatography which measures the incorporation of 3[H] thymidine. Both agonist and antagonist compounds may be identified by this procedure.

In another method, a mammalian cell or membrane preparation expressing a receptor for a polypeptide of the present invention is incubated with a labeled polypeptide of the present invention in the presence of the compound. The ability of the compound to enhance or block this interaction could then be measured. Alternatively, the response of a known second messenger system following interaction of a compound to be screened and the receptor is measured and the ability of the compound to bind to the receptor and elicit a second messenger response is measured to determine if the compound is a potential agonist or antagonist. Such second messenger systems include but are not limited to, cAMP guanylate cyclase, ion channels or phosphoinositide hydrolysis.

All of these above assays can be used as diagnostic or prognostic markers. The molecules discovered using these assays can be used to treat, prevent, and/or diagnose disease or to bring about a particular result in a patient (e.g., blood vessel growth) by activating or inhibiting the polypeptide/molecule. Moreover, the assays can discover agents which may inhibit or enhance the production of the polypeptides of the invention from suitably manipulated cells or tissues. Therefore, the invention includes a method of identifying compounds which bind to the polypeptides of the invention comprising the steps of: (a) incubating a candidate binding compound with the polypeptide; and (b) determining if binding has occurred. Moreover, the invention includes a method of identifying agonists/antagonists comprising the steps of: (a) incubating a candidate compound with the polypeptide, (b) assaying a biological activity, and (b) determining if a biological activity of the polypeptide has been altered.

Also, one could identify molecules bind a polypeptide of the invention experimentally by using the beta-pleated sheet regions contained in the polypeptide sequence of the protein. Accordingly, specific embodiments of the invention are directed to polynucleotides encoding polypeptides which comprise, or alternatively consist of, the amino acid sequence of each beta pleated sheet regions in a disclosed polypeptide sequence. Additional embodiments of the invention are directed to polynucleotides encoding polypeptides which comprise, or alternatively consist of, any combination or all of contained in the polypeptide sequences of the invention. Additional preferred embodiments of the invention are directed to polypeptides which comprise, or alternatively consist of, the amino acid sequence of each of the beta pleated sheet regions in one of the polypeptide sequences of the invention. Additional embodiments of the invention are directed to polypeptides which comprise, or alternatively consist of, any combination or all of the beta pleated sheet regions in one of the polypeptide sequences of the invention.

Targeted Delivery

In another embodiment, the invention provides a method of delivering compositions to targeted cells expressing a receptor for a polypeptide of the invention, or cells expressing a cell bound form of a polypeptide of the invention.

As discussed herein, polypeptides or antibodies of the invention may be associated with heterologous polypeptides, heterologous nucleic acids, toxins, or prodrugs via hydrophobic, hydrophilic, ionic and/or covalent interactions. In one embodiment, the invention provides a method for the specific delivery of compositions of the invention to cells by administering polypeptides of the invention (including antibodies) that are associated with heterologous polypeptides or nucleic acids. In one example, the invention provides a method for delivering a therapeutic protein into the targeted cell. In another example, the invention provides a method for delivering a single stranded nucleic acid (e.g., antisense or ribozymes) or double stranded nucleic acid (e.g., DNA that can integrate into the cell's genome or replicate episomally and that can be transcribed) into the targeted cell.

In another embodiment, the invention provides a method for the specific destruction of cells (e.g., the destruction of tumor cells) by administering polypeptides of the invention (e.g., polypeptides of the invention or antibodies of the invention) in association with toxins or cytotoxic prodrugs.

By "toxin" is meant compounds that bind and activate endogenous cytotoxic effector systems, radioisotopes, holotoxins, modified toxins, catalytic subunits of toxins, or any molecules or enzymes not normally present in or on the surface of a cell that under defined conditions cause the cell's death. Toxins that may be used according to the methods of the invention include, but are not limited to, radioisotopes known in the art, compounds such as, for example, antibodies (or complement fixing containing portions thereof) that bind an inherent or induced endogenous cytotoxic effector system, thymidine kinase, endonuclease, RNAse, alpha toxin, ricin, abrin, *Pseudomonas* exotoxin A, diphtheria toxin, saporin, momordin, gelonin, pokeweed antiviral protein, alpha-sarcin and cholera toxin. By "cytotoxic prodrug" is meant a non-toxic compound that is converted by an enzyme, normally present in the cell, into a cytotoxic compound. Cytotoxic prodrugs that may be used according to the methods of the invention include, but are not limited to, glutamyl derivatives of benzoic acid mustard alkylating agent, phosphate derivatives of etoposide or mitomycin C, cytosine arabinoside, daunorubisin, and phenoxyacetamide derivatives of doxorubicin.

Drug Screening

Further contemplated is the use of the polypeptides of the present invention, or the polynucleotides encoding these polypeptides, to screen for molecules which modify the activities of the polypeptides of the present invention. Such a method would include contacting the polypeptide of the present invention with a selected compound(s) suspected of having antagonist or agonist activity, and assaying the activity of these polypeptides following binding.

This invention is particularly useful for screening therapeutic compounds by using the polypeptides of the present invention, or binding fragments thereof, in any of a variety of drug screening techniques. The polypeptide or fragment employed in such a test may be affixed to a solid support, expressed on a cell surface, free in solution, or located intracellularly. One method of drug screening utilizes eukaryotic or prokaryotic host cells which are stably transformed with recombinant nucleic acids expressing the polypeptide or fragment. Drugs are screened against such transformed cells in competitive binding assays. One may measure, for example, the formulation of complexes between the agent being tested and a polypeptide of the present invention.

Thus, the present invention provides methods of screening for drugs or any other agents which affect activities mediated by the polypeptides of the present invention. These methods comprise contacting such an agent with a polypeptide of the present invention or a fragment thereof and assaying for the presence of a complex between the agent and the polypeptide or a fragment thereof, by methods well known in the art. In such a competitive binding assay, the agents to screen are typically labeled. Following incubation, free agent is separated from that present in bound form, and the amount of free or uncomplexed label is a measure of the ability of a particular agent to bind to the polypeptides of the present invention.

Another technique for drug screening provides high throughput screening for compounds having suitable binding affinity to the polypeptides of the present invention, and is described in great detail in European Patent Application 84/03564, published on Sep. 13, 1984, which is incorporated herein by reference herein. Briefly stated, large numbers of different small peptide test compounds are synthesized on a solid substrate, such as plastic pins or some other surface. The peptide test compounds are reacted with polypeptides of the present invention and washed. Bound polypeptides are then detected by methods well known in the art. Purified polypeptides are coated directly onto plates for use in the aforementioned drug screening techniques. In addition, non-neutralizing antibodies may be used to capture the peptide and immobilize it on the solid support.

This invention also contemplates the use of competitive drug screening assays in which neutralizing antibodies capable of binding polypeptides of the present invention specifically compete with a test compound for binding to the polypeptides or fragments thereof. In this manner, the antibodies are used to detect the presence of any peptide which shares one or more antigenic epitopes with a polypeptide of the invention.

Antisense and Ribozyme (Antagonists)

In specific embodiments, antagonists according to the present invention are nucleic acids corresponding to the sequences contained in SEQ ID NO:X, or the complementary strand thereof, and/or to nucleotide sequences contained a deposited clone. In one embodiment, antisense sequence is generated internally by the organism, in another embodiment, the antisense sequence is separately administered (see, for example, O'Connor, Neurochem., 56:560 (1991). Oligodeoxynucleotides as Antisense Inhibitors of Gene Expression, CRC Press, Boca Raton, Fla. (1988). Antisense technology can be used to control gene expression through antisense DNA or RNA, or through triple-helix formation. Antisense techniques are discussed for example, in Okano, Neurochem., 56:560 (1991); Oligodeoxynucleotides as Antisense Inhibitors of Gene Expression, CRC Press, Boca Raton, Fla. (1988). Triple helix formation is discussed in, for instance, Lee et al., Nucleic Acids Research, 6:3073 (1979); Cooney et al., Science, 241:456 (1988); and Dervan et al., Science, 251:1300 (1991). The methods are based on binding of a polynucleotide to a complementary DNA or RNA.

For example, the use of c-myc and c-myb antisense RNA constructs to inhibit the growth of the non-lymphocytic leukemia cell line HL-60 and other cell lines was previously described. (Wickstrom et al. (1988); Anfossi et al. (1989)). These experiments were performed in vitro by incubating cells with the oligoribonucleotide. A similar procedure for in vivo use is described in WO 91/15580. Briefly, a pair of oligonucleotides for a given antisense RNA is produced as follows: A sequence complimentary to the first 15 bases of the open reading frame is flanked by an EcoR1 site on the 5 end and a HindIII site on the 3 end. Next, the pair of oligonucleotides is heated at 90° C. for one minute and then annealed in 2× ligation buffer (20 mM TRIS HCl pH 7.5, 10 mM MgCl2, 10 MM dithiothreitol (DTT) and 0.2 mM ATP) and then ligated to the EcoR1/Hind III site of the retroviral vector PMV7 (WO 91/15580).

For example, the 5' coding portion of a polynucleotide that encodes the mature polypeptide of the present invention may be used to design an antisense RNA oligonucleotide of from about 10 to 40 base pairs in length. A DNA oligonucleotide is designed to be complementary to a region of the gene involved in transcription thereby preventing transcription and the production of the receptor. The antisense RNA oligonucleotide hybridizes to the mRNA in vivo and blocks translation of the mRNA molecule into receptor polypeptide.

In one embodiment, the antisense nucleic acid of the invention is produced intracellularly by transcription from an exogenous sequence. For example, a vector or a portion thereof, is transcribed, producing an antisense nucleic acid (RNA) of the invention. Such a vector would contain a sequence encoding the antisense nucleic acid of the invention. Such a vector can remain episomal or become chromosomally integrated, as long as it can be transcribed to produce the desired antisense RNA. Such vectors can be constructed by recombinant DNA technology methods standard in the art. Vectors can be plasmid, viral, or others known in the art, used for replication and expression in vertebrate cells. Expression of the sequence encoding a polypeptide of the invention, or fragments thereof, can be by any promoter known in the art to act in vertebrate, preferably human cells. Such promoters can be inducible or constitutive. Such promoters include, but are not limited to, the SV40 early promoter region (Bernoist and Chambon, Nature, 29:304-310 (1981), the promoter contained in the 3' long terminal repeat of Rous sarcoma virus (Yamamoto et al., Cell, 22:787-797 (1980), the herpes thymidine promoter (Wagner et al., Proc. Natl. Acad. Sci. U.S.A., 78:1441-1445 (1981), the regulatory sequences of the metallothionein gene (Brinster et al., Nature, 296:39-42 (1982)), etc.

The antisense nucleic acids of the invention comprise a sequence complementary to at least a portion of an RNA transcript of a gene of interest. However, absolute complementarity, although preferred, is not required. A sequence "complementary to at least a portion of an RNA," referred to herein, means a sequence having sufficient complementarity to be able to hybridize with the RNA, forming a stable duplex; in the case of double stranded antisense nucleic acids of the invention, a single strand of the duplex DNA may thus be tested, or triplex formation may be assayed. The ability to hybridize will depend on both the degree of complementarity and the length of the antisense nucleic acid Generally, the larger the hybridizing nucleic acid, the more base mismatches with a RNA sequence of the invention it may contain and still form a stable duplex (or triplex as the case may be). One skilled in the art can ascertain a tolerable degree of mismatch by use of standard procedures to determine the melting point of the hybridized complex.

Oligonucleotides that are complementary to the 5' end of the message, e.g., the 5' untranslated sequence up to and including the AUG initiation codon, should work most efficiently at inhibiting translation. However, sequences complementary to the 3' untranslated sequences of mRNAs have been shown to be effective at inhibiting translation of mRNAs as well. See generally, Wagner, R., *Nature,* 372: 333-335 (1994). Thus, oligonucleotides complementary to either the 5'- or 3'-non-translated, non-coding regions of a polynucleotide sequence of the invention could be used in an antisense approach to inhibit translation of endogenous mRNA. Oligonucleotides complementary to the 5' untranslated region of the mRNA should include the complement of the AUG start codon. Antisense oligonucleotides complementary to mRNA coding regions are less efficient inhibitors of translation but could be used in accordance with the invention. Whether designed to hybridize to the 5'-, 3'- or coding region of mRNA, antisense nucleic acids should be at least six nucleotides in length, and are preferably oligonucleotides ranging from 6 to about 50 nucleotides in length. In specific aspects the oligonucleotide is at least 10 nucleotides, at least 17 nucleotides, at least 25 nucleotides or at least 50 nucleotides.

The polynucleotides of the invention can be DNA or RNA or chimeric mixtures or derivatives or modified versions thereof, single-stranded or double-stranded. The oligonucleotide can be modified at the base moiety, sugar moiety, or phosphate backbone, for example, to improve stability of the molecule, hybridization, etc. The oligonucleotide may include other appended groups such as peptides (e.g., for targeting host cell receptors in vivo), or agents facilitating transport across the cell membrane (see, e.g., Letsinger et al., Proc. Natl. Acad. Sci. U.S.A. 86:6553-6556 (1989); Lemaitre et al., Proc. Natl. Acad. Sci., 84:648-652 (1987); PCT Publication NO: WO88/09810, published Dec. 15, 1988) or the blood-brain barrier (see, e.g., PCT Publication NO: WO89/10134, published Apr. 25, 1988), hybridization-triggered cleavage agents. (See, e.g., Krol et al., BioTechniques, 6:958-976 (1988)) or intercalating agents. (See, e.g., Zon, Pharm. Res., 5:539-549 (1988)). To this end, the oligonucleotide may be conjugated to another molecule, e.g., a peptide, hybridization triggered cross-linking agent, transport agent, hybridization-triggered cleavage agent, etc.

The antisense oligonucleotide may comprise at least one modified base moiety which is selected from the group including, but not limited to, 5-fluorouracil, 5-bromouracil, 5-chlorouracil, 5-iodouracil, hypoxanthine, xantine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3)w, and 2,6-diaminopurine.

The antisense oligonucleotide may also comprise at least one modified sugar moiety selected from the group including, but not limited to, arabinose, 2-fluoroarabinose, xylulose, and hexose.

In yet another embodiment, the antisense oligonucleotide comprises at least one modified phosphate backbone selected from the group including, but not limited to, a phosphorothioate, a phosphorodithioate, a phosphoramidothioate, a phosphoramidate, a phosphordiamidate, a methylphosphonate, an alkyl phosphotriester, and a formacetal or analog thereof.

In yet another embodiment, the antisense oligonucleotide is an a-anomeric oligonucleotide. An a-anomeric oligonucleotide forms specific double-stranded hybrids with complementary RNA in which, contrary to the usual b-units, the strands run parallel to each other (Gautier et al., Nucl. Acids Res., 15:6625-6641 (1987)). The oligonucleotide is a 2-0-methylribonucleotide (Inoue et al., Nucl. Acids Res., 15:6131-6148 (1987)), or a chimeric RNA-DNA analogue (Inoue et al., FEBS Lett. 215:327-330 (1987)).

Polynucleotides of the invention may be synthesized by standard methods known in the art, e.g. by use of an automated DNA synthesizer (such as are commercially available from Biosearch, Applied Biosystems, etc.). As examples, phosphorothioate oligonucleotides may be synthesized by the method of Stein et al. (Nucl. Acids Res., 16:3209 (1988)), methylphosphonate oligonucleotides can be prepared by use of controlled pore glass polymer supports (Sarin et al., Proc. Natl. Acad. Sci. U.S.A., 85:7448-7451 (1988)), etc.

While antisense nucleotides complementary to the coding region sequence of the invention could be used, those complementary to the transcribed untranslated region are most preferred.

Potential antagonists according to the invention also include catalytic RNA, or a ribozyme (See, e.g., PCT International Publication WO 90/11364, published Oct. 4, 1990; Sarver et al, Science, 247:1222-1225 (1990). While ribozymes that cleave mRNA at site specific recognition sequences can be used to destroy mRNAs corresponding to the polynucleotides of the invention, the use of hammerhead ribozymes is preferred. Hammerhead ribozymes cleave mRNAs at locations dictated by flanking regions that form complementary base pairs with the target mRNA. The sole requirement is that the target mRNA have the following sequence of two bases: 5'-UG-3'. The construction and production of hammerhead ribozymes is well known in the art and is described more fully in Haseloff and Gerlach, Nature, 334:585-591 (1988). There are numerous potential hammerhead ribozyme cleavage sites within each nucleotide sequence disclosed in the sequence listing. Preferably, the ribozyme is engineered so that the cleavage recognition site is located near the 5' end of the mRNA corresponding to the polynucleotides of the invention; i.e., to increase efficiency and minimize the intracellular accumulation of non-functional mRNA transcripts.

As in the antisense approach, the ribozymes of the invention can be composed of modified oligonucleotides (e.g. for improved stability, targeting, etc.) and should be delivered to cells which express the polynucleotides of the invention in vivo. DNA constructs encoding the ribozyme may be introduced into the cell in the same manner as described above for the introduction of antisense encoding DNA. A preferred method of delivery involves using a DNA construct "encoding" the ribozyme under the control of a strong constitutive promoter, such as, for example, pol III or pol II promoter, so that transfected cells will produce sufficient quantities of the ribozyme to destroy endogenous messages and inhibit translation. Since ribozymes unlike antisense molecules, are catalytic, a lower intracellular concentration is required for efficiency.

Antagonist/agonist compounds may be employed to inhibit the cell growth and proliferation effects of the polypeptides of the present invention on neoplastic cells and tissues, i.e. stimulation of angiogenesis of tumors, and, therefore, retard or prevent abnormal cellular growth and proliferation, for example, in tumor formation or growth.

The antagonist/agonist may also be employed to prevent hyper-vascular diseases, and prevent the proliferation of epithelial lens cells after extracapsular cataract surgery. Prevention of the mitogenic activity of the polypeptides of the present invention may also be desirous in cases such as restenosis after balloon angioplasty.

The antagonist/agonist may also be employed to prevent the growth of scar tissue during wound healing.

The antagonist/agonist may also be employed to treat, prevent, and/or diagnose the diseases described herein.

Thus, the invention provides a method of treating or preventing diseases, disorders, and/or conditions, including but not limited to the diseases, disorders, and/or conditions listed throughout this application, associated with overexpression of a polynucleotide of the present invention by administering to a patient (a) an antisense molecule directed to the polynucleotide of the present invention, and/or (b) a ribozyme directed to the polynucleotide of the present invention. invention, and/or (b) a ribozyme directed to the polynucleotide of the present invention Other Activities The polypeptide of the present invention, as a result of the ability to stimulate vascular endothelial cell growth, may be employed in treatment for stimulating re-vascularization of ischemic tissues due to various disease conditions such as thrombosis, arteriosclerosis, and other cardiovascular conditions. These polypeptide may also be employed to stimulate angiogenesis and limb regeneration, as discussed above.

The polypeptide may also be employed for treating wounds due to injuries, burns, post-operative tissue repair, and ulcers since they are mitogenic to various cells of different origins, such as fibroblast cells and skeletal muscle cells, and therefore, facilitate the repair or replacement of damaged or diseased tissue.

The polypeptide of the present invention may also be employed stimulate neuronal growth and to treat, prevent, and/or diagnose neuronal damage which occurs in certain neuronal disorders or neuro-degenerative conditions such as Alzheimer's disease, Parkinson's disease, and AIDS-related complex. The polypeptide of the invention may have the ability to stimulate chondrocyte growth, therefore, they may be employed to enhance bone and periodontal regeneration and aid in tissue transplants or bone grafts.

The polypeptide of the present invention may be also be employed to prevent skin aging due to sunburn by stimulating keratinocyte growth.

The polypeptide of the invention may also be employed for preventing hair loss, since FGF family members activate hair-forming cells and promotes melanocyte growth. Along the same lines, the polypeptides of the present invention may be employed to stimulate growth and differentiation of hematopoietic cells and bone marrow cells when used in combination with other cytokines.

The polypeptide of the invention may also be employed to maintain organs before transplantation or for supporting cell culture of primary tissues.

The polypeptide of the present invention may also be employed for inducing tissue of mesodermal origin to differentiate in early embryos.

The polypeptide or polynucleotides and/or agonist or antagonists of the present invention may also increase or decrease the differentiation or proliferation of embryonic stem cells, besides, as discussed above, hematopoietic lineage.

The polypeptide or polynucleotides and/or agonist or antagonists of the present invention may also be used to modulate mammalian characteristics, such as body height, weight, hair color, eye color, skin, percentage of adipose tissue, pigmentation, size, and shape (e.g., cosmetic surgery). Similarly, polypeptides or polynucleotides and/or agonist or antagonists of the present invention may be used to modulate mammalian metabolism affecting catabolism, anabolism, processing, utilization, and storage of energy.

Polypeptide or polynucleotides and/or agonist or antagonists of the present invention may be used to change a mammal's mental state or physical state by influencing biorhythms, caricadic rhythms, depression (including depressive diseases, disorders, and/or conditions), tendency for violence, tolerance for pain, reproductive capabilities (preferably by Activin or Inhibin-like activity), hormonal or endocrine levels, appetite, libido, memory, stress, or other cognitive qualities.

Polypeptide or polynucleotides and/or agonist or antagonists of the present invention may also be used as a food additive or preservative, such as to increase or decrease storage capabilities, fat content, lipid, protein, carbohydrate, vitamins, minerals, cofactors or other nutritional components.

Other Preferred Embodiments

Other preferred embodiments of the claimed invention include an isolated nucleic acid molecule comprising a nucleotide sequence which is at least 95% identical to a sequence of at least about 50 contiguous nucleotides in the nucleotide sequence of SEQ ID NO:X wherein X is any integer as defined in Table 1.

Also preferred is a nucleic acid molecule wherein said sequence of contiguous nucleotides is included in the nucleotide sequence of SEQ ID NO:X in the range of positions beginning with the nucleotide at about the position of the 5' Nucleotide of the Clone Sequence and ending with the nucleotide at about the position of the 3' Nucleotide of the Clone Sequence as defined for SEQ ID NO:X in Table 1.

Also preferred is a nucleic acid molecule wherein said sequence of contiguous nucleotides is included in the nucleotide sequence of SEQ ID NO:X in the range of positions beginning with the nucleotide at about the position of the 5' Nucleotide of the Start Codon and ending with the nucleotide at about the position of the 3' Nucleotide of the Clone Sequence as defined for SEQ ID NO:X in Table 1.

Similarly preferred is a nucleic acid molecule wherein said sequence of contiguous nucleotides is included in the nucleotide sequence of SEQ ID NO:X in the range of positions beginning with the nucleotide at about the position of the 5' Nucleotide of the First Amino Acid of the Signal Peptide and ending with the nucleotide at about the position of the 3' Nucleotide of the Clone Sequence as defined for SEQ ID NO:X in Table 1.

Also preferred is an isolated nucleic acid molecule comprising a nucleotide sequence which is at least 95% identical to a sequence of at least about 150 contiguous nucleotides in the nucleotide sequence of SEQ ID NO:X.

Further preferred is an isolated nucleic acid molecule comprising a nucleotide sequence which is at least 95% identical to a sequence of at least about 500 contiguous nucleotides in the nucleotide sequence of SEQ ID NO:X.

A further preferred embodiment is a nucleic acid molecule comprising a nucleotide sequence which is at least 95% identical to the nucleotide sequence of SEQ ID NO:X beginning with the nucleotide at about the position of the 5' Nucleotide of the First Amino Acid of the Signal Peptide and ending with the nucleotide at about the position of the 3' Nucleotide of the Clone Sequence as defined for SEQ ID NO:X in Table 1.

A further preferred embodiment is an isolated nucleic acid molecule comprising a nucleotide sequence which is at least 95% identical to the complete nucleotide sequence of SEQ ID NO:X.

Also preferred is an isolated nucleic acid molecule which hybridizes under stringent hybridization conditions to a nucleic acid molecule, wherein said nucleic acid molecule which hybridizes does not hybridize under stringent hybridization conditions to a nucleic acid molecule having a nucleotide sequence consisting of only A residues or of only T residues.

Also preferred is a composition of matter comprising a DNA molecule which comprises a human cDNA clone identified by a cDNA Clone Identifier in Table 1, which DNA molecule is contained in the material deposited with the American Type Culture Collection and given the ATCC Deposit Number shown in Table 1 for said cDNA Clone Identifier.

Also preferred is an isolated nucleic acid molecule comprising a nucleotide sequence which is at least 95% identical to a sequence of at least 50 contiguous nucleotides in the nucleotide sequence of a human cDNA clone identified by a cDNA Clone Identifier in Table 1, which DNA molecule is contained in the deposit given the ATCC Deposit Number shown in Table 1.

Also preferred is an isolated nucleic acid molecule, wherein said sequence of at least 50 contiguous nucleotides is included in the nucleotide sequence of the complete open reading frame sequence encoded by said human cDNA clone.

Also preferred is an isolated nucleic acid molecule comprising a nucleotide sequence which is at least 95% identical to sequence of at least 150 contiguous nucleotides in the nucleotide sequence encoded by said human cDNA clone.

A further preferred embodiment is an isolated nucleic acid molecule comprising a nucleotide sequence which is at least 95% identical to sequence of at least 500 contiguous nucleotides in the nucleotide sequence encoded by said human cDNA clone.

A further preferred embodiment is an isolated nucleic acid molecule comprising a nucleotide sequence which is at least 95% identical to the complete nucleotide sequence encoded by said human cDNA clone.

A further preferred embodiment is a method for detecting in a biological sample a nucleic acid molecule comprising a nucleotide sequence which is at least 95% identical to a sequence of at least 50 contiguous nucleotides in a sequence selected from the group consisting of: a nucleotide sequence of SEQ ID NO:X wherein X is any integer as defined in Table 1; and a nucleotide sequence encoded by a human cDNA clone identified by a cDNA Clone Identifier in Table 1 and contained in the deposit with the ATCC Deposit Number shown for said cDNA clone in Table 1; which method comprises a step of comparing a nucleotide sequence of at least one nucleic acid molecule in said sample with a sequence selected from said group and determining whether the sequence of said nucleic acid molecule in said sample is at least 95% identical to said selected sequence.

Also preferred is the above method wherein said step of comparing sequences comprises determining the extent of nucleic acid hybridization between nucleic acid molecules in said sample and a nucleic acid molecule comprising said sequence selected from said group. Similarly, also preferred is the above method wherein said step of comparing sequences is performed by comparing the nucleotide sequence determined from a nucleic acid molecule in said sample with said sequence selected from said group. The nucleic acid molecules can comprise DNA molecules or RNA molecules.

A further preferred embodiment is a method for identifying the species, tissue or cell type of a biological sample which method comprises a step of detecting nucleic acid molecules in said sample, if any, comprising a nucleotide sequence that is at least 95% identical to a sequence of at least 50 contiguous nucleotides in a sequence selected from the group consisting of: a nucleotide sequence of SEQ ID NO:X wherein X is any integer as defined in Table 1; and a nucleotide sequence encoded by a human cDNA clone identified by a cDNA Clone Identifier in Table 1 and contained in the deposit with the ATCC Deposit Number shown for said cDNA clone in Table 1.

The method for identifying the species, tissue or cell type of a biological sample can comprise a step of detecting nucleic acid molecules comprising a nucleotide sequence in a panel of at least two nucleotide sequences, wherein at least one sequence in said panel is at least 95% identical to a sequence of at least 50 contiguous nucleotides in a sequence selected from said group.

Also preferred is a method for diagnosing in a subject a pathological condition associated with abnormal structure or expression of a gene encoding a secreted protein identified in Table 1, which method comprises a step of detecting in a biological sample obtained from said subject nucleic acid molecules, if any, comprising a nucleotide sequence that is at least 95% identical to a sequence of at least 50 contiguous nucleotides in a sequence selected from the group consisting of: a nucleotide sequence of SEQ ID NO:X wherein X is any integer as defined in Table 1; and a nucleotide sequence encoded by a human cDNA clone identified by a cDNA Clone Identifier in Table 1 and contained in the deposit with the ATCC Deposit Number shown for said cDNA clone in Table 1.

The method for diagnosing a pathological condition can comprise a step of detecting nucleic acid molecules comprising a nucleotide sequence in a panel of at least two nucleotide sequences, wherein at least one sequence in said panel is at least 95% identical to a sequence of at least 50 contiguous nucleotides in a sequence selected from said group.

Also preferred is a composition of matter comprising isolated nucleic acid molecules wherein the nucleotide sequences of said nucleic acid molecules comprise a panel of at least two nucleotide sequences, wherein at least one sequence in said panel is at least 95% identical to a sequence of at least 50 contiguous nucleotides in a sequence selected from the group consisting of: a nucleotide sequence of SEQ ID NO:X wherein X is any integer as defined in Table 1; and a nucleotide sequence encoded by a human cDNA clone identified by a cDNA Clone Identifier in Table 1 and contained in the deposit with the ATCC Deposit Number shown for said cDNA clone in Table 1. The nucleic acid molecules can comprise DNA molecules or RNA molecules.

Also preferred is an isolated polypeptide comprising an amino acid sequence at least 90% identical to a sequence of at least about 10 contiguous amino acids in the amino acid sequence of SEQ ID NO:Y wherein Y is any integer as defined in Table 1.

Also preferred is a polypeptide, wherein said sequence of contiguous amino acids is included in the amino acid sequence of SEQ ID NO:Y in the range of positions beginning with the residue at about the position of the First Amino Acid of the Secreted Portion and ending with the residue at about the Last Amino Acid of the Open Reading Frame as set forth for SEQ ID NO:Y in Table 1.

Also preferred is an isolated polypeptide comprising an amino acid sequence at least 95% identical to a sequence of at least about 30 contiguous amino acids in the amino acid sequence of SEQ ID NO:Y.

Further preferred is an isolated polypeptide comprising an amino acid sequence at least 95% identical to a sequence of at least about 100 contiguous amino acids in the amino acid sequence of SEQ ID NO:Y.

Further preferred is an isolated polypeptide comprising an amino acid sequence at least 95% identical to the complete amino acid sequence of SEQ ID NO:Y.

Further preferred is an isolated polypeptide comprising an amino acid sequence at least 90% identical to a sequence of at least about 10 contiguous amino acids in the complete amino acid sequence of a secreted protein encoded by a human cDNA clone identified by a cDNA Clone Identifier in Table 1 and contained in the deposit with the ATCC Deposit Number shown for said cDNA clone in Table 1.

Also preferred is a polypeptide wherein said sequence of contiguous amino acids is included in the amino acid sequence of a secreted portion of the secreted protein encoded by a human cDNA clone identified by a cDNA Clone Identifier in Table 1 and contained in the deposit with the ATCC Deposit Number shown for said cDNA clone in Table 1.

Also preferred is an isolated polypeptide comprising an amino acid sequence at least 95% identical to a sequence of at least about 30 contiguous amino acids in the amino acid sequence of the secreted portion of the protein encoded by a human cDNA clone identified by a cDNA Clone Identifier in Table 1 and contained in the deposit with the ATCC Deposit Number shown for said cDNA clone in Table 1.

Also preferred is an isolated polypeptide comprising an amino acid sequence at least 95% identical to a sequence of at least about 100 contiguous amino acids in the amino acid sequence of the secreted portion of the protein encoded by a human cDNA clone identified by a cDNA Clone Identifier in Table 1 and contained in the deposit with the ATCC Deposit Number shown for said cDNA clone in Table 1.

Also preferred is an isolated polypeptide comprising an amino acid sequence at least 95% identical to the amino acid sequence of the secreted portion of the protein encoded by a human cDNA clone identified by a cDNA Clone Identifier in Table 1 and contained in the deposit with the ATCC Deposit Number shown for said cDNA clone in Table 1.

Further preferred is an isolated antibody which binds specifically to a polypeptide comprising an amino acid sequence that is at least 90% identical to a sequence of at least 10 contiguous amino acids in a sequence selected from the group consisting of: an amino acid sequence of SEQ ID NO:Y wherein Y is any integer as defined in Table 1; and a complete amino acid sequence of a protein encoded by a human cDNA clone identified by a cDNA Clone Identifier in Table 1 and contained in the deposit with the ATCC Deposit Number shown for said cDNA clone in Table 1.

Further preferred is a method for detecting in a biological sample a polypeptide comprising an amino acid sequence which is at least 90% identical to a sequence of at least 10 contiguous amino acids in a sequence selected from the group consisting of: an amino acid sequence of SEQ ID NO:Y wherein Y is any integer as defined in Table 1; and a complete amino acid sequence of a protein encoded by a human cDNA clone identified by a cDNA Clone Identifier in Table 1 and contained in the deposit with the ATCC Deposit Number shown for said cDNA clone in Table 1; which method comprises a step of comparing an amino acid sequence of at least one polypeptide molecule in said sample with a sequence selected from said group and determining whether the sequence of said polypeptide molecule in said sample is at least 90% identical to said sequence of at least 10 contiguous amino acids.

Also preferred is the above method wherein said step of comparing an amino acid sequence of at least one polypeptide molecule in said sample with a sequence selected from said group comprises determining the extent of specific binding of polypeptides in said sample to an antibody which binds specifically to a polypeptide comprising an amino acid sequence that is at least 90% identical to a sequence of at least 10 contiguous amino acids in a sequence selected from the group consisting of: an amino acid sequence of SEQ ID NO:Y wherein Y is any integer as defined in Table 1; and a complete amino acid sequence of a protein encoded by a human cDNA clone identified by a cDNA Clone Identifier in Table 1 and contained in the deposit with the ATCC Deposit Number shown for said cDNA clone in Table 1.

Also preferred is the above method wherein said step of comparing sequences is performed by comparing the amino acid sequence determined from a polypeptide molecule in said sample with said sequence selected from said group.

Also preferred is a method for identifying the species, tissue or cell type of a biological sample which method comprises a step of detecting polypeptide molecules in said sample, if any, comprising an amino acid sequence that is at least 90% identical to a sequence of at least 10 contiguous amino acids in a sequence selected from the group consisting of: an amino acid sequence of SEQ ID NO:Y wherein Y is any integer as defined in Table 1; and a complete amino acid sequence of a secreted protein encoded by a human cDNA clone identified by a cDNA Clone Identifier in Table 1 and contained in the deposit with the ATCC Deposit Number shown for said cDNA clone in Table 1.

Also preferred is the above method for identifying the species, tissue or cell type of a biological sample, which method comprises a step of detecting polypeptide molecules comprising an amino acid sequence in a panel of at least two amino acid sequences, wherein at least one sequence in said panel is at least 90% identical to a sequence of at least 10 contiguous amino acids in a sequence selected from the above group.

Also preferred is a method for diagnosing in a subject a pathological condition associated with abnormal structure or expression of a gene encoding a secreted protein identified in Table 1, which method comprises a step of detecting in a biological sample obtained from said subject polypeptide molecules comprising an amino acid sequence in a panel of at least two amino acid sequences, wherein at least one sequence in said panel is at least 90% identical to a sequence of at least 10 contiguous amino acids in a sequence selected from the group consisting of: an amino acid sequence of SEQ ID NO:Y wherein Y is any integer as defined in Table 1; and a complete amino acid sequence of a secreted protein encoded by a human cDNA clone identified by a cDNA Clone Identifier in Table 1 and contained in the deposit with the ATCC Deposit Number shown for said cDNA clone in Table 1.

In any of these methods, the step of detecting said polypeptide molecules includes using an antibody.

Also preferred is an isolated nucleic acid molecule comprising a nucleotide sequence which is at least 95% identical to a nucleotide sequence encoding a polypeptide wherein said polypeptide comprises an amino acid sequence that is at least 90% identical to a sequence of at least 10 contiguous amino acids in a sequence selected from the group consisting of: an amino acid sequence of SEQ ID NO:Y wherein Y is any integer as defined in Table 1; and a complete amino acid sequence of a secreted protein encoded by a human cDNA clone identified by a cDNA Clone Identifier in Table 1 and contained in the deposit with the ATCC Deposit Number shown for said cDNA clone in Table 1.

Also preferred is an isolated nucleic acid molecule, wherein said nucleotide sequence encoding a polypeptide has been optimized for expression of said polypeptide in a prokaryotic host.

Also preferred is an isolated nucleic acid molecule, wherein said polypeptide comprises an amino acid sequence selected from the group consisting of: an amino acid sequence of SEQ ID NO:Y wherein Y is any integer as defined in Table 1; and a complete amino acid sequence of a secreted protein encoded by a human cDNA clone identified by a cDNA Clone Identifier in Table 1 and contained in the deposit with the ATCC Deposit Number shown for said cDNA clone in Table 1.

Further preferred is a method of making a recombinant vector comprising inserting any of the above isolated nucleic acid molecule into a vector. Also preferred is the recombinant vector produced by this method. Also preferred is a method of making a recombinant host cell comprising introducing the vector into a host cell, as well as the recombinant host cell produced by this method.

Also preferred is a method of making an isolated polypeptide comprising culturing this recombinant host cell under conditions such that said polypeptide is expressed and recovering said polypeptide. Also preferred is this method of making an isolated polypeptide, wherein said recombinant host cell is a eukaryotic cell and said polypeptide is a secreted portion of a human secreted protein comprising an amino acid sequence selected from the group consisting of: an amino acid sequence of SEQ ID NO:Y beginning with the residue at the position of the First Amino Acid of the Secreted Portion of SEQ ID NO:Y wherein Y is an integer set forth in Table 1 and said position of the First Amino Acid of the Secreted Portion of SEQ ID NO:Y is defined in Table 1; and an amino acid sequence of a secreted portion of a protein encoded by a human cDNA clone identified by a cDNA Clone Identifier in Table 1 and contained in the deposit with the ATCC Deposit Number shown for said cDNA clone in Table 1. The isolated polypeptide produced by this method is also preferred.

Also preferred is a method of treatment of an individual in need of an increased level of a secreted protein activity, which method comprises administering to such an individual a pharmaceutical composition comprising an amount of an isolated polypeptide, polynucleotide, or antibody of the claimed invention effective to increase the level of said protein activity in said individual.

The above-recited applications have uses in a wide variety of hosts. Such hosts include, but are not limited to, human, murine, rabbit, goat, guinea pig, camel, horse, mouse, rat, hamster, pig, micro-pig, chicken, goat, cow, sheep, dog, cat, non-human primate, and human. In specific embodiments, the host is a mouse, rabbit, goat, guinea pig, chicken, rat, hamster, pig, sheep, dog or cat. In preferred embodiments, the host is a mammal. In most preferred embodiments, the host is a human.

In specific embodiments of the invention, for each "Contig ID" listed in the fourth column of Table 6, preferably excluded are one or more polynucleotides comprising, or alternatively consisting of, a nucleotide sequence referenced in the fifth column of Table 6 and described by the general formula of a-b, whereas a and b are uniquely determined for the corresponding SEQ ID NO:X referred to in column 3 of Table 6. Further specific embodiments are directed to polynucleotide sequences excluding one, two, three, four, or more of the specific polynucleotide sequences referred to in the fifth column of Table 6. In no way is this listing meant to encompass all of the sequences which may be excluded by the general formula, it is just a representative example. All references available through these accessions are hereby incorporated by reference in their entirety.

TABLE 6

| Clone ID NO: Z | SEQ ID NO.: X | Contig ID: | Accession #'s |
|---|---|---|---|
| HKABZ65 | 11 | 665424 | AA715814, AA503019, AW338860, AL044701, AA715173, AA715075, AI568659, AA525144, AF109907, AC005071, AC004878, AC005081, AC002549, AC020663, AC006064, AC004858, AC007666, AL022318, AL035086, AC004656, AC004067, AC004477, AC006023, Z98884, AC007637, AL080243, AC002369, Z84487, AL031311, AL049776, AC004686, AL080317, AC002310, AL050318, AL132712, D87675, AC007546, AC004675, AL035683, AC002288, AF030453, Z95331, AC006077, AC008101, AF088219, AC005175, AL021391, AC005670, AL133163, AL031123, AC004770, AC004659, AL078463, AC002492, AC006084, AC005089, AL031670, AC005088, AC004491, AC005887, AP000008, AC002457, AC009946, AC005200, AC006581, AL022316, AC005180, AC005015, AP000553, Z98742, AC007283, AC005920, AC004832, AL035462, AC002352, AC005037, AF111169, AC004854, AF067844, U95090, AL109623, AF053356, U78027, Z85987, AP000704, AC004263, AC004232, AC005661, AC005409, AP000563, AC005005, AL031848, AC004881, AC004685, AC005480, AC003950, AC000026, AC007563, AL021155, AC002470, AL031767, AP000557, Z73358, AL023553, AC002375, U52112, AC002395, AC002425, AC005280, AC006101, AL034418, AC005538, AC002476, AL049569, AL109801, AL035422, AC005102, AC002059, Z85996, AC004813, Z98304, AC003663, AC005562, AL034402, AC004804, AC002477, AC007225, AC005399, AL121825, AL034421, AL008718, Z84486, AC007051, AC005366, Z98950, AL049795, AC002073, AC006536, AC004905, AL035405, AC004587, U91327, AL096791, AC005393, AP000513, AL109753, AC003029, AL021918, AC005703, AL035659, Z93020, and AL031279. |
| HNGIC80 | 12 | 637909 | AL118503 |
| HDPUG50 | 13 | 684120 | AI217895, AI983150, AW385698, AW374106, AI660124, AI339010, AW374124, AA166971, AA542906, AA689356, AI285269, AI346870, N27706, AW236815, AI821227, AI821074, AL134542, AA166818, AA836112, D20721, AI221030, AA627350, AW027663, N35710, AI221246, AW372396, AI285231, T95430, AW372395, AI699709, AL134543, AA055338, AA449417, AW197834, R83129, AI418208, AA375954, AA450383, AA961046, N20259, AA336834, AA226636, AI911109, AA225691, N20865, AA825421, AI932769, AA938413, AW197872, AA370379, N29162, C03633, AI620095, AA055337, AI932771, AA976076, AI821821, AA173926, AA173884, AA569611, AI821883, AA772955, AW383971, AI432644, AI431307, AI431316, AI432666, AI431238, AI623302, AI432653, AI431323, AI921241, AI431347, AI431350, AI432655, AW081103, AI431321, AL042853, AL042729, AI431243, AI431230, AI431328, AI432654, AI431310, AI431312, AI432650, AI432677, AI431247, AI432657, AI492519, AI431231, AI791349, AI431257, AI431235, AI431315, AI431354, AI431318, AI431353, AI432661, AI431246, AI432649, AI432643, AI432675, AI431337, AI432651, AI432647, AI432674, AI431330, AW129223, AL045327, AI431248, AL042931, AI432665, AL042519, AJ224875, Y17793, AF019249, AL133082, and AF064854. |
| HAEAB66 | 14 | 580083 | AI659421, AI632698, AI969812, AI394313, AW139577, AI739006, AW271206, AW293868, AI805043, AI799897, AI923666, AA640596, AA308562, H80192, AA833662, AA910928, AI275400, AW377553, AW377527, AI191675, AI041565, AW138256, AI693984, AI392758, AI597816, AA776304, AI956051, AI085021, AI288918, AI076685, AA725434, AI824191, AI471844, AA524228, N70113, AA143492, AA143493, AA226122, AA226045, AI123234, AA858158, AA532806, W01829, N70775, AI183697, AI693773, AA757995, AA304772, H78816, AI276951, AA613815, AA152444, AI076680, AI283120, AA152445, AF228603, AF157600, and AF170564. |
| HHEPF59 | 15 | 695722 | AL120852, AI922659, AA932542, AA262051, AA526382, AW205846, N39596, AI459931, AW406797, AI866992, AI373687, AI475825, AA582869, AI862875, AA223668, R96889, T90824, AA642941, R43602, D60935, R44585, AA812110, AI669230, AI928028, AI199166, AI369241, AI799999, AI963565, N52647, D80065, N68066, R96890, AI083867, T85729, R19318, N80503, AW451196, N72375, AI571518, AI797299, AI685620, AW002004, AW194849, AW197067, AI498711, N46743, AW243761, AA974737, AW189464, AI383927, T23990, AI373614, AI633402, AA247241, AI961589, AL120853, AI587156, AI702073, AI537261, AI862139, AI500714, AI627988, AI921248, AI433157, AI633125, AW084425, AI659585, AI677796, AL121564, AW152182, AI277008, AI677797, AW167448, AI670009, AI280637, AI873923, AI620003, AI570989, AW029638, AI590630, AI812107, AW129271, AI620089, AI963193, AI281772, AI624293, AW105383, AI683173, AI682971, AI745656, AW080327, AI874166, AI868740, AI241744, AI612852, AI886181, AI637584, AI241923, AW090550, AW029329, AW170635, AI610770, AI587114, AI500061, AI583085, AI564719, AI469532, AI538564, AI432030, AI499285, AI827154, AI633000, AI538829, AI445025, AI434223, AW148536, AI002285, AI541056, AW129722, AI884318, AI554186, AI357940, AI569637, AI568138, AI445992, AI582932, AW151714, AI521560, AI569975, AA641818, AI287233, AI473536, AW104724, AI866469, AA502794, AW162194, AW104827, AI932949, AI288285, AW192652, AW026087, AI148272, AI591387, AI631095, AI800155, AI610690, AI275640, AI669459, AW149925, AI915291, AI963346, AW148408, AI499393, AI469112, AW193530, AW073270, AI632408, AW090071, AI866801, AI690426, AW058243, AL048656, AW087207, AI499986, AI368868, AI635067, AWO81653, AI8O1152, AI540382, AI890507, AI921464, AI690748, AI521103, AW148363, AW130068, AW051088, AI309244, AI290154, AI362347, AW105431, AI698391, AI142101, AI471909, AI355779, AW190194, AW090736, AI476478, AI922561, AI889189, AA805434, AW008353, AI362248, AI687362, AL037454, AI889376, AI609375, AL039086, AI619426, AW151893, AI744988, AA983883, AI796743, AWI62118, AI538716, AI499947, AI648567, |

TABLE 6-continued

| Clone ID NO: Z | SEQ ID NO.: X | Contig ID: | Accession #'s |
|---|---|---|---|
| | | | W74529, AI280732, AI797538, AI242248, AW075667, AI978703, AI696829, AI249877, AI648508, AW167021, AL046595, AI254731, AI540674, AW132056, AI624084, AI287793, AI569583, AI522052, AI539800, AI579901, AI760435, AW087160, AW193231, AW129916, AI269205, AI933589, AI963458, AW129230, AI925502, AW169604, AI340982, AL037030, AI520862, AW264727, AL040241, AW150453, AW262552, AI568855, AI286256, AW169653, AI261344, AW263823, AW168788, AC004596, AF090901, E05822, I89947, AL137429, AL133112, AR038854, AL137523, AL137539, AF061981, AL050116, I48978, AL137459, AC004883, AL133072, AL137480, AL050149, AL078630, AL110280, A08910, A08909, A08908, Z82022, A08916, A77033, A77035, AF106657, E12747, AF113019, Y10936, AJ000937, A08913, U35846, AL049938, AL049452, AF185576, A18788, AF026816, AL049283, I33392, AF111849, AC004093, U80742, AL117435, AJ006417, A21103, S36676, AL080159, AF183393, AL122100, AL137529, AF106862, L19437, AL117460, AF000301, AL137488, AF061573, AC006840, AC005968, I89931, AB022159, AL117416, Y14314, I49625, I48979, A08912, AL137463, AB016226, X82434, AF118094, AL137560, U53505, A49139, AF026124, AL080148, A58524, A58523, A18777, AL050366, AL117648, AF067790, AF153205, AF109906, AF139986, AL050092, AF008439, AL137557, A07647, L31396, X52034, L31397, X81464, AF182215, AR020905, X87582, Y11254, AL133080, AL049466, X94372, AL137550, S77771, AL122093, AL133113, AL133031, AL050277, AF067728, AF087943, AL137271, E02349, A93350, U87620, AL137533, AL050138, AL133606, AF032666, AJ005690, I89934, AF119337, AL133067, AL133640, I03321, AL133075, M27260, AP000020, AL137476, Y10655, A08907, AC004227, AF090903, I68732, AF177401, D83032, Y10080, AL122110, X79812, AL049430, AF031147, AL117457, AL096744, A03736, AF100931, A65341, AF111851, U58996, AL110197, AF159615, AL110221, U66274, I09499, AL137547, S76508, U88966, E01573, E02319, AL080124, AL050146, AF091084, AF113677, U67958, AL080154, AF079763, I17544, E01314, A45787, X57961, AL117440, AL110225, AL137292, Z97214, AL137276, AF054599, AF126247, AF175903, AF097996, AL133558, AL050024, AF113699, Y09972, AL023657, AF125948, AF162270, Y07905, U42766, X96540, AL110218, X72889, Y09885, E03348, AL049300, AL110296, AL117583, AJ238278, E08631, AF090896, A23630, AL110222, A08911, A15345, AC002467, AL137283, Y11587, AF118070, AL049382, AL049314, AF106827, I17767, AF142672, Z37987, E07108, AF061795, AF151685, AL050108, AL133665, AL133010, AL137521, X89102, AL137479, X53587, AR011880, I89944, AF090934, L13297, AL137478, AL110196, AL133081, AF210052, A08915, AF158248, L04504, X98834, AL049465, AL133560, L04849, AF003737, AF113690, AF031903, AF017437, AF113689, AL080074, I26207, E04233, AR038969, AL122050, and AF051325. |
| HE9BK23 | 16 | 675382 | AW299658, AW058550, AI796131, AW299514, AI767984, AI634858, AW235128, AI498692, AI373251, AI796532, R86161, AW295829, T73510, T73442, N71226, C15737, and AF152562. |
| HCYBI36 | 17 | 666358 | AI801638, AW089881, AA484795, AI700113, AI452474, AI220875, H03348, T79392, AA305424, H04030, AI392810, AA375432, AW366425, H95362, AI950113, AA375883, AF101051, AF115546, and AF072127. |
| HSSDX51 | 18 | 566879 | AI792073, AI791928, AW206230, AA317765, R60584, H22857, AI694498, F03192, R05669, AA365484, and U78304. |
| HSDAJ46 | 19 | 692358 | AI800075, AI686505, AW023374, AA418208, H97489, AA620395, AA418073, AW027850, AA401879, N67776, AI168759, N36146, AA700811, N28007, AA012999, H99095, AI015805, H82563, H60753, R87427, H59689, AA688368, W03403, H83666, R85022, AI582759, AA205528, H83667, N35665, AA322820, AW072108, H60754, R07653, AA339201, H59688, R07706, N26551, N69337, H84836, N88280, AA640177, AA221012, AA094140, and AB025904. |
| HRACG45 | 20 | 671767 | AL043880, AW005102, AA137033, AA523117, AA810411, AI671452, AI339682, AA437080, W90768, AI091057, AI288535, AA528033, AA137115, AW130160, AI338926, AI683304, AI199890, AI625514, AW083986, AW194157, AI859189, AI199896, AI990810, AI269181, AA114896, AA114897, AA922395, AI349372, AI168791, AI812097, AI274942, AA128536, AI266219, W90701, AI636417, AI743815, AI862000, AW204921, R51136, H48319, N78924, AI023431, AA128362, AI305176, AI873659, AI091111, AI056132, AI087400, H48227, R52200, AW339362, AI886641, H79689, R62399, R62400, AI680503, F11141, AA423981, AA938005, AA330985, W05294, M78260, Z46207, AI350674, AI915189, RI2869, AA523876, R38443, F08308, R51028, F05074, AA339020, H79690, F08811, AI982566, AA343945, F04534, R43758, AA368664, AW089229, D78779, AA465535, AA368064, AI751158, AW062626, and T05279. |
| HAPPW30 | 21 | 684272 | AW341517, AA868588, AA479992, AA305964, AA758865, AI276502, AA846842, AI183515, N41325, AW273135, AA775255, H57026, AA954695, AI337591, AI685296, N95033, AA969117, AI147710, AA962530, AA150989, AA758255, AI675402, AI167695, AI151098, AI798973, AA383301, AW172620, AI359078, AI688288, AI911606, H83172, AI078598, AI188832, H58146, AA446238, AA310796, AA724109, AA864698, AI240610, AA953573, AA421572, H41807, W15373, H48433, AA977855, AA757910, H87382, H46522, AI216014, AA098821, AA877407, W38885, AI739312, RI1443, H46521, R19191, H82944, W72627, C04986, AI479980, H56935, AI216655, AA339733, R99133, AA975974, AA922234, AA375160, AW183259, AA421590, AI459843, T61945, AI216656, AI191499, AI902298, H70309, AI902295, T71506, AA150942, AA383302, N57057, AA568552, T62175, R94393, AW021717, AI811212, AI924051, AW411235, AW411351, AW411265, AW410902, AI923989, AW166742, AI284509, AA742505, AA100772, AI804524, AW162189, AI654329, AI244704, AI049850, AI628333, AI343379, AI567204, AI457113, AA585298, T29005, AI889191, AI289436, R42275, AW411298, N63128, AW409775, AI954425, AR037084, AR054173, AL137258, AR068753, S71381, M19658, AR068751, AL133015, |

TABLE 6-continued

| Clone ID NO: Z | SEQ ID NO.: X | Contig ID: | Accession #'s |
|---|---|---|---|
| | | | Y11254, AF065135, A76337, A76335, I92592, A91160, S68736, A93016, Y10936, AR015970, AF093542, AL137254, AL133560, Y16645, AF118094, AJ132433, E03671, AF139986, U88966, AL096751, AL031903, AL133024, L04504, E08517, AF130470, AL050024, AF081366, S69385, AL050172, AF132341, AC006203, and AC006112. |
| HE2ES51 | 22 | 684278 | AI792241, AI793025, AW242855, AI767568, AA999850, AI911520, AI765078, AI373739, AI793193, AI985237, AI433883, AI478325, AI671437, AI613056, AI253234, AI524824, AI650909, AW299600, AI431850, AA131483, AI470468, AI473091, AA345162, AA065156, AA076448, AA282824, AL134259, AI862043, AI801088, AI583966, AI473471, AL120446, AI520946, W45039, AL035890, AW020619, AI239701, AI741637, AI468959, AA159625, AW410316, AC003669, U83112, AR030544, AF113677, 106996, AL137550, S71381, AR064250, X15132, AF091084, X67813, AL080234, AF113691, AF010191, E15324, AR054173, A23327, A49723, A49722, AB029755, E16086, E13052, U53505, X66417, I29004, AF113690, and A03736. |
| HAGGJ80 | 23 | 1158546 | |
| HTXDW56 | 24 | 695765 | AI765620, AA725071, AW271710, AI916562, AI634990, AI654165, AI991405, AI983985, AW299864, AI670830, AI570128, AW168930, AW009948, AA704525, AI749744, AW000916, AA861614, AI955276, AI492455, AI676055, AI276897, AI681128, AI796805, AW275120, AA430567, AI659635, AW419101, AA890343, AW167370, AI635116, AI361022, AI700668, AI968287, AW276391, AI935478, AI089414, AI955265, AI912091, AI718821, AI935972, AI216100, AA699534, AA030011, AA587495, AI025329, AI300305, AI342565, AI308169, N38817, AI298732, AA704532, AI628899, AI018477, AA115429, AI334626, AA774557, AA045856, AI160398, AA628480, AA555219, AA189132, AA780575, AI983713, AI686341, AI350088, AI917769, AI263986, AI131166, AI207172, AI347097, AI094833, W31093, AA216738, AA922079, AI095199, AA911845, AI356898, R24001, AI827291, AI251444, AI828631, AA190469, AA774568, N66175, W95063, T51687, R74559, H83131, AW341133, H83132, AI356017, AA028993, H44274, AW086147, N98698, R51880, AI431971, AI203034, AA766045, AI823509, AW071576, AW295813, R62584, AA765554, AI752881, AA017568, N49971, H48233, AI277213, R79503, H78111, R62585, R22076, AI206462, N54046, AI220633, AA580842, H05682, H67771, AI949890, AI675025, C21303, AW384997, AI583730, AA317754, AA191411, AI540820, H41654, H78112, AA359438, R74460, AW022361, AI434155, AA404726, D25572, R43514, N79216, AI468840, H53574, R22023, R20396, H53895, AA095942, R24167, AA362292, AA853334, N66781, N67446, H67770, H48324, N62548, N45446, N77843, AA045973, AI910254, W91944, AA115428, AF151803, and AL049839. |
| HEEAG23 | 25 | 684254 | AI279852, H57654, AI472339, H85172, AA383569, H96534, AA903404, AA719530, AI084916, AW135894, AA993772, AA890589, W61170, AA807443, AA814409, AI828884, R76166, AA470533, AI829062, AA737653, H96878, R62923, AA714658, AA705115, AI964064, AA569749, AI343340, AA769402, AW080830, AA494452, AI871834, AW193760, AL045053, D58349, AW275510, AI445674, AW168618, AA635739, AI039584, AI656744, AA158461, AA551552, AA490183, AA169263, AC004938, AR052481, AL031777, AL035079, AC004882, AL031680, AL109938, AC006312, AP000223, AL121578, AC005033, AC005082, U63313, AC006511, AC004477, AC006315, Z84572, AL035462, Z83823, AC002350, AC010206, D83253, AC004151, AC005291, AC005225, AC004652, AL021940, AP000962, AL031721, AL031666, AC004167, AL009183, U78027, AL021393, AC004223, AC002400, AF141309, AC006101, AL136297, AL035422, AL022100, AL049643, AC005694, AC003006, AL035659, AL022165, AC007066, AL133448, AL080243, AL137100, AC007014, AC004752, AL031427, Y18000, AC004832, AC003065, AC005800, AC006515, AC006011, AL035587, AC006017, AC004913, AC005387, AP000045, AC002039, AL117258, AC004076, AL031228, AD000092, AC006049, AL121934, AL022316, AC006205, Z82244, AC005393, AC006057, AC007324, AP000228, AC007919, AC007051, AC011718, AC006127, AC007227, AC005696, AC004754, AC004534, Z86090, AF107885, AP000547, AC005488, AP000689, AL035409, AC005037, AL049793, Z97196, AP000140, AC009743, AP000359, AP000088, Z69705, Z98051, Z84816, AF178030, AC002492, AC006211, Z92540, AC005725, AC000387, AC006125, AL033392, Z95116, AC008079, AC000115, AL008725, AC006581, AL133289, AC005776, AL139054, AF141308, AC002347, Z97632, Z93241, Z98752, AC005529, AL022311, AL096707, AL078593, AC010722, AC005323, AL031650, AC006544, AC002476, AC004883, AC004814, AF037338, Z98950, AC006543, AC007358, AL035420, AL109839, AL022238, AC005531, AF196969, AC002299, AL034420, AC004525, AP000104, AF200465, AC004833, AC005913, AL024507, Z93016, AL031577, AC007262, AL049766, AC004130, AC005486, AC002312, AL050308, AL009181, AC006285, AL078474, AL035252, AC006253, AC005632, AF190465, AC004854, AF035396, AL049776, U95740, AF109907, AC005702, AL022163, AC009263, AC007688, AC005829, AC005779, AC005088, AC005060, AC004808, AC004686, AC004057, AC016025, AC005527, AC005228, AC006974, AC007226, AC005512, Z81369, AC005378, AC004690, AC003102, AC005618, Z73359, AL079295, AL022395, U91327, AC018769, AC004673, AF111169, Z95400, AC002300, AC005859, AL035423, AC004675, AF053356, AC003684, AF205588, AL049830, AC004019, AC004463, AL035455, AC008033, AC005736, AC004890, AC002990, AP000552, AL031602, AF106656, AC004933, AD000812, AF064861, AL049757, AC005933, AA252707, and AA252834. |
| HDPKI93 | 26 | 683964 | AW026665, AI038157, AW160610, AA291566, AI313184, AA513729, AI028306, R72376, AI167786, AI744406, AI185677, AI660416, AA856738, AA397659, AA479875, AI918286, AA479739, W68014, AA628725, AA216390, R62410, AA399031, AW162156, AI032922, W67956, AA229418, AI628273, AA759314, AI564387, AI874106, AA100111, AA852988, AA852989, AA677565, AA627551, AW269334, |

TABLE 6-continued

| Clone ID NO: Z | SEQ ID NO.: X | Contig ID: | Accession #'s |
|---|---|---|---|
| | | | AI885854, AA100172, AI886985, AI369442, H40744, AI927077, AA188450, N94366, AA291402, AA187325, AI342982, AW136745, AW136249, AI499025, T24752, AI241302, AI990643, AI971492, AI074558, AW166318, AA428682, T55849, AA837459, T18597, AI525852, AI557312, AI557262, Z33559, Z32887, D59751, D50992, AI525661, AI535660, AI541205, AI525556, N71206, AI536138, AI535639, AI525500, AI557533, AA058620, AI557474, AI526078, AI536150, AI557084, AI525302, AI557809, AI541321, AI541075, AI541365, AI557602, AI546829, AI557082, AI557697, AI541353, AI541034, R29657, AI541450, AI540974, AI525856, AI541069, AI557039, AI547177, AI535994, AI536070, AI557543, AF132956, AF086160, U94592, AR050070, A62298, A82595, A82593, Z30183, and A62300. |
| HDLAC10 | 27 | 692299 | AL049012, AW161772, AI963569, AI627938, AA430167, AW150904, AA811288, AW148833, AA016001, AA534493, AI580793, AI473859, AA552599, AI762820, AA630256, AI249503, AI289630, AI093700, AI683179, AA902142, R50658, AA994326, Z43651, AI796343, Z39714, T36201, R50558, D60811, AI796404, AW023060, AI560541, AA445981, Z45738, F04619, AF205600, and AF205601. |
| HDPOH06 | 28 | 683371 | AI378660, AA669141, AI985796, AA688220, AI042515, AI372881, AI014423, AW025175, AI335099, AW263024, AI491990, AW128917, AI570270, AI128127, R91019, W85883, N59550, AW305279, AA679558, AI635705, AI559984, F00878, AW340645, R08677, W85967, AI262108, T98198, AA670170, T53837, AA337112, AA583164, R88760, AA902605, N78291, T98199, AI540509, AC003108, AC003684, Z95152, AC004694, AC002365, AL121603, AL049872, AC005071, AC007425, and R08585. |
| HCE4G61 | 29 | 846836 | AF039237, AL041798, AI831480, AW340563, AW025258, AI127613, AI818249, AA523520, AI750911, AA315462, AI216595, AA564125, AA058690, N24213, AW005271, AI735048, AA677314, AI278958, AA416726, R72506, AA071513, H39933, AI202794, AI871329, AA287126, AI269956, AA045523, C05686, AA040646, AA296927, AW386990, D80945, D61149, R37394, AI261950, Z44618, D60504, AI342287, AA297041, AA323642, AI289604, R85079, AI867501, T35835, R37967, AI021950, R72507, AA082290, AI350532, AI925788, AI369584, AA889809, AA297013, AW105104, AW391339, Z40486, R08860, R13486, R72016, AI188886, AI784381, AI186121, F01836, AA977138, AA534946, C15524, AA327396, AA057306, AA058536, Z42306, AI801558, AA416805, AI631998, AI750912, D31575, R72047, R72058, and AC004596. |
| HCWUI13 | 30 | 695679 | |
| HDPSP01 | 31 | 689129 | AI871101, AI560217, AA047000, AW190726, AA419038, AI479404, AA035467, AI361637, AI198435, AA725194, AI093316, AA442664, AI078128, AI274339, AA915909, AI677732, AI283200, AI769275, AI857306, AI275083, AA423792, AA046943, AI291474, AI291805, AI983969, AA427407, AA661657, AI141350, AA031475, N92812, W24931, AA035466, AA031617, AA961077, AA250784, AW070742, AA411122, AA378564, AW051192, AW452102, AW293787, H91665, AA514348, AW149476, H91759, T86488, AW392670, Z99396, AL119363, U46347, AL119457, AW363220, AW384394, AL119497, AL119319, AL119444, AW372827, AL119443, U46350, U46351, U46349, AL119324, AL119484, AL119391, AL119355, AL119483, AL119439, U46346, U46341, AL134525, AL134533, AL119341, AL119335, AL119522, AL037205, AL119418, AL134528, AL119399, AL134531, AL134527, AL134538, U46345, AL119396, AL119496, AL042614, AL043003, AI142134, AL042542, AL042544, AL042450, AL043019, AL042984, AL042965, AL042975, AL043029, AL119304, AL042551, AL119464, AB026436, AR054110, AR060234, A81671, AR066494, and AR069079. |
| HHPEN62 | 32 | 695134 | AI939620, AI480056, AW300615, AW300620, AI589129, AI911546, AI361251, AI498527, H41544, AA326679, AA348503, AI422476, AA912288, and AI423129. |
| HUKBT29 | 33 | 694590 | AI889172, AI080136, AA211445, AA211523, F24617, AA211502, F27978, AI862904, F28119, F30666, F29048, AI972919, AA211549, AI128717, Z24989, AW302460, F28086, F26294, Z28706, AA413432, and R45814. |
| HMAJR50 | 34 | 654004 | AW408305, AW403731, AW117933, AA947938, AW268857, AI983988, AI566347, AW129984, AW051493, AI741765, AI803337, AW081302, AI811384, AI828939, AL037800, AI146996, AA720675, AI819563, N21132, AI419827, AI460230, AI080555, AW195872, AI348121, AA833715, AW193550, AI285275, N31147, H97793, AW189406, AI240056, AI806449, AA928209, AW277257, AI225247, N50918, AA907019, AI597972, AW302355, AI050898, H82455, AA364171, AI610240, AI376029, AI989465, AA746601, R68913, AA157064, N21022, N47537, AW087619, Z44334, AA156969, H10287, AW197890, AA047176, AI074218, H59319, H13601, AI613266 T35974, R19227, AI338148, AI281563, AA992483, T35248, N42759, T34340, R59345, R62736, T30641, D56630, H10230, W02661, N31923, R38953, R19536, AA995898, T80302, AA248245, N67312, R68809, AI355476, R21115, AA694574, AA904354, Z40284, R59344, R45755, D56961, T34357, T35247, AA313414, T30099, AA301358, AI277161, T31945, T32601, AI865075, R44491, R43889, AA906085, AI560586, T36242, AA585150, N83938, AW197781, AI824759, W25731, Z28514, H59272, R78516, R29225, AI798671, N47536, AW378845, T24535, AA057047, AI583065, AI619777, AI312428, AI923989, AL045266, AI288305, AI866573, AI590043, AI538885, AI335426, AI348777, AI500061, AI432969, AI287326, AI866465, AI468872, AI682798, AI433157, AA572758, AI702073, AL119836, AI887308, AI539771, AI500523, AI582932, AI249877, AL040241, AI633125, AI698391, AI815232, AI915291, AI874261, AI207656, AA420722, AI819326, AI889189, AL079963, AI608936, AI799273, AI340603, AA420758, AW163834, AL038605, AW129230, AI675052, AI637584, AI798404, AL041150, AI625464, AI872910, AW161579, AI539153, AI632408, AW118496, AI570989, AI499986, AW102924, |

TABLE 6-continued

| Clone ID NO: Z | SEQ ID NO.: X | Contig ID: | Accession #'s |
|---|---|---|---|
| | | | AI570861, AL110306, AW410969, AI929108, AW190042, AW087462, AI866770, AL037521, AI633419, AI345347, AA176980, AI446373, AI340533, AL045500, AW088903, AA635382, AW151136, AW148536, AI538085, AI801325, AW022682, AI345608, AW051056, AL036403, AI284517, AW409914, AI697045, AI783504, AI538342, AI572021, AI863082, AW151485, AI288285, AL121014, AL036802, AI635067, AW411235, AI580435, AL048656, AI473799, AL036396, AL039086, AL038565, AI890214, AL119791, AW166903, AW059713, AI611738, AI963194, AI270099, AI251221, AI801793, AI340519, N33175, AI471909, AI352497, AI631273, AI571439, AI619748, AI500706, AI537677, AI934035, AI521560, AI500662, AI345745, AI623396, AI927233, AL036541, AA579232, AI888661, AI539687, AI475430, AI445992, AL135022, AF131856, AF195141, AC005915, E07108, Y11587, I48978, AF090901, AF090903, I89947, AF067728, A08916, A08913, I00734, A08910, A08909, AL117460, AF158248, AF106862, E03348, AF177401, AF113677, Z82022, I48979, AL133067, AL049283, E00617, E00717, E00778, E02349, AF017152, A65341, Y11254, S68736, X65873, A93016, I89931, AL049382, AF078844, I49625, AL133080, AL137271, AL133075, AL137550, AL137557, I61429, AL110228, AF090934, AL080159, Y14314, AL122093, U35846, U80742, AF113019, AL133014, AL133072, S78214, AL133560, Y16645, AL110196, A77033, A77035, AF125949, X93495, AF079765, AL122050, AF087943, AL117457, AL050116, I17767, AL137533, AL117585, AF090896, AF106657, E05822, I42402, AJ238278, AF039138, AF039137, AL137283, AL080074, AF118090, AF111851, AL137459, AL050149, AL096744, AL122121, AL080060, AF091084, AL050024, AF183393, AL117435, AF104032, AF061943, AF113013, AL050393, S61953, AL122110, AL136884, AJ000937, AL049430, AF107847, AL137281, AF125948, AL080124, AB019565, X82434, AL049452, AF118094, AL117463, AL117583, AF153205, A93350, AL137656, A03736, AL049938, I26207, I33392, AF113699, AF090900, AL117394, X98834, AF113691, A65340, AR038969, AL110221, A08912, AL050108, AL110225, AL133113, AL050138, AL133606, E15569, A58524, A58523, E01573, E02319, AF119337, AF008439, AF118070, I03321, AF146568, AL050092, U42766, AL122123, AL049466, AL050146, AR020905, AL133104, AF113690, AF113689, U67958, AP113676, U73682, AJ012755, U72620, X72889, X53587, AL049314, AR011880, A08911, AL050277, AR000496, U39656, AF141289, AL133077, AL137521, X63574, AF026816, A18777, I09360, AF106827, AL122098, AL137527, AL133565, AR059958, E08263, E08264, U00763, AF114168, AF113694, AF017437, AF097996, AL137560, AL133640, X84990, AF026124, AL133016, I09499, AL137548, S76508, X96540, AR038854, AL137463, Y10655, AF145233, AL137538, S83440, AL110280, AF111112, AL049464, AF069506, AJ242859, AF111849, AL137554, AL133557, AF126488, Y09972, E08631, L31396, AL117440, AF185576, A12297, AL133031, L31397, AL110159, AF090943, AF118064, AL133093, L40363, X70685, Z72491, AL137648, AL080127, AL080137, AR068753, E07361, AF000145, AL137556, AL122049, X79812, U58996, U87620, U89295, A08907, AF207750, A08908, AL050172, AF079763, AB007812, I92592, Z37987, I66342, U72621, Y07905, AR068751, A76335, AF120268, S53987, D16301, AL137480, and AA075938. |
| HBIMB51 | 35 | 672711 | AW293249. |
| HE8DX88 | 36 | 663511 | AI352035, and AL049871. |
| HNGHT03 | 37 | 692430 | |
| HWABU17 | 38 | 678671 | N58127, AI970999, AA543049, AA805508, AA481100, AW086144, AI224173, N52797, N49240, AW439223, AA480173, W87476, AA481045, AI702077, AA968423, AI208249, AA676568, AI339421, AA551673, H61729, H90630, AA354107, H18441, H90534, AA203228, Z41571, AA948533, AI990383, H24029, H18549, H22748, H61939, AW075792, W87571, AI270746, AA002111, AA002112, AW072594, N57619, AA977512, AL043010, AF092094, AF155157, and AF004231. |
| HDTAT90 | 39 | 692291 | AL041807, AA315553, AA578538, R60726, AA578520, W25198, N34727, AW160746, R90863, R84524, AW246146, AA081697, T52130, AW177731, AI525011, AW177733, AW068182, C04045, R51326, AA251576, AA081290, and AL050275. |
| HHFGR93 | 40 | 691402 | AW190823, W52782, AI921717, AA707399, AA780017, AI809901, AI656071, AI870870, AI633244, AA046658, AA913618, AA428298, AI014541, AW300019, AW173046, H12307, AA428713, H12782, AI141481, AI092488, W58612, AW172540, AI184646, W58613, AI359381, AW361707, AI126255, R77354, AI970137, AI949837, AW081182, AI923177, AI187105, AI624748, R69232, AA514466, AI521359, R69114, AI347221, R76149, AA664044, R73827, R79810, H12841, R78260, H12629, R76098, R63063, R32862, R78261, T47327, AI189377, R73853, R62315, R68433, AI828342, H12360, AA618505, H12680, T50332, R79923, R79910, AI216465, AA733001, R35438, AA683601, AW009057, R81664, T98690, H00855, R33685, H02334, AI189455, R73852, AW365832, AI873711, R67936, H02440, AI569353, H02804, R68432, R66838, H38189, R76065, R64387, R33581, R35749, AW235425, T98640, R27675, AA991630, AI189443, R75889, R81467, R31360, AA367816, R27576, R63218, AA359117, R31889, R34252, AI762218, AW002259, W52486, H01235, AI199859, R62314, AA046788, AA249358, R64386, AW407088, N55686, R67441, AI002022, D45691, AA446485, AA430177, AI432644, AI492519, AI623302, AI432655, AI432661, AI432653, AI431354, AI431312, AI431347, AI431230, AI431328, AI432654, AI431310, AW081103, AI432677, AI431337, AI431351, AI432675, AI431353, AW128900, AI432674, AI432651, AI432647, AI431330, AI431243, AI432650, AI431248, AI431255, AI431307, AI431316, AI432649, AI432672, AI432665, AI431254, AI431357, AI432662, AI431241, AI791349, AI432676, AI431345, AI431346, AI432673, AI432658, AI432666, AI431340, AI431238, AW128846, AI432664, AI431308, AI432657, |

TABLE 6-continued

| Clone ID NO: Z | SEQ ID NO.: X | Contig ID: | Accession #'s |
|---|---|---|---|
| | | | AI432645, AI431321, AI431247, AW128897, AI431231, AI432643, AI431257, AI431323, AI431350, AI431318, AW128884, AI431235, AI431315, AI492520, AI492510, AI431246, AI431751, AI492509, AW129223, AI431314, AL042729, AL042931, Y17793, AF064854, and AF019249. |
| HOVCB25 | 41 | 691357 | AA318972, AB014534, AF116574, AF116573, AC000029, and AC003678. |
| HSYAV66 | 42 | 686437 | AF126372. |
| HFPCT29 | 43 | 668239 | |
| HAWAT25 | 44 | 677480 | AI992139, AW173625, AI802924, AI263005, AI286190, AA694076, AW168835, AA699535, AA625080, AI912832, AA854042, AA320461, AA704943, AI762162, AA740929, AI700148, AI241269, AA330308, AI640185, AC006359, AL021920, and AC004455. |
| HNHFR04 | 45 | 646709 | |
| HOSFT61 | 46 | 862050 | AI768188, AI935495, AI819745, AI422744, AI423415, AI140447, AI969550, AI332649, AI942442, AA127755, AI075724, AI199841, AI422431, AI129261, AI140453, AI050878, AI419482, AI766108, AI080121, AI675245, AI280479, AI809228, AI372882, AI335707, AI423608, AA678475, AA807943, AI221599, N79574, AA449772, AI375330, AI094106, AA987838, R44044, AW274423, AI914896, R41865, R55755, AA831552, N51677, H23272, AI014757, AW444813, R26737, AW089977, Z38205, AI540756, AA029258, T24879, R26969, AP000118, AP000165, AP000315, and AC016831. |
| HBJIO81 | 47 | 625977 | AW301022, AA748554, and AA761415. |
| HADCL55 | 48 | 686761 | AI891111, AW273154, AI421861, AI937106, AA844641, AI435050, AW080343, AI903718, AA010290, AW363110, AI963329, AA460436, AA460435, C18387, AA010291, W26232, N20813, H09922, AI862319, AW363122, AI131459, AI422844, AA926645, AI671988, C01597, H22803, AI147703, AA017133, Z42698, H23009, H58948, AW295951, F05928, H09826, R92329, AA156440, M78768, AA824261, AA995248, Z38858, AA812976, AA092371, AL136827, and AB023199. |
| HAIBO81 | 49 | 695698 | AI061313, AL046519, AI733856, AA805848, AI609972, AA469327, AI753113, AI291439, AI537995, AI130709, AI687343, AWO21154, AI814682, AW302659, AW302705, AI536858, AA829036, AL041375, AA829044, AW148775, T71936, AI815210, AL020997, AC002425, AC006011, AC004975, Z82214, AP000510, AC005919, AC005225, AC008033, AC004020, AL021707, AC005209, AC003110, AL133163, AC000353, AC005288, AC005529, AC006530, Z98751, AL035407, AC007226, AC005484, AL049759, AC007666, AL024474, AC007055, Z97876, AP000552, AC002470, AC007036, AC008372, AL031295, AC005261, AC006312, AC005514, AC009247, AP000514, AC007686, AC003080, AC006139, AC004655, AC006130, AC005952, AC006241, AC002369, AL109627, AF038458, U91323, AC002544, AC005231, AL049229, Z83840, AC005015, AC004408, AL078463, M89651, M30688, AL035071, AL031767, AC005088, AL118516, AC006023, AC004491, AC006511, AP000557, AC005696, AL049766, AC005363, AL035413, AC002996, AF050154, AC007536, AC005726, Z96074, AC005280, AL049569, AC004156, AL031283, Z83826, AC005060, X54486, AC005324, AD000092, AC006942, AC005251, AC007371, AL031293, AL008725, AC005049, AL031428, Z84466, Z93023, AC003669, AC004024, AC004707, AL021453, AL031577, AF030453, AP000692, AL021546, AP000350, AP000260, AB014078, AC005067, AL031670, AP000116, AC006050, AC004099, AC007207, AL133353, AC007685, AL031311, AC004878, AB023049, AC005069, Z82976, AC007637, AP000049, AC005534, AC003101, AC005519, U78027, AF001548, AC002504, AC004771, AC004477, AL035587, AC005520, AC009516, AC006487, AF165926, AL031584, AC002039, AC003982, AC005759, AC005736, AC007690, AL049699, AP000555, AC004000, L78810, AC005837, AC005409, AP000563, AB001523, AC007938, AC005488, AC005578, AP000311, AP000036, AF196779, AL050318, AC005355, AC006480, AC005954, AC004228, AC005089, AP000215, AC005694, AC007227, AP000117, AL022311, AP000558, AC002314, AC005940, AL024498, AL035249, AC005207, AL109984, AL022323, AP000210, AC003043, AL109801, AL109758, AC007193, Z95331, AC006101, AC005912, AJ011930, AC005046, AC005971, AF129077, AC002404, AL049539, AF165147, AL022302, AC004770, AC004796, AC007731, U63721, AL049780, AC006441, AL031846, AC002400, AC005500, AL049538, AC009731, AL049839, AL023575, AC004216, AP000344, AL031659, AL022316, AL031985, AC002429, AB014079, AL121658, AC005200, U52112, AL022336, AC004150, AL035422, AL049694, U91326, AC006597, AL121653, AP000337, AF053356, AL132718, AL031597, and AC002549. |
| HBBBC37 | 50 | 695702 | AI953024, AI570581, AI052251, AW072845, AI283137, AW418961, AI276972, AI765673, AA443232, AI218363, H98529, AI819979, AA284497, AI187773, W31829, AA971941, H19433, AI674860, AI359631, AA443194, AA857996, AA975354, AW022944, AI032489, R59463, C02118, H23263, AA776510, R60979, Z38831, AA102625, N28938, D51172, T34946, R59403, AA953086, N81166, AI823922, T90503, R45520, AA872986, R45152, W04580, AI277164, R20541, H97160, AI560504, N22268, Z19348, AA287201, M62100, R44572, AA094604, R11284, Z42669, and AB032961. |
| HBJMX85 | 51 | 692971 | AI673085, AA716494, AW151554, AW445050, AA807345, AA926684, AI989351, AW071081, AI687590, AI523580, AW451331, AW075954, AI131215, AI333008, AA974138, AW291257, AA769392, T84096, H91806, AA765936, AW451758, C04782, AW402336, AI473525, AW028312, AA814453, AI568709, T78707, AI801411, AW085753, AW085750, AA471314, AA831522, and AL096808. |
| HCEES66 | 52 | 694592 | AI650353, AW129672, AI564414, AI805921, N51082, AI239923, H52585, H22566, AA007234, AI241833, R42536, H52176, H24419, and |

TABLE 6-continued

| Clone ID NO: Z | SEQ ID NO.: X | Contig ID: | Accession #'s |
|---|---|---|---|
| | | | N54208. |
| HCEMP62 | 53 | 684780 | AI688113, AI554392, AA911109, AW173438, AW382483, AA486370, AA778384, AI382028, AA776265, AA563686, AI493765, AI523553, AA484857, AI362311, AA811238, AA906681, AA838288, AA460659, AI276177, AW404956, AA479791, AA259052, AI097482, AI082243, AA488079, AA088205, AI609703, AI093069, AW438882, AW366250, AA477188, AI350871, AI953839, AI033274, AA285058, AA648139, AI087234, AA226399, AA594766, H53631, H04050, AI298774, H03363, T86181, AI687929, AI270613, H48473, AA496296, H53672, H70534, AI433271, R99170, AW188898, AA359247, AA374856, R23345, H28080, R70772, R33920, AI500391, AA852639, R81465, AA297085, T83919, AA428830, R33033, AA297469, AW088943, AA621048, AI400220, AA853069, R81663, AI963710, R23264, AA290677, AI687795, AW027045, AI289188, AA808274, AW074305, AA290975, AA461006, AA297403, R26089, AA226370, AA297468, R23497, AA359017, AA258974, AW392388, AI683668, T86180, AI653763, AA291083, H26077, T83747, AW058461, AW016612, AW023590, AL079963, AI241923, AI611738, AW163834, AW051088, AL039086, AI282679, AW054964, AI868931, AI917252, AW118518, AL040241, AI570807, AI582932, AI802542, AI174394, AL037030, AW198075, AI446373, AI912510, AI499890, AI890907, AW026882, AI474146, AW074869, AI280732, AI619502, AI677796, AI680162, AI352497, AI863382, AI886753, AI824576, AI923370, AW083778, AI624293, AI280607, AI433157, AI702073, AL037649, AI310575, AL037582, AL037602, AI457369, AI762739, AI932794, AI340533, AI520809, AI633125, AI698391, AI270706, AI915291, AW152182, AW166903, AL036638, AL047675, AW131294, AI889189, AI473536, AI270183, AW088899, W74529, AI627988, AI537837, AI288305, AL046990, AI572096, AI783997, AI288050, AW169234, AI675052, AW088903, AW079572, AW168373, AI699865, AI917963, AI926878, AI284131, AL036150, AW071417, AI620284, AI340603, AL036673, AI500061, AI493248, AI886181, AI632408, AI866770, AI620089, AA449768, AI886123, AI554821, AI269862, AI933589, AI635067, AI434468, AW149925, AI537261, AI863191, AL119863, AI445992, AA806720, AI623941, AI538085, AI564749, AW150794, R32821, AI288285, AW079409, AW078818, AW029611, AW151136, AL046944, AW130930, AI866469, AW161156, AW051258, AI590686, AI468872, AI886415, AI349645, AI473451, AI926367, AI537677, AA916133, AL042440, AI540821, AI569583, AW072719, AA641818, AI499285, AI690748, AI587606, AI340519, AI872423, AL048482, AI670009, AI521560, AI348847, AW268122, AW268302, AI559586, AI343091, AI610402, AI345677, AI310582, AI340627, N33175, AW162189, AI859991, AL110280, I89947, I48978, AL050092, AF113689, AF111849, AF026816, AF113691, Y14314, AR038854, A45787, AL137271, Y16645, A08916, U80742, AL117435, A08910, A08909, A08913, X84990, A03736, I33392, A93350, I48979, AF183393, I89931, AL110221, AF177401, I49625, AL080159, AF111851, AL133075, AL050149, AF113013, AL050277, AF087943, A08912, AJ000937, A77033, A77035, AR000496, U39656, AL137533, AF090901, AL137476, AR020905, X82434, X87582, AF153205, S78214, AF090900, U78525, AL050138, U35846, AL137480, A58524, A58523, AF162270, AF100931, AF113677, AL050024, AL137648, AL050146, E02221, AL137463, AR011880, AF113019, L19437, AL137478, Z82022, E07108, AF078844, AR038969, AF090934, AF017437, Y11587, AL137538, AL117460, AL137488, AL137292, X83508, X72889, AF091084, AL137550, AL080074, AF061981, AL080060, E03348, A18777, E06743, AL137560, AL049382, M30514, AL137294, AL133560, AF008439, AF111112, AL122123, S61953, A65341, E05822, E04233, AL133640, AF090903, I09499, AL110225, S68736, Y07905, AL050393, AL122121, AJ012755, AF081197, AF081195, X53587, AF113694, U67958, AF210052, L30117, E15569, AF061795, AF151685, AL133016, X65873, AL133565, AF104032, AL133606, AF119337, AL110196, I42402, AL133665, AL117457, AF158248, U49434, AF139986, AF079765, AF067790, I03321, Z37987, AL023657, AF125949, AF061573, AF097996, A08908, E02349, AL050116, L31396, I66342, AL133113, L31397, U91329, X96540, AF118064, AR059958, AF026124, AF125948, AL117440, AF185576, E12747, AF106862, X81464, AL122110, AL137521, AF113690, AL133067, AL137556, AL049466, AF067728, AF132676, AF061836, AL117585, AL122100, U96683, AF146568, AL122118, X93495, AL117432, U72620, AL080124, AL049300, AF090943, AL137557, AL049283, AL133080, AL049430, AF113699, U00763, U58996, AL1117583, AF079763, AL133557, Y09972, E08631, AL050108, AF090896, AL080148, I00734, A12297, AL133072, AB019565, Y11254, AL122050, AL080154, M86826, AB007812, AF113676, E00617, E00717, E00778, X63574, A07647, AF126247, AL137526, AF118094, AL049452, AL133081, AL137459, AL096744, AJ003118, AL080137, AF057300, AF057299, AL080086, I26207, AF003737, AL122049, AL049938, AL049314, AJ238278, U68233, AL117649, I92592, AL122093, AL049464, U42766, AF032666, U88966, A21103, AL133104, I09360, AL133093, AF118070, X62580, A90832, Z72491, AL122111, AL117416, AL133098, AL122098, X92070, and AF017152. |
| HE2FB90 | 54 | 691077 | AI857437, AI857436, AI278048, AA507045, AW273440, AW297803, AA493364, R47896, AI292326, AI364487, N66632, N58844, AI361304, AA347485, AA357233, N80769, AI374919, H08044, R47895, AW189621, AW439143, AA887910, AI394536, AI591191, AI279880, AI280275, W65494, AI797532, AA357422, H07938, W65483, and AI123607. |
| HTHDJ94 | 55 | 693652 | AI290720, AI741602, D79185, AW024422, AA401528, AA417131, AI333681, W47348, AA280813, AA905310, AA569922, AA573334, AA902128, AW027880, AA570689, AI312759, AA976250, AI092605, AA558902, AA151226, AI041784, AW262597, AA280806, N36166, W32108, AA151227, AA406299, AI090180, AA781961, AA115004, AI623995, AW239455, AI027447, AA065116, AI377228, N59607, AA451762, AI804317, AA724950, AA449952, AA450034, AA115005, AI186329, H10448, AA482977, AI242335, AA453022, AI032607, |

TABLE 6-continued

| Clone ID NO: Z | SEQ ID NO.: X | Contig ID: | Accession #'s |
|---|---|---|---|
| | | | AI804465, AA640751, C16610, AI149260, AA987598, AA781332, AI804069, AA973798, AA452663, AA127134, AA872873, H82385, T86790, T82258, H10449, F30722, T78950, W32213, AI424359, AA338139, AA296988, T78898, AI285049, AI278719, AA451764, W47452, AA541483, F06459, Z28571, Z39388, AA297494, T86695, AI318411, F01234, AA808781, AA297421, AI991656, AA661544, D31389, AA280856, AA280942, AA064799, Z24822, AA031579, AA298704, AI670708, AW238447, AA494107, AA296942, AA031458, AA297411, AA297354, AA099261, AA098866, T83540, AA297420, AI675090, AA194682, AA368017, AA297201, D20890, AI908416, AA897425, AA530981, AA411374, H70649, AA449811, F24096, AF125533, AF169481, and AF091084. |
| HTOHJ89 | 56 | 695763 | AA101269, AI792578, AI054419, AA847499, AW023111, AI612070, AA477503, AI611533, AI379719, AI440117, AW162288, AC002310, Z97196, AL022165, AC002470, AF129756, AC004139, AC006064, AF031078, AC006509, AL022320, Y14768, AF030876, AC005088, AL022336, AF024533, AL109801, AC007308, AL132712, AL022326, AL022316, AL031255, AL031577, AL034549, AC004221, AL009181, AL022327, AC006241, AP000045, AP000113, AP000501, AP000356, AC004622, AF111168, AC006965, AC005280, AC004216, AC005702, AC005969, AC004812, AL121754, AP000302, AL032821, AC004408, AC004382, I34294, AL121655, AC009946, AD000092, U91326, AL031677, AC007227, AC002350, AC005694, AB023048, AC009516, AL031767, AC005837, AC008372, AC005730, AC003006, AC003042, AC006011, AL024498, AL035249, AP000114, AP000046, AC007226, AC004476, AC007151, AC005829, AL031775, AC007182, Z95116, AC005911, Z95115, AF196779, AC006130, Z83826, AL050341, AC007766, AC005370, Z85986, AC002133, AC009542, AC002364, U85195, AC005231, AC006511, AC007685, AC005379, AL050318, U95742, AE000658, AC009247, AC004967, AP000555, AC005484, AP000252, AC004890, AF106918, AC007686, AP000143, AC007240, AC007216, AF165926, AL080243, AP000500, AC005726, AL049758, AC005914, AC002365, AC009330, AL031650, AC005071, AL021546, AC004381, AL008735, AC020663, AF196969, AC005067, AL049692, AL049748, AC007546, U91322, AL109798, AC007371, AC006449, Z94044, AP000354, AC004805, AC000134, AC007774, AC005212, AL035659, AC002544, AC005261, AC007367, AP000115, Z98946, AC005545, Z98742, AL031602, Z85987, Z86090, L44140, AC005933, AL049776, Z93017, AC005562, AC006101, Z98051, AL022311, AC004195, AC006538, AL022476, Z84487, AL035587, AC006958, AP000090, AC005527, and AC004780. |
| HUSHB62 | 57 | 680495 | AI096616, AI937128, AA478989, AW148649, AI635678, AA580461, AI871452, D61293, AA701343, AA947641, AI077699, AA587392, N92014, N22807, AW090032, AI913164, AI566329, AI304741, AI832816, AI920824, AI688989, AA505810, AI474080, AI591133, AW024245, AI423395, AA918351, AI285282, AA834943, AI870350, AI559195, AA838061, AA775249, AI435008, AA703175, R97195, AI421979, AA723388, N63869, AI339068, AA478599, T16357, AA868966, AI272181, AL039420, AA769928, H28566, AA363734, AA916277, AW337191, AI262344, D81371, H19664, AI239934, R56668, H03426, AI282295, H13067, AW276930, AI197924, AW363835, R21517, AI863591, AA299531, AI001889, AI420251, R53825, AA384624, AA962591, AL121415, C17798, AI276296, AA534355, AA013482, AA507743, Z45873, AI193397, R76057, AA947445, D78950, H53668, AI803908, R56831, AA327530, R21620, AA304103, AA327544, AI631817, F09191, AI695253, HI1336, T16635, H53629, T35087, AI610263, AW275794, R12800, AI601236, R97196, AI287902, AW128986, H04135, AA574194, AW118490, Z41505, AA865671, AW192504, AW151452, AI205173, AI244106, AA477926, AW316864, AA322273, AA363735, R39499, R39500, F11529, T35056, AL039419, AA960860, R75882, T19229, AW376282, AI934081, AA557576, T06706, H28565, R19084, AW384792, AJ011001, AL137591, AF106858, and AF166382. |
| HSXAG02 | 58 | 667848 | AW370368, AW137077, AI601240, AI803696, AI168184, AA121075, AA527028, AI334348, AA603723, AI432655, AW296548, AA420755, AI371852, N28275, AI268286, H93203, AW300705, AW453008, AA420796, T09453, AI761383, AA555003, AA122417, AI864017, AI698470, T09015, F11705, AA987938, AW083439, AA826633, AA972661, AW149398, C00601, AW183138, AI828119, D51113, R49527, AI251099, AA405926, AA936580, F09363, AW449144, C16721, R24145, H66763, W30922, Z39944, AW136862, H08616, T30425, AA405803, H46486, T30746, T51043, T50980, AA666060, AW131331, AW020419, H50168, AI469290, AI918408, AA720850, AI360816, AI434731, AA765198, AI334893, H95782, R37188, AI828795, AI699175, AL134598, AI432110, AA883351, AW195253, R75918, AI358271, AI263331, AI887775, AI619820, AA862606, AA806605, AA824513, AI783808, AI335235, AL042365, AI274811, AI683585, AI804505, AI500659, AI147877, AW151929, AI446046, AI815232, AI801325, AI866691, AI500523, AI538850, AI582932, AI923989, AI590043, AI284517, AI872423, AI440260, AI500706, AI289791, AI926593, AI889189, AI500662, AW151974, AI284509, AI538885, AI927233, AI866573, AI401697, AI866469, AI888661, AI500714, AI285439, AI859991, AI355779, AI889147, AI581033, AI491710, AI611728, AI584118, AI440238, AI860003, AI539260, H03560, AW151979, AI571699, AI285419, AI494201, AI866581, AW074057, AI567953, AI690930, AL047152, N23647, AA928539, AI251221, AW104746, AI932970, AI174819, AI799179, AW087915, AI621341, AW058275, AI921379, AI066497, AI261815, AL079910, AI538637, AW000738, AI800473, AI499325, AI250646, AI868180, AA587120, AL047422, AI537943, AI307569, R25628, AI521596, AA643038, AW130785, AI800159, AI349186, AW021662, AB026894, AL080083, A65890, AF140224, E01614, E13364, AL137479, AF161493, E12580, X73361, AJ001388, AF061795, AF151685, AL133053, AL133015, X56530, AL137292, AR005195, AF114168, AL133054, X87582, AL137716, AF161699, AL110218, AL137298, AL117438, U42766, AR038854, AR050959, Y10080, A08912, I32738, A08911, L24896, A18777, U75932, AF141315, AF097996, |

TABLE 6-continued

| Clone ID NO: Z | SEQ ID NO.: X | Contig ID: | Accession #'s |
|---|---|---|---|
| | | | AL049423, AL133084, U30290, AL133608, AL133049, S76508, AL110159, AF100781, AF017437, S63521, AL109672, AF093119, A44314, AL117457, AF113694, A08913, AL133557, I28326, A08910, AF054831, A08909, U78525, AJ004832, I77092, L04859, AF002985, A08908, AF035321, AF090900, AR034821, L13297, AF111845, AF043345, AL050277, A91160, AF177401, S68736, AF112208, E08443, A93016, AF028823, A20553, Y09972, U62807, A60092, A60094, AF031572, AC006288, I13140, S36676, X60786, AF131826, AF039202, AR068753, S82852, AL137537, AF026816, AF090943, U58996, M85165, AF199509, AL080140, AF004162, AF151109, I08319, AL133560, Y10655, M19658, AF131814, A07588, AF098484, AR068751, X83544, AL117583, AF076633, AF200464, X52128, AL080162, AF090886, AL133016, I09499, AL137533, AF199027, AF158248, AF090903, X99971, AL080126, AL050092, X72889, AL049276, I89947, AF161418, S71381, AL136884, AF090923, Y11254, AF065135, A76337, A76335, I08608, AF017790, X55446, I92592, S73498, A90832, X06146, X57961, AL049557, I48978, AF054289, A26498, AF118094, AL050024, AR029490, A49139, AJ006039, S83440, AF106657, Y07915, AF124435, U75604, AF107018, AL022165, I29004, X66417, X00861, AF167995, X15132, AF091084, X75295, AL117460, AL080234, AF125948, AL136842, AL110224, AL137521, M79462, AL110280, AL137267, E06743, A23630, X97332, AL110171, AF105427, AF113019, AL049347, AL133623, and AF056194. |
| HHTLH52 | 59 | 665722 | AI805189, AW136027, AI634613, AA292087, AI201246, AI693706, AI675765, AW390785, AA868564, AI654869, AW390814, AI077669, AW082330, AI695580, AA995665, AA758454, AW373785, AA757902, AC004893, AL133396, AF165142, AL034374, AC004837, AC002416, AP000045, AP000113, L44140, AC006501, AC003071, AC006255, AC005058, AL096776, AC008014, AC002326, AC005663, AC004797, AL049795, U95739, AC004878, AL031721, AC005488, AC005291, AP000116, AC007193, AC004084, AL009031, AF199364, AL022165, AL031390, AF030453, AL035450, AC002301, AL022163, AC005088, AC005224, AC004966, AC006210, AL049553, AC005520, AC011311, AC005216, AC002527, AP000013, AC004477, AF001549, AF045555, AC007425, AC004613, AL022315, AC016027, AC004213, U95742, AL121603, AC007216, AC002558, AC007358, AC005971, AC006312, AC003666, AL033521, AC005562, AC005519, L78753, AC005081, AL021329, AC002394, AC007773, AC005028, Z84486, AC007245, AP000226, Z83838, AP000250, Z98036, AL031282, AL031283, AP000087, AC005962, AC002565, AC004884, AL022723, AC003089, AC000119, AC005157, AC002086, AC005250, AC002432, U51560, AL079342, AC005102, AC007055, AL109865, Z84480, AP000211, AP000133, AP000030, AC004139, AP000344, AC002377, Z80896, AC003108, AC005242, AC002365, AC006120, Z93930, AC006344, AL035072, AC002430, AF064865, AC009113, AF111168, AL133445, AC003111, AC005074, AC002289, AC007384, AC004134, AL021937, AC006203, AC004895, AC006112, Z82214, U91323, U62317, AC005479, Z99297, Z93244, AF067844, AC006139, AC008372, AC004465, AL031774, AL021393, AC007151, AC005993, AC003029, AF088219, AP000359, AC009320, AC007237, AL022721, AC002504, and AC000025. |
| HCFMS95 | 60 | 674464 | AW276842, AL036382, AI963720, AI637587, AI954260, AI708009, AA610491, AA581903, AW439558, AI633390, AI859284, AW193265, AW085780, AI345654, AW082108, AA491814, AI956144, AI831819, AA569471, AL046409, AA493471, AA623002, AW304584, AA526979, AI344844, AI564454, AL042420, AI061334, AW088846, AA177120, AI284640, AI064952, AI814735, AI890570, AI890928, AI561060, AI568678, AL119691, AW265393, AI860020, AL121385, AI273968, AI783494, AA714453, AA828042, AW303196, AW274349, AI355206, AA551552, AI431303, AI670124, AI345681, AW301350, AI345675, AA578861, AI801600, AI956131, R66997, AI350211, AW070892, AI305766, AW238278, AA947364, AW088202, AW083402, AI613280, AI270117, AA601492, AW276827, AA598824, AA371434, AL041690, AA806796, AI368745, AW303876, AW419262, AI141675, AA594725, AA683258, AW083364, AW250970, AI446464, AA226153, AW438643, AW302013, AI807650, AA535661, AA225246, AI239488, AI085719, AW189303, AI619997, AI064864, AI281881, AA559290, AI334443, AA136338, AI634384, F36273, AW265009, AA469451, AA483223, AA219129, AL040130, AI873916, AW102955, AA781975, AI669453, AA525898, AL037683, AW082492, AA507824, AA468131, AI368256, AA643962, AA678671, AA775230, AI471481, AI431240, AA525790, AA632994, AA079831, AI623898, AA809029, AI110688, N54894, AI625244, AI561255, AW249224, AI754658, AL048925, AI345157, AI053790, AA526787, AW270619, AW104748, AI374809, AA503475, AI375710, AA649642, H71429, AI133164, AA526191, AW151855, AI889923, AA513141, AW276435, AW193432, D82290, AI688846, AW088718, AI160117, W79504, AI969436, AI538433, AA513181, AW029038, AL044940, AA570227, AI908381, AI240168, AA468022, AA584881, AI537955, T53128, AI801591, AA523837, AI798473, AW085794, AA552856, N53150, AW410400, AI251436, AA583955, W47183, AA877817, AA531372, AA720702, AW162049, AA652057, AI962050, AI929531, AA280632, AL138265, AA493206, AA857486, AW261871, AI859742, AI610159, AI689222, AA665021, AI636627, AI370094, AI345518, AW162246, AA908422, AI635818, AW088224, AW270382, AI370074, AW265385, AI798266, AI312309, AL022316, AC005031, U80017, AC004999, AF084195, AC005773, AL031055, AL079340, Z82217, AC007993, U85195, AE000658, AP000082, AC019014, U57004, AL031429, AL034412, AC005480, AC005264, AC008078, AL117471, U57007, AC004234, U73479, AC006392, AJ251973, AC006059, AF015155, AC004087, M94634, Z93017, U01102, S75201, AL033375, AL021938, AC007382, AC004941, AC004010, AF015153, AF015148, AL009029, AL049844, AC006238, Z98043, AF184110, X51956, AL022156, Z97987, U47924, AC006292, AC006276, U57009, AC006512, AF181449, AL031577, AB028893, AC004098, AC004009, AC002449, X74558, AC004870, D83989, AC005221, AL022476, AP000305, AC006449, |

TABLE 6-continued

| Clone ID NO: Z | SEQ ID NO.: X | Contig ID: | Accession #'s |
|---|---|---|---|
| | | | AC005250, M19364, AP000047, AC005815, AL031293, AL049761, U18391, U18392, U57005, X55925, AL118497, Z83844, X69951, U38672, AC007151, U18394, AC006077, AC006126, AC006057, AP000115, X53550, AF015157, AC005323, AF077058, Z82198, AL035659, AC007068, AL031255, AL133353, X54181, AC005391, AC005548, AL022302, AC005162, X54180, U18398, U57006, U18395, U18393, U57008, AL034562, AL023553, X54178, AC007671, U18387, U40369, X75335, AF076952, AF156539, X55926, U18396, Z95124, AC003695, AC004853, AL136295, X54175, X54176, AC006536, 151997, U18400, AF050154, AF144630, AL078581, AL121603, AF064863, AC003081, X55931, AC004745, AP000348, AL022322, AL096678, U18390, AL109865, AL078474, X55924, AC004594, AL121934, AL133396, AC005599, AC006539, AF015151, AL117344, AC005696, AC005919, AC005261, AC007537, AC005076, U18399, AC005154, AC006041, AC005210, AF045448, AL023807, AC004047, AC004501, AL022328, AC006367, AC005518, AP000359, AF121781, AF088219, AC006130, U62317, AC007065, AC007681, AC007564, AF015147, AF015156, AC005682, AC007103, AC002508, AC004019, AL031313, AC006312, AC003050, X54179, AL023803, AP001137, AC006989, AF196779, AL035681, AC006597, Z98751, AC004894, AL031315, X55932, L81583, AF085442, X55922, AL049631, AC002470, AF015152, AC008249, AC006537, AC004895, Z98200, AC004672, AC005690, AC007676, AF015154, AP001172, Z98744, AC002564, AF190465, AL031585, AC006120, AC005701, M37551, U67801, Z82245, AC000115, AC007324, AL008732, AL035695, AC008101, AC007043, AC006213, AF031077, AL049709, AF135028, AC005084, AF015167, AC005324, AF117829, AL078604, Z97632, AL050308, AL031446, AL136504, AC008079, AP000567, AC005304, AF015158, AC003957, AC005102, AL031668, AL022323, AP000356, AF074708, AC002368, AC007371, AC007656, and L48038. |
| HOUCT90 | 61 | 646817 | AW023515, AA715814, AA659232, AA513851, AA704393, AW237905, AI753672, T05118, AA602906, AI683131, AA535216, AI307201, AA019973, AW327422, AI076228, AA559241, AW023975, AI267269, AI635440, AA410788, AI249365, AI380617, AW023111, AI523316, AA644090, AA683069, AA654778, AA668291, AI144081, AA569591, AW062682, AI923052, AI792521, AA169245, AW302711, AW304580, AI056177, AA633892, AI365625, AI929410, AI792499, AA640430, AA630535, AA492015, AA515048, AA182731, AI887235, AA115863, AI912401, AA470567, AA455483, AA484267, AI246796, AL079734, AA659832, AA825827, AI053793, AI049709, AW316599, AA747757, AI669421, AA572813, AA084609, AA487272, AI754170, AI192440, AA669238, AL038842, AA583394, N35306, AA515728, W96277, AW270619, AA640410, H78898, AI053934, AW407632, N23913, AA780515, R95840, AL037714, AI874201, AI538491, AI628859, AI675615, AW410354, N34477, AA502532, AA313025, N72170, AA503298, AA282820, AI224619, AA622801, AA714011, AI362442, AC004876, Y07848, AC000026, AB023050, AC002059, AP000511, AL022238, U89335, AC006992, AC007021, AC006549, Z85987, AC002511, AL049776, AC006441, AC007663, AC006430, AL050332, Z85996, AL031281, AC003950, AC004686, AF031078, AC005104, AL109798, AF030876, U95742, AP000558, AC009516, AL031685, AC018633, AC006130, U07562, AC005058, AD001527, AC007688, Z95116, AP000047, AL021394, Z82176, AC000070, AC004707, AC000082, AC004408, AC006064, AP000115, AL121655, AL022336, AC004794, AJ246003, AC006312, AC006547, AC005390, AP000553, AL049872, AF134726, AC007684, AC005482, AP000304, AC004851, AC005081, AC002504, AL049745, AP000302, AC007216, L78833, AC002302, AC004382, AC000097, AC004814, AC004067, AC004032, AC004991, AC006468, AC005071, AL034548, AL049757, Y10196, Z73359, AF222686, AL049538, AC005180, L44140, AC005908, AP000141, AP000143, AC007151, AL031666, AL031588, AC006077, Z84469, AC004079, Z93024, AC004212, AC000393, AC004106, Z97184, AP001060, AC005284, AP000694, AC004638, AJ009610, AF042090, Z82215, AC003042, AC005829, AC005138, X58050, AC004671, AC006543, AC005041, AC005800, U78027, AC002404, AC005412, AC004057, AL031664, AC003109, AC005324, AC005529, AC005183, AC007731, AC004694, AL031282, AL035413, AF111168, AC006080, AC004655, AL035422, AC002350, AL109758, AL023284, AC004882, AC005212, AC007899, AC004531, AC006211 AL035417, AF196969, AC005005, AC004783, Z98044, AC004019, AF109907, AP000114, AP000046, AC007546, AL021940, AC007540, AL021707, AP000152, Z92542, AC005695, AC005031, AL022165, AC004878, AC005043, AL022237, AC006011, AP000557, AL079342, AB004907, AL022316, AC005046, AL133163, AF050154, AC002310, AC002394, AC006544, U80017, AF031076, AC000025, AP000505, AL020997, AP000279, AL109801, AL035658, AC002365, AF001549, AC004945, AC005952, AL031005, AC008038, AC009247, AC007386, X55922, AL035659, Z98036, AL031427, AC004834, AC007537, AC008040, AL008715, AC004678, AP000512, AL021391, AC007868, D87675, AL021546, AC003065, AC006449, AC005500, AC005527, AL031589, AC005033, AL031659, AC005765, AL133448, AC004955, Y14768, AP000501, AC002476, AC002984, AC002425, Z73360, AL023807, Z81365, AC004887, AL133500, AC006930, AL022302, AC010205, AC003972, AF129756, AC007156, AC005409, AL035461, AC005667, AC004033, AC000090, Z93241, AC000159, AC005015, AC007051, AL109984, and AC003983. |
| HCFLR78 | 62 | 679532 | AA573144, AA005018, AI978717, AI983151, AA007460, AW129961, AI023529, AI023528, AI097101, AI138990, AA429301, AI307122, AI281472, AA724365, AA074611, W47513, AI126957, AA843528, AA621024, N92125, AI151489, AA005019, AI023888, AI963099, W74039, AW296547, W47514, AI052664, AI369723, AI470114, AA203390, AA634442, AI289000, H75708, AI288995, AI131387, AI093686, H77802, AA470883, H09852, AI092232, AA758859, AA873611, AA463447, AA663901, AA365043, AI080292, H12975, |

TABLE 6-continued

| Clone ID NO: Z | SEQ ID NO.: X | Contig ID: | Accession #'s |
|---|---|---|---|
| | | | AA937147, H17224, AI014968, R74259, AA612948, AA682858, AA609107, AA358497, AW009774, AW383643, AA443488, AI076595, AJ243243, AA426125, AA862640, T99925, AI636974, AA336306, AI246182, AI050921, AA508211, D55400, AW445069, W19308, AA865885, H66722, N77454, AI266464, AI018497, R02421, AA889290, AI247759, H75637, H00584, H00583, R28482, D53939, AI798308, AI909657, R09589, AA449327, W72360, W90696, R32666, AA873850, AA074610, AW264053, AA524719, N63685, AA515478, AI742730, AA425024, F29136, AA429478, AA843783, AA635518, AI263801, D52605, AW008958, and AF151807. |
| HTOHT18 | 63 | 628300 | and AC004928. |
| HKPMB11 | 64 | 688048 | AI767027, AI985304, AA552150, AW058459, AI762127, and AW363648. |
| HNFHS38 | 65 | 872798 | AA576409, R33161, AL036490, AF064782, I89937, and I89938. |
| HAIBU10 | 66 | 695699 | AI767136, AW003744, AA553744, AI360184, AI565814, AW051486, AA505513, AW301029, AA679066, AI376801, AI341735, AI268928, AI761796, AI090327, AI767627, AI700593, AI538258, AA987212, AW003752, AI185049, AI682919, AA460766, AI343947, AI174548, R72610, AW027615, AA460166, C01651, R68273, R72274, AW207668, W46139, AA329290, AI393145, AI624837, AA810925, R11148, R94606, T84462, AI749190, AI659411, AA757401, R11149, AI424444, AI653008, AI337023, AI539289, AW173060, AA961062, AI150522, AA535727, AI797658, AW304422, AI620080, AA609486, AI911307, AW269588, AI357832, AI762382, AA723777, AW449936, AI937537, AI699787, AW235819, AI806859, AW182752, T96516, AA039581, AA993113, AW196492, AA931719, AA749267, AW003753, AA938372, N87192, AI750035, AW074390, AI239833, AI979278, AA722791, R68308, N95006, R94246, R97183, AA385572, AA811736, AA090761, AW294034, AI675733, R29264, AI628714, AW418794, AI700162, AI418602, AA905467, AW362416, and AW362436. |
| HAPOK30 | 67 | 685705 | AI350913, AA456130, AA459754, AA922659, AA729889, AA897044, AW207589, R60787, AA373089, AA514352, AI797424, AA737686, AI434406, AI025403, AW295994, AI492263, AA811057, AA629548, AI823834, AW027718, AI741138, AI637804, AI521795, AI094328, AI420179, AI277236, N26754, T16381, AW271660, AW337972, N66648, AI242353, AI094233, AI042022, AI690072, AI273673, AL036251, AA487475, AC004659, AF126403, AC005184, AC001231, AE000658, AC007564, U85195, AC005829, AC007227, AC007934, AL049775, AL109938, AL035079, AC005377, AC005250, AC002070, AC011504, Z83821, AL020991, AC006313, AP000514, AB014080, and Z99128. |
| HCEEM18 | 68 | 694615 | AI433694, AI287242, AA016140, AA769504, AA248824, AI174876, and AL031230. |
| HCWUA22 | 69 | 695683 | |
| HDSAG91 | 70 | 692361 | AL048773, AA837369, AA056206, AI200051, AW265393, F32668, AW023111, AA657918, AI307201, AA484148, AI815425, AL046746, AI267349, AW269488, R96401, H98660, AI349874, AW438542, AA664521, AA218851, AI264743, AI267450, AI267847, AW021116, AI623720, R90740, AI267356, AI499503, AI287832, AW028429, AA664604, H73070, AW270768, AW277174, AL045848, AA693370, AA713570, AA604843, AA167744, AI538852, AA713569, AA826144, AL118947, AA317170, AA381762, AA651864, AA584581, AI921188, AA577852, AI801482, AI446205, AA714595, AA877817, AL133243, AC008015, AP000046, AC006960, AC005215, AL031276, AL023284, AC005228, AL033527, AL022162, AC005091, AC002504, AC007191, U82695, U76377, AL035458, AC007539, AC002364, AC007130, AL049872, AL117351, AC004549, AC006061, AL034345, Z97205, AC006487, AC002543, AL078581, AP000338, AC007172, AP000216, AC006455, AC004531, AL031228, AC008282, AL031652, AC012384, AL109628, Z82243, AF107045, AC006344, AC004381, AC004087, AL117355, AL023694, AC005516, AC007216, AP000090, Z95118, Z84487, AL117258, AC004712, AC005161, AC004982, AL049569, AC002302, AC007030, Z74739, AC007057, AC005829, AC007347, AC004217, AF015416, AC004975, AC002105, AL049761, AC003957, AF196971, AL139165, AB022537, AL024508, AL049563, D87675, Z93931, Z98751, AC006088, AC004900, AL049552, AC004858, AL035361, Z82184, AC000118, AC005669, AL021328, AL021937, AC004894, AC002454, AC007102, AL121694, AF109907, AC005249, AL122003, AC007551, AC007314, AC002457, AR036572, AL078462, AC006101, U91328, AC007970, AL122023, AL022726, Z73358, AL049697, AC005075, AL031668, AJ010770, AC005005, AL109613, AC016025, AL022401, AC004848, AL050308, X54175, AC004702, AC007656, AF067844, AC007114, AC004013, Z95113, AL035454, AC006285, AC008040, AF165926, AF114156, AP000965, AC005154, AC013417, AL121769, AC018633, AL031255, AC002476, AC006084, AC004703, AL078474, AC005902, AP000011, AC004638, AP000030, AF104455, AL121595, AL021453, AC002531, Z93016, AC005722, AC004128, AP000211, AP000133, AP000884, AC005011, AL049835, Z93244, AC005158, AC005288, AC007676, AL031283, AC006115, AC002331, AL022723, AL121658, AC002377, AJ246003, AF205588, AL033521, AL023655, AC004522, U73634, U11309, AC007617, AL031132, AC006430, AC004458, AC004242, AC006241, Z95115, AL139054, AC007488, AC005094, AC007666, AC006530, AC004802, AL121852, AC005048, AC005191, Z85986, AP000153, AC008071, AC002472, AC002981, AC003007, AC005007, AC005785, AP000472, AC006160, AJ250235, AC008033, AC004806, AL137100, AC004987, AC004111, AC005907, AC006333, AL050318, AC005519, AC004002, U96629, AC005058, Z49258, AB020867, AL031428, AP000964, AC002430, AL133485, U85195, Z83841, AP000025, AL022345, AE000658, AC002429, AL035693, and AL133500. |

TABLE 6-continued

| Clone ID NO: Z | SEQ ID NO.: X | Contig ID: | Accession #'s |
|---|---|---|---|
| HNEDJ35 | 71 | 695744 | AI613459, AI090377, N68677, AW275432, AI310670, AI224583, AA573067, AI016704, AW085751, AW410844, AW151102, AI124798, AA489390, AA595661, AW021917, AW080811, AI547110, AI654285, AA809125, AI334435, AA013168, AL121039, AI433952, AI702049, AI284583, AL037910, AW272815, AW075979, AA365586, R23873, AA324108, AA019973, AW117740, AA831426, AA425283, AA350886, AI174703, AA693484, AW148821, AW151247, AA904275, AI753131, AI251696, AI523205, AI355572, AW265468, AW327868, AI349130, AI049999, AI690379, AI935827, AA904137, AI926728, AA631915, AL037067, AW327624, AI078409, AI473671, AI061313, AW270652, AA484143, AL041375, AA629992, AW270258, H07953, AW302659, AA743996, AW302705, AA584360, AL045709, AA828045, AW265385, AI921161, T74524, AA602906, AW302315, AI801563, AA525423, AL079734, AA311535, AL039117, AA640305, AA720732, AI439525, AA679946, AA280886, AI754037, AA720582, AI887468, H62123, AI452836, N99245, AA507623, AI445815, AW327852, AA642809, AI754421, AW167799, AA878149, Z49154, AC007207, AC005386, AL080243, AC007541, AC005516, AC002558, AL022328, AC006132, AL117340, AL049869, Z83826, AC005993, AC006271, AC016027, AC002302, AL132641, U95742, AC005004, AC004253, AF038458, AC007216, AC007421, AC002314, AC002430, AL035072, AC007384, AC005488, AC000052, AC005081, AL021707, AC016830, AL022320, AC006251, AC004150, AC006543, AC004000, AP000111, AP000043, AC008044, AC002563, AL021978, AC006285, Z98200, AC003101, AC005632, AC003035, AL031848, AC004820, AC005668, AC005531, AL049776, AF205588, AC006544, AL021453, AL133246, AC004019, AL034420, AC006449, AF045555, AP000326, AC007676, AL050343, AC006236, AL133243, AC005940, AP000169, AP000122, AP000054, AP000359, AL078581, AC012331, AL049760, AL096791, AC005288, AC005527, U80460, AC005060, AC007395, AC008082, AC005247, AP000688, AL049694, AL031587, AL050348, AC003029, AC002347, Z83856, AC008101, AL121754, AL133448, AC005971, AC004560, AC005234, AC004796, AC005696, AL049589, AC000085, AC005529, AP000557, AC002425, AL117258, AL121653, AJ003147, AL117337, AB023050, Z95152, Z92543, AC005703, AL035414, AL049570, AL008582, AC005057, AL022316, AC004771, AL136295, U85195, AC004893, AC005694, AC002044, AF207550, Z98256, AC003042, AE000658, AL049794, AC005502, AC004050, AC000025, AF109907, Y18000, AL031427, AC006137, AL121658, AL117694, AC005899, AC006126, AC005291, AC005225, AL049766, AC005218, AC008079, AL121603, AC007204, AC007308, AC006347, AC004079, AC005837, AC007151, AC004087, AC004590, AF134726, AC006241, AC005841, AC006120, AC006013, AP000509, AP000009, AJ011930, AC003982, AL049758, Z84480, Z94056, AC004678, AC004212, AC002395, U91324, AC005856, AC007731, AC004686, AC007666, AP000248, AC005500, AC005553, AL022326, AC005921, U91321, AP000692, AC007298, AP000552, AC008009, AC005800, D84394, AP000556, AL031255, AP000512, AP000354, Z75887, AL035696, AC005519, AL109985, AP000301, AC002428, AC003043, AC005399, AC002091, AC004878, AC002470, AC004895, AL034549, AC005832, AC004821, AC005046, AL049576, AL096701, AC005257, AL121655, AL109963, Z83840, AC005091, AC007845, U73023, AC006373, AC007537, AC005255, AF196779, AC003665, AC006160, AC003070, AL049780, AD000812, AC005300, AC007055, AL049757, AL031650, U62293, AC002300, AC004975, AC002312, AP000080, AL021391, AC007041, AL049778, AE000659, AL031588, AC005284, AL035415, AC005003, AC002301, AC006480, AC006441, AC004020, AF196970, AC007225, AC005231, AL033527, AC005220, and AD000092. |
| H7TBA62 | 72 | 861995 | R82515, AA514191, AA514190, AF121051, AF095853, AF033115, AF018071, D44443, L39119, AR038762, AJ005168, Y11107, AF046029, U67221, AJ245869, AC005501, I58669, I15353, AR018866, U89924, A58521, AB029348, D88984, AF054142, A49700, U85943, AF033196, AF095855, I65436, AR062871, D49729, AJ001044, AJ006789, AF013625, AF044960, AJ250192, U92795, AF019721, and AF045229. |
| HNGIO50 | 73 | 691288 | |
| HMIAW81 | 74 | 667504 | AA614239, and AC006518. |
| HMMCJ60 | 75 | 663467 | AL118912, U91321, and AC003982. |
| HDPIO09 | 76 | 686765 | AI804463, N32803, AW373516, N32577, AW182870, AA676790, W87853, AI038081, AA478157, AI334288, AA776795, AA306403, AI351376, AI203592, AA280706, AI089377, AW205251, AW391127, AI675872, AW391220, N30775, AI123770, AI148454, AI222245, AA133659, W90305, AI220222, W87683, AA418887, AI472099, AA133660, R13704, AA127057, AW367495, AA932329, AA287753, AA948045, H04073, AA826530, AI266054, AA742688, W90615, AI024654, AW408660, AI184331, AA255740, AA025466, AA418888, AI094116, AA431370, AW391079, AA343934, AA456495, AA545796, R81593, AA419218, AI191834, AI275548, AA001310, H69110, AA432367, AA255539, AA680159, AI218857, AW166628, AL120413, AI468727, AW102705, AA203443, AA384514, AI740920, AA846384, AA001680, AA478158, AI417822, AI863025, AW383212, AW205723, AW374902, T98259, AA361259, AA001638, AW166981, AL121099, T98314, AA360747, AI148591, R27882, R18829, AA476304, AA125934, AW390975, AA361382, AA013465, AW391073, AA767404, AA262028, T25723, AA832312, C21543, AA373327, AA419219, R81340, H03380, AA993124, AW139299, AA628282, and AB007963. |
| HHFHH34 | 77 | 688045 | AL109984, AC007216, AC004228, U95742, AL049759, AC004770, AC005694, U95090, AB023048, AP000694, AC004883, AC007238, AL022238, AC006536, AL031053, and AC006947. |

TABLE 6-continued

| Clone ID NO: Z | SEQ ID NO.: X | Contig ID: | Accession #'s |
|---|---|---|---|
| HISCL83 | 78 | 688047 | |
| HTOAI70 | 79 | 840223 | AI002744, AA636025, AA838190, AI223700, AC004049, AC004408, AC006511, AC006212, AC005747, AC002565, AC007066, AC005736, AL031311, AC004032, AL133448, AL096703, AL034417, AC004967, AC005071, AC006013, AC003101, Z85987, AC002492, AC007546, AC005191, AC002554, AL035423, AF001550, AC000029, AL022323, AC006101, AL035400, AC000353, AC005914, AL022336, AL121653, AF111169, AC008134, AC002351, AC004832, AP000696, AC005682, AC006449, AC004067, AL050307, AF038458, Z82194, U91321, AC006946, AC008072, AC007842, AL132985, AL031985, AC005280, U52112, AC005189, AC007227, AC005384, AC004976, AL008718, AP000248, AC004216, AC004526, AC016026, AC005486, AC005512, AF176915, AL035249, AC006139, AP000514, AC004531, AC005181, AL031283, AC004703, Z98304, AC007021, AL035420, AC003661, AF001549, AC004491, AC006960, AC007461, AL020997, AC000105, AC010582, AC004112, AC002551, AC010197, AC006006, AC005015, Z98950, AC005229, AC009263, AC005562, AC006973, AC004815, AC005880, AC005043, Z97054, AC005207, AP000100, AL096791, AP000688, AL034548, AC006568, AC005666, AL121655, AC004770, AF003529, AC005722, AC005608, AC007327, AC009464, AL022165, AC006991, U96629, AC005031, AC003663, Z85996, AC002543, AC005255, AC005081, U91327, AC004099, U95626, AC004887, AC004520, AC004905, AC005300, AC004707, AC006084, AL035417, AC004381, AP000359, AC004841, AC002369, AC007488, AC005046, AF111168, AL121756, AC002070, AP000117, AC004876, AL122021, Z77249, AC000025, AL031721, and AC001226. |
| HSDER95 | 80 | 664502 | AW005333, AA631227, AA143192, AA181022, AI301959, H98648, AA594850, AI478582, AA287457, AI393857, N75788, AA211849, F06608, N22567, AW450628, AA563681, AW195766, AI915322, AA186657, AA992992, AA143136, AI302352, AA631048, AI341927, AI870902, N75929, AA973384, AA160641, and AA338837. |
| HNECL25 | 81 | 618777 | AW243793, AW022608, AW270258, AA287872, AA490908, AW304580, F00564, AA487475, AL048275, AI050070, AL042756, AA631396, AW117829, AA601278, AC000159, Z95152, AC004832, AC005089, AC005527, AC007546, AC005529, Z97054, AC005899, AC005081, AL049540, AC007227, AC006211, AL049776, AF111168, AP000030, AC004263, AL109865, Z93016, U52112, U85195, AL031602, AC004966, AE000658, Z93017, AC005519, AC007225, AL109801, AC004531, AL133448, AL049779, AC005736, AC005071, AC002126, AL022323, AF134726, AC005844, AC007666, AC004228, AL121653, AC005088, AC003665, AL133163, AC005874, AF134471, AP000553, AC005225, AC006530, AC005049, AL035587, AC016027, AC006480, AL022313, AL020997, AL034429, AL049795, AC005944, AC005197, Y14768, AL049758, AC008072, AL022311, Z86090, AC002115, AC005484, AL096791, AC016830, AC004019, AL080243, AC002425, AP000505, AC007114, AC007934, AC007308, AC005291, AC003029, AL035659, AC005200, AF196971, AP000251, U95740, AC010197, Z98884, AL009183, AL034549, AC004821, AP000152, Z98036, AL031848, AL096701, AC006312, AC004659, AC005913, AC006241, AL035458, AC004217, AC004686, AC020663, AC005821, AF001548, AL031680, AP000503, U91323, AL022316, AC005104, AC004841, AC005668, AL021154, AL049757, AC007057, AC007371, AF030453, AC002316, AP000116, AC005670, AC007842, AF118808, AC002400, AL049713, AC005231, AC004674, AL022165, AP000350, AC004963, AL049764, AC005839, AL022320, AC009247, AL121652, Z99128, Z83846, AC015853, AC004106, AD000812, AC005632, AL121603, AC005781, AL049636, U96629, AF111169, AC002365, AL050321, AC006449, AP000351, AC005488, AC000052, AP000269, AL139054, AL031311, AC004876, AP000555, AL023284, U91318, AC003678, AC002350, AC007688, AL133445, U62317, AC005209, AC007676, AC004703, AC004922, AC004084, AF067844, AP000557, AC007637, AL031589, U62293, AL035089, AC004813, AC006441, Z93023, AC006111, AC004678, AC002483, AC002470, AP000500, AC004967, AL031846, Z85987, AC004087, AC002312, AC005778, AC005015, AC005740, AC007450, AC006057, AC007686, U47924, AC005531, AC005046, AC004962, AC002551, AC009516, AP000103, and AL022721. |
| HNFGZ45 | 82 | 618786 | AI887235, AI192440, AW410784, AA282951, AA579130, AA904211, AW023111, AA579152, AA568747, T50676, AW270258, AW303098, AI250552, AI362442, AI278972, AI251284, AI251203, AI284543, AA613630, AA084609, AA482776, AI251034, AW020088, AI431513, AI275982, AI366555, AI590906, AA602951, R83708, AI446452, AW029515, AI561210, AI872216, AA115863, AI821714, AI792133, AA595499, AI791913, AW189113, AI254770, AI799421, AA912287, AA225406, AA613624, AI792464, AI888468, AW303196, AW274349, AI693979, AI821785, AW272294, AA550850, AI284092, AA947265, T06518, AW079761, AW301350, AI249853, AI859946, AI272052, AI732789, AI380617, AI669421, AI635028, N22058, AC005189, AP000346, AP000347, AC004125, AL049779, AC007993, Z95115, AC006160, AC002073, Z94056, AC006088, AC003957, AC006537, AC004084, AC007151, AL023096, AL121578, AF196969, AL020997, AC007842, AC007637, AC005902, AC006064, AL117258, AC003070, AL031311, AC005703, AC002347, Z85996, AP000359, AL031597, AL034548, AL079342, AC006006, AF001552, AC005920, AC004408, AC002395, AC006312, AL132712, Z82244, AC004834, AC006965, AL022726, AC005736, AC005914, L78810, AL078463, AC006948, Z85987, AL031589, AF165926, AC004000, AC005081, AC005514, AC004982, AC004097, U89336, AC005031, AC006450, AP000302, AB023049, AF129756, AC004837, AP000115, AL132800, AL096701, AC005192, AC007425, AC007688, AL035683, AL049778, U91322, AC008170, D87011, AC010206, AC002375, AL021808, AF037338, AC008085, AL132641, AC007221, AL133355, AC002302, AL009181, AL034420, AC002554, AL035249, AL049569, |

TABLE 6-continued

| Clone ID NO: Z | SEQ ID NO.: X | Contig ID: | Accession #'s |
|---|---|---|---|
| | | | AC005971, AC004520, U91319, AL009172, Z82215, AC005005, U95739, AL035587, AB003151, AC002563, AP000513, AP000114, AP000046, AL031729, AC004466, Z83844, Z93017, AC004477, AL121603, AL021707, AC006449, AL022323, Z68869, AC006050, AC005082, AC002551, AL035462, AC002352, Y10196, AC004929, AC006111, AL022163, Z82188, AF196972, Z99570, AC007242, U91323, AC002492, AC008044, AC000392, AP001049, AC004492, AC004659, AF017104, AC006487, AC005316, AC005488, AL031228, AC004525, AL031291, AL021918, AC004815, AC005231, AC005291, AL049872, Z85986, AL031659, Z86090, AC008080, AC005225, AC005837, Z97183, AC006505, AC005066, AL035361, U91318, AC002303, AC006398, AC004927, AC005988, AC004526, AP000172, AL050307, AC008249, AC004448, AC009044, AC002300, AC006040, AC004812, AL122023, AP000057, AC004778, AC005071, AL031680, AP000085, AP000694, U91327, AC005520, AC005317, AL049540, AP000125, Z98257, AC004531, AL022336, AC005666, AL049712, AL109802, L77570, U95090, AL031276, AL020995, AC005778, AL021397, AL022316, AL080278, AC005562, AC002301, AL021391, AL034412, AL031670, AC003029, AL022721, U47924, AC004876, AL034554, AF207550, AF111167, AL021155, AP000493, AF196779, AC002565, AL049759, AP000558, Z83838, AF006501, AC008018, AL031678, AP000550, AC005245, AL031984, AC004230, AL021878, AC004099, AC007160, AC004816, AC005874, AF134471, AL022476, AP000338, AC007292, AL049539, Z97195, AF099810, AL096712, D86992, AL031846, AC000075, AC005003, AC004797, AL021407, AP000689, AP000696, AL078638, and AC007386. |
| HHGCU49 | 83 | 688046 | AA610125, and AA679911. |
| HDPND68 | 84 | 693214 | AA663075, AA047850, N58606, AA077458, AA856937, AA828871, AA807210, AA078031, AA077602, W58609, AW129389, AI186819, T87361, AI089362, AI287723, AI874364, AA450298, AA323098, AA411245, AA437334, AW105275, R50539, AI123195, AI566985, AA928290, AI418162, AA411170, AA731141, AA810894, AA812128, AA419599, AA463970, AA427583, AA862081, W58608, AA306683, AI866126, AI500451, C01071, AW058069, AW058057, AA291009, AA447967, AA0011588, AA078563, AA290621, AI805526, AA015835, AI805341, AA610550, AA078595, AA393321, AA077098, R27266, R66759, AI520978, AA291720, N26141, AI571067, AI096500, AI027709, AI885893, AI225016, AI434401, AI889278, AA291823, H82512, AA635813, AA583169, AA503752, AA780801, AW089311, AI206412, AI888819, T16137, AI141818, AA035214, AA161026, AI282157, AI375694, AA282042, AA437275, AI761298, AA908680, AA411808, AA770647, AI985940, AA098984, AI500026, AI355393, AI039000, AI039733, AA917605, AA621085, AA037468, AI282159, AA077481, AC006014, AC004878, AC005488, AC005071, AC004084, AC006480, AC005088, AF030453, AC002045, AL049760, AC004656, AL049694, AC002492, AC006210, AC004998, AL023283, AC004865, AL034408, AL121576, AC005090, AL022308, AC009411, AL049828, AC005066, AP000702, AP000701, and Z95889. |
| HETDT81 | 85 | 684320 | AI823398, W27116, AI581128, AL119465, AA897785, AW004741, AI808377, AI280964, W28405, R60290, AW006936, AI872266, AW137140, AA383051, AI167420, AA215764, AI362366, AI184026, R28463, R26454, W07404, AI701315, AI871468, and AF110799. |
| HHLBA14 | 86 | 690808 | AL046937, H08012, H08129, AA309286, Z43050, R22834, and AC006924. |
| HLTBU43 | 87 | 695735 | AI133350, AI739016, AW300169, N36266, AI972422, AI826155, AI678721, N28853, AA769899, T41222, T40368, AI086442, AL050309, Z69733, AC004038, AC010349, AC005062, AL121654, AC002524, AC005389, AC008109, AC009411, AC007527, AC003035, AC005250, AC006600, AL050334, AC005969, AC004025, AL031114, AL023876, AC000110, AL121578, AC004020, AC004865, AC004029, AC011422, AL049843, AL022575, AL030995, AC005145, AC003971, AC004015, AL022401, Z92846, AC002980, AC010196, AC006971, AL035552, AL136297, AC002075, AC005014, AL008708, AP000233, AP000147, AC003080, AP000152, AP000011, Z93341, AP000360, AL049834, Z99128, AC000053, Z93403, Z74696, AC002479, AL121782, AL034350, AL132800, AC004629, AC003013, AC002060, AC000004, AJ006997, AL031387, AL049875, AB014088, AC005518, L11910, AL133233, AL049830, Z95325, AC004384, AP001137, AL109620, AL031054, AP000516, AC004835, AP000526, AC007363, AC005537, Z98746, Z82203, AL031885, AL035423, AC006155, AC006367, AC004103, Z95124, AC005002, AP000069, AL122023, AC002476, and AC002448. |
| HNTSJ84 | 88 | 689474 | AI827770, AI962616, AA805764, AA824592, AW136273, AI952021, AI991996, AW182593, D61365, AI362069, AI934672, AI126330, AW169950, AA252349, AI362077, AW006061, AA598594, H79076, AI167818, AI040236, N35889, AA972128, N20949, AI928628, AA252198, AL134524, AL038878, AL045327, AL134110, AL045328, U46344, AL135012, AL042898, AL047163, AL045494, AL042523, AL038024, AI318479, AL042420, AL037295, AL038838, AL038761, AL037343, AL038041, AL045891, AI547295, AL038983, AI142134, D29033, AL037436, AL048657, AL037335, AL042655, AL037323, AL048677, AL038651, AL042468, AL042741, AL038040, AL042519, AL038745, AL037727, AL037443, AL038532, AL038822, AW363350, AL045326, AL043089, AL043321, AL046356, AL042488, AL037341, AL041955, AL039432, AI547258, AL039360, AL039643, AB033037, AL133028, AR066494, A93916, A93931, AL133053, A85203, AL122101, A93923, D17247, AL133074, AL133049, and AR023813. |
| HOHCG16 | 89 | 679018 | W03235, N69989, N58737, R01251, R72832, R46310, R73289, AA493321, AA002182, R46782, N72648, H43991, H43992, R46517, R50293, R37273, R46214, R72018, R72019, R45144, R01365, AI473522, R46877, R07516, R46516, R07468, T78715, R93643, AA382228, and AB028980. |
| HTHCB31 | 90 | 693201 | AA490084, AA694325, AC007541, AC007686, AC005225, and Z93023. |

TABLE 6-continued

| Clone ID NO: Z | SEQ ID NO.: X | Contig ID: | Accession #'s |
|---|---|---|---|
| HUKAM16 | 91 | 695767 | AI720817, AA625436, AI279619, AI686480, AI080242, W76270, AA778254, W72455, W72270, W76514, AA894476, H28670, H77984, AA886785, AA299801, AI589802, H24539, R54675, AI538603, AA441799, AI476560, R15815, AI969936, AI866817, AA363431, AI560023, H39513, AL048656, AI889168, AI819545, AL121328, AI890057, AI801167, AI679550, AI886055, AI446405, AW409775, AA908294, AI698437, AI929108, AW152182, AI250871, AA514684, AW161202, AA769318, AI365256, AI934147, AW084247, AI679916, AI857296, AA830406, AL036705, AA464646, AW162194, AW151034, AA128660, AI277008, AI559863, AW026630, AI918554, AI677797, AI804505, AW089932, AI628214, AA835966, AL110306, AA830821, AI250627, AL046463, AW162189, AW082532, AW074374, AW084772, AI570966, AI436644, AW166612, AI500061, AW263804, W38553, AI089766, AI950664, AI799244, AI652028, AI499920, AL138386, AL038575, AA693347, AI859654, AI696378, AI683634, AI669459, AL120736, AW105601, AI921746, AI634626, AW161892, AI524179, AW172723, AI244380, AI280661, AW149876, AW083573, AI687568, AW085786, AI612732, AW050725, AI679622, AI829495, W46513, AI540606, AI915295, AW026905, AI919345, AI539153, AI251205, AI689420, AI050666, AI567582, AI624529, AI089970, AI924971, N80094, AI491852, AI628344, AI336634, AW151652, AW265004, AL042384, AL042787, AW087199, AI636619, AI583578, AI249946, AW301410, AI699788, AW088162, AW081343, AI924686, AI874243, AW193467, AI802372, AI800411, AI623736, AI371228, AA827630, AI690813, N27632, AW163823, F37364, AI582912, AI824360, AW068845, AW161098, AI921386, AI419374, AW194185, AW193530, AI349622, AI270039, AI798373, AI431424, AI784028, AI889147, AL038445, AI255071, AI683465, AW088944, AI857241, AW051048, AI801605, AI590575, AI620093, AW268261, AW084097, AI358701, AI679800, AW078680, N71180, AI799234, AI961403, AI934000, AL038541, AI633125, AI684145, AI621171, AI873605, AI590035, AW188382, N75771, AI591407, AW263569, AI802826, AL036652, AI864857, AW073898, AI952862, AI634219, AW087203, AW073697, AW083804, AI282903, AI827058, AI096771, AI824557, H42825, AW020480, AI373914, AA911767, AI521538, AI141288, AL079794, AL039086, AI635013, AI783861, AI345415, AI689614, AI360560, AW088560, AI418254, AI951222, AI355277, AI624668, AI521095, AW078729, AW026730, AI497733, AW079334, AA808175, AI886206, AA627473, AI553669, AW102816, W33163, AI434242, AI251221, AW075084, AI310925, AI633477, AW190725, AI537617, AI696969, AI312399, AI952217, AI349937, AI469112, AI745713, AI918408, AW089572, AI334884, AI307543, U42031, AF036941, X06146, AL110197, AL137529, Z72491, AF158248, AF126247, AF067420, A8019565, AF113690, AF017152, AF118094, AJ010277, AL133568, AF031147, M86826, AF012536, AL137526, L13297, AL122098, U87620, I48978, AL117460, AL117585, E04233, AL110221, U92992, AF114170, AL137557, AF141289, AL050172, AL117435, I89947, E03348, U92068, AF065135, E03349, S69510, X59414, A08913, AF102578, E15569, AL133104, AI8777, I89931, AL049452, AJ003118, S68736, S77771, A08912, A08910, A08911, Y11435, I49625, A08909, AB026995, AB025103, L31396, L31397, AR038854, A08907, A08908, E01963, U96683, S76508, I00734, I89934, X79812, X62580, X70685, M27260, X54971, E00617, E00717, E00778, AL133077, AL133645, X80340, I26207, U90884, I42402, E02221, AB029065, AL050310, AL137556, AL109672, Y11587, E01812, U75370, AJ006417, X62773, AF207750, AL133558, AL050024, AL133081, AL137536, I17544, AF090886, AF036268, AF081571, X67813, AL133072, AL137665, AL137300, AR029580, U00763, AF030165, U68233, I92592, I66342, AF182215, AL035458, Z22828, AF114818, AF113676, A12297, X72387, U77594, A57389, X76228, X56039, AL137478, U35146, AF125949, AF015958, AL137548, E01614, E13364, I89944, X60786, AF038847, AR019470, AL137530, AL137641, X84990, AL117578, AL122045, S69407, AL137660, AL137555, AF118070, L40363, AL049460, AL122106, AL122111, AL137459, AF017790, U66274, AF106934, AF139986, AF119358, AL133049, AFI13013, A08916, S61953, AF078844, AF067790, AF113694, AF051325, AL050280, AF159148, AL137538, AF151109, AL137656, AL133014, A27171, U80742, A03736, U91329, AF008439, AF113691, D55641, AF026816, E01573, E02319, AL110171, AL122110, S75997, AR020905, AJ001838, AL137283, AL049464, S63521, AL133636, X99257, AL110196, AL137560, AF132676, AL117626, AF061836, A94751, AL117649, AL137547, AF016271, AL137658, A90832, Z97214, AF167995, AL137276, E02914, Y10655, AF119337, L10353, X66871, AF090943, AF069506, M30514, I52013, AJ242859, I17767, U95114, E15324, AF185614, J05032, Z37987, AF000301, AL117457, AL137558, AF199027, U68387, U57352, AF177401, AL110225, AL117394, A52563, AL080126, AL137294, AF137367, AF057300, AF057299, A93016, M85164, AF089818, AF107847, AF210052, I30339, I30334, AL050116, AL137256, AL122118, AL080137, S79832, AL110222, AF022363, AL117629, X72889, AF113699, and AF179633. |
| HLDOJ66 | 92 | 665402 | AA805014, AA728939, AA736485, AI754286, AI610651, AW192331, AA582746, AL042221, AI654655, AA664879, AA971711, AW083934, AA551582, AA070899, H05449, AA507282, AI499954, AI922217, H67234, AC004859, AF001549, AL035415, AL022330, AC004032, AC007792, AL031311, AC002300, AC005225, AC002477, AC004967, AC007425, AL050307, AL121754, AL079342, AC005015, AC006449, AL031680, AC004832, AL031276, AC006211, U15422, AL031685, AL022336, AC006966, AB015355, AC007225, AC004791, AC005486, AC004383, AL121652, AC005071, AC004491, AL022165, AL049591, AL049843, AL031594, U07561, AL021917, AL049780, AL008723, AC007388, AC005520, AC002302, AL031003, AC007676, AF111169, AL031657, AC006530, AC002115, AC005803, AL049776, AC005081, AC005878, AL049709, AC005736, AC005620, AC007563, AC005796, AL049749, AC005412, AL121603, AF064860, AC004813, AP000704, AF196971, AB023048, Z82188, AC005295, AC006480, AP000100, AC006441, AL109984, |

TABLE 6-continued

| Clone ID NO: Z | SEQ ID NO.: X | Contig ID: | Accession #'s |
|---|---|---|---|
| | | | AC003663, AL022399, AL035400, AC002308, AC004797, AC005082, U91321, AL133353, Z98941, U96629, AC005041, Z93023, AL024498, AC002347, AC006581, AC007151, AC007030, AC007546, AC007993, AC005844, Z93930, AL008718, AF196969, AC016025, AL049697, AC008126, AL049631, AP000350, AC002994, AC006537, U52112, AP000008, AC005291, AC005821, AC000025, AL049794, AL023807, AC005060, AC004805, AC010206, Z98752, Z83819, AC004000, AP000104, AC005529, AC005332, AC006205, AL049869, AC002425, AF111167, AC006013, AL021327, AC005874, AP000511, AF134471, AP000509, Z98036, AF093117, AC016830, Z82203, AC007021, AC002404, AC004477, AL133245, AC004844, AC004638, AL049712, AC005632, AF088219, U95090, AC005531, Z83844, AC005881, AC016027, AL035447, AC007263, AC002301, AL031123, D84394, AC003684, AP001053, AC004540, Z77249, AC002351, AL139054, AL008627, AL035086, AC004216, AC004878, and AC007227. |
| HTXKF10 | 93 | 663473 | AC006484, AC007878, AC005226, Z94056, AC012330, AC006055, AC005480, AC007981, AC004943, AP000550, AC007325, AC008018, AL022163, AC002073, AL049843, AC004216, AC005736, AL022476, AC002301, AC007308, AC004933, AC005274, AL121748, AL024498, AL020993, AC004797, AC002375, Z99716, AC004859, AC005305, AL035423, AC005800, AC002477, AL022328, AP000563, AC005225, AJ010770, AC006088, AC005156, and AL121603. |
| HPMAI22 | 94 | 635491 | AI540210, AW173208, AW006589, AW104434, AI148598, AI656207, AI350808, AW297121, AW237250, AA918535, AA918200, AI357673, AW235193, AW083055, AI350807, AI200477, AI991567, AA953496, AI825590, AA738163, N59298, AA369466, H71562, AA369367, AA369366, H71045, T48746, and H71557. |
| HL2AG57 | 95 | 695733 | AI829139, AW264273, AW070588, AA872984, H06954, AI369038, AW134647, AA974445, AA902284, H14753, AI904699, AW006498, AA970510, H06955, AW243991, AA306732, and AA333155. |
| HTHBH29 | 96 | 882405 | AI284640, AW276435, AI610159, AI613280, AI580652, AL046409, AW276817, AA623002, AI821271, AI249997, AA488395, AA469451, AI888518, AI653636, AI963720, AA569471, AW303196, AI334443, AL041690, AI246119, AW023672, AA856954, AI814735, AI887483, AI744995, AW301350, AA610491, AA613345, AI358343, AI053790, AW270270, AW408717, AW406162, AL048925, AW406447, AA877817, AI434695, AW169537, AI357288, AW148792, AI149478, AI053672, C75026, AI589230, AI133164, AA394271, AW274349, AW338086, AI085719, AI267818, AI537955, AI499938, AA583955, AW238278, AI890348, AI431303, AA908357, AA653618, AI374809, AA244357, AI133102, AL042420, AI564185, AA493471, AL119691, AL138455, AA488746, AA577906, AA808877, AA665021, AA653975, AL037683, AI336660, AA490183, AA503475, AI830390, AA587256, AA581903, AI521679, AI270559, AI286356, AW008952, AI148277, AI246796, AW071196, AL138265, AW265385, AI349850, AL044940, AA468131, AA649642, AI951889, AA758934, AI005388, AW301809, AI749559, AW265393, AL044858, AW162489, AI471481, AI951928, AA669840, AW327868, AW303876, AA708678, AL046898, AI434706, AI368256, AI564454, AI871722, AI270117, AI281903, AL046205, M77974, AW083402, AI565581, AW088202, AI817516, AA503258, AI446601, AI307201, AA491814, AA126051, AA126035, AA491284, AI298710, AA514737, AA908422, AI266576, AI669453, AI951863, AI457397, AI801591, AI471543, AA515905, AA633936, AA079462, AI061334, AW088846, H94870, AA572713, AA829225, AI744188, AI635818, AI341664, AW304584, AW157651, AI634384, AI928898, AI859251, AI633390, AA838333, AI561255, AI282310, AL135405, AA828856, H88666, AA486559, AW261871, AA503154, AI510838, AI224093, AA610271, AI744827, AW084252, T07287, AI654525, AA100599, AI734872, AI865905, AL119984, N48230, AW407578, AI305547, AI471534, AI801600, AW089322, AI287651, AA613232, AL040130, AI128353, AI207401, H71429, H09313, AI683577, AW243960, X75335, AF015150, X74558, U67221, AL021579, AF015153, D83989, AL049869, AF015151, AF015156, X55926, AC004664, AC000003, AC006946, AL096701, U18391, U18394, AF015148, AC005399, U18393, AC005756, M37551, Z81369, U18395, U85195, AF015147, Z81308, U47924, AE000658, AF015149, U57009, AF109907, X55925, AL079295, AL050312, U18387, Z82244, X54175, U91326, AC003101, I51997, AC004760, U18396, AC005411, AC002432, AC002465, AC002553, U57007, U38672, AC006111, AC002544, U18392, AC005291, AC007012, X54181, X54176, U38673, U91323, U57005, AF077058, U02532, Z22650, AL022336, AL031683, AF141976, AC005304, AF015155, AC005545, AC005181, X54178, X55924, X55931, AP000047, AP000049, AC004686, U38675, AL132641, X55927, AL035458, AL078621, AF015154, AC003086, AC005206, AP000116, AC006277, AP000115, AC005667, AP000311, AC005844, AP000305, AC007787, U67211, AC005225, AC004195, AB004907, AC005488, AC006548, X54179, AC002056, AF037338, AF015157, AL021707, Z95329, X53550, U02531, AP000556, AC006239, AF129756, AC002375, AC006312, AP000504, AF111168, AC003029, AC004862, AB023060, AC004777, M87916, AF001548, X54180, U67827, AC006047, U67801, AC004219, AC005697, AL023803, AC007685, AP000512, AC005771, AC007666, AC005666, U11309, AB023051, AC005274, AL050341, U18399, Z46936, U57008, AL117356, U95740, AC007216, AL080243, AL023553, U95742, Z99916, AC007283, AL031594, AP000509, AC000085, X55922, AL122020, AC008008, AL133448, AC006014, AL049776, AP001054, AC004019, AC004699, AP000967, AC009516, AC000090, AF169121, AC006359, AC007390, Z97053, Z93017, AC004957, AC004895, AJ006995, AL117258, AP000477, U34879, AC007664, D84394, AF015160, AL049594, AC004617, AL031311, AC008372, AC006130, AP000503, AL035423, AL024498, AC006166, AP000510, AC007011, AL133396, AL121754, AC009405, AC004447, AC004547, AC002457, AL096791, AC004825, X62025, AL031295, AL031277, |

TABLE 6-continued

| Clone ID NO: Z | SEQ ID NO.: X | Contig ID: | Accession #'s |
|---|---|---|---|
| | | | AC005412, AC006116, AC002395, AP000020, AC005786, Z97200, AL009028, AC004216, AC004991, AL121603, AC006084, AP000355, AF039590, AC005529, AC000070, AC004253, Z99716, AC006020, AC004854, AC006538, AC005944, AC005231, AC006333, M87917, AC004525, X54177, AC006241, AC007199, AC002091, AL049764, AC006088, AL121655, AC000083, AC006947, AC005057, AP000345, AP000207, AP000129, AL132777, U18398, AP000356, Z84814, AP000567, AC005159, X55448, U72787, AJ010598, AL034420, AC006275, AL049697, AP000351, and AL031283. |
| HUSAM59 | 97 | 664505 | AI097107, AW070331, AA885479, AI808635, AI808760, AI806642, AI359136, AA526850, AI743373, AA830249, AI097104, AI418914, AI263892, AI091575, AI742264, AI660637, AI218017, N25567, AI687290, AI149468, AI423504, AA056058, AI425096, AW080003, AA662766, AI699928, AW136639, AI674380, AA278628, AA789184, AW172424, H09719, AI950490, AI435913, AI092275, F34735, W31769, AI192998, AA749063, AA659932, AW003176, AL134147, AA907350, AA768824, AI968635, AA253111, W32476, AA576431, AI470700, AW303675, AW196635, H14752, AI216029, AI624069, AI005582, AA021513, AI659546, N68031, R63310, R12287, AA280617, AA158531, H13396, AA843425, AI474557, AA319692, AI087824, AA912809, R18232, R84736, AA770430, I73345, R25515, R36860, AA988334, H96095, AA868055, AA768638, AA299057, AA369839, AI762252, N52758, AI758489, AA809759, R20615, AI184905, H46838, AA029481, AA778585, R16041, AA253055, Z39839, H40110, AA483843, AA278627, R37936, H06060, R46123, AA282001, W04668, AA730323, H40174, AA215402, AA903630, AW304327, AI091241, AA885041, AA813856, and AC006263. |
| HNGGR26 | 98 | 688054 | |
| HTLCX30 | 99 | 675636 | AI656951, AA470111, AA897538, AW452331, AI970293, AA469941, AI890868, AW014651, R44057, AA812843, AW071964, AI916916, AI480054, AW002112, AI248788, AI248426, AI675608, AI926984, W88679, AA768893, AA709247, AW006299, T18862, T52506, AA779510, AI014337, AA992522, AI964071, D29261, AW103701, AA404555, AF155098, AF135016, AP000547, D87003, AC004527, AC002041, and AA132101. |
| HCEBC87 | 100 | 646713 | AL046649, AA446161, AI936225, AW015005, AW150185, AI382086, AI768700, AI207383, AA723583, AI221375, AA454867, AI025876, AW078908, AI373629, AA282528, AA747091, AI041381, AA160990, AA480040, N46327, AA455209, AI240230, AI024163, AA321984, N46331, D61581, N63661, T31481, AW088780, AI025261, AA948537, Z20134, H10717, AI764971, T89167, Z21302, Z20133, R40286, Z21303, AI702127, N40996, AA018284, AA452557, AA479066, T85209, and AA452740. |
| HATCB92 | 101 | 603948 | AI253043, AA621792, N84222, AA094505, and AB020635. |
| HMSCX69 | 102 | 692125 | AI23531, W07173, AA480028, AI803282, AI708223, N62829, AI203954, AI094156, AA872061, N49953, AW005810, AA433846, AA411225, AA761754, AA745807, AI708531, N50810, AA243455, AA422108, AA824620, AI281390, R26124, AI246265, AA257995, AI766585, W01365, N78578, AA243448, AA761087, AA883328, AA257994, AA766741, AI361501, Z41792, AA479057, AA740668, AI868726, AA837149, Z46162, AA282715, N52735, N31703, N48176, and AB020653. |
| HLHAL68 | 103 | 684216 | AA359084, AC008149, AC006057, AC007308, AF064861, AL021329, AC005180, and AC005197. |
| HEOMR73 | 104 | 691244 | AI341807, AI651516, AI337376, W86648, N46466, AA522544, AI279721, W86523, AI245138, and AI262580. |
| HETIB83 | 105 | 690863 | AL042250, R38741, F06975, R24942, T80007, R45205, Z40078, Z44674, F03694, AF070524, and D13896. |
| HJPDD28 | 106 | 842041 | AI620815, AL049064, AL042003, AA781401, AW248711, AI568876, R01265, AL044223, AA682242, AA887723, AW238884, AW372959, Y16610, AF090912, AF080514, AF080515, AF080512, AF080513, and AF080516. |
| HBAMB15 | 107 | 671835 | W27833, AI860764, AA809619, AA768248, AI370876, AI291737, H96013, AW051697, AI633038, and AI784315. |

Having generally described the invention, the same will be more readily understood by reference to the following examples, which are provided by way of illustration and are not intended as limiting.

EXAMPLES

Example 1

Isolation of a Selected cDNA Clone from the Deposited Sample

Each cDNA clone in a cited ATCC deposit is contained in a plasmid vector. Table 1 identifies the vectors used to construct the cDNA library from which each clone was isolated. In many cases, the vector used to construct the library is a phage vector from which a plasmid has been excised. The table immediately below correlates the related plasmid for each phage vector used in constructing the cDNA library. For example, where a particular clone is identified in Table 1 as being isolated in the vector "Lambda Zap," the corresponding deposited clone is in "pBluescript."

| Vector Used to Construct Library | Corresponding Deposited Plasmid |
|---|---|
| Lambda Zap | pBluescript (pBS) |
| Uni-Zap XR | pBluescript (pBS) |
| Zap Express | pBK |
| lafmid BA | plafmid BA |
| pSport1 | pSport1 |
| pCMVSport 2.0 | pCMVSport 2.0 |
| pCMVSport 3.0 | pCMVSport 3.0 |
| pCR ® 2.1 | pCR ® 2.1 |

Vectors Lambda Zap (U.S. Pat. Nos. 5,128,256 and 5,286,636), Uni-Zap XR (U.S. Pat. Nos. 5,128,256 and 5,286,636), Zap Express (U.S. Pat. Nos. 5,128,256 and 5,286,636), pBluescript (pBS) (Short, J. M. et al., Nucleic Acids Res. 16:7583-7600 (1988); Alting-Mees, M. A. and Short, J. M., Nucleic Acids Res. 17:9494 (1989)) and pBK (Alting-Mees, M. A. et al., Strategies 5:58-61 (1992)) are commercially available from Stratagene Cloning Systems, Inc., 11011 N. Torrey Pines Road, La Jolla, Calif., 92037. pBS contains an ampicillin resistance gene and pBK contains a neomycin resistance gene. Both can be transformed into *E. coli* strain XL-1 Blue, also available from Stratagene. pBS comes in 4 forms SK+, SK−, KS+ and KS. The S and K refers to the orientation of the polylinker to the T7 and T3 primer sequences which flank the polylinker region ("S" is for SacI and "K" is for KpnI which are the first sites on each respective end of the linker). "+" or "−" refer to the orientation of the f1 origin of replication ("ori"), such that in one orientation, single stranded rescue initiated from the f1 ori generates sense strand DNA and in the other, antisense.

Vectors pSport1, pCMVSport 2.0 and pCMVSport 3.0, were obtained from Life Technologies, Inc., P.O. Box 6009, Gaithersburg, Md. 20897. All Sport vectors contain an ampicillin resistance gene and may be transformed into *E. coli* strain DH10B, also available from Life Technologies. (See, for instance, Gruber, C. E., et al., Focus 15:59 (1993).) Vector lafmid BA (Bento Soares, Columbia University, NY) contains an ampicillin resistance gene and can be transformed into *E. coli* strain XL-1 Blue. Vector pCR®2.1, which is available from Invitrogen, 1600 Faraday Avenue, Carlsbad, Calif. 92008, contains an ampicillin resistance gene and may be transformed into *E. coli* strain DH10B, available from Life Technologies. (See, for instance, Clark, J. M., Nuc. Acids Res. 16:9677-9686 (1988) and Mead, D. et al., Bio/Technology 9: (1991).) Preferably, a polynucleotide of the present invention does not comprise the phage vector sequences identified for the particular clone in Table 1, as well as the corresponding plasmid vector sequences designated above.

The deposited material in the sample assigned the ATCC Deposit Number cited in Table 1 for any given cDNA clone also may contain one or more additional plasmids, each comprising a cDNA clone different from that given clone. Thus, deposits sharing the same ATCC Deposit Number contain at least a plasmid for each cDNA clone identified in Table 1. Typically, each ATCC deposit sample cited in Table 1 comprises a mixture of approximately equal amounts (by weight) of about 50 plasmid DNAs, each containing a different cDNA clone; but such a deposit sample may include plasmids for more or less than 50 cDNA clones, up to about 500 cDNA clones.

Two approaches can be used to isolate a particular clone from the deposited sample of plasmid DNAs cited for that clone in Table 1. First, a plasmid is directly isolated by screening the clones using a polynucleotide probe corresponding to SEQ ID NO:X.

Particularly, a specific polynucleotide with 30-40 nucleotides is synthesized using an Applied Biosystems DNA synthesizer according to the sequence reported. The oligonucleotide is labeled, for instance, with $^{32}P$-γ-ATP using T4 polynucleotide kinase and purified according to routine methods. (E.g., Maniatis et al., Molecular Cloning: A Laboratory Manual, Cold Spring Harbor Press, Cold Spring, N.Y. (1982).) The plasmid mixture is transformed into a suitable host, as indicated above (such as XL-1 Blue (Stratagene)) using techniques known to those of skill in the art, such as those provided by the vector supplier or in related publications or patents cited above. The transformants are plated on 1.5% agar plates (containing the appropriate selection agent, e.g., ampicillin) to a density of about 150 transformants (colonies) per plate. These plates are screened using Nylon membranes according to routine methods for bacterial colony screening (e.g., Sambrook et al., Molecular Cloning: A Laboratory Manual, 2nd Edit., (1989), Cold Spring Harbor Laboratory Press, pages 1.93 to 1.104), or other techniques known to those of skill in the art.

Alternatively, two primers of 17-20 nucleotides derived from both ends of the SEQ ID NO:X (i.e., within the region of SEQ ID NO:X bounded by the 5' NT and the 3' NT of the clone defined in Table 1) are synthesized and used to amplify the desired cDNA using the deposited cDNA plasmid as a template. The polymerase chain reaction is carried out under routine conditions, for instance, in 25 ul of reaction mixture with 0.5 ug of the above cDNA template. A convenient reaction mixture is 1.5-5 mM $MgCl_2$, 0.01% (w/v) gelatin, 20 uM each of dATP, dCTP, dGTP, dTTP, 25 pmol of each primer and 0.25 Unit of Taq polymerase. Thirty five cycles of PCR (denaturation at 94 degree C. for 1 min; annealing at 55 degree C. for 1 min; elongation at 72 degree C. for 1 min) are performed with a Perkin-Elmer Cetus automated thermal cycler. The amplified product is analyzed by agarose gel electrophoresis and the DNA band with expected molecular weight is excised and purified. The PCR product is verified to be the selected sequence by subcloning and sequencing the DNA product.

Several methods are available for the identification of the 5' or 3' non-coding portions of a gene which may not be present in the deposited clone. These methods include but are not limited to, filter probing, clone enrichment using specific probes, and protocols similar or identical to 5' and 3, "RACE" protocols which are well known in the art. For instance, a method similar to 5' RACE is available for generating the missing 5' end of a desired full-length transcript. (Fromont-Racine et al., Nucleic Acids Res. 21(7): 1683-1684 (1993).)

Briefly, a specific RNA oligonucleotide is ligated to the 5' ends of a population of RNA presumably containing full-length gene RNA transcripts. A primer set containing a primer specific to the ligated RNA oligonucleotide and a primer specific to a known sequence of the gene of interest is used to PCR amplify the 5' portion of the desired full-length gene. This amplified product may then be sequenced and used to generate the full length gene.

This above method starts with total RNA isolated from the desired source, although poly-A+ RNA can be used. The RNA preparation can then be treated with phosphatase if necessary to eliminate 5' phosphate groups on degraded or damaged RNA which may interfere with the later RNA ligase step. The phosphatase should then be inactivated and the RNA treated with tobacco acid pyrophosphatase in order to remove the cap structure present at the 5' ends of messenger RNAs. This reaction leaves a 5' phosphate group at the 5' end of the cap cleaved RNA which can then be ligated to an RNA oligonucleotide using T4 RNA ligase.

This modified RNA preparation is used as a template for first strand cDNA synthesis using a gene specific oligonucleotide. The first strand synthesis reaction is used as a template for PCR amplification of the desired 5' end using a primer specific to the ligated RNA oligonucleotide and a primer specific to the known sequence of the gene of interest. The resultant product is then sequenced and analyzed to confirm that the 5' end sequence belongs to the desired gene.

Example 2

Isolation of Genomic Clones Corresponding to a Polynucleotide

A human genomic P1 library (Genomic Systems, Inc.) is screened by PCR using primers selected for the cDNA sequence corresponding to SEQ ID NO:X, according to the method described in Example 1. (See also, Sambrook.)

Example 3

Tissue Distribution of Polypeptide

Tissue distribution of mRNA expression of polynucleotides of the present invention is determined using protocols for Northern blot analysis, described by, among others, Sambrook et al. For example, a cDNA probe produced by the method described in Example 1 is labeled with $P^{32}$ using the rediprime™ DNA labeling system (Amersham Life Science), according to manufacturer's instructions. After labeling, the probe is purified using CHROMA SPIN-100™ column (Clontech Laboratories, Inc.), according to manufacturer's protocol number PT1200-1. The purified labeled probe is then used to examine various human tissues for mRNA expression.

Multiple Tissue Northern (MTN) blots containing various human tissues (H) or human immune system tissues (IM) (Clontech) are examined with the labeled probe using ExpressHyb™ hybridization solution (Clontech) according to manufacturer's protocol number PT1190-1. Following hybridization and washing, the blots are mounted and exposed to film at −70 degree C. overnight, and the films developed according to standard procedures.

Example 4

Chromosomal Mapping of the Polynucleotides

An oligonucleotide primer set is designed according to the sequence at the 5' end of SEQ ID NO:X. This primer preferably spans about 100 nucleotides. This primer set is then used in a polymerase chain reaction under the following set of conditions: 30 seconds, 95 degree C.; 1 minute, 56 degree C.; 1 minute, 70 degree C. This cycle is repeated 32 times followed by one 5 minute cycle at 70 degree C. Human, mouse, and hamster DNA is used as template in addition to a somatic cell hybrid panel containing individual chromosomes or chromosome fragments (Bios, Inc). The reactions is analyzed on either 8% polyacrylamide gels or 3.5% agarose gels. Chromosome mapping is determined by the presence of an approximately 100 bp PCR fragment in the particular somatic cell hybrid.

Example 5

Bacterial Expression of a Polypeptide

A polynucleotide encoding a polypeptide of the present invention is amplified using PCR oligonucleotide primers corresponding to the 5' and 3' ends of the DNA sequence, as outlined in Example 1, to synthesize insertion fragments. The primers used to amplify the cDNA insert should preferably contain restriction sites, such as BamHI and XbaI, at the 5' end of the primers in order to clone the amplified product into the expression vector. For example, BamHI and XbaI correspond to the restriction enzyme sites on the bacterial expression vector pQE-9. (Qiagen, Inc., Chatsworth, Calif.). This plasmid vector encodes antibiotic resistance ($Amp^r$), a bacterial origin of replication (ori), an IPTG-regulatable promoter/operator (P/O), a ribosome binding site (RBS), a 6-histidine tag (6-His), and restriction enzyme cloning sites.

The pQE-9 vector is digested with BamHI and XbaI and the amplified fragment is ligated into the pQE-9 vector maintaining the reading frame initiated at the bacterial RBS. The ligation mixture is then used to transform the *E. coli* strain M15/rep4 (Qiagen, Inc.) which contains multiple copies of the plasmid pREP4, which expresses the lacI repressor and also confers kanamycin resistance ($Kan^r$). Transformants are identified by their ability to grow on LB plates and ampicillin/kanamycin resistant colonies are selected. Plasmid DNA is isolated and confirmed by restriction analysis.

Clones containing the desired constructs are grown overnight (O/N) in liquid culture in LB media supplemented with both Amp (100 ug/ml) and Kan (25 ug/ml). The O/N culture is used to inoculate a large culture at a ratio of 1:100 to 1:250. The cells are grown to an optical density 600 ($O.D.^{600}$) of between 0.4 and 0.6. IPTG (Isopropyl-B-D-thiogalacto pyranoside) is then added to a final concentration of 1 mM. IPTG induces by inactivating the lacI repressor, clearing the P/O leading to increased gene expression.

Cells are grown for an extra 3 to 4 hours. Cells are then harvested by centrifugation (20 mins at 6000×g). The cell pellet is solubilized in the chaotropic agent 6 Molar Guanidine HCl by stirring for 3-4 hours at 4 degree C. The cell debris is removed by centrifugation, and the supernatant containing the polypeptide is loaded onto a nickel-nitrilotri-acetic acid ("Ni-NTA") affinity resin column (available from QIAGEN, Inc., supra). Proteins with a 6×His tag bind to the Ni-NTA resin with high affinity and can be purified in a simple one-step procedure (for details see: The QIAexpressionist (1995) QIAGEN, Inc., supra).

Briefly, the supernatant is loaded onto the column in 6 M guanidine-HCl, pH 8, the column is first washed with 10 volumes of 6 M guanidine-HCl, pH 8, then washed with 10 volumes of 6 M guanidine-HCl pH 6, and finally the polypeptide is eluted with 6 M guanidine-HCl, pH 5.

The purified protein is then renatured by dialyzing it against phosphate-buffered saline (PBS) or 50 mM Na-acetate, pH 6 buffer plus 200 mM NaCl. Alternatively, the protein can be successfully refolded while immobilized on the Ni-NTA column. The recommended conditions are as follows: renature using a linear 6M-1M urea gradient in 500 mM NaCl, 20% glycerol, 20 mM Tris/HCl pH 7.4, containing protease inhibitors. The renaturation should be performed over a period of 1.5 hours or more. After renaturation the proteins are eluted by the addition of 250 mM immidazole. Immidazole is removed by a final dialyzing step against PBS or 50 mM sodium acetate pH 6 buffer plus 200 mM NaCl. The purified protein is stored at 4 degree C. or frozen at −80 degree C.

In addition to the above expression vector, the present invention further includes an expression vector comprising phage operator and promoter elements operatively linked to a polynucleotide of the present invention, called pHE4a. (ATCC Accession Number 209645, deposited on Feb. 25, 1998.) This vector contains: 1) a neomycinphosphotransferase gene as a selection marker, 2) an *E. coli* origin of replication, 3) a T5 phage promoter sequence, 4) two lac operator sequences, 5) a Shine-Delgarno sequence, and 6) the lactose operon repressor gene (lacIq). The origin of replication (oriC) is derived from pUC19 (LTI, Gaithersburg, Md.). The promoter sequence and operator sequences are made synthetically.

DNA can be inserted into the pHEa by restricting the vector with NdeI and XbaI, BamHI, XhoI, or Asp718, running the restricted product on a gel, and isolating the larger fragment (the stuffer fragment should be about 310 base pairs). The DNA insert is generated according to the PCR protocol described in Example 1, using PCR primers having restriction sites for NdeI (5' primer) and XbaI, BamHI, XhoI, or Asp718 (3' primer). The PCR insert is gel purified and restricted with compatible enzymes. The insert and vector are ligated according to standard protocols.

The engineered vector could easily be substituted in the above protocol to express protein in a bacterial system.

Example 6

Purification of a Polypeptide from an Inclusion Body

The following alternative method can be used to purify a polypeptide expressed in *E coli* when it is present in the form of inclusion bodies. Unless otherwise specified, all of the following steps are conducted at 4-10 degree C.

Upon completion of the production phase of the *E. coli* fermentation, the cell culture is cooled to 4-10 degree C. and the cells harvested by continuous centrifugation at 15,000 rpm (Heraeus Sepatech). On the basis of the expected yield of protein per unit weight of cell paste and the amount of purified protein required, an appropriate amount of cell paste, by weight, is suspended in a buffer solution containing 100 mM Tris, 50 mM EDTA, pH 7.4. The cells are dispersed to a homogeneous suspension using a high shear mixer.

The cells are then lysed by passing the solution through a microfluidizer (Microfuidics, Corp. or APV Gaulin, Inc.) twice at 4000-6000 psi. The homogenate is then mixed with NaCl solution to a final concentration of 0.5 M NaCl, followed by centrifugation at 7000×g for 15 min. The resultant pellet is washed again using 0.5M NaCl, 100 mM Tris, 50 mM EDTA, pH 7.4.

The resulting washed inclusion bodies are solubilized with 1.5 M guanidine hydrochloride (GuHCl) for 2-4 hours. After 7000×g centrifugation for 15 min., the pellet is discarded and the polypeptide containing supernatant is incubated at 4 degree C. overnight to allow further GuHCl extraction.

Following high speed centrifugation (30,000×g) to remove insoluble particles, the GuHCl solubilized protein is refolded by quickly mixing the GuHCl extract with 20 volumes of buffer containing 50 mM sodium, pH 4.5, 150 mM NaCl, 2 mM EDTA by vigorous stirring. The refolded diluted protein solution is kept at 4 degree C. without mixing for 12 hours prior to further purification steps.

To clarify the refolded polypeptide solution, a previously prepared tangential filtration unit equipped with 0.16 um membrane filter with appropriate surface area (e.g., Filtron), equilibrated with 40 mM sodium acetate, pH 6.0 is employed. The filtered sample is loaded onto a cation exchange resin (e.g., Poros HS-50, Perseptive Biosystems). The column is washed with 40 mM sodium acetate, pH 6.0 and eluted with 250 mM, 500 mM, 1000 mM, and 1500 mM NaCl in the same buffer, in a stepwise manner. The absorbance at 280 nm of the effluent is continuously monitored. Fractions are collected and further analyzed by SDS-PAGE.

Fractions containing the polypeptide are then pooled and mixed with 4 volumes of water. The diluted sample is then loaded onto a previously prepared set of tandem columns of strong anion (Poros HQ-50, Perseptive Biosystems) and weak anion (Poros CM-20, Perseptive Biosystems) exchange resins. The columns are equilibrated with 40 mM sodium acetate, pH 6.0. Both columns are washed with 40 mM sodium acetate, pH 6.0, 200 mM NaCl. The CM-20 column is then eluted using a 10 column volume linear gradient ranging from 0.2 M NaCl, 50 mM sodium acetate, pH 6.0 to 1.0 M NaCl, 50 mM sodium acetate, pH 6.5. Fractions are collected under constant $A_{280}$ monitoring of the effluent. Fractions containing the polypeptide (determined, for instance, by 16% SDS-PAGE) are then pooled.

The resultant polypeptide should exhibit greater than 95% purity after the above refolding and purification steps. No major contaminant bands should be observed from Commassie blue stained 16% SDS-PAGE gel when 5 ug of purified protein is loaded. The purified protein can also be tested for endotoxin/LPS contamination, and typically the LPS content is less than 0.1 ng/ml according to LAL assays.

Example 7

Cloning and Expression of a Polypeptide in a Baculovirus Expression System

In this example, the plasmid shuttle vector pA2 is used to insert a polynucleotide into a baculovirus to express a polypeptide. This expression vector contains the strong polyhedrin promoter of the *Autographa californica* nuclear polyhedrosis virus (AcMNPV) followed by convenient restriction sites such as BamHI, Xba I and Asp718. The polyadenylation site of the simian virus 40 ("SV40") is used for efficient polyadenylation. For easy selection of recombinant virus, the plasmid contains the beta-galactosidase gene from *E. coli* under control of a weak *Drosophila* promoter in the same orientation, followed by the polyadenylation signal of the polyhedrin gene. The inserted genes are flanked on both sides by viral sequences for cell-mediated homologous recombination with wild-type viral DNA to generate a viable virus that express the cloned polynucleotide.

Many other baculovirus vectors can be used in place of the vector above, such as pAc373, pVL941, and pAcIM1, as one skilled in the art would readily appreciate, as long as the construct provides appropriately located signals for transcription, translation, secretion and the like, including a signal peptide and an in-frame AUG as required. Such vectors are described, for instance, in Luckow et al., Virology 170:31-39 (1989).

Specifically, the cDNA sequence contained in the deposited clone, including the AUG initiation codon and the naturally associated leader sequence identified in Table 1, is amplified using the PCR protocol described in Example 1. If the naturally occurring signal sequence is used to produce the secreted protein, the pA2 vector does not need a second signal peptide. Alternatively, the vector can be modified (pA2 GP) to include a baculovirus leader sequence, using the standard methods described in Summers et al., "A Manual of Methods for Baculovirus Vectors and Insect Cell Culture Procedures," Texas Agricultural Experimental Station Bulletin No. 1555 (1987).

The amplified fragment is isolated from a 1% agarose gel using a commercially available kit ("Geneclean," BIO 101 Inc., La Jolla, Calif.). The fragment then is digested with appropriate restriction enzymes and again purified on a 1% agarose gel.

The plasmid is digested with the corresponding restriction enzymes and optionally, can be dephosphorylated using calf intestinal phosphatase, using routine procedures known in the art. The DNA is then isolated from a 1% agarose gel using a commercially available kit ("Geneclean" BIO 101 Inc., La Jolla, Calif.).

The fragment and the dephosphorylated plasmid are ligated together with T4 DNA ligase. *E. coli* HB101 or other suitable *E. coli* hosts such as XL-1 Blue (Stratagene Cloning Systems, La Jolla, Calif.) cells are transformed with the ligation mixture and spread on culture plates. Bacteria containing the plasmid are identified by digesting DNA from individual colonies and analyzing the digestion product by gel electrophoresis. The sequence of the cloned fragment is confirmed by DNA sequencing.

Five ug of a plasmid containing the polynucleotide is co-transfected with 1.0 ug of a commercially available linearized baculovirus DNA ("BaculoGold™ baculovirus DNA", Pharmingen, San Diego, Calif.), using the lipofection method described by Felgner et al., Proc. Natl. Acad. Sci. USA 84:7413-7417 (1987). One ug of BaculoGold™ virus DNA and 5 ug of the plasmid are mixed in a sterile well of a microtiter plate containing 50 ul of serum-free Grace's medium (Life Technologies Inc., Gaithersburg, Md.). Afterwards, 10 ul Lipofectin plus 90 ul Grace's medium are added, mixed and incubated for 15 minutes at room temperature. Then the transfection mixture is added drop-wise to Sf9 insect cells (ATCC CRL 1711) seeded in a 35 mm tissue culture plate with 1 ml Grace's medium without serum. The plate is then incubated for 5 hours at 27 degrees C. The transfection solution is then removed from the plate and 1 ml of Grace's insect medium supplemented with 10% fetal calf serum is added. Cultivation is then continued at 27 degrees C. for four days.

After four days the supernatant is collected and a plaque assay is performed, as described by Summers and Smith, supra. An agarose gel with "Blue Gal" (Life Technologies Inc., Gaithersburg) is used to allow easy identification and isolation of gal-expressing clones, which produce blue-stained plaques. (A detailed description of a "plaque assay" of this type can also be found in the user's guide for insect cell culture and baculovirology distributed by Life Technologies Inc., Gaithersburg, page 9-10.) After appropriate incubation, blue stained plaques are picked with the tip of a micropipettor (e.g., Eppendorf). The agar containing the recombinant viruses is then resuspended in a microcentrifuge tube containing 200 ul of Grace's medium and the suspension containing the recombinant baculovirus is used to infect Sf9 cells seeded in 35 mm dishes. Four days later the supernatants of these culture dishes are harvested and then they are stored at 4 degree C.

To verify the expression of the polypeptide, Sf9 cells are grown in Grace's medium supplemented with 10% heat-inactivated FBS. The cells are infected with the recombinant baculovirus containing the polynucleotide at a multiplicity of infection ("MOI") of about 2. If radiolabeled proteins are desired, 6 hours later the medium is removed and is replaced with SF900 II medium minus methionine and cysteine (available from Life Technologies Inc., Rockville, Md.). After 42 hours, 5 uCi of $^{35}$S-methionine and 5 uCi $^{35}$S-cysteine (available from Amersham) are added. The cells are further incubated for 16 hours and then are harvested by centrifugation. The proteins in the supernatant as well as the intracellular proteins are analyzed by SDS-PAGE followed by autoradiography (if radiolabeled).

Microsequencing of the amino acid sequence of the amino terminus of purified protein may be used to determine the amino terminal sequence of the produced protein.

Example 8

Expression of a Polypeptide in Mammalian Cells

The polypeptide of the present invention can be expressed in a mammalian cell. A typical mammalian expression vector contains a promoter element, which mediates the initiation of transcription of mRNA, a protein coding sequence, and signals required for the termination of transcription and polyadenylation of the transcript. Additional elements include enhancers, Kozak sequences and intervening sequences flanked by donor and acceptor sites for RNA splicing. Highly efficient transcription is achieved with the early and late promoters from SV40, the long terminal repeats (LTRs) from Retroviruses, e.g., RSV, HTLVI, HIVI and the early promoter of the cytomegalovirus (CMV). However, cellular elements can also be used (e.g., the human actin promoter).

Suitable expression vectors for use in practicing the present invention include, for example, vectors such as pSVL and pMSG (Pharmacia, Uppsala, Sweden), pRSVcat (ATCC 37152), pSV2dhfr (ATCC 37146), pBC12MI (ATCC 67109), pCMVSport 2.0, and pCMVSport 3.0. Mammalian host cells that could be used include, human Hela, 293, H9 and Jurkat cells, mouse NIH3T3 and C127 cells, Cos 1, Cos 7 and CV1, quail QC1-3 cells, mouse L cells and Chinese hamster ovary (CHO) cells.

Alternatively, the polypeptide can be expressed in stable cell lines containing the polynucleotide integrated into a chromosome. The co-transfection with a selectable marker such as dhfr, gpt, neomycin, hygromycin allows the identification and isolation of the transfected cells.

The transfected gene can also be amplified to express large amounts of the encoded protein. The DHFR (dihydrofolate reductase) marker is useful in developing cell lines that carry several hundred or even several thousand copies of the gene of interest. (See, e.g., Alt, F. W., et al., J. Biol. Chem. 253:1357-1370 (1978); Hamlin, J. L. and Ma, C., Biochem. et Biophys. Acta, 1097:107-143 (1990); Page, M. J. and Sydenham, M. A., Biotechnology 9:64-68 (1991).) Another useful selection marker is the enzyme glutamine synthase (GS) (Murphy et al., Biochem J. 227:277-279 (1991); Bebbington et al., Bio/Technology 10:169-175 (1992). Using these markers, the mammalian cells are grown in selective medium and the cells with the highest resistance are selected. These cell lines contain the amplified gene(s) integrated into a chromosome. Chinese hamster ovary (CHO) and NSO cells are often used for the production of proteins.

Derivatives of the plasmid pSV2-dhfr (ATCC Accession No. 37146), the expression vectors pC4 (ATCC Accession No. 209646) and pC6 (ATCC Accession No. 209647) contain the strong promoter (LTR) of the Rous Sarcoma Virus (Cullen et al., Molecular and Cellular Biology, 438-447 (March, 1985)) plus a fragment of the CMV-enhancer (Boshart et al., Cell 41:521-530 (1985).) Multiple cloning sites, e.g., with the restriction enzyme cleavage sites BamHI, XbaI and Asp718, facilitate the cloning of the gene of interest. The vectors also contain the 3' intron, the polyadenylation and termination signal of the rat preproinsulin gene, and the mouse DHFR gene under control of the SV40 early promoter.

Specifically, the plasmid pC6, for example, is digested with appropriate restriction enzymes and then dephosphorylated using calf intestinal phosphates by procedures known in the art. The vector is then isolated from a 1% agarose gel.

A polynucleotide of the present invention is amplified according to the protocol outlined in Example 1. If the naturally occurring signal sequence is used to produce the secreted protein, the vector does not need a second signal peptide. Alternatively, if the naturally occurring signal sequence is not used, the vector can be modified to include a heterologous signal sequence. (See, e.g., WO 96/34891.)

The amplified fragment is isolated from a 1% agarose gel using a commercially available kit ("Geneclean," BIO 101 Inc., La Jolla, Calif.). The fragment then is digested with appropriate restriction enzymes and again purified on a 1% agarose gel.

The amplified fragment is then digested with the same restriction enzyme and purified on a 1% agarose gel. The isolated fragment and the dephosphorylated vector are then ligated with T4 DNA ligase. *E. coli* HB101 or XL-1 Blue cells are then transformed and bacteria are identified that contain the fragment inserted into plasmid pC6 using, for instance, restriction enzyme analysis.

Chinese hamster ovary cells lacking an active DHFR gene is used for transfection. Five μg of the expression plasmid pC6 a pC4 is cotransfected with 0.5 ug of the plasmid pSVneo using lipofectin (Felgner et al., supra). The plasmid pSV2-neo contains a dominant selectable marker, the neo gene from Tn5 encoding an enzyme that confers resistance to a group of antibiotics including G418. The cells are seeded in alpha minus MEM supplemented with 1 mg/ml G418. After 2 days, the cells are trypsinized and seeded in hybridoma cloning plates (Greiner, Germany) in alpha minus MEM supplemented with 10, 25, or 50 ng/ml of metothrexate plus 1 mg/ml G418. After about 10-14 days single clones are trypsinized and then seeded in 6-well petri dishes or 10 ml flasks using different concentrations of methotrexate (50 nM, 100 nM, 200 nM, 400 nM, 800 nM). Clones growing at the highest concentrations of methotrexate are then transferred to new 6-well plates containing even higher concentrations of methotrexate (1 uM, 2 uM, 5 uM, 10 mM, 20 mM). The same procedure is repeated until clones are obtained which grow at a concentration of 100-200 uM. Expression of the desired gene product is analyzed, for instance, by SDS-PAGE and Western blot or by reversed phase HPLC analysis.

Example 9

Protein Fusions

The polypeptides of the present invention are preferably fused to other proteins. These fusion proteins can be used for a variety of applications. For example, fusion of the present polypeptides to His-tag, HA-tag, protein A, IgG domains, and maltose binding protein facilitates purification. (See Example 5; see also EP A 394,827; Traunecker, et al., Nature 331:84-86 (1988).) Similarly, fusion to IgG-1, IgG-3, and albumin increases the halflife time in vivo. Nuclear localization signals fused to the polypeptides of the present invention can target the protein to a specific subcellular localization, while covalent heterodimer or homodimers can increase or decrease the activity of a fusion protein. Fusion proteins can also create chimeric molecules having more than one function. Finally, fusion proteins can increase solubility and/or stability of the fused protein compared to the non-fused protein. All of the types of fusion proteins described above can be made by modifying the following protocol, which outlines the fusion of a polypeptide to an IgG molecule, or the protocol described in Example 5.

Briefly, the human Fc portion of the IgG molecule can be PCR amplified, using primers that span the 5' and 3' ends of the sequence described below. These primers also should have convenient restriction enzyme sites that will facilitate cloning into an expression vector, preferably a mammalian expression vector.

For example, if pC4 (Accession No. 209646) is used, the human Fc portion can be ligated into the BamHI cloning site. Note that the 3' BamHI site should be destroyed. Next, the vector containing the human Fc portion is re-restricted with BamHI, linearizing the vector, and a polynucleotide of the present invention, isolated by the PCR protocol described in Example 1, is ligated into this BamHI site. Note that the polynucleotide is cloned without a stop codon, otherwise a fusion protein will not be produced.

If the naturally occurring signal sequence is used to produce the secreted protein, pC4 does not need a second signal peptide. Alternatively, if the naturally occurring signal sequence is not used, the vector can be modified to include a heterologous signal sequence. (See, e.g., WO 96/34891.)

Human IgG Fc Region: GGGATCCGGAGCCCAAATCTTCTGACAAAACTCACACATGCCCACCGTGC CCAGCACCTGAATTCGAGGGTGCACCGTCAGTCTTCCTCTTCCCCCCAAAA CCCAAGGACACCCTCATGATCTCCCGGACTCCTGAGGTCACATGCGTGGT GGTGGACGTAAGCCACGAAGACCCTGAGGTCAAGTTCAACTGGTACGTGG ACGGCGTGGAGGTGCATAATGCCAAGACAAAGCCGCGGGAGGAGCAGTA CAACAGCACG- TACCGTGTGGTCAGCGTCCTCACCGTC-CTGCACCAGGACT GGCTGAATGGCAAGGAGTACAAGTG-CAAGGTCTCCAACAAAGCCCTCCCA ACCCCCATC-GAGAAAACCATCTCCAAAGC-CAAAGGGCAGCCCCGAGAAC CACAGGTGTACACCCTGCCCCCATC-CCGGGATGAGCTGACCAAGAACCAG GTCAGCCT-GACCTGCCTGGTCAAAGGCTTCTATC-CAAGCGACATCGCCGT GGAGTGGGAGAGCAATGGGCAGCCG-GAGAACAACTACAAGACCACGCCT CCCGTGCTG-GACTCCGACGGCTCCTTCTTCCTCTA-CAGCAAGCTCACCGTG GACAAGAGCAGGTGGCAGCAGGG-GAACGTCTTCTCATGCTCCGTGATGCA TGAG-GCTCTGCACAACCACTACACGCAGAA-GAGCCTCTCCCTGTCTCCGG GTAAATGAGTGCGACGGCCGCGACTCTAGAGGAT (SEQ ID NO:1)

Example 10

Production of an Antibody from a Polypeptide

The antibodies of the present invention can be prepared by a variety of methods. (See, Current Protocols, Chapter 2.) As one example of such methods, cells expressing a polypeptide of the present invention is administered to an animal to induce the production of sera containing polyclonal antibodies. In a preferred method, a preparation of the secreted protein is prepared and purified to render it substantially free of natural contaminants. Such a preparation is then introduced into an animal in order to produce polyclonal antisera of greater specific activity.

In the most preferred method, the antibodies of the present invention are monoclonal antibodies (or protein binding fragments thereof). Such monoclonal antibodies can be prepared using hybridoma technology. (Köhler et al., Nature 256:495 (1975); Köhler et al., Eur. J. Immunol. 6:511 (1976); Köhler et al., Eur. J. Immunol. 6:292 (1976); Hammerling et al., in: Monoclonal Antibodies and T-Cell Hybridomas, Elsevier, N.Y., pp. 563-681 (1981).) In general, such procedures involve immunizing an animal (preferably a mouse) with polypeptide or, more preferably, with a secreted polypeptide-expressing cell. Such cells may be cultured in any suitable tissue culture medium; however, it is preferable to culture cells in Earle's modified Eagle's medium supplemented with 10% fetal bovine serum (inactivated at about 56 degrees C.), and supplemented with about 10 g/l of nonessential amino acids, about 1,000 U/ml of penicillin, and about 100 ug/ml of streptomycin.

The splenocytes of such mice are extracted and fused with a suitable myeloma cell line. Any suitable myeloma cell line may be employed in accordance with the present invention; however, it is preferable to employ the parent myeloma cell line (SP2O), available from the ATCC. After fusion, the resulting hybridoma cells are selectively maintained in HAT medium, and then cloned by limiting dilution as described by Wands et al. (Gastroenterology 80:225-232 (1981).) The hybridoma cells obtained through such a selection are then assayed to identify clones which secrete antibodies capable of binding the polypeptide.

Alternatively, additional antibodies capable of binding to the polypeptide can be produced in a two-step procedure using anti-idiotypic antibodies. Such a method makes use of the fact that antibodies are themselves antigens, and therefore, it is possible to obtain an antibody which binds to a second antibody. In accordance with this method, protein specific antibodies are used to immunize an animal, preferably a mouse. The splenocytes of such an animal are then used to produce hybridoma cells, and the hybridoma cells are screened to identify clones which produce an antibody whose ability to bind to the protein-specific antibody can be blocked by the polypeptide. Such antibodies comprise anti-idiotypic antibodies to the protein-specific antibody and can be used to immunize an animal to induce formation of further protein-specific antibodies.

It will be appreciated that Fab and F(ab')2 and other fragments of the antibodies of the present invention may be used according to the methods disclosed herein. Such fragments are typically produced by proteolytic cleavage, using enzymes such as papain (to produce Fab fragments) or pepsin (to produce F(ab')2 fragments). Alternatively, secreted protein-binding fragments can be produced through the application of recombinant DNA technology or through synthetic chemistry.

For in vivo use of antibodies in humans, it may be preferable to use "humanized" chimeric monoclonal antibodies. Such antibodies can be produced using genetic constructs derived from hybridoma cells producing the monoclonal antibodies described above. Methods for producing chimeric antibodies are known in the art. (See, for review, Morrison, Science 229:1202 (1985); Oi et al., BioTechniques 4:214 (1986); Cabilly et al., U.S. Pat. No. 4,816,567; Taniguchi et al., EP 171496; Morrison et al., EP 173494; Neuberger et al., WO 8601533; Robinson et al., WO 8702671; Boulianne et al., Nature 312:643 (1984); Neuberger et al., Nature 314:268 (1985).)

Example 11

Production of Secreted Protein for High-Throughput Screening Assays

The following protocol produces a supernatant containing a polypeptide to be tested. This supernatant can then be used in the Screening Assays described herein.

First, dilute Poly-D-Lysine (644 587 Boehringer-Mannheim) stock solution (1 mg/ml in PBS) 1:20 in PBS (w/o calcium or magnesium 17-516F Biowhittaker) for a working solution of 50 ug/ml. Add 200 ul of this solution to each well (24 well plates) and incubate at RT for 20 minutes. Be sure to distribute the solution over each well (note: a 12-channel pipetter may be used with tips on every other channel). Aspirate off the Poly-D-Lysine solution and rinse with 1 ml PBS (Phosphate Buffered Saline). The PBS should remain in the well until just prior to plating the cells and plates may be poly-lysine coated in advance for up to two weeks.

Plate 293T cells (do not carry cells past P+20) at $2\times10^5$ cells/well in 0.5 ml DMEM (Dulbecco's Modified Eagle Medium) (with 4.5 G/L glucose and L-glutamine (12-604F Biowhittaker))/10% heat inactivated FBS(14-503F Biowhittaker)/1× Penstrep (17-602E Biowhittaker). Let the cells grow overnight.

The next day, mix together in a sterile solution basin: 300 ul Lipofectamine (18324-012 Gibco/BRL) and 5 ml Optimem I (31985070 Gibco/BRL)/96-well plate. With a small volume multi-channel pipetter, aliquot approximately 2 ug of an expression vector containing a polynucleotide insert, produced by the methods described in Examples 8 or 9, into an appropriately labeled 96-well round bottom plate. With a multi-channel pipetter, add 50 ul of the Lipofectamine/Optimem I mixture to each well. Pipette up and down gently to mix. Incubate at RT 15-45 minutes. After about 20 minutes, use a multi-channel pipetter to add 150 ul Optimem I to each well. As a control, one plate of vector DNA lacking an insert should be transfected with each set of transfections.

Preferably, the transfection should be performed by tag-teaming the following tasks. By tag-teaming, hands on time is cut in half, and the cells do not spend too much time on PBS. First, person A aspirates off the media from four 24-well plates of cells, and then person B rinses each well with 0.5-1 ml PBS. Person A then aspirates off PBS rinse, and person B, using a12-channel pipetter with tips on every other channel, adds the 200 ul of DNA/Lipofectamine/Optimem I complex to the odd wells first, then to the even wells, to each row on the 24-well plates. Incubate at 37 degrees C. for 6 hours.

While cells are incubating, prepare appropriate media, either 1% BSA in DMEM with 1× penstrep, or CHO-5 media (116.6 mg/L of CaCl2 (anhyd); 0.00130 mg/L $CuSO_4$-$5H_2O$; 0.050 mg/L of $Fe(NO_3)_3$-$9H_2O$; 0.417 mg/L of $FeSO_4$-$7H_2O$; 311.80 mg/L of Kcl; 28.64 mg/L of $MgCl_2$; 48.84 mg/L of $MgSO_4$; 6995.50 mg/L of NaCl; 2400.0 mg/L of $NaHCO_3$; 62.50 mg/L of $NaH_2PO_4$—$H_2O$; 71.02 mg/L of $Na_2$HPO4; 0.4320 mg/L of $ZnSO_4$-$7H_2O$; 0.002 mg/L of Arachidonic Acid; 1.022 mg/L of Cholesterol; 0.070 mg/L of DL-alpha-Tocopherol-Acetate; 0.0520 mg/L of Linoleic Acid; 0.010 mg/L of Linolenic Acid; 0.010 mg/L of Myristic Acid; 0.010 mg/L of Oleic Acid; 0.010 mg/L of Palmitric Acid; 0.010 mg/L of Palmitic Acid; 100 mg/L of Pluronic F-68; 0.010 mg/L of Stearic Acid; 2.20 mg/L of Tween 80; 4551 mg/L of D-Glucose; 130.85 mg/ml of L-Alanine; 147.50 mg/ml of L-Arginine-HCL; 7.50 mg/ml of L-Asparagine-$H_2O$; 6.65 mg/ml of L-Aspartic Acid; 29.56 mg/ml of L-Cystine-2HCL-$H_2O$; 31.29 mg/ml of L-Cystine-2HCL; 7.35 mg/ml of L-Glutamic Acid; 365.0 mg/ml of L-Glutamine; 18.75 mg/ml of Glycine; 52.48 mg/ml of L-Histidine-HCL-$H_2O$; 106.97 mg/ml of L-Isoleucine; 111.45 mg/ml of L-Leucine; 163.75 mg/ml of L-Lysine HCL; 32.34 mg/ml of L-Methionine; 68.48 mg/ml of L-Phenylalainine; 40.0 mg/ml of L-Proline; 26.25 mg/ml of L-Serine; 101.05 mg/ml of L-Threonine; 19.22 mg/ml of L-Tryptophan; 91.79 mg/ml of L-Tryrosine-2Na-$2H_2O$; 99.65 mg/ml of L-Valine; 0.0035 mg/L of Biotin; 3.24 mg/L of D-Ca Pantothenate; 11.78 mg/L of Choline Chloride; 4.65 mg/L of Folic Acid; 15.60 mg/L of i-Inositol; 3.02 mg/L of Niacinamide; 3.00 mg/L of Pyridoxal HCL; 0.031 mg/L of Pyridoxine HCL; 0.319 mg/L of Riboflavin; 3.17 mg/L of Thiamine HCL; 0.365 mg/L of Thymidine; and 0.680 mg/L of Vitamin $B_{12}$; 25 mM of HEPES Buffer; 2.39 mg/L of Na Hypoxanthine; 0.105 mg/L of Lipoic Acid; 0.081 mg/L of Sodium Putrescine-2HCL; 55.0 mg/L of Sodium Pyruvate; 0.0067 mg/L of Sodium Selenite; 20 uM of Ethanolamine; 0.122 mg/L of Ferric Citrate; 41.70 mg/L of Methyl-B-Cyclodextrin complexed with Linoleic Acid; 33.33 mg/L of Methyl-B-Cyclodextrin complexed with Oleic Acid; and 10 mg/L of Methyl-B-Cyclodextrin complexed with Retinal) with 2 mm glutamine and 1× penstrep. (BSA (81-068-3 Bayer) 100 gm dissolved in 1 L DMEM for a 10% BSA stock solution). Filter the media and collect 50 ul for endotoxin assay in 15 ml polystyrene conical.

The transfection reaction is terminated, preferably by tag-teaming, at the end of the incubation period. Person A aspirates off the transfection media, while person B adds 1.5 ml appropriate media to each well. Incubate at 37 degrees C. for 45 or 72 hours depending on the media used: 1% BSA for 45 hours or CHO-5 for 72 hours.

On day four, using a 300 ul multichannel pipetter, aliquot 600 ul in one 1 ml deep well plate and the remaining supernatant into a 2 ml deep well. The supernatants from each well can then be used in the assays described in Examples 13-20.

It is specifically understood that when activity is obtained in any of the assays described below using a supernatant, the activity originates from either the polypeptide directly (e.g., as a secreted protein) or by the polypeptide inducing expression of other proteins, which are then secreted into the supernatant. Thus, the invention further provides a method of identifying the protein in the supernatant characterized by an activity in a particular assay.

Example 12

Construction of GAS Reporter Construct

One signal transduction pathway involved in the differentiation and proliferation of cells is called the Jaks-STATs pathway. Activated proteins in the Jaks-STATs pathway bind to gamma activation site "GAS" elements or interferon-sensitive responsive element ("ISRE"), located in the promoter of many genes. The binding of a protein to these elements alter the expression of the associated gene.

GAS and ISRE elements are recognized by a class of transcription factors called Signal Transducers and Activators of Transcription, or "STATs." There are six members of the STATs family. Stat1 and Stat3 are present in many cell types, as is Stat2 (as response to IFN-alpha is widespread). Stat4 is more restricted and is not in many cell types though it has been found in T helper class I, cells after treatment with IL-12. Stat5 was originally called mammary growth factor, but has been found at higher concentrations in other cells including myeloid cells. It can be activated in tissue culture cells by many cytokines.

The STATs are activated to translocate from the cytoplasm to the nucleus upon tyrosine phosphorylation by a set of kinases known as the Janus Kinase ("Jaks") family. Jaks represent a distinct family of soluble tyrosine kinases and include Tyk2, Jak1, Jak2, and Jak3. These kinases display significant sequence similarity and are generally catalytically inactive in resting cells.

The Jaks are activated by a wide range of receptors summarized in the Table below. (Adapted from review by Schidler and Darnell, Ann. Rev. Biochem. 64:621-51 (1995).) A cytokine receptor family, capable of activating Jaks, is divided into two groups: (a) Class 1 includes receptors for IL-2, IL-3, IL-4, IL-6, IL-7, IL-9, IL-11, IL-12, IL-15, Epo, PRL, GH, G-CSF, GM-CSF, LIF, CNTF, and thrombopoietin; and (b) Class 2 includes IFN-a, IFN-g, and IL-10. The Class 1 receptors share a conserved cysteine motif (a set of four conserved cysteines and one tryptophan) and a WSXWS motif (a membrane proximal region encoding Trp-Ser-Xxx-Trp-Ser (SEQ ID NO:2)).

Thus, on binding of a ligand to a receptor, Jaks are activated, which in turn activate STATs, which then translocate and bind to GAS elements. This entire process is encompassed in the Jaks-STATs signal transduction pathway.

Therefore, activation of the Jaks-STATs pathway, reflected by the binding of the GAS or the ISRE element, can be used to indicate proteins involved in the proliferation and differentiation of cells. For example, growth factors and cytokines are known to activate the Jaks-STATs pathway. (See Table below.) Thus, by using GAS elements linked to reporter molecules, activators of the Jaks-STATs pathway can be identified.

| | JAKs | | | | | |
|---|---|---|---|---|---|---|
| Ligand | tyk2 | Jak1 | Jak2 | Jak3 | STATS | GAS(elements) or ISRE |
| IFN family | | | | | | |
| IFN-a/B | + | + | − | − | 1,2,3 | ISRE |
| IFN-g | | + | + | − | 1 | GAS (IRF1 > Lys6 > IFP) |
| I1-10 | + | ? | ? | − | 1,3 | |
| gp130 family | | | | | | |
| IL-6 (Pleiotrophic) | + | + | + | ? | 1,3 | GAS (IRF1 > Lys6 > IFP) |
| Il-11(Pleiotrophic) | ? | + | ? | ? | 1,3 | |
| OnM(Pleiotrophic) | ? | + | + | ? | 1,3 | |
| LIF(Pleiotrophic) | ? | + | + | ? | 1,3 | |
| CNTF(Pleiotrophic) | −/+ | + | + | ? | 1,3 | |
| G-CSF(Pleiotrophic) | ? | + | ? | ? | 1,3 | |
| IL-12(Pleiotrophic) | + | − | + | + | 1,3 | |
| g-C family | | | | | | |
| IL-2 (lymphocytes) | − | + | − | + | 1,3,5 | GAS |
| IL-4 (lymph/myeloid) | − | + | − | + | 6 | GAS (IRF1 = IFP >> Ly6)(IgH) |
| IL-7 (lymphocytes) | − | + | − | + | 5 | GAS |
| IL-9 (lymphocytes) | − | + | − | + | 5 | GAS |
| IL-13 (lymphocyte) | − | + | ? | ? | 6 | GAS |
| IL-15 | ? | + | ? | + | 5 | GAS |
| gp140 family | | | | | | |
| IL-3 (myeloid) | − | − | + | − | 5 | GAS (IRF1 > IFP >> Ly6) |
| IL-5 (myeloid) | − | − | + | − | 5 | GAS |
| GM-CSF (myeloid) | − | − | + | − | 5 | GAS |
| Growth hormone family | | | | | | |
| GH | ? | − | + | − | 5 | |
| PRL | ? | +/− | + | − | 1,3,5 | |
| EPO | ? | − | + | − | 5 | GAS(B-GAS > IRF1 = IFP >> Ly6) |
| Receptor Tyrosine Kinases | | | | | | |
| EGF | ? | + | + | − | 1,3 | GAS (IRF1) |
| PDGF | ? | + | + | − | 1,3 | |
| CSF-1 | ? | + | + | − | 1,3 | GAS (not IRF1) |

To construct a synthetic GAS containing promoter element, which is used in the Biological Assays described in Examples 13-14, a PCR based strategy is employed to generate a GAS-SV40 promoter sequence. The 5' primer contains four tandem copies of the GAS binding site found in the IRF1 promoter and previously demonstrated to bind STATs upon induction with a range of cytokines (Rothman et al., Immunity 1:457-468 (1994).), although other GAS or ISRE elements can be used instead. The 5' primer also contains 18 bp of sequence complementary to the SV40 early promoter sequence and is flanked with an XhoI site. The sequence of the 5' primer is: 5':GCGCCTCGAGATTTCCCCGAAATCTAGATTTCCCCGAAATGATTTCCCC GAAATGATTTCCCCGAAATATCTGCCATCTCAATTAG:3' (SEQ ID NO:3)

The downstream primer is complementary to the SV40 promoter and is flanked with a Hind III site: 5':GCGGCAAGCTTTTTGCAAAGCCTAGGC:3' (SEQ ID NO:4).

PCR amplification is performed using the SV40 promoter template present in the B-gal:promoter plasmid obtained from Clontech. The resulting PCR fragment is digested with XhoI/Hind III and subcloned into BLSK2-. (Stratagene.) Sequencing with forward and reverse primers confirms that the insert contains the following sequence: 5': CTCGAGATTTCCCCGAAATCTAGATTTCCCCGAAATGATTTCCCCGAAA TGATTTCCCCGAAATATCTGCCATCTCAATTAGTCAGCAACCATAGTCCCG CCCCTAACTCCGCCCATCCCGCCCCTAACTCCGCCCAGTTCCGCCCATTCT CCGCCCCATGGCTGACTAATTTTTTTTATTTATGCAGAGGCCGAGGCCGCC TCGGCCTCTGAGCTATTCCAGAAGTAGTGAGGAGGCTTTTTTGGAGGCCT AGGCTTTTGCAAAAAGCTT:3' (SEQ ID NO:5).

With this GAS promoter element linked to the SV40 promoter, a GAS:SEAP2 reporter construct is next engineered. Here, the reporter molecule is a secreted alkaline phosphatase, or "SEAP." Clearly, however, any reporter molecule can be instead of SEAP, in this or in any of the other Examples. Well known reporter molecules that can be used instead of SEAP include chloramphenicol acetyltransferase (CAT), luciferase, alkaline phosphatase, B-galactosidase, green fluorescent protein (GFP), or any protein detectable by an antibody.

The above sequence confirmed synthetic GAS-SV40 promoter element is subcloned into the pSEAP-Promoter vector obtained from Clontech using HindIII and XhoI, effectively replacing the SV40 promoter with the amplified GAS:SV40 promoter element, to create the GAS-SEAP vector. However, this vector does not contain a neomycin resistance gene, and therefore, is not preferred for mammalian expression systems.

Thus, in order to generate mammalian stable cell lines expressing the GAS-SEAP reporter, the GAS-SEAP cassette is removed from the GAS-SEAP vector using SalI and NotI, and inserted into a backbone vector containing the neomycin resistance gene, such as pGFP-1 (Clontech), using these restriction sites in the multiple cloning site, to create the GAS-SEAP/Neo vector. Once this vector is transfected into mammalian cells, this vector can then be used as a reporter molecule for GAS binding as described in Examples 13-14.

Other constructs can be made using the above description and replacing GAS with a different promoter sequence. For example, construction of reporter molecules containing NFK-B and EGR promoter sequences are described in Examples 15 and 16. However, many other promoters can be substituted using the protocols described in these Examples. For instance, SRE, IL-2, NFAT, or Osteocalcin promoters can be substituted, alone or in combination (e.g., GAS/NF-KB/EGR, GAS/NF-KB, I1-2/NFAT, or NF-KB/GAS). Similarly, other cell lines can be used to test reporter construct activity, such as HELA (epithelial), HUVEC (endothelial), Reh (B-cell), Saos-2 (osteoblast), HUVAC (aortic), or Cardiomyocyte.

Example 13

High-Throughput Screening Assay for T-Cell Activity

The following protocol is used to assess T-cell activity by identifying factors, and determining whether supernate containing a polypeptide of the invention proliferates and/or differentiates T-cells. T-cell activity is assessed using the GAS/SEAP/Neo construct produced in Example 12. Thus, factors that increase SEAP activity indicate the ability to activate the Jaks-STATS signal transduction pathway. The T-cell used in this assay is Jurkat T-cells (ATCC Accession No. TIB-152), although Molt-3 cells (ATCC Accession No. CRL-1552) and Molt-4 cells (ATCC Accession No. CRL-1582) cells can also be used.

Jurkat T-cells are lymphoblastic CD4+ Th1 helper cells. In order to generate stable cell lines, approximately 2 million Jurkat cells are transfected with the GAS-SEAP/neo vector using DMRIE-C (Life Technologies)(transfection procedure described below). The transfected cells are seeded to a density of approximately 20,000 cells per well and transfectants resistant to 1 mg/ml genticin selected. Resistant colonies are expanded and then tested for their response to increasing concentrations of interferon gamma. The dose response of a selected clone is demonstrated.

Specifically, the following protocol will yield sufficient cells for 75 wells containing 200 ul of cells. Thus, it is either scaled up, or performed in multiple to generate sufficient cells for multiple 96 well plates. Jurkat cells are maintained in RPMI+10% serum with 1% Pen-Strep. Combine 2.5 mls of OPTI-MEM (Life Technologies) with 10 ug of plasmid DNA in a T25 flask. Add 2.5 ml OPTI-MEM containing 50 ul of DMRIE-C and incubate at room temperature for 15-45 mins.

During the incubation period, count cell concentration, spin down the required number of cells ($10^7$ per transfection), and resuspend in OPTI-MEM to a final concentration of $10^7$ cells/ml. Then add 1 ml of $1\times10^7$ cells in OPTI-MEM to T25 flask and incubate at 37 degrees C. for 6 hrs. After the incubation, add 10 ml of RPMI+15% serum.

The Jurkat:GAS-SEAP stable reporter lines are maintained in RPMI+10% serum, 1 mg/ml Genticin, and 1% Pen-Strep. These cells are treated with supernatants containing polypeptides of the invention and/or induced polypeptides of the invention as produced by the protocol described in Example 11.

On the day of treatment with the supernatant, the cells should be washed and resuspended in fresh RPMI+10% serum to a density of 500,000 cells per ml. The exact number of cells required will depend on the number of supernatants being screened. For one 96 well plate, approximately 10 million cells (for 10 plates, 100 million cells) are required.

Transfer the cells to a triangular reservoir boat, in order to dispense the cells into a 96 well dish, using a 12 channel pipette. Using a 12 channel pipette, transfer 200 ul of cells into each well (therefore adding 100,000 cells per well).

After all the plates have been seeded, 50 ul of the supernatants are transferred directly from the 96 well plate containing the supernatants into each well using a 12 channel pipette. In addition, a dose of exogenous interferon gamma (0.1, 1.0, 10 ng) is added to wells H9, H10, and H11 to serve as additional positive controls for the assay.

The 96 well dishes containing Jurkat cells treated with supernatants are placed in an incubator for 48 hrs (note: this time is variable between 48-72 hrs). 35 ul samples from each well are then transferred to an opaque 96 well plate using a 12 channel pipette. The opaque plates should be covered (using sellophene covers) and stored at −20 degrees C. until SEAP assays are performed according to Example 17. The plates containing the remaining treated cells are placed at 4 degrees C. and serve as a source of material for repeating the assay on a specific well if desired.

As a positive control, 100 Unit/ml interferon gamma can be used which is known to activate Jurkat T cells. Over 30 fold induction is typically observed in the positive control wells.

The above protocol may be used in the generation of both transient, as well as, stable transfected cells, which would be apparent to those of skill in the art.

Example 14

High-Throughput Screening Assay Identifying Myeloid Activity

The following protocol is used to assess myeloid activity by determining whether polypeptides of the invention proliferates and/or differentiates myeloid cells. Myeloid cell activity is assessed using the GAS/SEAP/Neo construct produced in Example 12. Thus, factors that increase SEAP activity indicate the ability to activate the Jaks-STATS signal transduction pathway. The myeloid cell used in this assay is U937, a pre-monocyte cell line, although TF-1, HL60, or KG1 can be used.

To transiently transfect U937 cells with the GAS/SEAP/Neo construct produced in Example 12, a DEAE-Dextran method (Kharbanda et. al., 1994, Cell Growth & Differentiation, 5:259-265) is used. First, harvest $2\times10e^7$ U937 cells and wash with PBS. The U937 cells are usually grown in RPMI 1640 medium containing 10% heat-inactivated fetal bovine serum (FBS) supplemented with 100 units/ml penicillin and 100 mg/ml streptomycin.

Next, suspend the cells in 1 ml of 20 mM Tris-HCl (pH 7.4) buffer containing 0.5 mg/ml DEAE-Dextran, 8 ug GAS-SEAP2 plasmid DNA, 140 mM NaCl, 5 mM KCl, 375 uM $Na_2HPO_4.7H_2O$, 1 mM $MgCl_2$, and 675 uM $CaCl_2$. Incubate at 37 degrees C. for 45 min.

Wash the cells with RPMI 1640 medium containing 10% FBS and then resuspend in 10 ml complete medium and incubate at 37 degrees C. for 36 hr.

The GAS-SEAP/U937 stable cells are obtained by growing the cells in 400 ug/ml G418. The G418-free medium is used for routine growth but every one to two months, the cells should be re-grown in 400 ug/ml G418 for couple of passages.

These cells are tested by harvesting $1\times10^8$ cells (this is enough for ten 96-well plates assay) and wash with PBS. Suspend the cells in 200 ml above described growth medium, with a final density of $5\times10^5$ cells/ml. Plate 200 ul cells per well in the 96-well plate (or $1\times10^5$ cells/well).

Add 50 ul of the supernatant prepared by the protocol described in Example 11. Incubate at 37 degrees C. for 48 to 72 hr. As a positive control, 100 Unit/ml interferon gamma can be used which is known to activate U937 cells. Over 30 fold induction is typically observed in the positive control wells. SEAP assay the supernatant according to the protocol described in Example 17.

Example 15

High-Throughput Screening Assay Identifying Neuronal Activity

When cells undergo differentiation and proliferation, a group of genes are activated through many different signal transduction pathways. One of these genes, EGR1 (early growth response gene 1), is induced in various tissues and cell types upon activation. The promoter of EGR1 is responsible for such induction. Using the EGR1 promoter linked to reporter molecules, activation of cells can be assessed.

Particularly, the following protocol is used to assess neuronal activity in PC12 cell lines. PC12 cells (rat phenochromocytoma cells) are known to proliferate and/or differentiate by activation with a number of mitogens, such as TPA (tetradecanoyl phorbol acetate), NGF (nerve growth factor), and EGF (epidermal growth factor). The EGR1 gene expression is activated during this treatment. Thus, by stably transfecting PC12 cells with a construct containing an EGR promoter linked to SEAP reporter, activation of PC12 cells can be assessed.

The EGR/SEAP reporter construct can be assembled by the following protocol. The EGR-1 promoter sequence (−633 to +1)(Sakamoto K et al., Oncogene 6:867-871 (1991)) can be PCR amplified from human genomic DNA using the following primers:

5' GCGCTCGAGGGATGACAGCGATAGAACCCCGG-3' (SEQ ID NO:6)

5' GCGAAGCTTCGCGACTCCCCGGATCCGCCTC-3' (SEQ ID NO:7).

Using the GAS:SEAP/Neo vector produced in Example 12, EGR1 amplified product can then be inserted into this vector. Linearize the GAS:SEAP/Neo vector using restriction enzymes XhoI/HindIII, removing the GAS/SV40 stuffer. Restrict the EGR1 amplified product with these same enzymes. Ligate the vector and the EGR1 promoter.

To prepare 96 well-plates for cell culture, two mls of a coating solution (1:30 dilution of collagen type I (Upstate Biotech Inc. Cat#08-115) in 30% ethanol (filter sterilized)) is added per one 10 cm plate or 50 ml per well of the 96-well plate, and allowed to air dry for 2 hr.

PC12 cells are routinely grown in RPMI-1640 medium (Bio Whittaker) containing 10% horse serum (JRH BIOSCIENCES, Cat. #12449-78P), 5% heat-inactivated fetal bovine serum (FBS) supplemented with 100 units/ml penicillin and 100 ug/ml streptomycin on a precoated 10 cm tissue culture dish. One to four split is done every three to four days. Cells are removed from the plates by scraping and resuspended with pipetting up and down for more than 15 times.

Transfect the EGR/SEAP/Neo construct into PC12 using the Lipofectamine protocol described in Example 11. EGR-SEAP/PC12 stable cells are obtained by growing the cells in 300 ug/ml G418. The G418-free medium is used for routine growth but every one to two months, the cells should be re-grown in 300 ug/ml G418 for couple of passages.

To assay for neuronal activity, a 10 cm plate with cells around 70 to 80% confluent is screened by removing the old medium. Wash the cells once with PBS (Phosphate buffered saline). Then starve the cells in low serum medium (RPMI-1640 containing 1% horse serum and 0.5% FBS with antibiotics) overnight.

The next morning, remove the medium and wash the cells with PBS. Scrape off the cells from the plate, suspend the cells well in 2 ml low serum medium. Count the cell number and add more low serum medium to reach final cell density as $5\times10^5$ cells/ml.

Add 200 ul of the cell suspension to each well of 96-well plate (equivalent to $1\times10^5$ cells/well). Add 50 ul supernatant produced by Example 11, 37° C. for 48 to 72 hr. As a positive control, a growth factor known to activate PC12 cells through EGR can be used, such as 50 ng/ul of Neuronal Growth Factor (NGF). Over fifty-fold induction of SEAP is typically seen in the positive control wells. SEAP assay the supernatant according to Example 17.

Example 16

High-Throughput Screening Assay for T-cell Activity

NF-KB (Nuclear Factor KB) is a transcription factor activated by a wide variety of agents including the inflammatory cytokines IL-1 and TNF, CD30 and CD40, lymphotoxin-alpha and lymphotoxin-beta, by exposure to LPS or thrombin, and by expression of certain viral gene products. As a transcription factor, NF-KB regulates the expression of genes involved in immune cell activation, control of apoptosis (NF-KB appears to shield cells from apoptosis), B and T-cell development, anti-viral and antimicrobial responses, and multiple stress responses.

In non-stimulated conditions, NF-KB is retained in the cytoplasm with I-KB (Inhibitor KB). However, upon stimulation, I-KB is phosphorylated and degraded, causing NF-KB to shuttle to the nucleus, thereby activating transcription of target genes. Target genes activated by NF-KB include IL-2, IL-6, GM-CSF, ICAM-1 and class 1 MHC.

Due to its central role and ability to respond to a range of stimuli, reporter constructs utilizing the NF-KB promoter element are used to screen the supernatants produced in Example 11. Activators or inhibitors of NF-KB would be useful in treating diseases. For example, inhibitors of NF-KB could be used to treat those diseases related to the acute or chronic activation of NF-KB, such as rheumatoid arthritis.

To construct a vector containing the NF-KB promoter element, a PCR based strategy is employed. The upstream primer contains four tandem copies of the NF-KB binding site (GGGGACTTTCCC) (SEQ ID NO:8), 18 bp of sequence complementary to the 5' end of the SV40 early promoter sequence, and is flanked with an XhoI site: 5':GCGGCCTCGAGGGGACTTTCCCGGGGACTTTCCGGGGACTTTCCGGGAC TTTCCATCCTGCCATCTCAATTAG:3' (SEQ ID NO:9)

The downstream primer is complementary to the 3' end of the SV40 promoter and is flanked with a Hind III site: 5':GCGGCAAGCTTTTTGCAAAGCCTAGGC:3' (SEQ ID NO:4)

PCR amplification is performed using the SV40 promoter template present in the pB-gal:promoter plasmid obtained from Clontech. The resulting PCR fragment is digested with XhoI and Hind III and subcloned into BLSK2-. (Stratagene) Sequencing with the T7 and T3 primers confirms the insert contains the following sequence: 5':CTCGAGGGGACTTTCCCGGGGACTTTCCGGGGACTTTCCGGGACTTTCC ATCTGCCATCTCAATTAGTCAGCAACCATAGTCCCGCCCCTAACTCCGCCC ATCCCGCCCCTAACTCCGCCCAGTTCCGCCCATTCTCCGCCCCATGGCTGA CTAATTTTTTTTATTTATGCAGAGGCCGAGGCCGCCTCGGCCTCTGAGCTA TTCCAGAAGTAGTGAGGAGGCTTTTTTGGAGGCCTAGGCTTTTGCAAAAA GCTT:3' (SEQ ID NO:10)

Next, replace the SV40 minimal promoter element present in the pSEAP2-promoter plasmid (Clontech) with this NF-KB/SV40 fragment using XhoI and HindIII. However, this vector does not contain a neomycin resistance gene, and therefore, is not preferred for mammalian expression systems.

In order to generate stable mammalian cell lines, the NF-KB/SV40/SEAP cassette is removed from the above NF-KB/SEAP vector using restriction enzymes SalI and NotI, and inserted into a vector containing neomycin resistance. Particularly, the NF-KB/SV40/SEAP cassette was inserted into pGFP-1 (Clontech), replacing the GFP gene, after restricting pGFP-1 with SalI and NotI.

Once NF-KB/SV40/SEAP/Neo vector is created, stable Jurkat T-cells are created and maintained according to the protocol described in Example 13. Similarly, the method for assaying supernatants with these stable Jurkat T-cells is also described in Example 13. As a positive control, exogenous TNF alpha (0.1, 1, 10 ng) is added to wells H9, H10, and H11, with a 5-10 fold activation typically observed.

Example 17

Assay for SEAP Activity

As a reporter molecule for the assays described in Examples 13-16, SEAP activity is assayed using the Tropix Phospho-light Kit (Cat. BP-400) according to the following general procedure. The Tropix Phospho-light Kit supplies the Dilution, Assay, and Reaction Buffers used below.

Prime a dispenser with the 2.5× Dilution Buffer and dispense 15 ul of 2.5× dilution buffer into Optiplates containing 35 ul of a supernatant. Seal the plates with a plastic sealer and incubate at 65 degree C. for 30 min. Separate the Optiplates to avoid uneven heating.

Cool the samples to room temperature for 15 minutes. Empty the dispenser and prime with the Assay Buffer. Add 50 ml Assay Buffer and incubate at room temperature 5 min. Empty the dispenser and prime with the Reaction Buffer (see the table below). Add 50 ul Reaction Buffer and incubate at room temperature for 20 minutes. Since the intensity of the chemiluminescent signal is time dependent, and it takes about 10 minutes to read 5 plates on luminometer, one should treat 5 plates at each time and start the second set 10 minutes later.

Read the relative light unit in the luminometer. Set H12 as blank, and print the results. An increase in chemiluminescence indicates reporter activity.

| | Reaction Buffer Formulation: | |
|---|---|---|
| # of plates | Rxn buffer diluent (ml) | CSPD (ml) |
| 10 | 60 | 3 |
| 11 | 65 | 3.25 |
| 12 | 70 | 3.5 |
| 13 | 75 | 3.75 |
| 14 | 80 | 4 |
| 15 | 85 | 4.25 |
| 16 | 90 | 4.5 |
| 17 | 95 | 4.75 |
| 18 | 100 | 5 |
| 19 | 105 | 5.25 |
| 20 | 110 | 5.5 |
| 21 | 115 | 5.75 |
| 22 | 120 | 6 |
| 23 | 125 | 6.25 |
| 24 | 130 | 6.5 |
| 25 | 135 | 6.75 |
| 26 | 140 | 7 |
| 27 | 145 | 7.25 |
| 28 | 150 | 7.5 |
| 29 | 155 | 7.75 |
| 30 | 160 | 8 |
| 31 | 165 | 8.25 |
| 32 | 170 | 8.5 |
| 33 | 175 | 8.75 |
| 34 | 180 | 9 |
| 35 | 185 | 9.25 |
| 36 | 190 | 9.5 |
| 37 | 195 | 9.75 |
| 38 | 200 | 10 |
| 39 | 205 | 10.25 |
| 40 | 210 | 10.5 |
| 41 | 215 | 10.75 |
| 42 | 220 | 11 |
| 43 | 225 | 11.25 |
| 44 | 230 | 11.5 |
| 45 | 235 | 11.75 |
| 46 | 240 | 12 |
| 47 | 245 | 12.25 |
| 48 | 250 | 12.5 |
| 49 | 255 | 12.75 |
| 50 | 260 | 13 |

Example 18

High-Throughput Screening Assay Identifying Changes in Small Molecule Concentration and Membrane Permeability Binding of a ligand to a receptor is known to alter intracellular levels of small molecules, such as calcium, potassium, sodium, and pH, as well as alter membrane potential. These alterations can be measured in an assay to identify supernatants which bind to receptors of a particular cell. Although the following protocol describes an assay for calcium, this protocol can easily be modified to detect changes in potassium, sodium, pH, membrane potential, or any other small molecule which is detectable by a fluorescent probe.

The following assay uses Fluorometric Imaging Plate Reader ("FLIPR") to measure changes in fluorescent molecules (Molecular Probes) that bind small molecules. Clearly, any fluorescent molecule detecting a small molecule can be used instead of the calcium fluorescent molecule, fluo-4 (Molecular Probes, Inc.; catalog no. F-14202), used here.

For adherent cells, seed the cells at 10,000-20,000 cells/well in a Co-star black 96-well plate with clear bottom. The plate is incubated in a $CO_2$ incubator for 20 hours. The adherent cells are washed two times in Biotek washer with 200 ul of HBSS (Hank's Balanced Salt Solution) leaving 100 ul of buffer after the final wash.

A stock solution of 1 mg/ml fluo-4 is made in 10% pluronic acid DMSO. To load the cells with fluo-4, 50 ul of 12 ug/ml fluo-4 is added to each well. The plate is incubated at 37 degrees C. in a $CO_2$ incubator for 60 min. The plate is washed four times in the Biotek washer with HBSS leaving 100 ul of buffer.

For non-adherent cells, the cells are spun down from culture media. Cells are re-suspended to $2\text{-}5\times10^6$ cells/ml with HBSS in a 50-ml conical tube. 4 ul of 1 mg/ml fluo-4 solution in 10% pluronic acid DMSO is added to each ml of cell suspension. The tube is then placed in a 37 degrees C. water bath for 30-60 min. The cells are washed twice with HBSS, resuspended to $1\times10^6$ cells/ml, and dispensed into a microplate, 100 ul/well. The plate is centrifuged at 1000 rpm for 5 min. The plate is then washed once in Denley CellWash with 200 ul, followed by an aspiration step to 100 ul final volume.

For a non-cell based assay, each well contains a fluorescent molecule, such as fluo-4. The supernatant is added to the well, and a change in fluorescence is detected.

To measure the fluorescence of intracellular calcium, the FLIPR is set for the following parameters: (1) System gain is 300-800 mW; (2) Exposure time is 0.4 second; (3) Camera F/stop is F/2; (4) Excitation is 488 nm; (5) Emission is 530 nm; and (6) Sample addition is 50 ul. Increased emission at 530 nm indicates an extracellular signaling event which has resulted in an increase in the intracellular $Ca^{++}$ concentration.

Example 19

High-Throughput Screening Assay Identifying Tyrosine Kinase Activity

The Protein Tyrosine Kinases (PTK) represent a diverse group of transmembrane and cytoplasmic kinases. Within the Receptor Protein Tyrosine Kinase RPTK) group are receptors for a range of mitogenic and metabolic growth factors including the PDGF, FGF, EGF, NGF, HGF and Insulin receptor subfamilies. In addition there are a large family of RPTKs for which the corresponding ligand is unknown. Ligands for RPTKs include mainly secreted small proteins, but also membrane-bound and extracellular matrix proteins.

Activation of RPTK by ligands involves ligand-mediated receptor dimerization, resulting in transphosphorylation of the receptor subunits and activation of the cytoplasmic tyrosine kinases. The cytoplasmic tyrosine kinases include receptor associated tyrosine kinases of the src-family (e.g., src, yes, lck, lyn, fyn) and non-receptor linked and cytosolic protein tyrosine kinases, such as the Jak family, members of which mediate signal transduction triggered by the cytokine superfamily of receptors (e.g., the Interleukins, Interferons, GM-CSF, and Leptin).

Because of the wide range of known factors capable of stimulating tyrosine kinase activity, the identification of novel human secreted proteins capable of activating tyrosine kinase signal transduction pathways are of interest. Therefore, the following protocol is designed to identify those novel human secreted proteins capable of activating the tyrosine kinase signal transduction pathways.

Seed target cells (e.g., primary keratinocytes) at a density of approximately 25,000 cells per well in a 96 well Loprodyne Silent Screen Plates purchased from Nalge Nunc (Naperville, Ill.). The plates are sterilized with two 30 minute rinses with 100% ethanol, rinsed with water and dried overnight. Some plates are coated for 2 hr with 100 ml of cell culture grade type I collagen (50 mg/ml), gelatin (2%) or polylysine (50 mg/ml), all of which can be purchased from Sigma Chemicals (St. Louis, Mo.) or 10% Matrigel purchased from Becton Dickinson (Bedford, Mass.), or calf serum, rinsed with PBS and stored at 4 degree C. Cell growth on these plates is assayed by seeding 5,000 cells/well in growth medium and indirect quantitation of cell number through use of alamarBlue as described by the manufacturer Alamar Biosciences, Inc. (Sacramento, Calif.) after 48 hr. Falcon plate covers #3071 from Becton Dickinson (Bedford, Mass.) are used to cover the Loprodyne Silent Screen Plates. Falcon Microtest III cell culture plates can also be used in some proliferation experiments.

To prepare extracts, A431 cells are seeded onto the nylon membranes of Loprodyne plates (20,000/200 ml/well) and cultured overnight in complete medium. Cells are quiesced by incubation in serum-free basal medium for 24 hr. After 5-20 minutes treatment with EGF (60 ng/ml) or 50 ul of the supernatant produced in Example 11, the medium was removed and 100 ml of extraction buffer ((20 mM HEPES pH 7.5, 0.15 M NaCl, 1% Triton X-100, 0.1% SDS, 2 mM Na3VO4, 2 mM Na4P2O7 and a cocktail of protease inhibitors (#1836170) obtained from Boeheringer Mannheim (Indianapolis, Ind.) is added to each well and the plate is shaken on a rotating shaker for 5 minutes at 4 degrees C. The plate is then placed in a vacuum transfer manifold and the extract filtered through the 0.45 mm membrane bottoms of each well using house vacuum. Extracts are collected in a 96-well catch/assay plate in the bottom of the vacuum manifold and immediately placed on ice. To obtain extracts clarified by centrifugation, the content of each well, after detergent solubilization for 5 minutes, is removed and centrifuged for 15 minutes at 4 degrees C. at 16,000×g.

Test the filtered extracts for levels of tyrosine kinase activity. Although many methods of detecting tyrosine kinase activity are known, one method is described here.

Generally, the tyrosine kinase activity of a supernatant is evaluated by determining its ability to phosphorylate a tyrosine residue on a specific substrate (a biotinylated peptide). Biotinylated peptides that can be used for this purpose include PSK1 (corresponding to amino acids 6-20 of the cell division kinase cdc2-p34) and PSK2 (corresponding to amino acids 1-17 of gastrin). Both peptides are substrates for a range of tyrosine kinases and are available from Boehringer Mannheim.

The tyrosine kinase reaction is set up by adding the following components in order. First, add 10 ul of 5 uM Biotinylated Peptide, then 10 ul ATP/$Mg_{2+}$ (5 mM ATP/50 mM $MgCl_2$), then 10 ul of 5× Assay Buffer (40 mM imidazole hydrochloride, pH7.3, 40 mM beta-glycerophosphate, 1 mM EGTA, 100 mM $MgCl_2$, 5 mM $MnCl_2$, 0.5 mg/ml BSA), then 5 ul of Sodium Vanadate (1 mM), and then 5 ul of water. Mix the components gently and preincubate the reaction mix at 30 degrees C. for 2 min. Initial the reaction by adding 10 ul of the control enzyme or the filtered supernatant.

The tyrosine kinase assay reaction is then terminated by adding 10 ul of 120 mm EDTA and place the reactions on ice.

Tyrosine kinase activity is determined by transferring 50 ul aliquot of reaction mixture to a microtiter plate (MTP) module and incubating at 37 degrees C. for 20 min. This allows the streptavadin coated 96 well plate to associate with the biotinylated peptide. Wash the MTP module with 300 ul/well of PBS four times. Next add 75 ul of anti-phospotyrosine antibody conjugated to horse radish peroxidase (anti-P-Tyr-POD(0.5 u/ml)) to each well and incubate at 37 degrees C. for one hour. Wash the well as above.

Next add 100 ul of peroxidase substrate solution (Boehringer Mannheim) and incubate at room temperature for at least 5 mins (up to 30 min). Measure the absorbance of the sample at 405 nm by using ELISA reader. The level of bound peroxidase activity is quantitated using an ELISA reader and reflects the level of tyrosine kinase activity.

Example 20

High-Throughput Screening Assay Identifying Phosphorylation Activity

As a potential alternative and/or compliment to the assay of protein tyrosine kinase activity described in Example 19, an assay which detects activation (phosphorylation) of major intracellular signal transduction intermediates can also be used. For example, as described below one particular assay can detect tyrosine phosphorylation of the Erk-1 and Erk-2 kinases. However, phosphorylation of other molecules, such as Raf, JNK, p38 MAP, Map kinase kinase (MEK), MEK kinase, Src, Muscle specific kinase (MuSK), IRAK, Tec, and Janus, as well as any other phosphoserine, phosphotyrosine, or phosphothreonine molecule, can be detected by substituting these molecules for Erk-1 or Erk-2 in the following assay.

Specifically, assay plates are made by coating the wells of a 96-well ELISA plate with 0.1 ml of protein G (1 ug/ml) for 2 hr at room temp, (RT). The plates are then rinsed with PBS and blocked with 3% BSA/PBS for 1 hr at RT. The protein G plates are then treated with 2 commercial monoclonal antibodies (100 ng/well) against Erk-1 and Erk-2 (1 hr at RT) (Santa Cruz Biotechnology). (To detect other molecules, this step can easily be modified by substituting a monoclonal antibody detecting any of the above described molecules.) After 3-5 rinses with PBS, the plates are stored at 4 degrees C. until use.

A431 cells are seeded at 20,000/well in a 96-well Loprodyne filterplate and cultured overnight in growth medium. The cells are then starved for 48 hr in basal medium (DMEM) and then treated with EGF (6 ng/well) or 50 ul of the supernatants obtained in Example 11 for 5-20 minutes. The cells are then solubilized and extracts filtered directly into the assay plate.

After incubation with the extract for 1 hr at RT, the wells are again rinsed. As a positive control, a commercial preparation of MAP kinase (10 ng/well) is used in place of A431 extract. Plates are then treated with a commercial polyclonal (rabbit) antibody (1 ug/ml) which specifically recognizes the phosphorylated epitope of the Erk-1 and Erk-2 kinases (1 hr at RT). This antibody is biotinylated by standard procedures. The bound polyclonal antibody is then quantitated by successive incubations with Europium-streptavidin and Europium fluorescence enhancing reagent in the Wallac DELFIA instrument (time-resolved fluorescence). An increased fluorescent signal over background indicates a phosphorylation.

Example 21

Method of Determining Alterations in a Gene Corresponding to a Polynucleotide RNA isolated from entire families or individual patients presenting with a phenotype of interest (such as a disease) is be isolated. cDNA is then generated from these RNA samples using protocols known in the art. (See, Sambrook.) The cDNA is then used as a template for PCR, employing primers surrounding regions of interest in SEQ ID NO:X. Suggested PCR conditions consist of 35 cycles at 95 degrees C. for 30 seconds; 60-120 seconds at 52-58 degrees C.; and 60-120 seconds at 70 degrees C., using buffer solutions described in Sidransky et al., Science 252:706 (1991).

PCR products are then sequenced using primers labeled at their 5' end with T4 polynucleotide kinase, employing SequiTherm Polymerase. (Epicentre Technologies). The intron-exon borders of selected exons is also determined and genomic PCR products analyzed to confirm the results. PCR products harboring suspected mutations is then cloned and sequenced to validate the results of the direct sequencing.

PCR products is cloned into T-tailed vectors as described in Holton et al., Nucleic Acids Research, 19:1156 (1991) and sequenced with T7 polymerase (United States Biochemical). Affected individuals are identified by mutations not present in unaffected individuals.

Genomic rearrangements are also observed as a method of determining alterations in a gene corresponding to a polynucleotide. Genomic clones isolated according to Example 2 are nick-translated with digoxigenindeoxy-uridine 5'-triphosphate (Boehringer Manheim), and FISH performed as described in Johnson et al., Methods Cell Biol. 35:73-99 (1991). Hybridization with the labeled probe is carried out using a vast excess of human cot-1 DNA for specific hybridization to the corresponding genomic locus.

Chromosomes are counterstained with 4,6-diamino-2-phenylidole and propidium iodide, producing a combination of C- and R-bands. Aligned images for precise mapping are obtained using a triple-band filter set (Chroma Technology, Brattleboro, Vt.) in combination with a cooled charge-coupled device camera (Photometrics, Tucson, Ariz.) and variable excitation wavelength filters. (Johnson et al., Genet. Anal. Tech. Appl., 8:75 (1991).) Image collection, analysis and chromosomal fractional length measurements are performed using the ISee Graphical Program System. (Inovision Corporation, Durham, N.C.) Chromosome alterations of the genomic region hybridized by the probe are identified as insertions, deletions, and translocations. These alterations are used as a diagnostic marker for an associated disease.

Example 22

Method of Detecting Abnormal Levels of a Polypeptide in a Biological Sample

A polypeptide of the present invention can be detected in a biological sample, and if an increased or decreased level of the polypeptide is detected, this polypeptide is a marker for a particular phenotype. Methods of detection are numerous, and thus, it is understood that one skilled in the art can modify the following assay to fit their particular needs.

For example, antibody-sandwich ELISAs are used to detect polypeptides in a sample, preferably a biological sample. Wells of a microtiter plate are coated with specific antibodies, at a final concentration of 0.2 to 10 ug/ml. The antibodies are either monoclonal or polyclonal and are produced by the method described in Example 10. The wells are blocked so that non-specific binding of the polypeptide to the well is reduced.

The coated wells are then incubated for >2 hours at RT with a sample containing the polypeptide. Preferably, serial dilutions of the sample should be used to validate results. The plates are then washed three times with deionized or distilled water to remove unbounded polypeptide.

Next, 50 ul of specific antibody-alkaline phosphatase conjugate, at a concentration of 25-400 ng, is added and incubated for 2 hours at room temperature. The plates are again washed three times with deionized or distilled water to remove unbounded conjugate.

Add 75 ul of 4-methylumbelliferyl phosphate (MUP) or p-nitrophenyl phosphate (NPP) substrate solution to each well and incubate 1 hour at room temperature. Measure the reaction by a microtiter plate reader. Prepare a standard curve, using serial dilutions of a control sample, and plot polypeptide concentration on the X-axis (log scale) and fluorescence or absorbance of the Y-axis (linear scale). Interpolate the concentration of the polypeptide in the sample using the standard curve.

Example 23

Formulation

The invention also provides methods of treatment and/or prevention diseases, disorders, and/or conditions (such as, for example, any one or more of the diseases or disorders disclosed herein) by administration to a subject of an effective amount of a Therapeutic. By therapeutic is meant a polynucleotides or polypeptides of the invention (including fragments and variants), agonists or antagonists thereof, and/or antibodies thereto, in combination with a pharmaceutically acceptable carrier type (e.g., a sterile carrier).

The Therapeutic will be formulated and dosed in a fashion consistent with good medical practice, taking into account the clinical condition of the individual patient (especially the side effects of treatment with the Therapeutic alone), the site of delivery, the method of administration, the scheduling of administration, and other factors known to practitioners. The "effective amount" for purposes herein is thus determined by such considerations.

As a general proposition, the total pharmaceutically effective amount of the Therapeutic administered parenterally per dose will be in the range of about 1 ug/kg/day to 10 mg/kg/day of patient body weight, although, as noted above, this will be subject to therapeutic discretion. More preferably, this dose is at least 0.01 mg/kg/day, and most preferably for humans between about 0.01 and 1 mg/kg/day for the hormone. If given continuously, the Therapeutic is typically administered at a dose rate of about 1 ug/kg/hour to about 50 ug/kg/hour, either by 1-4 injections per day or by continuous subcutaneous infusions, for example, using a mini-pump. An intravenous bag solution may also be employed. The length of treatment needed to observe changes and the interval following treatment for responses to occur appears to vary depending on the desired effect.

Therapeutics can be are administered orally, rectally, parenterally, intracistemally, intravaginally, intraperitoneally, topically (as by powders, ointments, gels, drops or transdermal patch), bucally, or as an oral or nasal spray. "Pharmaceutically acceptable carrier" refers to a non-toxic solid, semisolid or liquid filler, diluent, encapsulating material or formulation auxiliary of any. The term "parenteral" as used herein refers to modes of administration which include intravenous, intramuscular, intraperitoneal, intrasternal, subcutaneous and intraarticular injection and infusion.

Therapeutics of the invention are also suitably administered by sustained-release systems. Suitable examples of sustained-release Therapeutics are administered orally, rectally, parenterally, intracistemally, intravaginally, intraperitoneally, topically (as by powders, ointments, gels, drops or transdermal patch), bucally, or as an oral or nasal spray. "Pharmaceutically acceptable carrier" refers to a non-toxic solid, semisolid or liquid filler, diluent, encapsulating material or formulation auxiliary of any type. The term "parenteral" as used herein refers to modes of administration which include intravenous, intramuscular, intraperitoneal, intrasternal, subcutaneous and intraarticular injection and infusion.

Therapeutics of the invention are also suitably administered by sustained-release systems. Suitable examples of sustained-release Therapeutics include suitable polymeric materials (such as, for example, semi-permeable polymer matrices in the form of shaped articles, e.g., films, or mirocapsules), suitable hydrophobic materials (for example as an emulsion in an acceptable oil) or ion exchange resins, and sparingly soluble derivatives (such as, for example, a sparingly soluble salt).

Sustained-release matrices include polylactides (U.S. Pat. No. 3,773,919, EP 58,481), copolymers of L-glutamic acid and gamma-ethyl-L-glutamate (Sidman et al., Biopolymers 22:547-556 (1983)), poly (2-hydroxyethyl methacrylate) (Langer et al., J. Biomed. Mater. Res. 15:167-277 (1981), and Langer, Chem. Tech. 12:98-105 (1982)), ethylene vinyl acetate (Langer et al., Id.) or poly-D-(−)-3-hydroxybutyric acid (EP 133,988).

Sustained-release Therapeutics also include liposomally entrapped Therapeutics of the invention (see generally, Langer, *Science* 249:1527-1533 (1990); Treat et al., in *Liposomes in the Therapy of Infectious Disease and Cancer*, Lopez-Berestein and Fidler (eds.), Liss, New York, pp. 317-327 and 353-365 (1989)). Liposomes containing the Therapeutic are prepared by methods known per se: DE 3,218,121; Epstein et al., Proc. Natl. Acad. Sci. (USA) 82:3688-3692 (1985); Hwang et al., Proc. Natl. Acad. Sci. (USA) 77:4030-4034 (1980); EP 52,322; EP 36,676; EP 88,046; EP 143,949; EP 142,641; Japanese Pat. Appl. 83-118008; U.S. Pat. Nos. 4,485,045 and 4,544,545; and EP 102,324. Ordinarily, the liposomes are of the small (about 200-800 Angstroms) unilamellar type in which the lipid content is greater than about 30 mol. percent cholesterol, the selected proportion being adjusted for the optimal Therapeutic.

In yet an additional embodiment, the Therapeutics of the invention are delivered by way of a pump (see Langer, supra; Sefton, CRC Crit. Ref. Biomed. Eng. 14:201 (1987); Buchwald et al., Surgery 88:507 (1980); Saudek et al., N. Engl. J. Med. 321:574 (1989)).

Other controlled release systems are discussed in the review by Langer (*Science* 249:1527-1533 (1990)).

For parenteral administration, in one embodiment, the Therapeutic is formulated generally by mixing it at the desired degree of purity, in a unit dosage injectable form (solution, suspension, or emulsion), with a pharmaceutically acceptable carrier, i.e., one that is non-toxic to recipients at the dosages and concentrations employed and is compatible with other ingredients of the formulation. For example, the formulation preferably does not include oxidizing agents and other compounds that are known to be deleterious to the Therapeutic.

Generally, the formulations are prepared by contacting the Therapeutic uniformly and intimately with liquid carriers or finely divided solid carriers or both. Then, if necessary, the product is shaped into the desired formulation. Preferably the carrier is a parenteral carrier, more preferably a solution that is isotonic with the blood of the recipient. Examples of such carrier vehicles include water, saline, Ringer's solution, and dextrose solution. Non-aqueous vehicles such as fixed oils and ethyl oleate are also useful herein, as well as liposomes.

The carrier suitably contains minor amounts of additives such as substances that enhance isotonicity and chemical stability. Such materials are non-toxic to recipients at the dosages and concentrations employed, and include buffers such as phosphate, citrate, succinate, acetic acid, and other organic acids or their salts; antioxidants such as ascorbic acid; low molecular weight (less than about ten residues) polypeptides, e.g., polyarginine or tripeptides; proteins, such as serum albumin, gelatin, or immunoglobulins; hydrophilic polymers such as polyvinylpyrrolidone; amino acids, such as glycine, glutamic acid, aspartic acid, or arginine; monosaccharides, disaccharides, and other carbohydrates including cellulose or its derivatives, glucose, manose, or dextrins; chelating agents such as EDTA; sugar alcohols such as mannitol or sorbitol; counterions such as sodium; and/or nonionic surfactants such as polysorbates, poloxamers, or PEG.

The Therapeutic is typically formulated in such vehicles at a concentration of about 0.1 mg/ml to 100 mg/ml, preferably 1-10 mg/ml, at a pH of about 3 to 8. It will be understood that the use of certain of the foregoing excipients, carriers, or stabilizers will result in the formation of polypeptide salts.

Any pharmaceutical used for therapeutic administration can be sterile. Sterility is readily accomplished by filtration through sterile filtration membranes (e.g., 0.2 micron membranes). Therapeutics generally are placed into a container having a sterile access port, for example, an intravenous solution bag or vial having a stopper pierceable by a hypodermic injection needle.

Therapeutics ordinarily will be stored in unit or multi-dose containers, for example, sealed ampoules or vials, as an aqueous solution or as a lyophilized formulation for reconstitution. As an example of a lyophilized formulation, 10-ml vials are filled with 5 ml of sterile-filtered 1% (w/v) aqueous Therapeutic solution, and the resulting mixture is lyophilized. The infusion solution is prepared by reconstituting the lyophilized Therapeutic using bacteriostatic Water-for-Injection.

The invention also provides a pharmaceutical pack or kit comprising one or more containers filled with one or more of the ingredients of the Therapeutics of the invention. Associated with such container(s) can be a notice in the form prescribed by a governmental agency regulating the manufacture, use or sale of pharmaceuticals or biological products, which notice reflects approval by the agency of manufacture, use or sale for human administration. In addition, the Therapeutics may be employed in conjunction with other therapeutic compounds.

The Therapeutics of the invention may be administered alone or in combination with adjuvants. Adjuvants that may be administered with the Therapeutics of the invention include, but are not limited to, alum, alum plus deoxycholate (ImmunoAg), MTP-PE (Biocine Corp.), QS21 (Genentech, Inc.), BCG, and MPL. In a specific embodiment, Therapeutics of the invention are administered in combination with alum. In another specific embodiment, Therapeutics of the invention are administered in combination with QS-21. Further adjuvants that may be administered with the Therapeutics of the invention include, but are not limited to, Monophosphoryl lipid immunomodulator, AdjuVax 100a, QS-21, QS-18, CRL1005, Aluminum salts, MF-59, and Virosomal adjuvant technology. Vaccines that may be administered with the Therapeutics of the invention include, but are not limited to, vaccines directed toward protection against MMR (measles, mumps, rubella), polio, varicella, tetanus/diptheria, hepatitis A, hepatitis B, *haemophilus influenzae* B, whooping cough, pneumonia, influenza, Lyme's Disease, rotavirus, cholera, yellow fever, Japanese encephalitis, poliomyelitis, rabies, typhoid fever, and pertussis. Combinations may be administered either concomitantly, e.g., as an admixture, separately but simultaneously or concurrently; or sequentially. This includes presentations in which the combined agents are administered together as a therapeutic mixture, and also procedures in which the combined agents are administered separately but simultaneously, e.g., as through separate intravenous lines into the same individual. Administration "in combination" further includes the separate administration of one of the compounds or agents given first, followed by the second.

The Therapeutics of the invention may be administered alone or in combination with other therapeutic agents. Therapeutic agents that may be administered in combination with the Therapeutics of the invention, include but not limited to, other members of the TNF family, chemotherapeutic agents, antibiotics, steroidal and non-steroidal anti-inflammatories, conventional immunotherapeutic agents, cytokines and/or growth factors. Combinations may be administered either concomitantly, e.g., as an admixture, separately but simultaneously or concurrently; or sequentially. This includes presentations in which the combined agents are administered together as a therapeutic mixture, and also procedures in which the combined agents are administered separately but simultaneously, e.g., as through separate intravenous lines into the same individual. Administration "in combination" further includes the separate administration of one of the compounds or agents given first, followed by the second.

In one embodiment, the Therapeutics of the invention are administered in combination with members of the TNF family. TNF, TNF-related or TNF-like molecules that may be administered with the Therapeutics of the invention include, but are not limited to, soluble forms of TNF-alpha, lymphotoxin-alpha (LT-alpha, also known as TNF-beta), LT-beta (found in complex heterotrimer LT-alpha2-beta), OPGL, FasL, CD27L, CD30L, CD40L, 4-1BBL, DcR3, OX40L, TNF-gamma (International Publication No. WO 96/14328), AIM-I (International Publication No. WO 97/33899), endokine-alpha (International Publication No. WO 98/07880), TR6 (International Publication No. WO 98/30694), OPG, and neutrokine-alpha (International Publication No. WO 98/18921, OX40, and nerve growth factor (NGF), and soluble forms of Fas, CD30, CD27, CD40 and 4-IBB, TR2 (International Publication No. WO 96/34095), DR3 (International Publication No. WO 97/33904), DR4 (International Publication No. WO 98/32856), TR5 (International Publication No. WO 98/30693), TR6 (International Publication No. WO 98/30694), TR7 (International Publication No. WO 98/41629), TRANK, TR9 (International Publication No. WO 98/56892), TR10 (International Publication No. WO 98/54202), 312C2 (International Publication No. WO 98/06842), and TR12, and soluble forms CD154, CD70, and CD153.

In certain embodiments, Therapeutics of the invention are administered in combination with antiretroviral agents, nucleoside reverse transcriptase inhibitors, non-nucleoside reverse transcriptase inhibitors, and/or protease inhibitors. Nucleoside reverse transcriptase inhibitors that may be administered in combination with the Therapeutics of the invention, include, but are not limited to, RETROVIR™ (zidovudine/AZT), VIDEX™ (didanosine/ddI), HIVID™ (zalcitabine/ddC), ZERIT™ (stavudine/d4T), EPIVIR™ (lamivudine/3TC), and COMBIVIR™ (zidovudine/lamivudine). Non-nucleoside reverse transcriptase inhibitors that may be administered in combination with the Therapeutics of the invention, include, but are not limited to, VIRAMUNE™ (nevirapine), RESCRIPTOR™ (delavirdine), and SUSTIVA™ (efavirenz). Protease inhibitors that may be administered in combination with the Therapeutics of the invention, include, but are not limited to, CRIXVAN™ (indinavir), NORVIR™ (ritonavir), INVIRASE™ (saquinavir), and VIRACEPT™ (nelfinavir). In a specific embodiment, antiretroviral agents, nucleoside reverse transcriptase inhibitors, non-nucleoside reverse transcriptase inhibitors, and/or protease inhibitors may be used in any combination with Therapeutics of the invention to treat AIDS and/or to prevent or treat HIV infection.

In other embodiments, Therapeutics of the invention may be administered in combination with anti-opportunistic infection agents. Anti-opportunistic agents that may be administered in combination with the Therapeutics of the invention, include, but are not limited to, TRIMETHOPRIM-SULFAMETHOXAZOLE™, DAPSONE™, PENTAMIDINE™, ATOVAQUONE™, ISONIAZID™, RIFAMPIN™, PYRAZINAMIDE™, ETHAMBUTOL™, RIFABUTIN™, CLARITHROMYCIN™, AZITHROMYCIN™, GANCICLOVIR™, FOSCARNET™, CIDOFOVIR™, FLUCONAZOLE™, ITRACONAZOLE™, KETOCONAZOLE™, ACYCLOVIR™, FAMCICOLVIR™, PYRIMETHAMINE™, LEUCOVORIN™, NEUPOGEN™ (filgrastim/G-CSF), and LEUKINE™ (sargramostim/GM-CSF). In a specific embodiment, Therapeutics of the invention are used in any combination with TRIMETHOPRIM-SULFAMETHOXAZOLE™, DAPSONE™, PENTAMIDINE™, and/or ATOVAQUONE™ to prophylactically treat or prevent an opportunistic *Pneumocystis carinii* pneumonia infection. In another specific embodiment, Therapeutics of the invention are used in any combination with ISONIAZID™, RIFAMPIN™, PYRAZINAMIDE™, and/or ETHAMBUTOL™ to prophylactically treat or prevent an opportunistic *Mycobacterium avium* complex infection. In another specific embodiment, Therapeutics of the invention are used in any combination with RIFABUTIN™, CLARITHROMYCIN™, and/or AZITHROMYCIN™ to prophylactically treat or prevent an opportunistic *Mycobacterium tuberculosis* infection. In another specific embodiment, Therapeutics of the invention are used in any combination with GANCICLOVIR™, FOSCARNET™, and/or CIDOFOVIR™ to prophylactically treat or prevent an opportunistic cytomegalovirus infection. In another specific embodiment, Therapeutics of the invention are used in any combination with FLUCONAZOLE™, ITRACONAZOLE™, and/or KETOCONAZOLE™ to prophylactically treat or prevent an opportunistic fungal infection. In another specific embodiment, Therapeutics of the invention are used in any combination with ACYCLOVIR™ and/or FAMCICOLVIR™ to prophylactically treat or prevent an opportunistic herpes simplex virus type I and/or type II infection. In another specific embodiment, Therapeutics of the invention are used in any combination with PYRIMETHAMINE™ and/or LEUCOVORIN™ to prophylactically treat or prevent an opportunistic *Toxoplasma gondii* infection. In another specific embodiment, Therapeutics of the invention are used in any combination with LEUCOVORIN™ and/or NEUPOGEN™ to prophylactically treat or prevent an opportunistic bacterial infection.

In a further embodiment, the Therapeutics of the invention are administered in combination with an antiviral agent. Antiviral agents that may be administered with the Therapeutics of the invention include, but are not limited to, acyclovir, ribavirin, amantadine, and remantidine.

In a further embodiment, the Therapeutics of the invention are administered in combination with an antibiotic agent. Antibiotic agents that may be administered with the Therapeutics of the invention include, but are not limited to, amoxicillin, beta-lactamases, aminoglycosides, beta-lactam (glycopeptide), beta-lactamases, Clindamycin, chloramphenicol, cephalosporins, ciprofloxacin, ciprofloxacin, erythromycin, fluoroquinolones, macrolides, metronidazole, penicillins, quinolones, rifampin, streptomycin, sulfonamide, tetracyclines, trimethoprim, trimethoprim-sulfamthoxazole, and vancomycin.

Conventional nonspecific immunosuppressive agents, that may be administered in combination with the Therapeutics of the invention include, but are not limited to, steroids, cyclosporine, cyclosporine analogs, cyclophosphamide methylprednisone, prednisone, azathioprine, FK-506, 15-deoxyspergualin, and other immunosuppressive agents that act by suppressing the function of responding T cells.

In specific embodiments, Therapeutics of the invention are administered in combination with immunosuppressants. Immunosuppressants preparations that may be administered with the Therapeutics of the invention include, but are not limited to, ORTHOCLONE™ (OKT3), SANDIMMUNE™/NEORAL™/SANGDYA™ (cyclosporin), PROGRAF™ (tacrolimus), CELLCEPT™ (mycophenolate), Azathioprine, glucorticosteroids, and RAPAMUNE™ (sirolimus). In a specific embodiment, immunosuppressants may be used to prevent rejection of organ or bone marrow transplantation.

In an additional embodiment, Therapeutics of the invention are administered alone or in combination with one or more intravenous immune globulin preparations. Intravenous immune globulin preparations that may be administered with the Therapeutics of the invention include, but not limited to, GAMMAR™, IVEEGAM™, SANDOGLOBULIN™, GAMMAGARD S/D™, and GAMIMUNE™. In a specific embodiment, Therapeutics of the invention are administered in combination with intravenous immune globulin preparations in transplantation therapy (e.g., bone marrow transplant).

In an additional embodiment, the Therapeutics of the invention are administered alone or in combination with an anti-inflammatory agent. Anti-inflammatory agents that may be administered with the Therapeutics of the invention include, but are not limited to, glucocorticoids and the nonsteroidal anti-inflammatories, aminoarylcarboxylic acid derivatives, arylacetic acid derivatives, arylbutyric acid derivatives, arylcarboxylic acids, arylpropionic acid derivatives, pyrazoles, pyrazolones, salicylic acid derivatives, thiazinecarboxamides, e-acetamidocaproic acid, S-adenosylmethionine, 3-amino-4-hydroxybutyric acid, amixetrine, bendazac, benzydamine, bucolome, difenpiramide, ditazol, emorfazone, guaiazulene, nabumetone, nimesulide, orgotein, oxaceprol, paranyline, perisoxal, pifoxime, proquazone, proxazole, and tenidap.

In another embodiment, compostions of the invention are administered in combination with a chemotherapeutic agent. Chemotherapeutic agents that may be administered with the Therapeutics of the invention include, but are not limited to, antibiotic derivatives (e.g., doxorubicin, bleomycin, daunorubicin, and dactinomycin); antiestrogens (e.g., tamoxifen); antimetabolites (e.g., fluorouracil, 5-FU, methotrexate, floxuridine, interferon alpha-2b, glutamic acid, plicamycin, mercaptopurine, and 6-thioguanine); cytotoxic agents (e.g., carmustine, BCNU, lomustine, CCNU, cytosine arabinoside, cyclophosphamide, estramustine, hydroxyurea, procarbazine, mitomycin, busulfan, cis-platin, and vincristine sulfate); hormones (e.g., medroxyprogesterone, estramustine phosphate sodium, ethinyl estradiol, estradiol, megestrol acetate, methyltestosterone, diethylstilbestrol diphosphate, chlorotrianisene, and testolactone); nitrogen mustard derivatives (e.g., mephalen, chorambucil, mechlorethamine (nitrogen mustard) and thiotepa); steroids and combinations (e.g., bethamethasone sodium phosphate); and others (e.g., dicarbazine, asparaginase, mitotane, vincristine sulfate, vinblastine sulfate, and etoposide).

In a specific embodiment, Therapeutics of the invention are administered in combination with CHOP (cyclophosphamide, doxorubicin, vincristine, and prednisone) or any combination of the components of CHOP. In another embodiment, Therapeutics of the invention are administered in combination with Rituximab. In a further embodiment, Therapeutics of the invention are administered with Rituxmab and CHOP, or Rituxmab and any combination of the components of CHOP.

In an additional embodiment, the Therapeutics of the invention are administered in combination with cytokines. Cytokines that may be administered with the Therapeutics of the invention include, but are not limited to, IL2, IL3, IL4, IL5, IL6, IL7, IL00, IL12, IL13, IL15, anti-CD40, CD40L, IFN-gamma and TNF-alpha. In another embodiment, Therapeutics of the invention may be administered with any interleukin, including, but not limited to, IL-1 alpha, IL-1beta, IL-2, IL-3, IL-4, IL-5, IL-6, IL-7, IL-8, IL-9, IL-10, IL-11, IL-12, IL-13, IL-14, IL-15, IL-16, IL-17, IL-18, IL-19, IL-20, and IL-21.

In an additional embodiment, the Therapeutics of the invention are administered in combination with angiogenic proteins. Angiogenic proteins that may be administered with the Therapeutics of the invention include, but are not limited to, Glioma Derived Growth Factor (GDGF), as disclosed in European Patent Number EP-399816; Platelet Derived Growth Factor-A (PDGF-A), as disclosed in European Patent Number EP-682110; Platelet Derived Growth Factor-B (PDGF-B), as disclosed in European Patent Number EP-282317; Placental Growth Factor (PlGF), as disclosed in International Publication Number WO 92/06194; Placental Growth Factor-2 (PlGF-2), as disclosed in Hauser et al., Growth Factors, 4:259-268 (1993); Vascular Endothelial Growth Factor (VEGF), as disclosed in International Publication Number WO 90/13649; Vascular Endothelial Growth Factor-A (VEGF-A), as disclosed in European Patent Number EP-506477; Vascular Endothelial Growth Factor-2 (VEGF-2), as disclosed in International Publication Number WO 96/39515; Vascular Endothelial Growth Factor B (VEGF-3); Vascular Endothelial Growth Factor B-186 (VEGF-B186), as disclosed in International Publication Number WO 96/26736; Vascular Endothelial Growth Factor-D (VEGF-D), as disclosed in International Publication Number WO 98/02543; Vascular Endothelial Growth Factor-D (VEGF-D), as disclosed in International Publication Number WO 98/07832; and Vascular Endothelial Growth Factor-E (VEGF-E), as disclosed in German Patent Number DE19639601. The above mentioned references are incorporated herein by reference herein.

In an additional embodiment, the Therapeutics of the invention are administered in combination with hematopoietic growth factors. Hematopoietic growth factors that may be administered with the Therapeutics of the invention include, but are not limited to, LEUKINE™ (SARGRAMOSTIM™) and NEUPOGEN™ (FILGRASTIM™).

In an additional embodiment, the Therapeutics of the invention are administered in combination with Fibroblast Growth Factors. Fibroblast Growth Factors that may be administered with the Therapeutics of the invention include, but are not limited to, FGF-1, FGF-2, FGF-3, FGF-4, FGF-5, FGF-6, FGF-7, FGF-8, FGF-9, FGF-10, FGF-11, FGF-12, FGF-13, FGF-14, and FGF-15.

In additional embodiments, the Therapeutics of the invention are administered in combination with other therapeutic or prophylactic regimens, such as, for example, radiation therapy.

Example 24

Method of Treating Decreased Levels of the Polypeptide

The present invention relates to a method for treating an individual in need of an increased level of a polypeptide of the invention in the body comprising administering to such an individual a composition comprising a therapeutically effective amount of an agonist of the invention (including polypeptides of the invention). Moreover, it will be appreciated that conditions caused by a decrease in the standard or normal expression level of a secreted protein in an individual can be treated by administering the polypeptide of the present invention, preferably in the secreted form. Thus, the invention also provides a method of treatment of an individual in need of an increased level of the polypeptide comprising administering to such an individual a Therapeutic comprising an amount of the polypeptide to increase the activity level of the polypeptide in such an individual.

For example, a patient with decreased levels of a polypeptide receives a daily dose 0.1-100 ug/kg of the polypeptide for six consecutive days. Preferably, the polypeptide is in the secreted form. The exact details of the dosing scheme, based on administration and formulation, are provided in Example 23.

Example 25

Method of Treating Increased Levels of the Polypeptide

The present invention also relates to a method of treating an individual in need of a decreased level of a polypeptide of the invention in the body comprising administering to such an individual a composition comprising a therapeutically effective amount of an antagonist of the invention (including polypeptides and antibodies of the invention).

In one example, antisense technology is used to inhibit production of a polypeptide of the present invention. This technology is one example of a method of decreasing levels of a polypeptide, preferably a secreted form, due to a variety of etiologies, such as cancer. For example, a patient diagnosed with abnormally increased levels of a polypeptide is administered intravenously antisense polynucleotides at 0.5, 1.0, 1.5, 2.0 and 3.0 mg/kg day for 21 days. This treatment is repeated after a 7-day rest period if the treatment was well tolerated. The formulation of the antisense polynucleotide is provided in Example 23.

Example 26

Method of Treatment Using Gene Therapy-Ex Vivo

One method of gene therapy transplants fibroblasts, which are capable of expressing a polypeptide, onto a patient. Generally, fibroblasts are obtained from a subject by skin biopsy. The resulting tissue is placed in tissue-culture medium and separated into small pieces. Small chunks of the tissue are placed on a wet surface of a tissue culture flask, approximately ten pieces are placed in each flask. The flask is turned upside down, closed tight and left at room temperature over night. After 24 hours at room temperature, the flask is inverted and the chunks of tissue remain fixed to the bottom of the flask and fresh media (e.g., Ham's F12 media, with 10% FBS, penicillin and streptomycin) is added. The flasks are then incubated at 37 degree C. for approximately one week.

At this time, fresh media is added and subsequently changed every several days. After an additional two weeks in culture, a monolayer of fibroblasts emerge. The monolayer is trypsinized and scaled into larger flasks.

pMV-7 (Kirschmeier, P. T. et al., DNA, 7:219-25 (1988)), flanked by the long terminal repeats of the Moloney murine sarcoma virus, is digested with EcoRI and HindIII and subsequently treated with calf intestinal phosphatase. The linear vector is fractionated on agarose gel and purified, using glass beads.

The cDNA encoding a polypeptide of the present invention can be amplified using PCR primers which correspond to the 5' and 3' end sequences respectively as set forth in Example 1 using primers and having appropriate restriction sites and initiation/stop codons, if necessary. Preferably, the 5' primer contains an EcoRI site and the 3' primer includes a HindIII site. Equal quantities of the Moloney murine sarcoma virus linear backbone and the amplified EcoRI and HindIII fragment are added together, in the presence of T4 DNA ligase. The resulting mixture is maintained under conditions appropriate for ligation of the two fragments. The ligation mixture is then used to transform bacteria HB101, which are then plated onto agar containing kanamycin for the purpose of confirming that the vector has the gene of interest properly inserted.

The amphotropic pA317 or GP+am12 packaging cells are grown in tissue culture to confluent density in Dulbecco's Modified Eagles Medium (DMEM) with 10% calf serum (CS), penicillin and streptomycin. The MSV vector containing the gene is then added to the media and the packaging cells transduced with the vector. The packaging cells now produce infectious viral particles containing the gene (the packaging cells are now referred to as producer cells).

Fresh media is added to the transduced producer cells, and subsequently, the media is harvested from a 10 cm plate of confluent producer cells. The spent media, containing the infectious viral particles, is filtered through a millipore filter to remove detached producer cells and this media is then used to infect fibroblast cells. Media is removed from a sub-confluent plate of fibroblasts and quickly replaced with the media from the producer cells. This media is removed and replaced with fresh media. If the titer of virus is high, then virtually all fibroblasts will be infected and no selection is required. If the titer is very low, then it is necessary to use a retroviral vector that has a selectable marker, such as neo or his. Once the fibroblasts have been efficiently infected, the fibroblasts are analyzed to determine whether protein is produced.

The engineered fibroblasts are then transplanted onto the host, either alone or after having been grown to confluence on cytodex 3 microcarrier beads.

Example 27

Gene Therapy Using Endogenous Genes Corresponding to Polynucleotides of the Invention Another method of gene therapy according to the present invention involves operably associating the endogenous polynucleotide sequence of the invention with a promoter via homologous recombination as described, for example, in U.S. Pat. No. 5,641,670, issued Jun. 24, 1997; International Publication NO: WO 96/29411, published Sep. 26, 1996; International Publication NO: WO 94/12650, published Aug. 4, 1994; Koller et al., *Proc. Natl. Acad. Sci. USA*, 86:8932-8935 (1989); and Zijlstra et al., *Nature*, 342:435-438 (1989). This method involves the activation of a gene which is present in the target cells, but which is not expressed in the cells, or is expressed at a lower level than desired.

Polynucleotide constructs are made which contain a promoter and targeting sequences, which are homologous to the 5' non-coding sequence of endogenous polynucleotide sequence, flanking the promoter. The targeting sequence will be sufficiently near the 5' end of the polynucleotide sequence so the promoter will be operably linked to the endogenous sequence upon homologous recombination. The promoter and the targeting sequences can be amplified using PCR. Preferably, the amplified promoter contains distinct restriction enzyme sites on the 5' and 3' ends. Preferably, the 3' end of the first targeting sequence contains the same restriction enzyme site as the 5' end of the amplified promoter and the 5' end of the second targeting sequence contains the same restriction site as the 3' end of the amplified promoter.

The amplified promoter and the amplified targeting sequences are digested with the appropriate restriction enzymes and subsequently treated with calf intestinal phosphatase. The digested promoter and digested targeting sequences are added together in the presence of T4 DNA ligase. The resulting mixture is maintained under conditions appropriate for ligation of the two fragments. The construct is size fractionated on an agarose gel then purified by phenol extraction and ethanol precipitation.

In this Example, the polynucleotide constructs are administered as naked polynucleotides via electroporation. However, the polynucleotide constructs may also be administered with transfection-facilitating agents, such as liposomes, viral sequences, viral particles, precipitating agents, etc. Such methods of delivery are known in the art.

Once the cells are transfected, homologous recombination will take place which results in the promoter being operably linked to the endogenous polynucleotide sequence. This results in the expression of polynucleotide corresponding to the polynucleotide in the cell. Expression may be detected by immunological staining, or any other method known in the art.

Fibroblasts are obtained from a subject by skin biopsy. The resulting tissue is placed in DMEM+10% fetal calf serum. Exponentially growing or early stationary phase fibroblasts are trypsinized and rinsed from the plastic surface with nutrient medium. An aliquot of the cell suspension is removed for counting, and the remaining cells are subjected to centrifugation. The supernatant is aspirated and the pellet is resuspended in 5 ml of electroporation buffer (20 mM HEPES pH 7.3, 137 mM NaCl, 5 mM KCl, 0.7 mM $Na_2HPO_4$, 6 mM dextrose). The cells are recentrifuged, the supernatant aspirated, and the cells resuspended in electroporation buffer containing 1 mg/ml acetylated bovine serum albumin. The final cell suspension contains approximately $3\times10^6$ cells/ml. Electroporation should be performed immediately following resuspension.

Plasmid DNA is prepared according to standard techniques. For example, to construct a plasmid for targeting to the locus corresponding to the polynucleotide of the invention, plasmid pUC18 (MBI Fermentas, Amherst, N.Y.) is digested with HindIII. The CMV promoter is amplified by PCR with an XbaI site on the 5' end and a BamHI site on the 3'end. Two non-coding sequences are amplified via PCR: one non-coding sequence (fragment 1) is amplified with a HindIII site at the 5' end and an Xba site at the 3'end; the other non-coding sequence (fragment 2) is amplified with a BamHI site at the 5'end and a HindIII site at the 3'end. The CMV promoter and the fragments (1 and 2) are digested with the appropriate enzymes (CMV promoter—XbaI and BamHI; fragment 1—XbaI; fragment 2—BamHI) and ligated together. The resulting ligation product is digested with HindIII, and ligated with the HindIII-digested pUC18 plasmid.

Plasmid DNA is added to a sterile cuvette with a 0.4 cm electrode gap (Bio-Rad). The final DNA concentration is generally at least 120 μg/ml. 0.5 ml of the cell suspension (containing approximately $1.5\times10^6$ cells) is then added to the cuvette, and the cell suspension and DNA solutions are gently mixed. Electroporation is performed with a Gene-Pulser apparatus (Bio-Rad). Capacitance and voltage are set at 960 μF and 250-300 V, respectively. As voltage increases, cell survival decreases, but the percentage of surviving cells that stably incorporate the introduced DNA into their genome increases dramatically. Given these parameters, a pulse time of approximately 14-20 mSec should be observed.

Electroporated cells are maintained at room temperature for approximately 5 min, and the contents of the cuvette are then gently removed with a sterile transfer pipette. The cells are added directly to 10 ml of prewarmed nutrient media (DMEM with 15% calf serum) in a 10 cm dish and incubated at 37 degree C. The following day, the media is aspirated and replaced with 10 ml of fresh media and incubated for a further 16-24 hours.

The engineered fibroblasts are then injected into the host, either alone or after having been grown to confluence on cytodex 3 microcarrier beads. The fibroblasts now produce the protein product. The fibroblasts can then be introduced into a patient as described above.

Example 28

Method of Treatment Using Gene Therapy—In Vivo

Another aspect of the present invention is using in vivo gene therapy methods to treat disorders, diseases and conditions. The gene therapy method relates to the introduction of naked nucleic acid (DNA, RNA, and antisense DNA or RNA) sequences into an animal to increase or decrease the expression of the polypeptide. The polynucleotide of the present invention may be operatively linked to a promoter or any other genetic elements necessary for the expression of the polypeptide by the target tissue. Such gene therapy and delivery techniques and methods are known in the art, see, for example, WO90/11092, WO98/11779; U.S. Pat. Nos. 5,693,622, 5,705,151, 5,580,859; Tabata et al., Cardiovasc. Res. 35(3):470-479 (1997); Chao et al., Pharmacol. Res. 35(6):517-522 (1997); Wolff, Neuromuscul. Disord. 7(5): 314-318 (1997); Schwartz et al., Gene Ther. 3(5):405-411 (1996); Tsurumi et al., Circulation 94(12):3281-3290 (1996) (incorporated herein by reference).

The polynucleotide constructs may be delivered by any method that delivers injectable materials to the cells of an animal, such as, injection into the interstitial space of tissues (heart, muscle, skin, lung, liver, intestine and the like). The polynucleotide constructs can be delivered in a pharmaceutically acceptable liquid or aqueous carrier.

The term "naked" polynucleotide, DNA or RNA, refers to sequences that are free from any delivery vehicle that acts to assist, promote, or facilitate entry into the cell, including viral sequences, viral particles, liposome formulations, lipofectin or precipitating agents and the like. However, the polynucleotides of the present invention may also be delivered in liposome formulations (such as those taught in Felgner P. L. et al. (1995) Ann. NY Acad. Sci. 772:126-139 and Abdallah B. et al. (1995) Biol. Cell 85(1):1-7) which can be prepared by methods well known to those skilled in the art.

The polynucleotide vector constructs used in the gene therapy method are preferably constructs that will not integrate into the host genome nor will they contain sequences that allow for replication. Any strong promoter known to those skilled in the art can be used for driving the expression of DNA. Unlike other gene therapies techniques, one major advantage of introducing naked nucleic acid sequences into target cells is the transitory nature of the polynucleotide synthesis in the cells. Studies have shown that non-replicating DNA sequences can be introduced into cells to provide production of the desired polypeptide for periods of up to six months.

The polynucleotide construct can be delivered to the interstitial space of tissues within the an animal, including of muscle, skin, brain, lung, liver, spleen, bone marrow, thymus, heart, lymph, blood, bone, cartilage, pancreas, kidney, gall bladder, stomach, intestine, testis, ovary, uterus, rectum, nervous system, eye, gland, and connective tissue. Interstitial space of the tissues comprises the intercellular fluid, mucopolysaccharide matrix among the reticular fibers of organ tissues, elastic fibers in the walls of vessels or chambers, collagen fibers of fibrous tissues, or that same matrix within connective tissue ensheathing muscle cells or in the lacunae of bone. It is similarly the space occupied by the plasma of the circulation and the lymph fluid of the lymphatic channels. Delivery to the interstitial space of muscle tissue is preferred for the reasons discussed below. They may be conveniently delivered by injection into the tissues comprising these cells. They are preferably delivered to and expressed in persistent, non-dividing cells which are differentiated, although delivery and expression may be achieved in non-differentiated or less completely differentiated cells, such as, for example, stem cells of blood or skin fibroblasts. In vivo muscle cells are particularly competent in their ability to take up and express polynucleotides.

For the naked polynucleotide injection, an effective dosage amount of DNA or RNA will be in the range of from about 0.05 g/kg body weight to about 50 mg/kg body weight. Preferably the dosage will be from about 0.005 mg/kg to about 20 mg/kg and more preferably from about 0.05 mg/kg to about 5 mg/kg. Of course, as the artisan of ordinary skill will appreciate, this dosage will vary according to the tissue site of injection. The appropriate and effective dosage of nucleic acid sequence can readily be determined by those of ordinary skill in the art and may depend on the condition being treated and the route of administration. The preferred route of administration is by the parenteral route of injection into the interstitial space of tissues. However, other parenteral routes may also be used, such as, inhalation of an aerosol formulation particularly for delivery to lungs or bronchial tissues, throat or mucous membranes of the nose. In addition, naked polynucleotide constructs can be delivered to arteries during angioplasty by the catheter used in the procedure.

The dose response effects of injected polynucleotide in muscle in vivo is determined as follows. Suitable template DNA for production of mRNA coding for polypeptide of the present invention is prepared in accordance with a standard recombinant DNA methodology. The template DNA, which may be either circular or linear, is either used as naked DNA or complexed with liposomes. The quadriceps muscles of mice are then injected with various amounts of the template DNA.

Five to six week old female and male Balb/C mice are anesthetized by intraperitoneal injection with 0.3 ml of 2.5% Avertin. A 1.5 cm incision is made on the anterior thigh, and the quadriceps muscle is directly visualized. The template DNA is injected in 0.1 ml of carrier in a 1 cc syringe through a 27 gauge needle over one minute, approximately 0.5 cm from the distal insertion site of the muscle into the knee and about 0.2 cm deep. A suture is placed over the injection site for future localization, and the skin is closed with stainless steel clips.

After an appropriate incubation time (e.g., 7 days) muscle extracts are prepared by excising the entire quadriceps. Every fifth 15 um cross-section of the individual quadriceps muscles is histochemically stained for protein expression. A time course for protein expression may be done in a similar fashion except that quadriceps from different mice are harvested at different times. Persistence of DNA in muscle following injection may be determined by Southern blot analysis after preparing total cellular DNA and HIRT supernatants from injected and control mice. The results of the above experimentation in mice can be use to extrapolate proper dosages and other treatment parameters in humans and other animals using naked DNA.

Example 29

Transgenic Animals

The polypeptides of the invention can also be expressed in transgenic animals. Animals of any species, including, but not limited to, mice, rats, rabbits, hamsters, guinea pigs, pigs, micro-pigs, goats, sheep, cows and non-human primates, e.g., baboons, monkeys, and chimpanzees may be used to generate transgenic animals. In a specific embodiment, techniques described herein or otherwise known in the art, are used to express polypeptides of the invention in humans, as part of a gene therapy protocol.

Any technique known in the art may be used to introduce the transgene (i.e., polynucleotides of the invention) into animals to produce the founder lines of transgenic animals. Such techniques include, but are not limited to, pronuclear microinjection (Paterson et al., Appl. Microbiol. Biotechnol. 40:691-698 (1994); Carver et al., Biotechnology (NY) 11: 1263-1270 (1993); Wright et al., Biotechnology (NY) 9:830-834 (1991); and Hoppe et al., U.S. Pat. No. 4,873,191 (1989)); retrovirus mediated gene transfer into germ lines (Van der Putten et al., Proc. Natl. Acad. Sci., USA 82:6148-6152 (1985)), blastocysts or embryos; gene targeting in embryonic stem cells (Thompson et al., Cell 56:313-321 (1989)); electroporation of cells or embryos (Lo, 1983, Mol Cell. Biol. 3:1803-1814 (1983)); introduction of the polynucleotides of the invention using a gene gun (see, e.g., Ulmer et al., Science 259:1745 (1993); introducing nucleic acid constructs into embryonic pleuripotent stem cells and transferring the stem cells back into the blastocyst; and sperm-mediated gene transfer (Lavitrano et al., Cell 57:717-723 (1989); etc. For a review of such techniques, see Gordon, "Transgenic Animals," Intl. Rev. Cytol. 115:171-229 (1989), which is incorporated by reference herein in its entirety.

Any technique known in the art may be used to produce transgenic clones containing polynucleotides of the invention, for example, nuclear transfer into enucleated oocytes of nuclei from cultured embryonic, fetal, or adult cells induced to quiescence (Campell et al., Nature 380:64-66 (1996); Wilmut et al., Nature 385:810-813 (1997)).

The present invention provides for transgenic animals that carry the transgene in all their cells, as well as animals which carry the transgene in some, but not all their cells, i.e., mosaic animals or chimeric. The transgene may be integrated as a single transgene or as multiple copies such as in concatamers, e.g., head-to-head tandems or head-to-tail tandems. The transgene may also be selectively introduced into and activated in a particular cell type by following, for example, the teaching of Lasko et al. (Lasko et al., Proc. Natl. Acad. Sci. USA 89:6232-6236 (1992)). The regulatory sequences required for such a cell-type specific activation will depend upon the particular cell type of interest, and will be apparent to those of skill in the art. When it is desired that the polynucleotide transgene be integrated into the chromosomal site of the endogenous gene, gene targeting is preferred. Briefly, when such a technique is to be utilized, vectors containing some nucleotide sequences homologous to the endogenous gene are designed for the purpose of integrating, via homologous recombination with chromosomal sequences, into and disrupting the function of the nucleotide sequence of the endogenous gene. The transgene may also be selectively introduced into a particular cell type, thus inactivating the endogenous gene in only that cell type, by following, for example, the teaching of Gu et al. (Gu et al., Science 265:103-106 (1994)). The regulatory sequences required for such a cell-type specific inactivation will depend upon the particular cell type of interest, and will be apparent to those of skill in the art.

Once transgenic animals have been generated, the expression of the recombinant gene may be assayed utilizing standard techniques. Initial screening may be accomplished by Southern blot analysis or PCR techniques to analyze animal tissues to verify that integration of the transgene has taken place. The level of mRNA expression of the transgene in the tissues of the transgenic animals may also be assessed using techniques which include, but are not limited to, Northern blot analysis of tissue samples obtained from the animal, in situ hybridization analysis, and reverse transcriptase-PCR (rt-PCR). Samples of transgenic gene-expressing tissue may also be evaluated immunocytochemically or immunohistochemically using antibodies specific for the transgene product.

Once the founder animals are produced, they may be bred, inbred, outbred, or crossbred to produce colonies of the particular animal. Examples of such breeding strategies include, but are not limited to: outbreeding of founder animals with more than one integration site in order to establish separate lines; inbreeding of separate lines in order to produce compound transgenics that express the transgene at higher levels because of the effects of additive expression of each transgene; crossing of heterozygous transgenic animals to produce animals homozygous for a given integration site in order to both augment expression and eliminate the need for screening of animals by DNA analysis; crossing of separate homozygous lines to produce compound heterozygous or homozygous lines; and breeding to place the transgene on a distinct background that is appropriate for an experimental model of interest.

Transgenic animals of the invention have uses which include, but are not limited to, animal model systems useful in elaborating the biological function of polypeptides of the present invention, studying diseases, disorders, and/or conditions associated with aberrant expression, and in screening for compounds effective in ameliorating such diseases, disorders, and/or conditions.

Example 30

Knock-Out Animals

Endogenous gene expression can also be reduced by inactivating or "knocking out" the gene and/or its promoter using targeted homologous recombination. (E.g., see Smithies et al., Nature 317:230-234 (1985); Thomas & Capecchi, Cell 51:503-512 (1987); Thompson et al., Cell 5:313-321 (1989); each of which is incorporated by reference herein in its entirety). For example, a mutant, non-functional polynucleotide of the invention (or a completely unrelated DNA sequence) flanked by DNA homologous to the endogenous polynucleotide sequence (either the coding regions or regulatory regions of the gene) can be used, with or without a selectable marker and/or a negative selectable marker, to transfect cells that express polypeptides of the invention in vivo. In another embodiment, techniques known in the art are used to generate knockouts in cells that contain, but do not express the gene of interest. Insertion of the DNA construct, via targeted homologous recombination, results in inactivation of the targeted gene. Such approaches are particularly suited in research and agricultural fields where modifications to embryonic stem cells can be used to generate animal offspring with an inactive targeted gene (e.g., see Thomas & Capecchi 1987 and Thompson 1989, supra). However this approach can be routinely adapted for use in humans provided the recombinant DNA constructs are directly administered or targeted to the required site in vivo using appropriate viral vectors that will be apparent to those of skill in the art.

In further embodiments of the invention, cells that are genetically engineered to express the polypeptides of the invention, or alternatively, that are genetically engineered not to express the polypeptides of the invention (e.g., knockouts) are administered to a patient in vivo. Such cells may be obtained from the patient (i.e., animal, including human) or an MHC compatible donor and can include, but are not limited to fibroblasts, bone marrow cells, blood cells (e.g., lymphocytes), adipocytes, muscle cells, endothelial cells etc. The cells are genetically engineered in vitro using recombinant DNA techniques to introduce the coding sequence of polypeptides of the invention into the cells, or alternatively, to disrupt the coding sequence and/or endogenous regulatory sequence associated with the polypeptides of the invention, e.g., by transduction (using viral vectors, and preferably vectors that integrate the transgene into the cell genome) or transfection procedures, including, but not limited to, the use of plasmids, cosmids, YACs, naked DNA, electroporation, liposomes, etc. The coding sequence of the polypeptides of the invention can be placed under the control of a strong constitutive or inducible promoter or promoter/enhancer to achieve expression, and preferably secretion, of the polypeptides of the invention. The engineered cells which express and preferably secrete the polypeptides of the invention can be introduced into the patient systemically, e.g., in the circulation, or intraperitoneally.

Alternatively, the cells can be incorporated into a matrix and implanted in the body, e.g., genetically engineered fibroblasts can be implanted as part of a skin graft; genetically engineered endothelial cells can be implanted as part of a lymphatic or vascular graft. (See, for example, Anderson et al. U.S. Pat. No. 5,399,349; and Mulligan & Wilson, U.S. Pat. No. 5,460,959 each of which is incorporated by reference herein in its entirety).

When the cells to be administered are non-autologous or non-MHC compatible cells, they can be administered using well known techniques which prevent the development of a host immune response against the introduced cells. For example, the cells may be introduced in an encapsulated form which, while allowing for an exchange of components with the immediate extracellular environment, does not allow the introduced cells to be recognized by the host immune system.

Transgenic and "knock-out" animals of the invention have uses which include, but are not limited to, animal model systems useful in elaborating the biological function of polypeptides of the present invention, studying diseases, disorders, and/or conditions associated with aberrant expression, and in screening for compounds effective in ameliorating such diseases, disorders, and/or conditions.

Example 31

Production of an Antibody

Hybridoma Technology

The antibodies of the present invention can be prepared by a variety of methods. (See, Current Protocols, Chapter 2.) As one example of such methods, cells expressing polypeptide(s) of the invention are administered to an animal to induce the production of sera containing polyclonal antibodies. In a preferred method, a preparation of polypeptide(s) of the invention is prepared and purified to render it substantially free of natural contaminants. Such a preparation is then introduced into an animal in order to produce polyclonal antisera of greater specific activity.

Monoclonal antibodies specific for polypeptide(s) of the invention are prepared using hybridoma technology. (Kohler et al., Nature 256:495 (1975); Kohler et al., Eur. J. Immunol. 6:511 (1976); Kohler et al., Eur. J. Immunol. 6:292 (1976); Hammerling et al., in: Monoclonal Antibodies and T-Cell Hybridomas, Elsevier, N.Y., pp. 563-681 (1981)). In general, an animal (preferably a mouse) is immunized with polypeptide(s) of the invention, or, more preferably, with a secreted polypeptide-expressing cell. Such polypeptide-expressing cells are cultured in any suitable tissue culture medium, preferably in Earle's modified Eagle's medium supplemented with 10% fetal bovine serum (inactivated at about 56° C.), and supplemented with about 10 g/l of nonessential amino acids, about 1,000 U/ml of penicillin, and about 100 μg/ml of streptomycin.

The splenocytes of such mice are extracted and fused with a suitable myeloma cell line. Any suitable myeloma cell line may be employed in accordance with the present invention; however, it is preferable to employ the parent myeloma cell line (SP2O), available from the ATCC. After fusion, the resulting hybridoma cells are selectively maintained in HAT medium, and then cloned by limiting dilution as described by Wands et al. (Gastroenterology 80:225-232 (1981)). The hybridoma cells obtained through such a selection are then assayed to identify clones which secrete antibodies capable of binding the polypeptide(s) of the invention.

Alternatively, additional antibodies capable of binding polypeptide(s) of the invention can be produced in a two-step procedure using anti-idiotypic antibodies. Such a method makes use of the fact that antibodies are themselves antigens, and therefore, it is possible to obtain an antibody which binds to a second antibody. In accordance with this method, protein specific antibodies are used to immunize an animal, preferably a mouse. The splenocytes of such an animal are then used to produce hybridoma cells, and the hybridoma cells are screened to identify clones which produce an antibody whose ability to bind to the polypeptide(s) of the invention protein-specific antibody can be blocked by polypeptide(s) of the invention. Such antibodies comprise anti-idiotypic antibodies to the polypeptide(s) of the invention protein-specific antibody and are used to immunize an animal to induce formation of further polypeptide(s) of the invention protein-specific antibodies.

For in vivo use of antibodies in humans, an antibody is "humanized". Such antibodies can be produced using genetic constructs derived from hybridoma cells producing the monoclonal antibodies described above. Methods for producing chimeric and humanized antibodies are known in the art and are discussed herein. (See, for review, Morrison, Science 229:1202 (1985); Oi et al., BioTechniques 4:214 (1986); Cabilly et al., U.S. Pat. No. 4,816,567; Taniguchi et al., EP 171496; Morrison et al., EP 173494; Neuberger et al., WO 8601533; Robinson et al., WO 8702671; Boulianne et al., Nature 312:643 (1984); Neuberger et al., Nature 314:268 (1985).)

Isolation of Antibody Fragments Directed polypeptide(s) of the invention from a Library of scFvs Naturally occurring V-genes isolated from human PBLs are constructed into a library of antibody fragments which contain reactivities against polypeptide(s) of the invention to which the donor may or may not have been exposed (see e.g., U.S. Pat. No. 5,885,793 incorporated herein by reference in its entirety).

Rescue of the Library. A library of scFvs is constructed from the RNA of human PBLs as described in PCT publication WO 92/01047. To rescue phage displaying antibody fragments, approximately 109 *E. coli* harboring the phagemid are used to inoculate 50 ml of 2×TY containing 1% glucose and 100 μg/ml of ampicillin (2×TY-AMP-GLU) and grown to an O.D. of 0.8 with shaking. Five ml of this culture is used to innoculate 50 ml of 2×TY-AMP-GLU, 2×108 TU of delta gene 3 helper (M13 delta gene III, see PCT publication WO 92/01047) are added and the culture incubated at 37° C. for 45 minutes without shaking and then at 37° C. for 45 minutes with shaking. The culture is centrifuged at 4000 r.p.m. for 10 min. and the pellet resuspended in 2 liters of 2×TY containing 100 μg/ml ampicillin and 50 ug/ml kanamycin and grown overnight. Phage are prepared as described in PCT publication WO 92/01047.

M13 delta gene III is prepared as follows: M13 delta gene III helper phage does not encode gene III protein, hence the phage(mid) displaying antibody fragments have a greater avidity of binding to antigen. Infectious M13 delta gene III particles are made by growing the helper phage in cells harboring a pUC19 derivative supplying the wild type gene III protein during phage morphogenesis. The culture is incubated for 1 hour at 37° C. without shaking and then for a further hour at 37° C. with shaking. Cells are spun down (IEC-Centra 8,400 r.p.m. for 10 min), resuspended in 300 ml 2×TY broth containing 100 μg ampicillin/ml and 25 μg kanamycin/ml (2×TY-AMP-KAN) and grown overnight, shaking at 37° C. Phage particles are purified and concentrated from the culture medium by two PEG-precipitations (Sambrook et al., 1990), resuspended in 2 ml PBS and passed through a 0.45 μm filter (Minisart NML; Sartorius) to give a final concentration of approximately 1013 transducing units/ml (ampicillin-resistant clones).

Panning of the Library. Immunotubes (Nunc) are coated overnight in PBS with 4 ml of either 100 μg/ml or 10 μg/ml of a polypeptide of the present invention. Tubes are blocked with 2% Marvel-PBS for 2 hours at 37° C. and then washed 3 times in PBS. Approximately 1013 TU of phage is applied to the tube and incubated for 30 minutes at room temperature tumbling on an over and under turntable and then left to stand for another 1.5 hours. Tubes are washed 10 times with PBS 0.1% Tween-20 and 10 times with PBS. Phage are eluted by adding 1 ml of 100 mM triethylamine and rotating 15 minutes on an under and over turntable after which the solution is immediately neutralized with 0.5 ml of 1.0M Tris-HCl, pH 7.4. Phage are then used to infect 10 ml of mid-log *E. coli* TG1 by incubating eluted phage with bacteria for 30 minutes at 37° C. The *E. coli* are then plated on TYE plates containing 1% glucose and 100 μg/ml ampicillin. The resulting bacterial library is then rescued with delta gene 3 helper phage as described above to prepare phage for a subsequent round of selection. This process is then repeated for a total of 4 rounds of affinity purification with tube-washing increased to 20 times with PBS, 0.1% Tween-20 and 20 times with PBS for rounds 3 and 4.

Characterization of Binders. Eluted phage from the 3rd and 4th rounds of selection are used to infect *E. coli* HB 2151 and soluble scFv is produced (Marks, et al., 1991) from single colonies for assay. ELISAs are performed with microtitre plates coated with either 10 pg/ml of the polypeptide of the present invention in 50 mM bicarbonate pH 9.6. Clones positive in ELISA are further characterized by PCR fingerprinting (see, e.g., PCT publication WO 92/01047) and then by sequencing. These ELISA positive clones may also be further characterized by techniques known in the art, such as, for example, epitope mapping, binding affinity, receptor signal transduction, ability to block or competitively inhibit antibody/antigen binding, and competitive agonistic or antagonistic activity.

Example 32

Assays Detecting Stimulation or Inhibition of B cell Proliferation and Differentiation Generation of functional humoral immune responses requires both soluble and cognate signaling between B-lineage cells and their microenvironment. Signals may impart a positive stimulus that allows a B-lineage cell to continue its programmed development, or a negative stimulus that instructs the cell to arrest its current developmental pathway. To date, numerous stimulatory and inhibitory signals have been found to influence B cell responsiveness including IL-2, IL-4, IL-5, IL-6, IL-7, IL10, IL-13, IL-14 and IL-15. Interestingly, these signals are by themselves weak effectors but can, in combination with various co-stimulatory proteins, induce activation, proliferation, differentiation, homing, tolerance and death among B cell populations.

One of the best studied classes of B-cell co-stimulatory proteins is the TNF-superfamily. Within this family CD40, CD27, and CD30 along with their respective ligands CD154, CD70, and CD153 have been found to regulate a variety of immune responses. Assays which allow for the detection and/or observation of the proliferation and differentiation of these B-cell populations and their precursors are valuable tools in determining the effects various proteins may have on these B-cell populations in terms of proliferation and differentiation. Listed below are two assays designed to allow for the detection of the differentiation, proliferation, or inhibition of B-cell populations and their precursors.

In Vitro Assay—Purified polypeptides of the invention, or truncated forms thereof, is assessed for its ability to induce activation, proliferation, differentiation or inhibition and/or death in B-cell populations and their precursors. The activity of the polypeptides of the invention on purified human tonsillar B cells, measured qualitatively over the dose range from 0.1 to 10,000 ng/mL, is assessed in a standard B-lymphocyte co-stimulation assay in which purified tonsillar B cells are cultured in the presence of either formalin-fixed *Staphylococcus aureus* Cowan I (SAC) or immobilized anti-human IgM antibody as the priming agent. Second signals such as IL-2 and IL-15 synergize with SAC and IgM crosslinking to elicit B cell proliferation as measured by tritiated-thymidine incorporation. Novel synergizing agents can be readily identified using this assay. The assay involves isolating human tonsillar B cells by magnetic bead (MACS) depletion of CD3-positive cells. The resulting cell population is greater than 95% B cells as assessed by expression of CD45R(B220).

Various dilutions of each sample are placed into individual wells of a 96-well plate to which are added $10^5$ B-cells suspended in culture medium (RPMI 1640 containing 10% FBS, $5\times10^{-5}$M 2ME, 100 U/ml penicillin, 10 ug/ml streptomycin, and $10^{-5}$ dilution of SAC) in a total volume of 150 ul. Proliferation or inhibition is quantitated by a 20 h pulse (1 uCi/well) with 3H-thymidine (6.7 Ci/mM) beginning 72 h post factor addition. The positive and negative controls are IL2 and medium respectively.

In Vivo Assay—BALB/c mice are injected (i.p.) twice per day with buffer only, or 2 mg/Kg of a polypeptide of the invention, or truncated forms thereof. Mice receive this treatment for 4 consecutive days, at which time they are sacrificed and various tissues and serum collected for analyses. Comparison of H&E sections from normal spleens and spleens treated with polypeptides of the invention identify the results of the activity of the polypeptides on spleen cells, such as the diffusion of peri-arterial lymphatic sheaths, and/or significant increases in the nucleated cellularity of the red pulp regions, which may indicate the activation of the differentiation and proliferation of B-cell populations. Immunohistochemical studies using a B cell marker, anti-CD45R(B220), are used to determine whether any physiological changes to splenic cells, such as splenic disorganization, are due to increased B-cell representation within loosely defined B-cell zones that infiltrate established T-cell regions.

Flow cytometric analyses of the spleens from mice treated with polypeptide is used to indicate whether the polypeptide specifically increases the proportion of ThB+, CD45R (B220) dull B cells over that which is observed in control mice.

Likewise, a predicted consequence of increased mature B-cell representation in vivo is a relative increase in serum Ig titers. Accordingly, serum IgM and IgA levels are compared between buffer and polypeptide-treated mice.

The studies described in this example tested activity of a polypeptide of the invention. However, one skilled in the art could easily modify the exemplified studies to test the activity of polynucleotides of the invention (e.g., gene therapy), agonists, and/or antagonists of polynucleotides or polypeptides of the invention.

Example 33

T Cell Proliferation Assay

Proliferation Assay for Resting PBLs.

A CD3-induced proliferation assay is performed on PBMCs and is measured by the uptake of $^3$H-thymidine. The assay is performed as follows. Ninety-six well plates are coated with 100 microliters per well of mAb to CD3 (HIT3a, Pharmingen) or isotype-matched control mAb (B33.1) overnight at 4° C. (1 microgram/ml in 0.05M bicarbonate buffer, pH 9.5), then washed three times with PBS. PBMC are isolated by F/H gradient centrifugation from human peripheral blood and added to quadruplicate wells ($5\times10^4$/well) of mAb coated plates in RPMI containing 10% FCS and P/S in the presence of varying concentrations of TNF Delta and/or TNF Epsilon protein (total volume 200 microliters). Relevant protein buffer and medium alone are controls. After 48 hr. culture at 37° C., plates are spun for 2 min. at 1000 rpm and 100 microliters of supernatant is removed and stored −20° C. for measurement of IL-2 (or other cytokines) if effect on proliferation is observed. Wells are supplemented with 100 microliters of medium containing 0.5 microcuries of $^3$H-thymidine and cultured at 37° C. for 18-24 hr. Wells are harvested and incorporation of $^3$H-thymidine used as a measure of proliferation. Anti-CD3 alone is the positive control for proliferation. IL-2 (100 U/ml) is also used as a control which enhances proliferation. Control antibody which does not induce proliferation of T cells is used as the negative controls for the effects of TNF Delta and/or TNF Epsilon proteins.

Alternatively, a proliferation assay on resting PBL (peripheral blood lymphocytes) is measured by the up-take of $^3$H-thymidine. The assay is performed as follows. PBMC are isolated by Ficoll (LSM, ICN Biotechnologies, Aurora, Ohio) gradient centrifugation from human peripheral blood, and are cultured overnight in 10% (Fetal Calf Serum, Biofluids, Rockville, Md.)/RPMI (Gibco BRL, Gaithersburg, Md.). This overnight incubation period allows the adherent cells to attach to the plastic, which results in a lower background in the assay as there are fewer cells that can act as antigen presenting cells or that might be producing growth factors. The following day the non-adherent cells are collected, washed and used in the proliferation assay. The assay is performed in a 96 well plate using $2\times10^4$ cells/well in a final volume of 200 microliters. The supernatants (e.g., CHO or 293T supernatants) expressing the protein of interest are tested at a 30% final dilution, therefore 60 ul are added to 140 ul of 10% FCS/RPMI containing the cells. Control supernatants are used at the same final dilution and express the following proteins: vector (negative control), IL-2 (*), IFNγ, TNFα, IL-10 and TR2. In addition to the control supernatants, recombinant human IL-2 (R & D Systems, Minneapolis, Minn.) at a final concentration of 10 ng/ml is also used. After 24 hours of culture, each well is pulsed with 1 uCi of $^3$H-thymidine (Nen, Boston, Mass.). Cells are then harvested 20 hours following pulsing and incorporation of $^3$H-thymidine is used as a measure of proliferation. Results are expressed as an average of triplicate samples plus or minus standard error.

(*) The amount of the control cytokines IL-2, IFNγ, TNFα and IL-10 produced in each transfection varies between 300 pg to 5 ng/ml.

Costimulation Assay.

A costimulation assay on resting PBL (peripheral blood lymphocytes) is performed in the presence of immobilized antibodies to CD3 and CD28. The use of antibodies specific for the invariant regions of CD3 mimic the induction of T cell activation that would occur through stimulation of the T cell receptor by an antigen. Cross-linking of the TCR (first signal) in the absence of a costimulatory signal (second signal) causes very low induction of proliferation and will eventually result in a state of "anergy", which is characterized by the absence of growth and inability to produce cytokines. The addition of a costimulatory signal such as an antibody to CD28, which mimics the action of the costimulatory molecule. B7-1 expressed on activated APCs, results in enhancement of T cell responses including cell survival and production of IL-2. Therefore this type of assay allows to detect both positive and negative effects caused by addition of supernatants expressing the proteins of interest on T cell proliferation.

The assay is performed as follows. Ninety-six well plates are coated with 100 ng/ml anti-CD3 and 5 ug/ml anti-CD28 (Pharmingen, San Diego, Calif.) in a final volume of 100 ul and incubated overnight at 4 C. Plates are washed twice with PBS before use. PBMC are isolated by Ficoll (LSM, ICN Biotechnologies, Aurora, Ohio) gradient centrifugation from human peripheral blood, and are cultured overnight in 10% FCS (Fetal Calf Serum, Biofluids, Rockville, Md.)/RPMI (Gibco BRL, Gaithersburg, Md.). This overnight incubation period allows the adherent cells to attach to the plastic, which results in a lower background in the assay as there are fewer cells that can act as antigen presenting cells or that might be producing growth factors. The following day the non adherent cells are collected, washed and used in the proliferation assay. The assay is performed in a 96 well plate using $2\times10^4$ cells/well in a final volume of 200 ul. The supernatants (e.g., CHO or 293T supernatants) expressing the protein of interest are tested at a 30% final dilution, therefore 60 ul are added to 140 ul of 10% FCS/RPMI containing the cells. Control supernatants are used at the same final dilution and express the following proteins: vector only (negative control), IL-2, IFNγ, TNFα, IL-10 and TR2. In addition to the control supernatants recombinant human IL-2 (R & D Systems, Minneapolis, Minn.) at a final concentration of 10 ng/ml is also used. After 24 hours of culture, each well is pulsed with 1 uCi of $^3$H-thymidine (Nen, Boston, Mass.). Cells are then harvested 20 hours following pulsing and incorporation of $^3$H-thymidine is used as a measure of proliferation. Results are expressed as an average of triplicate samples plus or minus standard error.

Proliferation Assay for Preactivated-Resting T Cells.

A proliferation assay on preactivated-resting T cells is performed on cells that are previously activated with the lectin phytohemagglutinin (PHA). Lectins are polymeric plant proteins that can bind to residues on T cell surface glycoproteins including the TCR and act as polyclonal activators. PBLs treated with PHA and then cultured in the presence of low doses of IL-2 resemble effector T cells. These cells are generally more sensitive to further activation induced by growth factors such as IL-2. This is due to the expression of high affinity IL-2 receptors that allows this population to respond to amounts of IL-2 that are 100 fold lower than what would have an effect on a naïve T cell. Therefore the use of this type of cells might enable to detect the effect of very low doses of an unknown growth factor, that would not be sufficient to induce proliferation on resting (naïve) T cells.

The assay is performed as follows. PBMC are isolated by F/H gradient centrifugation from human peripheral blood, and are cultured in 10% FCS (Fetal Calf Serum, Biofluids, Rockville, Md.)/RPMI (Gibco BRL, Gaithersburg, Md.) in the presence of 2 ug/ml PHA (Sigma, Saint Louis, Mo.) for three days. The cells are then washed in PBS and cultured in 10% FCS/RPMI in the presence of 5 ng/ml of human recombinant IL-2 (R & D Systems, Minneapolis, Minn.) for 3 days. The cells are washed and rested in starvation medium (1% FCS/RPMI) for 16 hours prior to the beginning of the proliferation assay. An aliquot of the cells is analyzed by FACS to determine the percentage of T cells (CD3 positive cells) present; this usually ranges between 93-97% depending on the donor. The assay is performed in a 96 well plate using $2\times10^4$ cells/well in a final volume of 200 ul. The supernatants (e.g., CHO or 293T supernatants) expressing the protein of interest are tested at a 30% final dilution, therefore 60 ul are added to 140 ul of in 10% FCS/RPMI containing the cells. Control supernatants are used at the same final dilution and express the following proteins: vector (negative control), IL-2, IFNγ, TNFα, IL-10 and TR2. In addition to the control supernatants recombinant human IL-2 at a final concentration of 10 ng/ml is also used. After 24 hours of culture, each well is pulsed with 1 uCi of $^3$H-thymidine (Nen, Boston, Mass.). Cells are then harvested 20 hours following pulsing and incorporation of $^3$H-thymidine is used as a measure of proliferation. Results are expressed as an average of triplicate samples plus or minus standard error.

The studies described in this example test activity of polypeptides of the invention. However, one skilled in the art could easily modify the exemplified studies to test the activity of polynucleotides of the invention (e.g., gene therapy), agonists, and/or antagonists of polynucleotides or polypeptides of the invention.

Example 34

Effect of Polypeptides of the Invention on the Expression of MHC Class II, Costimulatory and Adhesion Molecules and Cell Differentiation of Monocytes and Monocyte-Derived Human Dendritic Cells Dendritic cells are generated by the expansion of proliferating precursors found in the peripheral blood: adherent PBMC or elutriated monocytic fractions are cultured for 7-10 days with GM-CSF (50 ng/ml) and IL-4 (20 ng/ml). These dendritic cells have the characteristic phenotype of immature cells (expression of CD1, CD80, CD86, CD40 and MHC class II antigens). Treatment with activating factors, such as TNF-α, causes a rapid change in surface phenotype (increased expression of MHC class I and II, costimulatory and adhesion molecules, downregulation of FCγRII, upregulation of CD83). These changes correlate with increased antigen-presenting capacity and with functional maturation of the dendritic cells.

FACS analysis of surface antigens is performed as follows. Cells are treated 1-3 days with increasing concentrations of polypeptides of the invention or LPS (positive control), washed with PBS containing 1% BSA and 0.02 mM sodium azide, and then incubated with 1:20 dilution of appropriate FITC- or PE-labeled monoclonal antibodies for 30 minutes at 4 degrees C. After an additional wash, the labeled cells are analyzed by flow cytometry on a FACScan (Becton Dickinson).

Effect on the production of cytokines. Cytokines generated by dendritic cells, in particular IL-12, are important in the initiation of T-cell dependent immune responses. IL-12 strongly influences the development of Th1 helper T-cell immune response, and induces cytotoxic T and NK cell function. An ELISA is used to measure the IL-12 release as follows. Dendritic cells ($10^6$/ml) are treated with increasing concentrations of polypeptides of the invention for 24 hours. LPS (100 ng/ml) is added to the cell culture as positive control. Supernatants from the cell cultures are then collected and analyzed for IL-12 content using commercial ELISA kit (e.g, R & D Systems (Minneapolis, Minn.)). The standard protocols provided with the kits are used.

Effect on the expression of MHC Class II, costimulatory and adhesion molecules. Three major families of cell surface antigens can be identified on monocytes: adhesion molecules, molecules involved in antigen presentation, and Fc receptor. Modulation of the expression of MHC class II antigens and other costimulatory molecules, such as B7 and ICAM-1, may result in changes in the antigen presenting capacity of monocytes and ability to induce T cell activation. Increase expression of Fc receptors may correlate with improved monocyte cytotoxic activity, cytokine release and phagocytosis.

FACS analysis is used to examine the surface antigens as follows. Monocytes are treated 1-5 days with increasing concentrations of polypeptides of the invention or LPS (positive control), washed with PBS containing 1% BSA and 0.02 mM sodium azide, and then incubated with 1:20 dilution of appropriate FITC- or PE-labeled monoclonal antibodies for 30 minutes at 4 degrees C. After an additional wash, the labeled cells are analyzed by flow cytometry on a FACScan (Becton Dickinson).

Monocyte activation and/or increased survival. Assays for molecules that activate (or alternatively, inactivate) monocytes and/or increase monocyte survival (or alternatively, decrease monocyte survival) are known in the art and may routinely be applied to determine whether a molecule of the invention functions as an inhibitor or activator of monocytes. Polypeptides, agonists, or antagonists of the invention can be screened using the three assays described below. For each of these assays, Peripheral blood mononuclear cells (PBMC) are purified from single donor leukopacks (American Red Cross, Baltimore, Md.) by centrifugation through a Histopaque gradient (Sigma). Monocytes are isolated from PBMC by counterflow centrifugal elutriation.

Monocyte Survival Assay. Human peripheral blood monocytes progressively lose viability when cultured in absence of serum or other stimuli. Their death results from internally regulated process (apoptosis). Addition to the culture of activating factors, such as TNF-alpha dramatically improves cell survival and prevents DNA fragmentation. Propidium iodide (PI) staining is used to measure apoptosis as follows. Monocytes are cultured for 48 hours in polypropylene tubes in serum-free medium (positive control), in the presence of 100 ng/ml TNF-alpha (negative control), and in the presence of varying concentrations of the compound to be tested. Cells are suspended at a concentration of $2\times10^6$/ml in PBS containing PI at a final concentration of 5 μg/ml, and then incubated at room temperature for 5 minutes before FACScan analysis. PI uptake has been demonstrated to correlate with DNA fragmentation in this experimental paradigm.

Effect on cytokine release. An important function of monocytes/macrophages is their regulatory activity on other cellular populations of the immune system through the release of cytokines after stimulation. An ELISA to measure cytokine release is performed as follows. Human monocytes are incubated at a density of $5\times10^5$ cells/ml with increasing concentrations of the a polypeptide of the invention and under the same conditions, but in the absence of the polypeptide. For IL-12 production, the cells are primed overnight with IFN (100 U/ml) in presence of a polypeptide of the invention. LPS (10 ng/ml) is then added. Conditioned media are collected after 24 h and kept frozen until use. Measurement of TNF-alpha, IL-10, MCP-1 and IL-8 is then performed using a commercially available ELISA kit (e.g, R & D Systems (Minneapolis, Minn.)) and applying the standard protocols provided with the kit.

Oxidative burst. Purified monocytes are plated in 96-w plate at $2\text{-}1\times10^5$ cell/well. Increasing concentrations of polypeptides of the invention are added to the wells in a total volume of 0.2 ml culture medium (RPMI 1640+10% FCS, glutamine and antibiotics). After 3 days incubation, the plates are centrifuged and the medium is removed from the wells. To the macrophage monolayers, 0.2 ml per well of phenol red solution (140 mM NaCl, 10 mM potassium phosphate buffer pH 7.0, 5.5 mM dextrose, 0.56 mM phenol red and 19 U/ml of HRPO) is added, together with the stimulant (200 nM PMA). The plates are incubated at 37° C. for 2 hours and the reaction is stopped by adding 20 μl 1N NaOH per well. The absorbance is read at 610 nm. To calculate the amount of $H_2O_2$ produced by the macrophages, a standard curve of a $H_2O_2$ solution of known molarity is performed for each experiment.

The studies described in this example tested activity of a polypeptide of the invention. However, one skilled in the art could easily modify the exemplified studies to test the activity of polypeptides, polynucleotides (e.g., gene therapy), agonists, and/or antagonists of the invention.

Example 35

Biological Effects of Polypeptides of the Invention

Astrocyte and Neuronal Assays

Recombinant polypeptides of the invention, expressed in *Escherichia coli* and purified as described above, can be tested for activity in promoting the survival, neurite outgrowth, or phenotypic differentiation of cortical neuronal cells and for inducing the proliferation of glial fibrillary acidic protein immunopositive cells, astrocytes. The selection of cortical cells for the bioassay is based on the prevalent expression of FGF-1 and FGF-2 in cortical structures and on the previously reported enhancement of cortical neuronal survival resulting from FGF-2 treatment. A thymidine incorporation assay, for example, can be used to elucidate a polypeptide of the invention's activity on these cells.

Moreover, previous reports describing the biological effects of FGF-2 (basic FGF) on cortical or hippocampal neurons in vitro have demonstrated increases in both neuron survival and neurite outgrowth (Walicke et al., "Fibroblast growth factor promotes survival of dissociated hippocampal neurons and enhances neurite extension." *Proc. Natl. Acad. Sci. USA* 83:3012-3016. (1986), assay herein incorporated by reference in its entirety). However, reports from experiments done on PC-12 cells suggest that these two responses are not necessarily synonymous and may depend on not only which FGF is being tested but also on which receptor(s) are expressed on the target cells. Using the primary cortical neuronal culture paradigm, the ability of a polypeptide of the invention to induce neurite outgrowth can be compared to the response achieved with FGF-2 using, for example, a thymidine incorporation assay.

Fibroblast and Endothelial Cell Assays

Human lung fibroblasts are obtained from Clonetics (San Diego, Calif.) and maintained in growth media from Clonetics. Dermal microvascular endothelial cells are obtained from Cell Applications (San Diego, Calif.). For proliferation assays, the human lung fibroblasts and dermal microvascular endothelial cells can be cultured at 5,000 cells/well in a 96-well plate for one day in growth medium. The cells are then incubated for one day in 0.1% BSA basal medium. After replacing the medium with fresh 0.1% BSA medium, the cells are incubated with the test proteins for 3 days. Alamar Blue (Alamar Biosciences, Sacramento, Calif.) is added to each well to a final concentration of 10%. The cells are incubated for 4 hr. Cell viability is measured by reading in a CytoFluor fluorescence reader. For the $PGE_2$ assays, the human lung fibroblasts are cultured at 5,000 cells/well in a 96-well plate for one day. After a medium change to 0.1% BSA basal medium, the cells are incubated with FGF-2 or polypeptides of the invention with or without IL-1a for 24 hours. The supernatants are collected and assayed for $PGE_2$ by EIA kit (Cayman, Ann Arbor, Mich.). For the IL-6 assays, the human lung fibroblasts are cultured at 5,000 cells/well in a 96-well plate for one day. After a medium change to 0.1% BSA basal medium, the cells are incubated with FGF-2 or with or without polypeptides of the invention IL-1$\alpha$ for 24 hours. The supernatants are collected and assayed for IL-6 by ELISA kit (Endogen, Cambridge, Mass.).

Human lung fibroblasts are cultured with FGF-2 or polypeptides of the invention for 3 days in basal medium before the addition of Alamar Blue to assess effects on growth of the fibroblasts. FGF-2 should show a stimulation at 10-2500 ng/ml which can be used to compare stimulation with polypeptides of the invention.

Parkinson Models.

The loss of motor function in Parkinson's disease is attributed to a deficiency of striatal dopamine resulting from the degeneration of the nigrostriatal dopaminergic projection neurons. An animal model for Parkinson's that has been extensively characterized involves the systemic administration of 1-methyl-4 phenyl 1,2,3,6-tetrahydropyridine (MPTP). In the CNS, MPTP is taken-up by astrocytes and catabolized by monoamine oxidase B to 1-methyl-4-phenyl pyridine ($MPP^+$) and released. Subsequently, $MPP^+$ is actively accumulated in dopaminergic neurons by the high-affinity reuptake transporter for dopamine. $MPP^+$ is then concentrated in mitochondria by the electrochemical gradient and selectively inhibits nicotidamide adenine disphosphate: ubiquinone oxidoreductionase (complex I), thereby interfering with electron transport and eventually generating oxygen radicals.

It has been demonstrated in tissue culture paradigms that FGF-2 (basic FGF) has trophic activity towards nigral dopaminergic neurons (Ferrari et al., Dev. Biol. 1989). Recently, Dr. Unsicker's group has demonstrated that administering FGF-2 in gel foam implants in the striatum results in the near complete protection of nigral dopaminergic neurons from the toxicity associated with MPTP exposure (Otto and Unsicker, J. Neuroscience, 1990).

Based on the data with FGF-2, polypeptides of the invention can be evaluated to determine whether it has an action similar to that of FGF-2 in enhancing dopaminergic neuronal survival in vitro and it can also be tested in vivo for protection of dopaminergic neurons in the striatum from the damage associated with MPTP treatment. The potential effect of a polypeptide of the invention is first examined in vitro in a dopaminergic neuronal cell culture paradigm. The cultures are prepared by dissecting the midbrain floor plate from gestation day 14 Wistar rat embryos. The tissue is dissociated with trypsin and seeded at a density of 200,000 cells/$cm^2$ on polyorthinine-laminin coated glass coverslips. The cells are maintained in Dulbecco's Modified Eagle's medium and F12 medium containing hormonal supplements (N1). The cultures are fixed with paraformaldehyde after 8 days in vitro and are processed for tyrosine hydroxylase, a specific marker for dopminergic neurons, immunohistochemical staining. Dissociated cell cultures are prepared from embryonic rats. The culture medium is changed every third day and the factors are also added at that time.

Since the dopaminergic neurons are isolated from animals at gestation day 14, a developmental time which is past the stage when the dopaminergic precursor cells are proliferating, an increase in the number of tyrosine hydroxylase immunopositive neurons would represent an increase in the number of dopaminergic neurons surviving in vitro. Therefore, if a polypeptide of the invention acts to prolong the survival of dopaminergic neurons, it would suggest that the polypeptide may be involved in Parkinson's Disease.

The studies described in this example tested activity of a polypeptide of the invention. However, one skilled in the art could easily modify the exemplified studies to test the activity of polynucleotides (e.g., gene therapy), agonists, and/or antagonists of the invention.

Example 36

The Effect of Polypeptides of the Invention on the Growth of Vascular Endothelial Cells On day 1, human umbilical vein endothelial cells (HUVEC) are seeded at 2-5×$10^4$ cells/35 mm dish density in M199 medium containing 4% fetal bovine serum (FBS), 16 units/ml heparin, and 50 units/ml endothelial cell growth supplements (ECGS, Biotechnique, Inc.). On day 2, the medium is replaced with M199 containing 10% FBS, 8 units/ml heparin. A polypeptide having the amino acid sequence of SEQ ID NO:Y, and positive controls, such as VEGF and basic FGF (bFGF) are added, at varying concentrations. On days 4 and 6, the medium is replaced. On day 8, cell number is determined with a Coulter Counter.

An increase in the number of HUVEC cells indicates that the polypeptide of the invention may proliferate vascular endothelial cells.

The studies described in this example tested activity of a polypeptide of the invention. However, one skilled in the art could easily modify the exemplified studies to test the activity of polynucleotides (e.g., gene therapy), agonists, and/or antagonists of the invention.

Example 37

Stimulatory Effect of Polypeptides of the Invention on the Proliferation of Vascular Endothelial Cells For evaluation of mitogenic activity of growth factors, the colorimetric MTS (3-(4,5-dimethylthiazol-2-yl)-5-(3-carboxymethoxyphenyl)-2-(4-sulfophenyl)2H-tetrazolium) assay with the electron coupling reagent PMS (phenazine methosulfate) was performed (CellTiter 96 AQ, Promega). Cells are seeded in a 96-well plate (5,000 cells/well) in 0.1 mL serum-supplemented medium and are allowed to attach overnight. After serum-starvation for 12 hours in 0.5% FBS, conditions (bFGF, $VEGF_{165}$ or a polypeptide of the invention in 0.5% FBS) with or without Heparin (8 U/ml) are added to wells for 48 hours. 20 mg of MTS/PMS mixture (1:0.05) are added per well and allowed to incubate for 1 hour at 37° C. before measuring the absorbance at 490 nm in an ELISA plate reader. Background absorbance from control wells (some media, no cells) is subtracted, and seven wells are performed in parallel for each condition. See, Leak et al. *In Vitro Cell. Dev. Biol.* 30*A*:512-518 (1994).

The studies described in this example tested activity of a polypeptide of the invention. However, one skilled in the art could easily modify the exemplified studies to test the activity of polynucleotides (e.g., gene therapy), agonists, and/or antagonists of the invention.

Example 38

Inhibition of PDGF-Induced Vascular Smooth Muscle Cell Proliferation Stimulatory Effect HAoSMC proliferation can be measured, for example, by BrdUrd incorporation. Briefly, subconfluent, quiescent cells grown on the 4-chamber slides are transfected with CRP or FITC-labeled AT2-3LP. Then, the cells are pulsed with 10% calf serum and 6 mg/ml BrdUrd. After 24 h, immunocytochemistry is performed by using BrdUrd Staining Kit (Zymed Laboratories). In brief, the cells are incubated with the biotinylated mouse anti-BrdUrd antibody at 4 degrees C. for 2 h after being exposed to denaturing solution and then incubated with the streptavidin-peroxidase and diaminobenzidine. After counterstaining with hematoxylin, the cells are mounted for microscopic examination, and the BrdUrd-positive cells are counted. The BrdUrd index is calculated as a percent of the BrdUrd-positive cells to the total cell number. In addition, the simultaneous detection of the BrdUrd staining (nucleus) and the FITC uptake (cytoplasm) is performed for individual cells by the concomitant use of bright field illumination and dark field-UV fluorescent illumination. See, Hayashida et al., J. Biol. Chem. 6:271(36): 21985-21992 (1996).

The studies described in this example tested activity of a polypeptide of the invention. However, one skilled in the art could easily modify the exemplified studies to test the activity of polynucleotides (e.g., gene therapy), agonists, and/or antagonists of the invention.

Example 39

Stimulation of Endothelial Migration

This example will be used to explore the possibility that a polypeptide of the invention may stimulate lymphatic endothelial cell migration.

Endothelial cell migration assays are performed using a 48 well microchemotaxis chamber (Neuroprobe Inc., Cabin John, MD; Falk, W., et al., J. Immunological Methods 1980;33:239-247). Polyvinylpyrrolidone-free polycarbonate filters with a pore size of 8 um (Nucleopore Corp. Cambridge, Mass.) are coated with 0.1% gelatin for at least 6 hours at room temperature and dried under sterile air. Test substances are diluted to appropriate concentrations in M199 supplemented with 0.25% bovine serum albumin (BSA), and 25 ul of the final dilution is placed in the lower chamber of the modified Boyden apparatus. Subconfluent, early passage (2-6) HUVEC or BMEC cultures are washed and trypsinized for the minimum time required to achieve cell detachment. After placing the filter between lower and upper chamber, $2.5\times10^5$ cells suspended in 50 ul M199 containing 1% FBS are seeded in the upper compartment. The apparatus is then incubated for 5 hours at 37° C. in a humidified chamber with 5% CO2 to allow cell migration. After the incubation period, the filter is removed and the upper side of the filter with the non-migrated cells is scraped with a rubber policeman. The filters are fixed with methanol and stained with a Giemsa solution (Diff-Quick, Baxter, McGraw Park, Ill.). Migration is quantified by counting cells of three random high-power fields (40×) in each well, and all groups are performed in quadruplicate.

The studies described in this example tested activity of a polypeptide of the invention. However, one skilled in the art could easily modify the exemplified studies to test the activity of polynucleotides (e.g., gene therapy), agonists, and/or antagonists of the invention.

Example 40

Stimulation of Nitric Oxide Production by Endothelial Cells

Nitric oxide released by the vascular endothelium is believed to be a mediator of vascular endothelium relaxation. Thus, activity of a polypeptide of the invention can be assayed by determining nitric oxide production by endothelial cells in response to the polypeptide.

Nitric oxide is measured in 96-well plates of confluent microvascular endothelial cells after 24 hours starvation and a subsequent 4 hr exposure to various levels of a positive control (such as VEGF-1) and the polypeptide of the invention. Nitric oxide in the medium is determined by use of the Griess reagent to measure total nitrite after reduction of nitric oxide-derived nitrate by nitrate reductase. The effect of the polypeptide of the invention on nitric oxide release is examined on HUVEC.

Briefly, NO release from cultured HUVEC monolayer is measured with a NO-specific polarographic electrode connected to a NO meter (Iso-NO, World Precision Instruments Inc.) (1049). Calibration of the NO elements is performed according to the following equation:

$$2KNO_2+2KI+2H_2SO_462NO+I_2+2H_2O+2K_2SO_4$$

The standard calibration curve is obtained by adding graded concentrations of $KNO_2$ (0, 5, 10, 25, 50, 100, 250, and 500 nmol/L) into the calibration solution containing $K_1$ and $H_2SO_4$. The specificity of the Iso-NO electrode to NO is previously determined by measurement of NO from authentic NO gas (1050). The culture medium is removed and HUVECs are washed twice with Dulbecco's phosphate buffered saline. The cells are then bathed in 5 ml of filtered Krebs-Henseleit solution in 6-well plates, and the cell plates are kept on a slide warmer (Lab Line Instruments Inc.) To maintain the temperature at 37° C. The NO sensor probe is inserted vertically into the wells, keeping the tip of the electrode 2 mm under the surface of the solution, before addition of the different conditions. S-nitroso acetyl penicillamin (SNAP) is used as a positive control. The amount of released NO is expressed as picomoles per $1\times10^6$ endothelial cells. All values reported are means of four to six measurements in each group (number of cell culture wells). See, Leak et al. *Biochem. and Biophys. Res. Comm.* 217: 96-105 (1995).

The studies described in this example tested activity of polypeptides of the invention. However, one skilled in the art could easily modify the exemplified studies to test the activity of polynucleotides (e.g., gene therapy), agonists, and/or antagonists of the invention.

Example 41

Effect of Polypeptides of the Invention on Cord Formation in Angiogenesis

Another step in angiogenesis is cord formation, marked by differentiation of endothelial cells. This bioassay measures the ability of microvascular endothelial cells to form capillary-like structures (hollow structures) when cultured in vitro.

CADMEC (microvascular endothelial cells) are purchased from Cell Applications, Inc. as proliferating (passage 2) cells and are cultured in Cell Applications' CADMEC Growth Medium and used at passage 5. For the in vitro angiogenesis assay, the wells of a 48-well cell culture plate are coated with Cell Applications' Attachment Factor Medium (200 ml/well) for 30 min. at 37° C. CADMEC are seeded onto the coated wells at 7,500 cells/well and cultured overnight in Growth Medium. The Growth Medium is then replaced with 300 mg Cell Applications' Chord Formation Medium containing control buffer or a polypeptide of the invention (0.1 to 100 ng/ml) and the cells are cultured for an additional 48 hr. The numbers and lengths of the capillary-like chords are quantitated through use of the Boeckeler VIA-170 video image analyzer. All assays are done in triplicate.

Commercial (R&D) VEGF (50 ng/ml) is used as a positive control. b-esteradiol (1 ng/ml) is used as a negative control. The appropriate buffer (without protein) is also utilized as a control.

The studies described in this example tested activity of a polypeptide of the invention. However, one skilled in the art could easily modify the exemplified studies to test the activity of polynucleotides (e.g., gene therapy), agonists, and/or antagonists of the invention.

Example 42

Angiogenic Effect on Chick Chorioallantoic Membrane

Chick chorioallantoic membrane (CAM) is a well-established system to examine angiogenesis. Blood vessel formation on CAM is easily visible and quantifiable. The ability of polypeptides of the invention to stimulate angiogenesis in CAM can be examined.

Fertilized eggs of the White Leghorn chick (*Gallus gallus*) and the Japanese qual (*Coturnix coturnix*) are incubated at 37.8° C. and 80% humidity. Differentiated CAM of 16-day-old chick and 13-day-old qual embryos is studied with the following methods.

On Day 4 of development, a window is made into the egg shell of chick eggs. The embryos are checked for normal development and the eggs sealed with cellotape. They are further incubated until Day 13. Thermanox coverslips (Nunc, Naperville, Ill.) are cut into disks of about 5 mm in diameter. Sterile and salt-free growth factors are dissolved in distilled water and about 3.3 mg/5 ml are pipetted on the disks. After air-drying, the inverted disks are applied on CAM. After 3 days, the specimens are fixed in 3% glutaraldehyde and 2% formaldehyde and rinsed in 0.12 M sodium cacodylate buffer. They are photographed with a stereo microscope [Wild M8] and embedded for semi- and ultrathin sectioning as described above. Controls are performed with carrier disks alone.

The studies described in this example tested activity of a polypeptide of the invention. However, one skilled in the art could easily modify the exemplified studies to test the activity of polynucleotides (e.g., gene therapy), agonists, and/or antagonists of the invention.

Example 43

Angiogenesis Assay Using a Matrigel Implant in Mouse

In vivo angiogenesis assay of a polypeptide of the invention measures the ability of an existing capillary network to form new vessels in an implanted capsule of murine extracellular matrix material (Matrigel). The protein is mixed with the liquid Matrigel at 4 degree C. and the mixture is then injected subcutaneously in mice where it solidifies. After 7 days, the solid "plug" of Matrigel is removed and examined for the presence of new blood vessels. Matrigel is purchased from Becton Dickinson Labware/Collaborative Biomedical Products.

When thawed at 4 degree C. the Matrigel material is a liquid. The Matrigel is mixed with a polypeptide of the invention at 150 ng/ml at 4 degrees C. and drawn into cold 3 ml syringes. Female C57Bi/6 mice approximately 8 weeks old are injected with the mixture of Matrigel and experimental protein at 2 sites at the midventral aspect of the abdomen (0.5 ml/site). After 7 days, the mice are sacrificed by cervical dislocation, the Matrigel plugs are removed and cleaned (i.e., all clinging membranes and fibrous tissue is removed). Replicate whole plugs are fixed in neutral buffered 10% formaldehyde, embedded in paraffin and used to produce sections for histological examination after staining with Masson's Trichrome. Cross sections from 3 different regions of each plug are processed. Selected sections are stained for the presence of vWF. The positive control for this assay is bovine basic FGF (150 ng/ml). Matrigel alone is used to determine basal levels of angiogenesis.

The studies described in this example tested activity of a polypeptide of the invention. However, one skilled in the art could easily modify the exemplified studies to test the activity of polynucleotides (e.g., gene therapy), agonists, and/or antagonists of the invention.

Example 44

Rescue of Ischemia in Rabbit Lower Limb Model

To study the in vivo effects of polynucleotides and polypeptides of the invention on ischemia, a rabbit hindlimb ischemia model is created by surgical removal of one femoral arteries as described previously (Takeshita et al., *Am J. Pathol* 147:1649-1660 (1995)). The excision of the femoral artery results in retrograde propagation of thrombus and occlusion of the external iliac artery. Consequently, blood flow to the ischemic limb is dependent upon collateral vessels originating from the internal iliac artery (Takeshita et al. *Am J. Pathol* 147:1649-1660 (1995)). An interval of 10 days is allowed for post-operative recovery of rabbits and development of endogenous collateral vessels. At 10 day post-operatively (day 0), after performing a baseline angiogram, the internal iliac artery of the ischemic limb is transfected with 500 mg naked expression plasmid containing a polynucleotide of the invention by arterial gene transfer technology using a hydrogel-coated balloon catheter as described (Riessen et al. *Hum Gene Ther.* 4:749-758 (1993); Leclerc et al. *J. Clin. Invest.* 90: 936-944 (1992)). When a polypeptide of the invention is used in the treatment, a single bolus of 500 mg polypeptide of the invention or control is delivered into the internal iliac artery of the ischemic limb over a period of 1 min. through an infusion catheter. On day 30, various parameters are measured in these rabbits: (a) BP ratio—The blood pressure ratio of systolic pressure of the ischemic limb to that of normal limb; (b) Blood Flow and Flow Reserve—Resting FL: the blood flow during undilated condition and Max FL: the blood flow during fully dilated condition (also an indirect measure of the blood vessel amount) and Flow Reserve is reflected by the ratio of max FL: resting FL; (c) Angiographic Score—This is measured by the angiogram of collateral vessels. A score is determined by the percentage of circles in an overlaying grid that with crossing opacified arteries divided by the total number m the rabbit thigh; (d) Capillary density—The number of collateral capillaries determined in light microscopic sections taken from hindlimbs.

The studies described in this example tested activity of polynucleotides and polypeptides of the invention. However, one skilled in the art could easily modify the exemplified studies to test the agonists, and/or antagonists of the invention.

Example 45

Effect of Polypeptides of the Invention on Vasodilation

Since dilation of vascular endothelium is important in reducing blood pressure, the ability of polypeptides of the invention to affect the blood pressure in spontaneously hypertensive rats (SHR) is examined. Increasing doses (0, 10, 30, 100, 300, and 900 mg/kg) of the polypeptides of the invention are administered to 13-14 week old spontaneously hypertensive rats (SHR). Data are expressed as the mean+/−SEM. Statistical analysis are performed with a paired t-test and statistical significance is defined as $p<0.05$ vs. the response to buffer alone.

The studies described in this example tested activity of a polypeptide of the invention. However, one skilled in the art could easily modify the exemplified studies to test the activity of polynucleotides (e.g., gene therapy), agonists, and/or antagonists of the invention.

Example 46

Rat Ischemic Skin Flap Model

The evaluation parameters include skin blood flow, skin temperature, and factor VIII immunohistochemistry or endothelial alkaline phosphatase reaction. Expression of polypeptides of the invention, during the skin ischemia, is studied using in situ hybridization.

The study in this model is divided into three parts as follows:

a) Ischemic skin b) Ischemic skin wounds c) Normal wounds

The experimental protocol includes:

a) Raising a 3×4 cm, single pedicle full-thickness random skin flap (myocutaneous flap over the lower back of the animal).

b) An excisional wounding (4-6 mm in diameter) in the ischemic skin (skin-flap).

c) Topical treatment with a polypeptide of the invention of the excisional wounds (day 0, 1, 2, 3, 4 post-wounding) at the following various dosage ranges: 1 mg to 100 mg.

d) Harvesting the wound tissues at day 3, 5, 7, 10, 14 and 21 post-wounding for histological, immunohistochemical, and in situ studies.

The studies described in this example tested activity of a polypeptide of the invention. However, one skilled in the art could easily modify the exemplified studies to test the activity of polynucleotides (e.g., gene therapy), agonists, and/or antagonists of the invention.

Example 47

Peripheral Arterial Disease Model

Angiogenic therapy using a polypeptide of the invention is a novel therapeutic strategy to obtain restoration of blood flow around the ischemia in case of peripheral arterial diseases. The experimental protocol includes:

a) One side of the femoral artery is ligated to create ischemic muscle of the hindlimb, the other side of hindlimb serves as a control.

b) a polypeptide of the invention, in a dosage range of 20 mg-500 mg, is delivered intravenously and/or intramuscularly 3 times (perhaps more) per week for 2-3 weeks.

c) The ischemic muscle tissue is collected after ligation of the femoral artery at 1, 2, and 3 weeks for the analysis of expression of a polypeptide of the invention and histology. Biopsy is also performed on the other side of normal muscle of the contralateral hindlimb.

The studies described in this example tested activity of a polypeptide of the invention. However, one skilled in the art could easily modify the exemplified studies to test the activity of polynucleotides (e.g., gene therapy), agonists, and/or antagonists of the invention.

Example 48

Ischemic Myocardial Disease Model

A polypeptide of the invention is evaluated as a potent mitogen capable of stimulating the development of collateral vessels, and restructuring new vessels after coronary artery occlusion. Alteration of expression of the polypeptide is investigated in situ. The experimental protocol includes:

a) The heart is exposed through a left-side thoracotomy in the rat. Immediately, the left coronary artery is occluded with a thin suture (6-0) and the thorax is closed.

b) a polypeptide of the invention, in a dosage range of 20 mg-500 mg, is delivered intravenously and/or intramuscularly 3 times (perhaps more) per week for 2-4 weeks.

c) Thirty days after the surgery, the heart is removed and cross-sectioned for morphometric and in situ analyzes.

The studies described in this example tested activity of a polypeptide of the invention. However, one skilled in the art could easily modify the exemplified studies to test the activity of polynucleotides (e.g., gene therapy), agonists, and/or antagonists of the invention.

Example 49

Rat Corneal Wound Healing Model

This animal model shows the effect of a polypeptide of the invention on neovascularization. The experimental protocol includes:

a) Making a 1-1.5 mm long incision from the center of cornea into the stromal layer.

b) Inserting a spatula below the lip of the incision facing the outer corner of the eye.

c) Making a pocket (its base is 1-1.5 mm form the edge of the eye).

d) Positioning a pellet, containing 50 ng-5 ug of a polypeptide of the invention, within the pocket.

e) Treatment with a polypeptide of the invention can also be applied topically to the corneal wounds in a dosage range of 20 mg-500 mg (daily treatment for five days).

The studies described in this example tested activity of a polypeptide of the invention. However, one skilled in the art could easily modify the exemplified studies to test the activity of polynucleotides (e.g., gene therapy), agonists, and/or antagonists of the invention.

Example 50

Diabetic Mouse and Glucocorticoid-Impaired Wound Healing Models

A. Diabetic db+/db+ Mouse Model.

To demonstrate that a polypeptide of the invention accelerates the healing process, the genetically diabetic mouse model of wound healing is used. The full thickness wound healing model in the db+/db+ mouse is a well characterized, clinically relevant and reproducible model of impaired wound healing. Healing of the diabetic wound is dependent on formation of granulation tissue and re-epithelialization rather than contraction (Gartner, M. H. et al., *J. Surg. Res.* 52:389 (1992); Greenhalgh, D. G. et al., *Am. J. Pathol.* 136:1235 (1990)).

The diabetic animals have many of the characteristic features observed in Type II diabetes mellitus. Homozygous (db+/db+) mice are obese in comparison to their normal heterozygous (db+/+m) littermates. Mutant diabetic (db+/db+) mice have a single autosomal recessive mutation on chromosome 4 (db+) (Coleman et al. *Proc. Natl. Acad. Sci. USA* 77:283-293 (1982)). Animals show polyphagia, polydipsia and polyuria. Mutant diabetic mice (db+/db+) have elevated blood glucose, increased or normal insulin levels, and suppressed cell-mediated immunity (Mandel et al., *J. Immunol.* 120:1375 (1978); Debray-Sachs, M. et al., *Clin. Exp. Immunol.* 51(1):1-7 (1983); Leiter et al., *Am. J. of Pathol.* 114:46-55 (1985)). Peripheral neuropathy, myocardial complications, and microvascular lesions, basement membrane thickening and glomerular filtration abnormalities have been described in these animals (Norido, F. et al., *Exp. Neurol.* 83(2):221-232 (1984); Robertson et al., *Diabetes* 29(1):60-67 (1980); Giacomelli et al., *Lab Invest.* 40(4):460-473 (1979); Coleman, D. L., *Diabetes* 31 (*Suppl*): 1-6 (1982)). These homozygous diabetic mice develop hyperglycemia that is resistant to insulin analogous to human type II diabetes (Mandel et al., *J. Immunol.* 120: 1375-1377 (1978)).

The characteristics observed in these animals suggests that healing in this model may be similar to the healing observed in human diabetes (Greenhalgh, et al., *Am. J. of Pathol.* 136:1235-1246 (1990)).

Genetically diabetic female C57BL/KsJ (db+/db+) mice and their non-diabetic (db+/+m) heterozygous littermates are used in this study (Jackson Laboratories). The animals are purchased at 6 weeks of age and are 8 weeks old at the beginning of the study. Animals are individually housed and received food and water ad libitum. All manipulations are performed using aseptic techniques. The experiments are conducted according to the rules and guidelines of Human Genome Sciences, Inc. Institutional Animal Care and Use Committee and the Guidelines for the Care and Use of Laboratory Animals.

Wounding protocol is performed according to previously reported methods (Tsuboi, R. and Rifkin, D. B., *J. Exp. Med.* 172:245-251 (1990)). Briefly, on the day of wounding, animals are anesthetized with an intraperitoneal injection of Avertin (0.01 mg/mL), 2,2,2-tribromoethanol and 2-methyl-2-butanol dissolved in deionized water. The dorsal region of the animal is shaved and the skin washed with 70% ethanol solution and iodine. The surgical area is dried with sterile gauze prior to wounding. An 8 mm full-thickness wound is then created using a Keyes tissue punch. Immediately following wounding, the surrounding skin is gently stretched to eliminate wound expansion. The wounds are left open for the duration of the experiment. Application of the treatment is given topically for 5 consecutive days commencing on the day of wounding. Prior to treatment, wounds are gently cleansed with sterile saline and gauze sponges.

Wounds are visually examined and photographed at a fixed distance at the day of surgery and at two day intervals thereafter. Wound closure is determined by daily measurement on days 1-5 and on day 8. Wounds are measured horizontally and vertically using a calibrated Jameson caliper. Wounds are considered healed if granulation tissue is no longer visible and the wound is covered by a continuous epithelium.

A polypeptide of the invention is administered using at a range different doses, from 4 mg to 500 mg per wound per day for 8 days in vehicle. Vehicle control groups received 50 mL of vehicle solution.

Animals are euthanized on day 8 with an intraperitoneal injection of sodium pentobarbital (300 mg/kg). The wounds and surrounding skin are then harvested for histology and immunohistochemistry. Tissue specimens are placed in 10% neutral buffered formalin in tissue cassettes between biopsy sponges for further processing.

Three groups of 10 animals each (5 diabetic and 5 non-diabetic controls) are evaluated: 1) Vehicle placebo control, 2) untreated group, and 3) treated group.

Wound closure is analyzed by measuring the area in the vertical and horizontal axis and obtaining the total square area of the wound. Contraction is then estimated by establishing the differences between the initial wound area (day 0) and that of post treatment (day 8). The wound area on day 1 is 64 $mm^2$, the corresponding size of the dermal punch. Calculations are made using the following formula:

[Open area on day 8]−[Open area on day 1]/[Open area on day 1]

Specimens are fixed in 10% buffered formalin and paraffin embedded blocks are sectioned perpendicular to the wound surface (5 mm) and cut using a Reichert-Jung microtome. Routine hematoxylin-eosin (H&E) staining is performed on cross-sections of bisected wounds. Histologic examination of the wounds are used to assess whether the healing process and the morphologic appearance of the repaired skin is altered by treatment with a polypeptide of the invention. This assessment included verification of the presence of cell accumulation, inflammatory cells, capillaries, fibroblasts, re-epithelialization and epidermal maturity (Greenhalgh, D. G. et al., *Am. J. Pathol.* 136:1235 (1990)). A calibrated lens micrometer is used by a blinded observer.

Tissue sections are also stained immunohistochemically with a polyclonal rabbit anti-human keratin antibody using ABC Elite detection system. Human skin is used as a positive tissue control while non-immune IgG is used as a negative control. Keratinocyte growth is determined by evaluating the extent of reepithelialization of the wound using a calibrated lens micrometer.

Proliferating cell nuclear antigen/cyclin (PCNA) in skin specimens is demonstrated by using anti-PCNA antibody (1:50) with an ABC Elite detection system. Human colon cancer can serve as a positive tissue control and human brain tissue can be used as a negative tissue control. Each specimen includes a section with omission of the primary antibody and substitution with non-immune mouse IgG. Ranking of these sections is based on the extent of proliferation on a scale of 0-8, the lower side of the scale reflecting slight proliferation to the higher side reflecting intense proliferation.

Experimental data are analyzed using an unpaired t test. A p value of <0.05 is considered significant.

B. Steroid Impaired Rat Model

The inhibition of wound healing by steroids has been well documented in various in vitro and in vivo systems (Wahl, Glucocorticoids and Wound healing. In: Anti-Inflammatory Steroid Action: Basic and Clinical Aspects. 280-302 (1989); Wahl et al., *J. Immunol.* 115: 476-481 (1975); Werb et al., *J. Exp. Med.* 147:1684-1694 (1978)). Glucocorticoids retard wound healing by inhibiting angiogenesis, decreasing vascular permeability (Ebert et al., *An. Intern. Med.* 37:701-705 (1952)), fibroblast proliferation, and collagen synthesis (Beck et al., *Growth Factors.* 5: 295-304 (1991); Haynes et al., *J. Clin. Invest.* 61: 703-797 (1978)) and producing a transient reduction of circulating monocytes (Haynes et al., *J. Clin. Invest.* 61: 703-797 (1978); Wahl, "Glucocorticoids and wound healing", In: Antiinflammatory Steroid Action: Basic and Clinical Aspects, Academic Press, New York, pp. 280-302 (1989)). The systemic administration of steroids to impaired wound healing is a well establish phenomenon in rats (Beck et al., *Growth Factors.* 5: 295-304 (1991); Haynes et al., *J. Clin. Invest.* 61: 703-797 (1978); Wahl, "Glucocorticoids and wound healing", In: Antiinflammatory Steroid Action: Basic and Clinical Aspects, Academic Press, New York, pp. 280-302 (1989); Pierce et al., *Proc. Natl. Acad. Sci. USA* 86: 2229-2233 (1989)).

To demonstrate that a polypeptide of the invention can accelerate the healing process, the effects of multiple topical applications of the polypeptide on full thickness excisional skin wounds in rats in which healing has been impaired by the systemic administration of methylprednisolone is assessed.

Young adult male Sprague Dawley rats weighing 250-300 g (Charles River Laboratories) are used in this example. The animals are purchased at 8 weeks of age and are 9 weeks old at the beginning of the study. The healing response of rats is impaired by the systemic administration of methylprednisolone (17 mg/kg/rat intramuscularly) at the time of wounding. Animals are individually housed and received food and water ad libitum. All manipulations are performed using aseptic techniques. This study is conducted according to the rules and guidelines of Human Genome Sciences, Inc. Institutional Animal Care and Use Committee and the Guidelines for the Care and Use of Laboratory Animals.

The wounding protocol is followed according to section A, above. On the day of wounding, animals are anesthetized with an intramuscular injection of ketamine (50 mg/kg) and xylazine (5 mg/kg). The dorsal region of the animal is shaved and the skin washed with 70% ethanol and iodine solutions. The surgical area is dried with sterile gauze prior to wounding. An 8 mm full-thickness wound is created using a Keyes tissue punch. The wounds are left open for the duration of the experiment. Applications of the testing materials are given topically once a day for 7 consecutive days commencing on the day of wounding and subsequent to methylprednisolone administration. Prior to treatment, wounds are gently cleansed with sterile saline and gauze sponges.

Wounds are visually examined and photographed at a fixed distance at the day of wounding and at the end of treatment. Wound closure is determined by daily measurement on days 1-5 and on day 8. Wounds are measured horizontally and vertically using a calibrated Jameson caliper. Wounds are considered healed if granulation tissue is no longer visible and the wound is covered by a continuous epithelium.

The polypeptide of the invention is administered using at a range different doses, from 4 mg to 500 mg per wound per day for 8 days in vehicle. Vehicle control groups received 50 mL of vehicle solution.

Animals are euthanized on day 8 with an intraperitoneal injection of sodium pentobarbital (300 mg/kg). The wounds and surrounding skin are then harvested for histology. Tissue specimens are placed in 10% neutral buffered formalin in tissue cassettes between biopsy sponges for further processing.

Four groups of 10 animals each (5 with methylprednisolone and 5 without glucocorticoid) are evaluated: 1) Untreated group 2) Vehicle placebo control 3) treated groups.

Wound closure is analyzed by measuring the area in the vertical and horizontal axis and obtaining the total area of the wound. Closure is then estimated by establishing the differences between the initial wound area (day 0) and that of post treatment (day 8). The wound area on day 1 is 64 $mm^2$, the corresponding size of the dermal punch. Calculations are made using the following formula:

[Open area on day 8]−[Open area on day 1]/[Open area on day 1]

Specimens are fixed in 10% buffered formalin and paraffin embedded blocks are sectioned perpendicular to the wound surface (5 mm) and cut using an Olympus microtome. Routine hematoxylin-eosin (H&E) staining is performed on cross-sections of bisected wounds. Histologic examination of the wounds allows assessment of whether the healing process and the morphologic appearance of the repaired skin is improved by treatment with a polypeptide of the invention. A calibrated lens micrometer is used by a blinded observer to determine the distance of the wound gap.

Experimental data are analyzed using an unpaired t test. A p value of <0.05 is considered significant.

The studies described in this example tested activity of a polypeptide of the invention. However, one skilled in the art could easily modify the exemplified studies to test the activity of polynucleotides (e.g., gene therapy), agonists, and/or antagonists of the invention.

Example 51

Lymphadema Animal Model

The purpose of this experimental approach is to create an appropriate and consistent lymphedema model for testing the therapeutic effects of a polypeptide of the invention in lymphangiogenesis and re-establishment of the lymphatic circulatory system in the rat hind limb. Effectiveness is measured by swelling volume of the affected limb, quantification of the amount of lymphatic vasculature, total blood plasma protein, and histopathology. Acute lymphedema is observed for 7-10 days. Perhaps more importantly, the chronic progress of the edema is followed for up to 3-4 weeks.

Prior to beginning surgery, blood sample is drawn for protein concentration analysis. Male rats weighing approximately ~350 g are dosed with Pentobarbital. Subsequently, the right legs are shaved from knee to hip. The shaved area is swabbed with gauze soaked in 70% EtOH. Blood is drawn for serum total protein testing. Circumference and volumetric measurements are made prior to injecting dye into paws after marking 2 measurement levels (0.5 cm above heel, at mid-pt of dorsal paw). The intradermal dorsum of both right and left paws are injected with 0.05 ml of 1% Evan's Blue. Circumference and volumetric measurements are then made following injection of dye into paws.

Using the knee joint as a landmark, a mid-leg inguinal incision is made circumferentially allowing the femoral vessels to be located. Forceps and hemostats are used to dissect and separate the skin flaps. After locating the femoral vessels, the lymphatic vessel that runs along side and underneath the vessel(s) is located. The main lymphatic vessels in this area are then electrically coagulated suture ligated.

Using a microscope, muscles in back of the leg (near the semitendinosis and adductors) are bluntly dissected. The popliteal lymph node is then located. The 2 proximal and 2 distal lymphatic vessels and distal blood supply of the popliteal node are then and ligated by suturing. The popliteal lymph node, and any accompanying adipose tissue, is then removed by cutting connective tissues.

Care is taken to control any mild bleeding resulting from this procedure. After lymphatics are occluded, the skin flaps are sealed by using liquid skin (Vetbond) (A J Buck). The separated skin edges are sealed to the underlying muscle tissue while leaving a gap of ~0.5 cm around the leg. Skin also may be anchored by suturing to underlying muscle when necessary.

To avoid infection, animals are housed individually with mesh (no bedding). Recovering animals are checked daily through the optimal edematous peak, which typically occurred by day 5-7. The plateau edematous peak are then observed. To evaluate the intensity of the lymphedema, the circumference and volumes of 2 designated places on each paw before operation and daily for 7 days are measured. The effect plasma proteins on lymphedema is determined and whether protein analysis is a useful testing perimeter is also investigated. The weights of both control and edematous limbs are evaluated at 2 places. Analysis is performed in a blind manner.

Circumference Measurements: Under brief gas anesthetic to prevent limb movement, a cloth tape is used to measure limb circumference. Measurements are done at the ankle bone and dorsal paw by 2 different people then those 2 readings are averaged. Readings are taken from both control and edematous limbs.

Volumetric Measurements: On the day of surgery, animals are anesthetized with Pentobarbital and are tested prior to surgery. For daily volumetrics animals are under brief halothane anesthetic (rapid immobilization and quick recovery), both legs are shaved and equally marked using waterproof marker on legs. Legs are first dipped in water, then dipped into instrument to each marked level then measured by Buxco edema software (Chen/Victor). Data is recorded by one person, while the other is dipping the limb to marked area.

Blood-plasma protein measurements: Blood is drawn, spun, and serum separated prior to surgery and then at conclusion for total protein and Ca2+ comparison.

Limb Weight Comparison: After drawing blood, the animal is prepared for tissue collection. The limbs are amputated using a quillitine, then both experimental and control legs are cut at the ligature and weighed. A second weighing is done as the tibio-cacaneal joint is disarticulated and the foot is weighed.

Histological Preparations: The transverse muscle located behind the knee (popliteal) area is dissected and arranged in a metal mold, filled with freezeGel, dipped into cold methylbutane, placed into labeled sample bags at −80 EC until sectioning. Upon sectioning, the muscle is observed under fluorescent microscopy for lymphatics.

The studies described in this example tested activity of a polypeptide of the invention. However, one skilled in the art could easily modify the exemplified studies to test the activity of polynucleotides (e.g., gene therapy), agonists, and/or antagonists of the invention.

Example 52

Suppression of TNF Alpha-Induced Adhesion Molecule Expression by a Polypeptide of the Invention The recruitment of lymphocytes to areas of inflammation and angiogenesis involves specific receptor-ligand interactions between cell surface adhesion molecules (CAMs) on lymphocytes and the vascular endothelium. The adhesion process, in both normal and pathological settings, follows a multi-step cascade that involves intercellular adhesion molecule-1 (ICAM-1), vascular cell adhesion molecule-1 (VCAM-1), and endothelial leukocyte adhesion molecule-1 (E-selectin) expression on endothelial cells (EC). The expression of these molecules and others on the vascular endothelium determines the efficiency with which leukocytes may adhere to the local vasculature and extravasate into the local tissue during the development of an inflammatory response. The local concentration of cytokines and growth factor participate in the modulation of the expression of these CAMs.

Tumor necrosis factor alpha (TNF-a), a potent proinflammatory cytokine, is a stimulator of all three CAMs on endothelial cells and may be involved in a wide variety of inflammatory responses, often resulting in a pathological outcome.

The potential of a polypeptide of the invention to mediate a suppression of TNF-a induced CAM expression can be examined. A modified ELISA assay which uses ECs as a solid phase absorbent is employed to measure the amount of CAM expression on TNF-a treated ECs when co-stimulated with a member of the FGF family of proteins.

To perform the experiment, human umbilical vein endothelial cell (HUVEC) cultures are obtained from pooled cord harvests and maintained in growth medium (EGM-2;

Clonetics, San Diego, Calif.) supplemented with 10% FCS and 1% penicillin/streptomycin in a 37 degree C. humidified incubator containing 5% $CO_2$. HUVECs are seeded in 96-well plates at concentrations of $1\times10^4$ cells/well in EGM medium at 37 degree C. for 18-24 hrs or until confluent. The monolayers are subsequently washed 3 times with a serum-free solution of RPMI-1640 supplemented with 100 U/ml penicillin and 100 mg/ml streptomycin, and treated with a given cytokine and/or growth factor(s) for 24 h at 37 degree C. Following incubation, the cells are then evaluated for CAM expression.

Human Umbilical Vein Endothelial cells (HUVECs) are grown in a standard 96 well plate to confluence. Growth medium is removed from the cells and replaced with 90 ul of 199 Medium (10% FBS). Samples for testing and positive or negative controls are added to the plate in triplicate (in 10 ul volumes). Plates are incubated at 37 degree C. for either 5 h (selectin and integrin expression) or 24 h (integrin expression only). Plates are aspirated to remove medium and 100 µl of 0.1% paraformaldehyde-PBS (with Ca++ and Mg++) is added to each well. Plates are held at 4° C. for 30 min.

Fixative is then removed from the wells and wells are washed 1× with PBS(+Ca,Mg)+0.5% BSA and drained. Do not allow the wells to dry. Add 10 µl of diluted primary antibody to the test and control wells. Anti-ICAM-1-Biotin, Anti-VCAM-1-Biotin and Anti-E-selectin-Biotin are used at a concentration of 10 µg/ml (1:10 dilution of 0.1 mg/ml stock antibody). Cells are incubated at 37° C. for 30 min. in a humidified environment. Wells are washed ×3 with PBS (+Ca,Mg)+0.5% BSA.

Then add 20 µl of diluted ExtrAvidin-Alkaline Phosphotase (1:5,000 dilution) to each well and incubated at 37° C. for 30 min. Wells are washed ×3 with PBS(+Ca,Mg)+0.5% BSA. 1 tablet of p-Nitrophenol Phosphate pNPP is dissolved in 5 ml of glycine buffer (pH 10.4). 100 µl of pNPP substrate in glycine buffer is added to each test well. Standard wells in triplicate are prepared from the working dilution of the ExtrAvidin-Alkaline Phosphotase in glycine buffer: 1:5,000 $(10^0)>10^{-0.5}>10^{-1}>10^{1.5}$0.5 µl of each dilution is added to triplicate wells and the resulting AP content in each well is 5.50 ng, 1.74 ng, 0.55 ng, 0.18 ng. 100 µl of pNNP reagent must then be added to each of the standard wells. The plate must be incubated at 37° C. for 4 h. A volume of 50 µl of 3M NaOH is added to all wells. The results are quantified on a plate reader at 405 nm. The background subtraction option is used on blank wells filled with glycine buffer only. The template is set up to indicate the concentration of AP-conjugate in each standard well [5.50 ng; 1.74 ng; 0.55 ng; 0.18 ng]. Results are indicated as amount of bound AP-conjugate in each sample.

The studies described in this example tested activity of a polypeptide of the invention. However, one skilled in the art could easily modify the exemplified studies to test the activity of polynucleotides (e.g., gene therapy), agonists, and/or antagonists of the invention.

Example 53

Assay for the Stimulation of Bone Marrow CD34+ Cell Proliferation

This assay is based on the ability of human CD34+ to proliferate in the presence of hematopoietic growth factors and evaluates the ability of isolated polypeptides expressed in mammalian cells to stimulate proliferation of CD34+ cells.

It has been previously shown that most mature precursors will respond to only a single signal. More immature precursors require at least two signals to respond. Therefore, to test the effect of polypeptides on hematopoietic activity of a wide range of progenitor cells, the assay contains a given polypeptide in the presence or absence of other hematopoietic growth factors. Isolated cells are cultured for 5 days in the presence of Stem Cell Factor (SCF) in combination with tested sample. SCF alone has a very limited effect on the proliferation of bone marrow (BM) cells, acting in such conditions only as a "survival" factor. However, combined with any factor exhibiting stimulatory effect on these cells (e.g., IL-3), SCF will cause a synergistic effect. Therefore, if the tested polypeptide has a stimulatory effect on a hematopoietic progenitors, such activity can be easily detected. Since normal BM cells have a low level of cycling cells, it is likely that any inhibitory effect of a given polypeptide, or agonists or antagonists thereof, might not be detected. Accordingly, assays for an inhibitory effect on progenitors is preferably tested in cells that are first subjected to in vitro stimulation with SCF+IL+3, and then contacted with the compound that is being evaluated for inhibition of such induced proliferation.

Briefly, CD34+ cells are isolated using methods known in the art. The cells are thawed and resuspended in medium (QBSF 60 serum-free medium with 1% L-glutamine (500 ml) Quality Biological, Inc., Gaithersburg, Md. Cat#160-204-101). After several gentle centrifugation steps at 200×g, cells are allowed to rest for one hour. The cell count is adjusted to $2.5\times10^5$ cells/ml. During this time, 100 µl of sterile water is added to the peripheral wells of a 96-well plate. The cytokines that can be tested with a given polypeptide in this assay is rhSCF (R&D Systems, Minneapolis, Minn., Cat#255-SC) at 50 ng/ml alone and in combination with rhSCF and rhIL-3 (R&D Systems, Minneapolis, Minn., Cat#203-ML) at 30 ng/ml. After one hour, 10 µl of prepared cytokines, 50 µl SID (supernatants at 1:2 dilution=50 µl) and 20 µl of diluted cells are added to the media which is already present in the wells to allow for a final total volume of 100 µl. The plates are then placed in a 37° C./5% $CO_2$ incubator for five days.

Eighteen hours before the assay is harvested, 0.5 µCi/well of [3H] Thymidine is added in a 10 µl volume to each well to determine the proliferation rate. The experiment is terminated by harvesting the cells from each 96-well plate to a filtermat using the Tomtec Harvester 96. After harvesting, the filtermats are dried, trimmed and placed into OmniFilter assemblies consisting of one OmniFilter plate and one OmniFilter Tray. 60 µl Microscint is added to each well and the plate sealed with TopSeal-A press-on sealing film A bar code 15 sticker is affixed to the first plate for counting. The sealed plates is then loaded and the level of radioactivity determined via the Packard Top Count and the printed data collected for analysis. The level of radioactivity reflects the amount of cell proliferation.

The studies described in this example test the activity of a given polypeptide to stimulate bone marrow CD34+ cell proliferation. One skilled in the art could easily modify the exemplified studies to test the activity of polynucleotides (e.g., gene therapy), antibodies, agonists, and/or antagonists and fragments and variants thereof. As a nonlimiting example, potential antagonists tested in this assay would be expected to inhibit cell proliferation in the presence of cytokines and/or to increase the inhibition of cell proliferation in the presence of cytokines and a given polypeptide. In contrast, potential agonists tested in this assay would be expected to enhance cell proliferation and/or to decrease the inhibition of cell proliferation in the presence of cytokines and a given polypeptide.

The ability of a gene to stimulate the proliferation of bone marrow CD34+ cells indicates that polynucleotides and polypeptides corresponding to the gene are useful for the diagnosis and treatment of disorders affecting the immune system and hematopoiesis. Representative uses are described in the "Immune Activity" and "Infectious Disease" sections above, and elsewhere herein.

Example 54

Assay for Extracellular Matrix Enhanced Cell Response (EMECR)

The objective of the Extracellular Matrix Enhanced Cell Response (EMECR) assay is to identify gene products (e.g., isolated polypeptides) that act on the hematopoietic stem cells in the context of the extracellular matrix (ECM) induced signal.

Cells respond to the regulatory factors in the context of signal(s) received from the surrounding microenvironment. For example, fibroblasts, and endothelial and epithelial stem cells fail to replicate in the absence of signals from the ECM. Hematopoietic stem cells can undergo self-renewal in the bone marrow, but not in in vitro suspension culture. The ability of stem cells to undergo self-renewal in vitro is dependent upon their interaction with the stromal cells and the ECM protein fibronectin (fn). Adhesion of cells to fn is mediated by the $\alpha_5.\beta_1$ and $\alpha_4.\beta_1$ integrin receptors, which are expressed by human and mouse hematopoietic stem cells. The factor(s) which integrate with the ECM environment and responsible for stimulating stem cell self-renewal has not yet been identified. Discovery of such factors should be of great interest in gene therapy and bone marrow transplant applications Briefly, polystyrene, non tissue culture treated, 96-well plates are coated with fn fragment at a coating concentration of 0.2 $\mu g/cm^2$. Mouse bone marrow cells are plated (1,000 cells/well) in 0.2 ml of serum-free medium. Cells cultured in the presence of IL-3 (5 ng/ml)+SCF (50 ng/ml) would serve as the positive control, conditions under which little self-renewal but pronounced differentiation of the stem cells is to be expected. Gene products are tested with appropriate negative controls in the presence and absence of SCF (5.0 ng/ml), where test factor supernates represent 10% of the total assay volume. The plated cells are then allowed to grow by incubating in a low oxygen environment (5% $CO_2$, 7% $O_2$, and 88% $N_2$) tissue culture incubator for 7 days. The number of proliferating cells within the wells is then quantitated by measuring thymidine incorporation into cellular DNA. Verification of the positive hits in the assay will require phenotypic characterization of the cells, which can be accomplished by scaling up of the culture system and using appropriate antibody reagents against cell surface antigens and FACScan.

One skilled in the art could easily modify the exemplified studies to test the activity of polynucleotides (e.g., gene therapy), antibodies, agonists, and/or antagonists and fragments and variants thereof.

If a particular gene product is found to be a stimulator of hematopoietic progenitors, polynucleotides and polypeptides corresponding to the gene may be useful for the diagnosis and treatment of disorders affecting the immune system and hematopoiesis. Representative uses are described in the "Immune Activity" and "Infectious Disease" sections above, and elsewhere herein. The gene product may also be useful in the expansion of stem cells and committed progenitors of various blood lineages, and in the differentiation and/or proliferation of various cell types.

Additionally, the polynucleotides and/or polypeptides of the gene of interest and/or agonists and/or antagonists thereof, may also be employed to inhibit the proliferation and differentiation of hematopoietic cells and therefore may be employed to protect bone marrow stem cells from chemotherapeutic agents during chemotherapy. This antiproliferative effect may allow administration of higher doses of chemotherapeutic agents and, therefore, more effective chemotherapeutic treatment.

Moreover, polynucleotides and polypeptides corresponding to the gene of interest may also be useful for the treatment and diagnosis of hematopoietic related disorders such as, for example, anemia, pancytopenia, leukopenia, thrombocytopenia or leukemia since stromal cells are important in the production of cells of hematopoietic lineages. The uses include bone marrow cell ex-vivo culture, bone marrow transplantation, bone marrow reconstitution, radiotherapy or chemotherapy of neoplasia.

Example 55

Human Dermal Fibroblast and Aortic Smooth Muscle Cell Proliferation

The polypeptide of interest is added to cultures of normal human dermal fibroblasts (NHDF) and human aortic smooth muscle cells (AoSMC) and two co-assays are performed with each sample. The first assay examines the effect of the polypeptide of interest on the proliferation of normal human dermal fibroblasts (NHDF) or aortic smooth muscle cells (AoSMC). Aberrant growth of fibroblasts or smooth muscle cells is a part of several pathological processes, including fibrosis, and restenosis. The second assay examines IL6 production by both NHDF and SMC. IL6 production is an indication of functional activation. Activated cells will have increased production of a number of cytokines and other factors, which can result in a proinflammatory or immunomodulatory outcome. Assays are run with and without co-TNFa stimulation, in order to check for costimulatory or inhibitory activity.

Briefly, on day 1, 96-well black plates are set up with 1000 cells/well (NHDF) or 2000 cells/well (AoSMC) in 100 µl culture media. NHDF culture media contains: Clonetics FB basal media, 1 mg/ml hFGF, 5 mg/ml insulin, 50 mg/ml gentamycin, 2% FBS, while AoSMC culture media contains Clonetics SM basal media, 0.5 µg/ml hEGF, 5 mg/ml insulin, 1 µg/ml hFGF, 50 mg/ml gentamycin, 50 µg/ml Amphotericin B, 5% FBS. After incubation @ 37° C. for at least 4-5 hours culture media is aspirated and replaced with growth arrest media. Growth arrest media for NHDF contains fibroblast basal media, 50 mg/ml gentamycin, 2% FBS, while growth arrest media for AoSMC contains SM basal media, 50 mg/ml gentamycin, 50 µg/ml Amphotericin B, 0.4% FBS. Incubate at 37 C until day 2.

On day 2, serial dilutions and templates of the polypeptide of interest are designed which should always include media controls and known-protein controls. For both stimulation and inhibition experiments, proteins are diluted in growth arrest media. For inhibition experiments, TNFa is added to a final concentration of 2 ng/ml (NHDF) or 5 ng/ml (AoSMC). Then add ⅓ vol media containing controls or supernatants and incubate at 37 C/5% $CO_2$ until day 5.

Transfer 60 µl from each well to another labeled 96-well plate, cover with a plate-sealer, and store at 4 C until Day 6 (for IL6 ELISA). To the remaining 100 µl in the cell culture plate, aseptically add Alamar Blue in an amount equal to 10% of the culture volume (110%). Return plates to incubator for 3 to 4 hours. Then measure fluorescence with excitation at 530 nm and emission at 590 nm using the CytoFluor. This yields the growth stimulation/inhibition data.

On day 5, the IL6 ELISA is performed by coating a 96 well plate with 50-100 ul/well of Anti-Human IL6 Monoclonal antibody diluted in PBS, pH 7.4, incubate ON at room temperature.

On day 6, empty the plates into the sink and blot on paper towels. Prepare Assay Buffer containing PBS with 4% BSA. Block the plates with 200 µl/well of Pierce Super Block blocking buffer in PBS for 1-2 hr and then wash plates with wash buffer (PBS, 0.05% Tween-20). Blot plates on paper towels. Then add 50 µl/well of diluted Anti-Human IL-6 Monoclonal, Biotin-labeled antibody at 0.50 mg/ml. Make dilutions of IL-6 stock in media (30, 10, 3, 1, 0.3, 0 ng/ml). Add duplicate samples to top row of plate. Cover the plates and incubate for 2 hours at RT on shaker.

Wash plates with wash buffer and blot on paper towels. Dilute EU-labeled Streptavidin 1:1000 in Assay buffer, and add 100 µl/well. Cover the plate and incubate 1 h at RT. Wash plates with wash buffer. Blot on paper towels.

Add 100 µl/well of Enhancement Solution. Shake for 5 minutes. Read the plate on the Wallac DELFIA Fluorometer. Readings from triplicate samples in each assay were tabulated and averaged.

A positive result in this assay suggests AoSMC cell proliferation and that the gene product of interest may be involved in dermal fibroblast proliferation and/or smooth muscle cell proliferation. A positive result also suggests many potential uses of polypeptides, polynucleotides, agonists and/or antagonists of the gene/gene product of interest. For example, inflammation and immune responses, wound healing, and angiogenesis, as detailed throughout this specification. Particularly, polypeptides of the gene product and polynucleotides of the gene may be used in wound healing and dermal regeneration, as well as the promotion of vasculargenesis, both of the blood vessels and lymphatics. The growth of vessels can be used in the treatment of, for example, cardiovascular diseases. Additionally, antagonists of polypeptides of the gene product and polynucleotides of the gene may be useful in treating diseases, disorders, and/or conditions which involve angiogenesis by acting as an anti-vascular (e.g., anti-angiogenesis). These diseases, disorders, and/or conditions are known in the art and/or are described herein, such as, for example, malignancies, solid tumors, benign tumors, for example hemangiomas, acoustic neuromas, neurofibromas, trachomas, and pyogenic granulomas; artheroscleric plaques; ocular angiogenic diseases, for example, diabetic retinopathy, retinopathy of prematurity, macular degeneration, corneal graft rejection, neovascular glaucoma, retrolental fibroplasia, rubeosis, retinoblastoma, uvietis and Pterygia (abnormal blood vessel growth) of the eye; rheumatoid arthritis; psoriasis; delayed wound healing; endometriosis; vasculogenesis; granulations; hypertrophic scars (keloids); nonunion fractures; scleroderma; trachoma; vascular adhesions; myocardial angiogenesis; coronary collaterals; cerebral collaterals; arteriovenous malformations; ischemic limb angiogenesis; Osler-Webber Syndrome; plaque neovascularization; telangiectasia; hemophiliac joints; angiofibroma; fibromuscular dysplasia; wound granulation; Crohn's disease; and atherosclerosis. Moreover, antagonists of polypeptides of the gene product and polynucleotides of the gene may be useful in treating anti-hyperproliferative diseases and/or anti-inflammatory known in the art and/or described herein.

One skilled in the art could easily modify the exemplified studies to test the activity of polynucleotides (e.g., gene therapy), antibodies, agonists, and/or antagonists and fragments and variants thereof.

Example 56

Cellular Adhesion Molecule (CAM) Expression on Endothelial Cells

The recruitment of lymphocytes to areas of inflammation and angiogenesis involves specific receptor-ligand interactions between cell surface adhesion molecules (CAMs) on lymphocytes and the vascular endothelium. The adhesion process, in both normal and pathological settings, follows a multi-step cascade that involves intercellular adhesion molecule-1 (ICAM-1), vascular cell adhesion molecule-1 (VCAM-1), and endothelial leukocyte adhesion molecule-1 (E-selectin) expression on endothelial cells (EC). The expression of these molecules and others on the vascular endothelium determines the efficiency with which leukocytes may adhere to the local vasculature and extravasate into the local tissue during the development of an inflammatory response. The local concentration of cytokines and growth factor participate in the modulation of the expression of these CAMs.

Briefly, endothelial cells (e.g., Human Umbilical Vein Endothelial cells (HUVECs)) are grown in a standard 96 well plate to confluence, growth medium is removed from the cells and replaced with 100 µl of 199 Medium (10% fetal bovine serum (FBS)). Samples for testing and positive or negative controls are added to the plate in triplicate (in 10 µl volumes). Plates are then incubated at 37° C. for either 5 h (selectin and integrin expression) or 24 h (integrin expression only). Plates are aspirated to remove medium and 100 µl of 0.1% paraformaldehyde-PBS(with Ca++ and Mg++) is added to each well. Plates are held at 4° C. for 30 min. Fixative is removed from the wells and wells are washed 1× with PBS(+Ca,Mg)+0.5% BSA and drained. 10 µl of diluted primary antibody is added to the test and control wells. Anti-ICAM-1-Biotin, Anti-VCAM-1-Biotin and Anti-E-selectin-Biotin are used at a concentration of 10 µg/ml (1:10 dilution of 0.1 mg/ml stock antibody). Cells are incubated at 37° C. for 30 min. in a humidified environment. Wells are washed three times with PBS(+Ca,Mg)+0.5% BSA. 20 µl of diluted ExtrAvidin-Alkaline Phosphotase (1:5,000 dilution, referred to herein as the working dilution) are added to each well and incubated at 37° C. for 30 min. Wells are washed three times with PBS(+Ca,Mg)+0.5% BSA. Dissolve 1 tablet of p-Nitrophenol Phosphate pNPP per 5 ml of glycine buffer (pH 10.4). 100 µl of pNPP substrate in glycine buffer is added to each test well. Standard wells in triplicate are prepared from the working dilution of the ExtrAvidin-Alkaline Phosphotase in glycine buffer: 1:5,000 $(10^{0})>10^{-0.5}>10^{-1}>10^{1.5}$0.5 µl of each dilution is added to triplicate wells and the resulting AP content in each well is 5.50 ng, 1.74 ng, 0.55 ng, 0.18 ng. 100 µl of pNNP reagent is then added to each of the standard wells. The plate is incubated at 37° C. for 4 h. A volume of 50 µl of 3M NaOH is added to all wells. The plate is read on a plate reader at 405 nm using the background subtraction option on blank wells filled with glycine buffer only. Additionally, the template is set up to indicate the concentration of AP-conjugate in each standard well [5.50 ng; 1.74 ng; 0.55 ng; 0.18 ng]. Results are indicated as amount of bound AP-conjugate in each sample.

Example 57

Alamar Blue Endothelial Cells Proliferation Assay

This assay may be used to quantitatively determine protein mediated inhibition of bFGF-induced proliferation of Bovine Lymphatic Endothelial Cells (LECs), Bovine Aortic Endothelial Cells (BAECs) or Human Microvascular Uterine Myometrial Cells (UTMECs). This assay incorporates a fluorometric growth indicator based on detection of metabolic activity. A standard Alamar Blue Proliferation Assay is prepared in EGM-2MV with 10 ng/ml of bFGF added as a source of endothelial cell stimulation. This assay may be used with a variety of endothelial cells with slight changes in growth medium and cell concentration. Dilutions of the protein batches to be tested are diluted as appropriate. Serum-free medium (GIBCO SFM) without bFGF is used as a non-stimulated control and Angiostatin or TSP-1 are included as a known inhibitory controls.

Briefly, LEC, BAECs or UTMECs are seeded in growth media at a density of 5000 to 2000 cells/well in a 96 well plate and placed at 37-C overnight. After the overnight incubation of the cells, the growth media is removed and replaced with GIBCO EC-SFM. The cells are treated with the appropriate dilutions of the protein of interest or control protein sample(s) (prepared in SFM ) in triplicate wells with additional bFGF to a concentration of 10 ng/ml. Once the cells have been treated with the samples, the plate(s) is/are placed back in the 37° C. incubator for three days. After three days 10 ml of stock alamar blue (Biosource Cat#DAL1100) is added to each well and the plate(s) is/are placed back in the 37° C. incubator for four hours. The plate(s) are then read at 530 nm excitation and 590 nm emission using the CytoFluor fluorescence reader. Direct output is recorded in relative fluorescence units.

Alamar blue is an oxidation-reduction indicator that both fluoresces and changes color in response to chemical reduction of growth medium resulting from cell growth. As cells grow in culture, innate metabolic activity results in a chemical reduction of the immediate surrounding environment. Reduction related to growth causes the indicator to change from oxidized (non-fluorescent blue) form to reduced (fluorescent red) form. i.e. stimulated proliferation will produce a stronger signal and inhibited proliferation will produce a weaker signal and the total signal is proportional to the total number of cells as well as their metabolic activity. The background level of activity is observed with the starvation medium alone. This is compared to the output observed from the positive control samples (bFGF in growth medium) and protein dilutions.

Example 58

Detection of Inhibition of a Mixed Lymphocyte Reaction

This assay can be used to detect and evaluate inhibition of a Mixed Lymphocyte Reaction (MLR) by gene products (e.g., isolated polypeptides). Inhibition of a MLR may be due to a direct effect on cell proliferation and viability, modulation of costimulatory molecules on interacting cells, modulation of adhesiveness between lymphocytes and accessory cells, or modulation of cytokine production by accessory cells. Multiple cells may be targeted by these polypeptides since the peripheral blood mononuclear fraction used in this assay includes T, B and natural killer lymphocytes, as well as monocytes and dendritic cells.

Polypeptides of interest found to inhibit the MLR may find application in diseases associated with lymphocyte and monocyte activation or proliferation. These include, but are not limited to, diseases such as asthma, arthritis, diabetes, inflammatory skin conditions, psoriasis, eczema, systemic lupus erythematosus, multiple sclerosis, glomerulonephritis, inflammatory bowel disease, crohn's disease, ulcerative colitis, arteriosclerosis, cirrhosis, graft vs. host disease, host vs. graft disease, hepatitis, leukemia and lymphoma.

Briefly, PBMCs from human donors are purified by density gradient centrifugation using Lymphocyte Separation Medium (LSM®, density 1.0770 g/ml, Organon Teknika Corporation, West Chester, Pa.). PBMCs from two donors are adjusted to $2\times10^6$ cells/ml in RPMI-1640 (Life Technologies, Grand Island, N.Y.) supplemented with 10% FCS and 2 mM glutamine. PBMCs from a third donor is adjusted to $2\times10^5$ cells/ml. Fifty microliters of PBMCs from each donor is added to wells of a 96-well round bottom microtiter plate. Dilutions of test materials (50 μl) is added in triplicate to microtiter wells. Test samples (of the protein of interest) are added for final dilution of 1:4; rhuIL-2 (R&D Systems, Minneapolis, Minn., catalog number 202-IL) is added to a final concentration of 1 μg/ml; anti-CD4 mAb (R&D Systems, clone 34930.11, catalog number MAB379) is added to a final concentration of 10 μg/ml. Cells are cultured for 7-8 days at 37° C. in 5% $CO_2$, and 1 μC of $[^3H]$ thymidine is added to wells for the last 16 hrs of culture. Cells are harvested and thymidine incorporation determined using a Packard TopCount. Data is expressed as the mean and standard deviation of triplicate determinations.

Samples of the protein of interest are screened in separate experiments and compared to the negative control treatment, anti-CD4 mAb, which inhibits proliferation of lymphocytes and the positive control treatment, IL-2 (either as recombinant material or supernatant), which enhances proliferation of lymphocytes.

One skilled in the art could easily modify the exemplified studies to test the activity of polynucleotides (e.g., gene therapy), antibodies, agonists, and/or antagonists and fragments and variants thereof.

TABLE 7

| Res | Position | I | II | III | IV | V | VI | VII | VIII | IX | X | XI | XII | XIII | XIV |
|---|---|---|---|---|---|---|---|---|---|---|---|---|---|---|---|
| Met | 1 | . | . | B | . | . | . | . | 0.24 | 0.41 | . | . | . | −0.40 | 0.65 |
| Ile | 2 | . | . | B | . | . | T | . | 0.60 | 0.39 | . | . | . | 0.10 | 0.88 |
| Pro | 3 | . | . | B | . | . | T | . | 0.99 | 0.46 | . | . | . | −0.20 | 0.93 |
| Asn | 4 | . | . | . | . | T | T | . | 0.79 | 0.43 | . | . | . | 0.35 | 1.51 |
| Gln | 5 | . | . | B | . | . | T | . | 0.83 | 0.31 | . | . | F | 0.40 | 2.18 |
| His | 6 | . | . | . | . | . | . | C | 0.84 | 0.06 | . | . | F | 0.40 | 1.40 |

TABLE 7-continued

| Res | Position | I | II | III | IV | V | VI | VII | VIII | IX | X | XI | XII | XIII | XIV |
|---|---|---|---|---|---|---|---|---|---|---|---|---|---|---|---|
| Asn | 7 | . | . | . | . | . | . | C | 1.39 | 0.13 | . | . | . | 0.10 | 0.88 |
| Ala | 8 | . | . | . | . | . | . | C | 1.30 | 0.16 | . | . | . | 0.10 | 0.50 |
| Gly | 9 | . | . | . | . | T | T | . | 1.27 | 0.14 | . | . | . | 0.50 | 0.49 |
| Ala | 10 | . | . | . | . | T | T | . | 1.27 | 0.14 | . | . | F | 0.65 | 0.42 |
| Gly | 11 | . | . | . | . | . | T | C | 1.09 | 0.14 | . | . | F | 0.45 | 0.72 |
| Ser | 12 | . | . | . | . | . | T | C | 0.50 | 0.07 | . | . | F | 0.60 | 1.12 |
| His | 13 | . | A | . | . | . | . | C | 0.23 | 0.14 | . | . | F | 0.20 | 1.12 |
| Gln | 14 | . | A | B | . | . | . | . | −0.12 | 0.29 | * | * | F | −0.15 | 0.84 |
| Pro | 15 | . | A | B | . | . | . | . | 0.58 | 0.64 | * | * | F | −0.45 | 0.54 |
| Ala | 16 | . | A | B | . | . | . | . | 0.32 | 0.26 | * | * | . | −0.30 | 0.78 |
| Val | 17 | A | A | . | . | . | . | . | 0.03 | 0.37 | . | * | . | −0.30 | 0.45 |
| Phe | 18 | . | A | B | . | . | . | . | −0.79 | 0.47 | . | * | . | −0.60 | 0.29 |
| Arg | 19 | . | A | B | . | . | . | . | −1.60 | 0.69 | . | . | . | −0.60 | 0.21 |
| Met | 20 | . | A | B | . | . | . | . | −1.39 | 0.87 | . | * | . | −0.60 | 0.24 |
| Ala | 21 | A | A | . | . | . | . | . | −1.11 | 0.23 | . | * | . | −0.30 | 0.46 |
| Val | 22 | A | A | . | . | . | . | . | −0.26 | −0.07 | . | * | . | 0.30 | 0.34 |
| Leu | 23 | A | A | . | . | . | . | . | −0.37 | −0.07 | . | * | . | 0.30 | 0.57 |
| Asp | 24 | A | . | . | . | . | T | . | −0.48 | −0.00 | . | * | F | 0.85 | 0.47 |
| Thr | 25 | A | . | . | . | . | T | . | 0.09 | −0.50 | * | . | F | 1.30 | 1.05 |
| Asp | 26 | A | . | . | . | . | T | . | −0.21 | −0.64 | * | * | F | 1.30 | 1.73 |
| Leu | 27 | A | . | . | . | . | T | . | −0.17 | −0.64 | * | * | . | 1.00 | 0.73 |
| Asp | 28 | A | . | . | . | . | . | . | 0.43 | 0.04 | * | * | . | −0.10 | 0.41 |
| His | 29 | . | . | B | . | . | . | . | 0.13 | −0.01 | . | * | . | 0.50 | 0.38 |
| Ile | 30 | . | . | B | . | . | . | . | 0.14 | 0.37 | * | . | . | −0.10 | 0.62 |
| Leu | 31 | . | . | B | . | . | T | . | −0.71 | 0.07 | . | . | . | 0.10 | 0.50 |
| Pro | 32 | . | . | B | . | . | T | . | −0.71 | 0.71 | . | . | F | −0.05 | 0.27 |
| Ser | 33 | . | . | . | . | T | T | . | −0.92 | 0.90 | . | . | F | 0.35 | 0.32 |
| Ser | 34 | . | . | B | . | . | T | . | −1.10 | 0.64 | . | . | F | −0.05 | 0.60 |
| Val | 35 | . | . | B | . | . | . | . | −0.91 | 0.39 | . | . | F | 0.05 | 0.60 |
| Leu | 36 | . | . | B | . | . | . | . | −0.39 | 0.74 | . | . | F | −0.25 | 0.39 |
| Pro | 37 | . | . | B | . | . | T | . | −0.77 | 1.27 | . | . | F | −0.05 | 0.31 |
| Pro | 38 | . | . | B | . | . | T | . | −0.42 | 1.39 | * | * | . | −0.20 | 0.42 |
| Phe | 39 | A | . | . | . | . | T | . | −0.93 | 0.74 | * | . | . | −0.05 | 1.01 |
| Trp | 40 | A | . | . | . | . | T | . | −0.93 | 0.74 | . | * | . | −0.20 | 0.54 |
| Ala | 41 | A | A | . | B | . | . | . | −0.98 | 0.96 | * | . | . | −0.60 | 0.26 |
| Lys | 42 | . | A | B | B | . | . | . | −1.11 | 1.17 | . | * | . | −0.60 | 0.22 |
| Leu | 43 | . | A | B | B | . | . | . | −1.20 | 0.81 | . | . | . | −0.60 | 0.21 |
| Val | 44 | . | A | B | B | . | . | . | −1.36 | 0.29 | . | . | . | −0.30 | 0.28 |
| Val | 45 | . | . | B | B | . | . | . | −1.66 | 0.43 | . | . | . | −0.60 | 0.10 |
| Gly | 46 | . | . | B | B | . | . | . | −1.96 | 0.93 | . | . | . | −0.60 | 0.13 |
| Ser | 47 | . | A | B | B | . | . | . | −2.86 | 0.93 | . | . | . | −0.60 | 0.12 |
| Val | 48 | . | A | B | B | . | . | . | −2.71 | 0.93 | . | . | . | −0.60 | 0.12 |
| Ala | 49 | . | A | B | B | . | . | . | −2.56 | 0.86 | . | . | . | −0.60 | 0.06 |
| Ile | 50 | . | A | B | B | . | . | . | −2.29 | 1.21 | * | . | . | −0.60 | 0.04 |
| Val | 51 | . | A | B | B | . | . | . | −1.83 | 1.33 | * | . | . | −0.60 | 0.06 |
| Cys | 52 | . | A | B | B | . | . | . | −1.83 | 0.69 | * | . | . | −0.60 | 0.11 |
| Phe | 53 | . | A | B | B | . | . | . | −1.22 | 0.57 | * | . | . | −0.26 | 0.21 |
| Ala | 54 | . | A | B | B | . | . | . | −0.63 | 0.64 | * | . | . | 0.08 | 0.44 |
| Arg | 55 | . | A | B | B | . | . | . | −0.09 | 0.00 | * | . | . | 1.47 | 1.38 |
| Ser | 56 | . | . | . | . | T | T | . | 0.77 | −0.14 | * | . | F | 2.76 | 1.57 |
| Tyr | 57 | . | . | . | . | T | T | . | 0.73 | −0.93 | . | . | F | 3.40 | 2.60 |
| Asp | 58 | . | . | . | . | T | T | . | 0.58 | −0.64 | . | . | F | 3.06 | 1.15 |
| Gly | 59 | . | . | . | . | T | T | . | 0.47 | −0.00 | . | * | F | 2.27 | 0.64 |
| Asp | 60 | . | . | B | . | . | . | . | 0.36 | 0.40 | . | * | F | 0.73 | 0.35 |
| Phe | 61 | . | . | B | . | . | . | . | 0.66 | −0.36 | . | * | . | 0.84 | 0.35 |
| Val | 62 | . | . | B | . | . | . | . | 0.60 | −0.36 | . | * | . | 0.50 | 0.59 |
| Phe | 63 | . | . | B | . | . | . | . | 0.60 | −0.40 | . | * | . | 0.50 | 0.48 |
| Asp | 64 | A | . | . | . | . | T | . | 0.36 | −0.40 | * | . | F | 0.85 | 0.95 |
| Asp | 65 | A | . | . | . | . | T | . | −0.53 | −0.69 | * | . | F | 1.30 | 1.30 |
| Ser | 66 | A | . | . | . | . | T | . | −0.69 | −0.64 | * | . | F | 1.30 | 1.05 |
| Glu | 67 | A | . | . | . | . | T | . | 0.17 | −0.79 | * | . | F | 1.15 | 0.47 |
| Ala | 68 | A | . | . | . | . | . | . | 0.87 | −0.39 | . | . | . | 0.50 | 0.45 |
| Ile | 69 | A | . | . | . | . | . | . | 0.91 | 0.01 | . | . | . | −0.10 | 0.54 |
| Val | 70 | A | . | . | . | . | . | . | 0.91 | −0.37 | . | . | . | 0.50 | 0.62 |
| Asn | 71 | A | . | . | . | . | . | . | 0.40 | −0.37 | . | . | F | 0.80 | 1.03 |
| Asn | 72 | A | . | . | . | . | T | . | 0.40 | −0.19 | . | . | F | 1.00 | 1.21 |
| Lys | 73 | A | . | . | . | . | T | . | 0.40 | −0.47 | . | * | F | 1.00 | 2.83 |
| Asp | 74 | A | . | . | . | . | T | C | 1.29 | −0.61 | . | * | F | 1.50 | 1.78 |
| Leu | 75 | A | . | . | . | . | T | . | 1.83 | −1.01 | . | . | F | 1.30 | 1.91 |
| Gln | 76 | . | . | B | . | . | . | . | 1.62 | −0.93 | . | * | . | 0.95 | 1.38 |
| Ala | 77 | . | . | B | . | . | . | . | 0.81 | −0.50 | . | * | F | 1.35 | 1.28 |
| Glu | 78 | . | . | B | . | . | . | . | 0.42 | 0.19 | . | * | F | 0.70 | 1.28 |
| Thr | 79 | . | . | B | . | . | T | . | 0.42 | −0.07 | . | * | F | 1.60 | 0.73 |
| Pro | 80 | A | . | . | . | . | T | . | 0.42 | −0.47 | * | * | F | 2.00 | 1.21 |
| Leu | 81 | . | . | . | . | T | T | . | 0.13 | −0.29 | * | . | F | 2.50 | 0.57 |
| Gly | 82 | A | . | . | . | . | T | . | 0.69 | 0.63 | * | . | F | 0.95 | 0.42 |
| Asp | 83 | A | A | . | . | . | . | . | 0.66 | 0.64 | . | . | . | 0.15 | 0.37 |

TABLE 7-continued

| Res | Position | I | II | III | IV | V | VI | VII | VIII | IX | X | XI | XII | XIII | XIV |
|---|---|---|---|---|---|---|---|---|---|---|---|---|---|---|---|
| Leu | 84 | A | A | . | . | . | . | . | 0.97 | 0.71 | * | . | . | −0.10 | 0.61 |
| Tsp | 85 | A | A | . | . | . | . | . | 0.48 | 0.03 | . | . | . | 0.10 | 1.03 |
| His | 86 | . | A | B | . | . | . | . | 1.00 | 0.39 | . | . | . | −0.30 | 0.53 |
| His | 87 | . | A | B | . | . | . | . | 1.00 | 1.30 | . | . | . | −0.60 | 0.68 |
| Asp | 88 | . | A | . | . | T | . | . | 0.70 | 1.04 | . | . | . | −0.20 | 0.64 |
| Phe | 89 | . | A | . | . | T | . | . | 1.62 | 0.51 | . | . | . | −0.20 | 0.63 |
| Tsp | 90 | . | A | . | . | T | . | . | 1.10 | 0.01 | . | * | . | 0.10 | 0.91 |
| Gly | 91 | . | . | . | . | . | T | C | 0.83 | 0.20 | . | . | F | 0.45 | 0.45 |
| Ser | 92 | . | . | . | . | . | T | C | 0.57 | 0.59 | . | * | F | 0.15 | 0.69 |
| Arg | 93 | . | . | . | . | . | T | C | 0.57 | 0.19 | . | * | F | 0.45 | 0.88 |
| Leu | 94 | . | . | . | . | . | T | C | 0.96 | −0.33 | . | * | F | 1.20 | 1.43 |
| Ser | 95 | . | . | . | . | . | T | C | 0.94 | −0.27 | * | * | F | 1.20 | 1.54 |
| Ser | 96 | . | . | . | . | . | T | C | 1.26 | −0.27 | * | * | F | 1.20 | 1.06 |
| Asn | 97 | . | . | . | . | . | T | C | 1.60 | 0.23 | * | * | F | 0.60 | 1.74 |
| Thr | 98 | . | . | . | . | T | T | . | 1.19 | −0.46 | * | * | F | 1.74 | 2.60 |
| Ser | 99 | . | . | . | . | T | . | . | 1.76 | −0.46 | * | * | F | 1.88 | 2.60 |
| His | 100 | . | . | . | . | T | T | . | 2.17 | −0.09 | * | . | F | 2.42 | 2.53 |
| Lys | 101 | . | . | . | . | T | T | . | 2.26 | −0.49 | * | . | F | 2.76 | 3.44 |
| Ser | 102 | . | . | . | . | T | T | . | 1.44 | −0.54 | * | . | F | 3.40 | 3.97 |
| Tyr | 103 | . | . | B | . | . | T | . | 1.44 | −0.24 | * | . | F | 2.36 | 2.40 |
| Arg | 104 | . | . | B | B | . | . | . | 0.89 | −0.26 | * | . | F | 1.62 | 1.74 |
| Pro | 105 | . | . | B | B | . | . | . | 0.11 | 0.39 | * | . | F | 0.53 | 0.96 |
| Leu | 106 | . | . | B | B | . | . | . | −0.24 | 0.69 | * | . | . | −0.26 | 0.51 |
| Thr | 107 | . | . | B | B | . | . | . | −0.64 | 0.41 | * | * | . | −0.60 | 0.37 |
| Val | 108 | . | . | B | B | . | . | . | −0.29 | 1.20 | * | * | . | −0.60 | 0.21 |
| Leu | 109 | . | . | B | B | . | . | . | −1.29 | 0.77 | * | * | . | −0.60 | 0.50 |
| Thr | 110 | . | . | B | B | . | . | . | −1.08 | 0.77 | . | * | . | −0.60 | 0.24 |
| Phe | 111 | . | . | B | B | . | . | . | −0.51 | 0.69 | . | * | . | −0.60 | 0.52 |
| Arg | 112 | . | . | B | B | . | . | . | −0.44 | 0.80 | . | * | . | −0.60 | 0.99 |
| Ile | 113 | . | . | B | B | . | . | . | −0.40 | 0.87 | . | * | . | −0.45 | 1.08 |
| Asn | 114 | . | . | B | B | . | . | . | 0.11 | 1.07 | . | * | . | −0.45 | 1.02 |
| Tyr | 115 | . | . | B | B | . | . | . | 0.08 | 0.67 | . | * | . | −0.60 | 0.70 |
| Tyr | 116 | . | . | . | B | T | . | . | 0.43 | 1.10 | * | * | . | −0.20 | 0.99 |
| Leu | 117 | . | . | . | . | T | T | . | −0.38 | 0.84 | * | * | . | 0.20 | 0.61 |
| Ser | 118 | . | . | . | . | T | T | . | 0.48 | 1.23 | * | * | F | 0.35 | 0.34 |
| Gly | 119 | . | . | . | . | T | T | . | 0.27 | 0.97 | . | * | F | 0.35 | 0.29 |
| Gly | 120 | . | . | . | . | T | T | . | −0.34 | 0.64 | . | . | F | 0.35 | 0.55 |
| Phe | 121 | . | . | B | . | . | . | . | −0.44 | 0.60 | . | . | . | −0.40 | 0.30 |
| His | 122 | . | . | B | . | . | T | . | −0.33 | 0.64 | . | . | . | −0.20 | 0.30 |
| Pro | 123 | . | . | B | . | . | T | . | −0.07 | 1.00 | . | . | . | −0.20 | 0.27 |
| Val | 124 | . | . | B | . | . | T | . | −0.58 | 1.07 | . | . | . | −0.20 | 0.42 |
| Gly | 125 | . | . | B | . | . | T | . | −1.09 | 0.93 | * | . | . | −0.20 | 0.23 |
| Phe | 126 | . | . | B | B | . | . | . | −0.39 | 1.07 | * | . | . | −0.60 | 0.11 |
| His | 127 | . | . | B | B | . | . | . | −1.24 | 1.04 | * | . | . | −0.60 | 0.24 |
| Val | 128 | . | . | B | B | . | . | . | −1.84 | 1.09 | * | . | . | −0.60 | 0.17 |
| Val | 129 | . | . | B | B | . | . | . | −1.80 | 1.34 | * | . | . | −0.60 | 0.16 |
| Asn | 130 | . | . | B | B | . | . | . | −1.49 | 1.24 | * | . | . | −0.60 | 0.10 |
| Ile | 131 | . | . | B | B | . | . | . | −1.09 | 1.24 | * | . | . | −0.60 | 0.18 |
| Leu | 132 | . | . | B | B | . | . | . | −1.40 | 0.99 | * | * | . | −0.60 | 0.32 |
| Leu | 133 | A | . | . | B | . | . | . | −1.43 | 0.77 | . | * | . | −0.60 | 0.20 |
| His | 134 | . | . | . | . | . | T | C | −0.88 | 1.06 | * | * | . | 0.00 | 0.20 |
| Ser | 135 | . | . | . | . | . | T | C | −1.73 | 0.76 | . | * | . | 0.00 | 0.32 |
| Gly | 136 | . | . | B | . | . | T | . | −1.66 | 0.71 | . | * | . | −0.20 | 0.29 |
| Ile | 137 | . | . | B | . | . | T | . | −1.44 | 0.71 | . | . | . | −0.20 | 0.17 |
| Ser | 138 | . | . | B | B | . | . | . | −1.49 | 0.83 | . | . | . | −0.60 | 0.13 |
| Val | 139 | . | . | B | B | . | . | . | −1.46 | 1.09 | . | . | . | −0.60 | 0.10 |
| Leu | 140 | . | . | B | B | . | . | . | −2.01 | 0.66 | . | . | . | −0.60 | 0.23 |
| Met | 141 | . | . | B | B | . | . | . | −2.37 | 0.61 | . | . | . | −0.60 | 0.13 |
| Val | 142 | . | . | B | B | . | . | . | −1.78 | 1.01 | . | . | . | −0.60 | 0.15 |
| Asp | 143 | . | . | B | B | . | . | . | −2.33 | 0.76 | . | . | . | −0.60 | 0.24 |
| Val | 144 | . | . | B | B | . | . | . | −2.29 | 0.71 | . | . | . | −0.60 | 0.18 |
| Phe | 145 | . | . | B | B | . | . | . | −2.18 | 0.79 | . | . | . | −0.60 | 0.20 |
| Ser | 146 | . | . | B | B | . | . | . | −1.92 | 0.93 | * | . | . | −0.60 | 0.10 |
| Val | 147 | . | . | B | B | . | . | . | −1.41 | 1.36 | * | . | . | −0.60 | 0.14 |
| Leu | 148 | . | . | B | B | . | . | . | −2.22 | 1.14 | * | . | . | −0.60 | 0.16 |
| Phe | 149 | . | . | B | B | . | . | . | −1.37 | 1.04 | * | . | . | −0.60 | 0.10 |
| Gly | 150 | . | . | . | B | T | . | . | −0.91 | 1.06 | . | . | . | −0.20 | 0.23 |
| Gly | 151 | . | . | . | B | . | . | C | −0.92 | 1.17 | . | . | . | −0.40 | 0.44 |
| Leu | 152 | . | . | B | B | . | . | . | −0.37 | 0.97 | * | * | . | −0.60 | 0.73 |
| Gln | 153 | . | . | B | B | . | . | . | 0.49 | 0.57 | * | * | . | −0.26 | 0.98 |
| Tyr | 154 | . | . | B | B | . | . | . | 0.84 | 0.14 | . | * | F | 0.68 | 1.98 |
| Thr | 155 | . | . | . | B | T | . | . | 1.30 | 0.14 | * | * | F | 1.42 | 2.38 |
| Ser | 156 | . | . | . | . | T | T | . | 1.76 | −0.54 | * | * | F | 3.06 | 2.69 |
| Lys | 157 | . | . | . | . | T | T | . | 1.76 | −0.94 | * | * | F | 3.40 | 3.37 |
| Gly | 158 | . | . | . | . | T | T | . | 1.72 | −1.01 | * | * | F | 3.06 | 1.92 |
| Arg | 159 | . | . | B | . | . | T | . | 1.16 | −1.00 | * | . | F | 2.32 | 1.95 |
| Arg | 160 | . | A | B | . | . | . | . | 0.88 | −0.70 | * | . | F | 1.43 | 0.81 |

TABLE 7-continued

| Res | Position | I | II | III | IV | V | VI | VII | VIII | IX | X | XI | XII | XIII | XIV |
|---|---|---|---|---|---|---|---|---|---|---|---|---|---|---|---|
| Leu | 161 | . | A | B | . | . | . | . | 0.97 | −0.20 | * | * | . | 0.64 | 0.82 |
| His | 162 | . | A | B | . | . | . | . | 1.03 | −0.20 | * | * | . | 0.30 | 0.65 |
| Leu | 163 | . | A | B | . | . | . | . | 0.79 | −0.20 | * | * | . | 0.30 | 0.65 |
| Ala | 164 | . | A | B | . | . | . | . | 0.38 | 0.30 | * | * | . | −0.30 | 0.80 |
| Pro | 165 | A | A | . | . | . | . | . | −0.54 | 0.00 | . | * | F | −0.15 | 0.78 |
| Arg | 166 | A | A | . | . | . | . | . | −0.54 | 0.19 | * | * | F | −0.15 | 0.78 |
| Ala | 167 | A | A | . | . | . | . | . | −1.10 | 0.19 | . | * | . | 0.30 | 0.64 |
| Ser | 168 | A | A | . | . | . | . | . | −0.88 | 0.19 | . | * | . | −0.30 | 0.42 |
| Leu | 169 | A | A | . | . | . | . | . | −1.10 | 0.26 | . | * | . | −0.30 | 0.22 |
| Leu | 170 | A | A | . | . | . | . | . | −1.70 | 0.94 | . | * | . | −0.60 | 0.18 |
| Ala | 171 | A | A | . | . | . | . | . | −2.51 | 1.13 | . | * | . | −0.60 | 0.11 |
| Ala | 172 | A | A | . | B | . | . | . | −2.51 | 1.53 | . | . | . | −0.60 | 0.11 |
| Leu | 173 | A | A | . | B | . | . | . | 3.07 | 1.34 | . | . | . | −0.60 | 0.14 |
| Leu | 174 | A | A | . | B | . | . | . | 2.29 | 1.30 | . | . | . | −0.60 | 0.10 |
| Phe | 175 | A | A | . | B | . | . | . | −1.69 | 1.30 | . | . | . | −0.60 | 0.14 |
| Ala | 176 | A | A | . | B | . | . | . | −1.96 | 1.23 | . | . | . | −0.60 | 0.26 |
| Val | 177 | A | A | . | B | . | . | . | −1.40 | 1.19 | . | . | . | −0.60 | 0.23 |
| His | 178 | A | A | . | B | . | . | . | −0.90 | 1.00 | . | . | . | −0.60 | 0.37 |
| Pro | 179 | A | A | . | B | . | . | . | −0.09 | 0.70 | . | . | . | −0.60 | 0.52 |
| Val | 180 | A | A | . | B | . | . | . | −0.06 | 0.20 | . | . | . | −0.15 | 1.22 |
| His | 181 | A | A | . | B | . | . | . | −0.32 | 0.13 | . | . | . | −0.30 | 0.48 |
| Thr | 182 | A | A | . | B | . | . | . | −0.06 | 0.27 | . | . | . | −0.30 | 0.23 |
| Glu | 183 | A | A | B | B | . | . | . | −0.37 | 0.34 | . | . | . | −0.30 | 0.31 |
| Cys | 184 | . | A | B | B | . | . | . | −1.01 | 0.13 | . | . | . | −0.30 | 0.23 |
| Val | 185 | . | . | B | B | . | . | . | −1.01 | 0.27 | . | . | . | −0.30 | 0.12 |
| Ala | 186 | . | . | B | B | . | . | . | −1.32 | 0.43 | * | . | . | −0.60 | 0.05 |
| Gly | 187 | . | . | B | B | . | . | . | −0.90 | 0.86 | * | * | . | −0.60 | 0.09 |
| Val | 188 | . | . | B | B | . | . | . | −1.49 | 0.29 | * | * | . | −0.30 | 0.24 |
| Val | 189 | . | . | B | B | . | . | . | −0.82 | 0.14 | . | * | . | −0.30 | 0.24 |
| Gly | 190 | A | A | . | . | . | . | . | −0.78 | −0.36 | . | * | . | 0.30 | 0.41 |
| Arg | 191 | A | A | . | . | . | . | . | −1.00 | −0.10 | . | * | . | 0.30 | 0.46 |
| Ala | 192 | A | A | . | . | . | . | . | −1.32 | −0.06 | . | * | . | 0.30 | 0.51 |
| Asp | 193 | A | A | . | . | . | . | . | −1.06 | −0.13 | . | * | . | 0.30 | 0.28 |
| Leu | 194 | A | A | . | . | . | . | . | −1.01 | −0.06 | . | * | . | 0.30 | 0.14 |
| Leu | 195 | A | A | . | . | . | . | . | −1.37 | 0.63 | . | * | . | −0.60 | 0.12 |
| Cys | 196 | A | A | . | . | . | . | . | −2.18 | 0.91 | . | * | . | −0.60 | 0.06 |
| Ala | 197 | A | A | . | . | . | . | . | −2.40 | 1.70 | . | . | . | −0.60 | 0.06 |
| Leu | 198 | A | A | . | . | . | . | . | −3.21 | 1.70 | * | . | . | −0.60 | 0.06 |
| Phe | 199 | A | A | . | . | . | . | . | −2.70 | 1.70 | . | . | . | −0.60 | 0.10 |
| Phe | 200 | A | A | . | . | . | . | . | −2.59 | 1.51 | . | . | . | −0.60 | 0.13 |
| Leu | 201 | A | A | . | . | . | . | . | −2.73 | 1.80 | . | . | . | −0.60 | 0.14 |
| Leu | 202 | A | A | . | . | . | . | . | −2.49 | 1.80 | . | . | . | −0.60 | 0.13 |
| Ser | 203 | A | . | . | . | . | . | . | −1.92 | 1.44 | . | . | . | 0.40 | 0.15 |
| Phe | 204 | A | . | . | . | . | . | . | −1.89 | 1.41 | . | . | . | −0.40 | 0.28 |
| Leu | 205 | A | . | . | . | . | T | . | −1.14 | 1.30 | . | * | . | −0.20 | 0.18 |
| Gly | 206 | . | . | . | . | T | T | . | −0.92 | 0.61 | . | . | . | 0.20 | 0.27 |
| Tyr | 207 | . | . | . | . | T | T | . | −0.81 | 0.73 | * | * | . | 0.20 | 0.32 |
| Cys | 208 | A | . | . | . . | . | T | . | −0.40 | 0.73 | * | . | . | −0.20 | 0.33 |
| Lys | 209 | A | A | . | . | . | . | . | 0.30 | 0.04 | * | . | . | −0.30 | 0.66 |
| Ala | 210 | A | A | . | . | . | . | . | 0.81 | −0.39 | * | . | . | 0.30 | 0.73 |
| Phe | 211 | A | A | . | . | . | . | . | 1.16 | −0.76 | * | . | . | 0.75 | 1.82 |
| Arg | 212 | A | A | . | . | . | . | . | 1.44 | −0.93 | * | . | F | 0.90 | 1.47 |
| Glu | 213 | A | A | . | . | . | . | . | 2.11 | −0.93 | * | . | F | 0.90 | 2.90 |
| Ser | 214 | A | A | . | . | . | . | . | 1.72 | −1.43 | * | . | F | 0.90 | 5.80 |
| Asn | 215 | A | . | . | . | . | T | . | 1.72 | −1.79 | * | . | F | 1.30 | 2.93 |
| Lys | 216 | A | . | . | . | . | T | . | 2.39 | −1.29 | * | * | F | 1.30 | 1.71 |
| Glu | 217 | A | . | . | . | . | T | . | 1.98 | −0.79 | * | . | F | 1.30 | 1.74 |
| Gly | 218 | A | . | . | . | . | T | . | 1.68 | −0.79 | . | . | F | 1.30 | 1.45 |
| Ala | 219 | A | . | . | . | . | . | . | 1.67 | −0.80 | . | . | F | 0.95 | 0.97 |
| His | 220 | . | . | . | . | . | T | C | 0.97 | −0.31 | . | . | F | 1.05 | 0.81 |
| Ser | 221 | . | . | . | . | . | T | C | 0.63 | 0.47 | . | . | F | 0.15 | 0.71 |
| Ser | 222 | . | . | . | . | . | T | C | −0.22 | 0.96 | . | . | F | 0.15 | 0.74 |
| Thr | 223 | . | . | B | . | . | T | . | −0.69 | 1.10 | . | . | F | −0.05 | 0.40 |
| Phe | 224 | . | . | B | B | . | . | . | −0.91 | 1.29 | . | . | . | −0.60 | 0.25 |
| Trp | 225 | . | . | B | B | . | . | . | −1.18 | 1.59 | . | . | . | −0.60 | 0.15 |
| Val | 226 | . | . | B | B | . | . | . | −1.77 | 1.59 | . | . | . | −0.60 | 0.14 |
| Leu | 227 | . | . | B | B | . | . | . | −2.17 | 1.79 | . | . | . | −0.60 | 0.11 |
| Leu | 228 | . | . | B | B | . | . | . | −2.67 | 1.79 | . | . | . | −0.60 | 0.09 |
| Ser | 229 | . | . | B | B | . | . | . | −2.31 | 1.56 | . | . | . | −0.60 | 0.10 |
| Ile | 230 | A | . | . | B | . | . | . | −2.61 | 1.34 | . | . | . | −0.60 | 0.13 |
| Phe | 231 | A | . | . | B | . | . | . | −2.61 | 1.16 | . | . | . | −0.60 | 0.15 |
| Leu | 232 | A | . | . | B | . | . | . | −2.39 | 1.11 | . | . | . | −0.60 | 0.09 |
| Gly | 233 | A | . | . | B | . | . | . | −2.18 | 1.23 | . | . | . | −0.60 | 0.12 |
| Ala | 234 | A | . | . | B | . | . | . | −2.69 | 1.16 | . | . | . | −0.60 | 0.14 |
| Val | 235 | A | . | . | B | . | . | . | −2.47 | 1.06 | * | . | . | −0.60 | 0.14 |
| Ala | 236 | A | . | . | B | . | . | . | −1.72 | 0.94 | * | . | . | −0.60 | 0.08 |
| Met | 237 | A | . | . | B | . | . | . | −0.91 | 0.51 | . | . | . | −0.60 | 0.15 |

TABLE 7-continued

| Res | Position | I | II | III | IV | V | VI | VII | VIII | IX | X | XI | XII | XIII | XIV |
|---|---|---|---|---|---|---|---|---|---|---|---|---|---|---|---|
| Leu | 238 | A | . | . | B | . | . | . | −0.57 | 0.01 | . | . | . | −0.30 | 0.35 |
| Cys | 239 | A | . | . | B | . | . | . | −0.32 | −0.23 | . | . | . | 0.30 | 0.60 |
| Lys | 240 | A | . | . | B | . | . | . | −0.36 | −0.30 | . | . | F | 0.45 | 0.60 |
| Glu | 241 | A | . | . | . | . | . | . | −0.08 | −0.23 | . | . | F | 0.65 | 0.51 |
| Gln | 242 | A | . | . | B | . | . | . | −0.33 | −0.43 | . | . | F | 0.60 | 1.38 |
| Gly | 243 | . | . | B | B | . | . | . | −0.33 | −0.36 | . | . | F | 0.45 | 0.51 |
| Ile | 244 | . | . | B | B | . | . | . | −0.01 | 0.33 | . | . | F | −0.15 | 0.24 |
| Thr | 245 | . | . | B | B | . | . | . | −0.87 | 0.76 | . | . | . | −0.60 | 0.14 |
| Val | 246 | . | . | B | B | . | . | . | −0.87 | 1.04 | . | . | . | −0.60 | 0.12 |
| Leu | 247 | . | . | B | B | . | . | . | −1.46 | 1.01 | . | . | . | −0.60 | 0.27 |
| Gly | 248 | . | . | B | B | . | . | . | −1.97 | 0.83 | . | . | . | −0.60 | 0.19 |
| Leu | 249 | . | . | B | B | . | . | . | −1.78 | 0.99 | . | * | . | −0.60 | 0.19 |
| Asn | 250 | . | . | B | B | . | . | . | −1.47 | 1.13 | . | * | . | −0.60 | 0.20 |
| Ala | 251 | A | . | . | B | . | . | . | −1.50 | 0.44 | * | * | . | 0.60 | 0.33 |
| Val | 252 | A | . | . | B | . | . | . | −1.50 | 0.70 | * | * | . | −0.60 | 0.28 |
| Phe | 253 | . | . | B | B | . | . | . | −2.01 | 0.70 | * | * | . | −0.60 | 0.14 |
| Asp | 254 | . | . | B | B | . | . | . | −2.09 | 0.94 | * | * | . | −0.60 | 0.11 |
| Ile | 255 | . | . | B | B | . | . | . | −2.43 | 1.13 | * | * | . | −0.60 | 0.10 |
| Leu | 256 | . | . | B | B | . | . | . | −1.80 | 0.91 | . | * | . | −0.60 | 0.11 |
| Val | 257 | . | . | B | B | . | . | . | −1.64 | 0.13 | . | * | . | −0.30 | 0.14 |
| Ile | 258 | A | . | . | B | . | . | . | −0.94 | 0.91 | . | * | . | −0.60 | 0.17 |
| Gly | 259 | A | . | . | B | . | . | . | −1.80 | 0.63 | . | * | . | −0.60 | 0.33 |
| Lys | 260 | A | . | . | B | . | . | . | −1.72 | 0.59 | . | * | . | −0.60 | 0.33 |
| Phe | 261 | A | . | . | B | . | . | . | −0.91 | 0.63 | . | . | . | −0.60 | 0.39 |
| Asn | 262 | A | . | . | B | . | . | . | −0.94 | −0.06 | . | * | . | 0.30 | 0.68 |
| Val | 263 | A | . | . | B | . | . | . | −0.44 | 0.20 | . | . | . | −0.30 | 0.24 |
| Leu | 264 | A | . | . | B | . | . | . | −0.10 | 0.63 | . | * | . | −0.60 | 0.35 |
| Glu | 265 | A | . | . | B | . | . | . | −0.10 | 0.24 | * | * | . | −0.30 | 0.38 |
| Ile | 266 | A | . | . | B | . | . | . | −0.26 | −0.16 | * | . | F | 0.60 | 1.02 |
| Xxx | 267 | A | . | . | B | . | . | . | −1.07 | −0.16 | * | . | F | 0.45 | 0.91 |
| Gln | 268 | A | . | . | B | . | . | . | −0.24 | −0.16 | * | * | F | 0.45 | 0.44 |
| Lys | 269 | A | . | . | B | . | . | . | 0.61 | 0.34 | * | * | F | −0.15 | 0.85 |
| Val | 270 | A | . | . | B | . | . | . | 0.61 | −0.34 | * | * | F | 0.60 | 1.32 |
| Leu | 271 | A | . | . | B | . | . | . | 1.54 | −0.77 | * | * | . | 0.75 | 1.28 |
| His | 272 | A | . | . | B | . | . | . | 1.63 | −1.17 | * | . | . | 0.75 | 1.28 |
| Lys | 273 | A | . | . | B | . | . | . | 0.82 | −0.79 | * | . | F | 0.90 | 2.30 |
| Asp | 274 | A | . | . | . | . | T | . | 0.78 | −0.74 | * | . | F | 1.30 | 2.30 |
| Lys | 275 | A | . | . | . | . | T | . | 1.63 | −1.43 | * | . | F | 1.30 | 2.93 |
| Ser | 276 | A | . | . | . | . | T | . | 1.63 | −1.53 | . | . | F | 1.30 | 2.36 |
| Leu | 277 | A | . | . | . | . | T | . | 1.32 | −0.84 | . | . | F | 1.30 | 1.16 |
| Glu | 278 | A | A | . | . | . | . | . | 0.68 | −0.41 | . | . | F | 0.45 | 0.58 |
| Asn | 279 | A | A | . | . | . | . | . | −0.13 | 0.20 | . | . | . | −0.30 | 0.43 |
| Leu | 280 | A | A | . | . | . | . | . | −0.07 | 0.50 | . | . | . | −0.60 | 0.43 |
| Gly | 281 | A | A | . | . | . | . | . | 0.23 | −0.19 | . | . | . | 0.30 | 0.48 |
| Met | 282 | . | A | B | . | . | . | . | 0.70 | 0.21 | . | . | . | −0.30 | 0.48 |
| Leu | 283 | . | . | B | . | . | T | . | 0.36 | 0.24 | . | . | . | 0.10 | 0.58 |
| Arg | 284 | . | . | B | . | . | T | . | −0.46 | −0.01 | . | . | F | 0.85 | 0.58 |
| Asn | 285 | . | . | . | . | T | T | . | −0.46 | 0.24 | * | . | F | 0.65 | 0.48 |
| Gly | 286 | . | . | . | . | T | T | . | −0.81 | 0.31 | * | * | F | 0.65 | 0.48 |
| Gly | 287 | . | . | . | B | . | . | C | −0.10 | 0.41 | * | * | F | −0.25 | 0.21 |
| Leu | 288 | . | . | B | B | . | . | . | 0.11 | 0.41 | * | * | . | −0.60 | 0.26 |
| Leu | 289 | . | . | B | B | . | . | . | −0.31 | 0.63 | * | * | . | −0.60 | 0.26 |
| Phe | 290 | . | . | B | B | . | . | . | −1.12 | 0.69 | . | * | . | −0.60 | 0.38 |
| Arg | 291 | . | . | B | B | . | . | . | −1.59 | 0.94 | . | * | . | −0.60 | 0.38 |
| Met | 292 | . | . | B | B | . | . | . | −1.56 | 0.94 | . | * | . | −0.60 | 0.38 |
| Thr | 293 | . | . | B | B | . | . | . | −1.04 | 0.74 | . | * | . | −0.60 | 0.63 |
| Leu | 294 | . | . | B | B | . | . | . | −0.58 | 0.34 | . | * | . | −0.30 | 0.43 |
| Leu | 295 | . | . | B | B | . | . | . | −0.22 | 0.77 | . | * | F | −0.45 | 0.43 |
| Thr | 296 | . | . | . | . | . | T | C | −0.92 | 0.59 | . | * | F | 0.15 | 0.30 |
| Ser | 297 | . | . | . | . | . | T | C | −0.67 | 0.60 | . | . | F | 0.15 | 0.36 |
| Gly | 298 | . | . | . | . | . | T | C | −0.96 | 0.34 | . | . | F | 0.45 | 0.43 |
| Gly | 299 | . | . | . | . | . | T | C | −0.96 | 0.27 | . | . | F | 0.45 | 0.30 |
| Ala | 300 | . | . | . | . | . | . | C | −0.39 | 0.47 | . | . | F | −0.05 | 0.18 |
| Gly | 301 | . | . | B | B | . | . | . | −0.93 | 0.84 | . | * | . | −0.60 | 0.29 |
| Met | 302 | . | . | B | B | . | . | . | −0.52 | 1.06 | . | * | . | −0.60 | 0.22 |
| Leu | 303 | . | . | B | B | . | . | . | −0.47 | 0.63 | . | * | . | −0.60 | 0.42 |
| Tyr | 304 | . | . | B | B | . | . | . | −0.01 | 1.04 | . | * | . | −0.60 | 0.45 |
| Val | 305 | . | . | B | B | . | . | . | −0.31 | 0.61 | . | * | . | −0.60 | 0.89 |
| Arg | 306 | . | . | B | B | . | . | . | −0.57 | 0.69 | . | * | . | −0.60 | 0.75 |
| Trp | 307 | . | . | B | B | . | . | . | −0.31 | 0.61 | . | * | . | −0.60 | 0.48 |
| Arg | 308 | . | . | B | B | . | . | . | 0.19 | 0.29 | . | * | . | −0.30 | 0.63 |
| Ile | 309 | . | . | B | B | . | . | . | 0.09 | 0.13 | . | * | . | −0.30 | 0.47 |
| Met | 310 | . | . | B | B | . | . | . | 0.73 | 0.56 | . | * | . | −0.60 | 0.44 |
| Gly | 311 | . | . | . | . | T | . | . | 0.23 | 0.07 | . | * | . | 0.30 | 0.35 |
| Thr | 312 | . | . | . | . | . | . | C | −0.07 | 0.50 | * | * | F | −0.05 | 0.63 |
| Gly | 313 | . | . | . | . | . | T | C | −0.88 | 0.31 | * | * | F | 0.45 | 0.65 |
| Pro | 314 | . | . | . | . | . | T | C | −0.30 | 0.49 | * | . | F | 0.15 | 0.57 |

TABLE 7-continued

| Res | Position | I | II | III | IV | V | VI | VII | VIII | IX | X | XI | XII | XIII | XIV |
|---|---|---|---|---|---|---|---|---|---|---|---|---|---|---|---|
| Xxx | 315 | . | . | . | . | . | T | C | 0.30 | 0.54 | * | . | F | 0.15 | 0.57 |
| Ala | 316 | . | . | B | . | . | T | . | −0.21 | 0.06 | . | . | . | 0.10 | 0.99 |
| Phe | 317 | . | . | B | . | . | . | . | 0.10 | 0.27 | * | . | . | −0.10 | 0.48 |
| Thr | 318 | . | . | B | . | . | . | . | 0.44 | −0.16 | * | . | . | 0.77 | 0.62 |
| Glu | 319 | . | . | B | . | . | . | . | 0.44 | −0.19 | * | . | F | 1.19 | 0.99 |
| Val | 320 | . | . | B | . | . | . | . | 0.24 | −0.26 | * | . | F | 1.61 | 1.77 |
| Asp | 321 | . | . | . | . | . | . | C | 0.53 | −0.54 | * | * | F | 2.38 | 1.24 |
| Asn | 322 | . | . | . | . | . | T | C | 0.53 | −0.64 | * | . | F | 2.70 | 0.96 |
| Pro | 323 | A | . | . | . | . | T | . | 0.26 | 0.14 | * | . | F | 1.48 | 1.12 |
| Ala | 324 | A | . | . | . | . | T | . | 0.26 | −0.00 | * | . | F | 1.66 | 0.68 |
| Ser | 325 | A | . | . | . | . | T | . | 0.81 | −0.00 | * | . | . | 1.24 | 0.70 |
| Phe | 326 | A | . | . | . | . | . | . | 0.21 | −0.01* | . | . | 0.77 | 0.61 | |
| Ala | 327 | A | . | . | . | . | . | . | −0.60 | 0.17 | . | . | . | −0.10 | 0.60 |
| Asp | 328 | A | . | . | . | . | . | . | −1.24 | 0.36 | * | * | . | −0.10 | 0.37 |
| Ser | 329 | A | . | . | B | . | . | . | −0.54 | 0.61 | * | * | . | −0.60 | 0.31 |
| Met | 330 | A | . | . | B | . | . | . | −0.83 | −0.17 | * | . | . | 0.30 | 0.61 |
| Leu | 331 | A | . | . | B | . | . | . | −0.99 | −0.17 | * | . | . | 0.30 | 0.37 |
| Val | 332 | . | . | B | B | . | . | . | −0.40 | 0.47 | * | . | . | −0.60 | 0.20 |
| Arg | 333 | . | . | B | B | . | . | . | −0.64 | 0.49 | * | . | . | −0.60 | 0.33 |
| Ala | 334 | . | . | B | B | . | . | . | −0.34 | 0.63 | * | . | . | −0.60 | 0.63 |
| Val | 335 | . | . | B | B | . | . | . | 0.01 | 0.34 | * | . | . | −0.15 | 1.36 |
| Asn | 336 | . | . | B | . | . | T | . | 0.58 | 0.46 | * | . | . | −0.05 | 1.09 |
| Tyr | 337 | . | . | B | . | . | T | . | 1.19 | 1.21 | * | . | . | −0.05 | 1.69 |
| Asn | 338 | . | . | B | . | . | T | . | 0.78 | 1.47 | . | * | . | −0.05 | 3.57 |
| Tyr | 339 | . | . | B | . | . | T | . | 0.56 | 1.21 | . | * | . | −0.05 | 2.98 |
| Tyr | 340 | . | . | B | . | . | . | . | 1.41 | 1.50 | . | * | . | −0.25 | 1.57 |
| Tyr | 341 | . | . | B | . | . | . | . | 0.82 | 1.14 | . | * | . | −0.25 | 1.57 |
| Ser | 342 | . | A | B | . | . | . | . | 0.78 | 1.24 | . | * | . | −0.45 | 1.01 |
| Leu | 343 | . | A | B | . | . | . | . | −0.03 | 1.40 | . | * | . | −0.60 | 0.68 |
| Asn | 344 | . | A | B | . | . | . | . | −0.60 | 1.33 | . | * | . | −0.60 | 0.36 |
| Ala | 345 | . | A | B | . | . | . | . | −1.17 | 1.26 | . | . | . | −0.60 | 0.22 |
| Trp | 346 | . | A | B | . | . | . | . | −1.59 | 1.56 | . | * | . | −0.60 | 0.22 |
| Leu | 347 | . | A | B | . | . | . | . | −1.50 | 1.44 | . | . | . | −0.60 | 0.07 |
| Leu | 348 | . | A | B | . | . | . | . | −0.98 | 1.47 | . | . | . | −0.60 | 0.11 |
| Leu | 349 | . | A | B | . | . | . | . | −1.27 | 1.89 | . | . | . | −0.60 | 0.11 |
| Cys | 350 | . | . | B | . | . | T | . | −1.49 | 1.89 | . | . | . | −0.20 | 0.14 |
| Pro | 351 | . | . | . | . | T | T | . | −1.87 | 1.89 | . | . | . | 0.20 | 0.14 |
| Trp | 352 | . | . | . | . | T | T | . | −1.76 | 1.77 | . | . | . | 0.20 | 0.09 |
| Trp | 353 | . | . | B | . | . | T | . | −0.94 | 1.87 | . | * | . | −0.20 | 0.15 |
| Leu | 354 | . | . | B | . | . | . | . | −0.42 | 1.30 | . | * | . | −0.40 | 0.16 |
| Cys | 355 | . | . | . | . | T | T | . | −0.06 | 1.79 | . | * | . | 0.20 | 0.16 |
| Phe | 356 | . | . | . | . | T | T | . | −0.44 | 1.26 | . | * | . | 0.20 | 0.21 |
| Asp | 357 | . | . | . | . | T | T | . | −0.50 | 0.96 | . | * | . | 0.20 | 0.25 |
| Trp | 358 | . | . | . | . | T | T | . | −0.88 | 0.70 | . | * | . | 0.20 | 0.46 |
| Ser | 359 | . | . | . | . | T | T | . | −0.96 | 0.70 | . | * | . | 0.20 | 0.28 |
| Met | 360 | . | . | . | . | T | T | . | −0.50 | 0.60 | . | * | . | 0.20 | 0.12 |
| Gly | 361 | . | . | . | . | T | T | . | −0.61 | 1.03 | . | . | . | 0.20 | 0.17 |
| Cys | 362 | . | . | B | . | . | T | . | −1.50 | 0.80 | * | . | . | −0.20 | 0.11 |
| Ile | 363 | . | . | B | B | . | . | . | −1.17 | 1.10 | . | . | . | −0.60 | 0.08 |
| Pro | 364 | . | . | B | B | . | . | . | −1.17 | 0.49 | * | . | . | −0.60 | 0.15 |
| Leu | 365 | . | . | B | B | . | . | . | −1.46 | 0.44 | * | . | . | −0.60 | 0.38 |
| Ile | 366 | . | . | B | B | . | . | . | −1.41 | 0.56 | * | . | . | −0.60 | 0.38 |
| Lys | 367 | . | . | B | B | . | . | . | −0.74 | 0.26 | * | . | F | −0.15 | 0.33 |
| Ser | 368 | . | . | B | B | . | . | . | −0.14 | −0.17 | * | * | F | 0.45 | 0.68 |
| Ile | 369 | . | . | . | B | T | . | . | 0.18 | 0.06 | * | * | F | 0.40 | 1.01 |
| Ser | 370 | . | . | B | B | . | . | . | 0.13 | −0.63 | * | * | F | 0.75 | 0.99 |
| Asp | 371 | . | . | . | B | T | . | . | 0.13 | 0.01 | . | * | F | 0.25 | 0.55 |
| Trp | 372 | . | . | B | B | . | . | . | −0.50 | 0.31 | . | * | . | −0.30 | 0.55 |
| Arg | 373 | . | A | B | . | . | . | . | −1.01 | 0.13 | . | . | . | −0.30 | 0.41 |
| Val | 374 | . | A | B | . | . | . | . | −0.71 | 0.43 | . | . | . | −0.60 | 0.20 |
| Ile | 375 | . | A | B | . | . | . | . | −1.00 | 0.93 | . | * | . | −0.60 | 0.20 |
| Ala | 376 | A | A | . | . | . | . | . | −1.81 | 0.51 | . | * | . | −0.60 | 0.10 |
| Leu | 377 | A | A | . | . | . | . | . | −1.81 | 1.20 | * | * | . | −0.60 | 0.11 |
| Ala | 378 | A | A | . | . | . | . | . | −2.62 | 1.47 | * | . | . | −0.60 | 0.17 |
| Ala | 379 | A | A | . | . | . | . | . | −2.43 | 1.57 | . | . | . | −0.60 | 0.14 |
| Leu | 380 | A | A | . | . | . | . | . | −2.36 | 1.64 | . | . | . | −0.60 | 0.09 |
| Trp | 381 | A | A | . | . | . | . | . | −2.66 | 1.64 | . | . | . | −0.60 | 0.08 |
| Phe | 382 | A | A | . | . | . | . | . | −2.19 | 1.83 | . | . | . | −0.60 | 0.05 |
| Cys | 383 | A | A | . | . | . | . | . | −2.41 | 1.76 | . | . | . | −0.60 | 0.06 |
| Leu | 384 | A | A | . | . | . | . | . | −2.71 | 1.76 | . | . | . | −0.60 | 0.05 |
| Ile | 385 | . | A | B | . | . | . | . | −2.57 | 1.53 | * | . | . | −0.60 | 0.04 |
| Gly | 386 | . | A | . | . | T | . | . | −2.28 | 1.31 | * | . | . | −0.20 | 0.04 |
| Leu | 387 | . | A | . | . | T | . | . | −2.17 | 1.14 | * | . | . | −0.20 | 0.09 |
| Ile | 388 | . | A | B | . | . | . | . | −2.31 | 0.96 | * | . | . | −0.60 | 0.12 |
| Cys | 389 | . | A | B | . | . | . | . | −2.17 | 0.96 | * | . | . | −0.60 | 0.10 |
| Gln | 390 | . | A | B | . | . | . | . | −1.58 | 1.10 | . | . | . | −0.60 | 0.07 |
| Ala | 391 | . | A | B | . | . | . | . | −1.23 | 0.80 | . | . | . | −0.60 | 0.13 |

TABLE 7-continued

| Res | Position | I | II | III | IV | V | VI | VII | VIII | IX | X | XI | XII | XIII | XIV |
|---|---|---|---|---|---|---|---|---|---|---|---|---|---|---|---|
| Leu | 392 | . | A | B | . | . | . | . | −0.42 | 0.11 | . | . | . | −0.30 | 0.41 |
| Cys | 393 | A | A | . | . | . | . | . | 0.12 | −0.46 | . | . | . | 0.30 | 0.40 |
| Ser | 394 | A | . | . | . | . | T | . | 0.76 | −0.43 | . | . | F | 0.85 | 0.39 |
| Glu | 395 | A | . | . | . | . | T | . | 0.80 | −0.43 | . | . | F | 0.85 | 0.64 |
| Asp | 396 | A | . | . | . | . | T | . | 1.50 | −1.11 | . | . | F | 1.30 | 2.39 |
| Gly | 397 | A | . | . | . | . | T | . | 2.42 | −1.69 | . | . | F | 1.30 | 3.50 |
| His | 398 | A | . | . | . | . | . | . | 2.20 | −2.07 | . | . | F | 1.10 | 3.95 |
| Lys | 399 | A | . | . | B | . | . | . | 1.69 | −1.39 | . | . | F | 0.90 | 1.66 |
| Arg | 400 | . | . | B | B | . | . | . | 1.38 | −0.70 | . | . | F | 0.90 | 1.38 |
| Arg | 401 | . | . | B | B | . | . | . | 0.57 | −0.64 | * | . | . | 0.75 | 1.47 |
| Ile | 402 | . | . | B | B | . | . | . | 0.57 | −0.46 | * | . | . | 0.30 | 0.61 |
| Leu | 403 | . | . | B | B | . | . | . | −0.21 | −0.03 | * | . | . | 0.30 | 0.31 |
| Thr | 404 | . | . | B | B | . | . | . | −0.60 | 0.66 | * | . | . | −0.60 | 0.13 |
| Leu | 405 | . | . | B | B | . | . | . | −1.41 | 1.09 | * | . | . | −0.60 | 0.18 |
| Gly | 406 | . | . | B | B | . | . | . | −2.33 | 1.19 | * | * | . | −0.60 | 0.19 |
| Leu | 407 | . | . | B | B | . | . | . | −2.30 | 1.19 | . | . | . | −0.60 | 0.11 |
| Gly | 408 | . | . | B | B | . | . | . | −2.38 | 1.34 | . | . | . | −0.60 | 0.10 |
| Phe | 409 | . | . | B | B | . | . | . | −2.28 | 1.34 | . | . | . | −0.60 | 0.07 |
| Leu | 410 | . | . | B | B | . | . | . | −2.17 | 1.34 | . | . | . | −0.60 | 0.13 |
| Val | 411 | . | . | B | B | . | . | . | −2.63 | 1.44 | . | . | . | −0.60 | 0.11 |
| Ile | 412 | . | . | B | B | . | . | . | −2.03 | 1.70 | . | . | . | −0.60 | 0.11 |
| Pro | 413 | . | . | B | . | . | . | . | −2.28 | 1.34 | . | . | . | −0.40 | 0.20 |
| Phe | 414 | . | . | B | . | . | . | . | −1.88 | 1.16 | . | . | . | −0.40 | 0.28 |
| Leu | 415 | . | . | B | . | . | . | . | −1.07 | 0.90 | . | . | . | −0.40 | 0.53 |
| Pro | 416 | . | . | . | . | . | . | C | −1.02 | 0.61 | . | . | . | −0.20 | 0.55 |
| Ala | 417 | . | . | . | . | T | T | . | −0.83 | 0.87 | . | . | . | 0.20 | 0.52 |
| Ser | 418 | . | . | . | . | . | T | C | −1.32 | 0.87 | * | * | . | 0.00 | 0.55 |
| Asn | 419 | A | . | . | . | . | T | . | −0.51 | 0.97 | * | * | . | −0.20 | 0.31 |
| Leu | 420 | . | . | B | . | . | T | . | −0.56 | 0.54 | * | * | . | −0.20 | 0.60 |
| Phe | 421 | . | . | B | B | . | . | . | −0.69 | 0.69 | * | * | . | −0.60 | 0.33 |
| Phe | 422 | . | . | B | B | . | . | . | −0.80 | 0.73 | * | * | . | −0.60 | 0.20 |
| Arg | 423 | . | . | B | B | . | . | . | −1.36 | 1.11 | * | * | . | −0.60 | 0.21 |
| Val | 424 | . | . | B | B | . | . | . | −2.21 | 1.07 | * | * | . | −0.60 | 0.18 |
| Gly | 425 | . | . | B | B | . | . | . | −1.99 | 0.93 | * | * | . | −0.60 | 0.16 |
| Phe | 426 | . | . | B | B | . | . | . | −1.29 | 0.64 | * | * | . | −0.60 | 0.08 |
| Val | 427 | A | . | . | B | . | . | . | −0.48 | 0.64 | * | * | . | −0.60 | 0.19 |
| Val | 428 | A | . | . | B | . | . | . | −1.44 | −0.00 | * | * | . | 0.30 | 0.37 |
| Ala | 429 | A | . | . | B | . | . | . | −1.40 | 0.21 | * | . | . | −0.30 | 0.32 |
| Glu | 430 | A | . | . | B | . | . | . | −1.30 | 0.11 | * | . | . | −0.30 | 0.36 |
| Arg | 431 | . | . | B | B | . | . | . | −1.41 | 0.23 | * | . | . | −0.30 | 0.75 |
| Val | 432 | . | . | B | B | . | . | . | −0.77 | 0.27 | * | . | . | −0.30 | 0.62 |
| Leu | 433 | . | . | B | B | . | . | . | −0.21 | 0.20 | * | . | . | −0.30 | 0.55 |
| Tyr | 434 | . | . | B | B | . | . | . | −0.01 | 0.59 | * | . | . | −0.60 | 0.38 |
| Leu | 435 | . | . | B | B | . | . | . | −0.36 | 1.01 | * | . | . | −0.60 | 0.65 |
| Pro | 436 | . | . | . | B | T | . | . | −0.71 | 0.80 | * | . | F | −0.05 | 0.78 |
| Ser | 437 | . | . | . | . | T | T | . | −0.52 | 0.87 | . | . | F | 0.35 | 0.78 |
| Xxx | 438 | . | . | . | . | T | T | . | −0.57 | 0.69 | . | . | F | 0.35 | 0.50 |
| Gly | 439 | . | . | B | . | . | T | . | −1.13 | 0.64 | . | . | F | −0.05 | 0.24 |
| Tyr | 440 | . | . | B | . | . | T | . | −1.13 | 0.90 | . | . | . | −0.20 | 0.15 |
| Cys | 441 | . | . | B | B | . | . | . | −1.23 | 1.20 | . | . | . | −0.60 | 0.10 |
| Val | 442 | . | . | B | B | . | . | . | −1.63 | 1.26 | . | . | . | −0.60 | 0.14 |
| Leu | 443 | . | . | B | B | . | . | . | −1.59 | 1.61 | . | . | . | −0.60 | 0.08 |
| Leu | 444 | . | . | B | B | . | . | . | −1.94 | 1.29 | . | . | . | −0.60 | 0.14 |
| Thr | 445 | . | . | B | B | . | . | . | −2.04 | 1.50 | . | * | . | −0.60 | 0.17 |
| Phe | 446 | . | . | B | B | . | . | . | −1.97 | 1.29 | . | . | . | −0.60 | 0.20 |
| Gly | 447 | A | . | . | B | . | . | . | −1.92 | 1.10 | . | . | . | −0.60 | 0.25 |
| Phe | 448 | A | . | . | B | . | . | . | −1.41 | 1.10 | * | . | . | −0.60 | 0.14 |
| Gly | 449 | A | . | . | . | . | . | . | −0.56 | 1.00 | . | . | . | −0.40 | 0.22 |
| Ala | 450 | A | . | . | . | . | . | . | −0.28 | 0.21 | . | . | . | −0.10 | 0.44 |
| Leu | 451 | A | . | . | . | . | . | . | 0.11 | 0.29 | * | . | . | −0.10 | 0.69 |
| Ser | 452 | A | . | . | . | . | T | . | 0.50 | −0.01 | * | . | F | 1.00 | 1.01 |
| Lys | 453 | A | . | . | . | . | T | . | 1.24 | −0.44 | * | . | F | 1.00 | 1.99 |
| His | 454 | A | . | . | . | . | T | . | 1.63 | −0.94 | . | . | F | 1.30 | 4.83 |
| Thr | 455 | A | . | . | . | . | T | . | 2.27 | −1.63 | . | . | F | 1.30 | 7.20 |
| Lys | 456 | A | A | . | . | . | . | . | 2.27 | −2.01 | . | . | F | 0.90 | 7.20 |
| Lys | 457 | A | A | . | . | . | . | . | 1.68 | −1.33 | . | . | F | 0.90 | 4.36 |
| Lys | 458 | A | A | . | B | . | . | . | 1.04 | −1.14 | . | . | F | 0.90 | 2.12 |
| Lys | 459 | A | A | . | B | . | . | . | 0.49 | −1.13 | . | . | F | 0.90 | 1.07 |
| Leu | 460 | A | A | . | B | . | . | . | −0.06 | −0.63 | . | . | . | 0.60 | 0.54 |
| Ile | 461 | A | A | . | B | . | . | . | −0.96 | 0.01 | . | . | . | −0.30 | 0.20 |
| Ala | 462 | A | A | . | B | . | . | . | −1.81 | 0.66 | . | . | . | −0.60 | 0.07 |
| Ala | 463 | A | A | . | B | . | . | . | −2.20 | 1.34 | * | . | . | −0.60 | 0.07 |
| Val | 464 | A | A | . | B | . | . | . | −3.13 | 1.09 | * | . | . | −0.60 | 0.11 |
| Val | 465 | . | A | B | B | . | . | . | −3.13 | 1.09 | . | . | . | −0.60 | 0.07 |
| Leu | 466 | . | A | B | B | . | . | . | −2.94 | 1.27 | . | . | . | −0.60 | 0.06 |

TABLE 7-continued

| Res | Position | I | II | III | IV | V | VI | VII | VIII | IX | X | XI | XII | XIII | XIV |
|---|---|---|---|---|---|---|---|---|---|---|---|---|---|---|---|
| Gly | 467 | . | A | B | B | . | . | . | −3.24 | 1.56 | . | . | . | −0.60 | 0.07 |
| Ile | 468 | . | . | B | B | . | . | . | −2.66 | 1.60 | . | . | . | −0.60 | 0.07 |
| Leu | 469 | . | . | B | B | . | . | . | −2.11 | 1.36 | . | . | . | −0.60 | 0.13 |
| Phe | 470 | . | . | B | B | . | . | . | −2.07 | 1.16 | * | . | . | −0.60 | 0.19 |
| Ile | 471 | . | . | B | B | . | . | . | −1.14 | 1.41 | * | * | . | −0.60 | 0.22 |
| Asn | 472 | . | . | B | B | . | . | . | −1.47 | 0.73 | * | . | . | −0.60 | 0.52 |
| Thr | 473 | . | . | B | B | . | . | . | −1.43 | 0.61 | * | * | . | −0.60 | 0.32 |
| Leu | 474 | . | . | B | B | . | . | . | −1.43 | 0.47 | * | * | . | −0.60 | 0.34 |
| Arg | 475 | . | . | B | B | . | . | . | −0.62 | 0.47 | * | * | . | −0.60 | 0.18 |
| Cys | 476 | . | . | B | B | . | . | . | −0.03 | 0.07 | * | * | . | −0.30 | 0.24 |
| Val | 477 | . | . | B | B | . | . | . | −0.38 | −0.03 | * | * | . | 0.30 | 0.39 |
| Leu | 478 | . | . | B | B | . | . | . | −0.07 | −0.29 | * | * | . | 0.60 | 0.20 |
| Arg | 479 | . | . | B | B | . | . | . | 0.46 | −0.29 | * | * | F | 1.05 | 0.63 |
| Ser | 480 | . | . | . | . | . | T | C | 0.46 | 0.06 | * | * | F | 1.35 | 0.89 |
| Gly | 481 | . | . | . | . | . | T | C | 0.82 | −0.59 | . | * | F | 2.70 | 2.12 |
| Glu | 482 | . | . | . | . | . | T | C | 1.68 | −0.89 | * | * | F | 3.00 | 1.45 |
| Trp | 483 | . | . | . | . | . | T | C | 2.49 | −0.89 | . | * | F | 2.70 | 1.88 |
| Arg | 484 | A | A | . | . | . | . | . | 2.38 | −1.27 | . | * | F | 1.80 | 3.29 |
| Ser | 485 | A | A | . | . | . | . | . | 1.87 | −1.30 | * | * | F | 1.50 | 3.29 |
| Glu | 486 | A | A | . | . | . | . | . | 1.51 | −0.61 | * | * | F | 1.20 | 2.58 |
| Glu | 487 | A | A | . | . | . | . | . | 1.62 | −0.74 | * | * | F | 0.90 | 1.14 |
| Gln | 488 | A | A | . | . | . | . | . | 1.61 | −0.74 | * | * | F | 0.90 | 1.67 |
| Leu | 489 | A | A | . | . | . | . | . | 0.91 | −0.74 | * | * | F | 0.90 | 1.29 |
| Phe | 490 | A | A | . | . | . | . | . | 0.40 | −0.24 | * | . | . | 0.30 | 0.75 |
| Arg | 491 | A | A | . | . | . | . | . | 0.10 | 0.44 | * | * | . | 0.60 | 0.36 |
| Ser | 492 | A | A | . | . | . | . | . | −0.76 | 0.43 | * | * | . | −0.60 | 0.58 |
| Ala | 493 | A | A | . | . | . | . | . | −1.42 | 0.39 | * | * | . | −0.30 | 0.50 |
| Leu | 494 | . | A | B | . | . | . | . | −0.82 | 0.17 | * | * | . | −0.30 | 0.14 |
| Ser | 495 | . | A | B | . | . | . | . | −0.93 | 0.60 | . | * | . | −0.60 | 0.16 |
| Val | 496 | . | . | B | . | . | . | . | −1.04 | 0.90 | . | * | . | −0.40 | 0.13 |
| Cys | 497 | . | . | B | . | . | T | . | −1.33 | 0.80 | . | * | . | −0.20 | 0.25 |
| Pro | 498 | A | . | . | . | . | T | . | −0.70 | 0.61 | . | * | . | −0.20 | 0.19 |
| Leu | 499 | A | . | . | . | . | T | . | −0.74 | 0.23 | . | * | . | 0.10 | 0.51 |
| Asn | 500 | A | . | . | . | . | T | . | −0.48 | 0.23 | . | * | . | 0.10 | 0.70 |
| Ala | 501 | A | . | . | . | . | . | . | 0.13 | 0.16 | . | * | . | −0.10 | 0.62 |
| Lys | 502 | A | . | . | B | . | . | . | 0.80 | 0.49 | . | * | . | −0.45 | 1.18 |
| Val | 503 | . | . | B | B | . | . | . | 0.12 | 0.20 | . | * | . | −0.15 | 1.18 |
| His | 504 | . | . | B | B | . | . | . | 0.59 | 0.49 | * | * | . | −0.60 | 0.82 |
| Tyr | 505 | . | . | B | B | . | . | . | 0.63 | 0.41 | * | * | . | −0.60 | 0.40 |
| Asn | 506 | . | . | B | B | . | . | . | 1.22 | 0.41 | * | * | . | −0.45 | 1.09 |
| Ile | 507 | . | . | B | B | . | . | . | 0.37 | 0.17 | * | * | . | −0.15 | 1.29 |
| Gly | 508 | . | . | B | . | . | T | . | 0.63 | 0.36 | * | * | F | 0.25 | 0.68 |
| Lys | 509 | . | . | B | . | . | T | . | 0.67 | 0.10 | * | . | F | 0.59 | 0.43 |
| Asn | 510 | . | . | B | . | . | T | . | 0.96 | −0.30 | * | . | F | 1.68 | 1.02 |
| Leu | 511 | . | . | B | . | . | T | . | 0.61 | −0.99 | * | . | F | 2.32 | 2.05 |
| Ala | 512 | . | . | B | . | . | . | . | 1.50 | −0.99 | * | . | F | 2.46 | 1.02 |
| Asp | 513 | . | . | . | . | T | T | . | 1.84 | −0.59 | * | . | F | 3.40 | 1.02 |
| Lys | 514 | . | . | . | . | T | T | . | 1.49 | −0.59 | * | . | F | 3.06 | 2.13 |
| Gly | 515 | . | . | . | . | T | T | . | 0.90 | −0.79 | * | . | F | 2.72 | 3.05 |
| Asn | 516 | A | . | . | . | . | T | . | 1.12 | −0.79 | . | . | F | 1.98 | 1.84 |
| Gln | 517 | A | A | . | . | . | . | . | 0.82 | −0.29 | . | * | F | 0.79 | 0.93 |
| Thr | 518 | . | A | B | . | . | . | . | 0.93 | 0.40 | . | * | F | −0.15 | 0.66 |
| Ala | 519 | . | A | B | . | . | . | . | 0.64 | −0.03 | . | * | . | 0.30 | 0.80 |
| Ala | 520 | . | A | B | . | . | . | . | 0.74 | 0.33 | * | * | . | −0.30 | 0.73 |
| Ile | 521 | . | A | B | . | . | . | . | 0.86 | 0.69 | * | . | . | −0.60 | 0.79 |
| Arg | 522 | . | . | B | . | . | . | . | 0.86 | 0.20 | * | . | . | 0.05 | 1.53 |
| Tyr | 523 | . | . | B | . | . | . | . | 0.58 | −0.30 | * | . | . | 0.65 | 2.62 |
| Tyr | 524 | . | A | B | . | . | . | . | 0.31 | −0.30 | * | * | . | 0.45 | 3.78 |
| Arg | 525 | . | A | B | . | . | . | . | 1.01 | −0.34 | * | * | . | 0.45 | 1.43 |
| Glu | 526 | . | A | B | . | . | . | . | 1.09 | −0.34 | * | * | . | 0.45 | 1.79 |
| Ala | 527 | . | A | B | . | . | . | . | 0.98 | −0.41 | * | * | . | 0.30 | 0.94 |
| Val | 528 | . | A | B | . | . | . | . | 1.01 | −0.77 | * | * | . | 0.60 | 0.77 |
| Arg | 529 | . | A | B | . | . | . | . | 1.30 | −0.34 | * | * | . | 0.30 | 0.69 |
| Leu | 530 | A | . | . | . | . | . | . | 0.94 | −0.34 | * | * | . | 0.65 | 1.37 |
| Asn | 531 | . | . | . | . | . | T | C | 0.09 | −0.09 | * | * | . | 1.05 | 2.89 |
| Pro | 532 | A | . | . | . | . | T | . | 0.64 | −0.09 | * | * | F | 1.00 | 1.09 |
| Lys | 533 | A | . | . | . | . | T | . | 0.91 | 0.41 | * | * | . | −0.05 | 1.80 |
| Tyr | 534 | . | . | B | . | . | T | . | 0.20 | 0.23 | * | * | . | 0.25 | 1.13 |
| Val | 535 | . | . | B | . | . | . | . | 1.01 | 0.44 | * | . | . | −0.40 | 0.73 |
| His | 536 | . | . | B | . | . | . | . | 1.01 | 0.41 | * | . | . | −0.40 | 0.58 |
| Ala | 537 | . | . | B | . | . | T | . | 0.41 | 0.81 | * | . | . | −0.20 | 0.60 |
| Met | 538 | . | . | B | . | . | T | . | 0.02 | 0.74 | * | . | . | −0.20 | 0.67 |
| Asn | 539 | A | . | . | . | . | T | . | 0.27 | 0.53 | * | . | . | −0.20 | 0.48 |
| Asn | 540 | A | . | . | . | . | T | . | 0.23 | 0.43 | * | . | . | −0.20 | 0.77 |
| Leu | 541 | A | . | . | . | . | . | . | −0.54 | 0.61 | * | . | . | −0.40 | 0.55 |

TABLE 7-continued

| Res | Position | I | II | III | IV | V | VI | VII | VIII | IX | X | XI | XII | XIII | XIV |
|---|---|---|---|---|---|---|---|---|---|---|---|---|---|---|---|
| Gly | 542 | A | . | . | . | . | . | . | 0.09 | 0.69 | * | . | . | −0.40 | 0.28 |
| Asn | 543 | A | A | . | . | . | . | . | 0.69 | 0.29 | * | * | . | −0.30 | 0.35 |
| Ile | 544 | A | A | . | . | . | . | . | 0.80 | −0.11 | * | . | . | 0.30 | 0.73 |
| Leu | 545 | A | A | . | . | . | . | . | 0.80 | −0.80 | * | * | F | 0.90 | 1.45 |
| Lys | 546 | A | A | . | . | . | . | . | 1.61 | −0.83 | * | * | F | 0.90 | 1.45 |
| Glu | 547 | A | A | . | . | . | . | . | 1.14 | −1.23 | . | * | F | 0.90 | 3.57 |
| Arg | 548 | A | A | . | . | . | . | . | 1.14 | −1.23 | * | * | F | 0.90 | 3.57 |
| Asn | 549 | A | A | . | . | . | . | . | 2.03 | −1.51 | * | * | F | 0.90 | 3.09 |
| Glu | 550 | A | A | . | . | . | . | . | 2.26 | −1.51 | . | * | F | 0.90 | 3.09 |
| Leu | 551 | A | A | . | . | . | . | . | 2.21 | −1.01 | * | * | F | 0.90 | 1.60 |
| Gln | 552 | A | A | . | . | . | . | . | 2.21 | −1.01 | * | * | F | 0.90 | 1.72 |
| Glu | 553 | A | A | . | . | . | . | . | 1.29 | −1.41 | * | * | F | 0.90 | 1.72 |
| Ala | 554 | A | A | . | . | . | . | . | 0.48 | −0.73 | * | . | F | 0.90 | 1.72 |
| Glu | 555 | A | A | . | . | . | . | . | 0.18 | −0.73 | * | . | F | 0.75 | 0.82 |
| Glu | 556 | A | A | . | . | . | . | . | 0.18 | −0.74 | * | . | F | 0.75 | 0.63 |
| Leu | 557 | A | A | . | . | . | . | . | −0.41 | −0.06 | * | . | . | 0.30 | 0.52 |
| Leu | 558 | A | A | . | . | . | . | . | −1.27 | −0.06 | * | * | . | 0.30 | 0.30 |
| Ser | 559 | A | A | . | . | . | . | . | −0.68 | 0.59 | * | * | . | −0.60 | 0.13 |
| Leu | 560 | A | A | . | . | . | . | . | −1.57 | 0.99 | * | * | . | −0.60 | 0.27 |
| Ala | 561 | A | A | . | . | . | . | . | −1.57 | 0.99 | * | * | . | −0.60 | 0.23 |
| Val | 562 | A | A | . | . | . | . | . | −0.97 | 0.70 | * | * | . | −0.60 | 0.30 |
| Gln | 563 | . | A | B | . | . | . | . | −0.16 | 0.74 | * | * | . | −0.60 | 0.56 |
| Ile | 564 | . | A | B | . | . | . | . | −0.56 | 0.06 | . | * | . | −0.30 | 0.92 |
| Gln | 565 | . | . | B | . | . | T | . | −0.33 | 0.34 | . | * | F | 0.40 | 1.08 |
| Pro | 566 | . | . | B | . | . | T | . | −0.33 | 0.20 | . | * | F | 0.25 | 0.63 |
| Asp | 567 | A | . | . | . | . | T | . | −0.07 | 0.30 | . | * | . | 0.10 | 0.91 |
| Phe | 568 | A | . | . | . | . | T | . | −0.36 | 0.11 | . | * | . | 0.10 | 0.53 |
| Ala | 569 | A | A | . | . | . | . | . | −0.07 | 0.63 | . | * | . | −0.60 | 0.36 |
| Ala | 570 | A | A | . | . | . | . | . | −0.07 | 0.81 | . | * | . | −0.60 | 0.21 |
| Ala | 571 | A | A | . | . | . | . | . | −0.67 | 1.21 | * | . | . | −0.60 | 0.40 |
| Trp | 572 | A | A | . | . | . | . | . | −1.01 | 1.11 | . | * | . | −0.60 | 0.32 |
| Met | 573 | A | A | . | . | . | . | . | −1.20 | 1.04 | . | . | . | −0.60 | 0.32 |
| Asn | 574 | A | A | . | B | . | . | . | −1.47 | 1.23 | . | . | . | −0.60 | 0.22 |
| Leu | 575 | A | A | . | B | . | . | . | −0.88 | 1.37 | . | . | . | −0.60 | 0.15 |
| Gly | 576 | . | A | B | B | . | . | . | −0.29 | 0.86 | . | . | . | −0.60 | 0.27 |
| Ile | 577 | . | . | B | B | . | . | . | −0.30 | 0.64 | . | . | . | −0.60 | 0.27 |
| Val | 578 | . | . | B | . | . | T | . | −0.51 | 0.63 | . | * | . | −0.20 | 0.44 |
| Gln | 579 | . | . | B | . | . | T | . | −0.47 | 0.63 | * | . | F | −0.05 | 0.37 |
| Asn | 580 | . | . | B | . | . | T | . | 0.46 | 0.20 | * | . | F | 0.40 | 1.05 |
| Ser | 581 | . | . | . | . | . | T | C | 0.10 | −0.49 | * | . | F | 1.20 | 2.76 |
| Leu | 582 | . | A | . | . | . | . | C | 0.99 | −0.34 | * | . | F | 0.80 | 1.38 |
| Lys | 583 | . | A | . | . | . | . | C | 1.26 | −0.74 | * | . | F | 1.10 | 1.49 |
| Arg | 584 | A | A | . | . | . | . | . | 0.67 | −0.64 | * | . | . | 0.75 | 1.12 |
| Phe | 585 | A | A | . | . | . | . | . | 0.67 | −0.53 | * | . | . | 0.75 | 1.37 |
| Glu | 586 | A | A | . | . | . | . | . | 0.97 | −1.21 | * | . | . | 0.75 | 1.19 |
| Ala | 587 | A | A | . | . | . | . | . | 1.48 | −0.81 | * | . | . | 0.75 | 1.05 |
| Ala | 588 | A | A | . | . | . | . | . | 1.19 | −0.43 | * | * | . | 0.45 | 1.63 |
| Glu | 589 | A | A | . | . | . | . | . | 1.19 | −0.46 | . | * | F | 0.60 | 1.47 |
| Gln | 590 | A | . | . | . | . | T | . | 1.58 | −0.46 | * | . | F | 1.00 | 2.86 |
| Ser | 591 | A | . | . | . | . | T | . | 0.99 | −0.47 | * | * | F | 1.00 | 4.08 |
| Tyr | 592 | A | . | . | . | . | T | . | 0.69 | −0.47 | * | * | F | 1.00 | 2.38 |
| Arg | 593 | A | . | . | . | . | T | . | 1.32 | 0.21 | * | * | F | 0.25 | 0.96 |
| Thr | 594 | A | A | . | B | . | . | . | 1.29 | −0.19 | * | * | . | 0.45 | 1.44 |
| Ala | 595 | A | A | . | B | . | . | . | 1.40 | −0.07 | * | * | . | 0.45 | 1.25 |
| Ile | 596 | A | A | . | B | . | . | . | 1.81 | −0.83 | * | * | . | 1.05 | 1.25 |
| Lys | 597 | . | A | B | B | . | . | . | 2.10 | −0.83 | * | * | . | 1.35 | 1.69 |
| His | 598 | . | A | B | . | . | . | . | 1.74 | −1.31 | * | * | F | 1.80 | 3.35 |
| Arg | 599 | . | A | . | . | T | . | . | 1.84 | −1.06 | * | * | F | 2.50 | 7.50 |
| Arg | 600 | . | . | . | . | T | . | . | 2.43 | −1.31 | * | * | F | 3.00 | 5.80 |
| Lys | 601 | . | . | . | . | T | . | . | 2.66 | −1.31 | * | * | F | 2.70 | 7.12 |
| Tyr | 602 | . | . | B | . | . | T | . | 2.37 | −1.24 | * | . | F | 2.20 | 1.95 |
| Pro | 603 | . | . | . | . | T | T | . | 2.16 | −0.49 | . | . | F | 2.00 | 1.56 |
| Asp | 604 | . | . | . | . | T | T | . | 2.04 | 0.27 | * | * | . | 0.95 | 1.22 |
| Cys | 605 | . | . | B | . | . | T | . | 1.12 | 0.67 | * | . | . | −0.05 | 1.25 |
| Tyr | 606 | . | . | B | . | . | . | . | 0.73 | 0.60 | * | . | . | −0.40 | 0.67 |
| Tyr | 607 | . | . | B | . | . | . | . | 1.09 | 0.60 | * | . | . | −0.40 | 0.40 |
| Asn | 608 | . | . | B | . | . | . | . | 0.49 | 0.60 | * | . | . | −0.25 | 1.45 |
| Leu | 609 | . | . | B | . | . | . | . | 0.24 | 0.71 | * | * | . | −0.40 | 0.76 |
| Gly | 610 | . | . | B | . | . | . | . | 0.32 | 0.71 | * | * | . | −0.40 | 0.76 |
| Arg | 611 | . | A | B | . | . | . | . | 0.57 | 0.46 | * | * | . | −0.60 | 0.48 |
| Leu | 612 | . | A | B | . | . | . | . | −0.00 | 0.06 | * | * | . | −0.30 | 0.97 |
| Tyr | 613 | . | A | B | . | . | . | . | −0.00 | 0.06 | * | * | . | −0.30 | 0.81 |
| Ala | 614 | . | A | B | . | . | . | . | 0.92 | 0.03 | * | * | . | −0.30 | 0.66 |
| Asp | 615 | A | A | . | . | . | . | . | 1.23 | 0.03 | * | * | . | −0.15 | 1.57 |
| Leu | 616 | . | A | B | . | . | . | . | 0.27 | −0.16 | * | * | . | 0.45 | 1.37 |
| Asn | 617 | . | A | B | . | . | . | . | 1.08 | −0.27 | * | * | . | 0.45 | 1.00 |
| Arg | 618 | . | A | B | . | . | . | . | 0.73 | −0.77 | * | . | . | 0.75 | 1.00 |

TABLE 7-continued

| Res | Position | I | II | III | IV | V | VI | VII | VIII | IX | X | XI | XII | XIII | XIV |
|---|---|---|---|---|---|---|---|---|---|---|---|---|---|---|---|
| His | 619 | A | A | . | . | . | . | . | 0.51 | −0.27 | * | . | . | 0.45 | 1.23 |
| Val | 620 | A | A | . | . | . | . | . | 0.51 | −0.27 | * | . | . | 0.30 | 0.63 |
| Asp | 621 | A | A | . | . | . | . | . | 0.73 | −0.27 | * | . | . | 0.30 | 0.52 |
| Ala | 622 | A | A | . | . | . | . | . | 0.44 | 0.23 | * | . | . | −0.30 | 0.38 |
| Leu | 623 | A | A | . | . | . | . | . | 0.44 | 0.64 | * | . | . | −0.60 | 0.54 |
| Asn | 624 | A | A | . | . | . | . | . | 0.48 | −0.00 | * | . | . | 0.30 | 0.64 |
| Ala | 625 | A | A | . | . | . | . | . | 0.74 | 0.40 | * | . | . | −0.15 | 1.02 |
| Trp | 626 | A | A | . | . | . | . | . | 0.43 | 0.40 | * | . | . | −0.15 | 1.25 |
| Arg | 627 | A | A | . | . | . | . | . | 0.17 | 0.20 | * | . | . | −0.15 | 1.12 |
| Asn | 628 | A | A | . | B | . | . | . | 0.17 | 0.44 | . | . | . | −0.60 | 0.82 |
| Ala | 629 | A | A | . | B | . | . | . | 0.21 | 0.63 | * | . | . | −0.60 | 0.64 |
| Thr | 630 | . | A | B | B | . | . | . | 0.59 | −0.29 | . | * | . | 0.30 | 0.66 |
| Val | 631 | . | A | B | B | . | . | . | 0.88 | 0.14 | . | * | . | −0.30 | 0.63 |
| Leu | 632 | . | . | B | B | . | . | . | 0.73 | −0.26 | . | . | . | 0.45 | 1.08 |
| Lys | 633 | . | . | B | B | . | . | . | 0.43 | −0.26 | . | * | F | 0.60 | 1.02 |
| Pro | 634 | . | . | B | . | . | . | . | 0.21 | −0.36 | * | . | F | 0.80 | 1.85 |
| Glu | 635 | A | A | . | . | . | . | . | −0.07 | −0.31 | . | * | F | 0.60 | 1.85 |
| His | 636 | A | A | . | . | . | . | . | 0.50 | −0.50 | * | * | . | 0.60 | 0.93 |
| Ser | 637 | A | A | . | . | . | . | . | 1.31 | 0.41 | . | * | . | −0.60 | 0.63 |
| Leu | 638 | A | A | . | . | . | . | . | 1.27 | 0.39 | . | * | . | −0.30 | 0.59 |
| Ala | 639 | A | A | . | . | . | . | . | 0.88 | 0.79 | . | . | . | −0.60 | 0.70 |
| Trp | 640 | A | A | . | . | . | . | . | −0.01 | 0.90 | . | . | . | −0.60 | 0.51 |
| Asn | 641 | A | A | . | . | . | . | . | −0.87 | 1.20 | . | . | . | −0.60 | 0.44 |
| Asn | 642 | A | A | . | B | . | . | . | −1.38 | 1.20 | . | . | . | −0.60 | 0.30 |
| Met | 643 | . | A | B | B | . | . | . | −1.38 | 1.39 | . | . | . | −0.60 | 0.24 |
| Ile | 644 | . | . | B | B | . | . | . | −0.79 | 1.16 | * | . | . | −0.60 | 0.12 |
| Ile | 645 | . | . | B | B | . | . | . | −0.50 | 0.76 | * | . | . | −0.60 | 0.13 |
| Leu | 646 | . | . | B | B | . | . | . | −0.81 | 0.76 | . | . | . | −0.60 | 0.21 |
| Leu | 647 | . | . | B | B | . | . | . | −1.16 | 0.63 | * | . | . | −0.60 | 0.42 |
| Asp | 648 | . | . | B | B | . | . | . | −0.56 | 0.37 | . | * | F | −0.15 | 0.60 |
| Asn | 649 | . | . | . | . | . | T | C | −0.48 | 0.09 | . | . | F | 0.60 | 1.17 |
| Thr | 650 | . | . | . | . | . | T | C | −0.18 | 0.09 | * | . | F | 0.60 | 1.17 |
| Gly | 651 | . | . | . | . | . | T | C | 0.63 | −0.10 | * | . | F | 1.05 | 0.71 |
| Asn | 652 | . | . | . | . | . | T | C | 0.86 | 0.30 | . | . | F | 0.45 | 0.76 |
| Leu | 653 | A | A | . | . | . | . | . | 0.86 | 0.40 | . | . | . | −0.30 | 0.53 |
| Ala | 654 | A | A | . | . | . | . | . | 0.27 | −0.09 | . | . | . | 0.30 | 0.93 |
| Gln | 655 | A | A | . | . | . | . | . | −0.28 | −0.01 | . | . | . | 0.30 | 0.58 |
| Ala | 656 | A | A | . | . | . | . | . | −0.28 | 0.23 | . | * | . | −0.30 | 0.53 |
| Glu | 657 | A | A | . | . | . | . | . | −0.17 | −0.03 | . | * | . | 0.30 | 0.52 |
| Ala | 658 | A | A | . | . | . | . | . | 0.64 | −0.53 | * | * | . | 0.60 | 0.58 |
| Val | 659 | A | A | . | . | . | . | . | 0.64 | −0.93 | * | * | . | 0.60 | 1.00 |
| Gly | 660 | A | A | . | . | . | . | . | −0.17 | −0.93 | * | * | . | 0.60 | 0.58 |
| Arg | 661 | A | A | . | . | . | . | . | 0.42 | −0.24 | * | * | F | 0.45 | 0.48 |
| Glu | 662 | A | A | . | . | . | . | . | −0.39 | −0.74 | * | * | . | 0.75 | 1.11 |
| Ala | 663 | A | A | . | . | . | . | . | −0.69 | −0.70 | * | * | . | 0.60 | 0.93 |
| Leu | 664 | A | A | . | . | . | . | . | −0.04 | −0.44 | * | * | . | 0.30 | 0.33 |
| Glu | 665 | A | A | . | . | . | . | . | 0.30 | −0.01 | * | * | . | 0.30 | 0.30 |
| Leu | 666 | A | A | . | . | . | . | . | 0.19 | 0.39 | * | * | . | −0.30 | 0.47 |
| Ile | 667 | A | . | . | . | . | T | . | 0.16 | −0.11 | * | . | . | 0.70 | 0.95 |
| Pro | 668 | A | . | . | . | . | T | . | 0.44 | −0.30 | . | . | F | 0.85 | 0.75 |
| Asn | 669 | A | . | . | . | . | T | . | 0.44 | 0.09 | . | . | F | 0.40 | 1.22 |
| Asp | 670 | A | . | . | . | . | T | . | −0.16 | 0.09 | . | . | F | 0.40 | 1.43 |
| His | 671 | A | A | . | . | . | . | . | −0.04 | 0.01 | . | . | F | −0.15 | 0.92 |
| Ser | 672 | A | A | . | . | . | . | . | 0.54 | 0.37 | . | * | . | −0.30 | 0.49 |
| Leu | 673 | . | A | B | . | . | . | . | −0.06 | 0.36 | . | . | . | −0.30 | 0.40 |
| Met | 674 | . | A | B | . | . | . | . | −0.64 | 1.04 | . | . | . | −0.60 | 0.24 |
| Phe | 675 | A | A | . | . | . | . | . | −0.64 | 1.04 | . | . | . | −0.60 | 0.18 |
| Ser | 676 | A | A | . | . | . | . | . | −1.47 | 1.06 | * | . | . | −0.60 | 0.35 |
| Leu | 677 | A | A | . | . | . | . | . | −1.98 | 1.01 | * | . | . | −0.60 | 0.26 |
| Ala | 678 | A | A | . | . | . | . | . | −1.51 | 1.09 | * | . | . | −0.60 | 0.25 |
| Asn | 679 | A | A | . | . | . | . | . | −0.87 | 0.73 | * | . | . | −0.60 | 0.19 |
| Val | 680 | A | A | . | . | . | . | . | −0.47 | 0.34 | . | * | . | −0.30 | 0.45 |
| Leu | 681 | A | A | . | . | . | . | . | −0.17 | 0.04 | * | . | . | −0.30 | 0.60 |
| Gly | 682 | A | . | . | . | . | T | . | 0.69 | −0.06 | * | . | F | 0.85 | 0.64 |
| Lys | 683 | A | . | . | . | . | T | . | 1.03 | −0.46 | . | * | F | 1.00 | 1.74 |
| Ser | 684 | A | . | . | . | . | T | . | 1.08 | −0.34 | . | . | F | 1.00 | 3.30 |
| Gln | 685 | A | . | . | . | . | T | . | 1.93 | −1.03 | . | . | F | 1.30 | 6.67 |
| Lys | 686 | A | . | . | . | . | . | . | 2.44 | −1.46 | . | . | F | 1.10 | 5.77 |
| Tyr | 687 | A | . | . | . | . | T | . | 2.79 | −1.07 | . | . | F | 1.30 | 5.77 |
| Lys | 688 | A | . | . | . | . | T | . | 2.16 | −1.46 | . | . | F | 1.30 | 5.77 |
| Glu | 689 | A | . | . | . | . | T | . | 1.64 | −1.36 | . | . | F | 1.30 | 2.92 |
| Ser | 690 | A | . | . | . | . | T | . | 0.94 | −0.67 | . | . | F | 1.30 | 1.54 |
| Glu | 691 | A | A | . | . | . | . | . | 0.09 | −0.64 | . | . | F | 0.75 | 0.66 |
| Ala | 692 | A | A | . | . | . | . | . | 0.38 | 0.04 | * | . | . | −0.30 | 0.32 |
| Leu | 693 | A | A | . | . | . | . | . | −0.26 | 0.04 | * | . | . | −0.30 | 0.47 |
| Phe | 694 | A | A | . | . | . | . | . | −1.14 | 0.16 | * | . | . | −0.30 | 0.28 |
| Leu | 695 | A | A | . | . | . | . | . | −0.80 | 0.84 | * | . | . | −0.60 | 0.19 |

TABLE 7-continued

| Res | Position | I | II | III | IV | V | VI | VII | VIII | IX | X | XI | XII | XIII | XIV |
|---|---|---|---|---|---|---|---|---|---|---|---|---|---|---|---|
| Lys | 696 | A | A | . | . | . | . | . | −1.39 | 0.34 | . | . | . | −0.30 | 0.46 |
| Ala | 697 | A | A | . | . | . | . | . | −0.80 | 0.16 | * | . | . | −0.30 | 0.54 |
| Ile | 698 | A | A | . | . | . | . | . | −0.20 | −0.23 | * | * | . | 0.66 | 1.05 |
| Lys | 699 | A | A | . | . | . | . | . | 0.50 | −0.49 | * | * | F | 0.87 | 0.82 |
| Ala | 700 | A | A | . | . | . | . | . | 0.72 | −0.09 | * | * | F | 1.23 | 1.30 |
| Asn | 701 | . | . | . | . | . | T | C | 0.09 | −0.09 | * | * | F | 2.04 | 1.87 |
| Pro | 702 | . | . | . | . | . | T | C | 0.38 | −0.27 | * | * | F | 2.10 | 0.95 |
| Asn | 703 | . | . | . | . | T | T | . | 1.02 | 0.11 | . | * | . | 1.49 | 1.25 |
| Ala | 704 | A | . | . | . | . | T | . | 0.94 | 0.37 | . | * | . | 0.88 | 1.22 |
| Ala | 705 | . | . | B | . | . | . | . | 1.19 | 0.47 | . | . | . | 0.17 | 1.07 |
| Ser | 706 | . | . | B | . | . | . | . | 1.19 | 0.47 | . | * | . | −0.19 | 0.66 |
| Tyr | 707 | . | . | B | . | . | . | . | 0.59 | 0.47 | . | . | . | −0.25 | 1.05 |
| His | 708 | . | . | B | . | . | T | . | −0.00 | 0.66 | . | * | . | −0.20 | 0.86 |
| Gly | 709 | . | . | B | . | . | T | . | −0.27 | 0.66 | . | * | . | −0.20 | 0.65 |
| Asn | 710 | . | . | B | . | . | T | . | −0.49 | 0.91 | . | * | . | −0.20 | 0.31 |
| Leu | 711 | . | . | B | . | . | T | . | −0.43 | 0.84 | . | * | . | −0.20 | 0.19 |
| Ala | 712 | . | . | B | B | . | . | . | −0.22 | 1.10 | . | * | . | −0.60 | 0.29 |
| Val | 713 | . | . | B | B | . | . | . | −0.08 | 1.17 | . | * | . | −0.60 | 0.25 |
| Leu | 714 | . | . | B | B | . | . | . | −0.02 | 0.77 | * | . | . | −0.60 | 0.59 |
| Tyr | 715 | . | . | B | B | . | . | . | −0.37 | 1.00 | * | . | . | −0.60 | 0.62 |
| His | 716 | . | . | B | . | . | T | . | 0.41 | 0.93 | * | . | . | −0.20 | 0.82 |
| Arg | 717 | . | . | . | . | T | T | . | 0.19 | 0.79 | . | . | . | 0.35 | 1.36 |
| Trp | 718 | A | . | . | . | . | T | . | 1.04 | 0.79 | . | . | . | −0.20 | 0.71 |
| Gly | 719 | A | . | . | . | . | T | . | 1.04 | 0.03 | . | . | . | 0.10 | 0.88 |
| His | 720 | A | A | . | . | . | . | . | 0.70 | 0.21 | . | . | . | −0.30 | 0.37 |
| Leu | 721 | A | A | . | . | . | . | . | 0.78 | 0.71 | . | . | . | −0.60 | 0.35 |
| Asp | 722 | A | A | . | . | . | . | . | 0.71 | −0.20 | . | . | . | 0.30 | 0.72 |
| Leu | 723 | A | A | . | . | . | . | . | 0.97 | −0.63 | . | . | . | 0.75 | 1.05 |
| Ala | 724 | A | A | . | . | . | . | . | 1.07 | −0.63 | * | * | . | 0.75 | 1.74 |
| Lys | 725 | A | A | . | . | . | . | . | 1.10 | −0.56 | * | * | F | 0.90 | 1.63 |
| Lys | 726 | A | A | . | . | . | . | . | 1.02 | −0.56 | * | * | F | 0.90 | 3.42 |
| His | 727 | A | A | . | . | . | . | . | 0.72 | −0.56 | * | * | . | 0.75 | 2.37 |
| Tyr | 728 | A | A | . | . | . | . | . | 0.72 | −0.67 | * | * | . | 0.75 | 1.59 |
| Glu | 729 | . | A | B | . | . | . | . | 1.31 | 0.01 | * | * | . | −0.30 | 0.66 |
| Ile | 730 | . | A | B | . | . | . | . | 0.46 | 0.41 | . | * | . | −0.60 | 0.83 |
| Ser | 731 | . | A | B | . | . | . | . | 0.41 | 0.60 | . | * | . | −0.60 | 0.44 |
| Leu | 732 | . | A | B | . | . | . | . | 0.23 | −0.16 | . | * | . | 0.30 | 0.42 |
| Gln | 733 | . | A | B | . | . | . | . | 0.17 | 0.27 | . | * | . | −0.30 | 0.93 |
| Leu | 734 | . | A | B | . | . | . | . | −0.42 | 0.07 | . | * | . | −0.15 | 1.01 |
| Asp | 735 | . | . | . | . | . | T | C | 0.17 | 0.19 | . | * | F | 0.60 | 1.23 |
| Pro | 736 | . | . | . | . | . | T | C | 0.12 | −0.11 | . | * | F | 1.31 | 0.95 |
| Thr | 737 | . | . | . | . | . | T | C | 0.62 | −0.09 | . | * | F | 1.72 | 1.14 |
| Ala | 738 | . | . | B | . | . | T | C | 0.67 | −0.29 | . | * | F | 1.83 | 0.99 |
| Ser | 739 | . | . | . | . | . | . | C | 1.48 | −0.29 | . | * | F | 2.04 | 1.28 |
| Gly | 740 | . | . | . | . | . | . | C | 1.48 | −0.71 | . | . | F | 2.60 | 1.54 |
| Thr | 741 | . | . | . | . | . | . | C | 1.44 | −0.80 | . | . | F | 2.34 | 2.44 |
| Lys | 742 | . | . | B | . | . | . | . | 1.41 | −0.54 | . | . | F | 1.88 | 2.86 |
| Glu | 743 | . | . | B | . | . | . | . | 1.19 | −0.50 | . | . | F | 1.62 | 2.86 |
| Asn | 744 | . | . | B | . | . | T | . | 0.68 | −0.24 | * | . | F | 1.26 | 1.63 |
| Tyr | 745 | . | . | B | . | . | T | . | 1.13 | −0.04 | * | . | . | 0.70 | 0.67 |
| Gly | 746 | A | . | . | . | . | T | . | 1.56 | −0.04 | * | . | . | 0.70 | 0.76 |
| Leu | 747 | A | . | . | . | . | T | . | 1.56 | −0.04 | * | * | . | 0.70 | 0.93 |
| Leu | 748 | A | A | . | . | . | . | . | 0.74 | −0.44 | * | * | . | 0.45 | 1.18 |
| Arg | 749 | A | A | . | . | . | . | . | 0.74 | −0.51 | * | * | F | 0.75 | 0.99 |
| Arg | 750 | A | A | . | . | . | . | . | 0.18 | −0.94 | * | * | F | 0.90 | 2.07 |
| Lys | 751 | A | A | . | . | . | . | . | −0.08 | −0.94 | * | * | F | 0.90 | 2.07 |
| Leu | 752 | A | A | . | . | . | . | . | 0.73 | −1.01 | * | * | . | 0.75 | 1.05 |
| Glu | 753 | A | A | . | . | . | . | . | 1.59 | −0.61 | * | * | . | 0.60 | 0.93 |
| Leu | 754 | A | A | . | . | . | . | . | 1.52 | −0.61 | * | * | . | 0.60 | 0.93 |
| Met | 755 | A | A | . | . | . | . | . | 0.82 | −0.61 | * | . | . | 0.75 | 2.24 |
| Gln | 756 | A | A | . | . | . | . | . | −0.08 | −0.80 | . | * | . | 0.75 | 1.31 |
| Lys | 757 | A | A | . | . | . | . | . | 0.34 | −0.16 | . | . | F | 0.60 | 1.18 |
| Lys | 758 | A | A | . | . | . | . | . | −0.04 | −0.41 | . | . | . | 0.45 | 1.52 |
| Ala | 759 | A | A | . | . | . | . | . | 0.38 | −0.60 | . | . | . | 0.75 | 1.12 |
| Val | 760 | A | A | . | . | . | . | . | 0.59 | −0.57 | . | . | . | 0.60 | 0.72 |

It will be clear that the invention may be practiced otherwise than as particularly described in the foregoing description and examples. Numerous modifications and variations of the present invention are possible in light of the above teachings and, therefore, are within the scope of the appended claims.

The entire disclosure of each document cited (including patents, patent applications, journal articles, abstracts, laboratory manuals, books, or other disclosures) in the Background of the Invention, Detailed Description, and Examples is hereby incorporated herein by reference. Further, the hard copy of the sequence listing submitted herewith and the corresponding computer readable form are both incorporated herein by reference in their entireties.

What is claimed is:

1. An isolated antibody or fragment thereof that specifically binds to a polypeptide selected from the group consisting of:

(a) a polypeptide whose amino acid sequence consists of amino acid residues 1 to 508 of SEQ ID NO:139;

(b) a polypeptide whose amino acid sequence consists of a portion of SEQ ID NO:139, wherein said portion is at least 30 contiguous amino acid residues of SEQ ID NO:139; and (c) a polypeptide whose amino acid sequence consists of a portion of SEQ ID NO:139, wherein said portion is at least 50 contiguous amino acid residues of SEQ ID NO:139.

2. The antibody or fragment thereof of claim 1 that specifically binds polypeptide (a).

3. The antibody or fragment thereof of claim 1 that specifically binds polypeptide (b).

4. The antibody or fragment thereof of claim 1 that specifically binds polypeptide (c).

5. The antibody or fragment thereof of claim 3 that specifically binds a polypeptide whose amino acid sequence consists of amino acid residues 1 to 508 of SEQ ID NO:139.

6. The antibody or fragment thereof of claim 1, which is a polyclonal antibody.

7. The antibody or fragment thereof of claim 1, which is a monoclonal antibody.

8. The antibody or fragment thereof of claim 1, which is selected from the group consisting of:

(a) a chimeric antibody;

(b) a human antibody;

(c) a humanized antibody;

(d) a single chain antibody; and (e) a Fab fragment.

9. The antibody or fragment thereof of claim 1, which is labeled.

10. The antibody or fragment thereof of claim 1 wherein said polypeptide bound by said antibody or fragment thereof is glycosylated.

11. The antibody or fragment thereof of claim 1 wherein said antibody or fragment thereof specifically binds to said polypeptide in a Western blot.

12. The antibody or fragment thereof of claim 1 wherein said antibody or fragment thereof specifically binds to said polypeptide in an ELISA.

13. An isolated cell that produces the antibody or fragment thereof of claim 1.

14. A hybridoma that produces the antibody or fragment thereof of claim 1.

15. The antibody or fragment thereof of claim 2, which is a polyclonal antibody.

16. The antibody or fragment thereof of claim 2, which is a monoclonal antibody.

17. The antibody or fragment thereof of claim 2 which is selected from the group consisting of:

(a) a chimeric antibody;

(b) a human antibody;

(c) a humanized antibody;

(d) a single chain antibody; and (e) a Fab fragment.

18. The antibody or fragment thereof of claim 2, which is labeled.

19. The antibody or fragment thereof of claim 2 wherein said polypeptide bound by said antibody or fragment thereof is glycosylated.

20. The antibody or fragment thereof of claim 2 wherein said antibody or fragment thereof specifically binds to said polypeptide in a Western blot.

21. The antibody or fragment thereof of claim 2 wherein said antibody or fragment thereof specifically binds to said polypeptide in an ELISA.

22. An isolated cell that produces the antibody or fragment thereof of claim 2.

23. A hybridoma that produces the antibody or fragment thereof of claim 2.

24. A method of detecting a polypeptide comprising amino acid residues 1 to 508 of SEQ ID NO:139 in a biological sample comprising:

(a) contacting the biological sample with the antibody or fragment thereof of claim 1;

(b) allowing a complex to form between said polypeptide comprising amino acid residues 1 to 508 of SEQ ID NO:139 and said antibody of claim 1; and, (c) detecting said complex.

* * * * *

UNITED STATES PATENT AND TRADEMARK OFFICE

CERTIFICATE OF CORRECTION

PATENT NO. : 7,247,442 B1

APPLICATION NO. : 10/849979

DATED : July 24, 2007

INVENTOR(S) : Ruben et al.

It is certified that error appears in the above-identified patent and that said Letters Patent is hereby corrected as shown below:

On the Title Page (75):

Delete "Inventors: Steven M. Ruben, Brookeville, MD (US): Kimberly A. Florence, Rockville, MD (US); Jian Ni, Germantown, MD (US); Craig A. Rosen, Laytonsville, MD (US); Kenneth C. Carter, North Potomac, MD (US); Paul A. Moore, North Bethesda, MD (US); Henrik S. Olsen, Gaithersburg, MD (US); Yanggu Shi, Gaithersburg, MD (US); Paul E. Young, Gaithersburg, MD (US); Ying-Fei Wei, Berkeley, CA (US); Laurie A. Brewer, St. Paul, MN (US); Daniel R. Soppet, Centreville, VA (US); David W. LaFleur, Washington, DC (US); Gregory A. Endress, Florence, MA (US); Reinhard Ebner, Gaithersburg, MD (US); Charles E. Birse, North Potomac, MD (US)", and insert --Steven M. Ruben, Brookeville, MD (US); Jian Ni, Germantown, MD (US); Craig A. Rosen, Laytonsville, MD (US)--;

Page 2 (Other Publications)

Line 8, delete "Image 19287", and insert --Image 192879--;

Line 10, delete "EST29899", and insert --EST29889--;

Line 23, delete "*Biochem Biohys*", and insert --*Biochem Biophys*--.

Signed and Sealed this

Twentieth Day of November, 2007

JON W. DUDAS

*Director of the United States Patent and Trademark Office*